(12) United States Patent
Miller et al.

(10) Patent No.: US 10,538,555 B2
(45) Date of Patent: *Jan. 21, 2020

(54) MACROCYCLIC INHIBITORS OF THE PD-1/PD-L1 AND CD80(B7-1)/PD-L1 PROTEIN/PROTEIN INTERACTIONS

(71) Applicant: BRISTOL-MYERS SQUIBB COMPANY, Princeton, NJ (US)

(72) Inventors: Michael Matthew Miller, Lambertville, NJ (US); Claudio Mapelli, Langhorne, PA (US); Martin Patrick Allen, Flemington, NJ (US); Michael S. Bowsher, Prospect, CT (US); Eric P. Gillis, Cheshire, CT (US); David R. Langley, Meriden, CT (US); Eric Mull, Guilford, CT (US); Maude A. Poirier, Pennington, NJ (US); Nishith Sanghvi, Bridgewater, NJ (US); Li-Qiang Sun, Glastonbury, CT (US); Daniel J. Tenney, Yardley, PA (US); Kap-Sun Yeung, Madison, CT (US); Juliang Zhu, North Haven, CT (US); Kevin W. Gillman, Madison, CT (US); Qian Zhao, Wallingford, CT (US); Katharine A. Grant-Young, Madison, CT (US); Paul Michael Scola, Glastonbury, CT (US); Lyndon A. M. Cornelius, Jackson, NJ (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/510,138

(22) PCT Filed: Sep. 11, 2014

(86) PCT No.: PCT/US2014/055093
§ 371 (c)(1),
(2) Date: Mar. 9, 2017

(87) PCT Pub. No.: WO2016/039749
PCT Pub. Date: Mar. 17, 2016

(65) Prior Publication Data
US 2017/0260237 A1  Sep. 14, 2017

(51) Int. Cl.
*A61K 38/12* (2006.01)
*C07K 7/64* (2006.01)
*C07K 7/08* (2006.01)
*A61K 45/06* (2006.01)
*A61K 38/00* (2006.01)

(52) U.S. Cl.
CPC ............... *C07K 7/64* (2013.01); *A61K 38/12* (2013.01); *A61K 45/06* (2013.01); *C07K 7/08* (2013.01); *A61K 38/00* (2013.01); *Y02A 50/463* (2018.01)

(58) Field of Classification Search
None
See application file for complete search history.

(56) References Cited

U.S. PATENT DOCUMENTS

| 5,869,451 A | 2/1999 | Dower et al. |
| 9,090,668 B2 | 7/2015 | Suga et al. |
| 9,308,236 B2 * | 4/2016 | Miller .................... A61K 38/10 |
| 9,410,148 B2 | 8/2016 | Suga et al. |
| 2014/0018257 A1 | 1/2014 | Suga et al. |
| 2016/0158349 A1 | 6/2016 | Miller et al. |
| 2016/0272680 A1 | 9/2016 | Boy et al. |
| 2016/0340391 A1 | 11/2016 | Miller et al. |

FOREIGN PATENT DOCUMENTS

| WO | WO 00/26353 | 5/2000 |
| WO | WO 2010/027828 A2 | 3/2010 |
| WO | WO 2011/161699 A2 | 12/2011 |
| WO | WO 2012/168944 A1 | 12/2012 |
| WO | WO 2013/144704 A1 | 10/2013 |
| WO | WO 2013/182240 A1 | 12/2013 |
| WO | WO 2013/183707 A1 | 12/2013 |
| WO | WO 2014/151006 A2 | 9/2014 |
| WO | WO 2014/151634 A1 | 9/2014 |
| WO | WO 2015/033303 A1 | 3/2015 |
| WO | WO 2015/044900 A1 | 4/2015 |
| WO | WO 2016/039749 A1 | 3/2016 |
| WO | WO 2016/057624 A1 | 4/2016 |
| WO | WO 2016/077518 A1 | 5/2016 |
| WO | WO 2016/100285 A1 | 6/2016 |
| WO | WO 2016/100608 A1 | 6/2016 |
| WO | WO 2016/126646 A1 | 8/2016 |

OTHER PUBLICATIONS

Hayashi, Y. et al., "In Vitro Selection of Anti-Akt2 Thioether-Macrocyclic Peptides Leading to Isoform-Selective Inhibitors", ACS Chemical Biology, vol. 7, pp. 607-613 (2012).

Morimoto, J. et al., "Discovery of Macrocyclic Peptides Armed with a Mechanism-Based Warhead: Isoform-Selective Inhibition of Human Deacetylase SIRT2", Angewandte Chemie, International Edition, vol. 51, pp. 3423-3427 (2012).

Yamagishi, Y. et al., "Natural Product-Like Macrocyclic N-Methyl-Peptide Inhibitors against a Ubiquitin Ligase Uncovered from a Ribosome-Expressed De Novo Library", Chemistry & Biology, vol. 18, pp. 1562-1570 (2011).

F. Wang, et al., "Synthetic Small Peptides Acting on B7H1 Enhance Apoptosis in Pancreatic Cancer Cells," Molecular Medicine Reports 6: pp. 553-557, vol. 2012.

K.A. Hofmeyer et al., "The PD-1/PD-L1 (B7-H1) Pathway in chronic Infection-Induced Cytotoxic T Lymphocyte Exhaustion," Journal of Biomedicine and Biotechnology, Article ID 451694, 9 pages, 2011. https://doi.org/10.1155/2011/451694.

* cited by examiner

*Primary Examiner* — Thomas S Heard
(74) *Attorney, Agent, or Firm* — Sterne, Kessler, Goldstein & Fox P.L.L.C.

(57) ABSTRACT

The present disclosure provides novel macrocyclic peptides which inhibit the PD-1/PD-L1 and PD-L1/CD80 protein/protein interaction, and thus are useful for the amelioration of various diseases, including cancer and infectious diseases.

3 Claims, No Drawings
Specification includes a Sequence Listing.

```
                          SEQUENCE LISTING

<160> NUMBER OF SEQ ID NOS: 2

<210> SEQ ID NO 1
<211> LENGTH: 384
<212> TYPE: PRT
<213> ORGANISM: Homo sapiens

<400> SEQUENCE: 1

Leu Asp Ser Pro Asp Arg Pro Trp Asn Pro Thr Phe Ser Pro Ala
1               5                   10                  15

Leu Leu Val Val Thr Glu Gly Asp Asn Ala Thr Phe Thr Cys Ser Phe
                20                  25                  30

Ser Asn Thr Ser Glu Ser Phe Val Leu Asn Trp Tyr Arg Met Ser Pro
            35                  40                  45

Ser Asn Gln Thr Asp Lys Leu Ala Ala Phe Pro Glu Asp Arg Ser Gln
        50                  55                  60

Pro Gly Gln Asp Cys Arg Phe Arg Val Thr Gln Leu Pro Asn Gly Arg
65                  70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
                100                 105                 110

Ser Leu Arg Ala Glu Leu Arg Val Thr Glu Arg Arg Ala Glu Val Pro
            115                 120                 125

Thr Ala His Pro Ser Pro Ser Pro Arg Pro Ala Gly Gln Phe Gln Gly
        130                 135                 140

Ser Pro Gly Gly Gly Gly Arg Glu Pro Lys Ser Ser Asp Lys Thr
145                 150                 155                 160

His Thr Ser Pro Pro Ser Pro Ala Pro Glu Leu Leu Gly Gly Ser Ser
                165                 170                 175

Val Phe Leu Phe Pro Pro Lys Pro Lys Asp Thr Leu Met Ile Ser Arg
                180                 185                 190

Thr Pro Glu Val Thr Cys Val Val Val Asp Val Ser His Glu Asp Pro
            195                 200                 205

Glu Val Lys Phe Asn Trp Tyr Val Asp Gly Val Glu Val His Asn Ala
        210                 215                 220

Lys Thr Lys Pro Arg Glu Glu Gln Tyr Asn Ser Thr Tyr Arg Val Val
225                 230                 235                 240

Ser Val Leu Thr Val Leu His Gln Asp Trp Leu Asn Gly Lys Glu Tyr
                245                 250                 255

Lys Cys Lys Val Ser Asn Lys Ala Leu Pro Ala Pro Ile Glu Lys Thr
                260                 265                 270

Ile Ser Lys Ala Lys Gly Gln Pro Arg Glu Pro Gln Val Tyr Thr Leu
            275                 280                 285

Pro Pro Ser Arg Asp Glu Leu Thr Lys Asn Gln Val Ser Leu Thr Cys
        290                 295                 300
```

```
Leu Val Lys Gly Phe Tyr Pro Ser Asp Ile Ala Val Glu Trp Glu Ser
305                 310                 315                 320

Asn Gly Gln Pro Glu Asn Asn Tyr Lys Thr Thr Pro Pro Val Leu Asp
            325                 330                 335

Ser Asp Gly Ser Phe Phe Leu Tyr Ser Lys Leu Thr Val Asp Lys Ser
            340                 345                 350

Arg Trp Gln Gln Gly Asn Val Phe Ser Cys Ser Val Met His Glu Ala
            355                 360                 365

Leu His Asn His Tyr Thr Gln Lys Ser Leu Ser Leu Ser Pro Gly Lys
            370                 375                 380

<210> SEQ ID NO 2
<211> LENGTH: 237
<212> TYPE: PRT
<213> ORGANISM: Homo sapiens

<400> SEQUENCE: 2

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg Thr Gly Ser Ser
    210                 215                 220

Glu Thr Val Arg Phe Gln Gly His His His His His
225                 230                 235
```

MACROCYCLIC INHIBITORS OF THE PD-1/PD-L1 AND CD80(B7-1)/PD-L1 PROTEIN/PROTEIN INTERACTIONS

The present disclosure provides novel macrocyclic peptides which inhibit the PD-1/PD-L1 and CD80/PD-L1 protein/protein interaction, and are thus useful for the amelioration of various diseases, including cancer and infectious diseases.

The protein Programmed Death 1 (PD-1) is an inhibitory member of the CD28 family of receptors, that also includes CD28, CTLA-4, ICOS and BTLA. PD-1 is expressed on activated B cells, T cells, and myeloid cells (Agata et al., supra; Okazaki et al., Curr. Opin. Immunol., 14:779-782 (2002); Bennett et al., J. Immunol., 170:711-718 (2003)).

The PD-1 protein is a 55 kDa type I transmembrane protein that is part of the Ig gene superfamily (Agata et al., Int. Immunol., 8:765-772 (1996)). PD-1 contains a membrane proximal immunoreceptor tyrosine inhibitory motif (ITIM) and a membrane distal tyrosine-based switch motif (ITSM) (Thomas, M. L., J. Exp. Med., 181:1953-1956 (1995); Vivier, E. et al., Immunol. Today, 18:286-291 (1997)). Although structurally similar to CTLA-4, PD-1 lacks the MYPPY motif that is critical for CD80 CD86 (B7-2) binding. Two ligands for PD-1 have been identified, PD-L1 (B7-H1) and PD-L2 (b7-DC). The activation of T cells expressing PD-1 has been shown to be downregulated upon interaction with cells expressing PD-L1 or PD-L2 (Freeman et al., J. Exp. Med., 192:1027-1034 (2000); Latchman et al., Nat. Immunol., 2:261-268 (2001); Carter et al., Eur. J. Immunol., 32:634-643 (2002)). Both PD-L1 and PD-L2 are B7 protein family members that bind to PD-1, but do not bind to other CD28 family members. The PD-L1 ligand is abundant in a variety of human cancers (Dong et al., Nat. Med., 8:787-789 (2002)). The interaction between PD-1 and PD-L1 results in a decrease in tumor infiltrating lymphocytes, a decrease in T-cell receptor mediated proliferation, and immune evasion by the cancerous cells (Dong et al., J. Mol. Med., 81:281-287 (2003); Blank et al., Cancer Immunol. Immunother., 54:307-314 (2005); Konishi et al., Clin. Cancer Res., 10:5094-5100 (2004)). Immune suppression can be reversed by inhibiting the local interaction of PD-1 with PD-L1, and the effect is additive when the interaction of PD-1 with PD-L2 is blocked as well (Iwai et al., Proc. Natl. Acad. Sci. USA, 99:12293-12297 (2002); Brown et al., J. Immunol., 170:1257-1266 (2003)).

PD-L1 has also been shown to interact with CD80 (Butte, M. J. et al., Immunity, 27:111-122 (2007)). The interaction PD-L1/CD80 on expressing immune cells has been shown to be an inhibitory one. Blockade of this interaction has been shown to abrogate this inhibitory interaction (Paterson, A. M. et al., J. Immunol., 187:1097-1105 (2011); Yang, J. et al., J. Immunol., 187(3):1113-1119 (Aug. 1, 2011)).

When PD-1 expressing T cells contact cells expressing its ligands, functional activities in response to antigenic stimuli, including proliferation, cytokine secretion, and cytotoxicity, are reduced. PD-1/PD-L1 or PD-L2 interactions down regulate immune responses during resolution of an infection or tumor, or during the development of self tolerance (Keir, M. E. et al., Annu. Rev. Immunol., 26:Epub (2008)). Chronic antigen stimulation, such as that which occurs during tumor disease or chronic infections, results in T cells that express elevated levels of PD-1 and are dysfunctional with respect to activity towards the chronic antigen (reviewed in Kim et al., Curr. Opin. Imm. (2010)). This is termed "T cell exhaustion". B cells also display PD-1/PD-ligand suppression and "exhaustion".

Blockade of PD-1/PD-L1 ligation using antibodies to PD-L1 has been shown to restore and augment T cell activation in many systems. Patients with advanced cancer benefit from therapy with a monoclonal antibody to PD-L1 (Brahmer et al., New Engl. J. Med. (2012)). Preclinical animal models of tumors and chronic infections have shown that blockade of the PD-1/PD-L1 pathway by monoclonal antibodies can enhance the immune response and result in tumor rejection or control of infection. Antitumor immunotherapy via PD-1/PD-L1 blockade may augment therapeutic immune response to a number of histologically distinct tumors (Dong, H. et al., "B7-H1 pathway and its role in the evasion of tumor immunity", J. Mol. Med., 81(5):281-287 (2003); Dong, H. et al., "Tumor-associated B7-H1 promotes T-cell apoptosis: a potential mechanism of immune evasion", Nat. Med., 8(8):793-800 (2002)).

Interference with the PD-1/PD-L1 interaction causes enhanced T cell activity in systems with chronic infection. Blockade of PD-L1 caused improved viral clearance and restored immunity in mice with chromoic lymphocytic chorio meningitis virus infection (Barber, D. L. et al., "Restoring function in exhausted CD8 T cells during chronic viral infection", Nature, 439(7077):682-687 (2006)). Humanized mice infected with HIV-1 show enhanced protection against viremia and viral depletion of CD4+ T cells (Palmer et al., J. Immunol. (2013)). Blockade of PD-1/PD-L1 through monoclonal antibodies to PD-L1 can restore in vitro antigen-specific functionality to T cells from HIV patients (Day, Nature (2006); Petrovas, J. Exp. Med. (2006); Trautman, Nature Med. (2006); D'Souza, J. Immunol. (2007); Zhang, Blood (2007); Kaufmann, Nature Imm. (2007); Kasu, J. Immunol. (2010); Porichis, Blood (2011)), HCV patients (Golden-Mason, J. Virol. (2007); Jeung, J. Leuk. Biol. (2007); Urbani, J. Hepatol. (2008); Nakamoto, PLoS Path. (2009); Nakamoto, Gastroenterology (2008)) and HBV patients (Boni, J. Virol. (2007); Fisicaro, Gastro. (2010); Fisicaro et al., Gastroenterology (2012); Boni et al., Gastro. (2012); Penna et al., J. Hep. (2012); Raziorrough, Hepatology (2009); Liang, World J. Gastro. (2010); Zhang, Gastro. (2008)).

Blockade of the PD-L1/CD80 interaction has also been shown to stimulate immunity (Yang, J. et al., J. Immunol., 187(3):1113-1119 (Aug. 1, 2011)). Immune stimulation resulting from blockade of the PD-L1/CD80 interaction has been shown to be enhanced through combination with blockade of further PD-1/PD-L1 or PD-1/PD-L2 interactions.

Alterations in immune cell phenotypes are hypothesized to be an important factor in septic shock (Hotchkiss et al., Nat. Rev. Immunol. (2013)). These include increased levels of PD-1 and PD-L1 (Guignant, et al., Crit. Care (2011)), Cells from septic shock patients with increased levels of PD-1 and PD-L1 exhibit an increased level of T cell apoptosis. Antibodies directed to PD-L1, can reduce the level of Immune cell apoptosis (Zhang et al., Crit. Care (2011)). Furthermore, mice lacking PD-1 expression are more resistant to septic shock symptoms than wildtype mice. Yang, J. et al., J. Immunol., 187(3):1113-1119 (Aug. 1, 2011)). Studies have revealed that blockade of the interactions of PD-L1 using antibodies can suppress inappropriate immune responses and ameliorate disease signs.

In addition to enhancing immunologic responses to chronic antigens, blockade of the PD-1/PD-L1 pathway has also been shown to enhance responses to vaccination, including therapeutic vaccination in the context of chronic infection (Ha, S. J. et al., "Enhancing therapeutic vaccination by blocking PD-1-mediated inhibitory signals during chronic infection", *J. Exp. Med.*, 205(3):543-555 (2008); Finnefrock, A. C. et al., "PD-1 blockade in rhesus macaques: impact on chronic infection and prophylactic vaccination", *J. Immunol.*, 182(2):980-987 (2009); Song, M.-Y. et al., "Enhancement of vaccine-induced primary and memory CD8+t-cell responses by soluble PD-1", *J. Immunother.*, 34(3):297-306 (2011)).

The molecules described herein demonstrate the ability to block the interaction of PD-L1 with PD-1, in both biochemical and cell-based experimental systems. These results are consistent with a potential for therapeutic administration to enhance immunity in cancer or chronic infection, including therapeutic vaccine.

The macrocyclic peptides described herein are capable of inhibiting the interaction of PD-L1 with PD-1 and with CD80. These compounds have demonstrated highly efficacious binding to PD-L1, blockade of the interaction of PD-L1 with either PD-1 or CD80, and are capable of promoting enhanced T cell functional activity, thus making them candidates for parenteral, oral, pulmonary, nasal, buccal and sustained release formulations.

In one embodiment the present disclosure provides a compound of formula (I)

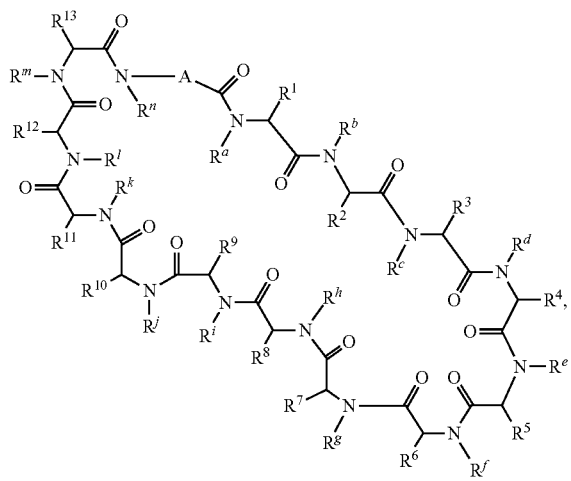

(I)

or a pharmaceutically acceptable salt thereof, wherein:

A is selected from a bond,

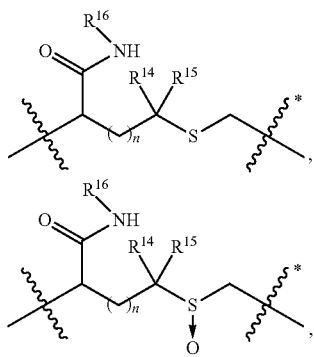

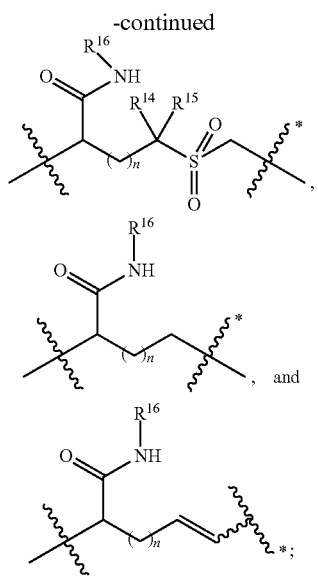

wherein:

$\sim^*$ denotes the point of attachment to the carbonyl group and $\sim$ denotes the point of attachment to the nitrogen atom;

n is 0 or 1;

$R^{14}$ and $R^{15}$ are independently selected from hydrogen and methyl; and $R^{16}$ is selected from hydrogen, —CHR$^{17}$C(O)NH$_2$, —CHR$^{17}$C(O)NHCHR$^{18}$C(O)NH$_2$, and —CHR$^{17}$C(O)NHCHR$^{18}$C(O)NHCH$_2$C(O)NH$_2$;

wherein $R^{17}$ is selected from hydrogen and —CH$_2$OH and wherein $R^{18}$ is selected from hydrogen and methyl;

$R^c$, $R^f$, $R^h$, $R^i$, $R^m$, and $R^n$ are hydrogen;

$R^a$, $R^e$, $R^j$, and $R^k$, are each independently selected from hydrogen and methyl;

$R^1$, $R^2$, $R^3$, $R^4$, $R^5$, $R^6$, $R^7$, $R^8$, $R^9$, $R^{10}$, $R^{11}$, $R^{12}$, and $R^{13}$ are independently selected from a natural amino acid side chain and an unnatural amino acid side chain or form a ring with the corresponding vicinal R group as described below;

$R^e$ and $R^k$ can each form a ring with the corresponding vicinal R group and the atoms to which they are attached selected from azetidine, pyrollidine, morpholine, piperidine, piperazine, and tetrahydrothiazole; wherein each ring is optionally substituted with one to four groups independently selected from amino, cyano, methyl, halo, and hydroxy;

$R^b$ is methyl or, $R^b$ and $R^2$, together with the atoms to which they are attached, form a ring selected from azetidine, pyrollidine, morpholine, piperidine, piperazine, and tetrahydrothiazole; wherein each ring is optionally substituted with one to four groups independently selected from amino, cyano, methyl, halo, and hydroxy;

$R^d$ is hydrogen or methyl, or, $R^d$ and $R^4$, together with the atoms to which they are attached, can form a ring selected from azetidine, pyrollidine, morpholine, piperidine, piperazine, and tetrahydrothiazole; wherein each ring is optionally substituted with one to four groups independently selected from amino, cyano, methyl, halo, hydroxy, and phenyl;

$R^g$ is hydrogen or methyl or $R^g$ and $R^7$, together with the atoms to which they are attached, can form a ring selected from azetidine, pyrollidine, morpholine, piperidine, piperazine, and tetrahydrothiazole; wherein each ring is optionally substituted with one to four groups independently selected from amino, benzyl optionally substituted with a halo group, benzyloxy, cyano, cyclohexyl, methyl, halo, hydroxy, isoquinolinyloxy optionally substituted with a methoxy group, quinolinyloxy optionally substituted with a halo group, and tetrazolyl; and wherein the pyrrolidine and the piperidine ring are optionally fused to a cyclohexyl, phenyl, or indole group; and $R^1$ is methyl or, $R^1$ and $R^{12}$, together with the atoms to which they are attached, form a ring selected from azetidine and pyrollidine, wherein each ring is optionally substituted with one to four independently selected from amino, cyano, methyl, halo, and hydroxy.

In another embodiment the present disclosure provides a compound of formula (I), or a pharmaceutically acceptable salt thereof, wherein A is

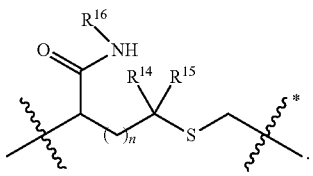

In another embodiment the present disclosure provides a compound of formula (I), or a pharmaceutically acceptable salt thereof, wherein A is

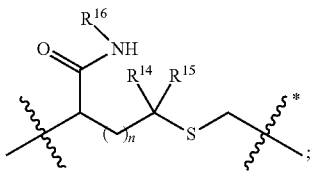

$R^d$ is methyl or, $R^d$ and $R^4$, together with the atoms to which they are attached, form a ring selected from azetidine, pyrollidine, morpholine, piperidine, piperazine, and tetrahydrothiazole; wherein each ring is optionally substituted with one or two groups independently selected from amino, cyano, methyl, halo, hydroxy, and phenyl;

$R^g$ is methyl or, $R^g$ and $R^7$, together with the atoms to which they are attached, form a ring selected from azetidine, pyrollidine, morpholine, piperidine, piperazine, and tetrahydrothiazole; wherein each ring is optionally substituted with one or two groups independently selected from amino, benzyl optionally substituted with a halo group, benzyloxy, cyano, cyclohexyl, methyl, halo, hydroxy, isoquinolinyloxy optionally substituted with a methoxy group, quinolinyloxy optionally substituted with a halo group, and tetrazolyl; and wherein the pyrrolidine and the piperidine ring are optionally fused to a cyclohexyl, phenyl, or indole group; and $R^k$ is methyl or, $R^k$ and $R^{11}$, together with the atoms to which they are attached, form a ring selected from azetidine, pyrollidine, morpholine, piperidine, piperazine, and tetrahydrothiazole; wherein each ring is optionally substituted with one or two groups independently selected from amino, cyano, methyl, halo, and hydroxy.

In another embodiment the present disclosure provides a compound of formula (I), or a pharmaceutically acceptable salt thereof, wherein A is

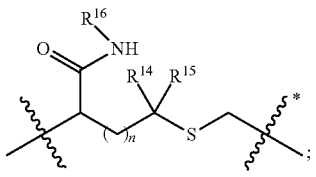

$R^d$ and $R^4$, together with the atoms to which they are attached, form a ring selected from azetidine, pyrollidine, morpholine, piperidine, piperazine, and tetrahydrothiazole; wherein each ring is optionally substituted with one or two groups independently selected from amino, cyano, methyl, halo, and hydroxy;

$R^g$ and $R^7$, together with the atoms to which they are attached, form a pyrollidine ring, wherein said ring is optionally substituted with one or two groups independently selected from amino, benzyl optionally substituted with a halo group, benzyloxy, cyano, cyclohexyl, methyl, halo, hydroxy, isoquinolinyloxy optionally substituted with a methoxy group, quinolinyloxy optionally substituted with a halo group, and tetrazolyl; and wherein the pyrrolidine and the piperidine ring are optionally fused to a cyclohexyl, phenyl, or indole group; and $R^k$ is methyl.

In another embodiment the present disclosure provides a compound of formula (I), or a pharmaceutically acceptable salt thereof, wherein A is

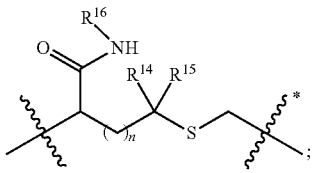

$R^d$ and $R^4$, together with the atoms to which they are attached, form a ring selected from azetidine, pyrollidine, morpholine, piperidine, piperazine, and tetrahydrothiazole; wherein each ring is optionally substituted with one or two groups independently selected from amino, cyano, methyl, halo, and hydroxy;

$R^g$ and $R^7$, together with the atoms to which they are attached, form a pyrollidine ring, wherein said ring is optionally substituted with one or two groups independently selected from amino, benzyl optionally substituted with a halo group, benzyloxy, cyano, cyclohexyl, methyl, halo, hydroxy, isoquinolinyloxy optionally substituted with a methoxy group, quinolinyloxy optionally substituted with a halo group, and tetrazolyl; and wherein the pyrrolidine and the piperidine ring are optionally fused to a cyclohexyl, phenyl, or indole group;

$R^k$ is methyl; and $R^8$ is selected from:

azaindolyl$C_1$-$C_3$alkyl, benzothiazolyl$C_1$-$C_3$alkyl, benzothienyl$C_1$-$C_3$alkyl, benzyloxy$C_1$-$C_3$alkyl, diphenylmethyl, furanyl$C_1$-$C_3$alkyl, imidazolyl$C_1$-$C_3$alkyl, naphthyl$C_1$-$C_3$alkyl, pyridinyl$C_1$-$C_3$alkyl, thiazolyl$C_1$-$C_3$alkyl, thienyl$C_1$-$C_3$alkyl; and indolyl$C_1$-$C_3$alkyl, wherein the indolyl part is optionally substituted with one group selected from $C_1$-$C_3$alkyl, cyano, halo, and hydroxy.

In another embodiment the present disclosure provides a compound of formula (I), or a pharmaceutically acceptable salt thereof, wherein A is

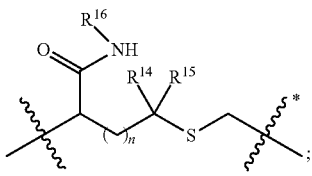

$R^d$ and $R^4$, together with the atoms to which they are attached, form a ring selected from azetidine, pyrollidine, morpholine, piperidine, piperazine, and tetrahydrothiazole; wherein each ring is optionally substituted with one or two groups independently selected from amino, cyano, methyl, halo, and hydroxy;

$R^g$ and $R^7$, together with the atoms to which they are attached, form a pyrollidine ring, wherein said ring is optionally substituted with one or two groups independently selected from amino, benzyl optionally substituted with a halo group, benzyloxy, cyano, cyclohexyl, methyl, halo, hydroxy, isoquinolinyloxy optionally substituted with a methoxy group, quinolinyloxy optionally substituted with a halo group, and tetrazolyl; and wherein the pyrrolidine and the piperidine ring are optionally fused to a cyclohexyl, phenyl, or indole group;

$R^k$ is methyl; and $R^8$ is 3-indolyl$C_1$-$C_3$alkyl optionally substituted with one group selected from $C_1$-$C_3$alkyl, halo, hydroxy, or cyano.

In another embodiment the present disclosure provides a compound of formula (II)

(II)

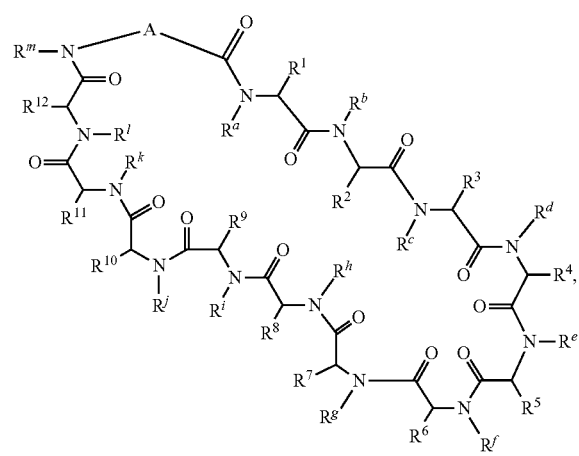

or a pharmaceutically acceptable salt thereof, wherein:
A is selected from a bond,

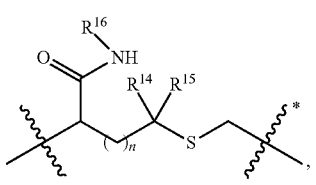

wherein:

$\sim\sim^*$ denotes the point of attachment to the carbonyl group and $\sim\sim$ denotes the point of attachment to the nitrogen atom;

n is 0 or 1;

$R^{14}$ and $R^{15}$ are independently selected from hydrogen and methyl; and $R^{16}$ is selected from hydrogen, —CHR$^{17}$C(O)NH$_2$, —CHR$^{17}$C(O)NHCHR$^{18}$C(O)NH$_2$, and —CHR$^{17}$C(O)NHCHR$^{18}$C(O)NHCH$_2$C(O)NH$_2$;

wherein $R^{17}$ is selected from hydrogen and —CH$_2$OH and wherein $R^{18}$ is selected from hydrogen and methyl;

$R^a$, $R^f$, $R^j$, $R^k$, $R^l$, and $R^m$ are hydrogen;

$R^b$ and $R^c$ are methyl;

$R^g$ is selected from hydrogen and methyl;

$R^1$, $R^2$, $R^3$, $R^4$, $R^5$, $R^6$, $R^7$, $R^8$, $R^9$, $R^{10}$, $R^{11}$, and $R^{12}$ are independently selected from a natural amino acid side chain and an unnatural amino acid side chain or form a ring with the corresponding vicinal R group as described below;

$R^d$ is selected from hydrogen and methyl, or, $R^d$ and $R^4$, together with the atoms to which they are attached, form a ring selected from azetidine, pyrollidine, morpholine, piperidine, piperazine, and tetrahydrothiazole; wherein each ring is optionally substituted with one to four groups independently selected from amino, cyano, methyl, halo, halomethyl, and hydroxy;

$R^e$ is selected from hydrogen and methyl, or, $R^e$ and $R^5$, together with the atoms to which they are attached, form a ring selected from azetidine, pyrollidine, morpholine, piperidine, piperazine, and tetrahydrothiazole; wherein each ring is optionally substituted with one to four groups independently selected from amino, cyano, methyl, halo, halomethyl, and hydroxy;

$R^h$ is selected from hydrogen and methyl, or, $R^h$ and $R^8$, together with the atoms to which they are attached, form a ring selected from azetidine, pyrollidine, morpholine, piperidine, piperazine, and tetrahydrothiazole; wherein each ring is optionally substituted with one to four groups independently selected from amino, cyano, methyl, halo, halomethyl, and hydroxy; and $R^i$ is selected from hydrogen and methyl, or, $R^i$ and $R^9$, together with the atoms to which they are attached selected from azetidine, pyrollidine, morpholine, piperidine, piperazine, and tetrahydrothiazole; wherein each ring is optionally substituted with one to four groups independently selected from amino, cyano, methyl, halo, halomethyl, and hydroxy.

In another embodiment the present disclosure provides a compound of formula (II), or a pharmaceutically acceptable salt thereof, wherein A is

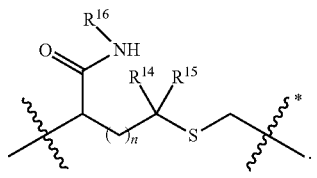

In another embodiment the present disclosure provides a compound of formula (II), or a pharmaceutically acceptable salt thereof, wherein A is

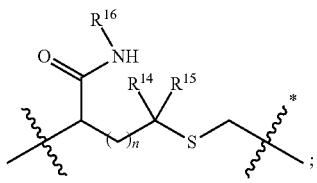

$R^d$ is methyl, or, $R^d$ and $R^4$, together with the atoms to which they are attached selected from azetidine, pyrollidine, morpholine, piperidine, piperazine, and tetrahydrothiazole; wherein each ring is optionally substituted with one or two groups independently selected from amino, cyano, methyl, halo, halomethyl, and hydroxy;

$R^g$ is methyl; and $R^i$ is methyl, or, $R^i$ and $R^9$, together with the atoms to which they are attached selected from selected from azetidine, pyrollidine, morpholine, piperidine, piperazine, and tetrahydrothiazole; wherein each ring is optionally substituted with one or two groups independently selected from amino, cyano, methyl, halo, halomethyl, and hydroxy.

In another embodiment the present disclosure provides a compound of formula (II), or a pharmaceutically acceptable salt thereof, wherein A is

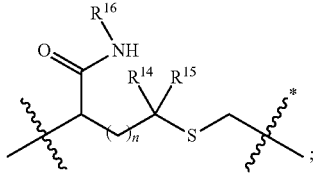

$R^d$ is methyl, or, $R^d$ and $R^4$, together with the atoms to which they are attached selected from azetidine, pyrollidine, morpholine, piperidine, piperazine, and tetrahydrothiazole; wherein each ring is optionally substituted with one or two groups independently selected from amino, cyano, methyl, halo, halomethyl, and hydroxy;

$R^g$ is methyl;

$R^i$ is methyl, or, $R^i$ and $R^9$, together with the atoms to which they are attached selected from selected from azetidine, pyrollidine, morpholine, piperidine, piperazine, and tetrahydrothiazole; wherein each ring is optionally substituted with one or two groups independently selected from amino, cyano, methyl, halo, halomethyl, and hydroxy; and $R^7$ is phenyl$C_1$-$C_3$alkyl optionally substituted with a fluoro group.

In another embodiment the present disclosure provides a method of enhancing, stimulating, and/or increasing the immune response in a subject in need thereof, said method comprising administering to the subject a therapeutically effective amount of at least one macrocyclic peptide described herein. In another embodiment the method further comprises administering an additional agent prior to, after, or simultaneously with the macrocyclic peptide or peptides described herein. In another embodiment the additional agent is an antimicrobial agent, an antiviral agent, a cytotoxic agent, and/or an immune response modifier.

In another embodiment the present disclosure provides a method of inhibiting growth, proliferation, or metastasis of cancer cells in a subject in need thereof, said method comprising administering to the subject a therapeutically effective amount of one or more macrocyclic peptides described herein. In another embodiment the cancer is selected from melanoma, renal cell carcinoma, squamous non-small cell lung cancer (NSCLC), non-squamous NSCLC, colorectal cancer, castration-resistant prostate cancer, ovarian cancer, gastric cancer, hepatocellular carcinoma, pancreatic carcinoma, squamous cell carcinoma of the head and neck, carcinomas of the esophagus, gastrointestinal tract and breast, and a hematological malignancy.

In another embodiment the present disclosure provides a method of treating an infectious disease in a subject in need thereof, the method comprising administering to the subject a therapeutically effective amount of at least one macrocyclic peptide described herein. In another embodiment the infectious disease is caused by a virus. In another embodiment the virus is selected from HIV, Hepatitis A, Hepatitis B, Hepatitis C, herpes virus, and influenza.

In another embodiment the present disclosure provides a method of treating septic shock in a subject in need thereof, the method comprising administering to the subject a therapeutically effective amount of one or more macrocyclic peptides described herein.

In another embodiment the present disclosure provides a method blocking the interaction of PD-L1 with PD-1 and/or CD80 in a subject, said method comprising administering to the subject a therapeutically effective amount of at least one macrocyclic peptide described herein.

In compounds of formula (I) and (II) where the R side chains are part of a ring that is substituted with methyl, it is understood that the methyl group may be on any substitutable carbon atom in the ring, including the carbon that is part of the macrocyclic parent structure.

In compounds of formula (I), preferred $R^1$ side chains are: phenylalanine, tyrosine, 3-thien-2-yl, 4-methylphenylalanine, 4-chlorophenylalanine, 3-methoxyphenylalananie, isotryptophan, 3-methylphenylalanine, 1-naphthylalanine, 3,4-difluorophenylalanine, 4-fluorophenylalanine, 3,4-dimethoxyphenylalanine, 3,4-dichlorophenylalanine, 4-difluoromethylphenylalanine, 2-methylphenylalanine, 2-naphthylalanine, tryptophan, 4-pyridinyl, 4-bromophenylalanine, 3-pyridinyl, 4-trifluoromethylphenylalanine, 4-carboxyphenylalanine, 4-methoxyphenylalanine, biphenylalanine, and 3-chlorophenylalanine; and 2,4-diaminobutane.

In compounds of formula (I) where $R^2$ is not part of a ring, preferred $R^2$ side chains are: alanine, serine, and glycine.

In compounds of formula (I), preferred $R^3$ side chains are: asparagine, aspartic acid, glutamic acid, glutamine, serine, ornithine, lysine, histidine, threonine, leucine, alanine, 2,3-diaminopropane, and 2,4-diaminobutane.

In compounds of formula (I) where $R^4$ is not part of a ring, preferred $R^4$ side chains are: valine, alanine, isoleucine, and glycine.

In compounds of formula (I), preferred $R^5$ side chains are: histidine, asparagine, 2,3-diaminopropane, serine, glycine, 2,4-diaminobutane, threonine, alanine, lysine, aspartic acid, alanine, and 3-thiazolylalanine.

In compounds of formula (I), preferred $R^6$ side chains are: leucine, aspartic acid, asparagine, glutamic acid, glutamine, serine, lysine, 3-cyclohexane, threonine, ornithine, 2,4-diaminobutane, alanine, arginine, and ornithine ($COCH_3$).

In compounds of formula (I) where $R^7$ is not part of a ring, preferred $R^7$ side chains are: glycine, 2,4-diaminobutane, serine, lysine, arginine, ornithine, histidine, asparagine, glutamine, alanine, and 2,4-diaminobutane (C(O)cyclobutane).

In compounds of formula (I) preferred $R^8$ side chains are tryptophan and 1,2-benzisothiazolinylalanine.

In compounds of formula (I) preferred $R^9$ side chains are: serine, histidine, lysine, ornithine, 2,4-dibutylamine, threonine, lysine, glycine, glutamic acid, valine, 2,3-diaminopropane, arginine, aspartic acid, and tyrosine.

In compounds of formula (I) preferred $R^{19}$ side chains are: tryptophan, benzisothiazolylalanine, 1-napththylalanine, 5-flurotryptophan, methionine, 7-methyltryptophan, 5-chlorotryptophan, and -methyltryptophan.

In compounds of formula (I) preferred $R^{11}$ side chains are: norleucine, leucine, asparagine, phenylalanine, methionine, ethoxymethane, alanine, tryptophan, isoleucine, phenylpropane, glutamic acid, hexane, and heptane.

In compounds of formula (I) where $R^{12}$ is not part of a ring, preferred $R^{12}$ side chains are: norleucine, alanine, ethoxymethane, methionine, serine, phenylalanine, methoxyethane, leucine, tryptophan, isoleucine, glutamic acid, hexane, heptane, and glycine.

In compounds of formula (I) preferred $R^{13}$ side chains: arginine, ornithine, alanine, 2,4-diaminobutane, 2,3-diaminopropane, leucine, aspartic acid, glutamic acid, serine, lysine, threonine, cyclopropylmethane, glycine, valine, isoleucine, histidine, and 2-aminobutane.

In compounds of formula (II) preferred $R^1$ side chains are: phenylalanine, 3-methoxyphenylalanine, 2-fluorophenylalanine, 3-fluorophenylalanine, 4-fluorophenylalanine, 3,4-difluorophenylalanine, 3,5-difluorophenylalanine, 3,4,5-trifluorophenylalanine, 3-fluro,4-chlorophenylalanine, 3-chloro,4-fluorophenylalanine, 3-chlorophenylalanine, 4-chlorophenylalanine, 3,4-dichlorophenylalanine, 3,5-dichlorophenylalanine, 3,5-dichloro,4-fluorophenylalanine, 3-chloro,4,5-difluorophenylalanine, 4-bromophenylalanine, 4-nitrophenylalanine, 3-trifluoromethylphenylalanine, 4-trifluoromethylphenylalanine, and 3-pyridylalanine.

In compounds of formula (II), preferred $R^2$ side chains are: phenylalanine, alanine, histidine, tyrosine, tryptophan, glutamic acid, 1-naphthylalanine, 2-naphthylalanine, 2-benzothiazolylalanine, 3-pyridinylalanine, and 4-pyridinylalanine.

In compounds of formula (II), preferred $R^3$ side chains are: norleucine, alanine, tyrosine, glutamic acid, leucine, and isoleucine.

In compounds of formula (II) where $R^4$ is not part of a ring, preferred $R^4$ side chains are: glycine, and alanine.

In compounds of formula (II) where $R^5$ is not part of a ring, preferred $R^5$ side chains are: aspartic acid, glutamic acid, arginine, lysine, asparagine, serine, 2,4-diaminobutane, 2,3-diaminopropane, and 2-aminobutane.

In compounds of formula (II) preferred $R^6$ side chains are: valine, leucine, isoleucine, N-methylthreonine, and cyclohexylmethane.

In compounds of formula (II) preferred $R^7$ side chains are: phenylalanine and 3-fluorophenylalanine.

In compounds of formula (II) where $R^8$ is not part of a ring, preferred $R^8$ side chains are: tyrosine, 3-iodotyrosine, leucine, arginine, glutamic acid, glutamine, pentafluorophenylalanine, 4-aminophenylalanine, 4-aminomethylphenylalanine, 3,4-dimethoxyphenylalanine, tryptophan, 5-chlorotryptophan, 5-hydroxytryptophan, isotryptophan, lysine, ornithine, and 2,3-diaminopropane.

In compounds of formula (II) preferred $R^{10}$ side chains are: tryptophan, 5-chlorotryptophan, 7-azatryptophan, isotryptophan, 3-benzothiazolylalanine, and 1-napththylalanine.

In compounds of formula (II) preferred $R^{11}$ side chains are tyrosine, 4-fluorophenylalanine, 4-aminomethylphenylalanine, 4-aminophenylalanine, and 3,4-dihydroxyphenylalanine.

In compounds of formula (II) preferred $R^{12}$ side chains are: leucine, tyrosine, arginine, lysine, ornithine, glutamic acid, phenylalanine, 4-methylphenylalanine, 4-chlorophenylalanine, 4-aminomethylphenylalanine, norleucine, cyclohexylalanine, 2,4-diaminobutane, and 2,3-diaminopropane.

In compounds of formula (II), when $R^4$ and $R^9$ are part of a ring the preferred stereochemistry is that of the D-isomer and when $R^5$ and $R^8$ are part of a ring the preferred stereochemistry is that of the L isomer.

One embodiment of the subject matter described herein is directed to a polypeptide comprising a sequence of Formula I(a):

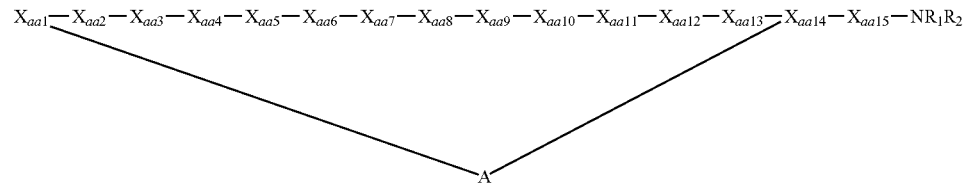

wherein:

A is an organic or peptidic linker between $X_{aa1}$ and $X_{aa14}$, thereby providing a macrocyclic peptide;

$X_{aa1}$ is a naturally or nonnaturally occurring aromatic or heteroaromatic or alkyl or heteroaryl alkyl amino acid;

$X_{aa2}$ is a naturally or nonnaturally occurring alkyl or N-methylated alkyl amino acid;

$X_{aa3}$ is a naturally or nonnaturally occurring hydrophilic or alkyl or polar amino acid;

$X_{aa4}$ is a naturally or nonnaturally occurring amino acid, an alkyl amino acid or a N-methylated alkyl amino acid;

$X_{aa5}$ is a naturally or nonnaturally occurring heteroaromatic amino acid or a positively charged amino acid or an alkyl amino acid;

$X_{aa6}$ is a naturally or nonnaturally occurring hydrophilic or hydrophobic or positively or negatively charged amino acid;

$X_{aa7}$ is a naturally or nonnaturally occurring N-methylated or non-N-methylated hydrophilic or hydrophobic or positively or negatively charged amino acid;

$X_{aa8}$ is a naturally or nonnaturally occurring aromatic or heteroaromatic or arylalkyl or heteroarylalkyl amino acid;

$X_{aa9}$ is a naturally or nonnaturally occurring hydrophilic or hydrophobic or positively or negatively charged amino acid;

$X_{aa10}$ is a naturally or nonnaturally occurring aromatic or heteroaromatic or arylalkyl or heteroarylalkyl or alkyl or heteroalkyl amino acid;

$X_{aa11}$ is a naturally or nonnaturally N-methylated or non-N-methylated alkyl or heteroalkyl or aromatic or heteroaromatic occurring amino acid;

$X_{aa12}$ is a naturally or nonnaturally N-methylated or non-N-methylated alkyl or heteroalkyl or aromatic or heteroaromatic occurring amino acid;

$X_{aa13}$ is a naturally or nonnaturally occurring hydrophilic or hydrophobic or positively or negatively charged amino acid;

$X_{aa14}$ is a naturally or nonnaturally occurring amino acid possessing a functional group that can be appropriately activated to react with one end of linker A to yield a cyclic peptide;

$X_{aa15}$ is a naturally or nonnaturally occurring amino acid or a spacer followed by a tag or a spacer followed by a solubilizing or a PK-enhancing element.

In another embodiment, the subject matter described herein is directed to a polypeptide comprising a sequence of Formula I(b):

$X_{aa1}-X_{aa2}-X_{aa3}-X_{aa4}-X_{aa5}-X_{aa6}-X_{aa7}-X_{aa8}-X_{aa9}-X_{aa10}-X_{aa11}-X_{aa12}-X_{aa13}-X_{aa14}-X_{aa15}-NR_1R_2$

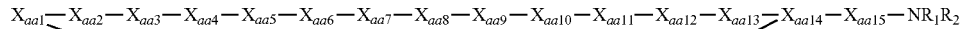

wherein:

A is an electrophilic moiety such as a Michael acceptor or a chloro- or bromoacetyl group which is capable of reacting with a sulfhydryl group present on residue $X_{aa14}$ to form a covalent thioether bond, thereby yielding a macrocyclic peptide; wherein such thioether bond may or may not be oxidized to the corresponding diastereomeric sulfoxides;

and wherein A can be optionally present; and wherein, if A is present, it can be a Gly or other spacer with a free amine, which can be used to cyclize the peptide via amide bond formation with a carboxyl group on the side chain of $X_{aa14}$, thereby providing an N-terminus to side chain lactam cyclic peptide; and wherein, if A is not present, the N-terminal amino group of the $X_{aa1}$ residue can be used to cyclize the peptide via amide bond formation with a carboxyl group on the side chain of $X_{aa14}$, thereby providing an N-terminus to side chain lactam cyclic peptide;

and wherein, if A is present, it can be a Gly or other spacer with a free amine, which can be used to cyclize the peptide via amide bond formation with the C-terminal α-carboxyl group of $X_{aa15}$, thereby providing a head-to-tail cyclic peptide; and wherein, if A is not present, the N-terminal amino group of the $X_{aa1}$ amino acid can be used to cyclize the peptide via amide bond formation with the C-terminal α-carboxyl group of $X_{aa15}$, thereby providing a head-to-tail cyclic peptide;

$X_{aa1}$ is a naturally or nonnaturally occurring amino acid comprising L-Phe, L-Ala, L-Trp, L-Tyr, L-Phe(4-OMe), L-Phe(4-F), L-Phe(4-Cl), L-Phe(4-Br), L-Phe(4-Me), L-Phe (4-$CF_3$), L-Phe(4-t-Bu), L-Phe(penta-F), L-1-Nal, L-2-Nal, L-Bip, L-$^m$Phe, L-Tic, L-3-Pya, L-4-Pya, L-Tza, L-3-Tha;

$X_{aa2}$ is a naturally or nonnaturally occurring amino acid selected from the group consisting of L-Ala, L-$^m$Ala, $^m$Gly, L-$^m$Val;

$X_{aa3}$ is selected from the group consisting of Gly, L-Asn and L-Ala;

$X_{aa4}$ is a naturally or nonnaturally occurring amino acid comprising L-Pro, L-Ala, L-α-Me-Pro, L-Pro(4R—OH), L-Pro(4R—OBzl), L-Pro(4R—$NH_2$), L-Pro(3R-Ph), L-Pro (4S-Ph), L-Pro(5R-Ph), L-Azt, L-Pip, L-Oic, L-2,3-Methano-Pro, L-3,4-Methano-Pro, L-Val, L-Leu, L-Ile, L-$^m$Ala, L-$^m$Val, L-$^m$Leu, L-Tza;

$X_{aa5}$ is a naturally or nonnaturally occurring amino acid selected from the group consisting of L-His, L-Ala, L-Tza, L-Arg, L-Lys, L-Orn, L-Dab and L-Dap;

$X_{aa6}$ is a naturally or nonnaturally occurring amino acid comprising L-Leu, L-Ala, L-Arg, L-His, L-Glu and L-Asp;

$X_{aa7}$ is a naturally or nonnaturally occurring amino acid comprising $^m$Gly, Gly, L-$^m$Ala, D-$^m$Ala, L-Pro, L-Ser, L-$^m$Ser L-Dab, L-Arg and L-His;

$X_{aa8}$ is L-Trp, L-Phe, L-Tyr, L-His, L-Phe(penta-F), L-Tza, L-Bzt, L-1-Nal, L-2-Nal, L-2-Pya, L-3-Pya, L-4-Pya;

$X_{aa9}$ is a naturally or nonnaturally occurring amino acid comprising L-Ser, L-Ala, L-Arg and D-Asn;

$X_{aa10}$ is a naturally or nonnaturally occurring amino acid selected from the group consisting of L-Trp, L-Ala, L-Met, L-Nle, L-Leu and L-Ile, L-Phe, L-Tyr, L-His, L-Phe(penta-F), L-Tza, L-Bzt, L-1-Nal, L-2-Nal, L-2-Pya, L-3-Pya, L-4-Pya;

$X_{aa11}$ is a naturally or nonnaturally occurring amino acid comprising L-$^m$Nle, L-Nle, L-$^m$Ala, L-Ala, L-Phe, L-$^m$Phe and L-$^m$Leu, L-Ser, D-Nle and L-Pro;

$X_{aa12}$ is a naturally or nonnaturally occurring amino acid comprising L-$^m$Nle, L-Nle, L-$^m$Ala, L-Ala, L-Phe, L-$^m$Phe, L-$^m$Leu and L-Pro;

$X_{aa13}$ is a naturally or nonnaturally occurring amino acid comprising L-Arg, L-Ala, L-Leu, L-Lys, L-Asp, L-Glu, L-His;

$X_{aa14}$ is selected from the group consisting of L-Cys, D-Cys, Asp, Glu, Gly, L-homo-Cys, D-homo-Cys, L-Pen, D-Pen, L-$^m$Cys and D-$^m$Cys;

$X_{aa15}$ is Gly or Gly followed by a PEG spacer comprised of at least two ethylene glycol units, or Gly followed by a PEG spacer comprised of at least two ethylene glycol units followed by a tag such as biotin, or Gly followed by a spacer followed by a PK-enhancing element;

wherein $X_{aa15}$ is optionally present and wherein the C-terminal carbonyl carbon of said amino acid is attached to a hydroxyl group to form a carboxylic acid or to a nitrogen to form a carboxamide ($NH_2$), an alkyl carboxamide ($NHR_1$), or a dialkylcarboxamide ($NR_1R_2$);

wherein each of $R_1$ and $R_2$ is an alkyl or arylalkyl group;

wherein, if $X_{aa15}$ is not present, the C-terminal carbonyl carbon of $X_{aa14}$ is attached to a nitrogen to form a carboxamide ($NH_2$), an alkyl carboxamide ($NHR_1$), or a dialkylcarboxamide ($NR_1R_2$);

wherein each of $R_1$ and $R_2$ is an alkyl or arylalkyl group.

In another embodiment, the subject matter described herein is directed to a polypeptide comprising a sequence of Formula I(c):

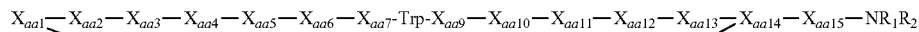

wherein:

A is an electrophilic moiety such as a Michael acceptor or a chloro- or bromoacetyl group which is capable of reacting with a sulfhydryl group present on residue $X_{aa14}$ to form a covalent thioether bond, thereby yielding a macrocyclic peptide; wherein such thioether bond may or may not be oxidized to the corresponding diastereomeric sulfoxides;

and wherein A can be optionally present; and wherein, if A is present, it can be a Gly or other spacer with a free amine, which can be used to cyclize the peptide via amide bond formation with a carboxyl group on the side chain of $X_{aa14}$, thereby providing an N-terminus to side chain lactam cyclic peptide; and wherein, if A is not present, the N-terminal amino group of the $X_{aa1}$ residue can be used to cyclize the peptide via amide bond formation with a carboxyl group on the side chain of $X_{aa14}$, thereby providing an N-terminus to side chain lactam cyclic peptide;

and wherein, if A is present, it can by a Gly or other spacer with a free amine, which can be used to cyclize the peptide via amide bond formation with the C-terminal α-carboxyl group of $X_{aa15}$, thereby providing a head-to-tail cyclic peptide; and wherein, if A is not present, the N-terminal amino group of the $X_{aa1}$ amino acid can be used to cyclize the peptide via amide bond formation with the C-terminal α-carboxyl group of $X_{aa15}$, thereby providing a head-to-tail cyclic peptide;

$X_{aa1}$ is a naturally or nonnaturally occurring amino acid comprising L-Phe, L-Ala, L-Trp, L-Tyr, L-Phe(4-OMe), L-Phe(4-F), L-Phe(4-Cl), L-Phe(4-Br), L-Phe(4-Me), L-Phe(4-$CF_3$), L-Phe(4-t-Bu), L-Phe(penta-F), L-1-Nal, L-2-Nal, L-Bip, L-$^m$Phe, L-Tic, L-3-Pya, L-4-Pya, L-Tza, L-3-Tha;

$X_{aa2}$ is a naturally or nonnaturally occurring amino acid selected from the group consisting of L-Ala, L-$^m$Ala, $^m$Gly, L-$^m$Val;

$X_{aa3}$ is selected from the group consisting of Gly, L-Asn and L-Ala;

$X_{aa4}$ is a naturally or nonnaturally occurring amino acid comprising L-Pro, L-Ala, L-α-Me-Pro, L-Pro(4R—OH), L-Pro(4R—$NH_2$), L-Pro(4S-Ph), L-Azt, L-Pip and L-Oic;

$X_{aa5}$ is a naturally or nonnaturally occurring amino acid selected from the group consisting of L-His and L-Ala;

$X_{aa6}$ is a naturally or nonnaturally occurring amino acid comprising L-Leu, L-Ala, L-Arg and L-Asp;

$X_{aa7}$ is a naturally or nonnaturally occurring amino acid comprising $^m$Gly, Gly, L-$^m$Ala, D-$^m$Ala, L-Pro, L-Ser, L-$^m$Ser L-Dab, L-Arg and L-His;

$X_{aa9}$ is a naturally or nonnaturally occurring amino acid comprising L-Ser, L-Ala, L-Arg and D-Asn;

$X_{aa10}$ is a naturally or nonnaturally occurring amino acid selected from the group consisting of L-Trp, L-Ala, L-Met, L-Leu and L-Ile;

$X_{aa11}$ is a naturally or nonnaturally occurring amino acid comprising L-$^m$Nle, L-Nle, L-$^m$Ala, L-Ala, L-Phe, L-$^m$Phe and L-$^m$Leu, L-Ser and D-Nle;

$X_{aa12}$ is a naturally or nonnaturally occurring amino acid comprising L-$^m$Nle, L-Nle, L-$^m$Ala and L-Ala;

$X_{aa13}$ is a naturally or nonnaturally occurring amino acid comprising L-Arg, L-Ala and L-Leu;

$X_{aa14}$ is selected from the group consisting of L-Cys, D-Cys, Asp, Glu and Gly;

$X_{aa15}$ is Gly or Gly followed by a PEG spacer comprised of at least two ethylene glycol units, or Gly followed by a PEG spacer comprised of at least two ethylene glycol units followed by a tag such as biotin;

wherein $X_{aa15}$ is optionally present and wherein the C-terminal carbonyl carbon of said amino acid is attached to a nitrogen to form a carboxamide ($NH_2$), an alkyl carboxamide ($NHR_1$), or a dialkylcarboxamide ($NR_1R_2$);

wherein each of $R_1$ and $R_2$ is an alkyl or arylalkyl group;

wherein, if $X_{aa15}$ is not present, the C-terminal carbonyl carbon of $X_{aa14}$ is attached to a nitrogen to form a carboxamide ($NH_2$), an alkyl carboxamide ($NHR_1$), or a dialkylcarboxamide ($NR_1R_2$);

wherein each of $R_1$ and $R_2$ is an alkyl or arylalkyl group.

In another embodiment, the subject matter described herein is directed to a polypeptide comprising a sequence of Formula II(a):

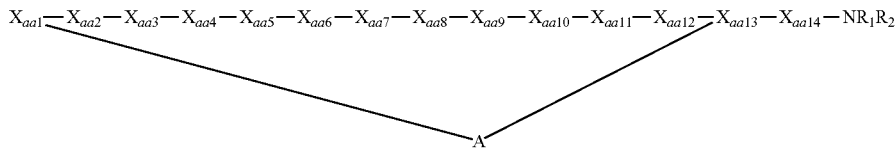

wherein:

A is an organic or peptidic linker between $X_{aa1}$ and $X_{aa13}$, thereby providing a macrocyclic peptide;

$X_{aa1}$ is a naturally or nonnaturally occurring aromatic or heteroaromatic or alkyl or heteroaryl alkyl amino acid;

$X_{aa2}$ is a naturally or nonnaturally occurring alkyl or aromatic N-methylated amino acid;

$X_{aa3}$ is a naturally or nonnaturally occurring hydrophobic N-methylated amino acid;

$X_{aa4}$ is a naturally or nonnaturally occurring hydrophobic N-methylated amino acid;

$X_{aa5}$ is a naturally or nonnaturally occurring alkyl amino acid or a positively or negatively charged amino acid;

$X_{aa6}$ is a naturally or nonnaturally occurring hydrophobic amino acid;

$X_{aa7}$ is a naturally or nonnaturally occurring N-methylated or non-N-methylated aromatic or heteroaromatic or alkyl or heteroarylalkyl amino acid;

$X_{aa8}$ is a naturally or nonnaturally occurring aromatic or heteroaromatic or arylalkyl or heteroarylalkyl amino acid or an alkyl amino acid;

$X_{aa9}$ is a naturally or nonnaturally occurring N-methylated or non-N-methylated aromatic or heteroaromatic or alkyl or heteroarylalkyl amino acid;

$X_{aa10}$ is a naturally or nonnaturally occurring aromatic or heteroaromatic or arylalkyl or heteroarylalkyl or alkyl or heteroalkyl amino acid;

$X_{aa11}$ is a naturally or nonnaturally occurring aromatic or heteroaromatic or arylalkyl or heteroarylalkyl or alkyl or heteroalkyl amino acid;

$X_{aa12}$ is a naturally or nonnaturally occurring aromatic or heteroaromatic or arylalkyl or heteroarylalkyl or alkyl or heteroalkyl amino acid;

$X_{aa13}$ is a naturally or nonnaturally occurring amino acid possessing a functional group that can be appropriately activated to react with one end of linker A to yield a cyclic peptide;

$X_{aa14}$ is a naturally or nonnaturally occurring amino acid or a spacer or a spacer followed by a tag or a spacer followed by a solubilizing or a PK-enhancing element.

In another embodiment, the subject matter described herein is directed to a polypeptide comprising a sequence of Formula II(b):

wherein:

A is an electrophilic moiety such as a Michael acceptor or a chloro- or bromoacetyl group which is capable of reacting with a sulfhydryl group present on residue $X_{aa13}$ to form a covalent thioether bond, thereby yielding a macrocyclic peptide; wherein such thioether bond may or may not be oxidized to the corresponding diastereomeric sulfoxides;

and wherein A can be optionally present; and wherein, if A is present, it can be a Gly or other spacer with a free amino terminus, which can be used to cyclize the peptide via amide bond formation with a carboxyl group on the side chain of $X_{aa13}$, thereby providing an N-terminus to side chain lactam cyclic peptide; and wherein, if A is not present, the N-terminal amino group of the $X_{aa1}$ residue can be used to cyclize the peptide via amide bond formation with a carboxyl group on the side chain of $X_{aa13}$, thereby providing an N-terminus to side chain lactam cyclic peptide;

and wherein, if A is present, it can be a Gly or other spacer with a free amino terminus, which can be used to cyclize the peptide via amide bond formation with the C-terminal α-carboxyl group of $X_{aa14}$, thereby providing a head-to-tail cyclic peptide; and wherein, if A is not present, the N-terminal amino group of the $X_{aa1}$ amino acid can be used to cyclize the peptide via amide bond formation with the C-terminal α-carboxyl group of $X_{aa14}$, thereby providing a head-to-tail cyclic peptide;

$X_{aa1}$ is a naturally or nonnaturally occurring amino acid comprising Phe and Ala;

$X_{aa2}$ is a naturally or nonnaturally occurring amino acid comprising $^m$Phe and $^m$Ala;

$X_{aa3}$ is a naturally or nonnaturally occurring amino acid comprising $^m$Nle and $^m$Ala;

$X_{aa4}$ is a naturally or nonnaturally occurring amino acid comprising $^m$Gly, Gly and $^m$Ala;

$X_{aa5}$ is a naturally or nonnaturally occurring amino acid comprising Asp and Ala;

$X_{aa6}$ is a naturally or nonnaturally occurring amino acid comprising Val (preferred) and Ala;

$X_{aa7}$ is a naturally or nonnaturally occurring amino acid comprising $^m$Phe and Phe;

$X_{aa8}$ is a naturally or nonnaturally occurring amino acid selected from the group consisting of Tyr and Ala;

$X_{aa9}$ is a naturally or nonnaturally occurring amino acid comprising $^m$Gly $^m$Ala and Gly;

$X_{aa11}$ is a naturally or nonnaturally occurring amino acid comprising Tyr and Ala;

$X_{aa12}$ is a naturally or nonnaturally occurring amino acid comprising Leu and Ala;

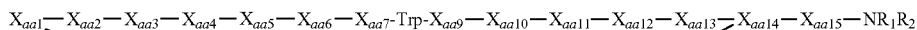

$X_{aa13}$ is a naturally or nonnaturally occurring amino acid comprising L-Cys, D-Cys, Asp, Glu and Gly;

$X_{aa14}$ is Gly or Gly followed by a PEG spacer comprised of at least two ethylene glycol units, or Gly followed by a PEG spacer comprised of at least two ethylene glycol units followed by a tag such as biotin, wherein $X_{aa14}$ is optionally present and wherein the C-terminal carbonyl carbon of said amino acid is attached to a nitrogen to form a carboxamide ($NH_2$), an alkyl carboxamide ($NHR_1$), or a dialkylcarboxamide ($NR_1R_2$);

wherein each of $R_1$ and $R_2$ is an alkyl or arylalkyl group;

wherein, if $X_{aa14}$ is not present, the C-terminal carbonyl carbon of $X_{aa13}$ is attached to a nitrogen to form a carboxamide ($NH_2$), an alkyl carboxamide ($NHR_1$), or a dialkylcarboxamide ($NR_1R_2$);

wherein each of $R_1$ and $R_2$ is an alkyl or arylalkyl group.

In another embodiment, the subject matter described herein is directed to a polypeptide comprising a sequence of Formula III(a):

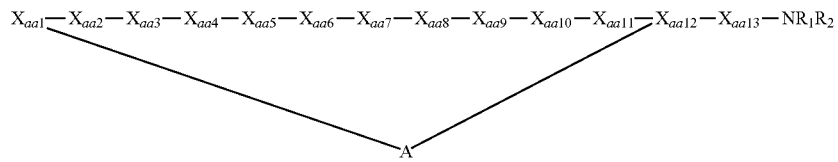

wherein:

A is an organic or peptidic linker between $X_{aa1}$ and $X_{aa12}$, thereby providing a macrocyclic peptide;

$X_{aa1}$ is a naturally or nonnaturally occurring aromatic or heteroaromatic or alkyl or heteroaryl alkyl amino acid;

$X_{aa2}$ is a naturally or nonnaturally occurring alkyl or aromatic or charged amino acid;

$X_{aa3}$ is a naturally or nonnaturally occurring aromatic or heteroaromatic or alkyl or heteroaryl alkyl amino acid;

$X_{aa4}$ is a naturally or nonnaturally occurring aromatic or heteroaromatic or alkyl or heteroarylalkyl amino acid;

$X_{aa5}$ is a naturally or nonnaturally occurring alkyl or heteroalkyl or aromatic or heteroaromatic or heteroarylalkyl amino acid;

$X_{aa6}$ is a naturally or nonnaturally occurring heteroaromatic or positively charged amino acid;

$X_{aa7}$ is a naturally or nonnaturally occurring polar or charged amino acid;

$X_{aa8}$ is a naturally or nonnaturally occurring positively charged amino acid;

$X_{aa9}$ is a naturally or nonnaturally occurring alkyl or heteroalkyl or aromatic or heteroaromatic or heteroarylalkyl amino acid;

$X_{aa10}$ is a naturally or nonnaturally occurring aromatic or heteroaromatic or arylalkyl or heteroarylalkyl or alkyl or heteroalkyl amino acid;

$X_{aa11}$ is a naturally or nonnaturally occurring aromatic or heteroaromatic or arylalkyl or heteroarylalkyl or heteroalkyl or a positively charged amino acid;

$X_{aa12}$ is a naturally or nonnaturally occurring amino acid possessing a functional group that can be appropriately activated to react with one end of linker A to yield a cyclic peptide;

$X_{aa13}$ is a naturally or nonnaturally occurring amino acid or a spacer or a spacer followed by a tag or a spacer followed by a solubilizing or a PK-enhancing element.

In another embodiment, the subject matter described herein is directed to a polypeptide comprising a sequence of Formula III(b):

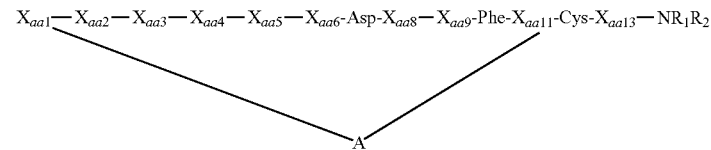

wherein:

A is an electrophilic moiety such as a Michael acceptor or a chloro- or bromoacetyl group which is capable of reacting with the sulfhydryl group of $Cys^{12}$ to form a covalent thioether bond, thereby yielding a macrocyclic peptide; wherein such thioether bond may or may not be oxidized to the corresponding diastereomeric sulfoxides;

$X_{aa1}$ is selected from Phe and D-Phe;

$X_{aa2}$ is selected from Leu, Arg and Phe;

$X_{aa3}$ is selected from Ile, Leu and Phe;

$X_{aa4}$ is selected from Val, Tyr and Phe;

$X_{aa5}$ is selected from Ile and Val;

$X_{aa6}$ is selected from Arg and His;

$X_{aa8}$ is selected from Arg;

$X_{aa9}$ is selected from Val, Leu, Tyr and Phe;

$X_{aa11}$ is selected from Arg and Tyr;

$X_{aa13}$ is Gly or Gly followed by a PEG spacer comprised of at least two ethylene glycol units, wherein $X_{aa13}$ is optionally present and wherein the C-terminal carbonyl carbon of said amino acid is attached to a nitrogen to form a carboxamide ($NH_2$), an alkyl carboxamide ($NHR_1$), or a dialkylcarboxamide ($NR_1R_2$);

wherein each of $R_1$ and $R_2$ is an alkyl or arylalkyl group;

wherein, if $X_{aa13}$ is not present, the C-terminal carbonyl carbon of $Cys^{12}$ is attached to a nitrogen to form a carboxamide ($NH_2$), an alkyl carboxamide ($NHR_1$), or a dialkylcarboxamide ($NR_1R_2$);

wherein each of $R_1$ and $R_2$ is an alkyl or arylalkyl group.

In another embodiment, the subject matter described herein is directed to a polypeptide comprising a sequence of Formula I(d):

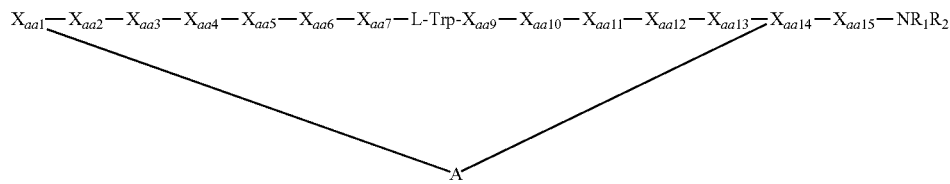

wherein:

A is a chloroacetyl group attached to the α-amine of the N-terminal $X_{aa1}$ residue which is capable of reacting with a sulfhydryl group present on residue $X_{aa14}$ to form a covalent thioether bond, thereby providing a macrocyclic peptide; wherein such thioether bond may or may not be oxidized to the corresponding diastereomeric sulfoxides;

and wherein, $X_{aa1}$ is selected from the group consisting of L-Phe, L-Trp, L-Tyr, L-Phe(4-OMe), L-Phe(4-F), L-Phe(4-Cl), L-Phe(4-Br), L-Phe(4-Me), L-Phe(4-CF$_3$), L-1-Nal, L-2-Nal, L-Bip, L-3-Pya, L-4-Pya, L-3-Tha;

$X_{aa2}$ is selected from the group consisting of L-Ala, L-$^m$Ala, $^m$Gly;

$X_{aa3}$ is selected from the group consisting of L-Ala and L-Asn;

$X_{aa4}$ is selected from the group consisting of L-Pro, L-Ala, L-α-Me-Pro, L-Pro(4-OH), L-Pro(4-NH$_2$), L-Pro(4S-Ph), L-Azt, L-Pip and L-Oic;

$X_{aa5}$ is selected from the group consisting of L-Ala, L-His and L-Leu;

$X_{aa6}$ is selected from the group consisting of L-Ala, L-Arg, L-Asp, L-His and L-Leu;

$X_{aa7}$ is selected from the group consisting of $^m$Gly, Gly, L-$^m$Ala, D-$^m$Ala, L-Pro, L-Ser, L-$^m$Ser, L-Dab, L-Arg and L-His;

$X_{aa9}$ is selected from the group consisting of L-Ala, L-Arg and L-Ser;

$X_{aa10}$ selected from the group consisting of L-Trp, L-Met and L-Bzt;

$X_{aa11}$ is selected from the group consisting of L-Nle, L-$^m$Nle, L-$^m$Ala, L-Phe, L-$^m$Phe and L-$^m$Leu and L-$^m$Ser;

$X_{aa12}$ is selected from the group consisting of L-$^m$Nle and L-$^m$Ala;

$X_{aa13}$ is selected from the group consisting of L-Ala, L-Arg and L-Leu;

$X_{aa14}$ is selected from the group consisting of L-Cys and D-Cys;

$X_{aa15}$ is Gly or Gly followed by a PEG spacer comprised of twelve ethylene glycol units;

wherein $X_{aa15}$ is optionally present and wherein the C-terminal carbonyl carbon of said amino acid is attached to a nitrogen to form a carboxamide (CONH$_2$);

wherein, if $X_{aa15}$ is not present, the C-terminal carbonyl carbon of $X_{aa14}$ is attached to a nitrogen to form a carboxamide (CONH$_2$).

In another embodiment, the subject matter described herein is directed to a polypeptide comprising a sequence of Formula II(c):

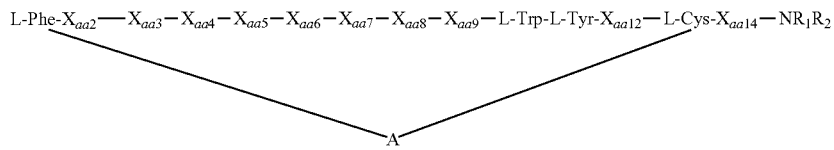

wherein:

A is a chloroacetyl group attached to the α-amine of the N-terminal $X_{aa1}$ residue which is capable of reacting with a sulfhydryl group present on the Cys[13] residue to form a covalent thioether bond, thereby yielding a macrocyclic peptide; wherein such thioether bond may or may not be oxidized to the corresponding diastereomeric sulfoxides;

and wherein, $X_{aa2}$ is selected from the group consisting of L-$^m$Ala and L-$^m$Phe;

$X_{aa3}$ is selected from the group consisting of L-$^m$Ala and L-$^m$Nle;

$X_{aa4}$ is selected from the group consisting of Gly, mGly and L-$^m$Ala;

$X_{aa5}$ is selected from the group consisting of L-Ala and L-Asp;

$X_{aa6}$ is selected from the group consisting of L-Ala and L-Val;

$X_{aa7}$ is selected from the group consisting of L-Phe and L-$^m$Phe;

$X_{aa8}$ is selected from the group consisting of L-Ala and L-Tyr;

$X_{aa9}$ is selected from the group consisting of Gly, mGly and L-$^m$Ala;

$X_{aa12}$ is selected from the group consisting of L-Leu and L-Ala;

$X_{aa14}$ is Gly or Gly followed by a PEG spacer comprised of twelve ethylene glycol units, wherein the C-terminal carbonyl carbon of $X_{aa14}$ or of $X_{aa14}$ followed by a PEG spacer is attached to a nitrogen to form a carboxamide (CONH$_2$).

In another embodiment, the subject matter described herein is directed to a polypeptide comprising a sequence of Formula III(c):

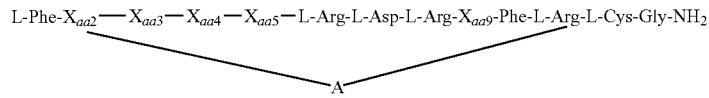

wherein:

A is a chloroacetyl group attached to the α-amine of the N-terminal L-Phe residue which is capable of reacting with a sulfhydryl group present on the L-Cys$^{12}$ residue to form a covalent thioether bond, thereby yielding a macrocyclic peptide;

and wherein, $X_{aa2}$ is selected from L-Leu, L-Arg and L-Phe;
$X_{aa3}$ is selected from L-Ile and L-Phe;
$X_{aa4}$ is selected from L-Phe, L-Tyr and L-Val;
$X_{aa5}$ is selected from L-Ile and L-Val;
$X_{aa9}$ is selected from L-Leu, L-Phe, L-Tyr and L-Val;

wherein the C-terminal carbonyl carbon of Gly$^{13}$ is attached to a nitrogen to form a carboxamide (CONH$_2$).

The present disclosure is also directed to a macrocyclic peptides comprising a sequence provided in Formula I.

The present disclosure is also directed to macrocyclic peptides comprising a sequence provided in Formula I(a).

The present disclosure is also directed to macrocyclic peptides comprising a sequence provided in Formula I(b).

The present disclosure is also directed to macrocyclic peptides comprising a sequence provided in Formula I(c).

The present disclosure is also directed to macrocyclic peptides comprising a sequence provided in Formula I(d).

The present disclosure is also directed to macrocyclic peptides comprising a sequence provided in Formula II.

The present disclosure is also directed to macrocyclic peptides comprising a sequence provided in Formula II(a).

The present disclosure is also directed to macrocyclic peptides comprising a sequence provided in Formula II(b).

The present disclosure is also directed to macrocyclic peptides comprising a sequence provided in Formula II(c).

The present disclosure is also directed to macrocyclic peptides comprising a sequence provided in Formula III.

The present disclosure is also directed to macrocyclic peptides comprising a sequence provided in Formula III(a).

The present disclosure is also directed to macrocyclic peptides comprising a sequence provided in Formula III(b).

The present disclosure is also directed to macrocyclic peptides comprising a sequence provided in Formula III(c).

The present disclosure is also directed to macrocyclic peptides comprising a sequence provided in Formula IV.

The present disclosure is also directed to macrocyclic peptides comprising a sequence provided in Formula V.

The present disclosure is also directed to macrocyclic peptides comprising a sequence provided in Formula VI.

The present disclosure is also directed to macrocyclic peptides comprising a sequence provided in Formula VII.

The present disclosure is also directed to macrocyclic peptides comprising a sequence selected from the group consisting of: Compound Nos. 1, 2, 3, 4, 71, and 99.

The present disclosure is also directed to macrocyclic peptides comprising a sequence selected from those described herein.

The present disclosure is also directed to methods of using the macrocyclic peptides of the present disclosure to ameliorate and/or treat hyperproliferative disorders and/or viral disorders.

The present disclosure is also directed to a method of modulating an immune response in a subject comprising administering to the subject one or more macrocyclic peptides comprising the sequence selected from the peptides described herein.

The present disclosure is also directed to a method of enhancing, stimulating or increasing the immune response in the subject comprising administering to the subject one or more macrocyclic peptides comprising the sequence selected from those described herein.

The present disclosure is also directed to a method of promoting immune system inhibition of the growth of tumor cells in a subject, comprising administering to a subject a therapeutically effective amount of one or more macrocyclic peptides comprising the sequence selected from those peptides described herein.

The present disclosure is also directed to a method of treating an infectious disease in a subject, comprising administering to a subject a therapeutically effective amount of one or more macrocyclic peptides comprising the sequence selected from those peptides described herein The present disclosure is also directed to combinations comprising a sequence selected from the macrocyclic peptides described herein, with another agent, such an antimicrobial therapy, antiviral therapy, an additional immunomodulatory therapy, a vaccine, or a cancer chemotherapeutic agent.

In accordance with the present disclosure, we have discovered peptides that specifically bind to PD-L1 and are capable of inhibiting the interaction of PD-L1 with PD-1 and CD80. These macrocyclic peptides exhibit in vitro immunomodulatory efficacy thus making them therapeutic candidates for the treatment of various diseases including cancer and infectious diseases.

The terms "specific binding" or "specifically bind" refer to the interaction between a protein and a binding molecule, such as a compound or ligand. The interaction is dependent upon the presence of a particular structure (i.e., an enzyme binding site, an antigenic determinant or epitope) of the protein that is recognized by the binding molecule. For example, if a compound has specific binding for protein binding site "A", the presence of the compound in a reaction containing a protein including binding site A, and a labeled peptide that specifically binds to protein binding site A will reduce the amount of labeled peptide bound to the protein. In contrast, nonspecific binding of a compound to the protein does not result in a concentration-dependent displacement of the labeled peptide from the protein.

Other embodiments include polypeptides comprising the following structures:

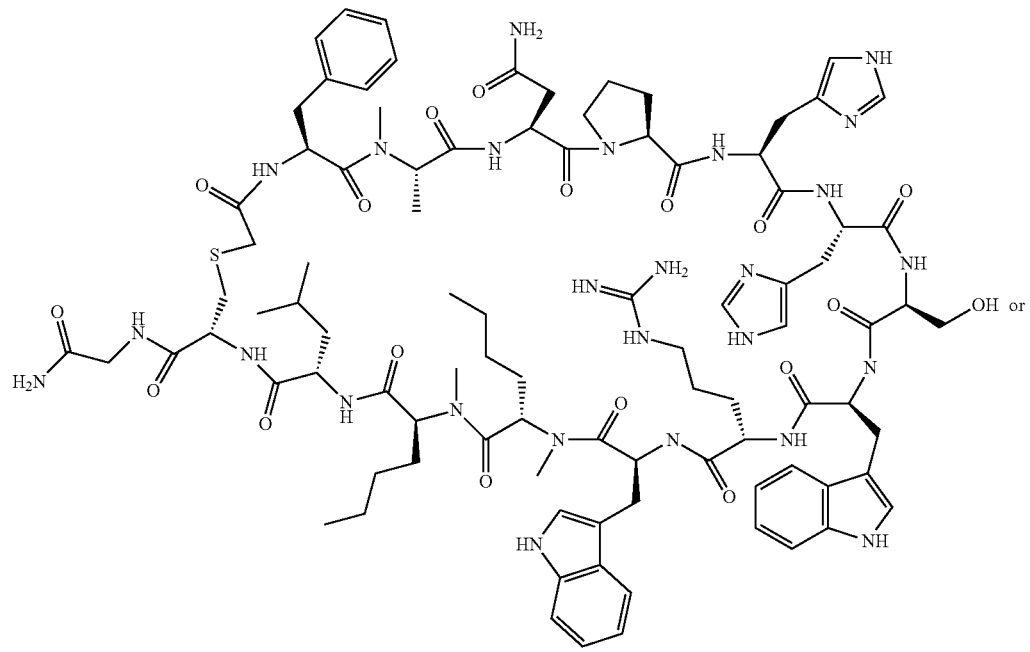
Formula IV
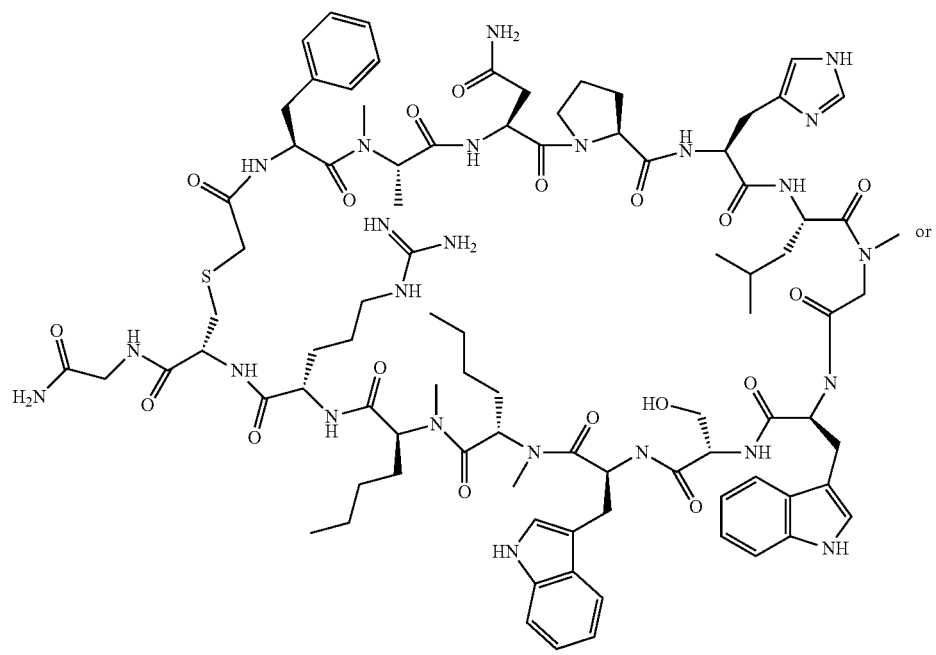
Formula V

Formula VI

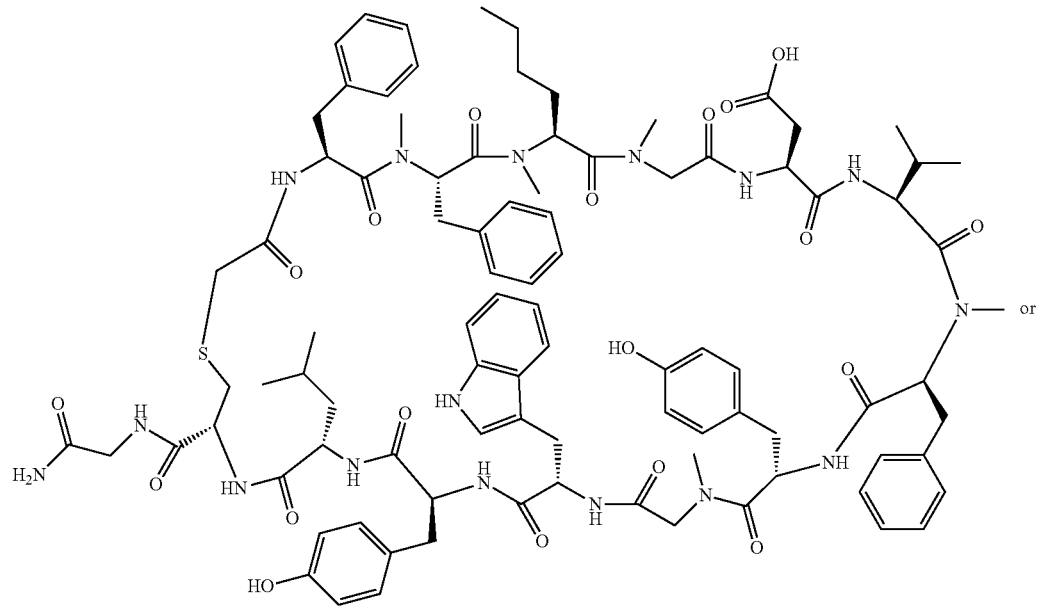

Formula VII

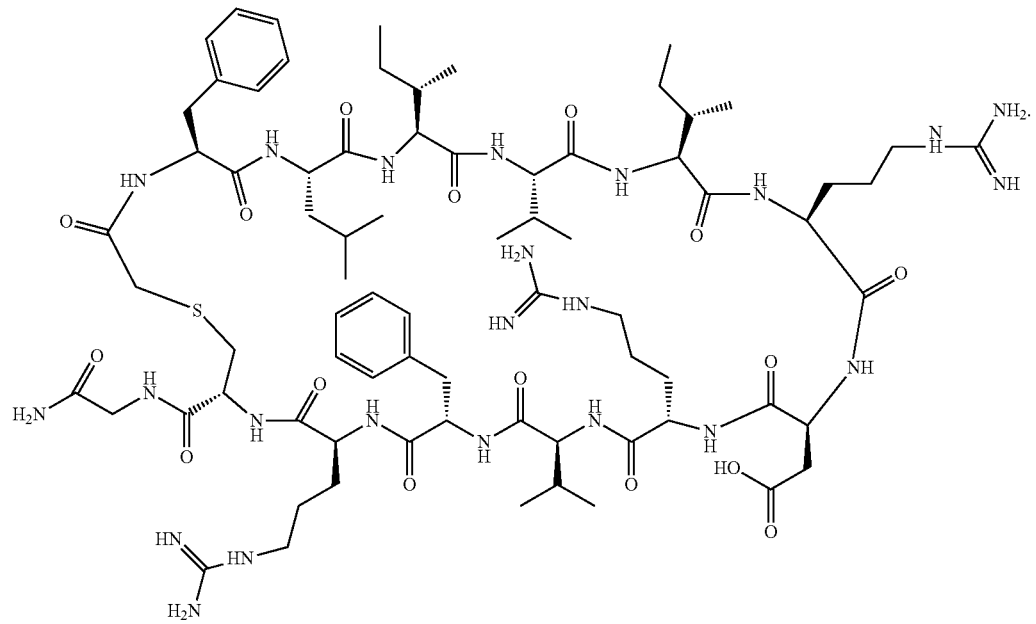

Another embodiment is a pharmaceutical composition comprising a polypeptide of Formula I(a), I(b), I(c), II(a), II(b), III(a), III(b), IV, V, VI, or VII, or a peptide comprising at least one of the macrocyclic peptides described herein.

Another embodiment is directed to a pharmaceutical combination comprising a polypeptide of Formula I(a), I(b), I(c), II(a), II(b), III(a), III(b), IV, V, VI, or VII or a macrocyclic peptide described herein, and at least one therapeutic agent selected from the group consisting of an antimicrobial, an antiviral, anti-cancer, anti-diabetic agent, an anti-obesity agent, an anti-hypertensive agent, an anti-atherosclerotic agent and a lipid-lowering agent.

Another embodiment is a pharmaceutical combination of a polypeptide of Formula I(a), I(b), I(c), II(a), II(b), III(a), III(b), IV, V, VI, or VII, or a macrocyclic peptide described herein, with another agent disclosed herein.

Another embodiment is directed to a method for treating or delaying the progression or onset of cancer and/or virology disorder, which comprises administering to a mammalian species in need of treatment a therapeutically effective amount of a polypeptide of Formula I(a), I(b), I(c), II(a), II(b), III(a), III(b), IV, V, VI, or VII, or a macrocyclic peptide described herein.

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

An additional aspect of the subject matter described herein is the use of the disclosed peptides as radiolabeled ligands for development of ligand binding assays or for monitoring of in vivo adsorption, metabolism, distribution, receptor binding or occupancy, or compound disposition. For example, a macrocyclic peptide described herein may be prepared using the radioactive isotope $^{125}$I and the resulting radiolabeled peptide may be used to develop a binding assay or for metabolism studies. Alternatively, and for the same purpose, a macrocyclic peptide described herein may be converted to a radiolabeled form by catalytic tritiation using methods known to those skilled in the art.

The macrocyclic peptides of the present disclosure can also be used as PET imaging agents by adding a radioactive tracer using methods known to those skilled in the art.

Preferred peptides include at least one of the macrocyclic peptides provided herein and these peptides may be included in pharmaceutical compositions and combinations.

The definitions provided herein apply, without limitation, to the terms as used throughout this specification, unless otherwise limited in specific instances.

Those of ordinary skill in the art of amino acid and peptide chemistry are aware that an amino acid includes a compound represented by the general structure:

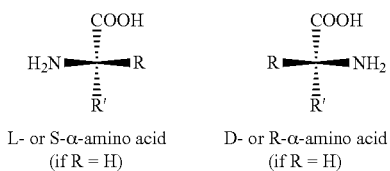

L- or S-α-amino acid (if R = H)   D- or R-α-amino acid (if R = H)

where R and R' are as discussed herein.

Unless otherwise indicated, the term "amino acid" as employed herein, alone or as part of another group, includes, without limitation, an amino group and a carboxyl group linked to the same carbon, referred to as "α" carbon, where R and/or R' can be a natural or an un-natural side chain, including hydrogen. The absolute "S" configuration at the "α" carbon is commonly referred to as the "L" or "natural" configuration. In the case where both the "R" and the "R'" (prime) substituents equal hydrogen, the amino acid is glycine and is not chiral.

The term "naturally occurring amino acid side chain", as used herein, refers to side chain of any of the naturally occurring amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) usually in the S-configuration (i.e., the L-amino acid).

The term "non-naturally occurring amino acid side chain", as used herein, refers to a side chain of any naturally occurring amino acid usually in the R-configuration (i.e., the D-amino acid) or to a group other than a naturally occurring amino acid side chain in R- or S-configuration (i.e., the D- or L-amino acid, respectively) selected from:

$C_2$-$C_7$alkenyl, $C_1$-$C_3$alkoxy$C_1$-$C_3$alkyl, $C_1$-$C_6$alkoxycarbonyl$C_1$-$C_3$alkyl, $C_1$-$C_7$alkyl, $C_1$-$C_3$alkylsulfanyl$C_1$-$C_3$alkyl, amido$C_1$-$C_3$alkyl, amino$C_1$-$C_3$alkyl, azaindolyl$C_1$-$C_3$alkyl, benzothiazolyl$C_1$-$C_3$alkyl, benzothienyl$C_1$-$C_3$alkyl, benzyloxy$C_1$-$C_3$alkyl, carboxy$C_1$-$C_3$alkyl, $C_3$-$C_6$cycloalkyl$C_1$-$C_3$alkyl, diphenylmethyl, furanyl$C_1$-$C_3$alkyl, imidazolyl$C_1$-$C_3$alkyl, naphthyl$C_1$-$C_3$alkyl, pyridinyl$C_1$-$C_3$alkyl, thiazolyl$C_1$-$C_3$alkyl, thienyl$C_1$-$C_3$alkyl;

biphenyl$C_1$-$C_3$alkyl wherein the biphenyl is optionally substituted with a methyl group;

indolyl$C_1$-$C_3$alkyl, wherein the indolyl part is optionally substituted with one group selected from $C_1$-$C_3$alkyl, carboxy$C_1$-$C_3$alkyl, halo, hydroxy, and phenyl, wherein the phenyl is further optionally substituted by one, two, or three groups independently selected from $C_1$-$C_3$alkoxy, $C_1$-$C_3$alkyl, and halo;

$NR^aR^b(C_1$-$C_7$alkyl), wherein $R^a$ and $R^b$ are independently selected from hydrogen, $C_2$-$C_4$alkenyloxycarbonyl, $C_1$-$C_3$alkyl, $C_1$-$C_3$alkylcarbonyl, $C_3$-$C_6$cycloalkylcarbonyl, furanylcarbonyl, and phenylcarbonyl. When the alkyl linker contains more than one carbon an additional $NR^aR^b$ group can be on the chain.

$NR^cR^d$carbonyl$C_1$-$C_3$alkyl, wherein $R^c$ and $R^d$ are independently selected from hydrogen, $C_1$-$C_3$alkyl, and triphenylmethyl;

phenyl$C_1$-$C_3$alkyl wherein the phenyl part is optionally substituted with one, two, three, four, or five groups independently selected from $C_1$-$C_4$alkoxy, $C_1$-$C_4$alkyl, $C_1$-$C_3$alkylsulfonylamino, amido, amino, amino$C_1$-$C_3$alkyl, aminosulfonyl, carboxy, cyano, halo, halo$C_1$-$C_3$alkyl, hydroxy, —NC(NH$_2$)$_2$, nitro, and —OP(O)(OH)$_2$; and phenoxy$C_1$-$C_3$alkyl wherein the phenyl is optionally substituted with a $C_1$-$C_3$alkyl group.

The term "$C_2$-$C_4$alkenyl", as used herein, refers to a straight or branched chain group of two to four carbon atoms containing at least one carbon-carbon double bond.

The term "$C_2$-$C_7$alkenyl", as used herein, refers to a straight or branched chain group of two to seven carbon atoms containing at least one carbon-carbon double bond.

The term "$C_2$-$C_4$alkenyloxy", as used herein, refers to a $C_2$-$C_4$alkenyl group attached to the parent molecular moiety through an oxygen atom.

The term "$C_1$-$C_3$alkoxy", as used herein, refers to a $C_1$-$C_3$alkyl group attached to the parent molecular moiety through an oxygen atom.

The term "$C_1$-$C_4$alkoxy", as used herein, refers to a $C_1$-$C_4$alkyl group attached to the parent molecular moiety through an oxygen atom.

The term "$C_1$-$C_6$alkoxy", as used herein, refers to a $C_1$-$C_6$alkyl group attached to the parent molecular moiety through an oxygen atom.

The term "$C_1$-$C_3$alkoxy$C_1$-$C_3$alkyl", as used herein, refers to a $C_1$-$C_3$alkoxy group attached to the parent molecular moiety through a $C_1$-$C_3$alkyl group.

The term "$C_1$-$C_6$alkoxycarbonyl", as used herein, refers to a $C_1$-$C_6$alkoxy group attached to the parent molecular moiety through a carbonyl group.

The term "$C_1$-$C_6$alkoxycarbonyl$C_1$-$C_3$alkyl", as used herein, refers to a $C_1$-$C_6$alkoxycarbonyl group attached to the parent molecular moiety through a $C_1$-$C_3$alkyl group.

The term "$C_1$-$C_3$alkyl", as used herein, refers to a group derived from a straight or branched chain saturated hydrocarbon containing from one to three carbon atoms.

The term "$C_1$-$C_4$alkyl", as used herein, refers to a group derived from a straight or branched chain saturated hydrocarbon containing from one to four carbon atoms.

The term "$C_1$-$C_6$alkyl", as used herein, refers to a group derived from a straight or branched chain saturated hydrocarbon containing from one to six carbon atoms.

The term "$C_1$-$C_3$alkylcarbonyl", as used herein, refers to a C1-C3alkyl group attached to the parent molecular moiety through a carbonyl group.

The term "$C_1$-$C_3$alkylsulfanyl", as used herein, refers to a $C_1$-$C_3$alkyl group attached to the parent molecular moiety through a sulfur atom.

The term "$C_1$-$C_3$alkylsulfanyl$C_1$-$C_3$alkyl", as used herein, refers to a $C_1$-$C_3$alkylsulfanyl group attached to the parent molecular moiety through a $C_1$-$C_3$alkyl group.

The term "$C_1$-$C_3$alkylsulfonyl", as used herein, refers to a $C_1$-$C_3$alkyl group attached to the parent molecular moiety through a sulfonyl group.

The term "$C_1$-$C_3$alkylsulfonylamino", as used herein, refers to a $C_1$-$C_3$alkylsulfonyl group attached to the parent molecular moiety through an amino group.

The term "amido", as used herein, refers to —C(O)NH$_2$.

The term "amido$C_1$-$C_3$alkyl", as used herein, refers to an amido group attached to the parent molecular moiety through a $C_1$-$C_3$alkyl group.

The term "amino", as used herein, refers to —NH$_2$.

The term "amino$C_1$-$C_3$alkyl", as used herein, refers to an amino group attached to the parent molecular moiety through a $C_1$-$C_3$alkyl group.

The term "aminosulfonyl", as used herein, refers to an amino group attached to the parent molecular moiety through a sulfonyl group.

The term "azaindolyl$C_1$-$C_3$alkyl", as used herein, refers to an azaindolyl group attached to the parent molecular through a $C_1$-$C_3$alkyl group. The azaindolyl group can be attached to the alkyl moiety through any substitutable atom in the group.

The term "benzothiazolyl$C_1$-$C_3$alkyl", as used herein, refers to an benzothiazolyl group attached to the parent molecular through a $C_1$-$C_3$alkyl group. The benzothiazolyl group can be attached to the alkyl moiety through any substitutable atom in the group.

The term "benzothienyl$C_1$-$C_3$alkyl", as used herein, refers to a benzothienyl group attached to the parent molecular through a $C_1$-$C_3$alkyl group. The benzothienyl group can be attached to the alkyl moiety through any substitutable atom in the group.

The term "benzyloxy", as used herein, refers to a benzyl group attached to the parent molecular moiety through an oxygen atom.

The term "benzyloxy$C_1$-$C_3$alkyl", as used herein, refers to a benzyloxy group attached to the parent molecular moiety through a $C_1$-$C_3$alkyl group.

The term "biphenyl$C_1$-$C_3$alkyl", as used herein, refers to a biphenyl group attached to the parent molecular moiety through a $C_1$-$C_3$alkyl group. The biphenyl group can be attached to the alkyl moiety through any substitutable atom in the group.

The term "carbonyl", as used herein, refers to —C(O)—.

The term "carboxy", as used herein, refers to —CO$_2$H.

The term "carboxy$C_1$-$C_3$alkyl", as used herein, refers to a carboxy group attached to the parent molecular moiety through a $C_1$-$C_3$alkyl group.

The term "cyano", as used herein, refers to —CN.

The term "$C_3$-$C_6$cycloalkyl", as used herein, refers to a saturated monocyclic, hydrocarbon ring system having three to six carbon atoms and zero heteroatoms.

The term "$C_3$-$C_6$cycloalkyl$C_1$-$C_3$alkyl", as used herein, refers to a $C_3$-$C_6$cycloalkyl group attached to the parent molecular moiety through a $C_1$-$C_3$alkyl group.

The term "$C_3$-$C_6$cycloalkylcarbonyl", as used herein, refers to a $C_3$-$C_6$ cycloalkyl group attached to the parent molecular moiety through a carbonyl group.

The term "furanyl$C_1$-$C_3$alkyl", as used herein, refers to a furanyl group attached to the parent molecular moiety through a $C_1$-$C_3$alkyl group. The furanyl group can be attached to the alkyl moiety through any substitutable atom in the group.

The term "furanylcarbonyl", as used herein, refers to a furanyl group attached to the parent molecular moiety through a carbonyl group.

The terms "halo" and "halogen", as used herein, refer to F, Cl, Br, or I.

The term "halo$C_1$-$C_3$alkyl", as used herein, refers to a $C_1$-$C_3$alkyl group substituted with one, two, or three halogen atoms.

The term "halomethyl", as used herein, refers to a methyl group substituted with one, two, or three halogen atoms.

The term "hydroxy", as used herein, refers to —OH.

The term "imidazolyl$C_1$-$C_3$alkyl", as used herein, refers to an imidazolyl group attached to the parent molecular moiety through a $C_1$-$C_3$alkyl group. The imidazolyl group can be attached to the alkyl moiety through any substitutable atom in the group.

The term "indolyl$C_1$-$C_3$alkyl", as used herein, refers to an indolyl group attached to the parent molecular moiety through a $C_1$-$C_3$alkyl group. The indolyl group can be attached to the alkyl moiety through any substitutable atom in the group.

The term "naphthyl$C_1$-$C_3$alkyl", as used herein, refers to a naphthyl group attached to the parent molecular moiety through a $C_1$-$C_3$alkyl group. The naphthyl group can be attached to the alkyl moiety through any substitutable atom in the group.

The term "nitro", as used herein, refers to —NO$_2$.

The term "$NR^aR^b$", as used herein, refers to two groups, $R^a$ and $R^b$, which are attached to the parent molecular moiety through a nitrogen atom. $R^a$ and $R^b$ are independently selected from hydrogen, $C_2$-$C_4$alkenyloxycarbonyl, $C_1$-$C_3$alkylcarbonyl, $C_3$-$C_6$cycloalkylcarbonyl, furanylcarbonyl, and phenylcarbonyl.

The term "$NR^aR^b(C_1$-$C_3)$alkyl", as used herein, refers to an $NR^aR^b$ group attached to the parent molecular moiety through a $C_1$-$C_3$alkyl group.

The term "$NR^cR^d$", as used herein, refers to two groups, $R^c$ and $R^d$, which are attached to the parent molecular moiety through a nitrogen atom. $R^c$ and $R^d$ are independently selected from hydrogen, $C_1$-$C_3$alkyl, and triphenylmethyl.

The term "$NR^cR^d$carbonyl", as used herein, refers to an $NR^cR^d$ group attached to the parent molecular moiety through a carbonyl group.

The term "$NR^cR^d$carbonyl$C_1$-$C_3$alkyl", as used herein, refers to an $NR^cR^d$carbonyl group attached to the parent molecular moiety through a $C_1$-$C_3$alkyl group.

The term "phenoxy", as used herein, refers to a phenyl group attached to the parent molecular moiety through an oxygen atom.

The term "phenoxy$C_1$-$C_3$alkyl", as used herein, refers to a phenoxy group attached to the parent molecular moiety through a $C_1$-$C_3$alkyl group.

The term "phenyl$C_1$-$C_3$alkyl", as used herein, refers to a phenyl group attached to the parent molecular moiety through a $C_1$-$C_3$alkyl group.

The term "phenylcarbonyl", as used herein, refers to a phenyl group attached to the parent molecular moiety through a carbonyl group.

The term "pyridinylC$_1$-C$_3$alkyl", as used herein, refers to a pyridinyl group attached to the parent molecular moiety through a C$_1$-C$_3$alkyl group. The pyridinyl group can be attached to the alkyl moiety through any substitutable atom in the group.

The term "sulfanyl", as used herein, refers to —S—.

The term "sulfonyl", as used herein, refers to —SO$_2$—.

The term "thiazolylC$_1$-C$_3$alkyl", as used herein, refers to a thiazolyl group attached to the parent molecular moiety through a C$_1$-C$_3$alkyl group. The thiazolyl group can be attached to the alkyl moiety through any substitutable atom in the group.

The term "thienylC$_1$-C$_3$alkyl", as used herein, refers to a thienyl group attached to the parent molecular moiety through a C$_1$-C$_3$alkyl group. The thienyl group can be attached to the alkyl moiety through any substitutable atom in the group.

The term "treating" refers to: (i) preventing a disease, disorder, or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition and/or symptoms associated with the disease, disorder, and/or condition.

Unless otherwise indicated, the term "alkyl" as employed herein alone or as part of another group includes, without limitation, both straight and branched chain hydrocarbons, containing 1 to 40 carbons, preferably 1 to 20 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like. Further, alkyl groups, as defined herein, may optionally be substituted on any available carbon atom with one or more functional groups commonly attached to such chains, such as, but not limited to alkyl, aryl, alkenyl, alkynyl, hydroxy, arylalkyl, cycloalkyl, cycloalkylalkyl, alkoxy, arylalkyloxy, heteroaryloxy, heteroarylalkyloxy, alkanoyl, halo, hydroxyl, thio, nitro, cyano, carboxyl, carbonyl

, carboxamido, amino, alkylamino, dialkylamino, amido, alkylamino, arylamido, heteroarylamido, azido, guanidino, amidino, phosphonic, phosphinic, sulfonic, sulfonamido, haloaryl, CF$_3$, OCF$_2$, OCF$_3$, aryloxy, heteroaryl, cycloalkylalkoxyalkyl, cycloheteroalkyl and the like to form alkyl groups such as trifluoro methyl, 3-hydroxyhexyl, 2-carboxypropyl, 2-fluoroethyl, carboxymethyl, cyanobutyl and the like.

Unless otherwise indicated, the term "cycloalkyl" as employed herein alone or as part of another group includes, without limitation, saturated or partially unsaturated (containing 1 or 2 double bonds) cyclic hydrocarbon groups containing 1 to 3 rings, appended or fused, including monocyclic alkyl, bicyclic alkyl and tricyclic alkyl, containing a total of 3 to 20 carbons forming the rings, preferably 4 to 7 carbons, forming each ring; which may be fused to 1 aromatic ring as described for aryl, which include cyclopropyl, cyclobutyl, cyclopentyl, cyclohexyl, cycloheptyl, cyclooctyl, cyclodecyl, cyclododecyl, cyclohexenyl,

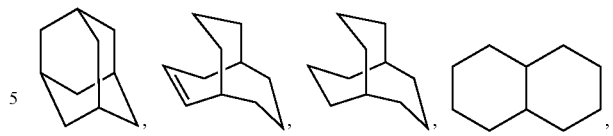

any of which groups may be optionally substituted through any available carbon atoms with 1 or more groups selected from hydrogen, halo, haloalkyl, alkyl, haloalkyl, alkoxy, haloalkoxy, alkenyl, trifluoromethyl, trifluoromethoxy, alkynyl, cycloalkylalkyl, fluorenyl, heterocycloalkyl, heterocycloalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, oxo, cyano, carboxyl, carbonyl

, carboxamido, amino, substituted amino wherein the amino includes 1 or 2 substituents (which are alkyl, aryl or any of the other aryl compounds mentioned in the definitions), amido, azido, guanidino, amidino, phosphonic, phosphinic, sulfonic, sulfonamido, thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl, or any of alkyl substituents as set out above.

The term "aryl" as employed herein alone or as part of another group refers, without limitation, to monocyclic and bicyclic aromatic groups containing 6 to 10 carbons in the ring portion (such as phenyl or naphthyl) and may optionally include one to three additional rings fused to "aryl" (such as aryl, cycloalkyl, heteroaryl or heterocycloalkyl rings) and may be optionally substituted through any available carbon atoms with 1 or more groups selected from hydrogen, alkyl, halo, haloalkyl, alkoxy, haloalkoxy, alkenyl, trifluoromethyl, trifluoromethoxy, alkynyl, cycloalkylalkyl, fluorenyl, heterocycloalkyl, heterocycloalkylalkyl, aryl, heteroaryl, arylalkyl, aryloxy, aryloxyalkyl, arylalkoxy, arylthio, arylazo, heteroarylalkyl, heteroarylalkenyl, heteroaryloxy, heteroarylalkyloxy, heteroarylalkyloxyalkyl, hydroxy, nitro, oxo, cyano, amino, substituted amino wherein the amino includes 1 or 2 substituents (which are alkyl, cycloalkyl, heterocycloalkyl, heteroaryl, or aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, cycloalkylaminocarbonyl, arylaminocarbonyl, heteroarylaminocarbonyl, heteroarylalkylaminocarbonyl alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl, or any of alkyl substituents as set out above.

The term "arylalkyl" as used herein alone or as part of another group refers, without limitation, to alkyl groups as defined above having an aryl substituent, such as benzyl, phenethyl or naphthylpropyl, wherein said aryl and/or alkyl groups may optionally be substituted as defined above.

The term "alkoxy", "aryloxy", "heteroaryloxy", "arylalkyloxy", or "heteroarylalkyloxy" as employed herein alone or as part of another group includes, without limitation, an alkyl or aryl group as defined above linked through an oxygen atom.

The term "heterocyclo", "heterocycle", "heterocyclyl" or "heterocyclic", as used herein, represents, without limitation, an unsubstituted or substituted stable 4-, 5-, 6-, or 7-membered monocyclic ring system which may be saturated or unsaturated, and which consists of carbon atoms and from one to four heteroatoms selected from nitrogen, sulfur, oxygen and/or a SO or $SO_2$ group, wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but are not limited to, tetrahydrofuranyl, tetrahydrothiophenyl pyrrolidinyl, piperidinyl, piperazinyl, oxopyrrolidinyl, oxopiperazinyl, oxopiperidinyl and oxadiazolyl. Optionally a heterocyclo group may be substituted with one or more functional groups, such as those described for "alkyl" or "aryl".

The term "heterocycloalkyl" as used herein alone or as part of another group refers, without limitation, to alkyl groups as defined above having a heterocycloalkyl substituent, wherein said "heterocyclo" and/or alkyl groups may optionally be substituted as defined above.

The term "heteroaryl" as used herein refers, without limitation, to a 5-, 6- or 7-membered aromatic heterocyclic ring which contains one or more heteroatoms selected from nitrogen, sulfur, oxygen and/or a SO or $SO_2$ group. Such rings may be fused to another aryl or heteroaryl ring and include possible N-oxides; examples of such heteroaryl groups include, but are not limited to, furan, pyrrole, thiophene, pyridine, pyrimidine, pyrazine, pyridazine, isoxazole, oxazole, imidazole and the like. Optionally a heteroaryl group may be substituted with one or more functional groups commonly attached to such chains, such as those described for "alkyl" or "aryl".

The term "heteroarylalkyl" as used herein alone or as part of another group refers, without limitation, to alkyl groups as defined above having a heteroaryl substituent, wherein said heteroaryl and/or alkyl groups may optionally be substituted as defined above.

The "inhibitory concentration" of PD-1/PD-L1 inhibitor is intended to mean the concentration at which a compound screened in an assay of the disclosure inhibits a measurable percentage of the interaction of PD-1 with PD-L1. Examples of "inhibitory concentration" values range from $IC_{50}$ to $IC_{90}$, and are preferably, $IC_{50}$, $IC_{60}$, $IC_{70}$, $IC_{80}$, or $IC_{90}$, which represent 50%, 60%, 70%, 80% or 90% reduction in PD-1/PD-L1 binding activity, respectively. More preferably, the "inhibitory concentration" is measured as the $IC_{50}$ value. It is understood that another designation for $IC_{50}$ is the half-maximal inhibitory concentration.

Binding of the macrocyclic peptides to PD-L1 can be measured, for example, by methods such as homogeneous time-resolved fluorescence (HTRF), Surface Plasmon Resonance (SPR), isothermal titration calorimetry (ITC), nuclear magnetic resonance spectroscopy (NMR), and the like. Further, binding of the macrocyclic peptides to PD-L1 expressed on the surface of cells can be measured as described herein in cellular binding assays.

Administration of a therapeutic agent described herein includes, without limitation, administration of a therapeutically effective amount of therapeutic agent. The term "therapeutically effective amount" as used herein refers, without limitation, to an amount of a therapeutic agent to treat or prevent a condition treatable by administration of a composition of the PD-1/PD-L1 binding inhibitors described herein. That amount is the amount sufficient to exhibit a detectable therapeutic or preventative or ameliorative effect. The effect may include, for example and without limitation, treatment or prevention of the conditions listed herein. The precise effective amount for a subject will depend upon the subject's size and health, the nature and extent of the condition being treated, recommendations of the treating physician, and therapeutics or combination of therapeutics selected for administration. Thus, it is not useful to specify an exact effective amount in advance.

The macrocyclic peptides of the present disclosure show potent binding activity to PD-L1, both in HTRF assays, as well as cellular binding assays. In addition, the macrocyclic peptides also demonstrate biological activity in CMV recall and HIV Elispot assays demonstrating their utility in ameliorating and/or treating hyperproliferative disorders, such as cancer, and virology indications, including HIV.

In another aspect, the disclosure pertains to methods of inhibiting growth of tumor cells in a subject using the macrocyclic peptides of the present disclosure. As demonstrated herein, the macrocyclic peptides of the present disclosure are capable of binding to PD-L1, disrupting the interaction between PD-L1 and PD-1, competing with the binding of PD-L1 with anti-PD-1 monoclonal antibodies that are known to block the interaction with PD-1, enhancing CMV-specific T cell IFNγ secretion, and enhancement of HIV-specific T cell IFNg secretion. As a result, the macrocyclic peptides of the present disclosure are useful for modifying an immune response, treating diseases such as cancer or infectious disease, stimulating a protective autoimmune response or to stimulate antigen-specific immune responses (e.g., by coadministration of PD-L1 blocking peptides with an antigen of interest).

In order that the present disclosure may be more readily understood, certain terms are first defined. Additional definitions are set forth throughout the detailed description.

The terms "Programmed Death Ligand 1", "Programmed Cell Death Ligand 1", "Protein PD-L1", "PD-L1", "PDL1", "PDCDL1", "hPD-L1", "hPD-L1", "CD274" and "B7-H1" are used interchangeably, and include variants, isoforms, species homologs of human PD-L1, and analogs having at least one common epitope with PD-L1. The complete PD-L1 sequence can be found under GENBANK® Accession No. NP_054862.

The terms "Programmed Death 1", "Programmed Cell Death 1", "Protein PD-1", "PD-1", "PD1", "PDCD1", "hPD-1" and "hPD-I" are used interchangeably, and include variants, isoforms, species homologs of human PD-1, and analogs having at least one common epitope with PD-1. The complete PD-1 sequence can be found under GENBANK® Accession No. U64863.

The terms "cytotoxic T lymphocyte-associated antigen-4", "CTLA-4", "CTLA4", "CTLA-4 antigen" and "CD152" (see, e.g., Murata, *Am. J. Pathol.*, 155:453-460 (1999)) are used interchangeably, and include variants, isoforms, species homologs of human CTLA-4, and analogs having at least one common epitope with CTLA-4 (see, e.g., Balzano, *Int. J. Cancer Suppl.*, 7:28-32 (1992)). The complete CTLA-4 nucleic acid sequence can be found under GENBANK® Accession No. L15006.

The term "immune response" refers to the action of, for example, lymphocytes, antigen presenting cells, phagocytic cells, granulocytes, and soluble macromolecules produced by the above cells or the liver (including macrocyclic peptides, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

A "signal transduction pathway" refers to the biochemical relationship between a variety of signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell. An example of a "cell surface receptor" of the present disclosure is the PD-1 receptor.

The term "macrocyclic peptide derivatives" refers to any modified form of the macrocyclic peptides disclosed herein, e.g., mutations, isoforms, peptides with altered linker backbones, conjugates with an antibody and/or another agent, etc.

As used herein, a macrocyclic peptide of the present disclosure that "specifically binds to human PD-L1" is intended to refer to a macrocyclic peptide that binds to human PD-L1 with an $IC_{50}$ of less than about 200 nM, less than about 150 nM, less than about 100 nM, less than about 80 nM, less than about 60 nM, less than about 40 nM, less than about 20 nM, less than about 15 nM, less than about 10 nM, less than about 5 nM, less than about 1 nM, or less. In this context, the term "about" shall be construed to mean anywhere between ±1, 2, 3, 4, 5, 6, 7, 8, 9, 10, 11, 12, 13, 14, 15, 16, 17, 18, 19, or 20 nM more or less than the cited amount.

The term "treatment" or "therapy" refers to administering an active agent with the purpose to cure, heal, alleviate, relieve, alter, remedy, ameliorate, improve, or affect a condition (e.g., a disease), the symptoms of the condition, or to prevent or delay the onset of the symptoms, complications, biochemical indicia of a disease, or otherwise arrest or inhibit further development of the disease, condition, or disorder in a statistically significant manner.

An "adverse event" (AE) as used herein is any unfavorable and generally unintended, even undesirable, sign (including an abnormal laboratory finding), symptom, or disease associated with the use of a medical treatment. For example, an adverse event may be associated with activation of the immune system or expansion of immune system cells (e.g., T cells) in response to a treatment. A medical treatment may have one or more associated AEs and each AE may have the same or different level of severity. Reference to methods capable of "altering adverse events" means a treatment regime that decreases the incidence and/or severity of one or more AEs associated with the use of a different treatment regime.

As used herein, "hyperproliferative disease" refers to conditions wherein cell growth is increased over normal levels. For example, hyperproliferative diseases or disorders include malignant diseases (e.g., esophageal cancer, colon cancer, biliary cancer) and non-malignant diseases (e.g., atherosclerosis, benign hyperplasia, and benign prostatic hypertrophy).

As used herein, "about" or "comprising essentially of" mean within an acceptable error range for the particular value as determined by one of ordinary skill in the art, which will depend in part on how the value is measured or determined, i.e., the limitations of the measurement system. For example, "about" or "comprising essentially of" can mean within one or more than one standard deviation per the practice in the art. Alternatively, "about" or "comprising essentially of" can mean a range of up to 20%. Furthermore, particularly with respect to biological systems or processes, the terms can mean up to an order of magnitude or up to 5-fold of a value. When particular values are provided in the application and claims, unless otherwise stated, the meaning of "about" or "comprising essentially of" should be assumed to be within an acceptable error range for that particular value.

As described herein, any concentration range, percentage range, ratio range or integer range is to be understood to include the value of any integer within the recited range and, when appropriate, fractions thereof (such as one tenth and one hundredth of an integer), unless otherwise indicated.

Competition Assays

The present disclosure is also directed to macrocyclic peptides that are capable of competing with the binding of a reference anti-PD-L1 antibody (MDX-1105) by at least about 20%, at least about 30%, at least about 40%, at least about 50%, at least about 60%, at least about 70%, at least about 80%, at least about 90%, and at least about 100%. Such macrocyclic peptides may share structural homology with one or more macrocyclic peptides disclosed herein, including mutant, conservative substitution, functional substitution, and deletion forms, provided they specific bind to PD-L1. For example, if a macrocyclic peptide binds substantially to the same region of PD-L1 as a reference anti-PD-L1 antibody, the macrocyclic peptide should bind to an epitope of PD-L1 that at least overlaps with the PD-L1 epitope that the anti-PD-L1 monoclonal antibody binds to. The overlapping region can range from one amino acid residue to several hundred amino acid residues. The macrocyclic peptide should then compete with and/or block the binding of the anti-PD-L1 monoclonal antibody to PD-L1 and thereby decrease the binding of the anti-PD-L1 monoclonal antibody to PD-L1, preferably by at least about 50% in a competition assay.

Anti-PD-L1 antibodies that may be used as reference antibodies for competition assay purposes are known in the art. For example, the following representative anti-PD-L1 antibodies may be used: MDX-1105 (BMS); L01X-C(Serono), L1X3 (Serono), MSB-0010718C (Serono), and PD-L1 Probody (CytomX), and the PD-L1 antibodies disclosed in co-owned WO 2007/005874.

Anti-PD-1 antibodies that may be used as reference antibodies for competition assay purposes are known in the art. For example, the following representative anti-PD-1 antibodies may be used: nivolumab (BMS); 17D8, 2D3, 4H1, 4A11, 7D3 and 5F4 each disclosed in co-owned U.S. Pat. No. 8,008,449 (BMS), MK-3475 (Merck, disclosed in U.S. Pat. No. 8,168,757), and the antibodies disclosed in U.S. Pat. No. 7,488,802.

Variant Macrocyclic Peptides

In yet another embodiment, a macrocyclic peptide of the disclosure comprises amino acid sequences that are homologous to the amino acid sequences of the macrocyclic peptides described herein, and wherein the macrocyclic peptides retain the desired functional and/or biological properties of the macrocyclic peptide of the disclosure.

For example, the disclosure provides a macrocyclic peptide, or antigen-binding portion thereof, comprising: an amino acid sequence that is at least 80% homologous to an amino acid sequence selected from the compounds described herein; and the macrocyclic peptide exhibits one or more of the following properties:

(a) the macrocyclic peptide binds to human PD-L1 with an $IC_{50}$ of 200 nM or less;

(b) the macrocyclic peptide does not substantially bind to human CD28, CTLA-4 or ICOS;

(c) the macrocyclic peptide increases CMV-specific T cell IFNγ secretion;

(d) the macrocyclic peptide increases HIV-specific T cell IFNγ secretion;

(e) the macrocyclic peptide binds to human PD-1 and one or more of the following: cynomolgus monkey PD-1; woodchuck PD-1, and/or mouse PD-1;

(f) the macrocyclic peptide inhibits the binding of PD-L1 and/or PD-L2 to PD-1;

(g) the macrocyclic peptide is capable of competing with binding of anti-PD-1 monoclonal antibodies, including nivolumab (BMS-936558, MDX-1106);

(h) the macrocyclic peptide inhibits tumor cell growth in a cellular assay and/or in vivo assay; and/or (i) the macrocyclic peptide inhibits HIV in a cellular assay and/or in vivo assay.

In other embodiments, the macrocyclic peptide amino acid sequences may be about 80%, about 85%, about 86%, about 87%, about 88%, about 89%, about 90%, about 91%, about 92%, about 93%, about 94%, about 95%, about 96%, about 97%, about 98% or about 99% homologous to the sequences set forth above. In this context, the term "about" shall be construed to mean anywhere between 1, 2, 3, 4, or 5 percent more or less than the cited amount. A macrocyclic peptide of the present disclosure having sequences with high identity (i.e., 80% or greater) to the sequences set forth above, can be obtained by mutating the sequences during chemical synthesis, for example, followed by testing of the altered macrocyclic peptide for retained function (i.e., the functions set forth in (a) through (i) above) using the functional assays described herein. The biological and/or functional activity of the variant macrocyclic peptide amino acid sequences may be at least about 1×, 2×, 3×, 4×, 5×, 6×, 7×, 8×, 9×, or 10× more than the reference macrocyclic peptide on which the variant is based. In this context, the term "about" shall be construed to mean anywhere between 0.1×, 0.2×, 0.3×, 0.4×, 0.5×, 0.6×, 0.7×, 0.8×, or 0.9× more or less than the cited amount.

As used herein, the percent homology between two amino acid sequences is equivalent to the percent identity between the two sequences. The percent identity between the two sequences is a function of the number of identical positions shared by the sequences (i.e., % homology=# of identical positions/total # of positions.times.100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of Meyers E. et al., (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman et al. (*J. Mol. Biol.*, 48:444-453 (1970)) algorithm which has been incorporated into the GAP program in the GCG® software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

Macrocyclic Peptides with Conservative Modifications

In yet another embodiment, a macrocyclic peptide of the disclosure comprises amino acid sequences that are homologous to the amino acid sequences of the macrocyclic peptides described herein, and wherein the macrocyclic peptides retain the desired functional and/or biological properties of the macrocyclic peptide of the disclosure.

For example, the disclosure provides a macrocyclic peptide, or antigen-binding portion thereof, comprising: an amino acid sequence that is at least 80% homologous to an amino acid sequence selected from the macrocyclic peptides described herein, wherein one or more amino acids have been substituted with a conservative amino acid; and the macrocyclic peptide exhibits one or more of the following properties:

(a) the macrocyclic peptide binds to human PD-L1 with an $IC_{50}$ of 200 nM or less (b) the macrocyclic peptide does not substantially bind to human CD28, CTLA-4 or ICOS;

(c) the macrocyclic peptide increases CMV-specific T cell IFNγ secretion;

(d) the macrocyclic peptide increases HIV-specific T cell IFNγ secretion;

(e) the macrocyclic peptide binds to human PD-L1 and one or more of the following: cynomolgus monkey PD-L1; woodchuck PD-L1, and/or mouse PD-L1;

(f) the macrocyclic peptide inhibits the binding of PD-L1 and/or PD-L2 to PD-1;

(g) the macrocyclic peptide is capable of competing with binding of anti-PD-1 monoclonal antibodies, including nivolumab (BMS-936558, MDX-1106);

(h) the macrocyclic peptide inhibits tumor cell growth in a cellular assay and/or in vivo assay; and/or (i) the macrocyclic peptide inhibits HIV in a cellular assay and/or in vivo assay.

As used herein, the term "conservative sequence modifications" is intended to refer to amino acid modifications that do not significantly affect or alter the binding characteristics of the macrocyclic peptide containing the amino acid sequence. Such conservative modifications include amino acid substitutions, additions and deletions. Modifications can be introduced into an antibody of the disclosure by standard techniques known in the art, such as substitution of peptide amidites during chemical synthesis, site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the antigen binding regions of macrocyclic peptides of the disclosure can be replaced with other amino acid residues from the same side chain family and the altered antibody can be tested for retained function (i.e., the functions set forth in (a) thru (i) above) using the functional assays described herein. Conservative amino acid substitutions may also be selected from one or more non-naturally occurring amino acids disclosed herein.

Pharmaceutical Compositions

The disclosure further relates to the polypeptides described herein wherein the sequence comprises one or more amino acid deletions from either the C-terminus and/or the N-terminus.

In preferred embodiments, the following N-terminal Compound No. 99 deletion polypeptides are encompassed by the present disclosure: X1-X13, X2-X13, X3-X13, X4-X13, X5-X13, X6-X13, X7-X13, X8-X13, X9-X13, X10-X13, X11-X13, and/or X12-X13 of Compound No. 99, wherein each X is representative of an amino acid at the indicated position for each peptide as outlined herein. The present disclosure also encompasses cyclic forms of these deletion mutants using the linking chemistries described elsewhere herein.

In preferred embodiments, the following C-terminal Compound No. 99 deletion polypeptides are encompassed by the present disclosure: X1-X13, X1-X12, X1-X11, X1-X10, X1-X9, X1-X8, X1-X7, X1-X6, X1-X5, X1-X4 and/or X1-X3 of Compound No. 99, wherein each X is representative of an amino acid at the indicated position for each peptide as outlined herein. The present disclosure also encompasses cyclic forms of these deletion mutants using the linking chemistries described elsewhere herein.

In preferred embodiments, the following N-terminal Compound No. 1 deletion polypeptides are encompassed by the present disclosure: X1-X15, X2-X15, X3-X15, X4-X15, X5-X15, X6-X15, X7-X15, X8-X15, X9-X15, X10-X15, X11-X15, and/or X12-X15 of Compound No. 1, wherein each 1 is representative of an amino acid at the indicated position for each peptide as outlined herein. The present disclosure also encompasses cyclic forms of these deletion mutants using the linking chemistries described elsewhere herein.

In preferred embodiments, the following C-terminal Compound No. 1 deletion polypeptides are encompassed by the present disclosure: X1-X15, X1-X14, X1-X13, X1-X12, X1-X11, X1-X10, X1-X9, X1-X8, X1-X7, X1-X6, X1-X5, X1-X4 and/or X1-X3 of Compound No. 1, wherein each X is representative of an amino acid at the indicated position for each peptide as outlined herein. The present disclosure also encompasses cyclic forms of these deletion mutants using the linking chemistries described elsewhere herein.

In preferred embodiments, the following N-terminal Compound No. 71 deletion polypeptides are encompassed by the present disclosure: X1-X14, X2-X14, X3-X14, X4-X14, X5-X14, X6-X14, X7-X14, X8-X14, X9-X14, X10-X14, X11-X14, and/or X12-X14 of Compound No. 71, wherein each X is representative of an amino acid at the indicated position for each peptide as outlined herein. The present disclosure also encompasses cyclic forms of these deletion mutants using the linking chemistries described elsewhere herein.

In preferred embodiments, the following C-terminal Compound No. 71 deletion polypeptides are encompassed by the present disclosure: X1-X14, X1-X13, X1-X12, X1-X11, X1-X10, X1-X9, X1-X8, X1-X7, X1-X6, X1-X5, X1-X4 and/or X1-X3 of Compound No. 71, wherein each X is representative of an amino acid at the indicated position for each peptide as outlined herein. The present disclosure also encompasses cyclic forms of these deletion mutants using the linking chemistries described elsewhere herein.

In another aspect, the present disclosure provides a composition, e.g., a pharmaceutical composition, containing one or a combination of macrocyclic peptides, or antigen-binding portion(s) thereof, of the present disclosure, formulated together with a pharmaceutically acceptable carrier. Such compositions may include one or a combination of (e.g., two or more different) macrocyclic peptides, or immunoconjugates or bispecific molecules of the disclosure. For example, a pharmaceutical composition of the disclosure can comprise a combination of macrocyclic peptides (or immunoconjugates or bispecifics) that bind to different epitopes on the target antigen or that have complementary activities.

Pharmaceutical compositions of the disclosure also can be administered in combination therapy, i.e., combined with other agents. For example, the combination therapy can include a macrocyclic peptide combined with at least one other anti-inflammatory or immunosuppressant agent. Examples of therapeutic agents that can be used in combination therapy are described in greater detail below in the section on uses of the macrocyclic peptides of the disclosure.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., a macrocyclic peptide, immunoconjugate, or bispecific molecule, may be coated in a material to protect the compound from the action of acids and other natural conditions that may inactivate the compound.

The pharmaceutical compounds of the disclosure may include one or more pharmaceutically acceptable salts. A "pharmaceutically acceptable salt" refers to a salt that retains the desired biological activity of the parent compound and does not impart any undesired toxicological effects (see e.g., Berge, S. M. et al., *J. Pharm. Sci.*, 66:1-19 (1977)). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the disclosure also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the disclosure is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the disclosure are dictated by and directly dependent on (a) the unique characteristics of the active compound and the particular therapeutic effect to be achieved, and (b) the limitations inherent in the art of compounding such an active compound for the treatment of sensitivity in individuals.

For administration of the macrocyclic peptide, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per day, bi-weekly, tri-weekly, weekly, once every two weeks, once every three weeks, once every four weeks, once a month, once every 3 months or once every three to 6 months. Preferred dosage regimens for a macrocyclic peptide of the disclosure include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more macrocyclic peptides with different binding specificities are administered simultaneously, in which case the dosage of each compound administered falls within the ranges indicated. The compounds are usually administered on multiple occasions. Intervals between single dosages can be, for example, weekly, monthly, every three months or yearly. Intervals can also be irregular as indicated by measuring blood levels of macrocyclic peptide to the target antigen in the patient. In some methods, dosage is adjusted to achieve a plasma antibody concentration of about 1-1000.mu·g/ml and in some methods about 25-300.mu·g/ml.

Alternatively, the macrocyclic peptide can be administered as a sustained release formulation, in which case less frequent administration is required. Dosage and frequency vary depending on the half-life of the macrocyclic peptide in the patient. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of a macrocyclic peptide of the disclosure preferably results in a decrease in severity of disease symptoms, an increase in frequency and duration of disease symptom-free periods, or a prevention of impairment or disability due to the disease affliction. For example, for the treatment of tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth and/or HIV can be evaluated in an animal model system predictive of efficacy in human tumors or viral efficacy. Alternatively, this property of a composition can be evaluated by examining the ability of the compound to inhibit, such inhibition in vitro by assays known to the skilled practitioner. A therapeutically effective amount of a therapeutic compound can decrease tumor size, decrease viral load, or otherwise ameliorate symptoms in a subject. One of ordinary skill in the art would be able to determine such amounts based on such factors as the subject's size, the severity of the subject's symptoms, and the particular composition or route of administration selected.

In another aspect, the instant disclosure provides a pharmaceutical kit of parts comprising a macrocyclic peptide and an anti-CTLA-4 antibody, as described herein. The kit may also further comprise instructions for use in the treatment of a hyperproliferative disease (such as cancer as described herein) and/or anti-viral disease.

A composition of the present disclosure can be administered via one or more routes of administration using one or more of a variety of methods known in the art. As will be appreciated by the skilled artisan, the route and/or mode of administration will vary depending upon the desired results. Preferred routes of administration for macrocyclic peptides of the disclosure include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, a macrocyclic peptide of the disclosure can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Robinson, J. R., ed., *Sustained and Controlled Release Drug Delivery Systems*, Marcel Dekker, Inc., New York (1978).

Therapeutic compositions can be administered with medical devices known in the art. For example, in a preferred embodiment, a therapeutic composition of the disclosure can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present disclosure include: U.S. Pat. No. 4,487,603, which discloses an implantable microinfusion pump for dispensing medication at a controlled rate; U.S. Pat. No. 4,486,194, which discloses a therapeutic device for administering medication through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the macrocyclic peptides of the disclosure can be formulated to ensure proper distribution in vivo. For example, the blood-brain barrier (BBB) excludes many highly hydrophilic compounds. To ensure that therapeutic compounds of the disclosure cross the BBB (if desired), they can be formulated, for example, in liposomes. For methods of manufacturing liposomes, see, e.g., U.S. Pat. Nos. 4,522,811, 5,374,548, and 5,399,331. The liposomes may comprise one or more moieties which are selectively transported into specific cells or organs, thus enhance targeted drug delivery (see, e.g., Ranade, V. V., *J. Clin. Pharmacol.*, 29:685 (1989)). Exemplary targeting moieties include folate or biotin (see, e.g., U.S. Pat. No. 5,416,016 to Low et al.); mannosides (Umezawa et al., *Biochem. Biophys. Res. Commun.*, 153:1038 (1988)); macrocyclic peptides (Bloeman, P. G. et al., *FEBS Lett.*, 357:140 (1995); Owais, M. et al., *Antimicrob. Agents Chemother.*, 39:180 (1995)); surfactant protein A receptor (Briscoe et al., *Am. J. Physiol.*, 1233:134 (1995)); p 120 (Schreier et al., *J. Biol. Chem.*, 269:9090 (1994)); see also Keinanen, K. et al., *FEBS Lett.*, 346:123 (1994); Killion, J. J. et al., *Immunomethods* 4:273 (1994).

Uses and Methods of the Disclosure

The macrocyclic peptides, compositions and methods of the present disclosure have numerous in vitro and in vivo utilities involving, for example, detection of PD-L1 or enhancement of immune response by blockade of PD-L1. For example, these molecules can be administered to cells in culture, in vitro or ex vivo, or to human subjects, e.g., in vivo, to enhance immunity in a variety of situations. Accordingly, in one aspect, the disclosure provides a method of modifying an immune response in a subject comprising administering to the subject the antibody, or antigen-binding portion thereof, of the disclosure such that the immune response in the subject is modified. Preferably, the response is enhanced, stimulated or up-regulated. In other respects, the macrocyclic peptide may have anti-cyno, anti-mouse, and/or anti-woodchuck binding and therapeutic activity.

As used herein, the term "subject" is intended to include human and non-human animals. Non-human animals includes all vertebrates, e.g., mammals and non-mammals, such as non-human primates, sheep, dogs, cats, cows, horses, chickens, woodchuck, amphibians, and reptiles, although mammals are preferred, such as non-human primates, sheep, dogs, cats, cows and horses. Preferred subjects include human patients in need of enhancement of an immune response. The methods are particularly suitable for treating human patients having a disorder that can be treated by augmenting the T-cell mediated immune response. In a particular embodiment, the methods are particularly suitable for treatment of cancer cells in vivo. To achieve antigen-specific enhancement of immunity, the macrocyclic peptides can be administered together with an antigen of interest. When macrocyclic peptides to PD-L1 are administered together with another agent, the two can be administered in either order or simultaneously.

The disclosure further provides methods for detecting the presence of human, woodchuck, cyno, and/or mouse PD-L1 antigen in a sample, or measuring the amount of human, woodchuck, cyno, and/or mouse PD-L1 antigen, comprising contacting the sample, and a control sample, with a reference monoclonal antibody, or an antigen-binding portion thereof, which specifically binds to human, woodchuck, cyno, and/or mouse PD-L1, under conditions that allow for formation of a complex between the antibody or portion thereof and human, woodchuck, cyno, and/or mouse PD-L1. The formation of a complex is then detected, wherein a difference complex formation between the sample compared to the control sample is indicative the presence of human, woodchuck, cyno, and/or mouse PD-L1 antigen in the sample.

Given the specific binding of the macrocyclic peptides of the disclosure for PD-L1, compared to CD28, ICOS and CTLA-4, the macrocyclic peptides of the disclosure can be used to specifically detect PD-L1 expression on the surface of cells and, moreover, can be used to purify PD-L1 via immunoaffinity purification.

Cancer

Blockade of PD-1 by macrocyclic peptides can enhance the immune response to cancerous cells in the patient. The ligand for PD-1, PD-L1, is not expressed in normal human cells, but is abundant in a variety of human cancers (Dong et al., *Nat. Med.*, 8:787-789 (2002)). The interaction between PD-1 and PD-L1 results in a decrease in tumor infiltrating lymphocytes, a decrease in T-cell receptor mediated proliferation, and immune evasion by the cancerous cells (Dong et al., *J. Mol. Med.*, 81:281-287 (2003); Blank et al., *Cancer Immunol. Immunother.*, 54:307-314 (2005); Konishi et al., *Clin. Cancer Res.*, 10:5094-5100 (2004)). Immune suppression can be reversed by inhibiting the local interaction of PD-1 to PD-L1 and the effect is additive when the interaction of PD-1 to PD-L2 is blocked as well (Iwai et al., *Proc. Natl. Acad. Sci.*, 99:12293-12297 (2002); Brown et al., *J. Immunol.*, 170:1257-1266 (2003)). While previous studies have shown that T-cell proliferation can be restored by inhibiting the interaction of PD-1 to PD-L1, there have been no reports of a direct effect on cancer tumor growth in vivo by blocking the PD-1/PD-L1 interaction. In one aspect, the present disclosure relates to treatment of a subject in vivo using a macrocyclic peptide such that growth of cancerous tumors is inhibited. A macrocyclic peptide may be used alone to inhibit the growth of cancerous tumors. Alternatively, a macrocyclic peptide may be used in conjunction with other immunogenic agents, standard cancer treatments, or other macrocyclic peptides, as described below.

Accordingly, in one embodiment, the disclosure provides a method of inhibiting growth of tumor cells in a subject, comprising administering to the subject a therapeutically effective amount of a macrocyclic peptide, or antigen-binding portion thereof.

Preferred cancers whose growth may be inhibited using the macrocyclic peptides of the disclosure include cancers typically responsive to immunotherapy. Non-limiting examples of preferred cancers for treatment include melanoma (e.g., metastatic malignant melanoma), renal cell carcinoma (e.g., clear cell carcinoma), prostate cancer (e.g., hormone refractory prostate adenocarcinoma and castration-resistant prostate cancer), breast cancer, colorectal cancer and lung cancer (e.g., squamous and non-squamous non-small cell lung cancer). Additionally, the disclosure includes refractory or recurrent malignancies whose growth may be inhibited using the macrocyclic peptides of the disclosure.

Examples of other cancers that may be treated using the methods of the disclosure include bone cancer, pancreatic cancer, skin cancer, cancer of the head or neck, cutaneous or intraocular malignant melanoma, uterine cancer, ovarian cancer, colon cancer, rectal cancer, cancer of the anal region, stomach/gastric cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present disclosure is also useful for treatment of metastatic cancers, especially metastatic cancers that express PD-L1 (Iwai et al., *Int. Immunol.*, 17:133-144 (2005)).

Optionally, macrocyclic peptides to PD-L1 can be combined with an immunogenic agent, such as cancerous cells, purified tumor antigens (including recombinant proteins, peptides, and carbohydrate molecules), cells, and cells transfected with genes encoding immune stimulating cytokines (He et al., *J. Immunol.*, 173:4919-4928 (2004)). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF (discussed further below).

In humans, some tumors have been shown to be immunogenic such as melanomas. It is anticipated that by raising the threshold of T cell activation by PD-L1 blockade, we may expect to activate tumor responses in the host.

PD-L1 blockade is likely to be most effective when combined with a vaccination protocol. Many experimental strategies for vaccination against tumors have been devised (see Rosenberg, S., Development of Cancer Vaccines, ASCO Educational Book Spring: 60-62 (2000); Logothetis, C., ASCO Educational Book Spring: 300-302 (2000); Khayat, D., ASCO Educational Book Spring: 414-428 (2000); Foon, K., ASCO Educational Book Spring: 730-738 (2000); see also Restifo, N. et al., Cancer Vaccines, Chapter 61, pp. 3023-3043, in DeVita, V. et al., eds., *Cancer: Principles and Practice of Oncology*, Fifth Edition (1997)). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al., *Proc. Natl. Acad. Sci. USA*, 90: 3539-3543 (1993)).

The study of gene expression and large scale gene expression patterns in various tumors has led to the definition of so called tumor specific antigens (Rosenberg, S. A., *Immunity*, 10:281-287 (1999)). In many cases, these tumor specific antigens are differentiation antigens expressed in the tumors and in the cell from which the tumor arose, for example melanocyte antigens gp100, MAGE antigens, and Trp-2. More importantly, many of these antigens can be shown to be the targets of tumor specific T cells found in the host. PD-L1 blockade may be used in conjunction with a collection of recombinant proteins and/or peptides expressed in a tumor in order to generate an immune response to these proteins. These proteins are normally viewed by the immune system as self antigens and are therefore tolerant to them. The tumor antigen may also include the protein telomerase, which is required for the synthesis of telomeres of chromosomes and which is expressed in more than 85% of human cancers and in only a limited number of somatic tissues (Kim, N. et al., *Science*, 266:2011-2013 (1994)). (These somatic tissues may be protected from immune attack by various means). Tumor antigen may also be "neo-antigens" expressed in cancer cells because of somatic mutations that alter protein sequence or create fusion proteins between two unrelated sequences (i.e., bcr-abl in the Philadelphia chromosome), or idiotype from B cell tumors.

Other tumor vaccines may include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which may be used in conjunction with PD-L1 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot, R. et al., *Science*, 269:1585-1588 (1995); Tamura, Y. et al., *Science*, 278:117-120 (1997)).

Dendritic cells (DC) are potent antigen presenting cells that can be used to prime antigen-specific responses. DC's can be produced ex vivo and loaded with various protein and peptide antigens as well as tumor cell extracts (Nestle, F. et al., *Nat. Med.*, 4:328-332 (1998)). DCs may also be transduced by genetic means to express these tumor antigens as well. DCs have also been fused directly to tumor cells for the purposes of immunization (Kugler, A. et al., *Nat. Med.*, 6:332-336 (2000)). As a method of vaccination, DC immunization may be effectively combined with PD-L1 blockade to activate more potent anti-tumor responses.

PD-L1 blockade may also be combined with standard cancer treatments. PD-L1 blockade may be effectively combined with chemotherapeutic regimes. In these instances, it may be possible to reduce the dose of chemotherapeutic reagent administered (Mokyr, M. et al., *Cancer Res.*, 58:5301-5304 (1998)). An example of such a combination is a macrocyclic peptide in combination with decarbazine for the treatment of melanoma. Another example of such a combination is a macrocyclic peptide in combination with interleukin-2 (IL-2) for the treatment of melanoma. The scientific rationale behind the combined use of PD-L1 blockade and chemotherapy is that cell death, that is a consequence of the cytotoxic action of most chemotherapeutic compounds, should result in increased levels of tumor antigen in the antigen presentation pathway. Other combination therapies that may result in synergy with PD-L1 blockade through cell death are radiation, surgery, and hormone deprivation. Each of these protocols creates a source of tumor antigen in the host. Angiogenesis inhibitors may also be combined with PD-L1 blockade Inhibition of angiogenesis leads to tumor cell death which may feed tumor antigen into host antigen presentation pathways.

PD-L1 blocking macrocyclic peptides can also be used in combination with bispecific macrocyclic peptides that target Fc alpha or Fc gamma receptor-expressing effectors cells to tumor cells (see, e.g., U.S. Pat. Nos. 5,922,845 and 5,837,243). Bispecific macrocyclic peptides can be used to target two separate antigens. For example anti-Fc receptor/anti tumor antigen (e.g., Her-2/neu) bispecific macrocyclic peptides have been used to target macrophages to sites of tumor. This targeting may more effectively activate tumor specific responses. The T cell arm of these responses would be augmented by the use of PD-L1 blockade. Alternatively, antigen may be delivered directly to DCs by the use of bispecific macrocyclic peptides which bind to tumor antigen and a dendritic cell specific cell surface marker.

Tumors evade host immune surveillance by a large variety of mechanisms. Many of these mechanisms may be overcome by the inactivation of proteins which are expressed by the tumors and which are immunosuppressive. These include among others TGF-beta (Kehrl, J. et al., *J. Exp. Med.*, 163:1037-1050 (1986)), IL-10 (Howard, M. et al., *Immunology Today*, 13:198-200 (1992)), and Fas ligand (Hahne, M. et al., *Science*, 274:1363-1365 (1996)). Macrocyclic peptides to each of these entities may be used in combination with anti-PD-L1 to counteract the effects of the immunosuppressive agent and favor tumor immune responses by the host.

Other macrocyclic peptides which may be used to activate host immune responsiveness can be used in combination with anti-PD-L1. These include molecules on the surface of dendritic cells which activate DC function and antigen presentation. Anti-CD40 macrocyclic peptides are able to substitute effectively for T cell helper activity (Ridge, J. et al., *Nature*, 393:474-478 (1998)) and can be used in conjunction with PD-1 antibodies (Ito, N. et al., *Immunobiology*, 201(5):527-540 (2000)). Activating macrocyclic peptides to T cell costimulatory molecules such as CTLA-4 (e.g., U.S. Pat. No. 5,811,097), OX-40 (Weinberg, A. et al., *Immunol.*, 164:2160-2169 (2000)), 4-1BB (Melero, I. et al., *Nat. Med.*, 3:682-685 (1997), and ICOS (Hutloff, A. et al., *Nature*, 397:262-266 (1999)) may also provide for increased levels of T cell activation.

Bone marrow transplantation is currently being used to treat a variety of tumors of hematopoietic origin. While graft versus host disease is a consequence of this treatment, therapeutic benefit may be obtained from graft vs. tumor responses. PD-L1 blockade can be used to increase the effectiveness of the donor engrafted tumor specific T cells.

There are also several experimental treatment protocols that involve ex vivo activation and expansion of antigen specific T cells and adoptive transfer of these cells into recipients in order to antigen-specific T cells against tumor (Greenberg, R. et al., *Science*, 285:546-551 (1999)). These methods may also be used to activate T cell responses to infectious agents such as CMV. Ex vivo activation in the presence of macrocyclic peptides may be expected to increase the frequency and activity of the adoptively transferred T cells.

Infectious Diseases

Other methods of the disclosure are used to treat patients that have been exposed to particular toxins or pathogens. Accordingly, another aspect of the disclosure provides a method of treating an infectious disease in a subject comprising administering to the subject a macrocyclic peptide of the present disclosure, or antigen-binding portion thereof, such that the subject is treated for the infectious disease. Preferably, the antibody is a human anti-human PD-L1 macrocyclic peptide (such as any of the macrocyclic peptides described herein). Additionally or alternatively, the antibody can be a chimeric or humanized antibody.

Similar to its application to tumors as discussed above, antibody mediated PD-L1 blockade can be used alone, or as an adjuvant, in combination with vaccines, to stimulate the immune response to pathogens, toxins, and self-antigens. Examples of pathogens for which this therapeutic approach may be particularly useful, include pathogens for which there is currently no effective vaccine, or pathogens for which conventional vaccines are less than completely effective. These include, but are not limited to HIV, Hepatitis (A, B, and C), Influenza, Herpes, Giardia, Malaria (Butler, N. S. et al., *Nature Immunology*, 13:188-195 (2012); Hafalla, J. C. R., et al., *PLOS Pathogens* (Feb. 2, 2012)), *Leishmania, Staphylococcus aureus, Pseudomonas Aeruginosa*. PD-L1 blockade is particularly useful against established infections by agents such as HIV that present altered antigens over the course of the infections. These novel epitopes are recognized as foreign at the time of anti-human PD-L1 administration, thus provoking a strong T cell response that is not dampened by negative signals through PD-L1.

Some examples of pathogenic viruses causing infections treatable by methods of the disclosure include HIV, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections treatable by methods of the disclosure include *chlamydia*, rickettsial bacteria, mycobacteria, staphylococci, streptococci, pneumonococci, meningococci and conococci, *klebsiella, proteus, serratia, pseudomonas, legionella*, diphtheria, *salmonella*, bacilli, cholera, tetanus, botulism, anthrax, plague, leptospirosis, and Lyme disease bacteria.

Some examples of pathogenic fungi causing infections treatable by methods of the disclosure include *Candida (albicans, krusei, glabrata, tropicalis,* etc.), *Cryptococcus neoformans, Aspergillus (fumigatus, niger,* etc.), Genus *Mucorales (mucor, absidia, rhizophus), Sporothrix schenkii, Blastomyces dermatitidis, Paracoccidioides brasiliensis, Coccidioides immitis* and *Histoplasma capsulatum*.

Some examples of pathogenic parasites causing infections treatable by methods of the disclosure include *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi,* and *Nippostrongylus brasiliensis*.

In all of the above methods, PD-L1 blockade can be combined with other forms of immunotherapy such as cytokine treatment (e.g., interferons, agents targeting VEGF activity or VEGF-receptors, GM-CSF, G-CSF, IL-2), or bispecific antibody therapy, which provides for enhanced presentation of tumor antigens (see, e.g., Holliger, *Proc. Natl. Acad. Sci. USA*, 90:6444-6448 (1993); Poljak, *Structure*, 2:1121-1123 (1994)).

Autoimmune Reactions

The macrocyclic peptides may provoke and amplify autoimmune responses. Indeed, induction of anti-tumor responses using tumor cell and peptide vaccines reveals that many anti-tumor responses involve anti-self reactivities (depigmentation observed in anti-CTLA-4+GM-CSF-modified B 16 melanoma in van Elsas et al., supra; depigmentation in Trp-2 vaccinated mice (Overwijk, W. et al., *Proc. Natl. Acad. Sci. USA*, 96:2982-2987 (1999)); autoimmune prostatitis evoked by TRAMP tumor cell vaccines (Hurwitz, A., supra (2000)), melanoma peptide antigen vaccination and vitiligo observed in human clinical trials (Rosenberg, S. A. et al., *J. Immunother. Emphasis Tumor Immunol.*, 19(1):81-84 (1996)).

Therefore, it is possible to consider using anti-PD-L1 blockade in conjunction with various self proteins in order to devise vaccination protocols to efficiently generate immune responses against these self proteins for disease treatment. For example, Alzheimer's disease involves inappropriate accumulation of A.beta. peptide in amyloid deposits in the brain; antibody responses against amyloid are able to clear these amyloid deposits (Schenk et al., *Nature*, 400:173-177 (1999)).

Other self proteins may also be used as targets such as IgE for the treatment of allergy and asthma, and TNF.alpha. for rheumatoid arthritis. Finally, antibody responses to various hormones may be induced by the use of the macrocycles disclosed herein. Neutralizing antibody responses to reproductive hormones may be used for contraception. Neutralizing antibody response to hormones and other soluble factors that are required for the growth of particular tumors may also be considered as possible vaccination targets.

Analogous methods as described above for the use of anti-PD-L1 macrocycles can be used for induction of therapeutic autoimmune responses to treat patients having an inappropriate accumulation of other self-antigens, such as amyloid deposits, including A.beta. in Alzheimer's disease, cytokines such as TNF.alpha., and IgE.

Vaccines

The macrocyclic peptides may be used to stimulate antigen-specific immune responses by coadministration of an anti-PD-1 macrocycle with an antigen of interest (e.g., a vaccine). Accordingly, in another aspect the disclosure provides a method of enhancing an immune response to an antigen in a subject, comprising administering to the subject: (i) the antigen; and (ii) an anti-PD-1 macrocycle, or antigen-binding portion thereof, such that an immune response to the antigen in the subject is enhanced. The antigen can be, for example, a tumor antigen, a viral antigen, a bacterial antigen or an antigen from a pathogen. Non-limiting examples of such antigens include those discussed in the sections above, such as the tumor antigens (or tumor vaccines) discussed above, or antigens from the viruses, bacteria or other pathogens described above.

Suitable routes of administering the compositions (e.g., macrocyclic peptides, multispecific and bispecific molecules and immunoconjugates) of the disclosure in vivo and in vitro are well known in the art and can be selected by those of ordinary skill. For example, the compositions can be administered by injection (e.g., intravenous or subcutaneous). Suitable dosages of the molecules used will depend on the age and weight of the subject and the concentration and/or formulation of the composition.

As previously described the macrocyclic peptides of the disclosure can be co-administered with one or other more therapeutic agents, e.g., a cytotoxic agent, a radiotoxic agent or an immunosuppressive agent. The peptide can be linked to the agent (as an immunocomplex) or can be administered separate from the agent. In the latter case (separate administration), the peptide can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, decarbazine and cyclophosphamide hydroxyurea which, by themselves, are only effective at levels which are toxic or subtoxic to a patient. Cisplatin is intravenously administered as a 100 mg/dose once every four weeks and adriamycin is intravenously administered as a 60-75 mg/ml dose once every 21 days. Co-administration of the macrocyclic peptides, or antigen binding fragments thereof, of the present disclosure with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the peptides.

Also within the scope of the present disclosure are kits comprising the compositions of the disclosure (e.g., macrocyclic peptides, bispecific or multispecific molecules, or immunoconjugates) and instructions for use. The kit can further contain at least one additional reagent, or one or more additional macrocyclic peptides of the disclosure (e.g., a human antibody having a complementary activity which binds to an epitope in PD-L1 antigen distinct from the macrocycle). Kits typically include a label indicating the intended use of the contents of the kit. The term label includes any writing, or recorded material supplied on or with the kit, or which otherwise accompanies the kit.

Combination Therapy

The combination of the macrocyclic peptides of the present disclosure with another PD-L1 antagonist and/or CTLA-4 antagonist is useful for enhancement of an immune response against a hyperproliferative disease by blockade of PD-L1 and CTLA-4. For example, these molecules can be administered to cells in culture, in vitro or ex vivo, or to human subjects, e.g., in vivo, to enhance immunity in a variety of situations. Accordingly, in one aspect, the disclosure provides a method of modifying an immune response in a subject comprising administering to the subject an antibody combination, or a combination of antigen-binding portions thereof, of the disclosure such that the immune response in the subject is modified. Preferably, the response is enhanced, stimulated or up-regulated. In another embodiment, the instant disclosure provides a method of altering adverse events associated with treatment of a hyperproliferative disease with an immunostimulatory therapeutic agent, comprising administering a macrocyclic peptide of the present disclosure and a subtherapeutic dose of anti-CTLA-4 antibody to a subject.

Blockade of PD-L1 and CTLA-4 by macrocyclic peptides can enhance the immune response to cancerous cells in the patient. Cancers whose growth may be inhibited using the macrocyclic peptides of the instant disclosure include cancers typically responsive to immunotherapy. Representative examples of cancers for treatment with the combination therapy of the instant disclosure include melanoma (e.g., metastatic malignant melanoma), renal cancer, prostate cancer, breast cancer, colon cancer and lung cancer. Examples of other cancers that may be treated using the methods of the instant disclosure include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present disclosure is also useful for treatment of metastatic cancers.

In certain embodiments, the combination of therapeutic agents containing at least one macrocyclic peptide discussed herein may be administered concurrently as a single composition in a pharmaceutically acceptable carrier, or concurrently as separate compositions wherein each agent can be administered sequentially. For example, an anti-CTLA-4 antibody and a macrocyclic peptide of the present disclosure can be administered sequentially, such as anti-CTLA-4 being administered first and the macrocyclic peptide second, or the macrocyclic peptide being administered first and anti-CTLA-4 second. Furthermore, if more than one dose of the combination therapy is administered sequentially, the order of the sequential administration can be reversed or kept in the same order at each time point of administration, sequential administrations may be combined with concurrent administrations, or any combination thereof. For example, the first administration of a combination anti-CTLA-4 antibody and the macrocyclic peptide may be concurrent, the second administration may be sequential with anti-CTLA-4 first and the macrocyclic peptide second, and the third administration may be sequential with the macrocyclic peptide first and anti-CTLA-4 second, etc. Another representative dosing scheme may involve a first administration that is sequential with the macrocyclic peptide first and anti-CTLA-4 second, and subsequent administrations may be concurrent.

Optionally, the combination of the macrocyclic peptide and anti-CTLA-4 agent can be further combined with an immunogenic agent, such as cancerous cells, purified tumor antigens (including recombinant proteins, peptides, and carbohydrate molecules), cells, and cells transfected with genes encoding immune stimulating cytokines (He et al., *J. Immunol.*, 173:4919-4928 (2004)). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF (discussed further below).

A combined PD-L1 macrocyclic peptide and CTLA-4 blockade can be further combined with a vaccination protocol. Many experimental strategies for vaccination against tumors have been devised (see Rosenberg, S., Development of Cancer Vaccines, ASCO Educational Book Spring: 60-62 (2000); Logothetis, C., ASCO Educational Book Spring: 300-302 (2000); Khayat, D., ASCO Educational Book Spring: 414-428 (2000); Foon, K., ASCO Educational Book Spring: 730-738 (2000); see also Restifo et al., Cancer Vaccines, Chapter 61, pp. 3023-3043 in DeVita et al., eds., *Cancer: Principles and Practice of Oncology*, Fifth Edition (1997)). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al., *Proc. Natl. Acad. Sci. USA*, 90:3539-3543 (1993)).

The study of gene expression and large scale gene expression patterns in various tumors has led to the definition of so called tumor specific antigens (Rosenberg, *Immunity*, 10:281-287 (1999)). In many cases, these tumor specific antigens are differentiation antigens expressed in the tumors and in the cell from which the tumor arose, for example melanocyte antigens gp100, MAGE antigens, and Trp-2. More importantly, many of these antigens can be shown to be the targets of tumor specific T cells found in the host. In certain embodiments, a combined PD-L1 macrocyclic peptide and CTLA-4 blockade using the antibody compositions described herein may be used in conjunction with a collection of recombinant proteins and/or peptides expressed in a tumor in order to generate an immune response to these proteins. These proteins are normally viewed by the immune system as self-antigens and are, therefore, tolerant to them. The tumor antigen may also include the protein telomerase, which is required for the synthesis of telomeres of chromosomes and which is expressed in more than 85% of human cancers and in only a limited number of somatic tissues (Kim et al., *Science*, 266:2011-2013 (1994)). (These somatic tissues may be protected from immune attack by various means). Tumor antigen may also be "neo-antigens" expressed in cancer cells because of somatic mutations that alter protein sequence or create fusion proteins between two unrelated sequences (i.e., bcr-abl in the Philadelphia chromosome), or idiotype from B cell tumors.

Other tumor vaccines may include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which may be used in conjunction with PD-L1 macrocyclic peptide blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot et al., *Science*, 269:1585-1588 (1995); Tamura et al., *Science*, 278:117-120 (1997)).

Dendritic cells (DC) are potent antigen presenting cells that can be used to prime antigen-specific responses. DC's can be produced ex vivo and loaded with various protein and peptide antigens as well as tumor cell extracts (Nestle et al., *Nat. Med.*, 4:328-332 (1998)). DCs may also be transduced by genetic means to express these tumor antigens as well. DCs have also been fused directly to tumor cells for the purposes of immunization (Kugler et al., *Nat. Med.*, 6:332-336 (2000)). As a method of vaccination, DC immunization may be effectively further combined with a combined anti-PD-L1 macrocyclic peptide and CTLA-4 blockade to activate more potent anti-tumor responses.

A combined anti-PD-L1 macrocyclic peptide and CTLA-4 blockade may also be further combined with standard cancer treatments. For example, a combined macrocyclic peptide and CTLA-4 blockade may be effectively combined with chemotherapeutic regimes. In these instances, as is observed with the combination of a macrocyclic peptide and anti-CTLA-4 agent, it may be possible to reduce the dose of other chemotherapeutic reagent administered with the combination of the instant disclosure (Mokyr et al., *Cancer Res.*, 58:5301-5304 (1998)). An example of such a combination is a combination of a macrocyclic peptide and anti-CTLA-4 agent further in combination with decarbazine for the treatment of melanoma. Another example is a combination of a macrocyclic peptide and anti-CTLA-4 agent further in combination with interleukin-2 (IL-2) for the treatment of melanoma. The scientific rationale behind the combined use of PD-L1 macrocyclic peptide and CTLA-4 blockade with chemotherapy is that cell death, which is a consequence of the cytotoxic action of most chemotherapeutic compounds, should result in increased levels of tumor antigen in the antigen presentation pathway. Other combination therapies that may result in synergy with a combined anti-PD-L1 macrocyclic peptide and CTLA-4 blockade through cell death include radiation, surgery, or hormone deprivation. Each of these protocols creates a source of tumor antigen in the host. Angiogenesis inhibitors may also be combined with a combined PD-L1 and CTLA-4 blockade. Inhibition of angiogenesis leads to tumor cell death, which may also be a source of tumor antigen to be fed into host antigen presentation pathways.

A combination of PD-L1 and CTLA-4 blocking agents can also be used in combination with bispecific macrocyclic peptides that target Fc.alpha. or Fc.gamma. receptor-expressing effector cells to tumor cells (see, e.g., U.S. Pat. Nos. 5,922,845 and 5,837,243). Bispecific macrocyclic peptides can be used to target two separate antigens. For example anti-Fc receptor/anti tumor antigen (e.g., Her-2/neu) bispecific macrocyclic peptides have been used to target macrophages to sites of tumor. This targeting may more effectively activate tumor specific responses. The T cell arm of these responses would be augmented by the use of a combined PD-1 and CTLA-4 blockade. Alternatively, antigen may be delivered directly to DCs by the use of bispecific macrocyclic peptides which bind to tumor antigen and a dendritic cell specific cell surface marker.

In another example, a combination of a macrocyclic peptide and anti-CTLA-4 agent can be used in conjunction with anti-neoplastic macrocyclic agents, such as RITUXAN® (rituximab), HERCEPTIN® (trastuzumab), BEXXAR® (tositumomab), ZEVALIN® (ibritumomab), CAMPATH® (alemtuzumab), Lymphocide (eprtuzumab), AVASTIN® (bevacizumab), and TARCEVA® (erlotinib), and the like. By way of example and not wishing to be bound by theory, treatment with an anti-cancer antibody or an anti-cancer antibody conjugated to a toxin can lead to cancer cell death (e.g., tumor cells) which would potentiate an immune response mediated by CTLA-4 or PD-L1. In an exemplary embodiment, a treatment of a hyperproliferative disease (e.g., a cancer tumor) may include an anti-cancer antibody in combination with a macrocyclic peptide and anti-CTLA-4 agents, concurrently or sequentially or any combination thereof, which may potentiate an anti-tumor immune responses by the host.

Tumors evade host immune surveillance by a large variety of mechanisms. Many of these mechanisms may be overcome by the inactivation of proteins, which are expressed by the tumors and which are immunosuppressive. These include, among others, TGF-.beta. (Kehrl, J. et al., *J. Exp. Med.*, 163:1037-1050 (1986)), IL-10 (Howard, M. et al., *Immunology Today*, 13:198-200 (1992)), and Fas ligand (Hahne, M. et al., *Science*, 274:1363-1365 (1996)). In another example, antibodies to each of these entities may be further combined with a macrocyclic peptide and anti-CTLA-4 combination to counteract the effects of immunosuppressive agents and favor anti-tumor immune responses by the host.

Other agents that may be used to activate host immune responsiveness can be further used in combination with a macrocyclic peptide of the present disclosure. These include molecules on the surface of dendritic cells that activate DC function and antigen presentation. Anti-CD40 macrocyclic peptides are able to substitute effectively for T cell helper activity (Ridge, J. et al., *Nature*, 393:474-478 (1998)) and can be used in conjunction with the macrocyclic peptides of the present disclosure, either alone or in combination with an anti-CTLA-4 combination (Ito, N. et al., *Immunobiology*, 201(5):527-540 (2000)). Activating macrocyclic peptides to T cell costimulatory molecules, such as OX-40 (Weinberg, A. et al., *Immunol.*, 164:2160-2169 (2000)), 4-1BB (Melero, I. et al., *Nat. Med.*, 3:682-685 (1997), and ICOS (Hutloff, A. et al., *Nature*, 397:262-266 (1999)) may also provide for increased levels of T cell activation.

Bone marrow transplantation is currently being used to treat a variety of tumors of hematopoietic origin. While graft versus host disease is a consequence of this treatment, therapeutic benefit may be obtained from graft vs. tumor responses. A macrocyclic peptide of the present disclosure, either alone or in combination with CTLA-4 blockade, can be used to increase the effectiveness of the donor engrafted tumor specific T cells.

There are also several experimental treatment protocols that involve ex vivo activation and expansion of antigen specific T cells and adoptive transfer of these cells into recipients in order to antigen-specific T cells against tumor (Greenberg, R. et al., *Science*, 285:546-551 (1999)). These methods may also be used to activate T cell responses to infectious agents such as CMV. Ex vivo activation in the presence a macrocyclic peptide of the present disclosure, either alone or in combination with an anti-CTLA-4 antagonist, may be expected to increase the frequency and activity of the adoptively transferred T cells.

In certain embodiments, the present disclosure provides a method for altering an adverse event associated with treatment of a hyperproliferative disease with an immunostimulatory agent, comprising administering a macrocyclic peptide of the present disclosure in combination with a subtherapeutic dose of anti-CTLA-4 antibody to a subject. For example, the methods of the present disclosure provide for a method of reducing the incidence of immunostimulatory therapeutic antibody-induced colitis or diarrhea by administering a non-absorbable steroid to the patient. Because any patient who will receive an immunostimulatory therapeutic antibody is at risk for developing colitis or diarrhea induced by such treatment, this entire patient population is suitable for therapy according to the methods of the present disclosure. Although steroids have been administered to treat inflammatory bowel disease (IBD) and prevent exacerbations of IBD, they have not been used to prevent (decrease the incidence of) IBD in patients who have not been diagnosed with IBD. The significant side effects associated with steroids, even non-absorbable steroids, have discouraged prophylactic use.

In further embodiments, a macrocyclic peptide of the present disclosure, either alone or in combination with CTLA-4 blockade, can be further combined with the use of any non-absorbable steroid. As used herein, a "non-absorbable steroid" is a glucocorticoid that exhibits extensive first pass metabolism such that, following metabolism in the liver, the bioavailability of the steroid is low, i.e., less than about 20%. In one embodiment of the disclosure, the non-absorbable steroid is budesonide. Budesonide is a locally-acting glucocorticosteroid, which is extensively metabolized, primarily by the liver, following oral administration. ENTOCORT® EC (Astra-Zeneca) is a pH- and time-dependent oral formulation of budesonide developed to optimize drug delivery to the ileum and throughout the colon. ENTOCORT® EC is approved in the U.S. for the treatment of mild to moderate Crohn's disease involving the ileum and/or ascending colon. The usual oral dosage of ENTOCORT® EC for the treatment of Crohn's disease is 6 to 9 mg/day. ENTOCORT® EC is released in the intestines before being absorbed and retained in the gut mucosa. Once it passes through the gut mucosa target tissue, ENTOCORT® EC is extensively metabolized by the cytochrome P450 system in the liver to metabolites with negligible glucocorticoid activity. Therefore, the bioavailability is low (about 10%). The low bioavailability of budesonide results in an improved therapeutic ratio compared to other glucocorticoids with less extensive first-pass metabolism. Budesonide results in fewer adverse effects, including less hypothalamic-pituitary suppression, than systemically-acting corticosteroids. However, chronic administration of ENTOCORT® EC can result in systemic glucocorticoid effects such as hypercorticism and adrenal suppression. See *Physicians' Desk Reference Supplement*, 58th Edition, 608-610 (2004).

In still further embodiments, a combination PD-L1 and CTLA-4 blockade (i.e., immunostimulatory therapeutic macrocyclic peptides anti-PD-L1 and anti-CTLA-4) in conjunction with a non-absorbable steroid can be further combined with a salicylate. Salicylates include 5-ASA agents such as, for example: sulfasalazine (AZULFIDINE®, Pharmacia & Upjohn); olsalazine (DIPENTUM®, Pharmacia & UpJohn); balsalazide (COLAZAL®, Salix Pharmaceuticals, Inc.); and mesalamine (ASACOL®, Procter & Gamble Pharmaceuticals; PENTASA®, Shire US; CANASA®, Axcan Scandipharm, Inc.; ROWASA®, Solvay).

Dosage and Formulation

A suitable peptide of Formula I, or more specifically a macrocyclic peptide described herein, can be administered to patients to treat diabetes and other related diseases as the compound alone and or mixed with an acceptable carrier in the form of pharmaceutical formulations. Those skilled in the art of treating diabetes can easily determine the dosage and route of administration of the compound to mammals, including humans, in need of such treatment. The route of administration may include but is not limited to oral, intraoral, rectal, transdermal, buccal, intranasal, pulmonary, subcutaneous, intramuscular, intradermal, sublingual, intracolonic, intraoccular, intravenous, or intestinal administration. The compound is formulated according to the route of administration based on acceptable pharmacy practice (Fingl et al., in *The Pharmacological Basis of Therapeutics*, Chapter 1, p. 1 (1975); *Remington's Pharmaceutical Sciences,* 18th Edition, Mack Publishing Co., Easton, Pa. (1990)).

The pharmaceutically acceptable peptide compositions described herein can be administered in multiple dosage forms such as tablets, capsules (each of which includes sustained release or timed release formulations), pills, powders, granules, elixirs, in situ gels, microspheres, crystalline complexes, liposomes, micro-emulsions, tinctures, suspensions, syrups, aerosol sprays and emulsions. The compositions described herein can also be administered in oral, intravenous (bolus or infusion), intraperitoneal, subcutaneous, transdermally or intramuscular form, all using dosage forms well known to those of ordinary skill in the pharmaceutical arts. The compositions may be administered alone, but generally will be administered with a pharmaceutical carrier selected on the basis of the chosen route of administration and standard pharmaceutical practice.

The dosage regimen for the compositions described herein will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disease state.

By way of general guidance, the daily oral dosage of the active ingredient, when used for the indicated effects, will range between about 0.001 to 1000 mg/kg of body weight, preferably between about 0.01 to 100 mg/kg of body weight per day, and most preferably between about 0.6 to 20 mg/kg/day. Intravenously, the daily dosage of the active ingredient when used for the indicated effects will range between 0.001 ng to 100.0 ng per min/per Kg of body weight during a constant rate infusion. Such constant intravenous infusion can be preferably administered at a rate of 0.01 ng to 50 ng per min per Kg body weight and most preferably at 0.01 ng to 10.0 mg per min per Kg body weight. The compositions described herein may be administered in a single daily dose, or the total daily dosage may be administered in divided doses of two, three, or four times daily. The compositions described herein may also be administered by a depot formulation that will allow sustained release of the drug over a period of days/weeks/months as desired.

The compositions described herein can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compositions are typically administered in a mixture with suitable pharmaceutical diluents, excipients, or carriers (collectively referred to herein as pharmaceutical carriers) suitably selected with respect to the intended form of administration, that is, oral tablets, capsules, elixirs, aerosol sprays generated with or without propellant and syrups, and consistent with conventional pharmaceutical practices.

For instance, for oral administration in the form of a tablet or capsule, the active drug component can be combined with an oral, non-toxic, pharmaceutically acceptable, inert carrier such as but not limited to, lactose, starch, sucrose, glucose, methyl cellulose, magnesium stearate, dicalcium phosphate, calcium sulfate, mannitol, and sorbitol; for oral administration in liquid form, the oral drug components can be combined with any oral, non-toxic, pharmaceutically acceptable inert carrier such as, but not limited to, ethanol, glycerol, and water. Moreover, when desired or necessary, suitable binders, lubricants, disintegrating agents, and coloring agents can also be incorporated into the mixture. Suitable binders include, but not limited to, starch, gelatin, natural sugars such as, but not limited to, glucose or beta-lactose, corn sweeteners, natural and synthetic gums such as acacia, tragacanth, or sodium alginate, carboxymethylcellulose, polyethylene glycol, and waxes. Lubricants used in these dosage forms include sodium oleate, sodium stearate, magnesium stearate, sodium benzoate, sodium acetate, and sodium chloride. Disintegrants include, but are not limited to, starch, methyl cellulose, agar, bentonite, and xanthan gum.

The compositions described herein may also be administered in the form of mixed micellar or liposome delivery systems, such as small unilamellar vesicles, large unilamellar vesicles, and multilamellar vesicles. Liposomes can be formed from a variety of phospholipids, such as cholesterol, stearylamine, or phosphatidylcholines. Permeation enhancers may be added to enhance drug absorption.

Since prodrugs are known to enhance numerous desirable qualities of pharmaceuticals (i.e., solubility, bioavailability, manufacturing, etc.) the compounds described herein may be delivered in prodrug form. Thus, the subject matter described herein is intended to cover prodrugs of the presently claimed compounds, methods of delivering the same, and compositions containing the same.

The compositions described herein may also be coupled with soluble polymers as targetable drug carriers. Such polymers can include polyvinyl-pyrrolidone, pyran copolymer, polyhydroxypropyl-methacrylamide-phenol, polyhydroxyethylaspartamidephenol, or polyethyleneoxide-polylysine substituted with palmitoyl residues. Furthermore, the compositions described herein may be combined with a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 0.01 milligram to about 500 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivative, magnesium stearate, and stearic acid. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solution for parenteral administration preferably contains a water-soluble salt of the active ingredient, suitable stabilizing agents, and if necessary, buffer substances. Antioxidizing agents such as sodium bisulfate, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington: The Science and Practice of Pharmacy*, Nineteenth Edition, Mack Publishing Company (1995), a standard reference text in this field.

Representative useful pharmaceutical dosage forms for administration of the compounds described herein can be illustrated as follows:

Capsules

A large number of unit capsules can be prepared by filling standard two-piece hard gelatin capsules with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit, for example is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

An injectable formulation of a peptide composition described herein may or may not require the use of excipients such as those that have been approved by regulatory bodies. These excipients include, but are not limited to, solvents and co-solvents, solubilizing, emulsifying or thickening agents, chelating agents, anti-oxidants and reducing agents, antimicrobial preservatives, buffers and pH adjusting agents, bulking agents, protectants and tonicity adjustors and special additives. An injectable formulation has to be sterile, pyrogen free and, in the case of solutions, free of particulate matter.

A parenteral composition suitable for administration by injection may be prepared by stirring for example, 1.5% by weight of active ingredient in a pharmaceutically acceptable buffer that may or may not contain a co-solvent or other excipient. The solution should be made isotonic with sodium chloride and sterilized.

Suspension

An aqueous suspension can be prepared for oral and/or parenteral administration so that, for example, each 5 mL contains 100 mg of finely divided active ingredient, 20 mg of sodium carboxymethyl cellulose, 5 mg of sodium benzoate, 1.0 g of sorbitol solution, U.S.P., and 0.025 mL of vanillin or other palatable flavoring.

Biodegradable Microparticles

A sustained-release parenteral composition suitable for administration by injection may be prepared, for example, by dissolving a suitable biodegradable polymer in a solvent, adding to the polymer solution the active agent to be incorporated, and removing the solvent from the matrix thereby forming the matrix of the polymer with the active agent distributed throughout the matrix.

Peptide Synthesis

The macrocyclic peptides of the present disclosure can be produced by methods known in the art, such as they can be synthesized chemically, recombinantly in a cell free system, recombinantly within a cell or can be isolated from a biological source. Chemical synthesis of a macrocyclic peptide of the present disclosure can be carried out using a variety of art recognized methods, including stepwise solid phase synthesis, semi-synthesis through the conformationally-assisted re-ligation of peptide fragments, enzymatic ligation of cloned or synthetic peptide segments, and chemical ligation. A preferred method to synthesize the macrocyclic peptides and analogs thereof described herein is chemical synthesis using various solid-phase techniques such as those described in Chan, W. C. et al., eds., *Fmoc Solid Phase Synthesis*, Oxford University Press, Oxford (2000); Barany, G. et al., The Peptides: Analysis, *Synthesis, Biology*, Vol. 2: "Special Methods in Peptide Synthesis, Part A", pp. 3-284, Gross, E. et al., eds., Academic Press, New York (1980); and in Stewart, J. M. et al., *Solid-Phase Peptide Synthesis*, 2nd Edition, Pierce Chemical Co., Rockford, Ill. (1984). The preferred strategy is based on the Fmoc (9-Fluorenylmethyl methyl-oxycarbonyl) group for temporary protection of the α-amino group, in combination with the tert-butyl group for temporary protection of the amino acid side chains (see for example Atherton, E. et al., "The Fluorenylmethoxycarbonyl Amino Protecting Group", in *The Peptides: Analysis, Synthesis, Biology*, Vol. 9: "Special Methods in Peptide Synthesis, Part C", pp. 1-38, Undenfriend, S. et al., eds., Academic Press, San Diego (1987).

The peptides can be synthesized in a stepwise manner on an insoluble polymer support (also referred to as "resin") starting from the C-terminus of the peptide. A synthesis is begun by appending the C-terminal amino acid of the peptide to the resin through formation of an amide or ester linkage. This allows the eventual release of the resulting peptide as a C-terminal amide or carboxylic acid, respectively.

The C-terminal amino acid and all other amino acids used in the synthesis are required to have their α-amino groups and side chain functionalities (if present) differentially protected such that the α-amino protecting group may be selectively removed during the synthesis. The coupling of an amino acid is performed by activation of its carboxyl group as an active ester and reaction thereof with the unblocked α-amino group of the N-terminal amino acid appended to the resin. The sequence of α-amino group deprotection and coupling is repeated until the entire peptide sequence is assembled. The peptide is then released from the resin with concomitant deprotection of the side chain functionalities, usually in the presence of appropriate scavengers to limit side reactions. The resulting peptide is finally purified by reverse phase HPLC.

The synthesis of the peptidyl-resins required as precursors to the final peptides utilizes commercially available cross-linked polystyrene polymer resins (Novabiochem, San Diego, Calif.; Applied Biosystems, Foster City, Calif.). Preferred solid supports are: 4-(2',4'-dimethoxyphenyl-Fmoc-aminomethyl)-phenoxyacetyl-p-methyl benzhydrylamine resin (Rink amide MBHA resin); 9-Fmoc-amino-xanthen-3-yloxy-Merrifield resin (Sieber amide resin); 4-(9-Fmoc)aminomethyl-3,5-dimethoxyphenoxy)valeryl-aminomethyl-Merrifield resin (PAL resin), for C-terminal carboxamides. Coupling of first and subsequent amino acids can be accomplished using HOBt, 6-Cl-HOBt or HOAt active esters produced from DIC/HOBt, HBTU/HOBt, BOP, PyBOP, or from DIC/6-Cl-HOBt, HCTU, DIC/HOAt or HATU, respectively. Preferred solid supports are: 2-Chlorotrityl chloride resin and 9-Fmoc-amino-xanthen-3-yloxy-Merrifield resin (Sieber amide resin) for protected peptide fragments. Loading of the first amino acid onto the 2-chlorotrityl chloride resin is best achieved by reacting the Fmoc-protected amino acid with the resin in dichloromethane and DIEA. If necessary, a small amount of DMF may be added to facilitate dissolution of the amino acid.

The syntheses of the peptide analogs described herein can be carried out by using a single or multi-channel peptide synthesizer, such as an CEM Liberty Microwave synthesizer, or a Protein Technologies, Inc. Prelude (6 channels) or Symphony (12 channels) synthesizer.

Useful Fmoc amino acids derivatives are shown below. Examples of Orthogonally Protected Amino Acids used in Solid Phase Synthesis

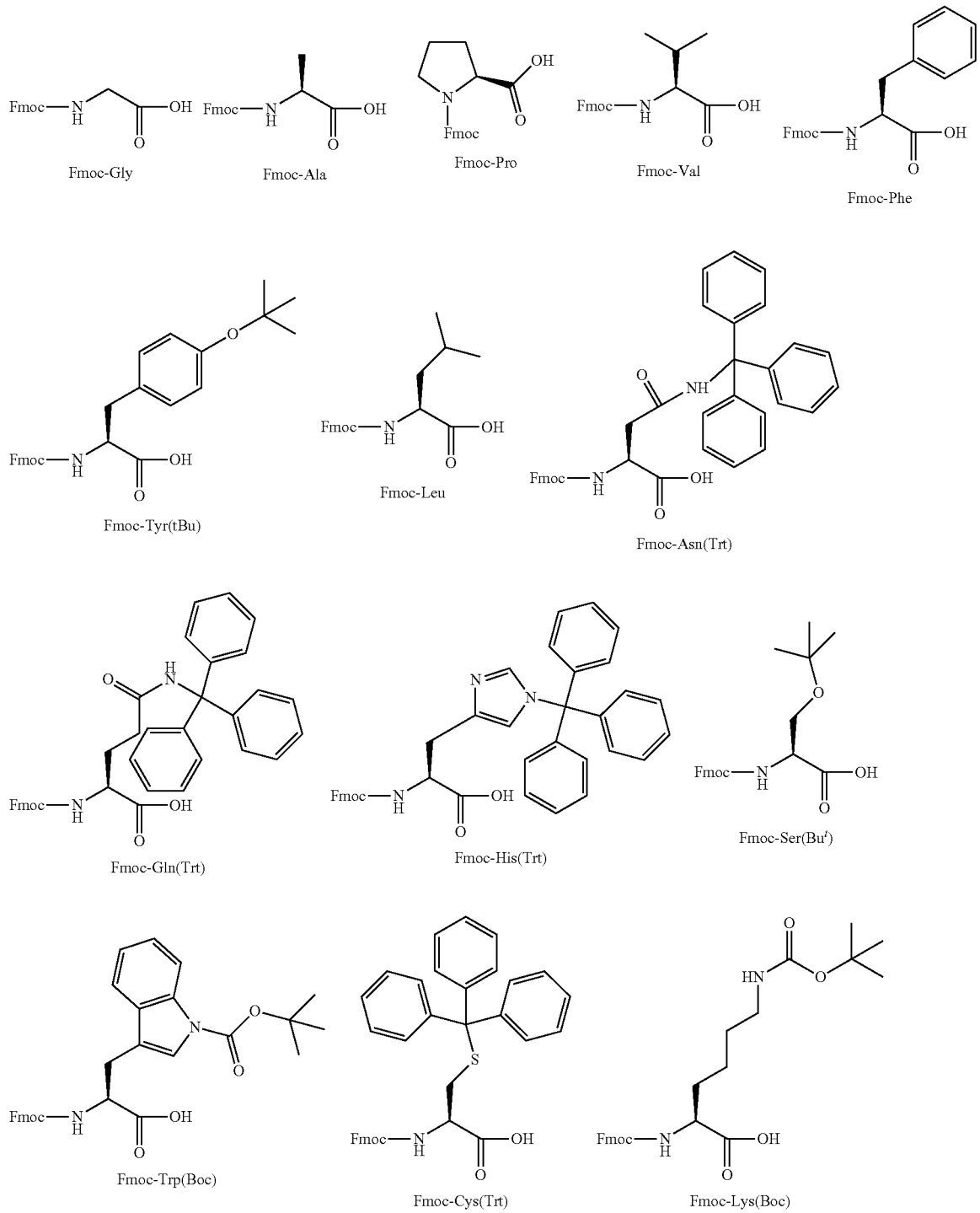

-continued

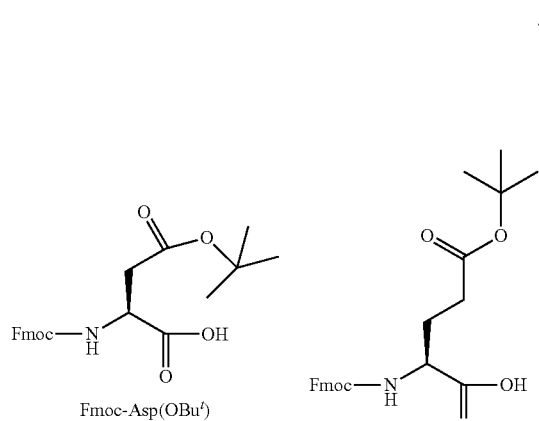

Fmoc-Asp(OBu$^t$)

Fmoc-Glu(OBu$^t$)

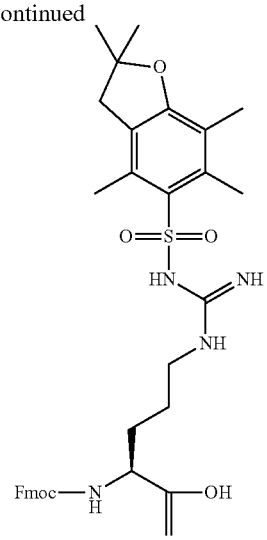

Fmoc-Arg(Pbf)

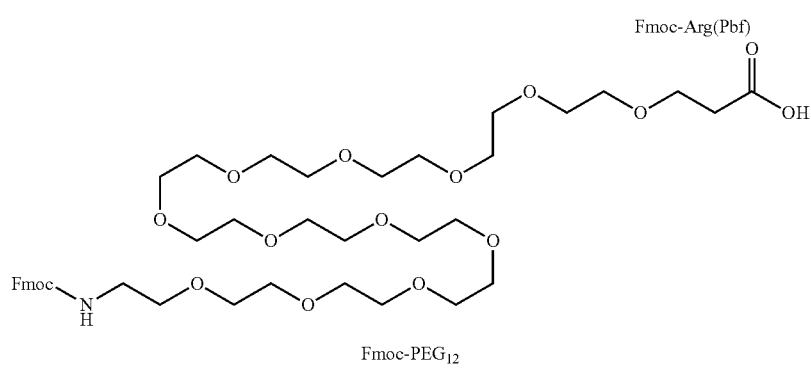

Fmoc-PEG$_{12}$

Fmoc =

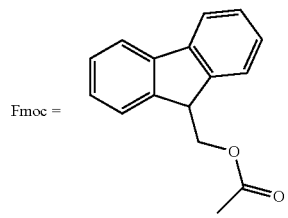

The peptidyl-resin precursors for their respective peptides may be cleaved and deprotected using any standard procedure (see, for example, King, D. S. et al., *Int. J. Peptide Protein Res.*, 36:255-266 (1990)). A desired method is the use of TFA in the presence of water and TIS as scavengers. Typically, the peptidyl-resin is stirred in TFA/water/TIS (94:3:3, v:v:v; 1 mL/100 mg of peptidyl resin) for 2-6 hrs at room temperature. The spent resin is then filtered off and the TFA solution is concentrated or dried under reduced pressure. The resulting crude peptide is either precipitated and washed with Et$_2$O or is redissolved directly into DMSO or 50% aqueous acetic acid for purification by preparative HPLC.

Peptides with the desired purity can be obtained by purification using preparative HPLC, for example, on a Waters Model 4000 or a Shimadzu Model LC-8A liquid chromatograph. The solution of crude peptide is injected into a YMC S5 ODS (20×100 mm) column and eluted with a linear gradient of MeCN in water, both buffered with 0.1% TFA, using a flow rate of 14-20 mL/min with effluent monitoring by UV absorbance at 220 nm. The structures of the purified peptides can be confirmed by electro-spray MS analysis.

List of non-naturally occurring amino acids referred to herein is provided below.

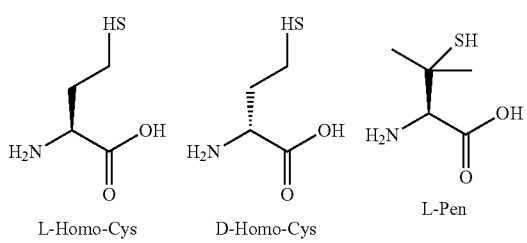

L-Homo-Cys    D-Homo-Cys    L-Pen

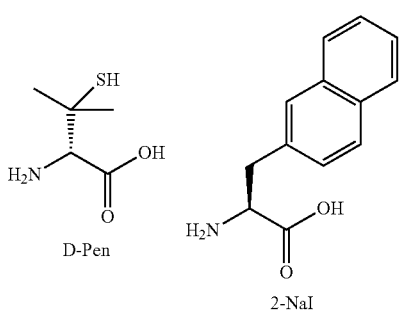

D-Pen

2-Nal

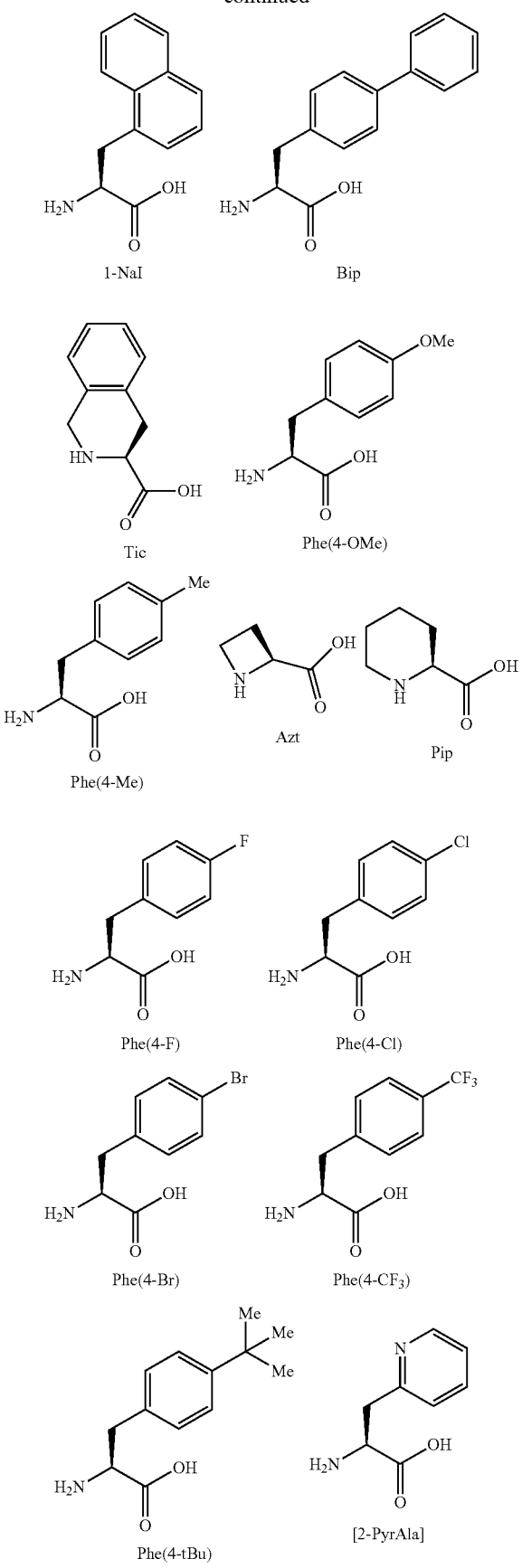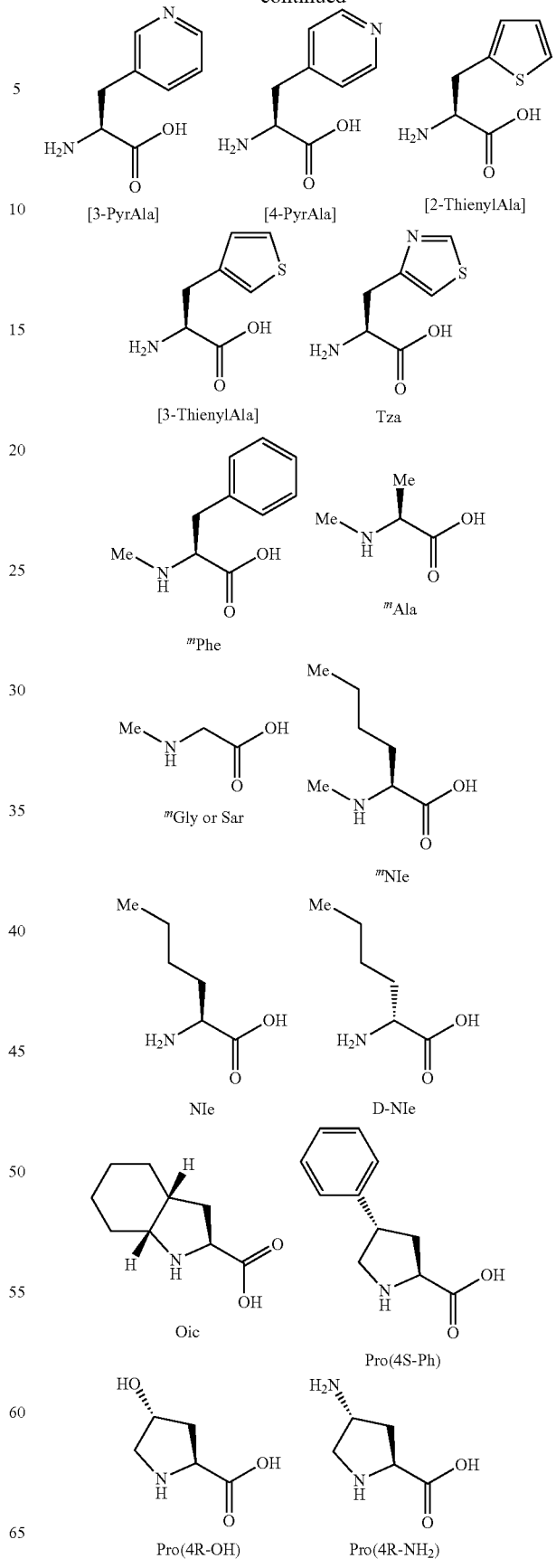

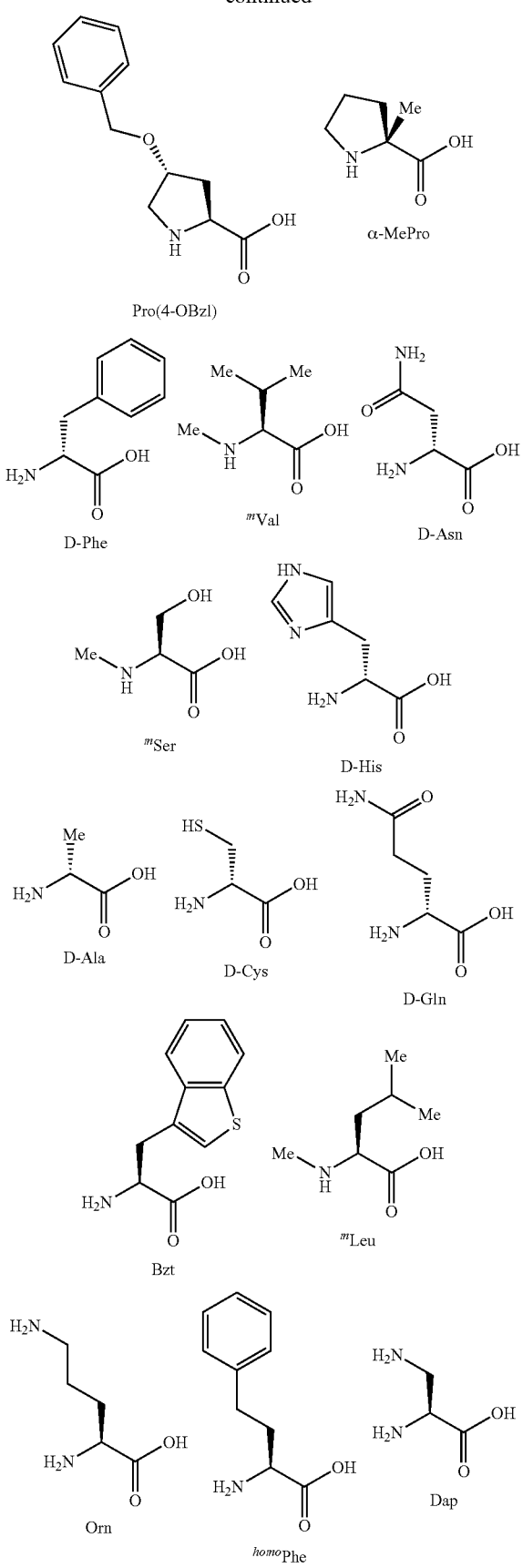
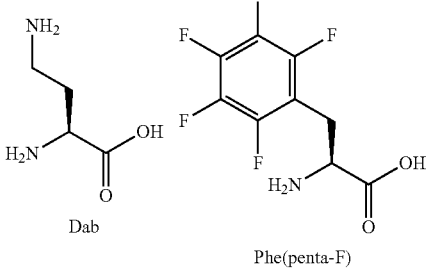

The following abbreviations are employed in the Examples and elsewhere herein:
Ph=phenyl
Bn=benzyl
i-Bu=iso-butyl
i-Pr=iso-propyl
Me=methyl
Et=ethyl
Pr=n-propyl
Bu=n-butyl
t-Bu=tert-butyl
Trt=trityl
TMS=trimethylsilyl
TIS=triisopropylsilane
Et$_2$O=diethyl ether
HOAc or AcOH=acetic acid
MeCN or AcCN=acetonitrile
DMF=N,N-dimethylformamide
EtOAc=ethyl acetate
THF=tetrahydrofuran
TFA=trifluoroacetic acid
TFE=α,α,α-trifluoroethanol
Et$_2$NH=diethylamine
NMM=N-methylmorpholine
NMP=N-methylpyrrolidone
DCM=dichloromethane
TEA=triethylamine
min.=minute(s)
h or hr=hour(s)
L=liter
mL or ml=milliliter
μL=microliter
g=gram(s)
mg=milligram(s)
mol=mole(s)
mmol=millimole(s)
meq=milliequivalent
rt or RT=room temperature
sat or sat'd=saturated
aq.=aqueous
mp=melting point
BOP reagent=benzotriazol-1-yloxy-tris-dimethylamino-phosphonium hexafluorophosphate (Castro's reagent)
PyBOP reagent=benzotriazol-1-yloxy-tripyrrolidino phosphonium hexafluorophosphate
HBTU=2-(1H-Benzotriazol-1-yl)-1,1,3,3-tetramethyl-uronim hexafluorophosphate HATU=O-(7-Azabenzotriazol-1-yl)-1,1,3,3-tetramethyl-uronim hexafluorophosphate
HCTU=2-(6-Chloro-1-H-benzotriazol-1-yl)-1,1,3,3-tetramethyluronium hexafluorophosphate
T3P=2,4,6-tripropyl-1,3,5,2,4,6-trioxatriphosphorinane-2,4,6-trioxide
DMAP=4-(dimethylamino)pyridine
DIEA=diisopropylethylamine
Fmoc or FMOC=fluorenylmethyloxycarbonyl
Boc or BOC=tert-butyloxycarbonyl
HOBT or HOBT.H$_2$O=1-hydroxybenzotriazole hydrate
Cl-HOBt=6-Chloro-benzotriazole
HOAT=1-hydroxy-7-azabenzotriazole
HPLC=high performance liquid chromatography
LC/MS=high performance liquid chromatography/mass spectrometry
MS or Mass Spec=mass spectrometry
NMR=nuclear magnetic resonance
Sc or SC=sub-cutaneous
IP or ip=intra-peritoneal

EXAMPLES

Preparation of Example 1240

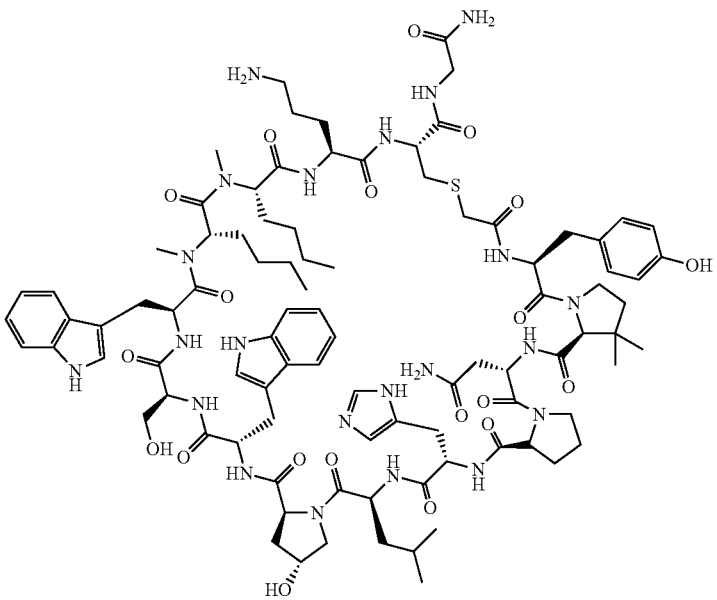

Example 1240 was prepared on Rink Resin following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Manual Coupling procedure A", "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-65% B over 25 minutes, then a 5-minute hold at 100% B; Flow: 20 mL/min. Fractions containing the desired product were combined and dried via centrifugal evaporation. The yield of the product was 11.5 mg, and its estimated purity by LCMS analysis was 100%.

Analysis LCMS Condition D: Retention time=1.45 min; ESI-MS(+) m/z 955.0 (M+2H).
Analysis LCMS Condition E: Retention time=1.39 min; ESI-MS(+) m/z 954.7 (M+2H).
ESI-HRMS(+) m/z: Calculated: 954.4849 (M+2H; Found: 954.4816 (M+2H).

Preparation of Example 1241

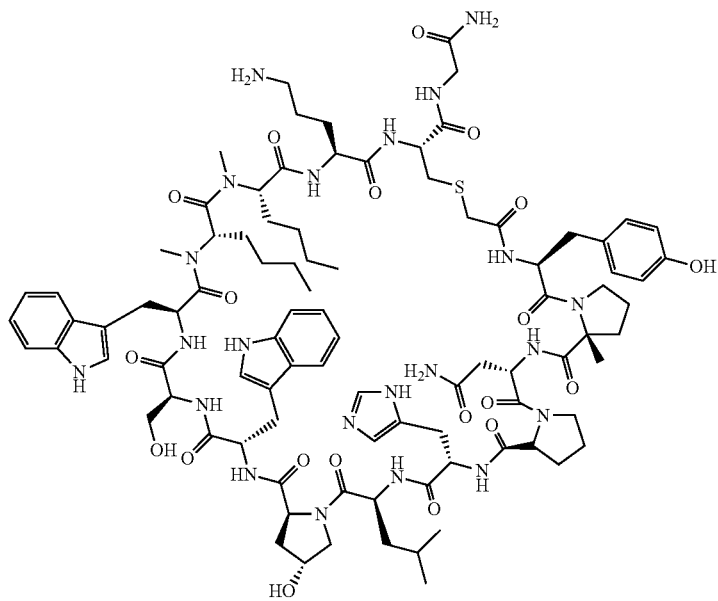

Example 1241 was prepared on Rink Resin following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Manual Coupling procedure A", "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-65% B over 25 minutes, then a 5-minute hold at 100% B; Flow: 20 mL/min. Fractions containing the desired product were combined and dried via centrifugal evaporation. The yield of the product was 11.3 mg, and its estimated purity by LCMS analysis was 92%.

Analysis LCMS Condition D: Retention time=1.37 min; ESI-MS(+) m/z 947.8 (M+2H).

Analysis LCMS Condition E: Retention time=1.30 min; ESI-MS(+) m/z 948.0 (M+2H).

ESI-HRMS(+) m/z: Calculated: 947.4771 (M+2H); Found: 947.4755 (M+2H).

Preparation of Example 1244

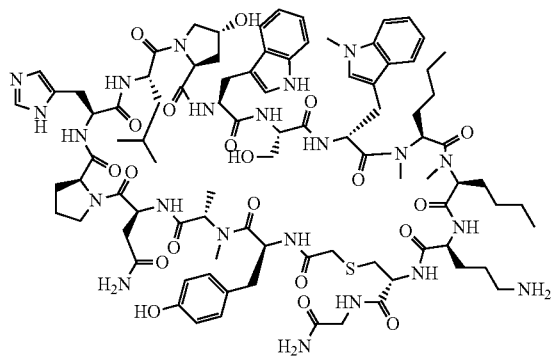 [SMILES: CCCC[C@H]1C(=O)N(C)[C@@H](CCCC)C(=O)N[C@@H](CCCN)C(=O)N[C@H](C(=O)NCC(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@H](Cc2cn(C)c3ccccc23)C(=O)N1C]

Example 1244 was prepared on Rink Resin following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Manual Coupling procedure A", "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-65% B over 25 minutes, then a 5-minute hold at 100% B; Flow: 20 mL/min. Fractions containing the desired product were combined and dried via centrifugal evaporation. The yield of the product was 21.9 mg, and its estimated purity by LCMS analysis was 97%.

Analysis LCMS Condition D: Retention time=1.49 min; ESI-MS(+) m/z 942.0 (M+2H).

Analysis LCMS Condition E: Retention time=1.56 min; ESI-MS(+) m/z 942.0 (M+2H).

ESI-HRMS(+) m/z: Calculated: 941.4771 (M+2H); Found: 941.4757 (M+2H).

Preparation of Example 1245

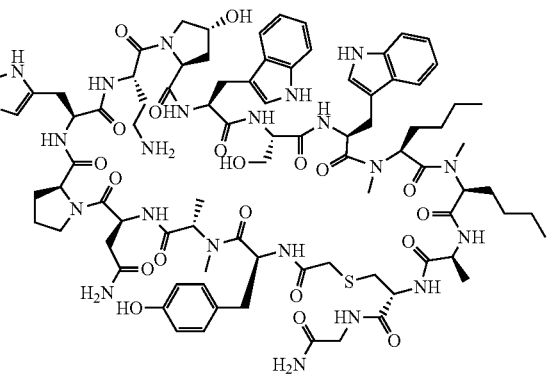

Example 1245 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", Chloroacetic acid coupling procedure B "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-65% B over 25 minutes, then a 5-minute hold at 100% B; Flow: 20 mL/min. Fractions containing the desired product were combined and dried via centrifugal evaporation. The yield of the product was 1.4 mg, and its estimated purity by LCMS analysis was 90%.

Analysis LCMS Condition D: Retention time=1.48 min; ESI-MS(+) m/z 907.3 (M+2H).

Analysis LCMS Condition E: Retention time=1.42 min; ESI-MS(+) m/z 907.3 (M+2H).

Preparation of Example 1246

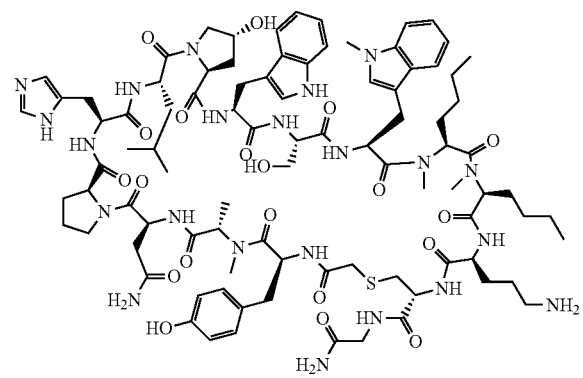 [SMILES: CCCC[C@H]1C(=O)N(C)[C@@H](CCCC)C(=O)N[C@@H](CCCN)C(=O)N[C@H](C(=O)NCC(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2cn(C)c3ccccc23)C(=O)N1C]

Example 1246 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", Chloroacetic acid coupling procedure B "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 minutes, then a 5-minute hold at 100% B; Flow: 20 mL/min. Fractions containing the desired product were combined and dried via centrifugal evaporation. The yield of the product was 15.5 mg, and its estimated purity by LCMS analysis was 94%.

Analysis LCMS Condition D: Retention time=1.57 min; ESI-MS(+) m/z 941.9 (M+2H).

Analysis LCMS Condition E: Retention time=1.51 min; ESI-MS(+) m/z 942.2 (M+2H).

ESI-HRMS(+) m/z: Calculated: 941.4771 (M+2H); Found: 941.4755 (M+2H).

Preparation of Example 1247

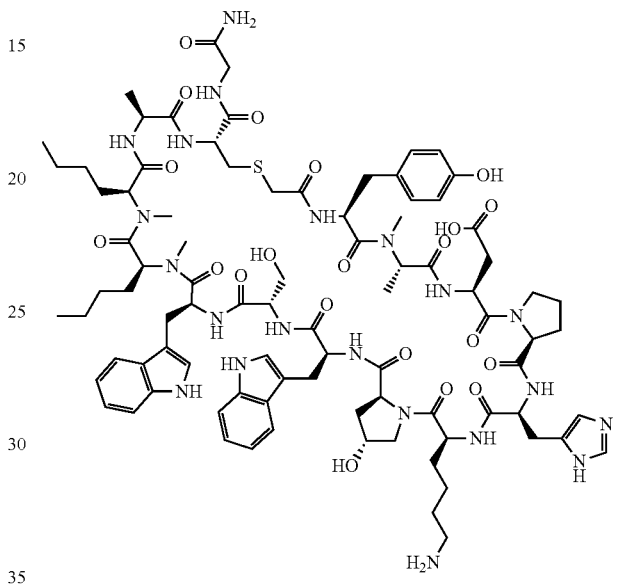

Example 1247 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", Chloroacetic acid coupling procedure B "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-65% B over 25 minutes, then a 5-minute hold at 100% B; Flow: 20 mL/min. Fractions containing the desired product were combined and dried via centrifugal evaporation. The yield of the product was 1.1 mg, and its estimated purity by LCMS analysis was 94%.

Analysis LCMS Condition D: Retention time=1.49 min; ESI-MS(+) m/z 921.1 (M+2H).

Analysis LCMS Condition E: Retention time=1.42 min; ESI-MS(+) m/z 921.4 (M+2H).

ESI-HRMS(+) m/z: Calculated: 920.9456 (M+2H); Found: 920.9436 (M+2H).

Preparation of Example 1248

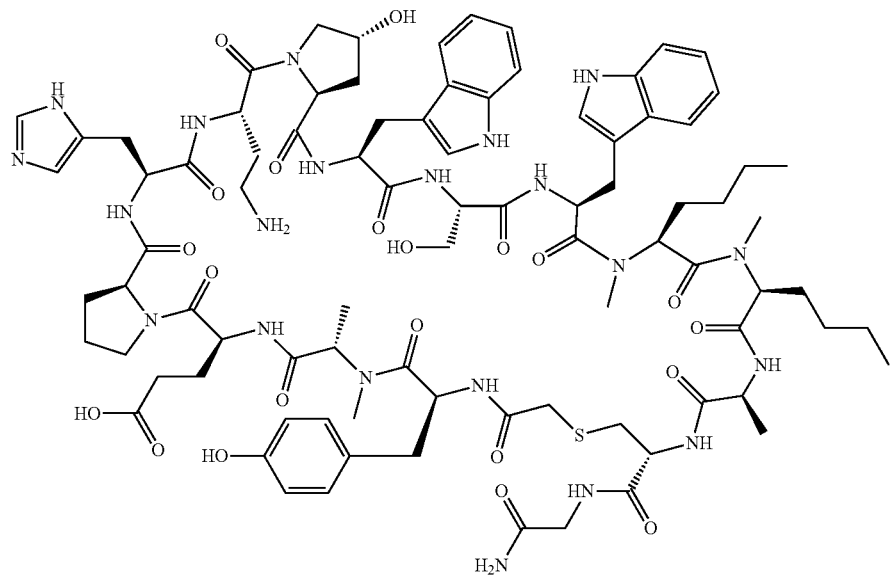 [SMILES: CCCC[C@H]1C(=O)N(C)[C@@H](CCCC)C(=O)N[C@@H](C)C(=O)N[C@H](C(=O)NCC(N)=O)CSCC(=O)N[C@@H](Cc2ccc(O)cc2)C(=O)N(C)[C@@H](C)C(=O)N[C@@H](CCC(=O)O)C(=O)N2CCC[C@H]2C(=O)N[C@@H](Cc2cnc[nH]2)C(=O)N[C@@H](CCN)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

Example 1248 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", Chloroacetic acid coupling procedure B "Global Deprotection Method C", and "Cyclization Method D".

The crude material was purified via preparative LC/MS with the following conditions: Column: Waters XBridge C18, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-65% B over 25 minutes, then a 5-minute hold at 100% B; Flow: 20 mL/min. Fractions containing the desired product were combined and dried via centrifugal evaporation. The yield of the product was 4.7 mg, and its estimated purity by LCMS analysis was 94%.

Analysis LCMS Condition D: Retention time=1.45 min; ESI-MS(+) m/z 914.3 (M+2H).

Analysis LCMS Condition E: Retention time=1.40 min; ESI-MS(+) m/z 914.1 (M+2H).

ESI-HRMS(+) m/z: Calculated: 913.9378 (M+2H); Found: 913.9372 (M+2H).

Preparation of Example 1250

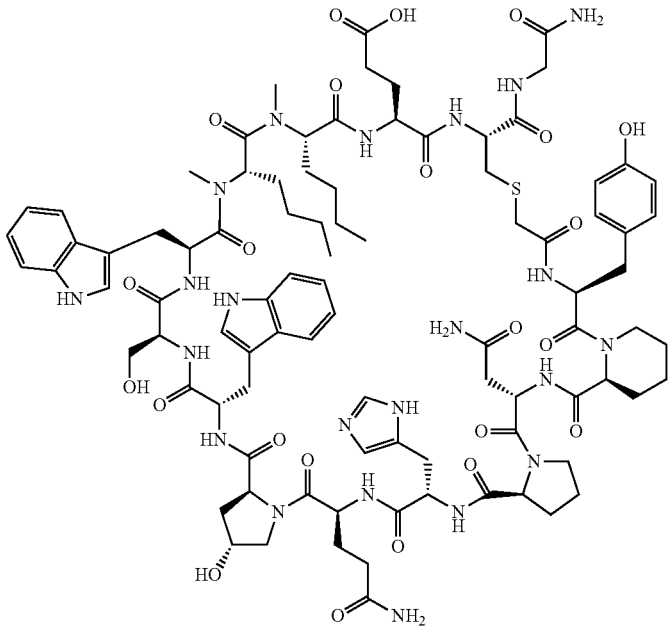 [SMILES: CCCC[C@H]1C(=O)N(C)[C@@H](CCCC)C(=O)N[C@@H](CCC(=O)O)C(=O)N[C@H](C(=O)NCC(N)=O)CSCC(=O)N[C@@H](Cc2ccc(O)cc2)C(=O)N2CCCC[C@H]2C(=O)N[C@@H](CC(N)=O)C(=O)N2CCC[C@H]2C(=O)N[C@@H](Cc2cnc[nH]2)C(=O)N[C@@H](CCC(N)=O)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

Example 1250 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles;

Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 11.4 mg, and its estimated purity by LCMS analysis was 96%.

Analysis LCMS Condition H: retention time=1.46 min.; ESI-MS(+) m/z 962.7 (M+2H).

Analysis LCMS Condition I: retention time=2.10 min.; ESI-MS(+) m/z 962.5 (M+2H).

ESI-HRMS(+) m/z: Calculated: 962.4460 (M+2H); Found: 962.4459 (M+2H).

Preparation of Example 1251

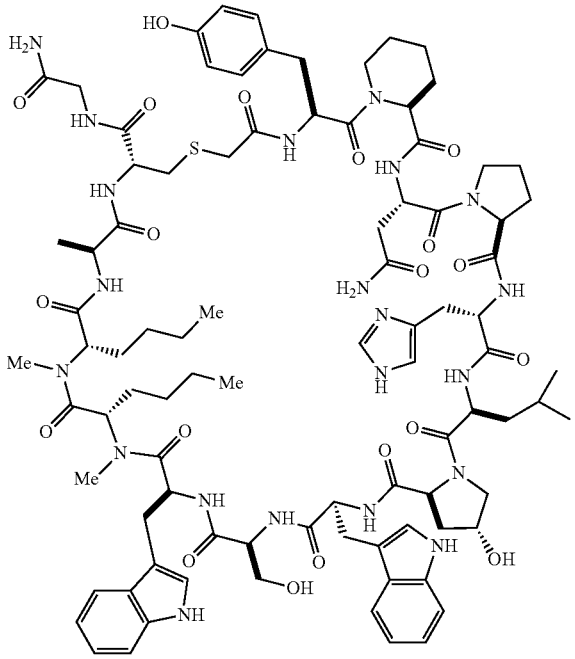

Example 1251 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method D", and "Cyclization Method D".

The crude material was purified via preparative LC/MS with the following conditions: Column: XBridge C18, 19×200 mm, 5-μm particles;

Mobile Phase A: 5:95 methanol:water with 10-mM ammonium acetate; Mobile Phase B: 95:5 methanol:water with 10-mM ammonium acetate; Gradient: 40-85% B over 30 minutes, then a 5-minute hold at 100% B; Flow: 20 mL/min. Fractions containing the desired product were combined and dried via centrifugal evaporation. The yield of the product was 7.0 mg, and its estimated purity by LCMS analysis was 98%.

Analysis LCMS Condition H: retention time=1.68 min.; ESI-MS(+) m/z 926.4 (M+2H).

Analysis LCMS Condition I: retention time=3.10 min.; ESI-MS(+) m/z 926.4 (M+2H).

ESI-HRMS(+) m/z: Calculated: 925.9560 (M+2H); Found: 925.9548 (M+2H).

Preparation of Example 1252

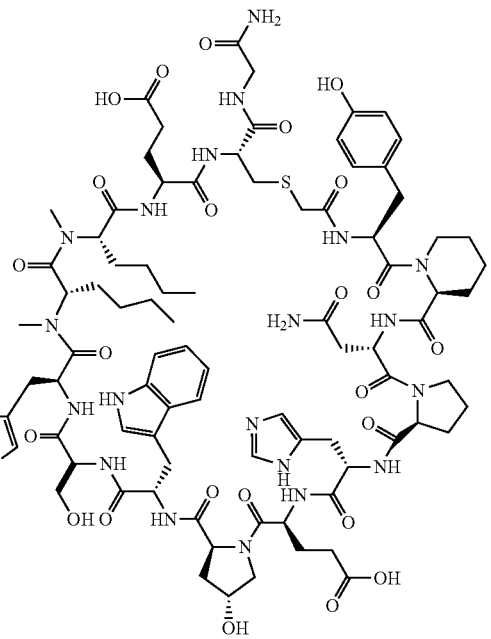

Example 1252 was prepared on Rink resin following the general synthetic sequence described for the preparation of Example 0002, composed of the following general procedures: "CEM Method A: Resin-swelling procedure", "CEM Method A: Single-coupling procedure", "CEM Method A: Double-coupling procedure", "Chloroacetyl chloride coupling procedure A", "Global Deprotection Method F", and "Cyclization Method C".

The crude material was purified via preparative LC/MS with the following conditions: Column: XBridge C18, 19×mm, 5-μm particles;

Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 16.6 mg, and its estimated purity by LCMS analysis was 100%.

Analysis LCMS Condition H: retention time=1.48 min.; ESI-MS(+) m/z 963.1 (M+2H).

Analysis LCMS Condition I: retention time=2.08 min.; ESI-MS(+) m/z 963.5 (M+2H).

ESI-HRMS(+) m/z: Calculated: 962.9380 (M+2H); Found: 962.9370 (M+2H).

Preparation of Example 1255

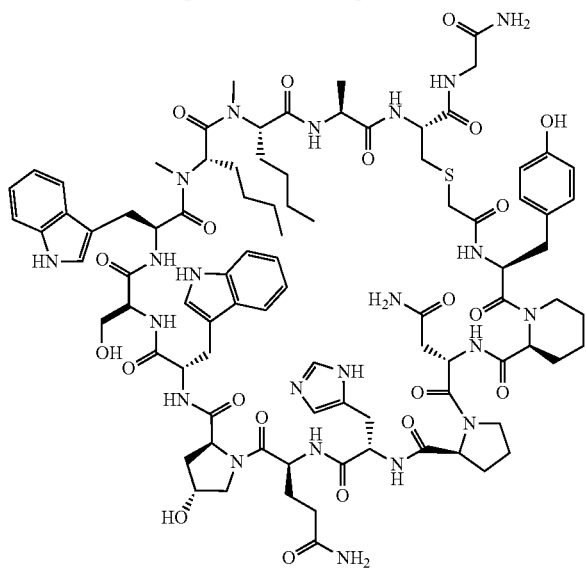 [SMILES: CCCC[C@H]1C(=O)N(C)[C@@H](CCCC)C(=O)N[C@@H](C)C(=O)N[C@H](C(=O)NCC(N)=O)CSCC(=O)N[C@@H](Cc2ccc(O)cc2)C(=O)N2CCCC[C@H]2C(=O)N[C@@H](CC(N)=O)C(=O)N2CCC[C@H]2C(=O)N[C@@H](Cc2cnc[nH]2)C(=O)N[C@@H](CCC(N)=O)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

Example 1255 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method D", and "Cyclization Method D".

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 8.6 mg, and its estimated purity by LCMS analysis was 100%.

Analysis LCMS Condition H: retention time=1.58 min.; ESI-MS(+) m/z 933.6 (M+2H).
Analysis LCMS Condition I: retention time=2.25 min.; ESI-MS(+) m/z 933.5 (M+2H).
ESI-HRMS(+) m/z: Calculated: 933.4419 (M+2H); Found: 933.4432 (M+2H).

Preparation of Example 1256

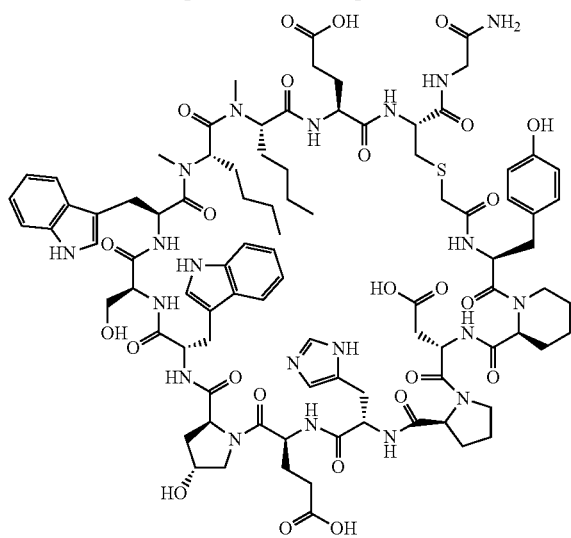 [SMILES: CCCC[C@H]1C(=O)N(C)[C@@H](CCCC)C(=O)N[C@@H](CCC(=O)O)C(=O)N[C@H](C(=O)NCC(N)=O)CSCC(=O)N[C@@H](Cc2ccc(O)cc2)C(=O)N2CCCC[C@H]2C(=O)N[C@@H](CC(=O)O)C(=O)N2CCC[C@H]2C(=O)N[C@@H](Cc2cnc[nH]2)C(=O)N[C@@H](CCC(=O)O)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

Example 1256 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method D", and "Cyclization Method D".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 2.2 mg, and its estimated purity by LCMS analysis was 100%.

Analysis LCMS Condition H: retention time=1.37 min.; ESI-MS(+) m/z 963.6 (M+2H).
Analysis LCMS Condition I: retention time=1.98 min.; ESI-MS(+) m/z 963.6 (M+2H).
ESI-HRMS(+) m/z: Calculated: 963.4300 (M+2H); Found: 963.4295 (M+2H).

Preparation of Example 1257

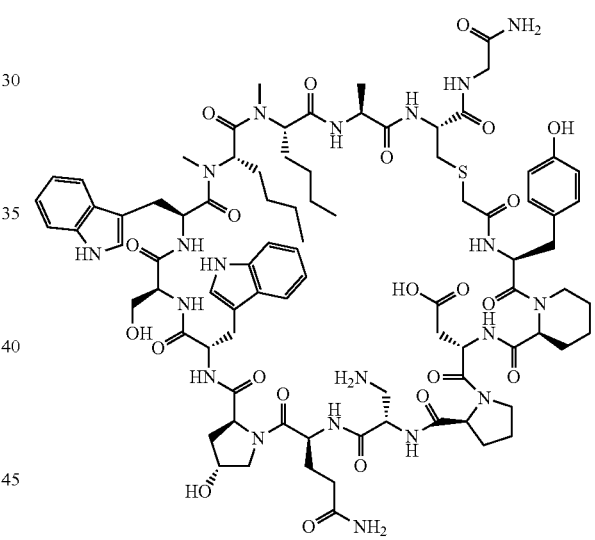

Example 1257 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method D", and "Cyclization Method D".

The crude material was purified via preparative LC/MS with the following conditions: Column: XBridge C18, 19×200 mm, 5-μm particles;
Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 3.6 mg, and its estimated purity by LCMS analysis was 99%.

Analysis LCMS Condition H: retention time=1.60 min.; ESI-MS(+) m/z 908.6 (M+2H).

Analysis LCMS Condition I: retention time=3.12 min.; ESI-MS(+) m/z 908.6 (M+2H).

ESI-HRMS(+) m/z: Calculated: 908.4298 (M+2H); Found: 908.4283 (M+2H).

Preparation of Example 1258

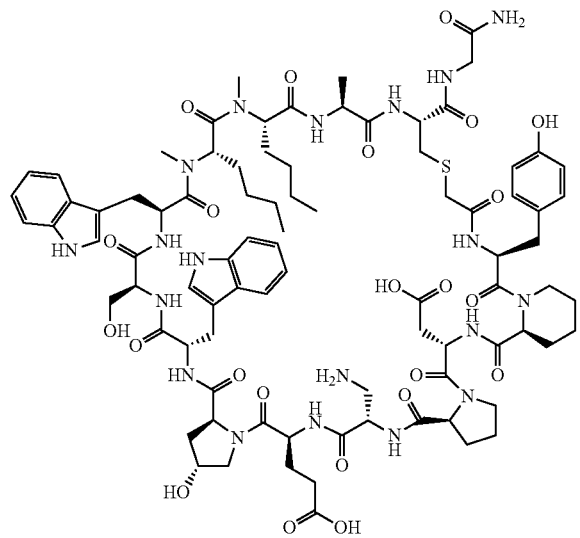 [SMILES: CCCC[C@H]1C(=O)N(C)[C@@H](CCCC)C(=O)N[C@@H](C)C(=O)N[C@H](C(=O)NCC(N)=O)CSCC(=O)N[C@@H](Cc2ccc(O)cc2)C(=O)N2CCCC[C@H]2C(=O)N[C@@H](CC(=O)O)C(=O)N2CCC[C@H]2C(=O)N[C@@H](CN)C(=O)N[C@@H](CCC(=O)O)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

Example 1258 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method D", and "Cyclization Method D".

The crude material was purified via preparative LC/MS with the following conditions: Column: XBridge C18, 19×200 mm, 5-μm particles;

Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The material was further purified via preparative LC/MS with the following conditions:

Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 4.8 mg, and its estimated purity by LCMS analysis was 100%.

Analysis LCMS Condition H: retention time=1.61 min.; ESI-MS(+) m/z 909.0 (M+2H).

Analysis LCMS Condition I: retention time=2.66 min.; ESI-MS(+) m/z 909.6 (M+2H).

ESI-HRMS(+) m/z: Calculated: 908.9218 (M+2H); Found: 908.9206 (M+2H).

Preparation of Example 1259

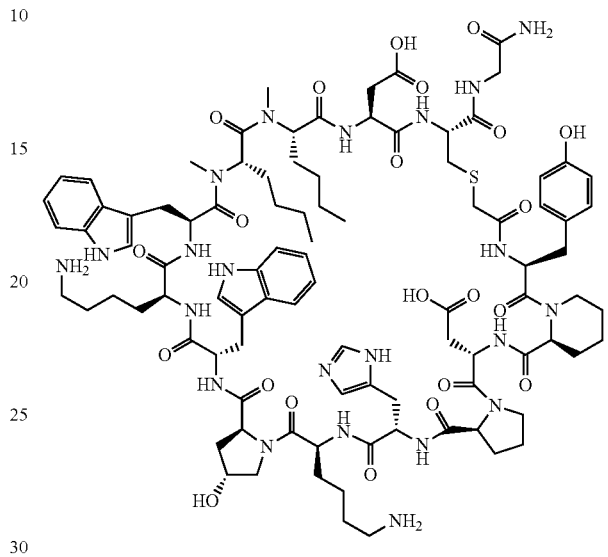

Example 1259 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method D", and "Cyclization Method D".

The crude material was purified via preparative LC/MS with the following conditions: Column: XBridge C18, 19×200 mm, 5-μm particles;

Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 30 minutes, then a 5-minute hold at 100% B; Flow: 20 mL/min. Fractions containing the desired product were combined and dried via centrifugal evaporation. The yield of the product was 2.6 mg, and its estimated purity by LCMS analysis was 100%.

Analysis LCMS Condition H: retention time=1.49 min.; ESI-MS(+) m/z 976.7 (M+2H).

Analysis LCMS Condition I: retention time=2.15 min.; ESI-MS(+) m/z 976.7 (M+2H).

ESI-HRMS(+) m/z: Calculated: 976.4798 (M+2H); Found: 976.4781 (M+2H).

Preparation of Example 1260

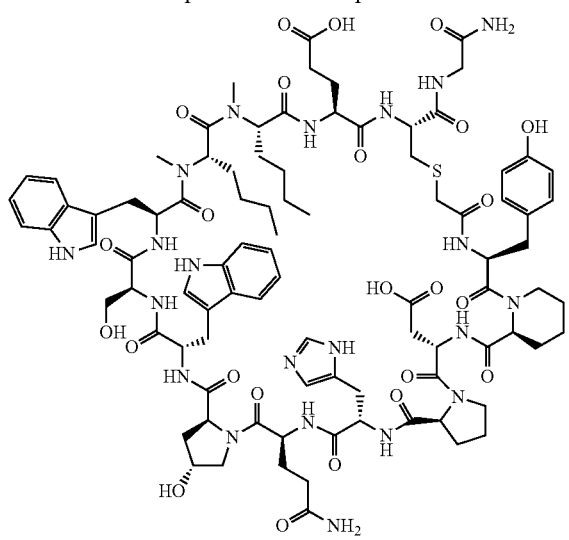

Example 1260 was prepared on Rink resin following the general synthetic sequence described for the preparation of Example 0002, composed of the following general procedures: "CEM Method A: Resin-swelling procedure", "CEM Method A: Single-coupling procedure", "CEM Method A: Double-coupling procedure", "Chloroacetyl chloride coupling procedure A", "Global Deprotection Method F", and "Cyclization Method C".

The crude material was purified via preparative LC/MS with the following conditions: Column: XBridge C18, 19×mm, 5-µm particles;

Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 35.2 mg, and its estimated purity by LCMS analysis was 98%.

Analysis LCMS Condition H: retention time=1.51 min.; ESI-MS(+) m/z 963.2 (M+2H).

Analysis LCMS Condition I: retention time=2.05 min.; ESI-MS(+) m/z 962.9 (M+2H).

ESI-HRMS(+) m/z: Calculated: 962.9380 (M+2H); Found: 962.9367 (M+2H).

Preparation of Example 1261

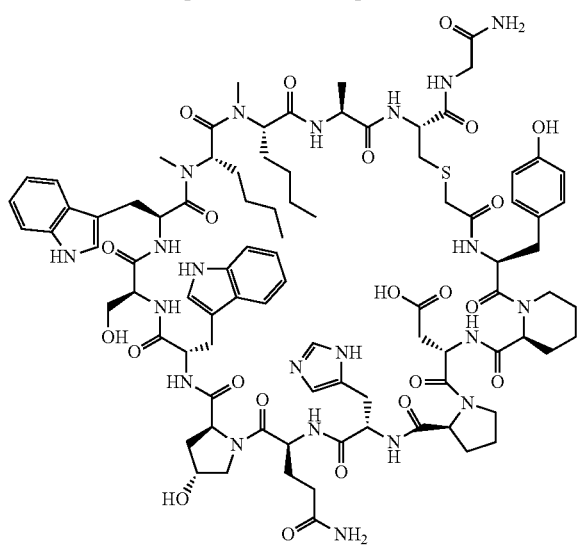 [SMILES: CCCC[C@H]1C(=O)N(C)[C@@H](CCCC)C(=O)N[C@@H](C)C(=O)N[C@H](C(=O)NCC(N)=O)CSCC(=O)N[C@@H](Cc2ccc(O)cc2)C(=O)N2CCCC[C@H]2C(=O)N[C@@H](CC(=O)O)C(=O)N2CCC[C@H]2C(=O)N[C@@H](Cc2cnc[nH]2)C(=O)N[C@@H](CCC(N)=O)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

Example 1261 was prepared on Rink resin following the general synthetic sequence described for the preparation of Example 0002, composed of the following general procedures: "CEM Method A: Resin-swelling procedure", "CEM Method A: Single-coupling procedure", "CEM Method A: Double-coupling procedure", "Chloroacetyl chloride coupling procedure A", "Global Deprotection Method F", and "Cyclization Method C".

The crude material was purified via preparative LC/MS with the following conditions: Column: XBridge C18, 19×mm, 5-µm particles;

Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 20.2 mg, and its estimated purity by LCMS analysis was 96%.

Analysis LCMS Condition H: retention time=1.55 min.; ESI-MS(+) m/z 934.1 (M+2H).

Analysis LCMS Condition I: retention time=3.02 min.; ESI-MS(+) m/z 934.1 (M+2H).

ESI-HRMS(+) m/z: Calculated: 933.9352 (M+2H); Found: 933.9344 (M+2H).

Preparation of Example 1262

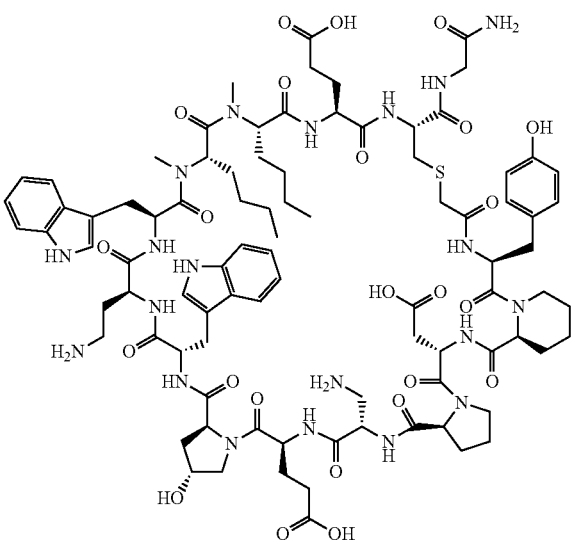 [SMILES: CCCC[C@H]1C(=O)N(C)[C@@H](CCCC)C(=O)N[C@@H](CCC(=O)O)C(=O)N[C@H](C(=O)NCC(N)=O)CSCC(=O)N[C@@H](Cc2ccc(O)cc2)C(=O)N2CCCC[C@H]2C(=O)N[C@@H](CC(=O)O)C(=O)N2CCC[C@H]2C(=O)N[C@@H](CN)C(=O)N[C@@H](CCC(=O)O)C(=O)N2C[C@H](O)C[C@H]2C(=O)N[C@@H](Cc2c[nH]c3ccccc23)C(=O)N[C@@H](CCN)C(=O)N[C@@H](Cc2c[nH]c3ccccc23)C(=O)N1C]

Example 1262 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method D", and "Cyclization Method D".

The crude material was purified via preparative LC/MS with the following conditions: Column: XBridge C18, 19×200 mm, 5-µm particles;

Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-65% B over 30 minutes, then a 5-minute hold at 100% B; Flow: 20 mL/min. Fractions containing the desired product were combined and dried via centrifugal evaporation. The yield of the product was 3.8 mg, and its estimated purity by LCMS analysis was 100%.

Analysis LCMS Condition H: retention time=1.65 min.; ESI-MS(+) m/z 944.8 (M+2H).

Analysis LCMS Condition I: retention time=2.59 min.; ESI-MS(+) m/z 945.0 (M+2H).

ESI-HRMS(+) m/z: Calculated: 944.4404 (M+2H); Found: 944.4388 (M+2H).

Preparation of Example 1272

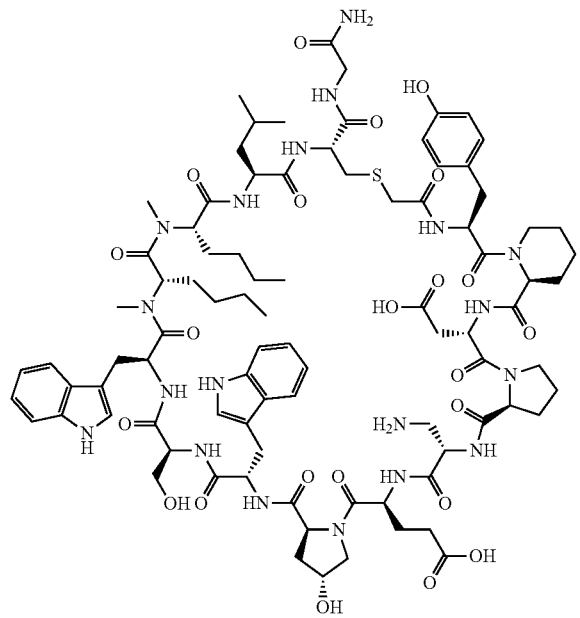 [SMILES: CCCC[C@H]1C(=O)N(C)[C@@H](CCCC)C(=O)N[C@@H](CC(C)C)C(=O)N[C@H](C(=O)NCC(N)=O)CSCC(=O)N[C@@H](Cc2ccc(O)cc2)C(=O)N2CCCC[C@H]2C(=O)N[C@@H](CC(=O)O)C(=O)N2CCC[C@H]2C(=O)N[C@@H](CN)C(=O)N[C@@H](CCC(=O)O)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

Example 1272 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", Chloroacetic acid coupling procedure B "Global Deprotection Method F", and "Cyclization Method D"

The crude material was purified via preparative LC/MS with the following conditions: Column: XBridge C18, 19×200 mm, 5-µm particles;

Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 30.6 mg, and its estimated purity by LCMS analysis was 98%.

Analysis LCMS Condition H: retention time=1.65 min.; ESI-MS(+) m/z 930.4 (M+2H).

Analysis LCMS Condition I: retention time=3.08 min.; ESI-MS(+) m/z 930.4 (M+2H).

ESI-HRMS(+) m/z: Calculated: 929.9453 (M+2H); Found: 929.9429 (M+2H).

Preparation of Example 1273

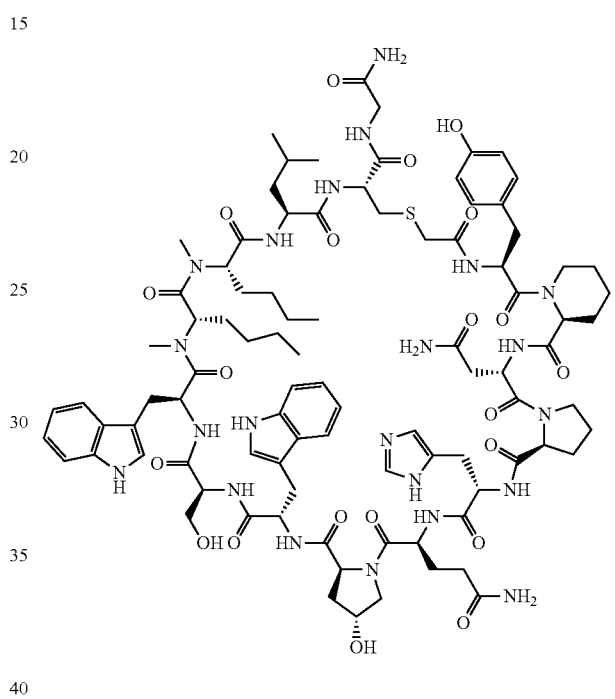

Example 1273 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", Chloroacetic acid coupling procedure B "Global Deprotection Method F", and "Cyclization Method D".

The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 20.5 mg, and its estimated purity by LCMS analysis was 100%.

Analysis LCMS Condition H: retention time=1.66 min.; ESI-MS(+) m/z 954.8 (M+2H).

Analysis LCMS Condition I: retention time=3.14 min.; ESI-MS(+) m/z 954.8 (M+2H).

ESI-HRMS(+) m/z: Calculated: 954.4667 (M+2H); Found: 954.4644 (M+2H).

Preparation of Example 1275

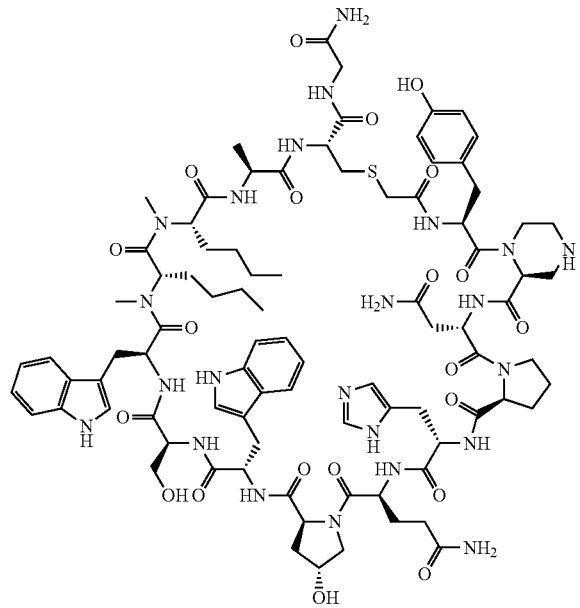 [SMILES: CCCC[C@H]1C(=O)N(C)[C@@H](CCCC)C(=O)N[C@@H](C)C(=O)N[C@H](C(=O)NCC(N)=O)CSCC(=O)N[C@@H](Cc2ccc(O)cc2)C(=O)N2CCNC[C@H]2C(=O)N[C@@H](CC(N)=O)C(=O)N2CCC[C@H]2C(=O)N[C@@H](Cc2cnc[nH]2)C(=O)N[C@@H](CCC(N)=O)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

Example 1275 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 0.4 mg, and its estimated purity by LCMS analysis was 97%.

Analysis LCMS Condition H: retention time=1.48 min.; ESI-MS(+) m/z 934.4 (M+2H).

Analysis LCMS Condition I: retention time=2.97 min.; ESI-MS(+) m/z 934.4 (M+2H).

Preparation of Example 1276

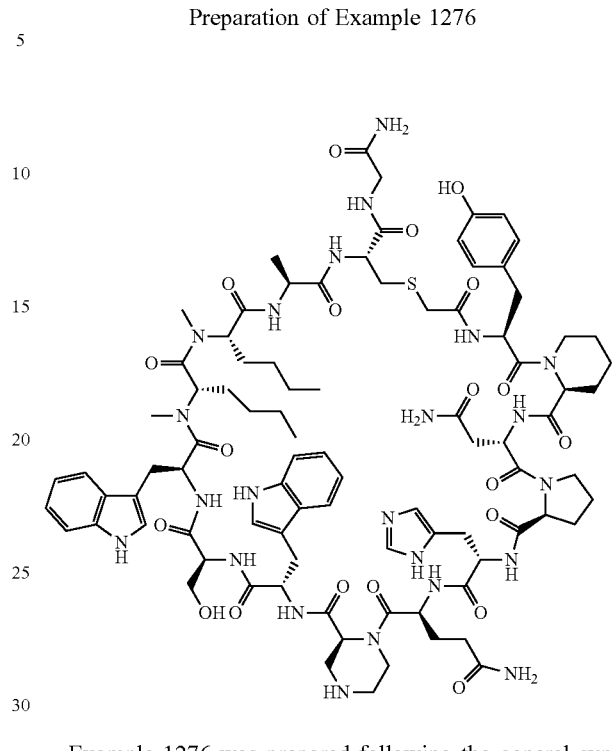

Example 1276 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 10.6 mg, and its estimated purity by LCMS analysis was 97%.

Analysis LCMS Condition H: retention time=1.54 min.; ESI-MS(+) m/z 933.7 (M+2H).

Analysis LCMS Condition I: retention time=3.02 min.; ESI-MS(+) m/z 933.4 (M+2H).

ESI-HRMS(+) m/z: Calculated: 932.9512 (M+2H); Found: 932.9524 (M+2H).

Preparation of Example 1277

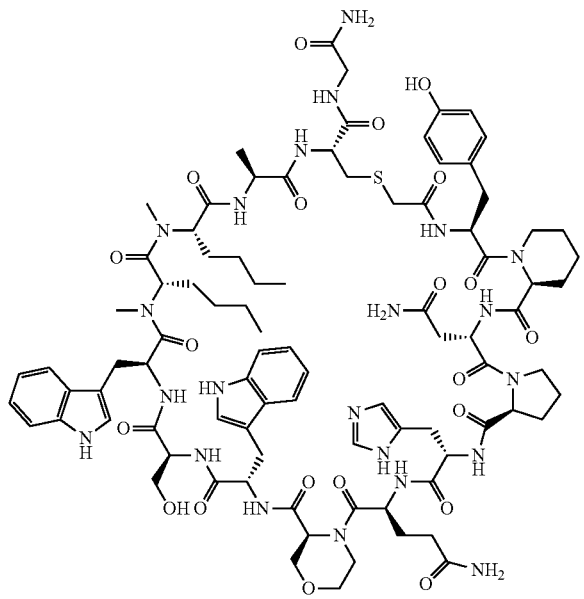 [SMILES: CCCC[C@H]1C(=O)N(C)[C@@H](CCCC)C(=O)N[C@@H](C)C(=O)N[C@H](C(=O)NCC(N)=O)CSCC(=O)N[C@@H](Cc2ccc(O)cc2)C(=O)N2CCCC[C@H]2C(=O)N[C@@H](CC(N)=O)C(=O)N2CCC[C@H]2C(=O)N[C@@H](Cc2cnc[nH]2)C(=O)N[C@@H](CCC(N)=O)C(=O)N2CCOC[C@H]2C(=O)N[C@@H](Cc2c[nH]c3ccccc23)C(=O)N[C@@H](CO)C(=O)N[C@@H](Cc2c[nH]c3ccccc23)C(=O)N1C]

Example 1277 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 7.0 mg, and its estimated purity by LCMS analysis was 100%.

Analysis LCMS Condition H: retention time=1.61 min.; ESI-MS(+) m/z 933.9 (M+2H).

Analysis LCMS Condition I: retention time=3.07 min.; ESI-MS(+) m/z 933.9 (M+2H).

ESI-HRMS(+) m/z: Calculated: 933.4432 (M+2H); Found: 933.4416 (M+2H).

Preparation of Example 1278

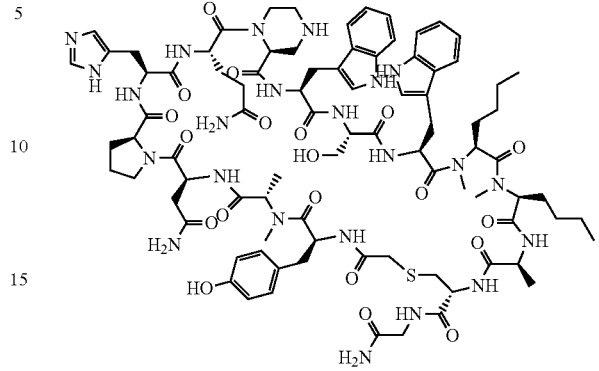

Example 1278 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 3.3 mg, and its estimated purity by LCMS analysis was 99%.

Analysis LCMS Condition H: retention time=1.52 min.; ESI-MS(+) m/z 920.3 (M+2H).

Analysis LCMS Condition I: retention time=2.97 min.; ESI-MS(+) m/z 920.4 (M+2H).

ESI-HRMS(+) m/z: Calculated: 919.9434 (M+2H); Found: 919.9422 (M+2H).

Preparation of Example 1279

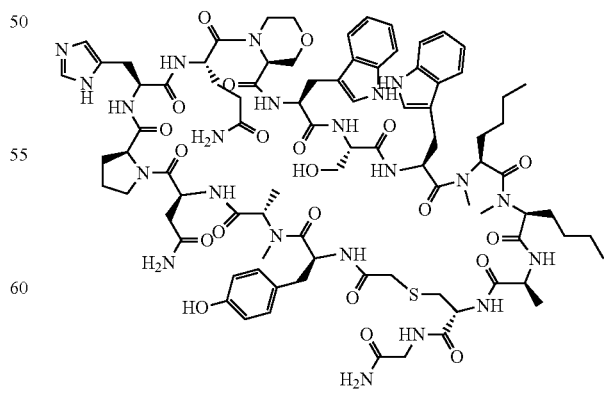

Example 1279 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 9.1 mg, and its estimated purity by LCMS analysis was 99%.

Analysis LCMS Condition H: retention time=1.55 min.; ESI-MS(+) m/z 921.0 (M+2H).

Analysis LCMS Condition I: retention time=2.99 min.; ESI-MS(+) m/z 920.9 (M+2H).

ESI-HRMS(+) m/z: Calculated: 920.4354 (M+2H); Found: 920.4340 (M+2H).

Preparation of Example 1280

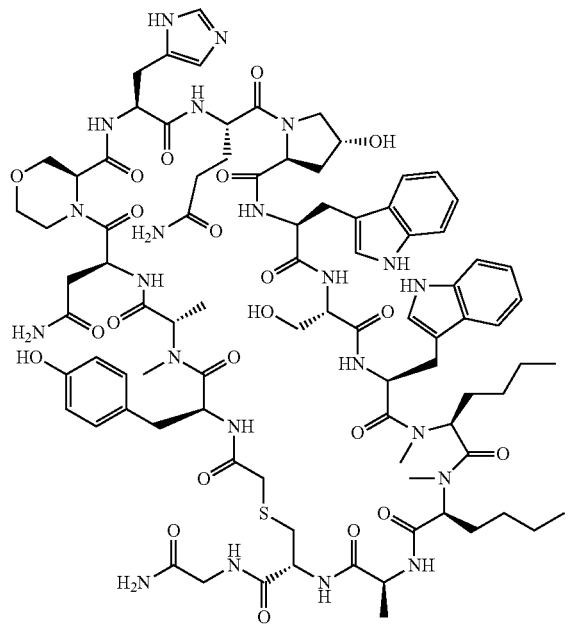 [SMILES: CCCC[C@H]1C(=O)N(C)[C@@H](CCCC)C(=O)N[C@@H](C)C(=O)N[C@H](C(=O)NCC(N)=O)CSCC(=O)N[C@@H](Cc2ccc(O)cc2)C(=O)N(C)[C@@H](C)C(=O)N[C@@H](CC(N)=O)C(=O)N2CCOC[C@H]2C(=O)N[C@@H](Cc2cnc[nH]2)C(=O)N[C@@H](CCC(N)=O)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

Example 1280 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 6.0 mg, and its estimated purity by LCMS analysis was 97%.

Analysis LCMS Condition H: retention time=1.48 min.; ESI-MS(+) m/z 929.0 (M+2H).

Analysis LCMS Condition I: retention time=2.93 min.; ESI-MS(+) m/z 928.9 (M+2H).

ESI-HRMS(+) m/z: Calculated: 928.4329 (M+2H); Found: 928.4324 (M+2H).

Preparation of Example 1281

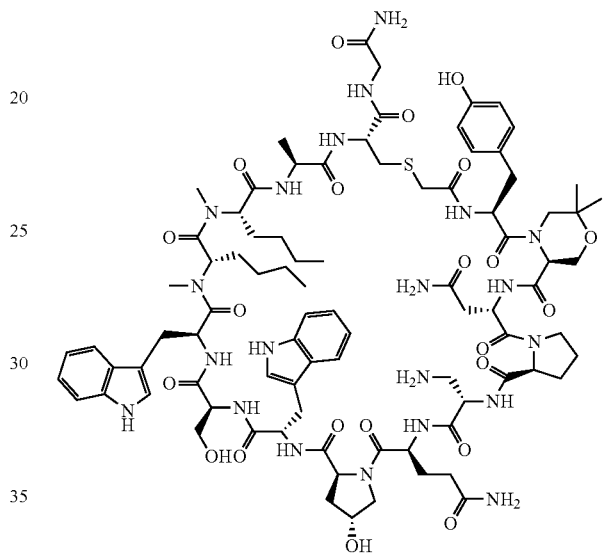

Example 1281 was prepared following the general synthetic sequence described for the preparation of Example 0001, composed of the following general procedures: "Symphony Method B: Resin-swelling procedure", "Symphony Method B: Custom amino acids-coupling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: XBridge C18, 19×250 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 4.9 mg, and its estimated purity by LCMS analysis was 100%.

Analysis LCMS Condition H: retention time=1.81 min.; ESI-MS(+) m/z 923.7 (M+2H).

Analysis LCMS Condition I: retention time=2.63 min.; ESI-MS(+) m/z 924.1 (M+2H).

ESI-HRMS(+) m/z: Calculated: 922.9431 (M+2H); Found: 922.9422 (M+2H).

Preparation of Example 1282

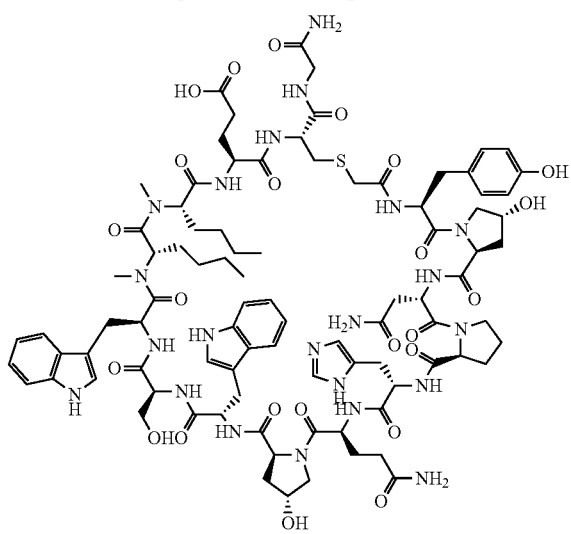 [SMILES: CCCC[C@H]1C(=O)N(C)[C@@H](CCCC)C(=O)N[C@@H](CCC(=O)O)C(=O)N[C@H](C(=O)NCC(N)=O)CSCC(=O)N[C@@H](Cc2ccc(O)cc2)C(=O)N2C[C@H](O)C[C@H]2C(=O)N[C@@H](CC(N)=O)C(=O)N2CCC[C@H]2C(=O)N[C@@H](Cc2cnc[nH]2)C(=O)N[C@@H](CCC(N)=O)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

Example 1282 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 5.6 mg, and its estimated purity by LCMS analysis was 95%.

Analysis LCMS Condition H: retention time=1.51 min.; ESI-MS(+) m/z 964.3 (M+2H).

Analysis LCMS Condition I: retention time=2.27 min.; ESI-MS(+) m/z 964.7 (M+2H).

ESI-HRMS(+) m/z: Calculated: 963.4356 (M+2H); Found: 963.4356 (M+2H).

Preparation of Example 1283

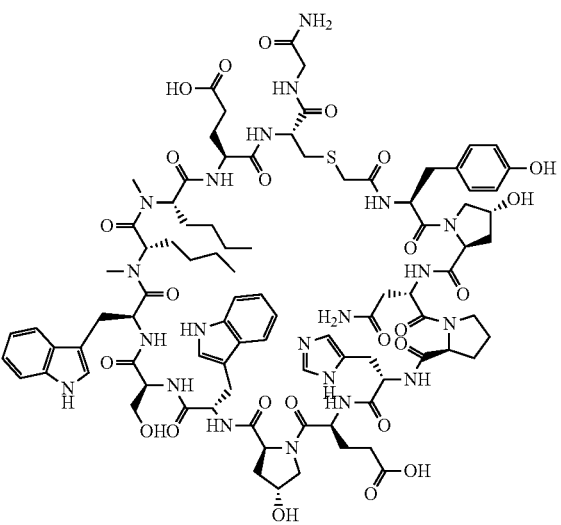 [SMILES: CCCC[C@H]1C(=O)N(C)[C@@H](CCCC)C(=O)N[C@@H](CCC(=O)O)C(=O)N[C@H](C(=O)NCC(N)=O)CSCC(=O)N[C@@H](Cc2ccc(O)cc2)C(=O)N2C[C@H](O)C[C@H]2C(=O)N[C@@H](CC(N)=O)C(=O)N2CCC[C@H]2C(=O)N[C@@H](Cc2cnc[nH]2)C(=O)N[C@@H](CCC(=O)O)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

Example 1283 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 8-minute hold at 100% B; Flow: 20 mL/min. Fractions containing the desired product were combined and dried via centrifugal evaporation. The yield of the product was 3.0 mg, and its estimated purity by LCMS analysis was 98%.

Analysis LCMS Condition H: retention time=1.32 min.; ESI-MS(+) m/z 963.7 (M+2H).

Analysis LCMS Condition I: retention time=2.67 min.; ESI-MS(+) m/z 963.8 (M+2H).

ESI-HRMS(+) m/z: Calculated: 963.9276 (M+2H); Found: 963.9270 (M+2H).

Preparation of Example 1285

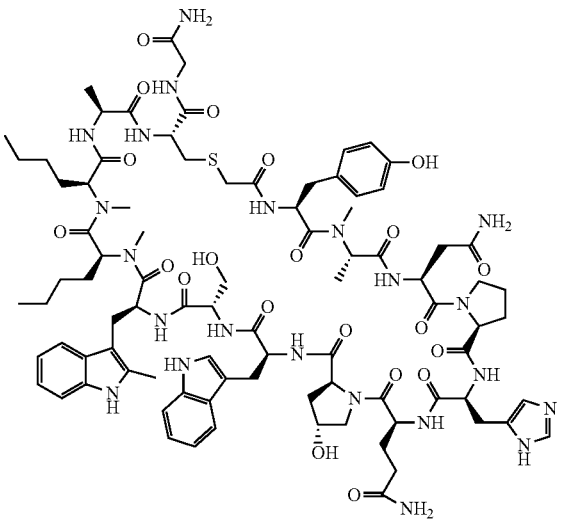 [SMILES: CCCC[C@H]1C(=O)N(C)[C@@H](CCCC)C(=O)N[C@@H](C)C(=O)N[C@H](C(=O)NCC(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CCC(N)=O)C(=O)N2C[C@H](O)C[C@H]2C(=O)N[C@@H](Cc2c[nH]c3ccccc23)C(=O)N[C@@H](CO)C(=O)N[C@@H](Cc2c(C)[nH]c3ccccc23)C(=O)N1C]

Example 1285 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Manual Coupling procedure A", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 4.4 mg, and its estimated purity by LCMS analysis was 95%.

Analysis LCMS Condition H: retention time=1.86 min.; ESI-MS(+) m/z 928.5 (M+2H).

ESI-HRMS(+) m/z: Calculated: 927.4432 (M+2H); Found: 927.4426 (M+2H).

Preparation of Example 1289

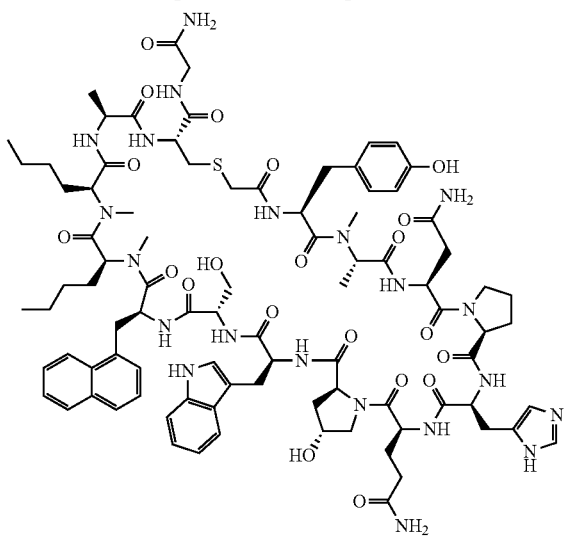 [SMILES: CCCC[C@H]1C(=O)N(C)[C@@H](CCCC)C(=O)N[C@@H](C)C(=O)N[C@H](C(=O)NCC(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CCC(N)=O)C(=O)N2C[C@H](O)C[C@H]2C(=O)N[C@@H](Cc2c[nH]c3ccccc23)C(=O)N[C@@H](CO)C(=O)N[C@@H](Cc2cccc3ccccc23)C(=O)N1C]

Example 1289 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Custom amino acids-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 5.7 mg, and its estimated purity by LCMS analysis was 99%.

Analysis LCMS Condition H: retention time=1.74 min.; ESI-MS(+) m/z 926.4 (M+2H).

Analysis LCMS Condition I: retention time=3.32 min.; ESI-MS(+) m/z 926.2 (M+2H).

ESI-HRMS(+) m/z: Calculated: 925.9378 (M+2H); Found: 925.9350 (M+2H).

Preparation of Example 1290

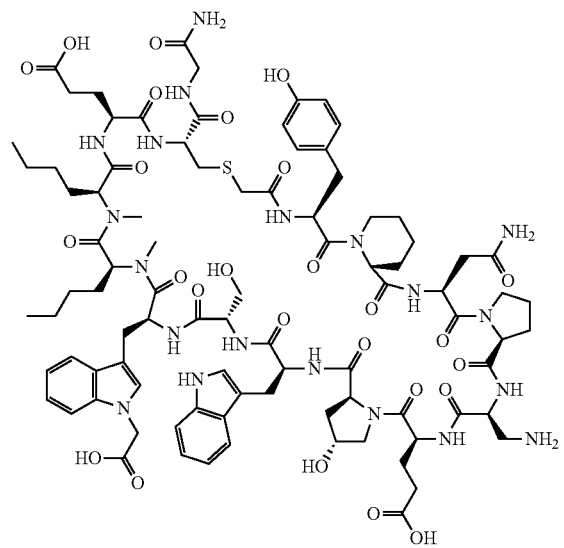 [SMILES: CCCC[C@H]1C(=O)N(C)[C@@H](CCCC)C(=O)N[C@@H](CCC(=O)O)C(=O)N[C@H](C(=O)NCC(N)=O)CSCC(=O)N[C@@H](Cc2ccc(O)cc2)C(=O)N2CCCC[C@@H]2C(=O)N[C@@H](CC(N)=O)C(=O)N2CCC[C@H]2C(=O)N[C@@H](CN)C(=O)N[C@@H](CCC(=O)O)C(=O)N2C[C@H](O)C[C@H]2C(=O)N[C@@H](Cc2c[nH]c3ccccc23)C(=O)N[C@@H](CO)C(=O)N[C@@H](Cc2cn(CC(=O)O)c3ccccc23)C(=O)N1C]

Example 1290 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×200 mm, 5-μm particles; Mobile Phase A: water with 0.1% trifluoroacetic acid; Mobile Phase B: 95:5 acetonitrile:water with 0.1% trifluoroacetic acid; Gradient: 5-45% B over 30 minutes, then a 5-minute hold at 100% B; Flow: 20 mL/min. Fractions containing the desired product were combined and dried via centrifugal evaporation. The yield of the product was 7.7 mg, and its estimated purity by LCMS analysis was 94%.

Analysis LCMS Condition H: retention time=1.24 min.; ESI-MS(+) m/z 967.3 (M+2H).

Analysis LCMS Condition I: retention time=2.66 min.; ESI-MS(+) m/z 967.4 (M+2H).

ESI-HRMS(+) m/z: Calculated: 966.9273 (M+2H); Found: 966.9273 (M+2H).

Preparation of Example 1291

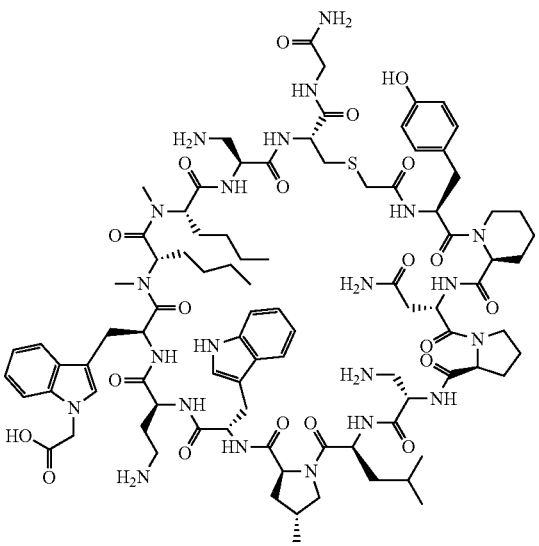 [SMILES: CCCC[C@H]1C(=O)N(C)[C@@H](CCCC)C(=O)N[C@@H](CN)C(=O)N[C@H](C(=O)NCC(N)=O)CSCC(=O)N[C@@H](Cc2ccc(O)cc2)C(=O)N2CCCC[C@H]2C(=O)N[C@@H](CC(N)=O)C(=O)N2CCC[C@H]2C(=O)N[C@@H](CN)C(=O)N[C@@H](CC(C)C)C(=O)N2C[C@H](C)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 1291 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-100% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 3.1 mg, and its estimated purity by LCMS analysis was 93%.

Analysis LCMS Condition H: retention time=1.39 min.; ESI-MS(+) m/z 944.1 (M+2H).

Analysis LCMS Condition I: retention time=2.99 min.; ESI-MS(+) m/z 943.8 (M+2H).

ESI-HRMS(+) m/z: Calculated: 943.4745 (M+2H); Found: 943.4714 (M+2H).

Preparation of Example 1292

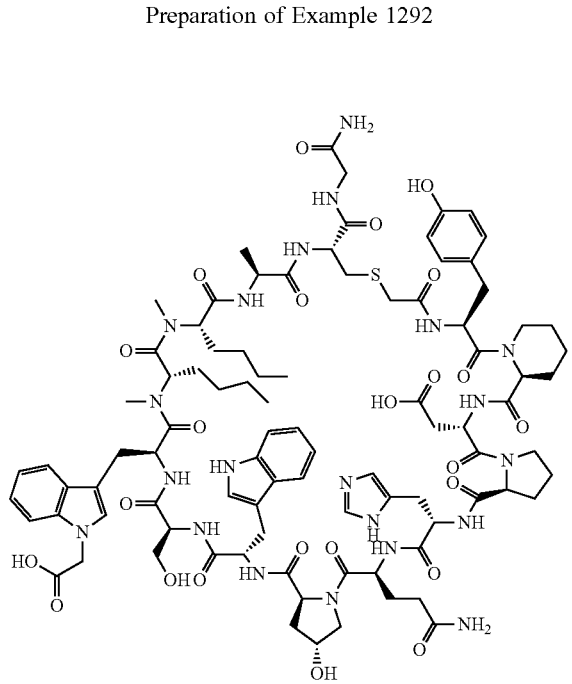

Example 1292 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 1.6 mg, and its estimated purity by LCMS analysis was 100%.

Analysis LCMS Condition H: retention time=1.20 min.; ESI-MS(+) m/z 963.3 (M+2H).

Analysis LCMS Condition I: retention time=2.52 min.; ESI-MS(+) m/z 963.5 (M+2H).

ESI-HRMS(+) m/z: Calculated: 962.9380 (M+2H); Found: 962.9357 (M+2H).

Preparation of Example 1293

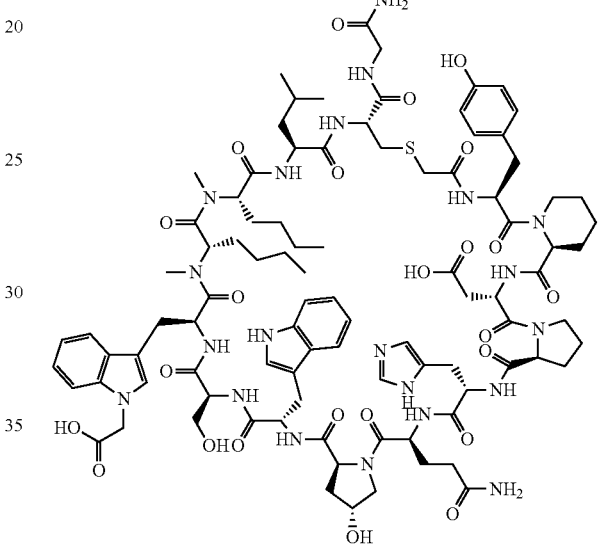

Example 1293 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 2.1 mg, and its estimated purity by LCMS analysis was 98%.

Analysis LCMS Condition H: retention time=1.48 min.; ESI-MS(+) m/z 983.9 (M+2H).

Analysis LCMS Condition I: retention time=2.12 min.; ESI-MS(+) m/z 984.1 (M+2H).

Preparation of Example 1294

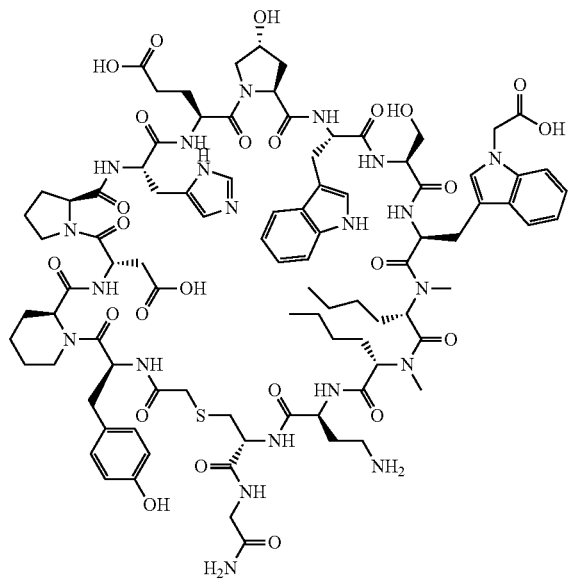 [SMILES: CCCC[C@H]1C(=O)N(C)[C@@H](CCCC)C(=O)N[C@@H](CCN)C(=O)N[C@H](C(=O)NCC(N)=O)CSCC(=O)N[C@@H](Cc2ccc(O)cc2)C(=O)N2CCCC[C@H]2C(=O)N[C@@H](CC(=O)O)C(=O)N2CCC[C@H]2C(=O)N[C@@H](Cc2cnc[nH]2)C(=O)N[C@@H](CCC(=O)O)C(=O)N2C[C@H](O)C[C@H]2C(=O)N[C@@H](Cc2c[nH]c3ccccc23)C(=O)N[C@@H](CO)C(=O)N[C@@H](Cc2cn(CC(=O)O)c3ccccc23)C(=O)N1C]

Example 1294 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-40% B over 30 minutes, then a 5-minute hold at 100% B; Flow: 20 mL/min. Fractions containing the desired product were combined and dried via centrifugal evaporation. The yield of the product was 4.1 mg, and its estimated purity by LCMS analysis was 94%.

Analysis LCMS Condition H: retention time=1.22 min.; ESI-MS(+) m/z 978.8 (M+2H).

Analysis LCMS Condition I: retention time=2.56 min.; ESI-MS(+) m/z 979.0 (M+2H).

ESI-HRMS(+) m/z: Calculated: 977.9433 (M+2H); Found: 977.9417 (M+2H).

Preparation of Example 1295

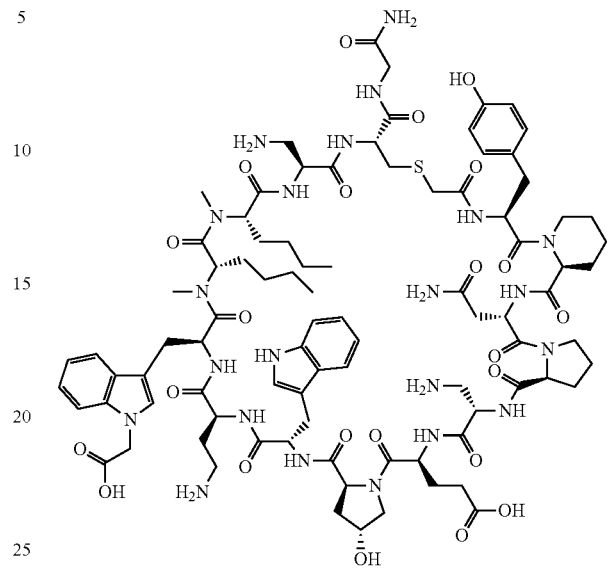

Example 1295 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 20 minutes, then a 5-minute hold at 100% B; Flow: 20 mL/min. Fractions containing the desired product were combined and dried via centrifugal evaporation. The yield of the product was 4.4 mg, and its estimated purity by LCMS analysis was 100%.

Analysis LCMS Condition H: retention time=1.38 min.; ESI-MS(+) m/z 951.6 (M+2H).

Analysis LCMS Condition I: retention time=2.96 min.; ESI-MS(+) m/z 952.0 (M+2H).

ESI-HRMS(+) m/z: Calculated: 951.4538 (M+2H); Found: 951.4508 (M+2H).

103
Preparation of Example 1296

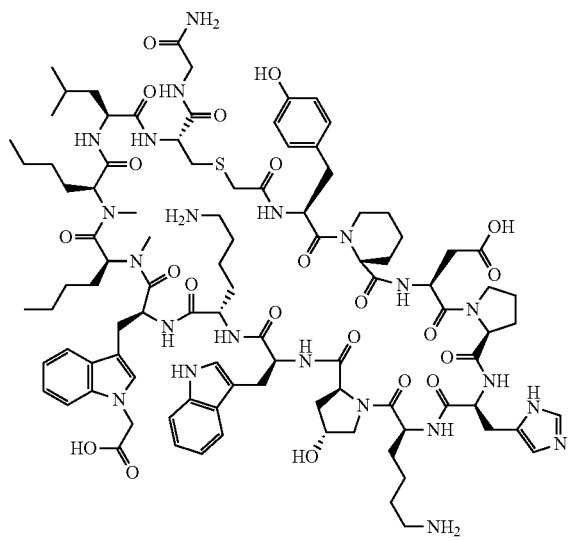 [SMILES: CCCC[C@H]1C(=O)N(C)[C@@H](CCCC)C(=O)N[C@@H](CC(C)C)C(=O)N[C@H](C(=O)NCC(N)=O)CSCC(=O)N[C@@H](Cc2ccc(O)cc2)C(=O)N2CCCC[C@@H]2C(=O)N[C@@H](CC(=O)O)C(=O)N2CCC[C@H]2C(=O)N[C@@H](Cc2cnc[nH]2)C(=O)N[C@@H](CCCCN)C(=O)N2C[C@H](O)C[C@H]2C(=O)N[C@@H](Cc2c[nH]c3ccccc23)C(=O)N[C@@H](CCCCN)C(=O)N[C@@H](Cc2cn(CC(=O)O)c3ccccc23)C(=O)N1C]

Example 1296 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 1.4 mg, and its estimated purity by LCMS analysis was 97%.

Analysis LCMS Condition H: retention time=1.35 min.; ESI-MS(+) m/z 1005.2 (M+2H).

Analysis LCMS Condition I: retention time=2.75 min.; ESI-MS(+) m/z 1005.3 (M+2H).

ESI-HRMS(+) m/z: Calculated: 1004.5111 (M+2H); Found: 1004.5078 (M+2H).

104
Preparation of Example 1297

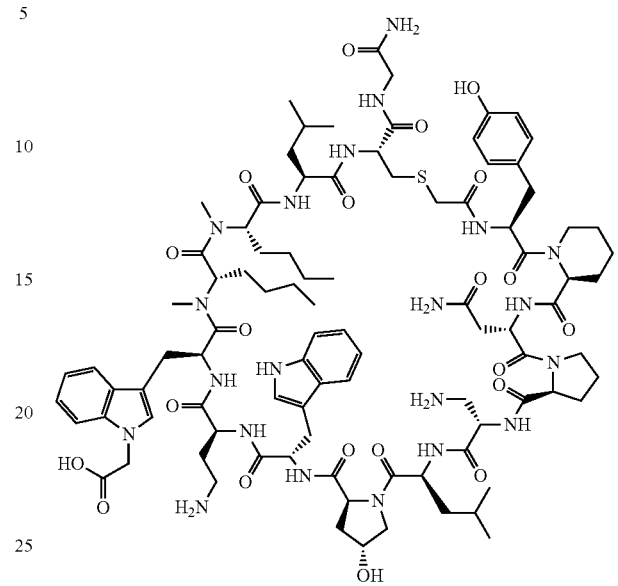

Example 1297 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Custom amino acids-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 4.9 mg, and its estimated purity by LCMS analysis was 100%.

Analysis LCMS Condition H: retention time=1.58 min.; ESI-MS(+) m/z 957.5 (M+2H).

Analysis LCMS Condition I: retention time=3.18 min.; ESI-MS(+) m/z 957.5 (M+2H).

ESI-HRMS(+) m/z: Calculated: 956.9826 (M+2H); Found: 956.9896 (M+2H).

Preparation of Example 1298

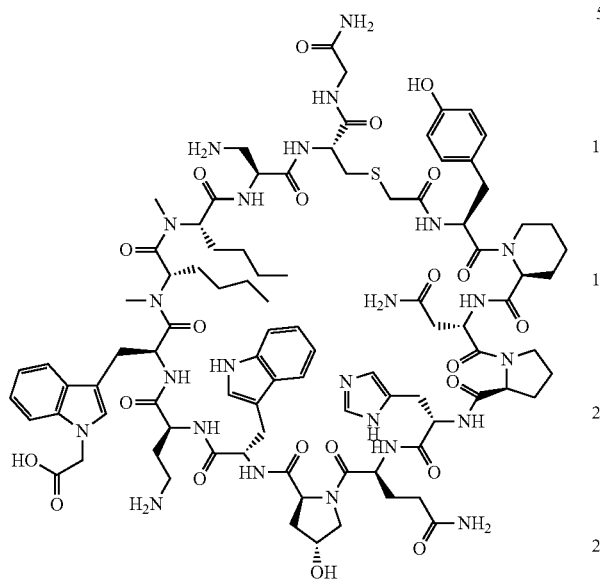

Example 1298 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Custom amino acids-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-40% B over 20 minutes, then a 5-minute hold at 100% B; Flow: 20 mL/min. Fractions containing the desired product were combined and dried via centrifugal evaporation. The yield of the product was 9.4 mg, and its estimated purity by LCMS analysis was 100%.

Analysis LCMS Condition H: retention time=1.33 min.; ESI-MS(+) m/z 977.3 (M+2H).

Analysis LCMS Condition I: retention time=2.71 min.; ESI-MS(+) m/z 977.3 (M+2H).

ESI-HRMS(+) m/z: Calculated: 976.4672 (M+2H); Found: 976.4644 (M+2H).

Preparation of Example 1299

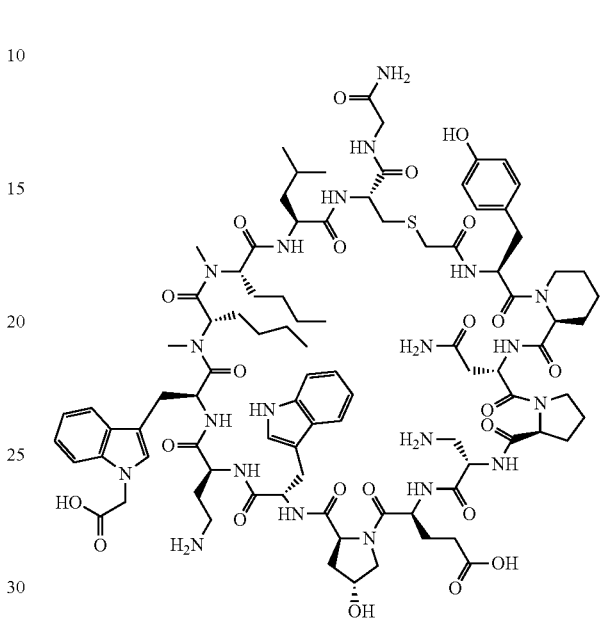

Example 1299 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Custom amino acids-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-85% B over 30 minutes, then a 5-minute hold at 100% B; Flow: 20 mL/min. Fractions containing the desired product were combined and dried via centrifugal evaporation. The yield of the product was 5.3 mg, and its estimated purity by LCMS analysis was 92%.

Analysis LCMS Condition H: retention time=1.40 min.; ESI-MS(+) m/z 965.7 (M+2H).

Analysis LCMS Condition I: retention time=2.79 min.; ESI-MS(+) m/z 965.3 (M+2H).

ESI-HRMS(+) m/z: Calculated: 964.9718 (M+2H); Found: 964.9680 (M+2H).

Preparation of Example 1300

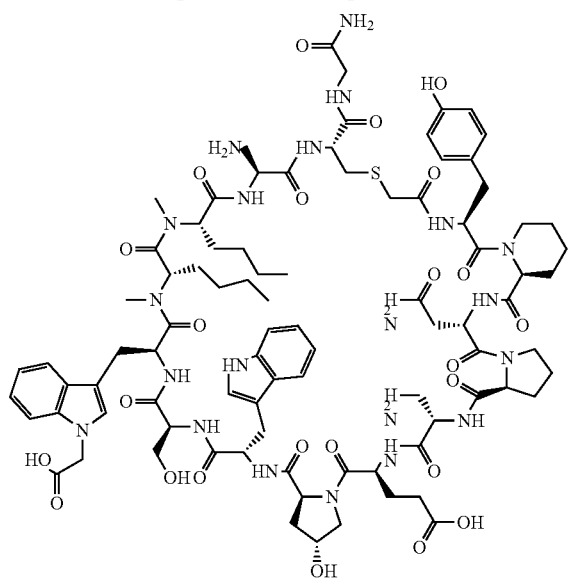 [SMILES: CCCC[C@H]1C(=O)N(C)[C@@H](CCCC)C(=O)N[C@@H](CN)C(=O)N[C@H](C(=O)NCC(N)=O)CSCC(=O)N[C@@H](Cc2ccc(O)cc2)C(=O)N2CCCC[C@H]2C(=O)N[C@@H](CC(N)=O)C(=O)N2CCC[C@H]2C(=O)N[C@@H](CN)C(=O)N[C@@H](CCC(=O)O)C(=O)N2C[C@H](O)C[C@H]2C(=O)N[C@@H](Cc2c[nH]c3ccccc23)C(=O)N[C@@H](CO)C(=O)N[C@@H](Cc2cn(CC(=O)O)c3ccccc23)C(=O)N1C]

Example 1300 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Custom amino acids-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 4.3 mg, and its estimated purity by LCMS analysis was 97%.

Analysis LCMS Condition I: retention time=2.65 min.; ESI-MS(+) m/z 944.8 (M+2H).

Preparation of Example 1301

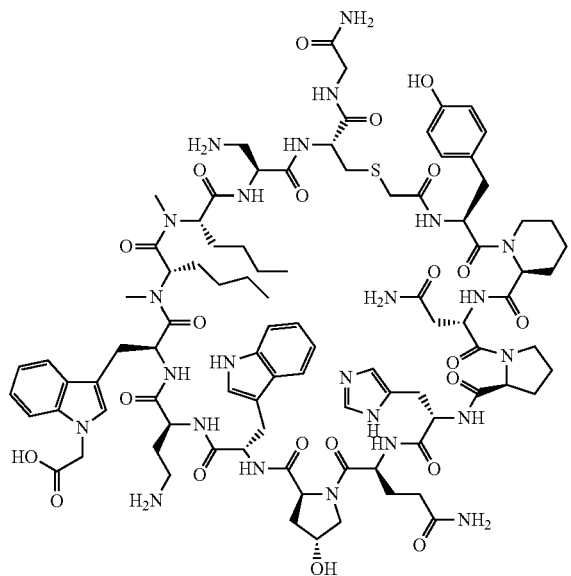 [SMILES: CCCC[C@H]1C(=O)N(C)[C@@H](CCCC)C(=O)N[C@@H](CN)C(=O)N[C@H](C(=O)NCC(N)=O)CSCC(=O)N[C@@H](Cc2ccc(O)cc2)C(=O)N2CCCC[C@H]2C(=O)N[C@@H](CC(N)=O)C(=O)N2CCC[C@H]2C(=O)N[C@@H](Cc2cnc[nH]2)C(=O)N[C@@H](CCC(N)=O)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 1301 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Custom amino acids-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 2.1 mg, and its estimated purity by LCMS analysis was 97%.

Analysis LCMS Condition H: retention time=1.33 min.; ESI-MS(+) m/z 977.3 (M+2H).

Analysis LCMS Condition I: retention time=2.71 min.; ESI-MS(+) m/z 977.3 (M+2H).

ESI-HRMS(+) m/z: Calculated: 976.4672 (M+2H); Found: 976.4645 (M+2H).

Preparation of Example 1302

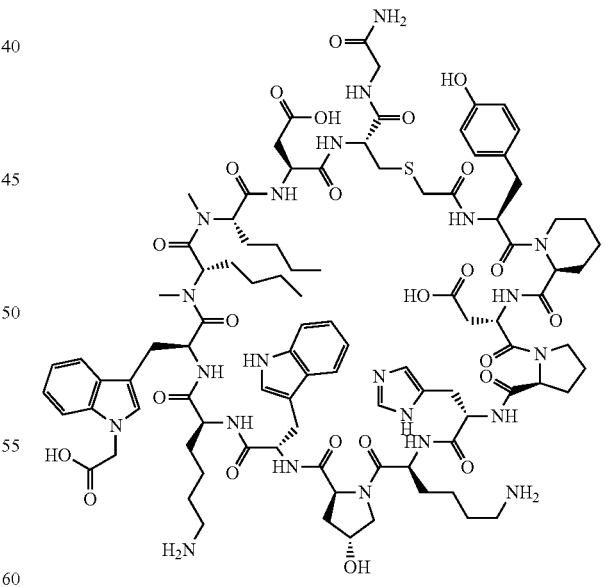

Example 1302 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Custom amino acids-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 1.0 mg, and its estimated purity by LCMS analysis was 100%.

Analysis LCMS Condition H: retention time=1.20 min.; ESI-MS(+) m/z 1006.3 (M+2H).

Analysis LCMS Condition I: retention time=2.47 min.; ESI-MS(+) m/z 1006.3 (M+2H).

ESI-HRMS(+) m/z: Calculated: 1005.4826 (M+2H); Found: 1005.4786 (M+2H).

Preparation of Example 1303

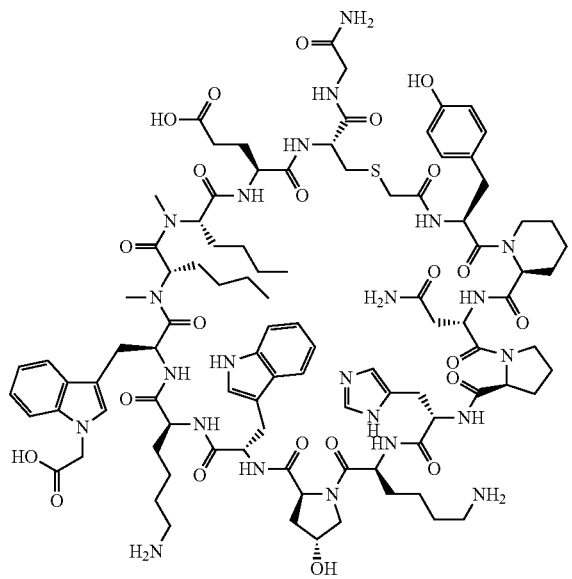 [SMILES: CCCC[C@H]1C(=O)N(C)[C@@H](CCCC)C(=O)N[C@@H](CCC(=O)O)C(=O)N[C@H](C(=O)NCC(N)=O)CSCC(=O)N[C@@H](Cc2ccc(O)cc2)C(=O)N2CCCC[C@H]2C(=O)N[C@@H](CC(N)=O)C(=O)N2CCC[C@H]2C(=O)N[C@@H](Cc2cnc[nH]2)C(=O)N[C@@H](CCCCN)C(=O)N2C[C@H](O)C[C@H]2C(=O)N[C@@H](Cc2c[nH]c3ccccc23)C(=O)N[C@@H](CCCCN)C(=O)N[C@@H](Cc2cn(CC(=O)O)c3ccccc23)C(=O)N1C]

Example 1303 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Custom amino acids-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 8.0 mg, and its estimated purity by LCMS analysis was 93%.

Analysis LCMS Condition H: retention time=1.25 min.; ESI-MS(+) m/z 1012.9 (M+2H).

Analysis LCMS Condition I: retention time=2.52 min.; ESI-MS(+) m/z 1013.3 (M+2H).

ESI-HRMS(+) m/z: Calculated: 1011.9984 (M+2H); Found: 1011.9941 (M+2H).

Preparation of Example 1304

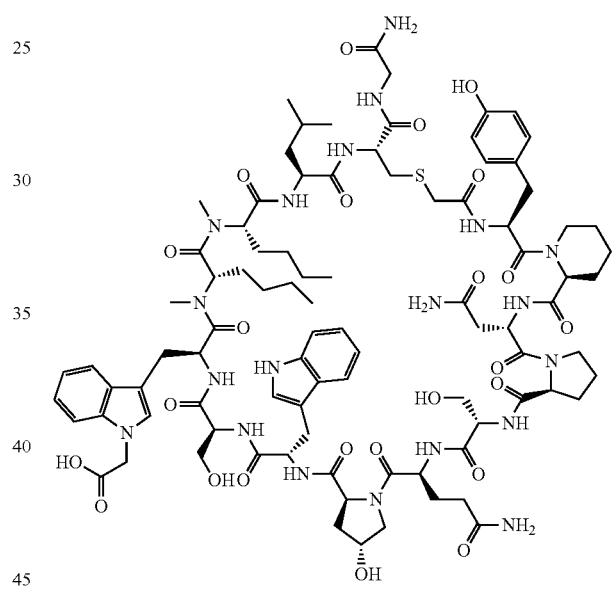

Example 1304 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Custom amino acids-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 1.1 mg, and its estimated purity by LCMS analysis was 95%.

Analysis LCMS Condition H: retention time=1.34 min.; ESI-MS(+) m/z 959.0 (M+2H).

Analysis LCMS Condition I: retention time=2.98 min.; ESI-MS(+) m/z 959.0 (M+2H).

ESI-HRMS(+) m/z: Calculated: 958.4560 (M+2H); Found: 958.4542 (M+2H).

Preparation of Example 1305

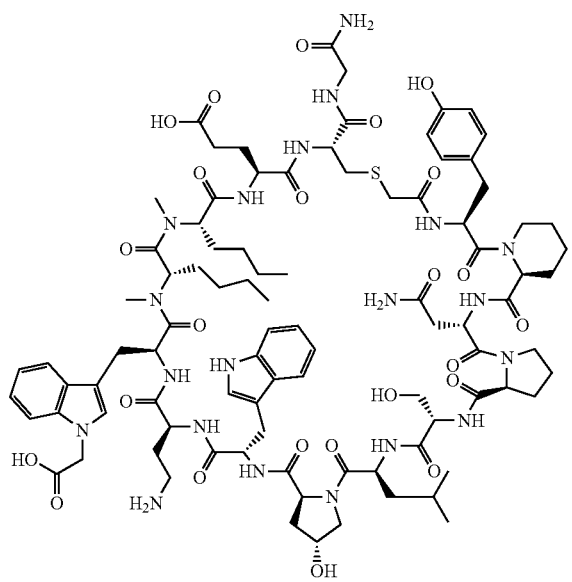 [SMILES: CCCC[C@H]1C(=O)N(C)[C@@H](CCCC)C(=O)N[C@@H](CCC(=O)O)C(=O)N[C@H](C(=O)NCC(N)=O)CSCC(=O)N[C@@H](Cc2ccc(O)cc2)C(=O)N2CCCC[C@H]2C(=O)N[C@@H](CC(N)=O)C(=O)N2CCC[C@H]2C(=O)N[C@@H](CO)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 1305 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Custom amino acids-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-40% B over 30 minutes, then a 5-minute hold at 100% B; Flow: 20 mL/min. Fractions containing the desired product were combined and dried via centrifugal evaporation. The yield of the product was 0.7 mg, and its estimated purity by LCMS analysis was 100%.

Analysis LCMS Condition H: retention time=1.25 min.; ESI-MS(+) m/z 966.4 (M+2H).

Analysis LCMS Condition I: retention time=2.91 min.; ESI-MS(+) m/z 965.7 (M+2H).

ESI-HRMS(+) m/z: Calculated: 965.4638 (M+2H); Found: 965.4619 (M+2H).

Preparation of Example 1306

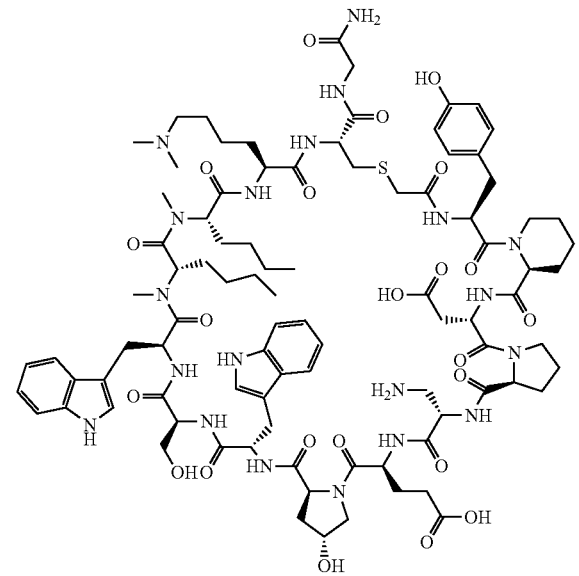 [SMILES: CCCC[C@H]1C(=O)N(C)[C@@H](CCCC)C(=O)N[C@@H](CCCCN(C)C)C(=O)N[C@H](C(=O)NCC(N)=O)CSCC(=O)N[C@@H](Cc2ccc(O)cc2)C(=O)N2CCCC[C@H]2C(=O)N[C@@H](CC(=O)O)C(=O)N2CCC[C@H]2C(=O)N[C@@H](CN)C(=O)N[C@@H](CCC(=O)O)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

Example 1306 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Custom amino acids-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 2.8 mg, and its estimated purity by LCMS analysis was 92%.

Analysis LCMS Condition H: retention time=1.57 min.; ESI-MS(+) m/z 951.9 (M+2H).

Analysis LCMS Condition I: retention time=3.07 min.; ESI-MS(+) m/z 951.9 (M+2H).

ESI-HRMS(+) m/z: Calculated: 951.4664 (M+2H); Found: 951.4633 (M+2H).

Preparation of Example 1309

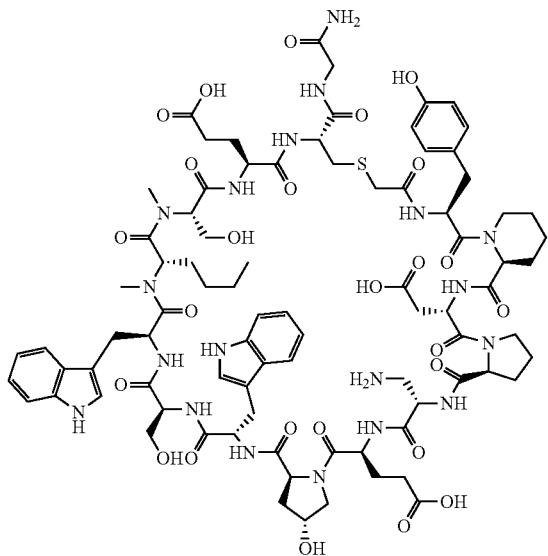 [SMILES: CCCC[C@H]1C(=O)N(C)[C@@H](CO)C(=O)N[C@@H](CCC(=O)O)C(=O)N[C@H](C(=O)NCC(N)=O)CSCC(=O)N[C@@H](Cc2ccc(O)cc2)C(=O)N2CCCC[C@H]2C(=O)N[C@@H](CC(=O)O)C(=O)N2CCC[C@H]2C(=O)N[C@@H](CN)C(=O)N[C@@H](CCC(=O)O)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

Example 1309 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Custom amino acids-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-50% B over 25 minutes, then a 5-minute hold at 100% B; Flow: 20 mL/min. Fractions containing the desired product were combined and dried via centrifugal evaporation. The material was further purified via preparative LC/MS with the following conditions: Column: waters xbridge c-18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 25 minutes, then a 5-minute hold at 55% B; Flow: 20 mL/min. Fractions containing the desired product were combined and dried via centrifugal evaporation.

The yield of the product was 3.6 mg, and its estimated purity by LCMS analysis was 98%.

Analysis LCMS Condition D: Retention time=1.1 min; ESI-MS(+) m/z 925.3 (M+2H).

Analysis LCMS Condition E: Retention time=1.25 min; ESI-MS(+) m/z 925.4 (M+2H).

ESI-HRMS(+) m/z: Calculated: 924.8985 (M+2H); Found: 950.8961 (M+2H).

Preparation of Example 1500

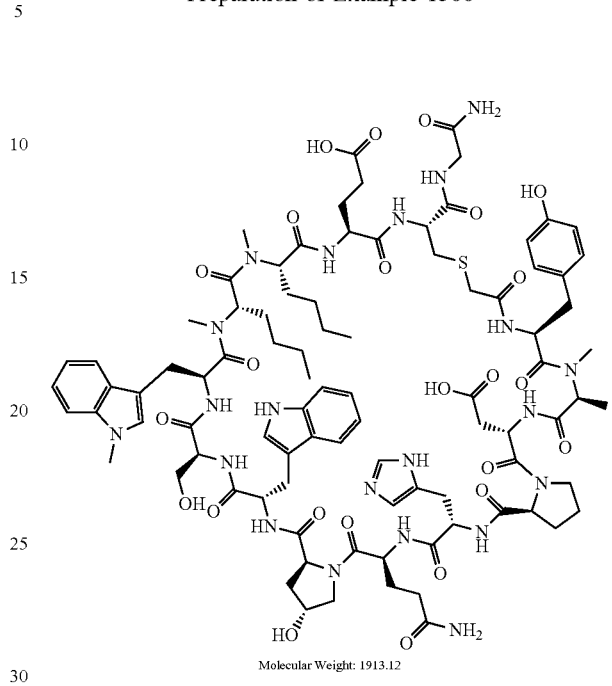

Molecular Weight: 1913.12

Example 1500 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 0.6 mg, and its estimated purity by LCMS analysis was 100%.

Analysis LCMS Condition H: Retention time=1.60 min; ESI-MS(+) m/z 957.00 (M+2H).

Analysis LCMS Condition I: Retention time=3.06 min; ESI-MS(+) m/z 957.00 (M+2H).

Preparation of Example 1501

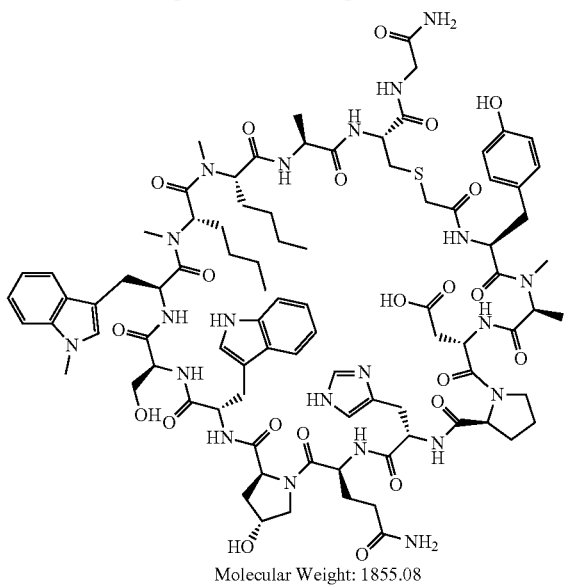 [SMILES: CCCC[C@H]1C(=O)N(C)[C@@H](CCCC)C(=O)N[C@@H](C)C(=O)N[C@H](C(=O)NCC(N)=O)CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2c[nH]cn2)C(=O)N[C@@H](CCC(N)=O)C(=O)N2C[C@H](O)C[C@H]2C(=O)N[C@@H](Cc2c[nH]c3ccccc23)C(=O)N[C@@H](CO)C(=O)N[C@@H](Cc2cn(C)c3ccccc23)C(=O)N1C]

Molecular Weight: 1855.08

Example 1501 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 6.4 mg, and its estimated purity by LCMS analysis was 97%.

Analysis LCMS Condition H: Retention time=1.76 min; ESI-MS(+) m/z 928.15 (M+2H).

Analysis LCMS Condition I: Retention time=3.20 min; ESI-MS(+) m/z 928.20 (M+2H).

Preparation of Example 1502

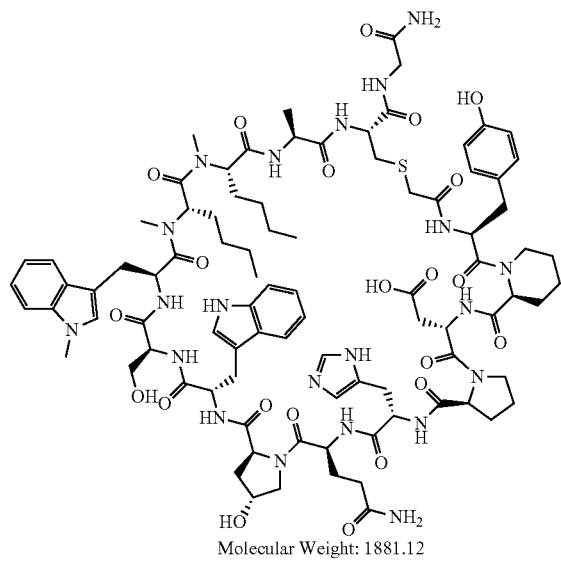 [SMILES: CCCC[C@H]1C(=O)N(C)[C@@H](CCCC)C(=O)N[C@@H](C)C(=O)N[C@H](C(=O)NCC(N)=O)CSCC(=O)N[C@@H](Cc2ccc(O)cc2)C(=O)N2CCCC[C@H]2C(=O)N[C@@H](CC(=O)O)C(=O)N2CCC[C@H]2C(=O)N[C@@H](Cc2cnc[nH]2)C(=O)N[C@@H](CCC(N)=O)C(=O)N2C[C@H](O)C[C@H]2C(=O)N[C@@H](Cc2c[nH]c3ccccc23)C(=O)N[C@@H](CO)C(=O)N[C@@H](Cc2cn(C)c3ccccc23)C(=O)N1C]

Molecular Weight: 1881.12

Example 1502 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 55-95% B over 30 minutes, then a 5-minute hold at 100% B; Flow: 20 mL/min. Fractions containing the desired product were combined and dried via centrifugal evaporation. The yield of the product was 5.4 mg, and its estimated purity by LCMS analysis was 100%.

Analysis LCMS Condition H: Retention time=1.796 min; ESI-MS(+) m/z 941.20 (M+2H).

Analysis LCMS Condition I: Retention time=2.389 min; ESI-MS(+) m/z 940.95 (M+2H).

Preparation of Example 1503

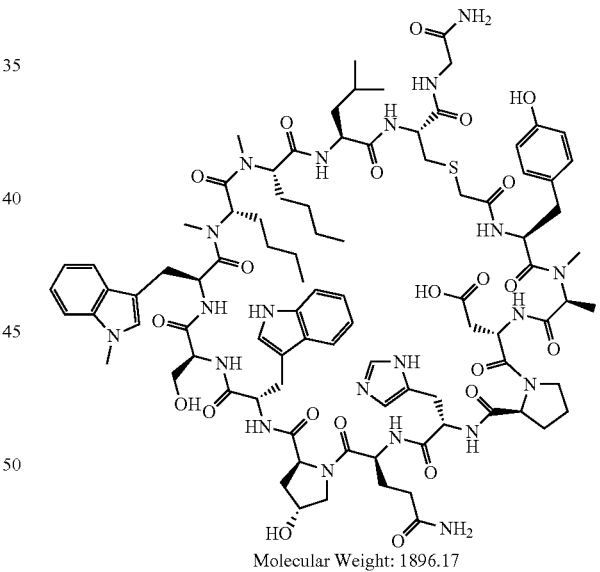

Molecular Weight: 1896.17

Example 1503 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 3.1 mg, and its estimated purity by LCMS analysis was 100%.

Analysis LCMS Condition H: Retention time=1.870 min; ESI-MS(+) m/z 948.75 (M+2H).

Analysis LCMS Condition I: Retention time=3.358 min; ESI-MS(+) m/z 948.60 (M+2H).

Preparation of Example 1504

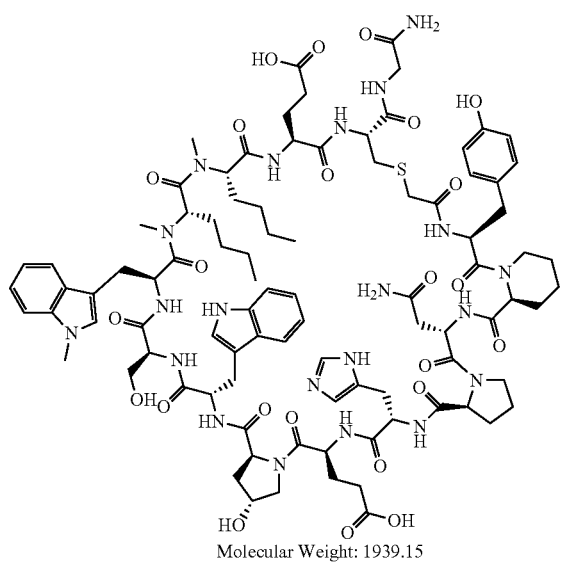 [SMILES: CCCC[C@H]1C(=O)N(C)[C@@H](CCCC)C(=O)N[C@@H](CCC(=O)O)C(=O)N[C@H](C(=O)NCC(N)=O)CSCC(=O)N[C@@H](Cc2ccc(O)cc2)C(=O)N2CCCC[C@H]2C(=O)N[C@@H](CC(=O)O)C(=O)N2CCC[C@H]2C(=O)N[C@@H](Cc2cnc[nH]2)C(=O)N[C@@H](CCC(=O)O)C(=O)N2C[C@H](O)C[C@H]2C(=O)N[C@@H](Cc2c[nH]c3ccccc23)C(=O)N[C@@H](CO)C(=O)N[C@@H](Cc2cn(C)c3ccccc23)C(=O)N1C]

Molecular Weight: 1939.15

Example 1504 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 55-95% B over 30 minutes, then a 5-minute hold at 100% B; Flow: 20 mL/min. Fractions containing the desired product were combined and dried via centrifugal evaporation. The yield of the product was 8.4 mg, and its estimated purity by LCMS analysis was 98%.

Analysis LCMS Condition H: Retention time=1.447 min; ESI-MS(+) m/z 970.80 (M+2H).

Analysis LCMS Condition I: Retention time=2.838 min; ESI-MS(+) m/z 970.20 (M+2H).

Preparation of Example 1505

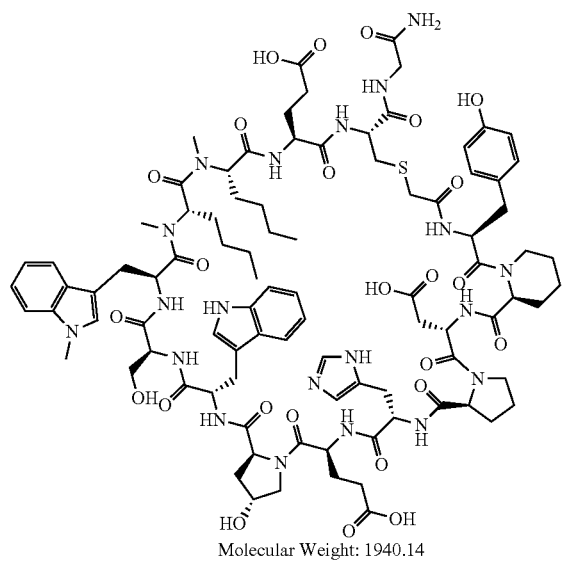

Molecular Weight: 1940.14

Example 1505 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 8.9 mg, and its estimated purity by LCMS analysis was 98%.

Analysis LCMS Condition H: Retention time=1.624 min; ESI-MS(+) m/z 970.95 (M+2H).

Analysis LCMS Condition I: Retention time=3.075 min; ESI-MS(+) m/z 970.65 (M+2H).

Preparation of Example 1506

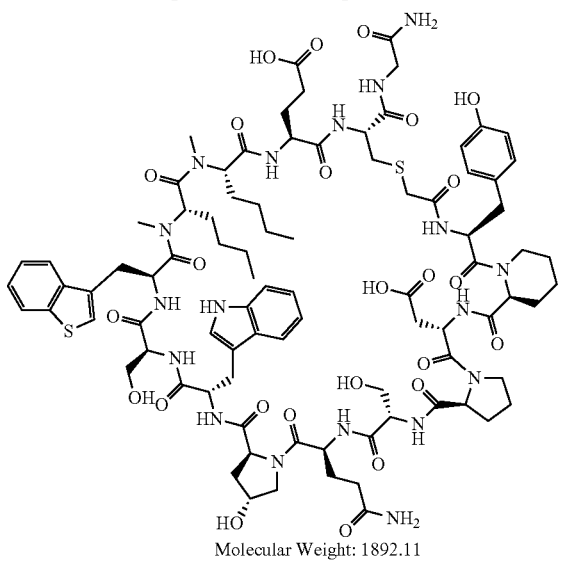 [SMILES: CCCC[C@H]1C(=O)N(C)[C@@H](CCCC)C(=O)N[C@@H](CCC(=O)O)C(=O)N[C@H](C(=O)NCC(N)=O)CSCC(=O)N[C@@H](Cc2ccc(O)cc2)C(=O)N2CCCC[C@H]2C(=O)N[C@@H](CC(=O)O)C(=O)N2CCC[C@H]2C(=O)N[C@@H](CO)C(=O)N[C@@H](CCC(N)=O)C(=O)N2C[C@H](O)C[C@H]2C(=O)N[C@@H](Cc2c[nH]c3ccccc23)C(=O)N[C@@H](CO)C(=O)N[C@@H](Cc2csc3ccccc23)C(=O)N1C]

Molecular Weight: 1892.11

Example 1506 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 2.7 mg, and its estimated purity by LCMS analysis was 98%.

Analysis LCMS Condition H: Retention time=1.566 min; ESI-MS(+) m/z 947.20 (M+2H).

Analysis LCMS Condition I: Retention time=3.069 min; ESI-MS(+) m/z 946.90 (M+2H).

Preparation of Example 1507

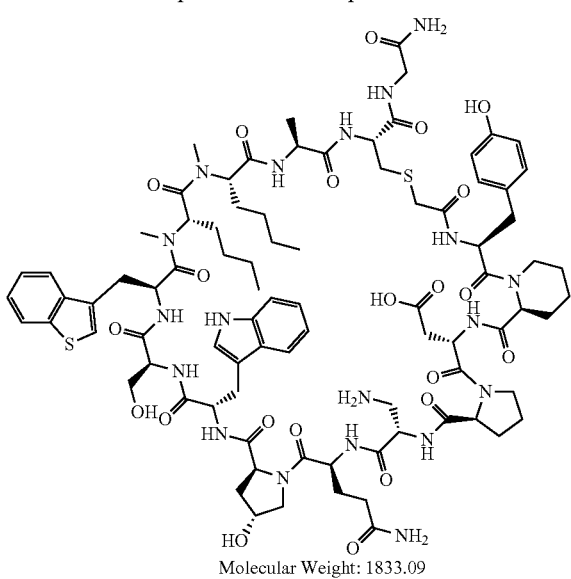

Molecular Weight: 1833.09

Example 1507 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 2.9 mg, and its estimated purity by LCMS analysis was 100%.

Analysis LCMS Condition H: Retention time=1.761 min; ESI-MS(+) m/z 917.60 (M+2H).

Analysis LCMS Condition I: Retention time=3.321 min; ESI-MS(+) m/z 917.40 (M+2H).

Preparation of Example 1508

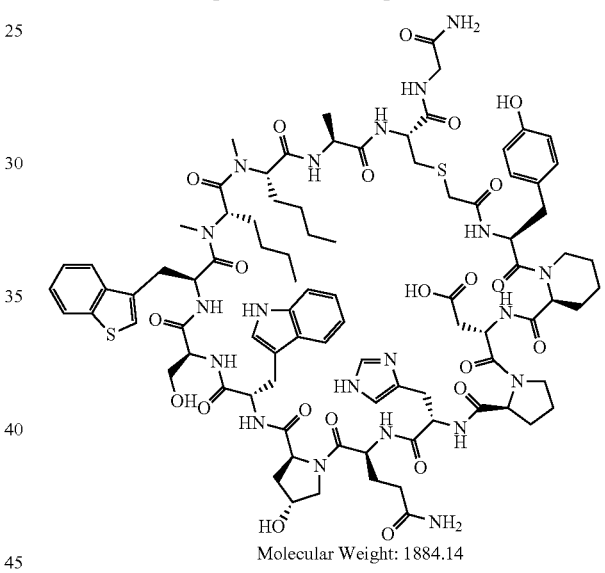

Molecular Weight: 1884.14

Example 1508 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 2.2 mg, and its estimated purity by LCMS analysis was 100%.

Analysis LCMS Condition H: Retention time=1.702 min; ESI-MS(+) m/z 942.90 (M+2H).

Analysis LCMS Condition I: Retention time=3.245 min; ESI-MS(+) m/z 942.95 (M+2H).

Preparation of Example 1509

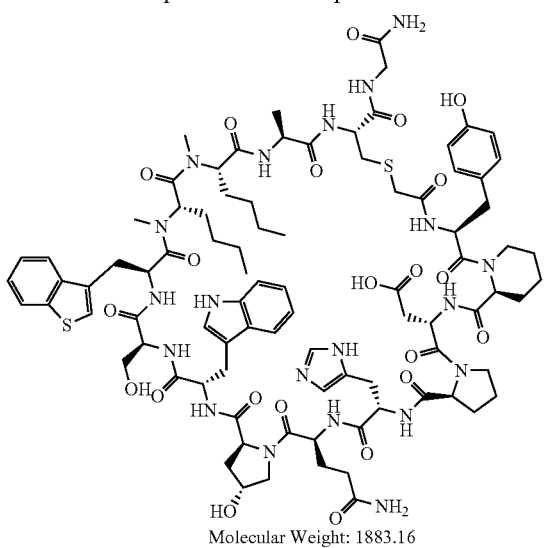
Molecular Weight: 1883.16

Example 1509 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 8.9 mg, and its estimated purity by LCMS analysis was 98%.

Analysis LCMS Condition H: Retention time=1.702 min; ESI-MS(+) m/z 942.90 (M+2H).

Analysis LCMS Condition I: Retention time=3.245 min; ESI-MS(+) m/z 942.95 (M+2H).

Preparation of Example 1510

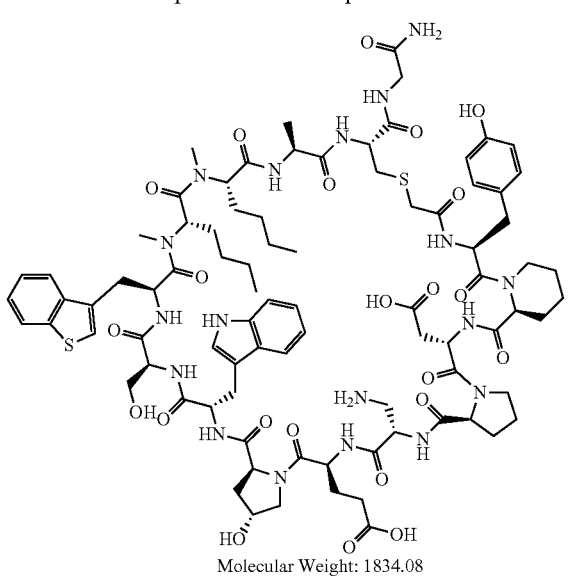
Molecular Weight: 1834.08

Example 1510 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 2.0 mg, and its estimated purity by LCMS analysis was 99%.

Analysis LCMS Condition H: Retention time=1.706 min; ESI-MS(+) m/z 917.55 (M+2H).

Analysis LCMS Condition I: Retention time=3.271 min; ESI-MS(+) m/z 917.90 (M+2H).

Preparation of Example 1511

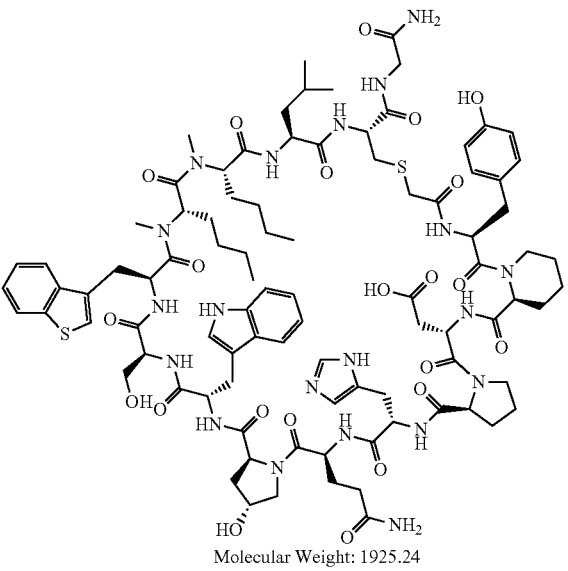 [SMILES: CCCC[C@H]1C(=O)N(C)[C@@H](CCCC)C(=O)N[C@@H](CC(C)C)C(=O)N[C@H](C(=O)NCC(N)=O)CSCC(=O)N[C@@H](Cc2ccc(O)cc2)C(=O)N2CCCC[C@H]2C(=O)N[C@@H](CC(=O)O)C(=O)N2CCC[C@H]2C(=O)N[C@@H](Cc2cnc[nH]2)C(=O)N[C@@H](CCC(N)=O)C(=O)N2C[C@H](O)C[C@H]2C(=O)N[C@@H](Cc2c[nH]c3ccccc23)C(=O)N[C@@H](CO)C(=O)N[C@@H](Cc2csc3ccccc23)C(=O)N1C]
Molecular Weight: 1925.24

Example 1511 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 7.9 mg, and its estimated purity by LCMS analysis was 100%.

Analysis LCMS Condition H: Retention time=1.819 min; ESI-MS(+) m/z 963.45 (M+2H).

Analysis LCMS Condition I: Retention time=3.377 min; ESI-MS(+) m/z 963.45 (M+2H).

Preparation of Example 1512

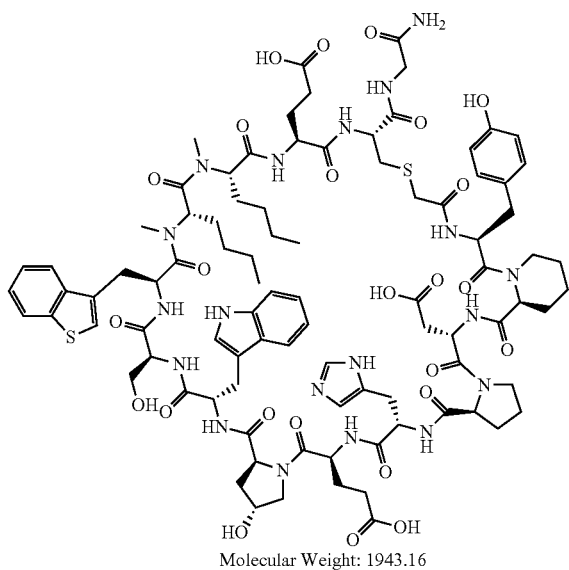 [SMILES: CCCC[C@H]1C(=O)N(C)[C@@H](CCCC)C(=O)N[C@@H](CCC(=O)O)C(=O)N[C@H](C(=O)NCC(N)=O)CSCC(=O)N[C@@H](Cc2ccc(O)cc2)C(=O)N2CCCC[C@H]2C(=O)N[C@@H](CC(=O)O)C(=O)N2CCC[C@H]2C(=O)N[C@@H](Cc2cnc[nH]2)C(=O)N[C@@H](CCC(=O)O)C(=O)N2C[C@H](O)C[C@H]2C(=O)N[C@@H](Cc2c[nH]c3ccccc23)C(=O)N[C@@H](CO)C(=O)N[C@@H](Cc2csc3ccccc23)C(=O)N1C]

Molecular Weight: 1943.16

Example 1512 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 2.4 mg, and its estimated purity by LCMS analysis was 100%.

Analysis LCMS Condition H: Retention time=1.479 min; ESI-MS(+) m/z 972.25 (M+2H).

Analysis LCMS Condition I: Retention time=3.000 min; ESI-MS(+) m/z 972.40 (M+2H).

Preparation of Example 1513

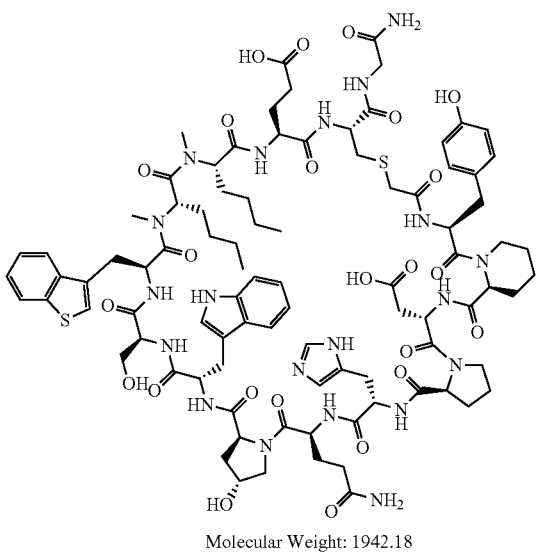 [SMILES: CCCC[C@H]1C(=O)N(C)[C@@H](CCCC)C(=O)N[C@@H](CCC(=O)O)C(=O)N[C@H](C(=O)NCC(N)=O)CSCC(=O)N[C@@H](Cc2ccc(O)cc2)C(=O)N2CCCC[C@H]2C(=O)N[C@@H](CC(=O)O)C(=O)N2CCC[C@H]2C(=O)N[C@@H](Cc2cnc[nH]2)C(=O)N[C@@H](CCC(N)=O)C(=O)N2C[C@H](O)C[C@H]2C(=O)N[C@@H](Cc2c[nH]c3ccccc23)C(=O)N[C@@H](CO)C(=O)N[C@@H](Cc2csc3ccccc23)C(=O)N1C]

Molecular Weight: 1942.18

Example 1513 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 2.8 mg, and its estimated purity by LCMS analysis was 98%.

Analysis LCMS Condition H: Retention time=1.539 min; ESI-MS(+) m/z 971.90 (M+2H).

Analysis LCMS Condition I: Retention time=3.071 min; ESI-MS(+) m/z 971.85 (M+2H).

Preparation of Example 1514

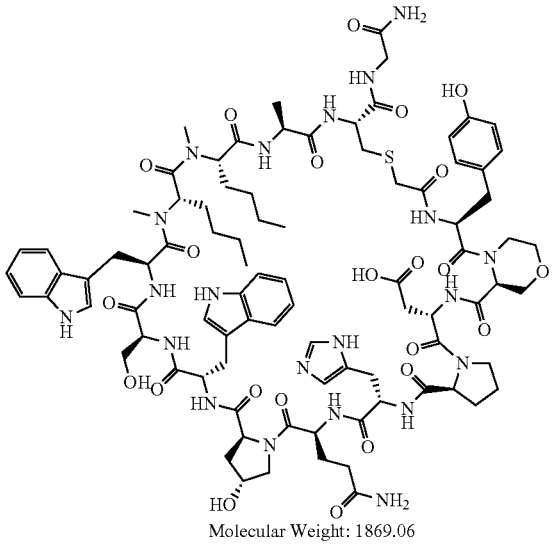 [SMILES: CCCC[C@H]1C(=O)N(C)[C@@H](CCCC)C(=O)N[C@@H](C)C(=O)N[C@H](C(=O)NCC(N)=O)CSCC(=O)N[C@@H](Cc2ccc(O)cc2)C(=O)N2CCOC[C@H]2C(=O)N[C@@H](CC(=O)O)C(=O)N2CCC[C@H]2C(=O)N[C@@H](Cc2cnc[nH]2)C(=O)N[C@@H](CCC(N)=O)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

Molecular Weight: 1869.06

Example 1514 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 24.3 mg, and its estimated purity by LCMS analysis was 100%.

Analysis LCMS Condition H: Retention time=1.66 min; ESI-MS(+) m/z 935.5 (M+2H).

Analysis LCMS Condition I: Retention time=2.53 min; ESI-MS(+) m/z 935.7 (M+2H).

Preparation of Example 1515

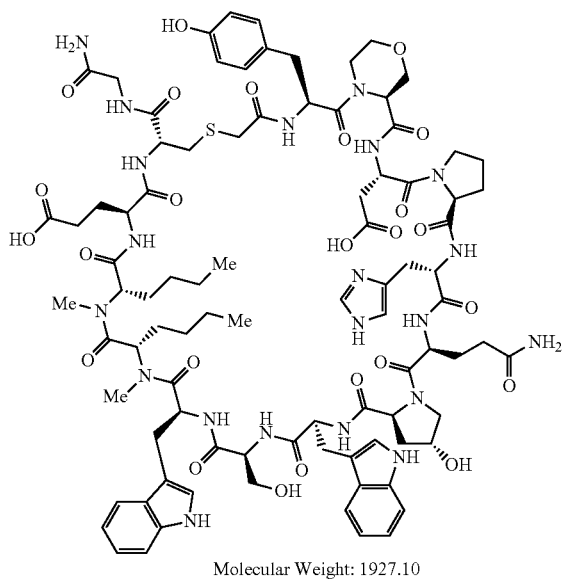 [SMILES: CCCC[C@H]1C(=O)N(C)[C@@H](CCCC)C(=O)N[C@@H](CCC(=O)O)C(=O)N[C@H](C(=O)NCC(N)=O)CSCC(=O)N[C@@H](Cc2ccc(O)cc2)C(=O)N2CCOC[C@H]2C(=O)N[C@@H](CC(=O)O)C(=O)N2CCC[C@H]2C(=O)N[C@@H](Cc2c[nH]cn2)C(=O)N[C@@H](CCC(N)=O)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

Molecular Weight: 1927.10

Example 1515 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 17.0 mg, and its estimated purity by LCMS analysis was 100%.

Analysis LCMS Condition H: Retention time=1.455 min; ESI-MS(+) m/z 964.65 (M+2H).

Analysis LCMS Condition I: Retention time=2.809 min; ESI-MS(+) m/z 964.75 (M+2H).

Preparation of Example 1519

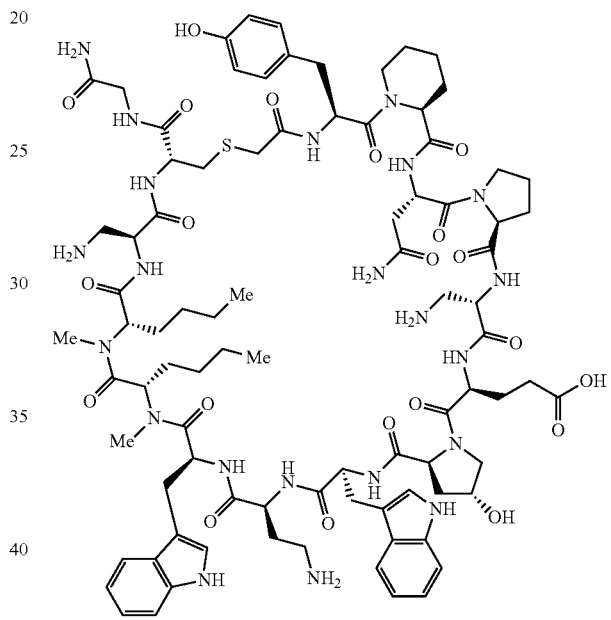

Molecular Weight: 1844.10

Example 1519 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 28.3 mg, and its estimated purity by LCMS analysis was 100%.

Analysis LCMS Condition H: Retention time=1.551 min; ESI-MS(+) m/z 922.85 (M+2H).

Analysis LCMS Condition I: Retention time=3.012 min; ESI-MS(+) m/z 922.90 (M+2H).

Preparation of Example 1520

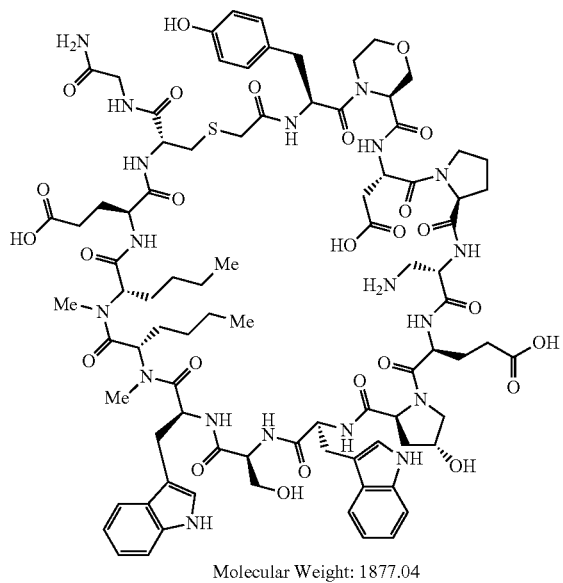 [SMILES: CCCC[C@H]1C(=O)N(C)[C@@H](CCCC)C(=O)N[C@@H](CCC(=O)O)C(=O)N[C@H](C(=O)NCC(N)=O)CSCC(=O)N[C@@H](Cc2ccc(O)cc2)C(=O)N2CCOC[C@H]2C(=O)N[C@@H](CC(=O)O)C(=O)N2CCC[C@H]2C(=O)N[C@@H](CN)C(=O)N[C@@H](CCC(=O)O)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

Molecular Weight: 1877.04

Example 1520 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-65% B over 25 minutes, then a 5-minute hold at 100% B; Flow: 20 mL/min. Fractions containing the desired product were combined and dried via centrifugal evaporation. The yield of the product was 8.4 mg, and its estimated purity by LCMS analysis was 100%.

Analysis LCMS Condition D: Retention time=1.30 min; ESI-MS(+) m/z 939.6 (M+2H).
Analysis LCMS Condition E: Retention time=1.40 min; ESI-MS(+) m/z 939.4 (M+2H).

Preparation of Example 1521

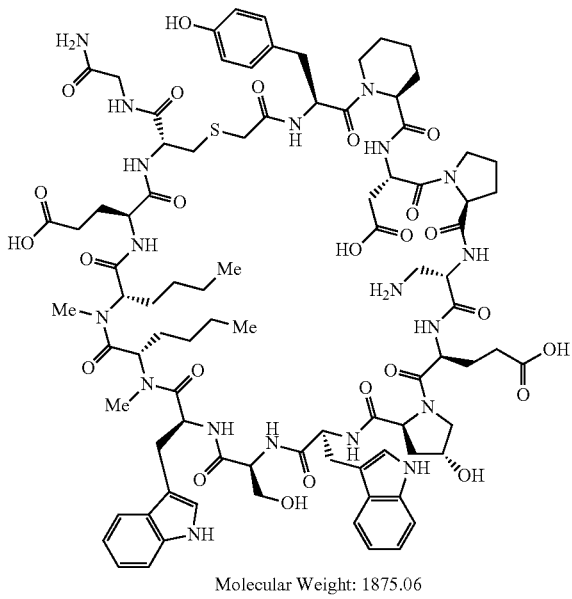 [SMILES: CCCC[C@H]1C(=O)N(C)[C@@H](CCCC)C(=O)N[C@@H](CCC(=O)O)C(=O)N[C@H](C(=O)NCC(N)=O)CSCC(=O)N[C@@H](Cc2ccc(O)cc2)C(=O)N2CCCC[C@H]2C(=O)N[C@@H](CC(=O)O)C(=O)N2CCC[C@H]2C(=O)N[C@@H](CN)C(=O)N[C@@H](CCC(=O)O)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

Molecular Weight: 1875.06

Example 1521 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 8.9 mg, and its estimated purity by LCMS analysis was 97%.

Analysis LCMS Condition H: Retention time=1.525 min; ESI-MS(+) m/z 938.15 (M+2H).
Analysis LCMS Condition I: Retention time=2.936 min; ESI-MS(+) m/z 938.05 (M+2H).

Preparation of Example 1522

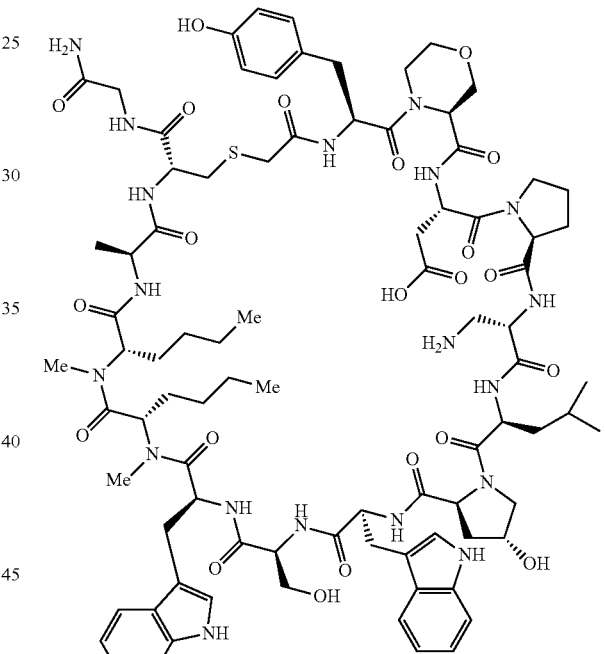

Molecular Weight: 1802.06

Example 1522 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 11.0 mg, and its estimated purity by LCMS analysis was 100%.

Analysis LCMS Condition H: Retention time=1.637 min; ESI-MS(+) m/z 901.95 (M+2H).

Analysis LCMS Condition I: Retention time=3.038 min; ESI-MS(+) m/z 901.75 (M+2H).

Preparation of Example 1523

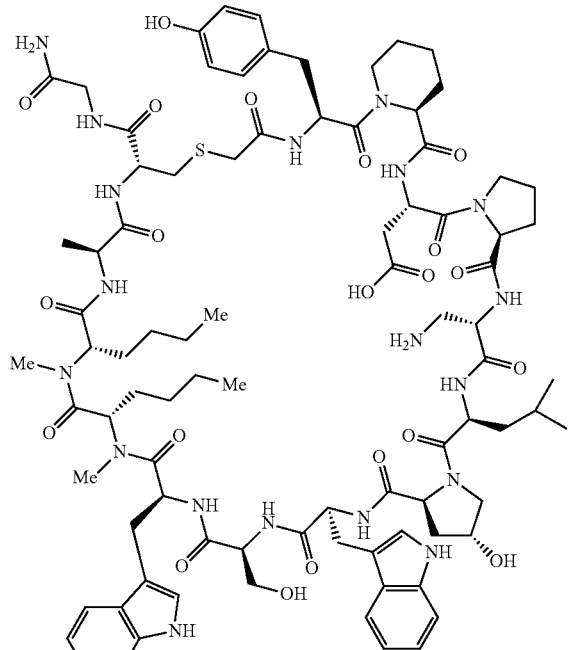

Molecular Weight: 1800.09

Example 1523 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 2.6 mg, and its estimated purity by LCMS analysis was 92%.

Analysis LCMS Condition H: Retention time=1.683 min; ESI-MS(+) m/z 900.80 (M+2H).

Analysis LCMS Condition I: Retention time=3.098 min; ESI-MS(+) m/z 900.60 (M+2H).

Preparation of Example 1525

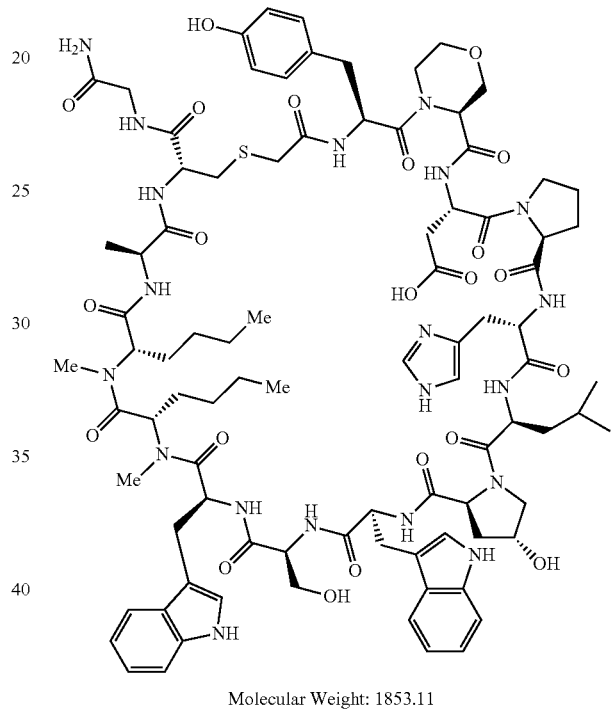

Molecular Weight: 1853.11

Example 1525 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 16.0 mg, and its estimated purity by LCMS analysis was 100%.

Analysis LCMS Condition H: Retention time=1.643 min; ESI-MS(+) m/z 927.20 (M+2H).

Analysis LCMS Condition I: Retention time=2.250 min; ESI-MS(+) m/z 926.85 (M+2H).

Preparation of Example 1526

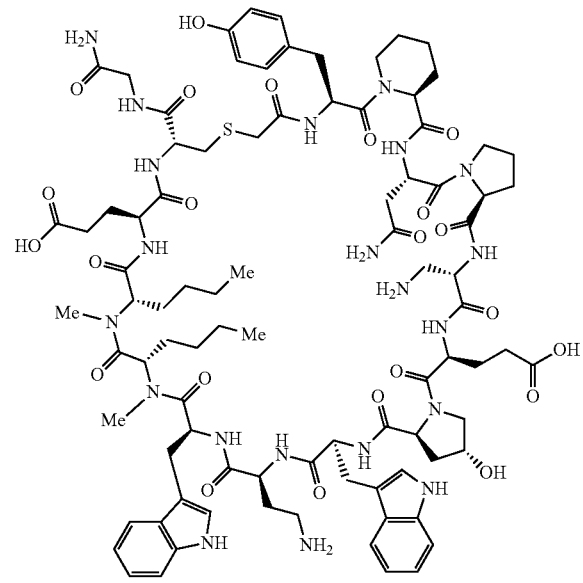

Molecular Weight: 1887.12

Example 1526 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-65% B over 25 minutes, then a 5-minute hold at 100% B; Flow: 20 mL/min. Fractions containing the desired product were combined and dried via centrifugal evaporation. The yield of the product was 3.0 mg, and its estimated purity by LCMS analysis was 94%.

Analysis LCMS Condition D: Retention time=1.39 min; ESI-MS(+) m/z 944.3 (M+2H).

Analysis LCMS Condition E: Retention time=1.44 min; ESI-MS(+) m/z 944.2 (M+2H).

Preparation of Example 1528

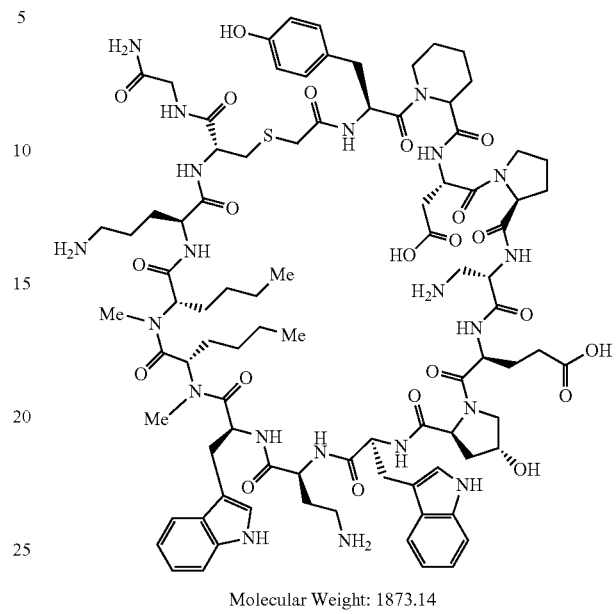

Molecular Weight: 1873.14

Example 1528 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-60% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-60% B over 25 minutes, then a 5-minute hold at 100% B; Flow: 20 mL/min. Fractions containing the desired product were combined and dried via centrifugal evaporation. The yield of the product was 2.1 mg, and its estimated purity by LCMS analysis was 95%.

Analysis LCMS Condition D: Retention time=1.43 min; ESI-MS(+) m/z 937.1 (M+2H).

Analysis LCMS Condition E: Retention time=1.41 min; ESI-MS(+) m/z 937.5 (M+2H).

Preparation of Example 1529

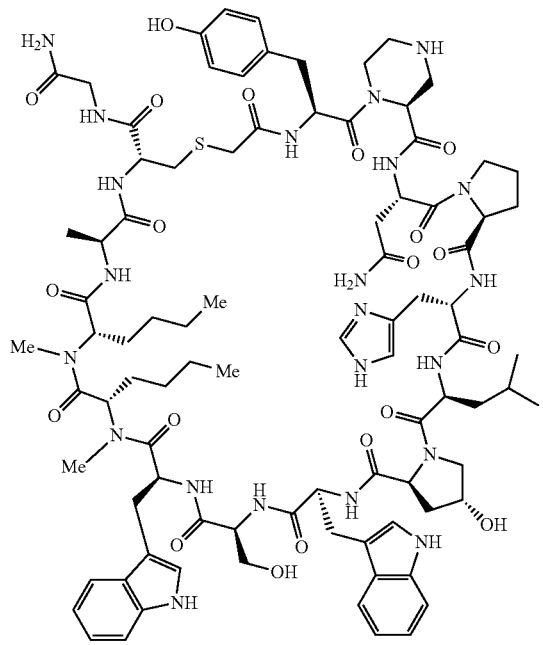

Molecular Weight: 1852.12

Example 1529 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-60% B over 25 minutes, then a 5-minute hold at 100% B; Flow: 20 mL/min. Fractions containing the desired product were combined and dried via centrifugal evaporation. The yield of the product was 13.1 mg, and its estimated purity by LCMS analysis was 91%.

Analysis LCMS Condition D: Retention time=1.44 min; ESI-MS(+) m/z 927.0 (M+2H).

Analysis LCMS Condition E: Retention time=1.35 min; ESI-MS(+) m/z 926.8 (M+2H).

Preparation of Example 1530

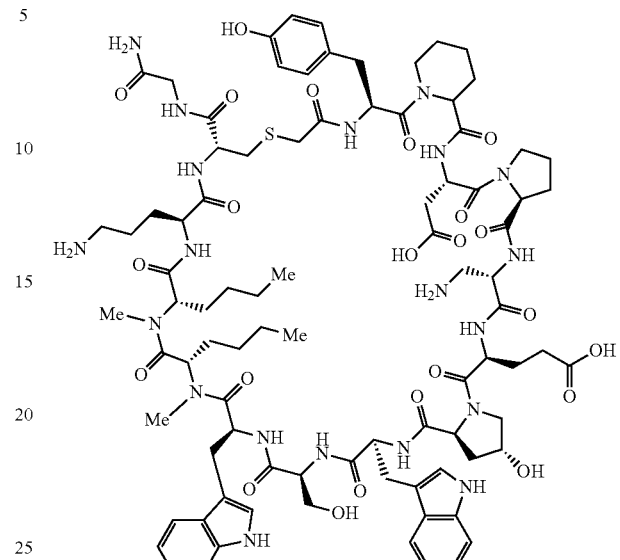

Molecular Weight: 1860.10

Example 1530 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: waters xbridge c-18, 19×200 mm, 5-μm particles; Mobile Phase A: 5:95 methanol:water with 0.1% trifluoroacetic acid; Mobile Phase B: 95:5 methanol:water with 0.1% trifluoroacetic acid; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 30 minutes, then a 5-minute hold at 100% B; Flow: 20 mL/min. Fractions containing the desired product were combined and dried via centrifugal evaporation. The yield of the product was 11.9 mg, and its estimated purity by LCMS analysis was 100%.

Analysis LCMS Condition H: Retention time=1.57 min; ESI-MS(+) m/z 931.9 (M+2H).

Analysis LCMS Condition I: Retention time=2.70 min; ESI-MS(+) m/z 931.2 (M+2H).

Preparation of Example 1531

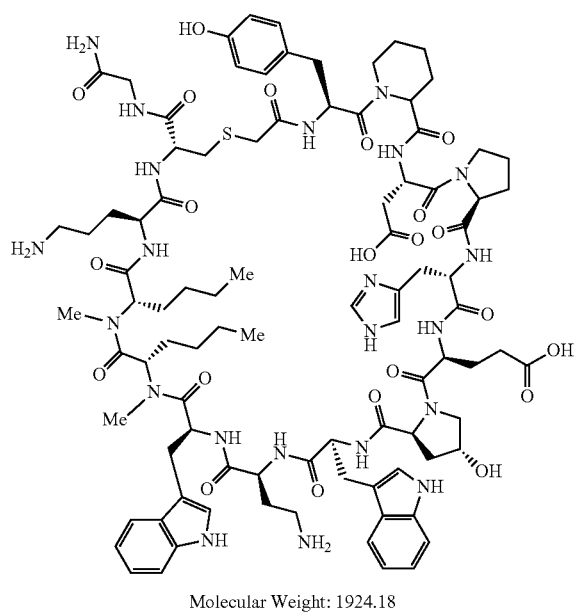 [SMILES: CCCC[C@H]1C(=O)N(C)[C@@H](CCCC)C(=O)N[C@@H](CCCN)C(=O)N[C@H](C(=O)NCC(N)=O)CSCC(=O)N[C@@H](Cc2ccc(O)cc2)C(=O)N2CCCCC2C(=O)N[C@@H](CC(=O)O)C(=O)N2CCC[C@H]2C(=O)N[C@@H](Cc2c[nH]cn2)C(=O)N[C@@H](CCC(=O)O)C(=O)N2C[C@H](O)C[C@H]2C(=O)N[C@@H](Cc2c[nH]c3ccccc23)C(=O)N[C@@H](CCN)C(=O)N[C@@H](Cc2c[nH]c3ccccc23)C(=O)N1C]

Molecular Weight: 1924.18

Example 1531 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-60% B over 25 minutes, then a 5-minute hold at 100% B; Flow: 20 mL/min. Fractions containing the desired product were combined and dried via centrifugal evaporation. The yield of the product was 1.2 mg, and its estimated purity by LCMS analysis was 98%.

Analysis LCMS Condition D: Retention time=1.34 min; ESI-MS(+) m/z 963.0 (M+2H).

Analysis LCMS Condition E: Retention time=1.35 min; ESI-MS(+) m/z 962.6 (M+2H).

Preparation of Example 1532

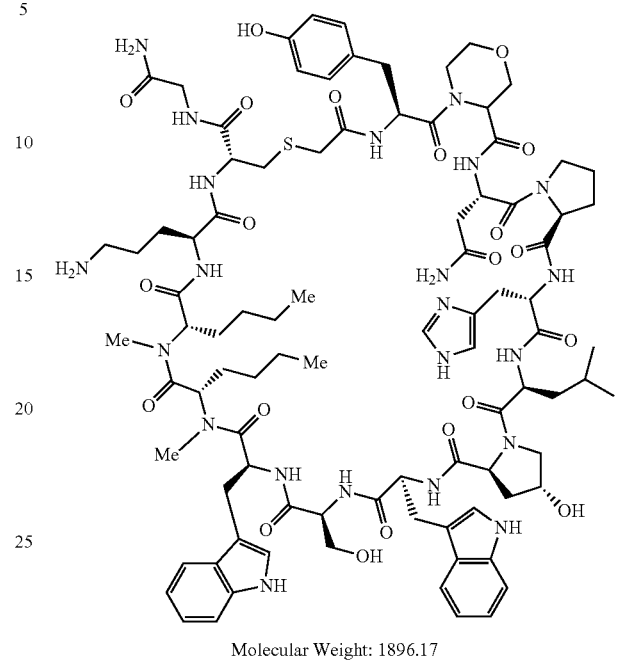

Molecular Weight: 1896.17

Example 1532 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: waters xbridge c-18, 19×200 mm, 5-μm particles; Mobile Phase A: 5:95 methanol:water with 0.1% trifluoroacetic acid; Mobile Phase B: 95:5 methanol:water with 0.1% trifluoroacetic acid; Gradient: 40-80% B over 30 minutes, then a 5-minute hold at 100% B; Flow: 20 mL/min. Fractions containing the desired product were combined and dried via centrifugal evaporation. The yield of the product was 12.2 mg, and its estimated purity by LCMS analysis was 94%.

Analysis LCMS Condition H: Retention time=1.48 min; ESI-MS(+) m/z 949.4 (M+2H).

Analysis LCMS Condition I: Retention time=2.57 min; ESI-MS(+) m/z 949.0 (M+2H).

Preparation of Example 1533

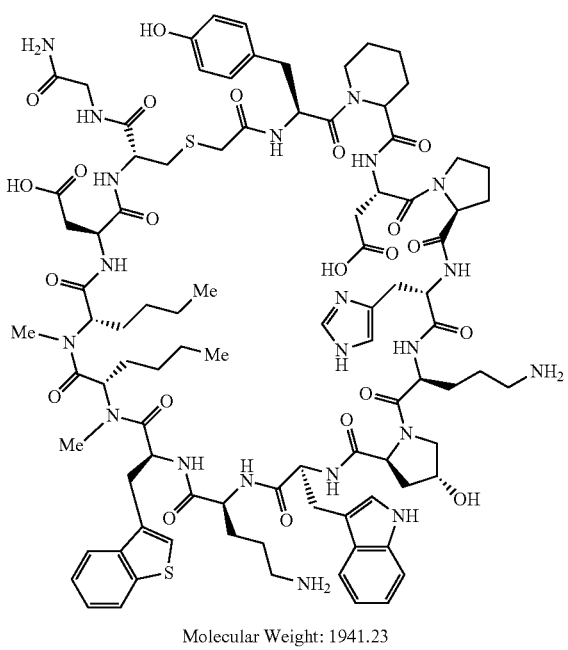 [SMILES: CCCC[C@H]1C(=O)N(C)[C@@H](CCCC)C(=O)N[C@@H](CC(=O)O)C(=O)N[C@H](C(=O)NCC(N)=O)CSCC(=O)N[C@@H](Cc2ccc(O)cc2)C(=O)N2CCCCC2C(=O)N[C@@H](CC(=O)O)C(=O)N2CCC[C@H]2C(=O)N[C@@H](Cc2c[nH]cn2)C(=O)N[C@@H](CCCN)C(=O)N2C[C@H](O)C[C@H]2C(=O)N[C@@H](Cc2c[nH]c3ccccc23)C(=O)N[C@@H](CCCN)C(=O)N[C@@H](Cc2csc3ccccc23)C(=O)N1C]

Molecular Weight: 1941.23

Example 1533 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: waters xbridge c-18, 19×200 mm, 5-µm particles; Mobile Phase A: 5:95 methanol:water with 0.1% trifluoroacetic acid; Mobile Phase B: 95:5 methanol:water with 0.1% trifluoroacetic acid; Gradient: 45-85% B over 30 minutes, then a 5-minute hold at 100% B; Flow: 20 mL/min. Fractions containing the desired product were combined and dried via centrifugal evaporation. The yield of the product was 6.9 mg, and its estimated purity by LCMS analysis was 100%.

Analysis LCMS Condition H: Retention time=1.63 min; ESI-MS(+) m/z 971.6 (M+2H).

Analysis LCMS Condition I: Retention time=2.87 min; ESI-MS(+) m/z 971.9 (M+2H).

Preparation of Example 1534

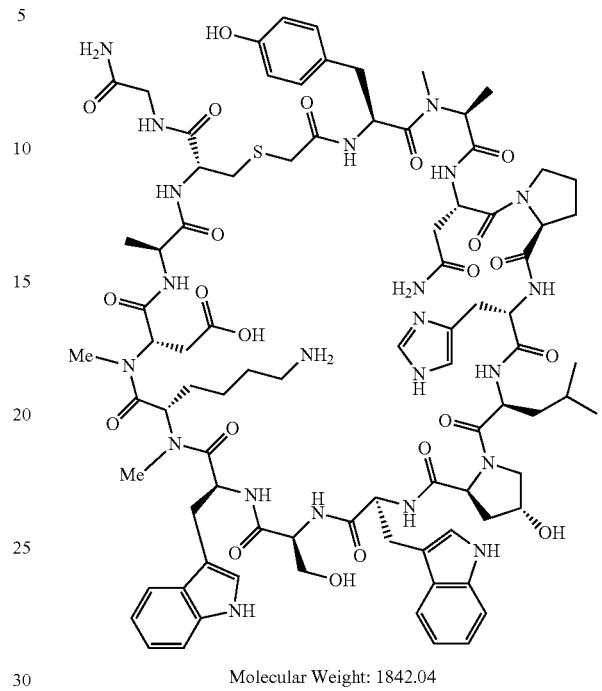

Molecular Weight: 1842.04

Example 1534 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 0-50% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 0-45% B over 25 minutes, then a 5-minute hold at 100% B; Flow: 20 mL/min. Fractions containing the desired product were combined and dried via centrifugal evaporation. The yield of the product was 1.1 mg, and its estimated purity by LCMS analysis was 95%.

Analysis LCMS Condition D: Retention time=0.94 min; ESI-MS(+) m/z 922.1 (M+2H).

Analysis LCMS Condition E: Retention time=0.97 min; ESI-MS(+) m/z 921.5 (M+2H).

Preparation of Example 1535

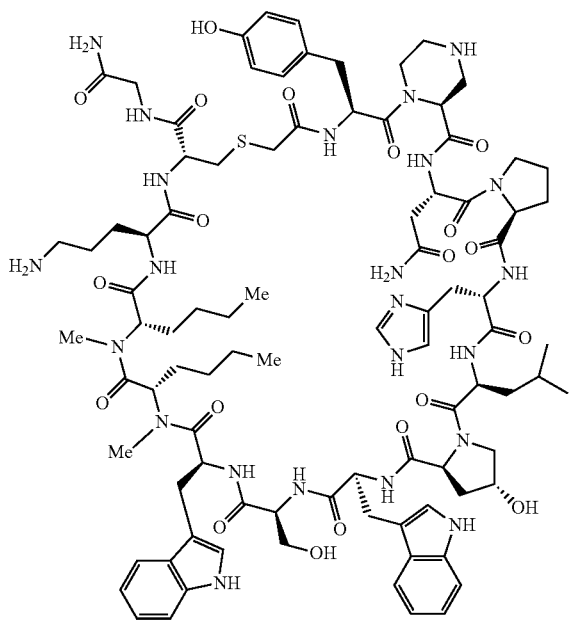

Molecular Weight: 1895.19

Example 1535 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-60% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 5-50% B over 25 minutes, then a 5-minute hold at 100% B; Flow: 20 mL/min. Fractions containing the desired product were combined and dried via centrifugal evaporation. The yield of the product was 3.0 mg, and its estimated purity by LCMS analysis was 100%.

Analysis LCMS Condition D: Retention time=1.32 min; ESI-MS(+) m/z 948.5 (M+2H).

Analysis LCMS Condition E: Retention time=1.21 min; ESI-MS(+) m/z 948.7 (M+2H).

Preparation of Example 1536

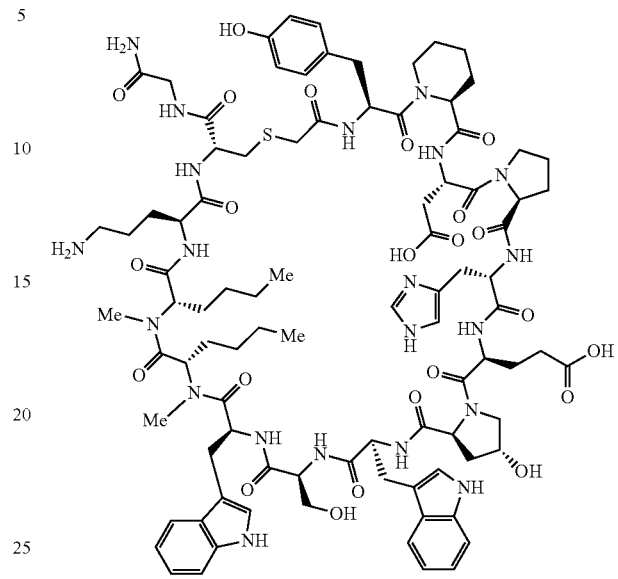

Molecular Weight: 1911.14

Example 1536 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-60% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-60% B over 25 minutes, then a 5-minute hold at 100% B; Flow: 20 mL/min. Fractions containing the desired product were combined and dried via centrifugal evaporation. The yield of the product was 1.6 mg, and its estimated purity by LCMS analysis was 99%.

Analysis LCMS Condition D: Retention time=1.32 min; ESI-MS(+) m/z 956.7 (M+2H).

Analysis LCMS Condition E: Retention time=1.43 min; ESI-MS(+) m/z 956.7 (M+2H).

Preparation of Example 1537

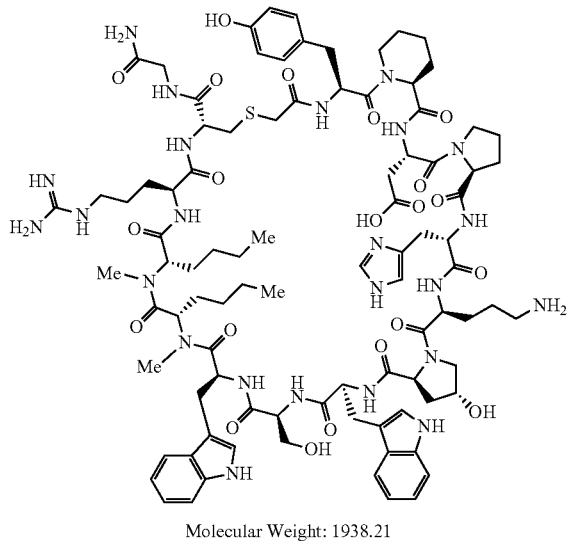 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(O)cc2)C(=O)N2CCCC[C@H]2C(=O)N[C@@H](CC(=O)O)C(=O)N2CCC[C@H]2C(=O)N[C@@H](Cc2c[nH]cn2)C(=O)N[C@@H](CCCN)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

Molecular Weight: 1938.21

Example 1537 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-60% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-55% B over 25 minutes, then a 5-minute hold at 100% B; Flow: 20 mL/min. Fractions containing the desired product were combined and dried via centrifugal evaporation. The yield of the product was 1.9 mg, and its estimated purity by LCMS analysis was 99%.

Analysis LCMS Condition D: Retention time=1.42 min; ESI-MS(+) m/z 969.7 (M+2H).

Analysis LCMS Condition E: Retention time=1.40 min; ESI-MS(+) m/z 969.7 (M+2H).

Preparation of Example 1538

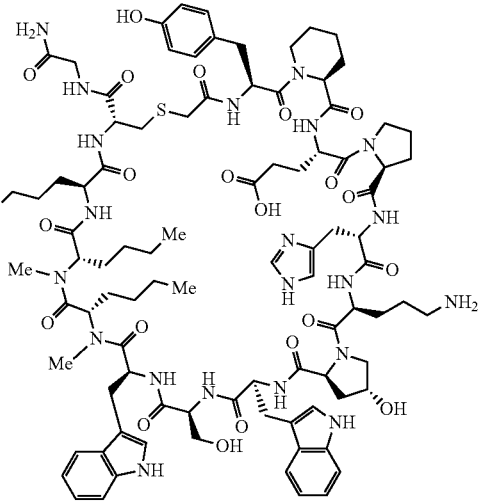

Molecular Weight: 1952.24

Example 1538 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-60% B over 25 minutes, then a 5-minute hold at 100% B; Flow: 20 mL/min. Fractions containing the desired product were comb fined and dried via centrifugal evaporation. The yield of the product was 5.5 mg, and its estimated purity by LCMS analysis was 100%.

Analysis LCMS Condition D: Retention time=1.38 min; ESI-MS(+) m/z 977.6 (M+2H).

Analysis LCMS Condition E: Retention time=1.31 min; ESI-MS(+) m/z 976.7 (M+2H).

Preparation of Example 1541

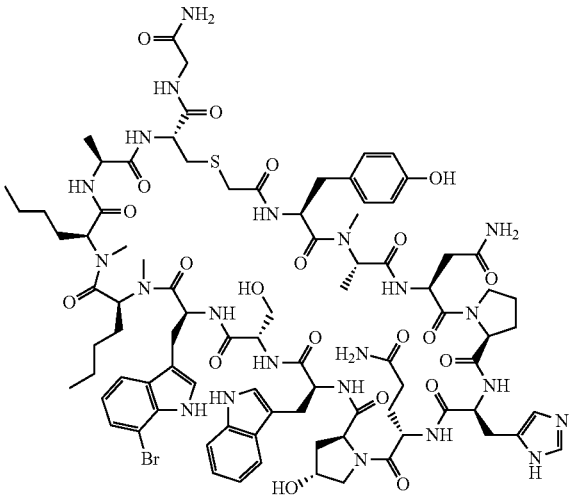

Molecular Weight: 1918.96

Example 1541 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 30 minutes, then a 5-minute hold at 100% B; Flow: 20 mL/min. Fractions containing the desired product were combined and dried via centrifugal evaporation. The yield of the product was 2.4 mg, and its estimated purity by LCMS analysis was 96%.

Analysis LCMS Condition I: Retention time=2.87 min; ESI-MS(+) m/z 960.7 (M+2H).

Preparation of Example 1542

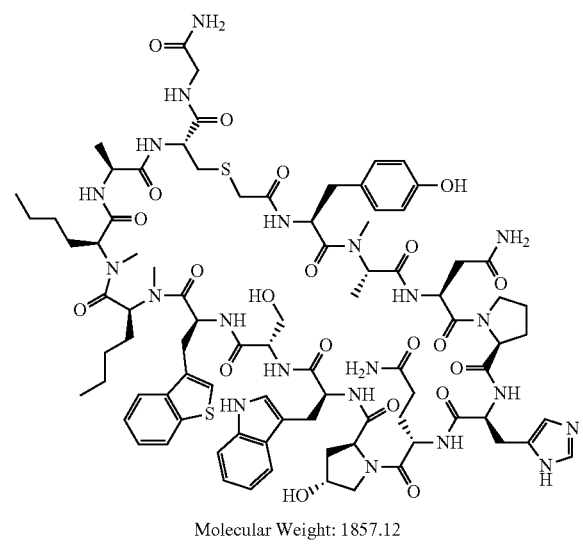 [SMILES: CCCC[C@H]1C(=O)N(C)[C@@H](CCCC)C(=O)N[C@@H](C)C(=O)N[C@H](C(=O)NCC(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CCC(N)=O)C(=O)N2C[C@H](O)C[C@H]2C(=O)N[C@@H](Cc2c[nH]c3ccccc23)C(=O)N[C@@H](CO)C(=O)N[C@@H](Cc2csc3ccccc23)C(=O)N1C]

Molecular Weight: 1857.12

Example 1542 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 5.7 mg, and its estimated purity by LCMS analysis was 97%.

Analysis LCMS Condition H: Retention time=1.769 min; ESI-MS(+) m/z 929.30 (M+2H).

Analysis LCMS Condition I: Retention time=3.313 min; ESI-MS(+) m/z 929.30 (M+2H).

Analytical Data:

Mass Spectrometry: "ESI-MS(+)" signifies electrospray ionization mass spectrometry performed in positive ion mode; "ESI-MS(−)" signifies electrospray ionization mass spectrometry performed in negative ion mode; "ESI-HRMS (+)" signifies high-resolution electrospray ionization mass spectrometry performed in positive ion mode; "ESI-HRMS (−)" signifies high-resolution electrospray ionization mass spectrometry performed in negative ion mode. The detected masses are reported following the "m/z" unit designation. Compounds with exact masses greater than 1000 were often detected as double-charged or triple-charged ions.

Analysis LCMS Condition A:
Column: Waters BEH C18, 2.1×50 mm, 1.7-μm particles; Mobile Phase A: water with 0.05% TFA; Mobile Phase B: Acetonitrile with 0.05% TFA; Temperature: 50° C.; Gradient: 2% B to 98% B over 2 min., then a 0.5 min. hold at 98% B; Flow: 0.8 mL/min; Detection: UV at 220 nm.

Analysis LCMS Condition C:
Column: Waters BEH C18, 2.1×50 mm, 1.7-μm particles; Mobile Phase A: water with 0.2% Formic Acid and 0.01% TFA; Mobile Phase B: Acetonitrile with 0.2% Formic acid an 0.01% TFA; Temperature: 50° C.; Gradient: 2% B to 80% B over 2 min., 80% B to 98% B over 0.1 minute then a 0.5 min. hold at 98% B; Flow: 0.8 mL/min; Detection: UV at 220 nm.

Analysis LCMS Condition D:
Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min., then a 0.75-minute hold at 100% B; Flow: 1.0 mL/min; Detection: UV at 220 nm.

Analysis LCMS Condition E:
Column: Waters BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; temperature: 50° C.; Gradient: 0-100% B over 3 min., then a 0.75-minute hold at 100% B; Flow: 1.11 mL/min; Detection: UV at 220 nm.

Analysis LCMS Condition F:
Column: Waters XBridge C18, 2.1×50 mm; Mobile Phase A: 5:95 acetonitrile:water with 10 mM ammonium acetate; Mobile Phase B: 95:5 acetonitrile:water with 10 mM ammonium acetate; Temperature: 35° C.; Gradient: 0-100% B over 4 min., then a 1-minute hold at 100% B; Flow: 4 mL/min; Detection: UV at 220 nm.

Analysis LCMS Condition G:
Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0-100% B over 3 min., then a 0.5-minute hold at 100% B; Flow: 0.5 mL/min; Detection: UV at 220 nm.

Analysis HPLC Condition B:
Column: YMC Pack ODS-AQ 3 um 150×4.6 mm; Mobile Phase A: water with 0.1% TFA; Mobile Phase B: Acetonitrile with 0.1% TFA; Temperature: 40° C.; Gradient: from 10% B to 100% B over 10 to 40 min.; Flow rate: 1 mL/min; Detection: UV at 220 nm.

General Procedures:
Prelude Method A:
All manipulations were performed under automation on a Prelude peptide synthesizer (Protein Technologies). All procedures unless noted were performed in a 10 or 45 mL polypropylene tube fitted with a bottom frit. The tube connects to the Prelude peptide synthesizer through both the bottom and the top of the tube. DMF and DCM can be added through the top of the tube, which washes down the sides of the tube equally. The remaining reagents are added through the bottom of the tube and pass up through the frit to contact the resin. All solutions are removed through the bottom of the tube. "Periodic agitation" describes a brief pulse of N2 gas through the bottom frit; the pulse lasts approximately 5 seconds and occurs every 30 seconds. Amino acid solutions were generally not used beyond three weeks from preparation. HATU solution was used within 5 days of preparation. DMF=dimethylformamide; HCTU=2-(6-Chloro-1-H-benzotriazol-1-yl)-1,1,3,3-tetramethyluronium; HATU=1-[Bis(dimethylamino)methylene]-1H-1,2,3-triazolo[4,5-b]pyridinium 3-oxid hexafluorophosphate; NMM=N-methylmorpholine; Sieber=Fmoc-amino-xanthen-3-yloxy, where "3-yloxy" describes the position and type of connectivity to the polystyrene resin. The resin used is Merrifield polymer (polystyrene) with a Sieber linker (Fmoc-protected at nitrogen); 100-200 mesh, 1% DVB, 0.71 mmol/g loading. Common amino acids used are listed below with side-chain protecting groups indicated inside parenthesis.

Fmoc-Ala-OH; Fmoc-Arg(Pbf)-OH; Fmoc-Asn(Trt)-OH; Fmoc-Asp(OtBu)-OH; Fmoc-Bzt-OH; Fmoc-Cys(Trt)-OH; Fmoc-Dab(Boc)-OH; Fmoc-Dap(Boc)-OH; Fmoc-Gln(Trt)-OH; Fmoc-Gly-OH; Fmoc-His(Trt)-OH; Fmoc-Ile-OH; Fmoc-Leu-OH; Fmoc-Lys(Boc)-OH; Fmoc-Nle-OH; Fmoc[N-Me]Ala-OH; Fmoc[N-Me]Nle-OH; Fmoc-Phe-OH; Fmoc-Pro-OH; Fmoc-(D)-cis-Pro(4-OtBu)-OH; Fmoc-(D)-trans-Pro(4-OtBu)-OH; Fmoc-Sar-OH; Fmoc-Ser(tBu)-OH; Fmoc-Thr(tBu)-OH; Fmoc-Trp(Boc)-OH; Fmoc-Tyr(tBu)-OH; Fmoc-Val-OH.

The procedures of "Prelude Method A" describe an experiment performed on a 0.100 mmol scale, where the scale is determined by the amount of Sieber linker bound to the resin. This scale corresponds to approximately 140 mg of the Sieber-Merrifield resin described above. All procedures can be scaled beyond 0.100 mmol scale by adjusting the described volumes by the multiple of the scale. Prior to amino acid coupling, all peptide synthesis sequences began with a resin-swelling procedure, described below as "Resin-swelling procedure". Coupling of amino acids to a primary amine N-terminus used the "Single-coupling procedure" described below. Coupling of amino acids to a secondary amine N-terminus used the "Secondary amine-coupling procedure" described below. Coupling of chloroacetyl group to the N-terminus of the peptide is described by the "Chloroacetyl chloride coupling procedure" or "Chloroacetic acid coupling procedure" detailed below.

Resin-Swelling Procedure:

To a 40 mL polypropylene solid-phase reaction vessel was added Merrifield Sieber resin (140 mg, 0.100 mmol). The resin was washed (swelled) three times as follows: to the reaction vessel was added DMF (5.0 mL) and DCM (5.0 mL), upon which the mixture was periodically agitated with N2 bubbling from the bottom of the reaction vessel for 10 min. before the solvent was drained through the frit.

Single-Coupling Procedure:

To the reaction vessel containing resin from the previous step was added piperidine:DMF (20:80 v/v, 5.0 mL). The mixture was periodically agitated for 3 or 5 min. and then the solution was drained through the frit. To the reaction vessel was added piperidine:DMF (20:80 v/v, 5.0 mL). The mixture was periodically agitated for 3 or 5 min. and then the solution was drained through the frit. The resin was washed successively five times as follows: for each wash, DMF (4.0 mL) was added through the top of the vessel and the resulting mixture was periodically agitated for 60 seconds before the solution was drained through the frit. To the reaction vessel was added the amino acid (0.2M in DMF, 5.0 mL, 10 eq), then HATU or HCTU (0.2M in DMF, 5.0 mL, 10 eq), and finally NMM (0.8M in DMF, 2.5 mL, 20 eq). The mixture was periodically agitated for 60 min., then the reaction solution was drained through the frit. The resin was washed successively four times as follows: for each wash, DMF (4.0 mL) was added through the top of the vessel and the resulting mixture was periodically agitated for 30 seconds before the solution was drained through the frit. To the reaction vessel was added a solution of acetic anhydride:DIEA:DMF (10:1:89 v/v/v, 5.0 mL). The mixture was periodically agitated for 10 min., then the solution was drained through the frit. The resin was washed successively four times as follows: for each wash, DMF (4.0 mL) was added through the top of the vessel and the resulting mixture was periodically agitated for 90 seconds before the solution was drained through the frit. The resulting resin was used directly in the next step.

Secondary Amine-Coupling Procedure:

To the reaction vessel containing resin from the previous step was added piperidine:DMF (20:80 v/v, 5.0 mL). The mixture was periodically agitated for 3 or 5 min. and then the solution was drained through the frit. To the reaction vessel was added piperidine:DMF (20:80 v/v, 5.0 mL). The mixture was periodically agitated for 3 or 5 min. and then the solution was drained through the frit. The resin was washed successively five times as follows: for each wash, DMF (4.0 mL) was added through the top of the vessel and the resulting mixture was periodically agitated for 30 seconds before the solution was drained through the frit. To the reaction vessel was added the amino acid (0.2M in DMF, 2.5 mL, 5 eq), then HATU (0.2M in DMF, 2.5 mL, 5 eq), and finally NMM (0.8M in DMF, 1.5 mL, 12 eq). The mixture was periodically agitated for 300 min., then the reaction solution was drained through the frit. The resin was twice washed as follows: for each wash, DMF (4.0 mL) was added through the top of the vessel and the resulting mixture was periodically agitated for 30 seconds before the solution was drained through the frit. To the reaction vessel was added a solution of acetic anhydride:DIEA:DMF (10:1:89 v/v/v, 5.0 mL). The mixture was periodically agitated for 10 min., then the solution was drained through the frit. The resin was washed successively four times as follows: for each wash, DMF (4.0 mL) was added through the top of the vessel and the resulting mixture was periodically agitated for 90 seconds before the solution was drained through the frit. The resulting resin was used directly in the next step.

Custom Amino Acids-Coupling Procedure:

To the reaction vessel containing resin from the previous step was added piperidine:DMF (20:80 v/v, 5.0 mL). The mixture was periodically agitated for 3 or 5 min. and then the solution was drained through the frit. To the reaction vessel was added piperidine:DMF (20:80 v/v, 5.0 mL). The mixture was periodically agitated for 3 or 5 min. and then the solution was drained through the frit. The resin was washed successively five times as follows: for each wash, DMF (4.0 mL) was added through the top of the vessel and the resulting mixture was periodically agitated for 30 seconds before the solution was drained through the frit. To the reaction vessel was added the amino acid (0.2M in DMF, 0.5 to 2.5 mL, 1 to 5 eq), then HATU (0.2M in DMF, 0.5 to 2.5 mL, 1 to 5 eq), and finally DIPEA (0.8M in DMF, 0.5 to 1.5 mL, 4 to 12 eq). The mixture was periodically agitated for 60 min. to 600 min., then the reaction solution was drained through the frit. The resin was twice washed as follows: for each wash, DMF (2.0 mL) was added through the top of the vessel and the resulting mixture was periodically agitated for 30 seconds before the solution was drained through the frit. To the reaction vessel was added a solution of acetic anhydride:DIEA:DMF (10:1:89 v/v/v, 5.0 mL). The mixture was periodically agitated for 10 min., then the solution was drained through the frit. The resin was washed successively four times as follows: for each wash, DMF (4.0 mL) was added through the top of the vessel and the resulting mixture was periodically agitated for 90 seconds before the solution was drained through the frit. The resulting resin was used directly in the next step.

Chloroacetyl Chloride Coupling Procedure A:

To the reaction vessel containing the resin from the previous step was added piperidine:DMF (20:80 v/v, 5.0 mL). The mixture was periodically agitated for 3 min. and then the solution was drained through the frit. To the reaction vessel was added piperidine:DMF (20:80 v/v, 5.0 mL). The mixture was periodically agitated for 3 min. and then the solution was drained through the frit. The resin was washed successively five times as follows: for each wash, DMF (4.0 mL) was added through the top of the vessel and the resulting mixture was periodically agitated for 30 seconds before the solution was drained through the frit. To the reaction vessel was added 3.0 mL of a solution of DIPEA (4.0 mmol, 0.699 mL, 40 eq), and chloroacetyl chloride (2.0 mmol, 0.160 mL, 20 eq) in DMF. The mixture was periodically agitated for 12 to 18 hours, then the solution was drained through the frit. The resin was washed successively three times as follows: for each wash, DMF (4.0 mL) was added to top of the vessel and the resulting mixture was periodically agitated for 90 seconds before the solution was drained through the frit. The resin was washed successively four times as follows: for each wash, $CH_2Cl_2$ (2.0 mL) was added to top of the vessel and the resulting mixture was periodically agitated for 90 seconds before the solution was drained through the frit.

Chloroacetic Acid Coupling Procedure A:

To the reaction vessel containing the resin from the previous step was added piperidine:DMF (20:80 v/v, 5.0 mL). The mixture was periodically agitated for 3 min. and then the solution was drained through the frit. To the reaction vessel was added piperidine:DMF (20:80 v/v, 5.0 mL). The mixture was periodically agitated for 3 min. and then the solution was drained through the frit. The resin was washed successively five times as follows: for each wash, DMF (4.0 mL) was added through the top of the vessel and the resulting mixture was periodically agitated for 30 seconds before the solution was drained through the frit. To the reaction vessel was added DMF (2.0 mL), chloroacetic acid (1.2 mmol, 113 mg, 12 eq), and N,N'-Diisopropylcarbodiimide (1.2 mmol, 0.187 mL, 12 eq). The mixture was periodically agitated for 12 to 18 hours, then the solution was drained through the frit. The resin was washed successively three times as follows: for each wash, DMF (4.0 mL) was added to top of the vessel and the resulting mixture was periodically agitated for 90 seconds before the solution was drained through the frit. The resin was washed successively four times as follows: for each wash, $CH_2Cl_2$ (2.0 mL) was added to top of the vessel and the resulting mixture was periodically agitated for 90 seconds before the solution was drained through the frit.

CEM Method A:

All manipulations were performed under automation on a CEM Liberty microwave peptide synthesizer (CEM Corporation). All procedures unless noted were performed in a 30 or 125 mL polypropylene tube fitted with a bottom frit to a CEM Discovery microwave unit. The tube connects to the CEM Liberty synthesizer through both the bottom and the top of the tube. DMF and DCM can be added through the top and bottom of the tube, which washes down the sides of the tube equally. All solutions are removed through the bottom of the tube except while transferring resin from the top. "Periodic bubbling" describes a brief bubbling of N2 gas through the bottom frit. Amino acid solutions were generally not used beyond three weeks from preparation. HATU solution was used within 5 days of preparation. DMF=dimethylformamide; HCTU=2-(6-Chloro-1-H-benzotriazol-1-yl)-1,1,3,3-tetramethyluronium; HATU=1-[Bis(dimethylamino)methylene]-1H-1,2,3-triazolo[4,5-b]pyridinium 3-oxid hexafluorophosphate; DIPEA=diisopropylethylamine; Sieber=Fmoc-amino-xanthen-3-yloxy, where "3-yloxy" describes the position and type of connectivity to the polystyrene resin. The resin used is Merrifield polymer (polystyrene) with a Sieber linker (Fmoc-protected at nitrogen); 100-200 mesh, 1% DVB, 0.71 mmol/g loading. Common amino acids used are listed below with side-chain protecting groups indicated inside parenthesis.

Fmoc-Ala-OH; Fmoc-Arg(Pbf)-OH; Fmoc-Asn(Trt)-OH; Fmoc-Asp(OtBu)-OH; Fmoc-Bzt-OH; Fmoc-Cys(Trt)-OH; Fmoc-Dab(Boc)-OH; Fmoc-Dap(Boc)-OH; Fmoc-Gln(Trt)-OH; Fmoc-Gly-OH; Fmoc-His(Trt)-OH; Fmoc-Hyp(tBu)-OH; Fmoc-Ile-OH; Fmoc-Leu-OH; Fmoc-Lys(Boc)-OH; Fmoc-Nle-OH; Fmoc-Met-OH; Fmoc-[N-Me]Ala-OH; Fmoc[N-Me]Nle-OH; Fmoc-Phe-OH; Fmoc-Pro-OH; Fmoc-Sar-OH; Fmoc-Ser(tBu)-OH; Fmoc-Thr(tBu)-OH; Fmoc-Trp(Boc)-OH; Fmoc-Tyr(tBu)-OH; Fmoc-Val-OH The procedures of "CEM Method A" describe an experiment performed on a 0.100 mmol scale, where the scale is determined by the amount of Sieber linker bound to the resin. This scale corresponds to approximately 140 mg of the Sieber-Merrifield resin described above. All procedures can be scaled beyond 0.100 mmol scale by adjusting the described volumes by the multiple of the scale. Prior to amino acid coupling, all peptide synthesis sequences began with a resin-swelling procedure, described below as "Resin-swelling procedure". Coupling of amino acids to a primary amine N-terminus used the "Single-coupling procedure" described below. Coupling of amino acids to a secondary amine N-terminus used the "Secondary amine-coupling procedure" described below. Coupling of chloroacetyl group to the N-terminus of the peptide is described by the "Chloroacetyl chloride coupling procedure" or "Chloroacetic acid coupling procedure" detailed above.

Resin-Swelling Procedure:

To 50 mL polypropylene conical tube was added Merrifield Sieber resin (140 mg, 0.100 mmol). Then DMF (7 mL) was added to the tube followed by DCM (7 mL). The resin was then transferred to the reaction vessel from top of the vessel. The procedure is repeated additionally two times. DMF (7 mL) was added followed by DCM (7 mL). The resin was allowed to swell with N2 bubbling from the bottom of the reaction vessel for 15 min. before the solvent was drained through the frit.

Standard Coupling Procedure:

To the reaction vessel containing resin from the previous step was added a solution of piperidine:DMF (20:80 v/v, 5.0 mL). The mixture was periodically agitated for 3 min. and then the solution was drained through the frit. To the reaction vessel was added a solution of piperidine:DMF (20:80 v/v, 5.0 mL). The mixture was periodically agitated for 3 min. and then the solution was drained through the frit. The resin was washed successively three times as follows: DMF (7 mL) wash from top, followed by DMF (7 mL) wash from bottom and finally with DMF (7 mL) wash from top. To the reaction vessel was added the amino acid (0.2M in DMF, 2.5 mL, 5 eq), HATU (0.5M in DMF, 1.0 mL, 5 eq), and DIPEA (2M in NMP, 0.5 mL, 10 eq). The mixture was mixed by N2 bubbling for 5 min. at 75° C. for all amino acids, except Fmoc-Cys(Trt)-OH and Fmoc-His(Trt)-OH which are coupled at 50° C., the reaction solution was drained through the frit. The resin was washed successively three times as follows: DMF (7 mL) wash from top, followed by DMF (7 mL) wash from bottom and finally with DMF (7 mL) wash from top. To the reaction vessel was added a solution of acetic anhydride:DIEA:DMF (10:1:89 v/v/v, 5.0 mL). The mixture was periodically bubbled for 2 min. at 65° C., then the solution was drained through the frit. The resin was washed successively three times as follows: DMF (7 mL) wash from top, followed by DMF (7 mL) wash from bottom and finally with DMF (7 mL) wash from top. The resulting resin was used directly in the next step.

Double-Couple Coupling Procedure:

To the reaction vessel containing resin from the previous step was added a solution of piperidine:DMF (20:80 v/v, 5.0 mL). The mixture was periodically agitated for 3 min. and then the solution was drained through the frit. To the reaction vessel was added a solution of piperidine:DMF (20:80 v/v, 5.0 mL). The mixture was periodically agitated for 3 min. and then the solution was drained through the frit. The resin was washed successively three times as follows: DMF (7 mL) wash from top, followed by DMF (7 mL) wash from bottom and finally with DMF (7 mL) wash from top. To the reaction vessel was added the amino acid (0.2M in DMF, 2.5 mL, 5 eq), HATU (0.5M in DMF, 1.0 mL, 5 eq), and DIPEA (2M in NMP, 0.5 mL, 10 eq). The mixture was mixed by N2 bubbling for 5 min. at 75° C. for all amino acids, except Fmoc-Cys(Trt)-OH and Fmoc-His(Trt)-OH which are coupled at 50° C., the reaction solution was drained through the frit. The resin was washed successively three times as follows: DMF (7 mL) wash from top, followed by DMF (7 mL) wash from bottom and finally with DMF (7 mL) wash from top. To the reaction vessel was added the amino acid (0.2M in DMF, 2.5 mL, 5 eq), HATU (0.5M in DMF, 1.0 mL, 5 eq), and DIPEA (2M in NMP, 0.5 mL, 10 eq). The mixture was mixed by N2 bubbling for 5 min. at 75° C. for all amino acids, except Fmoc-Cys(Trt)-OH and Fmoc-His (Trt)-OH which are coupled at 50° C., the reaction solution was drained through the frit. The resin was washed successively three times as follows: DMF (7 mL) wash from top, followed by DMF (7 mL) wash from bottom and finally with DMF (7 mL) wash from top. To the reaction vessel was added a solution of acetic anhydride:DIEA:DMF (10:1:89 v/v/v, 5.0 mL). The mixture was periodically bubbled for 2 min. at 65° C., then the solution was drained through the frit. The resin was washed successively three times as follows: DMF (7 mL) wash from top, followed by DMF (7 mL) wash from bottom and finally with DMF (7 mL) wash from top. The resulting resin was used directly in the next step.

Custom Amino Acids-Coupling Procedure:

To the reaction vessel containing resin from the previous step was added a solution of piperidine:DMF (20:80 v/v, 5.0 mL). The mixture was periodically agitated for 3 min. and then the solution was drained through the frit. To the reaction vessel was added a solution of piperidine:DMF (20:80 v/v, 5.0 mL). The mixture was periodically agitated for 3 min. and then the solution was drained through the frit. The resin was washed successively three times as follows: DMF (7 mL) wash from top, followed by DMF (7 mL) wash from bottom and finally with DMF (7 mL) wash from top. To the reaction vessel was added the amino acid solution (1.25 mL to 5 mL, 2.5 eq to 10 eq) containing HATU (2.5 eq to 10 eq), and finally DIPEA (2M in NMP, 0.5 mL to 1 mL, 20 eq). The mixture was mixed by N2 bubbling for 5 min. to 2 hours at 25° C. to 75° C., then the reaction solution was drained through the frit. The resin was washed successively three times as follows: DMF (7 mL) wash from top, followed by DMF (7 mL) wash from bottom and finally with DMF (7 mL) wash from top. To the reaction vessel was added a solution of acetic anhydride:DIEA:DMF (10:1:89 v/v/v, 5.0 mL). The mixture was periodically bubbled for 2 min. at 65° C., then the solution was drained through the frit. The resin was washed successively three times as follows: DMF (7 mL) wash from top, followed by DMF (7 mL) wash from bottom and finally with DMF (7 mL) wash from top. The resulting resin was used directly in the next step.

Symphony Method A:

All manipulations were performed under automation on a Symphony peptide synthesizer (Protein Technologies). All procedures unless noted were performed in a Symphony polypropylene tube fitted with a bottom frit. The tube connects to the Symphony peptide synthesizer through both the bottom and the top of the tube. All Solvents, DMF, DCM, amino acids and reagents are added through the bottom of the tube and pass up through the frit to contact the resin. All solutions are removed through the bottom of the tube. "Periodic agitation" describes a brief pulse of N2 gas through the bottom frit; the pulse lasts approximately 5 seconds and occurs every 15 seconds. Amino acid solutions were generally not used beyond three weeks from preparation. HATU solution was used within 5 days of preparation. DMF=dimethylformamide; HCTU=2-(6-Chloro-1-H-benzotriazol-1-yl)-1,1,3,3-tetramethyluronium; HATU=1-[Bis (dimethylamino)methylene]-1H-1,2,3-triazolo[4,5-b]pyridinium 3-oxid hexafluorophosphate; NMM=n-Methyl morpholine; DIPEA=diisopropylethylamine; Sieber=Fmoc-amino-xanthen-3-yloxy, where "3-yloxy" describes the position and type of connectivity to the polystyrene resin. The resin used is Merrifield polymer (polystyrene) with a Sieber linker (Fmoc-protected at nitrogen); 100-200 mesh, 1% DVB, 0.71 mmol/g loading. Other common Acid sensitive resins can also be used in the synthesis such as Rink or functionalized Chloro trityl Resin. Common amino acids used are listed below with side-chain protecting groups indicated inside parenthesis. Fmoc-Ala-OH; Fmoc-Arg (Pbf)-OH; Fmoc-Asn(Trt)-OH; Fmoc-Asp(OtBu)-OH; Fmoc-Bzt-OH; Fmoc-Cys(Trt)-OH; Fmoc-Dab(Boc)-OH; Fmoc-Dap(Boc)-OH; Fmoc-Gln(Trt)-OH; Fmoc-Gly-OH; Fmoc-His(Trt)-OH; Fmoc-Hyp(tBu)-OH; Fmoc-Ile-OH; Fmoc-Leu-OH; Fmoc-Lys(Boc)-OH; Fmoc-Nle-OH; Fmoc-Met-OH; Fmoc[N-Me]Ala-OH; Fmoc-[N-Me]Nle-OH; Fmoc-Phe-OH; Fmoc-Pro-OH; Fmoc-Sar-OH; Fmoc-Ser (tBu)-OH; Fmoc-Thr(tBu)-OH; Fmoc-Trp(Boc)-OH; Fmoc-Tyr(tBu)-OH; Fmoc-Val-OH The procedures of "Symphony Method A" describes an experiment performed on a 0.050-0.100 mmol scale, where the scale is determined by the amount of Sieber linker bound to the resin. This scale corresponds to approximately 70-140 mg of the Sieber-Merrifield resin described above. All procedures can be scaled beyond the 0.050-0.100 mmol scale by adjusting the described volumes by the multiple of the scale. Prior to amino acid coupling, all peptide synthesis sequences began with a resin-swelling procedure, described below as "Swelling procedure". Coupling of amino acids to a primary amine N-terminus used the "Standard-coupling procedure" described below. Coupling of amino acids to a secondary amine N-terminus used the "Double-coupling", custom amino acids are coupled via a manual Blank addition of the amino acid "Blank coupling" described below.

Swelling Procedure:

To a Symphony polypropylene solid-phase reaction vessel was added Merrifield Sieber resin (70 mg, 0.050 mmol or 140 mg, 0.100 mmol). The resin was washed (swelled) three times as follows: to the reaction vessel was added DMF (2.5 mL) upon which the mixture was periodically agitated with N2 bubbling from the bottom of the reaction vessel for 10 minutes before the solvent was drained through the frit.

Standard-Coupling Procedure:

The resin was washed three times as follows: to the reaction vessel was added DMF (2.5 mL) upon which the mixture was periodically agitated with $N_2$ bubbling from the bottom of the reaction vessel for 30 seconds before the solvent was drained through the frit. To the reaction vessel was added piperidine:DMF (20:80 v/v, 2.5 mL). The mixture was periodically agitated for 5 minutes and then the solution was drained through the frit. The procedure was repeated one more time. The resin was washed 6 times as follows: for each wash, DMF (2.5 mL) was added through the bottom of the vessel and the resulting mixture was periodically agitated for 30 seconds before the solution was drained through the frit. To the reaction vessel was added the amino acid (0.2M in DMF, 1.25 mL, 5 eq), then HATU (0.2M in DMF, 1.25 mL, 5 eq), and finally NMM (0.8M in DMF, 1.25 mL, 10 eq). The mixture was periodically agitated for 10 minutes, then the reaction solution was drained through the frit. The resin was washed with DMF (6.25 mL) was added through the bottom of the vessel and the resulting mixture was periodically agitated for 30 seconds before the solution was drained through the frit. To the reaction vessel was added the amino acid (0.2M in DMF, 1.25 mL, 5 eq), then HATU (0.2M in DMF, 1.25 mL, 5 eq), and finally NMM (0.8M in DMF, 1.25 mL, 10 eq). The mixture was periodically agitated for 10 minutes, then the reaction solution was drained through the frit. The resin was washed successively three times as follows: for each wash, DMF (2.5 mL) was added through the bottom of the vessel and the resulting mixture was periodically agitated for 30 seconds before the solution was drained through the frit. The resulting resin was used directly in the next step.

Secondary Amine-Coupling Procedure:

The resin was washed three times as follows: to the reaction vessel was added DMF (2.5 mL) upon which the mixture was periodically agitated with $N_2$ bubbling from the bottom of the reaction vessel for 30 seconds before the solvent was drained through the frit. To the reaction vessel was added piperidine:DMF (20:80 v/v, 2.5 mL). The mixture was periodically agitated for 5 minutes and then the solution was drained through the frit. The procedure was repeated one more time. The resin was washed 6 times as follows: for each wash, DMF (2.5 mL) was added through the bottom of the vessel and the resulting mixture was periodically agitated for 30 seconds before the solution was drained through the frit. To the reaction vessel was added the amino acid (0.2M in DMF, 1.25 mL, 5 eq), then HATU (0.2M in DMF, 1.25 mL, 5 eq), and finally NMM (0.8M in DMF, 1.25 mL, 10 eq). The mixture was periodically agitated for 300 minutes, then the reaction solution was drained through the frit. The resin was washed with DMF (6.25 mL) was added through the bottom of the vessel and the resulting mixture was periodically agitated for 30 seconds before the solution was drained through the frit. To the reaction vessel was added the amino acid (0.2M in DMF, 1.25 mL, 5 eq), then HATU (0.2M in DMF, 1.25 mL, 5 eq), and finally NMM (0.8M in DMF, 1.25 mL, 10 eq). The mixture was periodically agitated for 300 minutes, then the reaction solution was drained through the frit. The resin was washed successively three times as follows: for each wash, DMF (2.5 mL) was added through the bottom of the vessel and the resulting mixture was periodically agitated for 30 seconds before the solution was drained through the frit. The resulting resin was used directly in the next step.

Symphony Method B

Final Capping Procedure:

The resin was washed three times as follows: to the reaction vessel was added DMF (2.5 mL) upon which the mixture was periodically agitated with $N_2$ bubbling from the bottom of the reaction vessel for 30 seconds before the solvent was drained through the frit. To the reaction vessel was added piperidine:DMF (20:80 v/v, 2.5 mL). The mixture was periodically agitated for 2.5 minutes and then the solution was drained through the frit. The resin was washed 6 times as follows: for each wash, DMF (2.5 mL) was added through the bottom of the vessel and the resulting mixture was periodically agitated for 30 seconds before the solution was drained through the frit. To the reaction vessel was added NMM (0.8M in DMF, 1.25 mL, 10 eq) followed by the addition of the Chloroacetic anhydride (0.4M in DMF, 1.25 mL, 10 eq). The mixture was periodically agitated for 15 minutes, then the reaction solution was drained through the frit. The resin was washed with DMF (6.25 mL) was added through the bottom of the vessel and the resulting mixture was periodically agitated for 30 seconds before the solution was drained through the frit. To the reaction vessel was added NMM (0.8M in DMF, 1.25 mL, 10 eq) followed by the addition of the Chloroacetic anhydride (0.4M in DMF, 1.25 mL, 10 eq). The mixture was periodically agitated for 15 minutes, then the reaction solution was drained through the frit. The resin was washed 6 times as follows: DMF (2.5 mL) was added through the bottom of the vessel and the resulting mixture was periodically agitated for 30 seconds before the solution was drained through the frit. To the reaction vessel was added $Ac_2O$/DIPEA/DMF (v/v/v 1:1:3 2.5 mL) the mixture was periodically agitated for 10 minutes, then the reaction solution was drained through the frit. The resin was washed successively six times as follows: for each wash, DMF (2.5 mL) was added through the bottom of the vessel and the resulting mixture was periodically agitated for 30 seconds before the solution was drained through the frit. The resin was washed successively four times as follows: for each wash, DCM (2.5 mL) was added through the bottom of the vessel and the resulting mixture was periodically agitated for 30 seconds before the solution was drained through the frit. The resulting resin was then dried with a stream of Nitrogen for 10 mins.

N-methylation on-resin (Turner, R. A.; Hauksson, N. E.; Gipe, J. H.; Lokey, R. S. Org. Lett. 2013, 15(19), 5012-5015):

All manipulations were performed manually unless noted. The procedure of "N-methylation on-resin" describes an experiment performed on a 0.100 mmol scale, where the scale is determined by the amount of Sieber linker bound to the resin that was used to generate the peptide. This scale is not based on a direct determination of the quantity of peptide used in the procedure. The procedure can be scaled beyond 0.100 mmol scale by adjusting the described volumes by the multiple of the scale.

The resin was transferred into a 25 mL syringe equipped with a frit. To the resin was added piperidine:DMF (20:80 v/v, 5.0 mL). The mixture was shaken for 3 min. and then the solution was drained through the frit. The resin was washed 3 times with DMF (4.0 mL). To the reaction vessel was added piperidine:DMF (20:80 v/v, 4.0 mL). The mixture was shaken for 3 min. and then the solution was drained through the frit. The resin was washed successively six times as follows: 3 times DMF (4.0 mL) was added and the resulting mixture was shaken for 3 seconds before the solution was drained through the frit followed by 3 addition of DCM (4.0 mL) and the resulting mixture was shaken for 3 seconds before the solution was drained through the frit.

The resin was suspended in DMF (2.0 mL) and ETHYL TRIFLUOROACETATE (0.119 ml, 1.00 mmol), 1,8-DIAZABICYCLO[5.4.0]UNDEC-7-ENE (0.181 ml, 1.20 mmol). The mixture was put on a shaker for 60 min. The solution was drained through the frit. The resin was washed successively six times as follows: 3 times DMF (4.0 mL) was added and the resulting mixture was shaken for 3 seconds before the solution was drained through the frit followed by 3 addition of DCM (4.0 mL) and the resulting mixture was shaken for 3 seconds before the solution was drained through the frit. The resin was washed 3 times with dry THF (2.0 mL) to remove any residual water. In an oven dried 4.0 mL vial is added THF (1.0 mL), TRIPHENYLPHOSPHINE (131 mg, 0.500 mmol) on dry 4 Å molecular sieves (20 mg). The turbid solution is transferred on the resin and isopropyl azodicarboxylate (0.097 mL, 0.5 mmol) is added slowly. The resin is shaken for 15 min. The solution was drained through the frit and the resin was washed with 3 times with dry THF (2.0 mL) to remove any residual water. In an oven dried 4.0 mL vial is added THF (1.0 mL), TRIPHENYLPHOSPHINE (131 mg, 0.500 mmol) on dry 4 Å molecular sieves (20 mg). The turbid solution is transferred on the resin and diisopropyl azodicarboxylate (0.097 mL, 0.5 mmol) is added slowly. The resin is shaken for 15 min. The solution was drained through the frit. The resin was washed successively six times as follows: 3 times DMF (4.0 mL) was added and the resulting mixture was shaken for 3 seconds before the solution was drained through the frit followed by 3 addition of DCM (4.0 mL) and the resulting mixture was shaken for 3 seconds before the solution was drained through the frit.

The resin was suspended in Ethanol (1.0 mL) and THF (1.0 mL) and SODIUM BOROHYDRIDE (37.8 mg, 1.000 mmol) was added. The mixture was mixed on a shaker for 30 min. Solution was drained through the frit and the resin was washed successively six times as follows: 3 times DMF (4.0 mL) was added and the resulting mixture was shaken for 3 seconds before the solution was drained through the frit followed by 3 addition of DCM (4.0 mL) and the resulting mixture was shaken for 3 seconds before the solution was drained through the frit.

Global Deprotection Method B:

All manipulations were performed manually unless noted. The procedure of "Global Deprotection Method B" describes an experiment performed on a 0.100 mmol scale, where the scale is determined by the amount of Sieber linker bound to the resin. The procedure can be scaled beyond 0.100 mmol scale by adjusting the described volumes by the multiple of the scale. A "deprotection solution" was prepared using trifluoroacetic acid:triisopropylsilane:dithiothreitol (94:3:3 v:v:w). The resin was removed from the reaction vessel and transferred to a 25 mL syringe equipped with a frit. To the syringe was added the "deprotection solution" (5.0 mL). The mixture was mixed in a shaker for 5 min. The solution was filtered through and diluted in diethyl ether (30 mL). The precipitated solid was centrifuged for 3 min. The supernatant solution was decanted and the solid was re-suspended in diethyl ether (25 mL). The suspension was centrifuged for 3 min. The supernatant was decanted and the remaining solid was suspended diethyl ether (25 mL). The suspension was centrifuged for 3 min. The supernatant was decanted and the remaining solid was dried under high vacuum. The crude peptide was obtained as a white to off-white solid.

Global Deprotection Method G

All manipulations were performed manually unless noted. The procedure of "Global Deprotection Method G" describes an experiment performed on a 0.50 or 0.100 mmol scale, where the scale is determined by the amount of Sieber linker bound to the resin. The procedure can be scaled beyond 0.100 mmol scale by adjusting the described volumes by the multiple of the scale. A "deprotection solution" was prepared using trifluoroacetic acid:triisopropylsilane:water (95:2.5:2.5 v:v:v). To the resin was added the "deprotection solution" (2.5 mL). The mixture was stirred for 5 min. The solution was filtered and the filtrate was added to cold diethyl ether (40 mL). The resin was treated with an additional 2.5 mL of "deprotection solution" for 2 min and the filtrate was added to cold ether from the previous treatment. The precipitated solid was collected by centrifugation, washed twice with ether (40 mL) and dried under high vacuum to yield a white to off-white solid.

Cyclization Method C:

All manipulations were performed manually unless noted. The procedure of "Cyclization Method C" describes an experiment performed on a 0.100 mmol scale, where the scale is determined by the amount of Sieber linker bound to the resin that was used to generate the peptide. This scale is not based on a direct determination of the quantity of peptide used in the procedure. The procedure can be scaled beyond 0.100 mmol scale by adjusting the described volumes by the multiple of the scale. The crude peptide solids were dissolved in a solution of acetonitrile: aqueous 0.1M ammonium bicarbonate buffer (11 mL:24 mL), and the solution was then carefully adjusted to pH=8.5-9.0 using aqueous NaOH (1.0 M). The solution was then mixed using a shaker for 12 to 18 hours. The reaction solution was concentrated and the residue was then dissolved in acetonitrile:water. This solution was subjected to reverse-phase HPLC purification to afford the desired cyclic peptide.

Preparation of racemic 2-((((9H-fluoren-9-yl) methoxy)carbonyl)amino)-3-(1-(tert-butoxycarbonyl)-1H-pyrrolo[2,3-b]pyridin-3-yl)propanoic acid (Robison, M. M and Robison, B. L. *J. Am. Chem. Soc.,* 1955, 77, 457-459).

Scheme:

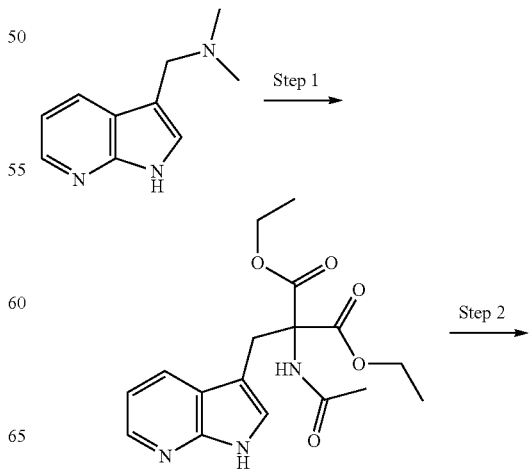

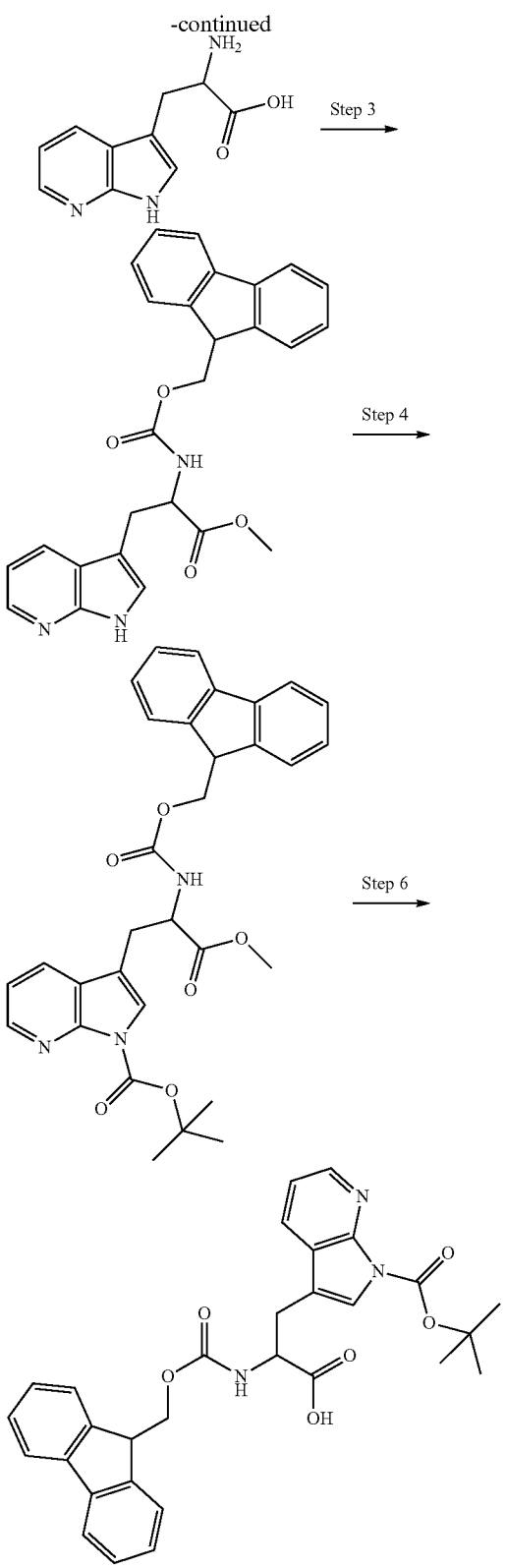

Step 1:
A mixture of 7-azagramine (3.5 g, 19.97 mmol), diethyl acetamidomalonate (4.34 g, 19.97 mmol) and xylenes (35 ml) was treated with powder sodium hydroxide (0.080 g, 1.997 mmol) and stirred at reflux for 15 h under nitrogen. The hot solution was filtered to give a yellow filtrate. A yellow solid precipitated from the filtrate when cooled to room temperature. The solid mass was suspended in benzene (40 mL) and filtered. The collected solid was washed with cyclohexane (2×100 mL) to give diethyl 2-((1H-pyrrolo[2,3-b]pyridin-3-yl)methyl)-2-acetamidomalonate (3.5 g, 50.4%) as a white solid.

Analysis LCMS Condition A: Retention time=0.79 min; ESI-MS(+) m/z 348.3 (M+H).

Step 2:
A mixture of diethyl 2-((1H-pyrrolo[2,3-b]pyridin-3-yl)methyl)-2-acetamidomalonate (3.5 g, 10.08 mmol) and hydrochloric acid, 37% (30 mL) was refluxed for 15 h an the concentrated to 10 mL. The product was treated with acetonitrile (5 mL) and lyophilized to give an off-white solid. This was re-dissolved in 15% NH4OH to pH 7 and the solution was then diluted with water (20 mL). The precipitated white solid was collected by filtration, washed with water and EtOH and dried to yield 2-amino-3-(1H-pyrrolo[2,3-b]pyridin-3-yl)propanoic acid (1.5 g, 72.5%) as a white solid.

Analysis LCMS Condition A: Retention time=0.29 min; ESI-MS(+) m/z 206.0 (M+H).

Step 3:
A solution of 2-amino-3-(1H-pyrrolo[2,3-b]pyridin-3-yl)propanoic acid (1.3 g, 6.33 mmol) and triethylamine (1.766 ml, 12.67 mmol) in acetonitrile (20 ml) and water (15 ml) was treated with FMOC-OSu (2.137 g, 6.33 mmol) and the resulting solution was stirred at rt for 30 min. The mixture was concentrated to dryness to give a white foamy solid which was triturated with ether (50 mL). The solid was treated 1 M HCl (100 mL) and the gummy solid that formed was triturated with water, MeOH and ether and dried under vacuum. The resulting product was suspended in anhydrous MeOH (50 mL) and 4 M HCl/dioxane (10 mL) and the solution was refluxed for 1 h. The mixture was concentrated under reduced pressure and the residue was partitioned between EtOAc and saturated NaHCO₃ and filtered. The EtOAc phase was washed twice with brine, dried over sodium sulfate and concentrated under reduced pressure to give methyl 2-((((9H-fluoren-9-yl)methoxy)carbonyl)amino)-3-(1H-pyrrolo[2,3-b]pyridin-3-yl)propanoate (1.0 g, 28% yield) as a foamy yellow solid.

Analysis LCMS Condition A: Retention time=0.81 min; ESI-MS(+) m/z 442.5 (M+H).

Step 4:
A solution of methyl 2-((((9H-fluoren-9-yl)methoxy)carbonyl)amino)-3-(1H-pyrrolo[2,3-b]pyridin-3-yl)propanoate (1.0 g, 2.265 mmol) in anhydrous THF (10 mL) was treated with DMAP (0.028 g, 0.227 mmol), placed under nitrogen and cooled in an ice bath. A solution of Boc₂O (0.789 mL, 3.40 mmol) in THF (5 mL) was added to the mixture over 3 min and the mixture was stirred and allowed to warm up over 16 h. The reaction mixture was diluted with EtOAc (150 mL), washed with saturated NH4Cl (3×50 mL) and brine (50 mL), dried over sodium sulfate and concentrated under reduced pressure. The crude product was purified by flash chromatography using a 40 g ISCO silica gel cartridge eluted with 0-60% EtOAc/hexanes to give tert-butyl 3-(2-((((9H-fluoren-9-yl)methoxy)carbonyl)amino)-3-methoxy-3-oxopropyl)-1H-pyrrolo[2,3-b]pyridine-1-carboxylate (0.85 g, 69% yield) as a white solid.

Analysis LCMS Condition A: Retention time=1.01 min; ESI-MS(+) m/z 542.5 (M+H).

Step 5:
A solution of tert-butyl 3-(2-((((9H-fluoren-9-yl)methoxy)carbonyl)amino)-3-methoxy-3-oxopropyl)-1H-pyrrolo[2,3-b]pyridine-1-carboxylate (200 mg, 0.369 mmol) in anhydrous 1,2-Dichloroethane (5 mL) was treated with trimethyltin hydroxide (200 mg, 1.108 mmol) and the mixture was stirred at 65° C. for 1 h. The mixture was concentrated under reduced pressure and the residue was dissolved in EtOAc (50 mL), washed with 1 M HCl and brine, dried over sodium sulfate and concentrated under reduce pressure to yield 2-((((9H-fluoren-9-yl)methoxy)carbonyl)amino)-3-(1-(tert-butoxycarbonyl)-1H-pyrrolo[2,3-b]pyridin-3-yl)propanoic acid as a white foamy solid. This was used without further purification. $^1$H NMR (400 MHz, DMSO-$d_6$) δ 8.40-8.37 (m, 1H), 8.12-8.05 (m, 1H), 7.90-7.75 (m, 2H), 7.70-7.55 (m, 2H), 7.43-7.35 (m, 2H), 7.30-7.18 (m, 4H), 4.37-4.29 (m, 1H), 4.16-4.12 (m, 3H), 3.23-3.15 (m, 1H), 3.07-2.98 (m, 1H), 1.60 (s, 9H).

Analysis LCMS Condition A: Retention time=0.93 min; ESI-MS(+) m/z 528.4 (M+H).

Preparation of Example 3210

Example 3210

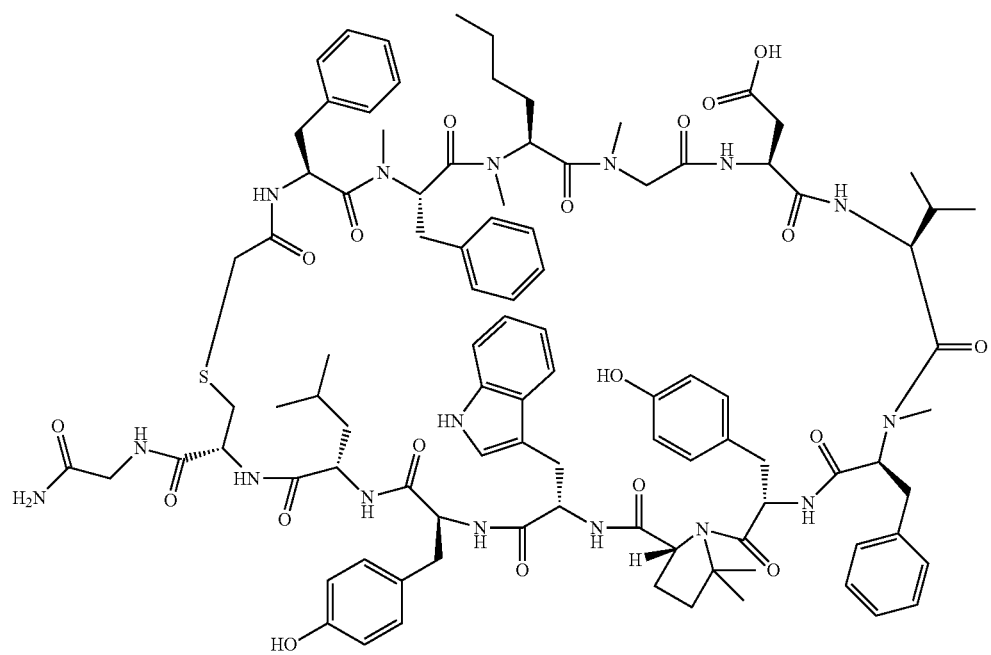

To a 50 mL polypropylene tube was added Sieber resin (140 mg, 0.100 mmol), and the tube was placed on the CEM Liberty microwave peptide synthesizer. The following procedures were then performed sequentially:

"CEM Method A: Resin-swelling procedure" was followed;
"CEM Method A: Standard coupling procedure" was followed with Fmoc-Gly-OH;
"CEM Method A: Standard coupling procedure" was followed with Fmoc-Cys(Trt)-OH;
"CEM Method A: Standard coupling procedure" was followed with Fmoc-Leu-OH;
"CEM Method A: Standard coupling procedure" was followed with Fmoc-Tyr(tBu)-OH;
"CEM Method A: Standard coupling procedure" was followed with Fmoc-Trp(Boc)-OH; Fmoc-D-Pro(5,5-di-Me) was coupled manually as follows: to the peptidyl-resin was added a 5 mL solution of Fmoc-D-Pro(5,5-di-Me)-OH (1.2 eq), HATU (1.2 eq) and DIEA (2.5 eq). The resin suspension was stirred for 16 hrs. The resin was washed with DMF (3×5 mL), DCM (3×5 mL) and once again with DMF (5 mL). The synthesis was then continued on the CEM synthesizer.
"CEM Method A: Standard coupling procedure" was followed with Fmoc-Tyr(tBu)-OH;
"CEM Method A: Standard coupling procedure" was followed with Fmoc-[N-Me]Phe-OH;
"CEM Method A: Custom amino acids-coupling procedure" was followed with Fmoc-Val-OH using 10 eq for 10 min at 75° C., followed by 2 hours at room temperature;
"CEM Method A: Standard coupling procedure" was followed with Fmoc-Asp(OtBu)-OH;
"CEM Method A: Standard coupling procedure" was followed with Fmoc-Sar-OH;
"CEM Method A: Custom amino acids-coupling procedure" was followed with Fmoc-[N-Me]Nle-OH using 5 eq for 10 min;
"CEM Method A: Custom amino acids-coupling procedure" was followed with Fmoc-[N-Me]Phe-OH using 5 eq for 10 min;
"CEM Method A: Custom amino acids-coupling procedure" was followed with Fmoc-Phe-OH using 5 eq for 10 min;
"Prelude Method A: Chloroacetyl chloride coupling procedure A" was followed;
"Global Deprotection Method B" was followed;
"Cyclization Method C" was followed.

The crude material was purified via preparative LC/MS with the following conditions: Column: Phenomenex Luna 20×250 5µ particles; Mobile Phase A: water with 0.1% TFA; Mobile Phase B: Acetonitrile with 0.1% TFA; Gradient: 30-80% B over 50 min., then a 5-minute hold at 80% B; Flow: 15 mL/min. Fractions containing the desired product were combined and dried via centrifugal evaporation. The yield of the product was 1.1 mg, and its estimated purity was 99% by "Analysis HPLC Condition B" using a gradient of 35% to 85% buffer B over 30 min.

Analysis LCMS Condition A: Retention time=1.55 min; ESI-MS(+) m/z 925.8 (M+2H).

ESI-HRMS(+) m/z:
Calculated: 925.4547 (M+2H).
Found: 925.4551 (M+2H).

Preparation of Example 3211

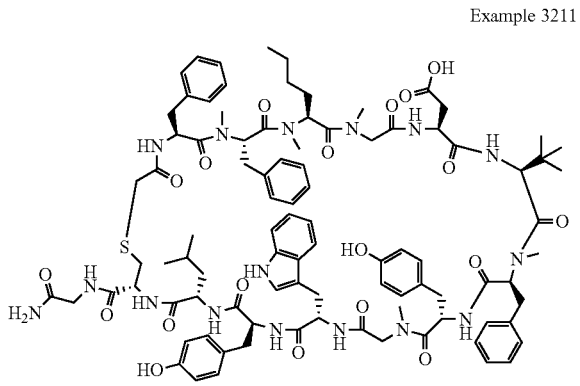 [SMILES: CCCC[C@H]1C(=O)N(C)CC(=O)N[C@@H](CC(=O)O)C(=O)N[C@@H](C(C)(C)C)C(=O)N(C)[C@@H](Cc2ccccc2)C(=O)N[C@@H](Cc2ccc(O)cc2)C(=O)N(C)CC(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccccc2)C(=O)N(C)[C@@H](Cc2ccccc2)C(=O)N1C]

Example 3211

Example 3211 was prepared following the general synthetic sequence described for the preparation of Example 3210, composed of the following general procedures: "CEM Method A: Resin-swelling procedure", "CEM Method A: Standard-coupling procedure", "Custom amino acids-coupling procedure", "CEM Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 25 min., then a 5-minute hold at 100% B; Flow: 20 mL/min. Fractions containing the desired product were combined and dried via centrifugal evaporation. The yield of the product was 3.4 mg, and its estimated purity by LCMS analysis was 97% using "Analysis conditions D and E".

Analysis LCMS Condition D: Retention time=1.60 min; ESI-MS(+) m/z 905.9 (M+2H).

Analysis LCMS Condition E: Retention time=1.82 min; ESI-MS(+) m/z 906.0 (M+2H).

Preparation of Example 3212

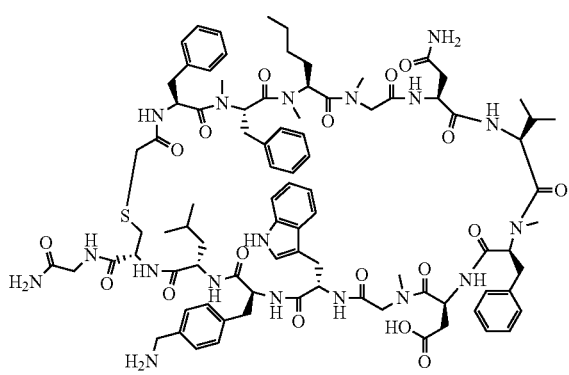

Example 3212

To a 40 mL polypropylene solid-phase reaction vessel was added Sieber resin (140 mg, 0.100 mmol), and the reaction vessel was placed on the Prelude peptide synthesizer. The following procedures were then performed sequentially:

"Prelude Method A: Resin-swelling procedure" was followed;

"Prelude Method A: Single-coupling procedure" was followed with Fmoc-Gly-OH;

"Prelude Method A: Single-coupling procedure" was followed with Fmoc-Cys(Trt)-OH;

"Prelude Method A: Single-coupling procedure" was followed with Fmoc-Leu-OH;

"Prelude Method A: Single-coupling procedure" was followed with Fmoc-Phe(CH$_2$NH$_2$)—OH;

"Prelude Method A: Single-coupling procedure" was followed with Fmoc-Trp(Boc)-OH;

"Prelude Method A: Single-coupling procedure" was followed with Fmoc-Sar-OH;

"Prelude Method A: Single-coupling procedure" was followed with Fmoc-Asp(OtBu)-OH;

"Prelude Method A: Single-coupling procedure" was followed with Fmoc-[N-Me]Phe-OH;

"Prelude Method A: Secondary amine-coupling procedure" was followed with Fmoc-Val-OH;

"Prelude Method A: Single-coupling procedure" was followed with Fmoc-Asn(Trt)-OH;

"Prelude Method A: Secondary amine-coupling procedure" was followed with Fmoc-Sar-OH;

"Prelude Method A: Secondary amine-coupling procedure" was followed with Fmoc-[N-Me]Nle-OH;

"Prelude Method A: Secondary amine-coupling procedure" was followed with Fmoc-[N-Me]Phe-OH;

"Prelude Method A: Secondary amine-coupling procedure" was followed with Fmoc-Phe-OH;

"Prelude Method A: Chloroacetyl chloride coupling procedure A" was followed;

"Global Deprotection Method B" was followed;

"Cyclization Method C" was followed.

The crude material was purified via preparative LC/MS with the following conditions:

Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-60% B over 25 min., then a 5-minute hold at 100% B; Flow: 20 mL/min. Fractions containing the desired product were combined and dried via centrifugal evaporation. The yield of the product was 6.8 mg, and its estimated purity by LCMS analysis was 97% by "Analysis conditions D and E".

Analysis LCMS condition D: Retention time=1.62 min; ESI-MS(+) m/z 880.7 (M+2H).

Analysis LCMS condition E: Retention time=1.61 min; ESI-MS(+) m/z 880.7 (M+2H).

Preparation of Example 3213

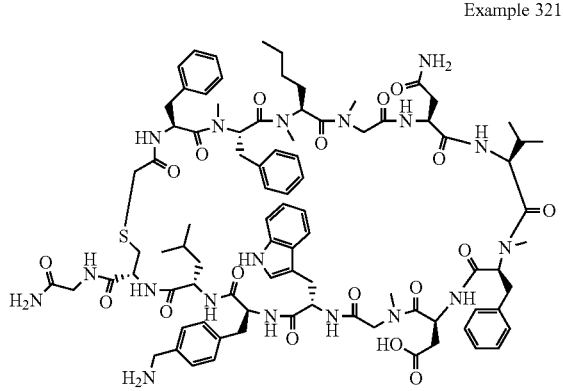 [SMILES: CCCC[C@H]1C(=O)N(C)CC(=O)N[C@@H](CC(N)=O)C(=O)N[C@@H](C(C)C)C(=O)N(C)[C@@H](Cc2ccccc2)C(=O)N[C@@H](CC(=O)O)C(=O)N(C)CC(=O)N[C@@H](Cc2c[nH]c3ccccc23)C(=O)N[C@@H](Cc2ccc(CN)cc2)C(=O)N[C@@H](CC(C)C)C(=O)N[C@H](C(=O)NCC(N)=O)CSCC(=O)N[C@@H](Cc2ccccc2)C(=O)N(C)[C@@H](Cc2ccccc2)C(=O)N1C]

Example 3212

Example 3213 was prepared following the general synthetic sequence described for the preparation of Example 3212, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 25 min., then a 5-minute hold at 100% B; Flow: 20 mL/min. Fractions containing the desired product were combined and dried via centrifugal evaporation. The yield of the product was 9.5 mg, and its estimated purity by LCMS analysis was 99% by "Analysis Conditions D and E".

Analysis LCMS Condition D: Retention time=1.60 min; ESI-MS(+) m/z 887.9 (M+2H).

Analysis LCMS Condition E: Retention time=1.60 min; ESI-MS(+) m/z 887.7 (M+2H).

Preparation of Example 3216

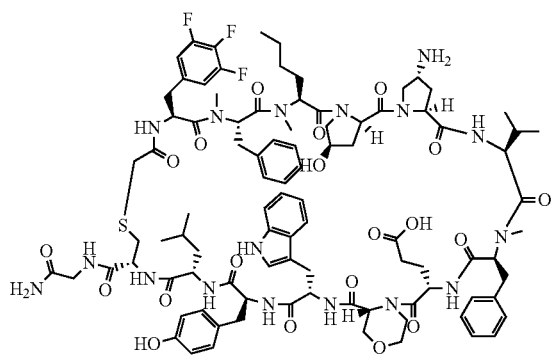

Example 3216

Example 3216 was prepared following the general synthetic sequence described for the preparation of Example 3212, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 min., then a 5-minute hold at 100% B; Flow: 20 mL/min. Fractions containing the desired product were combined and dried via centrifugal evaporation. The material was further purified via preparative LC/MS with the following conditions: Column: XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-70% B over 25 min., then a 5-minute hold at 100% B; Flow: 20 mL/min. Fractions containing the desired product were combined and dried via centrifugal evaporation. The yield of the product was 1.3 mg, and its estimated purity by LCMS analysis was 96% by "Analysis Conditions D and E".

Analysis LCMS Condition D: Retention time=1.69 min; ESI-MS(+) m/z 949.2 (M+2H).

Analysis LCMS Condition E: Retention time=1.70 min; ESI-MS(+) m/z 949.2 (M+2H).

Preparation of Example 3217

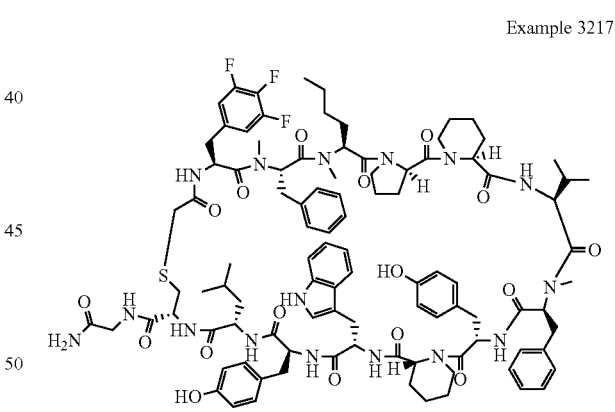

Example 3217

Example 3217 was prepared following the general synthetic sequence described for the preparation of Example 3212, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 35-85% B over 25 min., then a 5-minute hold at 100% B; Flow: 20 mL/min. Fractions containing the desired product were combined and dried via centrifugal evaporation. The yield of the product was 5.2 mg, and its estimated purity by LCMS analysis was 98% by "Analysis Conditions D and E".

Analysis LCMS Condition D: Retention time=2.43 min; ESI-MS(+) m/z 956.8 (M+2H).

Analysis LCMS Condition E: Retention time=2.43 min; ESI-MS(+) m/z 957.0 (M+2H).

ESI-HRMS(+) m/z:

Calculated: 956.4613 (M+2H).

Found: 956.4604 (M+2H).

Preparation of Example 3218

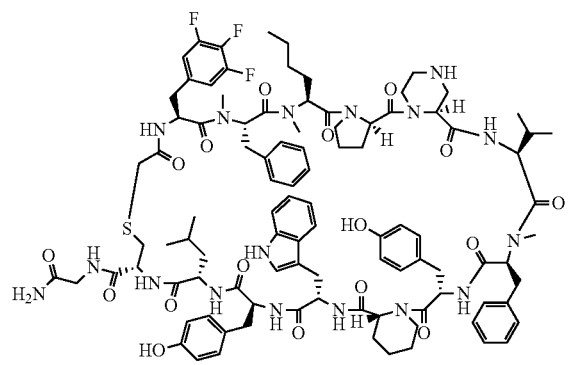

Example 3218

Example 3218 was prepared following the general synthetic sequence described for the preparation of Example 3212, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-70% B over 25 min., then a 5-minute hold at 100% B; Flow: 20 mL/min. Fractions containing the desired product were combined and dried via centrifugal evaporation. The yield of the product was 7.6 mg, and its estimated purity by LCMS analysis was 94% by "Analysis Conditions D and E" Analysis LCMS Condition D: Retention time=2.12 min; ESI-MS(+) m/z 957.2 (M+2H).

Analysis LCMS Condition E: Retention time=1.83 min; ESI-MS(+) m/z 957.4 (M+2H).

ESI-HRMS(+) m/z:

Calculated: 956.9590 (M+2H).

Found: 956.9582 (M+2H).

Preparation of Example 3219

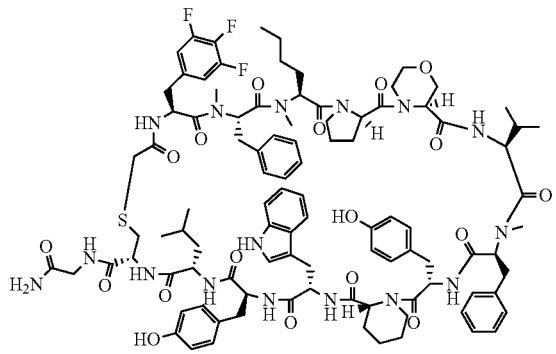

Example 3219

Example 3219 was prepared following the general synthetic sequence described for the preparation of Example 3212, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-80% B over 25 min., then a 5-minute hold at 100% B; Flow: 20 mL/min. Fractions containing the desired product were combined and dried via centrifugal evaporation. The yield of the product was 7.9 mg, and its estimated purity by LCMS analysis was 96% by "Analysis Conditions D and E" Analysis LCMS Condition D: Retention time=2.26 min; ESI-MS(+) m/z 957.9 (M+2H).

Analysis LCMS Condition E: Retention time=2.26 min; ESI-MS(+) m/z 958.0 (M+2H).

ESI-HRMS(+) m/z:

Calculated: 956.4510 (M+2H).

Found: 956.4493 (M+2H).

Preparation of Example 3220

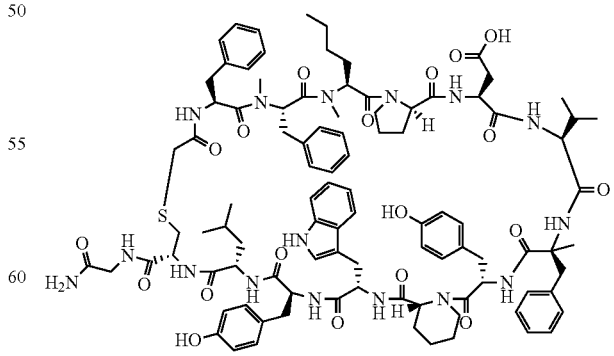

Example 3220

Example 3220 was prepared following the general synthetic sequence described for the preparation of Example 3212, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-75% B over 25 min., then a 5-minute hold at 100% B; Flow: 20 mL/min. Fractions containing the desired product were combined and dried via centrifugal evaporation. The yield of the product was 8.4 mg, and its estimated purity by LCMS analysis was 92% by "Analysis Conditions D and E".

Analysis LCMS Condition D: Retention time=1.71 min; ESI-MS(+) m/z 932.0 (M+2H).

Analysis LCMS Condition E: Retention time=1.94 min; ESI-MS(+) m/z 932.0 (M+2H).

ESI-HRMS(+) m/z:
Calculated: 931.4547 (M+2H).
Found: 931.4536 (M+2H).

Preparation of Example 3221

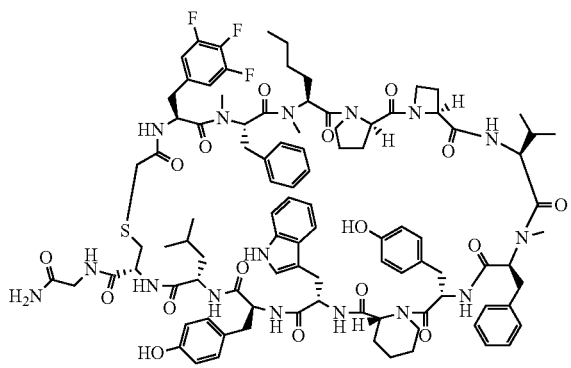

Example 3221

Example 3221 was prepared following the general synthetic sequence described for the preparation of Example 3212, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-80% B over 25 min., then a 5-minute hold at 100% B; Flow: 20 mL/min. Fractions containing the desired product were combined and dried via centrifugal evaporation. The yield of the product was 7.2 mg, and its estimated purity by LCMS analysis was 94% by "Analysis Conditions D and E".

Analysis LCMS Condition D: Retention time=2.22 min; ESI-MS(+) m/z 942.1 (M+2H).

Analysis LCMS Condition E: Retention time=2.20 min; ESI-MS(+) m/z 943.2 (M+2H).

ESI-HRMS(+) m/z:
Calculated: 942.4457 (M+2H).
Found: 942.4445 (M+2H).

Preparation of Example 3222

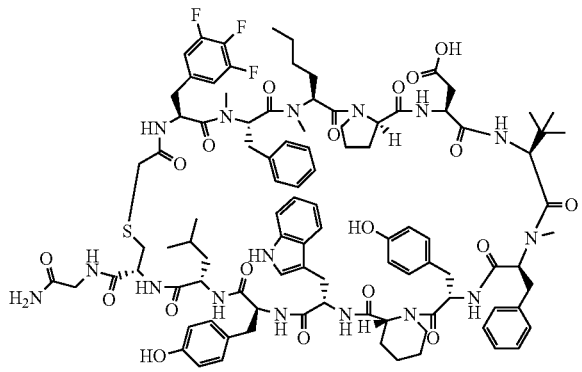

Example 3222

Example 3222 was prepared following the general synthetic sequence described for the preparation of Example 3212, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Phenomenex Luna 20×250 5 u particles; Mobile Phase A: water with 0.1% TFA; Mobile Phase B: Acetonitrile with 0.1% TFA; Gradient: 0.35-95% B over 50 min., then a 5-minute hold at 95% B; Flow: 15 mL/min. Fractions containing the desired product were combined and dried via centrifugal evaporation. The yield of the product was 8.9 mg, and its estimated purity was 99% by "Analysis HPLC Condition B" using a gradient of 35% to 85% buffer B over 30 min.

Analysis LCMS Condition A: Retention time=1.65 min; ESI-MS(+) m/z 966.1 (M+2H).
ESI-HRMS(+) m/z:
Calculated: 965.4484 (M+2H).
Found: 965.4473 (M+2H).

Preparation of Example 3223

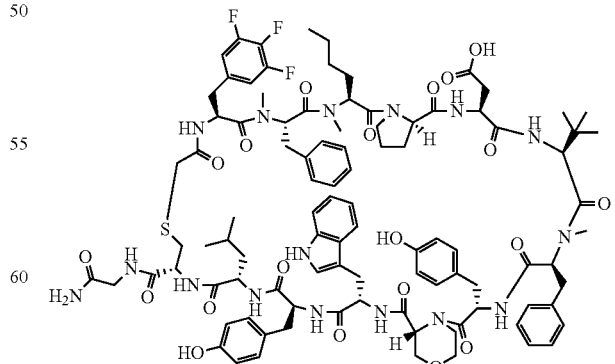

Example 3223

Example 3223 was prepared following the general synthetic sequence described for the preparation of Example 3212, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Phenomenex Luna 20×250 5 u particles; Mobile Phase A: water with 0.1% TFA; Mobile Phase B: Acetonitrile with 0.1% TFA; Gradient: 35-95% B over 50 min., then a 5-minute hold at 95% B; Flow: 15 mL/min. Fractions containing the desired product were combined and dried via centrifugal evaporation. The yield of the product was 9.1 mg, and its estimated purity was 98% by "Analysis HPLC Condition B" using a gradient of 35% to 85% buffer B over 30 min.

Analysis LCMS Condition A: Retention time=1.65 min; ESI-MS(+) m/z 966.8 (M+2H).
ESI-HRMS(+) m/z:
Calculated: 966.4381 (M+2H).
Found: 966.4375 (M+2H).

Preparation of Example 3224

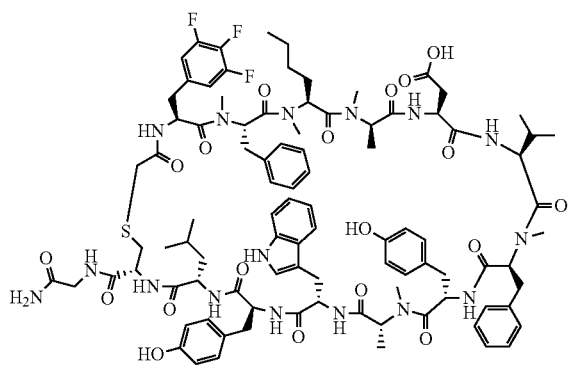

Example 3224

Example 3224 was prepared following the general synthetic sequence described for the preparation of Example 3212, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

Mobile Phase A: 5:95 acetonitrile:water with 10-mM ammonium acetate; Mobile Phase B: 95:5 acetonitrile:water with 10-mM ammonium acetate; Gradient: 20-60% B over 30 min., then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 30 min., then a 5-minute hold at 100% B; Flow: 20 mL/min. Fractions containing the desired product were combined and dried via centrifugal evaporation. The yield of the product was 9.7 mg, and its estimated purity by LCMS analysis was 97% by "Analysis LCMS Condition E".

Analysis LCMS Condition E: Retention time=1.93 min; ESI-MS(+) m/z 939.31 (M+2H).
ESI-HRMS(+) m/z:
Calculated: 939.4328 (M+2H).
Found: 939.4322 (M+2H).

Preparation of Example 3225

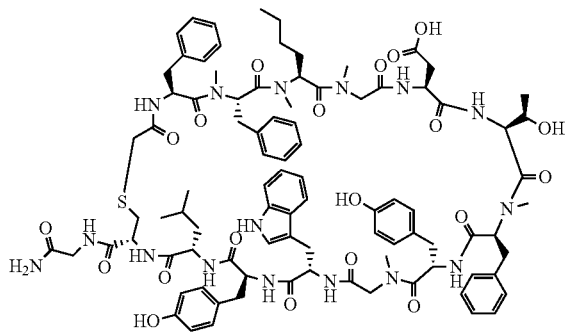

Example 3225

Example 3225 was prepared following the general synthetic sequence described for the preparation of Example 3212, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 30 min., then a 5-minute hold at 100% B; Flow: 20 mL/min. Fractions containing the desired product were combined and dried via centrifugal evaporation. The yield of the product was 10.2 mg, and its estimated purity by LCMS analysis was 96% by "Analysis Conditions E and G".

Analysis LCMS Condition E: Retention time=1.59 min; ESI-MS(−) m/z 898.5 (M−2H).
Analysis LCMS Condition G: Retention time=3.18 min; ESI-MS(+) m/z 899.5 (M+2H).

Preparation of Example 3226

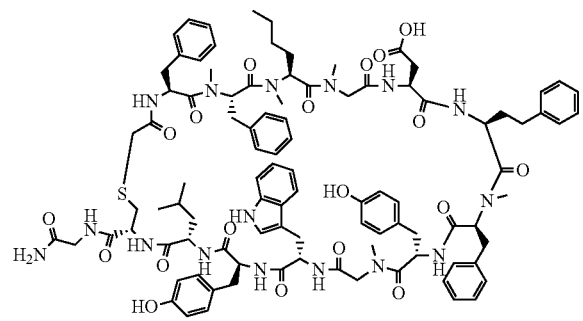

Example 3226

Example 3226 was prepared following the general synthetic sequence described for the preparation of Example 3212, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-65% B over 30 min., then a 5-minute hold at 100% B; Flow: 20 mL/min. Fractions containing the desired product were combined and dried via centrifugal evaporation. The yield of the product was 16.2 mg, and its estimated purity by LCMS analysis was 95% by "Analysis LCMS Condition E".

Analysis LCMS Condition E: Retention time=1.84 min; ESI-MS(−) m/z 928.9 (M−2H).

Preparation of Example 3227

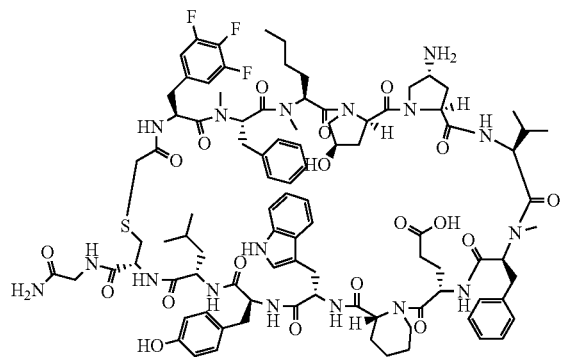

Example 3227

Example 3227 was prepared following the general synthetic sequence described for the preparation of Example 3212, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 35-75% B over 30 min., then a 5-minute hold at 100% B; Flow: 20 mL/min. Fractions containing the desired product were combined and dried via centrifugal evaporation. The yield of the product was 5.3 mg, and its estimated purity by LCMS analysis was 97% by "Analysis LCMS Condition E and G".

Analysis LCMS Condition E: Retention time=1.74 min; ESI-MS(+) m/z 947.7 (M+2H).

Analysis LCMS Condition G: Retention time=3.37 min; ESI-MS(+) m/z 948.00 (M+2H).

ESI-HRMS(+) m/z:
Calculated: 947.9461 (M+2H).
Found: 949.9449 (M+2H).

Preparation of Example 3228

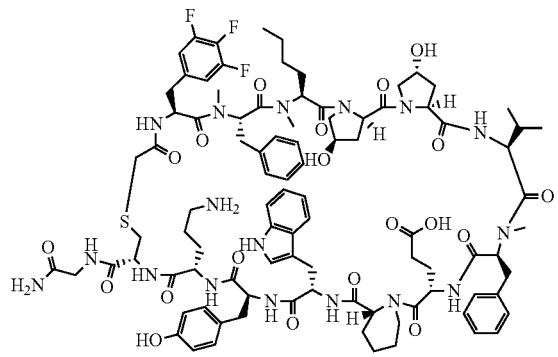

Example 3228

Example 3228 was prepared following the general synthetic sequence described for the preparation of Example 3212, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 35-75% B over 30 min., then a 5-minute hold at 100% B; Flow: 20 mL/min. Fractions containing the desired product were combined and dried via centrifugal evaporation. The yield of the product was 5.2 mg, and its estimated purity by LCMS analysis was 98% by "Analysis LCMS Conditions E and G".

Analysis LCMS Condition E: Retention time=1.80 min; ESI-MS(−) m/z 947.7 (M−2H).

Analysis LCMS Condition G: Retention time=3.41 min; ESI-MS(+) m/z 949.10 (M+2H).

ESI-HRMS(+) m/z:
Calculated: 948.9357 (M+2H).
Found: 948.9354 (M+2H).

Preparation of Example 3229

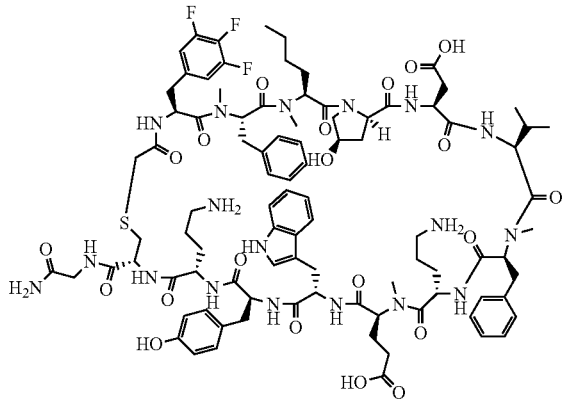

Example 3229

Example 3229 was prepared following the general synthetic sequence described for the preparation of Example 3212, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 30 min., then a 5-minute hold at 100% B; Flow: 20 mL/min. Fractions containing the desired product were combined and dried via centrifugal evaporation. The yield of the product was 8.6 mg, and its estimated purity by LCMS analysis was 95% by "Analysis LCMS Conditions E and G".

Analysis LCMS Condition G: Retention time=3.443 min; ESI-MS(+) m/z 965.55 (M+2H).

Preparation of Example 3230

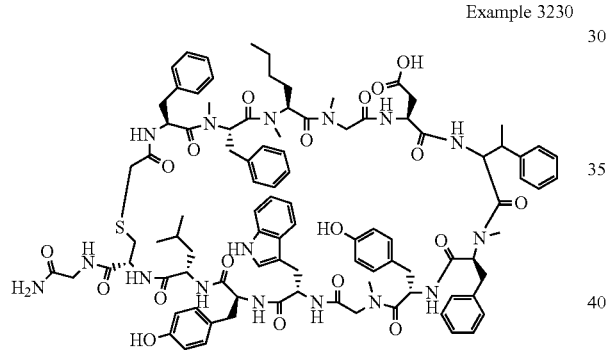

Example 3230

Example 3230 was prepared following the general synthetic sequence described for the preparation of Example 3212, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative HPLC with the following conditions: Column: Phenomenex Luna 20×250 5 u particles; Mobile Phase A: water with 0.1% TFA; Mobile Phase B: Acetonitrile with 0.1% TFA; Gradient: 45-95% B over 55 min., then a 5-minute hold at 95% B; Flow: 15 mL/min. Fractions containing the desired product were combined and dried via centrifugal evaporation. Four isomers (Isomers 3230-A, 3230-B, 3230-C and 3230-D) were obtained. The yields of the products isomer 3230-A, 3230-B, 3230-C and 3060-D were 7.5 mg, 9.3 mg, 0.66 mg and 0.72 mg, respectively, and their estimated purities were 97%, 97.5%, 99% and 84%, respectively, by "Analysis HPLC Condition B" using a gradient of 35% to 90% buffer B over 30 min. at 60° C.

Analysis LCMS Condition A: isomer 3230-A: Retention time=1.52 min; ESI-MS(+) m/z 930.1 (M+2H).
Analysis LCMS Condition A: isomer 3230-B: Retention time=1.55 min; ESI-MS(+) m/z 930.0 (M+2H).
Analysis LCMS Condition A: isomer 3230-C: Retention time=1.55 min; ESI-MS(+) m/z 929.8 (M+2H).
Analysis LCMS Condition A: isomer 3230-D: Retention time=1.67 min; ESI-MS(+) m/z 930.2 (M+2H). 3230-A:
ESI-HRMS(+) m/z:
Calculated: 929.4391 (M+2H).
Found: 929.4371 (M+2H).
3230-B:
ESI-HRMS(+) m/z:
Calculated: 929.4391 (M+2H).
Found: 929.4372 (M+2H).
3230-C:
ESI-HRMS(+) m/z:
Calculated: 929.4391 (M+2H).
Found: 929.4380 (M+2H).
3230-D:
ESI-HRMS(+) m/z:
Calculated: 929.4391 (M+2H).
Found: 929.4379 (M+2H).

Preparation of Example 3231

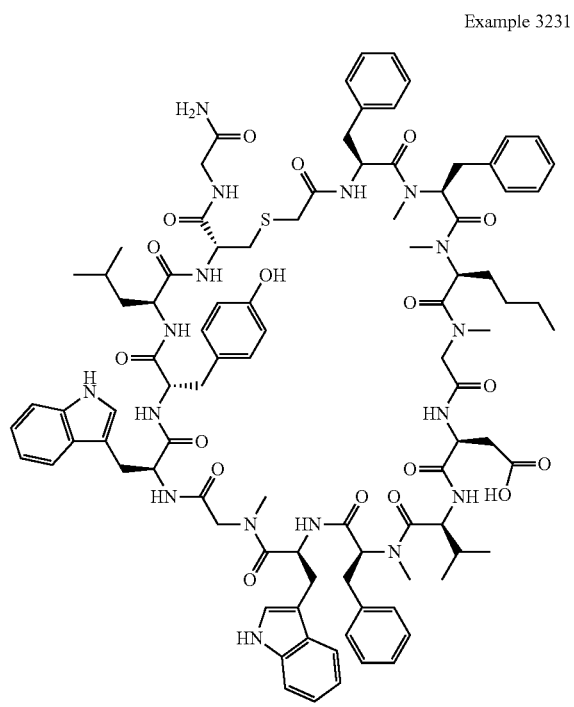 [SMILES: CCCC[C@H]1C(=O)N(C)CC(=O)N[C@@H](CC(=O)O)C(=O)N[C@@H](C(C)C)C(=O)N(C)[C@@H](Cc2ccccc2)C(=O)N[C@@H](Cc2c[nH]c3ccccc23)C(=O)N(C)CC(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccccc2)C(=O)N(C)[C@@H](Cc2ccccc2)C(=O)N1C]

Example 3231

Example 3231 was prepared following the general synthetic sequence described for the preparation of Example 3212, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method G", and "Cyclization Method C".

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-70% B over 25 minutes, then a 5-minute hold at 100% B; Flow: 20 mL/min. Fractions containing the desired product were combined and dried via centrifugal evaporation. The yield of the product was 5.2 mg, and its estimated purity by LCMS analysis was 99%.

Analysis LCMS Condition D: Retention time=1.652 min; ESI-MS(+) m/z 910.40 (M+2H).

Analysis LCMS Condition E: Retention time=1.801 min; ESI-MS(+) m/z 910.75 (M+2H).

Preparation of Example 3232

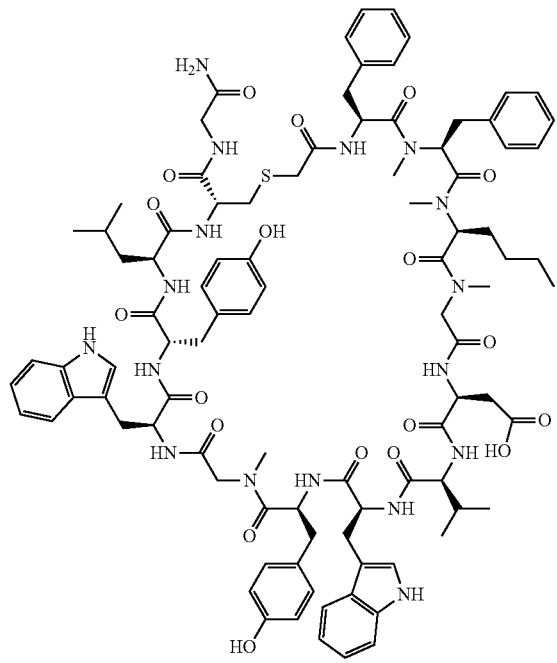

Example 3232

Example 3232 was prepared following the general synthetic sequence described for the preparation of Example 3212, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method G", and "Cyclization Method C".

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-65% B over 25 minutes, then a 5-minute hold at 100% B; Flow: 20 mL/min. Fractions containing the desired product were combined and dried via centrifugal evaporation. The yield of the product was 11.1 mg, and its estimated purity by LCMS analysis was 95%.

Analysis LCMS Condition D: Retention time=1.499 min; ESI-MS(+) m/z 911.70 (M+2H).

Analysis LCMS Condition E: Retention time=1.633 min; ESI-MS(+) m/z 911.40 (M+2H).

Preparation of Example 3233

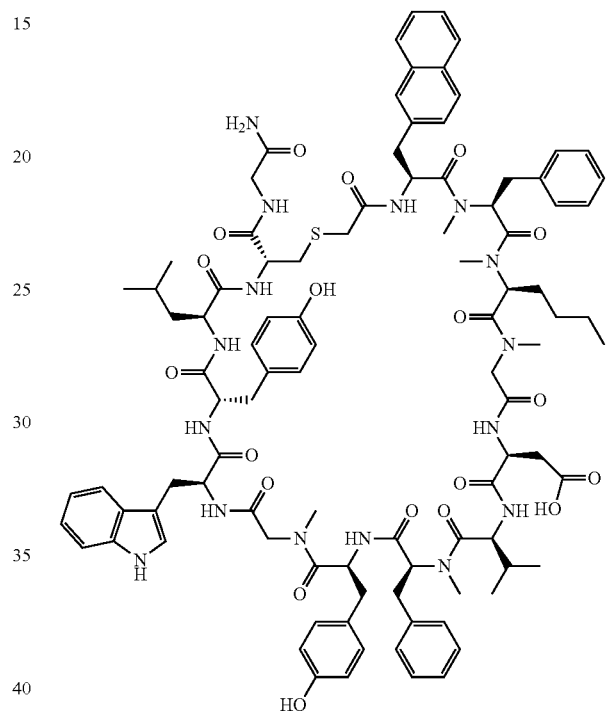

Example 3233

Example 3233 was prepared following the general synthetic sequence described for the preparation of Example 3212, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method G", and "Cyclization Method C".

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-70% B over 25 minutes, then a 5-minute hold at 100% B; Flow: 20 mL/min. Fractions containing the desired product were combined and dried via centrifugal evaporation. The yield of the product was 5.3 mg, and its estimated purity by LCMS analysis was 94%.

Analysis LCMS Condition D: Retention time=1.662 min; ESI-MS(+) m/z 923.70 (M+2H).

Analysis LCMS Condition E: Retention time=1.823 min; ESI-MS(+) m/z 923.75 (M+2H).

Preparation of Example 3234

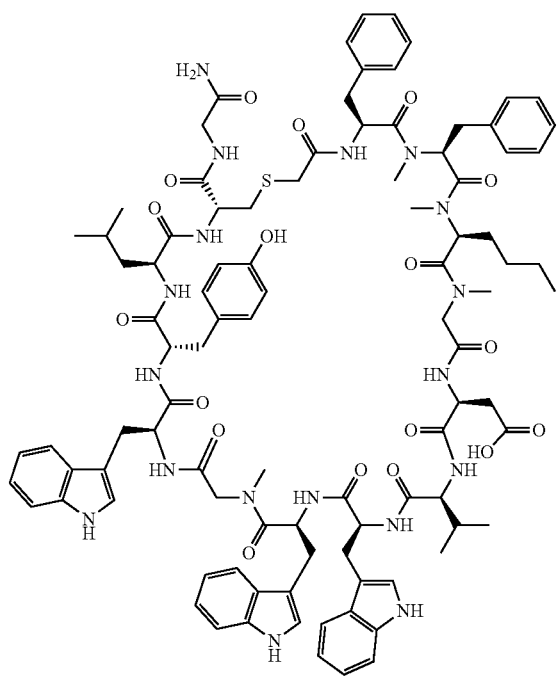

Example 3234

Example 3234 was prepared following the general synthetic sequence described for the preparation of Example 3212, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method G", and "Cyclization Method C".

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 25 minutes, then a 5-minute hold at 100% B; Flow: 20 mL/min. Fractions containing the desired product were combined and dried via centrifugal evaporation. The yield of the product was 9.0 mg, and its estimated purity by LCMS analysis was 99%.

Analysis LCMS Condition D: Retention time=1.585 min; ESI-MS(+) m/z 922.60 (M+2H).

Analysis LCMS Condition E: Retention time=1.724 min; ESI-MS(+) m/z 924.45 (M+2H).

Preparation of Example 3235

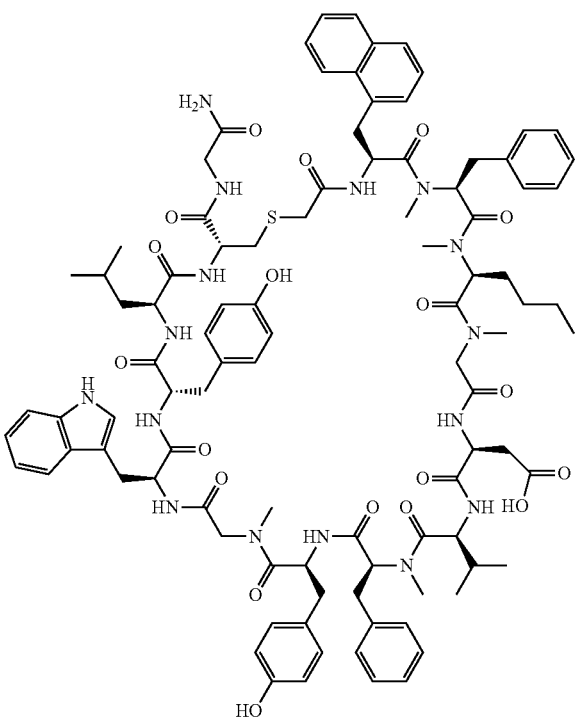

Example 3235

Example 3235 was prepared following the general synthetic sequence described for the preparation of Example 3212, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method G", and "Cyclization Method C".

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-70% B over 25 minutes, then a 5-minute hold at 100% B; Flow: 20 mL/min. Fractions containing the desired product were combined and dried via centrifugal evaporation. The yield of the product was 4.0 mg, and its estimated purity by LCMS analysis was 98%.

Analysis LCMS Condition D: Retention time=1.77 min; ESI-MS(+) m/z 923.8 (M+2H).

Analysis LCMS Condition E: Retention time=1.99 min; ESI-MS(+) m/z 924.0 (M+2H).

Preparation of Example 3236

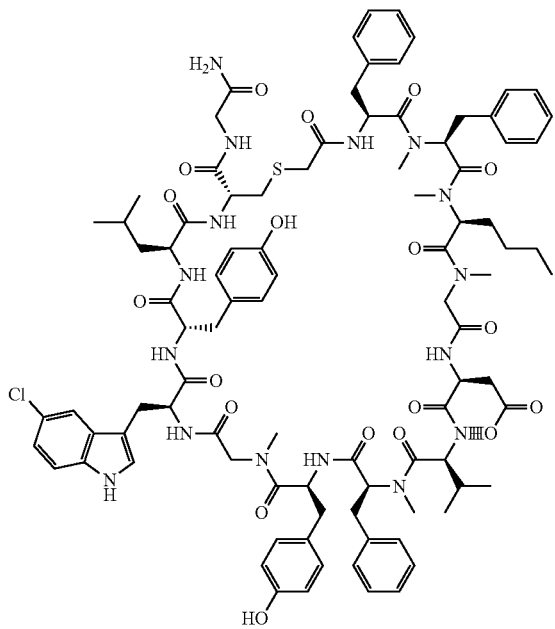

Example 3236

Example 3236 was prepared following the general synthetic sequence described for the preparation of Example 3212, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method G", and "Cyclization Method C".

The crude material was purified via preparative LC/MS with the following conditions: Column: XBridge C18 300, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 25 minutes, then a 5-minute hold at 100% B; Flow: 20 mL/min. Fractions containing the desired product were combined and dried via centrifugal evaporation. The yield of the product was 3.9 mg, and its estimated purity by LCMS analysis was 100%.

Analysis LCMS Condition D: Retention time=1.69 min; ESI-MS(+) m/z 916.3 (M+2H).

Analysis LCMS Condition E: Retention time=1.89 min; ESI-MS(+) m/z 916.3 (M+2H).

Preparation of Example 3237

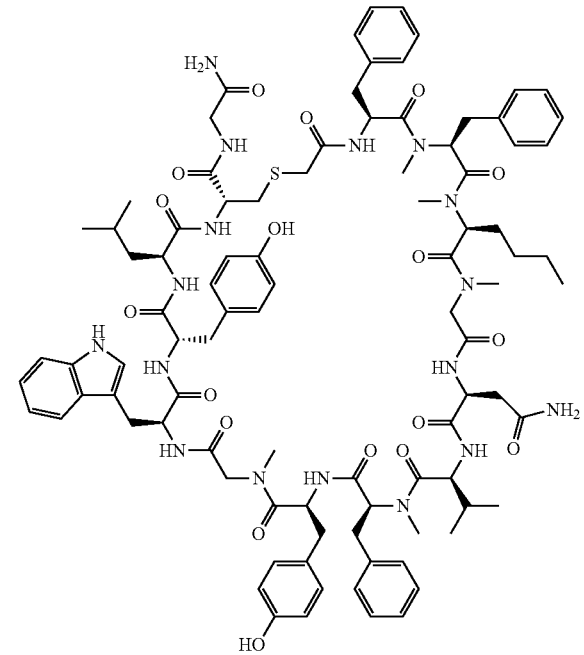

Example 3237

Example 3237 was prepared following the general synthetic sequence described for the preparation of Example 3212, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method G", and "Cyclization Method C".

The crude material was purified via preparative LC/MS with the following conditions: Column: XBridge C18 300, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 minutes, then a 5-minute hold at 100% B; Flow: 20 mL/min. Fractions containing the desired product were combined and dried via centrifugal evaporation. The yield of the product was 9.9 mg, and its estimated purity by LCMS analysis was 100%.

Analysis LCMS Condition D: Retention time=1.78 min; ESI-MS(+) m/z 898.4 (M+2H).

Analysis LCMS Condition E: Retention time=1.78 min; ESI-MS(+) m/z 898.5 (M+2H).

Preparation of Example 3238

Preparation of Example 3239

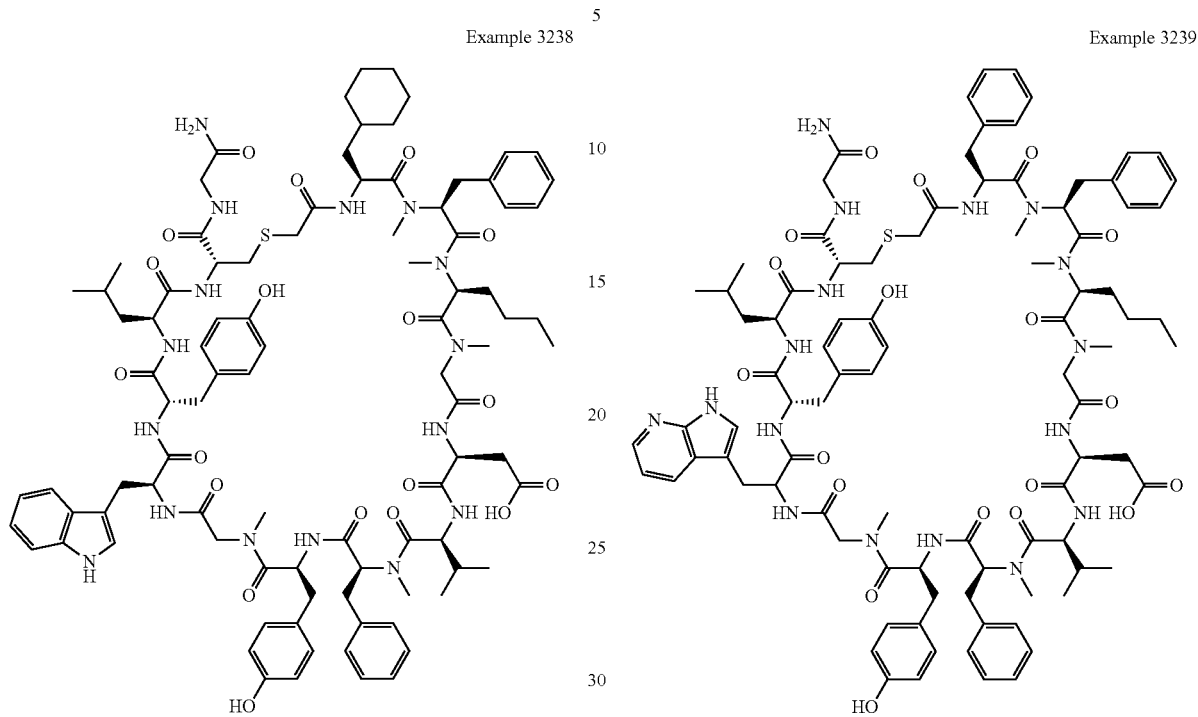

Example 3238

Example 3239

Example 3238 was prepared following the general synthetic sequence described for the preparation of Example 3212, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method G", and "Cyclization Method C".

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 minutes, then a 5-minute hold at 100% B; Flow: 20 mL/min. Fractions containing the desired product were combined and dried via centrifugal evaporation. The yield of the product was 10.3 mg, and its estimated purity by LCMS analysis was 91%.

Analysis LCMS Condition D: Retention time=1.78 min; ESI-MS(+) m/z 902.3 (M+2H).

Analysis LCMS Condition E: Retention time=1.98 min; ESI-MS(+) m/z 902.1 (M+2H).

Example 3239 was prepared following the general synthetic sequence described for the preparation of Example 3212, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method G", and "Cyclization Method C". The Fmoc-protected 7-aza-Trp residue was coupled as the racemate.

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 minutes, then a 5-minute hold at 100% B; Flow: 20 mL/min. Fractions containing the desired product were combined and dried via centrifugal evaporation. The yield of product was 9.4 mg, and its estimated purity by LCMS analysis was 98% as a diastereomeric mixture.

Analysis LCMS Condition D: Retention time=1.51 min; ESI-MS(+) m/z 899.8 (M+2H).

Analysis LCMS Condition E: Retention time=1.61 min; ESI-MS(+) m/z 899.3 (M+2H).

181
Preparation of Example 3240

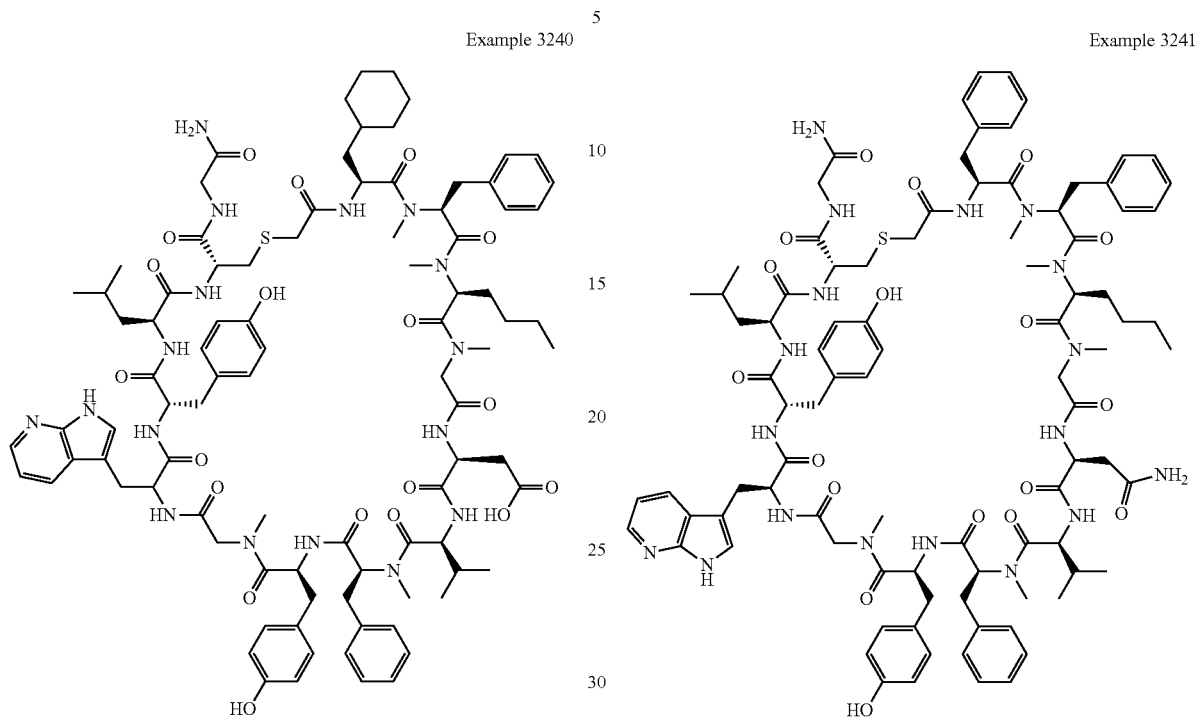

Example 3240 was prepared following the general synthetic sequence described for the preparation of Example 3212, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method G", and "Cyclization Method C". The Fmoc-protected 7-aza-Trp residue was coupled as the racemate.

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 minutes, then a 5-minute hold at 100% B; Flow: 20 mL/min. Fractions containing the desired product were combined and dried via centrifugal evaporation. The yield of product was 3.5 mg, and its estimated purity by LCMS analysis was 97% as a diastereomeric mixture.

Analysis LCMS Condition D: Retention time=1.67 min; ESI-MS(+) m/z 902.5 (M+2H).

Analysis LCMS Condition E: Retention time=1.77 min; ESI-MS(+) m/z 902.5 (M+2H).

182
Preparation of Example 3241

Example 3241 was prepared following the general synthetic sequence described for the preparation of Example 3212, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method G", and "Cyclization Method C". The Fmoc-protected 7-aza-Trp residue was coupled as the racemate.

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 25 minutes, then a 5-minute hold at 100% B; Flow: 20 mL/min. Fractions containing the desired product were combined and dried via centrifugal evaporation. The yield of product was 7.0 mg, and its estimated purity by LCMS analysis was 98% as a diastereomeric mixture.

Analysis LCMS Condition D: Retention time=1.66 min; ESI-MS(+) m/z 898.6 (M+2H).

Analysis LCMS Condition E: Retention time=1.57 min; ESI-MS(+) m/z 899.2 (M+2H).

Preparation of Example 3242

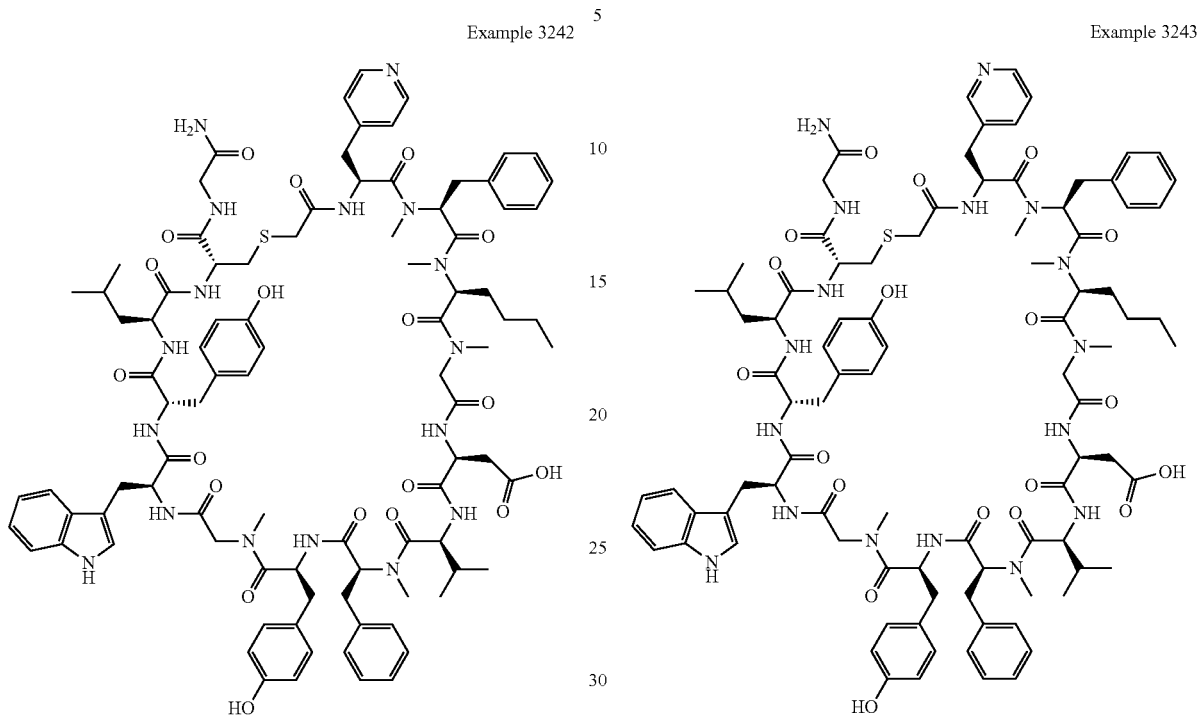

Example 3242

Preparation of Example 3243

Example 3243

Example 3242 was prepared following the general synthetic sequence described for the preparation of Example 3212, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method G", and "Cyclization Method C".

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 minutes, then a 5-minute hold at 100% B; Flow: 20 mL/min. Fractions containing the desired product were combined and dried via centrifugal evaporation. The yield of the product was 2.3 mg, and its estimated purity by LCMS analysis was 99%.

Analysis LCMS Condition D: Retention time=1.43 min; ESI-MS(+) m/z 899.5 (M+2H).

Analysis LCMS Condition E: Retention time=1.54 min; ESI-MS(+) m/z 899.6 (M+2H).

Example 3243 was prepared following the general synthetic sequence described for the preparation of Example 3212, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method G", and "Cyclization Method C".

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 minutes, then a 5-minute hold at 100% B; Flow: 20 mL/min. Fractions containing the desired product were combined and dried via centrifugal evaporation. The yield of the product was 4.8 mg, and its estimated purity by LCMS analysis was 99%.

Analysis LCMS Condition D: Retention time=1.44 min; ESI-MS(+) m/z 899.5 (M+2H).

Analysis LCMS Condition E: Retention time=1.54 min; ESI-MS(+) m/z 899.9 (M+2H).

Preparation of Example 3244

Preparation of Example 3245

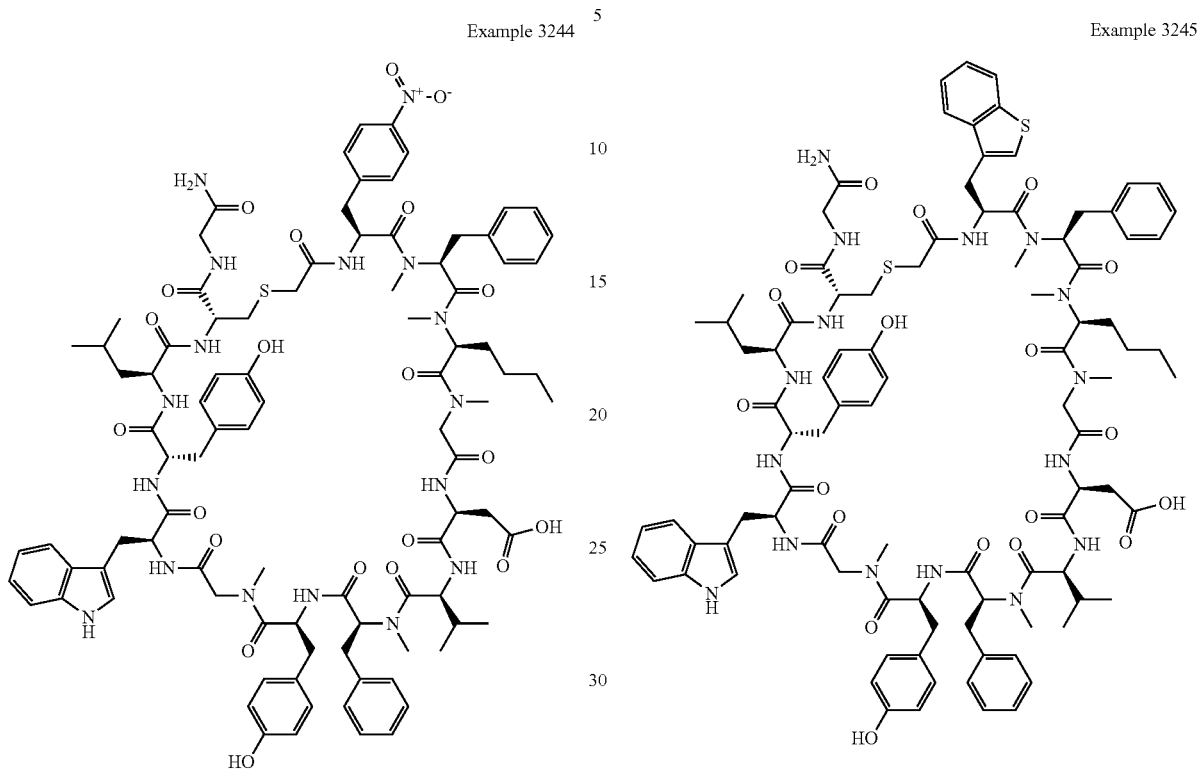

Example 3244

Example 3245

Example 3244 was prepared following the general synthetic sequence described for the preparation of Example 3212, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method G", and "Cyclization Method C".

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-70% B over 25 minutes, then a 5-minute hold at 100% B; Flow: 20 mL/min. Fractions containing the desired product were combined and dried via centrifugal evaporation. The yield of the product was 4.6 mg, and its estimated purity by LCMS analysis was 99%.

Analysis LCMS Condition D: Retention time=1.60 min; ESI-MS(+) m/z 921.3 (M+2H).

Analysis LCMS Condition E: Retention time=1.81 min; ESI-MS(+) m/z 922.0 (M+2H).

Example 3245 was prepared following the general synthetic sequence described for the preparation of Example 3212, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method G", and "Cyclization Method C".

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-75% B over 25 minutes, then a 5-minute hold at 100% B; Flow: 20 mL/min. Fractions containing the desired product were combined and dried via centrifugal evaporation. The yield of the product was 2.3 mg, and its estimated purity by LCMS analysis was 99%.

Analysis LCMS Condition D: Retention time=1.73 min; ESI-MS(+) m/z 927.1 (M+2H).

Analysis LCMS Condition E: Retention time=1.93 min; ESI-MS(+) m/z 927.4 (M+2H).

Preparation of Example 3246

Example 3246

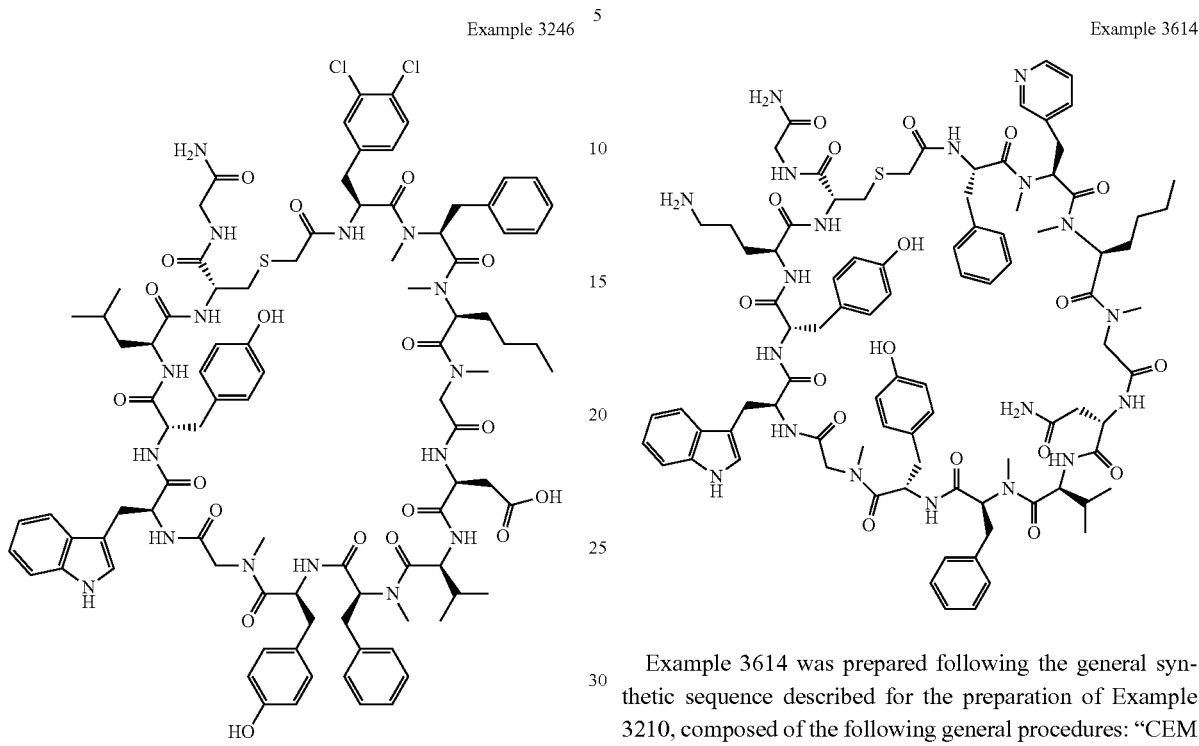

Example 3614

Example 3246 was prepared following the general synthetic sequence described for the preparation of Example 3212, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method G", and "Cyclization Method C".

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 minutes, then a 5-minute hold at 100% B; Flow: 20 mL/min. Fractions containing the desired product were combined and dried via centrifugal evaporation. The yield of the product was 4.4 mg, and its estimated purity by LCMS analysis was 94%.

Analysis LCMS Condition D: Retention time=1.78 min; ESI-MS(+) m/z 932.9 (M+2H).

Analysis LCMS Condition E: Retention time=1.97 min; ESI-MS(+) m/z 932.9 (M+2H).

Preparation of Example 3614

Example 3614 was prepared following the general synthetic sequence described for the preparation of Example 3210, composed of the following general procedures: "CEM Method A: Resin-swelling procedure", "CEM Method A: Standard coupling procedure", "CEM Method A: Custom amino acids-coupling procedure", "N-Methylation on-resin procedure" for the N-methylation of the Fmoc-3-PyAla-OH, "Chloroacetic acid coupling procedure A", "Global Deprotection Method B", and "Cyclization Method C". Fmoc-3-PyAla-OH (2.5 eq.) was coupled manually using HATU (2.5 eq.) and NMM (2.5 eq.) as the coupling method, followed by a second manual coupling step of Fmoc-Phe-OH (5 eq.) using HATU (5 eq.) and NMM (5 eq.) as the coupling method.

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried via centrifugal evaporation. The yield of the product was 6.6 mg, and its estimated purity by LCMS analysis was 94%.

Analysis LCMS Condition D: Retention time=1.53 min; ESI-MS(+) m/z 899.6 (M+2H).

Analysis LCMS Condition E: Retention time=1.45 min; ESI-MS(+) m/z 899.4 (M+2H).

ESI-HRMS(+) m/z:
Calculated: 898.9345 (M+2H).
Found: 898.9345 (M+2H).

Preparation of Example 3616

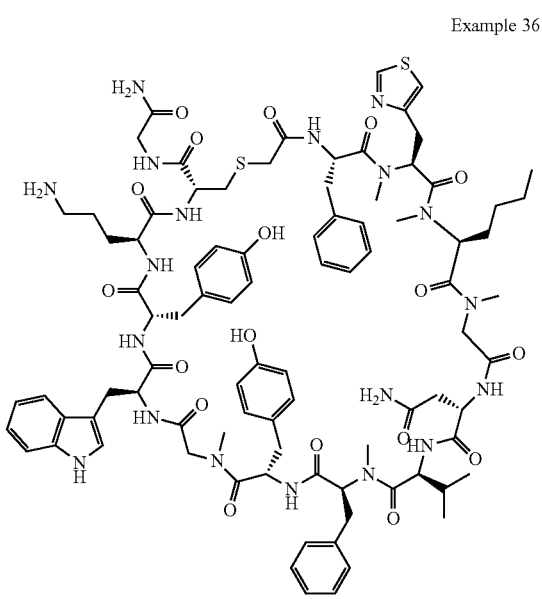

Example 3616

Example 3616 was prepared following the general synthetic sequence described for the preparation of Example 3210, composed of the following general procedures: "CEM Method A: Resin-swelling procedure", "CEM Method A: Standard coupling procedure", "CEM Method A: Custom amino acids-coupling procedure", "N-Methylation on-resin procedure" for the N-methylation of the Fmoc-4-thiazole-ala-OH, "Chloroacetic acid coupling procedure A", "Global Deprotection Method B", and "Cyclization Method C". Fmoc-3-(Thiazol-4yl)-Ala-OH (2.5 eq.) was coupled manually using HATU (2.5 eq.) and NMM (2.5 eq.) as the coupling method, followed by a second manual coupling step of Fmoc-Phe-OH (5 eq.) using HATU (5 eq.) and NMM (5 eq.) as the coupling method. The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-60% B over 25 min., then a 5-minute hold at 100% B; Flow: 20 mL/min. Fractions containing the desired product were combined and dried via centrifugal evaporation. The yield of the product was 11.8 mg, and its estimated purity by LCMS analysis was 97%.

Analysis LCMS Condition D: Retention time=1.53 min; ESI-MS(+) m/z 902.1 (M+2H).

Analysis LCMS Condition E: Retention time=1.52 min; ESI-MS(+) m/z 902.1 (M+2H).

ESI-HRMS(+) m/z:

Calculated: 901.9127 (M+2H).

Found: 901.9130 (M+2H).

Preparation of Example 3617

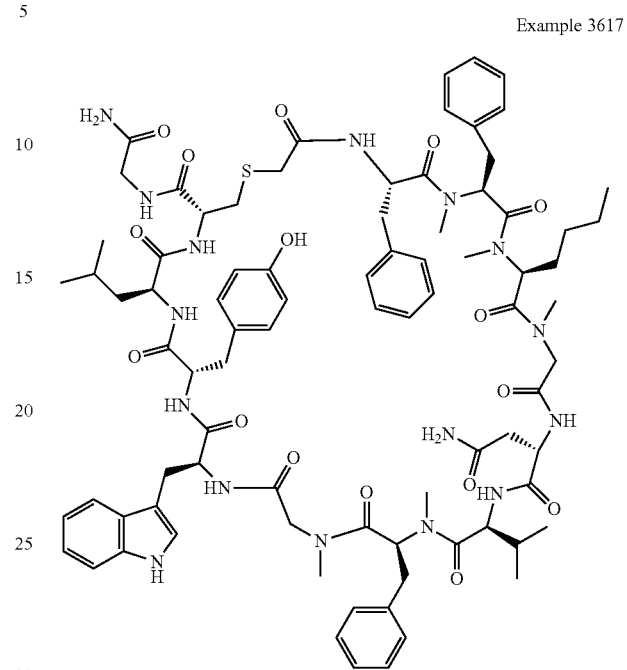

Example 3617

Example 3617 was prepared following the general synthetic sequence described for the preparation of Example 3210, composed of the following general procedures: "CEM Method A: Resin-swelling procedure", "CEM Method A: Standard coupling procedure", "CEM Method A: Custom amino acids-coupling procedure", "Chloroacetic acid coupling procedure A", "Global Deprotection Method B", and "Cyclization Method C".

The crude material was purified via preparative HPLC with the following conditions: Column: Phenomenex Luna 5 u C18(2) 250×21.2 AXIA, 100A Ser. #520221-1; Mobile Phase A: 0.1% TFA in water; Mobile Phase B: 0.1% TFA in acetonitrile; Gradient: 35-75% B over 40 min., then a 5-minute gradient up to 85% B; Flow: 15 mL/min. Fractions containing the desired product were combined and dried via centrifugal evaporation. The product was dissolved in a minimum if acetonitrile and water, frozen and lyophilized to give a white amorphous solid. The yield of the product was 1.9 mg, and its estimated purity by LCMS analysis was 90%.

Analysis LCMS Condition A: Retention time=1.42 min; ESI-MS(+) m/z 817.2 (M+2H).

Analysis LCMS Condition C: Retention time=1.65 min; ESI-MS(+) m/z 1632.8 (M+H).

ESI-HRMS(+) m/z:

Calculated: 816.8996 (M+2H).

Found: 816.8968 (M+2H).

Preparation of Example 3618

Preparation of Example 3628

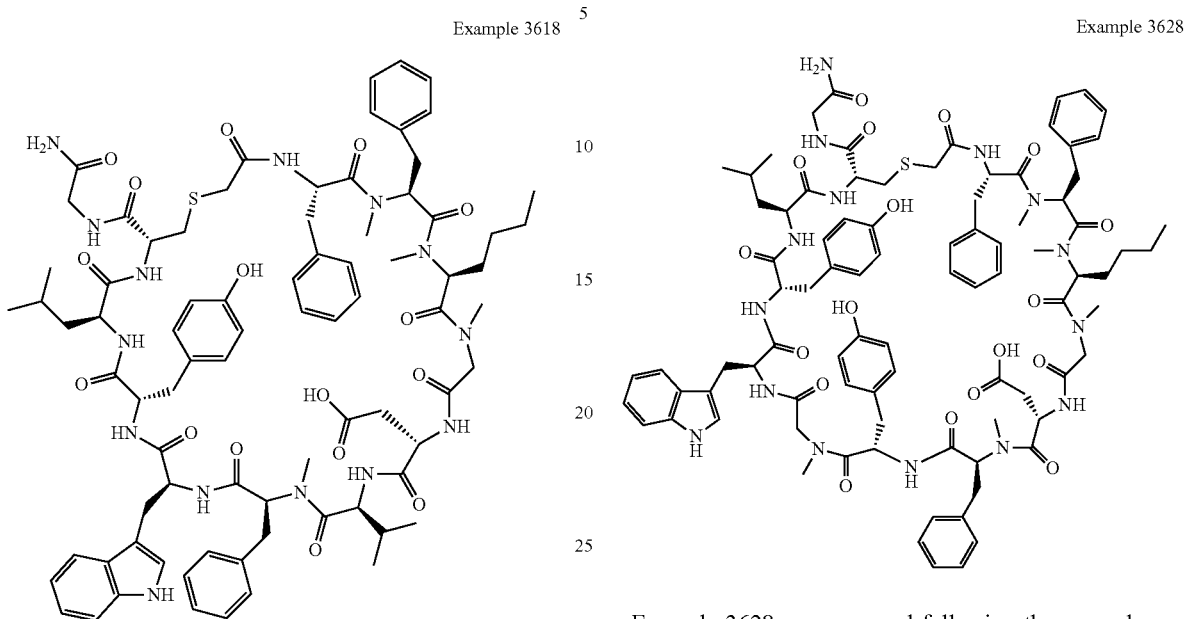

Example 3618

Example 3628

Example 3618 was prepared following the general synthetic sequence described for the preparation of Example 3210, composed of the following general procedures: "CEM Method A: Resin-swelling procedure", "CEM Method A: Standard coupling procedure", "CEM Method A: Custom amino acids-coupling procedure", "Chloroacetic acid coupling procedure A", "Global Deprotection Method B", and "Cyclization Method C".

The crude material was purified via preparative HPLC with the following conditions: Column: Phenom Luna 5 u C18(2) 250×21.2 AXIA, 100 Å Ser. #520221-1; Mobile Phase A: 0.1% TFA in water; Mobile Phase B: 0.1% TFA in acetonitrile; Gradient: 35-75% B over 40 min., then a 5-minute gradient up to 85% B; Flow: 15 mL/min. Fractions containing the desired product were combined and dried via centrifugal evaporation. The product was dissolved in a minimum if acetonitrile and water, frozen and lyophilized to give a white amorphous solid. The yield of the product was 3.5 mg, and its estimated purity by LCMS analysis was 99%.

Analysis LCMS Condition A: Retention time=1.49 min; ESI-MS(+) m/z 781.7 (M+2H).

Analysis LCMS Condition C: Retention time=1.74 min; ESI-MS(+) m/z 1561.8 (M+H).

ESI-HRMS(+) m/z:

Calculated: 781.3810 (M+2H).

Found: 781.3778 (M+2H).

Example 3628 was prepared following the general synthetic sequence described for the preparation of Example 3210, composed of the following general procedures: "CEM Method A: Resin-swelling procedure", "CEM Method A: Standard coupling procedure", "CEM Method A: Custom amino acids-coupling procedure", "Chloroacetic acid coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-60% B over 25 min., then a 5-minute hold at 100% B; Flow: 20 mL/min. Fractions containing the desired product were combined and dried via centrifugal evaporation. The yield of the product was 2.97 mg, and its estimated purity by LCMS analysis was 100%.

Analysis LCMS Condition D: Retention time=1.45 min; ESI-MS(+) m/z 849.2 (M+2H).

Analysis LCMS Condition E: Retention time=1.66 min; ESI-MS(+) m/z 849.3 (M+2H).

ESI-HRMS(+) m/z:

Calculated: 848.8971 (M+2H).

Found: 848.8962 (M+2H).

Preparation of Example 3637

Preparation of Example 3638

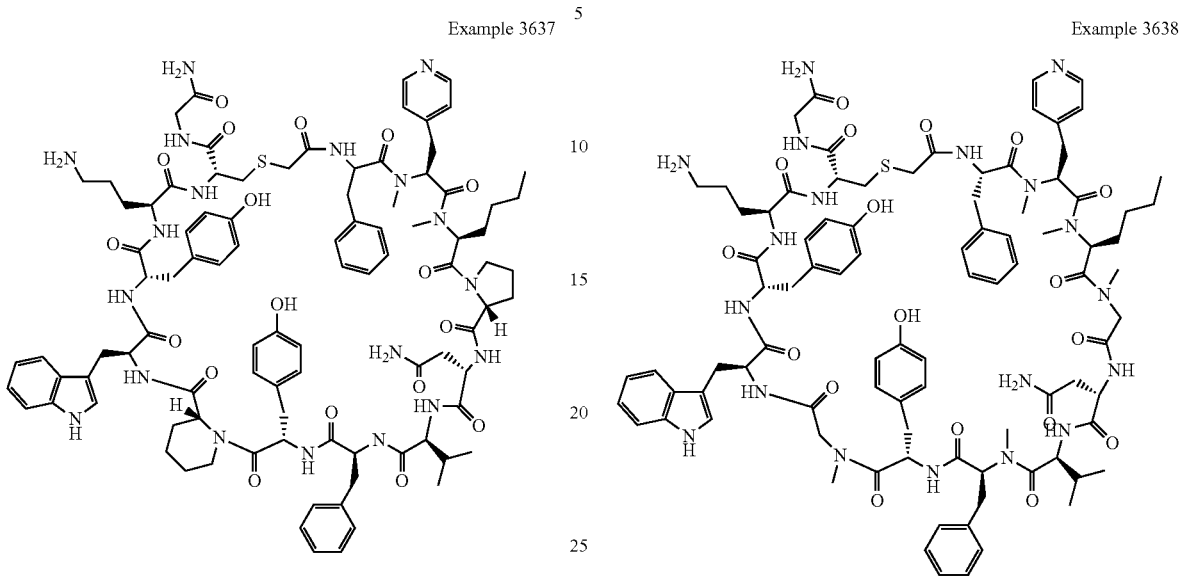

Example 3637

Example 3638

Example 3637 was prepared following the general synthetic sequence described for the preparation of Example 3210, composed of the following general procedures: "CEM Method A: Resin-swelling procedure", "CEM Method A: Standard coupling procedure", "CEM Method A: Custom amino acids-coupling procedure", "N-Methylation on-resin procedure" for the N-methylation of the Fmoc-4-Py-ala-OH, "Chloroacetic acid coupling procedure A", "Global Deprotection Method B", and "Cyclization Method C". Fmoc-4-PyAla-OH (10 eq.) was coupled manually using HATU (10 eq.) and NMM (20 eq.) as the coupling method, followed by a second manual coupling step of Fmoc-Phe-OH (5 eq.) using HATU (5 eq.) and NMM (10 eq.) as the coupling method.

The crude material was purified via preparative LC/MS with the following conditions: Column: Waters XBridge C18, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-60% B over 25 min., then a 5-minute hold at 100% B; Flow: 20 mL/min. Fractions containing the desired product were combined and dried via centrifugal evaporation. The yield of the product was 2.78 mg, and its estimated purity by LCMS analysis was 100%.

Analysis LCMS Condition D: Retention time=1.74 min; ESI-MS(+) m/z 932.5 (M+2H).

Analysis LCMS Condition E: Retention time=1.61 min; ESI-MS(+) m/z 932.5 (M+2H).

ESI-HRMS(+) m/z:
Calculated: 931.9580 (M+2H).
Found: 931.9557 (M+2H).

Example 3638 was prepared following the general synthetic sequence described for the preparation of Example 3210, composed of the following general procedures: "CEM Method A: Resin-swelling procedure", "CEM Method A: Standard coupling procedure", "CEM Method A: Custom amino acids-coupling procedure", "N-Methylation on-resin procedure" for the N-methylation of the Fmoc-4-Py-ala-OH, "Chloroacetic acid coupling procedure A", "Global Deprotection Method B", and "Cyclization Method C". Fmoc-4-PyAla-OH (10 eq.) was coupled manually using HATU (10 eq.) and NMM (20 eq.) as the coupling method, followed by a second manual coupling step of Fmoc-Phe-OH (5 eq.) using HATU (5 eq.) and NMM (10 eq.) as the coupling method.

The crude material was purified via preparative LC/MS with the following conditions: Column: Waters XBridge C18, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-60% B over 25 min., then a 5-minute hold at 100% B; Flow: 20 mL/min. Fractions containing the desired product were combined and dried via centrifugal evaporation. The separation led to two isomers.

The yield of the first isomer, 3638-A, was 1.66 mg, and its estimated purity by LCMS analysis was 91%.

Analysis LCMS Condition D: Retention time=1.07 min; ESI-MS(+) m/z 899.5 (M+2H).

Analysis LCMS Condition E: Retention time=1.08 min; ESI-MS(+) m/z 899.4 (M+2H).

The yield of the second isomer, 3638-B, was 7.56 mg, and its estimated purity by LCMS analysis was 92%.

Analysis LCMS Condition D: Retention time=1.52 min; ESI-MS(+) m/z 899.2 (M+2H).

Analysis LCMS Condition E: Retention time=1.45 min; ESI-MS(+) m/z 899.5 (M+2H).

3638-B:

ESI-HRMS(+) m/z:

Calculated: 898.9345 (M+2H).

Found: 898.9331 (M+2H).

Preparation of Example 3639

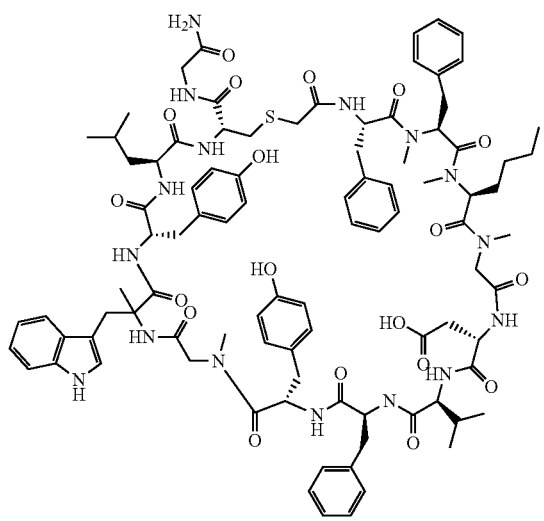

Example 3639

Example 3639 was prepared following the general synthetic sequence described for the preparation of Example 3210, composed of the following general procedures: "CEM Method A: Resin-swelling procedure", "CEM Method A: Standard coupling procedure", "CEM Method A: Custom amino acids-coupling procedure", "Chloroacetic acid coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-60% B over 25 min., then a 5-minute hold at 100% B; Flow: 20 mL/min. Fractions containing the desired product as a diastereomeric mixture were combined and dried via centrifugal evaporation. The yield of the product was 6.7 mg, and its estimated purity by LCMS analysis was 96%.

Analysis LCMS Condition D: Retention time=1.65 min; ESI-MS(+) m/z 903.45 (M+2H).

ESI-HRMS(+) m/z:

Calculated: 905.4391 (M+2H).

Found: 905.4376 (M+2H).

Preparation of Example 3640

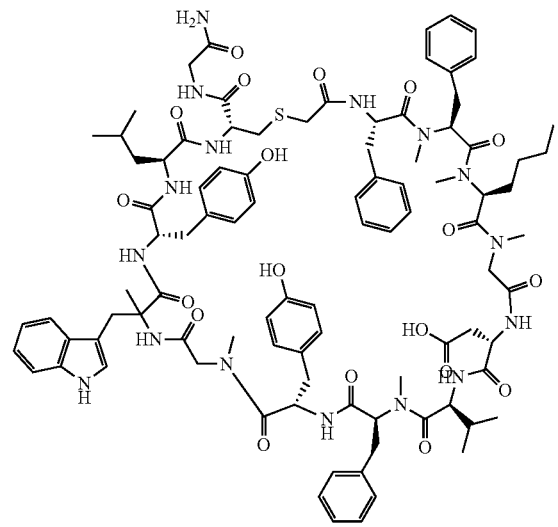

Example 3640

The two diastereoisomers from Example 3639 were separated by Supercritical Fluid Chromatography (SFC) on a Berger SFC MGII system using the following conditions: Column: ES DEAP 25×2.1 cm 5-μm particles; Mobile Phase 44/55 of $CO_2$/95:5 MeOH: $H_2O$ with 10 mM $NH_4OAc$.

The yield of the first isomer, 3640-A, was 2.39 mg, and its estimated purity by LCMS analysis was 100%.

Analysis LCMS Condition A: Retention time=1.43 min; ESI-MS(+) m/z 1812.1 (M+H).

Analysis LCMS Condition C: Retention time=1.67 min; ESI-MS(+) m/z 1810.2 (M+H).

The yield of the second isomer, 3640-B, was 2.15 mg, and its estimated purity by LCMS analysis was 100%.

Analysis LCMS Condition A: Retention time=1.42 min; ESI-MS(+) m/z 1812.1 (M+H).

Analysis LCMS Condition C: Retention time=1.66 min; ESI-MS(+) m/z 1811.1 (M+H).

Preparation of Example 3641

Example 3641

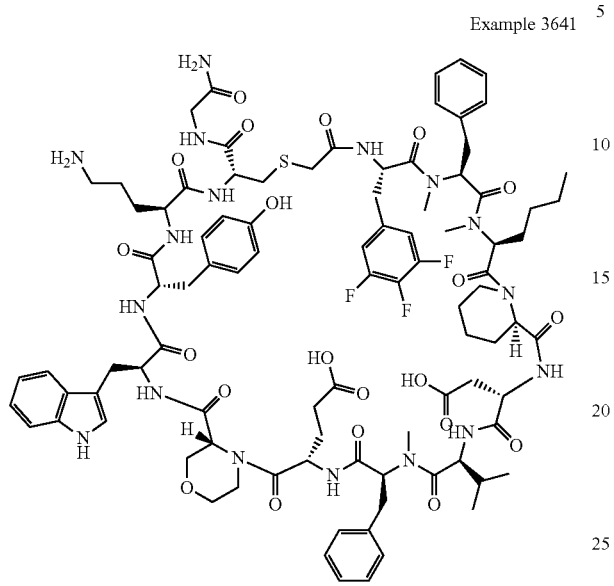

Example 3641 was prepared following the general synthetic sequence described for the preparation of Example 3212, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C". The coupling of Fmoc-Val-OH to the peptidyl-resin was performed using 10 eq. of amino acid, 10 eq. of HATU and 20 eq. of NMM, and was extended to 10 hours. The final coupling of Fmoc-Phe(3,4,5-tri-F)—OH was preformed manually using 1.5 eq. of amino acid, 1.65 eq. of 7-azabenzotriazole (HOAt) and 1.58 eq. of N,N-diisopropylcarbodiimide (DIC) in DMF, and was allowed to proceed for 60 hours.

The crude material was purified via preparative LC/MS with the following conditions: Column: Waters XBridge C18, 19×250 mm, 5-μm particles; Mobile Phase A: 5:95 methanol:water with 10-mM ammonium acetate; Mobile Phase B: 95:5 methanol:water with 10-mM ammonium acetate; Gradient: 40-90% B over 30 minutes, then a 5-minute hold at 100% B; Flow: 20 mL/min. Fractions containing the desired product were combined and dried via centrifugal evaporation. The yield of the product was 2.9 mg, and its estimated purity by LCMS analysis was 100% by "Analysis LCMS Conditions D and G".

Analysis LCMS Condition D: Retention time=1.61 min; ESI-MS(−) m/z 948.7 (M−2H).

Analysis LCMS Condition G: Retention time=2.98 min; ESI-MS(+) m/z 950.7 (M+2H).

ESI-HRMS(+) m/z:
Calculated: (M+2H) 949.9253.
Found: (M+2H) 949.9230.

Preparation of Example 3642

Example 3642

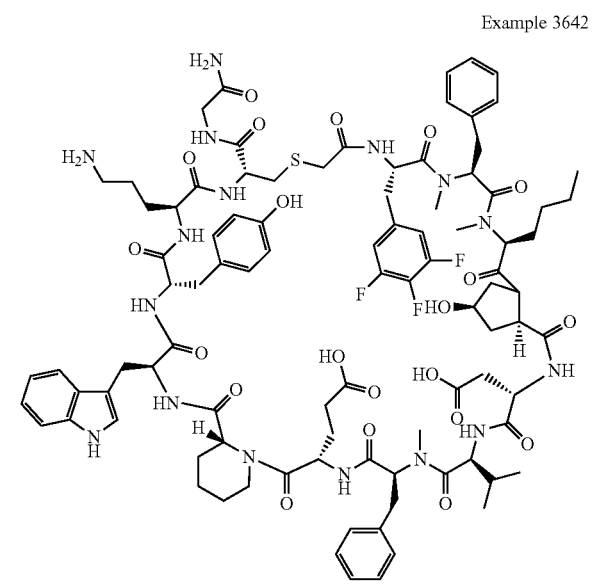 [SMILES: CCCC[C@H]1C(=O)C2C[C@H](O)C[C@@H]2C(=O)N[C@@H](CC(=O)O)C(=O)N[C@@H](C(C)C)C(=O)N(C)[C@@H](Cc2ccccc2)C(=O)N[C@@H](CCC(=O)O)C(=O)N2CCCC[C@@H]2C(=O)N[C@@H](Cc2c[nH]c3ccccc23)C(=O)N[C@@H](Cc2ccc(O)cc2)C(=O)N[C@@H](CCCN)C(=O)N[C@H](C(=O)NCC(N)=O)CSCC(=O)N[C@@H](Cc2cc(F)c(F)c(F)c2)C(=O)N(C)[C@@H](Cc2ccccc2)C(=O)N1C]

Example 3642 was prepared following the general synthetic sequence described for the preparation of Example 3212, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C". The coupling of Fmoc-Val-OH to the peptidyl-resin was performed using 10 eq. of amino acid, 10 eq. of HATU and 20 eq. of NMM, and was extended to 10 hours. The final coupling of Fmoc-Phe(3,4,5-tri-F)—OH was preformed manually using 1.5 eq. of amino acid, 1.65 eq. of 7-azabenzotriazole (HOAt) and 1.58 eq. of N,N-diisopropylcarbodiimide (DIC) in DMF, and was allowed to proceed for 60 hours.

The crude material was purified via preparative LC/MS with the following conditions: Column: Waters XBridge C18, 19×250 mm, 5-μm particles; Mobile Phase A: 5:95 methanol:water with 10-mM ammonium acetate; Mobile Phase B: 95:5 methanol:water with 10-mM ammonium acetate; Gradient: 40-90% B over 30 minutes, then a 5-minute hold at 100% B; Flow: 20 mL/min. Fractions containing the desired product were combined and dried via centrifugal evaporation. The yield of the product was 14.8 mg, and its estimated purity by LCMS analysis was 100% by "Analysis LCMS Conditions D and G".

Analysis LCMS Condition D: Retention time=1.63 min; ESI-MS(+) m/z 950.8 (M−2H).

Analysis LCMS Condition G: Retention time=2.98 min; ESI-MS(+) m/z 950.8 (M+2H).

ESI-HRMS(+) m/z:

Calculated: (M+2H) 949.9253.

Found: (M+2H) 949.9229.

Preparation of Example 3643

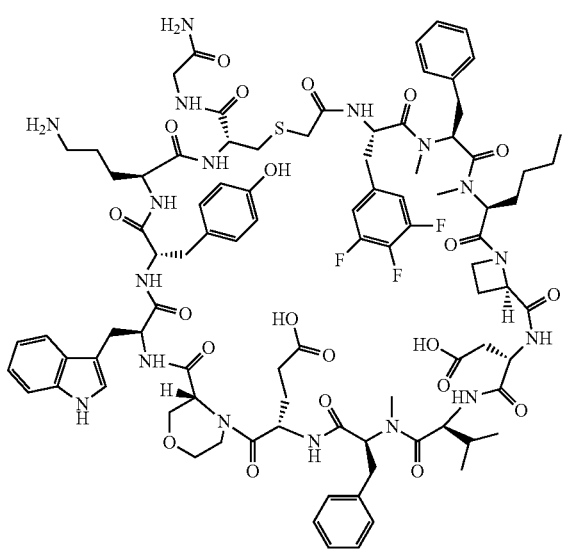

Example 3643

Example 3643 was prepared following the general synthetic sequence described for the preparation of Example 3212, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C". The coupling of Fmoc-Val-OH to the peptidyl-resin was performed using 10 eq. of amino acid, 10 eq. of HATU and 20 eq. of NMM, and was extended to 10 hours. The final coupling of Fmoc-Phe(3,4,5-tri-F)—OH was preformed manually using 1.5 eq. of amino acid, 1.65 eq. of 7-azabenzotriazole (HOAt) and 1.58 eq. of N,N-diisopropylcarbodiimide (DIC) in DMF, and was allowed to proceed for 60 hours.

The crude material was purified via preparative LC/MS with the following conditions: Column: Waters XBridge C18, 19×250 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 31.8 mg, and its estimated purity by LCMS analysis was 98% by "Analysis LCMS Conditions D and G".

Analysis LCMS Condition D: Retention time=1.52 min; ESI-MS(+) m/z 936.9 (M+2H).

Analysis LCMS Condition G: Retention time=2.90 min; ESI-MS(+) m/z 936.8 (M+2H).

ESI-HRMS(+) m/z:

Calculated: (M+2H) 935.9097.

Found: (M+2H) 935.9073.

Preparation of Example 3644

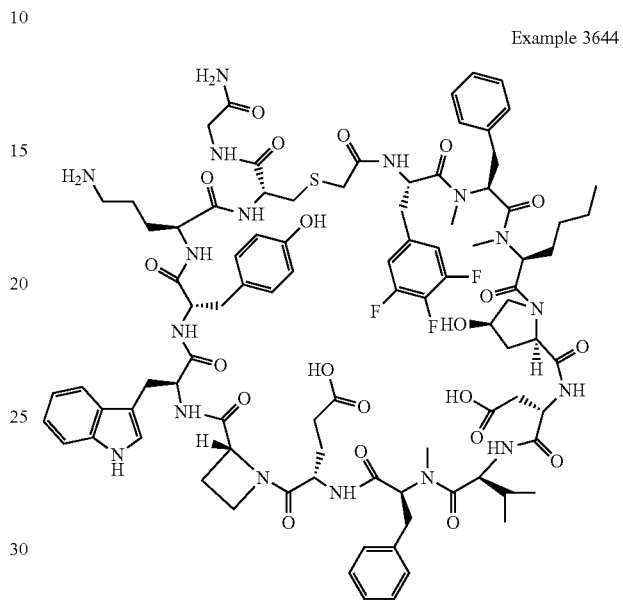

Example 3644

Example 3644 was prepared following the general synthetic sequence described for the preparation of Example 3212, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C". The coupling of Fmoc-Val-OH to the peptidyl-resin was performed using 10 eq. of amino acid, 10 eq. of HATU and 20 eq. of NMM, and was extended to 10 hours. The final coupling of Fmoc-Phe(3,4,5-tri-F)—OH was preformed manually using 1.5 eq. of amino acid, 1.65 eq. of 7-azabenzotriazole (HOAt) and 1.58 eq. of N,N-diisopropylcarbodiimide (DIC) in DMF, and was allowed to proceed for 60 hours.

The crude material was purified via preparative LC/MS with the following conditions: Column: Waters XBridge C18, 19×250 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 35.9 mg, and its estimated purity by LCMS analysis was 100% by "Analysis LCMS Conditions D and G".

Analysis LCMS Condition D: Retention time=1.57 min; ESI-MS(+) m/z 936.5 (M+2H).

Analysis LCMS Condition G: Retention time=2.93 min; ESI-MS(+) m/z 936.5 (M+2H).

ESI-HRMS(+) m/z:

Calculated: (M+2H) 935.9097.

Found: (M+2H) 935.9069.

Preparation of Example 3645

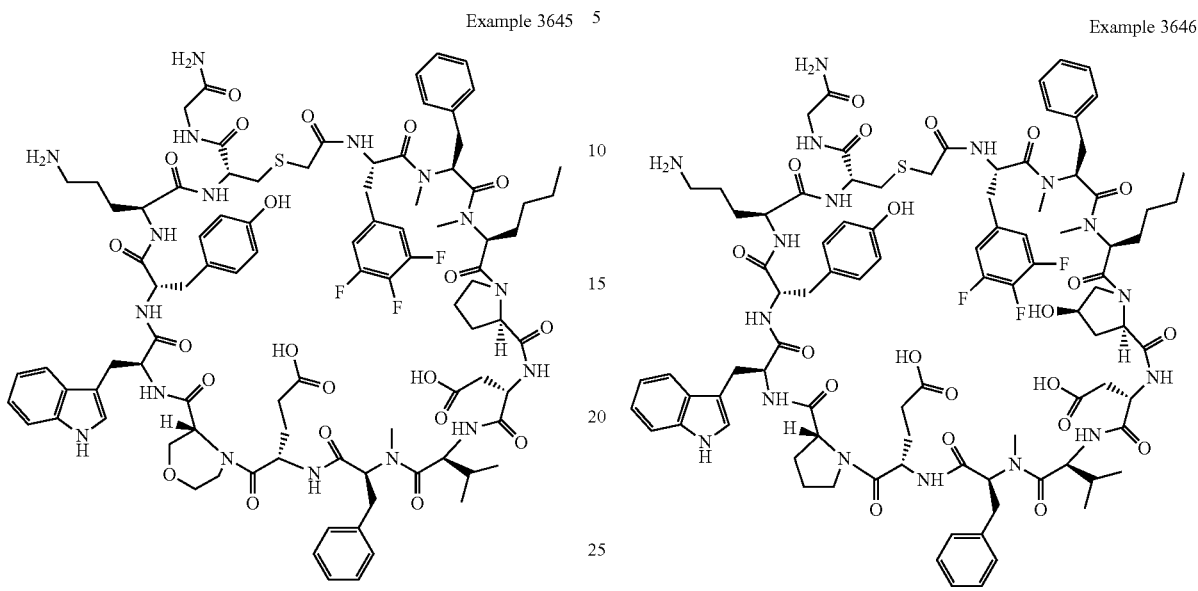

Example 3645

Example 3645 was prepared following the general synthetic sequence described for the preparation of Example 3212, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C". The coupling of Fmoc-Val-OH to the peptidyl-resin was performed using 10 eq. of amino acid, 10 eq. of HATU and 20 eq. of NMM, and was extended to 10 hours. The final coupling of Fmoc-Phe(3,4,5-tri-F)—OH was preformed manually using 1.5 eq. of amino acid, 1.65 eq. of 7-azabenzotriazole (HOAt) and 1.58 eq. of N,N-diisopropylcarbodiimide (DIC) in DMF, and was allowed to proceed for 60 hours.

The crude material was purified via preparative LC/MS with the following conditions: Column: Waters XBridge C18, 19×250 mm, 5-μm particles; Mobile Phase A: 5:95 methanol:water with 10-mM ammonium acetate; Mobile Phase B: 95:5 methanol:water with 10-mM ammonium acetate; Gradient: 50-100% B over 30 minutes, then a 5-minute hold at 100% B; Flow: 20 mL/min. Fractions containing the desired product were combined and dried via centrifugal evaporation. The yield of the product was 46.3 mg, and its estimated purity by LCMS analysis was 95% by "Analysis LCMS Conditions D and G".

Analysis LCMS Condition D: Retention time=1.82 min; ESI-MS(−) m/z 941.05 (M−2H).

Analysis LCMS Condition G: Retention time=3.06 min; ESI-MS(+) m/z 943.8 (M+2H).

ESI-HRMS(+) m/z:

Calculated: (M+2H) 942.9175.

Found: (M+2H) 942.9159.

Preparation of Example 3646

Example 3646

Example 3646 was prepared following the general synthetic sequence described for the preparation of Example 3212, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C". The coupling of Fmoc-Val-OH to the peptidyl-resin was performed using 10 eq. of amino acid, 10 eq. of HATU and 20 eq. of NMM, and was extended to 10 hours. The final coupling of Fmoc-Phe(3,4,5-tri-F)—OH was preformed manually using 1.5 eq. of amino acid, 1.65 eq. of 7-azabenzotriazole (HOAt) and 1.58 eq. of N,N-diisopropylcarbodiimide (DIC) in DMF, and was allowed to proceed for 60 hours.

The crude material was purified via preparative LC/MS with the following conditions: Column: Waters XBridge C18, 19×250 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 28.3 mg, and its estimated purity by LCMS analysis was 98% by "Analysis LCMS Conditions D and G".

Analysis LCMS Condition D: Retention time=1.57 min; ESI-MS(+) m/z 943.4 (M+2H).

Analysis LCMS Condition G: Retention time=2.93 min; ESI-MS(+) m/z 943.6 (M+2H).

ESI-HRMS(+) m/z:

Calculated: (M+2H) 942.9175.

Found: (M+2H) 942.9152.

Preparation of Example 3647

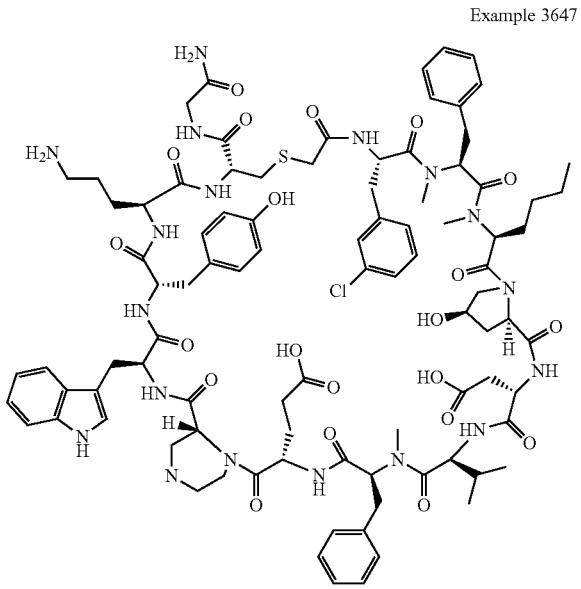 [SMILES: CCCC[C@H]1C(=O)N2C[C@H](O)C[C@@H]2C(=O)N[C@@H](CC(=O)O)C(=O)N[C@@H](C(C)C)C(=O)N(C)[C@@H](Cc2ccccc2)C(=O)N[C@@H](CCC(=O)O)C(=O)N2CCNC[C@@H]2C(=O)N[C@@H](Cc2c[nH]c3ccccc23)C(=O)N[C@@H](Cc2ccc(O)cc2)C(=O)N[C@@H](CCCN)C(=O)N[C@H](C(=O)NCC(N)=O)CSCC(=O)N[C@@H](Cc2cccc(Cl)c2)C(=O)N(C)[C@@H](Cc2ccccc2)C(=O)N1C]

Example 3647

To a Symphony polypropylene solid-phase reaction vessel was added Sieber resin (140 mg, 0.100 mmol), and the reaction vessel was placed on the Symphony peptide synthesizer. The following procedures were then performed sequentially:
"Symphony Method A: Resin-swelling procedure" was followed;
"Symphony Method A: Standard-coupling procedure" was followed with Fmoc-Gly-OH;
"Symphony Method A: Standard-coupling procedure" was followed with Fmoc-Cys(Trt)-OH;
"Symphony Method A: Standard-coupling procedure" was followed with Fmoc-Leu-OH;
"Symphony Method A: Standard-coupling procedure" was followed with Fmoc-Tyr(tBu)-OH;
"Symphony Method A: Standard-coupling procedure" was followed with Fmoc-Trp(Boc)-OH;
"Symphony Method A: Standard-coupling procedure" was followed with Fmoc-(D)-Morpholino-3-carboxylic acid;
"Symphony Method A: Secondary amine-coupling procedure" was followed with Fmoc-Glu(OtBu)-OH;
"Symphony Method A: Standard-coupling procedure" was followed with Fmoc-[N-Me]Phe-OH;
"Symphony Method A: Secondary amine-coupling procedure" was followed with Fmoc-Val-OH;
"Symphony Method A: Single Standard-coupling procedure" was followed with Fmoc-Asp(OtBu)-OH;
"Symphony Method A: Single Standard-coupling procedure" was followed with Fmoc-(D)-cis-Pro(4-OH)—OH;
"Prelude Method A: Secondary amine-coupling procedure" was followed with Fmoc-[N-Me]Nle-OH;
"Prelude Method A: Secondary amine-coupling procedure" was followed with Fmoc-[N-Me]Phe-OH;
"Prelude Method A: Secondary amine-coupling procedure" was followed with Fmoc-Phe(3-Cl)—OH;
"Symphony Method B: Final capping procedure" was followed;
"Global Deprotection Method B" was followed;
"Cyclization Method C" was followed.

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 5.8 mg, and its estimated purity by LCMS analysis was 100%.
Analysis LCMS Condition D: Retention time=1.73 min; ESI-MS(−) m/z 939.8 (M−2H).
Analysis LCMS Condition G: Retention time=2.9 min; ESI-MS(+) m/z 941.8 (M+2H).
ESI-HRMS(+) m/z:
Calculated: (M+2H) 940.9096.
Found: (M+2H) 940.9063.

Preparation of Example 3648

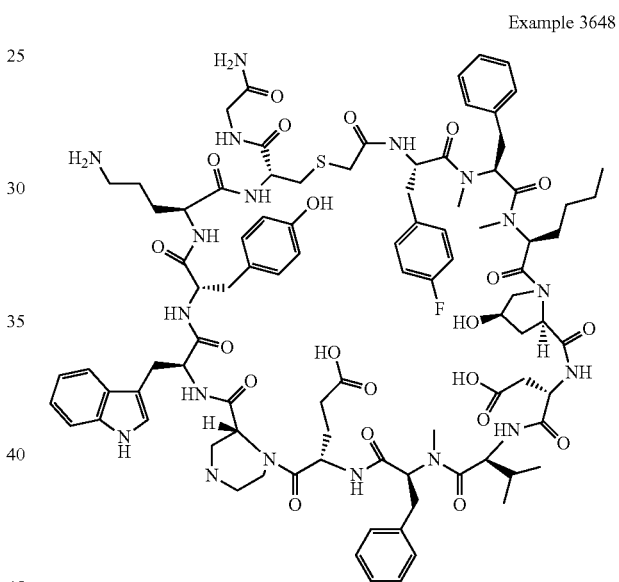

Example 3648

Example 3648 was prepared on Rink Resin following the general synthetic sequence described for the preparation of Example 3647, composed of the following general procedures: "Symphony Method A: Resin-swelling procedure", "Symphony Method A: Standard-coupling procedure", "Symphony Method A: Secondary amine-coupling procedure", "Symphony Method B: Final capping procedure", "Global Deprotection Method B", and "Cyclization Method C".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 4.9 mg, and its estimated purity by LCMS analysis was 100%.
Analysis LCMS Condition D: Retention time=1.67 min; ESI-MS(−) m/z 931.1 (M−2H).

Analysis LCMS Condition G: Retention time=2.84 min; ESI-MS(+) m/z 933.3 (M+2H).
ESI-HRMS(+) m/z:
Calculated: (M+2H) 932.9244.
Found: (M+2H) 932.9200.
Analytical Data:
Mass Spectrometry: "ESI-MS(+)" signifies electrospray ionization mass spectrometry performed in positive ion mode; "ESI-MS(−)" signifies electrospray ionization mass spectrometry performed in negative ion mode; "ESI-HRMS (+)" signifies high-resolution electrospray ionization mass spectrometry performed in positive ion mode; "ESI-HRMS (−)" signifies high-resolution electrospray ionization mass spectrometry performed in negative ion mode. The detected masses are reported following the "m/z" unit designation. Compounds with exact masses greater than 1000 were often detected as double-charged or triple-charged ions.
Analysis Condition A:
Column: Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm.
Analysis Condition B:
Column: Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm.
Analysis Condition C:
Column: Waters Aquity BEH C18 2.1×50 mm 1.7 µm particles; Mobile Phase A: water with 0.05% TFA; Mobile Phase B: acetonitrile with 0.05% TFA; Temperature: 40° C.; Gradient: 0% B, 0-100% B over 3 minutes, then a 0.5-minute hold at 100% B; Flow: 0.8 mL/min; Detection: UV at 220 nm.
Analysis Condition D:
Column: Waters Aquity BEH C18 2.1×50 mm 1.7 µm particles; Mobile Phase A: water with 0.05% TFA; Mobile Phase B: methanol with 0.05% TFA; Temperature: 40° C.; Gradient: 0% B, 0-100% B over 3 minutes, then a 0.5-minute hold at 100% B; Flow: 0.8 mL/min; Detection: UV at 220 nm.
General Procedures:
Prelude Method A:
All manipulations were performed under automation on a Prelude peptide synthesizer (Protein Technologies). All procedures unless noted were performed in a 10 mL polypropylene tube fitted with a bottom frit; where the scale of the reaction exceeded 0.100 mmol, a 40 mL polypropylene tube fitted with a bottom frit was used. The tube connects to a the Prelude peptide synthesizer through both the bottom and the top of the tube. DMF and DCM can be added through the top of the tube, which washes down the sides of the tube equally. The remaining reagents are added through the bottom of the tube and pass up through the frit to contact the resin. All solutions are removed through the bottom of the tube. "Periodic agitation" describes a brief pulse of $N_2$ gas through the bottom frit; the pulse lasts approximately 5 seconds and occurs every 30 seconds. Chloroacetyl chloride solutions in DMF were used within 24 h of preparation. Amino acid solutions were generally not used beyond three weeks from preparation. HATU solutions were used within 5 days of preparation. DMF=dimethylformamide; HATU=1-[Bis(dimethylamino)methylene]-1H-1,2,3-triazolo[4,5-b]pyridinium 3-oxid hexafluorophosphate; DIPEA=diisopropylethylamine; Rink=(2,4-dimethoxyphenyl)(4-alkoxyphenyl)methanamine, where "4-alkoxy" describes the position and type of connectivity to the polystyrene resin. The resin used is Merrifield polymer (polystyrene) with a Rink linker (Fmoc-protected at nitrogen); 100-200 mesh, 1% DVB, 0.56 mmol/g loading. Common amino acids used are listed below with side-chain protecting groups indicated inside parenthesis.

Fmoc-Ala-OH; Fmoc-Arg(Pbf)-OH; Fmoc-Asn(Trt)-OH; Fmoc-Asp(OtBu)-OH; Fmoc-Bzt-OH; Fmoc-Cys(Trt)-OH; Fmoc-Dab(Boc)-OH; Fmoc-Dap(Boc)-OH; Fmoc-Gln(Trt)-OH; Fmoc-Gly-OH; Fmoc-His(Trt)-OH; Fmoc-Hyp(tBu)-OH; Fmoc-Ile-OH; Fmoc-Leu-OH; Fmoc-Lys(Boc)-OH; Fmoc-Nle-OH; Fmoc-Met-OH; Fmoc[N-Me]Ala-OH; Fmoc-[N-Me]Nle-OH; Fmoc-Phe-OH; Fmoc-Pro-OH; Fmoc-Sar-OH; Fmoc-Ser(tBu)-OH; Fmoc-Thr(tBu)-OH; Fmoc-Trp(Boc)-OH; Fmoc-Tyr(tBu)-OH; Fmoc-Val-OH.

The procedures of "Prelude Method A" describe an experiment performed on a 0.100 mmol scale, where the scale is determined by the amount of Rink linker bound to the resin. This scale corresponds to approximately 178 mg of the Rink-Merrifield resin described above. All procedures can be scaled beyond 0.100 mmol scale by adjusting the described volumes by the multiple of the scale. Prior to amino acid coupling, all peptide synthesis sequences began with a resin-swelling procedure, described below as "Resin-swelling procedure". Coupling of amino acids to a primary amine N-terminus used the "Single-coupling procedure" described below. Coupling of amino acids to a secondary amine N-terminus used the "Double-coupling procedure" described below. Coupling of chloroacetylchloride to the N-terminus of the peptide is described by the "Chloroacetyl chloride coupling procedure" detailed below.
Resin-Swelling Procedure:
To a 10 mL polypropylene solid-phase reaction vessel was added Merrifield:Rink resin (178 mg, 0.100 mmol). The resin was washed (swelled) three times as follows: to the reaction vessel was added DMF (2.0 mL), upon which the mixture was periodically agitated for 10 minutes before the solvent was drained through the frit.
Single-Coupling Procedure:
To the reaction vessel containing resin from the previous step was added piperidine:DMF (20:80 v/v, 2.0 mL). The mixture was periodically agitated for 3 minutes and then the solution was drained through the frit. To the reaction vessel was added piperidine:DMF (20:80 v/v, 2.0 mL). The mixture was periodically agitated for 3 minutes and then the solution was drained through the frit. The resin was washed successively six times as follows: for each wash, DMF (2.0 mL) was added through the top of the vessel and the resulting mixture was periodically agitated for 30 seconds before the solution was drained through the frit. To the reaction vessel was added the amino acid (0.2M in DMF, 1.0 mL, 2 eq), then HATU (0.2M in DMF, 1.0 mL, 2 eq), and finally DIPEA (0.8M in DMF, 0.5 mL, 4 eq). The mixture was periodically agitated for 15 minutes, then the reaction solution was drained through the frit. The resin was washed successively four times as follows: for each wash, DMF (2.0 mL) was added through the top of the vessel and the resulting mixture was periodically agitated for 30 seconds before the solution was drained through the frit. To the reaction vessel was added acetic anhydride (2.0 mL). The mixture was periodically agitated for 10 minutes, then the solution was drained through the frit. The resin was washed successively four times as follows: for each wash, DMF (2.0 mL) was added through the top of the vessel and the resulting mixture was periodically agitated for 90 seconds before the solution was drained through the frit. The resulting resin was used directly in the next step.

Double-Coupling Procedure:

To the reaction vessel containing resin from the previous step was added piperidine:DMF (20:80 v/v, 2.0 mL). The mixture was periodically agitated for 3 minutes and then the solution was drained through the frit. To the reaction vessel was added piperidine:DMF (20:80 v/v, 2.0 mL). The mixture was periodically agitated for 3 minutes and then the solution was drained through the frit. The resin was washed successively six times as follows: for each wash, DMF (2.0 mL) was added through the top of the vessel and the resulting mixture was periodically agitated for 30 seconds before the solution was drained through the frit. To the reaction vessel was added the amino acid (0.2M in DMF, 1.0 mL, 2 eq), then HATU (0.2M in DMF, 1.0 mL, 2 eq), and finally DIPEA (0.8M in DMF, 0.5 mL, 4 eq). The mixture was periodically agitated for 15 minutes, then the reaction solution was drained through the frit. The resin was twice washed as follows: for each wash, DMF (2.0 mL) was added through the top of the vessel and the resulting mixture was periodically agitated for 30 seconds before the solution was drained through the frit. To the reaction vessel was added the amino acid (0.2M in DMF, 1.0 mL, 2 eq), then HATU (0.2M in DMF, 1.0 mL, 2 eq), and finally DIPEA (0.8M in DMF, 0.5 mL, 4 eq). The mixture was periodically agitated for 15 minutes, then the reaction solution was drained through the frit. The resin was twice washed as follows: for each wash, DMF (2.0 mL) was added through the top of the vessel and the resulting mixture was periodically agitated for 30 seconds before the solution was drained through the frit. To the reaction vessel was added acetic anhydride (2.0 mL). The mixture was periodically agitated for 10 minutes, then the solution was drained through the frit. The resin was washed successively four times as follows: for each wash, DMF (2.0 mL) was added through the top of the vessel and the resulting mixture was periodically agitated for 90 seconds before the solution was drained through the frit. The resulting resin was used directly in the next step.

Chloroacetyl Chloride Coupling Procedure:

To the reaction vessel containing the resin from the previous step was added piperidine:DMF (20:80 v/v, 2.0 mL). The mixture was periodically agitated for 3 minutes and then the solution was drained through the frit. To the reaction vessel was added piperidine:DMF (20:80 v/v, 2.0 mL). The mixture was periodically agitated for 3 minutes and then the solution was drained through the frit. The resin was washed successively six times as follows: for each wash, DMF (2.0 mL) was added through the top of the vessel and the resulting mixture was periodically agitated for 30 seconds before the solution was drained through the frit. To the reaction vessel was added DIPEA (0.8M in DMF, 3.0 mL, 24 eq), then chloroacetyl chloride (0.8M in DMF, 1.65 mL, 13.2 eq). The mixture was periodically agitated for 30 minutes, then the solution was drained through the frit. The resin was washed successively three times as follows: for each wash, DMF (2.0 mL) was added to top of the vessel and the resulting mixture was periodically agitated for 90 seconds before the solution was drained through the frit. The resin was washed successively four times as follows: for each wash, $CH_2Cl_2$ (2.0 mL) was added to top of the vessel and the resulting mixture was periodically agitated for 90 seconds before the solution was drained through the frit. The resulting resin was placed under a $N_2$ stream for 15 minutes.

Symphony Method A:

This collection of procedures is identical that of "Prelude Method A" except as noted. For all procedures a Symphony X peptide synthesizer (Protein Technologies) was used instead of a Prelude peptide synthesizer and all reagents were added through the top of the reaction vessel.

Resin-Swelling Procedure:

This procedure is identical to "Prelude Method A: Resin-swelling procedure".

Single-Coupling Procedure:

This procedure is identical to "Prelude Method A: Single-coupling procedure" except that the concentration of DIPEA solution was 0.4M and 1.0 mL of this solution was delivered to the reaction.

Double-Coupling Procedure:

This procedure is identical to "Prelude Method A: Double-coupling procedure" except that the concentration of DIPEA solution was 0.4M and 1.0 mL of this solution was delivered to the reaction.

Chloroacetyl Chloride Coupling Procedure:

This procedure is identical to "Prelude Method A: Chloroacetyl chloride coupling procedure".

Global Deprotection Method A:

All manipulations were performed manually unless noted. The procedure of "Global Deprotection Method A" describes an experiment performed on a 0.100 mmol scale, where the scale is determined by the amount of Rink linker bound to the resin. The procedure can be scaled beyond 0.100 mmol scale by adjusting the described volumes by the multiple of the scale. A "deprotection solution" was prepared by combining in a 40 mL glass vial trifluoroacetic acid (22 mL), phenol (1.325 g), water (1.25 mL) and triisopropylsilane (0.5 mL). The resin was removed from the reaction vessel and transferred to a 4 mL glass vial. To the vial was added the "deprotection solution" (2.0 mL). The mixture was vigorously mixed in a shaker (1000 RPM for 1 minute, then 500 RPM for 1-2 h). The mixture was filtered through a 0.2 micron syringe filter and the solids were extracted with the "deprotection solution" (1.0 mL) or TFA (1.0 mL). To a 24 mL test tube charged with the combined filtrates was added $Et_2O$ (15 mL). The mixture was vigorously mixed upon which a significant amount of a white solid precipitated. The mixture was centrifuged for 5 minutes, then the solution was decanted away from the solids and discarded. The solids were suspended in $Et_2O$ (20 mL); then the mixture was centrifuged for 5 minutes; and the solution was decanted away from the solids and discarded. For a final time, the solids were suspended in $Et_2O$ (20 mL); the mixture was centrifuged for 5 minutes; and the solution was decanted away from the solids and discarded to afford the crude peptide as a white to off-white solid.

Cyclization Method A:

All manipulations were performed manually unless noted. The procedure of "Cyclization Method A" describes an experiment performed on a 0.100 mmol scale, where the scale is determined by the amount of Rink linker bound to the resin that was used to generate the peptide. This scale is not based on a direct determination of the quantity of peptide used in the procedure. The procedure can be scaled beyond 0.100 mmol scale by adjusting the described volumes by the multiple of the scale. The crude peptide solids were dissolved in MeCN:aq. 0.1M $NH_4OAc$ (1:1) to a total volume of 18-22 mL, and the solution was carefully then adjusted to pH=8.5-9.0 using aq NaOH (1.0M). The solution was then allowed to stand without stirring for 12-18 h. The reaction solution was concentrated and the residue was then dissolved in DMSO:MeOH. This solution was subjected to reverse-phase HPLC purification to afford the desired cyclic peptide.

General Synthetic Sequence A:

"General Synthetic Sequence A" describes a general sequence of procedures that were used to afford the cyclic peptides described herein. For the purposes of this general procedure, the procedures of "Symphony Method A" are interchangeable with those of "Prelude Method A". To a 10 mL polypropylene solid-phase reaction vessel was added Rink-Merrifield resin (178 mg, 0.100 mmol), and the reaction vessel was placed on the Prelude peptide synthesizer. "Prelude Method A: Resin-swelling procedure" was followed. Then a series of amino acids couplings was sequentially performed on the Prelude following "Prelude Method A: Single-coupling procedure" if the N-terminus of the resin-bound peptide was a primary amine or "Prelude Method A: Double-coupling procedure" if the N-terminus of the resin-bound peptide was a secondary amine. "Prelude Method A: Chloroacetyl chloride coupling procedure" was followed; then "Global Deprotection Method A" was followed; then "Cyclization Method A" was followed.

General Synthetic Sequence B:

"General Synthetic Sequence B" describes a general sequence of procedures that were used to afford the cyclic peptides described herein. For the purposes of this general procedure, the procedures of "Symphony Method A" are interchangeable with those of "Prelude Method A". To a 10 mL polypropylene solid-phase reaction vessel was added 2-Chlorotritylchloride resin (100 mg, 1.42 mmol/g loading). The reaction vessel was placed on the Prelude peptide synthesizer. Manually, to the reaction vessel was added a solution of the Fmoc-protected C-terminus amino acid (0.10 mmol) and diisopropylethylamine (0.65 mmol) in DCM (2.5 mL). Under automation, the mixture was agitated by periodic nitrogen bubbling for 60 minutes. To the reaction vessel was added methanol (0.20 mL). The mixture was agitated by periodic nitrogen bubbling for 15 minutes, then the reaction vessel was drained through the frit. The resin was washed successively three times as follows: for each wash, DCM (2.0 mL) was added to top of the vessel and the resulting mixture was periodically agitated for 90 seconds before the solution was drained through the frit. The resin was washed successively three times as follows: for each wash, DMF (2.0 mL) was added to top of the vessel and the resulting mixture was periodically agitated for 90 seconds before the solution was drained through the frit. The resin was washed successively two times as follows: for each wash, DCM (2.0 mL) was added to top of the vessel and the resulting mixture was periodically agitated for 90 seconds before the solution was drained through the frit. The resin was washed successively three times as follows: for each wash, DMF (2.0 mL) was added to top of the vessel and the resulting mixture was periodically agitated for 90 seconds before the solution was drained through the frit. Then a series of amino acids couplings was sequentially performed on the Prelude following "Prelude Method A: Single-coupling procedure" if the N-terminus of the resin-bound peptide was a primary amine or "Prelude Method A: Double-coupling procedure" if the N-terminus of the resin-bound peptide was a secondary amine. "Prelude Method A: Chloroacetyl chloride coupling procedure" was followed; then "Global Deprotection Method A" was followed; then "Cyclization Method A" was followed.

Preparation of (S)-2-((((9H-fluoren-9-yl)methoxy)carbonyl)amino)-3-(1-(2-(tert-butoxy)-2-oxoethyl)-1H-indol-3-yl)propanoic acid Scheme:

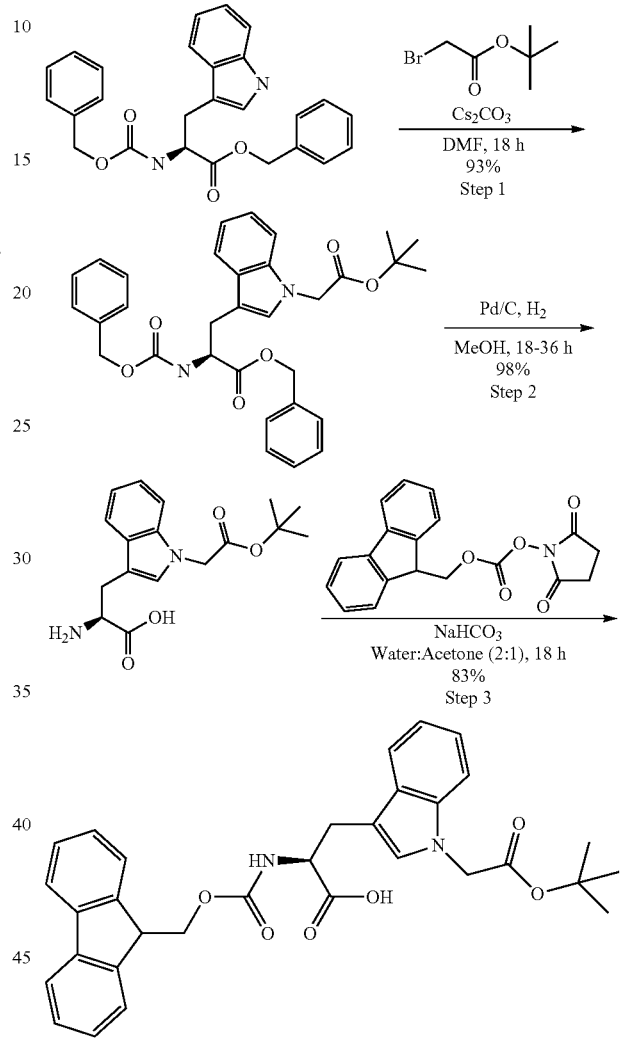

Step 1:

To a 0° C. solution of (S)-benzyl 2-(((benzyloxy)carbonyl)amino)-3-(1H-indol-3-yl)propanoate (25.0 g, 58.3 mmol) and cesium carbonate (20.9 g, 64.2 mmol) in DMF (200 mL) was added tert-butyl 2-bromoacetate (9.36 mL, 64.2 mmol). The solution was allowed to slowly warm up to RT with stirring for 18 h. The reaction mixture was poured into ice water:aq. 1N HCl (1:1) and then extracted with EtOAc. The organic layer was washed with brine, collected, dried over MgSO$_4$, filtered and then concentrated in vacuo. The resulting solid was subjected to SiO$_2$ chromatography (330 g column, 0-50% EtOAc:Hex over 20 column volumes) to afford (S)-benzyl 2-(((benzyloxy)carbonyl)amino)-3-(1-(2-(tert-butoxy)-2-oxoethyl)-1H-indol-3-yl)propanoate as a white solid, 29.6 g (93%).

Step 2:

H₂ was slowly bubbled through a mixture of (S)-benzyl 2-(((benzyloxy)carbonyl)amino)-3-(1-(2-(tert-butoxy)-2-oxoethyl)-1H-indol-3-yl)propanoate (29.6 g, 54.5 mmol) and Pd—C (1.45 g, 1.36 mmol) in MeOH (200 mL) at RT for 10 min. The mixture was then stirred under positive pressure of H₂ while conversion was monitored by LCMS. After 48 h conversion was judged complete and the reaction mixture was filtered through celite and evaporated to afford crude (S)-2-amino-3-(1-(2-(tert-butoxy)-2-oxoethyl)-1H-indol-3-yl)propanoic acid (17.0 g) which was carried into step three without additional purification.

Step 3:

To a solution of (S)-2-amino-3-(1-(2-(tert-butoxy)-2-oxoethyl)-1H-indol-3-yl)propanoic acid (5.17 g, 16.2 mmol) and sodium bicarbonate (6.8 g, 81 mmol) in acetone:water (50.0 mL:100 mL) was added (9H-fluoren-9-yl)methyl (2,5-dioxopyrrolidin-1-yl) carbonate (5.48 g, 16.2 mmol). The mixture stirred overnight upon which LCMS analysis indicated complete conversion. The vigorously stirred mixture was acidified via slow addition of aq 1N HCl. Once acidified, the mixture was diluted with DCM (150 mL), and the isolated organic phase was then washed with water, followed by brine. The organic layer was collected, dried over sodium sulfate, and concentrated under vacuum to afford the crude product. The crude material was purified via silica gel chromatography (330 g column, 20-80% EtOAc:Hex over 20 column volumes) to afford (S)-2-((((9H-fluoren-9-yl)methoxy)carbonyl)amino)-3-(1-(2-(tert-butoxy)-2-oxoethyl)-1H-indol-3-yl)propanoic acid as a white foam, 7.26 g (83%). ¹H NMR (500 MHz, methanol-d₄) δ 7.80 (d, J=7.6 Hz, 2H), 7.67-7.60 (m, 2H), 7.39 (t, J=7.5 Hz, 2H), 7.32-7.22 (m, 3H), 7.18 (td, J=7.6, 0.9 Hz, 1H), 7.08 (td, J=7.5, 0.9 Hz, 1H), 7.04 (s, 1H), 4.54 (dd, J=8.4, 4.9 Hz, 1H), 4.36-4.23 (m, 2H), 4.23-4.14 (m, 1H), 3.43-3.35 (m, 2H), 3.25-3.09 (m, 1H), 1.55-1.38 (m, 9H). ESI-MS(+) m/z=541.3 (M+H).

Preparation of Example 5148

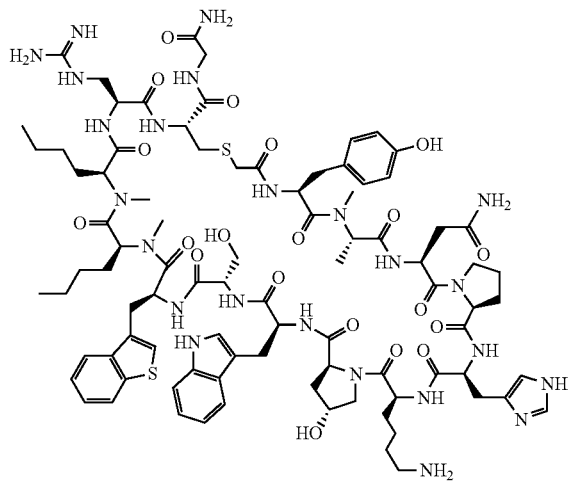

Example 5148

Example 5148 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 8.9 mg, and its estimated purity by LCMS analysis was 100%.

Analysis condition A: Retention time=1.57 min; ESI-MS (+) m/z 972.2 (M+2H)

Analysis condition B: Retention time=2.76 min; ESI-MS (+) m/z 972.3 (M+2H)

ESI-HRMS(+) m/z: Calculated: 971.4662. Found: 971.4619.

Preparation of Example 5150

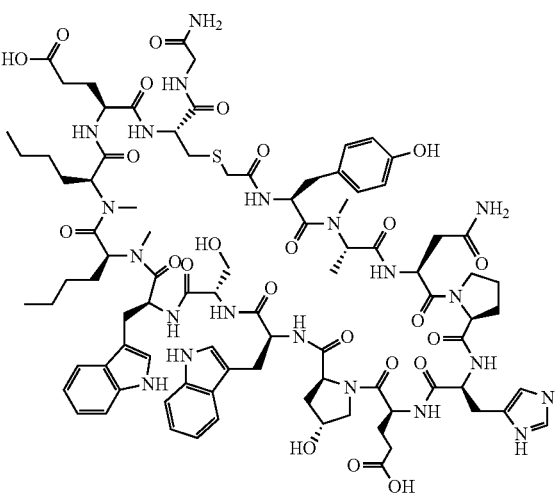

Example 5150

Example 5150 was prepared following "General Synthetic Sequence A". The crude material was purified via preparative LC/MS with the following conditions: Column: waters xbridge c-18, 19×200 mm, 5-μm particles; Mobile Phase A: 5:95 methanol:water with 0.1% trifluoroacetic acid; Mobile Phase B: 95:5 methanol:water with 0.1% trifluoroacetic acid; Gradient: 35-75% B over 30 minutes, then a 5-minute hold at 100% B; Flow: 20 mL/min. Fractions containing the desired product were combined and dried via centrifugal evaporation. The yield of the product was 2.9 mg, and its estimated purity by LCMS analysis was 100%.

Analysis condition A: Retention time=1.36 min; ESI-MS (−) m/z 948.7 (M−2H)

Analysis condition B: Retention time=2.46 min; ESI-MS (−) m/z 948.3 (M−2H)

ESI-HRMS(+) m/z: Calculated: 949.9302. Found: 949.9312.

Preparation of Example 5151

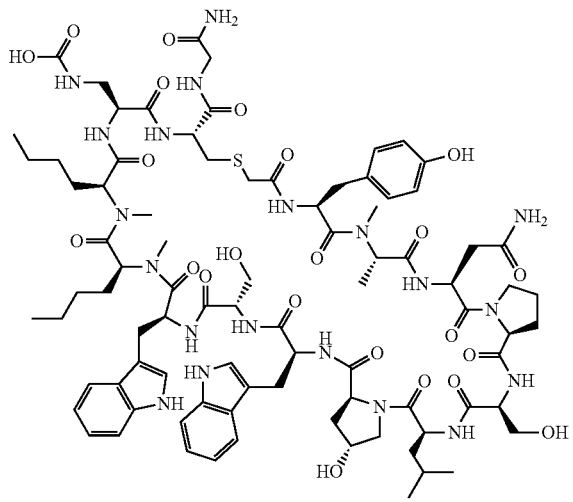

Example 5151

Example 5151 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 1.7 mg, and its estimated purity by LCMS analysis was 100%.

Analysis condition A: Retention time=1.41 min; ESI-MS (+) m/z 1833.3 (M+H)

Analysis condition B: Retention time=2.55 min; ESI-MS (−) m/z 915.7 (M−2H)

ESI-HRMS(+) m/z: Calculated: 916.9374. Found: 916.9376.

Preparation of Example 5152

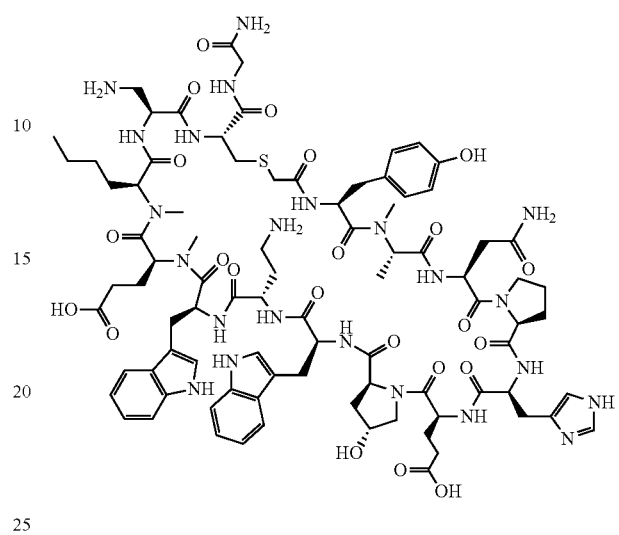

Example 5152

Example 5152 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 30-70% B over 30 minutes, then a 5-minute hold at 100% B; Flow: 20 mL/min. Fractions containing the desired product were combined and dried via centrifugal evaporation. The yield of the product was 32.5 mg, and its estimated purity by LCMS analysis was 100%.

Analysis condition A: Retention time=1.13 min; ESI-MS (+) m/z 943.6 (M+2H)

Analysis condition B: Retention time=2.23 min; ESI-MS (+) m/z 943.6 (M+2H)

ESI-HRMS(+) m/z: Calculated: 942.9279. Found: 942.9257.

Preparation of Example 5153

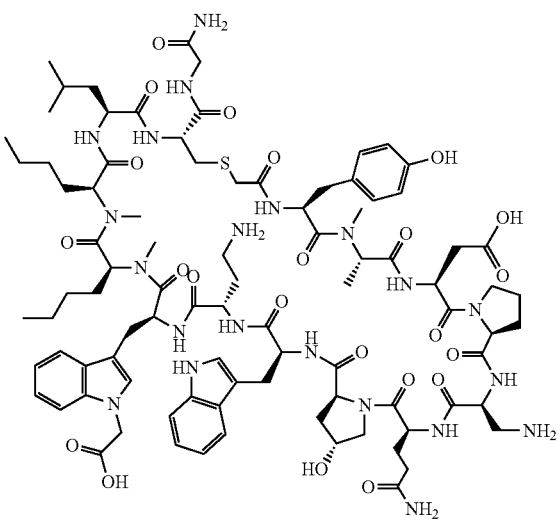

Example 5153

Example 5153 was prepared following "General Synthetic Sequence A", where the "Single-coupling procedure" and "Double-coupling procedure" of "Prelude Method A" were modified to use acetic anhydride in DMF (1.0 M, 2 mL) instead of neat acetic anhydride (2.0 mL). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 49.6 mg, and its estimated purity by LCMS analysis was 100%.

Analysis condition A: Retention time=1.458 min; ESI-MS(+) m/z 953.15 (M+2H)

Analysis condition B: Retention time=2.883 min; ESI-MS(−) m/z 950.30 (M−2H)

ESI-HRMS(+) m/z: Calculated: 951.964. Found: 951.9617.

Preparation of Example 5154

Example 5154

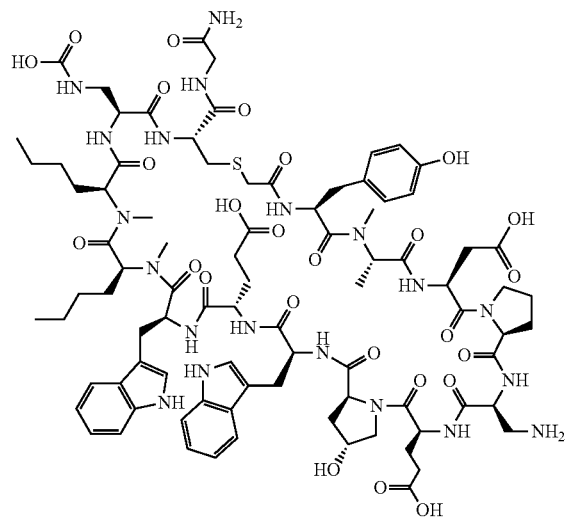

Example 5154 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 20.7 mg, and its estimated purity by LCMS analysis was 96%.

Analysis condition A: Retention time=1.523 min; ESI-MS(+) m/z 946.40 (M+2H)

Analysis condition B: Retention time=2.738 min; ESI-MS(+) m/z 946.10 (M+2H)

ESI-HRMS(+) m/z: Calculated: 945.922. Found: 945.9222.

Preparation of Example 5155

Example 5155

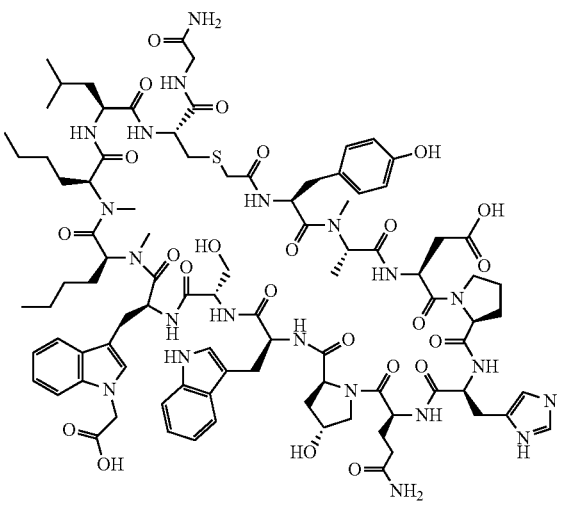

Example 5155 was prepared following "General Synthetic Sequence A", where the "Single-coupling procedure" and "Double-coupling procedure" of "Prelude Method A" were modified to use acetic anhydride in DMF (1.0 M, 2 mL) instead of neat acetic anhydride (2.0 mL). The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 20 minutes, then a 5-minute hold at 100% B; Flow: 20 mL/min. Fractions containing the desired product were combined and dried via centrifugal evaporation. The yield of the product was 17.4 mg, and its estimated purity by LCMS analysis was 94%.

Analysis condition A: Retention time=1.42 min; ESI-MS(+) m/z 978.1 (M+2H)

Analysis condition B: Retention time=2.61 min; ESI-MS(+) m/z 977.7 (M+2H)

ESI-HRMS(+) m/z: Calculated: 977.4694. Found: 977.4682.

Preparation of Example 5156

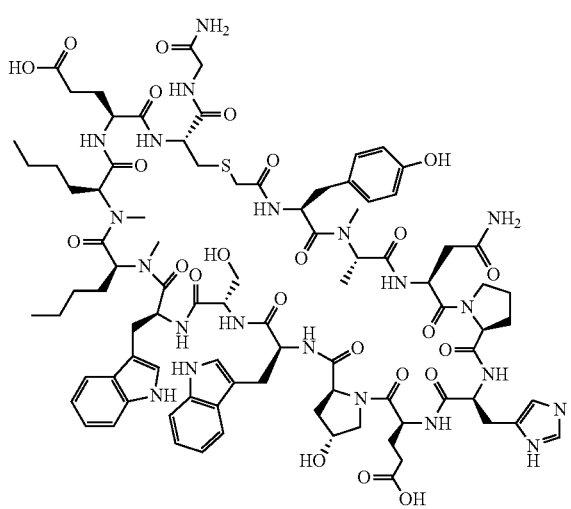

Example 5156

Example 5156 was prepared following "General Synthetic Sequence A". The crude material was purified via preparative LC/MS with the following conditions: Column: XBridge C18, 19×mm, 5-µm particles; Mobile Phase A: 5:95 methanol:water with 10-mM ammonium acetate; Mobile Phase B: 95:5 methanol:water with 10-mM ammonium acetate; Gradient: 30-75% B over 30 minutes, then a 5-minute hold at 100% B; Flow: 20 mL/min. Fractions containing the desired product were combined and dried via centrifugal evaporation. The yield of the product was 13.5 mg, and its estimated purity by LCMS analysis was 97%.

Analysis condition A: Retention time=1.23 min; ESI-MS (+) m/z 97.6 (M+2H)

Analysis condition B: Retention time=2.35 min; ESI-MS (−) m/z 969.5 (M−2H)

ESI-HRMS(+) m/z: Calculated: 970.9354. Found: 970.9336.

Preparation of Example 5157

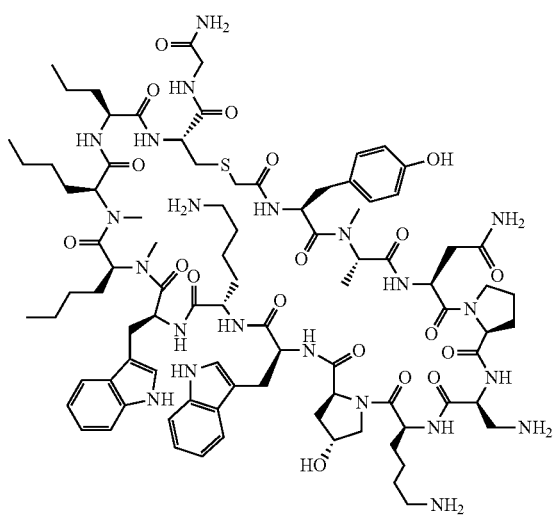

Example 5157

Example 5157 was prepared following "General Synthetic Sequence A". The crude material was purified via preparative LC/MS with the following conditions: Column: XBridge C18, 19×mm, 5-µm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 22.2 mg, and its estimated purity by LCMS analysis was 99%.

Analysis condition A: Retention time=1.35 min; ESI-MS (+) m/z 929.7 (M+2H)

Analysis condition B: Retention time=2.50 min; ESI-MS (+) m/z 930.3 (M+2H)

ESI-HRMS(+) m/z: Calculated: 929.5135. Found: 929.5102.

Preparation of Example 5158

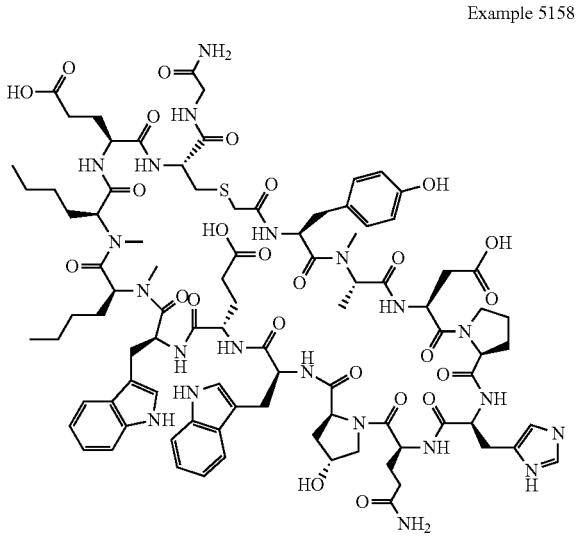 [SMILES: CCCC[C@H]1C(=O)N(C)[C@@H](CCCC)C(=O)N[C@@H](CCC(=O)O)C(=O)N[C@H](C(=O)NCC(N)=O)CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2c[nH]cn2)C(=O)N[C@@H](CCC(N)=O)C(=O)N2C[C@H](O)C[C@H]2C(=O)N[C@@H](Cc2c[nH]c3ccccc23)C(=O)N[C@@H](CCC(=O)O)C(=O)N[C@@H](Cc2c[nH]c3ccccc23)C(=O)N1C]

Example 5158

Example 5158 was prepared following "General Synthetic Sequence A". The crude material was purified via preparative LC/MS with the following conditions: Column: waters xbridge c-18, 19×200 mm, 5-µm particles; Mobile Phase A: 5:95 methanol:water with 0.1% trifluoroacetic acid; Mobile Phase B: 95:5 methanol:water with 0.1% trifluoroacetic acid; Gradient: 35-75% B over 30 minutes, then a 5-minute hold at 100% B; Flow: 20 mL/min. Fractions containing the desired product were combined and dried via centrifugal evaporation. The yield of the product was 9.6 mg, and its estimated purity by LCMS analysis was 100%.

Analysis condition A: Retention time=1.25 min; ESI-MS (+) m/z 972.1 (M+2H)

Analysis condition B: Retention time=2.39 min; ESI-MS (+) m/z 971.6 (M+2H)

ESI-HRMS(+) m/z: Calculated: 970.9354. Found: 970.9359.

Preparation of Example 5159

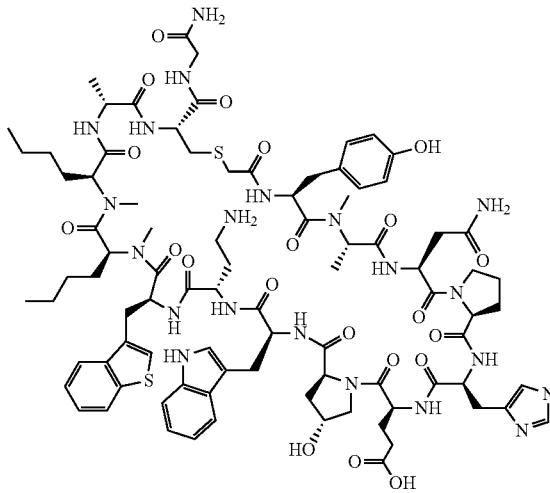

Example 5159

Example 5159 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 26.9 mg, and its estimated purity by LCMS analysis was 99%.

Analysis condition A: Retention time=1.48 min; ESI-MS (+) m/z 936.5 (M+2H)

Analysis condition B: Retention time=2.77 min; ESI-MS (+) m/z 936.3 (M+2H)

ESI-HRMS(+) m/z: Calculated: 935.9238. Found: 935.9214.

Preparation of Example 5160

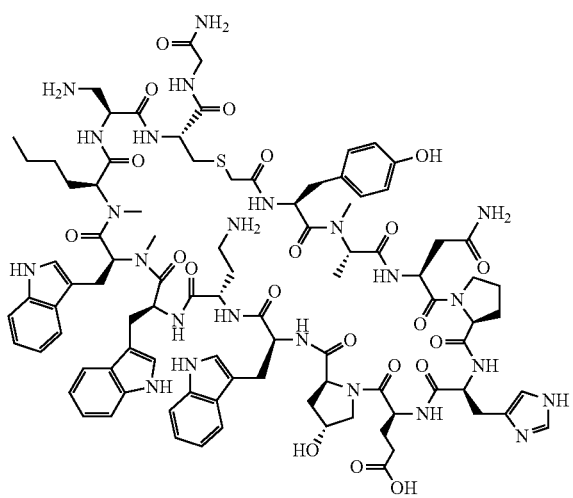

Example 5160

Example 5160 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-40% B over 30 minutes, then a 5-minute hold at 100% B; Flow: 20 mL/min. Fractions containing the desired product were combined and dried via centrifugal evaporation. The yield of the product was 17.0 mg, and its estimated purity by LCMS analysis was 97%.

Analysis condition A: Retention time=1.36 min; ESI-MS (+) m/z 972.1 (M+2H)

Analysis condition B: Retention time=2.46 min; ESI-MS (+) m/z 971.8 (M+2H)

ESI-HRMS(+) m/z: Calculated: 971.4463. Found: 971.444.

Preparation of Example 5161

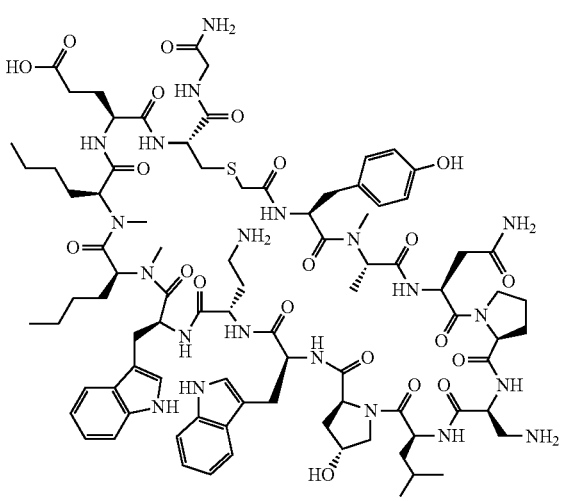

Example 5161

Example 5161 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 17.7 mg, and its estimated purity by LCMS analysis was 100%.

Analysis condition A: Retention time=1.44 min; ESI-MS (+) m/z 923.2 (M+2H)

Analysis condition B: Retention time=2.60 min; ESI-MS (−) m/z 921.6 (M−2H)

ESI-HRMS(+) m/z: Calculated: 922.9613. Found: 922.9568.

Preparation of Example 5162

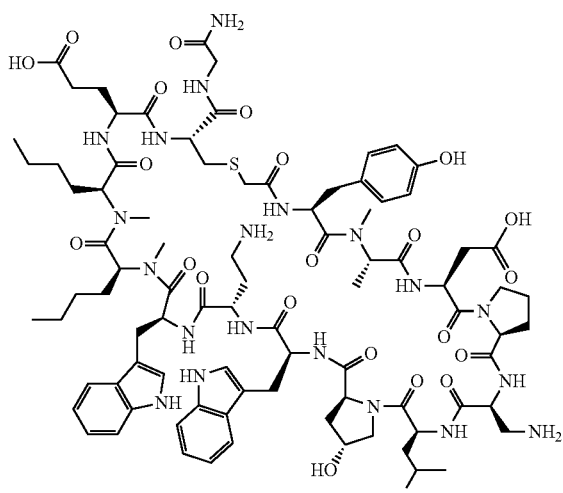

Example 5162

Example 5162 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 29.2 mg, and its estimated purity by LCMS analysis was 98%.

Analysis condition A: Retention time=1.47 min; ESI-MS (+) m/z 923.8 (M+2H)

Analysis condition B: Retention time=2.63 min; ESI-MS (+) m/z 923.8 (M+2H)

ESI-HRMS(+) m/z: Calculated: 923.4533. Found: 923.449.

Preparation of Example 5163

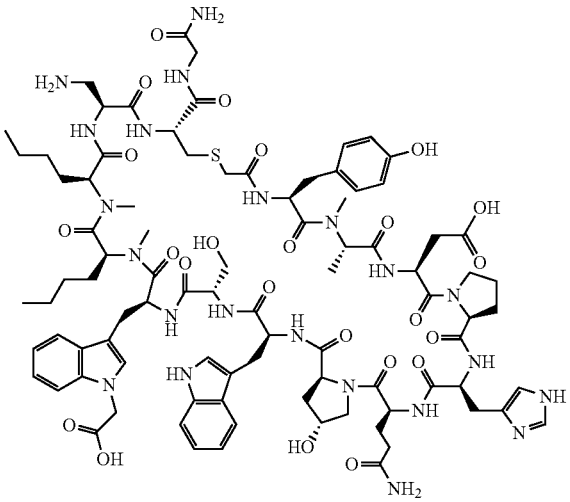

Example 5163

Example 5163 was prepared following "General Synthetic Sequence A", where the "Single-coupling procedure" and "Double-coupling procedure" of "Prelude Method A" were modified to use acetic anhydride in DMF (1.0 M, 2 mL) instead of neat acetic anhydride (2.0 mL). The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-45% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-35% B over 30 minutes, then a 5-minute hold at 100% B; Flow: 20 mL/min. Fractions containing the desired product were combined and dried via centrifugal evaporation. The yield of the product was 49.4 mg, and its estimated purity by LCMS analysis was 100%.

Analysis condition A: Retention time=1.28 min; ESI-MS (+) m/z 958.7 (M+2H)

Analysis condition B: Retention time=2.41 min; ESI-MS (+) m/z 957.8 (M+2H)

ESI-HRMS(+) m/z: Calculated: 957.4356. Found: 957.4321.

Preparation of Example 5164

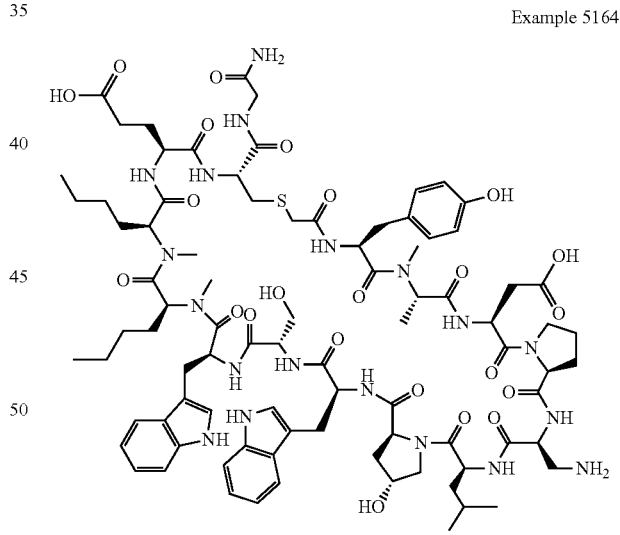

Example 5164

Example 5164 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 30.4 mg, and its estimated purity by LCMS analysis was 100%.

Analysis condition A: Retention time=1.36 min; ESI-MS (−) m/z 915.3 (M−2H)

Analysis condition B: Retention time=2.54 min; ESI-MS (+) m/z 917.6 (M+2H)

ESI-HRMS(+) m/z: Calculated: 916.9374. Found: 916.9374.

Preparation of Example 5165

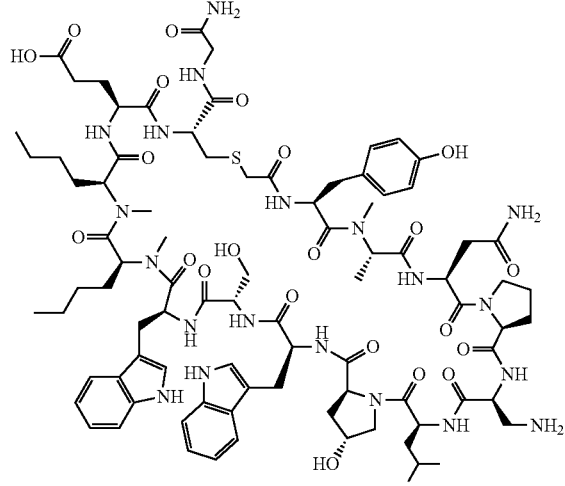

Example 5165

Example 5165 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The material was further purified via preparative LC/MS with the following conditions: Column: waters xbridge c-18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 30-70% B over 30 minutes, then a 5-minute hold at 100% B; Flow: 20 mL/min. Fractions containing the desired product were combined and dried via centrifugal evaporation. The yield of the product was 8.1 mg, and its estimated purity by LCMS analysis was 100%.

Analysis condition A: Retention time=1.45 min; ESI-MS (−) m/z 914.8 (M−2H)

Analysis condition B: Retention time=2.58 min; ESI-MS (+) m/z 917.0 (M+2H)

ESI-HRMS(+) m/z: Calculated: 916.4454. Found: 916.4459.

Preparation of Example 5166

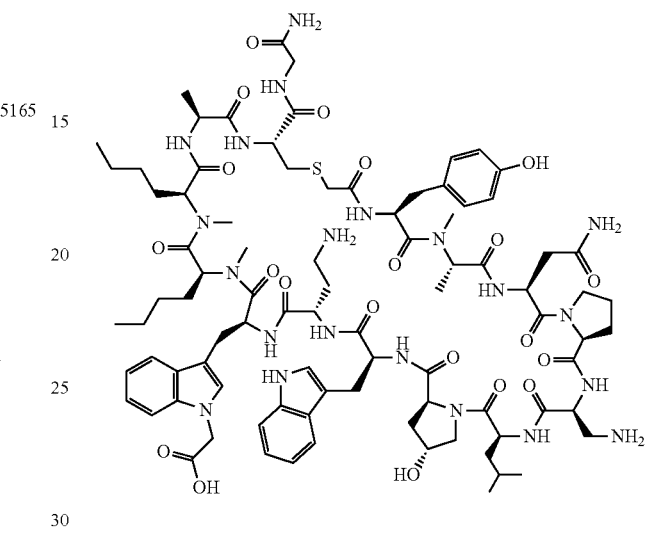

Example 5166

Example 5166 was prepared following "General Synthetic Sequence A", where the "Single-coupling procedure" and "Double-coupling procedure" of "Prelude Method A" were modified to use acetic anhydride in DMF (1.0 M, 2 mL) instead of neat acetic anhydride (2.0 mL). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 20 minutes, then a 5-minute hold at 100% B; Flow: 20 mL/min. Fractions containing the desired product were combined and dried via centrifugal evaporation. The yield of the product was 7.4 mg, and its estimated purity by LCMS analysis was 100%.

Analysis condition A: Retention time=1.41 min; ESI-MS (+) m/z 923.0 (M+2H)

Analysis condition B: Retention time=2.58 min; ESI-MS (+) m/z 923.1 (M+2H).

Preparation of Example 5167

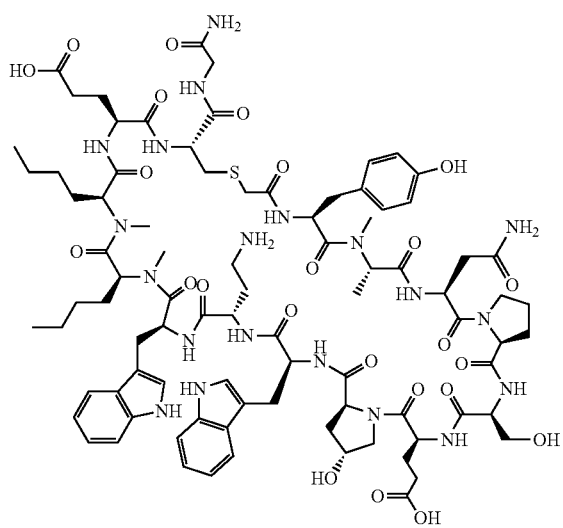

Example 5167

Example 5167 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 37.8 mg, and its estimated purity by LCMS analysis was 100%.

Analysis condition A: Retention time=1.38 min; ESI-MS (+) m/z 931.8 (M+2H)

Analysis condition B: Retention time=2.54 min; ESI-MS (+) m/z 931.3 (M+2H)

ESI-HRMS(+) m/z: Calculated: 931.4325. Found: 931.4285.

Preparation of Example 5168

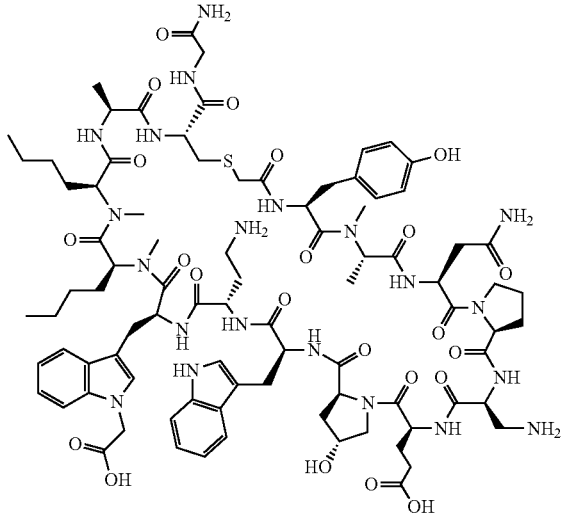

Example 5168

Example 5168 was prepared following "General Synthetic Sequence A", where the "Single-coupling procedure" and "Double-coupling procedure" of "Prelude Method A" were modified to use acetic anhydride in DMF (1.0 M, 2 mL) instead of neat acetic anhydride (2.0 mL). The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 15.9 mg, and its estimated purity by LCMS analysis was 100%.

Analysis condition A: Retention time=1.374 min; ESI-MS(+) m/z 931.4 (M+2H)

Analysis condition B: Retention time=2.892 min; ESI-MS(+) m/z 931.4 (M+2H)

ESI-HRMS(+) m/z: Calculated: 930.9405. Found: 930.9383.

Preparation of Example 5169

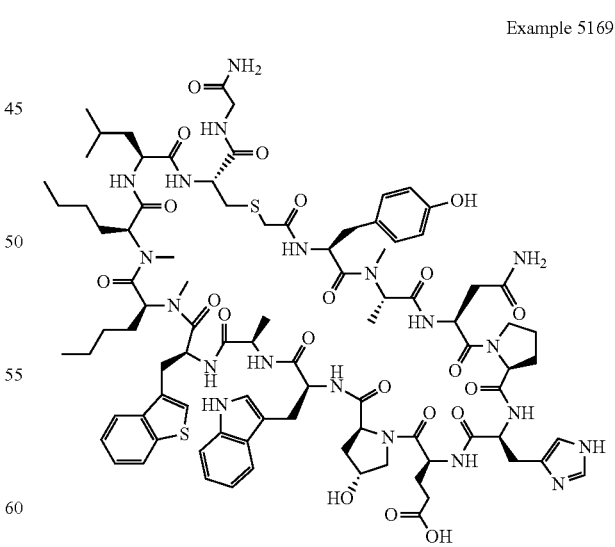

Example 5169

Example 5169 was prepared following "General Synthetic Sequence A". The crude material was purified via preparative LC/MS with the following conditions: Column: XBridge C18, 19×200 mm, 5-μm particles; Mobile Phase A:

5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 10.5 mg, and its estimated purity by LCMS analysis was 100%.

Analysis condition A: Retention time=1.538 min; ESI-MS(+) m/z 940.60 (M+2H)

Analysis condition B: Retention time=2.832 min; ESI-MS(−) m/z 940.65 (M−2H)

ESI-HRMS(+) m/z: Calculated: 942.434. Found: 942.4326.

Preparation of Example 5170

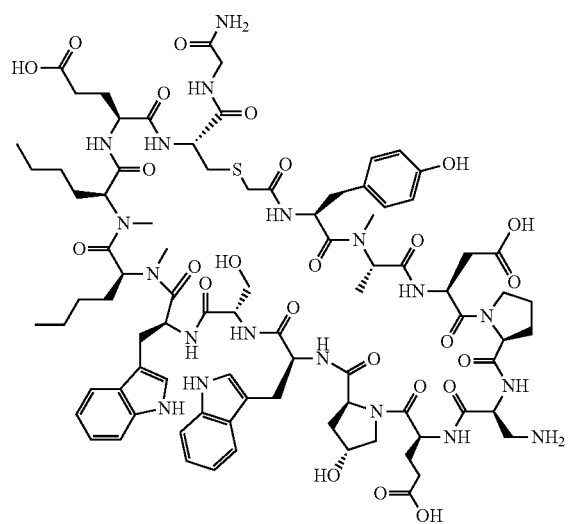

Example 5170

Example 5170 was prepared following "General Synthetic Sequence A". The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 17.2 mg, and its estimated purity by LCMS analysis was 100%.

Analysis condition A: Retention time=1.36 min; ESI-MS (+) m/z 1849.6 (M+H)

Analysis condition B: Retention time=2.49 min; ESI-MS (−) m/z 923.6 (M−2H)

ESI-HRMS(+) m/z: Calculated: 924.9167. Found: 924.9175.

Preparation of Example 5171

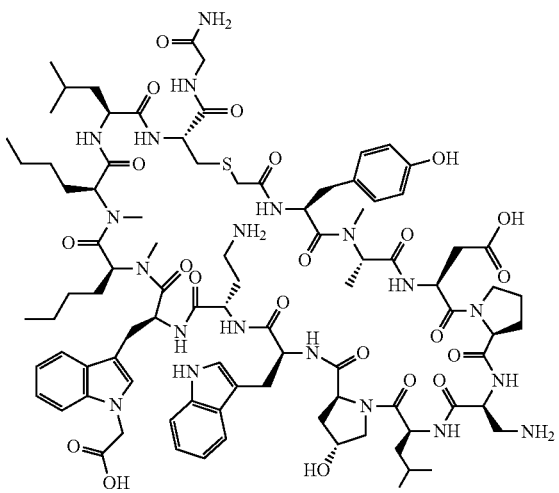

Example 5171

Example 5171 was prepared following "General Synthetic Sequence A", where the "Single-coupling procedure" and "Double-coupling procedure" of "Prelude Method A" were modified to use acetic anhydride in DMF (1.0 M, 2 mL) instead of neat acetic anhydride (2.0 mL). The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 25 minutes, then a 5-minute hold at 100% B; Flow: 20 mL/min. Fractions containing the desired product were combined and dried via centrifugal evaporation. The yield of the product was 31.7 mg, and its estimated purity by LCMS analysis was 97%.

Analysis condition A: Retention time=1.551 min; ESI-MS(+) m/z 944.95 (M+2H)

Analysis condition B: Retention time=3.165 min; ESI-MS(+) m/z 943.2 (M+2H)

ESI-HRMS(+) m/z: Calculated: 944.4767. Found: 944.4745.

Preparation of Example 5174

Example 5174

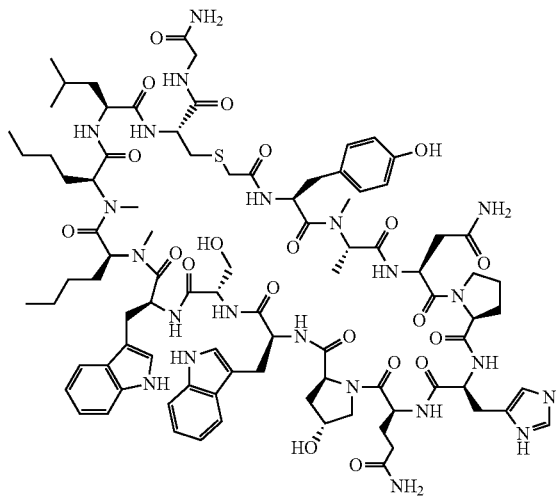

Example 5174 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 9.4 mg, and its estimated purity by LCMS analysis was 98%.

Analysis condition A: Retention time=1.58 min; ESI-MS (+) m/z 935.0 (M+2H)

Analysis condition B: Retention time=2.70 min; ESI-MS (−) m/z 933.2 (M−2H)

ESI-HRMS(+) m/z: Calculated: 934.4511. Found: 934.4518.

Preparation of Example 5175

Example 5175

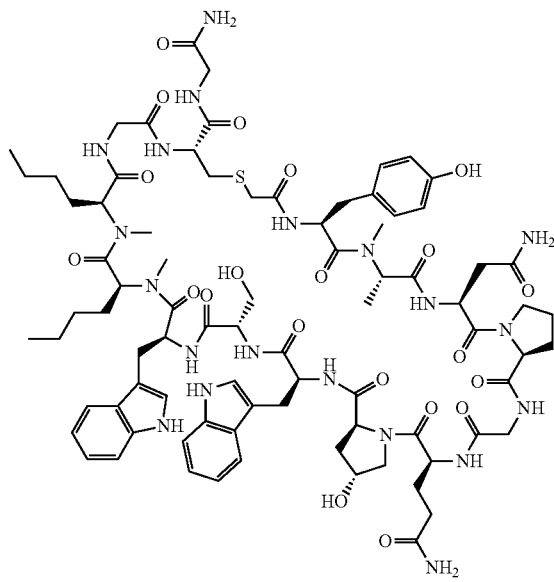

Example 5175 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×200 mm, 5-μm particles; Mobile Phase A: water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 29.5 mg, and its estimated purity by LCMS analysis was 92%.

Analysis condition A: Retention time=1.408 min; ESI-MS(+) m/z 873.65 (M+2H)

Analysis condition B: Retention time=2.63 min; ESI-MS (+) m/z 873.7 (M+2H)

Analysis condition C: Retention time=1.408 min; ESI-MS(+) m/z 873.65 (M+2H)

ESI-HRMS(+) m/z: Calculated: 873.4089. Found: 873.4089.

Preparation of Example 5176

Example 5176

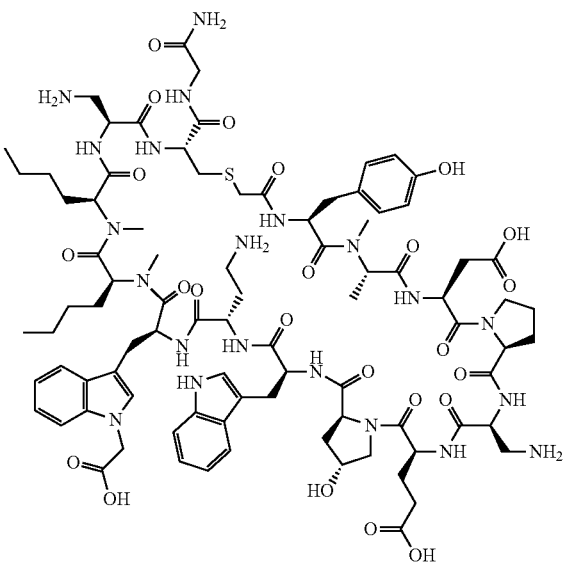

Example 5176 was prepared following "General Synthetic Sequence A", where the "Single-coupling procedure" and "Double-coupling procedure" of "Prelude Method A" were modified to use acetic anhydride in DMF (1.0 M, 2 mL) instead of neat acetic anhydride (2.0 mL). The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 27.9 mg, and its estimated purity by LCMS analysis was 99%.

Analysis condition A: Retention time=1.35 min; ESI-MS (+) m/z 939.5 (M+2H)

Analysis condition B: Retention time=2.49 min; ESI-MS (+) m/z 939.7 (M+2H)

ESI-HRMS(+) m/z: Calculated: 938.938. Found: 938.9345.

Preparation of Example 5177

Example 5177

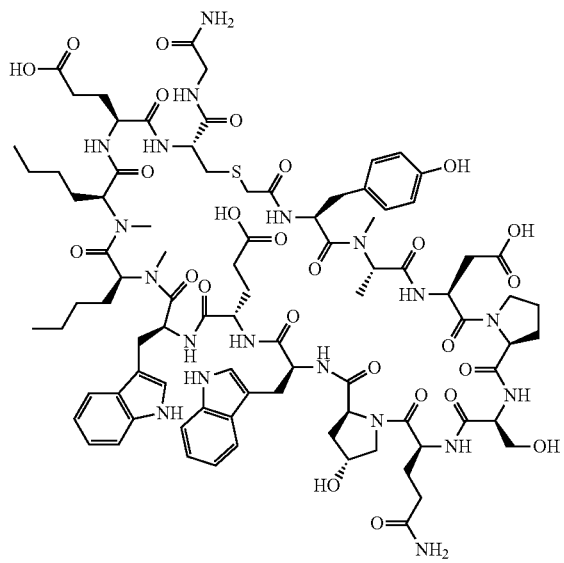

Example 5177 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 27.4 mg, and its estimated purity by LCMS analysis was 98%.

Analysis condition A: Retention time=1.393 min; ESI-MS(+) m/z 946.20 (M+2H)

Analysis condition B: Retention time=2.41 min; ESI-MS (+) m/z 946.2 (M+2H)

ESI-HRMS(+) m/z: Calculated: 945.922. Found: 945.9222.

Preparation of Example 5178

Example 5178

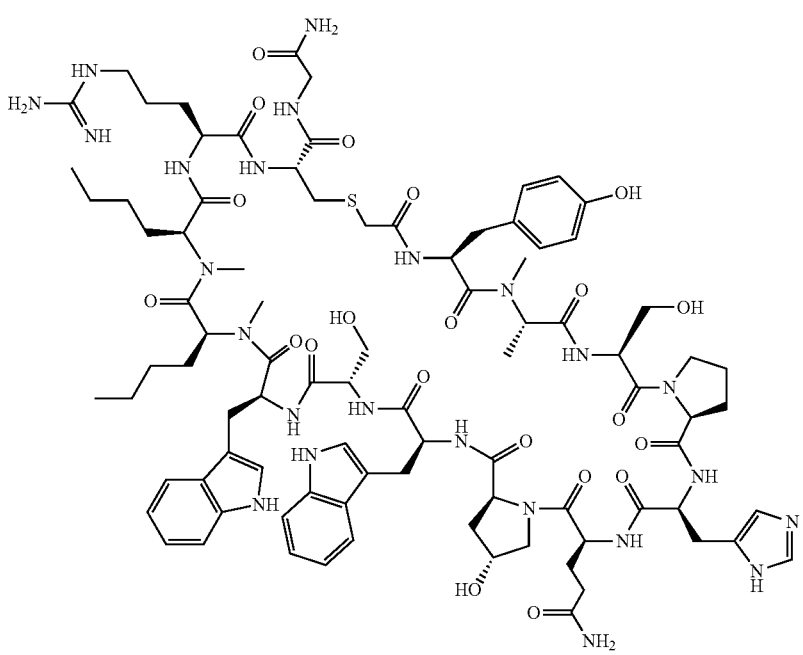

Example 5178 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 6.6 mg, and its estimated purity by LCMS analysis was 100%.

Analysis condition A: Retention time=1.48 min; ESI-MS (+) m/z 949.7 (M+2H)

Analysis condition B: Retention time=2.59 min; ESI-MS (−) m/z 947.8 (M−2H)

ESI-HRMS(+) m/z: Calculated: 949.462. Found: 949.4626.

Preparation of Example 5179

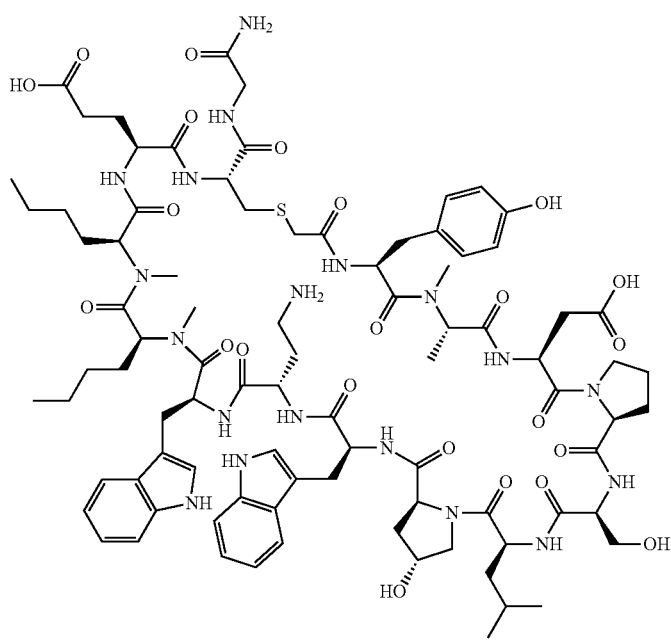

Example 5179

Example 5179 was prepared following "General Synthetic Sequence A". The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 18.2 mg, and its estimated purity by LCMS analysis was 99%.

Analysis condition A: Retention time=1.39 min; ESI-MS (+) m/z 1847.5 (M+H)

Analysis condition B: Retention time=2.54 min; ESI-MS (+) m/z 924.6 (M+2H)

ESI-HRMS(+) m/z: Calculated: 923.9453. Found: 923.944.

Preparation of Example 5180

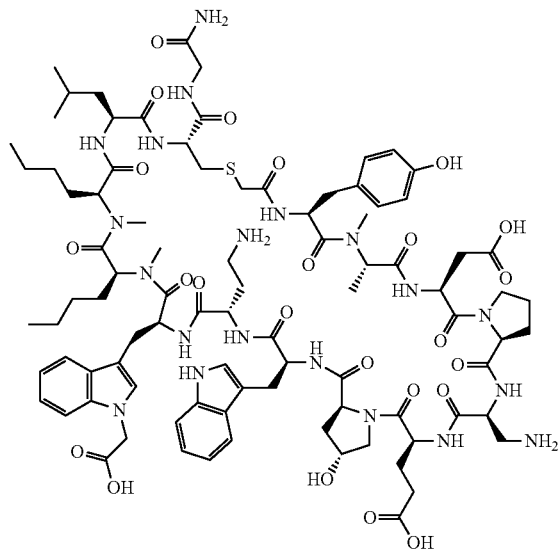

Example 5180

Example 5180 was prepared following "General Synthetic Sequence A", where the "Single-coupling procedure" and "Double-coupling procedure" of "Prelude Method A" were modified to use acetic anhydride in DMF (1.0 M, 2 mL) instead of neat acetic anhydride (2.0 mL). The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 30 minutes, then a 5-minute hold at 100% B; Flow: 20 mL/min. Fractions containing the desired product were combined and dried via centrifugal evaporation. The yield of the product was 19.2 mg, and its estimated purity by LCMS analysis was 100%.

Analysis condition A: Retention time=1.471 min; ESI-MS(−) m/z 950.95 (M−2H)

Analysis condition B: Retention time=3.060 min; ESI-MS(−) m/z 951.15 (M−2H)

ESI-HRMS(+) m/z: Calculated: 952.456. Found: 952.4533.

Preparation of Example 5181

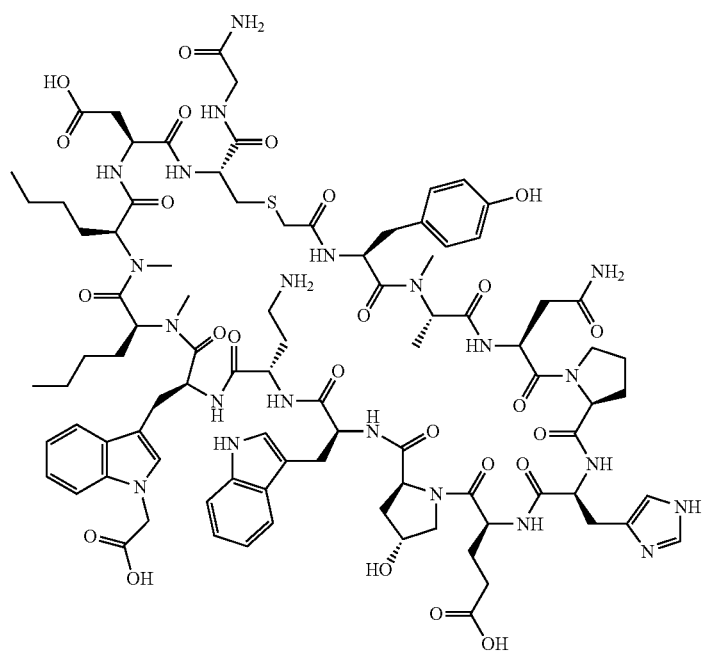

Example 5181

Example 5181 was prepared following "General Synthetic Sequence A", where the "Single-coupling procedure" and "Double-coupling procedure" of "Prelude Method A" were modified to use acetic anhydride in DMF (1.0 M, 2 mL) instead of neat acetic anhydride (2.0 mL). The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-40% B over 20 minutes, then a 5-minute hold at 100% B; Flow: 20 mL/min. Fractions containing the desired product were combined and dried via centrifugal evaporation. The yield of the product was 20.4 mg, and its estimated purity by LCMS analysis was 100%.

Analysis condition A: Retention time=1.238 min; ESI-MS(+) m/z 978.95 (M+2H)

Analysis condition B: Retention time=2.659 min; ESI-MS(−) m/z 977.00 (M−2H)

ESI-HRMS(+) m/z: Calculated: 978.4409. Found: 978.4382.

Preparation of Example 5182

Example 5182

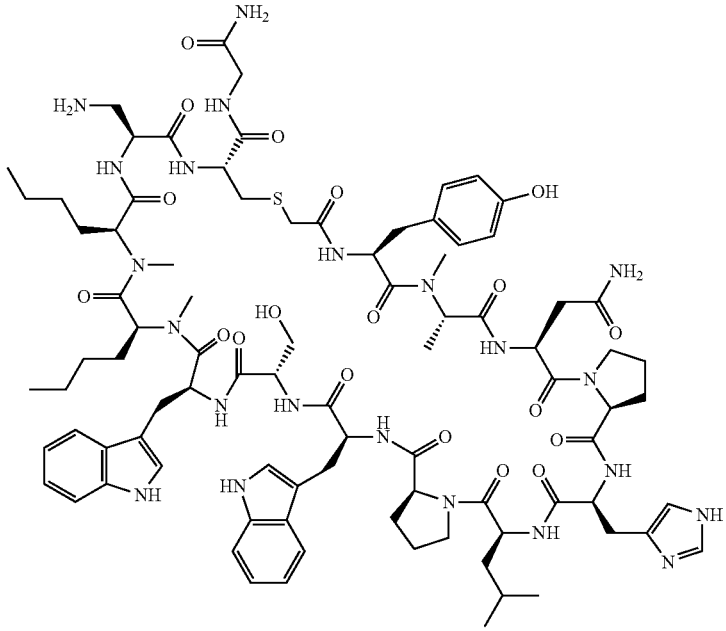

Example 5182 was prepared following "General Synthetic Sequence A", where the "Single-coupling procedure" and "Double-coupling procedure" of "Prelude Method A" were modified to use acetic anhydride in DMF (1.0 M, 2 mL) instead of neat acetic anhydride (2.0 mL). The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 114.3 mg, and its estimated purity by LCMS analysis was 99%.

Analysis condition A: Retention time=1.58 min; ESI-MS (+) m/z 912.6 (M+2H)

Analysis condition B: Retention time=2.65 min; ESI-MS (+) m/z 912.9 (M+2H)

ESI-HRMS(+) m/z: Calculated: 912.4561. Found: 912.4545.

Preparation of Example 5183

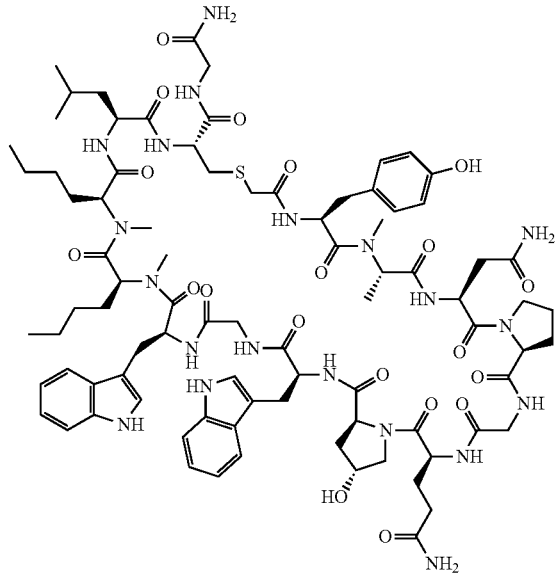

Example 5183

Example 5183 was prepared following "General Synthetic Sequence A". The crude material was purified via preparative LC/MS with the following conditions:

Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 17.9 mg, and its estimated purity by LCMS analysis was 95%.

Analysis condition A: Retention time=1.61 min; ESI-MS (+) m/z 1772.2 (M+H)

Analysis condition B: Retention time=2.74 min; ESI-MS (+) m/z 887.0 (M+2H)

ESI-HRMS(+) m/z: Calculated: 886.9388. Found: 886.9384.

Preparation of Example 5184

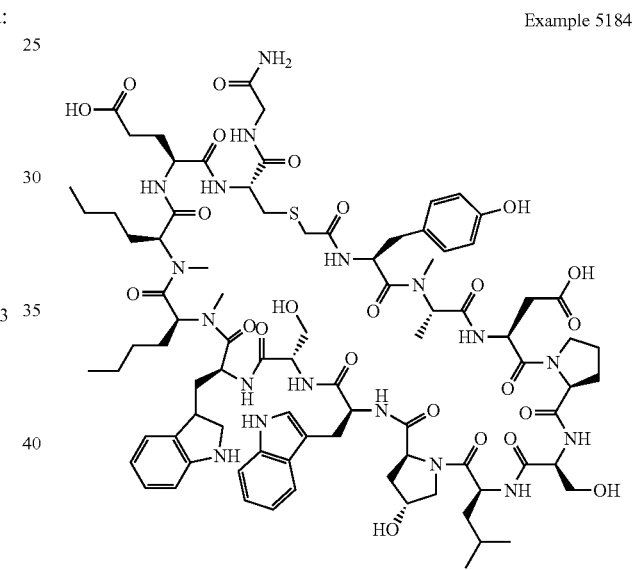

Example 5184

Example 5184 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 19.5 mg, and its estimated purity by LCMS analysis was 100%.

Analysis condition A: Retention time=1.34 min; ESI-MS (−) m/z 915.5 (M−2H)

Analysis condition B: Retention time=2.48 min; ESI-MS (+) m/z 918.0 (M+2H)

ESI-HRMS(+) m/z: Calculated: 917.4295. Found: 917.4291.

Preparation of Example 5186

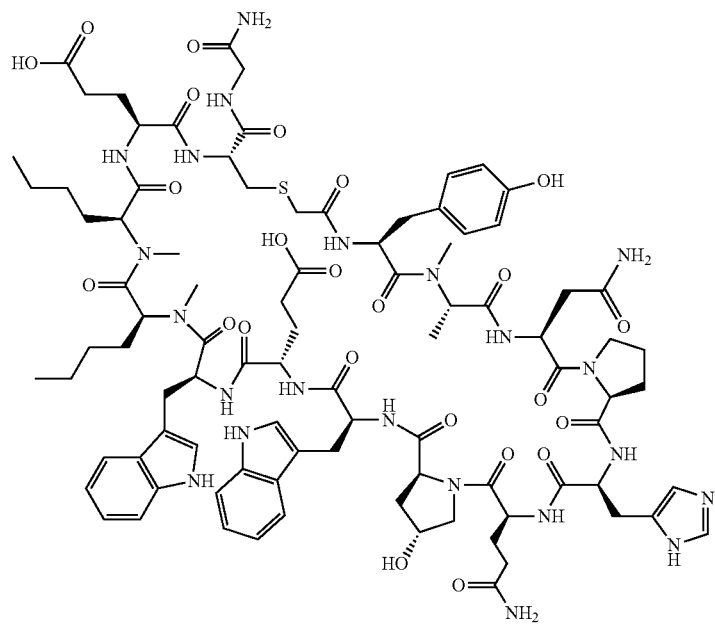

Example 5186

Example 5186 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 6.3 mg, and its estimated purity by LCMS analysis was 100%.

Analysis condition A: Retention time=1.21 min; ESI-MS (+) m/z 1940.3 (M+H)

Analysis condition B: Retention time=2.33 min; ESI-MS (+) m/z 970.5 (M+2H)

ESI-HRMS(+) m/z: Calculated: 970.4434. Found: 970.4435.

Preparation of Example 5187

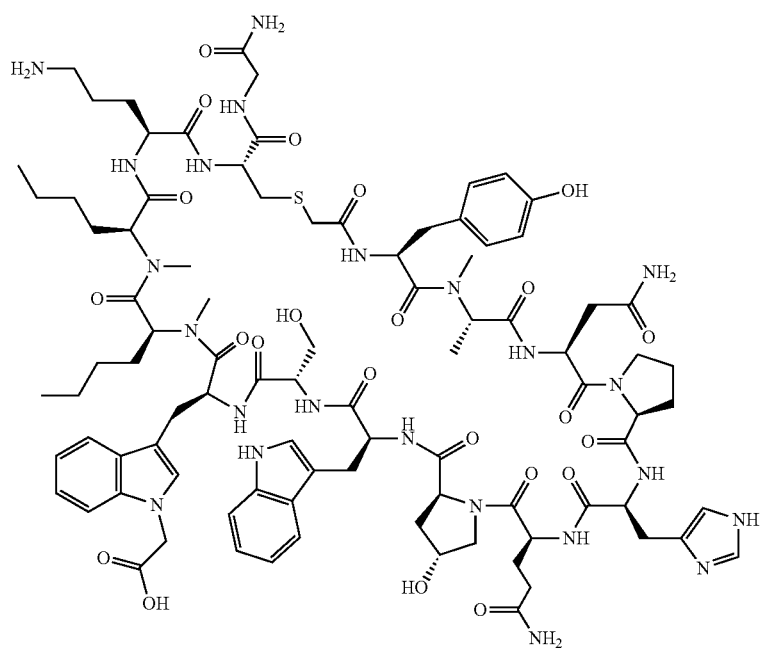

Example 5187

Example 5187 was prepared following "General Synthetic Sequence A", where the "Single-coupling procedure" and "Double-coupling procedure" of "Prelude Method A" were modified to use acetic anhydride in DMF (1.0 M, 2 mL) instead of neat acetic anhydride (2.0 mL). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 15.2 mg, and its estimated purity by LCMS analysis was 99%.

Analysis condition A: Retention time=1.305 min; ESI-MS(−) m/z 955.20 (M−2H)

Analysis condition B: Retention time=2.639 min; ESI-MS(+) m/z 957.85 (M+2H)

ESI-HRMS(+) m/z: Calculated: 956.9436. Found: 956.9401.

Preparation of Example 5189

Example 5189

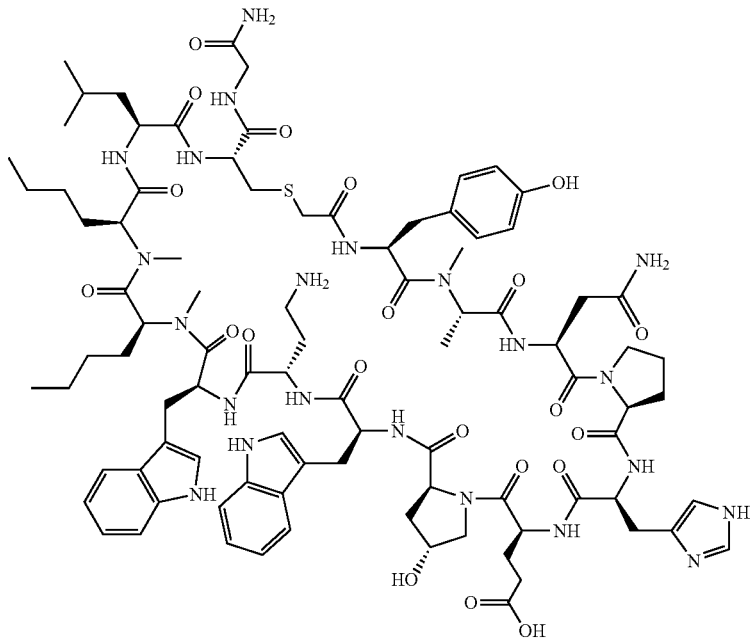

Example 5189 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 5.9 mg, and its estimated purity by LCMS analysis was 100%.

Analysis condition A: Retention time=1.61 min; ESI-MS (+) m/z 951.4 (M+2H)

Analysis condition B: Retention time=2.91 min; ESI-MS (−) m/z 949.5 (M−2H)

ESI-HRMS(+) m/z: Calculated: 950.9473. Found: 950.9449.

Preparation of Example 5190

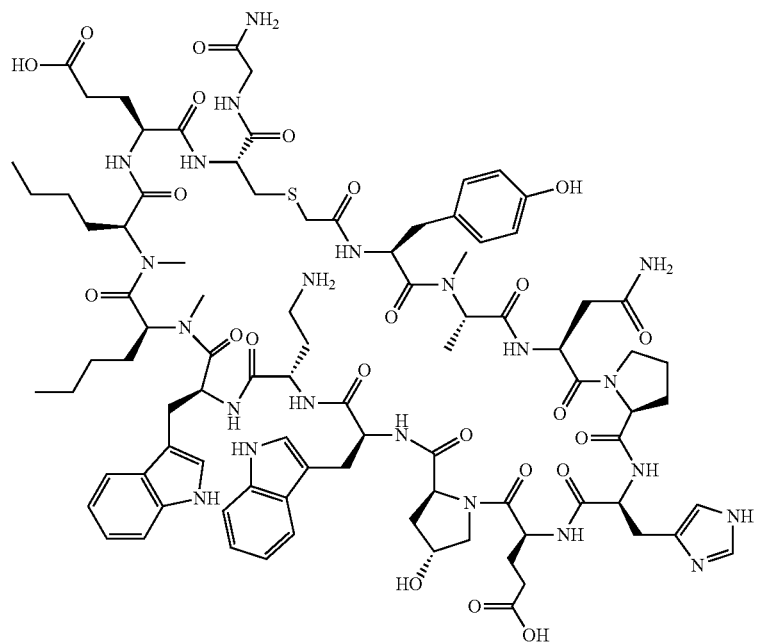

Example 5190

Example 5190 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 19.9 mg, and its estimated purity by LCMS analysis was 100%.

Analysis condition A: Retention time=1.36 min; ESI-MS (+) m/z 957.0 (M+2H)

Analysis condition B: Retention time=2.52 min; ESI-MS (−) m/z 954.8 (M−2H)

ESI-HRMS(+) m/z: Calculated: 956.446. Found: 956.4415.

Preparation of Example 5191

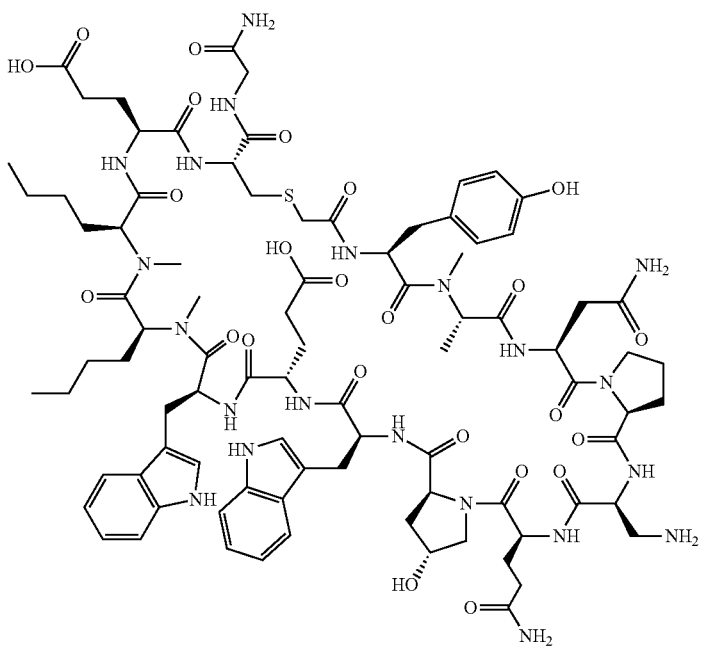

Example 5191

Example 5191 was prepared following "General Synthetic Sequence A". The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 30 minutes, then a 5-minute hold at 100% B; Flow: 20 mL/min. Fractions containing the desired product were combined and dried via centrifugal evaporation. The yield of the product was 7.2 mg, and its estimated purity by LCMS analysis was 98%.

Analysis condition A: Retention time=1.599 min; ESI-MS(+) m/z 944.40 (M+2H)

Analysis condition B: Retention time=1.917 min; ESI-MS(+) m/z 945.20 (M+2H)

ESI-HRMS(+) m/z: Calculated: 944.938. Found: 944.9383.

Preparation of Example 5192

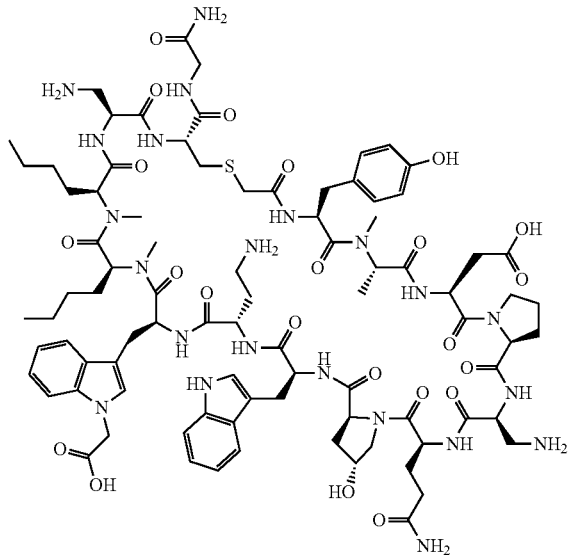

Example 5192

Example 5192 was prepared following "General Synthetic Sequence A", where the "Single-coupling procedure" and "Double-coupling procedure" of "Prelude Method A" were modified to use acetic anhydride in DMF (1.0 M, 2 mL) instead of neat acetic anhydride (2.0 mL). The crude material was purified via preparative LC/MS with the following conditions: Column: Waters XBridge C18, 19×150 mm, 5-µm particles; Mobile Phase A: water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 26.7 mg, and its estimated purity by LCMS analysis was 100%.

Analysis condition A: Retention time=1.354 min; ESI-MS(+) m/z 938.25 (M+2H)

Analysis condition B: Retention time=2.876 min; ESI-MS(+) m/z 938.90 (M+2H)

ESI-HRMS(+) m/z: Calculated: 938.446. Found: 938.4432.

Preparation of Example 5196

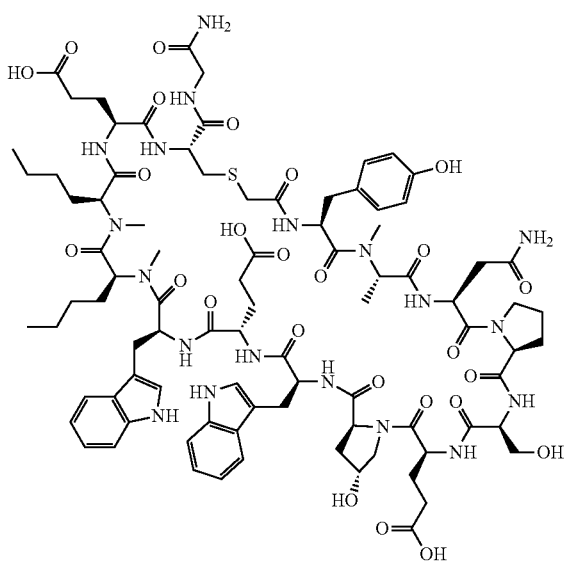

Example 5196

Example 5196 was prepared following "General Synthetic Sequence A". The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 20.8 mg, and its estimated purity by LCMS analysis was 99%.

Analysis condition A: Retention time=1.417 min; ESI-MS(+) m/z 947.15 (M+2H)

Analysis condition B: Retention time=2.469 min; ESI-MS(+) m/z 946.25 (M+2H)

ESI-HRMS(+) m/z: Calculated: 945.922. Found: 945.9222.

Preparation of Example 5198

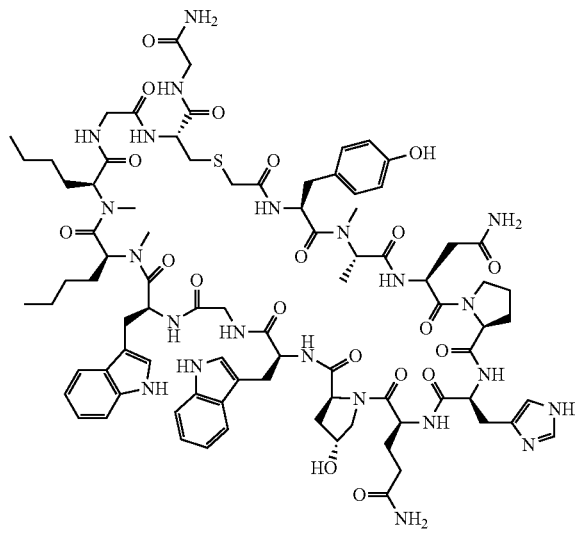

Example 5198

Example 5198 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 23.1 mg, and its estimated purity by LCMS analysis was 98%.

Analysis condition A: Retention time=1.44 min; ESI-MS (+) m/z 898.7 (M+2H)

Analysis condition B: Retention time=2.56 min; ESI-MS (+) m/z 899.0 (M+2H)

ESI-HRMS(+) m/z: Calculated: 898.4223. Found: 898.4223.

Preparation of Example 5199

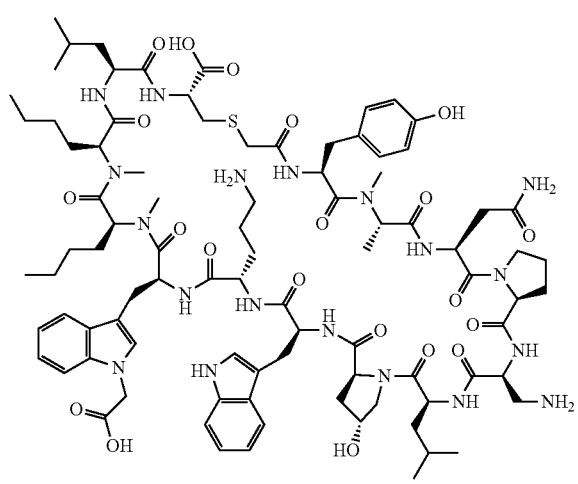

Example 5199

Example 5199 was prepared following "General Synthetic Sequence B". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 8.4 mg, and its estimated purity by LCMS analysis was 96%.

Analysis condition A: Retention time=1.484 min; ESI-MS(−) m/z 921.40 (M−2H)

Analysis condition B: Retention time=3.064 min; ESI-MS(+) m/z 923.45 (M+2H)

ESI-HRMS(+) m/z: Calculated: 922.9738. Found: 922.9705.

Preparation of Example 5200

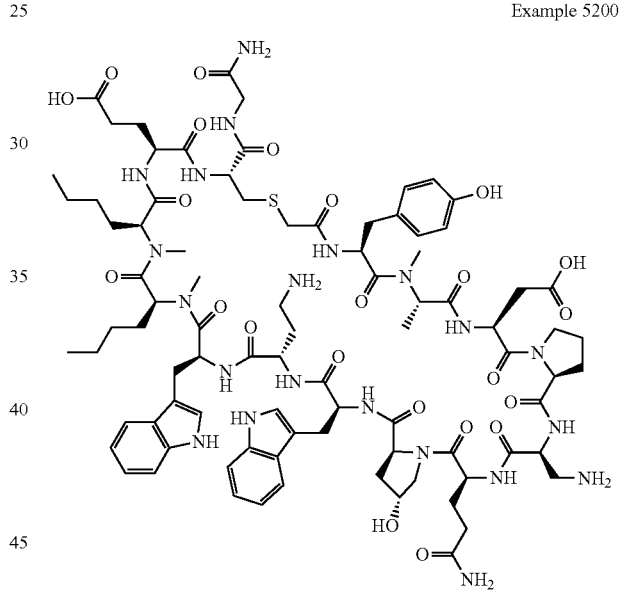

Example 5200

Example 5200 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 15 mg, and its estimated purity by LCMS analysis was 98%.

Analysis condition A: Retention time=1.47 min; ESI-MS (+) m/z 931.3 (M+2H)

Analysis condition B: Retention time=2.62 min; ESI-MS (+) m/z 931.3 (M+2H)

ESI-HRMS(+) m/z: Calculated: 930.9405. Found: 930.9383.

Preparation of Example 5201

Example 5201

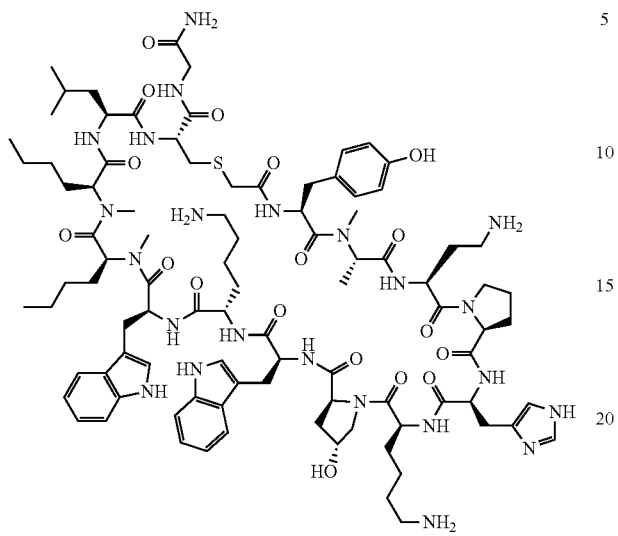

Example 5201 was prepared following "General Synthetic Sequence A". The crude material was purified via preparative LC/MS with the following conditions: Column: XBridge C18, 19×mm, 5-μm particles; Mobile Phase A: 5:95 methanol:water with 10-mM ammonium acetate; Mobile Phase B: 95:5 methanol:water with 10-mM ammonium acetate; Gradient: 40-90% B over 30 minutes, then a 5-minute hold at 100% B; Flow: 20 mL/min. Fractions containing the desired product were combined and dried via centrifugal evaporation. The yield of the product was 7.6 mg, and its estimated purity by LCMS analysis was 100%.

Analysis condition A: Retention time=1.33 min; ESI-MS (+) m/z 956.0 (M+2H)

Analysis condition B: Retention time=2.51 min; ESI-MS (+) m/z 955.8 (M+2H)

ESI-HRMS(+) m/z: Calculated: 955.0189. Found: 955.015.

Preparation of Example 5202

Example 5202

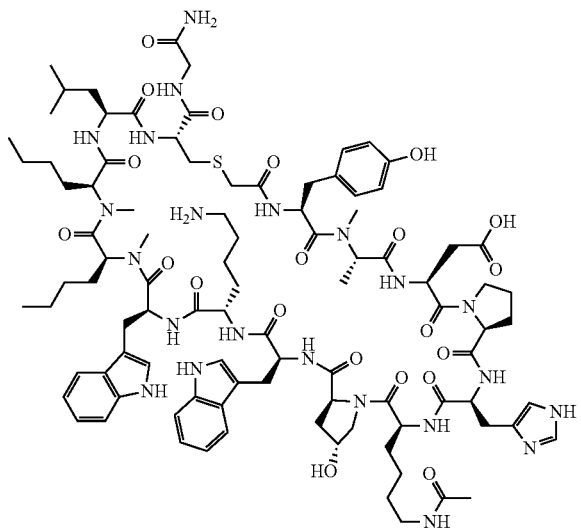

Example 5202 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-60% B over 30 minutes, then a 5-minute hold at 100% B; Flow: 20 mL/min. Fractions containing the desired product were combined and dried via centrifugal evaporation. The yield of the product was 15.8 mg, and its estimated purity by LCMS analysis was 97%.

Analysis condition A: Retention time=1.54 min; ESI-MS (+) m/z 984.3 (M+2H)

Analysis condition B: Retention time=2.70 min; ESI-MS (+) m/z 984.2 (M+2H)

ESI-HRMS(+) m/z: Calculated: 983.5058. Found: 983.5018.

Preparation of Example 5203

Example 5203

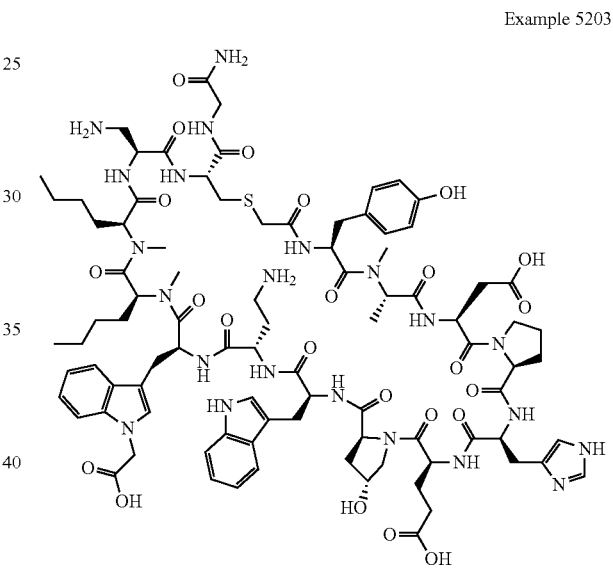

Example 5203 was prepared following "General Synthetic Sequence A", where the "Single-coupling procedure" and "Double-coupling procedure" of "Prelude Method A" were modified to use acetic anhydride in DMF (1.0 M, 2 mL) instead of neat acetic anhydride (2.0 mL). The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 30-70% B over 30 minutes, then a 5-minute hold at 100% B; Flow: 20 mL/min. Fractions containing the desired product were combined and dried via centrifugal evaporation. The yield of the product was 25.4 mg, and its estimated purity by LCMS analysis was 95%.

Analysis condition A: Retention time=1.225 min; ESI-MS(−) m/z 956.15 (M−2H)

Analysis condition B: Retention time=2.460 min; ESI-MS(−) m/z 955.15 (M−2H)

ESI-HRMS(+) m/z: Calculated: 957.9276. Found: 957.9241.

Preparation of Example 5204

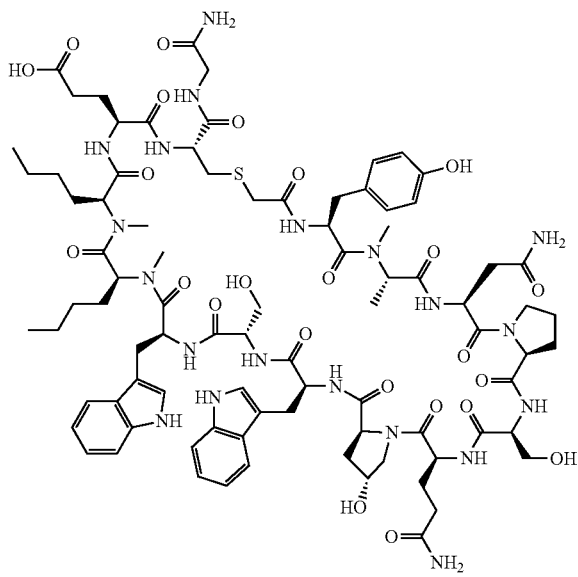

Example 5204

Example 5204 was prepared following "General Synthetic Sequence A". The crude material was purified via preparative LC/MS with the following conditions: Column: XBridge C18, 19×mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 14.6 mg, and its estimated purity by LCMS analysis was 100%.

Analysis condition A: Retention time=1.39 min; ESI-MS (+) m/z 1848.3 (M+H)

Analysis condition B: Retention time=2.51 min; ESI-MS (−) m/z 922.7 (M−2H).

Preparation of Example 5205

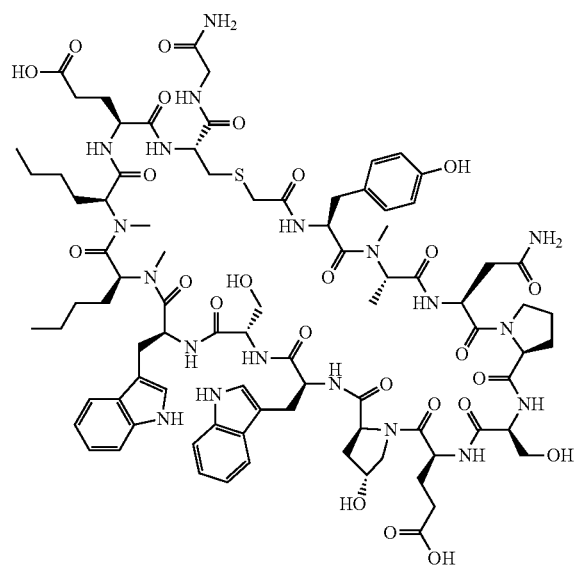

Example 5205

Example 5205 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-50% B over 5 minutes, then a 30-minute hold at 100% B; Flow: 20 mL/min. Fractions containing the desired product were combined and dried via centrifugal evaporation. The yield of the product was 10.6 mg, and its estimated purity by LCMS analysis was 100%.

Analysis condition A: Retention time=1.36 min; ESI-MS (−) m/z 923.9 (M−2H)

Analysis condition B: Retention time=2.45 min; ESI-MS (+) m/z 925.1 (M+2H)

ESI-HRMS(+) m/z: Calculated: 924.9167. Found: 924.9173.

Preparation of Example 5207

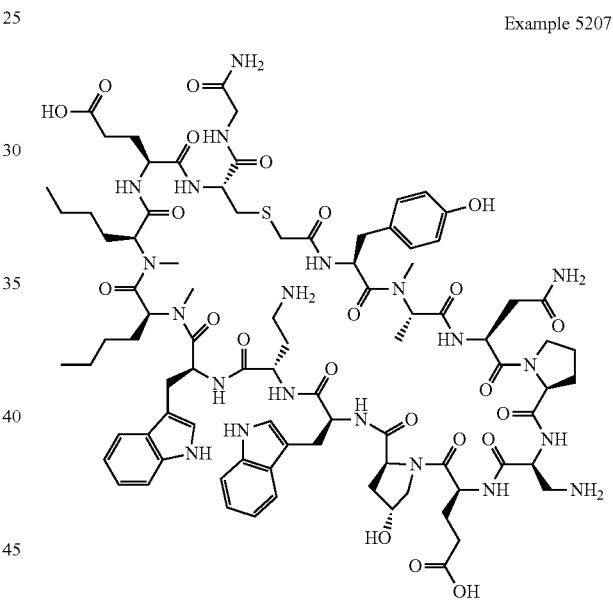

Example 5207

Example 5207 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 24.6 mg, and its estimated purity by LCMS analysis was 100%.

Analysis condition A: Retention time=1.39 min; ESI-MS (+) m/z 931.6 (M+2H)

Analysis condition B: Retention time=2.58 min; ESI-MS (+) m/z 931.5 (M+2H)

ESI-HRMS(+) m/z: Calculated: 930.9405. Found: 930.9359.

Preparation of Example 5208

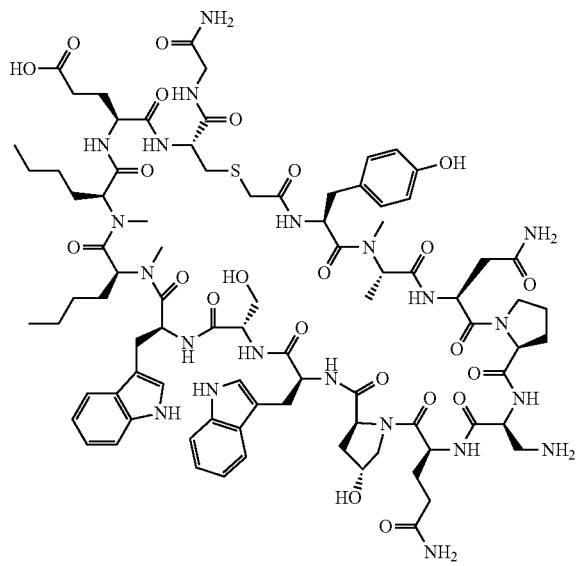

Example 5208

Example 5208 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 15 minutes, then a 5-minute hold at 100% B; Flow: 20 mL/min. Fractions containing the desired product were combined and dried via centrifugal evaporation. The yield of the product was 18.5 mg, and its estimated purity by LCMS analysis was 98%.

Analysis condition A: Retention time=1.35 min; ESI-MS (+) m/z 925.0 (M+2H)

Analysis condition B: Retention time=2.51 min; ESI-MS (+) m/z 924.7 (M+2H)

ESI-HRMS(+) m/z: Calculated: 923.9327. Found: 923.9336.

Preparation of Example 5209

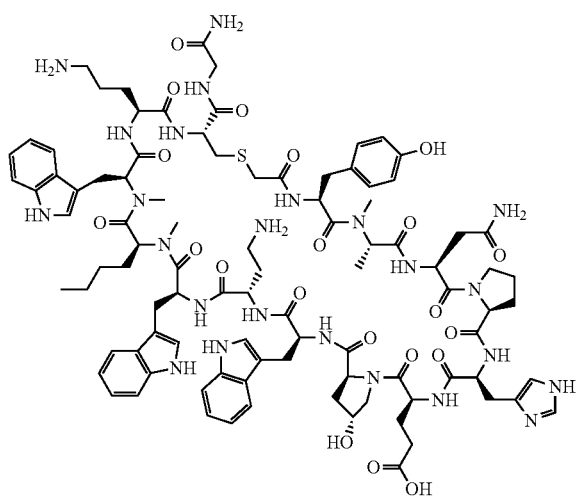

Example 5209

Example 5209 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-40% B over 30 minutes, then a 5-minute hold at 100% B; Flow: 20 mL/min. Fractions containing the desired product were combined and dried via centrifugal evaporation. The yield of the product was 35.5 mg, and its estimated purity by LCMS analysis was 100%.

Analysis condition A: Retention time=1.297 min; ESI-MS(+) m/z 971.45 (M+2H)

Analysis condition B: Retention time=2.45 min; ESI-MS (+) m/z 971.8 (M+2H)

Analysis condition C: Retention time=1.297 min; ESI-MS(+) m/z 971.45 (M+2H)

ESI-HRMS(+) m/z: Calculated: 971.4463. Found: 971.4443.

Preparation of Example 5211

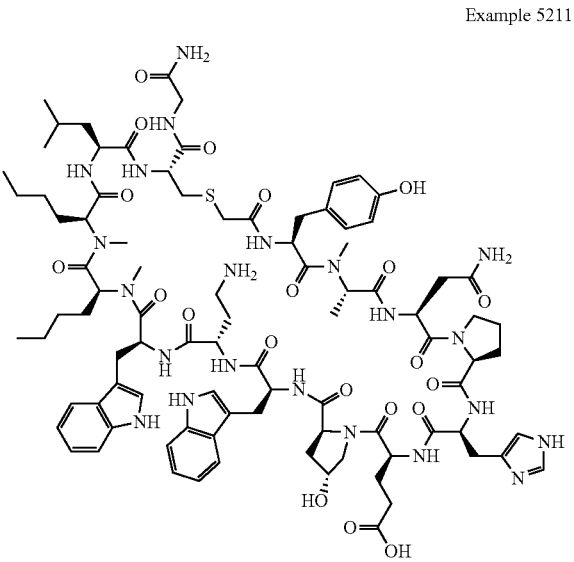 [SMILES: CCCC[C@H]1C(=O)N(C)[C@@H](CCCC)C(=O)N[C@@H](CC(C)C)C(=O)N[C@H](C(=O)NCC(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](Cc2c[nH]cn2)C(=O)N[C@@H](CCC(=O)O)C(=O)N2C[C@H](O)C[C@H]2C(=O)N[C@@H](Cc2c[nH]c3ccccc23)C(=O)N[C@@H](CCN)C(=O)N[C@@H](Cc2c[nH]c3ccccc23)C(=O)N1C]

Example 5211

Example 5211 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 55-100% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 30 minutes, then a 5-minute hold at 100% B; Flow: 20 mL/min. Fractions containing the desired product were combined and dried via centrifugal evaporation. The yield of the product was 5.5 mg, and its estimated purity by LCMS analysis was 100%.

Analysis condition A: Retention time=1.74 min; ESI-MS (+) m/z 957.6 (M+2H)

Analysis condition B: Retention time=2.98 min; ESI-MS (+) m/z 957.6 (M+2H)

ESI-HRMS(+) m/z: Calculated: 956.9473. Found: 956.9451.

Preparation of Example 5213

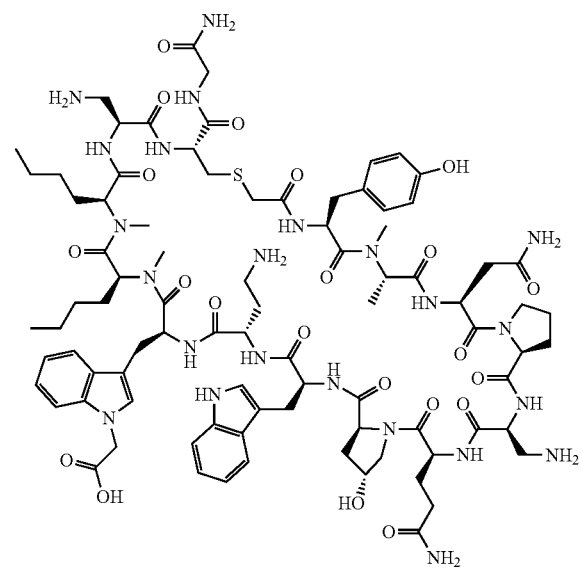

Example 5213

Example 5213 was prepared following "General Synthetic Sequence A", where the "Single-coupling procedure" and "Double-coupling procedure" of "Prelude Method A" were modified to use acetic anhydride in DMF (1.0 M, 2 mL) instead of neat acetic anhydride (2.0 mL). The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 22.2 mg, and its estimated purity by LCMS analysis was 100%.

Analysis condition A: Retention time=1.30 min; ESI-MS (+) m/z 938.2 (M+2H)

Analysis condition B: Retention time=2.46 min; ESI-MS (+) m/z 938.6 (M+2H)

ESI-HRMS(+) m/z: Calculated: 937.954. Found: 937.9511.

Preparation of Example 5214

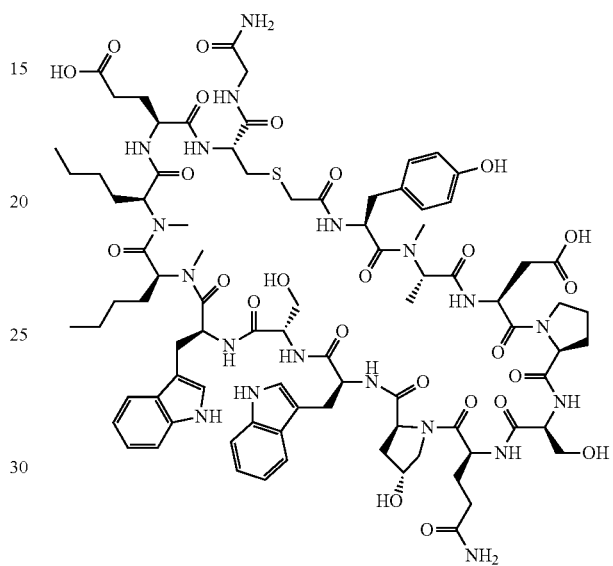

Example 5214

Example 5214 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 25-65% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 10.9 mg, and its estimated purity by LCMS analysis was 100%.

Analysis condition A: Retention time=1.39 min; ESI-MS (+) m/z 925.5 (M+2H)

Analysis condition B: Retention time=2.49 min; ESI-MS (+) m/z 925.5 (M+2H)

ESI-HRMS(+) m/z: Calculated: 924.9167. Found: 924.9166.

Preparation of Example 5215

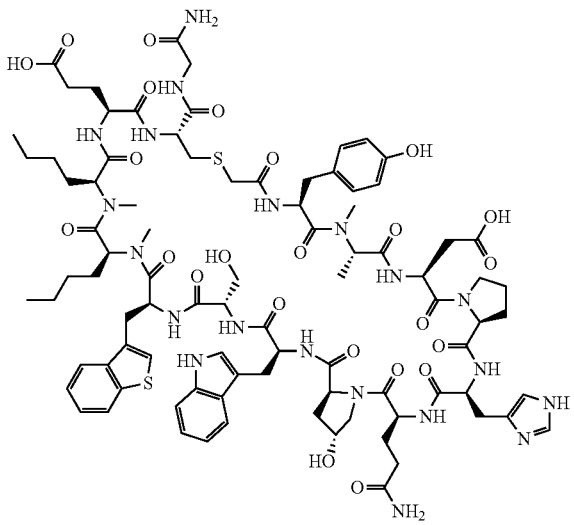

Example 5215

Example 5215 was prepared following "General Synthetic Sequence A". The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 8.6 mg, and its estimated purity by LCMS analysis was 99%.

Analysis condition A: Retention time=1.44 min; ESI-MS (+) m/z 958.7 (M+2H)

Analysis condition B: Retention time=2.62 min; ESI-MS (+) m/z 959.2 (M+2H)

ESI-HRMS(+) m/z: Calculated: 958.4107. Found: 958.4078.

Preparation of Example 5216

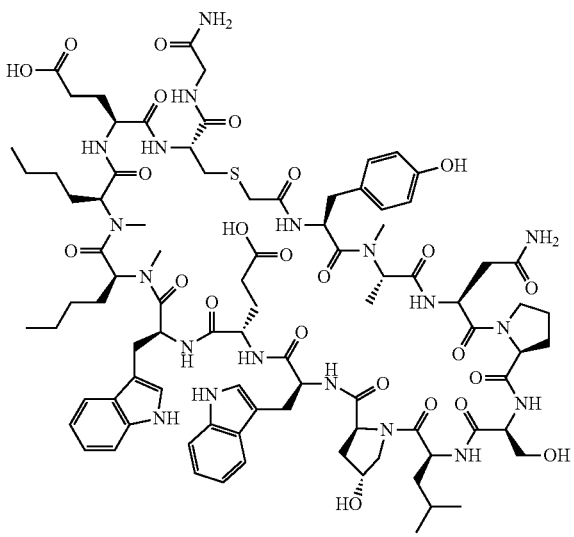

Example 5216

Example 5216 was prepared following "General Synthetic Sequence A". The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 14.3 mg, and its estimated purity by LCMS analysis was 100%.

Analysis condition A: Retention time=1.38 min; ESI-MS (+) m/z 938.7 (M+2H)

Analysis condition B: Retention time=2.49 min; ESI-MS (+) m/z 938.6 (M+2H)

ESI-HRMS(+) m/z: Calculated: 937.9427. Found: 937.9436.

Preparation of Example 5218

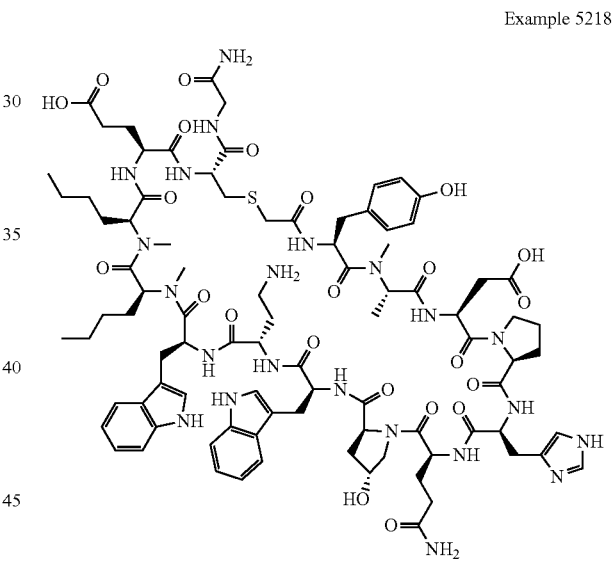

Example 5218

Example 5218 was prepared following "General Synthetic Sequence A". The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 40-80% B over 20 minutes, then a 5-minute hold at 100% B; Flow: 20 mL/min. Fractions containing the desired product were combined and dried via centrifugal evaporation. The yield of the product was 19.2 mg, and its estimated purity by LCMS analysis was 99%.

Analysis condition A: Retention time=1.38 min; ESI-MS (+) m/z 357.2 (M+2H)

Analysis condition B: Retention time=2.52 min; ESI-MS (+) m/z 956.8 (M+2H)

ESI-HRMS(+) m/z: Calculated: 956.446. Found: 956.4413.

Preparation of Example 5219

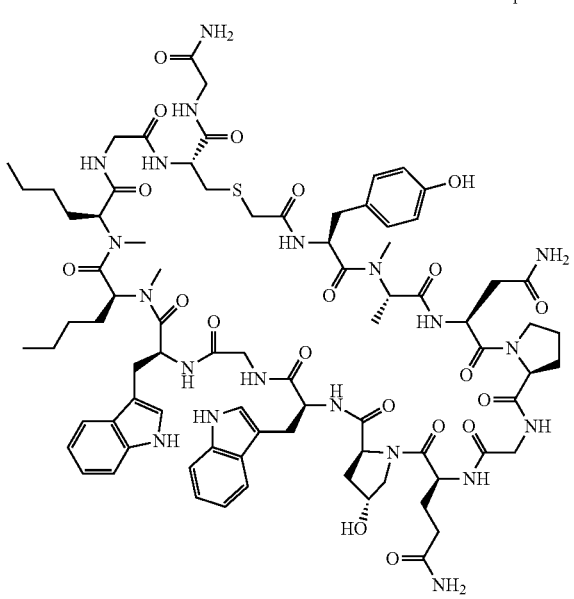

Example 5219

Example 5219 was prepared following "General Synthetic Sequence A". The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 28.6 mg, and its estimated purity by LCMS analysis was 96%.

Analysis condition A: Retention time=1.52 min; ESI-MS (+) m/z 858.1 (M+2H)

Analysis condition B: Retention time=2.55 min; ESI-MS (+) m/z 858.7 (M+2H)

ESI-HRMS(+) m/z: Calculated: 858.4036. Found: 858.4032.

Preparation of Example 5220

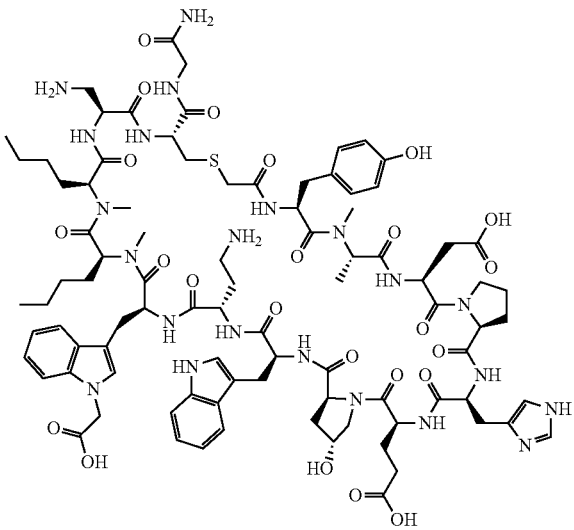

Example 5220

Example 5220 was prepared following "General Synthetic Sequence A", where the "Single-coupling procedure" and "Double-coupling procedure" of "Prelude Method A" were modified to use acetic anhydride in DMF (1.0 M, 2 mL) instead of neat acetic anhydride (2.0 mL). The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 0-40% B over 30 minutes, then a 5-minute hold at 100% B; Flow: 20 mL/min. Fractions containing the desired product were combined and dried via centrifugal evaporation. The yield of the product was 40.2 mg, and its estimated purity by LCMS analysis was 100%.

Analysis condition A: Retention time=1.342 min; ESI-MS(−) m/z 962.60 (M−2H)

Analysis condition B: Retention time=2.856 min; ESI-MS(+) m/z 965.00 (M+2H)

ESI-HRMS(+) m/z: Calculated: 964.4434. Found: 964.4399.

Preparation of Example 5221

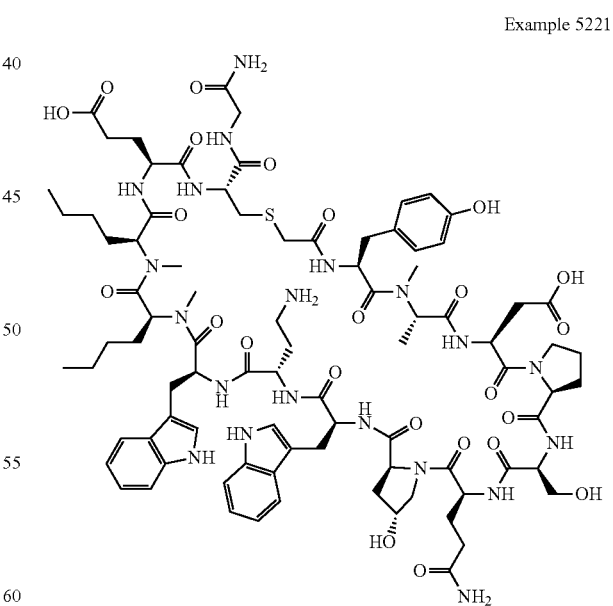

Example 5221

Example 5221 was prepared following "General Synthetic Sequence A". The crude material was purified via preparative LC/MS with the following conditions: Column: XBridge C18, 19×200 mm, 5-µm particles; Mobile Phase A: 5:95 methanol:water with 10-mM ammonium acetate;

Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 26.6 mg, and its estimated purity by LCMS analysis was 100%.

Analysis condition A: Retention time=1.40 min; ESI-MS (+) m/z 932.1 (M+2H)

Analysis condition B: Retention time=2.55 min; ESI-MS (+) m/z 932.1 (M+2H)

ESI-HRMS(+) m/z: Calculated: 931.4325. Found: 931.429.

Preparation of Example 5222

Example 5222

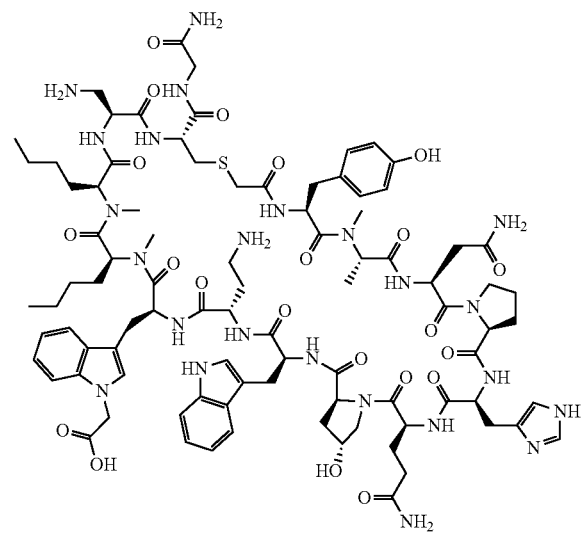

Example 5222 was prepared following "General Synthetic Sequence A", where the "Single-coupling procedure" and "Double-coupling procedure" of "Prelude Method A" were modified to use acetic anhydride in DMF (1.0 M, 2 mL) instead of neat acetic anhydride (2.0 mL). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 22.2 mg, and its estimated purity by LCMS analysis was 100%.

Analysis condition A: Retention time=1.31 min; ESI-MS (+) m/z 964.1 (M+2H)

Analysis condition B: Retention time=2.48 min; ESI-MS (+) m/z 963.6 (M+2H)

ESI-HRMS(+) m/z: Calculated: 963.4594. Found: 963.4567.

Preparation of Example 5223

Example 5223

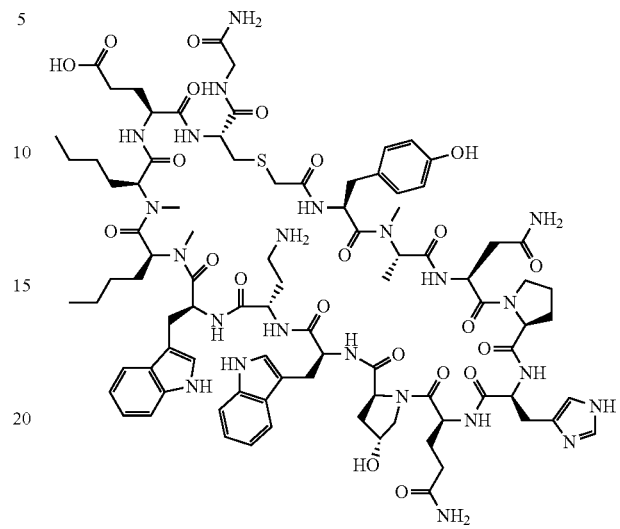

Example 5223 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 15.8 mg, and its estimated purity by LCMS analysis was 100%.

Analysis condition A: Retention time=1.42 min; ESI-MS (+) m/z 956.1 (M+2H)

Analysis condition B: Retention time=2.59 min; ESI-MS (+) m/z 956.6 (M+2H)

ESI-HRMS(+) m/z: Calculated: 955.954. Found: 955.9503.

Preparation of Example 5224

Example 5224

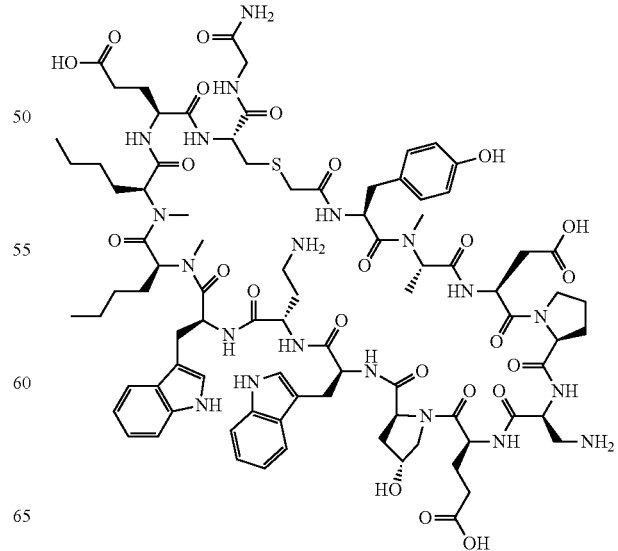

Example 5224 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 22.7 mg, and its estimated purity by LCMS analysis was 100%.

Analysis condition A: Retention time=1.37 min; ESI-MS (+) m/z 932.1 (M+2H)

Analysis condition B: Retention time=2.53 min; ESI-MS (+) m/z 931.8 (M+2H)

ESI-HRMS(+) m/z: Calculated: 931.4325. Found: 931.4303.

Preparation of Example 5225

Example 5225

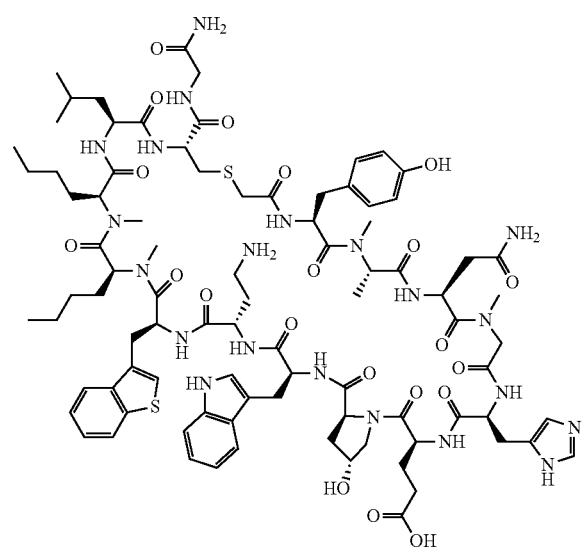

Example 5225 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 2.6 mg, and its estimated purity by LCMS analysis was 98%.

Analysis condition A: Retention time=1.69 min; ESI-MS (+) m/z 944.7 (M+2H)

Analysis condition B: Retention time=2.90 min; ESI-MS (+) m/z 944.3 (M+2H)

ESI-HRMS(+) m/z: Calculated: 943.9395. Found: 943.9396.

Preparation of Example 5226

Example 5226

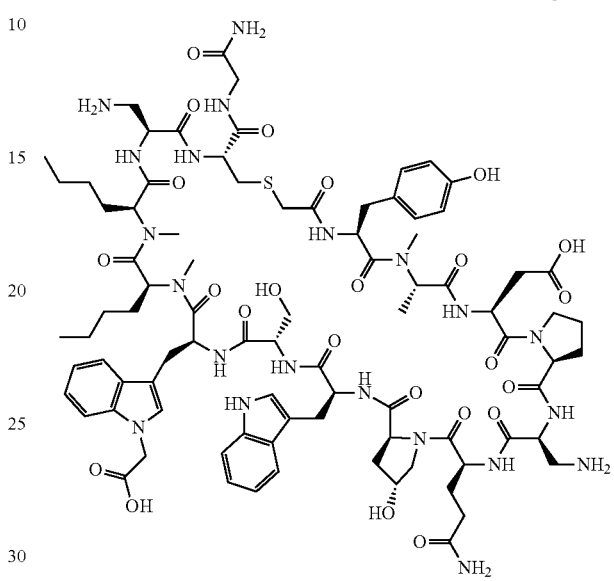

Example 5226 was prepared following "General Synthetic Sequence A", where the "Single-coupling procedure" and "Double-coupling procedure" of "Prelude Method A" were modified to use acetic anhydride in DMF (1.0 M, 2 mL) instead of neat acetic anhydride (2.0 mL). The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 20 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 23.6 mg, and its estimated purity by LCMS analysis was 99%.

Analysis condition A: Retention time=1.375 min; ESI-MS(−) m/z 930.30 (M−2H)

Analysis condition B: Retention time=1.988 min; ESI-MS(+) m/z 932.35 (M+2H)

ESI-HRMS(+) m/z: Calculated: 931.9302. Found: 931.9273.

Preparation of Example 5227

Example 5227

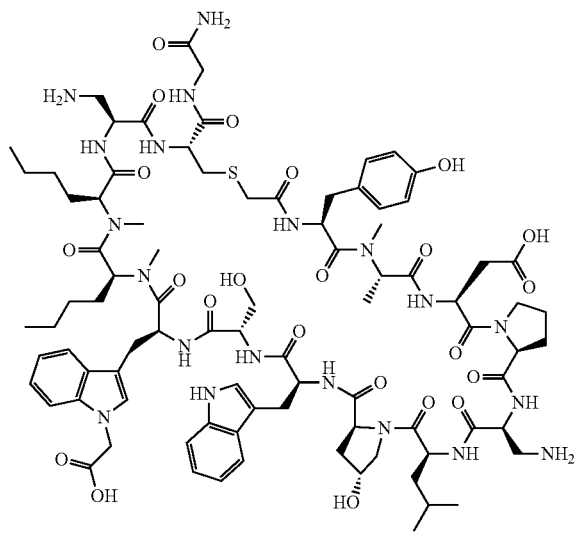

Example 5227 was prepared following "General Synthetic Sequence A", where the "Single-coupling procedure" and "Double-coupling procedure" of "Prelude Method A" were modified to use acetic anhydride in DMF (1.0 M, 2 mL) instead of neat acetic anhydride (2.0 mL). The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 20 minutes, then a 5-minute hold at 100% B; Flow: 20 mL/min. Fractions containing the desired product were combined and dried via centrifugal evaporation. The yield of the product was 13.6 mg, and its estimated purity by LCMS analysis was 100%.

Analysis condition A: Retention time=1.429 min; ESI-MS(−) m/z 922.45 (M−2H)

Analysis condition B: Retention time=2.914 min; ESI-MS(+) m/z 924.45 (M+2H)

ESI-HRMS(+) m/z: Calculated: 924.4429. Found: 924.4396.

Preparation of Example 5228

Example 5228

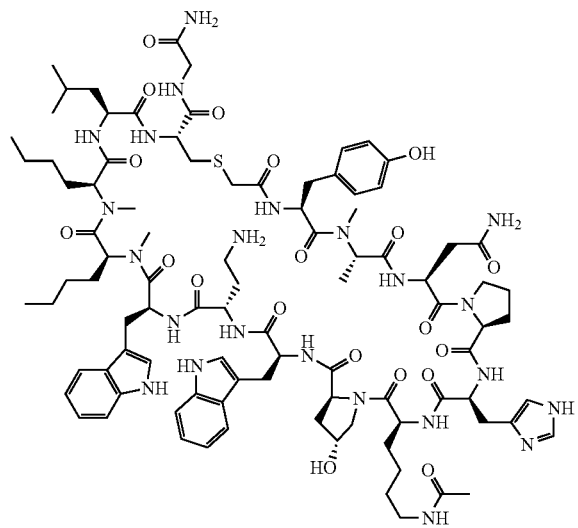

Example 5228 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 6.3 mg, and its estimated purity by LCMS analysis was 100%.

Analysis condition A: Retention time=1.58 min; ESI-MS(+) m/z 969.8 (M+2H)

Analysis condition B: Retention time=2.72 min; ESI-MS(−) m/z 267.1 (M−2H)

ESI-HRMS(+) m/z: Calculated: 968.9982. Found: 968.9941.

Preparation of Example 5229

Example 5229

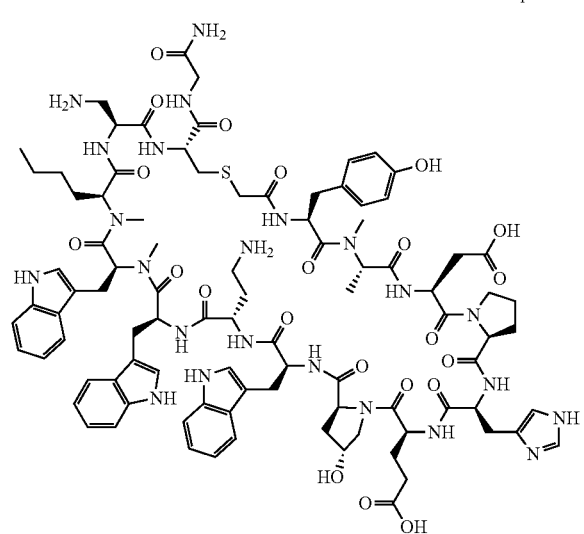

Example 5229 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-40% B over 30 minutes, then a 5-minute hold at 100% B; Flow: 20 mL/min. Fractions containing the desired product were combined and dried via centrifugal evaporation. The yield of the product was 10.0 mg, and its estimated purity by LCMS analysis was 96%.

Analysis condition A: Retention time=1.41 min; ESI-MS(+) m/z 971.8 (M+2H)

Analysis condition B: Retention time=2.53 min; ESI-MS(+) m/z 972.1 (M+2H)

ESI-HRMS(+) m/z: Calculated: 971.4463. Found: 971.4448.

Preparation of Example 5230

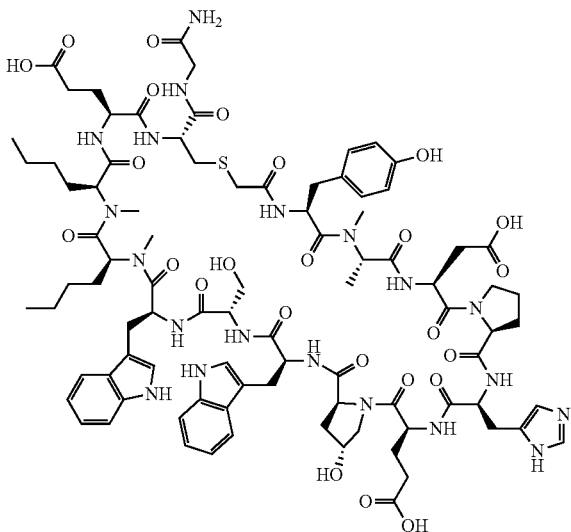

Example 5230

Example 5230 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 12.1 mg, and its estimated purity by LCMS analysis was 100%.

Analysis condition A: Retention time=1.32 min; ESI-MS (+) m/z 950.8 (M+2H)

Analysis condition B: Retention time=2.40 min; ESI-MS (+) m/z 951.1 (M+2H)

ESI-HRMS(+) m/z: Calculated: 950.4222. Found: 950.4232.

Preparation of Example 5231

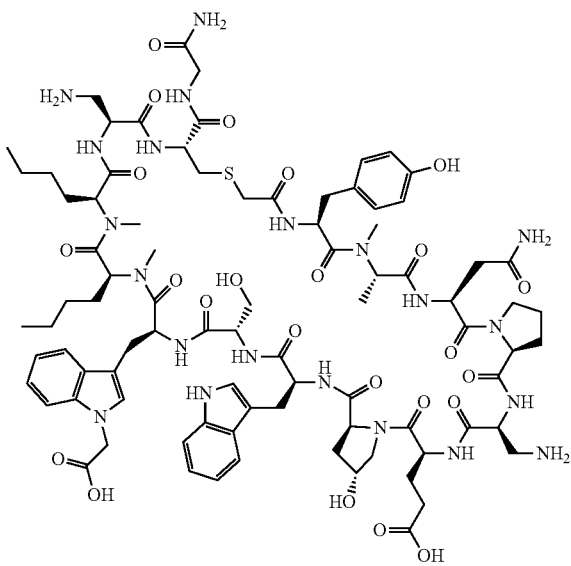

Example 5231

Example 5231 was prepared following "General Synthetic Sequence A", where the "Single-coupling procedure" and "Double-coupling procedure" of "Prelude Method A" were modified to use acetic anhydride in DMF (1.0 M, 2 mL) instead of neat acetic anhydride (2.0 mL). The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 9.8 mg, and its estimated purity by LCMS analysis was 100%.

Analysis condition A: Retention time=1.31 min; ESI-MS (+) m/z 932.1 (M+2H)

Analysis condition B: Retention time=2.44 min; ESI-MS (+) m/z 932.4 (M+2H)

ESI-HRMS(+) m/z: Calculated: 931.9302. Found: 931.9273.

Preparation of Example 5232

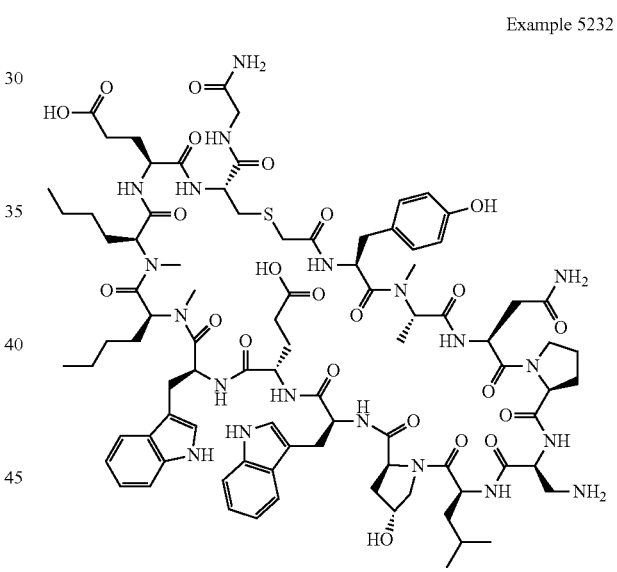

Example 5232

Example 5232 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 24.7 mg, and its estimated purity by LCMS analysis was 100%.

Analysis condition A: Retention time=1.34 min; ESI-MS (+) m/z 937.9 (M+2H)

Analysis condition B: Retention time=2.47 min; ESI-MS (−) m/z 936.2 (M−2H)

ESI-HRMS(+) m/z: Calculated: 937.4507. Found: 937.4509.

Preparation of Example 5233

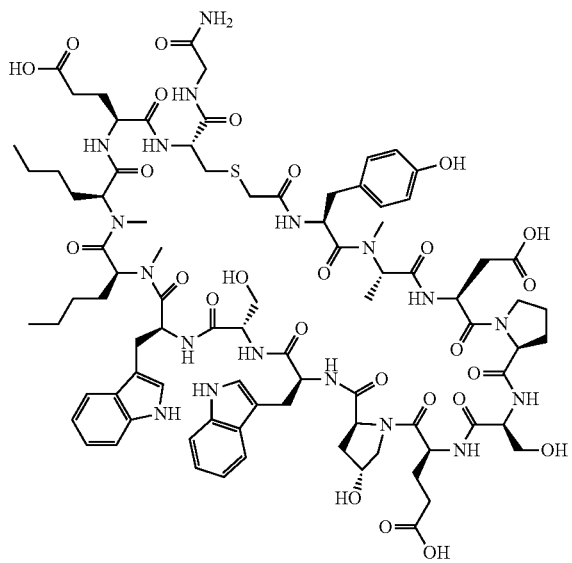

Example 5233

Example 5233 was prepared following "General Synthetic Sequence A". The crude material was purified via preparative LC/MS with the following conditions: Column: XBridge C18, 19×200 mm, 5-μm particles; Mobile Phase A: 5:95 methanol:water with 0.1% trifluoroacetic acid; Mobile Phase B: 95:5 methanol:water with 0.1% trifluoroacetic acid; Gradient: 45-85% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 9.0 mg, and its estimated purity by LCMS analysis was 100%.

Analysis condition A: Retention time=1.29 min; ESI-MS (+) m/z 925.8 (M+2H)

4Analysis condition B: Retention time=2.40 min; ESI-MS(−) m/z 924.1 (M−2H).

Preparation of Example 5234

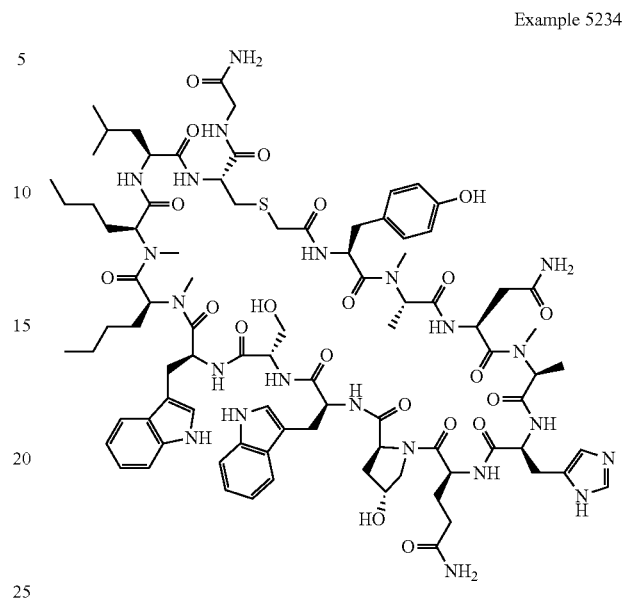

Example 5234

Example 5234 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 7.3 mg, and its estimated purity by LCMS analysis was 100%.

Analysis condition A: Retention time=1.61 min; ESI-MS (+) m/z 935.6 (M+2H)

Analysis condition B: Retention time=2.71 min; ESI-MS (−) m/z 933.7 (M−2H)

ESI-HRMS(+) m/z: Calculated: 935.4589. Found: 935.4591.

Preparation of Example 5236

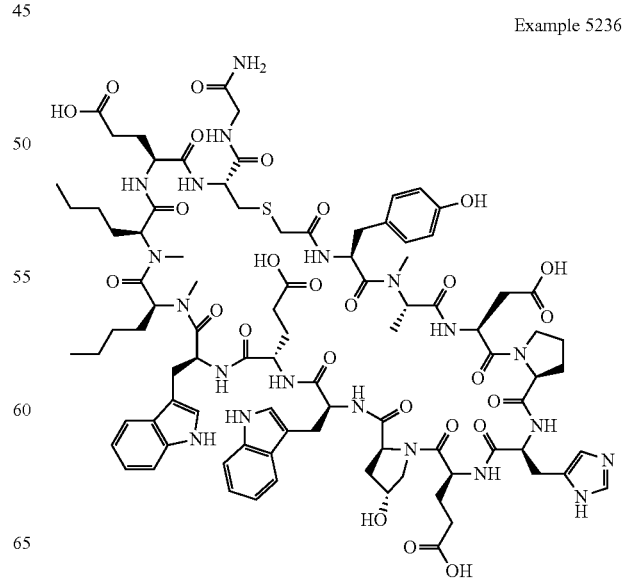

Example 5236

Example 5236 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 25-70% B over 30 minutes, then a 5-minute hold at 100% B; Flow: 20 mL/min. Fractions containing the desired product were combined and dried via centrifugal evaporation. The yield of the product was 7.8 mg, and its estimated purity by LCMS analysis was 100%.

Analysis condition A: Retention time=1.21 min; ESI-MS (+) m/z 972.9 (M+2H)

Analysis condition B: Retention time=2.31 min; ESI-MS (+) m/z 972.0 (M+2H)

ESI-HRMS(+) m/z: Calculated: 971.4274. Found: 971.4247.

Preparation of Example 5237

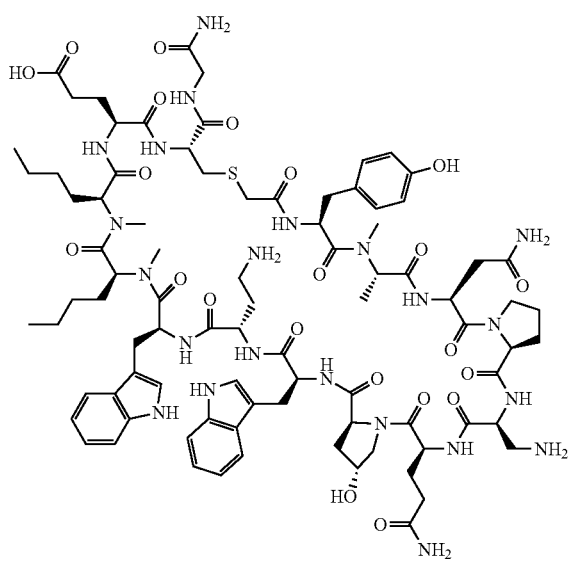

Example 5237

Example 5237 was prepared following "General Synthetic Sequence A". The crude material was purified via preparative LC/MS with the following conditions: Column: XBridge C18, 19×150 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 24.8 mg, and its estimated purity by LCMS analysis was 100%.

Analysis condition A: Retention time=1.43 min; ESI-MS (+) m/z 931.0 (M+2H)

Analysis condition B: Retention time=2.58 min; ESI-MS (+) m/z 931.0 (M+2H)

ESI-HRMS(+) m/z: Calculated: 930.4485. Found: 930.4441.

Preparation of Example 5238

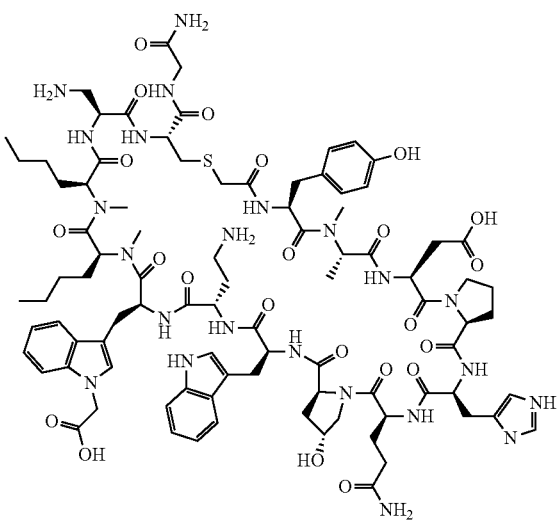

Example 5238

Example 5238 was prepared following "General Synthetic Sequence A", where the "Single-coupling procedure" and "Double-coupling procedure" of "Prelude Method A" were modified to use acetic anhydride in DMF (1.0 M, 2 mL) instead of neat acetic anhydride (2.0 mL). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The material was further purified via preparative LC/MS with the following conditions: Column: waters xbridge c-18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-45% B over 30 minutes, then a 5-minute hold at 100% B; Flow: 20 mL/min. Fractions containing the desired product were combined and dried via centrifugal evaporation. The yield of the product was 9.7 mg, and its estimated purity by LCMS analysis was 93%.

Analysis condition A: Retention time=1.29 min; ESI-MS (+) m/z 964.1 (M+2H)

Analysis condition B: Retention time=2.46 min; ESI-MS (+) m/z 964.2 (M+2H)

ESI-HRMS(+) m/z: Calculated: 963.9484. Found: 963.9514.

Preparation of Example 5240

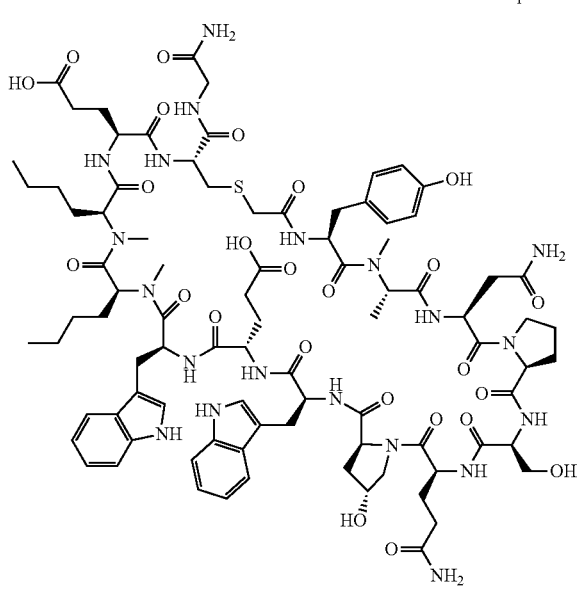

Example 5240

Example 5240 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 10.4 mg, and its estimated purity by LCMS analysis was 97%.

Analysis condition A: Retention time=1.30 min; ESI-MS (+) m/z 946.0 (M+2H)

Analysis condition B: Retention time=2.44 min; ESI-MS (+) m/z 946.2 (M+2H)

ESI-HRMS(+) m/z: Calculated: 945.43. Found: 945.4304.

Preparation of Example 5241

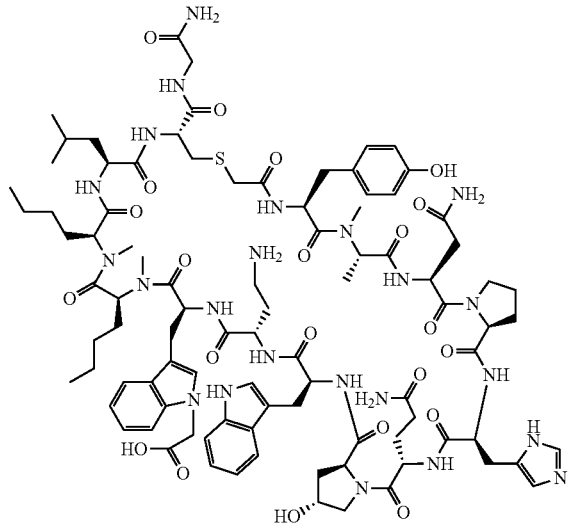

Example 5241

Example 5241 was prepared following "General Synthetic Sequence A", where the "Single-coupling procedure" and "Double-coupling procedure" of "Prelude Method A" were modified to use acetic anhydride in DMF (1.0 M, 2 mL) instead of neat acetic anhydride (2.0 mL). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 10.3 mg, and its estimated purity by LCMS analysis was 98%.

Analysis condition A: Retention time=1.51 min; ESI-MS (+) m/z 978.5 (M+2H)

Analysis condition B: Retention time=2.77 min; ESI-MS (−) m/z 975.3 (M−2H)

ESI-HRMS(+) m/z: Calculated: 976.9774. Found: 976.9757.

Preparation of Example 5242

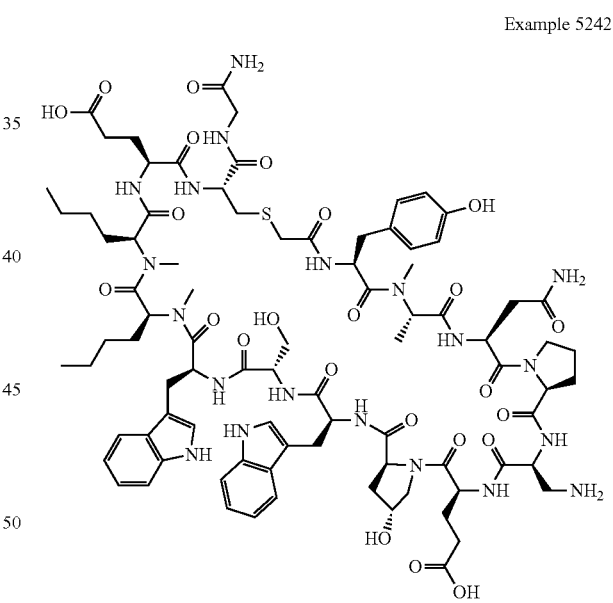

Example 5242

Example 5242 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 19.7 mg, and its estimated purity by LCMS analysis was 100%.

Analysis condition A: Retention time=1.34 min; ESI-MS (+) m/z 1849.3 (M+H)
Analysis condition B: Retention time=2.47 min; ESI-MS (−) m/z 923.1 (M−2H)
ESI-HRMS(+) m/z: Calculated: 924.4247. Found: 924.4248.

Preparation of Example 5243

Example 5243

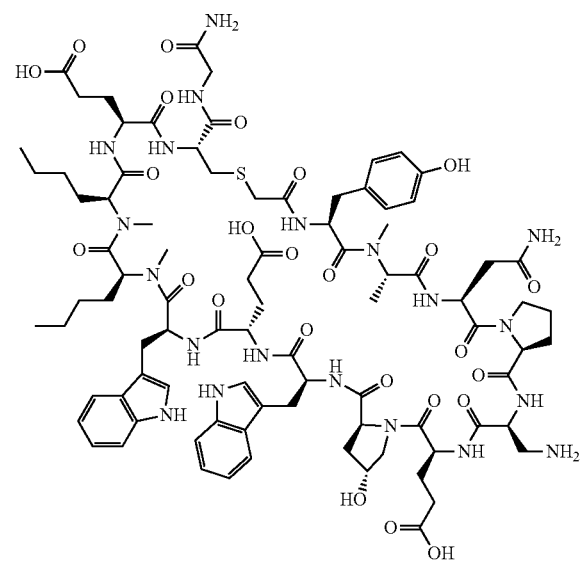

Example 5243 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 0.1% trifluoroacetic acid; Mobile Phase B: 95:5 methanol:water with 0.1% trifluoroacetic acid; Gradient: 40-100% B over 30 minutes, then a 5-minute hold at 100% B; Flow: 20 mL/min. Fractions containing the desired product were combined and dried via centrifugal evaporation. The yield of the product was 5.6 mg, and its estimated purity by LCMS analysis was 100%.

Analysis condition A: Retention time=1.22 min; ESI-MS (+) m/z 946.0 (M+2H)
Analysis condition B: Retention time=2.31 min; ESI-MS (−) m/z 944.1 (M−2H)

ESI-HRMS(+) m/z: Calculated: 945.43. Found: 945.4302.

Preparation of Example 5245

Example 5245

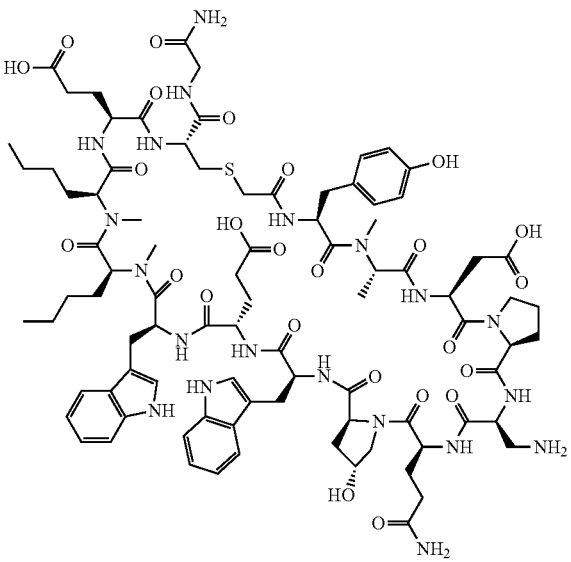

Example 5245 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 30 minutes, then a 5-minute hold at 100% B; Flow: 20 mL/min. Fractions containing the desired product were combined and dried via centrifugal evaporation. The yield of the product was 11.6 mg, and its estimated purity by LCMS analysis was 98%.

Analysis condition A: Retention time=1.576 min; ESI-MS(+) m/z 946.60 (M+2H)
Analysis condition B: Retention time=2.171 min; ESI-MS(+) m/z 945.55 (M+2H)
Analysis condition C: Retention time=1.576 min; ESI-MS(+) m/z 946.60 (M+2H)
ESI-HRMS(+) m/z: Calculated: 945.43. Found: 945.4308.

Preparation of Example 5246

Example 5246

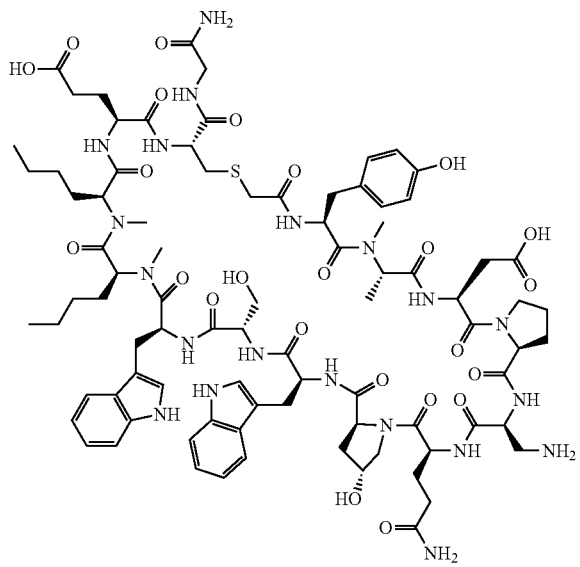

Example 5246 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 16.9 mg, and its estimated purity by LCMS analysis was 100%.

Analysis condition A: Retention time=1.42 min; ESI-MS (−) m/z 923.0 (M−2H)

Analysis condition B: Retention time=2.54 min; ESI-MS (+) m/z 925.1 (M+2H)

ESI-HRMS(+) m/z: Calculated: 924.4247. Found: 924.4249.

Preparation of Example 5247

Example 5247

Example 5247 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 14.0 mg, and its estimated purity by LCMS analysis was 99%.

Analysis condition A: Retention time=1.49 min; ESI-MS (+) m/z 924.0 (M+2H)

Analysis condition B: Retention time=2.64 min; ESI-MS (−) m/z 922.1 (M−2H)

ESI-HRMS(+) m/z: Calculated: 923.4533. Found: 923.449.

Preparation of Example 5248

Example 5248

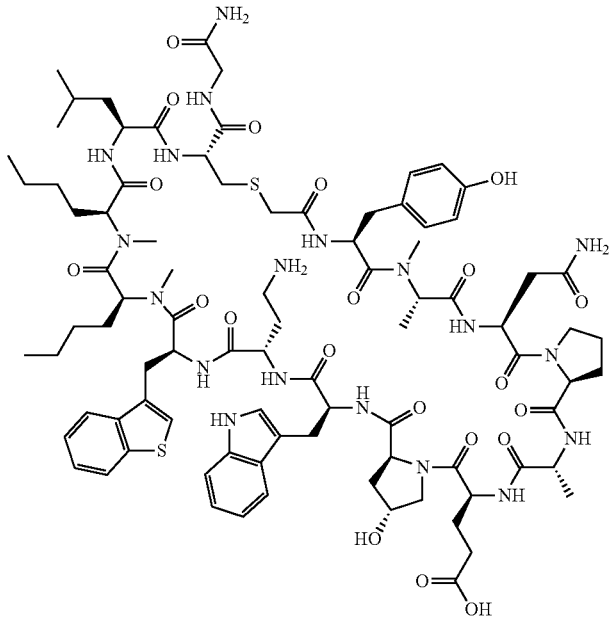

Example 5248 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 60-100% B over 30 minutes, then a 5-minute hold at 100% B; Flow: 20 mL/min. Fractions containing the desired product were combined and dried via centrifugal evaporation. The yield of the product was 21.7 mg, and its estimated purity by LCMS analysis was 97%.

Analysis condition A: Retention time=1.65 min; ESI-MS (+) m/z 1847.4 (M+H)

Analysis condition B: Retention time=2.93 min; ESI-MS (+) m/z 924.5 (M+2H).

Preparation of Example 5249

Example 5249

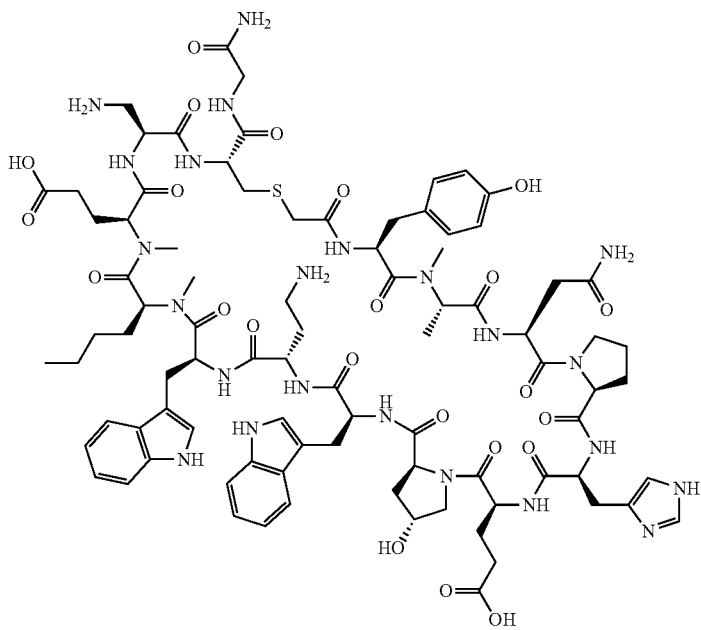

Example 5249 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 15 minutes, then a 5-minute hold at 100% B; Flow: 20 mL/min. Fractions containing the desired product were combined and dried via centrifugal evaporation. The yield of the product was 37.9 mg, and its estimated purity by LCMS analysis was 100%.

Analysis condition A: Retention time=1.06 min; ESI-MS (+) m/z 943.5 (M+2H)

Analysis condition B: Retention time=2.16 min; ESI-MS (−) m/z 941.4 (M−2H)

ESI-HRMS(+) m/z: Calculated: 942.9279. Found: 942.9254.

Preparation of Example 5251

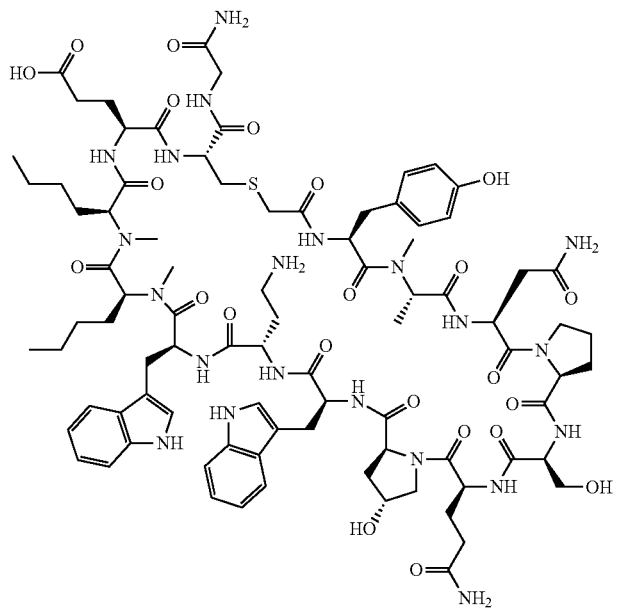

Example 5251

Example 5251 was prepared following "General Synthetic Sequence A". The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 20.2 mg, and its estimated purity by LCMS analysis was 100%.

Analysis condition A: Retention time=1.49 min; ESI-MS (+) m/z 931.5 (M+2H)

Analysis condition B: Retention time=2.61 min; ESI-MS (−) m/z 929.2 (M−2H)

ESI-HRMS(+) m/z: Calculated: 930.9405. Found: 930.936.

Preparation of Example 5252

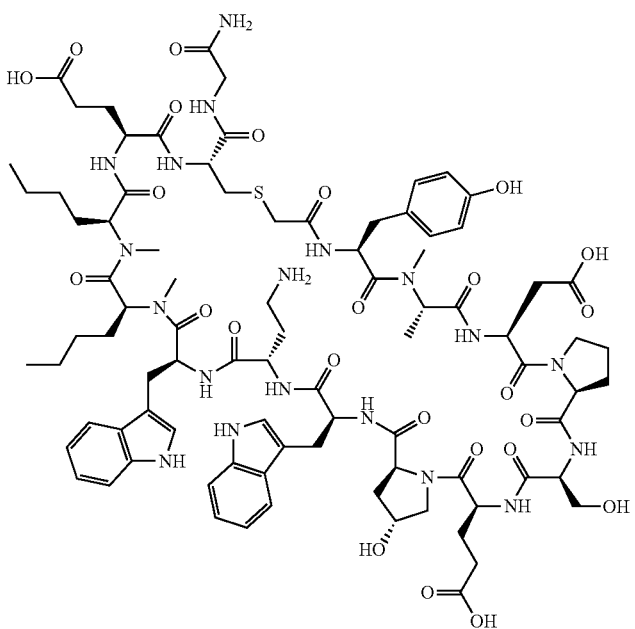

Example 5252

Example 5252 was prepared following "General Synthetic Sequence A". The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 15.9 mg, and its estimated purity by LCMS analysis was 100%.

Analysis condition A: Retention time=1.30 min; ESI-MS (+) m/z 932.3 (M+2H)

Analysis condition B: Retention time=2.45 min; ESI-MS (−) m/z 930.6 (M−2H)

ESI-HRMS(+) m/z: Calculated: 931.9245. Found: 931.9205.

Preparation of Example 5253

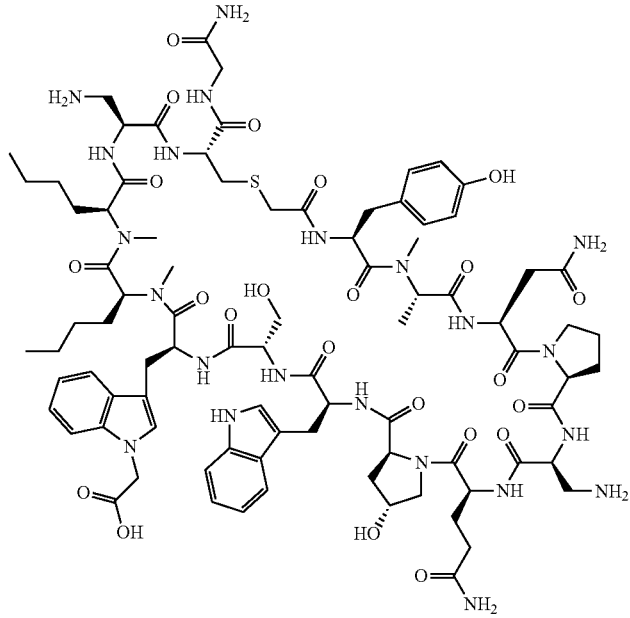

Example 5253

Example 5253 was prepared following "General Synthetic Sequence A", where the "Single-coupling procedure" and "Double-coupling procedure" of "Prelude Method A" were modified to use acetic anhydride in DMF (1.0 M, 2 mL) instead of neat acetic anhydride (2.0 mL). The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 45-85% B over 20 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 5-45% B over 20 minutes, then a 5-minute hold at 100% B; Flow: 20 mL/min. Fractions containing the desired product were combined and dried via centrifugal evaporation. The yield of the product was 26.8 mg, and its estimated purity by LCMS analysis was 100%.

Analysis condition A: Retention time=1.378 min; ESI-MS(+) m/z 931.9 (M+2H)

Analysis condition B: Retention time=2.862 min; ESI-MS(−) m/z 929.9 (M−2H)

ESI-HRMS(+) m/z: Calculated: 931.4381. Found: 931.435.

Preparation of Example 5254

Example 5254

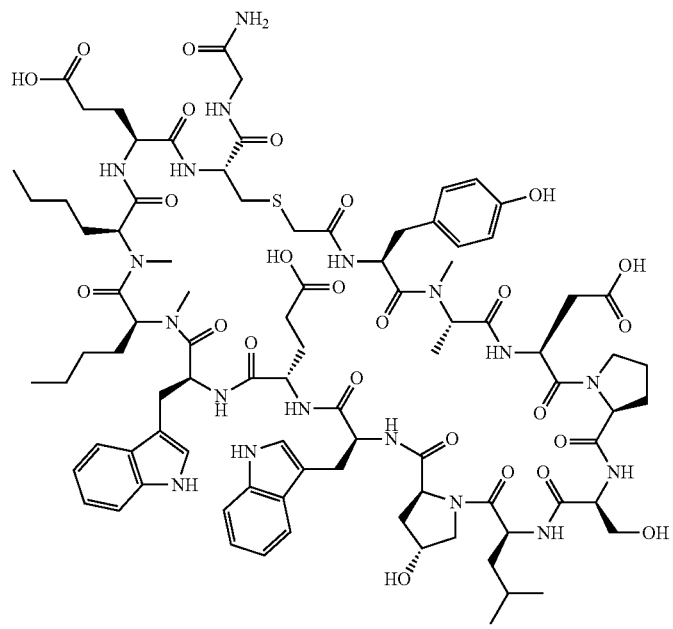

Example 5254 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 9.4 mg, and its estimated purity by LCMS analysis was 100%.

Analysis condition A: Retention time=1.655 min; ESI-MS(+) m/z 938.60 (M+2H)

Analysis condition B: Retention time=2.40 min; ESI-MS (+) m/z 939.2 (M+2H)

Analysis condition C: Retention time=1.655 min; ESI-MS(+) m/z 938.60 (M+2H)

ESI-HRMS(+) m/z: Calculated: 938.4347. Found: 938.4348.

Preparation of Example 5255

Example 5255

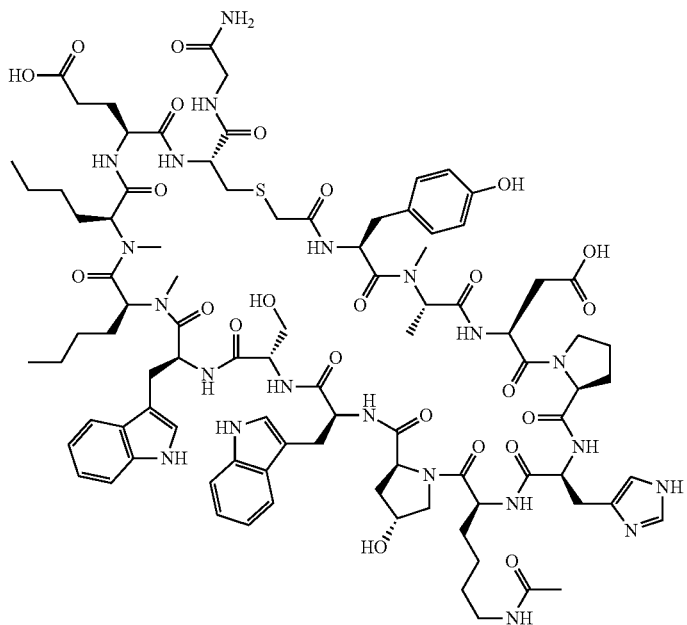

Example 5255 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 25-75% B over 30 minutes, then a 5-minute hold at 100% B; Flow: 20 mL/min. Fractions containing the desired product were combined and dried via centrifugal evaporation. The yield of the product was 2.2 mg, and its estimated purity by LCMS analysis was 100%.

Analysis condition A: Retention time=1.32 min; ESI-MS (+) m/z 971.2 (M+2H)

Analysis condition B: Retention time=2.44 min; ESI-MS (+) m/z 971.6 (M+2H)

ESI-HRMS(+) m/z: Calculated: 970.9536. Found: 970.9501.

Preparation of Example 5256

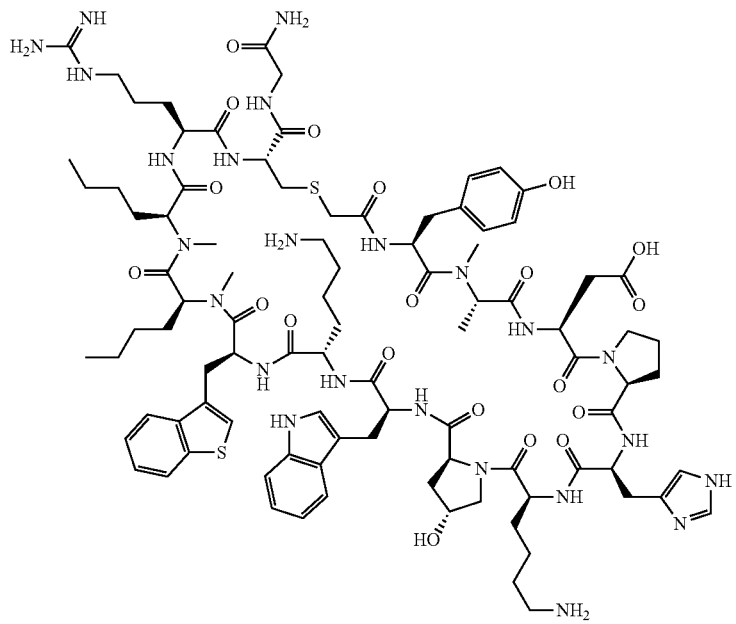

Example 5256

Example 5256 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 3.4 mg, and its estimated purity by LCMS analysis was 100%.

Analysis condition A: Retention time=1.54 min; ESI-MS (+) m/z 993.1 (M+2H)

Analysis condition B: Retention time=2.73 min; ESI-MS (+) m/z 992.8 (M+2H)

ESI-HRMS(+) m/z: Calculated: 992.4897. Found: 992.4871.

Preparation of Example 5257

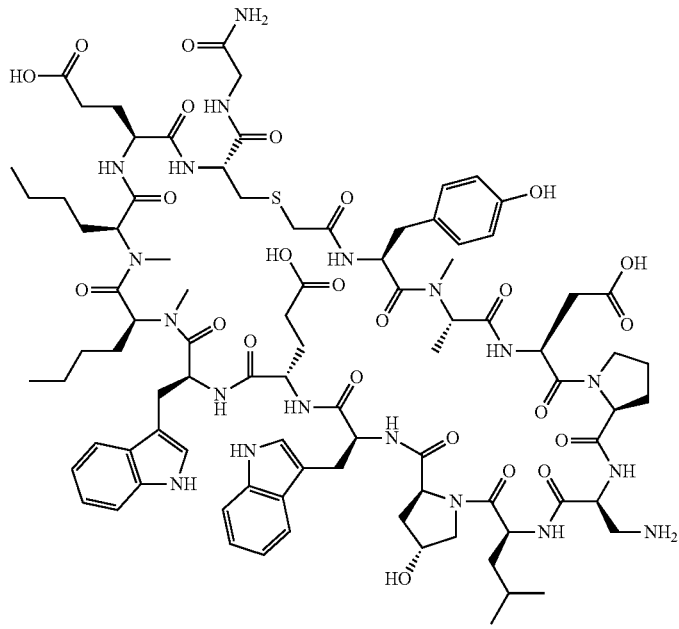

Example 5257

Example 5257 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 17.2 mg, and its estimated purity by LCMS analysis was 95%.

Analysis condition A: Retention time=1.34 min; ESI-MS (+) m/z 1876.4 (M+2H)

Analysis condition B: Retention time=2.45 min; ESI-MS (−) m/z 936.3 (M−2H)

ESI-HRMS(+) m/z: Calculated: 937.9427. Found: 937.9431.

Preparation of Example 5259

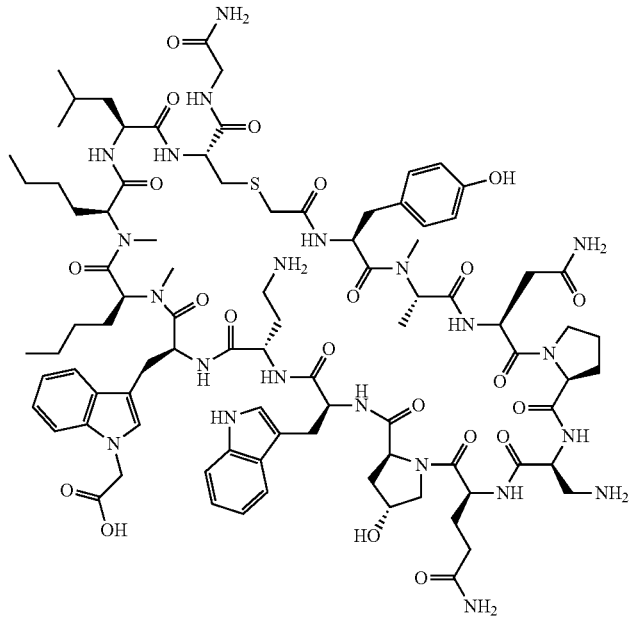

Example 5259

Example 5259 was prepared following "General Synthetic Sequence A", where the "Single-coupling procedure" and "Double-coupling procedure" of "Prelude Method A" were modified to use acetic anhydride in DMF (1.0 M, 2 mL) instead of neat acetic anhydride (2.0 mL). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 31.9 mg, and its estimated purity by LCMS analysis was 100%.

Analysis condition A: Retention time=1.48 min; ESI-MS (+) m/z 951.3 (M+2H)

Analysis condition B: Retention time=2.69 min; ESI-MS (−) m/z 950.0 (M−2H)

ESI-HRMS(+) m/z: Calculated: 951.472. Found: 951.4698.

Preparation of Example 5260

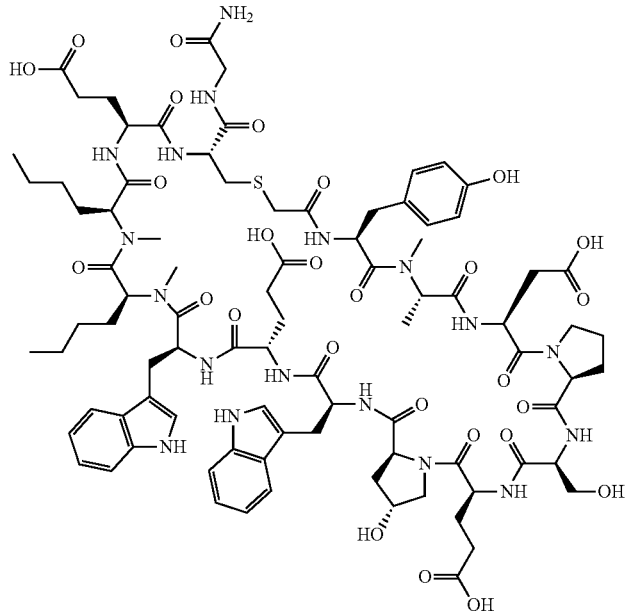

Example 5260

Example 5260 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 25.9 mg, and its estimated purity by LCMS analysis was 96%.

Analysis condition A: Retention time=1.61 min; ESI-MS (+) m/z 928.2 (M+2H)

Analysis condition B: Retention time=2.72 min; ESI-MS (+) m/z 928.6 (M+2H)

Analysis condition C: Retention time=1.432 min; ESI-MS(+) m/z 946.70 (M+2H)

ESI-HRMS(+) m/z: Calculated: 946.414. Found: 946.4138.

Preparation of Example 5261

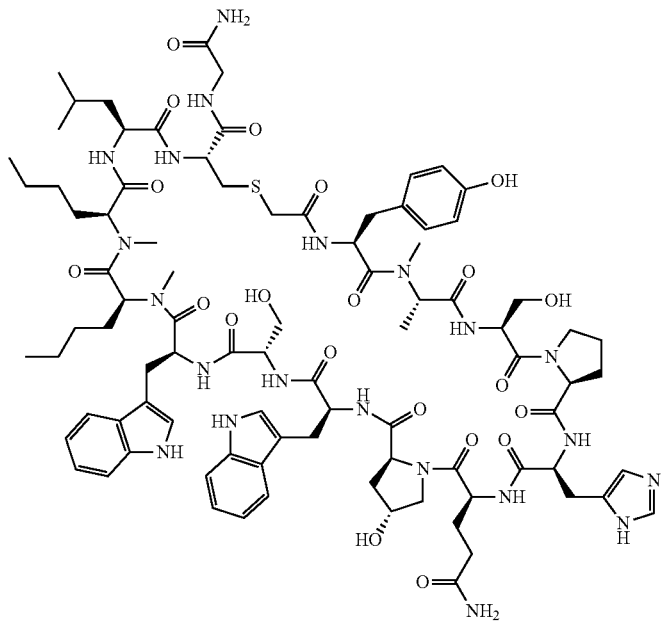

Example 5261

Example 5261 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 13.6 mg, and its estimated purity by LCMS analysis was 95%.

Analysis condition A: Retention time=1.432 min; ESI-MS(+) m/z 946.70 (M+2H)

Analysis condition B: Retention time=2.462 min; ESI-MS(−) m/z 944.80 (M−2H)

ESI-HRMS(+) m/z: Calculated: 946.414. Found: 946.4138.

Preparation of Example 5262

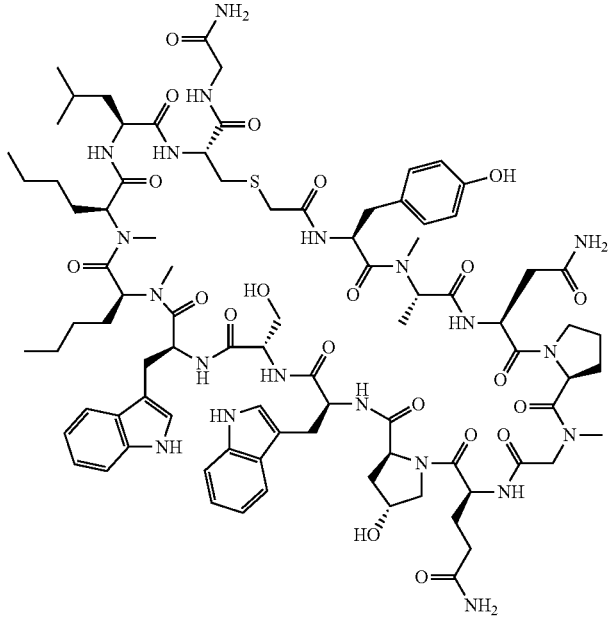

Example 5262

Example 5262 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 19.0 mg, and its estimated purity by LCMS analysis was 98%.

Analysis condition A: Retention time=1.62 min; ESI-MS (+) m/z 908.8 (M+2H)

Analysis condition B: Retention time=2.75 min; ESI-MS (−) m/z 907.1 (M−2H)

ESI-HRMS(+) m/z: Calculated: 908.4480. Found: 908.4463.

Preparation of Example 5263

Example 5263

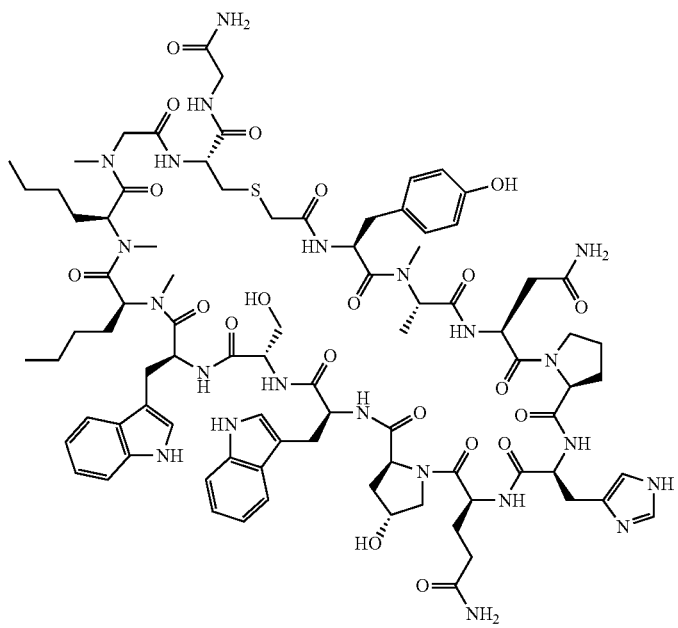

Example 5263 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 7.7 mg, and its estimated purity by LCMS analysis was 100%.

Analysis condition A: Retention time=1.43 min; ESI-MS (+) m/z 920.9 (M+2H)

Analysis condition B: Retention time=2.59 min; ESI-MS (−) m/z 919.2 (M−2H)

ESI-HRMS(+) m/z: Calculated: 920.4354. Found: 920.4356.

Preparation of Example 5264

Example 5264

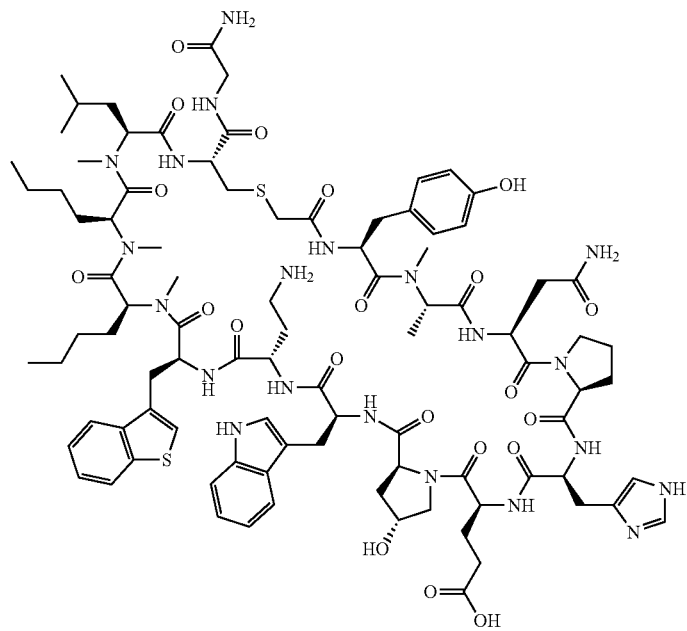

Example 5264 was prepared following "General Synthetic Sequence A". The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 55-95% B over 30 minutes, then a 5-minute hold at 100% B; Flow: 20 mL/min. Fractions containing the desired product were combined and dried via centrifugal evaporation. The yield of the product was 14.8 mg, and its estimated purity by LCMS analysis was 100%.

Analysis condition A: Retention time=1.82 min; ESI-MS (−) m/z 964.9 (M+2H)

Analysis condition B: Retention time=2.94 min; ESI-MS (+) m/z 964.6 (M+2H)

ESI-HRMS(+) m/z: Calculated: 963.9551. Found: 963.9530.

Preparation of Example 5265

Example 5265

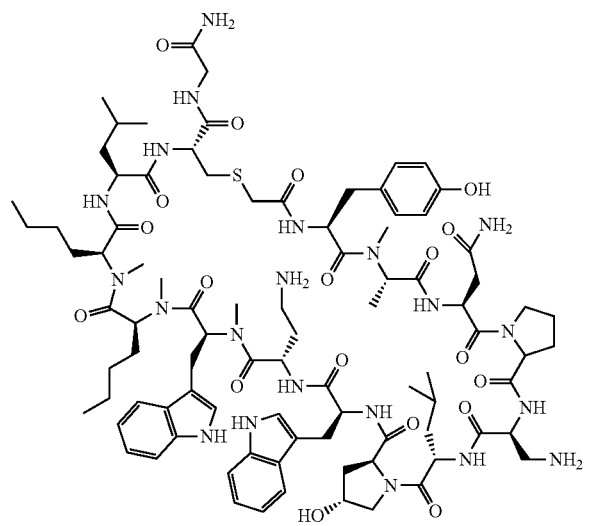

Example 5265 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 23.2 mg, and its estimated purity by LCMS analysis was 100%.

Analysis condition A: Retention time=1.631 min; ESI-MS(−) m/z 920.30 (M−2H)

Analysis condition B: Retention time=3.126 min; ESI-MS(+) m/z 922.35 (M+2H).

Preparation of Example 6118

Example 6118

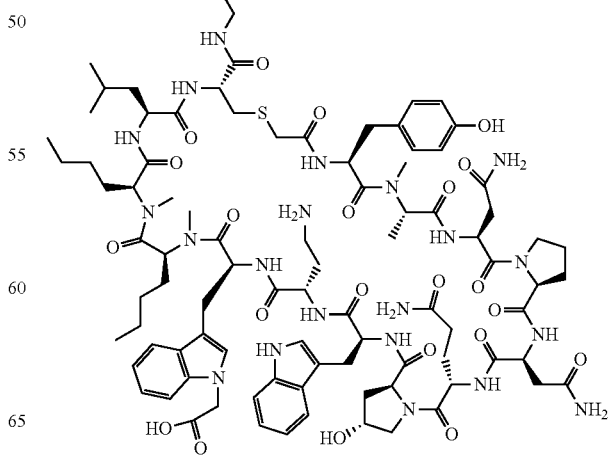

Example 6118 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 4.4 mg, and its estimated purity by LCMS analysis was 100%.

Analysis condition A: Retention time=1.52 min; ESI-MS (+) m/z 965.3 (M+2H)

Analysis condition B: Retention time=2.16 min; ESI-MS (+) m/z 965.65 (M+2H)

ESI-HRMS(+) m/z: Calculated: 965.4694. Found: 965.4676.

Preparation of Example 6119

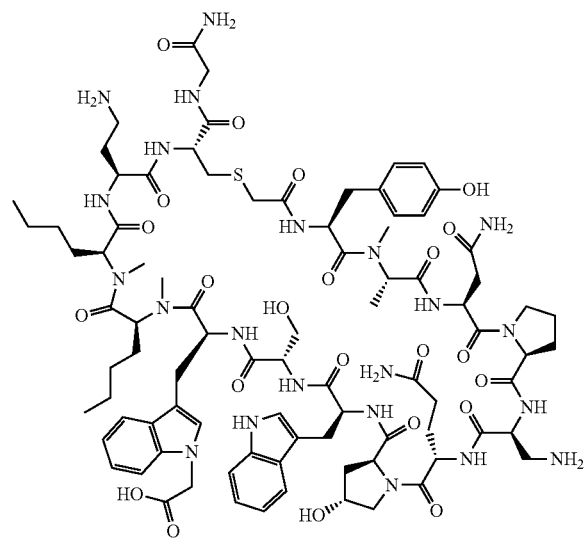

Example 6119

Example 6119 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 30-70% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 2.9 mg, and its estimated purity by LCMS analysis was 96%.

Analysis condition A: Retention time=1.27 min; ESI-MS (+) m/z 938.75 (M+2H)

Analysis condition B: Retention time=2.79 min; ESI-MS (+) m/z 939 (M+2H)

ESI-HRMS(+) m/z: Calculated: 938.446. Found: 938.444.

Preparation of Example 6128

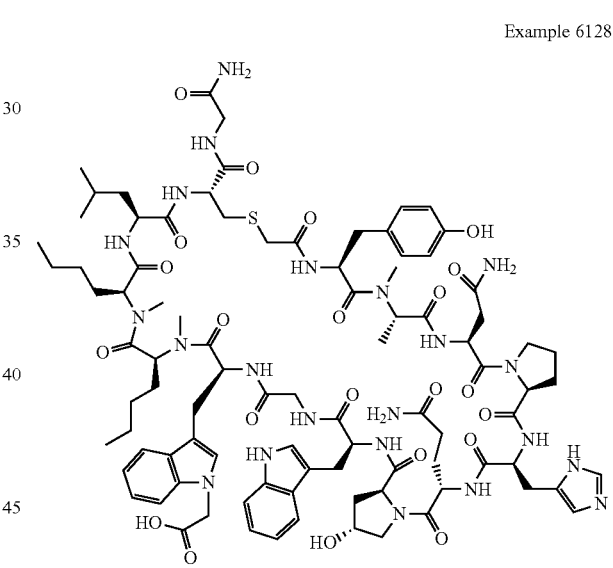

Example 6128

Example 6128 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 9.4 mg, and its estimated purity by LCMS analysis was 99%.

Analysis condition A: Retention time=1.43 min; ESI-MS (+) m/z 956.0 (M+2H)

Analysis condition B: Retention time=2.89 min; ESI-MS (+) m/z 956.0 (M+2H)

ESI-HRMS(+) m/z: Calculated: 955.4563. Found: 955.4553.

Preparation of Example 6134

Example 6134

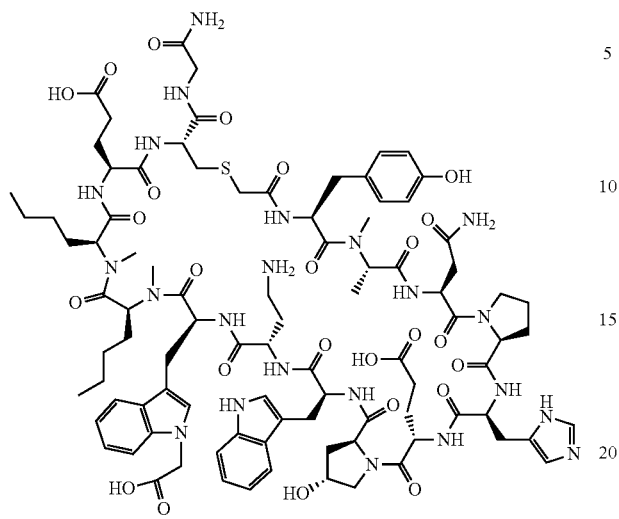

Example 6134 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: waters xbridge c-18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 5-45% B over 30 minutes, then a 5-minute hold at 100% B; Flow: 20 mL/min. Fractions containing the desired product were combined and dried via centrifugal evaporation. The yield of the product was 11.4 mg, and its estimated purity by LCMS analysis was 95%.

Analysis condition A: Retention time=1.22 min; ESI-MS (−) m/z 984.4 (M+2H)

Analysis condition B: Retention time=2.30 min; ESI-MS (−) m/z 984.6 (M+2H)

ESI-HRMS(+) m/z: Calculated: 985.4487. Found: 985.4464.

Preparation of Example 6135

Example 6135

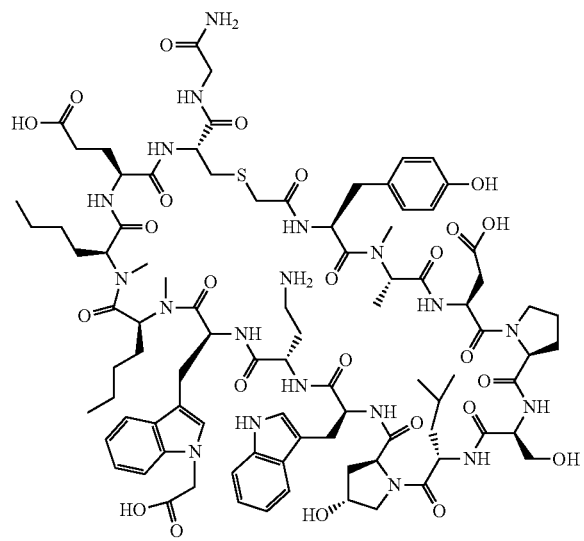

Example 6135 was prepared following "General Synthetic Sequence A". The crude material was purified via preparative LC/MS with the following conditions: Column: waters xbridge c-18, 19×200 mm, 5-µm particles; Mobile Phase A: 5:95 methanol:water with 0.1% trifluoroacetic acid; Mobile Phase B: 95:5 methanol:water with 0.1% trifluoroacetic acid; Gradient: 40-80% B over 30 minutes, then a 5-minute hold at 100% B; Flow: 20 mL/min. Fractions containing the desired product were combined and dried via centrifugal evaporation. The yield of the product was 21.9 mg, and its estimated purity by LCMS analysis was 95%.

Analysis condition A: Retention time=1.18 min; ESI-MS (+) m/z 954.2 (M+2H)

Analysis condition B: Retention time=2.27 min; ESI-MS (+) m/z 953.5 (M+2H)

ESI-HRMS(+) m/z: Calculated: 952.948. Found: 952.9465.

Preparation of Example 6136

Example 6136

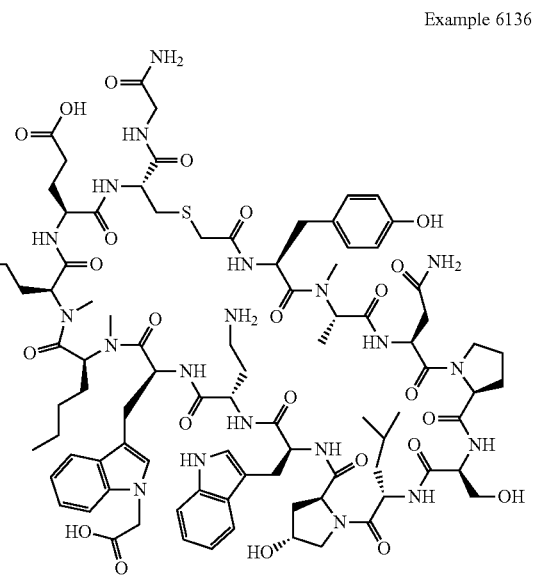

Example 6136 was prepared following "General Synthetic Sequence A". The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 30-70% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 0-40% B over 30 minutes, then a 5-minute hold at 100% B; Flow: 20 mL/min. Fractions containing the desired product were combined and dried via centrifugal evaporation. The yield of the product was 16.2 mg, and its estimated purity by LCMS analysis was 100%.

Analysis condition A: Retention time=1.30 min; ESI-MS (+) m/z 952.9 (M+2H)

Analysis condition B: Retention time=1.90 min; ESI-MS (+) m/z 952.7 (M+2H)

ESI-HRMS(+) m/z: Calculated: 952.456. Found: 952.4533.

Preparation of Example 6137

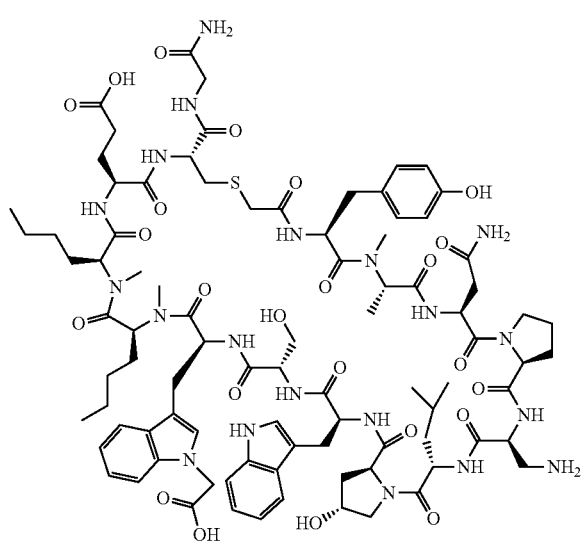

Example 6137

Example 6137 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 7.0 mg, and its estimated purity by LCMS analysis was 99%.

Analysis condition A: Retention time=1.31 min; ESI-MS (+) m/z 945.95 (M+2H)

ESI-HRMS(+) m/z: Calculated: 945.4482. Found: 945.4472.

Preparation of Example 6140

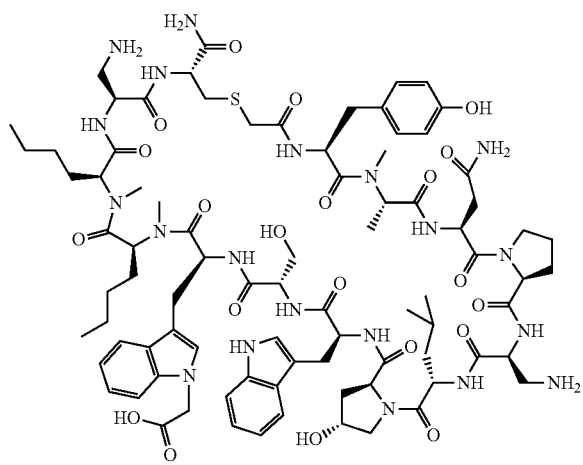

Example 6140

Example 6140 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 11.4 mg, and its estimated purity by LCMS analysis was 100%.

Analysis condition A: Retention time=1.36 min; ESI-MS (+) m/z 896.4 (M+2H)

Analysis condition B: Retention time=2.56 min; ESI-MS (+) m/z 896.4 (M+2H)

ESI-HRMS(+) m/z: Calculated: 895.4402. Found: 895.4393.

Preparation of Example 6141

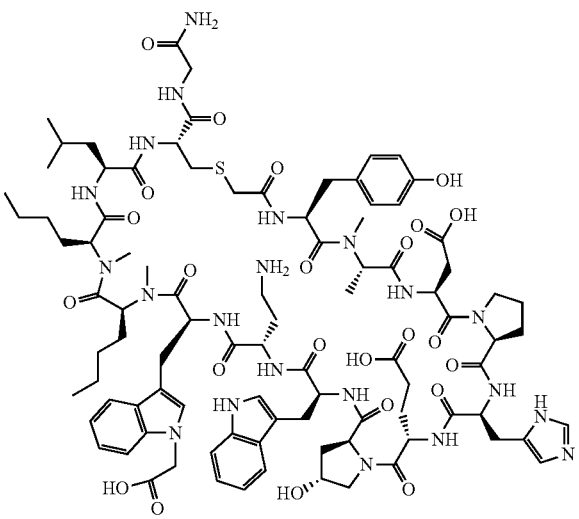

Example 6141

Example 6141 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 13.6 mg, and its estimated purity by LCMS analysis was 100%.

Analysis condition A: Retention time=1.44 min; ESI-MS (+) m/z 978.5 (M+2H)

Analysis condition B: Retention time=2.94 min; ESI-MS (+) m/z 978.4 (M+2H)

ESI-HRMS(+) m/z: Calculated: 977.9615. Found: 977.9603.

Preparation of Example 6146

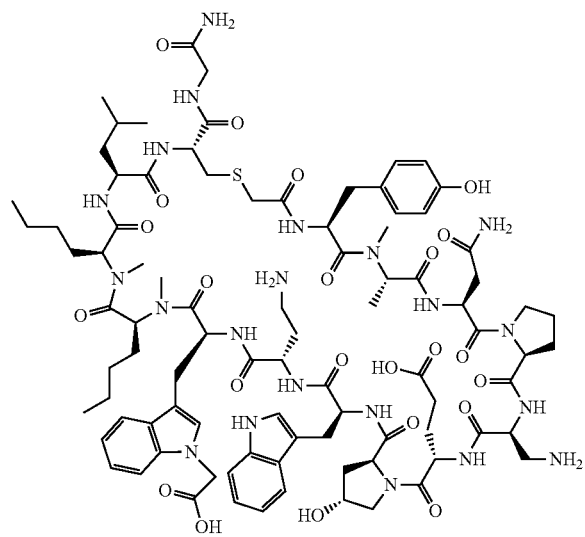

Example 6146

Example 6146 was prepared following "General Synthetic Sequence A". The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 7.8 mg, and its estimated purity by LCMS analysis was 100%.

Analysis condition A: Retention time=1.52 min; ESI-MS (+) m/z 952.4 (M+2H)

Analysis condition B: Retention time=3.07 min; ESI-MS (+) m/z 952.4 (M+2H)

ESI-HRMS(+) m/z: Calculated: 951.964. Found: 951.9612.

Preparation of Example 6156

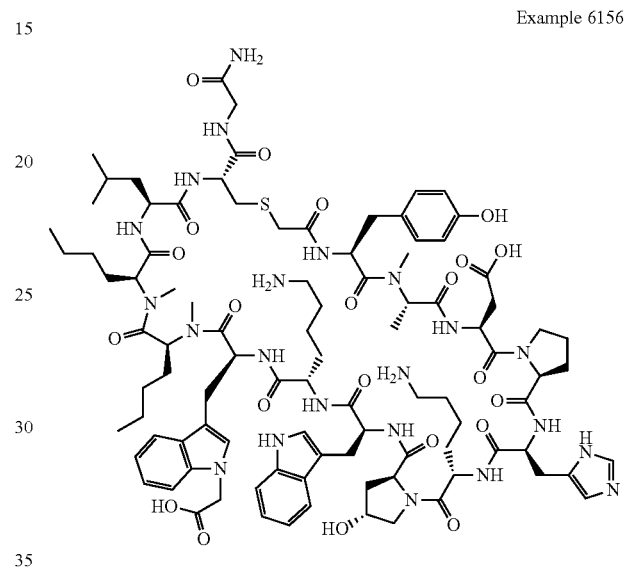

Example 6156

Example 6156 was prepared following "General Synthetic Sequence A". The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 17.9 mg, and its estimated purity by LCMS analysis was 98%.

Analysis condition A: Retention time=1.46 min; ESI-MS (+) m/z 992.0 (M+2H)

Analysis condition B: Retention time=2.98 min; ESI-MS (+) m/z 992.0 (M+2H)

ESI-HRMS(+) m/z: Calculated: 991.5033. Found: 991.5002.

Preparation of Example 6158

Example 6158

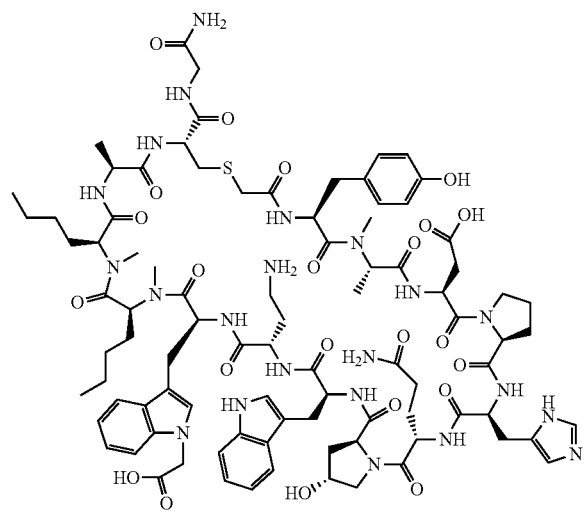

Example 6158 was prepared following "General Synthetic Sequence A". The crude material was purified via preparative LC/MS with the following conditions: Column: waters xbridge c-18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 17.3 mg, and its estimated purity by LCMS analysis was 99%.

Analysis condition A: Retention time=1.30 min; ESI-MS (+) m/z 957.1 (M+2H)

Analysis condition B: Retention time=2.43 min; ESI-MS (+) m/z 956.9 (M+2H)

ESI-HRMS(+) m/z: Calculated: 956.446. Found: 956.4428.

Preparation of Example 6162

Example 6162

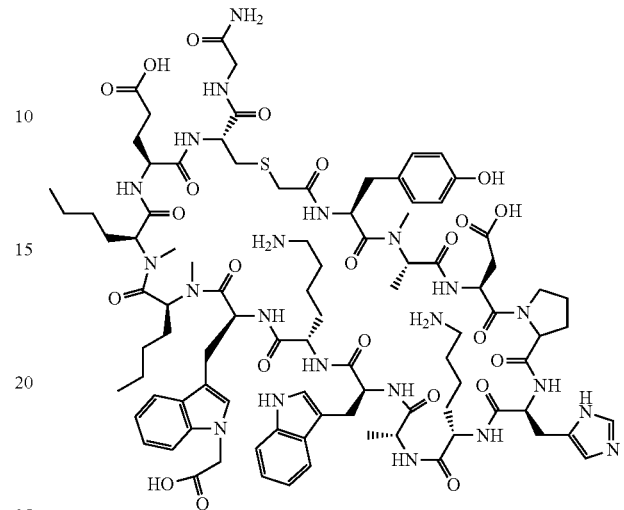

Example 6162 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 30-70% B over 30 minutes, then a 5-minute hold at 100% B; Flow: 20 mL/min. Fractions containing the desired product were combined and dried via centrifugal evaporation. The yield of the product was 15.9 mg, and its estimated purity by LCMS analysis was 95%.

Analysis condition A: Retention time=1.21 min; ESI-MS (+) m/z 999.7 (M+2H)

Analysis condition B: Retention time=2.68 min; ESI-MS (+) m/z 999.6 (M+2H)

ESI-HRMS(+) m/z: Calculated: 999.4826. Found: 999.4816.

Preparation of Example 6168

Example 6168

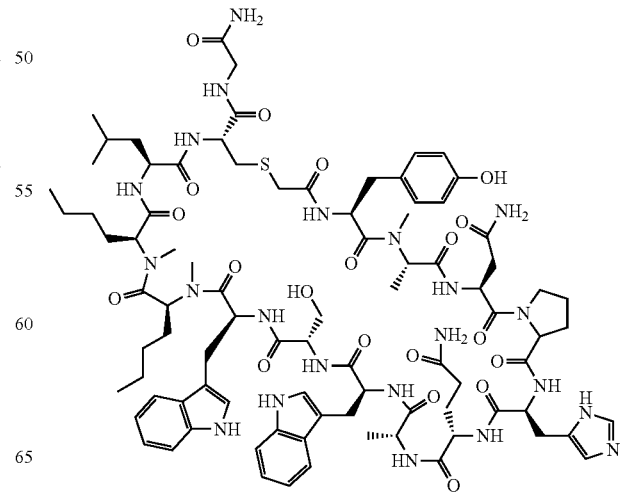

Example 6168 was prepared following "General Synthetic Sequence A". The crude material was purified via preparative LC/MS with the following conditions: Column: XBridge C18, 19×150 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 21.8 mg, and its estimated purity by LCMS analysis was 100%.

Analysis condition A: Retention time=1.51 min; ESI-MS (+) m/z 920.65 (M+2H)

Analysis condition B: Retention time=2.78 min; ESI-MS (+) m/z 920.65 (M+2H)

ESI-HRMS(+) m/z: Calculated: 920.4536. Found: 920.4506.

Preparation of Example 6170

Example 6170

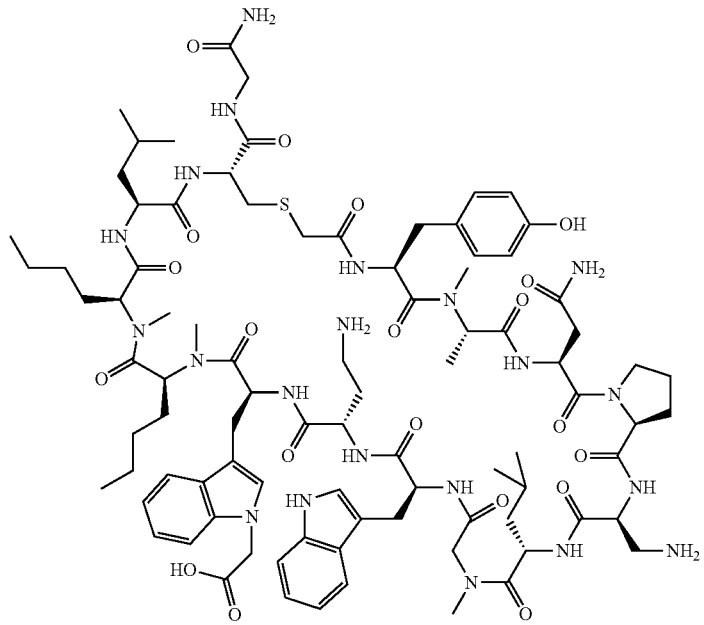

Example 6170 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 7.2 mg, and its estimated purity by LCMS analysis was 100%.

Analysis condition A: Retention time=1.55 min; ESI-MS (+) m/z 924.3 (M+2H)

Analysis condition B: Retention time=2.87 min; ESI-MS (+) m/z 924.3 (M+2H)

ESI-HRMS(+) m/z: Calculated: 922.9794. Found: 922.9764.

Preparation of Example 6172

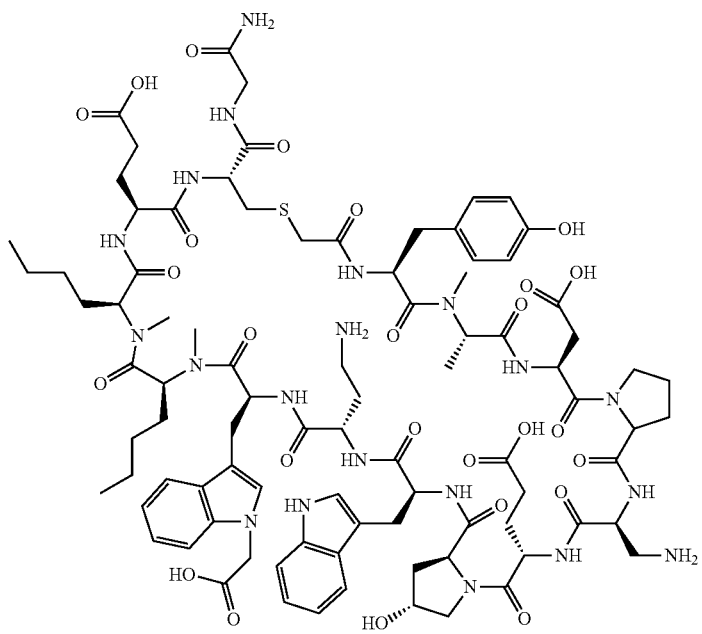

Example 6172

Example 6172 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 30-70% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-40% B over 30 minutes, then a 5-minute hold at 100% B; Flow: 20 mL/min. Fractions containing the desired product were combined and dried via centrifugal evaporation. The yield of the product was 15.6 mg, and its estimated purity by LCMS analysis was 100%.

Analysis condition A: Retention time=1.21 min; ESI-MS (+) m/z 960.7 (M+2H)

Analysis condition B: Retention time=1.79 min; ESI-MS (+) m/z 960.9 (M+2H)

ESI-HRMS(+) m/z: Calculated: 960.4353. Found: 960.4323.

Preparation of Example 6176

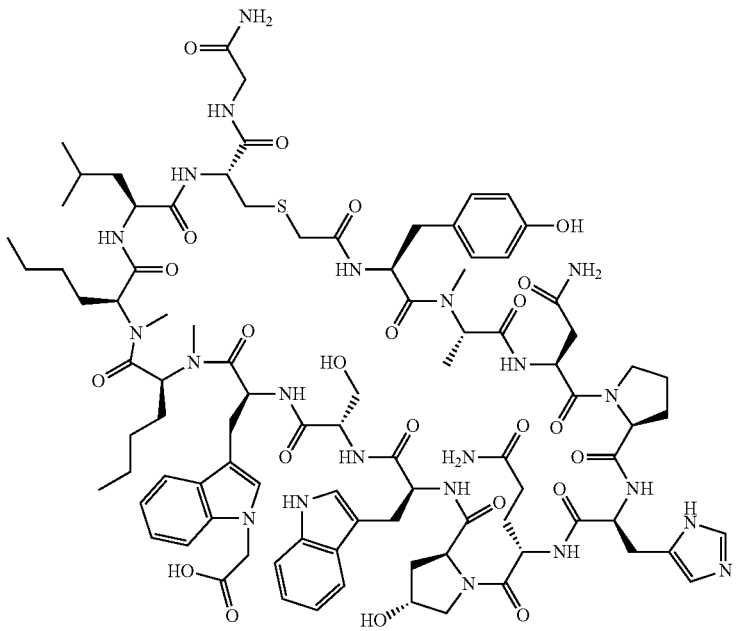

Example 6176

Example 6176 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 4.9 mg, and its estimated purity by LCMS analysis was 100%.

Analysis condition A: Retention time=1.47 min; ESI-MS (+) m/z 971.0 (M+2H)

Analysis condition B: Retention time=2.91 min; ESI-MS (+) m/z 970.9 (M+2H).

Preparation of Example 6180

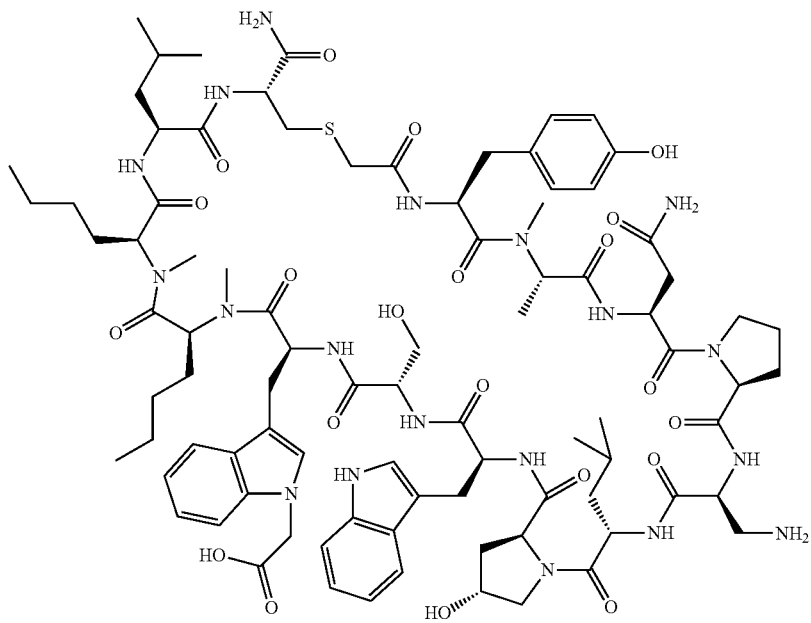

Example 6180

Example 6180 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 12.2 mg, and its estimated purity by LCMS analysis was 100%.

Analysis condition A: Retention time=1.50 min; ESI-MS (−) m/z 907.7 (M−2H)

Analysis condition B: Retention time=2.71 min; ESI-MS (+) m/z 910.3 (M+2H)

ESI-HRMS(+) m/z: Calculated: 908.9582. Found: 908.9577.

Preparation of Example 6183

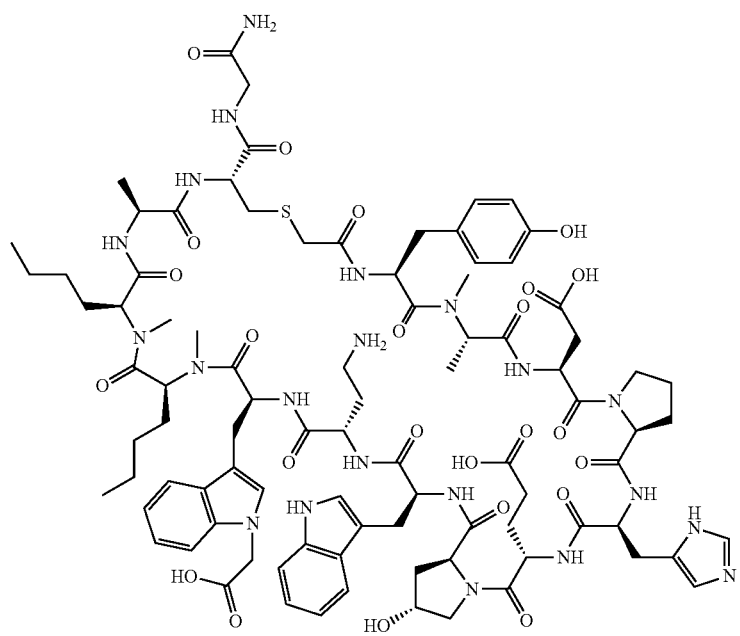

Example 6183

Example 6183 was prepared following "General Synthetic Sequence A". The crude material was purified via preparative LC/MS with the following conditions: Column: waters xbridge c-18, 19×200 mm, 5-μm particles; Mobile Phase A: 5:95 methanol:water with 0.1% trifluoroacetic acid; Mobile Phase B: 95:5 methanol:water with 0.1% trifluoroacetic acid; Gradient: 40-80% B over 30 minutes, then a 50-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 30-70% B over 30 minutes, then a 5-minute hold at 100% B; Flow: 20 mL/min. Fractions containing the desired product were combined and dried via centrifugal evaporation. The yield of the product was 18.3 mg, and its estimated purity by LCMS analysis was 97%.

Analysis condition A: Retention time=1.24 min; ESI-MS (+) m/z 957.8 (M+2H)

Analysis condition B: Retention time=2.36 min; ESI-MS (+) m/z 957.6 (M+2H).

Preparation of Example 6184

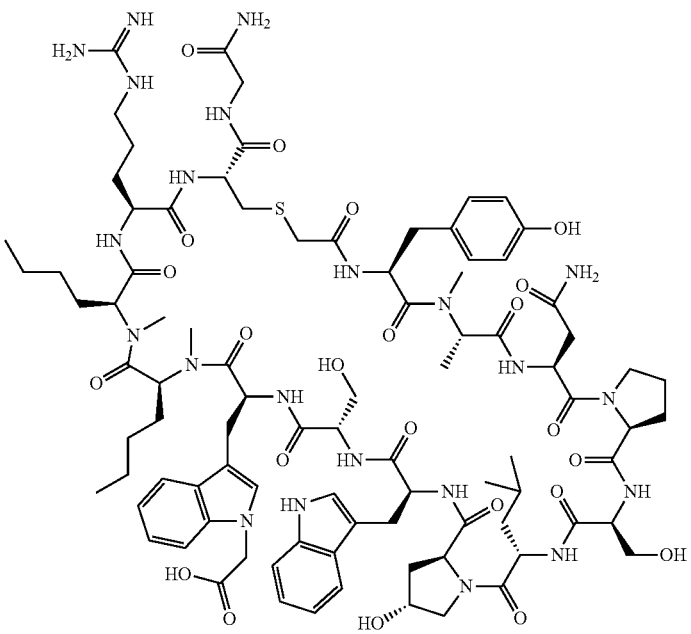

Example 6184

Example 6184 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 8.9 mg, and its estimated purity by LCMS analysis was 100%.

Analysis condition A: Retention time=1.25 min; ESI-MS (−) m/z 958.8 (M−2H)

Analysis condition B: Retention time=1.62 min; ESI-MS (+) m/z 960.5 (M+2H)

ESI-HRMS(+) m/z: Calculated: 959.4694. Found: 959.4692.

Preparation of Example 6185

Example 6185

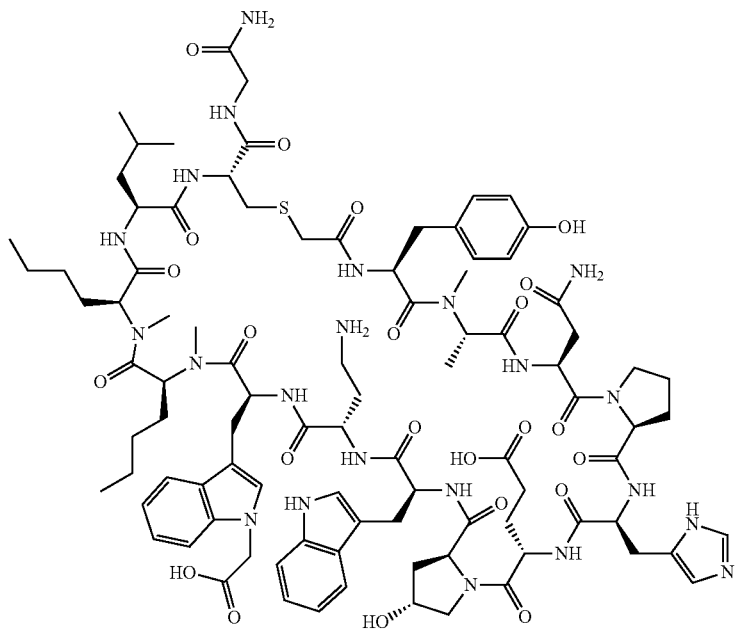

Example 6185 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 30 minutes, then a 5-minute hold at 100% B; Flow: 20 mL/min. Fractions containing the desired product were combined and dried via centrifugal evaporation. The yield of the product was 17.0 mg, and its estimated purity by LCMS analysis was 92%.

Analysis condition A: Retention time=1.38 min; ESI-MS (−) m/z 976.9 (M−2H)

Analysis condition B: Retention time=3.09 min; ESI-MS (+) m/z 977.6 (M+2H)

ESI-HRMS(+) m/z: Calculated: 977.4694. Found: 977.4692.

Preparation of Example 6189

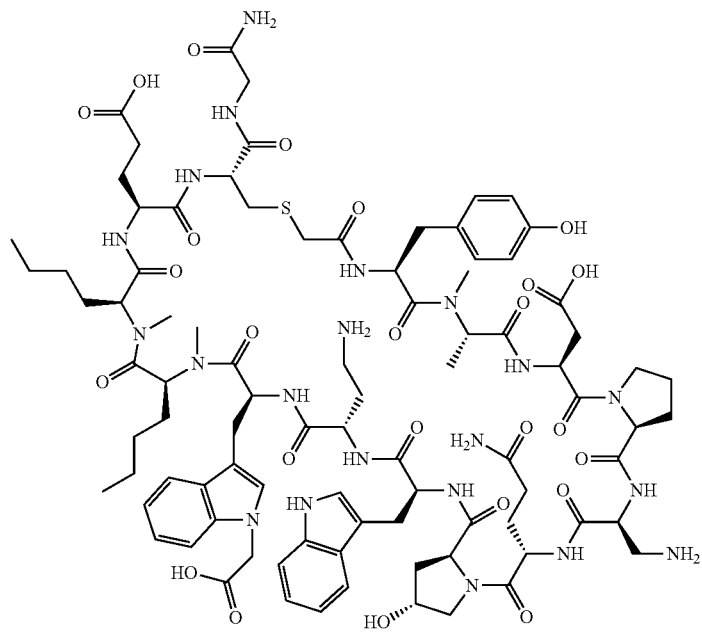

Example 6189 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-40% B over 30 minutes, then a 5-minute hold at 100% B; Flow: 20 mL/min. Fractions containing the desired product were combined and dried via centrifugal evaporation. The yield of the product was 37.4 mg, and its estimated purity by LCMS analysis was 100%.

Analysis condition A: Retention time=1.18 min; ESI-MS (+) m/z 960.5 (M+2H)

Analysis condition B: Retention time=2.33 min; ESI-MS (+) m/z 960.7 (M+2H)

Example 6189

ESI-HRMS(+) m/z: Calculated: 959.9433. Found: 959.9404.

Preparation of Example 6201

Example 6201

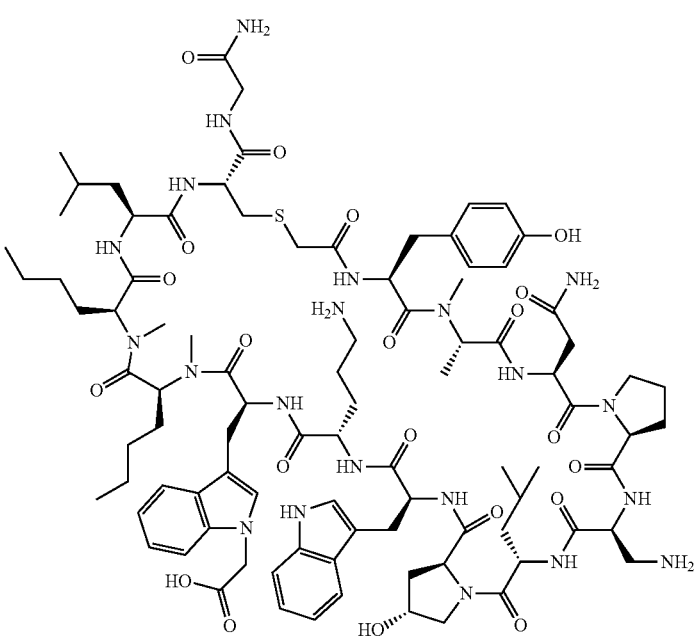

Example 6201 was prepared following "General Synthetic Sequence A". The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 13.7 mg, and its estimated purity by LCMS analysis was 96%.

Analysis condition A: Retention time=1.49 min; ESI-MS (+) m/z 951.6 (M+2H)

Analysis condition B: Retention time=3.06 min; ESI-MS (+) m/z 951.6 (M+2H).

Preparation of Example 6202

Example 6202

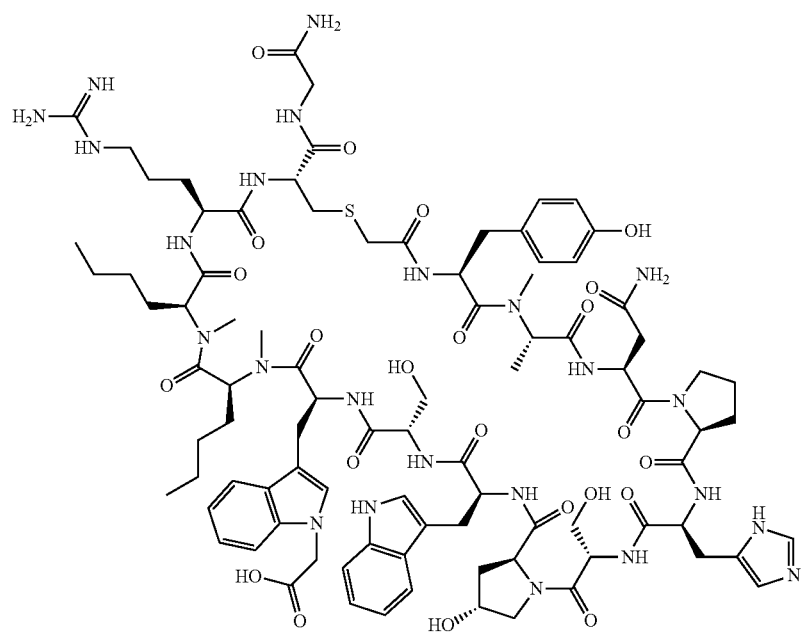

Example 6202 was prepared following "General Synthetic Sequence A". The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 0-40% B over 30 minutes, then a 5-minute hold at 100% B; Flow: 20 mL/min. Fractions containing the desired product were combined and dried via centrifugal evaporation. The yield of the product was 17.1 mg, and its estimated purity by LCMS analysis was 99%.

Analysis condition A: Retention time=1.27 min; ESI-MS (+) m/z 972.3 (M+2H)

Analysis condition B: Retention time=2.44 min; ESI-MS (+) m/z 972.1 (M+2H)

ESI-HRMS(+) m/z: Calculated: 971.4569. Found: 971.4558.

Preparation of Example 6203

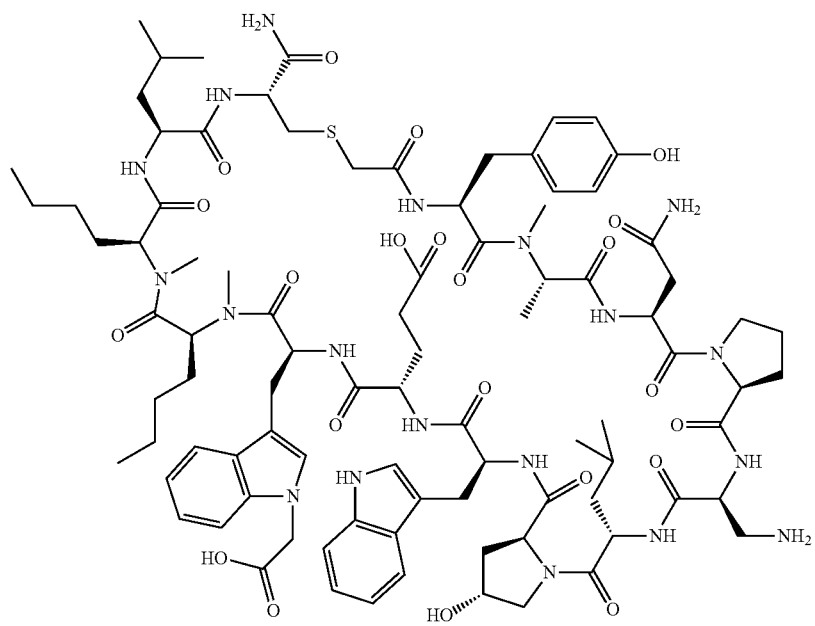

Example 6203

Example 6203 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 20 minutes, then a 5-minute hold at 100% B; Flow: 20 mL/min. Fractions containing the desired product were combined and dried via centrifugal evaporation. The yield of the product was 2.6 mg, and its estimated purity by LCMS analysis was 99%.

Analysis condition A: Retention time=1.39 min; ESI-MS (−) m/z 929.0 (M−2H)

Analysis condition B: Retention time=2.51 min; ESI-MS (+) m/z 931.1 (M+2H)

ESI-HRMS(+) m/z: Calculated: 929.9635. Found: 929.9623.

Preparation of Example 6204

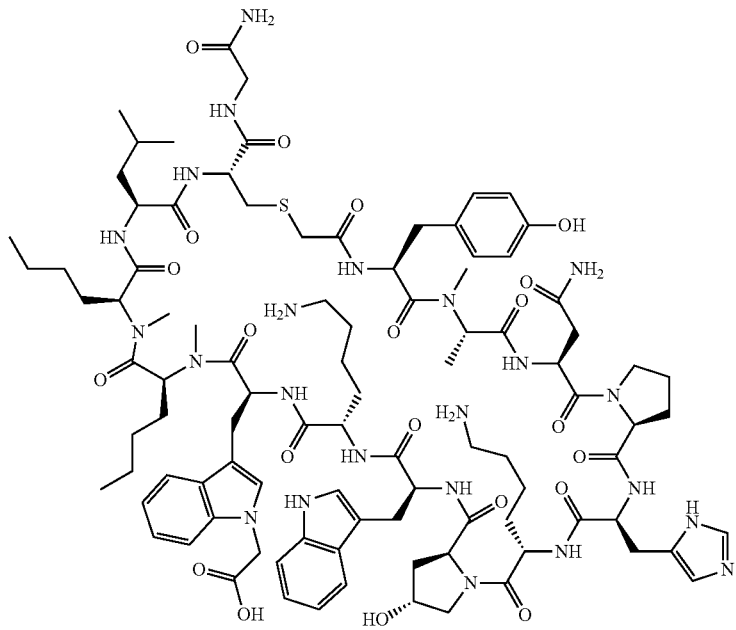

Example 6204

Example 6204 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The material was further purified via preparative LC/MS with the following conditions:

Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 30 minutes, then a 5-minute hold at 100% B; Flow: 20 mL/min. Fractions containing the desired product were combined and dried via centrifugal evaporation. The yield of the product was 4.2 mg, and its estimated purity by LCMS analysis was 100%.

Analysis condition A: Retention time=1.43 min; ESI-MS (+) m/z 991.5 (M+2H)

Analysis condition B: Retention time=2.98 min; ESI-MS (+) m/z 991.5 (M+2H)

ESI-HRMS(+) m/z: Calculated: 991.0113. Found: 991.0095.

Preparation of Example 6207

Example 6207

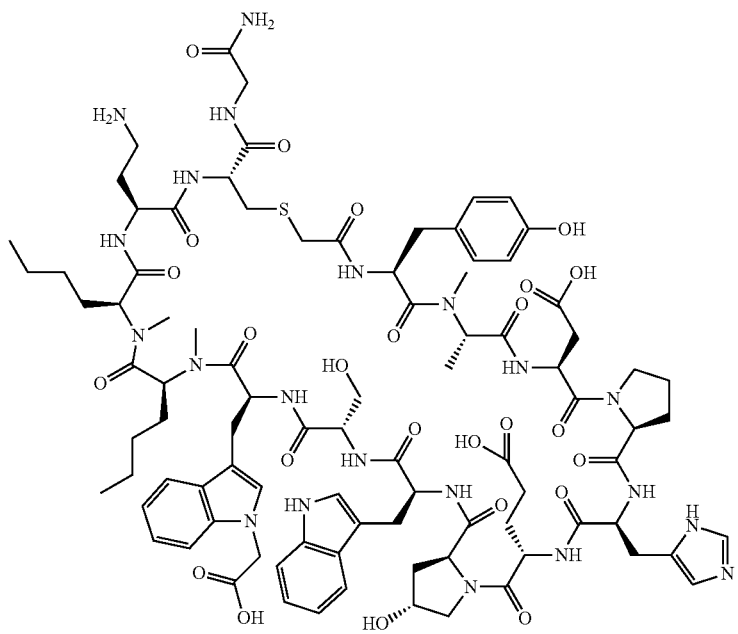

Example 6207 was prepared following "General Synthetic Sequence A". The crude material was purified via preparative LC/MS with the following conditions:

Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 12.2 mg, and its estimated purity by LCMS analysis was 100%.

Analysis condition A: Retention time=1.50 min; ESI-MS (−) m/z 907.7 (M−2H)

Analysis condition B: Retention time=2.71 min; ESI-MS (+) m/z 910.3 (M+2H)

ESI-HRMS(+) m/z: Calculated: 908.9582. Found: 908.9577.

Preparation of Example 6209

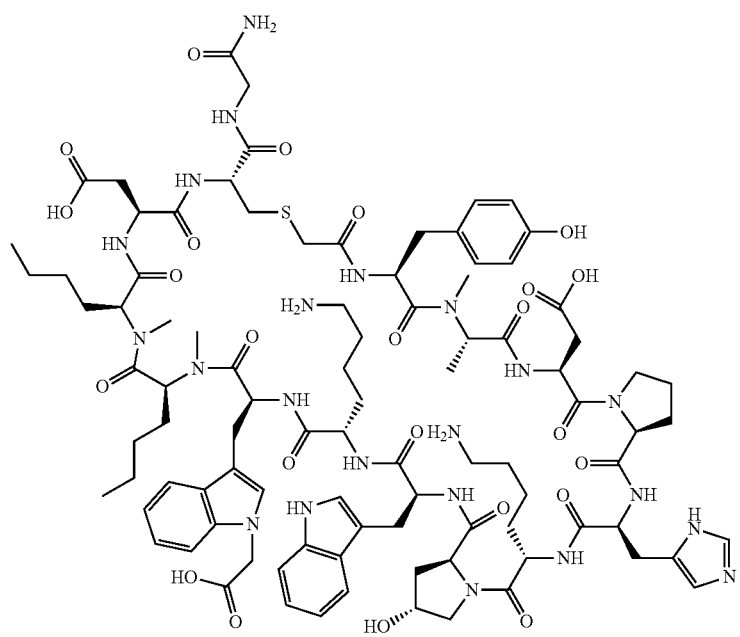

Example 6209

Example 6209 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 15.0 mg, and its estimated purity by LCMS analysis was 100%.

Analysis condition A: Retention time=1.28 min; ESI-MS (+) m/z 992.0 (M+2H)

Analysis condition B: Retention time=2.69 min; ESI-MS (+) m/z 993.0 (M+2H)

ESI-HRMS(+) m/z: Calculated: 992.4747. Found: 992.4713.

Preparation of Example 6213

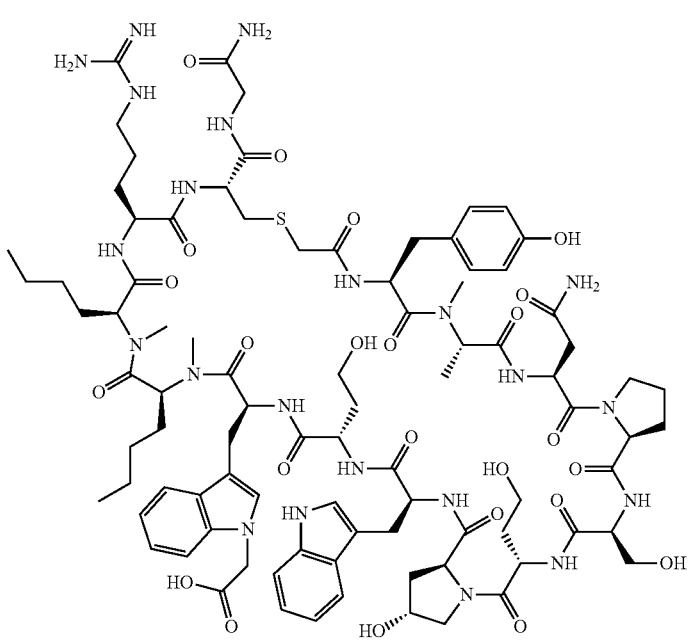

Example 6213

Example 6213 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 12.2 mg, and its estimated purity by LCMS analysis was 96%.

Analysis condition A: Retention time=1.32 min; ESI-MS (−) m/z 959.5 (M−2H)

Analysis condition B: Retention time=2.51 min; ESI-MS (−) m/z 959.8 (M−2H)

ESI-HRMS(+) m/z: Calculated: 960.4591. Found: 960.4585.

Preparation of Example 6216

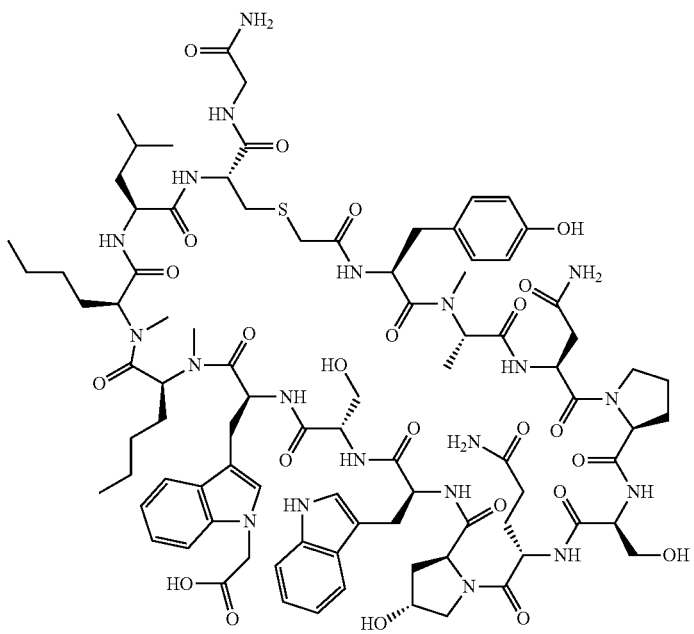

Example 6216

Example 6216 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 4.9 mg, and its estimated purity by LCMS analysis was 98%.

Analysis condition A: Retention time=1.45 min; ESI-MS (+) m/z 945.4 (M+2H)

Analysis condition B: Retention time=2.95 min; ESI-MS (+) m/z 945.6 (M+2H)

ESI-HRMS(+) m/z: Calculated: 945.4482. Found: 945.4472.

Preparation of Example 6224

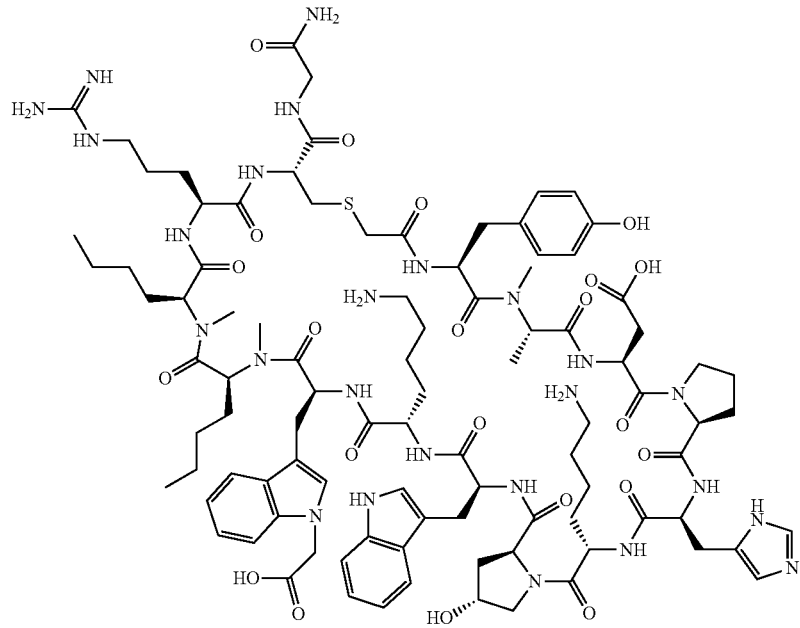

Example 6224

Example 6224 was prepared following "General Synthetic Sequence A". The crude material was purified via preparative LC/MS with the following conditions: Column: waters xbridge c-18, 19×200 mm, 5-μm particles; Mobile Phase A: 5:95 methanol:water with 0.1% trifluoroacetic acid; Mobile Phase B: 95:5 methanol:water with 0.1% trifluoroacetic acid; Gradient: 35-75% B over 30 minutes, then a 5-minute hold at 100% B; Flow: 20 mL/min. Fractions containing the desired product were combined and dried via centrifugal evaporation. The yield of the product was 24.0 mg, and its estimated purity by LCMS analysis was 96%.

Analysis condition A: Retention time=1.29 min; ESI-MS (+) m/z 1013.45 (M+2H)

Analysis condition B: Retention time=0.42 min; ESI-MS (+) m/z 1013.7 (M+2H).

Preparation of Example 6228

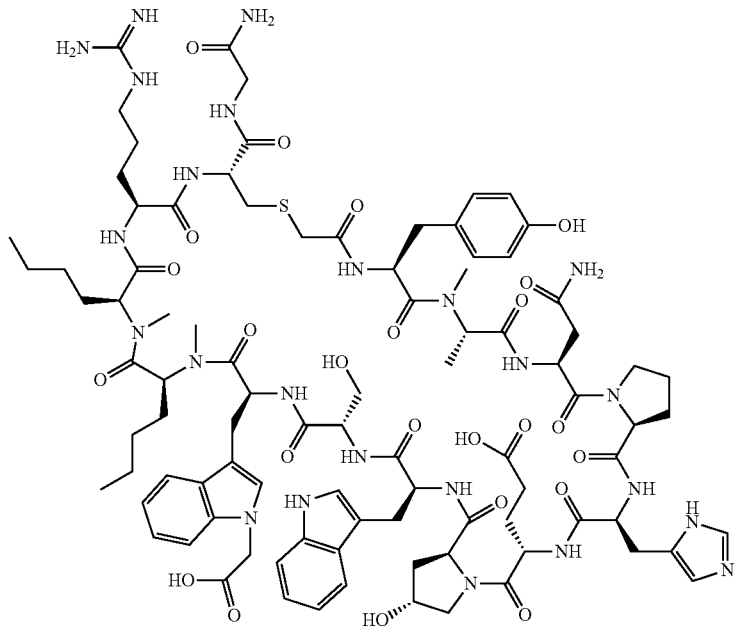

Example 6228

Example 6228 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 20 minutes, then a 5-minute hold at 100% B; Flow: 20 mL/min. Fractions containing the desired product were combined and dried via centrifugal evaporation. The yield of the product was 8.0 mg, and its estimated purity by LCMS analysis was 99%.

Analysis condition A: Retention time=1.34 min; ESI-MS (+) m/z 992.6 (M+2H)

Analysis condition B: Retention time=1.85 min; ESI-MS (+) m/z 992.7 (M+2H)

ESI-HRMS(+) m/z: Calculated: 992.4622. Found: 992.4599.

Preparation of Example 6236

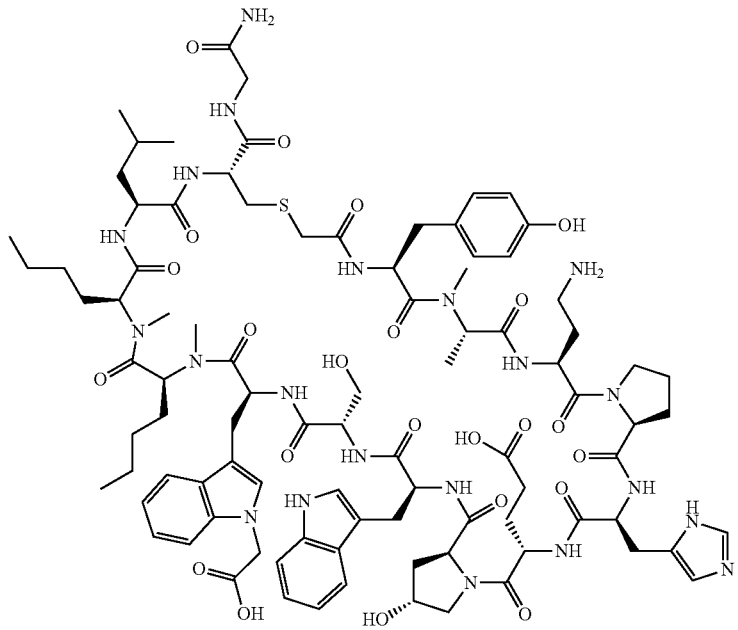

Example 6236

Example 6236 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 8.5 mg, and its estimated purity by LCMS analysis was 99%.

Analysis condition A: Retention time=1.42 min; ESI-MS (+) m/z 962.4 (M+2H)

Analysis condition B: Retention time=2.92 min; ESI-MS (+) m/z 964.5 (M+2H)

ESI-HRMS(+) m/z: Calculated: 963.964. Found: 963.9611.

Preparation of Example 6244

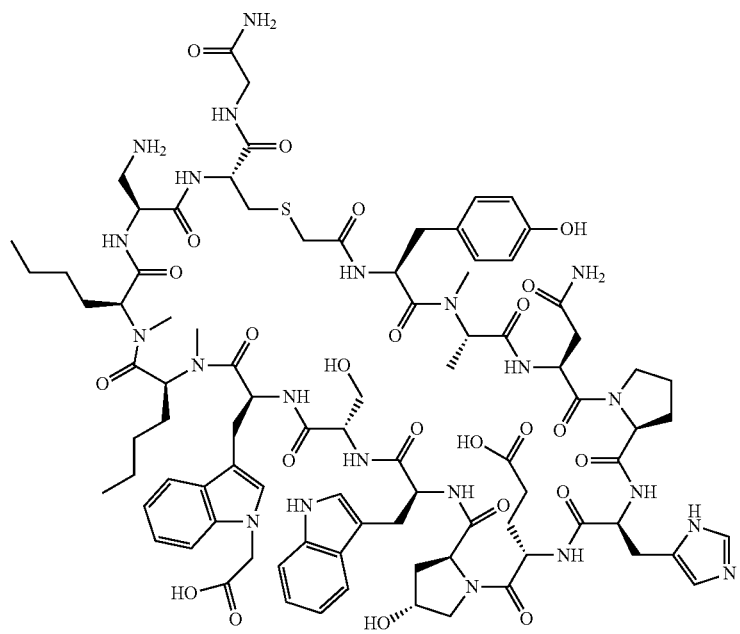

Example 6244

Example 6244 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 10.0 mg, and its estimated purity by LCMS analysis was 100%.

Analysis condition A: Retention time=1.35 min; ESI-MS (+) m/z 957.6 (M+2H)

Analysis condition B: Retention time=2.82 min; ESI-MS (+) m/z 957.8 (M+2H)

ESI-HRMS(+) m/z: Calculated: 957.4356. Found: 957.4328.

Preparation of Example 6247

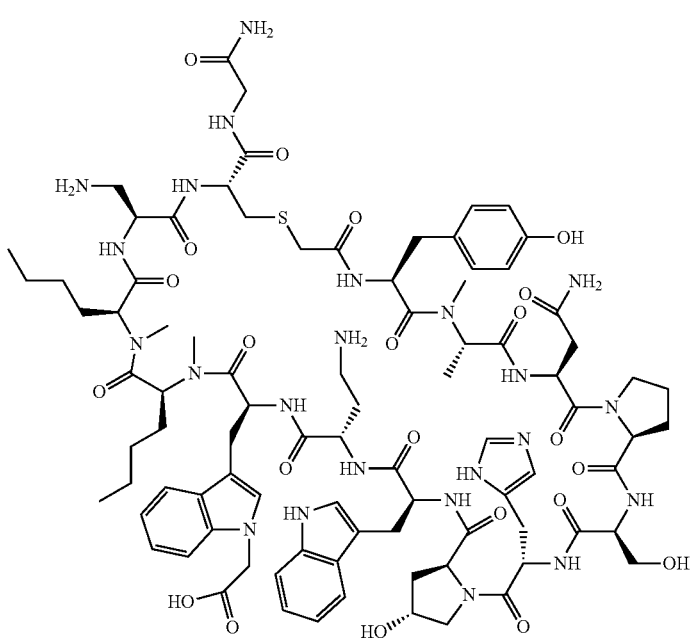

Example 6247

Example 6247 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 8.8 mg, and its estimated purity by LCMS analysis was 100%.

Analysis condition A: Retention time=1.34 min; ESI-MS (+) m/z 943.0 (M+2H)

Analysis condition B: Retention time=1.89 min; ESI-MS (+) m/z 942.9 (M+2H)

ESI-HRMS(+) m/z: Calculated: 942.9461. Found: 942.9426.

Preparation of Example 6249

Example 6249

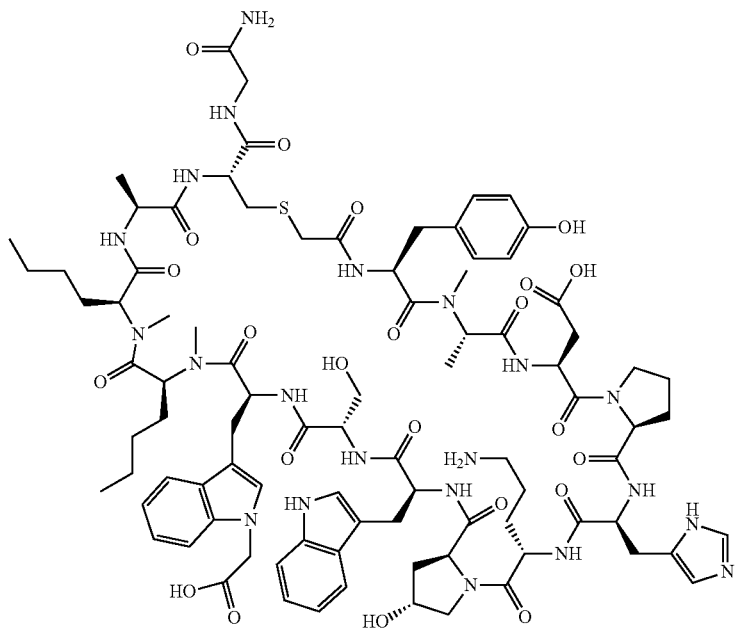

Example 6249 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 8.6 mg, and its estimated purity by LCMS analysis was 99%.

Analysis condition A: Retention time=1.36 min; ESI-MS (+) m/z 943.4 (M+2H)

Analysis condition B: Retention time=2.82 min; ESI-MS (+) m/z 943.4 (M+2H)

ESI-HRMS(+) m/z: Calculated: 942.9405. Found: 942.9378.

Preparation of Example 6250

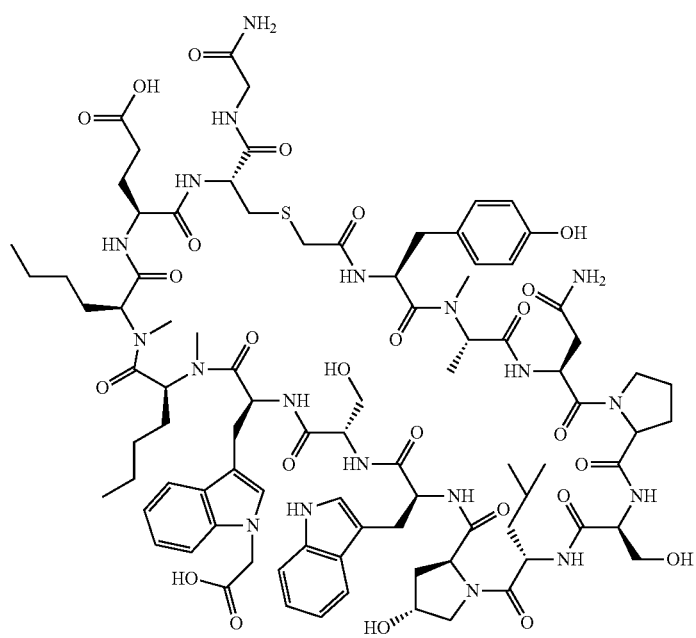

Example 6250

Example 6250 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 30-70% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-40% B over 30 minutes, then a 5-minute hold at 100% B; Flow: 20 mL/min. Fractions containing the desired product were combined and dried via centrifugal evaporation. The yield of the product was 11.2 mg, and its estimated purity by LCMS analysis was 100%.

Analysis condition A: Retention time=1.24 min; ESI-MS (+) m/z 946.1 (M+2H)

Analysis condition B: Retention time=2.61 min; ESI-MS (+) m/z 946.1 (M+2H)

ESI-HRMS(+) m/z: Calculated: 945.9402. Found: 945.9386.

Preparation of Example 6258

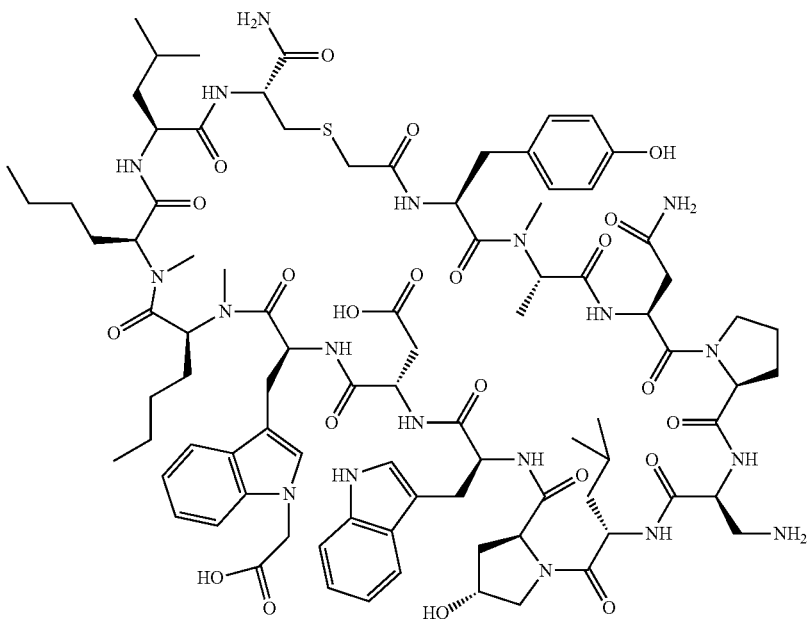

Example 6258

Example 6258 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 2.2 mg, and its estimated purity by LCMS analysis was 93%.

Analysis condition A: Retention time=1.44 min; ESI-MS (+) m/z 922.8 (M+2H)

Analysis condition B: Retention time=2.93 min; ESI-MS (+) m/z 923.1 (M+2H)

ESI-HRMS(+) m/z: Calculated: 922.9556. Found: 922.9537.

Preparation of Example 6262

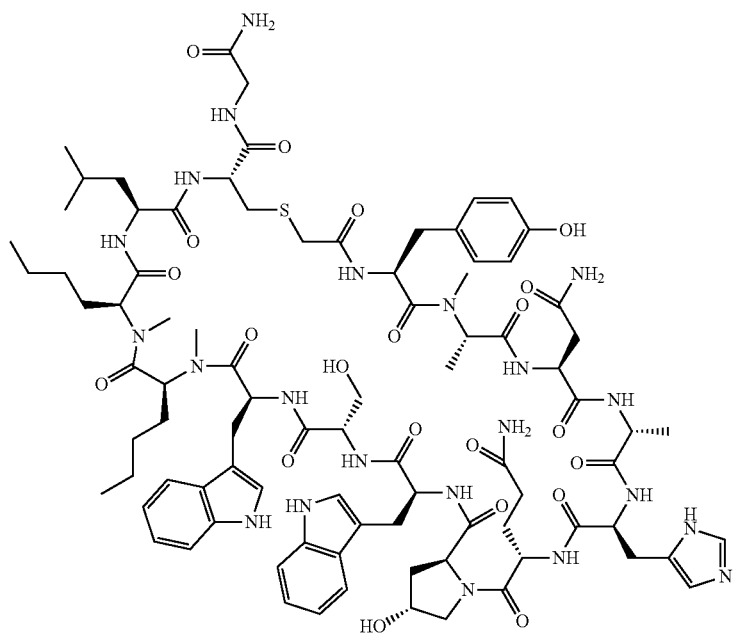

Example 6262

Example 6262 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 25.9 mg, and its estimated purity by LCMS analysis was 96%.

Analysis condition A: Retention time=1.47 min; ESI-MS (+) m/z 928.7 (M+2H)

Analysis condition B: Retention time=2.74 min; ESI-MS (+) m/z 928.7 (M+2H)

ESI-HRMS(+) m/z: Calculated: 928.4511. Found: 928.4479.

Preparation of Example 6266

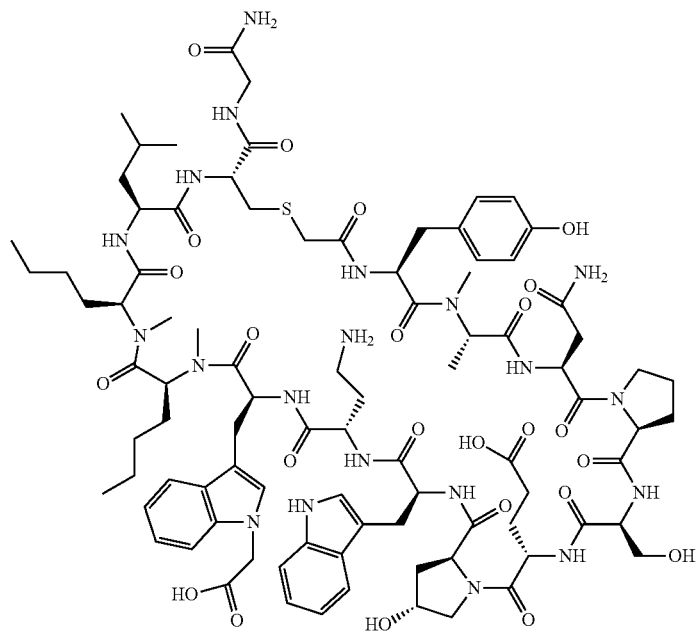

Example 6266

Example 6266 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 12.5 mg, and its estimated purity by LCMS analysis was 96%.

Analysis condition A: Retention time=1.49 min; ESI-MS (+) m/z 952.9 (M+2H)

Analysis condition B: Retention time=3.09 min; ESI-MS (+) m/z 952.7 (M+2H)

ESI-HRMS(+) m/z: Calculated: 952.456. Found: 952.4541.

Preparation of Example 6267

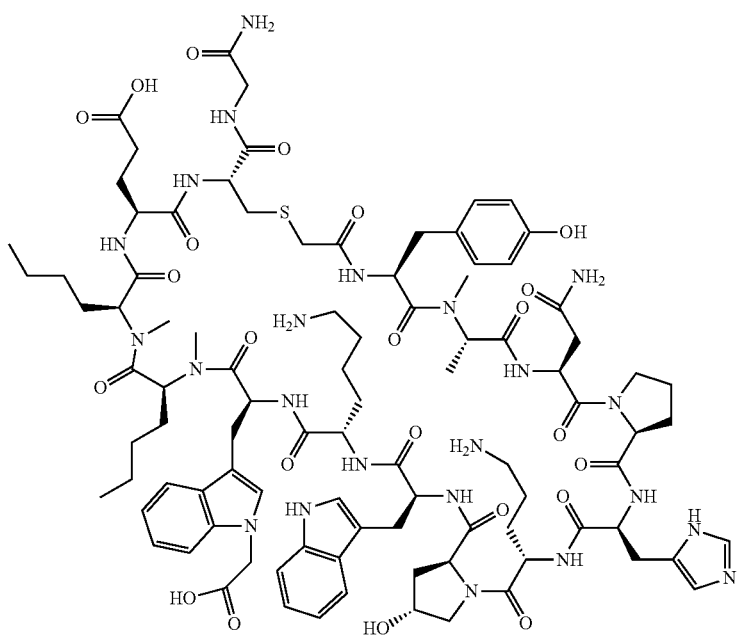

Example 6267

Example 6267 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-40% B over 20 minutes, then a 5-minute hold at 100% B; Flow: 20 mL/min. Fractions containing the desired product were combined and dried via centrifugal evaporation. The yield of the product was 20.0 mg, and its estimated purity by LCMS analysis was 100%.

Analysis condition A: Retention time=1.26 min; ESI-MS (+) m/z 992.7 (M+2H)

Analysis condition B: Retention time=2.75 min; ESI-MS (+) m/z 992.7 (M+2H).

Preparation of Example 6269

Example 6269

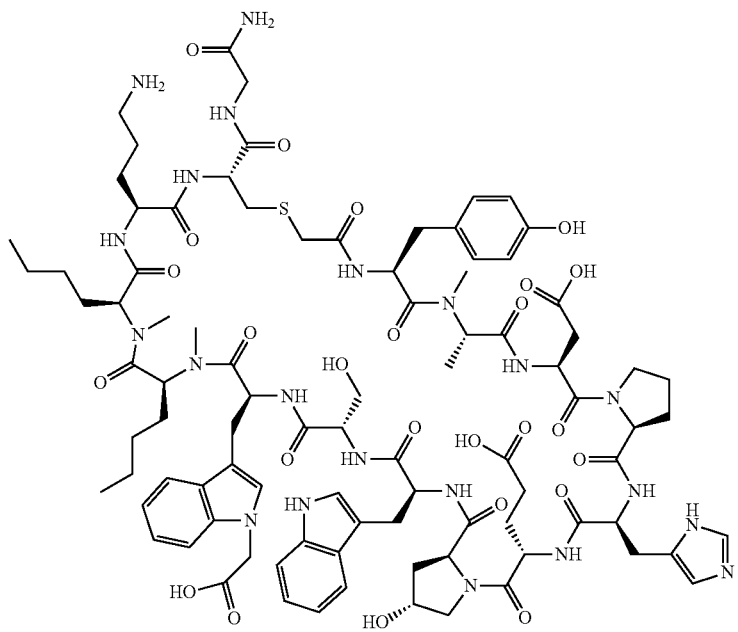

Example 6269 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 30-70% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 6.2 mg, and its estimated purity by LCMS analysis was 100%.

Analysis condition A: Retention time=1.19 min; ESI-MS (+) m/z 972.9 (M+2H)

Analysis condition B: Retention time=2.32 min; ESI-MS (+) m/z 972.7 (M+2H)

ESI-HRMS(+) m/z: Calculated: 971.9433. Found: 971.9421.

Preparation of Example 6272

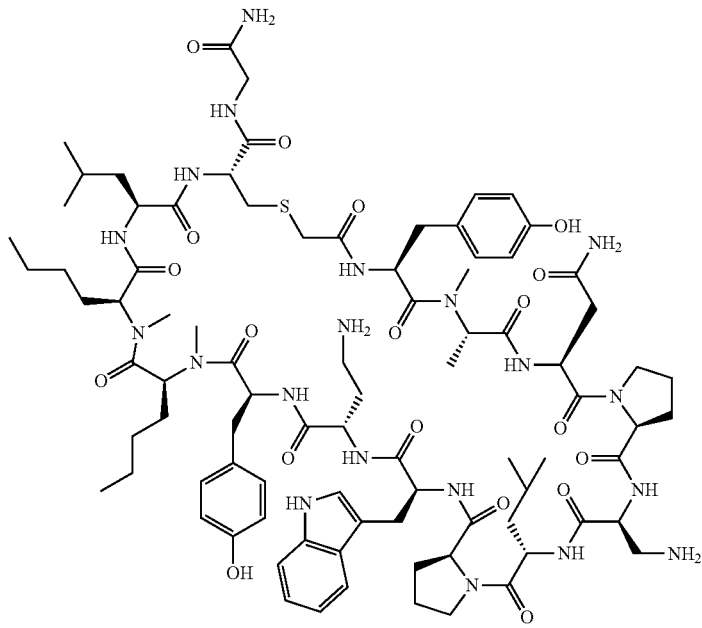

Example 6272

Example 6272 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 14.7 mg, and its estimated purity by LCMS analysis was 97%.

Analysis condition A: Retention time=1.47 min; ESI-MS (+) m/z 896.1 (M+2H)

Analysis condition B: Retention time=2.63 min; ESI-MS (+) m/z 896.1 (M+2H)

ESI-HRMS(+) m/z: Calculated: 895.4765. Found: 895.4740.

Preparation of Example 6274

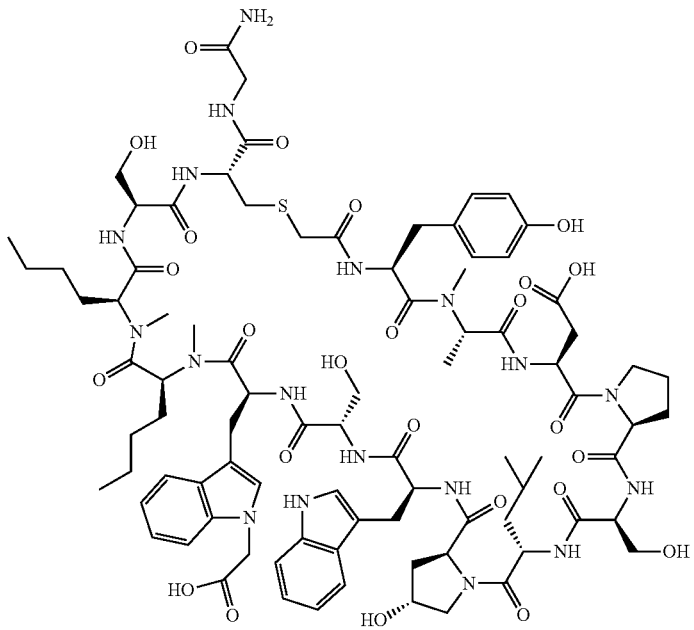

Example 6274

Example 6274 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 20.0 mg, and its estimated purity by LCMS analysis was 100%.

Analysis condition A: Retention time=1.29 min; ESI-MS (+) m/z 925.5 (M+2H)

Analysis condition B: Retention time=2.68 min; ESI-MS (+) m/z 925.9 (M+2H)

ESI-HRMS(+) m/z: Calculated: 925.4269. Found: 925.4266.

Preparation of Example 6276

Example 6276 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-40% B over 30 minutes, then a 5-minute hold at 100% B; Flow: 20 mL/min. Fractions containing the desired product were combined and dried via centrifugal evaporation. The yield of the product was 12.5 mg, and its estimated purity by LCMS analysis was 100%.

Analysis condition A: Retention time=1.29 min; ESI-MS (−) m/z 970.9 (M−2H)

Analysis condition B: Retention time=1.55 min; ESI-MS (+) m/z 972.5 (M+2H)

ESI-HRMS(+) m/z: Calculated: 971.4456. Found: 971.4445.

Example 6276

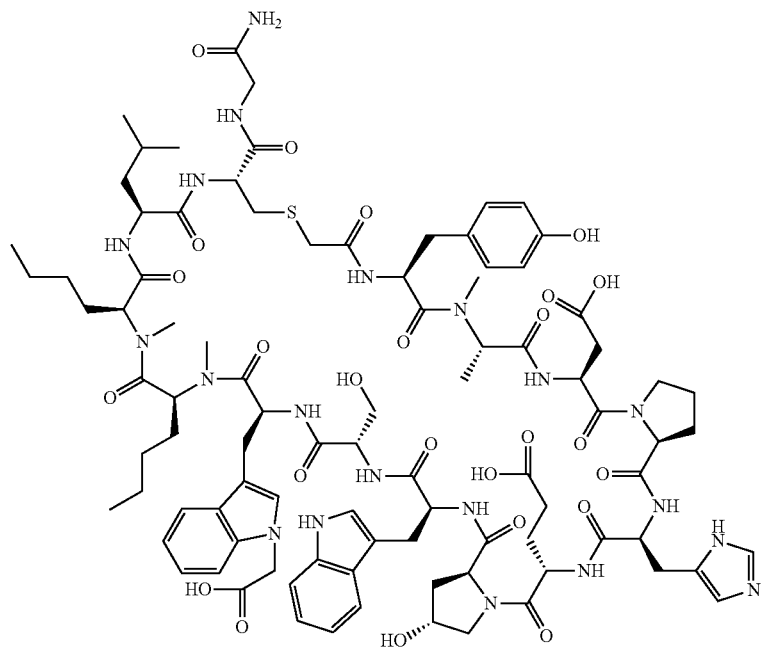

Preparation of Example 6283

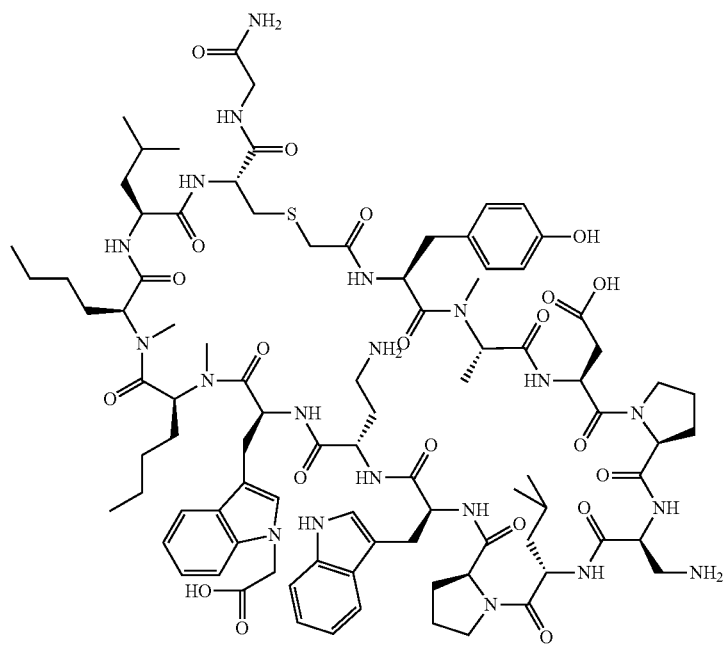

Example 6283

Example 6283 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 10.3 mg, and its estimated purity by LCMS analysis was 99%.

Analysis condition B: Retention time=3.22 min; ESI-MS (+) m/z 936.1 (M+2H)

Analysis condition C: Retention time=1.63 min; ESI-MS (+) m/z 935.9 (M+2H)

ESI-HRMS(+) m/z: Calculated: 935.9873. Found: 935.9857.

Preparation of Example 6284

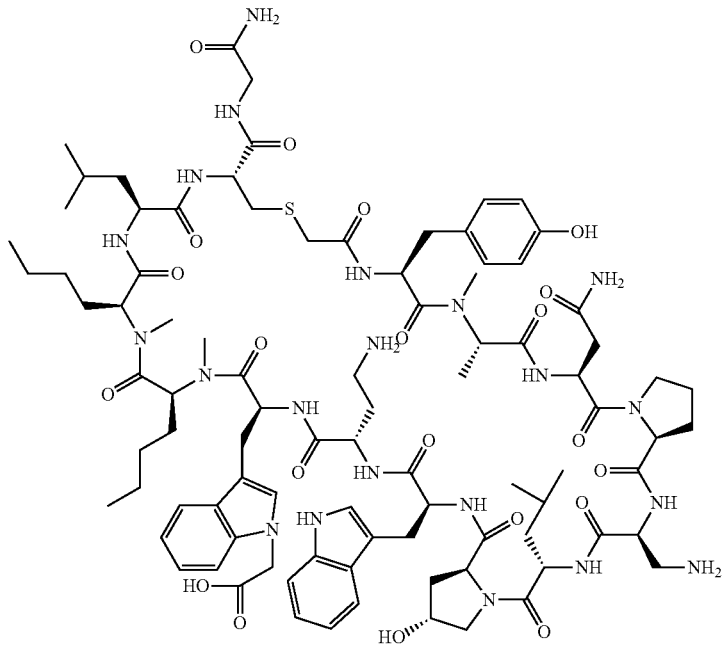

Example 6284

Example 6284 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 30 minutes, then a 5-minute hold at 100% B; Flow: 20 mL/min. Fractions containing the desired product were combined and dried via centrifugal evaporation. The yield of the product was 18.3 mg, and its estimated purity by LCMS analysis was 98%.

Analysis condition A: Retention time=1.55 min; ESI-MS (+) m/z 958.3 (M+2H)

Analysis condition B: Retention time=2.22 min; ESI-MS (+) m/z 958.2 (M+2H)

ESI-HRMS(+) m/z: Calculated: 957.9822. Found: 957.9801.

Preparation of Example 6288

Example 6288

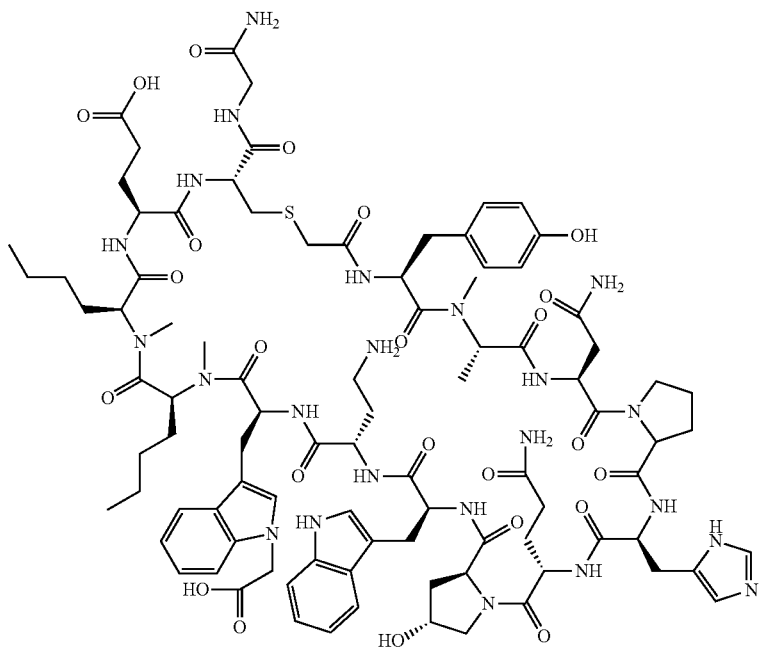

Example 6288 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 30-70% B over 30 minutes, then a 5-minute hold at 100% B; Flow: 20 mL/min. Fractions containing the desired product were combined and dried via centrifugal evaporation. The yield of the product was 8.2 mg, and its estimated purity by LCMS analysis was 100%.

Analysis condition A: Retention time=1.24 min; ESI-MS (+) m/z 985.2 (M+2H)

Analysis condition B: Retention time=1.80 min; ESI-MS (+) m/z 985.1 (M+2H)

ESI-HRMS(+) m/z: Calculated: 984.9567. Found: 984.9557.

Preparation of Example 6289

Example 6289

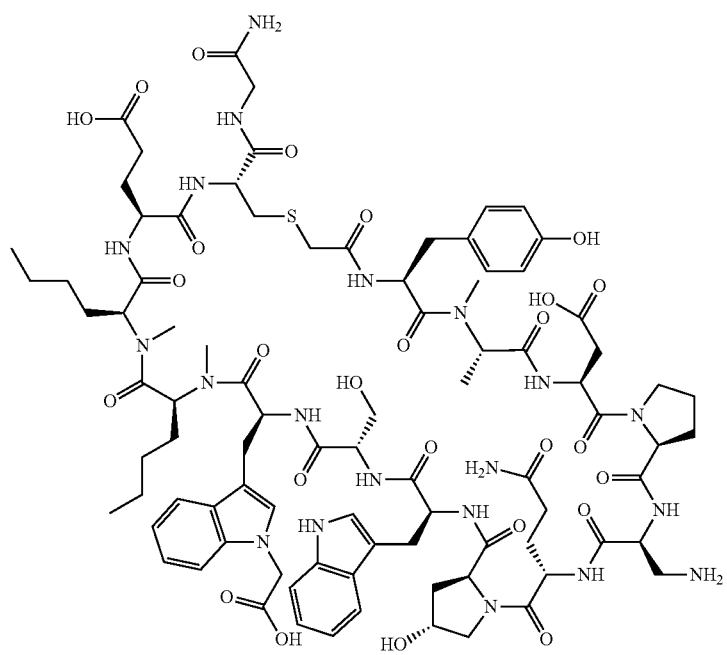

Example 6289 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 30-70% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 12.1 mg, and its estimated purity by LCMS analysis was 100%.

Analysis condition A: Retention time=1.24 min; ESI-MS (+) m/z 953.9 (M+2H)

Analysis condition B: Retention time=2.57 min; ESI-MS (+) m/z 953.9 (M+2H)

ESI-HRMS(+) m/z: Calculated: 953.4274. Found: 953.4251.

Preparation of Example 6293

Example 6293

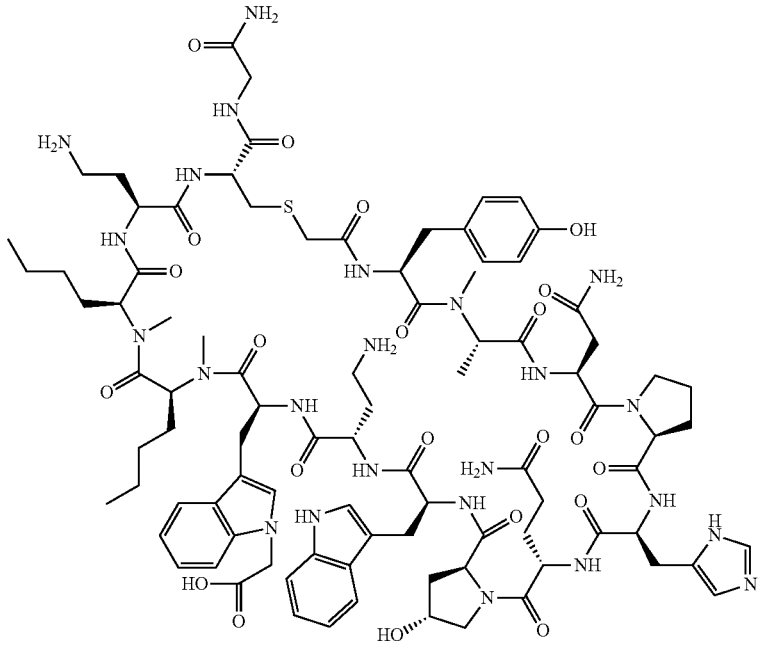

Example 6293 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 10.7 mg, and its estimated purity by LCMS analysis was 100%.

Analysis condition A: Retention time=1.30 min; ESI-MS (+) m/z 971.0 (M+2H)

Analysis condition B: Retention time=2.74 min; ESI-MS (+) m/z 971.0 (M+2H)

ESI-HRMS(+) m/z: Calculated: 970.4672. Found: 970.4643.

Preparation of Example 6296

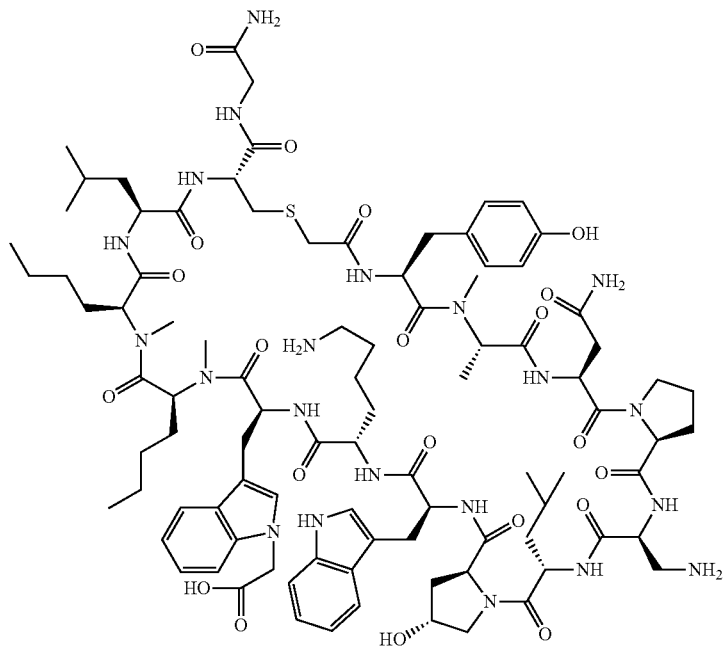

Example 6296

Example 6296 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 15.0 mg, and its estimated purity by LCMS analysis was 95%.

Analysis condition A: Retention time=1.46 min; ESI-MS (+) m/z 958.5 (M+2H)

Analysis condition B: Retention time=3.01 min; ESI-MS (+) m/z 958.5 (M+2H)

ESI-HRMS(+) m/z: Calculated: 958.0004. Found: 957.9994.

Preparation of Example 6297

Example 6297

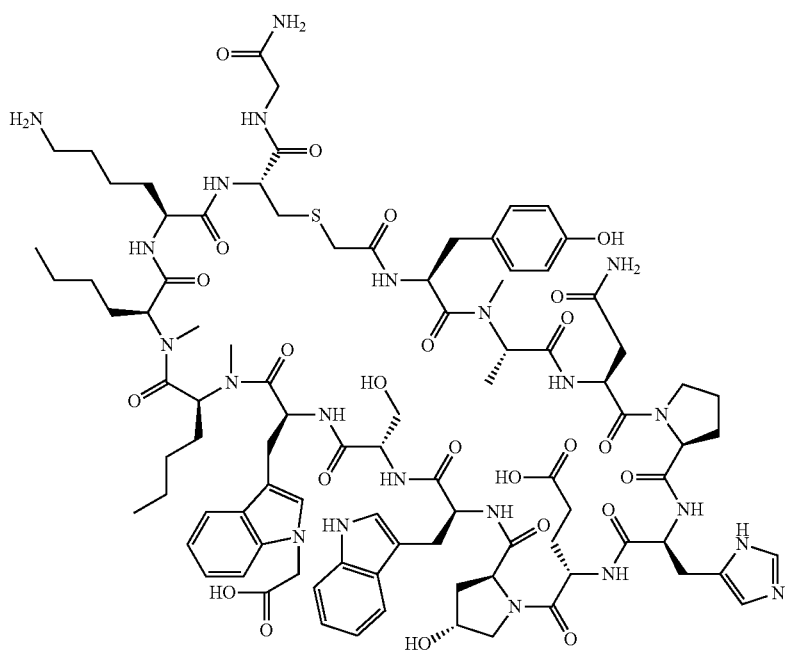

Example 6297 was prepared following "General Synthetic Sequence A". The crude material was purified via preparative LC/MS with the following conditions: Column: XBridge C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 10.7 mg, and its estimated purity by LCMS analysis was 100%.

Analysis condition A: Retention time=1.32 min; ESI-MS (+) m/z 978.9 (M+2H)

Analysis condition B: Retention time=2.77 min; ESI-MS (+) m/z 978.9 (M+2H)

ESI-HRMS(+) m/z: Calculated: 978.4591. Found: 978.4570.

Preparation of Example 6301

Example 6301

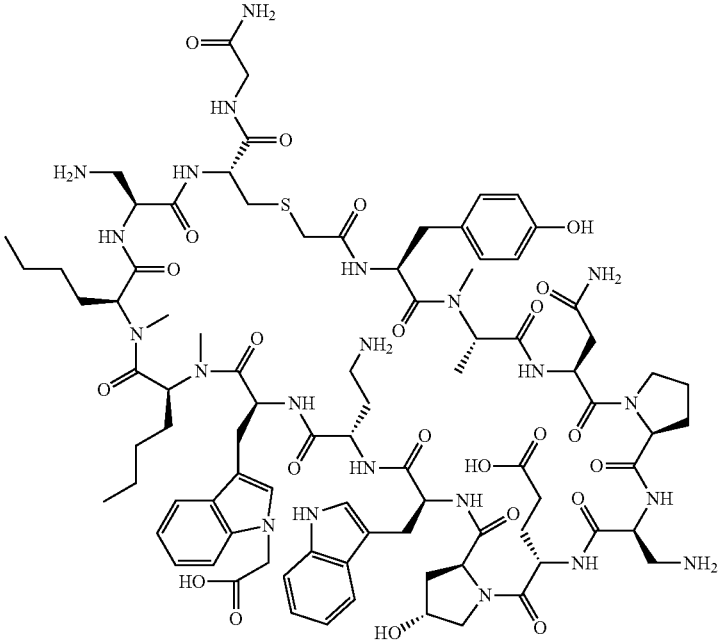

Example 6301 was prepared following "General Synthetic Sequence A". The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 30 minutes, then a 5-minute hold at 100% B; Flow: 20 mL/min. Fractions containing the desired product were combined and dried via centrifugal evaporation. The yield of the product was 38.9 mg, and its estimated purity by LCMS analysis was 100%.

Analysis condition A: Retention time=1.34 min; ESI-MS (+) m/z 938.9 (M+2H)

Analysis condition B: Retention time=2.84 min; ESI-MS (+) m/z 938.8 (M+2H)

ESI-HRMS(+) m/z: Calculated: 938.446. Found: 938.4450.

Preparation of Example 6303

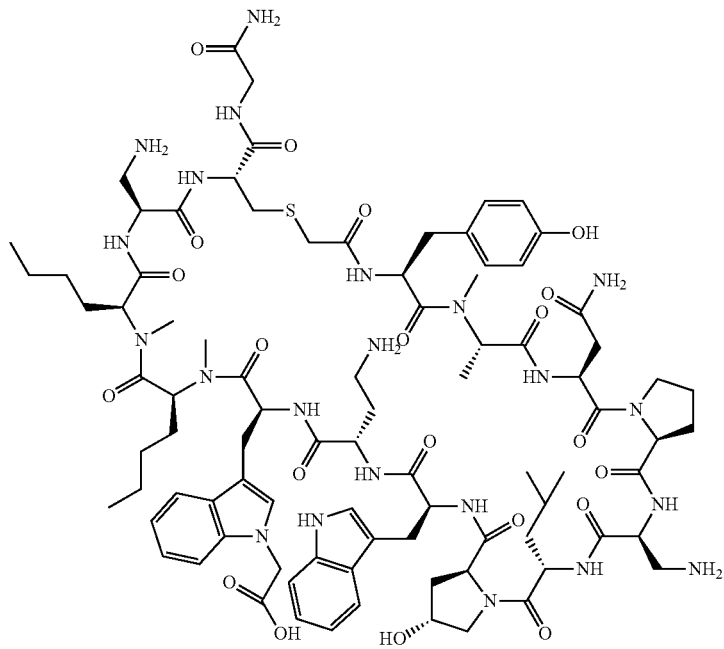

Example 6303

Example 6303 was prepared following "General Synthetic Sequence A". The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 7.4 mg, and its estimated purity by LCMS analysis was 100%.

Analysis condition A: Retention time=1.34 min; ESI-MS (+) m/z 930.9 (M+2H)

Analysis condition B: Retention time=2.85 min; ESI-MS (+) m/z 930.9 (M+2H)

ESI-HRMS(+) m/z: Calculated: 930.4667. Found: 930.4644.

Preparation of Example 6309

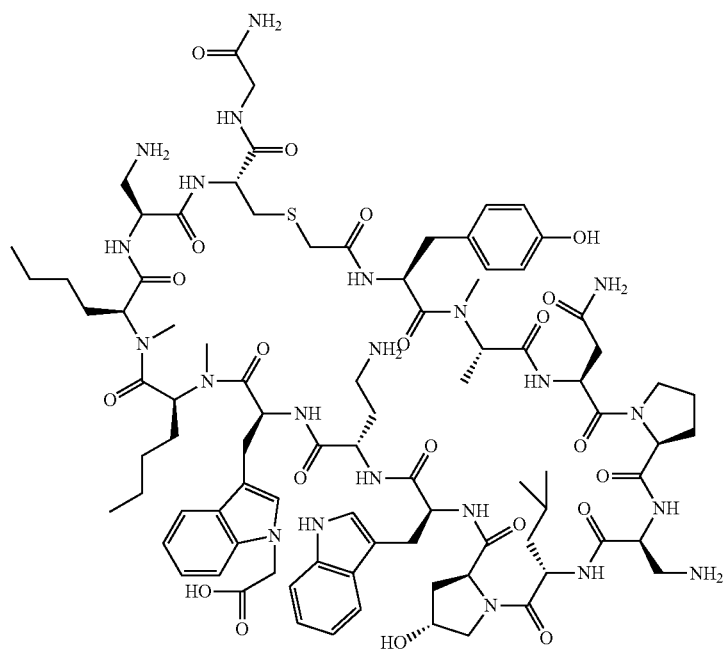

Example 6309

Example 6309 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 11.0 mg, and its estimated purity by LCMS analysis was 100%.

Analysis condition A: Retention time=1.39 min; ESI-MS (+) m/z 924.1 (M+2H)

Analysis condition B: Retention time=2.91 min; ESI-MS (+) m/z 924.1 (M+2H)

ESI-HRMS(+) m/z: Calculated: 923.9509. Found: 923.9473.

Preparation of Example 6310

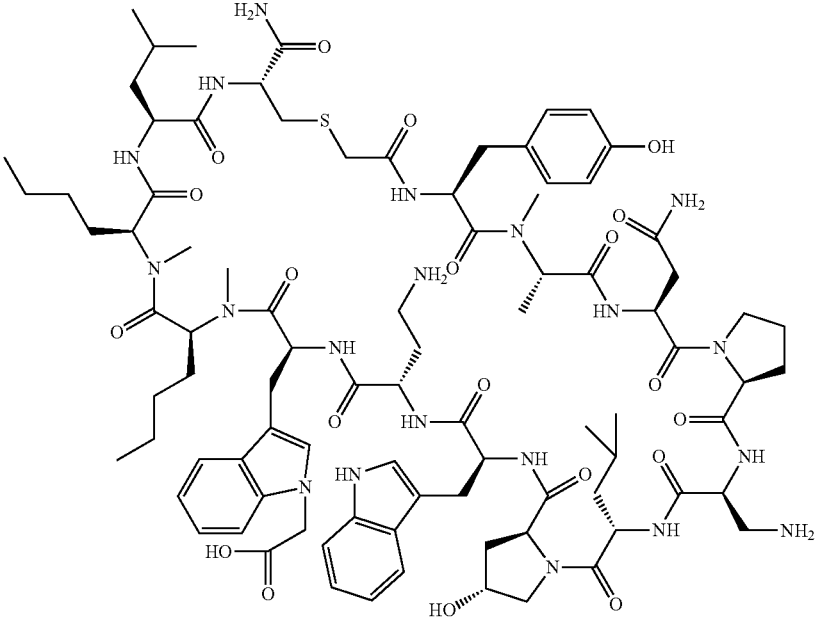

Example 6310

Example 6310 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 20 minutes, then a 5-minute hold at 100% B; Flow: 20 mL/min. Fractions containing the desired product were combined and dried via centrifugal evaporation. The yield of the product was 10.7 mg, and its estimated purity by LCMS analysis was 94%.

Analysis condition A: Retention time=1.54 min; ESI-MS (+) m/z 916.7 (M+2H)

Analysis condition B: Retention time=2.82 min; ESI-MS (+) m/z 916.5 (M+2H)

ESI-HRMS(+) m/z: Calculated: 915.474. Found: 915.4721.

Preparation of Example 6324

Example 6324

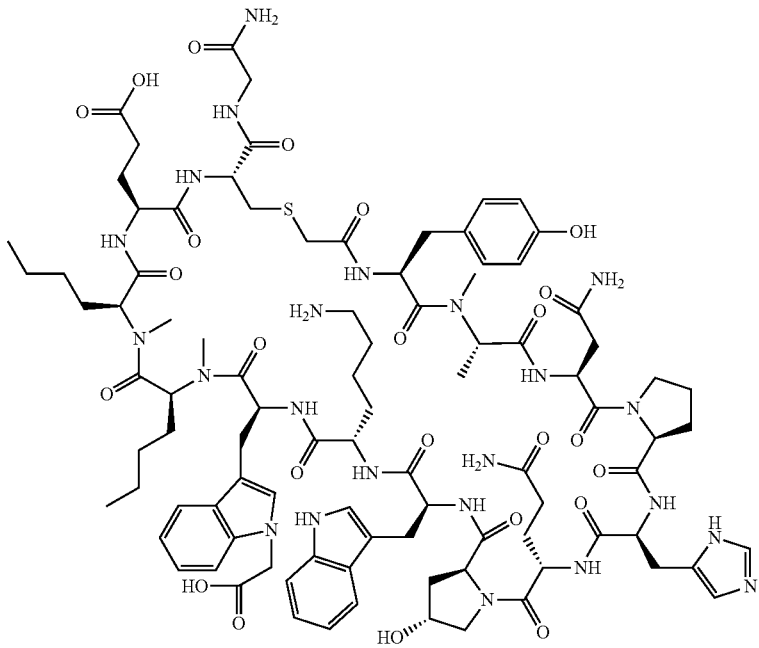

Example 6324 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-40% B over 30 minutes, then a 5-minute hold at 100% B; Flow: 20 mL/min. Fractions containing the desired product were combined and dried via centrifugal evaporation. The yield of the product was 13.4 mg, and its estimated purity by LCMS analysis was 100%.

Analysis condition A: Retention time=1.24 min; ESI-MS (+) m/z 1000.0 (M+2H)

Analysis condition B: Retention time=2.69 min; ESI-MS (+) m/z 999.2 (M+2H).

Preparation of Example 6331

Example 6331

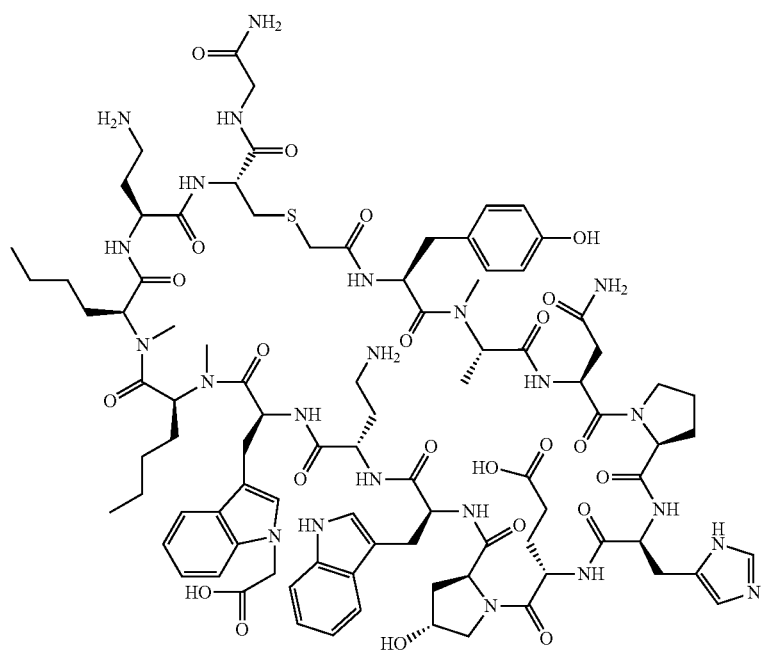

Example 6331 was prepared following "General Synthetic Sequence A". The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 12.0 mg, and its estimated purity by LCMS analysis was 100%.

Analysis condition A: Retention time=1.32 min; ESI-MS (+) m/z 971.2 (M+2H)

Analysis condition B: Retention time=2.89 min; ESI-MS (+) m/z 971.2 (M+2H)

ESI-HRMS(+) m/z: Calculated: 970.9592. Found: 970.9561.

Preparation of Example 6334

Example 6334

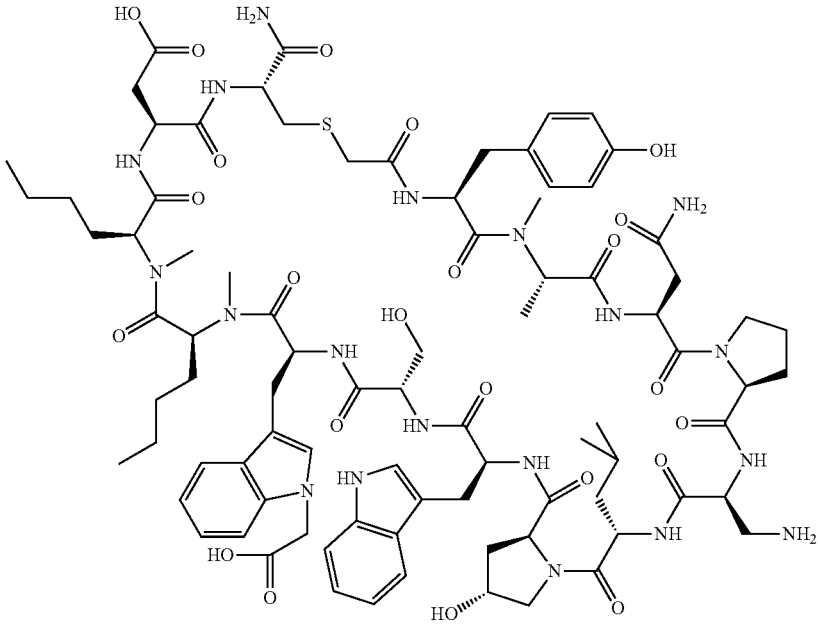

Example 6334 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-40% B over 30 minutes, then a 5-minute hold at 100% B; Flow: 20 mL/min. Fractions containing the desired product were combined and dried via centrifugal evaporation. The yield of the product was 16.8 mg, and its estimated purity by LCMS analysis was 99%.

Analysis condition A: Retention time=1.32 min; ESI-MS (+) m/z 910.2 (M+2H)

Analysis condition B: Retention time=2.77 min; ESI-MS (+) m/z 910.3 (M+2H)

ESI-HRMS(+) m/z: Calculated: 909.9296. Found: 909.9284.

Preparation of Example 6335

Example 6335

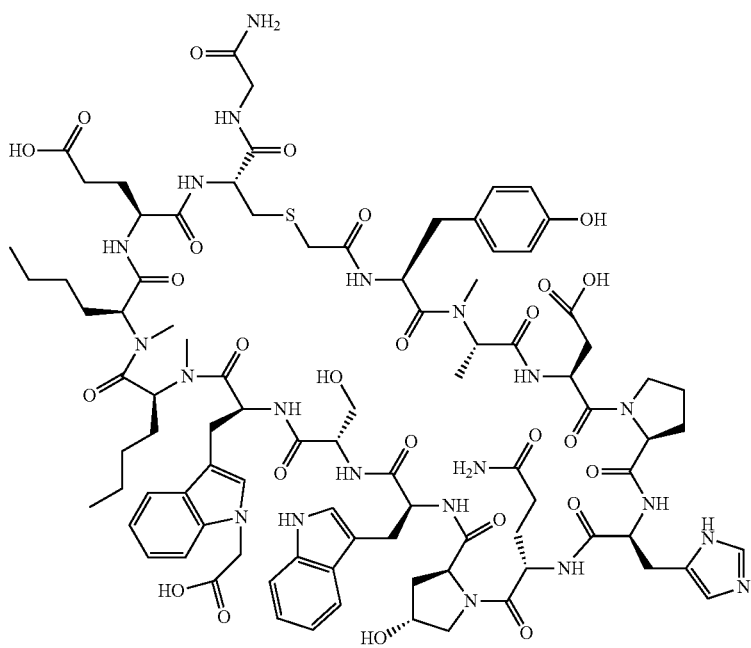

Example 6335 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 25-70% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-45% B over 30 minutes, then a 5-minute hold at 100% B; Flow: 20 mL/min. Fractions containing the desired product were combined and dried via centrifugal evaporation. The yield of the product was 10.3 mg, and its estimated purity by LCMS analysis was 100%.

Analysis condition A: Retention time=1.19 min; ESI-MS (+) m/z 979.4 (M+2H)

Analysis condition B: Retention time=2.50 min; ESI-MS (+) m/z 979.4 (M+2H).

Preparation of Example 6338

Example 6338

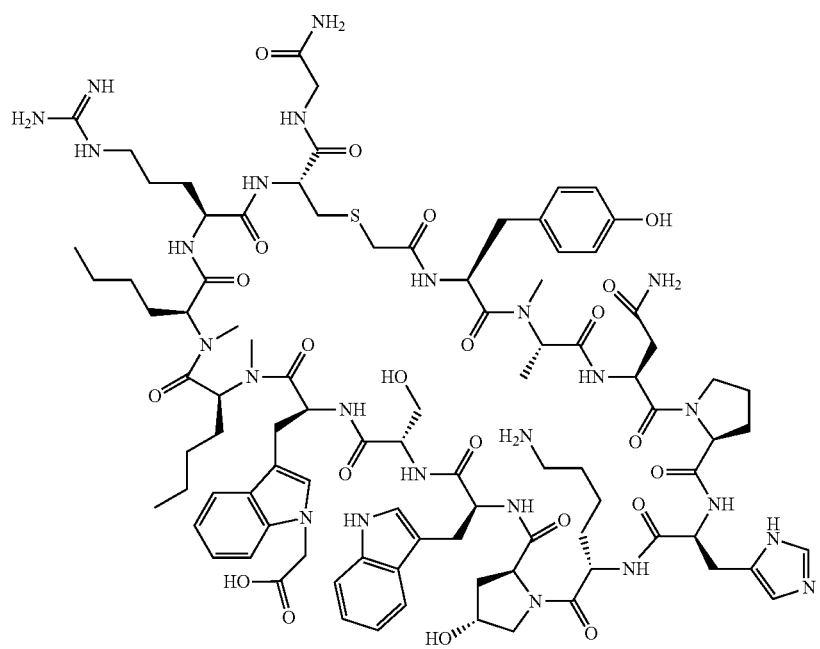

Example 6338 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 5.8 mg, and its estimated purity by LCMS analysis was 100%.

Analysis condition A: Retention time=1.33 min; ESI-MS (+) m/z 992.5 (M+2H)

Analysis condition B: Retention time=2.78 min; ESI-MS (+) m/z 992.5 (M+2H)

ESI-HRMS(+) m/z: Calculated: 991.9883. Found: 991.9861.

Preparation of Example 6344

Example 6344

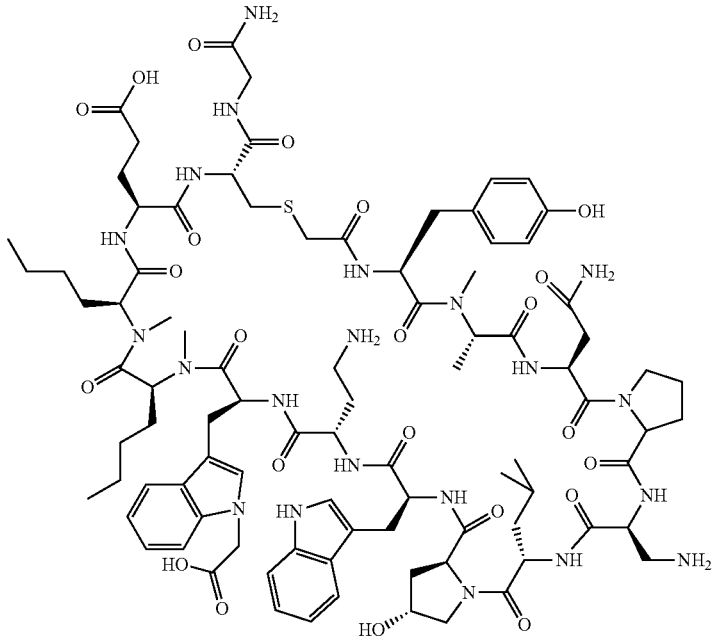

Example 6344 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 9.1 mg, and its estimated purity by LCMS analysis was 100%.

Analysis condition A: Retention time=1.47 min; ESI-MS (+) m/z 952.7 (M+2H)

Analysis condition B: Retention time=2.37 min; ESI-MS (+) m/z 952.6 (M+2H)

ESI-HRMS(+) m/z: Calculated: 951.964. Found: 951.9612.

Preparation of Example 6347

Example 6347

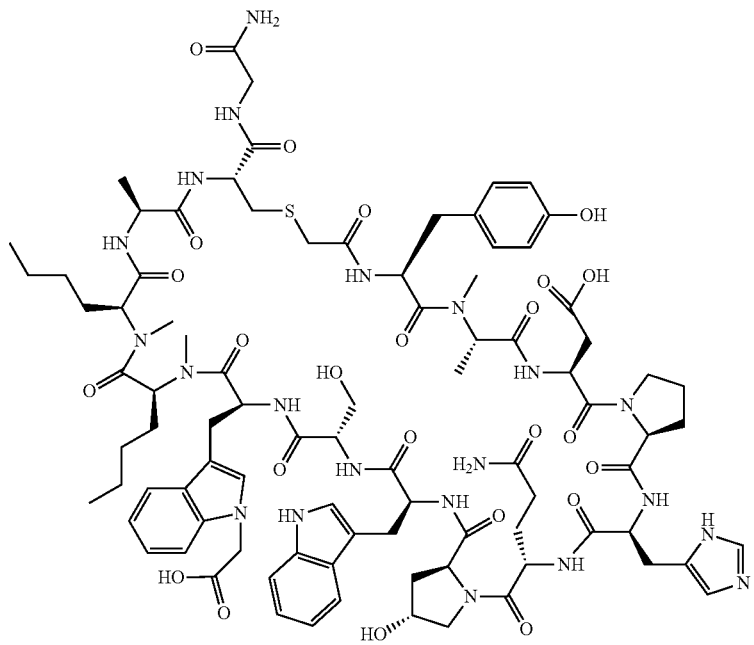

Example 6347 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 30-70% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 11.6 mg, and its estimated purity by LCMS analysis was 100%.

Analysis condition A: Retention time=1.29 min; ESI-MS (+) m/z 950.4 (M+2H)

Analysis condition B: Retention time=2.66 min; ESI-MS (+) m/z 950.4 (M+2H)

ESI-HRMS(+) m/z: Calculated: 949.9302. Found: 949.9288.

Preparation of Example 6350

Example 6350

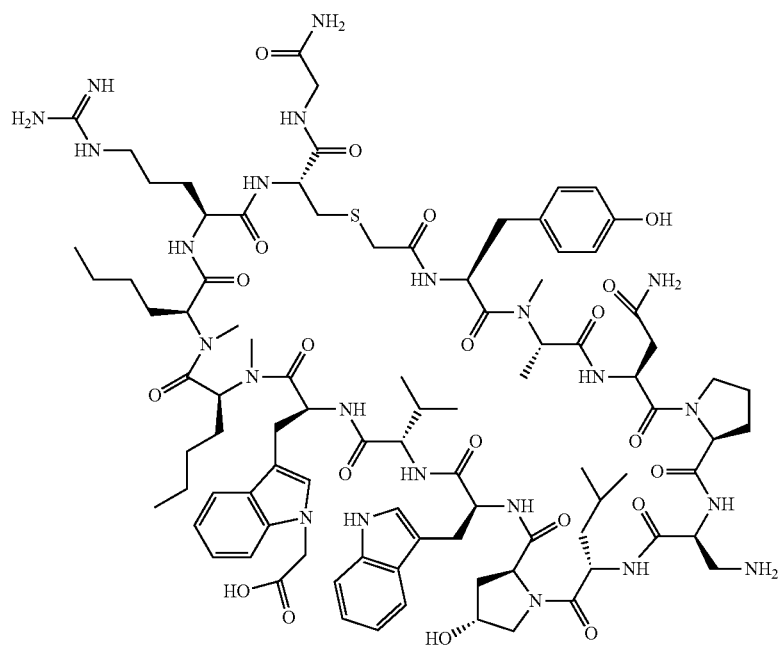

Example 6350 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 4.0 mg, and its estimated purity by LCMS analysis was 100%.

Analysis condition A: Retention time=1.45 min; ESI-MS (+) m/z 965.4 (M+2H)

Analysis condition B: Retention time=2.95 min; ESI-MS (+) m/z 965.4 (M+2H)

ESI-HRMS(+) m/z: Calculated: 964.9956. Found: 964.9953.

Preparation of Example 6361

Example 6361

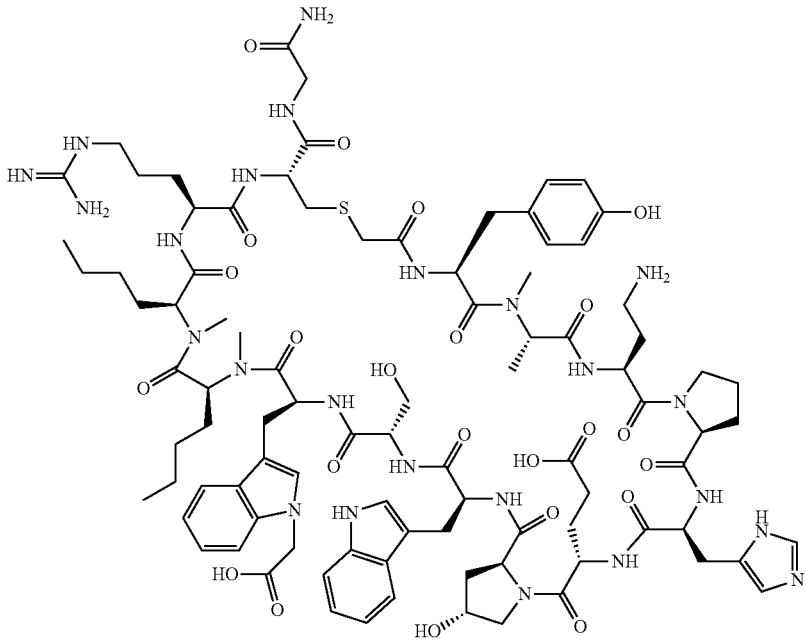

Example 6361 was prepared following "General Synthetic Sequence A". The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 13.3 mg, and its estimated purity by LCMS analysis was 100%.

Analysis condition A: Retention time=1.33 min; ESI-MS (+) m/z 985.9 (M+2H)

Analysis condition B: Retention time=2.78 min; ESI-MS (+) m/z 985.9 (M+2H)

ESI-HRMS(+) m/z: Calculated: 985.4725. Found: 985.4694.

Preparation of Example 6363

Example 6363 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 0-40% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 4.3 mg, and its estimated purity by LCMS analysis was 96%.

Analysis condition A: Retention time=1.36 min; ESI-MS (+) m/z 916.9 (M+2H)

Analysis condition B: Retention time=2.88 min; ESI-MS (+) m/z 916.9 (M+2H)

ESI-HRMS(+) m/z: Calculated: 916.4454. Found: 916.4428.

Example 6363

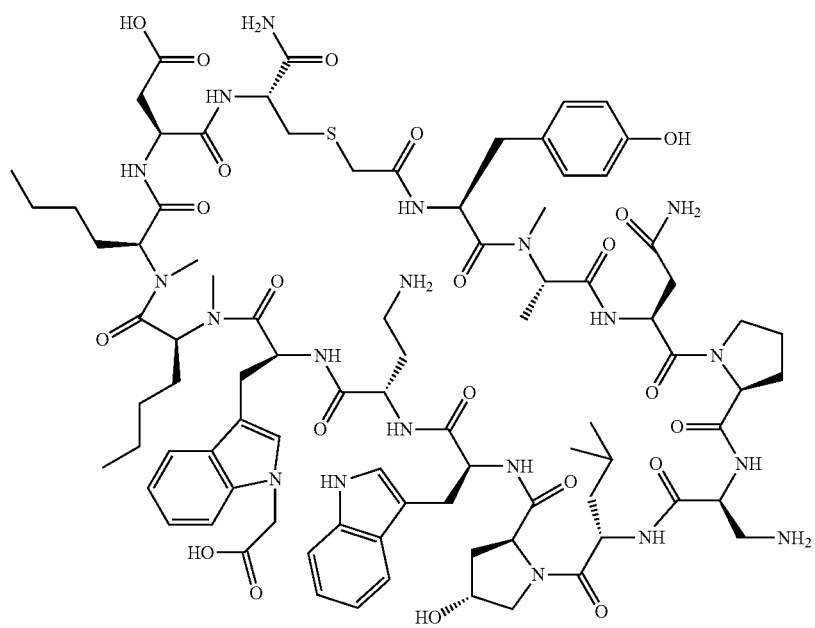

Preparation of Example 6365

Example 6365

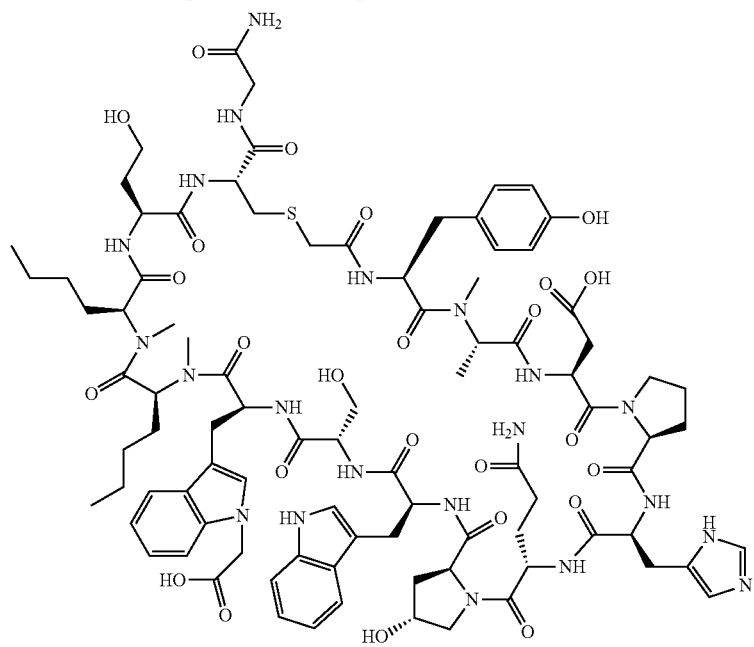

Example 6365 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-40% B over 30 minutes, then a 5-minute hold at 100% B; Flow: 20 mL/min. Fractions containing the desired product were combined and dried via centrifugal evaporation. The material was further purified via preparative LC/MS with the following conditions:

Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 10-50% B over 20 minutes, then a 5-minute hold at 100% B; Flow: 20 mL/min. Fractions containing the desired product were combined and dried via centrifugal evaporation. The yield of the product was 10.2 mg, and its estimated purity by LCMS analysis was 95%.

Analysis condition A: Retention time=1.20 min; ESI-MS (−) m/z 963.8 (M−2H)

Analysis condition B: Retention time=2.32 min; ESI-MS (+) m/z 966.6 (M+2H)

ESI-HRMS(+) m/z: Calculated: 965.9354. Found: 965.9352.

Preparation of Example 6369

Example 6369

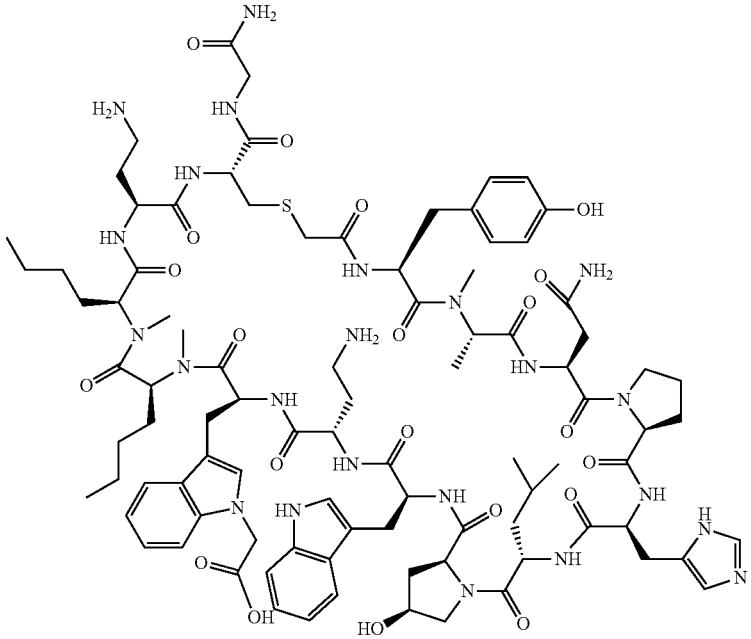

Example 6369 was prepared following "General Synthetic Sequence A". The crude material was purified via preparative LC/MS with the following conditions:

Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-80% B over 30 minutes, then a 5-minute hold at 100% B; Flow: 20 mL/min. Fractions containing the desired product were combined and dried via centrifugal evaporation. The yield of the product was 11.9 mg, and its estimated purity by LCMS analysis was 100%.

Analysis condition A: Retention time=1.34 min; ESI-MS (+) m/z 963.4 (M+2H)

Analysis condition B: Retention time=2.79 min; ESI-MS (+) m/z 963.4 (M+2H)

ESI-HRMS(+) m/z: Calculated: 962.98. Found: 962.9762.

Preparation of Example 6370

Example 6370 was prepared following "General Synthetic Sequence A". The crude material was purified via preparative LC/MS with the following conditions:

Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 20 minutes, then a 5-minute hold at 100% B; Flow: 20 mL/min. Fractions containing the desired product were combined and dried via centrifugal evaporation. The yield of the product was 6.9 mg, and its estimated purity by LCMS analysis was 100%.

Analysis condition A: Retention time=1.35 min; ESI-MS (+) m/z 984.9 (M+2H)

Analysis condition B: Retention time=2.85 min; ESI-MS (+) m/z 984.0 (M+2H).

Example 6370

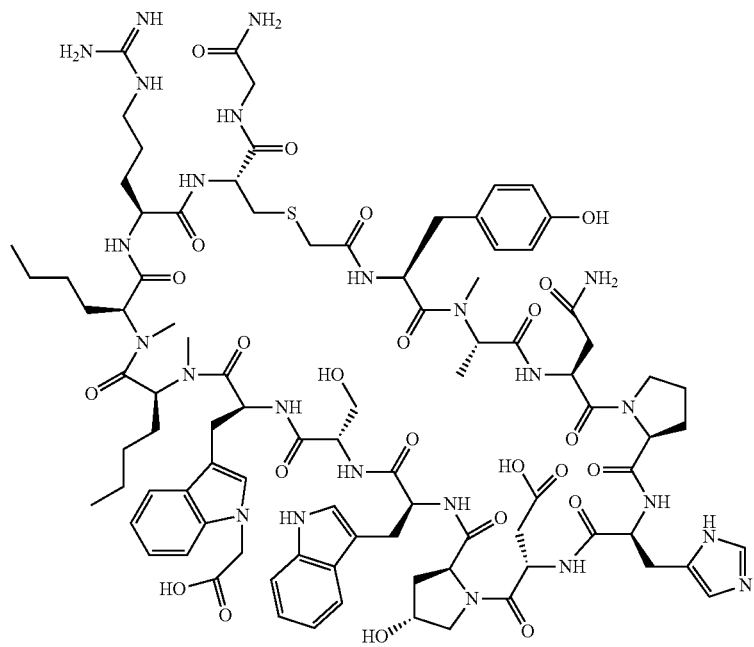

Preparation of Example 6372

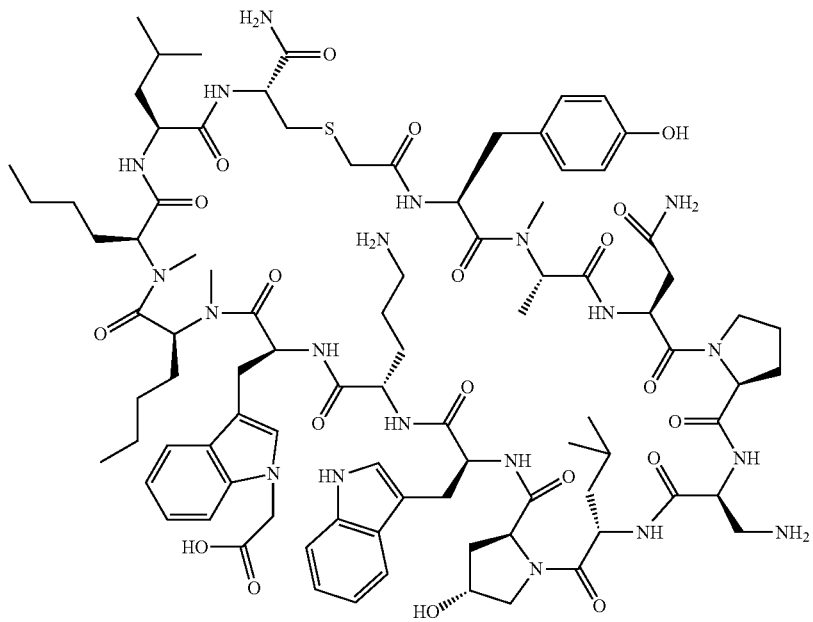

Example 6372

Example 6372 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 20 minutes, then a 5-minute hold at 100% B; Flow: 20 mL/min. Fractions containing the desired product were combined and dried via centrifugal evaporation. The yield of the product was 6.8 mg, and its estimated purity by LCMS analysis was 95%.

Analysis condition A: Retention time=1.51 min; ESI-MS (+) m/z 923.8 (M+2H)

Analysis condition B: Retention time=2.77 min; ESI-MS (+) m/z 923.7 (M+2H)

ESI-HRMS(+) m/z: Calculated: 922.4818. Found: 922.4799.

Preparation of Example 6380

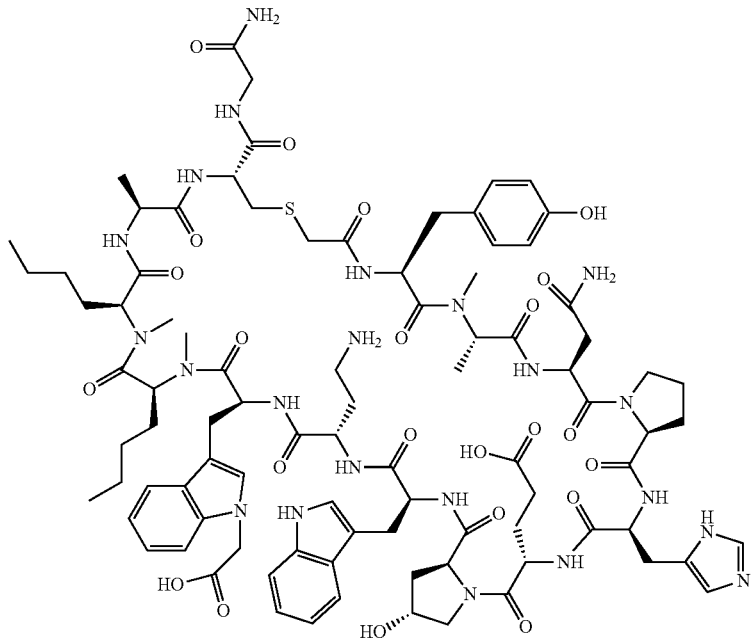

Example 6380

Example 6380 was prepared following "General Synthetic Sequence A". The crude material was purified via preparative LC/MS with the following conditions:

Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 17.9 mg, and its estimated purity by LCMS analysis was 100%.

Analysis condition A: Retention time=1.33 min; ESI-MS (+) m/z 957.3 (M+2H)

Analysis condition B: Retention time=2.86 min; ESI-MS (+) m/z 957.3 (M+2H)

ESI-HRMS(+) m/z: Calculated: 956.446. Found: 956.4431.

Preparation of Example 6383

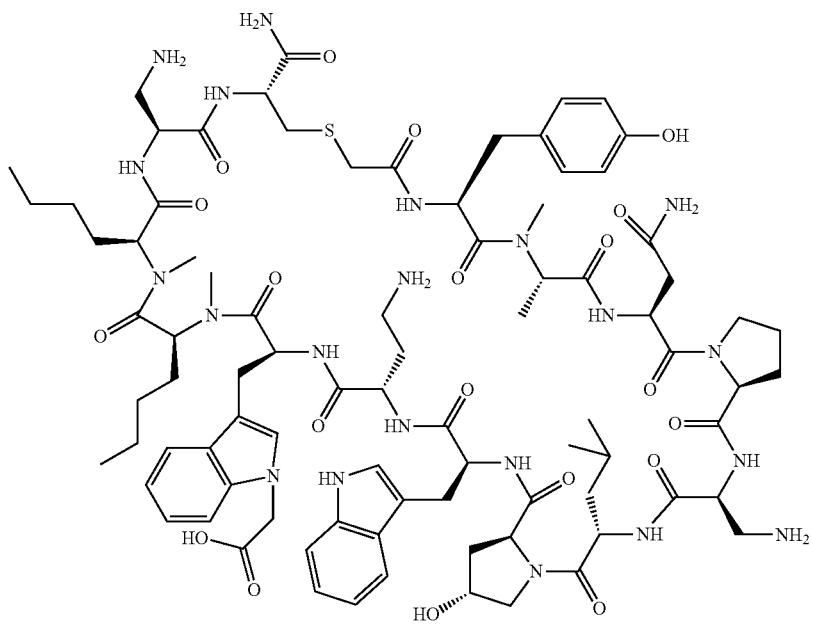

Example 6383

Example 6383 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 15.8 mg, and its estimated purity by LCMS analysis was 100%.

Analysis condition A: Retention time=1.34 min; ESI-MS (+) m/z 903.2 (M+2H)

Analysis condition B: Retention time=2.55 min; ESI-MS (+) m/z 903.4 (M+2H)

ESI-HRMS(+) m/z: Calculated: 901.956. Found: 901.9538.

Preparation of Example 6384

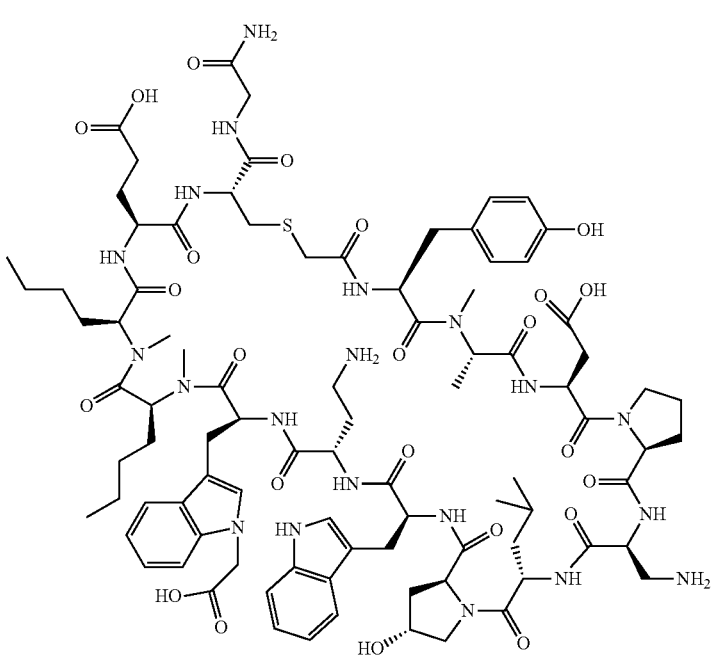

Example 6384

Example 6384 was prepared following "General Synthetic Sequence A". The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 0-40% B over 30 minutes, then a 5-minute hold at 100% B; Flow: 20 mL/min. Fractions containing the desired product were combined and dried via centrifugal evaporation. The yield of the product was 27.7 mg, and its estimated purity by LCMS analysis was 100%.

Analysis condition A: Retention time=1.23 min; ESI-MS (+) m/z 954.1 (M+2H)

Analysis condition B: Retention time=1.48 min; ESI-MS (+) m/z 954.0 (M+2H)

ESI-HRMS(+) m/z: Calculated: 952.456. Found: 952.4545.

Preparation of Example 6389

Example 6389

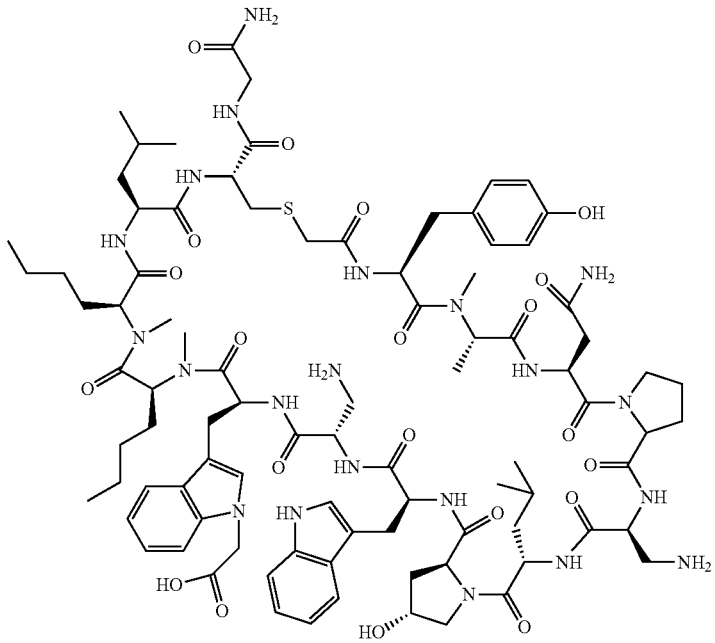

Example 6389 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 5.8 mg, and its estimated purity by LCMS analysis was 99%.

Analysis condition A: Retention time=1.49 min; ESI-MS (+) m/z 936.9 (M+2H)

Analysis condition B: Retention time=2.84 min; ESI-MS (−) m/z 934.9 (M−2H)

ESI-HRMS(+) m/z: Calculated: 936.9769. Found: 936.9742.

Preparation of Example 6390

Example 6390

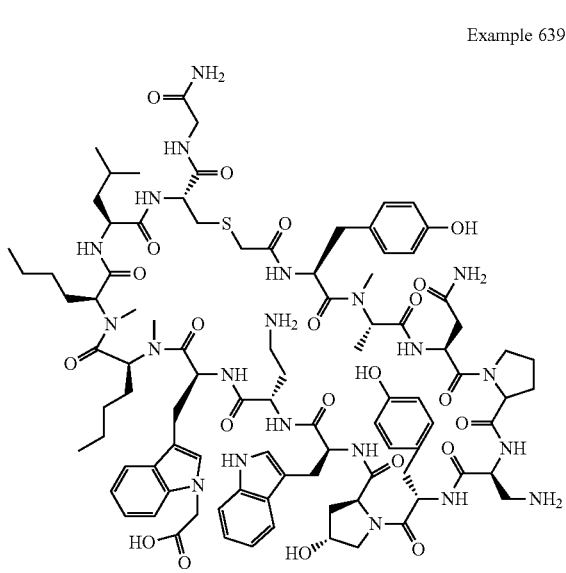

Example 6390 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 8.0 mg, and its estimated purity by LCMS analysis was 98%.

Analysis condition A: Retention time=1.48 min; ESI-MS (+) m/z 969.0 (M+2H)

Analysis condition B: Retention time=2.84 min; ESI-MS (+) m/z 969.2 (M+2H)

ESI-HRMS(+) m/z: Calculated: 968.9744. Found: 968.9721.

Preparation of Example 6391

Example 6391

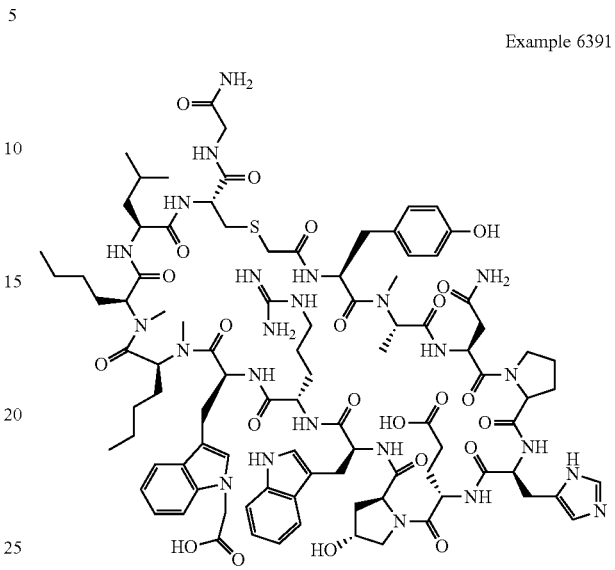

Example 6391 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 8.3 mg, and its estimated purity by LCMS analysis was 100%.

Analysis condition A: Retention time=1.30 min; ESI-MS (+) m/z 1005.4 (M+2H)

Analysis condition B: Retention time=2.54 min; ESI-MS (−) m/z 1003.5 (M−2H)

ESI-HRMS(+) m/z: Calculated: 1005.4882. Found: 1005.4868.

Preparation of Example 6392

Example 6392

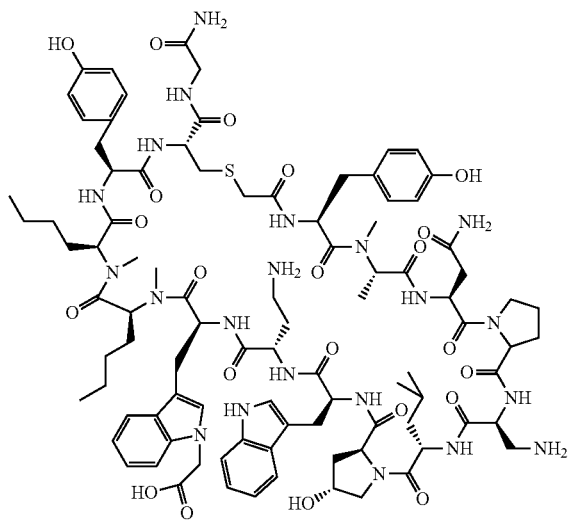

Example 6392 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 30-70% B over 30 minutes, then a 5-minute hold at 100% B; Flow: 20 mL/min. Fractions containing the desired product were combined and dried via centrifugal evaporation. The yield of the product was 19.0 mg, and its estimated purity by LCMS analysis was 100%.

Analysis condition A: Retention time=1.481 min; ESI-MS(+) m/z 969.25 (M+2H)

Analysis condition B: Retention time=3.004 min; ESI-MS(+) m/z 969.80 (M+2H)

ESI-HRMS(+) m/z: Calculated: 968.9744. Found: 968.9728.

Preparation of Example 6393

Example 6393

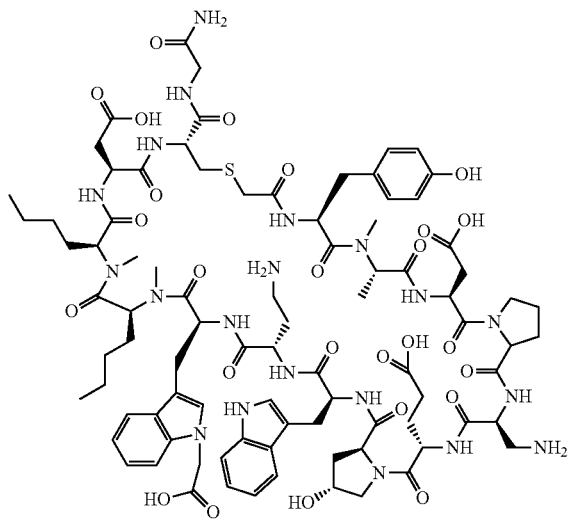

Example 6393 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 24.4 mg, and its estimated purity by LCMS analysis was 100%.

Analysis condition A: Retention time=1.270 min; ESI-MS(+) m/z 953.40 (M+2H)

Analysis condition B: Retention time=2.685 min; ESI-MS(−) m/z 951.55 (M−2H)

ESI-HRMS(+) m/z: Calculated: 953.4274. Found: 953.425.

Preparation of Example 6394

Example 6394

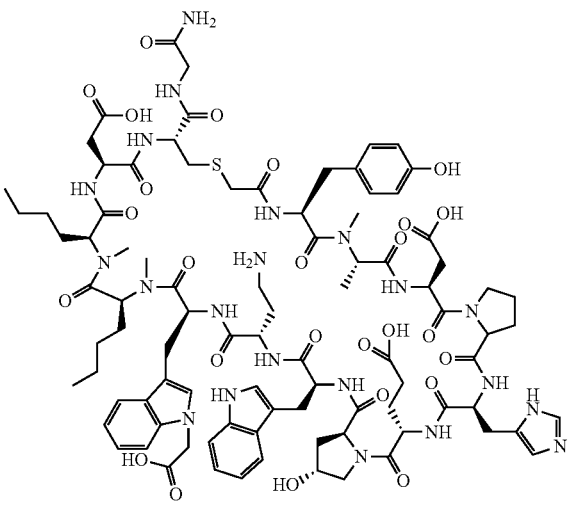

'Example 6394 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 30-70% B over 30 minutes, then a 5-minute hold at 100% B; Flow: 20 mL/min. Fractions containing the desired product were combined and dried via centrifugal evaporation. The yield of the product was 33.3 mg, and its estimated purity by LCMS analysis was 97%.

Analysis condition A: Retention time=1.227 min; ESI-MS(−) m/z 976.85 (M−2H)

Analysis condition B: Retention time=0.366 min; ESI-MS(−) m/z 976.75 (M−2H)

ESI-HRMS(+) m/z: Calculated: 978.9329. Found: 978.9314.

Preparation of Example 6395

Example 6395

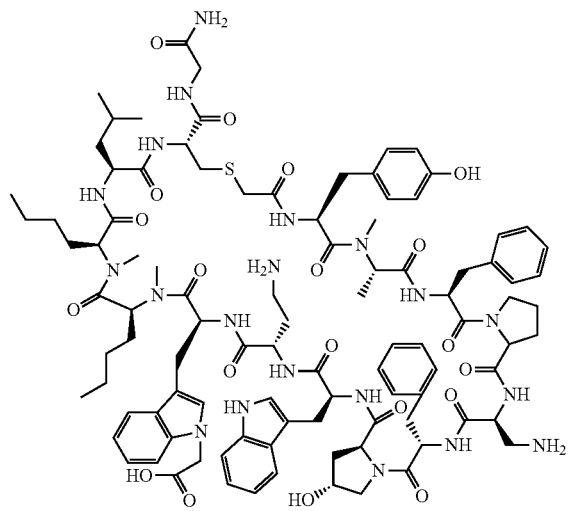

Example 6395 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 7.0 mg, and its estimated purity by LCMS analysis was 93%.

Analysis condition A: Retention time=1.67 min; ESI-MS (+) m/z 978.3 (M+2H)

Analysis condition B: Retention time=3.09 min; ESI-MS (+) m/z 978.2 (M+2H)

ESI-HRMS(+) m/z: Calculated: 977.4896. Found: 977.4877.

Preparation of Example 6396

Example 6396

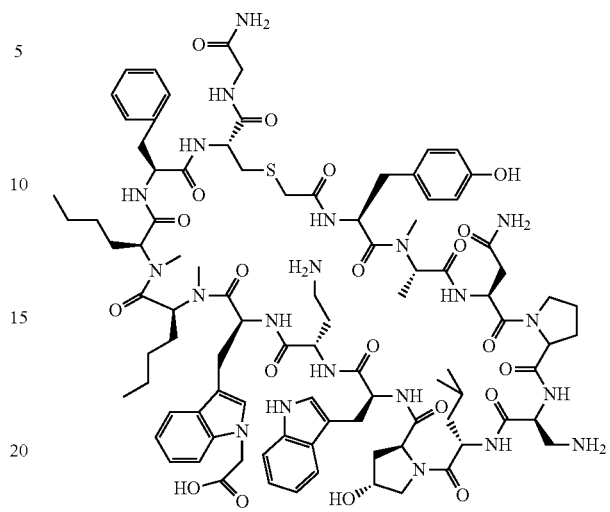

Example 6396 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 15.3 mg, and its estimated purity by LCMS analysis was 96%.

Analysis condition A: Retention time=1.54 min; ESI-MS (+) m/z 960.9 (M+2H)

Analysis condition B: Retention time=2.96 min; ESI-MS (+) m/z 961.7 (M+2H)

ESI-HRMS(+) m/z: Calculated: 960.9769. Found: 960.9741.

Preparation of Example 6397

Example 6397

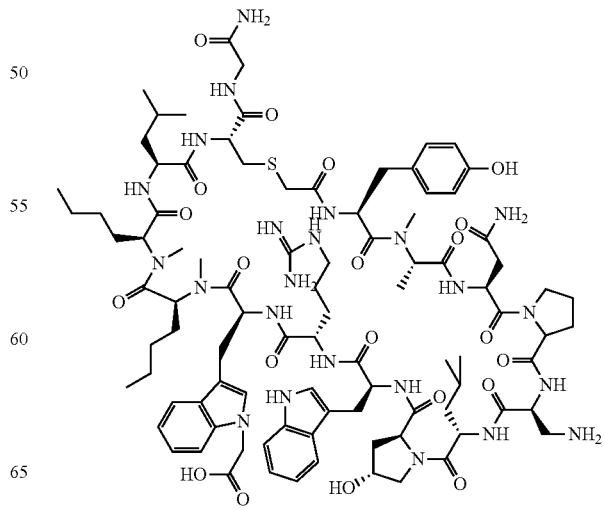

Example 6397 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 8.5 mg, and its estimated purity by LCMS analysis was 100%.

Analysis condition A: Retention time=1.47 min; ESI-MS (+) m/z 972.2 (M+2H)

Analysis condition B: Retention time=2.80 min; ESI-MS (+) m/z 972.2 (M+2H)

ESI-HRMS(+) m/z: Calculated: 972.0035. Found: 972.0013.

Preparation of Example 6398

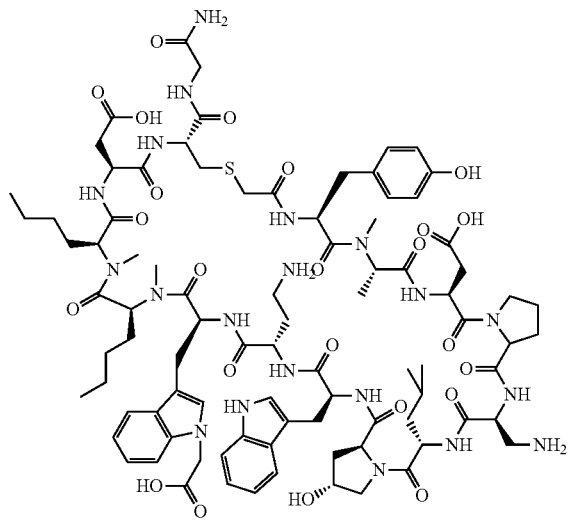

Example 6398

Example 6398 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 0-40% B over 30 minutes, then a 5-minute hold at 100% B; Flow: 20 mL/min. Fractions containing the desired product were combined and dried via centrifugal evaporation. The yield of the product was 8.2 mg, and its estimated purity by LCMS analysis was 98%.

Analysis condition A: Retention time=1.16 min; ESI-MS (−) m/z 943.4 (M−2H)

Analysis condition B: Retention time=2.43 min; ESI-MS (+) m/z 945.6 (M+2H)

ESI-HRMS(+) m/z: Calculated: 945.4482. Found: 945.4459.

Preparation of Example 6399

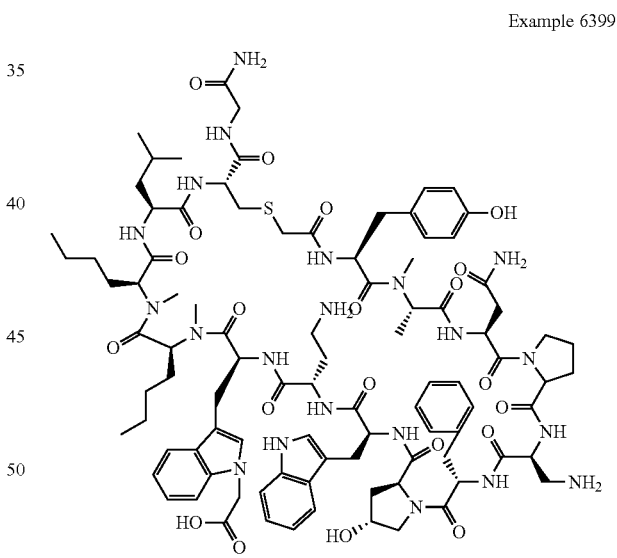

Example 6399

Example 6399 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 26.5 mg, and its estimated purity by LCMS analysis was 95%.

Analysis condition A: Retention time=1.51 min; ESI-MS (+) m/z 961.3 (M+2H)

Analysis condition B: Retention time=2.92 min; ESI-MS (+) m/z 961.6 (M+2H)

ESI-HRMS(+) m/z: Calculated: 960.9769. Found: 960.9745.

Preparation of Example 6400

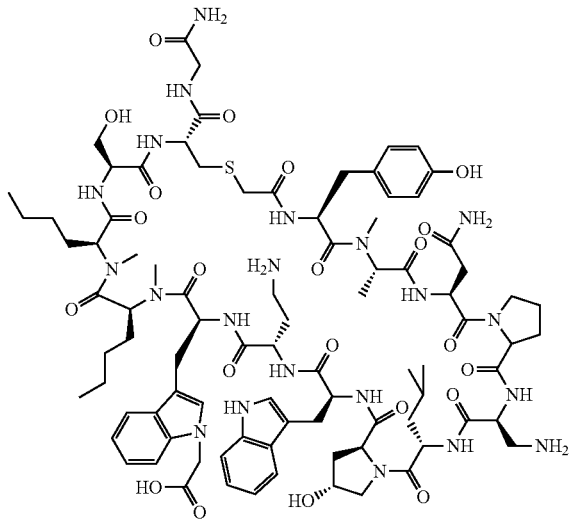

Example 6400

Example 6400 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 14.0 mg, and its estimated purity by LCMS analysis was 100%.

Analysis condition A: Retention time=1.34 min; ESI-MS (+) m/z 931.6 (M+2H)

Analysis condition B: Retention time=2.72 min; ESI-MS (−) m/z 928.9 (M−2H)

ESI-HRMS(+) m/z: Calculated: 930.9587. Found: 930.9564.

Preparation of Example 6401

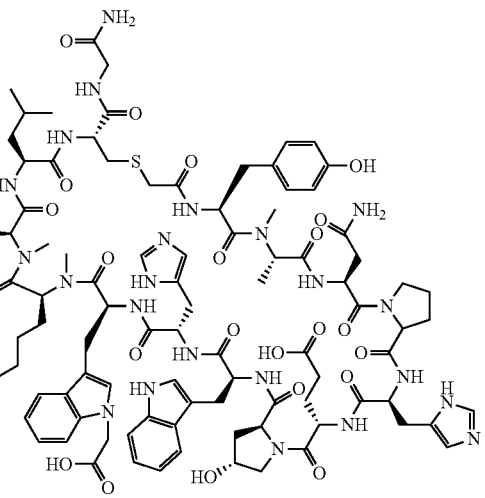

Example 6401

Example 6401 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 16.3 mg, and its estimated purity by LCMS analysis was 100%.

Analysis condition A: Retention time=1.26 min; ESI-MS (−) m/z 993.9 (M−2H)

Analysis condition B: Retention time=2.51 min; ESI-MS (+) m/z 996.5 (M+2H).

Preparation of Example 6402

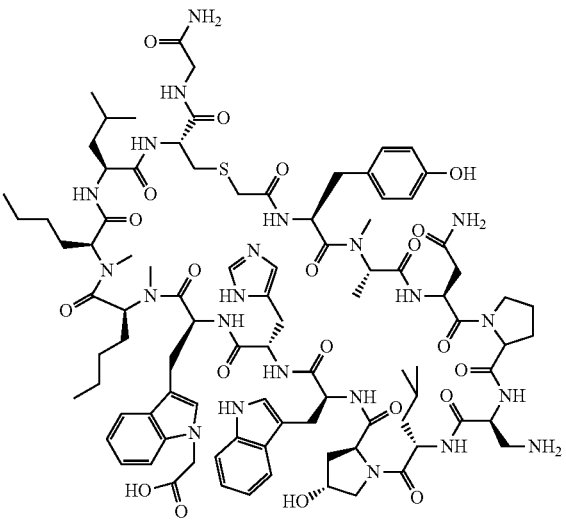

Example 6402

Example 6402 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 9.6 mg, and its estimated purity by LCMS analysis was 95%.

Analysis condition A: Retention time=1.45 min; ESI-MS (+) m/z 962.3 (M+2H)

Analysis condition B: Retention time=2.74 min; ESI-MS (−) m/z 960.7 (M−2H)

ESI-HRMS(+) m/z: Calculated: 962.4824. Found: 962.4792.

Preparation of Example 6403

Example 6403

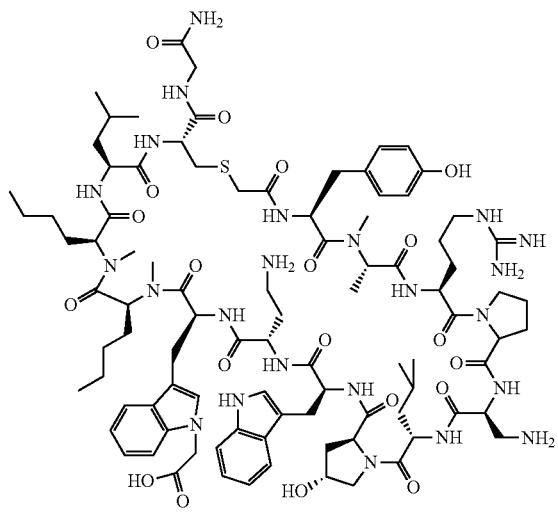

Example 6403 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 13.2 mg, and its estimated purity by LCMS analysis was 96%.

Analysis condition A: Retention time=1.52 min; ESI-MS (+) m/z 965.3 (M+2H)

Analysis condition B: Retention time=2.92 min; ESI-MS (+) m/z 965.0 (M+2H)

ESI-HRMS(+) m/z: Calculated: 965.0138. Found: 965.0104.

Preparation of Example 6404

Example 6404

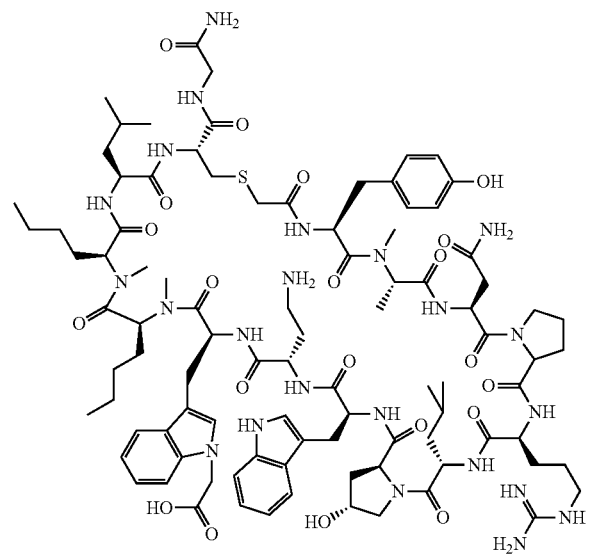

Example 6404 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 16.9 mg, and its estimated purity by LCMS analysis was 95%.

Analysis condition A: Retention time=1.48 min; ESI-MS (+) m/z 979.1 (M+2H)

Analysis condition B: Retention time=2.87 min; ESI-MS (−) m/z 977.3 (M−2H).

Preparation of Example 6405

Example 6405

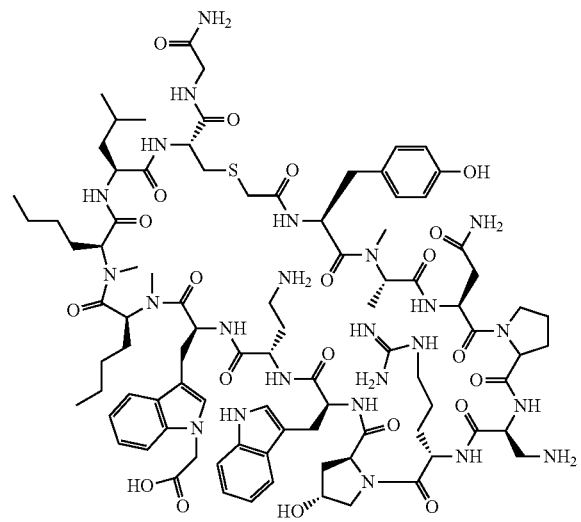

Example 6405 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 15.5 mg, and its estimated purity by LCMS analysis was 98%.

Analysis condition A: Retention time=1.47 min; ESI-MS (+) m/z 966.2 (M+2H)

Analysis condition B: Retention time=2.87 min; ESI-MS (+) m/z 965.4 (M+2H)

ESI-HRMS(+) m/z: Calculated: 965.4933. Found: 965.4899.

Preparation of Example 6406

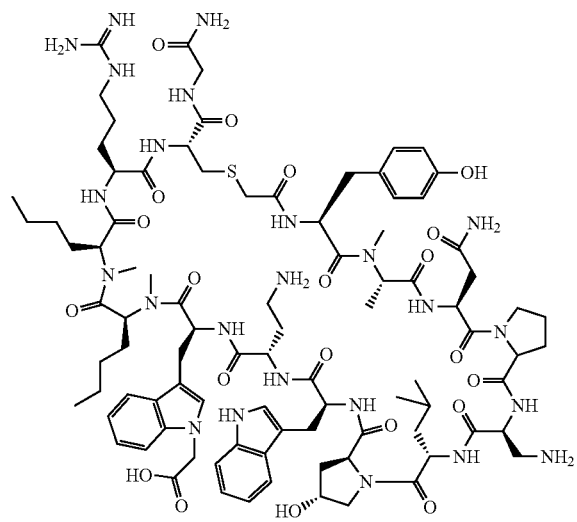

Example 6406

Example 6406 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 18.7 mg, and its estimated purity by LCMS analysis was 99%.

Analysis condition A: Retention time=1.32 min; ESI-MS (+) m/z 965.6 (M+2H)

Analysis condition B: Retention time=2.70 min; ESI-MS (+) m/z 965.6 (M+2H)

ESI-HRMS(+) m/z: Calculated: 965.4933. Found: 965.4894.

Preparation of Example 6407

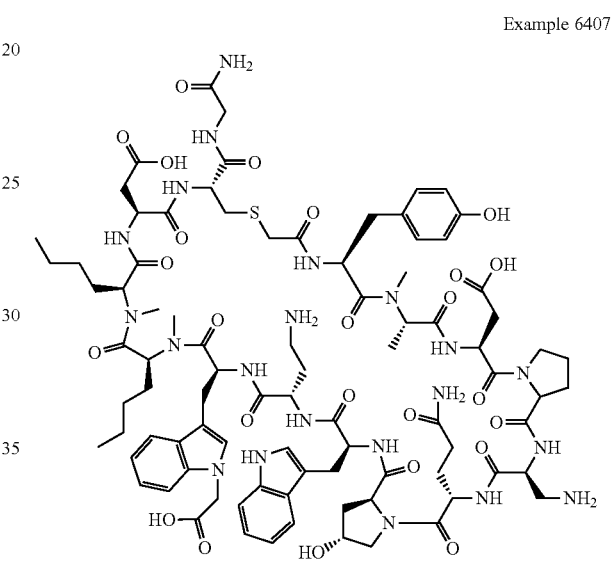

Example 6407

Example 6407 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 26.7 mg, and its estimated purity by LCMS analysis was 100%.

Analysis condition A: Retention time=1.16 min; ESI-MS (+) m/z 953.1 (M+2H)

Analysis condition B: Retention time=2.46 min; ESI-MS (−) m/z 951.1 (M−2H)

ESI-HRMS(+) m/z: Calculated: 952.9354. Found: 952.9326.

Preparation of Example 6408

Example 6408

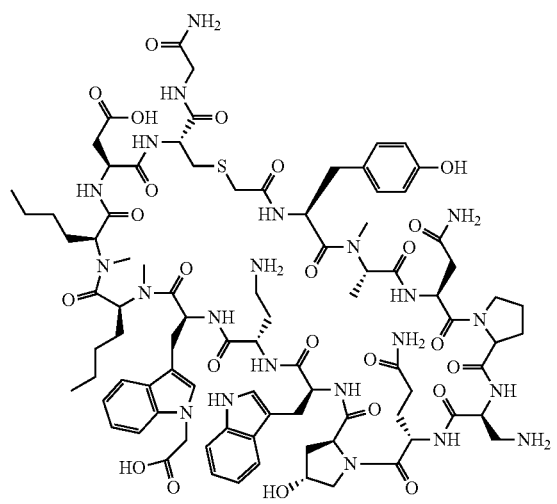

Example 6408 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 19.2 mg, and its estimated purity by LCMS analysis was 100%.

Analysis condition A: Retention time=1.22 min; ESI-MS (+) m/z 952.8 (M+2H)

Analysis condition B: Retention time=2.53 min; ESI-MS (+) m/z 953.1 (M+2H).

Preparation of Example 6409

Example 6409

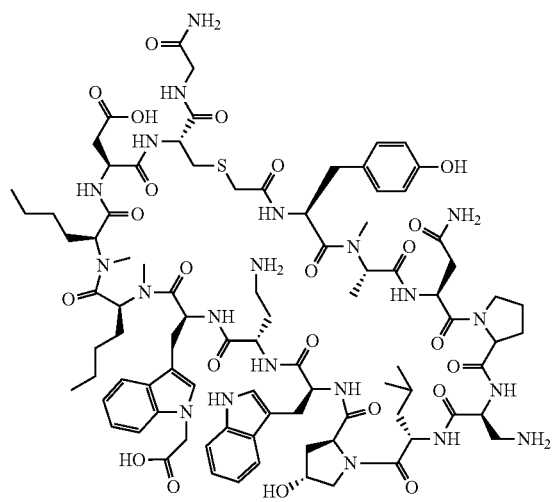

Example 6409 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 24.8 mg, and its estimated purity by LCMS analysis was 100%.

Analysis condition A: Retention time=1.23 min; ESI-MS (+) m/z 945.7 (M+2H)

Analysis condition B: Retention time=2.57 min; ESI-MS (+) m/z 945.2 (M+2H)

ESI-HRMS(+) m/z: Calculated: 944.9562. Found: 944.9537.

Preparation of Example 6410

Example 6410

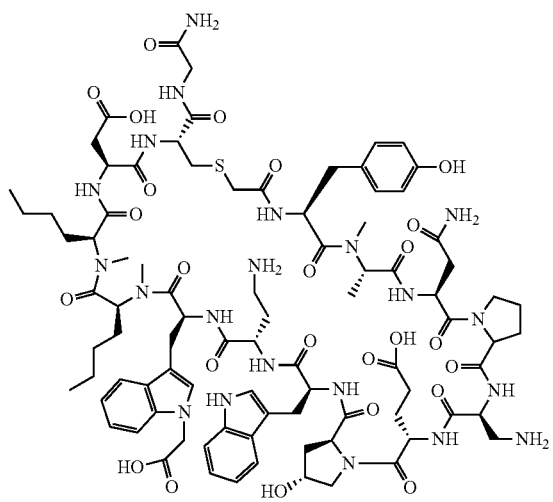

Example 6410 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 25.1 mg, and its estimated purity by LCMS analysis was 100%.

Analysis condition A: Retention time=1.16 min; ESI-MS (+) m/z 953.0 (M+2H)

Analysis condition B: Retention time=2.41 min; ESI-MS (+) m/z 953.2 (M+2H)

ESI-HRMS(+) m/z: Calculated: 952.9354. Found: 952.9332.

Preparation of Example 6411

Example 6411

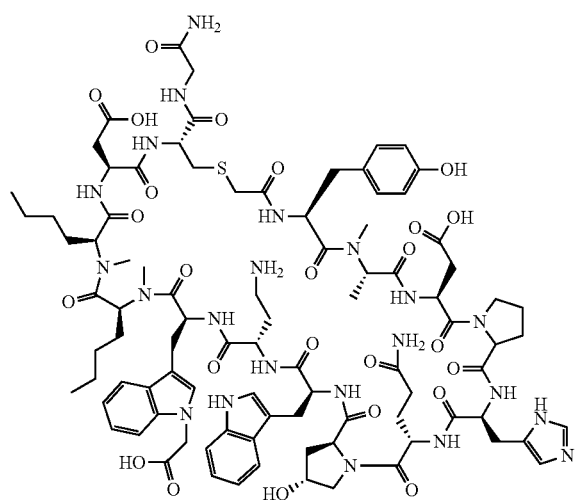

Example 6411 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-70% B over 30 minutes, then a 5-minute hold at 100% B; Flow: 20 mL/min. Fractions containing the desired product were combined and dried via centrifugal evaporation. The yield of the product was 25.5 mg, and its estimated purity by LCMS analysis was 100%.

Analysis condition A: Retention time=1.15 min; ESI-MS (−) m/z 977.0 (M−2H)

Analysis condition B: Retention time=2.36 min; ESI-MS (+) m/z 978.7 (M+2H)

ESI-HRMS(+) m/z: Calculated: 978.4409. Found: 978.4388.

Preparation of Example 6412

Example 6412

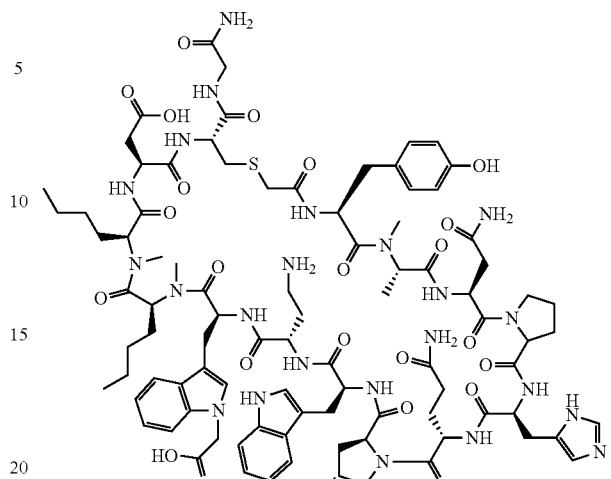

Example 6412 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 14.4 mg, and its estimated purity by LCMS analysis was 100%.

Analysis condition A: Retention time=1.17 min; ESI-MS (−) m/z 976.5 (M−2H)

Analysis condition B: Retention time=2.42 min; ESI-MS (+) m/z 978.3 (M+2H)

ESI-HRMS(+) m/z: Calculated: 977.9489. Found: 977.9467.

Preparation of Example 6415

Exampe 6415

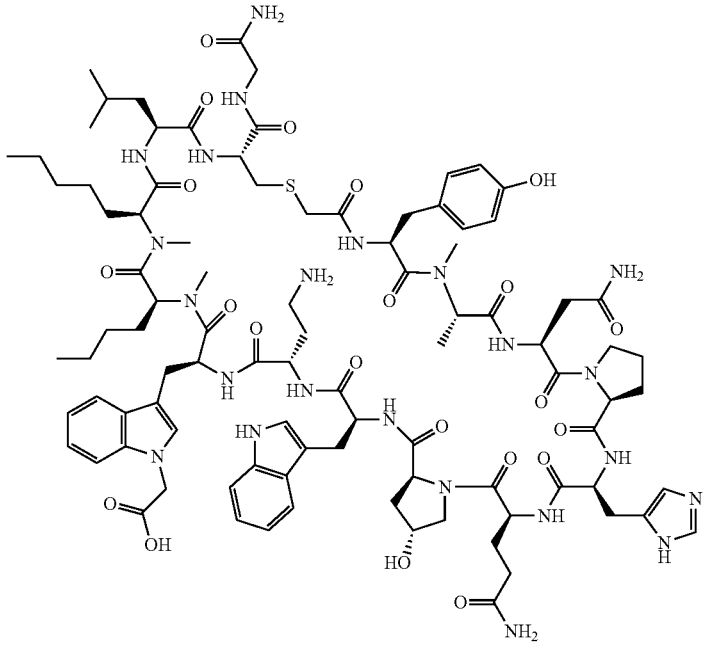

Example 6415 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: waters xbridge c-18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-85% B over 30 minutes, then a 5-minute hold at 100% B; Flow: 20 mL/min. Fractions containing the desired product were combined and dried via centrifugal evaporation. The yield of the product was 21.1 mg, and its estimated purity by LCMS analysis was 96%.

Analysis condition A: Retention time=1.51 min; ESI-MS (+) m/z 975.8 (M+2H)

Analysis condition B: Retention time=2.74 min; ESI-MS (+) m/z 977.9 (M+2H)

ESI-HRMS(+) m/z: Calculated: 976.9774. Found: 976.9735.

Preparation of Example 6416

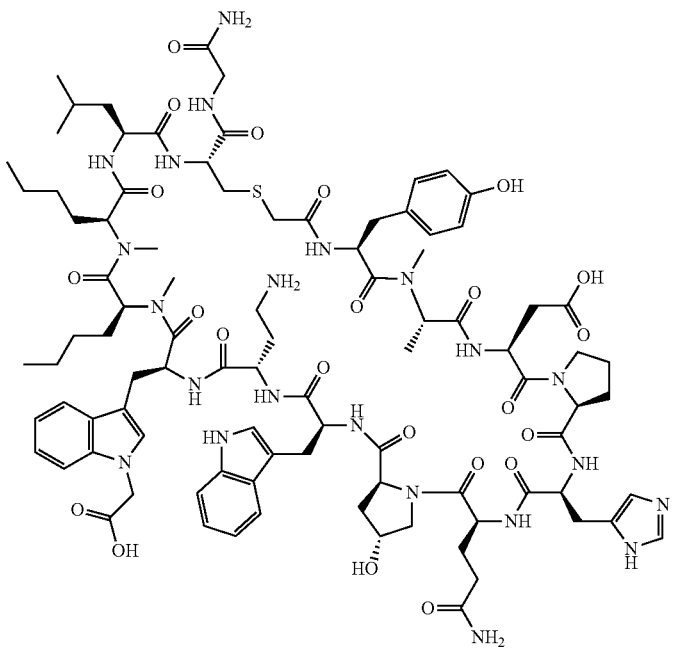

Exampe 6416

Example 6416 was prepared following "General Synthetic Sequence A", where the "Single-coupling procedure" and "Double-coupling procedure" of "Symphony Method A" were modified to use acetic anhydride (1.0 mL)+DIPEA in DMF (0.4M, 1.0 mL) instead of neat acetic anhydride (2.0 mL). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 10.5 mg, and its estimated purity by LCMS analysis was 94%.

Analysis condition A: Retention time=1.48 min; ESI-MS (−) m/z 977.9 (M−2H)

Analysis condition B: Retention time=2.77 min; ESI-MS (+) m/z 977.9 (M+2H).

Preparation of Example 7067

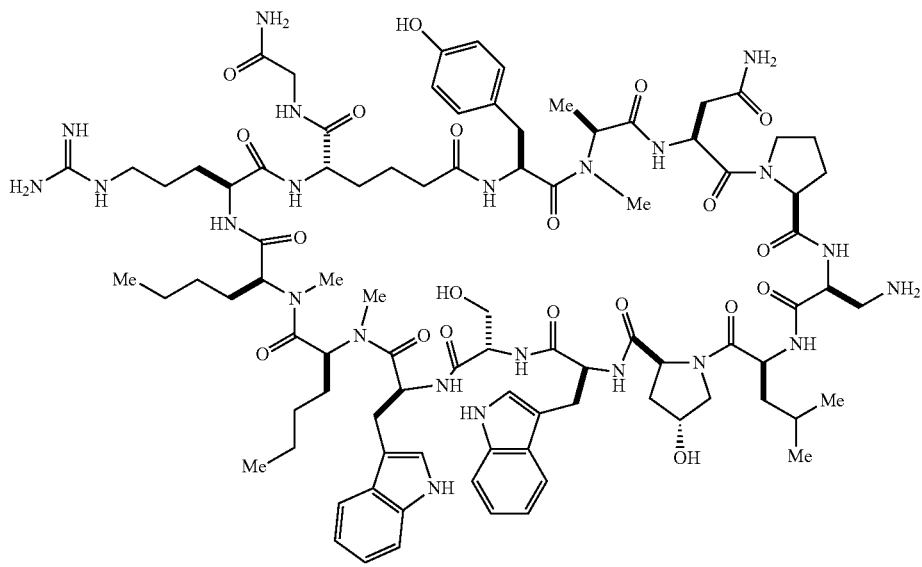

Example 7013 (3.0 mg, 1.631 umol) was dissolved in methanol (3 mL). The mixture was treated with Pd/C (1 mg), sparged under a hydrogen atmosphere (1 atm, balloon) and then stirred for 24 hrs. The LCMS showed the unsaturated starting material was consumed. The mixture was filtered to remove Pd/C. The solvent was removed to give Example 7067 (1.4 mg).

Analysis condition A: Retention time=2.92 min; ESI-MS (+) m/z=921.5 (M+2H)

ESI-HRMS(+) m/z Calculated 920.9965, Found 920.9965 (M+2H).

Examples 7068 to 7154 were prepared by following the general synthetic sequence described for the preparation of Example 5001, composed of the following general procedures: "Prelude Method A: Resin-swelling procedure", "Prelude Method A: Single-coupling procedure", "Prelude Method A: Double-coupling procedure", "Prelude Method A: Chloroacetyl chloride coupling procedure". The "Global Deprotection Method A" and "Cyclization Method A" used for the preparation of Examples 7068 to 7154 were modified as described in the following. Global Deprotection Method A: The procedure of "Global Deprotection Method A" describes an experiment performed on a 0.100 mmol scale, where the scale is determined by the amount of Rink linker bound to the resin. A "deprotection solution" was prepared by combining in a 40 mL glass jar trifluoroacetic acid (22 mL), phenol (1.325 g), water (1.25 mL) and triisopropylsilane (0.5 mL). The resin was removed from the reaction vessel and transferred to a 4 mL glass vial. To the vial was added the "deprotection solution" (2.0 mL). The mixture was mixed on an orbital shaker (175 RPM for 2 h). The mixture was filtered through a funnel, the solids washed with additional "de-protection solution" (1.0 mL) and collected into a 40 mL screw capped vial. To the combined filtrates was added $Et_2O$ (15 mL). The mixture was vigorously mixed upon which a significant amount of a white solid precipitated. The mixture was centrifuged for 3 minutes at 2000 RPM, the solution decanted away from the solids and discarded. The process was repeated ×3, the solids were then allowed to sit on the bench and air dry for 1-2 hrs before carrying on affording the crude peptide as an off-white solid. Cyclization Method A: The procedure of "Cyclization Method A" describes an experiment performed on a 0.100 mmol scale. The crude peptide solids were dissolved in MeCN:aq. 0.1M $NH_4OAc$ (15 mL:15 mL), and the solution was then carefully adjusted to pH=9.0 using aq NaOH (1.0M). The vials were capped and the solution was then mixed at 175 RPM on an orbital shaker overnight (~18 h). The reaction solution was concentrated and the residue was then dissolved in MeOH. This solution was subjected to reverse-phase HPLC purification to afford the desired cyclic peptide.

Two of the four analytical LC/MS conditions were used to determine the final purity.

Analysis condition A: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm.

Analysis condition B: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm.

Analysis condition C1: Column: Waters BEH C18, 2.0×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0% B, 0-100% B over 3 minutes, then a 0.5 minute hold at 100% B; Flow: 0.5 mL/min; Detection: UV at 220 nm.

Analysis condition D1: Column: Waters BEH C18, 2.0×50 mm, 1.7-μm particles; Mobile Phase A: 5:95 methanol:water with 0.05% TFA; Mobile Phase B: 95:5 methanol:water with 0.05% TFA; Temperature: 50° C.; Gradient: 0% B, 0-100% B over 3 minutes, then a 0.5 minute hold at 100% B; Flow: 0.5 mL/min; Detection: UV at 220 nm.

Preparation of Example 7068

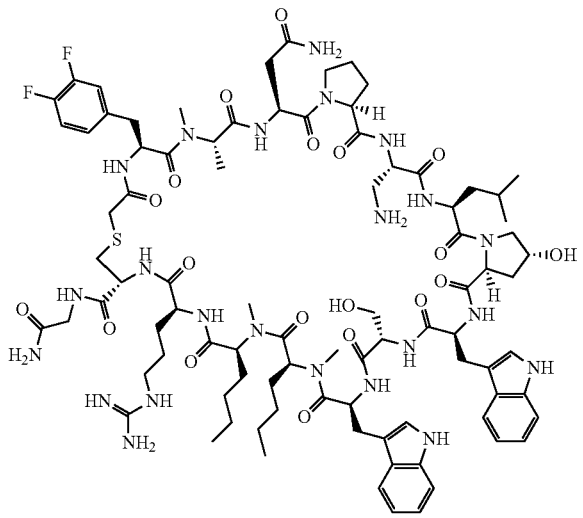 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(F)c(F)c2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 μm, 19×200 mm, Mobile Phase A: 5:95 methanol:water with 10-mM ammonium acetate; Mobile Phase B: 95:5 methanol:water with 10-mM ammonium acetate; Gradient: 40-80% B over 15 minutes, then a 5-minute hold at 100% B; Flow: 20 mL/min. Fractions containing the desired product were combined and dried via centrifugal evaporation. The yield of the product was 1.9 mg, and its estimated purity by LCMS analysis was 98%.

Analysis condition A: Retention time=1.84 min; ESI-MS (+) m/z=940.6 (M+2H)

Analysis condition B: Retention time=3.06 min; ESI-MS (+) m/z=940.5 (M+2H).

Preparation of Example 7069

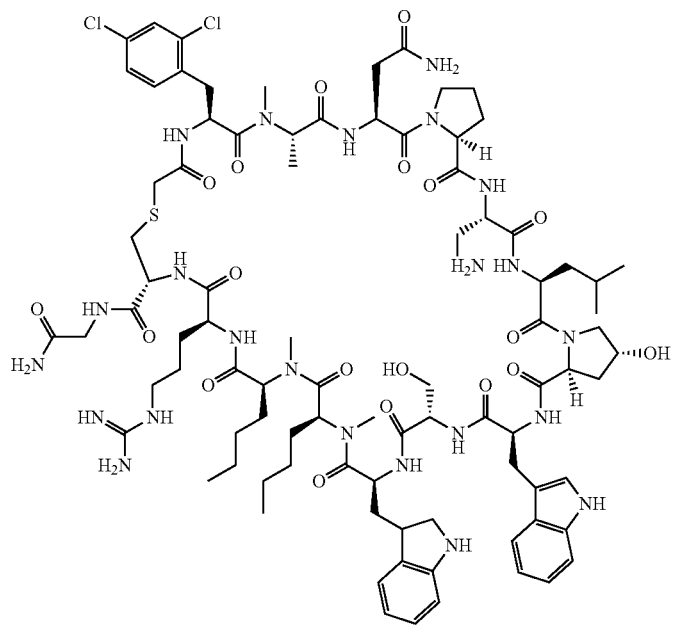 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(Cl)cc2Cl)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](CC2CNc3ccccc32)C(=O)N1C]

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 14.0 mg, and its estimated purity by LCMS analysis was 100%.

Analysis condition A: Retention time=1.85 min; ESI-MS (+) m/z=957.5 (M+2H)

Analysis condition B: Retention time=3.07 min; ESI-MS (+) m/z=957.5 (M+2H)

ESI-HRMS(+) m/z Calculated 955.9383, Found 955.9382 (M+2H).

Preparation of Example 7070

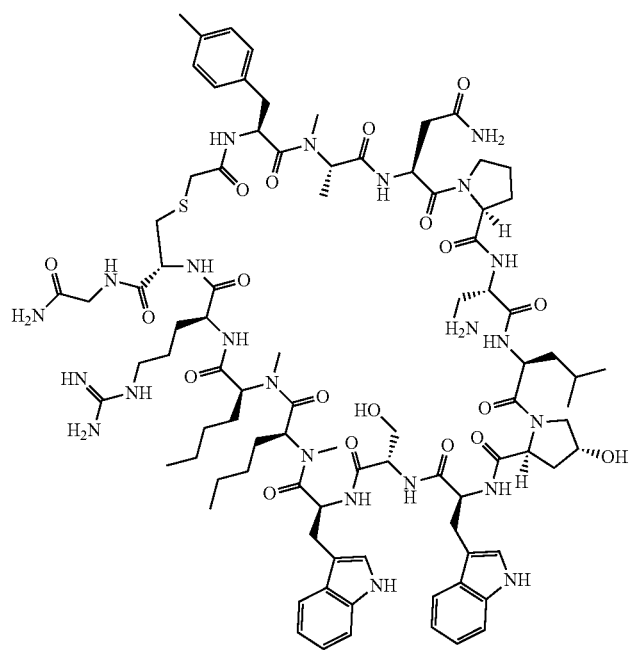 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(C)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 17.8 mg, and its estimated purity by LCMS analysis was 100%.

Analysis condition A: Retention time=1.86 min; ESI-MS (+) m/z=929.9 (M+2H)

Analysis condition B: Retention time=3.06 min; ESI-MS (+) m/z=929.7 (M+2H)

ESI-HRMS(+) m/z Calculated 928.9851, Found 928.9842 (M+2H).

Preparation of Example 7071

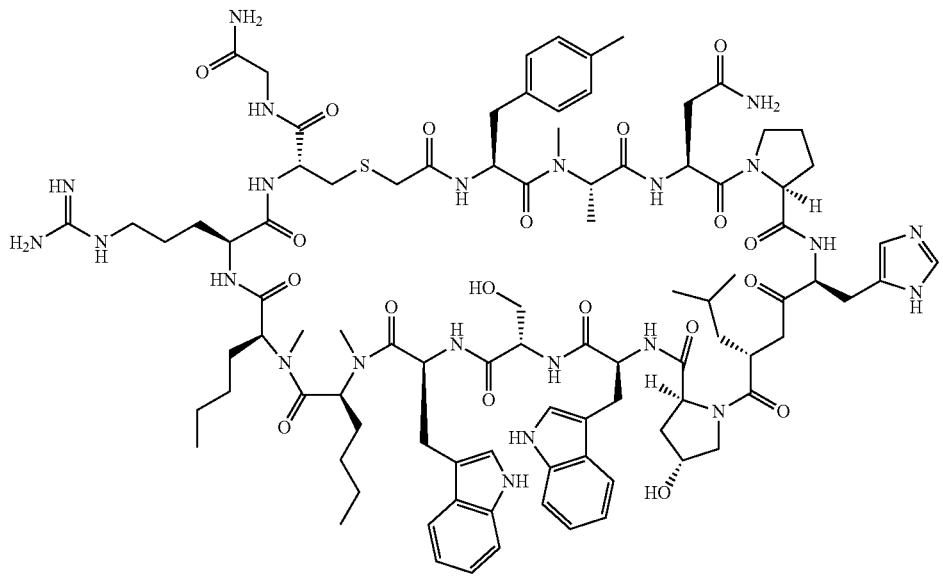 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(C)cc2)C(=O)N(C)[C@@H](C)C(=O)N[C@@H](CC(N)=O)C(=O)N2CCC[C@H]2C(=O)N[C@@H](Cc2cnc[nH]2)C(=O)C[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 55-95% B over 30 minutes, then a 5-minute hold at 100% B; Flow: 20 mL/min. Fractions containing the desired product were combined and dried via centrifugal evaporation. The yield of the product was 25.7 mg, and its estimated purity by LCMS analysis was 99%.

Analysis condition A: Retention time=1.91 min; ESI-MS (+) m/z=955.4 (M+2H)

Analysis condition B: Retention time=3.02 min; ESI-MS (+) m/z=955.2 (M+2H)

ESI-HRMS(+) m/z Calculated 954.4905, Found 954.4909 (M+2H).

Preparation of Example 7072

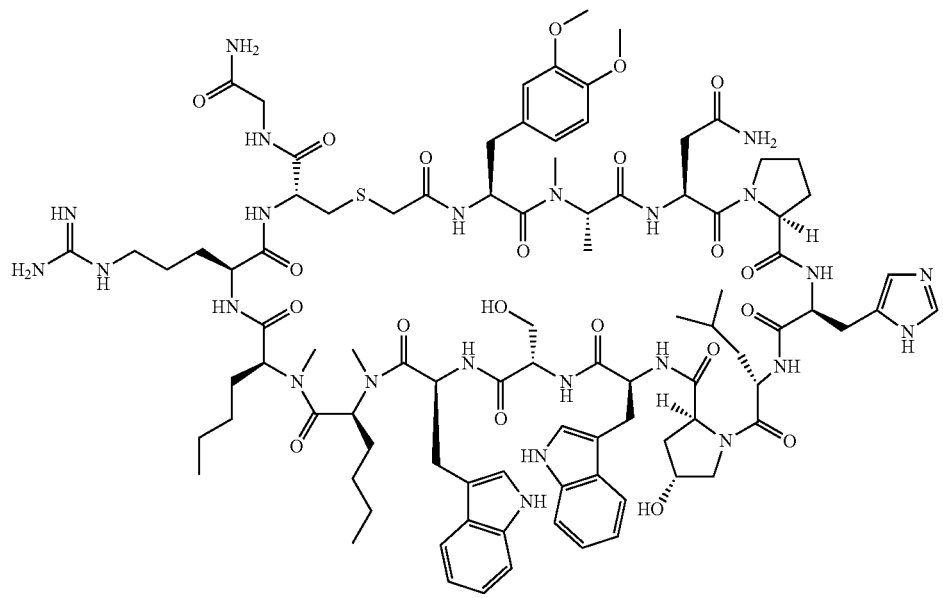 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(OC)c(OC)c2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 55-95% B over 30 minutes, then a 5-minute hold at 100% B; Flow: 20 mL/min. Fractions containing the desired product were combined and dried via centrifugal evaporation. The yield of the product was 22.3 mg, and its estimated purity by LCMS analysis was 96%.
Analysis condition A: Retention time=1.66 min; ESI-MS (+) m/z=978.2 (M+2H)
Analysis condition B: Retention time=2.80 min; ESI-MS (+) m/z=978.3 (M+2H)
ESI-HRMS(+) m/z Calculated 977.4933, Found 9774928 (M+2H).

Preparation of Example 7073

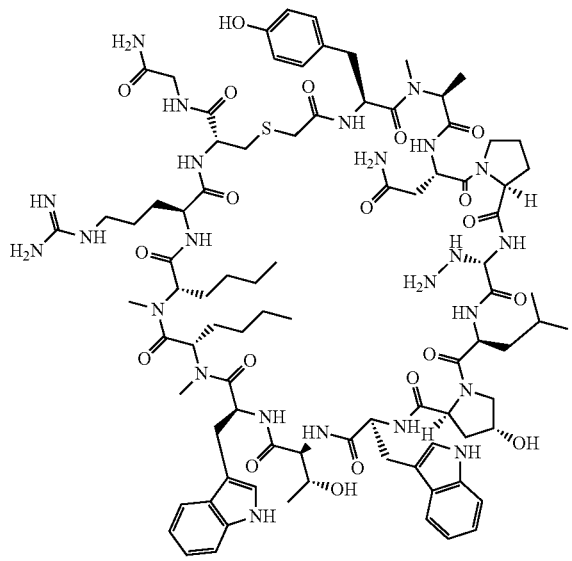 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](NN)C(=O)N[C@@H](CC(C)C)C(=O)N2C[C@H](O)C[C@H]2C(=O)N[C@@H](Cc2c[nH]c3ccccc23)C(=O)N[C@@H]([C@@H](C)O)C(=O)N[C@@H](Cc2c[nH]c3ccccc23)C(=O)N1C]

The crude material was purified via preparative LC/MS with the following conditions: Column: XBridge C18, 19×mm, 5-μm particles; Mobile Phase A: 5:95 methanol:water with 10-mM ammonium acetate; Mobile Phase B: 95:5 methanol:water with 10-mM ammonium acetate; Gradient: 30-70% B over 30 minutes, then a 5-minute hold at 100% B; Flow: 20 mL/min. Fractions containing the desired product were combined and dried via centrifugal evaporation. The yield of the product was 14.7 mg, and its estimated purity by LCMS analysis was 99%.

Analysis condition A: Retention time=1.50 min; ESI-MS (+) m/z=937.4 (M+2H)

Analysis condition B: Retention time=2.59 min; ESI-MS (+) m/z=937.7 (M+2H)

Preparation of Example 7075

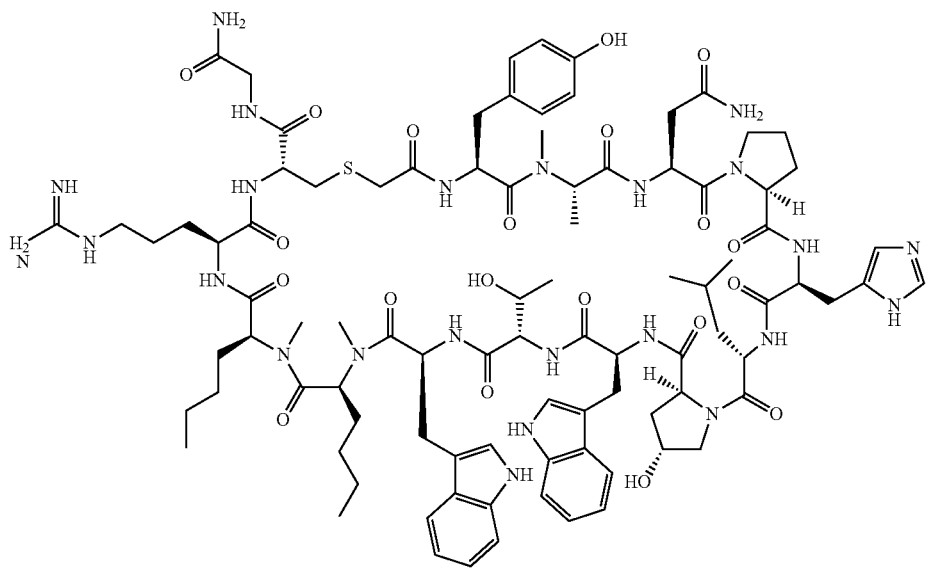 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](C(C)O)C(=O)N[C@@H](Cc2c[nH]c3ccccc23)C(=O)N1C]

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 25-65% B over 30 minutes, then a 5-minute hold at 100% B; Flow: 20 mL/min. Fractions containing the desired product were combined and dried via centrifugal evaporation. The yield of the product was 16.2 mg, and its estimated purity by LCMS analysis was 97%.

Analysis condition A: Retention time=1.50 min; ESI-MS (+) m/z=963.2 (M+2H)

Analysis condition B: Retention time=2.59 min; ESI-MS (+) m/z=963.6 (M+2H)

ESI-HRMS(+) m/z Calculated 962.4880, Found 962.4865 (M+2H).

Preparation of Example 7077

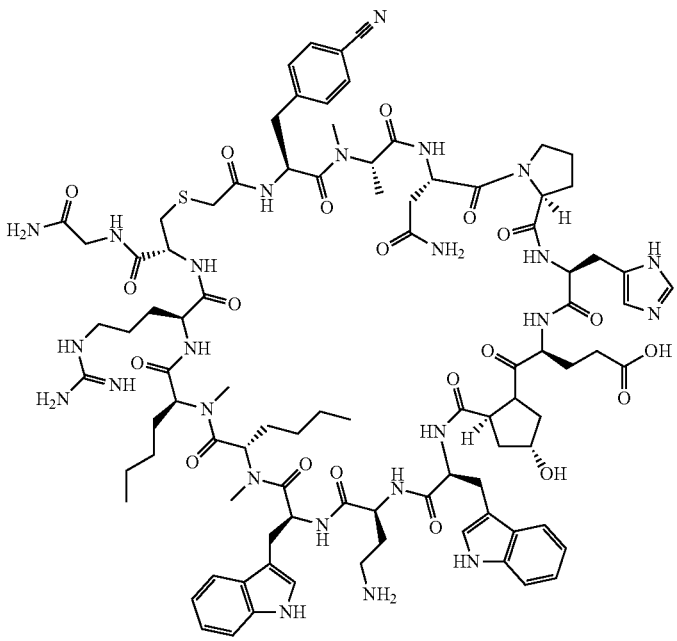 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(C#N)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CCC(=O)O)C(=O)C2C[C@H](O)C[C@H]2C(=O)N[C@@H](Cc2c[nH]c3ccccc23)C(=O)N[C@@H](CCN)C(=O)N[C@@H](Cc2c[nH]c3ccccc23)C(=O)N1C]

The crude material was purified via preparative LC/MS with the following conditions: Column: XBridge C18, 19×mm, 5-µm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 25.4 mg, and its estimated purity by LCMS analysis was 100%.

Analysis condition A: Retention time=1.43 min; ESI-MS (+) m/z=975.2 (M+2H)

Analysis condition B: Retention time=2.58 min; ESI-MS (+) m/z=975.1 (M+2H)

ESI-HRMS(+) m/z Calculated 974.4754, Found 974.4743 (M+2H).

Preparation of Example 7078

Preparation of Example 7079

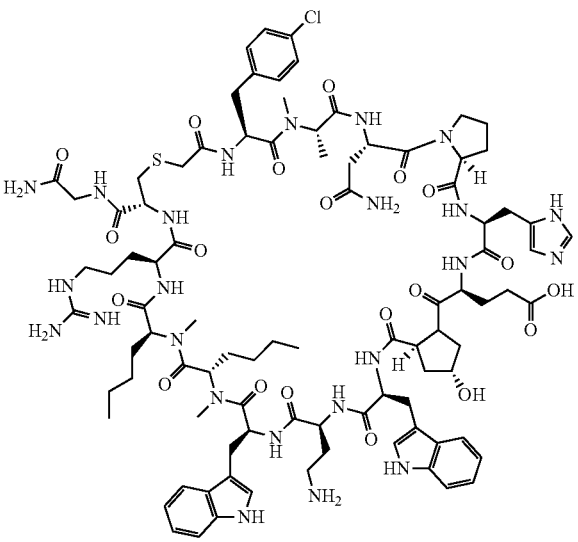

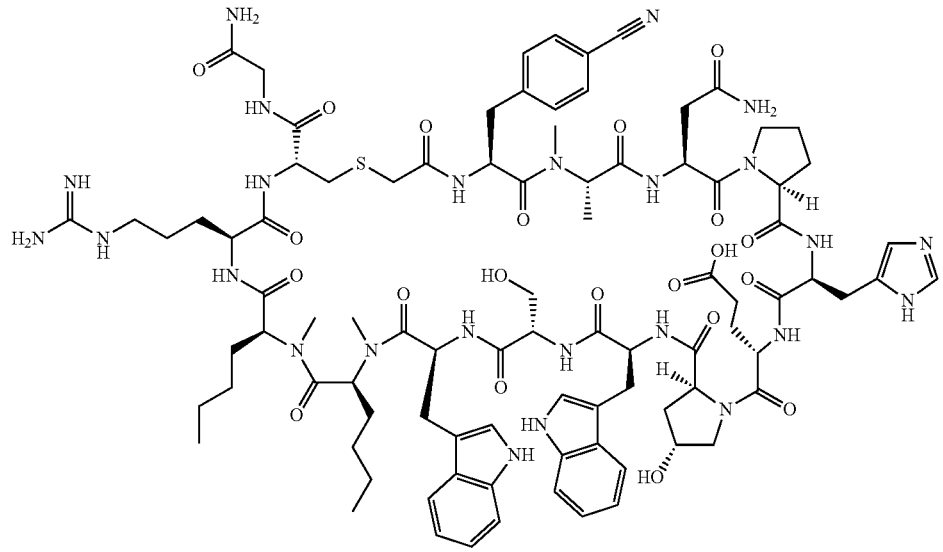 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(C#N)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CCC(=O)O)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 29.4 mg, and its estimated purity by LCMS analysis was 99%.

Analysis condition A: Retention time=1.63 min; ESI-MS (+) m/z=968.6 (M+2H)

Analysis condition B: Retention time=2.77 min; ESI-MS (+) m/z=968.6 (M+2H)

ESI-HRMS(+) m/z Calculated 967.9596, Found 967.9601 (M+2H).

The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-70% B over 30 minutes, then a 5-minute hold at 100% B; Flow: 20 mL/min. Fractions containing the desired product were combined and dried via centrifugal evaporation. The yield of the product was 30.1 mg, and its estimated purity by LCMS analysis was 100%.

Analysis condition A: Retention time=1.65 min; ESI-MS (+) m/z=979.6 (M+2H)

Analysis condition B: Retention time=2.89 min; ESI-MS (+) m/z=979.4 (M+2H)

ESI-HRMS(+) m/z Calculated 978.9583, Found 978.9560 (M+2H).

Preparation of Example 7080

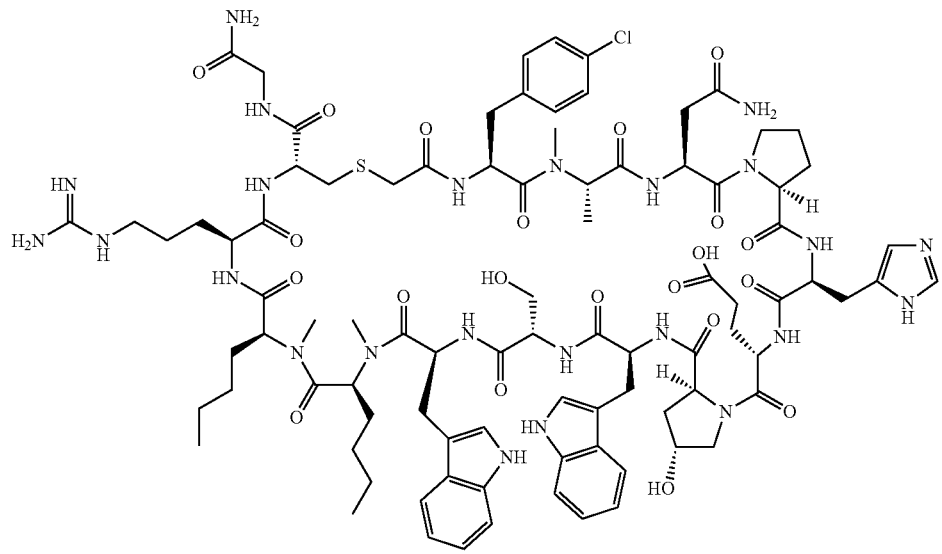 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(Cl)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CCC(=O)O)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 38.6 mg, and its estimated purity by LCMS analysis was 100%.

Analysis condition A: Retention time=1.86 min; ESI-MS (+) m/z=973.1 (M+2H)

Analysis condition B: Retention time=3.03 min; ESI-MS (+) m/z=973.6 (M+2H)

ESI-HRMS(+) m/z Calculated 972.4425, Found 972.4426 (M+2H).

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 55-95% B over 30 minutes, then a 5-minute hold at 100% B; Flow: 20 mL/min. Fractions containing the desired product were combined and dried via centrifugal evaporation. The yield of the product was 24.8 mg, and its estimated purity by LCMS analysis was 100%.

Analysis condition A: Retention time=1.59 min; ESI-MS (+) m/z=971.8 (M+2H)

Analysis condition B: Retention time=2.82 min; ESI-MS (+) m/z=971.6 (M+2H)

ESI-HRMS(+) m/z Calculated 970.9731, Found 970.9718 (M+2H).

Preparation of Example 7081

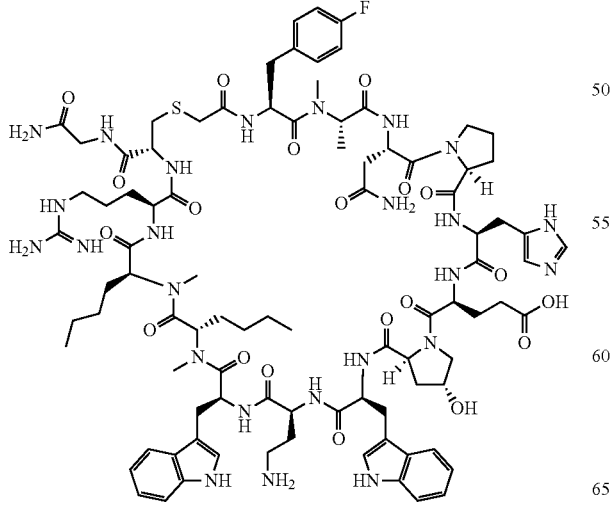

Preparation of Example 7082

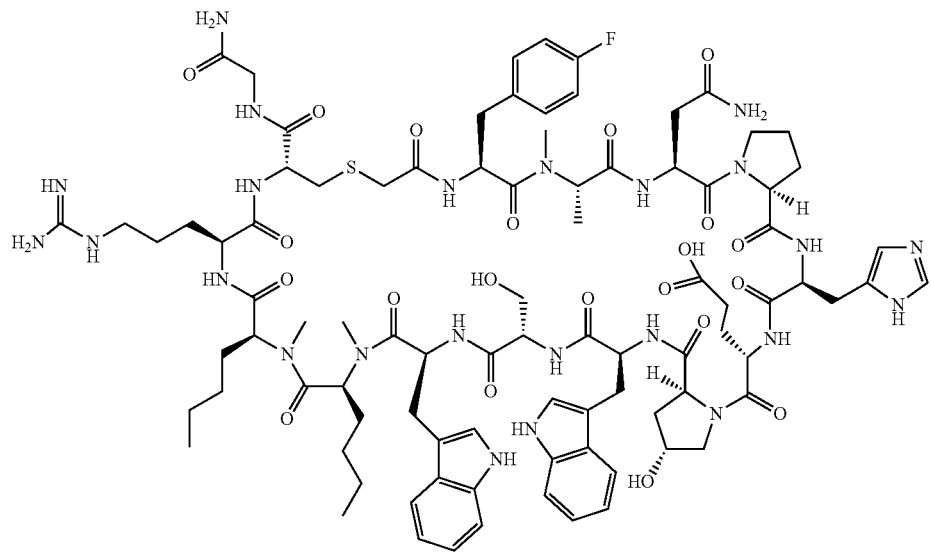 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(F)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CCC(=O)O)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 55-95% B over 30 minutes, then a 5-minute hold at 100% B; Flow: 20 mL/min. Fractions containing the desired product were combined and dried via centrifugal evaporation. The yield of the product was 21.1 mg, and its estimated purity by LCMS analysis was 100%.

Analysis condition A: Retention time=1.75 min; ESI-MS (+) m/z=965.2 (M+2H)

Analysis condition B: Retention time=2.95 min; ESI-MS (+) m/z=965.5 (M+2H)

ESI-HRMS(+) m/z Calculated 964.4572, Found 964.4570 (M+2H).

Preparation of Example 7083

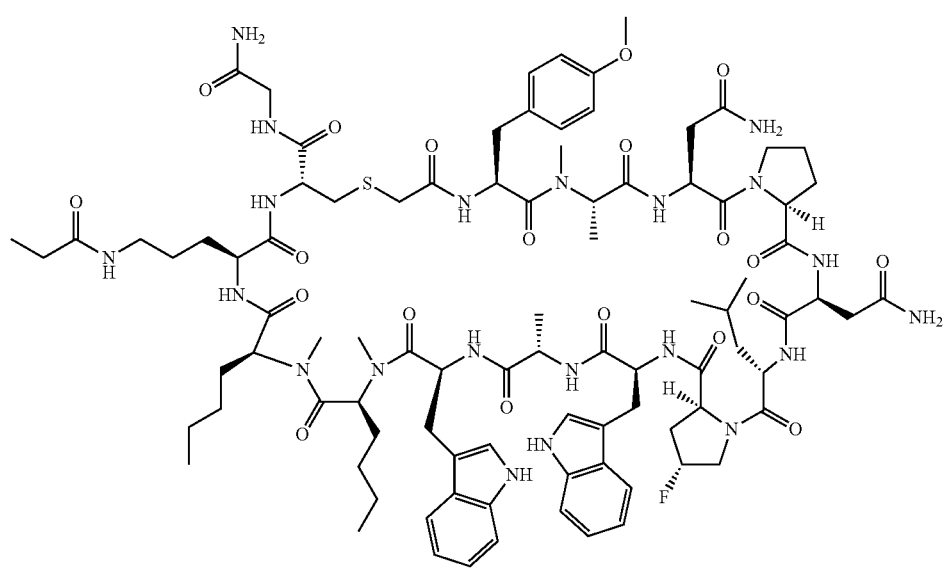 [SMILES: CCCC[C@H]1C(=O)N(C)[C@@H](CCCC)C(=O)N[C@@H](CCCNC(=O)CC)C(=O)N[C@H](C(=O)NCC(N)=O)CSCC(=O)N[C@@H](Cc2ccc(OC)cc2)C(=O)N(C)[C@@H](C)C(=O)N[C@@H](CC(N)=O)C(=O)N2CCC[C@H]2C(=O)N[C@@H](CC(N)=O)C(=O)N[C@@H](CC(C)C)C(=O)N2C[C@H](F)C[C@H]2C(=O)N[C@@H](Cc2c[nH]c3ccccc23)C(=O)N[C@@H](C)C(=O)N[C@@H](Cc2c[nH]c3ccccc23)C(=O)N1C]

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 5.0 mg, and its estimated purity by LCMS analysis was 100%.

Analysis condition A: Retention time=1.89 min; ESI-MS (+) m/z=951.5 (M+2H)

Analysis condition B: Retention time=3.00 min; ESI-MS (+) m/z=951.3 (M+2H)

ESI-HRMS(+) m/z Calculated 950.9826, Found 950.9820 (M+2H).

Preparation of Example 7084

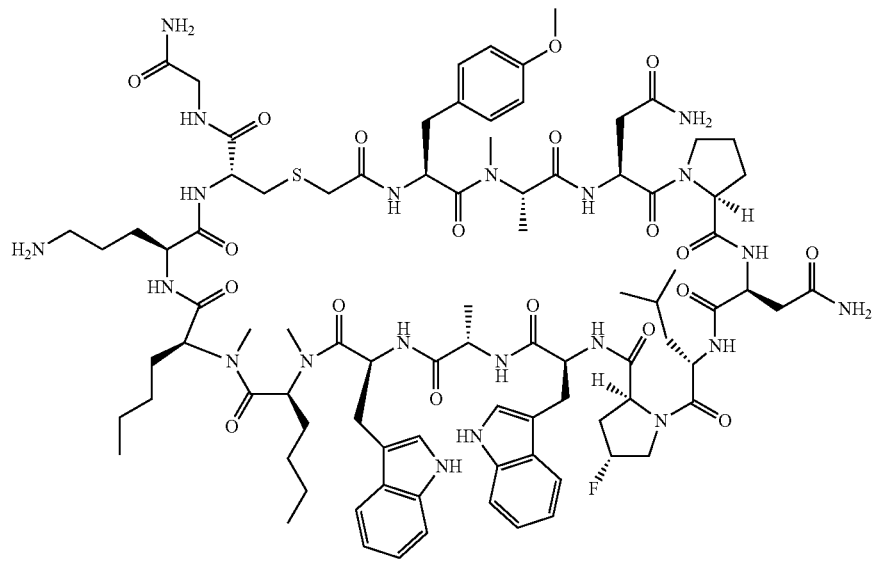 [SMILES: CCCC[C@H]1C(=O)N(C)[C@@H](CCCC)C(=O)N[C@@H](CCCN)C(=O)N[C@H](C(=O)NCC(N)=O)CSCC(=O)N[C@@H](Cc2ccc(OC)cc2)C(=O)N(C)[C@@H](C)C(=O)N[C@@H](CC(N)=O)C(=O)N2CCC[C@H]2C(=O)N[C@@H](CC(N)=O)C(=O)N[C@@H](CC(C)C)C(=O)N2C[C@H](F)C[C@H]2C(=O)N[C@@H](Cc2c[nH]c3ccccc23)C(=O)N[C@@H](C)C(=O)N[C@@H](Cc2c[nH]c3ccccc23)C(=O)N1C]

Preparation of Example 7085

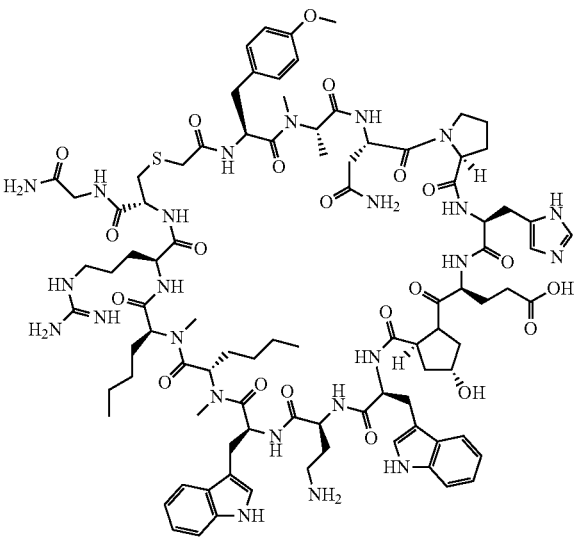 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(OC)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CCC(=O)O)C(=O)C2C[C@H](O)C[C@H]2C(=O)N[C@@H](Cc2c[nH]c3ccccc23)C(=O)N[C@@H](CCN)C(=O)N[C@@H](Cc2c[nH]c3ccccc23)C(=O)N1C]

The crude material was purified via preparative LC/MS with the following conditions: Column: XBridge C18, 5 μm, 19×200 mm, Mobile Phase A: 5:95 methanol:water with 10-mM ammonium acetate; Mobile Phase B: 95:5 methanol:water with 10-mM ammonium acetate; Gradient: 55-95% B over 30 minutes, then a 5-minute hold at 100% B; Flow: 20 mL/min. Fractions containing the desired product were combined and dried via centrifugal evaporation. The yield of the product was 10.9 mg, and its estimated purity by LCMS analysis was 100%.

Analysis condition A: Retention time=1.79 min; ESI-MS (+) m/z=923.6 (M+2H)

Analysis condition B: Retention time=2.92 min; ESI-MS (+) m/z=923.6 (M+2H)

ESI-HRMS(+) m/z Calculated 922.9695, Found 922.9695 (M+2H).

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 10.4 mg, and its estimated purity by LCMS analysis was 100%.

Analysis condition A: Retention time=1.60 min; ESI-MS (+) m/z=977.6 (M+2H)

Analysis condition B: Retention time=2.77 min; ESI-MS (+) m/z=977.8 (M+2H)

ESI-HRMS(+) m/z Calculated 976.9831, Found 976.9844 (M+2H).

Preparation of Example 7086

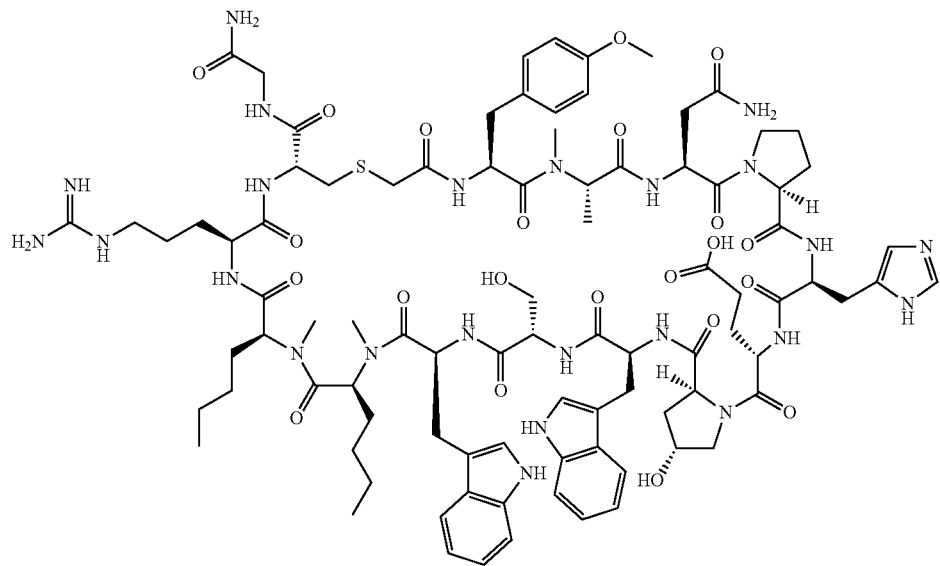 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(OC)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CCC(=O)O)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 13.2 mg, and its estimated purity by LCMS analysis was 96%.

Analysis condition A: Retention time=1.74 min; ESI-MS (+) m/z=971.0 (M+2H).

Analysis condition B: Retention time=2.89 min; ESI-MS (+) m/z=971.1 (M+2H).

ESI-HRMS(+) m/z Calculated 970.4672, Found 970.4671 (M+2H).

Preparation of Example 7087

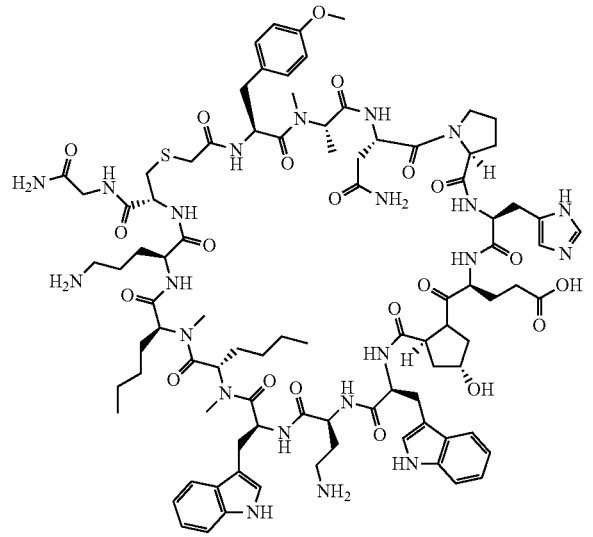 [SMILES: CCCC[C@H]1C(=O)N(C)[C@@H](CCCC)C(=O)N[C@@H](CCCN)C(=O)N[C@H](C(=O)NCC(N)=O)CSCC(=O)N[C@@H](Cc2ccc(OC)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CCC(=O)O)C(=O)C2C[C@H](O)C[C@H]2C(=O)N[C@@H](Cc2c[nH]c3ccccc23)C(=O)N[C@@H](CCN)C(=O)N[C@@H](Cc2c[nH]c3ccccc23)C(=O)N1C]

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-85% B over 30 minutes, then a 5-minute hold at 100% B; Flow: 20 mL/min. Fractions containing the desired product were combined and dried via centrifugal evaporation. The yield of the product was 13.2 mg, and its estimated purity by LCMS analysis was 96%.

Analysis condition A: Retention time=1.64 min; ESI-MS (+) m/z=957.6 (M+2H)

Analysis condition B: Retention time=2.93 min; ESI-MS (+) m/z=957.0 (M+2H)

ESI-HRMS(+) m/z Calculated 955.9722, Found 955.9700 (M+2H).

Preparation of Example 7088

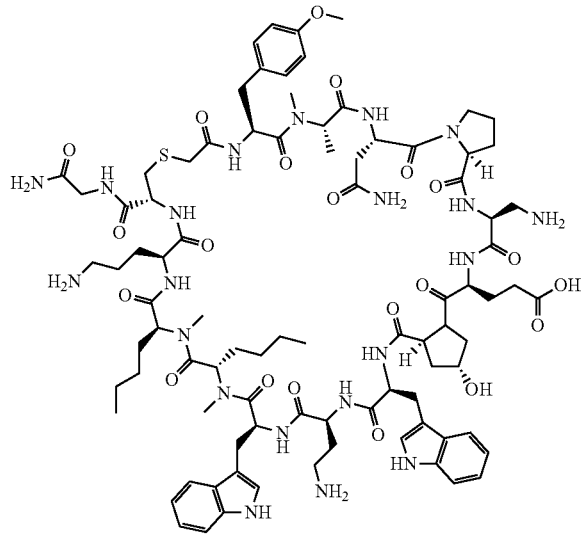 [SMILES: CCCC[C@H]1C(=O)N(C)[C@@H](CCCC)C(=O)N[C@@H](CCCN)C(=O)N[C@H](C(=O)NCC(N)=O)CSCC(=O)N[C@@H](Cc2ccc(OC)cc2)C(=O)N(C)[C@@H](C)C(=O)N[C@@H](CC(N)=O)C(=O)N2CCC[C@H]2C(=O)N[C@@H](CN)C(=O)N[C@@H](CCC(=O)O)C(=O)C2C[C@H](O)C[C@H]2C(=O)N[C@@H](Cc2c[nH]c3ccccc23)C(=O)N[C@@H](CCN)C(=O)N[C@@H](Cc2c[nH]c3ccccc23)C(=O)N1C]

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 30 minutes, then a 5-minute hold at 100% B; Flow: 20 mL/min. Fractions containing the desired product were combined and dried via centrifugal evaporation. The yield of the product was 33.1 mg, and its estimated purity by LCMS analysis was 100%.

Analysis condition A: Retention time=1.63 min; ESI-MS (+) m/z=931.3 (M+2H)

Analysis condition B: Retention time=3.01 min; ESI-MS (+) m/z=931.8 (M+2H).

Preparation of Example 7089

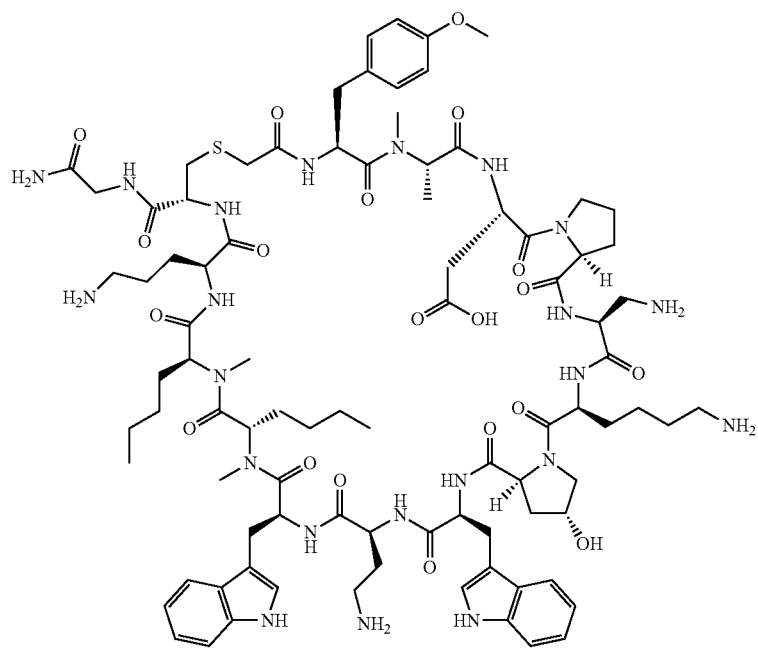 [SMILES: CCCC[C@H]1C(=O)N(C)[C@@H](CCCC)C(=O)N[C@@H](CCCN)C(=O)N[C@H](C(=O)NCC(N)=O)CSCC(=O)N[C@@H](Cc2ccc(OC)cc2)C(=O)N(C)[C@@H](C)C(=O)N[C@@H](CC(=O)O)C(=O)N2CCC[C@H]2C(=O)N[C@@H](CN)C(=O)N[C@@H](CCCCN)C(=O)N2C[C@H](O)C[C@H]2C(=O)N[C@@H](Cc2c[nH]c3ccccc23)C(=O)N[C@@H](CCN)C(=O)N[C@@H](Cc2c[nH]c3ccccc23)C(=O)N1C]

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 44.0 mg, and its estimated purity by LCMS analysis was 98%.

Analysis condition A: Retention time=1.50 min; ESI-MS (+) m/z=930.7 (M+2H)

Analysis condition B: Retention time=2.93 min; ESI-MS (+) m/z=930.6 (M+2H)

ESI-HRMS(+) m/z Calculated 929.9929, Found 929.9914 (M+2H).

Preparation of Example 7090

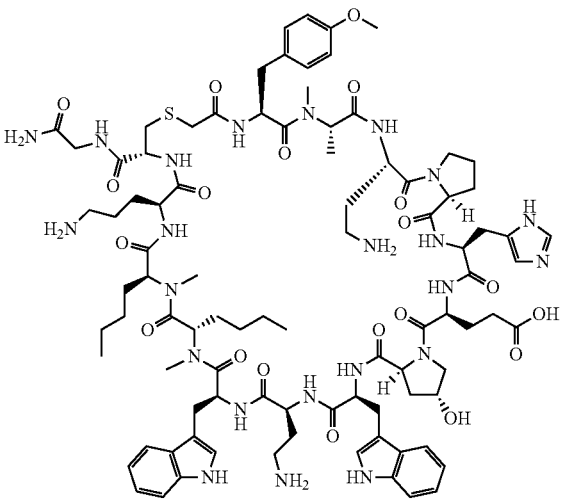 [SMILES: CCCC[C@H]1C(=O)N(C)[C@@H](CCCC)C(=O)N[C@@H](CCCN)C(=O)N[C@H](C(=O)NCC(N)=O)CSCC(=O)N[C@@H](Cc2ccc(OC)cc2)C(=O)N(C)[C@@H](C)C(=O)N[C@@H](CCN)C(=O)N2CCC[C@H]2C(=O)N[C@@H](Cc2cnc[nH]2)C(=O)N[C@@H](CCC(=O)O)C(=O)N2C[C@H](O)C[C@H]2C(=O)N[C@@H](Cc2c[nH]c3ccccc23)C(=O)N[C@@H](CCN)C(=O)N[C@@H](Cc2c[nH]c3ccccc23)C(=O)N1C]

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-85% B over 30 minutes, then a 5-minute hold at 100% B; Flow: 20 mL/min. Fractions containing the desired product were combined and dried via centrifugal evaporation. The yield of the product was 38.9 mg, and its estimated purity by LCMS analysis was 96%.

Analysis condition A: Retention time=1.58 min; ESI-MS (+) m/z=949.9 (M+2H)

Analysis condition B: Retention time=2.81 min; ESI-MS (+) m/z=949.6 (M+2H)

ESI-HRMS(+) m/z Calculated 948.9825, Found 948.9801 (M+2H).

Preparation of Example 7091

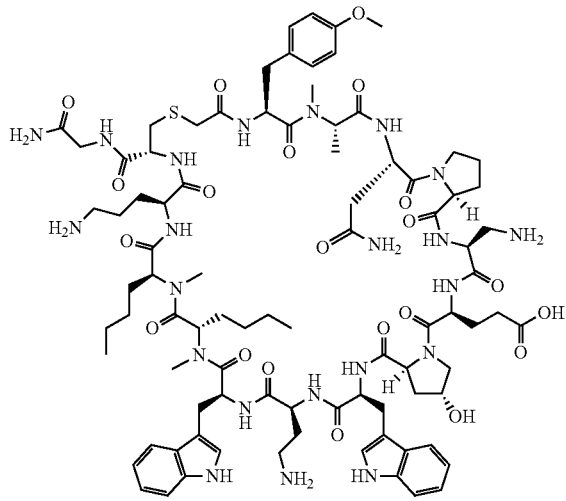 [SMILES: CCCC[C@H]1C(=O)N(C)[C@@H](CCCC)C(=O)N[C@@H](CCCN)C(=O)N[C@H](C(=O)NCC(N)=O)CSCC(=O)N[C@@H](Cc2ccc(OC)cc2)C(=O)N(C)[C@@H](C)C(=O)N[C@@H](CC(N)=O)C(=O)N2CCC[C@H]2C(=O)N[C@@H](CN)C(=O)N[C@@H](CCC(=O)O)C(=O)N2C[C@H](O)C[C@H]2C(=O)N[C@@H](Cc2c[nH]c3ccccc23)C(=O)N[C@@H](CCN)C(=O)N[C@@H](Cc2c[nH]c3ccccc23)C(=O)N1C]

The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 45-90% B over 30 minutes, then a 5-minute hold at 100% B; Flow: 20 mL/min. Fractions containing the desired product were combined and dried via centrifugal evaporation. The yield of the product was 41.3 mg, and its estimated purity by LCMS analysis was 99%.

Analysis condition A: Retention time=1.59 min; ESI-MS (+) m/z=931.1 (M+2H)

Analysis condition B: Retention time=2.81 min; ESI-MS (+) m/z=931.4 (M+2H)

ESI-HRMS(+) m/z Calculated 930.4667, Found 930.4647 (M+2H).

Preparation of Example 7092

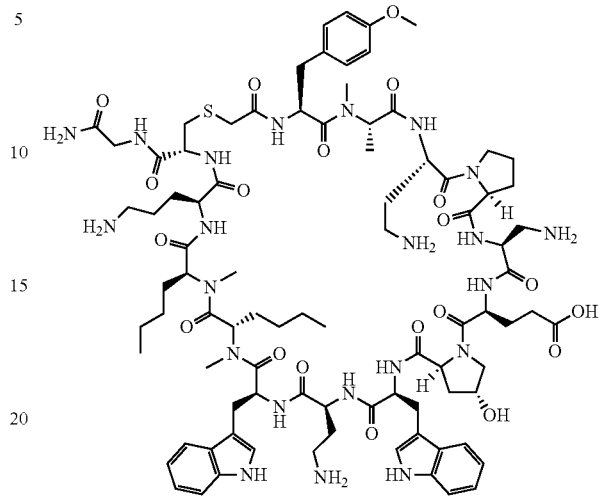

The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 40-85% B over 30 minutes, then a 5-minute hold at 100% B; Flow: 20 mL/min. Fractions containing the desired product were combined and dried via centrifugal evaporation. The yield of the product was 49.5 mg, and its estimated purity by LCMS analysis was 99%.

Analysis condition A: Retention time=1.47 min; ESI-MS (+) m/z=924.1 (M+2H)

Analysis condition B: Retention time=2.78 min; ESI-MS (+) m/z=924.2 (M+2H)

ESI-HRMS(+) m/z Calculated 923.4771, Found 923.4752 (M+2H).

Preparation of Example 7093

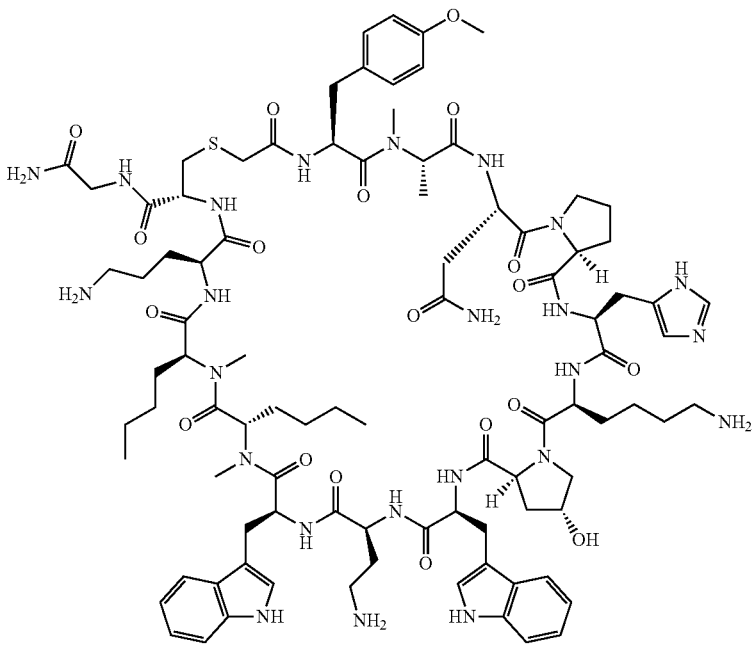 [SMILES: CCCC[C@H]1C(=O)N(C)[C@@H](CCCC)C(=O)N[C@@H](CCCN)C(=O)N[C@H](C(=O)NCC(N)=O)CSCC(=O)N[C@@H](Cc2ccc(OC)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CCCCN)C(=O)N2C[C@H](O)C[C@H]2C(=O)N[C@@H](Cc2c[nH]c3ccccc23)C(=O)N[C@@H](CCN)C(=O)N[C@@H](Cc2c[nH]c3ccccc23)C(=O)N1C]

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-85% B over 30 minutes, then a 5-minute hold at 100% B; Flow: 20 mL/min. Fractions containing the desired product were combined and dried via centrifugal evaporation. The yield of the product was 30.7 mg, and its estimated purity by LCMS analysis was 100%.

Analysis condition A: Retention time=1.55 min; ESI-MS (+) m/z=956.6 (M+2H)

Analysis condition B: Retention time=2.91 min; ESI-MS (+) m/z=956.2 (M+2H)

ESI-HRMS(+) m/z Calculated 955.4983, Found 955.4978 (M+2H).

Preparation of Example 7094

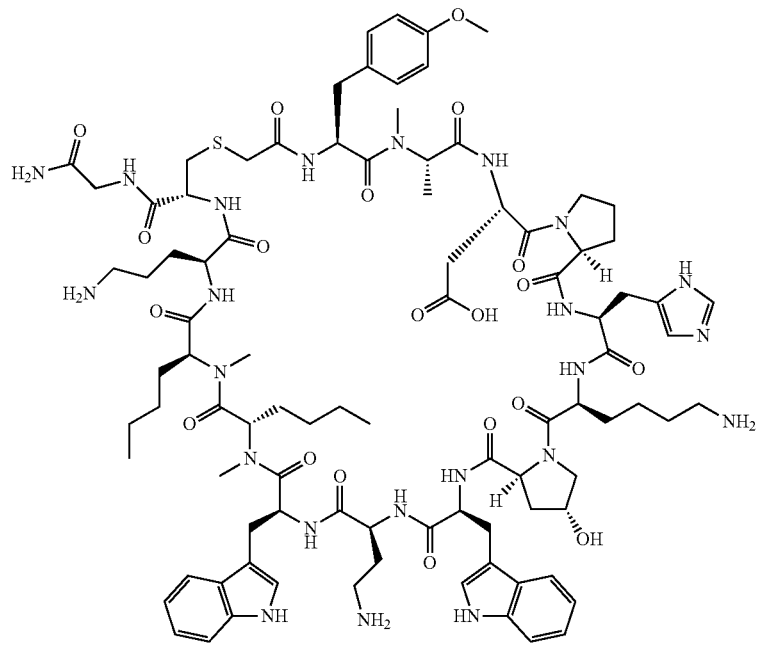 [SMILES: CCCC[C@H]1C(=O)N(C)[C@@H](CCCC)C(=O)N[C@@H](CCCN)C(=O)N[C@H](C(=O)NCC(N)=O)CSCC(=O)N[C@@H](Cc2ccc(OC)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CCCCN)C(=O)N2C[C@H](O)C[C@H]2C(=O)N[C@@H](Cc2c[nH]c3ccccc23)C(=O)N[C@@H](CCN)C(=O)N[C@@H](Cc2c[nH]c3ccccc23)C(=O)N1C]

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 39.2 mg, and its estimated purity by LCMS analysis was 100%.

Analysis condition A: Retention time=1.52 min; ESI-MS (+) m/z=956.6 (M+2H)

Analysis condition B: Retention time=2.93 min; ESI-MS (+) m/z=956.7 (M+2H).

Preparation of Example 7095

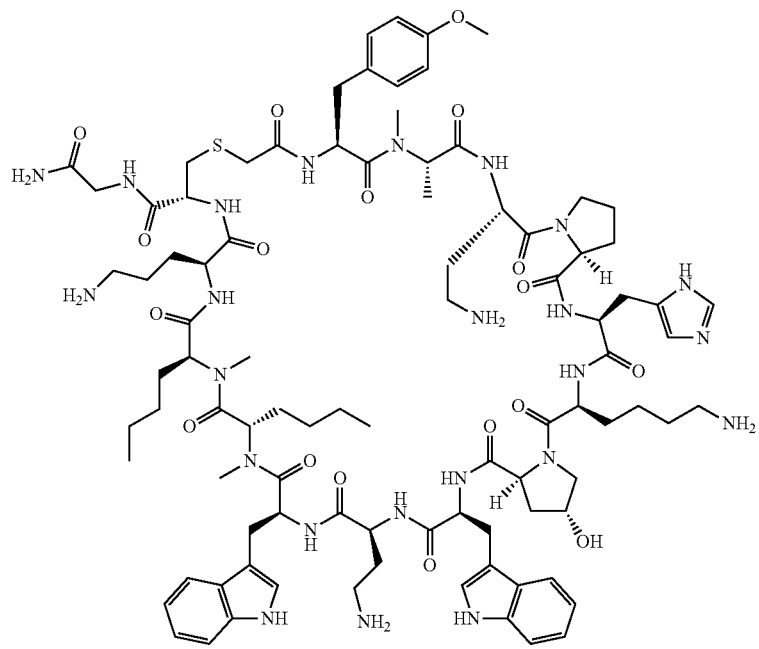 [SMILES: CCCC[C@H]1C(=O)N(C)[C@@H](CCCC)C(=O)N[C@@H](CCCN)C(=O)N[C@H](C(=O)NCC(N)=O)CSCC(=O)N[C@@H](Cc2ccc(OC)cc2)C(=O)N(C)[C@@H](C)C(=O)N[C@@H](CCN)C(=O)N2CCC[C@H]2C(=O)N[C@@H](Cc2cnc[nH]2)C(=O)N[C@@H](CCCCN)C(=O)N2C[C@H](O)C[C@H]2C(=O)N[C@@H](Cc2c[nH]c3ccccc23)C(=O)N[C@@H](CCN)C(=O)N[C@@H](Cc2c[nH]c3ccccc23)C(=O)N1C]

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 35.6 mg, and its estimated purity by LCMS analysis was 98%.

Analysis condition C1: Retention time=1.31 min; ESI-MS(+) m/z=948.7 (M+2H)

Analysis condition D1: Retention time=3.48 min; ESI-MS (+) m/z=948.8 (M+2H)

ESI-HRMS(+) m/z Calculated 948.5087, Found 948.5072 (M+2H).

Preparation of Example 7096

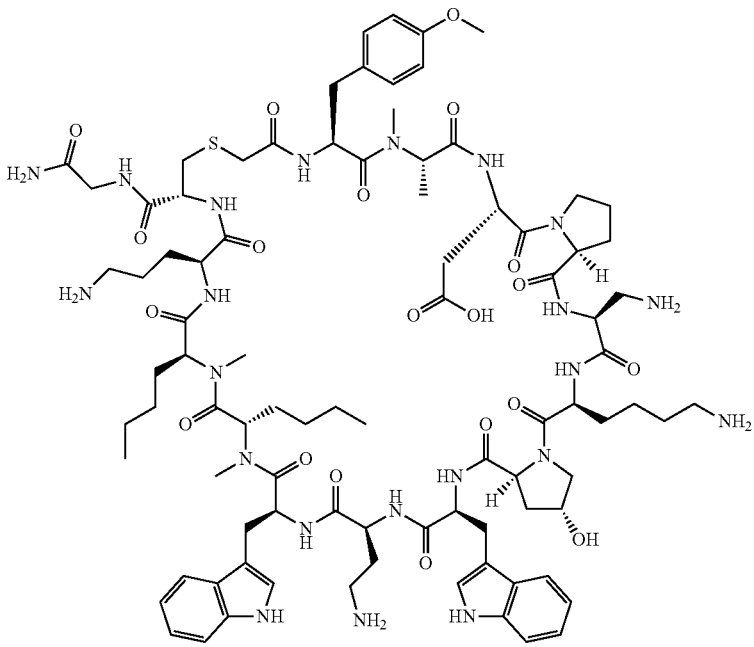 [SMILES: CCCC[C@H]1C(=O)N(C)[C@@H](CCCC)C(=O)N[C@@H](CCCN)C(=O)N[C@H](C(=O)NCC(N)=O)CSCC(=O)N[C@@H](Cc2ccc(OC)cc2)C(=O)N(C)[C@@H](C)C(=O)N[C@@H](CC(=O)O)C(=O)N2CCC[C@H]2C(=O)N[C@@H](CN)C(=O)N[C@@H](CCCCN)C(=O)N2C[C@H](O)C[C@H]2C(=O)N[C@@H](Cc2c[nH]c3ccccc23)C(=O)N[C@@H](CCN)C(=O)N[C@@H](Cc2c[nH]c3ccccc23)C(=O)N1C]

The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 28.8 mg, and its estimated purity by LCMS analysis was 96%.

Analysis condition A: Retention time=1.59 min; ESI-MS (+) m/z=931.5 (M+2H)

Analysis condition B: Retention time=3.03 min; ESI-MS (+) m/z=931.1 (M+2H).

Preparation of Example 7097

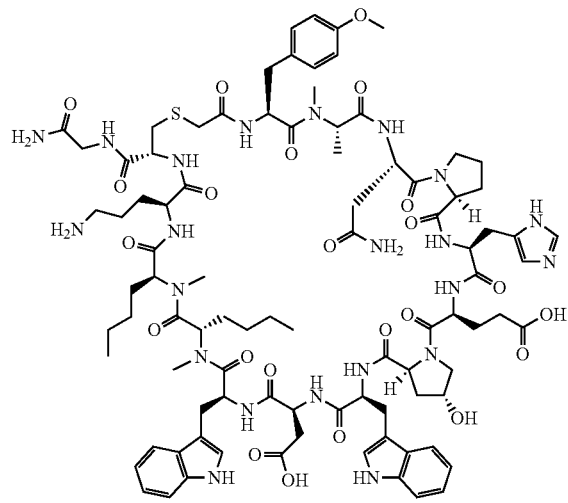 [SMILES: CCCC[C@H]1C(=O)N(C)[C@@H](CCCC)C(=O)N[C@@H](CCCN)C(=O)N[C@H](C(=O)NCC(N)=O)CSCC(=O)N[C@@H](Cc2ccc(OC)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CCC(=O)O)C(=O)N2C[C@H](O)C[C@H]2C(=O)N[C@@H](Cc2c[nH]c3ccccc23)C(=O)N[C@@H](CC(=O)O)C(=O)N[C@@H](Cc2c[nH]c3ccccc23)C(=O)N1C]

The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 50-100% B over 30 minutes, then a 5-minute hold at 100% B; Flow: 20 mL/min. Fractions containing the desired product were combined and dried via centrifugal evaporation. The yield of the product was 26.7 mg, and its estimated purity by LCMS analysis was 100%.

Analysis condition A: Retention time=1.64 min; ESI-MS (+) m/z=964.3 (M+2H)

Analysis condition B: Retention time=2.96 min; ESI-MS (+) m/z=964.2 (M+2H)

ESI-HRMS(+) m/z Calculated 963.4538, Found 963.4514 (M+2H).

Preparation of Example 7098

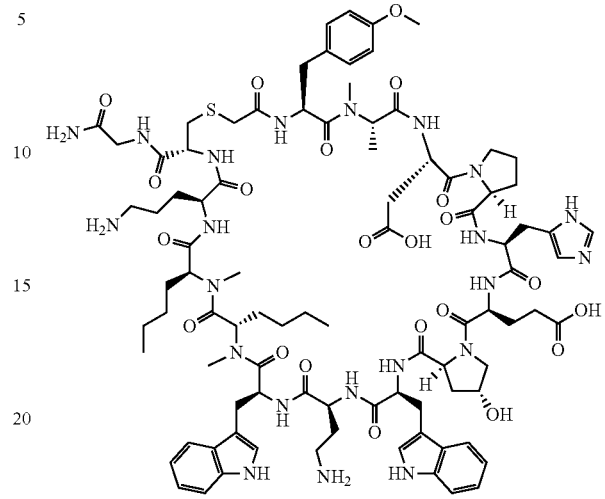

The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 40-85% B over 30 minutes, then a 5-minute hold at 100% B; Flow: 20 mL/min. Fractions containing the desired product were combined and dried via centrifugal evaporation. The yield of the product was 31.7 mg, and its estimated purity by LCMS analysis was 100%.

Analysis condition A: Retention time=1.52 min; ESI-MS (+) m/z=957.6 (M+2H)

Analysis condition B: Retention time=2.79 min; ESI-MS (+) m/z=957.0 (M+2H)

ESI-HRMS(+) m/z Calculated 956.4642, Found 956.4646 (M+2H).

Preparation of Example 7099

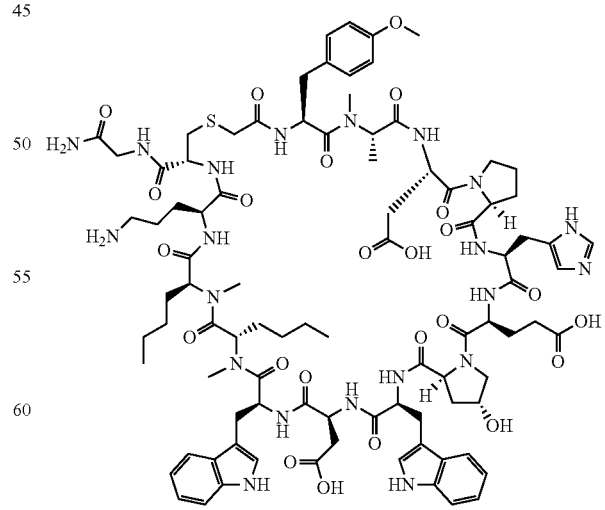

The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 60-100% B over 30 minutes, then a 5-minute hold at 100% B; Flow: 20 mL/min. Fractions containing the desired product were combined and dried via centrifugal evaporation. The yield of the product was 21.1 mg, and its estimated purity by LCMS analysis was 100%.

Analysis condition A: Retention time=1.65 min; ESI-MS (+) m/z=964.5 (M+2H)

Analysis condition B: Retention time=2.93 min; ESI-MS (+) m/z=964.5 (M+2H)

ESI-HRMS(+) m/z Calculated 963.9458, Found 963.9441 (M+2H).

Preparation of Example 7100

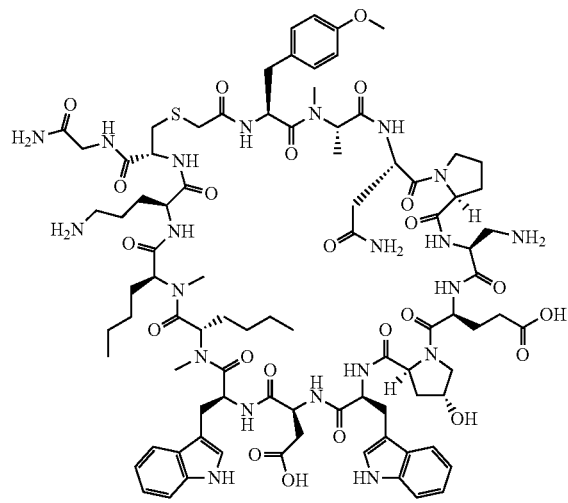

The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-70% B over 30 minutes, then a 5-minute hold at 100% B; Flow: 20 mL/min. Fractions containing the desired product were combined and dried via centrifugal evaporation. The yield of the product was 31.8 mg, and its estimated purity by LCMS analysis was 100%.

Analysis condition A: Retention time=1.70 min; ESI-MS (+) m/z=938.7 (M+2H)

Analysis condition B: Retention time=2.99 min; ESI-MS (+) m/z=938.9 (M+2H)

ESI-HRMS(+) m/z Calculated 937.9483, Found 937.9466 (M+2H).

Preparation of Example 7101

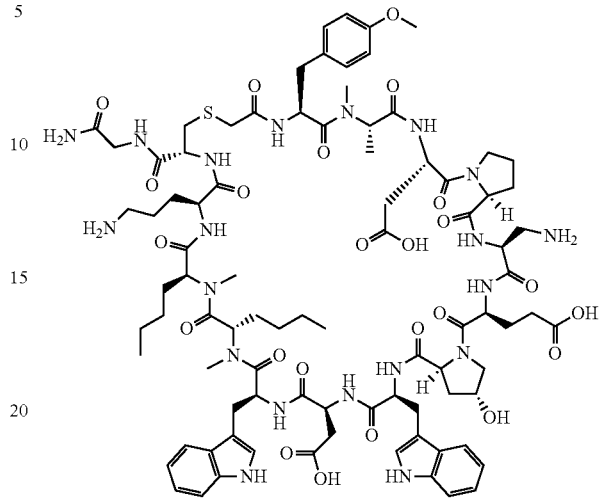

The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 32.4 mg, and its estimated purity by LCMS analysis was 98%.

Analysis condition A: Retention time=1.66 min; ESI-MS (+) m/z=939.1 (M+2H)

Analysis condition B: Retention time=2.98 min; ESI-MS (+) m/z=939.1 (M+2H)

ESI-HRMS(+) m/z Calculated 938.4404, Found 938.4387 (M+2H).

Preparation of Example 7102

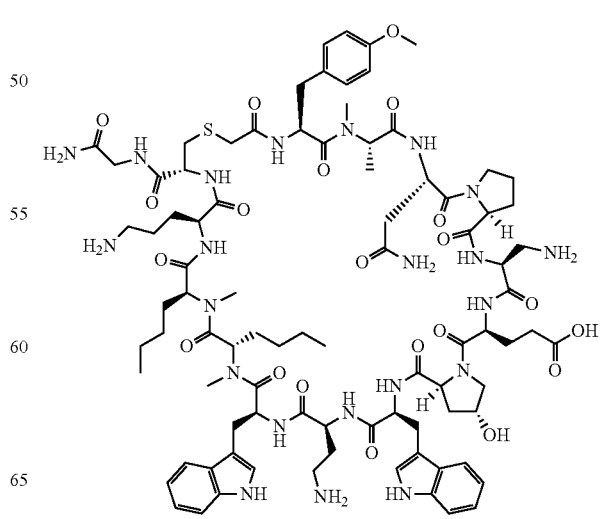

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 39.3 mg, and its estimated purity by LCMS analysis was 100%.

Analysis condition A: Retention time=1.58 min; ESI-MS (+) m/z=938.9 (M+2H)

Analysis condition B: Retention time=2.84 min; ESI-MS (+) m/z=938.6 (M+2H)

ESI-HRMS(+) m/z Calculated 937.9483, Found 937.9471 (M+2H).

Preparation of Example 7103

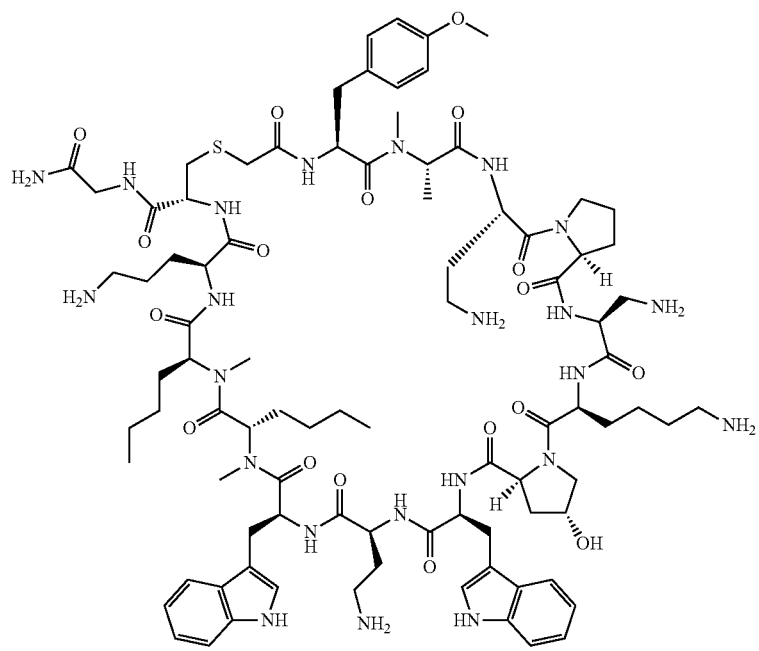 [SMILES: CCCC[C@H]1C(=O)N(C)[C@@H](CCCC)C(=O)N[C@@H](CCCN)C(=O)N[C@H](C(=O)NCC(N)=O)CSCC(=O)N[C@@H](Cc2ccc(OC)cc2)C(=O)N(C)[C@@H](C)C(=O)N[C@@H](CCN)C(=O)N2CCC[C@H]2C(=O)N[C@@H](CN)C(=O)N[C@@H](CCCCN)C(=O)N2C[C@H](O)C[C@H]2C(=O)N[C@@H](Cc2c[nH]c3ccccc23)C(=O)N[C@@H](CCN)C(=O)N[C@@H](Cc2c[nH]c3ccccc23)C(=O)N1C]

Preparation of Example 7104

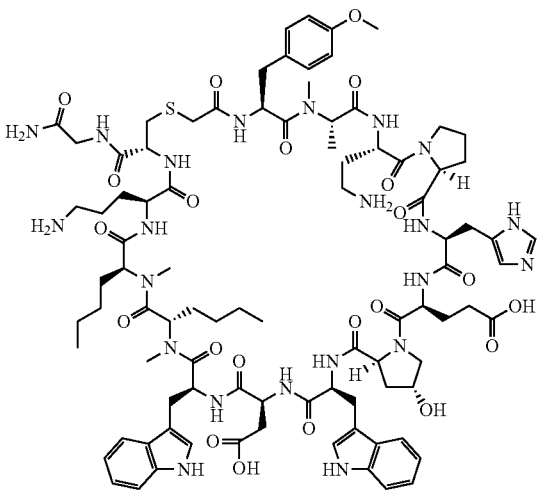 [SMILES: CCCC[C@H]1C(=O)N(C)[C@@H](CCCC)C(=O)N[C@@H](CCCN)C(=O)N[C@H](C(=O)NCC(N)=O)CSCC(=O)N[C@@H](Cc2ccc(OC)cc2)C(=O)N(C)[C@@H](C)C(=O)N[C@@H](CCN)C(=O)N2CCC[C@H]2C(=O)N[C@@H](Cc2cnc[nH]2)C(=O)N[C@@H](CCC(=O)O)C(=O)N2C[C@H](O)C[C@H]2C(=O)N[C@@H](Cc2c[nH]c3ccccc23)C(=O)N[C@@H](CC(=O)O)C(=O)N[C@@H](Cc2c[nH]c3ccccc23)C(=O)N1C]

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 29.4 mg, and its estimated purity by LCMS analysis was 99%.

Analysis condition C1: Retention time=1.28 min; ESI-MS(+) m/z=923.4 (M+2H)

Analysis condition D1: Retention time=2.77 min; ESI-MS (+) m/z=923.3 (M+2H)

ESI-HRMS(+) m/z Calculated 923.0033, Found 923.0011 (M+2H).

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 55-100% B over 30 minutes, then a 5-minute hold at 100% B; Flow: 20 mL/min. Fractions containing the desired product were combined and dried via centrifugal evaporation. The yield of the product was 40.6 mg, and its estimated purity by LCMS analysis was 95%.

Analysis condition A: Retention time=1.60 min; ESI-MS (+) m/z=957.0 (M+2H)

Analysis condition B: Retention time=2.91 min; ESI-MS (+) m/z=957.1 (M+2H)

ESI-HRMS(+) m/z Calculated 956.4642, Found 956.4623 (M+2H).

Preparation of Example 7105

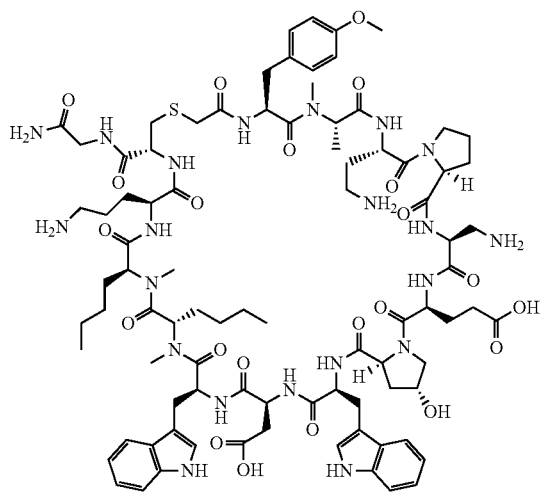 [SMILES: CCCC[C@H]1C(=O)N(C)[C@@H](CCCC)C(=O)N[C@@H](CCCN)C(=O)N[C@H](C(=O)NCC(N)=O)CSCC(=O)N[C@@H](Cc2ccc(OC)cc2)C(=O)N(C)[C@@H](C)C(=O)N[C@@H](CCN)C(=O)N2CCC[C@H]2C(=O)N[C@@H](CN)C(=O)N[C@@H](CCC(=O)O)C(=O)N2C[C@H](O)C[C@H]2C(=O)N[C@@H](Cc2c[nH]c3ccccc23)C(=O)N[C@@H](CC(=O)O)C(=O)N[C@@H](Cc2c[nH]c3ccccc23)C(=O)N1C]

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 30.7 mg, and its estimated purity by LCMS analysis was 100%.

Analysis condition A: Retention time=1.55 min; ESI-MS (+) m/z=931.6 (M+2H)

Analysis condition B: Retention time=2.87 min; ESI-MS (+) m/z=931.8 (M+2H)

ESI-HRMS(+) m/z Calculated 930.9587, Found 930.9573 (M+2H).

Preparation of Example 7106

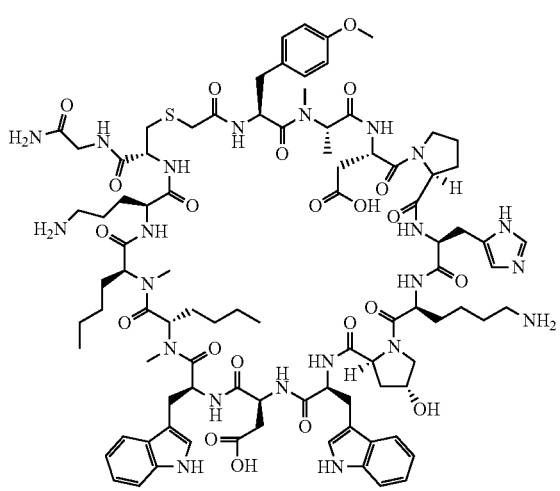 [SMILES: CCCC[C@H]1C(=O)N(C)[C@@H](CCCC)C(=O)N[C@@H](CCCN)C(=O)N[C@H](C(=O)NCC(N)=O)CSCC(=O)N[C@@H](Cc2ccc(OC)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CCCCN)C(=O)N2C[C@H](O)C[C@H]2C(=O)N[C@@H](Cc2c[nH]c3ccccc23)C(=O)N[C@@H](CC(=O)O)C(=O)N[C@@H](Cc2c[nH]c3ccccc23)C(=O)N1C]

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 33.1 mg, and its estimated purity by LCMS analysis was 100%.

Analysis condition A: Retention time=1.68 min; ESI-MS (+) m/z=964.0 (M+2H)

Analysis condition B: Retention time=2.99 min; ESI-MS (+) m/z=964.2 (M+2H)

ESI-HRMS(+) m/z Calculated 963.4720, Found 963.4704 (M+2H).

Preparation of Example 7107

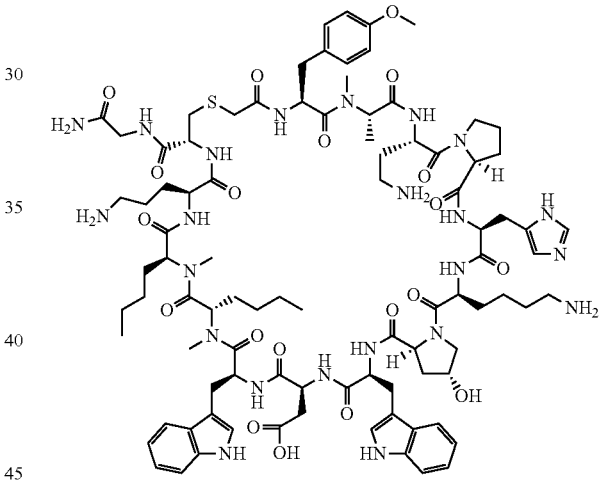

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 36.1 mg, and its estimated purity by LCMS analysis was 100%.

Analysis condition A: Retention time=1.45 min; ESI-MS (+) m/z=956.5 (M+2H)

Analysis condition B: Retention time=2.74 min; ESI-MS (+) m/z=956.6 (M+2H)

ESI-HRMS(+) m/z Calculated 955.9903, Found 955.9890 (M+2H).

Preparation of Example 7108

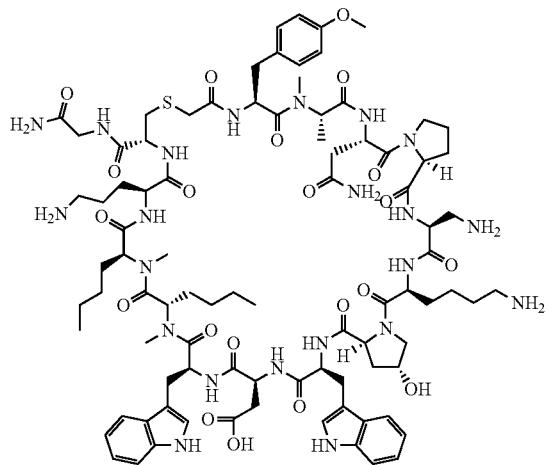 [SMILES: CCCC[C@H]1C(=O)N(C)[C@@H](CCCC)C(=O)N[C@@H](CCCN)C(=O)N[C@H](C(=O)NCC(N)=O)CSCC(=O)N[C@@H](Cc2ccc(OC)cc2)C(=O)N(C)[C@@H](C)C(=O)N[C@@H](CC(N)=O)C(=O)N2CCC[C@H]2C(=O)N[C@@H](CN)C(=O)N[C@@H](CCCCN)C(=O)N2C[C@H](O)C[C@H]2C(=O)N[C@@H](Cc2c[nH]c3ccccc23)C(=O)N[C@@H](CC(=O)O)C(=O)N[C@@H](Cc2c[nH]c3ccccc23)C(=O)N1C]

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 41.4 mg, and its estimated purity by LCMS analysis was 100%.

Analysis condition A: Retention time=1.64 min; ESI-MS (+) m/z=938.2 (M+2H)

Analysis condition B: Retention time=2.94 min; ESI-MS (+) m/z=938.5 (M+2H)

ESI-HRMS(+) m/z Calculated 937.4745, Found 937.4723 (M+2H).

Preparation of Example 7109

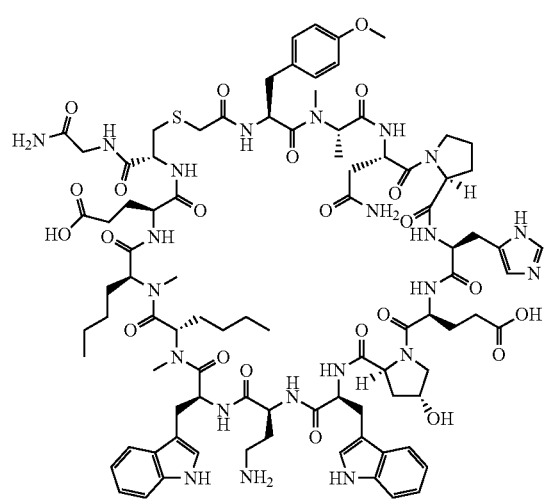 [SMILES: CCCC[C@H]1C(=O)N(C)[C@@H](CCCC)C(=O)N[C@@H](CCC(=O)O)C(=O)N[C@H](C(=O)NCC(N)=O)CSCC(=O)N[C@@H](Cc2ccc(OC)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CCC(=O)O)C(=O)N2C[C@H](O)C[C@H]2C(=O)N[C@@H](Cc2c[nH]c3ccccc23)C(=O)N[C@@H](CCN)C(=O)N[C@@H](Cc2c[nH]c3ccccc23)C(=O)N1C]

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 36.6 mg, and its estimated purity by LCMS analysis was 100%.

Analysis condition A: Retention time=1.59 min; ESI-MS (+) m/z=964.0 (M+2H)

Analysis condition B: Retention time=2.83 min; ESI-MS (+) m/z=964.1 (M+2H)

ESI-HRMS(+) m/z Calculated 963.4538, Found 963.4521 (M+2H).

Preparation of Example 7110

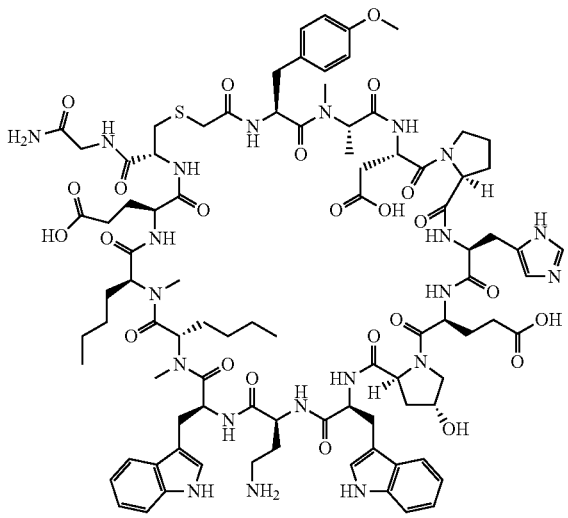

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 41.4 mg, and its estimated purity by LCMS analysis was 100%.

Analysis condition A: Retention time=1.48 min; ESI-MS (+) m/z=964.6 (M+2H)

Analysis condition B: Retention time=2.74 min; ESI-MS (+) m/z=964.6 (M+2H)

ESI-HRMS(+) m/z Calculated 963.9458, Found 963.9432 (M+2H).

Preparation of Example 7111

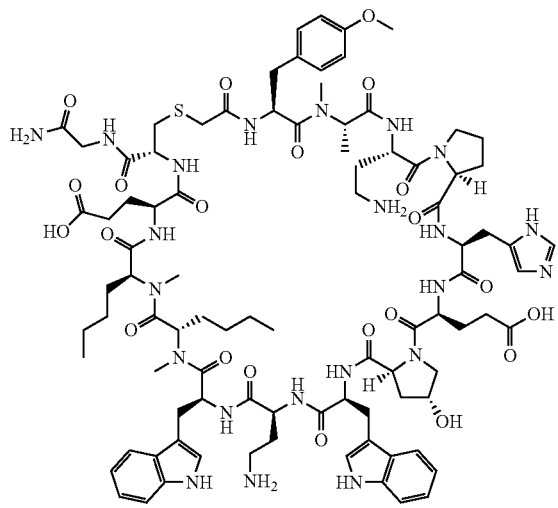 [SMILES: CCCC[C@H]1C(=O)N(C)[C@@H](CCCC)C(=O)N[C@@H](CCC(=O)O)C(=O)N[C@H](C(=O)NCC(N)=O)CSCC(=O)N[C@@H](Cc2ccc(OC)cc2)C(=O)N(C)[C@@H](C)C(=O)N[C@@H](CCN)C(=O)N2CCC[C@H]2C(=O)N[C@@H](Cc2cnc[nH]2)C(=O)N[C@@H](CCC(=O)O)C(=O)N2C[C@H](O)C[C@H]2C(=O)N[C@@H](Cc2c[nH]c3ccccc23)C(=O)N[C@@H](CCN)C(=O)N[C@@H](Cc2c[nH]c3ccccc23)C(=O)N1C]

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and re-purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 24.3 mg, and its estimated purity by LCMS analysis was 100%.

Analysis condition A: Retention time=1.52 min; ESI-MS (+) m/z=957.3 (M+2H)

Analysis condition B: Retention time=2.80 min; ESI-MS (+) m/z=957.0 (M+2H)

ESI-HRMS(+) m/z Calculated 956.4642, Found 956.4619 (M+2H).

Preparation of Example 7112

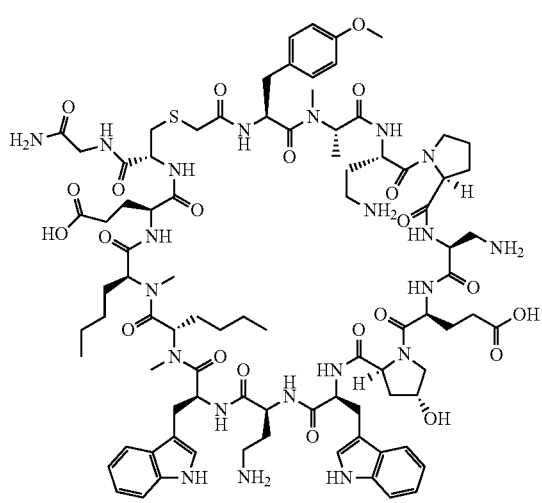 [SMILES: CCCC[C@H]1C(=O)N(C)[C@@H](CCCC)C(=O)N[C@@H](CCC(=O)O)C(=O)N[C@H](C(=O)NCC(N)=O)CSCC(=O)N[C@@H](Cc2ccc(OC)cc2)C(=O)N(C)[C@@H](C)C(=O)N[C@@H](CCN)C(=O)N2CCC[C@H]2C(=O)N[C@@H](CN)C(=O)N[C@@H](CCC(=O)O)C(=O)N2C[C@H](O)C[C@H]2C(=O)N[C@@H](Cc2c[nH]c3ccccc23)C(=O)N[C@@H](CCN)C(=O)N[C@@H](Cc2c[nH]c3ccccc23)C(=O)N1C]

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 43.8 mg, and its estimated purity by LCMS analysis was 100%.

Analysis condition A: Retention time=1.47 min; ESI-MS (+) m/z=931.6 (M+2H)

Analysis condition B: Retention time=2.80 min; ESI-MS (+) m/z=931.5 (M+2H)

ESI-HRMS(+) m/z Calculated 930.9587, Found 930.9565 (M+2H).

Preparation of Example 7113

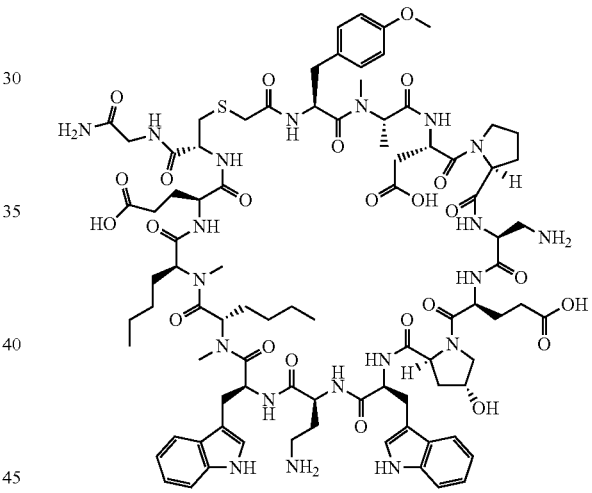

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 55-95% B over 30 minutes, then a 5-minute hold at 100% B; Flow: 20 mL/min. Fractions containing the desired product were combined and dried via centrifugal evaporation. The yield of the product was 34.3 mg, and its estimated purity by LCMS analysis was 100%.

Analysis condition A: Retention time=1.58 min; ESI-MS (+) m/z=939.0 (M+2H)

Analysis condition B: Retention time=2.91 min; ESI-MS (+) m/z=939.1 (M+2H)

ESI-HRMS(+) m/z Calculated 938.4404, Found 938.4382 (M+2H).

Preparation of Example 7114

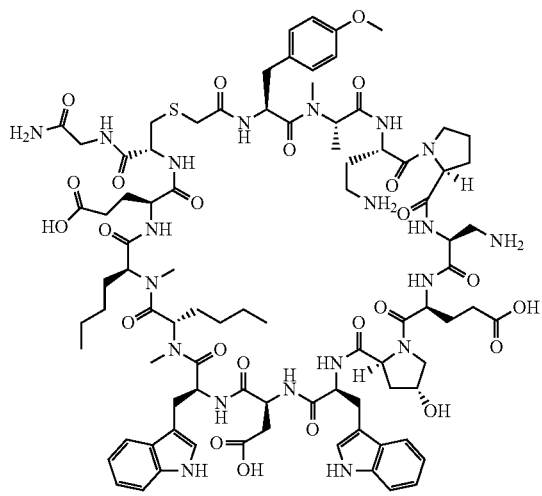 [SMILES: CCCC[C@H]1C(=O)N(C)[C@@H](CCCC)C(=O)N[C@@H](CCC(=O)O)C(=O)N[C@H](C(=O)NCC(N)=O)CSCC(=O)N[C@@H](Cc2ccc(OC)cc2)C(=O)N(C)[C@@H](C)C(=O)N[C@@H](CCN)C(=O)N2CCC[C@H]2C(=O)N[C@@H](CN)C(=O)N[C@@H](CCC(=O)O)C(=O)N2C[C@H](O)C[C@H]2C(=O)N[C@@H](Cc2c[nH]c3ccccc23)C(=O)N[C@@H](CC(=O)O)C(=O)N[C@@H](Cc2c[nH]c3ccccc23)C(=O)N1C]

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 3.1 mg, and its estimated purity by LCMS analysis was 100%.

Analysis condition A: Retention time=1.48 min; ESI-MS (+) m/z=939.7 (M+2H)

Analysis condition B: Retention time=2.48 min; ESI-MS (+) m/z=939.7 (M+2H)

ESI-HRMS(+) m/z Calculated 938.4404, Found 938.4375 (M+2H).

Preparation of Example 7115

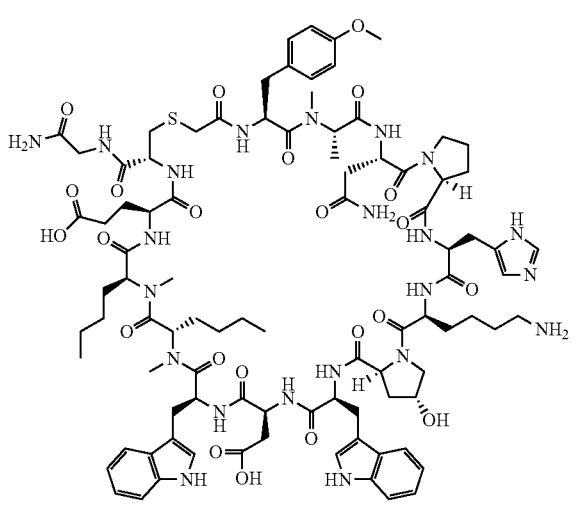 [SMILES: CCCC[C@H]1C(=O)N(C)[C@@H](CCCC)C(=O)N[C@@H](CCC(=O)O)C(=O)N[C@H](C(=O)NCC(N)=O)CSCC(=O)N[C@@H](Cc2ccc(OC)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CCCCN)C(=O)N2C[C@H](O)C[C@H]2C(=O)N[C@@H](Cc2c[nH]c3ccccc23)C(=O)N[C@@H](CC(=O)O)C(=O)N[C@@H](Cc2c[nH]c3ccccc23)C(=O)N1C]

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 3.9 mg, and its estimated purity by LCMS analysis was 100%.

Analysis condition A: Retention time=1.53 min; ESI-MS (+) m/z=971.1 (M+2H)

Analysis condition B: Retention time=2.57 min; ESI-MS (+) m/z=971.0 (M+2H)

ESI-HRMS(+) m/z Calculated 970.4616, Found 970.4587 (M+2H).

Preparation of Example 7116

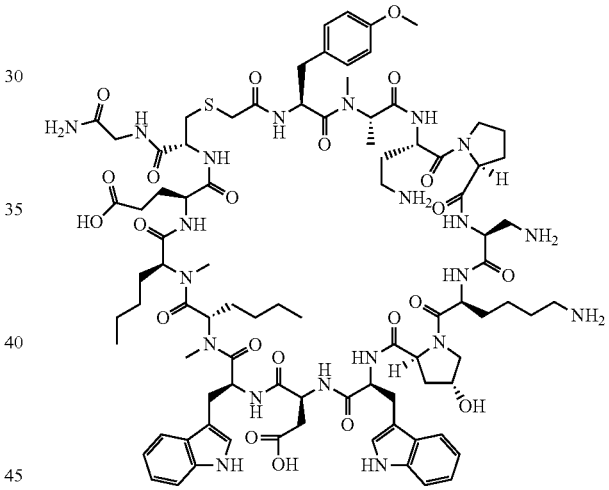

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 4.1 mg, and its estimated purity by LCMS analysis was 100%.

Analysis condition A: Retention time=1.55 min; ESI-MS (+) m/z=938.8 (M+2H)

Analysis condition B: Retention time=2.54 min; ESI-MS (+) m/z=938.5 (M+2H)

ESI-HRMS(+) m/z Calculated 937.9665, Found 937.9649 (M+2H).

Preparation of Example 7117

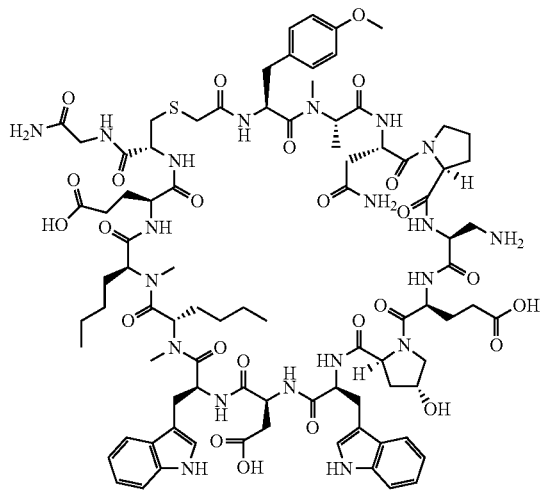 [SMILES: CCCC[C@H]1C(=O)N(C)[C@@H](CCCC)C(=O)N[C@@H](CCC(=O)O)C(=O)N[C@H](C(=O)NCC(N)=O)CSCC(=O)N[C@@H](Cc2ccc(OC)cc2)C(=O)N(C)[C@@H](C)C(=O)N[C@@H](CC(N)=O)C(=O)N2CCC[C@H]2C(=O)N[C@@H](CN)C(=O)N[C@@H](CCC(=O)O)C(=O)N2C[C@H](O)C[C@H]2C(=O)N[C@@H](Cc2c[nH]c3ccccc23)C(=O)N[C@@H](CC(=O)O)C(=O)N[C@@H](Cc2c[nH]c3ccccc23)C(=O)N1C]

The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 35-80% B over 30 minutes, then a 5-minute hold at 100% B; Flow: 20 mL/min. Fractions containing the desired product were combined and dried via centrifugal evaporation. The yield of the product was 2.8 mg, and its estimated purity by LCMS analysis was 98%.

Analysis condition A: Retention time=1.41 min; ESI-MS (+) m/z=945.7 (M+2H)

Analysis condition B: Retention time=2.66 min; ESI-MS (+) m/z=945.8 (M+2H)

ESI-HRMS(+) m/z Calculated 945.4300, Found 945.4282 (M+2H).

Preparation of Example 7118

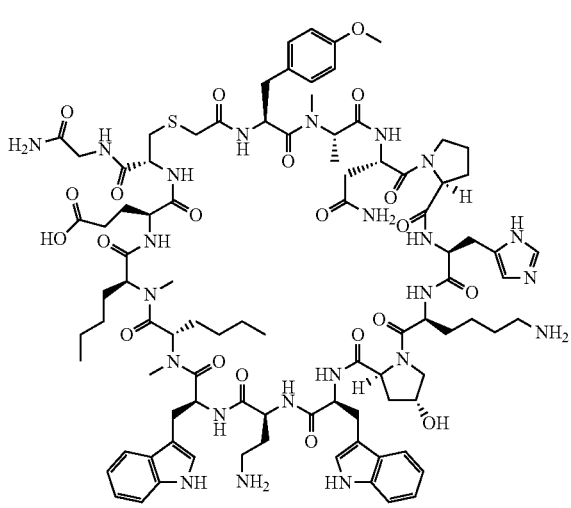 [SMILES: CCCC[C@H]1C(=O)N(C)[C@@H](CCCC)C(=O)N[C@@H](CCC(=O)O)C(=O)N[C@H](C(=O)NCC(N)=O)CSCC(=O)N[C@@H](Cc2ccc(OC)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CCCCN)C(=O)N2C[C@H](O)C[C@H]2C(=O)N[C@@H](Cc2c[nH]c3ccccc23)C(=O)N[C@@H](CCN)C(=O)N[C@@H](Cc2c[nH]c3ccccc23)C(=O)N1C]

The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 40-85% B over 30 minutes, then a 5-minute hold at 100% B; Flow: 20 mL/min. Fractions containing the desired product were combined and dried via centrifugal evaporation. The yield of the product was 35.6 mg, and its estimated purity by LCMS analysis was 100%.

Analysis condition A: Retention time=1.69 min; ESI-MS (+) m/z=963.4 (M+2H)

Analysis condition B: Retention time=3.25 min; ESI-MS (+) m/z=963.4 (M+2H)

ESI-HRMS(+) m/z Calculated 962.9800, Found 962.9780 (M+2H).

Preparation of Example 7119

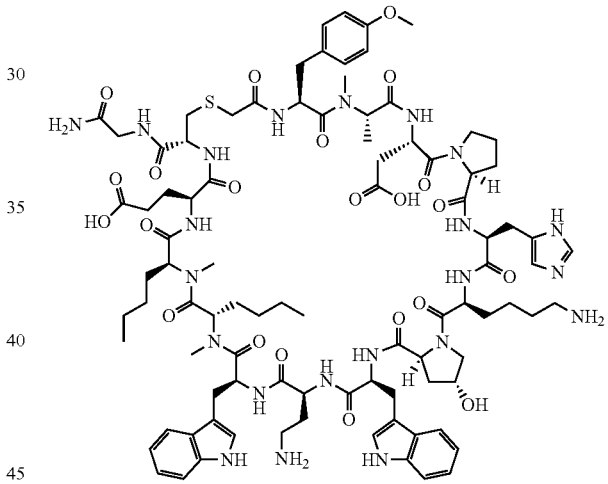

The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 52.7 mg, and its estimated purity by LCMS analysis was 99%.

Analysis condition A: Retention time=1.67 min; ESI-MS (+) m/z=963.9 (M+2H)

Analysis condition B: Retention time=3.31 min; ESI-MS (+) m/z=964.0 (M+2H)

ESI-HRMS(+) m/z Calculated 963.4720, Found 963.4699 (M+2H).

Preparation of Example 7120

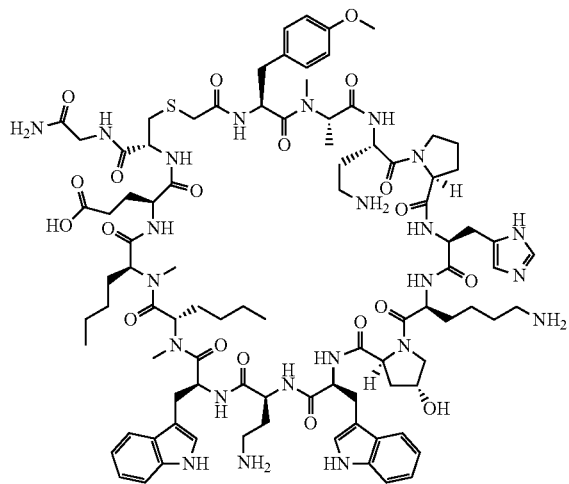 [SMILES: CCCC[C@H]1C(=O)N(C)[C@@H](CCCC)C(=O)N[C@@H](CCC(=O)O)C(=O)N[C@H](C(=O)NCC(N)=O)CSCC(=O)N[C@@H](Cc2ccc(OC)cc2)C(=O)N(C)[C@@H](C)C(=O)N[C@@H](CCN)C(=O)N2CCC[C@H]2C(=O)N[C@@H](Cc2cnc[nH]2)C(=O)N[C@@H](CCCCN)C(=O)N2C[C@H](O)C[C@H]2C(=O)N[C@@H](Cc2c[nH]c3ccccc23)C(=O)N[C@@H](CCN)C(=O)N[C@@H](Cc2c[nH]c3ccccc23)C(=O)N1C]

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-85% B over 30 minutes, then a 5-minute hold at 100% B; Flow: 20 mL/min. Fractions containing the desired product were combined and dried via centrifugal evaporation. The yield of the product was 48.9 mg, and its estimated purity by LCMS analysis was 100%.

Analysis condition A: Retention time=1.51 min; ESI-MS (+) m/z=956.4 (M+2H)

Analysis condition B: Retention time=3.03 min; ESI-MS (+) m/z=956.3 (M+2H)

ESI-HRMS(+) m/z Calculated 955.9903, Found 955.9896 (M+2H).

Preparation of Example 7121

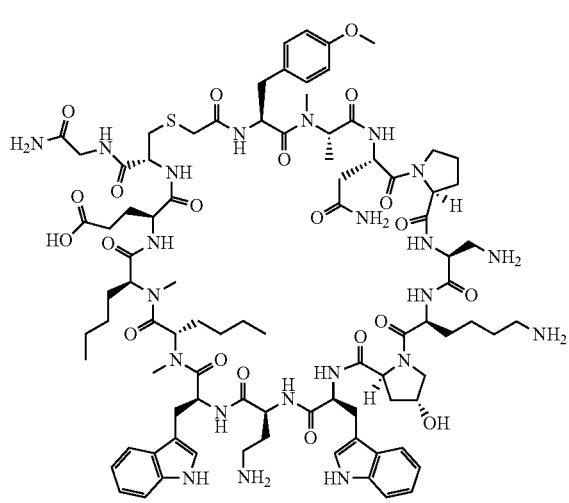 [SMILES: CCCC[C@H]1C(=O)N(C)[C@@H](CCCC)C(=O)N[C@@H](CCC(=O)O)C(=O)N[C@H](C(=O)NCC(N)=O)CSCC(=O)N[C@@H](Cc2ccc(OC)cc2)C(=O)N(C)[C@@H](C)C(=O)N[C@@H](CC(N)=O)C(=O)N2CCC[C@H]2C(=O)N[C@@H](CN)C(=O)N[C@@H](CCCCN)C(=O)N2C[C@H](O)C[C@H]2C(=O)N[C@@H](Cc2c[nH]c3ccccc23)C(=O)N[C@@H](CCN)C(=O)N[C@@H](Cc2c[nH]c3ccccc23)C(=O)N1C]

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 26.7 mg, and its estimated purity by LCMS analysis was 100%.

Analysis condition A: Retention time=1.66 min; ESI-MS (+) m/z=937.9 (M+2H)

Analysis condition B: Retention time=3.26 min; ESI-MS (+) m/z=937.9 (M+2H)

ESI-HRMS(+) m/z Calculated 937.4745, Found 937.4724 (M+2H).

Preparation of Example 7122

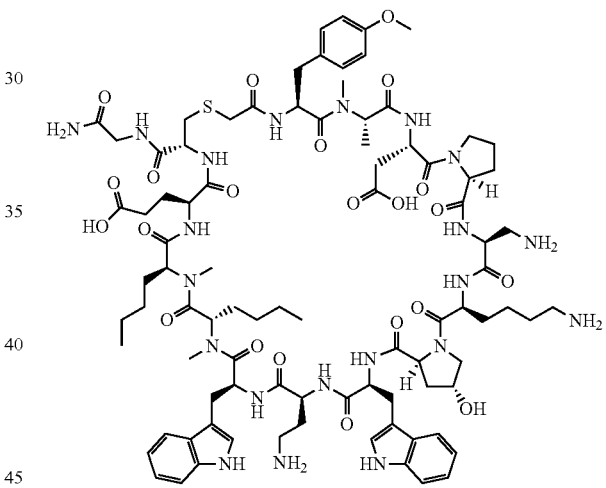

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-90% B over 30 minutes, then a 5-minute hold at 100% B; Flow: 20 mL/min. Fractions containing the desired product were combined and dried via centrifugal evaporation. The yield of the product was 46.5 mg, and its estimated purity by LCMS analysis was 100%.

Analysis condition A: Retention time=1.71 min; ESI-MS (+) m/z=938.4 (M+2H)

Analysis condition B: Retention time=3.35 min; ESI-MS (+) m/z=938.4 (M+2H)

ESI-HRMS(+) m/z Calculated 937.4745, Found 937.4724 (M+2H).

Preparation of Example 7123

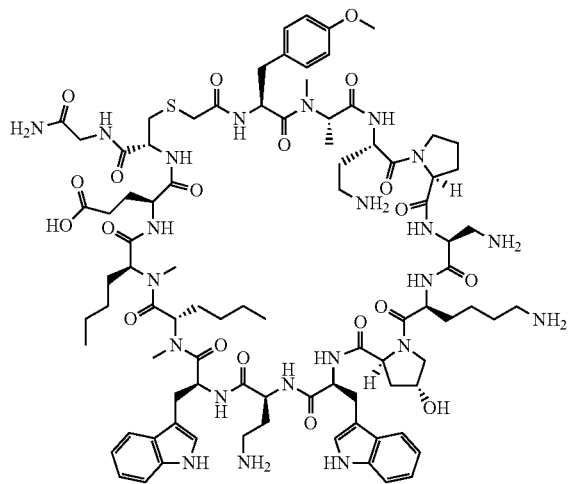 [SMILES: CCCC[C@H]1C(=O)N(C)[C@@H](CCCC)C(=O)N[C@@H](CCC(=O)O)C(=O)N[C@H](C(=O)NCC(N)=O)CSCC(=O)N[C@@H](Cc2ccc(OC)cc2)C(=O)N(C)[C@@H](C)C(=O)N[C@@H](CCN)C(=O)N2CCC[C@H]2C(=O)N[C@@H](CN)C(=O)N[C@@H](CCCCN)C(=O)N2C[C@H](O)C[C@H]2C(=O)N[C@@H](Cc2c[nH]c3ccccc23)C(=O)N[C@@H](CCN)C(=O)N[C@@H](Cc2c[nH]c3ccccc23)C(=O)N1C]

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-85% B over 30 minutes, then a 5-minute hold at 100% B; Flow: 20 mL/min. Fractions containing the desired product were combined and dried via centrifugal evaporation. The yield of the product was 39.2 mg, and its estimated purity by LCMS analysis was 100%.

Analysis condition A: Retention time=1.44 min; ESI-MS (+) m/z=930.9 (M+2H)

Analysis condition B: Retention time=3.01 min; ESI-MS (+) m/z=931.0 (M+2H)

ESI-HRMS(+) m/z Calculated 930.4849, Found 930.4835 (M+2H).

Preparation of Example 7124

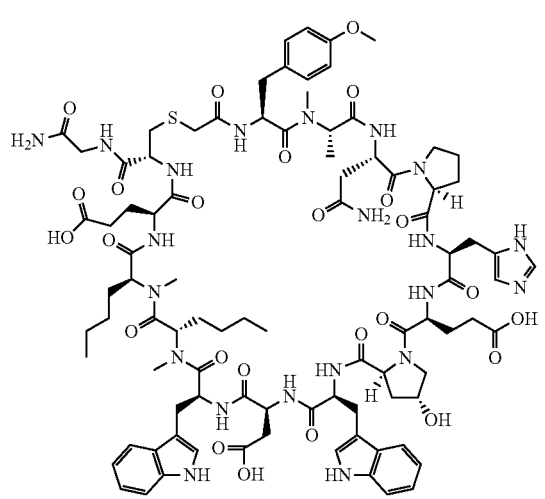

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 30-70% B over 30 minutes, then a 5-minute hold at 100% B; Flow: 20 mL/min. Fractions containing the desired product were combined and dried via centrifugal evaporation. The yield of the product was 25.2 mg, and its estimated purity by LCMS analysis was 100%.

Analysis condition A: Retention time=1.48 min; ESI-MS (+) m/z=971.4 (M+2H)

Analysis condition B: Retention time=2.95 min; ESI-MS (+) m/z=971.4 (M+2H)

ESI-HRMS(+) m/z Calculated 970.9354, Found 970.9357 (M+2H).

Preparation of Example 7125

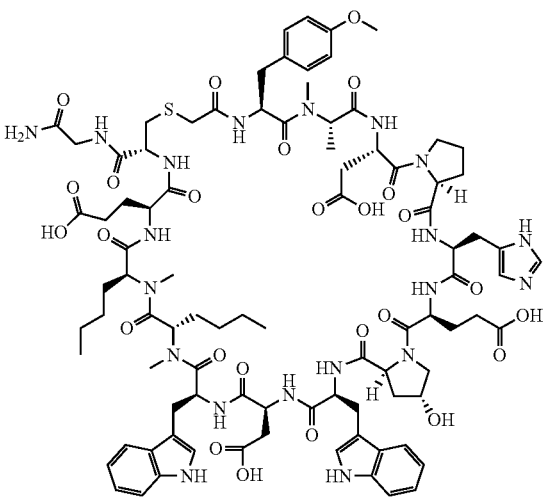 [SMILES: CCCC[C@H]1C(=O)N(C)[C@@H](CCCC)C(=O)N[C@@H](CCC(=O)O)C(=O)N[C@H](C(=O)NCC(N)=O)CSCC(=O)N[C@@H](Cc2ccc(OC)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CCC(=O)O)C(=O)N2C[C@H](O)C[C@H]2C(=O)N[C@@H](Cc2c[nH]c3ccccc23)C(=O)N[C@@H](CC(=O)O)C(=O)N[C@@H](Cc2c[nH]c3ccccc23)C(=O)N1C]

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 39.6 mg, and its estimated purity by LCMS analysis was 98%.

Analysis condition A: Retention time=1.51 min; ESI-MS (+) m/z=971.9 (M+2H)

Analysis condition B: Retention time=2.95 min; ESI-MS (+) m/z=971.9 (M+2H)

ESI-HRMS(+) m/z Calculated 971.4274, Found 971.4269 (M+2H).

Preparation of Example 7126

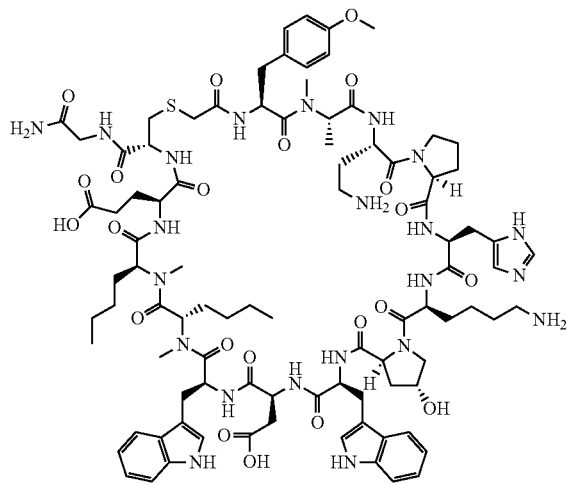 [SMILES: CCCC[C@H]1C(=O)N(C)[C@@H](CCCC)C(=O)N[C@@H](CCC(=O)O)C(=O)N[C@H](C(=O)NCC(N)=O)CSCC(=O)N[C@@H](Cc2ccc(OC)cc2)C(=O)N(C)[C@@H](C)C(=O)N[C@@H](CCN)C(=O)N2CCC[C@H]2C(=O)N[C@@H](Cc2cnc[nH]2)C(=O)N[C@@H](CCCCN)C(=O)N2C[C@H](O)C[C@H]2C(=O)N[C@@H](Cc2c[nH]c3ccccc23)C(=O)N[C@@H](CC(=O)O)C(=O)N[C@@H](Cc2c[nH]c3ccccc23)C(=O)N1C]

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 12.8 mg, and its estimated purity by LCMS analysis was 98%.

Analysis condition A: Retention time=1.35 min; ESI-MS (+) m/z=964.7 (M+2H)

Analysis condition B: Retention time=2.85 min; ESI-MS (+) m/z=964.9 (M+2H)

ESI-HRMS(+) m/z Calculated 963.4720, Found 963.4704 (M+2H).

Preparation of Example 7127

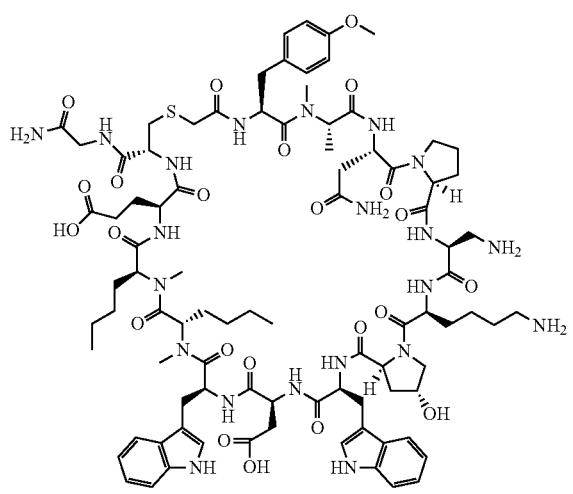 [SMILES: CCCC[C@H]1C(=O)N(C)[C@@H](CCCC)C(=O)N[C@@H](CCC(=O)O)C(=O)N[C@H](C(=O)NCC(N)=O)CSCC(=O)N[C@@H](Cc2ccc(OC)cc2)C(=O)N(C)[C@@H](C)C(=O)N[C@@H](CC(N)=O)C(=O)N2CCC[C@H]2C(=O)N[C@@H](CN)C(=O)N[C@@H](CCCCN)C(=O)N2C[C@H](O)C[C@H]2C(=O)N[C@@H](Cc2c[nH]c3ccccc23)C(=O)N[C@@H](CC(=O)O)C(=O)N[C@@H](Cc2c[nH]c3ccccc23)C(=O)N1C]

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 37.1 mg, and its estimated purity by LCMS analysis was 100%.

Analysis condition A: Retention time=1.45 min; ESI-MS (+) m/z=945.4 (M+2H)

Analysis condition B: Retention time=2.95 min; ESI-MS (+) m/z=945.4 (M+2H)

ESI-HRMS(+) m/z Calculated 944.9562, Found 944.9556 (M+2H).

Preparation of Example 7128

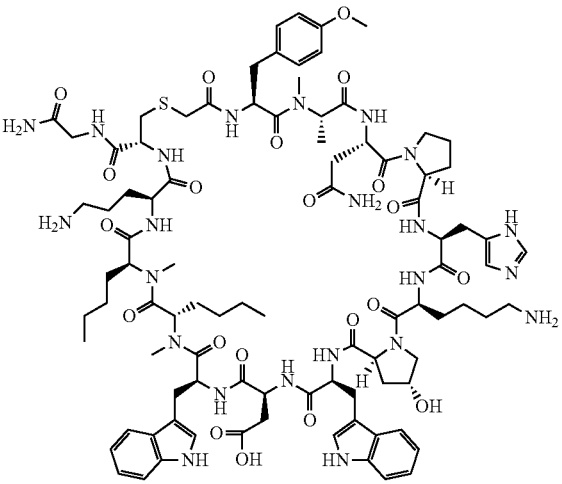 [SMILES: CCCC[C@H]1C(=O)N(C)[C@@H](CCCC)C(=O)N[C@@H](CCCN)C(=O)N[C@H](C(=O)NCC(N)=O)CSCC(=O)N[C@@H](Cc2ccc(OC)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CCCCN)C(=O)N2C[C@H](O)C[C@H]2C(=O)N[C@@H](Cc2c[nH]c3ccccc23)C(=O)N[C@@H](CC(=O)O)C(=O)N[C@@H](Cc2c[nH]c3ccccc23)C(=O)N1C]

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-100% B over 30 minutes, then a 5-minute hold at 100% B; Flow: 20 mL/min. Fractions containing the desired product were combined and dried via centrifugal evaporation. The yield of the product was 26.3 mg, and its estimated purity by LCMS analysis was 100%.

Analysis condition A: Retention time=1.74 min; ESI-MS (+) m/z=963.4 (M+2H)

Analysis condition B: Retention time=3.29 min; ESI-MS (+) m/z=963.4 (M+2H)

ESI-HRMS(+) m/z Calculated 962.9800, Found 962.9778 (M+2H).

Preparation of Example 7129

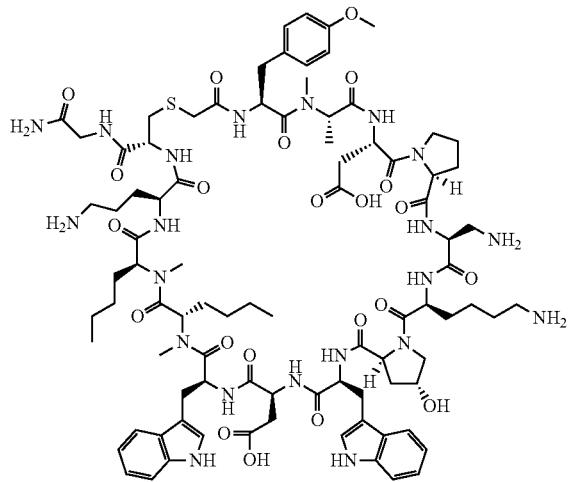 [SMILES: CCCC[C@H]1C(=O)N(C)[C@@H](CCCC)C(=O)N[C@@H](CCCN)C(=O)N[C@H](C(=O)NCC(N)=O)CSCC(=O)N[C@@H](Cc2ccc(OC)cc2)C(=O)N(C)[C@@H](C)C(=O)N[C@@H](CC(=O)O)C(=O)N2CCC[C@H]2C(=O)N[C@@H](CN)C(=O)N[C@@H](CCCCN)C(=O)N2C[C@H](O)C[C@H]2C(=O)N[C@@H](Cc2c[nH]c3ccccc23)C(=O)N[C@@H](CC(=O)O)C(=O)N[C@@H](Cc2c[nH]c3ccccc23)C(=O)N1C]

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-90% B over 30 minutes, then a 5-minute hold at 100% B; Flow: 20 mL/min. Fractions containing the desired product were combined and dried via centrifugal evaporation. The yield of the product was 37.4 mg, and its estimated purity by LCMS analysis was 100%.

Analysis condition A: Retention time=1.65 min; ESI-MS (+) m/z=938.5 (M+2H)

Analysis condition B: Retention time=2.98 min; ESI-MS (+) m/z=938.4 (M+2H)

ESI-HRMS(+) m/z Calculated 937.9665, Found 937.9647 (M+2H).

Preparation of Example 7130

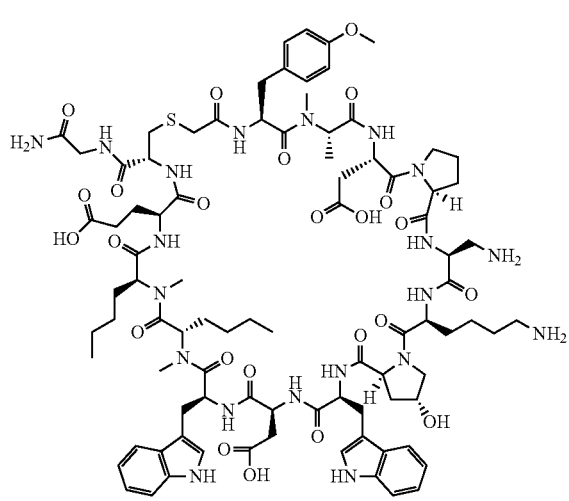

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-80% B over 30 minutes, then a 5-minute hold at 100% B; Flow: 20 mL/min. Fractions containing the desired product were combined and dried via centrifugal evaporation. The yield of the product was 44.0 mg, and its estimated purity by LCMS analysis was 99%.

Analysis condition A: Retention time=1.42 min; ESI-MS (+) m/z=946.1 (M+2H)

Analysis condition B: Retention time=2.64 min; ESI-MS (+) m/z=946.0 (M+2H)

ESI-HRMS(+) m/z Calculated 945.4482, Found 945.4475 (M+2H).

Preparation of Example 7131

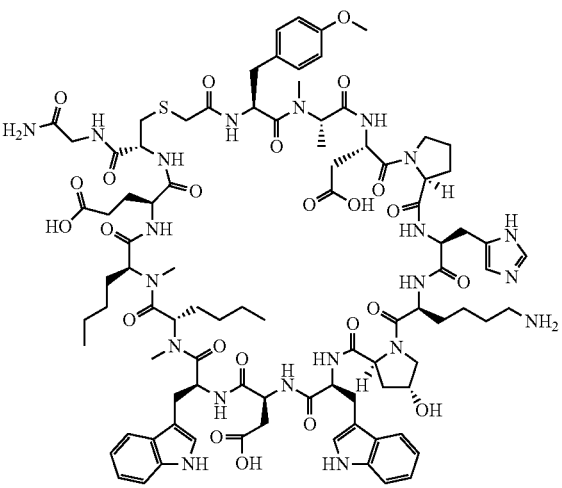 [SMILES: CCCC[C@H]1C(=O)N(C)[C@@H](CCCC)C(=O)N[C@@H](CCC(=O)O)C(=O)N[C@H](C(=O)NCC(N)=O)CSCC(=O)N[C@@H](Cc2ccc(OC)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CCCCN)C(=O)N2C[C@H](O)C[C@H]2C(=O)N[C@@H](Cc2c[nH]c3ccccc23)C(=O)N[C@@H](CC(=O)O)C(=O)N[C@@H](Cc2c[nH]c3ccccc23)C(=O)N1C]

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 29.8 mg, and its estimated purity by LCMS analysis was 100%.

Analysis condition A: Retention time=1.40 min; ESI-MS (+) m/z=971.3 (M+2H)

Analysis condition B: Retention time=2.69 min; ESI-MS (+) m/z=971.2 (M+2H)

ESI-HRMS(+) m/z Calculated 970.9536, Found 970.9536 (M+2H).

Preparation of Example 7132

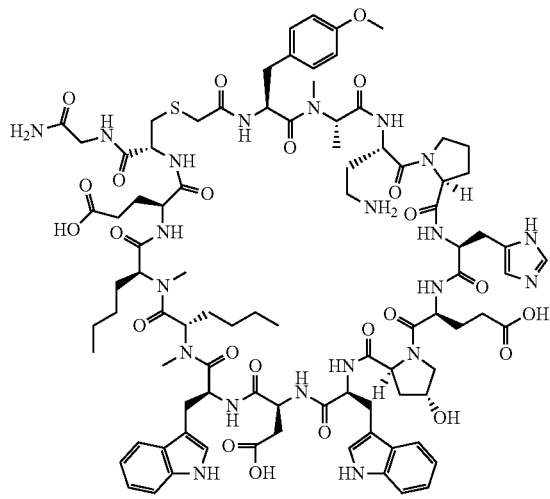 [SMILES: CCCC[C@H]1C(=O)N(C)[C@@H](CCCC)C(=O)N[C@@H](CCC(=O)O)C(=O)N[C@H](C(=O)NCC(N)=O)CSCC(=O)N[C@@H](Cc2ccc(OC)cc2)C(=O)N(C)[C@@H](C)C(=O)N[C@@H](CCN)C(=O)N2CCC[C@H]2C(=O)N[C@@H](Cc2cnc[nH]2)C(=O)N[C@@H](CCC(=O)O)C(=O)N2C[C@H](O)C[C@H]2C(=O)N[C@@H](Cc2c[nH]c3ccccc23)C(=O)N[C@@H](CC(=O)O)C(=O)N[C@@H](Cc2c[nH]c3ccccc23)C(=O)N1C]

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 32.9 mg, and its estimated purity by LCMS analysis was 100%.

Analysis condition A: Retention time=1.28 min; ESI-MS (+) m/z=964.3 (M+2H)

Analysis condition B: Retention time=2.58 min; ESI-MS (+) m/z=964.2 (M+2H)

ESI-HRMS(+) m/z Calculated 963.9458, Found 963.9452 (M+2H).

Preparation of Example 7133

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 19.1 mg, and its estimated purity by LCMS analysis was 99%.

Analysis condition A: Retention time=1.45 min; ESI-MS (+) m/z=946.2 (M+2H)

Analysis condition B: Retention time=2.72 min; ESI-MS (+) m/z=946.2 (M+2H)

ESI-HRMS(+) m/z Calculated 945.9220, Found 945.9208 (M+2H).

Preparation of Example 7134

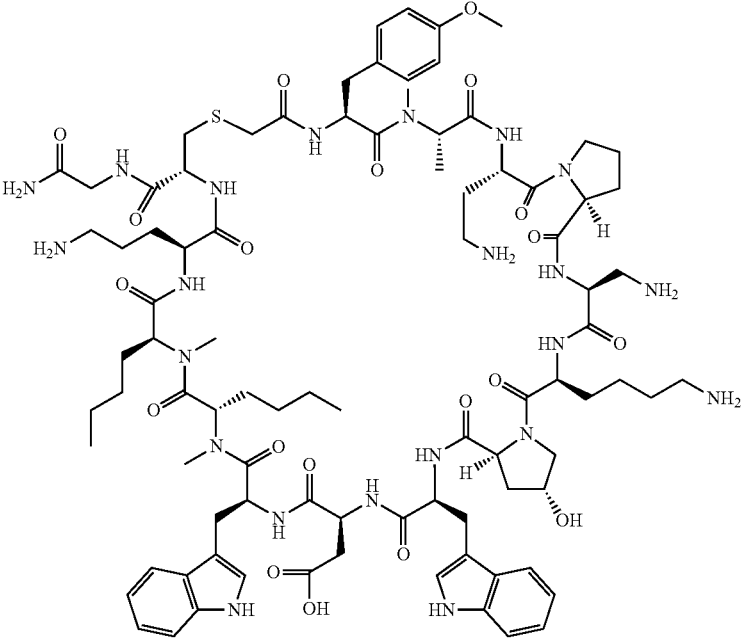 [SMILES: CCCC[C@H]1C(=O)N(C)[C@@H](CCCC)C(=O)N[C@@H](CCCN)C(=O)N[C@H](C(=O)NCC(N)=O)CSCC(=O)N[C@@H](Cc2ccc(OC)cc2)C(=O)N(C)[C@@H](C)C(=O)N[C@@H](CCN)C(=O)N2CCC[C@H]2C(=O)N[C@@H](CN)C(=O)N[C@@H](CCCCN)C(=O)N2C[C@H](O)C[C@H]2C(=O)N[C@@H](Cc2c[nH]c3ccccc23)C(=O)N[C@@H](CC(=O)O)C(=O)N[C@@H](Cc2c[nH]c3ccccc23)C(=O)N1C]

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 99.9 mg, and its estimated purity by LCMS analysis was 99%.

Analysis condition A: Retention time=1.59 min; ESI-MS (+) m/z=931.8 (M+2H)

Analysis condition B: Retention time=2.59 min; ESI-MS (+) m/z=931.2 (M+2H)

ESI-HRMS(+) m/z Calculated 930.4849, Found 930.4832 (M+2H).

Preparation of Example 7135

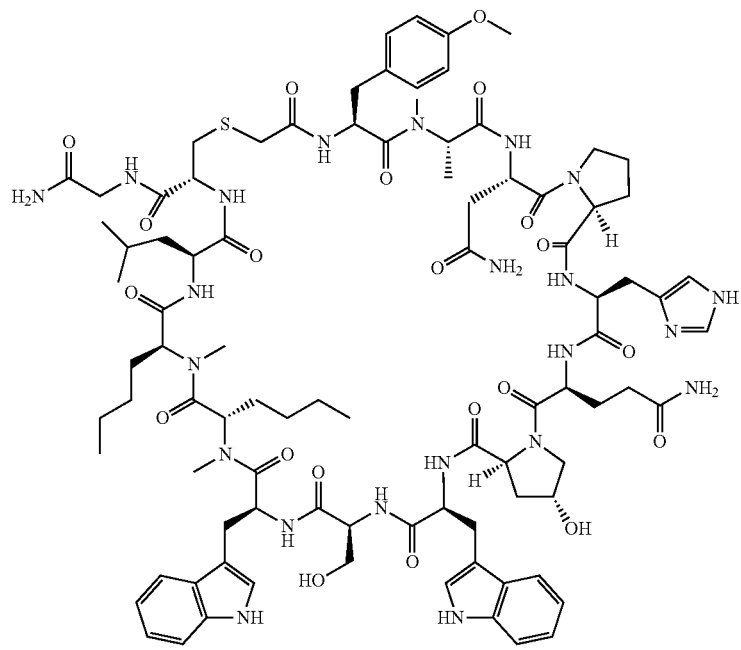 [SMILES: CCCC[C@H]1C(=O)N(C)[C@@H](CCCC)C(=O)N[C@@H](CC(C)C)C(=O)N[C@H](C(=O)NCC(N)=O)CSCC(=O)N[C@@H](Cc2ccc(OC)cc2)C(=O)N(C)[C@@H](C)C(=O)N[C@@H](CC(N)=O)C(=O)N2CCC[C@H]2C(=O)N[C@@H](Cc2c[nH]cn2)C(=O)N[C@@H](CCC(N)=O)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 55-95% B over 30 minutes, then a 5-minute hold at 100% B; Flow: 20 mL/min. Fractions containing the desired product were combined and dried via centrifugal evaporation. The yield of the product was 32.3 mg, and its estimated purity by LCMS analysis was 98%.

Analysis condition A: Retention time=1.94 min; ESI-MS (+) m/z=948.8 (M+2H), 957.5 (M+H+NH$_4$)

Analysis condition B: Retention time=2.90 min; ESI-MS (+) m/z=949.8 (M+2H), 957.5 (M+H+NH$_4$)

ESI-HRMS(+) m/z Calculated 948.4667, Found 948.4650 (M+2H).

Preparation of Example 7136

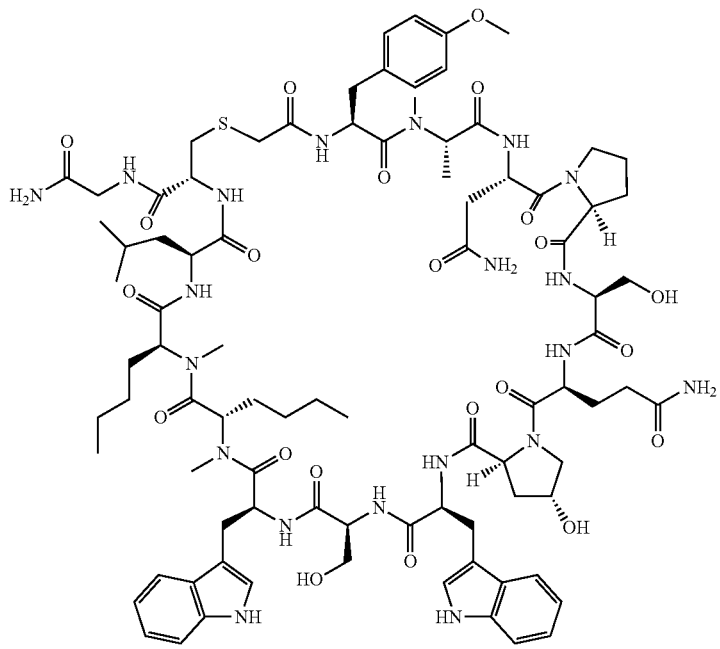 [SMILES: CCCC[C@H]1C(=O)N(C)[C@@H](CCCC)C(=O)N[C@@H](CC(C)C)C(=O)N[C@H](C(=O)NCC(N)=O)CSCC(=O)N[C@@H](Cc2ccc(OC)cc2)C(=O)N(C)[C@@H](C)C(=O)N[C@@H](CC(N)=O)C(=O)N2CCC[C@H]2C(=O)N[C@@H](CO)C(=O)N[C@@H](CCC(N)=O)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 55-95% B over 30 minutes, then a 5-minute hold at 100% B; Flow: 20 mL/min. Fractions containing the desired product were combined and dried via centrifugal evaporation. The yield of the product was 41.0 mg, and its estimated purity by LCMS analysis was 100%.

Analysis condition A: Retention time=1.84 min; ESI-MS (+) m/z=924.0 (M+2H)

Analysis condition B: Retention time=3.39 min; ESI-MS (+) m/z=924.0 (M+2H)

ESI-HRMS(+) m/z Calculated 923.4533, Found 923.4520 (M+2H).

Preparation of Example 7137

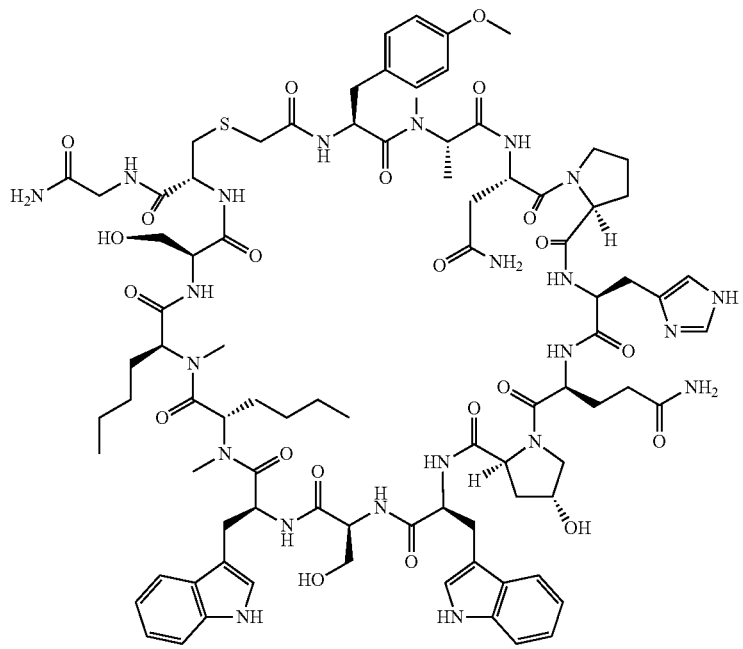

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 55-95% B over 30 minutes, then a 5-minute hold at 100% B; Flow: 20 mL/min. Fractions containing the desired product were combined and dried via centrifugal evaporation. The yield of the product was 38.2 mg, and its estimated purity by LCMS analysis was 100%.

Analysis condition A: Retention time=1.84 min; ESI-MS (+) m/z=936.0 (M+2H)

Analysis condition B: Retention time=3.36 min; ESI-MS (+) m/z=936.0 (M+2H)

ESI-HRMS(+) m/z Calculated 935.4407, Found 935.4402 (M+2H).

Preparation of Example 7138

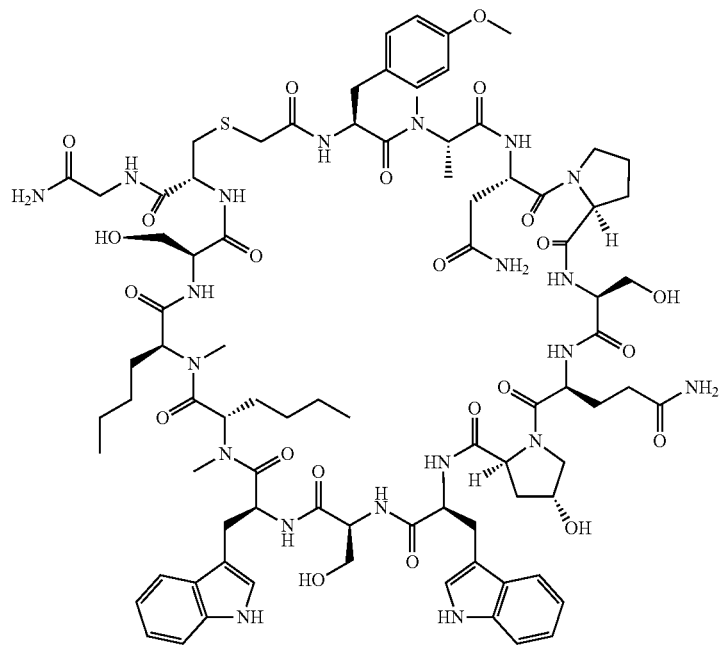

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 55-95% B over 30 minutes, then a 5-minute hold at 100% B; Flow: 20 mL/min. Fractions containing the desired product were combined and dried via centrifugal evaporation. The yield of the product was 34.3 mg, and its estimated purity by LCMS analysis was 100%.

Analysis condition A: Retention time=1.89 min; ESI-MS (+) m/z=911.0 (M+2H)

Analysis condition B: Retention time=3.40 min; ESI-MS (+) m/z=911.0 (M+2H)

ESI-HRMS(+) m/z Calculated 910.4272, Found 910.4266 (M+2H).

Preparation of Example 7139

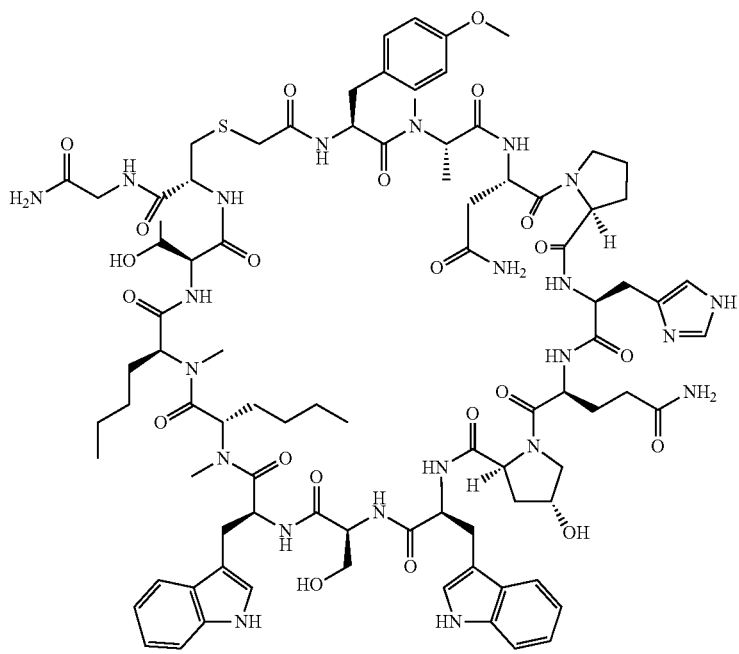 [SMILES: CCCC[C@H]1C(=O)N(C)[C@@H](CCCC)C(=O)N[C@@H](C(C)O)C(=O)N[C@H](C(=O)NCC(N)=O)CSCC(=O)N[C@@H](Cc2ccc(OC)cc2)C(=O)N(C)[C@@H](C)C(=O)N[C@@H](CC(N)=O)C(=O)N2CCC[C@H]2C(=O)N[C@@H](Cc2c[nH]cn2)C(=O)N[C@@H](CCC(N)=O)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 55-95% B over 30 minutes, then a 5-minute hold at 100% B; Flow: 20 mL/min. Fractions containing the desired product were combined and dried via centrifugal evaporation. The yield of the product was 33.2 mg, and its estimated purity by LCMS analysis was 97%.

Analysis condition A: Retention time=1.76 min; ESI-MS (+) m/z=943.0 (M+2H)

Analysis condition B: Retention time=2.90 min; ESI-MS (+) m/z=943.7 (M+2H)

ESI-HRMS(+) m/z Calculated 942.4485, Found 942.4482 (M+2H).

Preparation of Example 7140

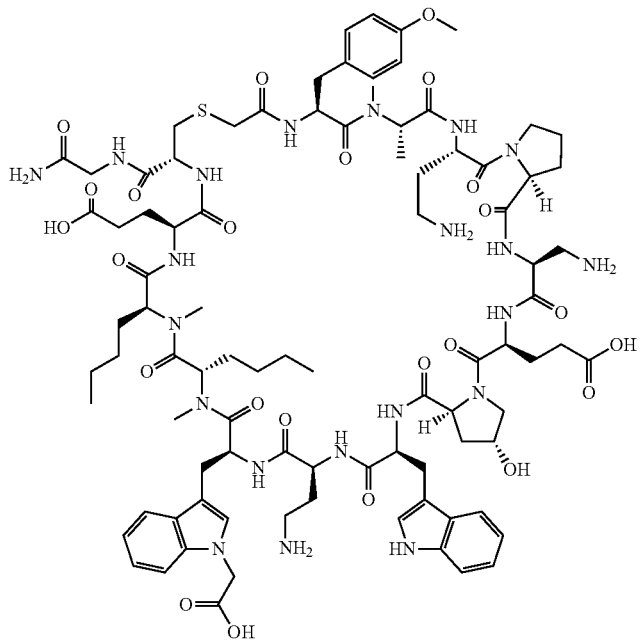 [SMILES: CCCC[C@H]1C(=O)N(C)[C@@H](CCCC)C(=O)N[C@@H](CCC(=O)O)C(=O)N[C@H](C(=O)NCC(N)=O)CSCC(=O)N[C@@H](Cc2ccc(OC)cc2)C(=O)N(C)[C@@H](C)C(=O)N[C@@H](CCN)C(=O)N2CCC[C@H]2C(=O)N[C@@H](CN)C(=O)N[C@@H](CCC(=O)O)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 30.3 mg, and its estimated purity by LCMS analysis was 100%.

Analysis condition A: Retention time=1.33 min; ESI-MS (+) m/z=968.0 (M+2H)

Analysis condition B: Retention time=2.70 min; ESI-MS (+) m/z=968.0 (M+2H)

ESI-HRMS(+) m/z Calculated 967.4431, Found 967.4406 (M+2H).

Preparation of Example 7141

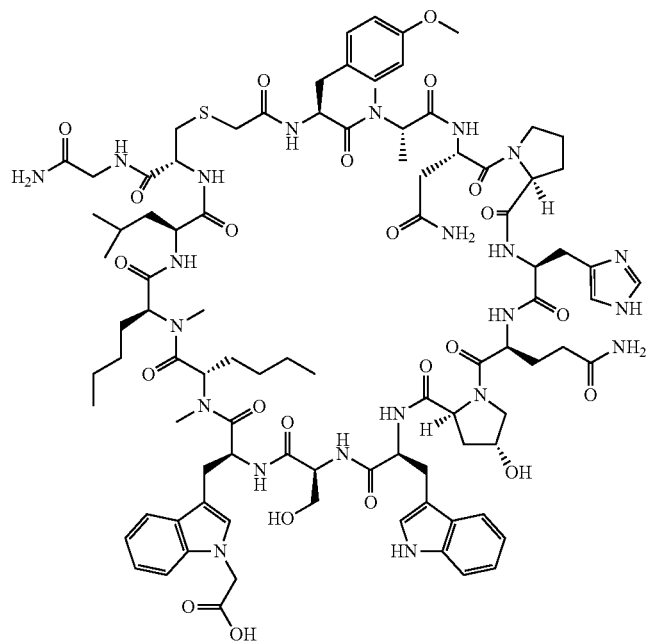 [SMILES: CCCC[C@H]1C(=O)N(C)[C@@H](CCCC)C(=O)N[C@@H](CC(C)C)C(=O)N[C@H](C(=O)NCC(N)=O)CSCC(=O)N[C@@H](Cc2ccc(OC)cc2)C(=O)N(C)[C@@H](C)C(=O)N[C@@H](CC(N)=O)C(=O)N2CCC[C@H]2C(=O)N[C@@H](Cc2c[nH]cn2)C(=O)N[C@@H](CCC(N)=O)C(=O)N2C[C@H](O)C[C@H]2C(=O)N[C@@H](Cc2c[nH]c3ccccc23)C(=O)N[C@@H](CO)C(=O)N[C@@H](Cc2cn(CC(=O)O)c3ccccc23)C(=O)N1C]

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 11.4 mg, and its estimated purity by LCMS analysis was 99%.

Analysis condition A: Retention time=1.70 min; ESI-MS (+) m/z=978.7 (M+2H)

Analysis condition B: Retention time=3.27 min; ESI-MS (+) m/z=978.6 (M+2H)

ESI-HRMS(+) m/z Calculated 977.4694, Found 977.4683 (M+2H).

Preparation of Example 7142

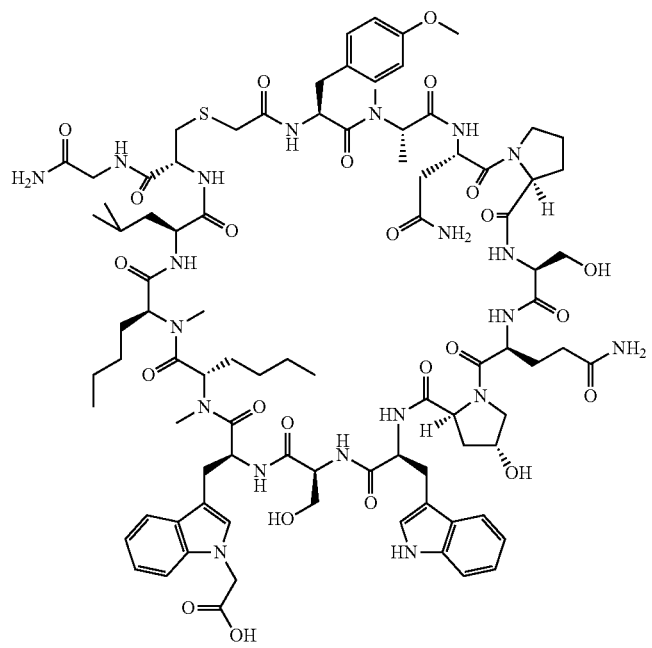 [SMILES: CCCC[C@H]1C(=O)N(C)[C@@H](CCCC)C(=O)N[C@@H](CC(C)C)C(=O)N[C@H](C(=O)NCC(N)=O)CSCC(=O)N[C@@H](Cc2ccc(OC)cc2)C(=O)N(C)[C@@H](C)C(=O)N[C@@H](CC(N)=O)C(=O)N2CCC[C@H]2C(=O)N[C@@H](CO)C(=O)N[C@@H](CCC(N)=O)C(=O)N2C[C@H](O)C[C@H]2C(=O)N[C@@H](Cc2c[nH]c3ccccc23)C(=O)N[C@@H](CO)C(=O)N[C@@H](Cc2cn(CC(=O)O)c3ccccc23)C(=O)N1C]

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 10.3 mg, and its estimated purity by LCMS analysis was 99%.

Analysis condition A: Retention time=1.71 min; ESI-MS (+) m/z=952.8 (M+2H)

Analysis condition B: Retention time=2.31 min; ESI-MS (+) m/z=952.9 (M+2H).

Preparation of Example 7143

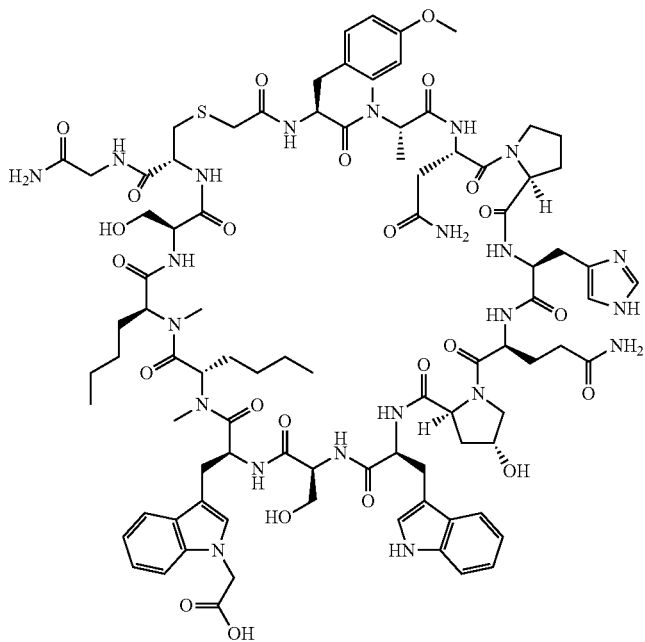 [SMILES: CCCC[C@H]1C(=O)N(C)[C@@H](CCCC)C(=O)N[C@@H](CO)C(=O)N[C@H](C(=O)NCC(N)=O)CSCC(=O)N[C@@H](Cc2ccc(OC)cc2)C(=O)N(C)[C@@H](C)C(=O)N[C@@H](CC(N)=O)C(=O)N2CCC[C@H]2C(=O)N[C@@H](Cc2c[nH]cn2)C(=O)N[C@@H](CCC(N)=O)C(=O)N2C[C@H](O)C[C@H]2C(=O)N[C@@H](Cc2c[nH]c3ccccc23)C(=O)N[C@@H](CO)C(=O)N[C@@H](Cc2cn(CC(=O)O)c3ccccc23)C(=O)N1C]

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 15.0 mg, and its estimated purity by LCMS analysis was 100%.

Analysis condition A: Retention time=1.47 min; ESI-MS (+) m/z=965.2 (M+2H)

Analysis condition B: Retention time=2.78 min; ESI-MS (+) m/z=965.8 (M+2H)

ESI-HRMS(+) m/z Calculated 964.4434, Found 964.4420 (M+2H).

Preparation of Example 7144

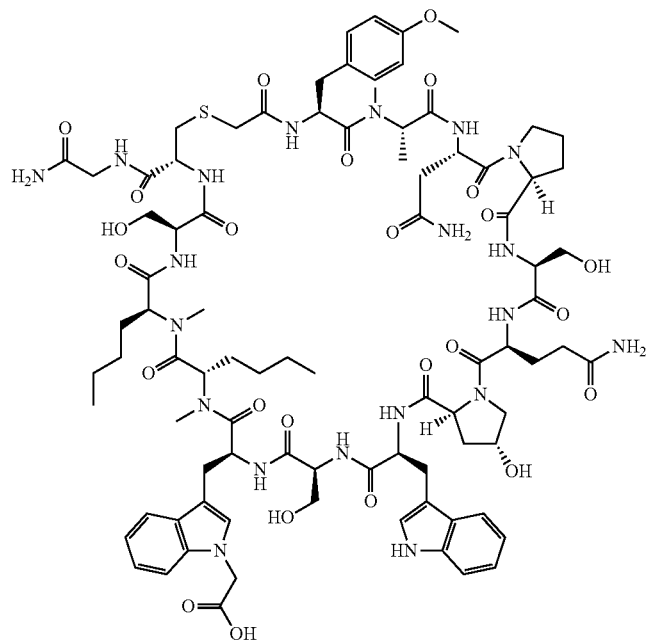 [SMILES: CCCC[C@H]1C(=O)N(C)[C@@H](CCCC)C(=O)N[C@@H](CO)C(=O)N[C@H](C(=O)NCC(N)=O)CSCC(=O)N[C@@H](Cc2ccc(OC)cc2)C(=O)N(C)[C@@H](C)C(=O)N[C@@H](CC(N)=O)C(=O)N2CCC[C@H]2C(=O)N[C@@H](CO)C(=O)N[C@@H](CCC(N)=O)C(=O)N2C[C@H](O)C[C@H]2C(=O)N[C@@H](Cc2c[nH]c3ccccc23)C(=O)N[C@@H](CO)C(=O)N[C@@H](Cc2cn(CC(=O)O)c3ccccc23)C(=O)N1C]

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 14.4 mg, and its estimated purity by LCMS analysis was 99%.

Analysis condition A: Retention time=1.67 min; ESI-MS (+) m/z=940.8 (M+2H)

Analysis condition B: Retention time=2.22 min; ESI-MS (+) m/z=940.7 (M+2H)

ESI-HRMS(+) m/z Calculated 939.4300, Found 939.4296 (M+2H).

Preparation of Example 7145

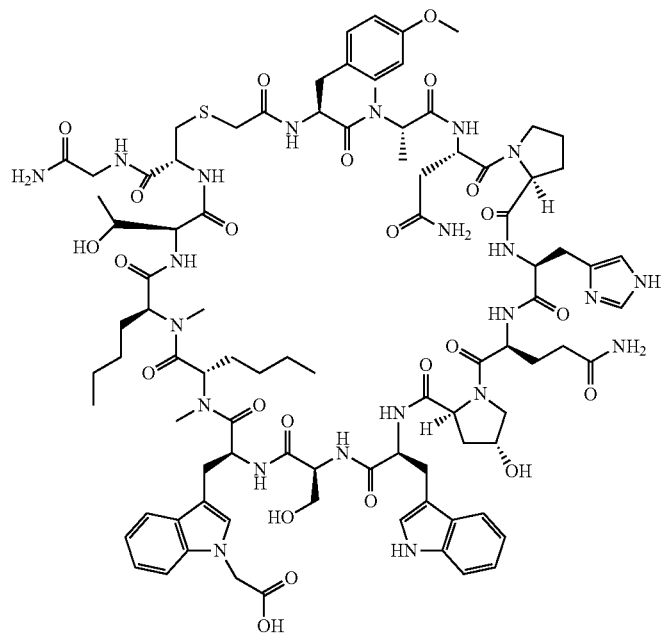 [SMILES: CCCC[C@H]1C(=O)N(C)[C@@H](CCCC)C(=O)N[C@@H](C(C)O)C(=O)N[C@H](C(=O)NCC(N)=O)CSCC(=O)N[C@@H](Cc2ccc(OC)cc2)C(=O)N(C)[C@@H](C)C(=O)N[C@@H](CC(N)=O)C(=O)N2CCC[C@H]2C(=O)N[C@@H](Cc2c[nH]cn2)C(=O)N[C@@H](CCC(N)=O)C(=O)N2C[C@H](O)C[C@H]2C(=O)N[C@@H](Cc2c[nH]c3ccccc23)C(=O)N[C@@H](CO)C(=O)N[C@@H](Cc2cn(CC(=O)O)c3ccccc23)C(=O)N1C]

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 14.1 mg, and its estimated purity by LCMS analysis was 95%.

Analysis condition A: Retention time=1.60 min; ESI-MS (+) m/z=971.4 (M+2H)

Analysis condition B: Retention time=3.22 min; ESI-MS (+) m/z=971.8 (M+2H)

ESI-HRMS(+) m/z Calculated 971.4513, Found 971.4496 (M+2H).

Preparation of Example 7146

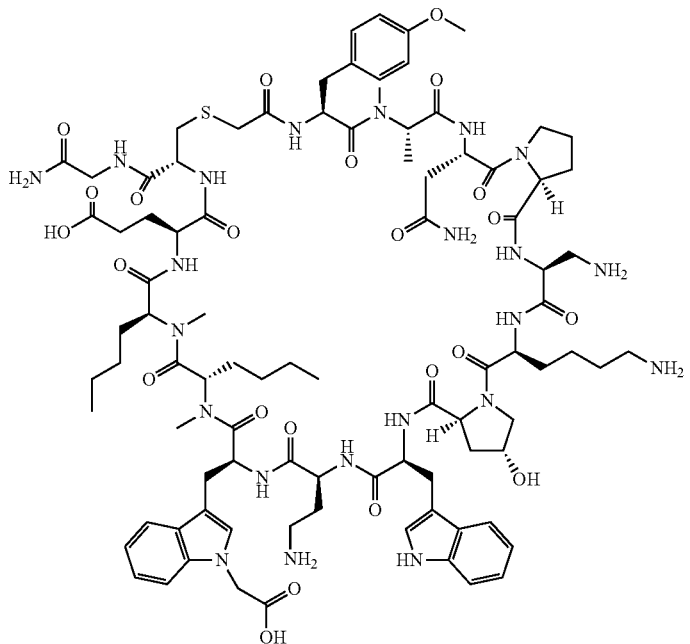 [SMILES: CCCC[C@H]1C(=O)N(C)[C@@H](CCCC)C(=O)N[C@@H](CCC(=O)O)C(=O)N[C@H](C(=O)NCC(N)=O)CSCC(=O)N[C@@H](Cc2ccc(OC)cc2)C(=O)N(C)[C@@H](C)C(=O)N[C@@H](CC(N)=O)C(=O)N2CCC[C@H]2C(=O)N[C@@H](CN)C(=O)N[C@@H](CCCCN)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 38.5 mg, and its estimated purity by LCMS analysis was 100%.

Analysis condition A: Retention time=1.43 min; ESI-MS (+) m/z=967.7 (M+2H)

Analysis condition B: Retention time=2.74 min; ESI-MS (+) m/z=967.6 (M+2H)

ESI-HRMS(+) m/z Calculated 966.4773, Found 966.4745 (M+2H).

Preparation of Example 7147

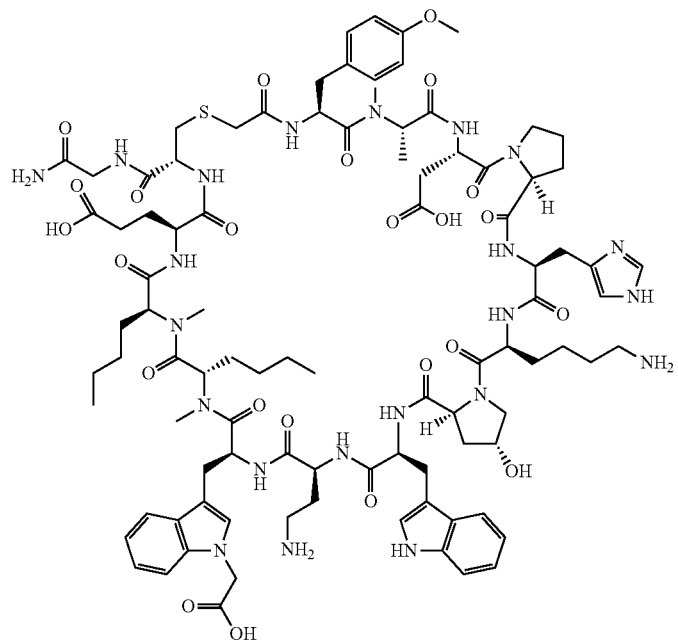 [SMILES: CCCC[C@H]1C(=O)N(C)[C@@H](CCCC)C(=O)N[C@@H](CCC(=O)O)C(=O)N[C@H](C(=O)NCC(N)=O)CSCC(=O)N[C@@H](Cc2ccc(OC)cc2)C(=O)N(C)[C@@H](C)C(=O)N[C@@H](CC(=O)O)C(=O)N2CCC[C@H]2C(=O)N[C@@H](Cc2c[nH]cn2)C(=O)N[C@@H](CCCCN)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 36.5 mg, and its estimated purity by LCMS analysis was 100%.

Analysis condition A: Retention time=1.44 min; ESI-MS (+) m/z=993.7 (M+2H)

Analysis condition B: Retention time=3.08 min; ESI-MS (+) m/z=993.6 (M+2H)

ESI-HRMS(+) m/z Calculated 992.4747, Found 992.4711 (M+2H).

Preparation of Example 7148

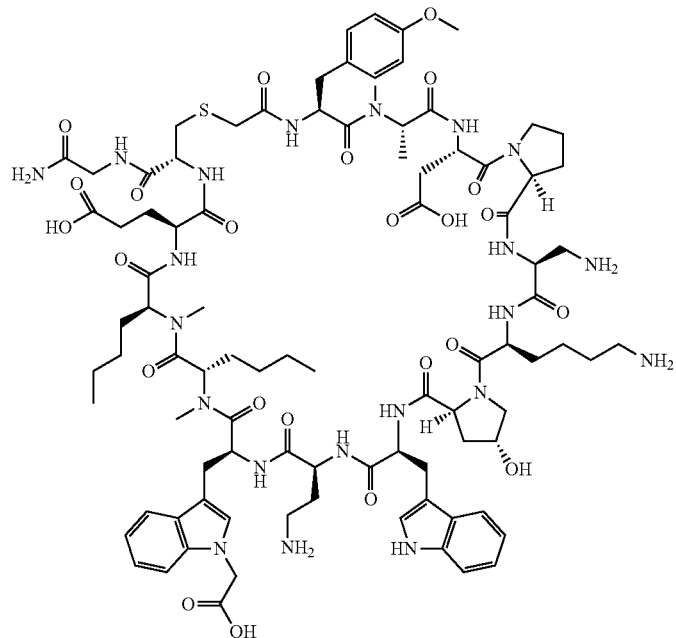 [SMILES: CCCC[C@H]1C(=O)N(C)[C@@H](CCCC)C(=O)N[C@@H](CCC(=O)O)C(=O)N[C@H](C(=O)NCC(N)=O)CSCC(=O)N[C@@H](Cc2ccc(OC)cc2)C(=O)N(C)[C@@H](C)C(=O)N[C@@H](CC(=O)O)C(=O)N2CCC[C@H]2C(=O)N[C@@H](CN)C(=O)N[C@@H](CCCCN)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 22.0 mg, and its estimated purity by LCMS analysis was 100%.

Analysis condition A: Retention time=1.47 min; ESI-MS (+) m/z=967.4 (M+2H)

Analysis condition B: Retention time=3.15 min; ESI-MS (+) m/z=967.4 (M+2H).

Preparation of Example 7151

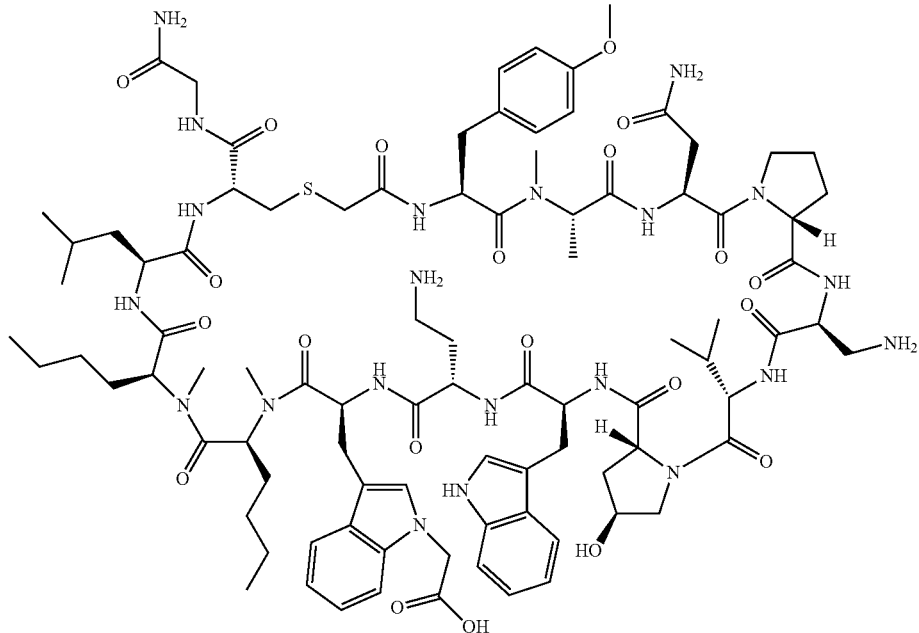 [SMILES: CCCC[C@H]1C(=O)N(C)[C@@H](CCCC)C(=O)N[C@@H](CC(C)C)C(=O)N[C@H](C(=O)NCC(N)=O)CSCC(=O)N[C@@H](Cc2ccc(OC)cc2)C(=O)N(C)[C@@H](C)C(=O)N[C@@H](CC(N)=O)C(=O)N2CCC[C@@H]2C(=O)N[C@@H](CN)C(=O)N[C@@H](C(C)C)C(=O)N2C[C@@H](O)C[C@@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 23.5 mg, and its estimated purity by LCMS analysis was 100%.

Analysis condition A: Retention time=1.69 min; ESI-MS (+) m/z=951.7 (M+2H)

Analysis condition B: Retention time=2.93 min; ESI-MS (+) m/z=951.2 (M+2H).

Preparation of Example 7152

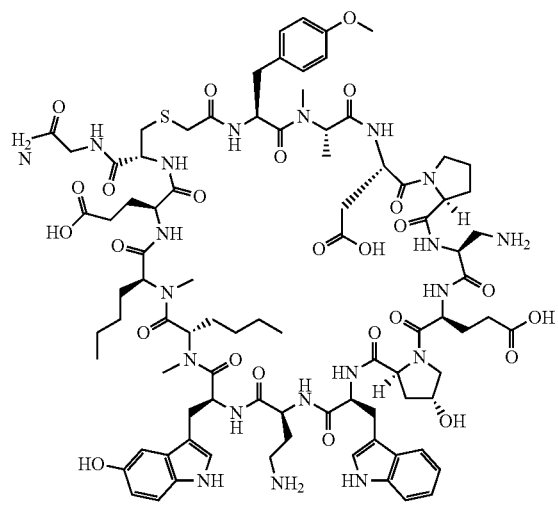 [SMILES: CCCC[C@H]1C(=O)N(C)[C@@H](CCCC)C(=O)N[C@@H](CCC(=O)O)C(=O)N[C@H](C(=O)NCC(N)=O)CSCC(=O)N[C@@H](Cc2ccc(OC)cc2)C(=O)N(C)[C@@H](C)C(=O)N[C@@H](CC(=O)O)C(=O)N2CCC[C@H]2C(=O)N[C@@H](CN)C(=O)N[C@@H](CCC(=O)O)C(=O)N2C[C@H](O)C[C@H]2C(=O)N[C@@H](Cc2c[nH]c3ccccc23)C(=O)N[C@@H](CCN)C(=O)N[C@@H](Cc2c[nH]c3ccc(O)cc23)C(=O)N1C]

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 8.3 mg, and its estimated purity by LCMS analysis was 96%.

Analysis condition A: Retention time=1.45 min; ESI-MS (+) m/z=946.6 (M+2H)

Analysis condition B: Retention time=2.49 min; ESI-MS (+) m/z=946.9 (M+2H).

Preparation of Example 7153

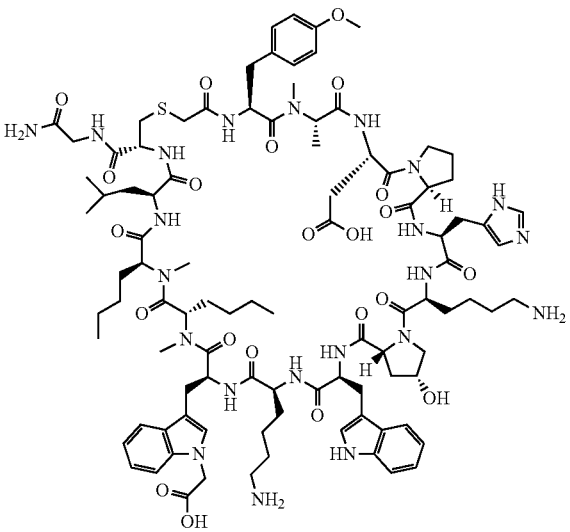 [SMILES: CCCC[C@H]1C(=O)N(C)[C@@H](CCCC)C(=O)N[C@@H](CC(C)C)C(=O)N[C@H](C(=O)NCC(N)=O)CSCC(=O)N[C@@H](Cc2ccc(OC)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CCCCN)C(=O)N2C[C@H](O)C[C@@H]2C(=O)N[C@@H](Cc2c[nH]c3ccccc23)C(=O)N[C@@H](CCCCN)C(=O)N[C@@H](Cc2cn(CC(=O)O)c3ccccc23)C(=O)N1C]

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation.

The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation.

The yield of the product was 6.8 mg, and its estimated purity by LCMS analysis was 100%.

Analysis condition A: Retention time=1.55 min; ESI-MS (+) m/z=999.5 (M+2H)

Analysis condition B: Retention time=2.87 min; ESI-MS (+) m/z=999.8 (M+2H).

Preparation of Example 7154

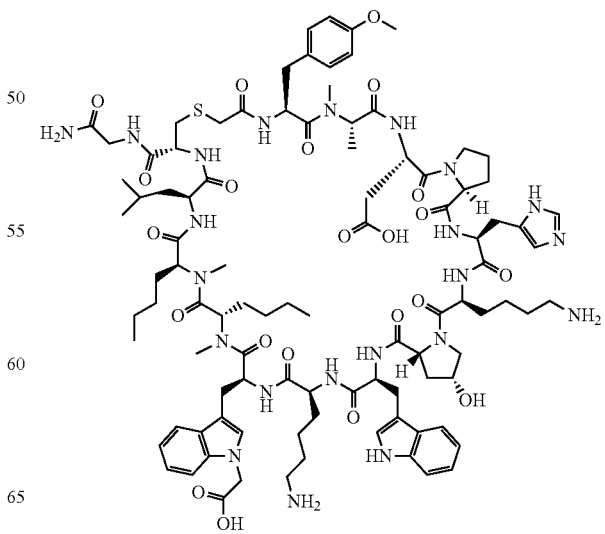

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation.

The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation.

The yield of the product was 1.2 mg, and its estimated purity by LCMS analysis was 98%.

Analysis condition A: Retention time=1.67 min; ESI-MS (+) m/z=999.7 (M+2H)

Analysis condition B: Retention time=3.03 min; ESI-MS (+) m/z=999.8 (M+2H).

General procedures for Symphony X Method D

Analytical Data:

Mass Spectrometry: "ESI-MS(+)" signifies electrospray ionization mass spectrometry performed in positive ion mode; "ESI-MS(−)" signifies electrospray ionization mass spectrometry performed in negative ion mode; "ESI-HRMS (+)" signifies high-resolution electrospray ionization mass spectrometry performed in positive ion mode; "ESI-HRMS (−)" signifies high-resolution electrospray ionization mass spectrometry performed in negative ion mode. The detected masses are reported following the "m/z" unit designation. Compounds with exact masses greater than 1000 were often detected as double-charged or triple-charged ions.

Analysis Condition A:

Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm.

Analysis Condition B:

Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm.

General Coupling Procedures D:

All manipulations were performed under automation on a Symphony X peptide synthesizer (Protein Technologies). All procedures unless noted were performed in a 10 mL polypropylene tube fitted with a bottom frit; where the scale of the reaction exceeded 0.100 mmol, a 40 mL polypropylene tube fitted with a bottom frit was used. The tube connects to a the Symphony X peptide synthesizer through both the bottom and the top of the tube. DMF and DCM can be added through the top of the tube, which washes down the sides of the tube equally. The remaining reagents are added through the top of the tube and pass up through the frit to contact the resin. All solutions are removed through the bottom of the tube. "Periodic agitation" describes a brief pulse of N2 gas through the bottom frit; the pulse lasts approximately 5 seconds and occurs every 30 seconds. Chloroacetyl chloride solutions in DMF were used within 24 h of preparation. Amino acid solutions were generally not used beyond three weeks from preparation. HATU solutions were used within 5 days of preparation. DMF=dimethylformamide; HATU=1-[Bis(dimethylamino) methylene]-1H-1,2,3-triazolo[4,5-b]pyridinium 3-oxid hexafluorophosphate; DIPEA=diisopropylethylamine; Rink resin: 4-((2,4-dimethoxyphenyl)(Fmocamino) methyl)phenoxymethylpolystyrene. Sieber amide resin: 9-Fmoc-aminoxanthen-3-yloxy-methyl, polymer-bound.

The procedures of "Symphony X Method D" describe an experiment performed on a 0.100 mmol scale. All procedures can be scaled beyond 0.100 mmol scale by adjusting the described volumes by the multiple of the scale. Prior to amino acid coupling, all peptide synthesis sequences began with a resin-swelling procedure, described below as "Resin-swelling procedure". Coupling of amino acids to a primary amine N-terminus used the "Single-coupling procedure" described below. Coupling of amino acids to a secondary amine N-terminus used the "Double-coupling procedure" described below. Coupling of chloroacetylchloride to the N-terminus of the peptide is described by the "Chloroacetyl chloride coupling procedure" detailed below.

Resin-Swelling Procedure:

To a 10 mL polypropylene solid-phase reaction vessel was added resin (0.100 mmol). The resin was washed (swelled) three times as follows: to the reaction vessel was added DMF (2.0 mL), upon which the mixture was periodically agitated for 10 minutes before the solvent was drained through the frit.

Single-Coupling Procedure:

To the reaction vessel containing resin from the previous step was added piperidine:DMF (20:80 v/v, 2.0 mL). The mixture was periodically agitated for 3 minutes and then the solution was drained through the frit. To the reaction vessel was added piperidine:DMF (20:80 v/v, 2.0 mL). The mixture was periodically agitated for 3 minutes and then the solution was drained through the frit. The resin was washed successively six times as follows: for each wash, DMF (2.0 mL) was added through the top of the vessel and the resulting mixture was periodically agitated for 30 seconds before the solution was drained through the frit. To the reaction vessel was added the amino acid (0.2M in DMF, 1.0 mL, 2 eq), then HATU (0.2M in DMF, 1.0 mL, 2 eq), and finally DIPEA (0.4M in DMF, 1.0 mL, 4 eq). The mixture was periodically agitated for 15 minutes, then the reaction solution was drained through the frit. The resin was washed successively four times as follows: for each wash, DMF (2.0 mL) was added through the top of the vessel and the resulting mixture was periodically agitated for 30 seconds before the solution was drained through the frit. To the reaction vessel was added acetic anhydride (2.0 mL). The mixture was periodically agitated for 10 minutes, then the solution was drained through the frit. The resin was washed successively four times as follows: for each wash, DMF (2.0 mL) was added through the top of the vessel and the resulting mixture was periodically agitated for 90 seconds before the solution was drained through the frit. The resulting resin was used directly in the next step.

Single-Coupling 1 h Procedure:

To the reaction vessel containing resin from the previous step was added piperidine:DMF (20:80 v/v, 2.0 mL). The mixture was periodically agitated for 3 minutes and then the solution was drained through the frit. To the reaction vessel was added piperidine:DMF (20:80 v/v, 2.0 mL). The mixture was periodically agitated for 3 minutes and then the solution was drained through the frit. The resin was washed successively six times as follows: for each wash, DMF (2.0 mL) was added through the top of the vessel and the resulting mixture was periodically agitated for 30 seconds before the solution was drained through the frit. To the reaction vessel was added the amino acid (0.2M in DMF, 1.0 mL, 2 eq), then HATU (0.2M in DMF, 1.0 mL, 2 eq), and finally DIPEA (0.4M in DMF, 1.0 mL, 4 eq). The mixture was periodically agitated for 60 minutes, then the reaction solution was drained through the frit. The resin was washed successively four times as follows: for each wash, DMF (2.0 mL) was added through the top of the vessel and the resulting mixture was periodically agitated for 30 seconds before the solution was drained through the frit. To the reaction vessel was added acetic anhydride (2.0 mL). The mixture was periodically agitated for 10 minutes, then the solution was drained through the frit. The resin was washed successively four times as follows: for each wash, DMF (2.0 mL) was added through the top of the vessel and the resulting mixture was periodically agitated for 90 seconds before the solution was drained through the frit. The resulting resin was used directly in the next step.

Double-Coupling Procedure:

To the reaction vessel containing resin from the previous step was added piperidine:DMF (20:80 v/v, 2.0 mL). The mixture was periodically agitated for 3 minutes and then the solution was drained through the frit. To the reaction vessel was added piperidine:DMF (20:80 v/v, 2.0 mL). The mixture was periodically agitated for 3 minutes and then the solution was drained through the frit. The resin was washed successively six times as follows: for each wash, DMF (2.0 mL) was added through the top of the vessel and the resulting mixture was periodically agitated for 30 seconds before the solution was drained through the frit. To the reaction vessel was added the amino acid (0.2M in DMF, 1.0 mL, 2 eq), then HATU (0.2M in DMF, 1.0 mL, 2 eq), and finally DIPEA (0.4M in DMF, 1.0 mL, 4 eq). The mixture was periodically agitated for 15 minutes, then the reaction solution was drained through the frit. The resin was twice washed as follows: for each wash, DMF (2.0 mL) was added through the top of the vessel and the resulting mixture was periodically agitated for 30 seconds before the solution was drained through the frit. To the reaction vessel was added the amino acid (0.2M in DMF, 1.0 mL, 2 eq), then HATU (0.2M in DMF, 1.0 mL, 2 eq), and finally DIPEA (0.4M in DMF, 1.0 mL, 4 eq). The mixture was periodically agitated for 15 minutes, then the reaction solution was drained through the frit. The resin was twice washed as follows: for each wash, DMF (2.0 mL) was added through the top of the vessel and the resulting mixture was periodically agitated for 30 seconds before the solution was drained through the frit. To the reaction vessel was added acetic anhydride (2.0 mL). The mixture was periodically agitated for 10 minutes, then the solution was drained through the frit. The resin was washed successively four times as follows: for each wash, DMF (2.0 mL) was added through the top of the vessel and the resulting mixture was periodically agitated for 90 seconds before the solution was drained through the frit. The resulting resin was used directly in the next step.

Double-Coupling 6 h Procedure:

To the reaction vessel containing resin from the previous step was added piperidine:DMF (20:80 v/v, 2.0 mL). The mixture was periodically agitated for 3 minutes and then the solution was drained through the frit. To the reaction vessel was added piperidine:DMF (20:80 v/v, 2.0 mL). The mixture was periodically agitated for 3 minutes and then the solution was drained through the frit. The resin was washed successively six times as follows: for each wash, DMF (2.0 mL) was added through the top of the vessel and the resulting mixture was periodically agitated for 30 seconds before the solution was drained through the frit. To the reaction vessel was added the amino acid (0.2M in DMF, 1.0 mL, 2 eq), then HATU (0.2M in DMF, 1.0 mL, 2 eq), and finally DIPEA (0.4M in DMF, 1.0 mL, 4 eq). The mixture was periodically agitated for 6 hs, then the reaction solution was drained through the frit. The resin was twice washed as follows: for each wash, DMF (2.0 mL) was added through the top of the vessel and the resulting mixture was periodically agitated for 30 seconds before the solution was drained through the frit. To the reaction vessel was added the amino acid (0.2M in DMF, 1.0 mL, 2 eq), then HATU (0.2M in DMF, 1.0 mL, 2 eq), and finally DIPEA (0.4M in DMF, 1.0 mL, 4 eq). The mixture was periodically agitated for 6 hs, then the reaction solution was drained through the frit. The resin was twice washed as follows: for each wash, DMF (2.0 mL) was added through the top of the vessel and the resulting mixture was periodically agitated for 30 seconds before the solution was drained through the frit. To the reaction vessel was added acetic anhydride (2.0 mL). The mixture was periodically agitated for 10 minutes, then the solution was drained through the frit. The resin was washed successively four times as follows: for each wash, DMF (2.0 mL) was added through the top of the vessel and the resulting mixture was periodically agitated for 90 seconds before the solution was drained through the frit. The resulting resin was used directly in the next step.

Chloroacetyl Chloride Coupling Procedure:

To the reaction vessel containing the resin from the previous step was added piperidine:DMF (20:80 v/v, 2.0 mL). The mixture was periodically agitated for 3 minutes and then the solution was drained through the frit. To the reaction vessel was added piperidine:DMF (20:80 v/v, 2.0 mL). The mixture was periodically agitated for 3 minutes and then the solution was drained through the frit. The resin was washed successively six times as follows: for each wash, DMF (2.0 mL) was added through the top of the vessel and the resulting mixture was periodically agitated for 30 seconds before the solution was drained through the frit. To the reaction vessel was added DIPEA (0.8M in DMF, 3.0 mL, 24 eq), then chloroacetyl chloride (0.8M in DMF, 1.65 mL, 13.2 eq). The mixture was periodically agitated for 30 minutes, then the solution was drained through the frit. The resin was washed successively three times as follows: for each wash, DMF (2.0 mL) was added to top of the vessel and the resulting mixture was periodically agitated for 90 seconds before the solution was drained through the frit. The resin was washed successively four times as follows: for each wash, $CH_2Cl_2$ (2.0 mL) was added to top of the vessel and the resulting mixture was periodically agitated for 90 seconds before the solution was drained through the frit. The resulting resin was placed under a $N_2$ stream for 15 minutes.

Deprotection Method D:

All manipulations were performed manually unless noted. The procedure of "Deprotection Method D" describes an experiment performed on a 0.100 mmol scale. The procedure can be scaled beyond 0.100 mmol scale by adjusting the described volumes by the multiple of the scale. A "deprotection solution" was prepared by combining in a 40 mL glass vial trifluoroacetic acid (38 mL), DTT (1 g) and triisopropylsilane (1 mL). The resin was removed from the reaction vessel and transferred to a 4 mL glass vial. To the vial was added the "deprotection solution" (2.0 mL). The mixture was vigorously mixed in a shaker (1000 RPM for 15-30 minutes). The mixture was filtered through a 0.2 micron syringe filter and the solids were extracted with the "deprotection solution" (1.0 mL). To a 24 mL test tube charged with the combined filtrates was added $Et_2O$ (15 mL). The mixture was vigorously mixed upon which a significant amount of a white solid precipitated. The mixture was centrifuged for 3 minutes, then the solution was decanted away from the solids and discarded. The solids were suspended in $Et_2O$ (20 mL); then the mixture was centrifuged for 3 minutes; and the solution was decanted away from the solids and discarded. For a final time, the solids were suspended in Et$_2$O (20 mL); the mixture was centrifuged for 3 minutes; and the solution was decanted away from the solids and discarded to afford the crude peptide as a white to off-white solid.

Cyclization Method D:

All manipulations were performed manually unless noted. The procedure of "Cyclization Method D" describes an experiment performed on a 0.100 mmol scale. The procedure can be scaled beyond 0.100 mmol scale by adjusting the described volumes by the multiple of the scale. The crude peptide solids were dissolved in MeCN:aq. 0.1M NH$_4$OAc (1:1) to a total volume of 18-22 mL, and the solution was carefully then adjusted to pH=8.5-9.0 using aq NaOH (1.0M). The solution was then allowed to stand without stirring for 12-18 h. The reaction solution was concentrated and the residue was then dissolved in DMSO: MeOH (1:1). This solution was subjected to reverse-phase HPLC purification to afford the desired cyclic peptide.

General Synthetic Sequence D:

"General Synthetic Sequence D" describes a general sequence of procedures that were used to afford the cyclic peptides described herein. To a 10 mL polypropylene solid-phase reaction vessel was added Rink or Sieber resin, and the reaction vessel was placed on the Symphony X peptide synthesizer. "General coupling Procedures D": Resin-swelling procedure was followed. Then a series of amino acids couplings was sequentially performed on the Symphony X peptide synthesizer following "Single-coupling procedure" if the N-terminus of the resin-bound peptide was a primary amine or "Double-coupling procedure" if the N-terminus of the resin-bound peptide was a secondary amine. "Single-coupling 1 h" procedure was used with the amino acid (S)-2-((((9H-fluoren-9-yl)methoxy)carbonyl)amino)-3-(3,4, 5-trifluorophenyl)propanoic acid was coupled onto the resin. "Double-coupling 6 h procedure" was used when Valine was coupled onto the resin. Chloroacetyl chloride coupling procedure was followed; then Deprotection Method D was followed; then Cyclization Method D was followed.

Series 9000

Examples 9115-9187 were prepared by following the "General Synthetic Sequence A". Examples 9188-9196, Example 9213-9224, Examples 9241-9288 and Examples 9318-9374 were prepared by following the "General Synthetic Sequence D".

Preparation of Example 9115

Example 9115

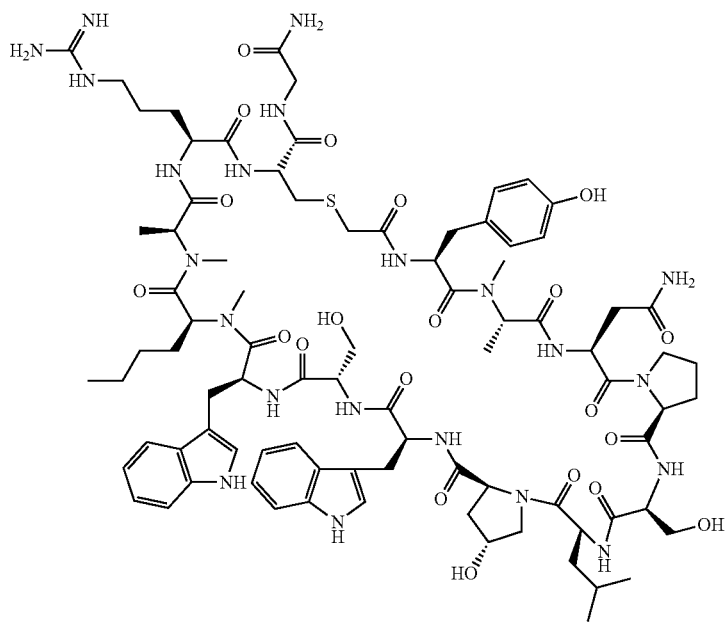

The crude material of Example 9115 was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 17.9 mg, and its estimated purity by LCMS analysis was 91%.

Analysis condition A: Retention time=1.37 min; ESI-MS (+) m/z 910.1 (M+2H).

Analysis condition B: Retention time=2.42 min; ESI-MS (+) m/z 910.1 (M+2H).

Preparation of Example 9116

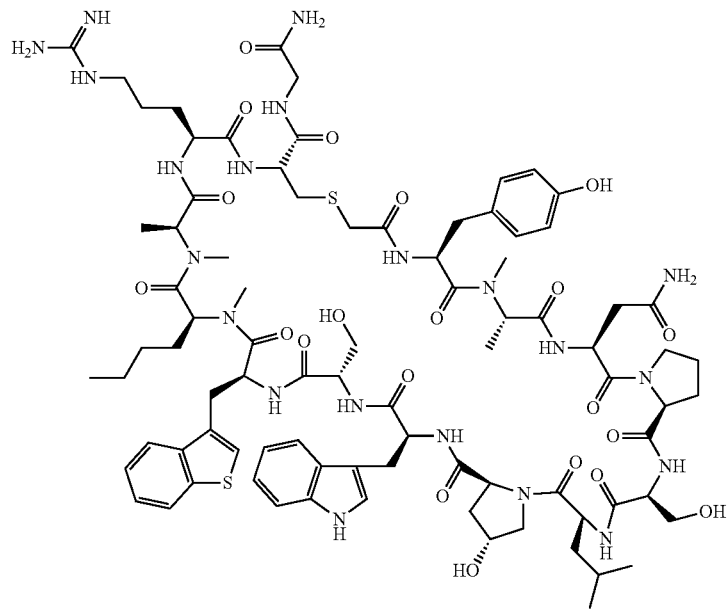

Example 9116

The crude material of Example 9116 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 7.3 mg, and its estimated purity by LCMS analysis was 100%.

Analysis condition A: Retention time=1.54 min; ESI-MS (+) m/z 918.3 (M+2H).

Analysis condition B: Retention time=2.64 min; ESI-MS (+) m/z 918.6 (M+2H).

Preparation of Example 9117

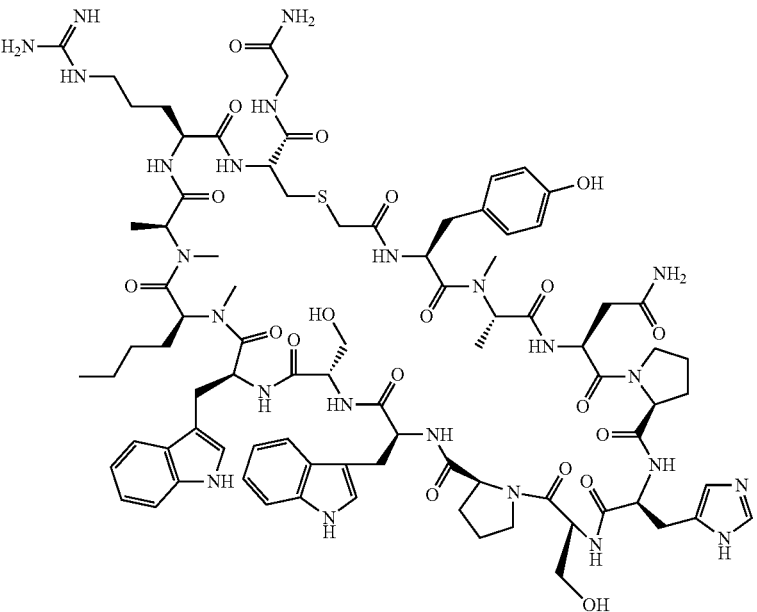

Example 9117

The crude material of Example 9117 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 21.9 mg, and its estimated purity by LCMS analysis was 98%.

Analysis condition A: Retention time=1.33 min; ESI-MS (+) m/z 913.7 (M+2H).

Analysis condition B: Retention time=2.36 min; ESI-MS (+) m/z 914.1 (M+2H).

Preparation of Example 9118

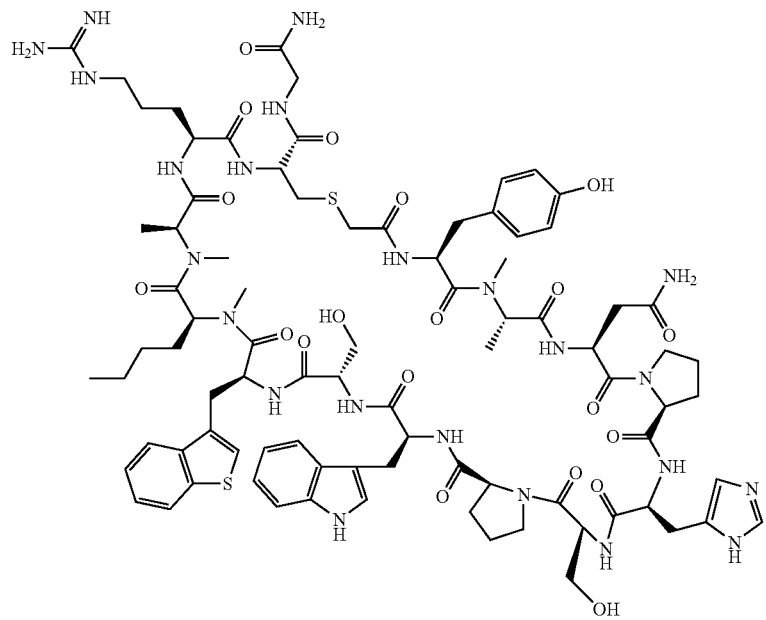

Example 9118

The crude material of Example 9118 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 15.8 mg, and its estimated purity by LCMS analysis was 100%.

Analysis condition A: Retention time=1.43 min; ESI-MS (+) m/z 922.6 (M+2H).

Analysis condition B: Retention time=2.58 min; ESI-MS (+) m/z 922.6 (M+2H).

Preparation of Example 9119

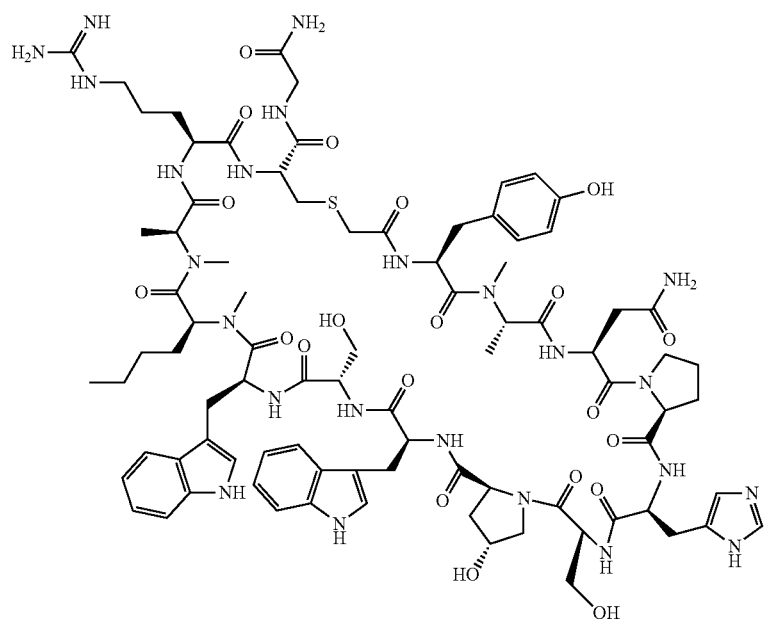

Example 9119

The crude material of Example 9119 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 15.5 mg, and its estimated purity by LCMS analysis was 100%.

Analysis condition A: Retention time=1.28 min; ESI-MS (+) m/z 922.2 (M+2H).

Analysis condition B: Retention time=2.34 min; ESI-MS (+) m/z 922.2 (M+2H).

Preparation of Example 9120

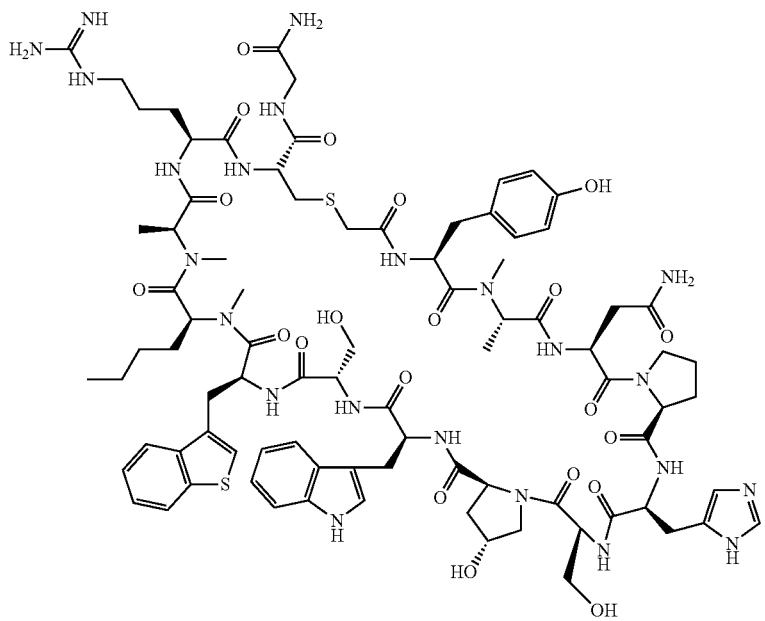

Example 9120

The crude material of Example 9120 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 15.7 mg, and its estimated purity by LCMS analysis was 100%.

Analysis condition A: Retention time=1.45 min; ESI-MS (+) m/z 930.7 (M+2H).

Analysis condition B: Retention time=2.56 min; ESI-MS (+) m/z 930.7 (M+2H).

Preparation of Example 9121

Example 9121

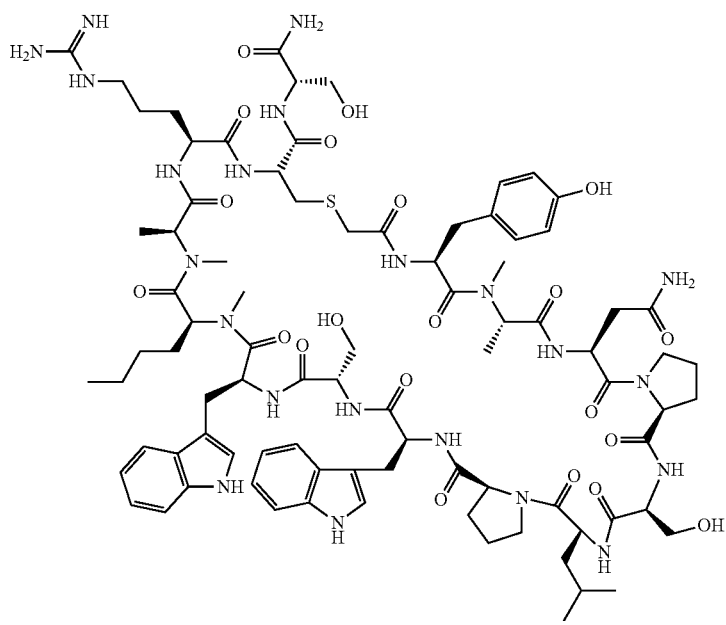

The crude material of Example 9121 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 18.8 mg, and its estimated purity by LCMS analysis was 98%.

Analysis condition A: Retention time=1.39 min; ESI-MS (+) m/z 916.9 (M+2H).

Analysis condition B: Retention time=2.45 min; ESI-MS (+) m/z 917.1 (M+2H).

Preparation of Example 9122

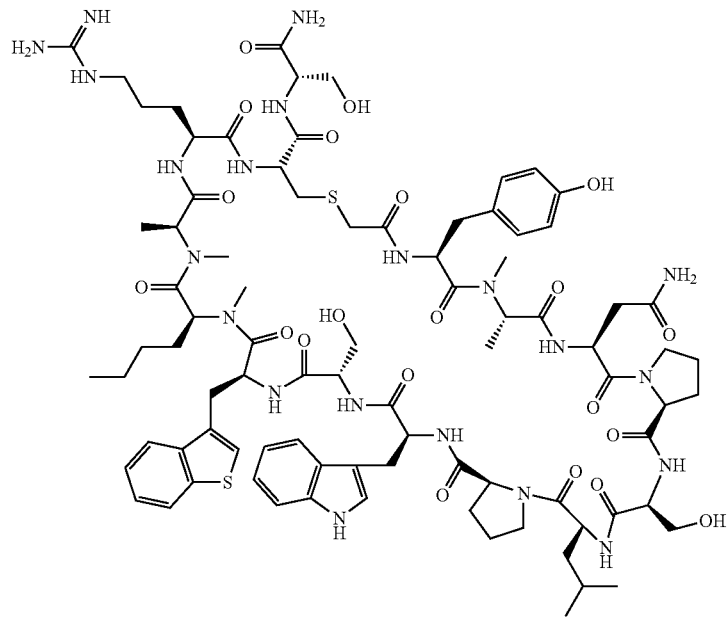

Example 9122

The crude material of Example 9122 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 14.2 mg, and its estimated purity by LCMS analysis was 100%.

Analysis condition A: Retention time=1.52 min; ESI-MS (+) m/z 925.6 (M+2H).

Analysis condition B: Retention time=2.65 min; ESI-MS (+) m/z 925.5 (M+2H).

Preparation of Example 9123

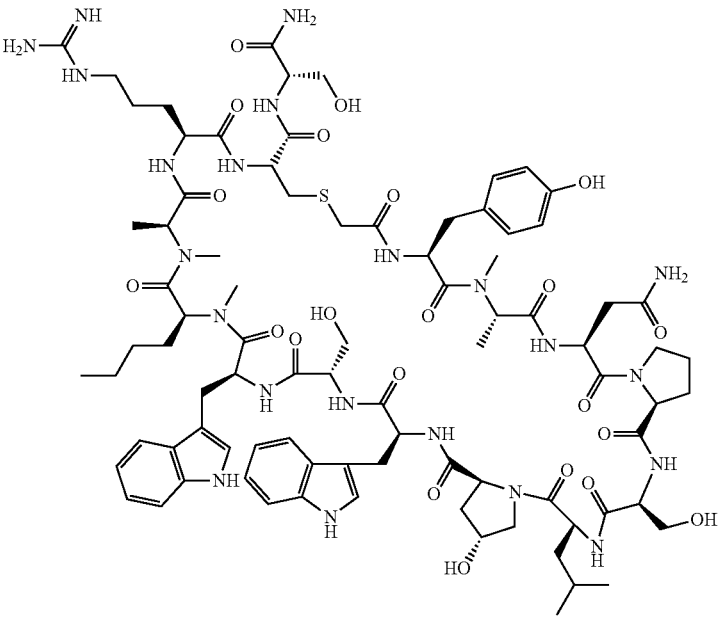

Example 9123

The crude material of Example 9123 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 7.8 mg, and its estimated purity by LCMS analysis was 100%.

Analysis condition A: Retention time=1.38 min; ESI-MS (+) m/z 925.2 (M+2H).

Analysis condition B: Retention time=2.40 min; ESI-MS (+) m/z 925.3 (M+2H).

Preparation of Example 9124

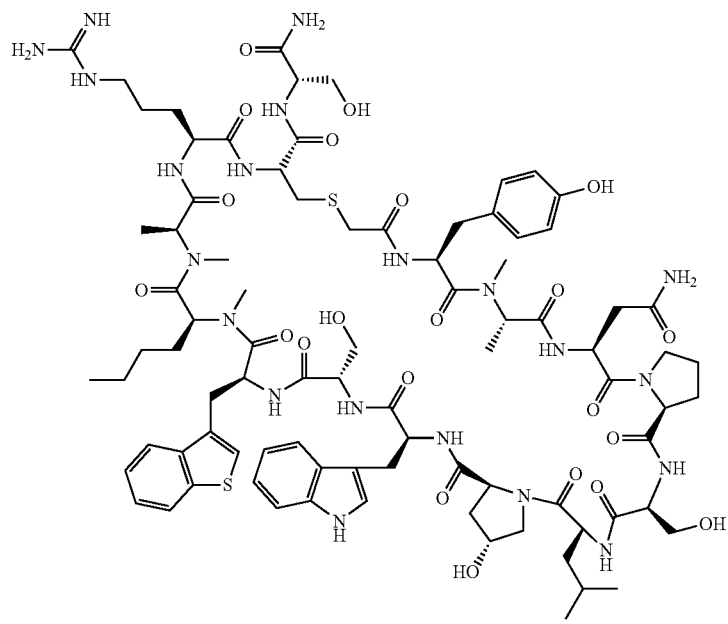

Example 9124

The crude material of Example 9124 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 22.6 mg, and its estimated purity by LCMS analysis was 93%.

Analysis condition A: Retention time=1.48 min; ESI-MS (+) m/z 933.9 (M+2H).

Analysis condition B: Retention time=2.62 min; ESI-MS (+) m/z 933.7 (M+2H).

Preparation of Example 9125

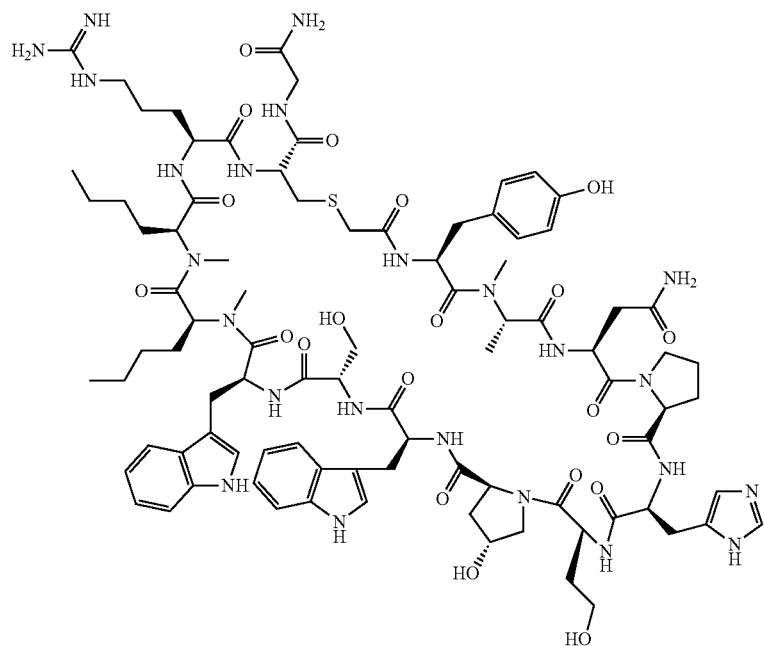

Example 9125

The crude material of Example 9125 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 13.3 mg, and its estimated purity by LCMS analysis was 98%.

Analysis condition A: Retention time=1.47 min; ESI-MS (+) m/z 942.1 (M+2H).

Analysis condition B: Retention time=2.59 min; ESI-MS (+) m/z 942.2 (M+2H).

Preparation of Example 9126

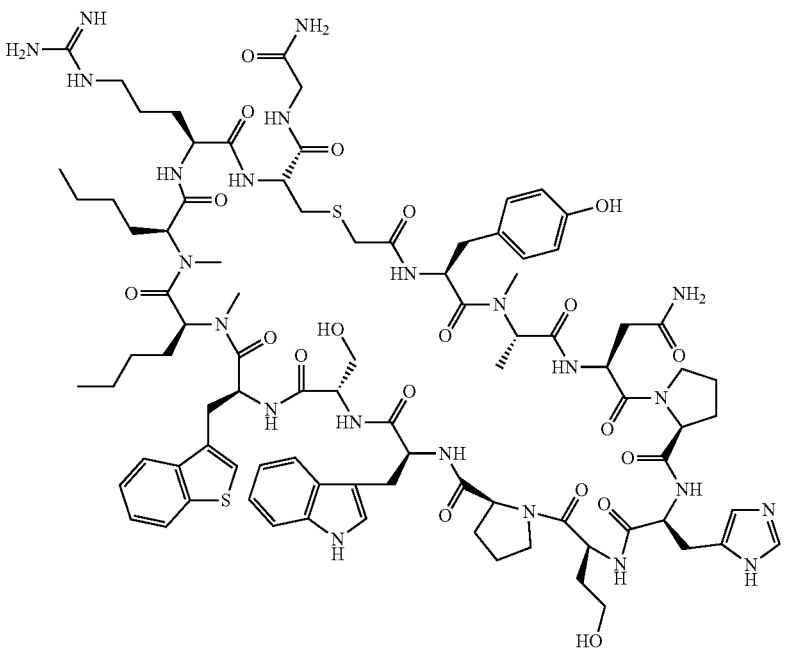

Example 9126

The crude material of Example 9126 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 18.4 mg, and its estimated purity by LCMS analysis was 99%.

Analysis condition A: Retention time=1.59 min; ESI-MS (+) m/z 950.7 (M+2H).

Analysis condition B: Retention time=2.75 min; ESI-MS (+) m/z 950.7 (M+2H).

Preparation of Example 9127

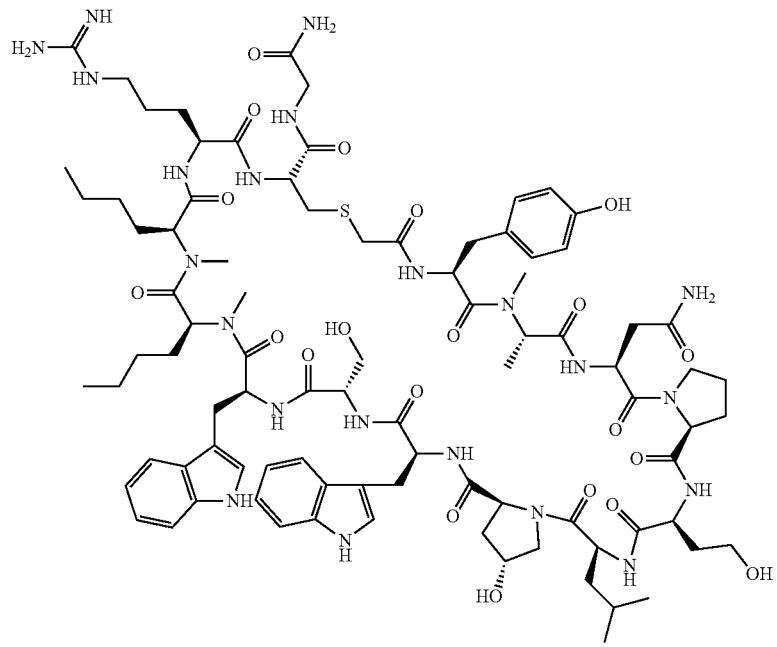

Example 9127

The crude material of Example 9127 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 23.5 mg, and its estimated purity by LCMS analysis was 99%.

Analysis condition A: Retention time=1.53 min; ESI-MS (+) m/z 938.5 (M+2H).

Analysis condition B: Retention time=2.65 min; ESI-MS (+) m/z 938.6 (M+2H).

Preparation of Example 9128

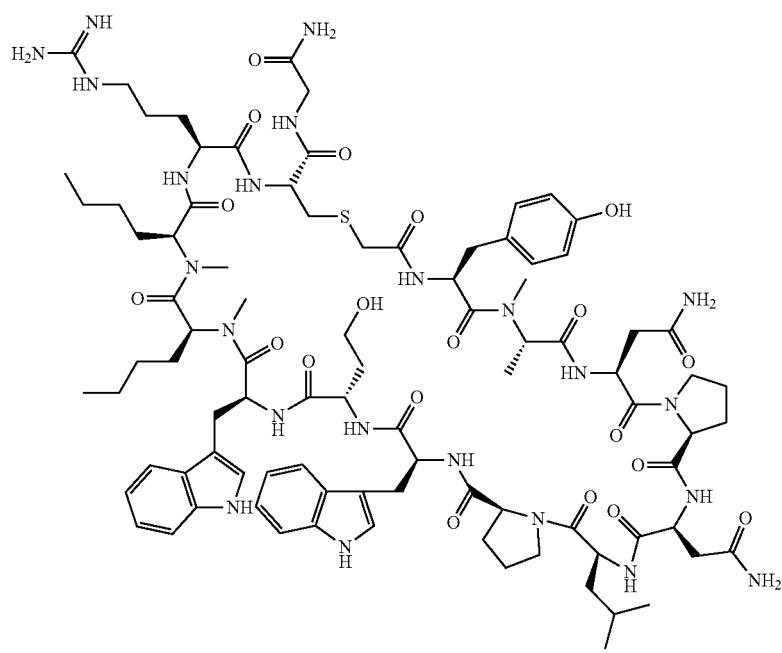

Example 9128

The crude material of Example 9128 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 13.5 mg, and its estimated purity by LCMS analysis was 93%.

Analysis condition A: Retention time=1.50 min; ESI-MS (+) m/z 941.5 (M+2H).

Analysis condition B: Retention time=2.59 min; ESI-MS (+) m/z 941.8 (M+2H).

Preparation of Example 9129

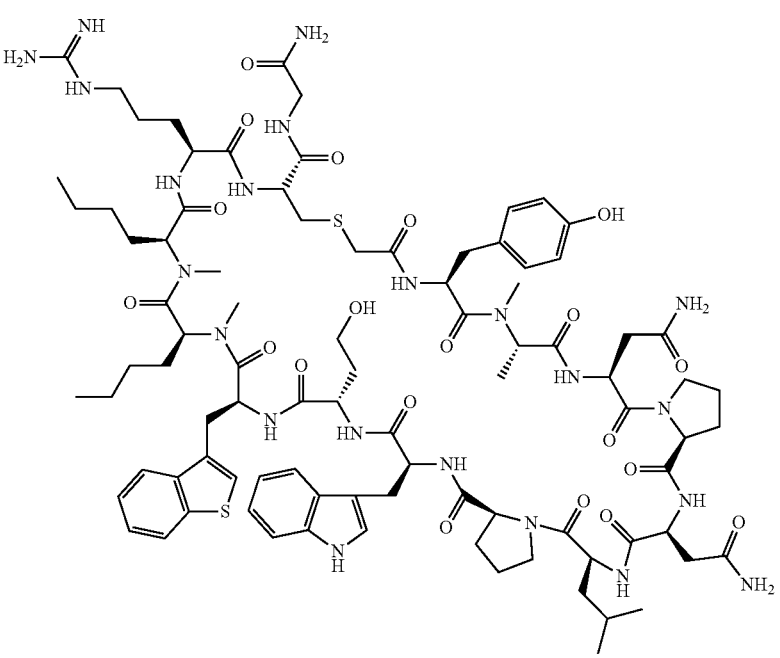

Example 9129

The crude material of Example 9129 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 17.6 mg, and its estimated purity by LCMS analysis was 96%.

Analysis condition A: Retention time=1.67 min; ESI-MS (−) m/z 949.9 (M−2H).

Analysis condition B: Retention time=2.79 min; ESI-MS (+) m/z 952.1 (M+2H).

Preparation of Example 9130

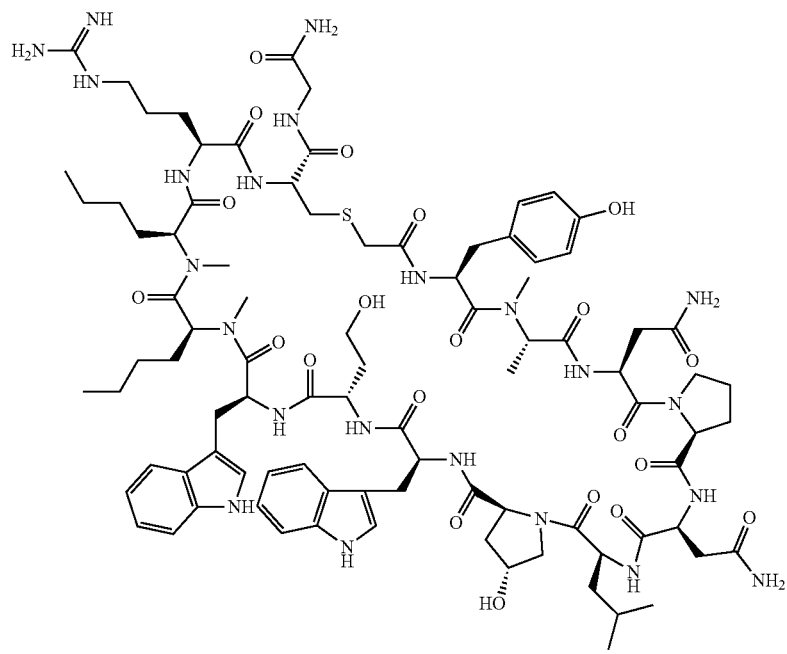

Example 9130

The crude material of Example 9130 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 14.3 mg, and its estimated purity by LCMS analysis was 96%.

Analysis condition A: Retention time=1.50 min; ESI-MS (+) m/z 951.7 (M+2H).

Analysis condition B: Retention time=2.56 min; ESI-MS (+) m/z 951.6 (M+2H).

Preparation of Example 9131

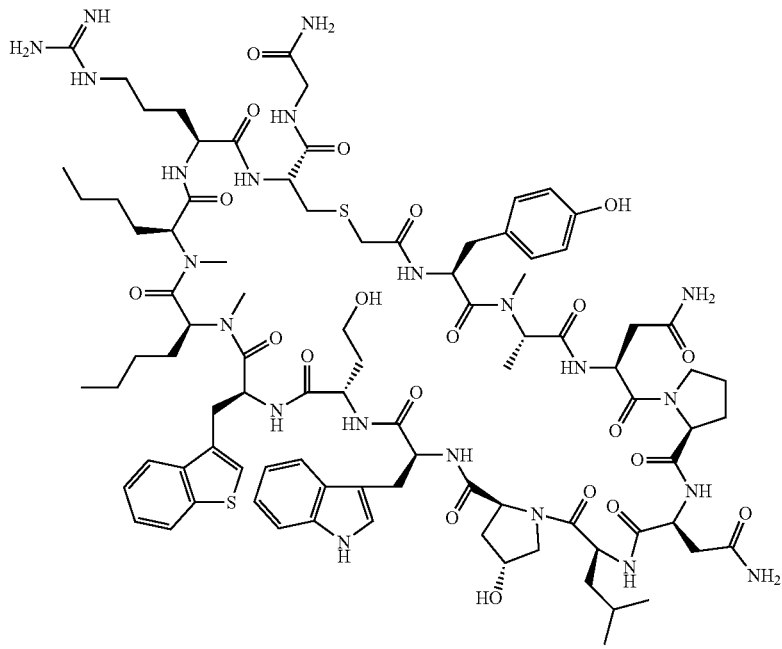

Example 9131

The crude material of Example 9131 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 15.8 mg, and its estimated purity by LCMS analysis was 97%.

Analysis condition A: Retention time=1.63 min; ESI-MS (+) m/z 960.0 (M+2H).

Analysis condition B: Retention time=2.79 min; ESI-MS (+) m/z 960.2 (M+2H).

Preparation of Example 9132

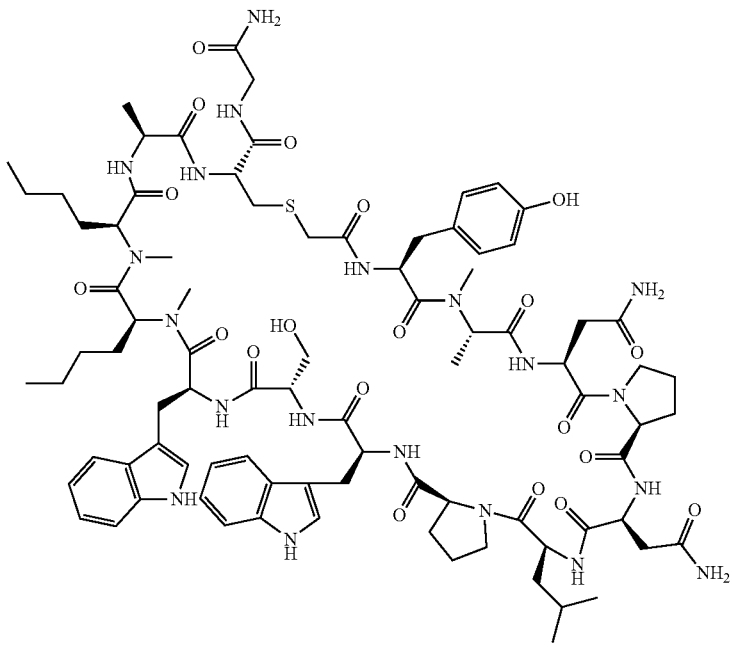

Example 9132

The crude material of Example 9132 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-55% B over 30 minutes, then a 5-minute hold at 100% B; Flow: 20 mL/min. Fractions containing the desired product were combined and dried via centrifugal evaporation. The yield of the product was 15.1 mg, and its estimated purity by LCMS analysis was 100%.

Analysis condition A: Retention time=1.58 min; ESI-MS (−) m/z 892.1 (M−2H).

Analysis condition B: Retention time=2.67 min; ESI-MS (+) m/z 894.1 (M+2H).

Preparation of Example 9133

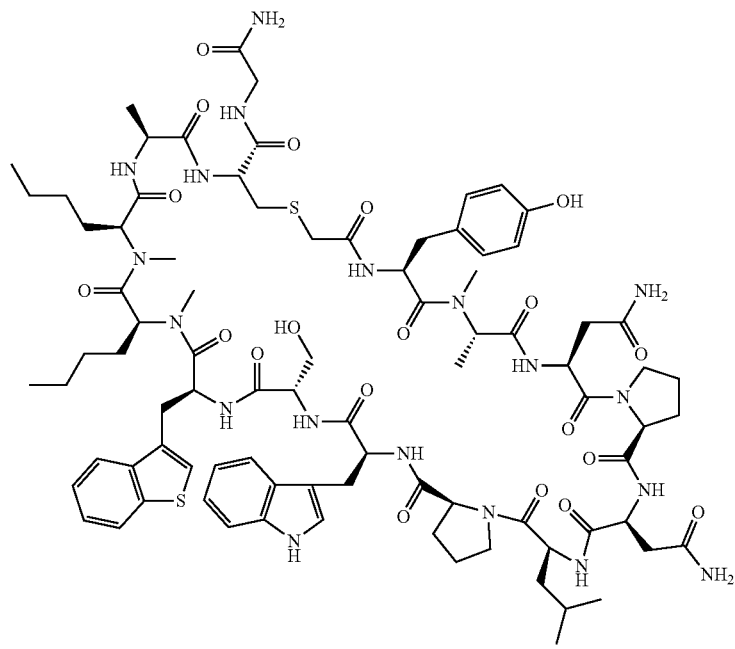

Example 9133

The crude material of Example 9133 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 24.5 mg, and its estimated purity by LCMS analysis was 100%.

Analysis condition A: Retention time=1.76 min; ESI-MS (+) m/z 902.6 (M+2H).

Analysis condition B: Retention time=2.88 min; ESI-MS (+) m/z 902.6 (M+2H).

Preparation of Example 9134

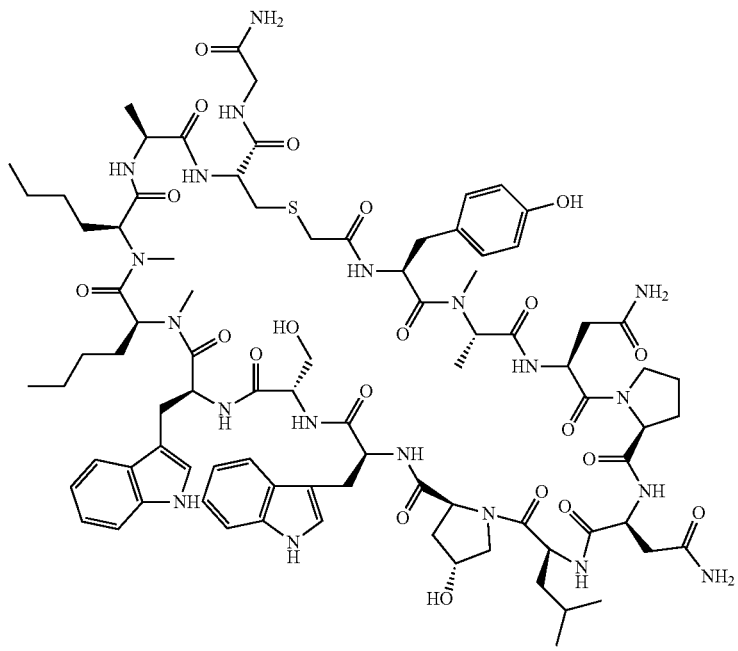

Example 9134

The crude material of Example 9134 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 21.2 mg, and its estimated purity by LCMS analysis was 100%.

Analysis condition A: Retention time=1.67 min; ESI-MS (+) m/z 902.0 (M+2H).

Analysis condition B: Retention time=2.65 min; ESI-MS (+) m/z 902.0 (M+2H).

Preparation of Example 9135

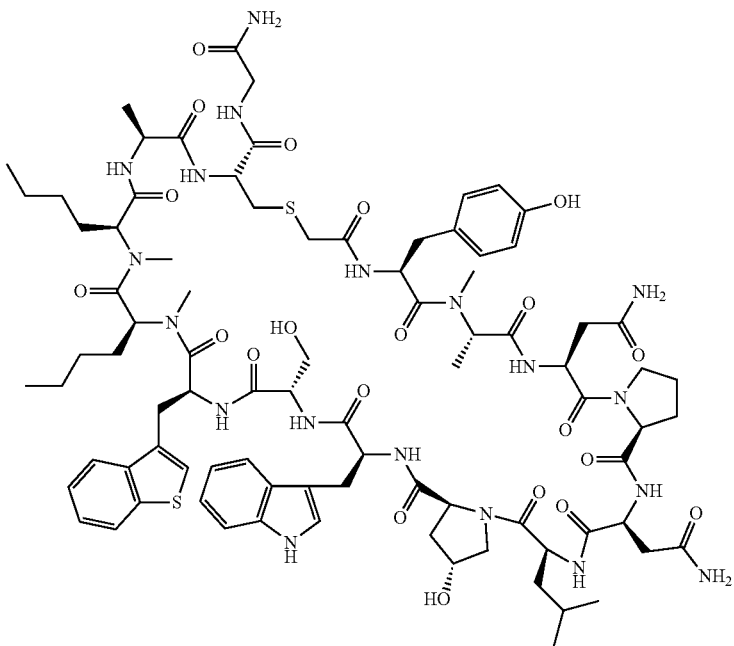

Example 9135

The crude material of Example 9135 was submitted to the Single Compound Purification team for purification and analysis. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-60% B over 30 minutes, then a 5-minute hold at 100% B; Flow: 20 mL/min. Fractions containing the desired product were combined and dried via centrifugal evaporation. The yield of the product was 15.6 mg, and its estimated purity by LCMS analysis was 100%.

Analysis condition A: Retention time=1.73 min; ESI-MS (+) m/z 910.9 (M+2H).

Analysis condition B: Retention time=2.90 min; ESI-MS (+) m/z 910.6 (M+2H).

Preparation of Example 9136

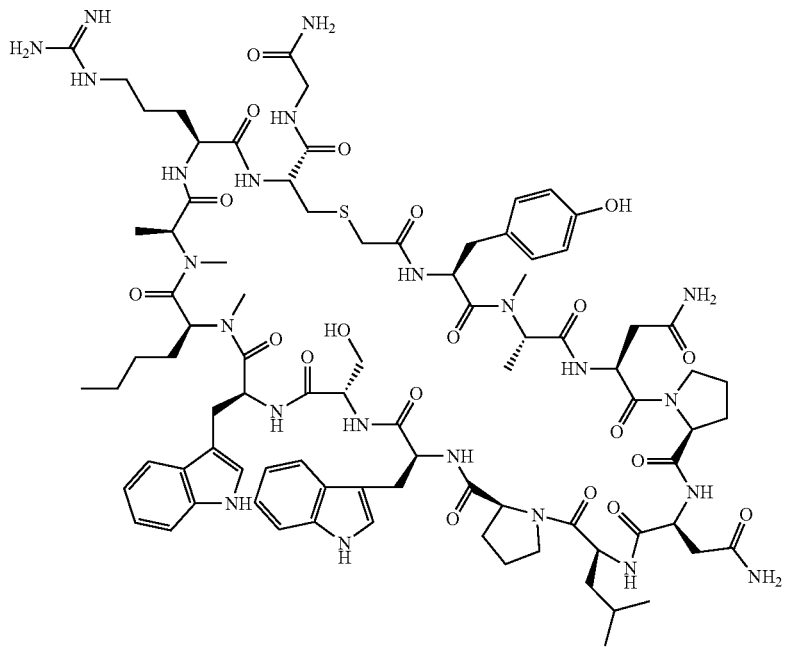

Example 9136

The crude material of Example 9136 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 17.7 mg, and its estimated purity by LCMS analysis was 92%.

Analysis condition A: Retention time=1.35 min; ESI-MS (+) m/z 915.7 (M+2H).

Analysis condition B: Retention time=2.42 min; ESI-MS (+) m/z 915.6 (M+2H).

Preparation of Example 9137

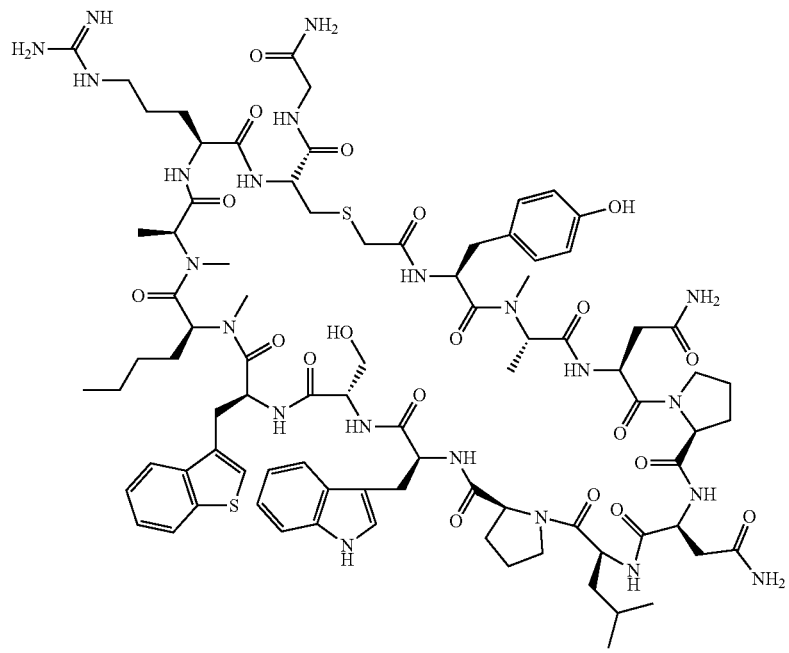

Example 9137

The crude material of Example 9137 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-50% B over 30 minutes, then a 5-minute hold at 100% B; Flow: 20 mL/min. Fractions containing the desired product were combined and dried via centrifugal evaporation. The yield of the product was 4.0 mg, and its estimated purity by LCMS analysis was 100%.

Analysis condition A: Retention time=1.53 min; ESI-MS (+) m/z 924.0 (M+2H).

Analysis condition B: Retention time=2.65 min; ESI-MS (+) m/z 924.3 (M+2H).

Preparation of Example 9138

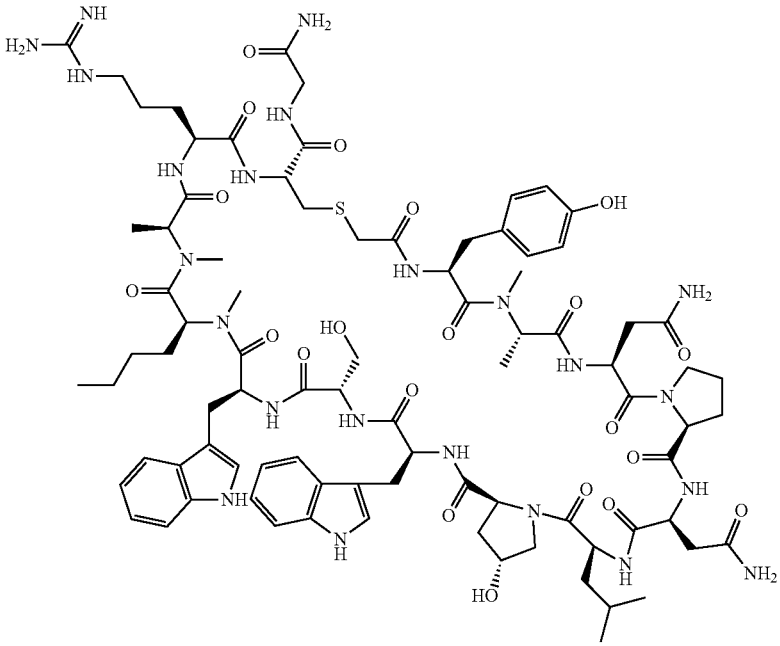

Example 9138

The crude material of Example 9138 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 8.6 mg, and its estimated purity by LCMS analysis was 100%.

Analysis condition A: Retention time=1.32 min; ESI-MS (+) m/z 924.1 (M+2H).

Analysis condition B: Retention time=2.35 min; ESI-MS (+) m/z 924.0 (M+2H).

Preparation of Example 9139

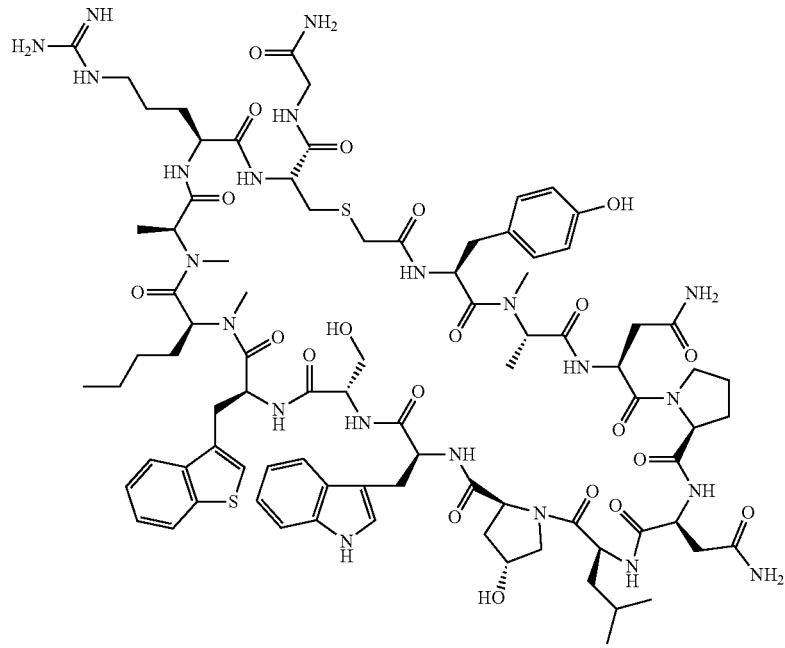

Example 9139

The crude material of Example 9139 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-60% B over 30 minutes, then a 5-minute hold at 100% B; Flow: 20 mL/min. Fractions containing the desired product were combined and dried via centrifugal evaporation. The material was further purified via preparative LC/MS with the following conditions: Column: waters xbridge c-18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 30-80% B over 30 minutes, then a 5-minute hold at 100% B; Flow: 20 mL/min. Fractions containing the desired product were combined and dried via centrifugal evaporation. The yield of the product was 10.1 mg, and its estimated purity by LCMS analysis was 100%.

Analysis condition A: Retention time=1.51 min; ESI-MS (+) m/z 932.4 (M+2H).

Analysis condition B: Retention time=2.63 min; ESI-MS (+) m/z 932.2 (M+2H).

Preparation of Example 9140

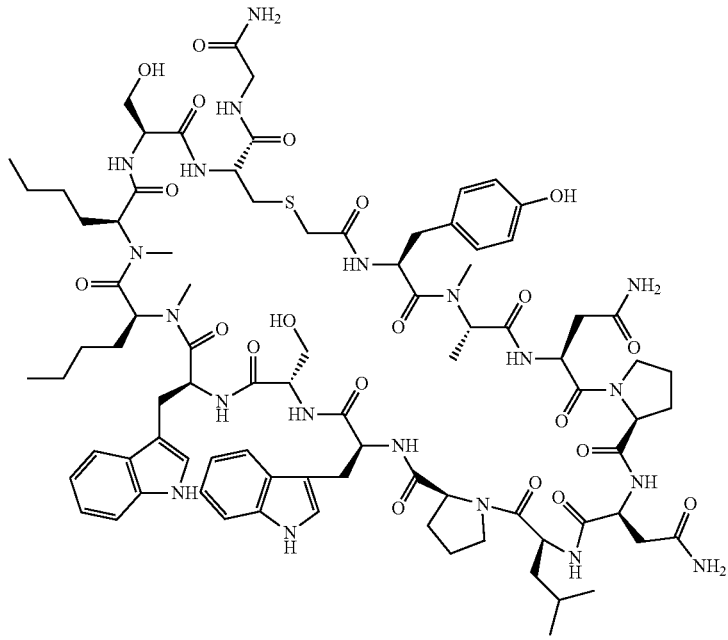

Example 9140

The crude material of Example 9140 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 17.8 mg, and its estimated purity by LCMS analysis was 100%.

Analysis condition A: Retention time=1.60 min; ESI-MS (+) m/z 902.2 (M+2H).

Analysis condition B: Retention time=2.60 min; ESI-MS (+) m/z 902.0 (M+2H).

Preparation of Example 9141

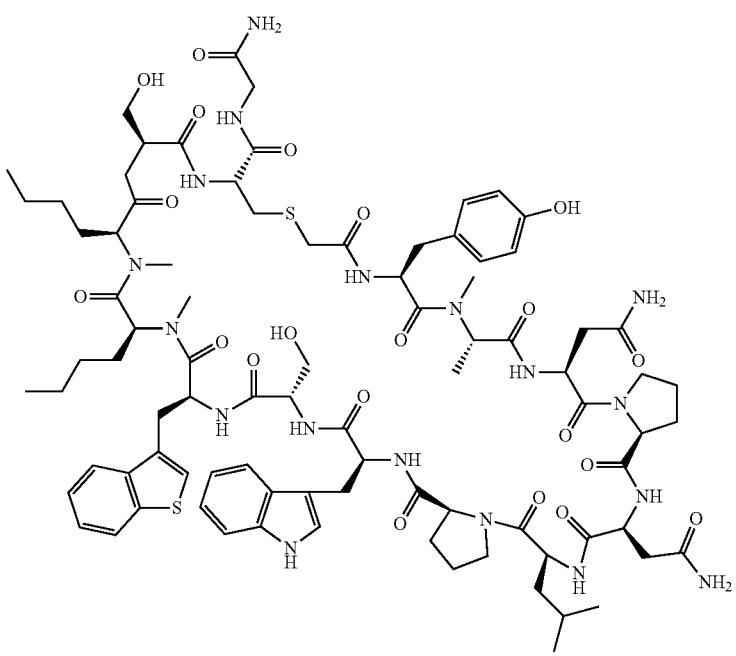

Example 9141

The crude material of Example 9141 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 29.9 mg, and its estimated purity by LCMS analysis was 99%.

Analysis condition A: Retention time=1.76 min; ESI-MS (+) m/z 910.5 (M+2H).

Analysis condition B: Retention time=2.86 min; ESI-MS (+) m/z 910.6 (M+2H).

Preparation of Example 9142

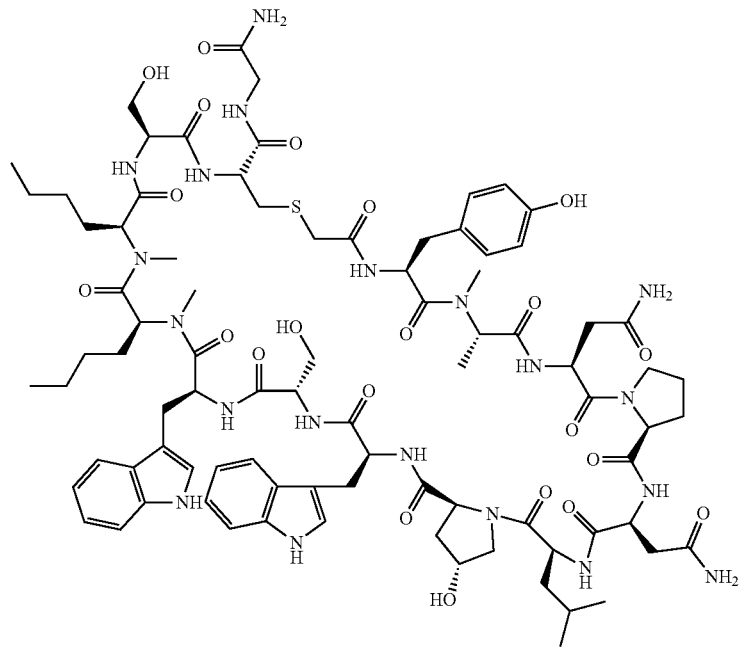

Example 9142

The crude material of Example 9142 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 14.8 mg, and its estimated purity by LCMS analysis was 98%.

Analysis condition A: Retention time=1.57 min; ESI-MS (+) m/z 910.1 (M+2H).

Analysis condition B: Retention time=2.63 min; ESI-MS (+) m/z 910.0 (M+2H).

Preparation of Example 9143

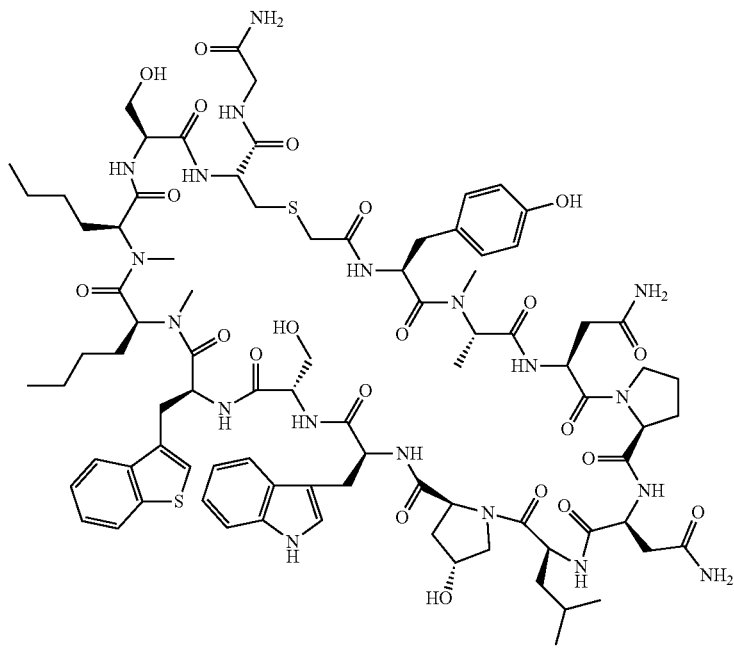

Example 9143

The crude material of Example 9143 was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 12.3 mg, and its estimated purity by LCMS analysis was 98%.

Analysis condition A: Retention time=1.68 min; ESI-MS (+) m/z 918.9 (M+2H).

Analysis condition B: Retention time=2.84 min; ESI-MS (+) m/z 918.5 (M+2H).

Preparation of Example 9144

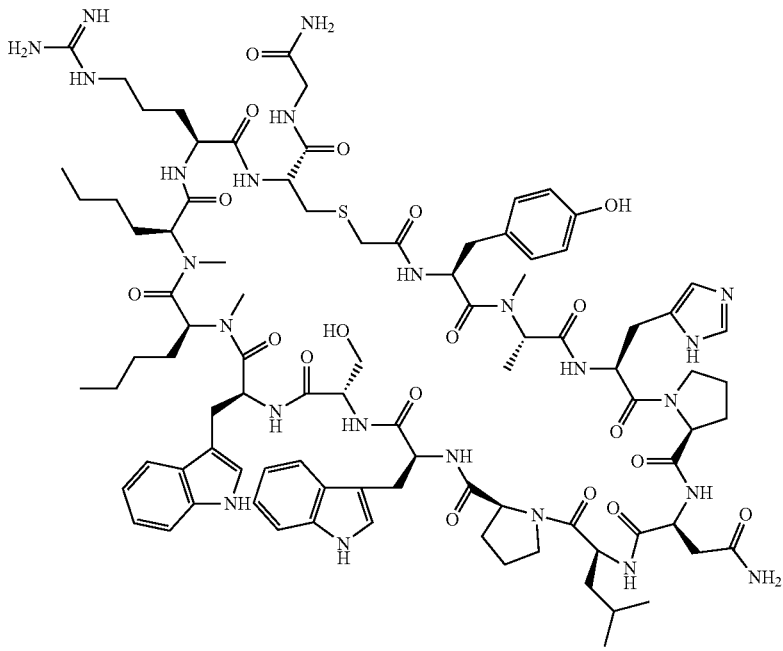

Example 9144

The crude material of Example 9144 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 8.8 mg, and its estimated purity by LCMS analysis was 99%.

Analysis condition A: Retention time=1.54 min; ESI-MS (+) m/z 948.5 (M+2H).

Analysis condition B: Retention time=2.60 min; ESI-MS (+) m/z 948.2 (M+2H).

Preparation of Example 9145

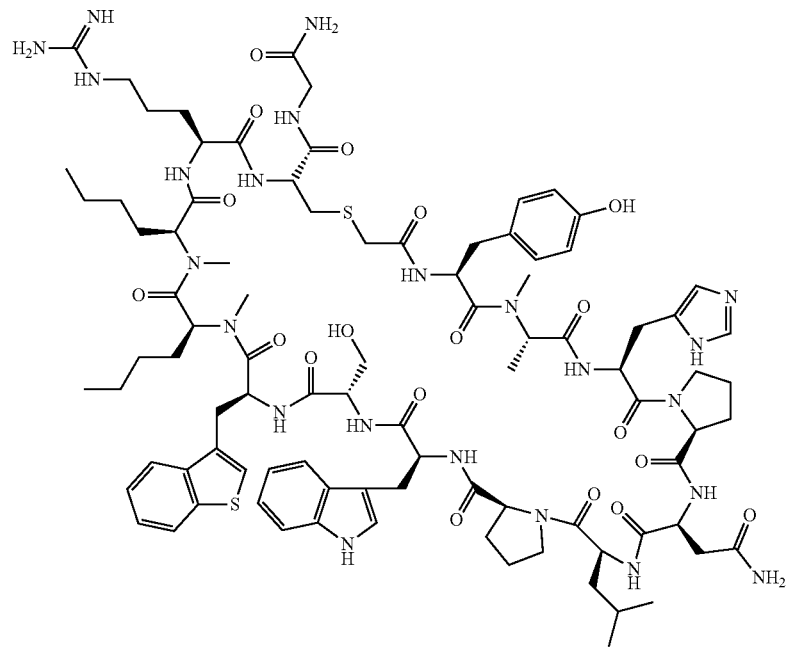

Example 9145

The crude material of Example 9145 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 12.6 mg, and its estimated purity by LCMS analysis was 100%.

Analysis condition A: Retention time=1.66 min; ESI-MS (+) m/z 956.5 (M+2H).

Analysis condition B: Retention time=2.83 min; ESI-MS (+) m/z 956.6 (M+2H).

Preparation of Example 9146

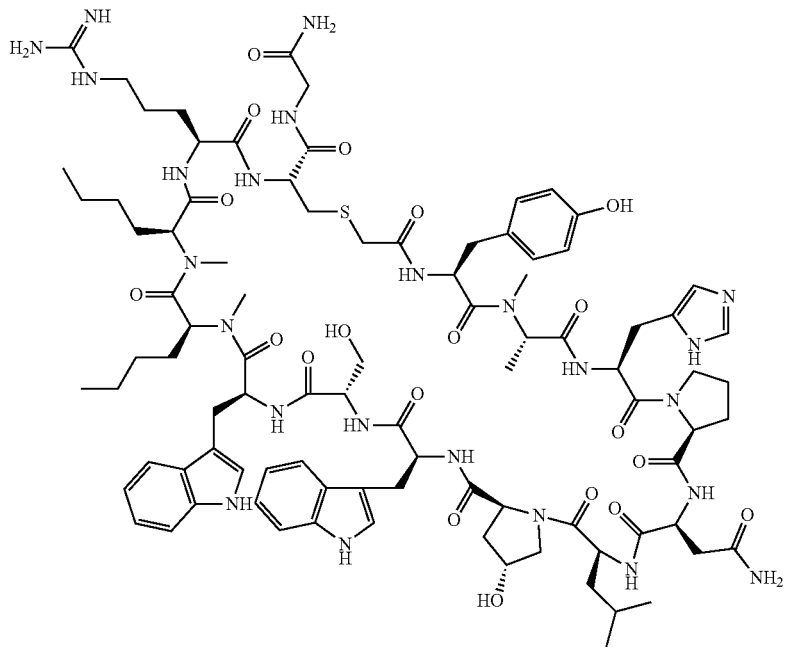

Example 9146

The crude material of Example 9146 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 26.6 mg, and its estimated purity by LCMS analysis was 100%.

Analysis condition A: Retention time=1.48 min; ESI-MS (+) m/z 956.0 (M+2H).

Analysis condition B: Retention time=2.57 min; ESI-MS (+) m/z 956.1 (M+2H).

Preparation of Example 9147

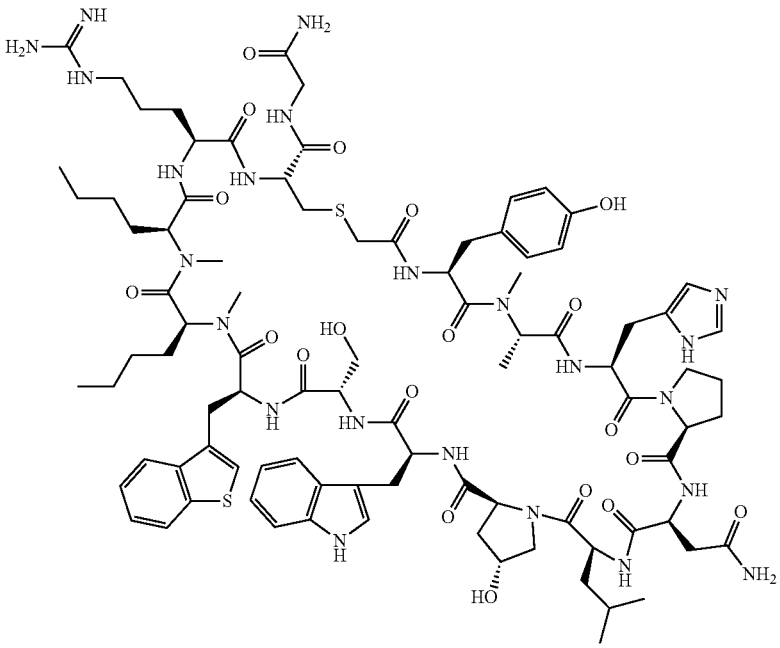

Example 9147

The crude material of Example 9147 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 15.7 mg, and its estimated purity by LCMS analysis was 97%.

Analysis condition A: Retention time=1.61 min; ESI-MS (+) m/z 965.0 (M+2H).

Analysis condition B: Retention time=2.78 min; ESI-MS (+) m/z 964.7 (M+2H).

Preparation of Example 9148

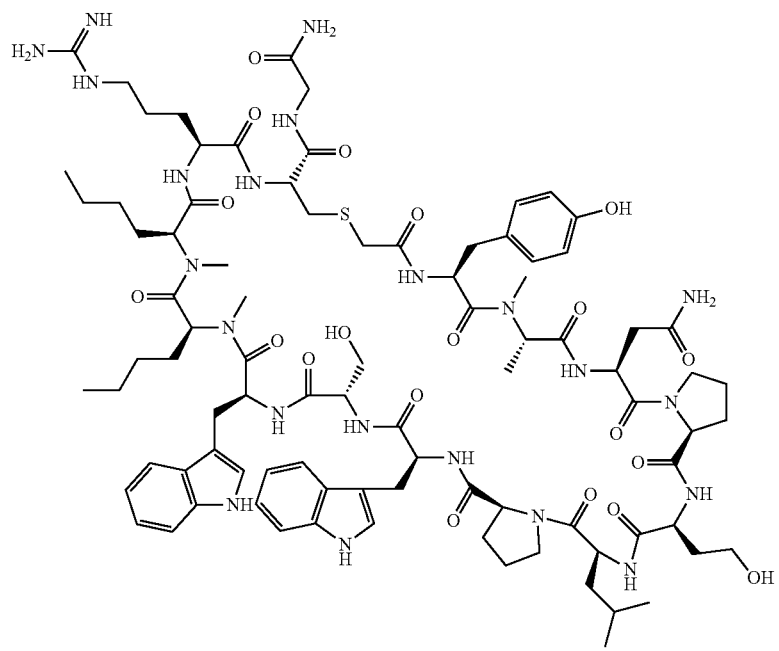

Example 9148

The crude material of Example 9148 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 30-70% B over 30 minutes, then a 5-minute hold at 100% B; Flow: 20 mL/min. Fractions containing the desired product were combined and dried via centrifugal evaporation. The yield of the product was 5.8 mg, and its estimated purity by LCMS analysis was 100%.

Analysis condition A: Retention time=1.31 min; ESI-MS (+) m/z 931.2 (M+2H).

Analysis condition B: Retention time=2.50 min; ESI-MS (+) m/z 931.0 (M+2H).

Preparation of Example 9149

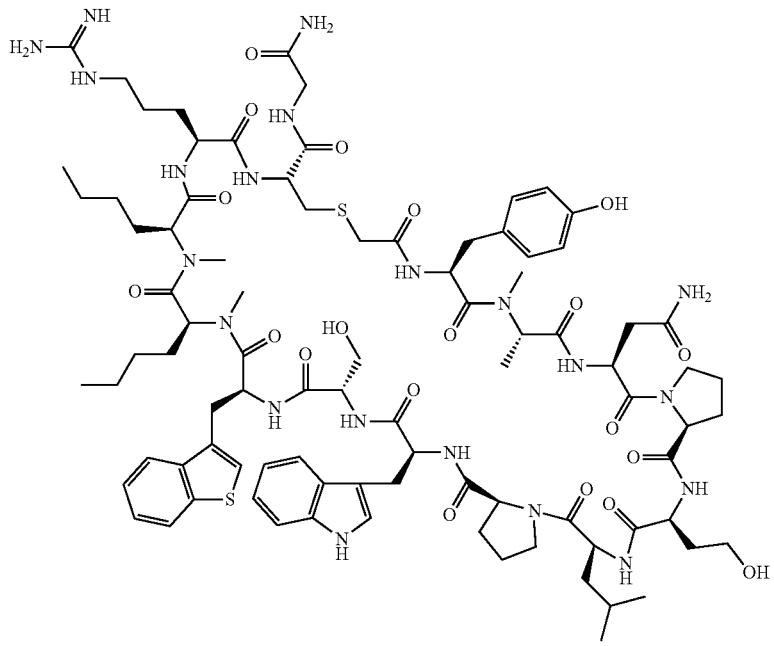

Example 9149

The crude material of Example 9149 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 25-75% B over 30 minutes, then a 5-minute hold at 100% B; Flow: 20 mL/min. Fractions containing the desired product were combined and dried via centrifugal evaporation. The yield of the product was 9.4 mg, and its estimated purity by LCMS analysis was 100%.

Analysis condition A: Retention time=1.37 min; ESI-MS (+) m/z 939.7 (M+2H).

Analysis condition B: Retention time=2.62 min; ESI-MS (+) m/z 939.1 (M+2H).

Preparation of Example 9150

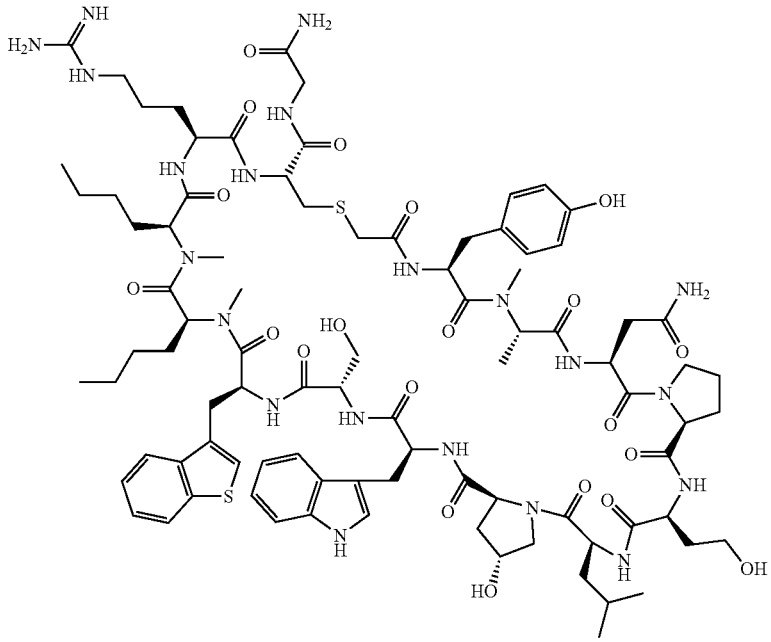

Example 9150

The crude material of Example 9150 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 25.8 mg, and its estimated purity by LCMS analysis was 100%.

Analysis condition A: Retention time=1.63 min; ESI-MS (+) m/z 946.6 (M+2H).

Analysis condition B: Retention time=2.80 min; ESI-MS (+) m/z 946.6 (M+2H).

Preparation of Example 9155

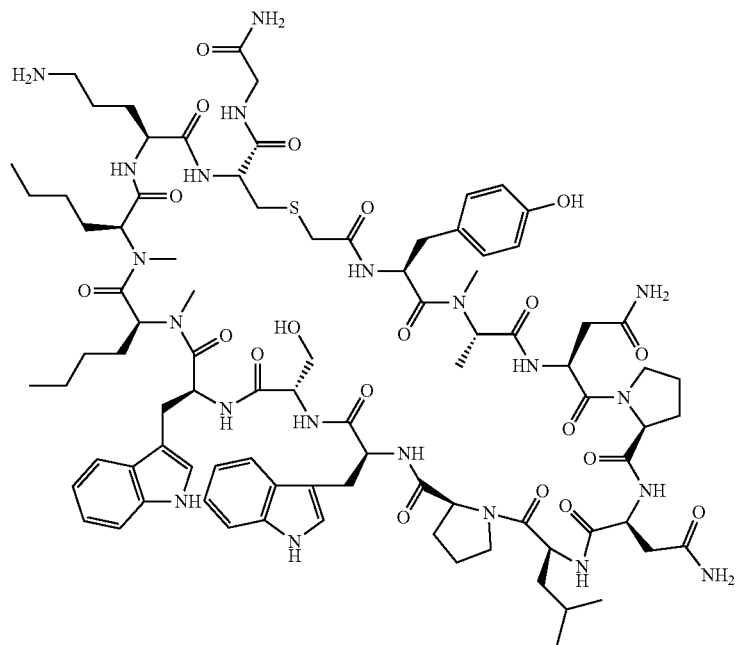

Example 9155

The crude material of Example 9155 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 26.9 mg, and its estimated purity by LCMS analysis was 100%.

Analysis condition A: Retention time=1.54 min; ESI-MS (+) m/z 915.8 (M+2H).

Analysis condition B: Retention time=2.63 min; ESI-MS (+) m/z 916.1 (M+2H).

Preparation of Example 9156

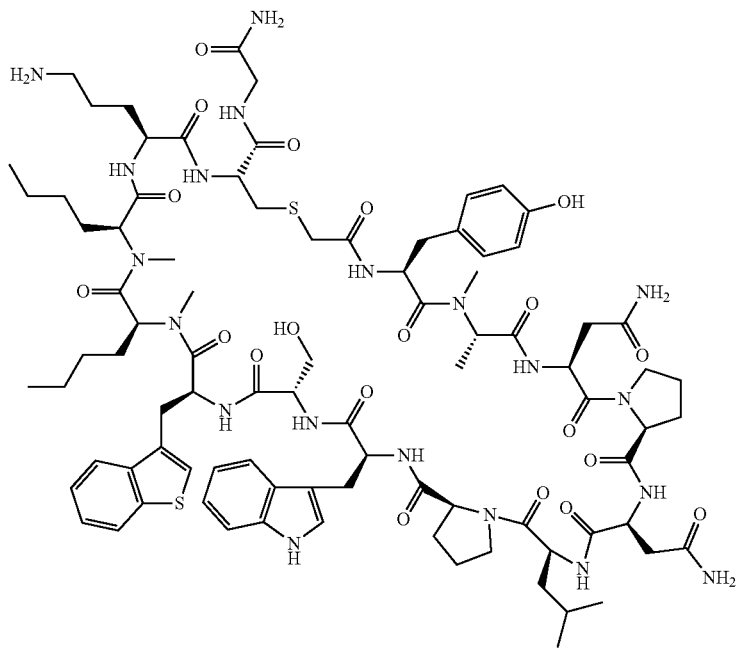

Example 9156

The crude material of Example 9156 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-70% B over 30 minutes, then a 5-minute hold at 100% B; Flow: 20 mL/min. Fractions containing the desired product were combined and dried via centrifugal evaporation. The yield of the product was 15.9 mg, and its estimated purity by LCMS analysis was 100%.

Analysis condition A: Retention time=1.68 min; ESI-MS (−) m/z 922.1 (M−2H).

Analysis condition B: Retention time=2.83 min; ESI-MS (+) m/z 924.0 (M+2H).

Preparation of Example 9157

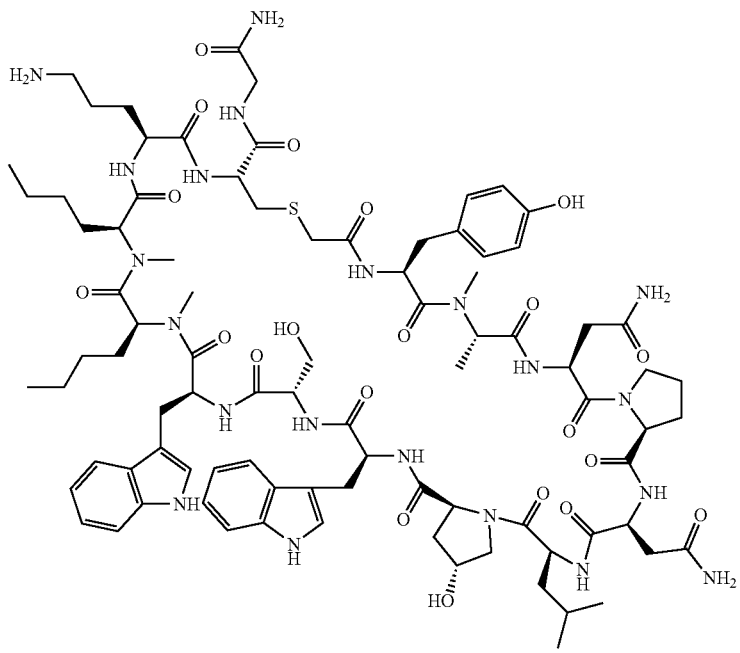

Example 9157

The crude material of Example 9157 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 23.8 mg, and its estimated purity by LCMS analysis was 97%.

Analysis condition A: Retention time=1.53 min; ESI-MS (+) m/z 923.8 (M+2H).

Analysis condition B: Retention time=2.60 min; ESI-MS (+) m/z 923.6 (M+2H).

Preparation of Example 9158

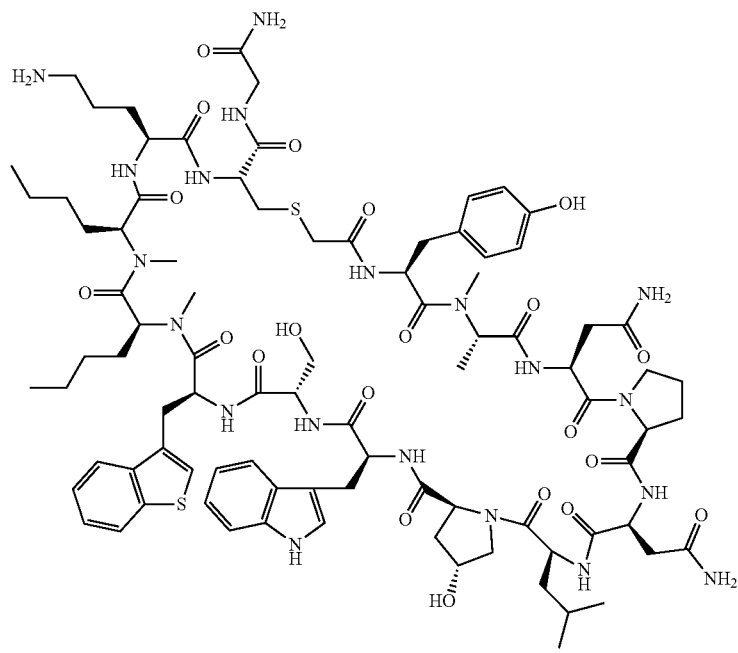

Example 9158

The crude material of Example 9158 was submitted to the Single Compound Purification team for purification and analysis. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 25.9 mg, and its estimated purity by LCMS analysis was 97%.

Analysis condition A: Retention time=1.64 min; ESI-MS (+) m/z 932.2 (M+2H).

Analysis condition B: Retention time=2.80 min; ESI-MS (+) m/z 932.0 (M+2H).

Preparation of Example 9159

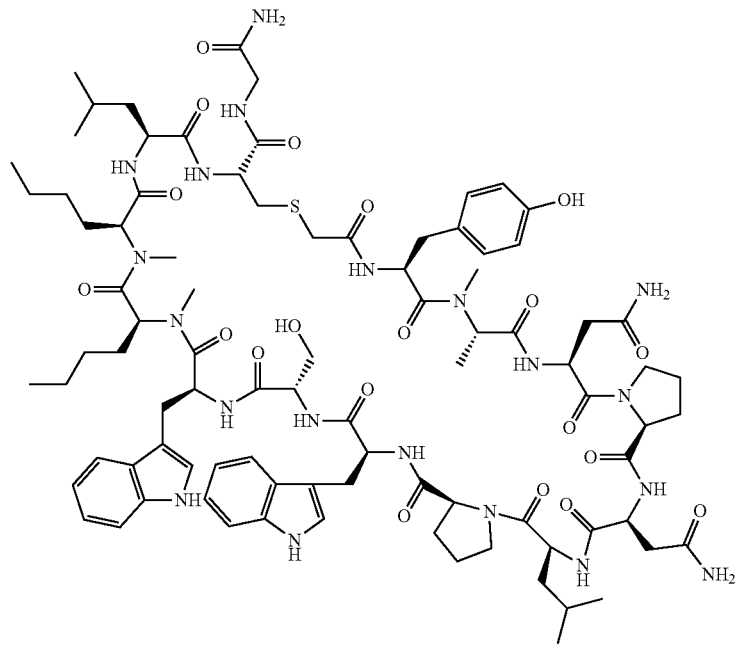

Example 9159

The crude material of Example 9159 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 22.7 mg, and its estimated purity by LCMS analysis was 100%.

Analysis condition A: Retention time=1.74 min; ESI-MS (+) m/z 913.5 (M+2H).

Analysis condition B: Retention time=2.80 min; ESI-MS (+) m/z 915.1 (M+2H).

Preparation of Example 9160

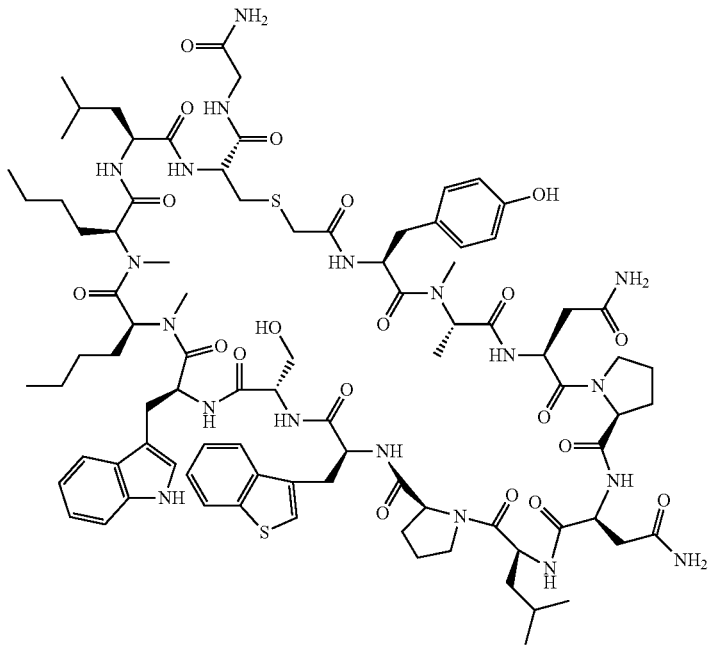

Example 9160

The crude material of Example 9160 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-80% B over 30 minutes, then a 5-minute hold at 100% B; Flow: 20 mL/min. Fractions containing the desired product were combined and dried via centrifugal evaporation. The yield of the product was 26.6 mg, and its estimated purity by LCMS analysis was 100%.

Analysis condition A: Retention time=1.89 min; ESI-MS (+) m/z 923.3 (M+2H).

Analysis condition B: Retention time=3.04 min; ESI-MS (+) m/z 923.7 (M+2H).

Preparation of Example 9161

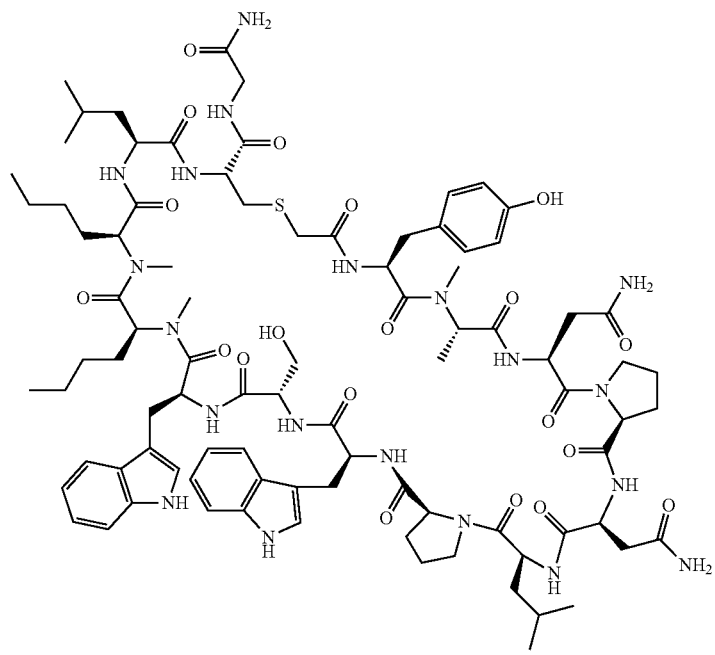

Example 9161

The crude material of Example 9161 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 30 minutes, then a 5-minute hold at 100% B; Flow: 20 mL/min. Fractions containing the desired product were combined and dried via centrifugal evaporation. The yield of the product was 14.2 mg, and its estimated purity by LCMS analysis was 93%.

Analysis condition A: Retention time=1.70 min; ESI-MS (+) m/z 923.1 (M+2H).

Analysis condition B: Retention time=2.75 min; ESI-MS (+) m/z 923.1 (M+2H).

Preparation of Example 9162

Example 9162

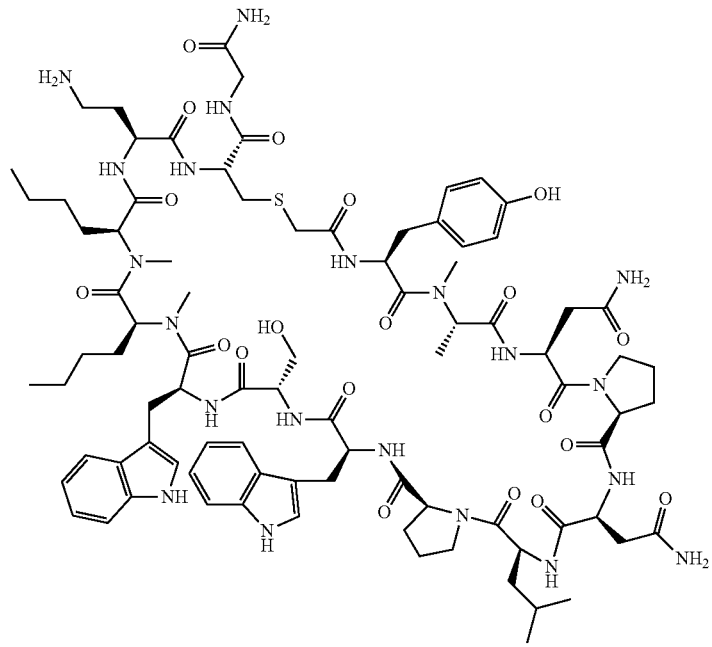

The crude material of Example 9162 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 24.9 mg, and its estimated purity by LCMS analysis was 97%.

Analysis condition A: Retention time=1.53 min; ESI-MS (+) m/z 908.7 (M+2H).

Analysis condition B: Retention time=2.63 min; ESI-MS (+) m/z 908.8 (M+2H).

Preparation of Example 9163

Example 9163

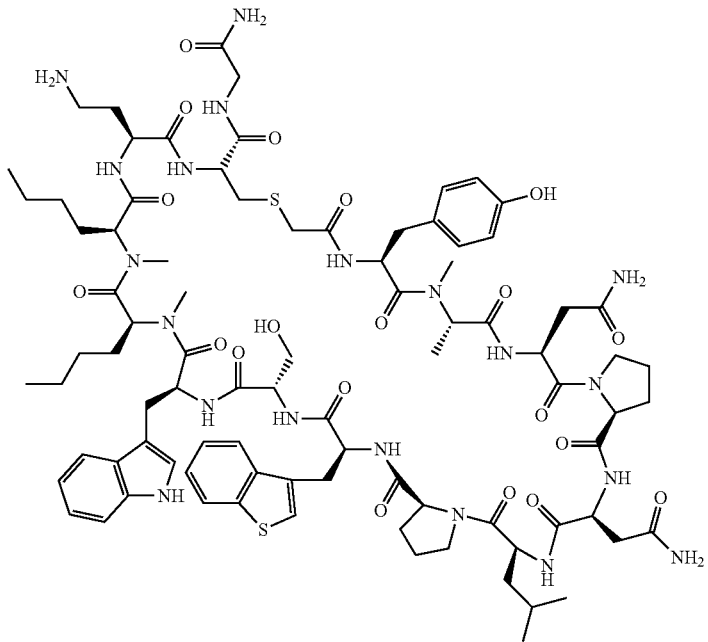

The crude material of Example 9163 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 12.3 mg, and its estimated purity by LCMS analysis was 99%.

Analysis condition A: Retention time=1.66 min; ESI-MS (+) m/z 917.2 (M+2H).

Analysis condition B: Retention time=2.84 min; ESI-MS (+) m/z 917.3 (M+2H).

Preparation of Example 9164

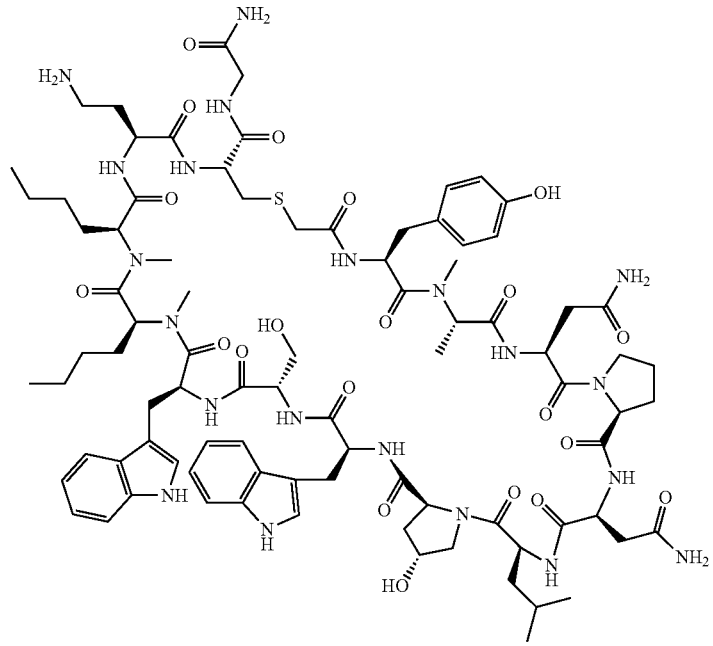

Example 9164

The crude material of Example 9164 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min.

Fractions containing the desired product were combined and dried via centrifugal evaporation.

The yield of the product was 21.0 mg, and its estimated purity by LCMS analysis was 93%.

Analysis condition A: Retention time=1.48 min; ESI-MS (+) m/z 916.9 (M+2H).

Analysis condition B: Retention time=2.60 min; ESI-MS (+) m/z 916.6 (M+2H).

Preparation of Example 9165

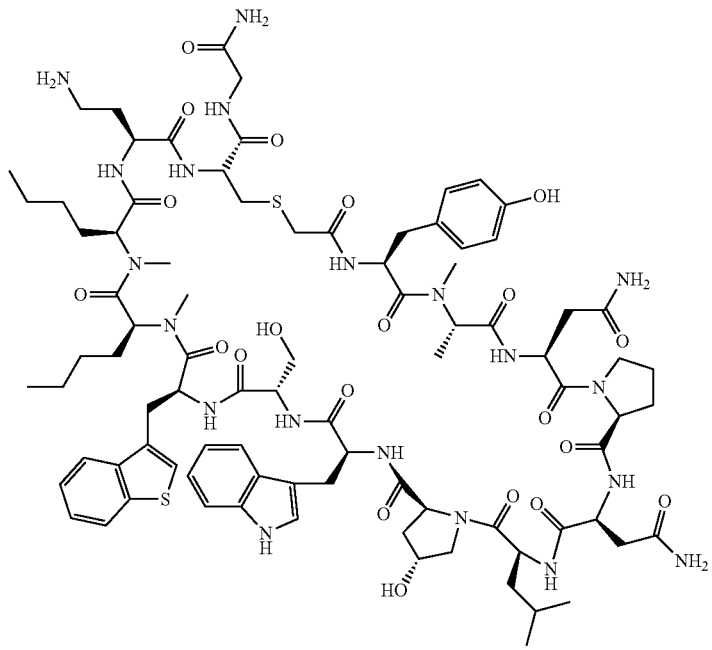

Example 9161=5

The crude material of Example 9165 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 34.9 mg, and its estimated purity by LCMS analysis was 98%.

Analysis condition A: Retention time=1.66 min; ESI-MS (+) m/z 925.1 (M+2H).

Analysis condition B: Retention time=2.81 min; ESI-MS (+) m/z 925.1 (M+2H).

Preparation of Example 9166

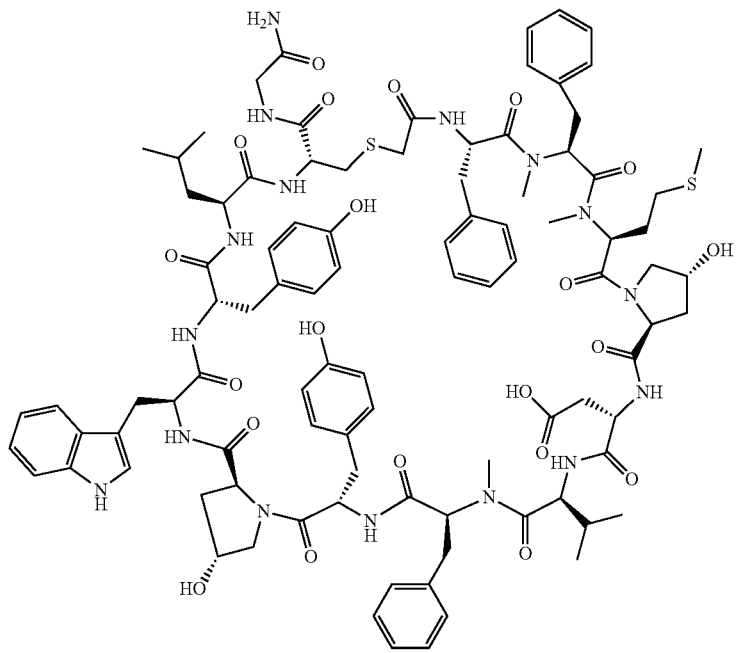

Example 9166

The crude material of Example 9166 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 30-70% B over 30 minutes, then a 5-minute hold at 100% B; Flow: 20 mL/min. Fractions containing the desired product were combined and dried via centrifugal evaporation. The yield of the product was 7.7 mg, and its estimated purity by LCMS analysis was 99%.

Analysis condition A: Retention time=1.58 min; ESI-MS (+) m/z 950.2 (M+2H).

Analysis condition B: Retention time=2.72 min; ESI-MS (+) m/z 949.9 (M+2H).

Preparation of Example 9167

Example 9167

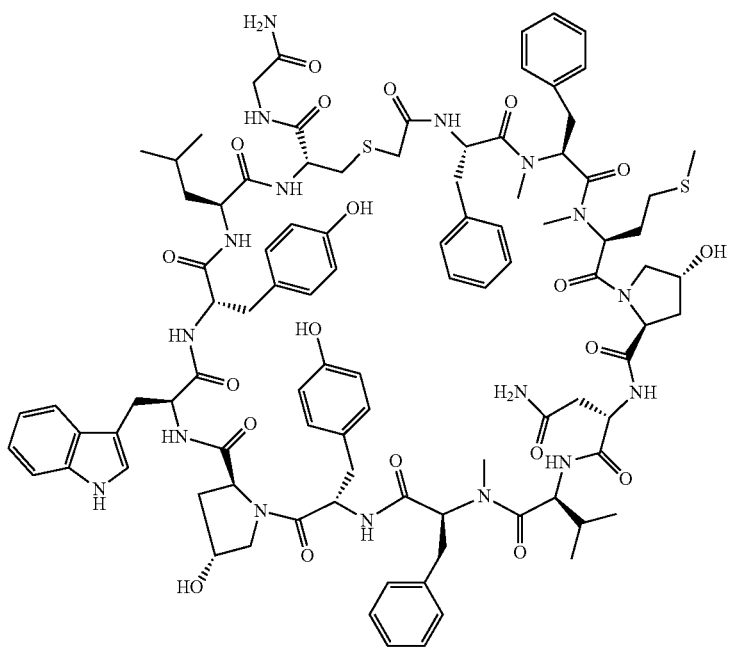

The crude material of Example 9167 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 30-75% B over 30 minutes, then a 5-minute hold at 100% B; Flow: 20 mL/min. Fractions containing the desired product were combined and dried via centrifugal evaporation. The yield of the product was 10.7 mg, and its estimated purity by LCMS analysis was 98%.

Analysis condition A: Retention time=1.44 min; ESI-MS (+) m/z 949.9 (M+2H).

Analysis condition B: Retention time=2.61 min; ESI-MS (+) m/z 950.0 (M+2H).

Preparation of Example 9168

Example 9168

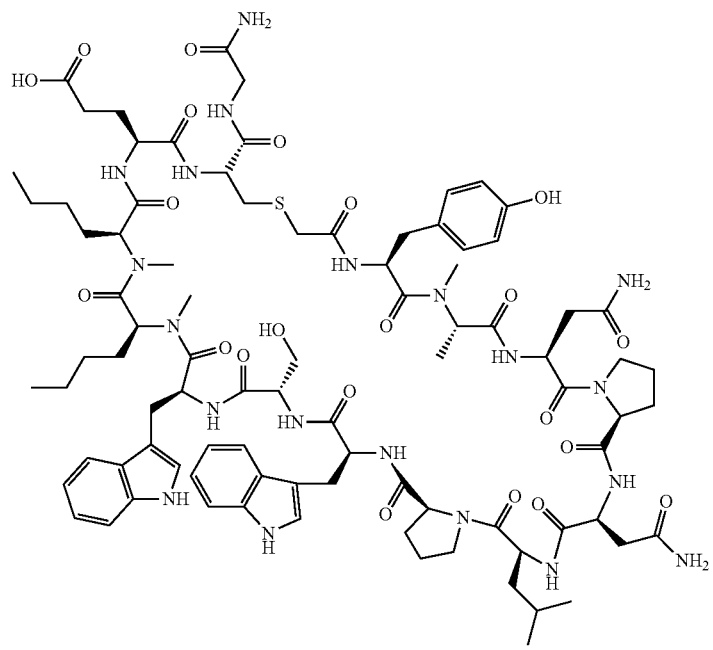

The crude material of Example 9168 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 15.1 mg, and its estimated purity by LCMS analysis was 100%.

Analysis condition A: Retention time=1.76 min; ESI-MS (+) m/z 922.8 (M+2H).

Analysis condition B: Retention time=2.47 min; ESI-MS (+) m/z 923.1 (M+2H).

Preparation of Example 9169

Example 9169

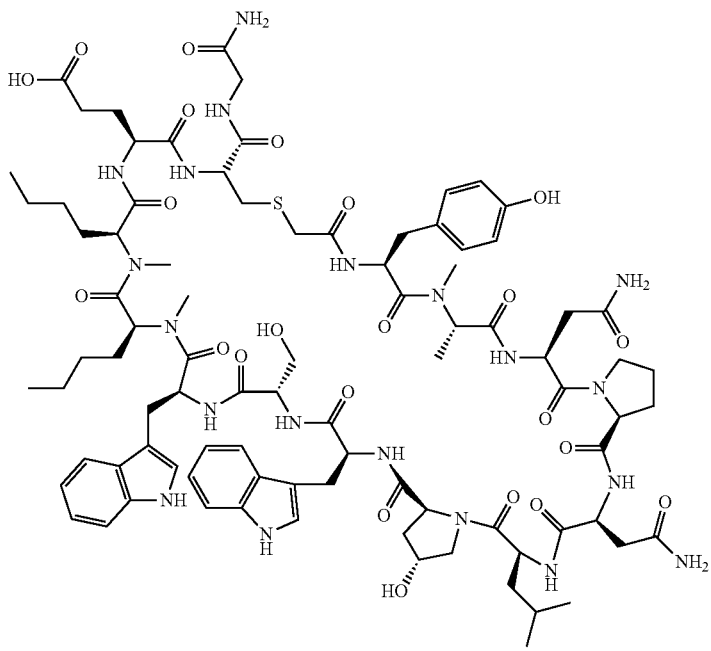

The crude material of Example 9169 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 22.1 mg, and its estimated purity by LCMS analysis was 100%.

Analysis condition A: Retention time=1.45 min; ESI-MS (+) m/z 930.90 (M+2H).

Analysis condition B: Retention time=2.88 min; ESI-MS (+) m/z 930.95 (M+2H).

Preparation of Example 9170

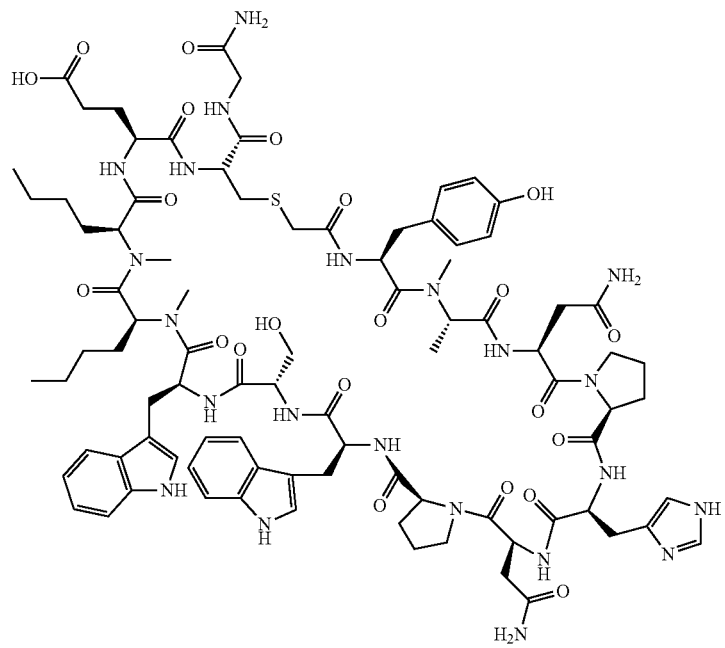

Example 9170

The crude material of Example 9170 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 17.0 mg, and its estimated purity by LCMS analysis was 99%.

Analysis condition A: Retention time=1.40 min; ESI-MS (+) m/z 934.65 (M+2H).

Analysis condition B: Retention time=2.83 min; ESI-MS (+) m/z 934.80 (M+2H).

Preparation of Example 9171

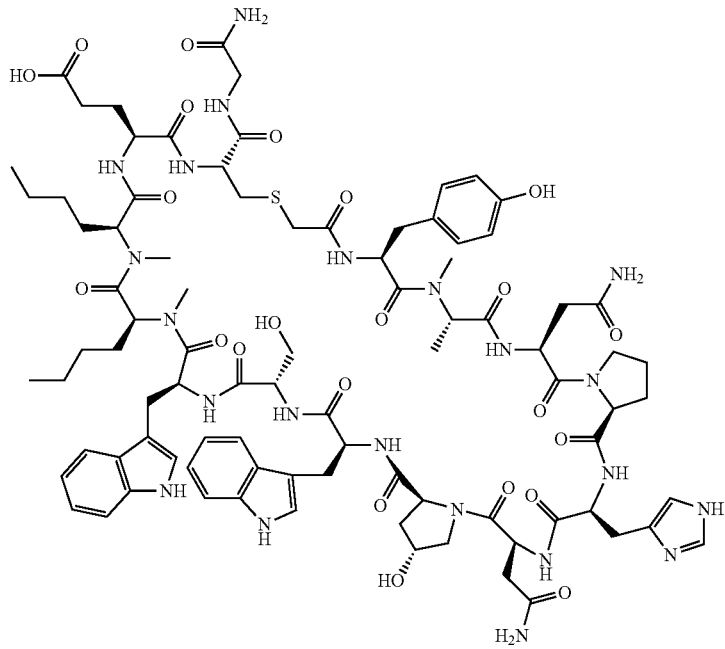

Example 9171

The crude material of Example 9171 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 24.5 mg, and its estimated purity by LCMS analysis was 100%.

Analysis condition A: Retention time=1.36 min; ESI-MS (+) m/z 942.85 (M+2H).

Analysis condition B: Retention time=2.78 min; ESI-MS (+) m/z 942.95 (M+2H).

Preparation of Example 9172

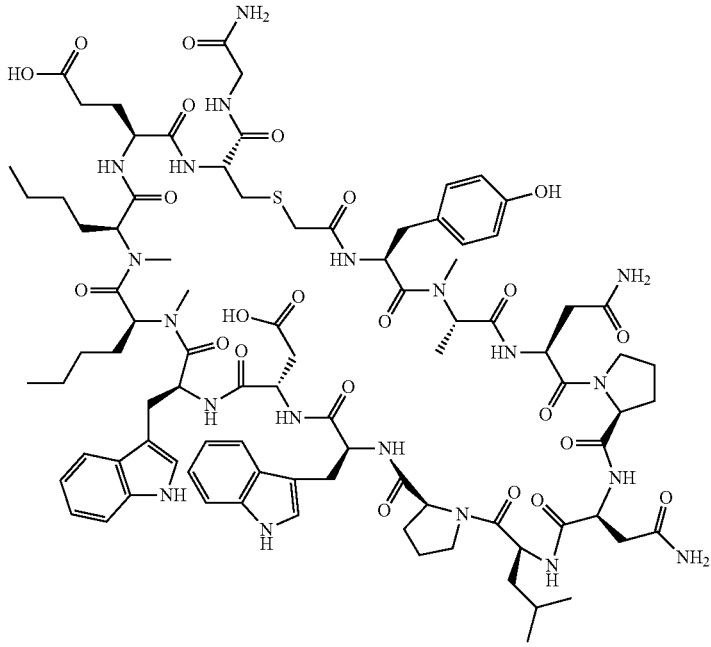

Example 9172

The crude material of Example 9172 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 10.9 mg, and its estimated purity by LCMS analysis was 100%.

Analysis condition A: Retention time=1.35 min; ESI-MS (+) m/z 936.60 (M+2H).

Analysis condition B: Retention time=1.93 min; ESI-MS (+) m/z 936.80 (M+2H).

Preparation of Example 9173

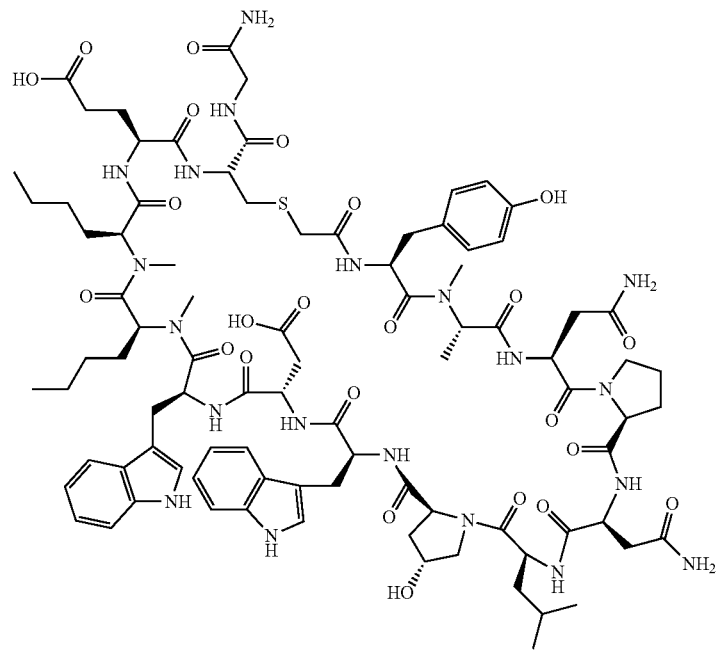

Example 9173

The crude material of Example 9173 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 15.0 mg, and its estimated purity by LCMS analysis was 100%.

Analysis condition A: Retention time=1.28 min; ESI-MS (+) m/z 944.60 (M+2H).

Analysis condition B: Retention time=1.87 min; ESI-MS (+) m/z 944.60 (M+2H).

Preparation of Example 9174

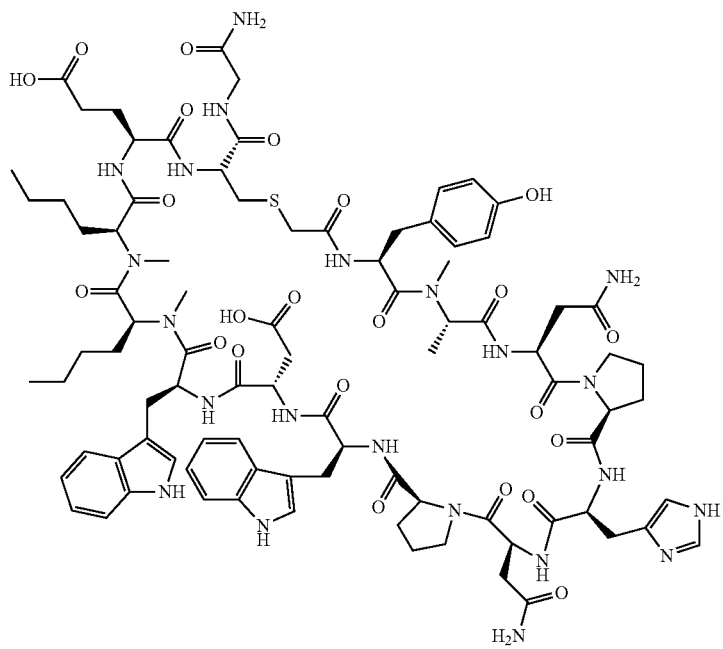

Example 9174

The crude material of Example 9174 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-40% B over 30 minutes, then a 5-minute hold at 100% B; Flow: 20 mL/min. Fractions containing the desired product were combined and dried via centrifugal evaporation. The yield of the product was 7.4 mg, and its estimated purity by LCMS analysis was 92%.

Analysis condition A: Retention time=1.26 min; ESI-MS (+) m/z 948.55 (M+2H).

Analysis condition B: Retention time=2.63 min; ESI-MS (+) m/z 948.30 (M+2H).

Preparation of Example 9175

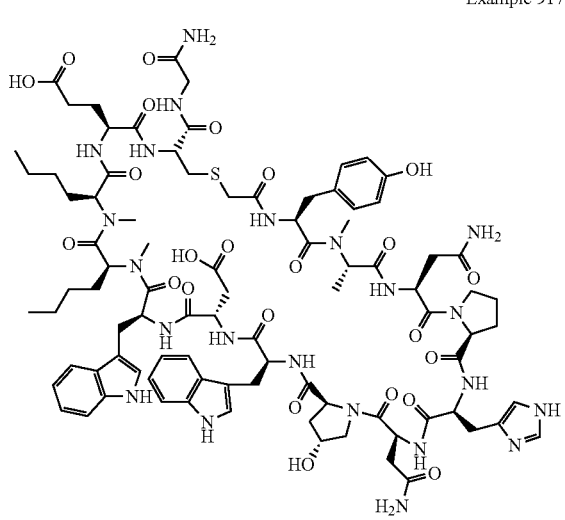

Example 9175

The crude material of Example 9175 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-40% B over 30 minutes, then a 5-minute hold at 100% B; Flow: 20 mL/min. Fractions containing the desired product were combined and dried via centrifugal evaporation. The yield of the product was 12.9 mg, and its estimated purity by LCMS analysis was 100%.

Analysis condition A: Retention time=1.22 min; ESI-MS (+) m/z 956.80 (M+2H).

Analysis condition B: Retention time=1.76 min; ESI-MS (+) m/z 956.70 (M+2H).

Preparation of Example 9176

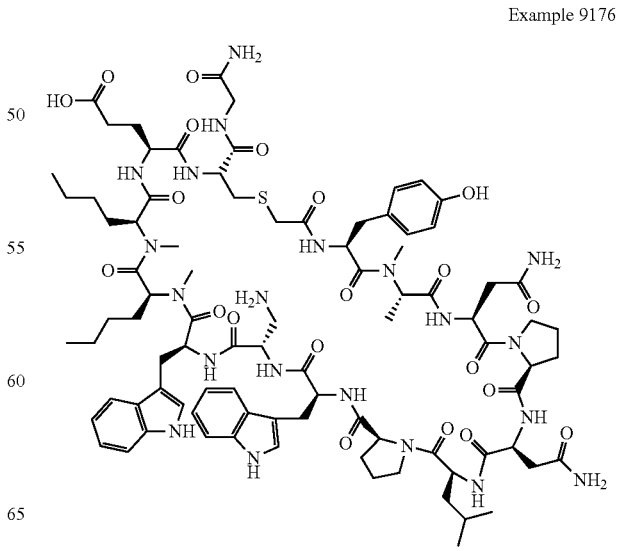

Example 9176

The crude material of Example 9176 was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 8.9 mg, and its estimated purity by LCMS analysis was 92%.

Analysis condition A: Retention time=1.31 min; ESI-MS (+) m/z 922.40 (M+2H).

Analysis condition B: Retention time=2.78 min; ESI-MS (+) m/z 922.40 (M+2H).

Preparation of Example 9177

Example 9177

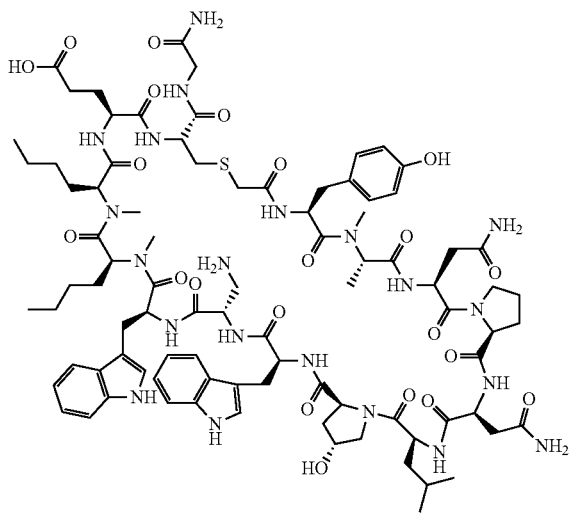

The crude material of Example 9177 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 11.8 mg, and its estimated purity by LCMS analysis was 100%.

Analysis condition A: Retention time=1.44 min; ESI-MS (+) m/z 930.05 (M+2H).

Analysis condition B: Retention time=2.69 min; ESI-MS (+) m/z 930.05 (M+2H).

Preparation of Example 9178

Example 9178

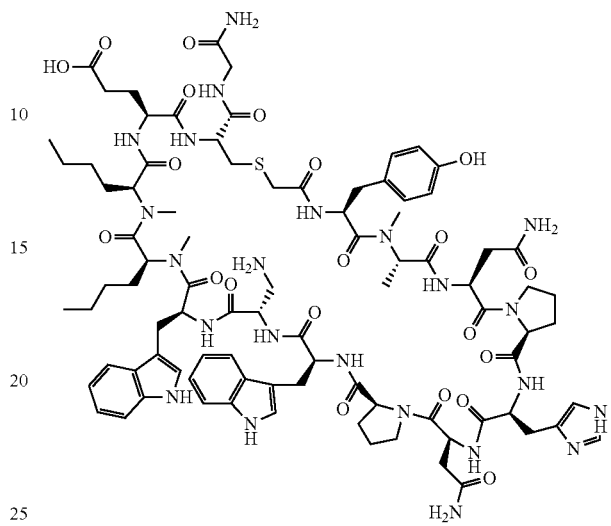

The crude material of Example 9178 was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 16.7 mg, and its estimated purity by LCMS analysis was 100%.

Analysis condition A: Retention time=1.41 min; ESI-MS (+) m/z 934.15 (M+2H).

Analysis condition B: Retention time=2.89 min; ESI-MS (+) m/z 934.20 (M+2H).

Preparation of Example 9179

Example 9179

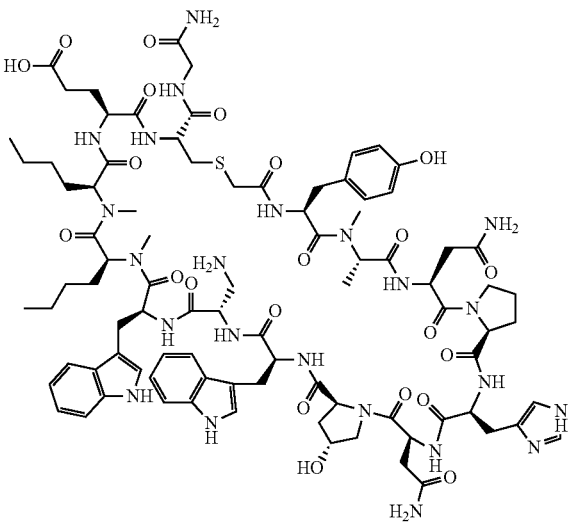

The crude material of Example 9179 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 6.1 mg, and its estimated purity by LCMS analysis was 100%.

Analysis condition A: Retention time=1.37 min; ESI-MS (+) m/z 942.20 (M+2H).

Analysis condition B: Retention time=2.70 min; ESI-MS (+) m/z 942.05 (M+2H).

Preparation of Example 9180

Example 9180

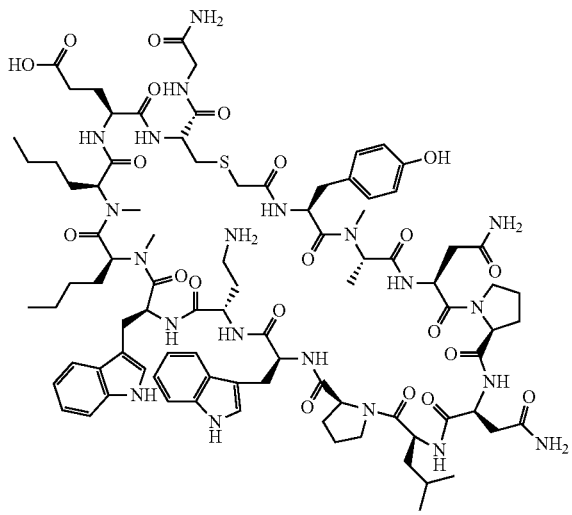

The crude material of Example 9180 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 19.9 mg, and its estimated purity by LCMS analysis was 100%.

Analysis condition A: Retention time=1.52 min; ESI-MS (+) m/z 929.20 (M+2H).

Analysis condition B: Retention time=2.99 min; ESI-MS (+) m/z 929.25 (M+2H).

Preparation of Example 9181

Example 9181

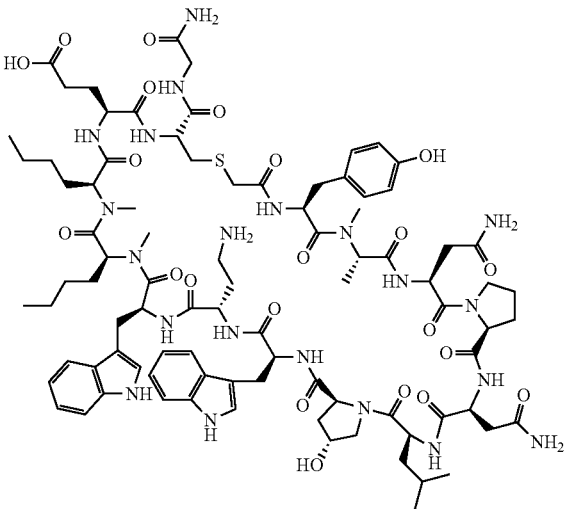

The crude material of Example 9181 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 10.9 mg, and its estimated purity by LCMS analysis was 99%.

Analysis condition A: Retention time=1.49 min; ESI-MS (+) m/z 937.20 (M+2H).

Analysis condition B: Retention time=2.99 min; ESI-MS (+) m/z 937.40 (M+2H).

Preparation of Example 9182

Example 9182

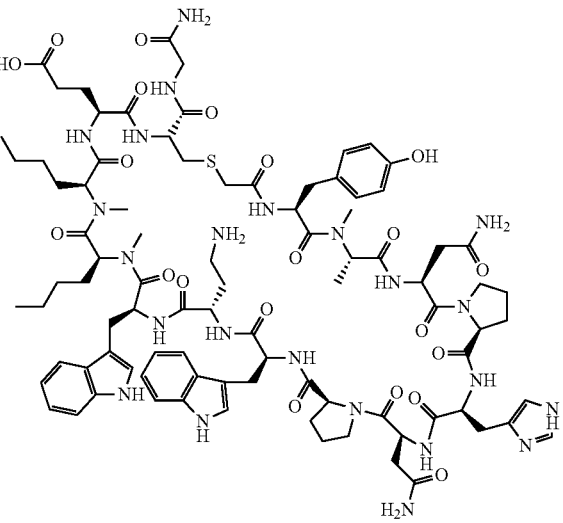

The crude material of Example 9182 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 20.7 mg, and its estimated purity by LCMS analysis was 99%.

Analysis condition A: Retention time=1.53 min; ESI-MS (+) m/z 941.45 (M+2H).

Analysis condition B: Retention time=2.99 min; ESI-MS (+) m/z 941.40 (M+2H).

Preparation of Example 9183

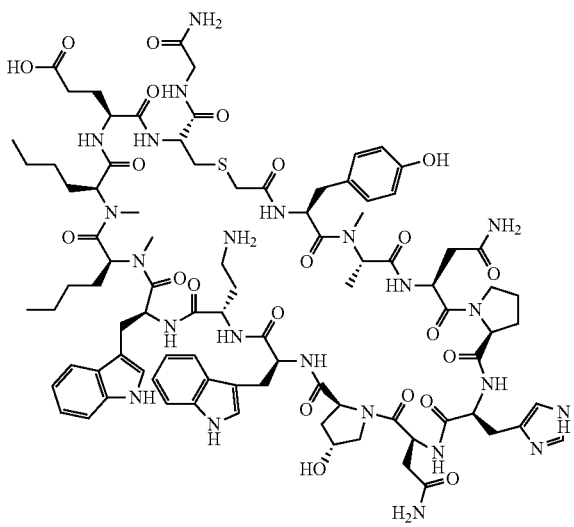

Example 9183

The crude material of Example 9183 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 10.9 mg, and its estimated purity by LCMS analysis was 98%.

Analysis condition A: Retention time=1.49 min; ESI-MS (+) m/z 949.35 (M+2H).

Analysis condition B: Retention time=2.91 min; ESI-MS (+) m/z 949.45 (M+2H).

Preparation of Example 9184

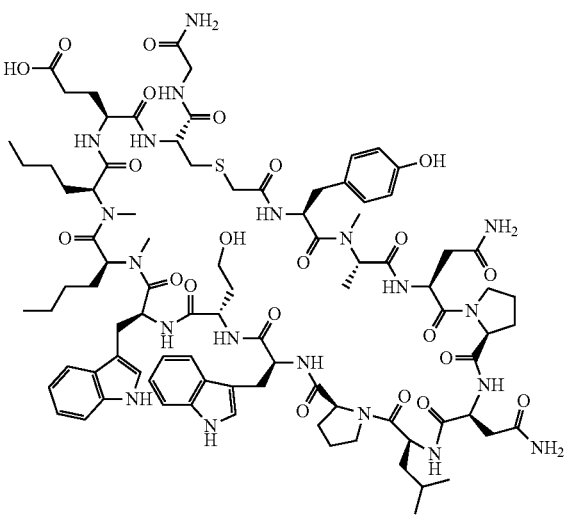

Example 9184

The crude material of Example 9184 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 14.1 mg, and its estimated purity by LCMS analysis was 100%.

Analysis condition A: Retention time=1.45 min; ESI-MS (+) m/z 929.90 (M+2H).

Analysis condition B: Retention time=2.92 min; ESI-MS (+) m/z 929.95 (M+2H).

Preparation of Example 9185

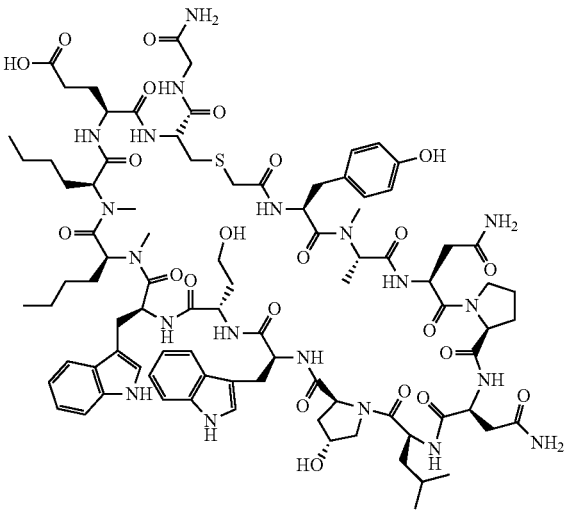

Example 9185

The crude material of Example 9185 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 21.0 mg, and its estimated purity by LCMS analysis was 99%.

Analysis condition A: Retention time=1.42 min; ESI-MS (+) m/z 937.85 (M+2H).

Analysis condition B: Retention time=2.88 min; ESI-MS (+) m/z 937.90 (M+2H).

Preparation of Example 9186

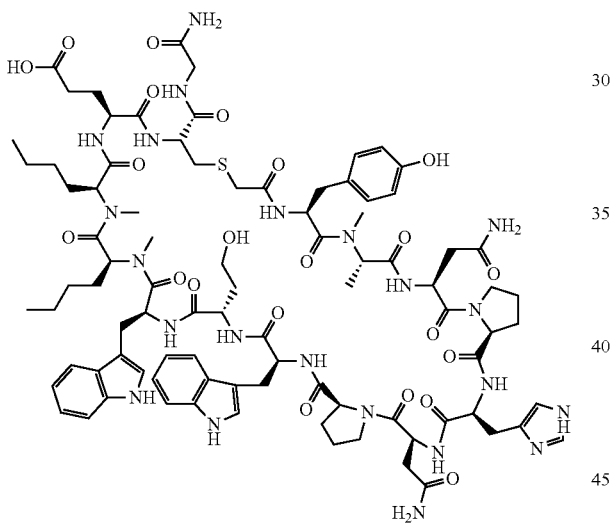

Example 9186

The crude material of Example 9186 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 24.6 mg, and its estimated purity by LCMS analysis was 100%.

Analysis condition A: Retention time=1.28 min; ESI-MS (+) m/z 941.65 (M+2H).

Analysis condition B: Retention time=2.53 min; ESI-MS (+) m/z 941.65 (M+2H).

Preparation of Example 9187

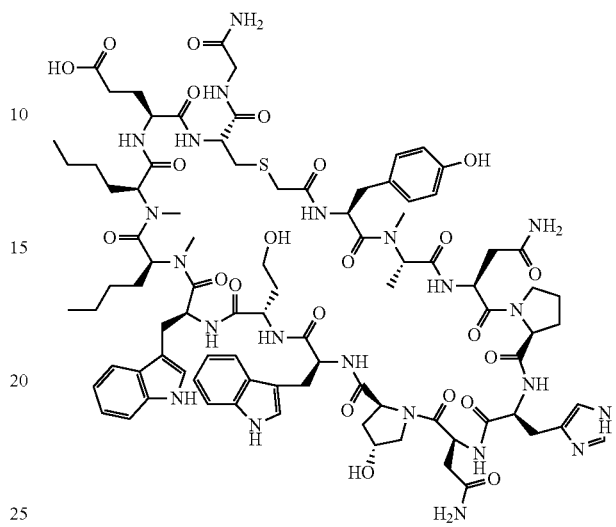

Example 9187

The crude material of Example 9187 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 30-75% B over 30 minutes, then a 5-minute hold at 100% B; Flow: 20 mL/min. Fractions containing the desired product were combined and dried via centrifugal evaporation. The yield of the product was 21.6 mg, and its estimated purity by LCMS analysis was 99%.

Analysis condition A: Retention time=1.24 min; ESI-MS (+) m/z 949.65 (M+2H).

Analysis condition B: Retention time=2.49 min; ESI-MS (+) m/z 949.65 (M+2H).

Preparation of Example 9188

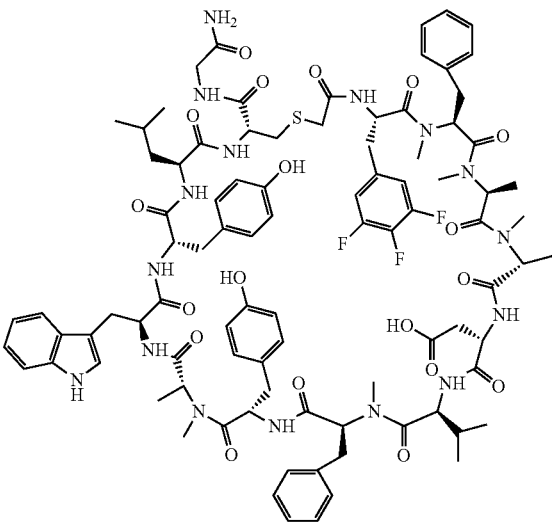

Example 9188

The crude material of Example 9188 was purified via preparative LC/MS with the following conditions: Column: XBridge C18, 19×mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 1.3 mg, and its estimated purity by LCMS analysis was 100%.

Analysis condition A: Retention time=2.10 min; ESI-MS (+) m/z 919.8 (M+2H).

Analysis condition B: Retention time=2.74 min; ESI-MS (+) m/z 919.2 (M+2H).

Preparation of Example 9189

Example 9189

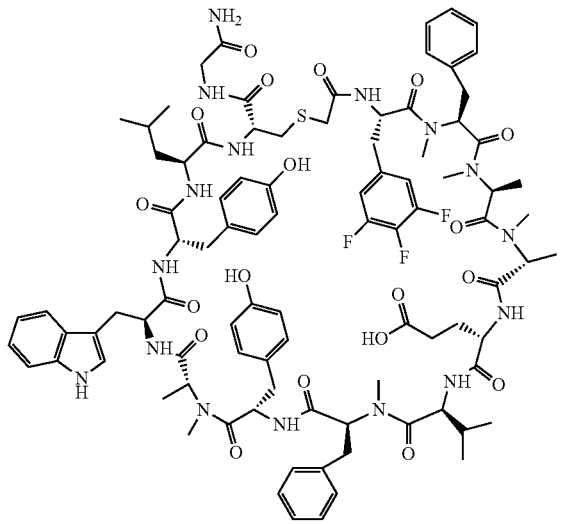

The crude material of Example 9189 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 18.2 mg, and its estimated purity by LCMS analysis was 93%.

Analysis condition A: Retention time=2.07 min; ESI-MS (+) m/z 925.9 (M+2H).

Analysis condition B: Retention time=2.73 min; ESI-MS (+) m/z 926.0 (M+2H).

Preparation of Example 9190

Example 9190

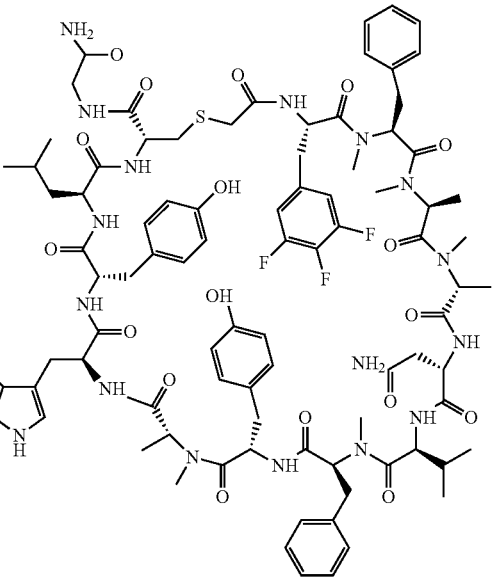

The crude material of Example 9190 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 55-95% B over 30 minutes, then a 5-minute hold at 100% B; Flow: 20 mL/min. Fractions containing the desired product were combined and dried via centrifugal evaporation. The yield of the product was 30.4 mg, and its estimated purity by LCMS analysis was 10

Analysis condition A: Retention time=2.13 min; ESI-MS (+) m/z 918.3 (M+2H).

Analysis condition B: Retention time=2.85 min; ESI-MS (+) m/z 918.5 (M+2H).

Preparation of Example 9191

Example 9191

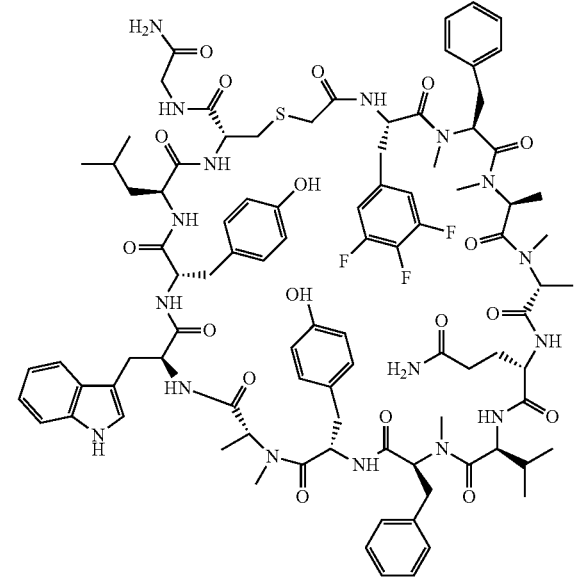

The crude material of Example 9191 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 60-100% B over 30 minutes, then a 5-minute hold at 100% B; Flow: 20 mL/min. Fractions containing the desired product were combined and dried via centrifugal evaporation. The yield of the product was 27.4 mg, and its estimated purity by LCMS analysis was 100%.

Analysis condition A: Retention time=2.02 min; ESI-MS (+) m/z 923.6 (M+2H).

Analysis condition B: Retention time=2.83 min; ESI-MS (+) m/z 923.6 (M+2H).

Preparation of Example 9192

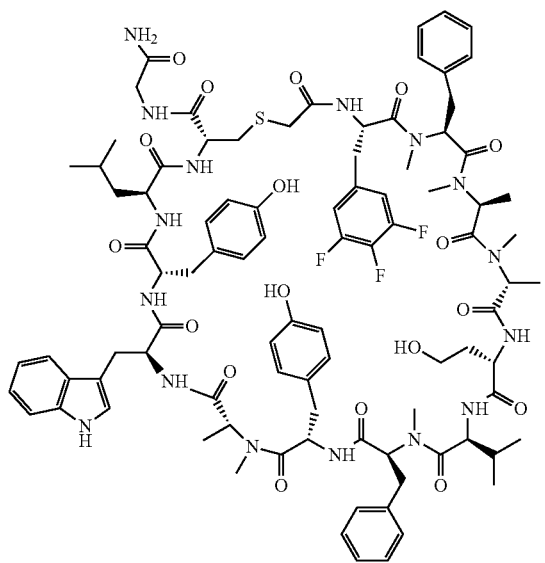

Example 9192

The crude material of Example 9192 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 30 minutes, then a 5-minute hold at 100% B; Flow: 20 mL/min. Fractions containing the desired product were combined and dried via centrifugal evaporation. The yield of the product was 26.6 mg, and its estimated purity by LCMS analysis was 100%.

Analysis condition A: Retention time=1.92 min; ESI-MS (+) m/z 911.70 (M+2H).

Analysis condition B: Retention time=2.53 min; ESI-MS (+) m/z 911.45 (M+2H).

Preparation of Example 9193

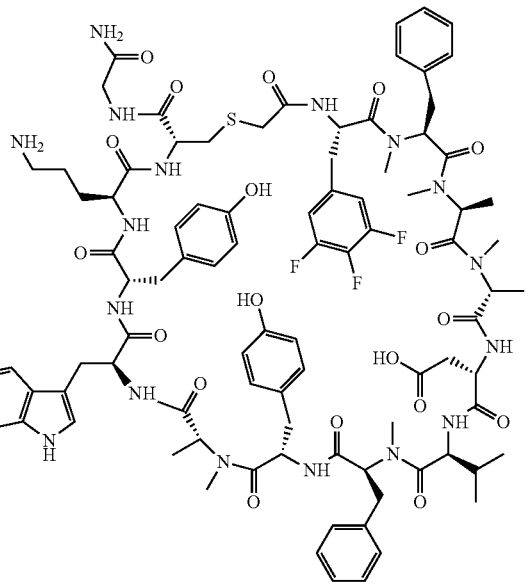

Example 9193

The crude material of Example 9193 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 60-100% B over 30 minutes, then a 5-minute hold at 100% B; Flow: 20 mL/min. Fractions containing the desired product were combined and dried via centrifugal evaporation. The yield of the product was 24.5 mg, and its estimated purity by LCMS analysis was 100%.

Analysis condition A: Retention time=1.82 min; ESI-MS (+) m/z 919.3 (M+2H).

Analysis condition B: Retention time=2.76 min; ESI-MS (+) m/z 919.7 (M+2H).

Preparation of Example 9194

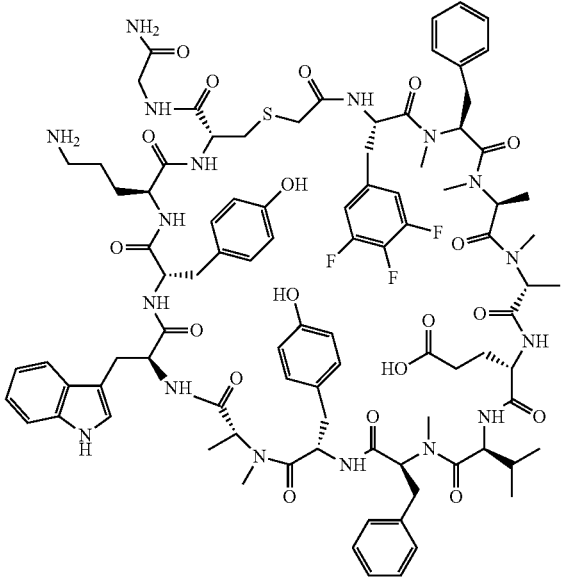

Example 9194

The crude material of Example 9194 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 11.8 mg, and its estimated purity by LCMS analysis was 95%.

Analysis condition A: Retention time=1.81 min; ESI-MS (+) m/z 926.3 (M+2H).

Analysis condition B: Retention time=2.73 min; ESI-MS (+) m/z 926.7 (M+2H).

Preparation of Example 9195

Example 9195

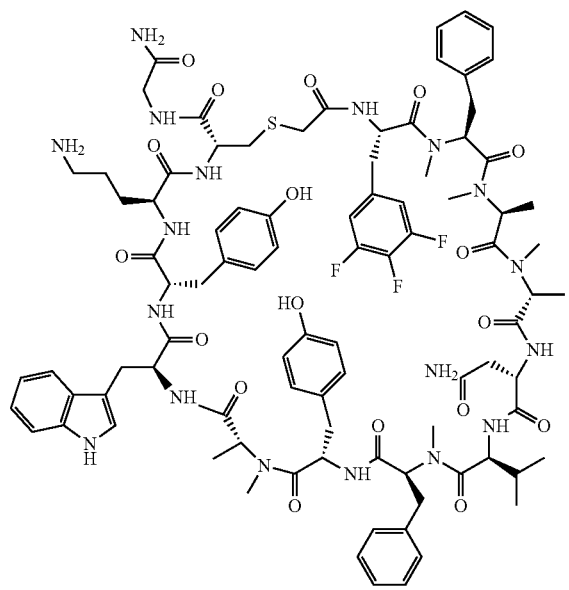

The crude material of Example 9195 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 55-95% B over 30 minutes, then a 5-minute hold at 100% B; Flow: 20 mL/min. Fractions containing the desired product were combined and dried via centrifugal evaporation. The yield of the product was 17.2 mg, and its estimated purity by LCMS analysis was 100%.

Analysis condition A: Retention time=1.919.2 min; ESI-MS(+) m/z 919.2 (M+2H).

Analysis condition B: Retention time=2.76 min; ESI-MS (+) m/z 919.1 (M+2H).

Preparation of Example 9196

Example 9196

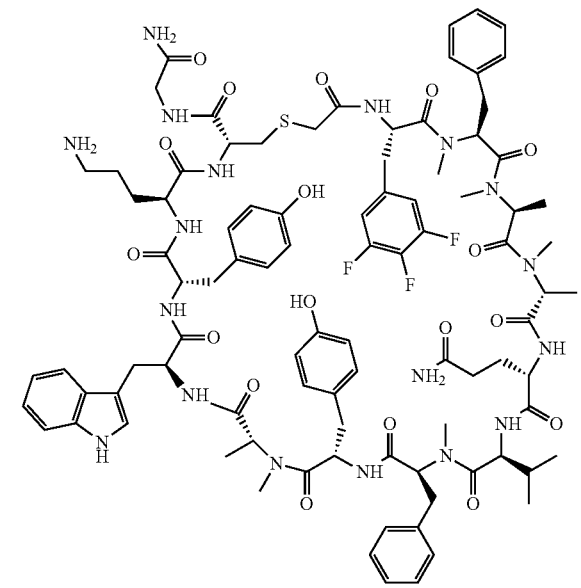

The crude material of Example 9196 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 55-95% B over 30 minutes, then a 5-minute hold at 100% B; Flow: 20 mL/min. Fractions containing the desired product were combined and dried via centrifugal evaporation. The yield of the product was 13.5 mg, and its estimated purity by LCMS analysis was 100%.

Analysis condition A: Retention time=2.04 min; ESI-MS (+) m/z 926.4 (M+2H).

Analysis condition B: Retention time=2.72 min; ESI-MS (+) m/z 926.5 (M+2H).

Preparation of Example 9213

Example 9213

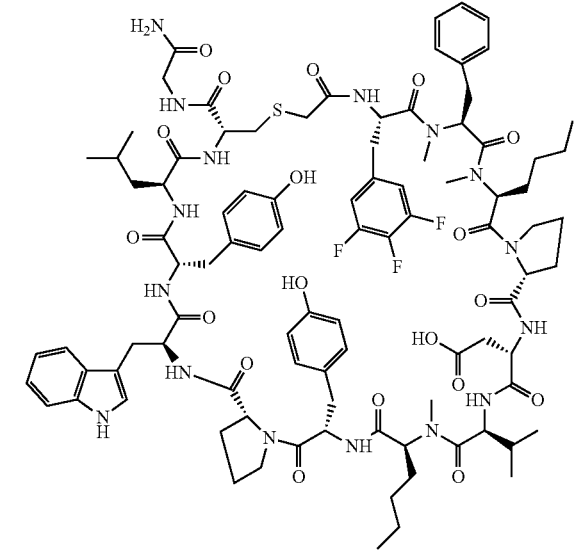

The crude material of Example 9213 was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 34.2 mg, and its estimated purity by LCMS analysis was 98%.

Analysis condition A: Retention time=1.80 min; ESI-MS (+) m/z 916.55 (M+2H).

Analysis condition B: Retention time=3.40 min; ESI-MS (+) m/z 916.60 (M+2H).

Preparation of Example 9214

Example 9214

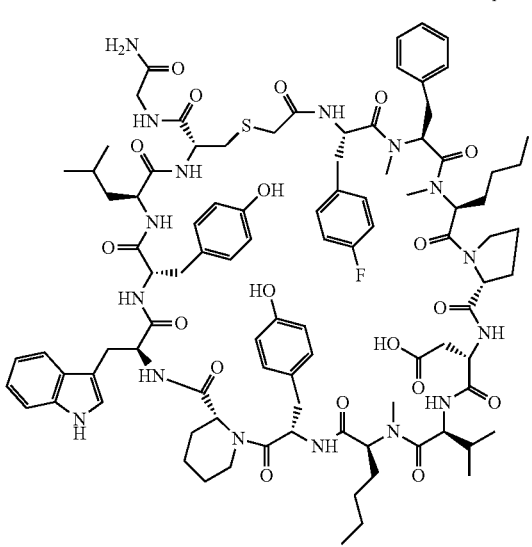

The crude material of Example 9214 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 24.2 mg, and its estimated purity by LCMS analysis was 96%.

Analysis condition A: Retention time=1.87 min; ESI-MS (+) m/z 923.60 (M+2H).

Analysis condition B: Retention time=2.55 min; ESI-MS (+) m/z 923.55 (M+2H).

Preparation of Example 9215

Example 9215

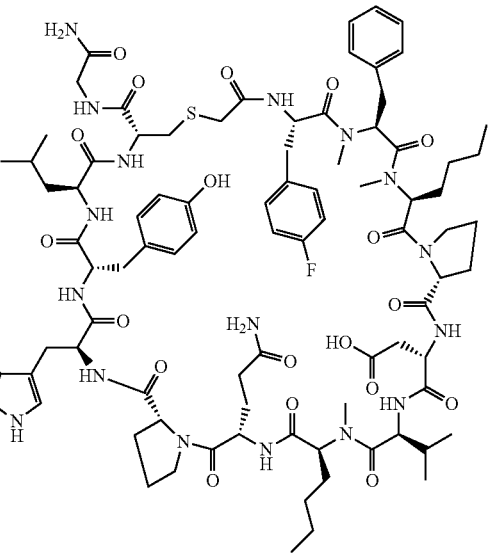

The crude material of Example 9215 was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 29.7 mg, and its estimated purity by LCMS analysis was 100%.

Analysis condition A: Retention time=1.76 min; ESI-MS (+) m/z 899.15 (M+2H).

Analysis condition B: Retention time=2.44 min; ESI-MS (+) m/z 899.05 (M+2H).

Preparation of Example 9216

Example 9216

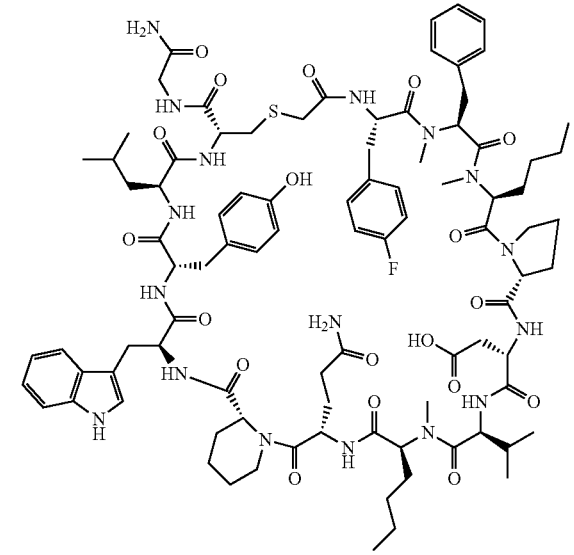

583

The crude material of Example 9216 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 54.1 mg, and its estimated purity by LCMS analysis was 100%.

Analysis condition A: Retention time=1.81 min; ESI-MS (+) m/z 906.20 (M+2H).

Analysis condition B: Retention time=3.42 min; ESI-MS (+) m/z 906.10 (M+2H).

Preparation of Example 9217

Example 9217

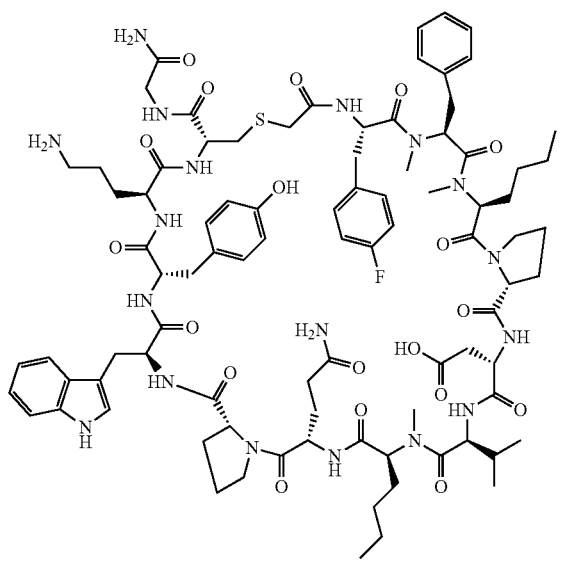

The crude material of Example 9217 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 60.7 mg, and its estimated purity by LCMS analysis was 100%.

Analysis condition A: Retention time=1.73 min; ESI-MS (+) m/z 899.55 (M+2H).

Analysis condition B: Retention time=3.41 min; ESI-MS (+) m/z 899.65 (M+2H).

584

Preparation of Example 9218

Example 9218

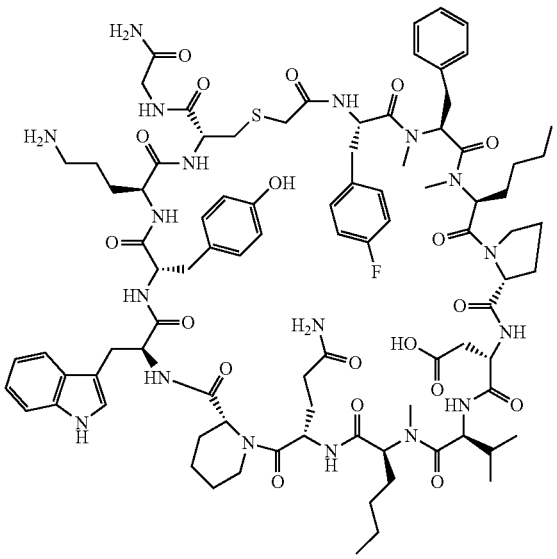

The crude material of Example 9218 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 44.1 mg, and its estimated purity by LCMS analysis was 97%.

Analysis condition A: Retention time=1.59 min; ESI-MS (+) m/z 906.60 (M+2H).

Analysis condition B: Retention time=3.43 min; ESI-MS (+) m/z 906.70 (M+2H).

Preparation of Example 9219

Example 9219

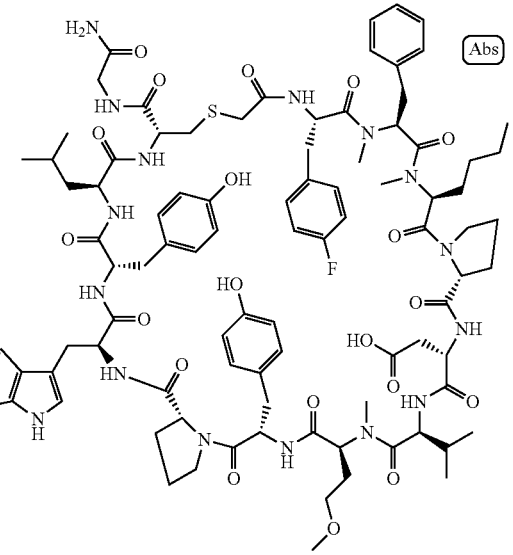

The crude material of Example 9219 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 30.1 mg, and its estimated purity by LCMS analysis was 100%.

Analysis condition A: Retention time=1.68 min; ESI-MS (+) m/z 917.95 (M+2H).

Analysis condition B: Retention time=3.27 min; ESI-MS (+) m/z 917.95 (M+2H).

Preparation of Example 9220

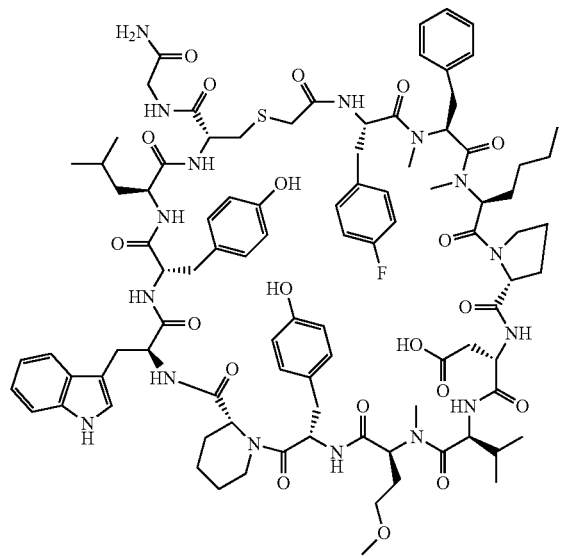

Example 9220

The crude material of Example 9220 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 36.2 mg, and its estimated purity by LCMS analysis was 97%.

Analysis condition A: Retention time=1.73 min; ESI-MS (+) m/z 924.95 (M+2H).

Analysis condition B: Retention time=3.25 min; ESI-MS (+) m/z 924.90 (M+2H).

Preparation of Example 9221

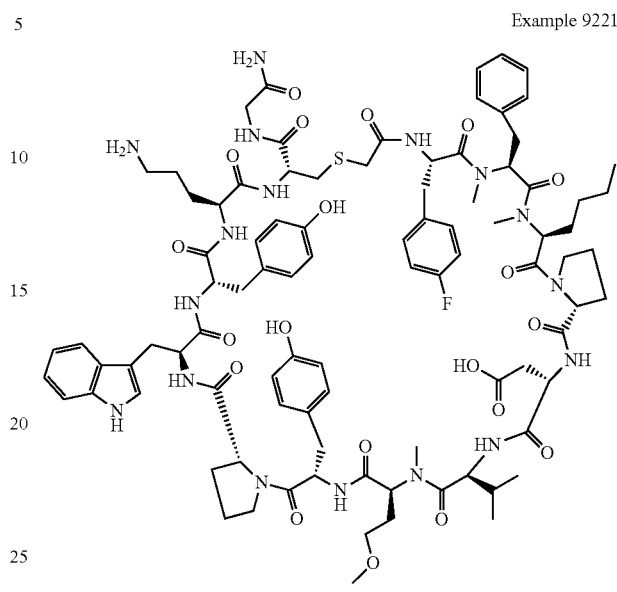

Example 9221

The crude material of Example 9221 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 43.3 mg, and its estimated purity by LCMS analysis was 95%.

Analysis condition A: Retention time=1.63 min; ESI-MS (+) m/z 918.40 (M+2H).

Analysis condition B: Retention time=3.27 min; ESI-MS (+) m/z 918.40 (M+2H).

Preparation of Example 9222

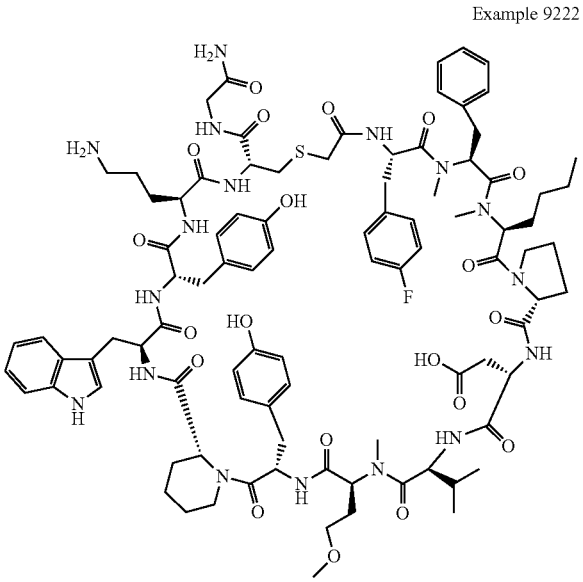 [SMILES: CCCC[C@H]1C(=O)N2CCC[C@@H]2C(=O)N[C@@H](CC(=O)O)C(=O)N[C@@H](C(C)C)C(=O)N(C)[C@@H](CCOC)C(=O)N[C@@H](Cc2ccc(O)cc2)C(=O)N2CCCC[C@@H]2C(=O)N[C@@H](Cc2c[nH]c3ccccc23)C(=O)N[C@@H](Cc2ccc(O)cc2)C(=O)N[C@@H](CCCN)C(=O)N[C@H](C(=O)NCC(N)=O)CSCC(=O)N[C@@H](Cc2ccc(F)cc2)C(=O)N(C)[C@@H](Cc2ccccc2)C(=O)N1C]

Example 9222

The crude material of Example 9222 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 33.2 mg, and its estimated purity by LCMS analysis was 96%.

Analysis condition A: Retention time=1.66 min; ESI-MS (+) m/z 925.50 (M+2H).

Analysis condition B: Retention time=3.35 min; ESI-MS (+) m/z 925.40 (M+2H).

Preparation of Example 9223

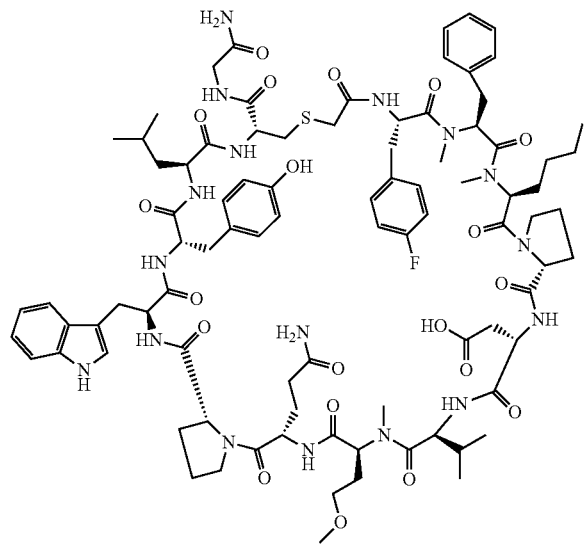

Eample 9223

The crude material of Example 9223 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 36.0 mg, and its estimated purity by LCMS analysis was 96%.

Analysis condition A: Retention time=1.61 min; ESI-MS (+) m/z 900.40 (M+2H).

Analysis condition B: Retention time=3.18 min; ESI-MS (+) m/z 900.40 (M+2H).

Preparation of Example 9224

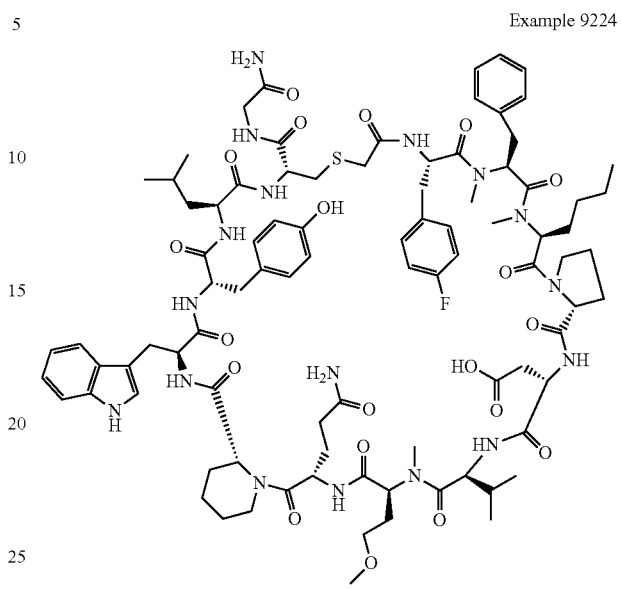

Example 9224

The crude material of Example 9224 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 38.5 mg, and its estimated purity by LCMS analysis was 97%.

Analysis condition A: Retention time=1.68 min; ESI-MS (+) m/z 907.25 (M+2H).

Analysis condition B: Retention time=3.28 min; ESI-MS (+) m/z 907.40 (M+2H).

Preparation of Examples 9225 and 9226

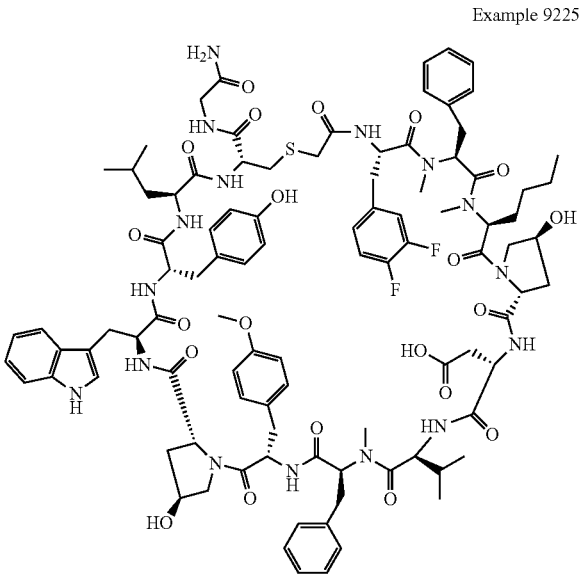

Example 9225

589
-continued

Example 9226

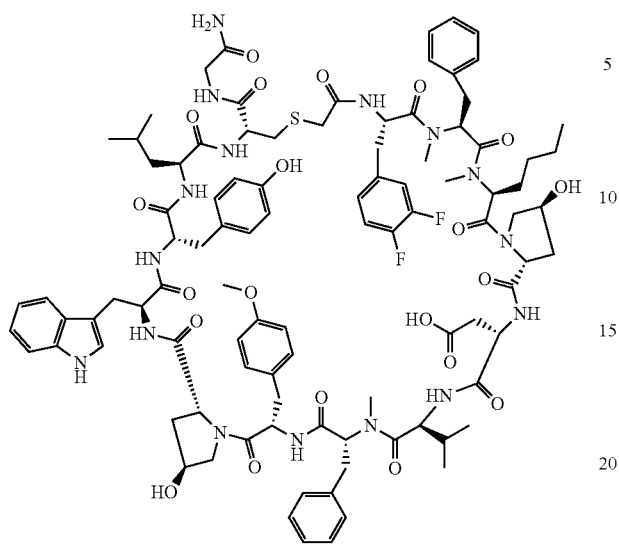

Examples 9225 and 9226 were prepared according to the method outlined in Example 10541. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired products were combined and dried via centrifugal evaporation. The yield of Examples 9225 was 27.4 mg, and its estimated purity by LCMS analysis was 96%. The yield of Examples 9226 was 24.9 mg, and its estimated purity by LCMS analysis was 96%.

Examples 9225

Analysis condition A: Retention time=1.77 min; ESI-MS (+) m/z 966.45 (M+2H).

Analysis condition B: Retention time=3.34 min; ESI-MS (+) m/z 966.45 (M+2H).

Examples 9226

Analysis condition A: Retention time=1.93 min; ESI-MS (+) m/z 966.40 (M+2H).

Analysis condition B: Retention time=3.50 min; ESI-MS (+) m/z 966.85 (M+2H).

590
Preparation of Examples 9227 and 9228

Example 9227

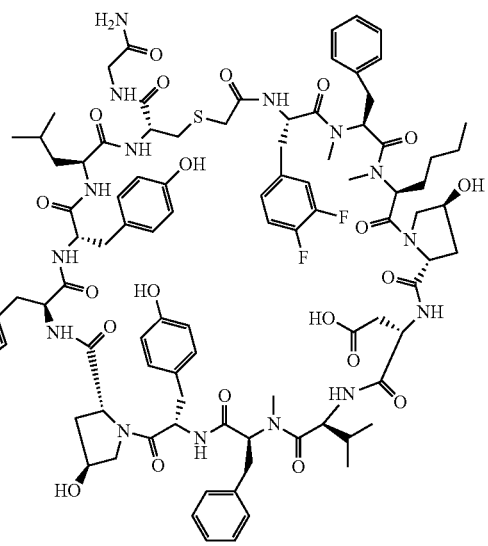

Example 9228

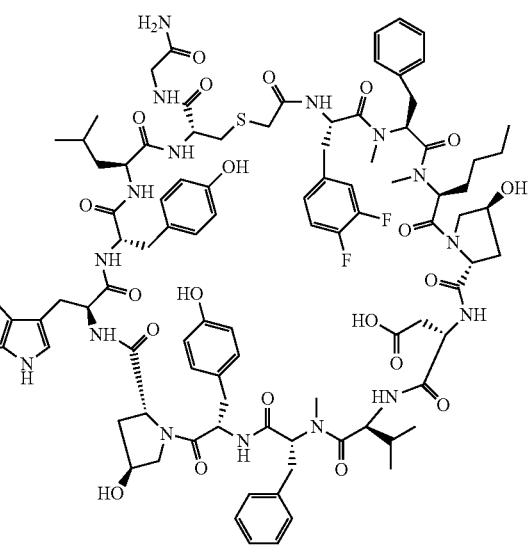

Examples 9227 and 9228 were prepared according to the method outlined in Example 10541. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired products were combined and dried via centrifugal evaporation. The yield of Examples 9227 was 39.1 mg, and its estimated purity by LCMS analysis was 98%. The yield of Examples 9228 was 21.6 mg, and its estimated purity by LCMS analysis was 95%.

Examples 9227

Analysis condition A: Retention time=1.70 min; ESI-MS (+) m/z 958.90 (M+2H).

Analysis condition B: Retention time=3.27 min; ESI-MS (+) m/z 958.90 (M+2H).

Examples 9228

Analysis condition A: Retention time=1.79 min; ESI-MS (+) m/z 958.90 (M+2H).
Analysis condition B: Retention time=3.36 min; ESI-MS (+) m/z 958.95 (M+2H).

Preparation of Examples 9229 and 9230

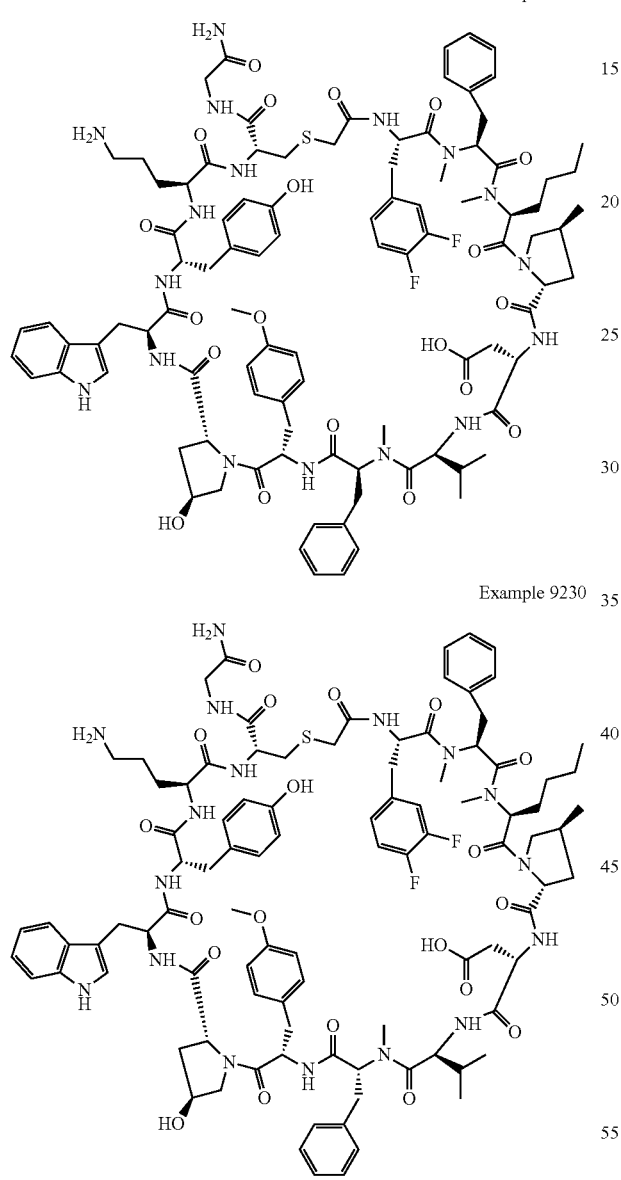

Examples 9229 and 930 were prepared according to the method outlined in Example 10541. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired products were combined and dried via centrifugal evaporation. The yield of Examples 9229 was 25.1 mg, and its estimated purity by LCMS analysis was 98%. The yield of Examples 9230 was 12.7 mg, and its estimated purity by LCMS analysis was 98%.

Examples 9229

Analysis condition A: Retention time=1.76 min; ESI-MS (+) m/z 965.95 (M+2H).
Analysis condition B: Retention time=3.35 min; ESI-MS (+) m/z 965.95 (M+2H).

Examples 9230

Analysis condition A: Retention time=1.98 min; ESI-MS (+) m/z 965.85 (M+2H).
Analysis condition B: Retention time=3.47 min; ESI-MS (+) m/z 965.55 (M+2H).

Preparation of Examples 9231 and 9232

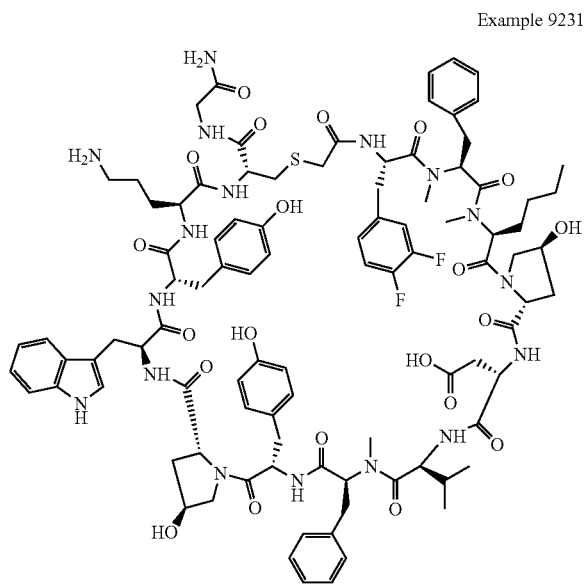

Examples 9231 and 9232 were prepared according to the method outlined in Example 10541. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired products were combined and dried via centrifugal evaporation. The yield of Examples 9231 was 24.9 mg, and its estimated purity by LCMS analysis was 100%. The yield of Examples 9232 was 16.0 mg, and its estimated purity by LCMS analysis was 96%.

Examples 9231

Analysis condition A: Retention time=1.67 min; ESI-MS (+) m/z 959.40 (M+2H).

Analysis condition B: Retention time=3.25 min; ESI-MS (+) m/z 959.40 (M+2H).

Examples 9232

Analysis condition A: Retention time=1.78 min; ESI-MS (+) m/z 959.40 (M+2H).

Analysis condition B: Retention time=3.32 min; ESI-MS (+) m/z 959.35 (M+2H).

Preparation of Examples 9233 and 9234

Example 9233

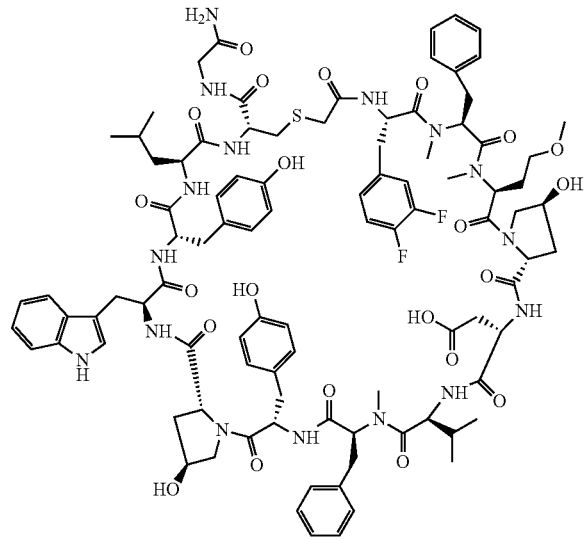

Example 9234

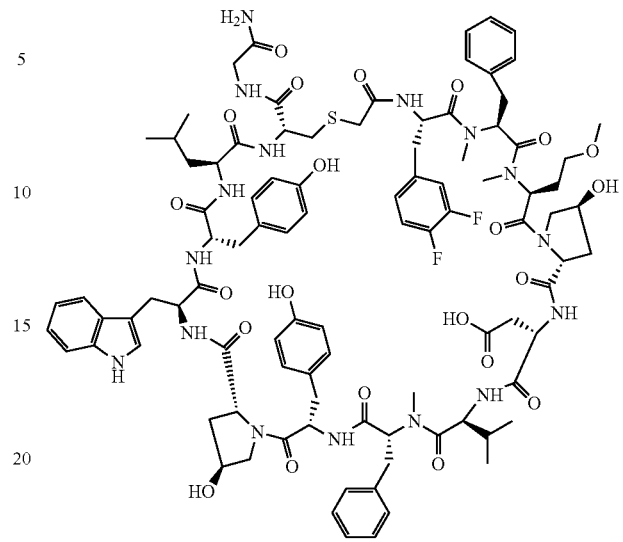

Examples 9233 and 9234 were prepared according to the method outlined in Example 10541. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired products were combined and dried via centrifugal evaporation. The yield of Examples 9233 was 13.3 mg, and its estimated purity by LCMS analysis was 93%. The yield of Examples 9234 was 11.1 mg, and its estimated purity by LCMS analysis was 94%.

Examples 9233

Analysis condition A: Retention time=1.54 min; ESI-MS (+) m/z 960.0 (M+2H).

Analysis condition B: Retention time=2.70 min; ESI-MS (+) m/z 960.0 (M+2H).

Examples 9234

Analysis condition A: Retention time=1.59 min; ESI-MS (+) m/z 960.1 (M+2H).

Analysis condition B: Retention time=2.78 min; ESI-MS (+) m/z 960.4 (M+2H).

Preparation of Examples 9235 and 9236

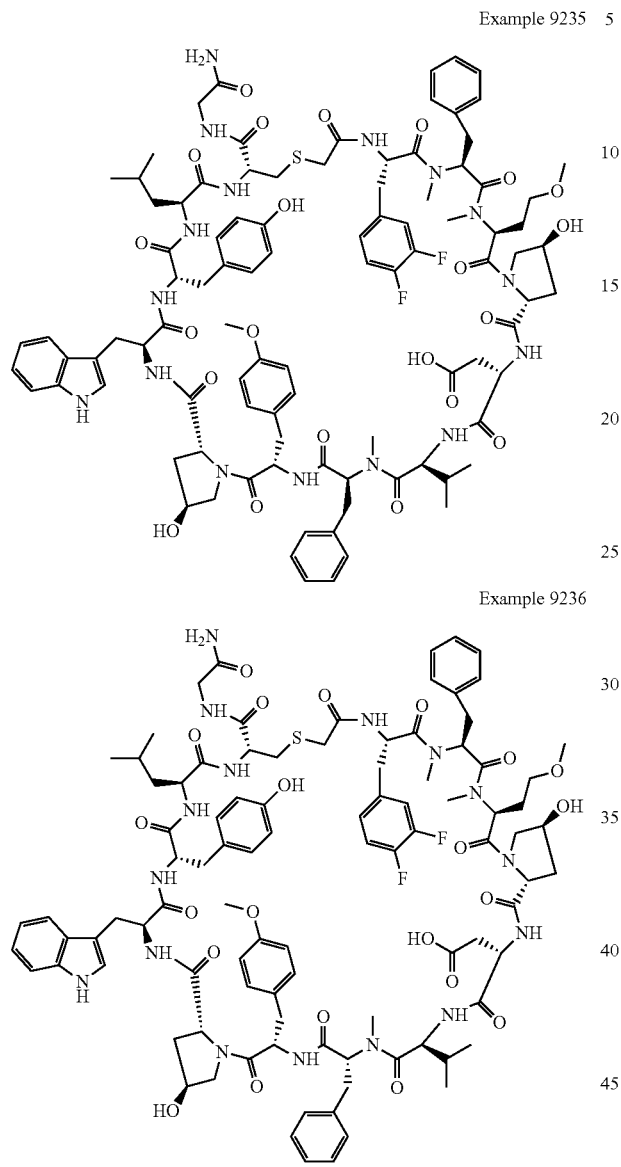

Example 9235

Example 9236

Examples 9235 and 9236 were prepared according to the method outlined in Example 10541. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired products were combined and dried via centrifugal evaporation. The yield of Examples 9235 was 13.0 mg, and its estimated purity by LCMS analysis was 90%. The yield of Examples 9236 was 10.3 mg, and its estimated purity by LCMS analysis was 92%.

Examples 9235

Analysis condition A: Retention time=1.62 min; ESI-MS (+) m/z 966.95 (M+2H).

Analysis condition B: Retention time=3.16 min; ESI-MS (+) m/z 966.90 (M+2H).

Examples 9236

Analysis condition A: Retention time=1.79 min; ESI-MS (+) m/z 966.75 (M+2H).
Analysis condition B: Retention time=3.37 min; ESI-MS (+) m/z 966.95 (M+2H).

Preparation of Examples 9237 and 9238

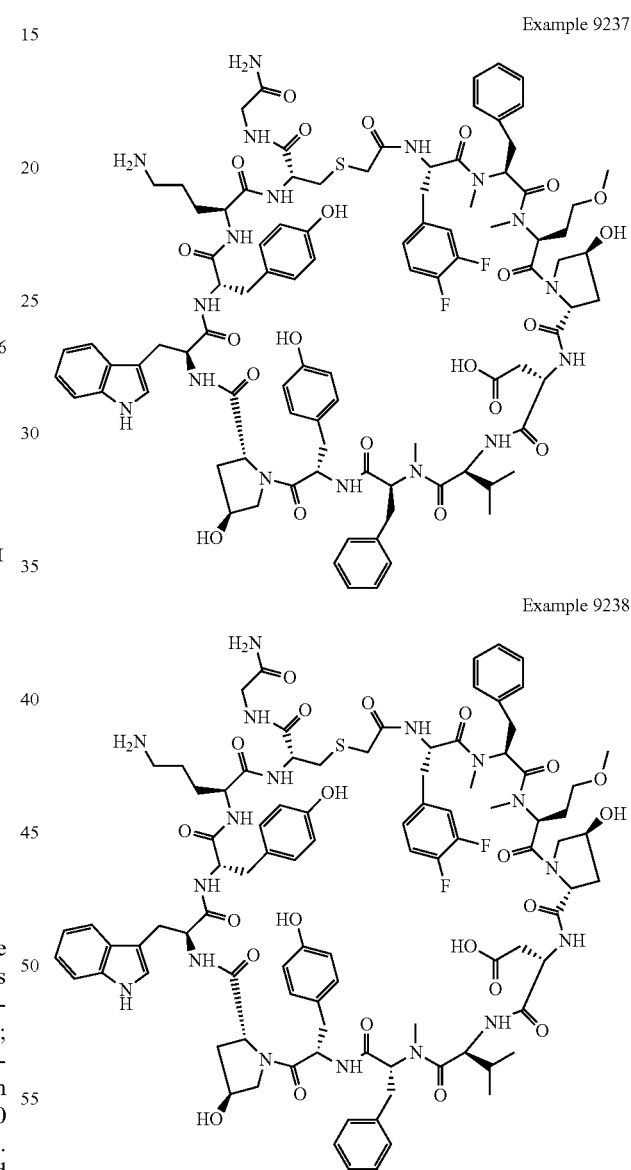

Example 9237

Example 9238

Examples 9237 and 9238 were prepared according to the method outlined in Example 10541. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired products were combined and dried via centrifugal evaporation. The yield of Examples 9237 was 20.4 mg, and its estimated purity by LCMS analysis was 96%. The yield of Examples 9238 was 20.5 mg, and its estimated purity by LCMS analysis was 97%.

Examples 9237

Analysis condition A: Retention time=1.52 min; ESI-MS (+) m/z 960.40 (M+2H).
Analysis condition B: Retention time=3.05 min; ESI-MS (+) m/z 960.40 (M+2H).

Examples 9238

Analysis condition A: Retention time=1.62 min; ESI-MS (+) m/z 960.40 (M+2H).
Analysis condition B: Retention time=3.13 min; ESI-MS (+) m/z 960.40 (M+2H).

Preparation of Examples 9239 and 9240

Examples 9239 and 9240 were prepared according to the method outlined in Example 10541. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired products were combined and dried via centrifugal evaporation. The yield of Examples 9239 was 22.7 mg, and its estimated purity by LCMS analysis was 97%. The yield of Examples 9240 was 16.0 mg, and its estimated purity by LCMS analysis was 97%.

Examples 9239

Analysis condition A: Retention time=1.59 min; ESI-MS (+) m/z 967.45 (M+2H).
Analysis condition B: Retention time=3.13 min; ESI-MS (+) m/z 967.45 (M+2H).

Examples 9240

Analysis condition A: Retention time=1.75 min; ESI-MS (+) m/z 967.40 (M+2H).
Analysis condition B: Retention time=3.29 min; ESI-MS (+) m/z 967.40 (M+2H).

Preparation of Example 9241

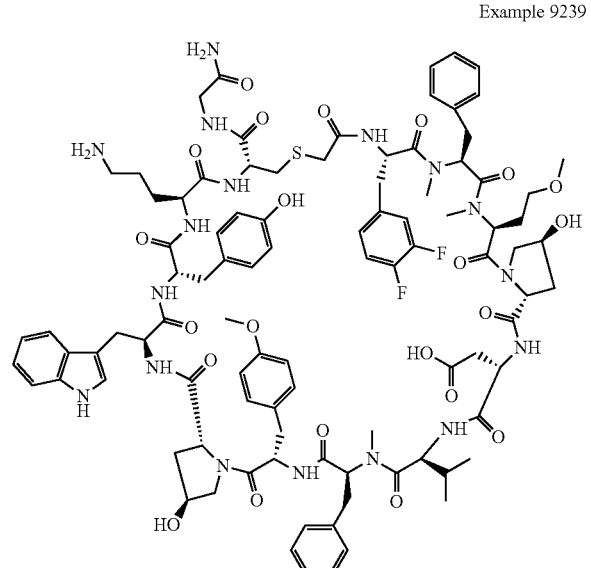

Example 9239

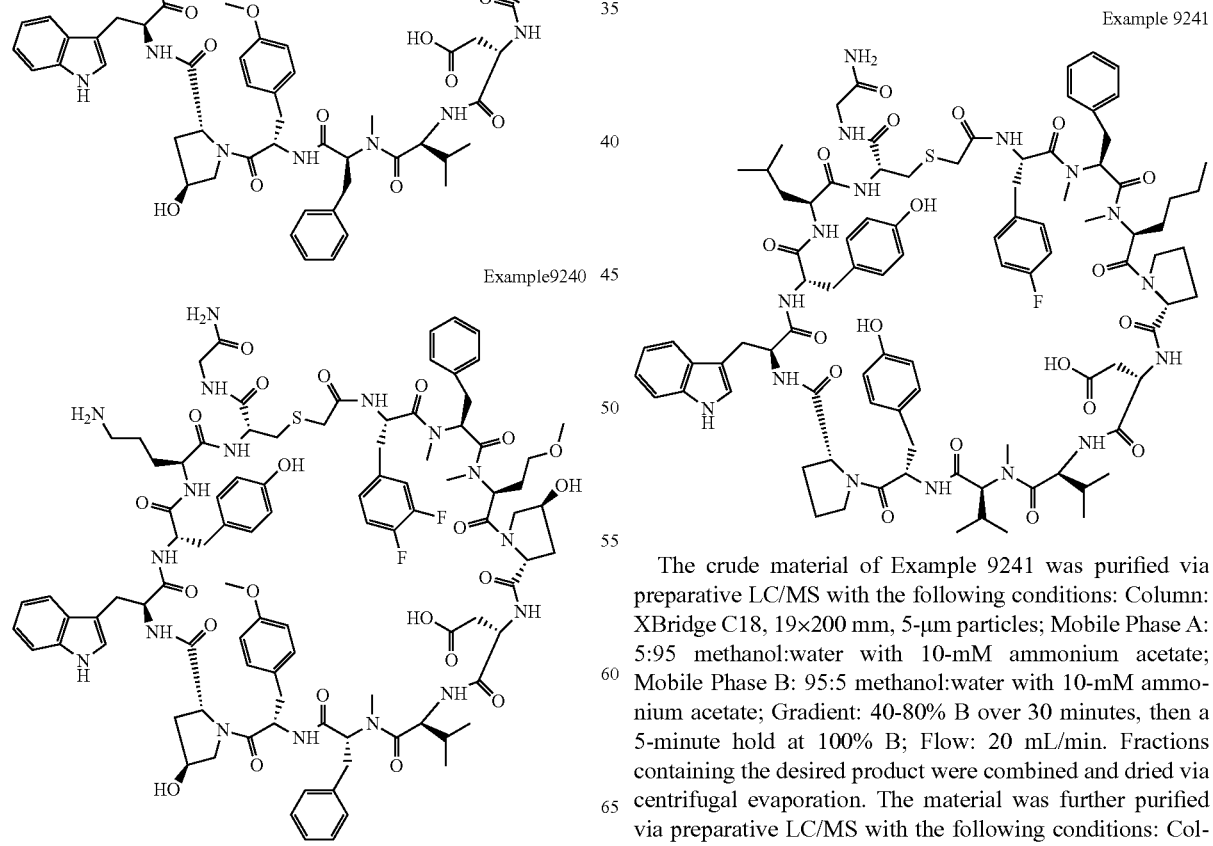

Example 9240

Example 9241

The crude material of Example 9241 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 30 minutes, then a 5-minute hold at 100% B; Flow: 20 mL/min. Fractions containing the desired product were combined and dried via centrifugal evaporation. The yield of the product was 9.7 mg, and its estimated purity by LCMS analysis was 100%.

Analysis condition A: Retention time=1.65 min; ESI-MS (−) m/z 908.5 (M−2H).

Analysis condition B: Retention time=2.86 min; ESI-MS (+) m/z 908.1 (M−2H).

Preparation of Example 9242

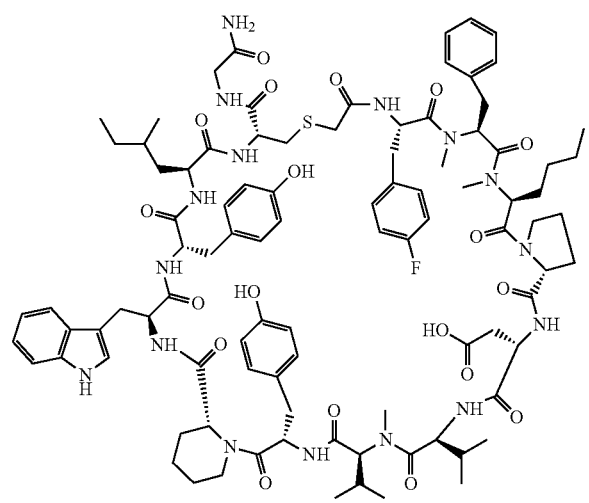

Example 9242

The crude material of Example 9242 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 30 minutes, then a 5-minute hold at 100% B; Flow: 20 mL/min. Fractions containing the desired product were combined and dried via centrifugal evaporation. The yield of the product was 2.6 mg, and its estimated purity by LCMS analysis was 97%.

Analysis condition A: Retention time=1.82 min; ESI-MS (+) m/z 916.20 (M+2H).

Analysis condition B: Retention time=2.47 min; ESI-MS (+) m/z 916.45 (M−2H).

Preparation of Example 9243

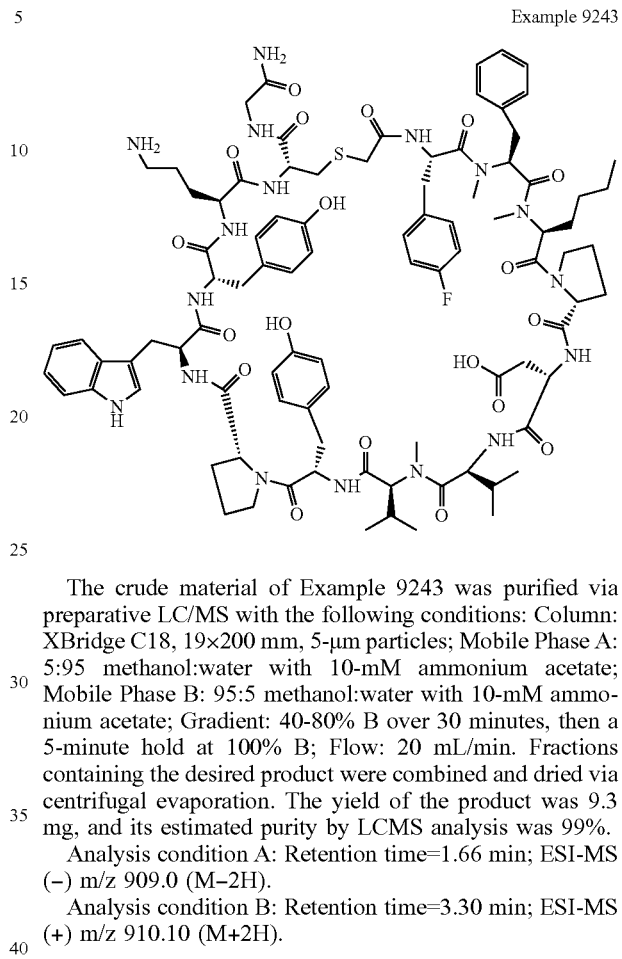

Example 9243

The crude material of Example 9243 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 9.3 mg, and its estimated purity by LCMS analysis was 99%.

Analysis condition A: Retention time=1.66 min; ESI-MS (−) m/z 909.0 (M−2H).

Analysis condition B: Retention time=3.30 min; ESI-MS (+) m/z 910.10 (M+2H).

Preparation of Example 9244

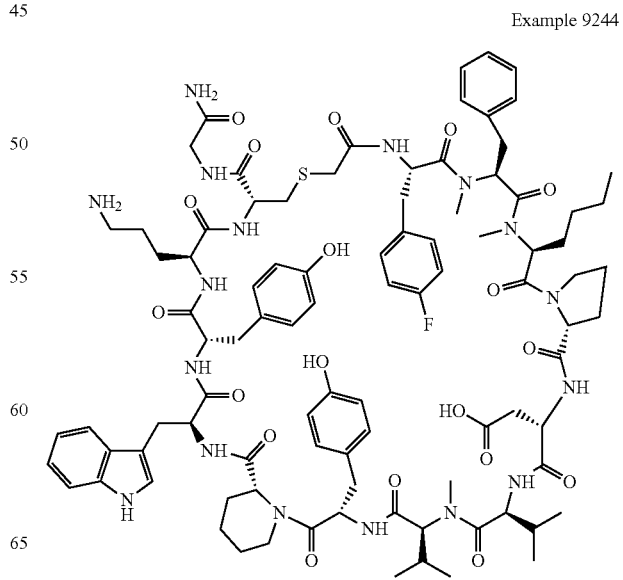

Example 9244

The crude material of Example 9244 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 55-95% B over 30 minutes, then a 5-minute hold at 100% B; Flow: 20 mL/min. Fractions containing the desired product were combined and dried via centrifugal evaporation. The yield of the product was 8.6 mg, and its estimated purity by LCMS analysis was 99%.

Analysis condition A: Retention time=1.69 min; ESI-MS (−) m/z 916.0 (M−2H).

Analysis condition B: Retention time=3.43 min; ESI-MS (+) m/z 917.05 (M+2H).

Preparation of Example 9245

Example 9245

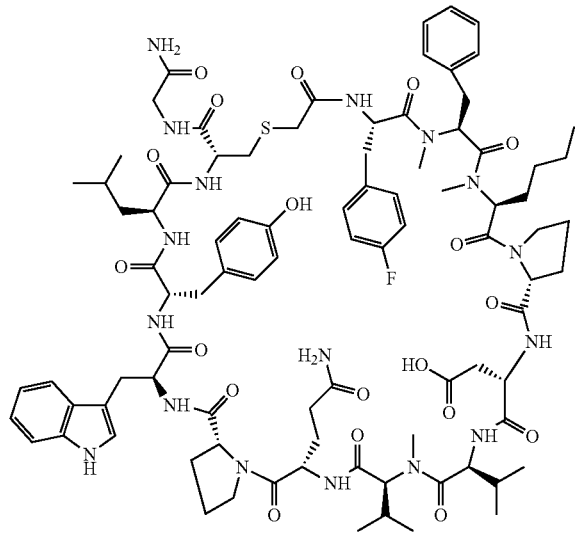

The crude material of Example 9245 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 10.3 mg, and its estimated purity by LCMS analysis was 100%.

Analysis condition A: Retention time=1.58 min; ESI-MS (−) m/z 891.4 (M−2H).

Analysis condition B: Retention time=3.04 min; ESI-MS (+) m/z 892.55 (M+2H).

Preparation of Example 9246

Example 9246

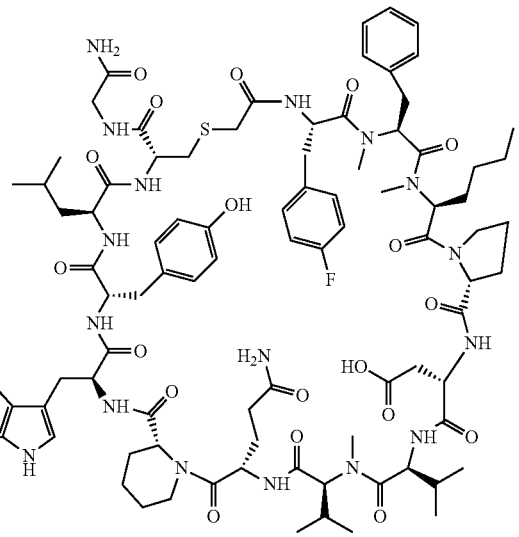

The crude material of Example 9246 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 13.0 mg, and its estimated purity by LCMS analysis was 98%.

Analysis condition B: Retention time=3.14 min; ESI-MS (+) m/z 899.55 (M+2H).

Preparation of Example 9247

Example 9247

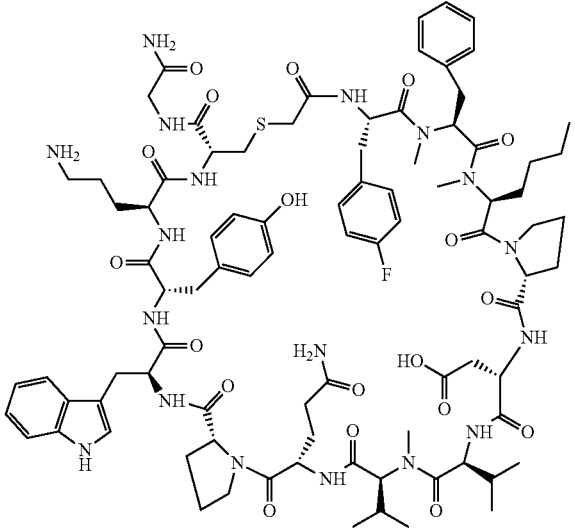

The crude material of Example 9247 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 19.4 mg, and its estimated purity by LCMS analysis was 100%.

Analysis condition B: Retention time=3.12 min; ESI-MS (+) m/z 893.00 (M+2H).

Preparation of Example 9248

Example 9248

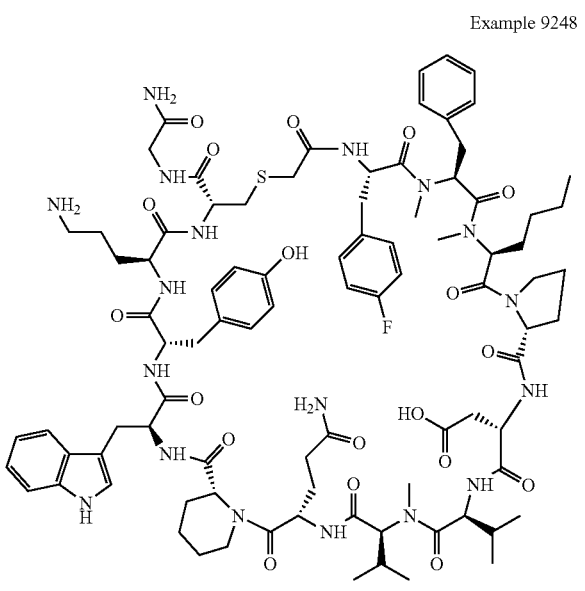 [SMILES: CCCC[C@H]1C(=O)N2CCC[C@@H]2C(=O)N[C@@H](CC(=O)O)C(=O)N[C@@H](C(C)C)C(=O)N(C)[C@@H](C(C)C)C(=O)N[C@@H](CCC(N)=O)C(=O)N2CCCC[C@@H]2C(=O)N[C@@H](Cc2c[nH]c3ccccc23)C(=O)N[C@@H](Cc2ccc(O)cc2)C(=O)N[C@@H](CCCN)C(=O)N[C@H](C(=O)NCC(N)=O)CSCC(=O)N[C@@H](Cc2ccc(F)cc2)C(=O)N(C)[C@@H](Cc2ccccc2)C(=O)N1C]

The crude material of Example 9248 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 25.0 mg, and its estimated purity by LCMS analysis was 100%.

Analysis condition B: Retention time=3.26 min; ESI-MS (+) m/z 900.0 (M+2H).

Preparation of Example 9249

Example 9249

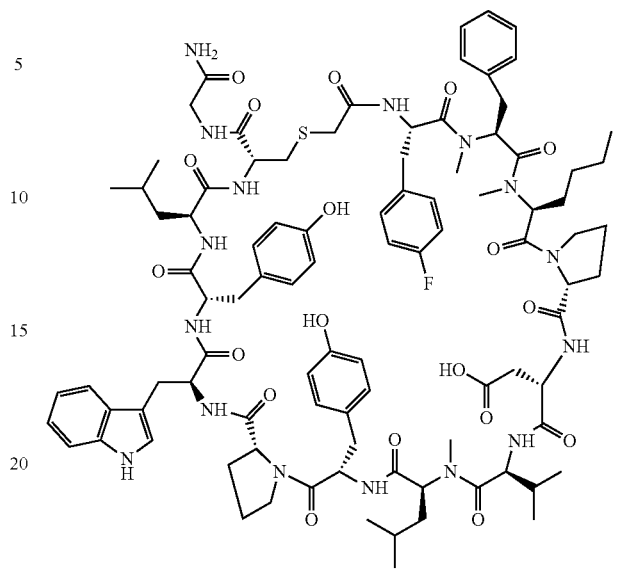

The crude material of Example 9249 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 20 minutes, then a 5-minute hold at 100% B; Flow: 20 mL/min. Fractions containing the desired product were combined and dried via centrifugal evaporation. The yield of the product was 14.6 mg, and its estimated purity by LCMS analysis was 97%.

Analysis condition B: Retention time=3.38 min; ESI-MS (+) m/z 916.55 (M+2H).

Preparation of Example 9250

Example 9250

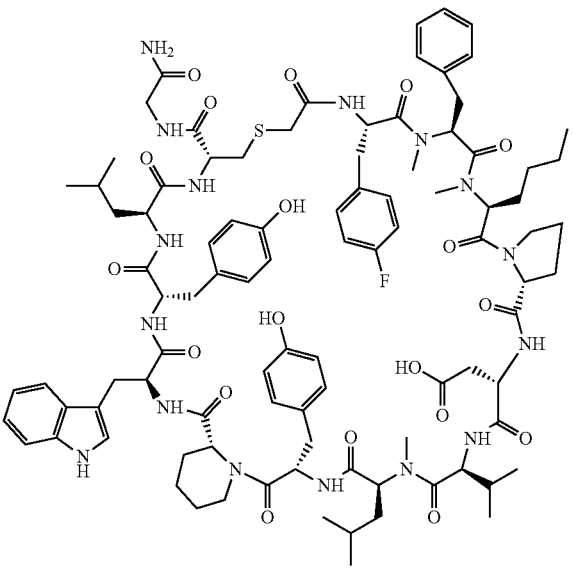

The crude material of Example 9250 was purified via preparative LC/MS with the following conditions: Column: XBridge C18, 19×mm, 5-μm particles; Mobile Phase A: 5:95 methanol:water with 10-mM ammonium acetate; Mobile Phase B: 95:5 methanol:water with 10-mM ammonium acetate; Gradient: 55-95% B over 30 minutes, then a 5-minute hold at 100% B; Flow: 20 mL/min. Fractions containing the desired product were combined and dried via centrifugal evaporation. The yield of the product was 41.0 mg, and its estimated purity by LCMS analysis was 100%.

Analysis condition A: Retention time=1.85 min; ESI-MS (−) m/z 922.5 (M−2H).

Analysis condition B: Retention time=3.48 min; ESI-MS (+) m/z 923.45 (M+2H).

Preparation of Example 9251

Example 9251

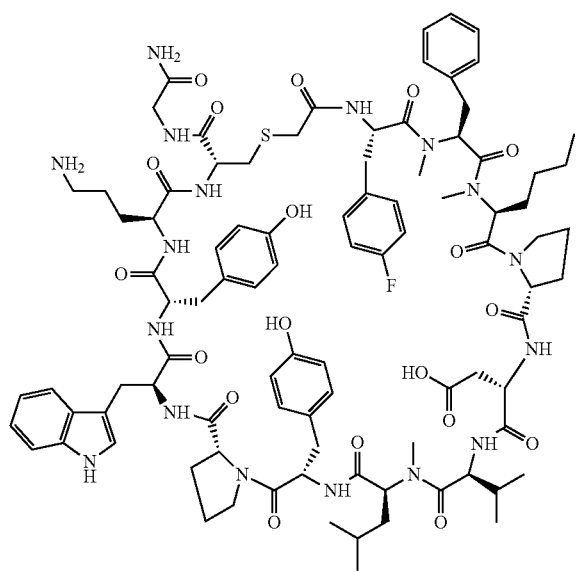

The crude material of Example 9251 was purified via preparative LC/MS with the following conditions: Column: waters xbridge c-18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 55-95% B over 30 minutes, then a 5-minute hold at 100% B; Flow: 20 mL/min. Fractions containing the desired product were combined and dried via centrifugal evaporation. The yield of the product was 38.1 mg, and its estimated purity by LCMS analysis was 94%. Analysis condition A: Retention time=1. min; ESI-MS (+) m/z (M+2H).

Analysis condition A: Retention time=1.71 min; ESI-MS (−) m/z 916.6 (M−2H).

Analysis condition B: Retention time=2.39 min; ESI-MS (+) m/z 917.05 (M+2H).

Preparation of Example 9252

Example 9252

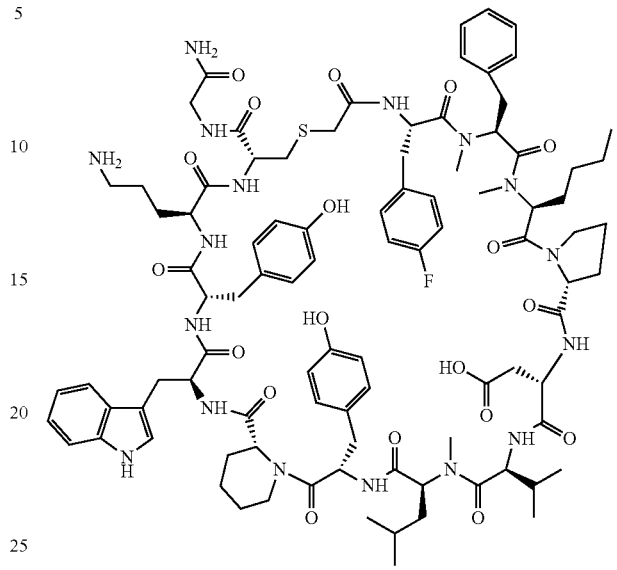

The crude material of Example 9252 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 55-95% B over 30 minutes, then a 5-minute hold at 100% B; Flow: 20 mL/min. Fractions containing the desired product were combined and dried via centrifugal evaporation. The yield of the product was 33.1 mg, and its estimated purity by LCMS analysis was 98%.

Analysis condition A: Retention time=1.76 min; ESI-MS (−) m/z 923.0 (M−2H).

Analysis condition B: Retention time=3.06 min; ESI-MS (+) m/z 925.7 (M+2H).

Preparation of Example 9253

Example 9253


The crude material of Example 9253 was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 47.5 mg, and its estimated purity by LCMS analysis was 100%.

Analysis condition A: Retention time=1.63 min; ESI-MS (−) m/z 898.6 (M−2H).

Analysis condition B: Retention time=3.19 min; ESI-MS (+) m/z 899.50 (M+2H).

Preparation of Example 9254

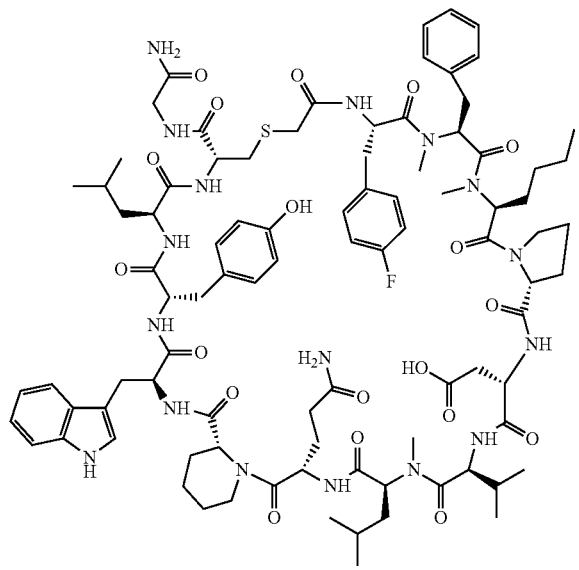

Exmaple 9254

The crude material of Example 9254 was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 48.9 mg, and its estimated purity by LCMS analysis was 98%.

Analysis condition A: Retention time=1.64 min; ESI-MS (−) m/z 905.8 (M−2H).

Analysis condition B: Retention time=2. min; ESI-MS(+) m/z 906.55 (M+2H).

Preparation of Example 9255

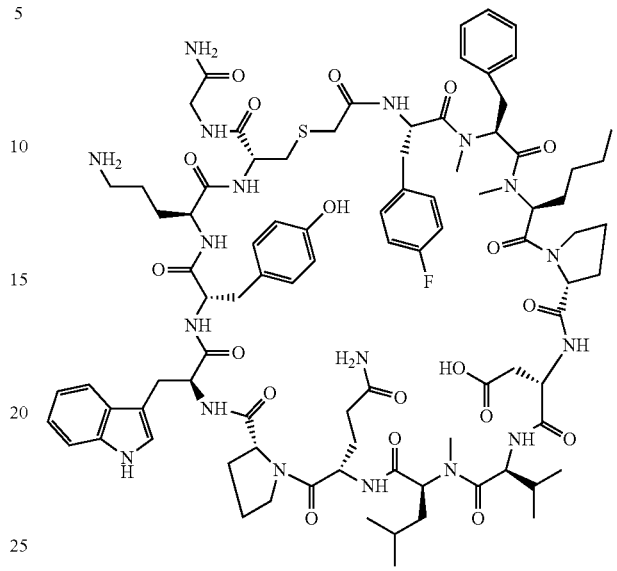

Example 9255

The crude material of Example 9255 was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 52.2 mg, and its estimated purity by LCMS analysis was 99%.

Analysis condition A: Retention time=1.63 min; ESI-MS (+) m/z 899.2 (M+2H).

Analysis condition B: Retention time=3.23 min; ESI-MS (+) m/z 900.05 (M+2H).

Preparation of Example 9256

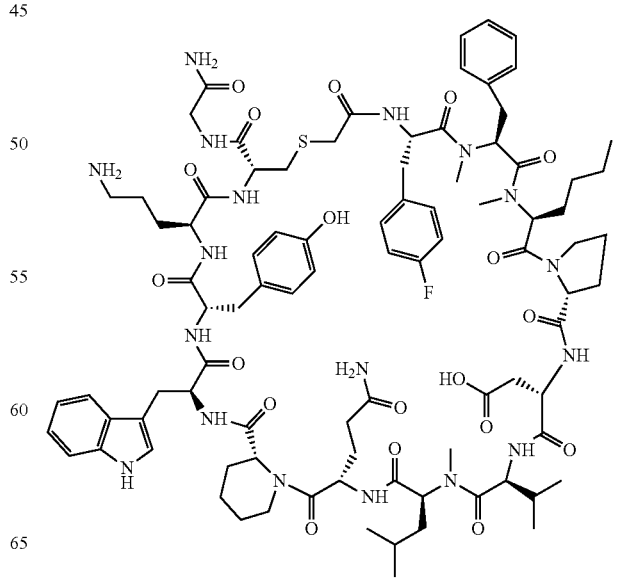

Example 9256

The crude material of Example 9256 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 53.7 mg, and its estimated purity by LCMS analysis was 100%.

Analysis condition A: Retention time=1.69 min; ESI-MS (+) m/z 906.8 (M+2H).

Analysis condition B: Retention time=3.40 min; ESI-MS (+) m/z 907.00 (M+2H).

Preparation of Example 9257

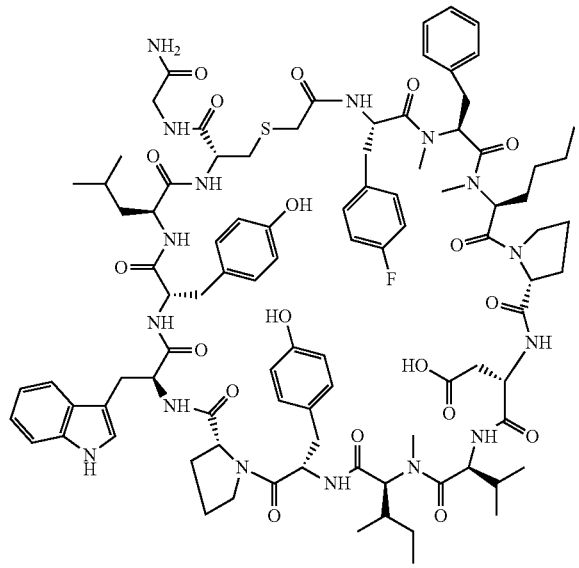

Example 9257

The crude material of Example 9257 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 10.0 mg, and its estimated purity by LCMS analysis was 97%.

Analysis condition A: Retention time=2.88 min; ESI-MS (+) m/z 915.7 (M+2H).

Analysis condition B: Retention time=3.28 min; ESI-MS (+) m/z 916.55 (M+2H).

Preparation of Example 9258

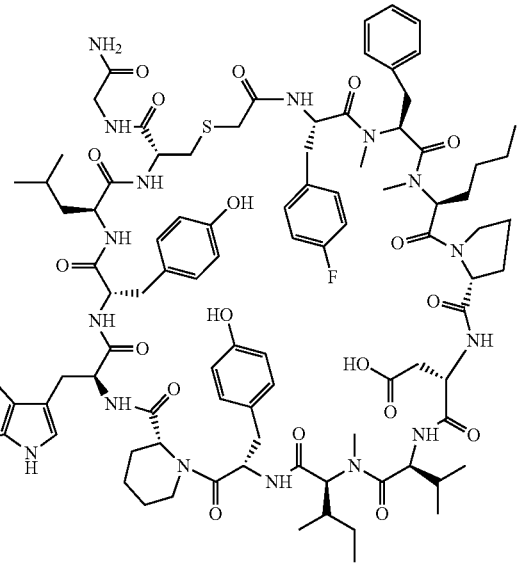

Example 9258

The crude material of Example 9258 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 10.7 mg, and its estimated purity by LCMS analysis was 99%.

Analysis condition A: Retention time=1.77 min; ESI-MS (+) m/z 922.8 (M+2H).

Analysis condition B: Retention time=2.76 min; ESI-MS (+) m/z 923.60 (M+2H).

Preparation of Example 9259

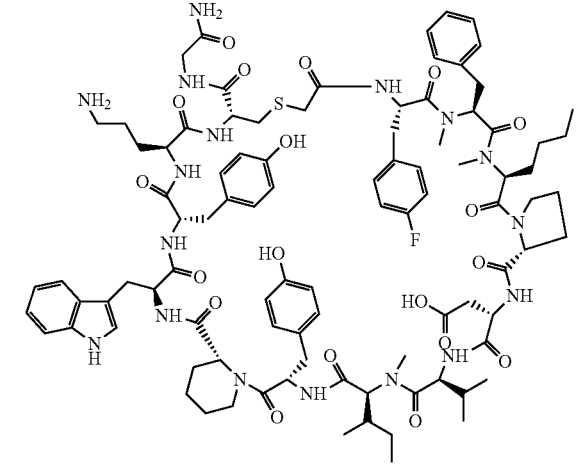

Example 9259

The crude material of Example 9259 was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 9.1 mg, and its estimated purity by LCMS analysis was 100%.

Analysis condition A: Retention time=1.75 min; ESI-MS (−) m/z 923.0 (M−2H).

Analysis condition B: Retention time=3.47 min; ESI-MS (+) m/z 924.05 (M+2H).

Preparation of Example 9260

Example 9260

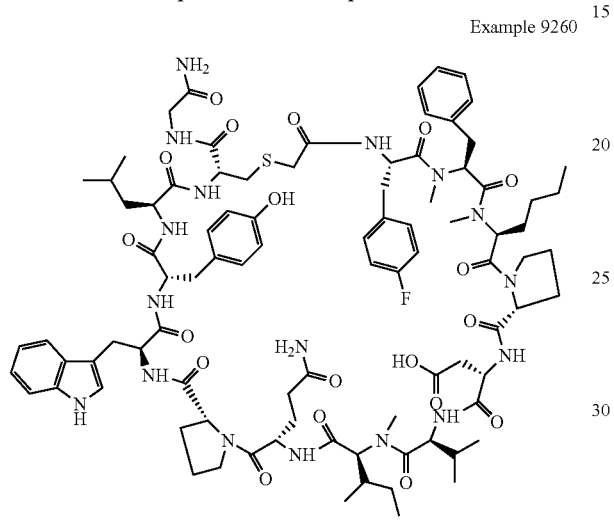

The crude material of Example 9260 was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 21.0 mg, and its estimated purity by LCMS analysis was 98%.

Analysis condition B: Retention time=3.08 min; ESI-MS (−) m/z 899.55 (M−2H).

Preparation of Example 9261

Example 9261

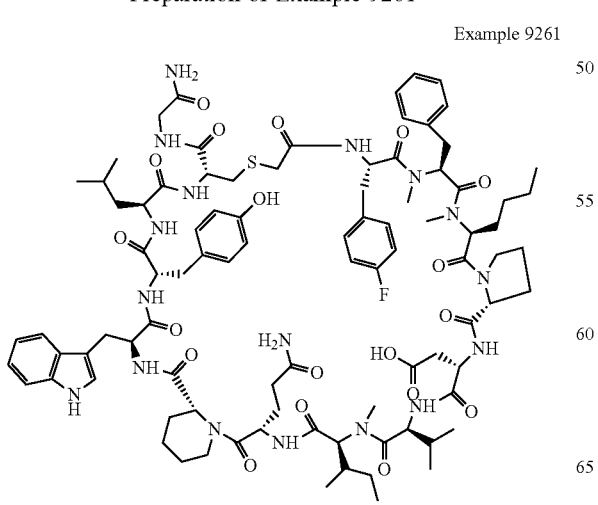

The crude material of Example 9261 was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 16.8 mg, and its estimated purity by LCMS analysis was 100%.

Analysis condition A: Retention time=1.67 min; ESI-MS (+) m/z 905.5 (M+2H).

Analysis condition B: Retention time=3.19 min; ESI-MS (+) m/z 906.55 (M+2H).

Preparation of Example 9262

Example 9262

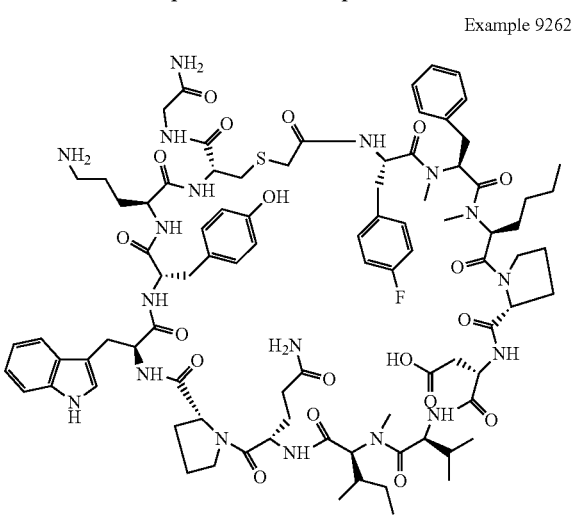

The crude material of Example 9262 was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 14.0 mg, and its estimated purity by LCMS analysis was 100%.

Analysis condition B: Retention time=3.18 min; ESI-MS (+) m/z 899.9 (M+2H).

Preparation of Example 9263

Example 9263

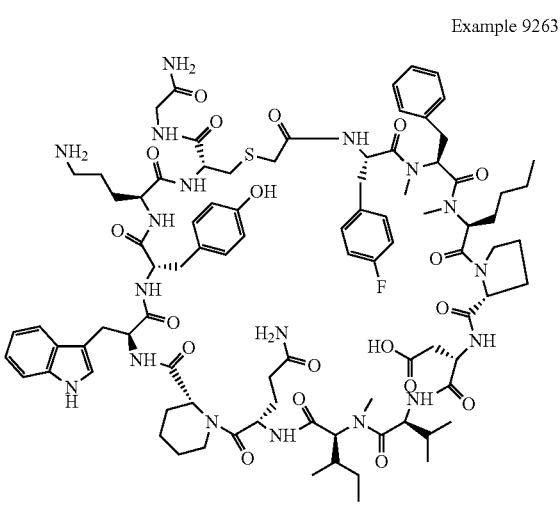 [SMILES: CCCC[C@H]1C(=O)N2CCC[C@@H]2C(=O)N[C@@H](CC(=O)O)C(=O)N[C@@H](C(C)C)C(=O)N(C)[C@@H](C(C)CC)C(=O)N[C@@H](CCC(N)=O)C(=O)N2CCCC[C@@H]2C(=O)N[C@@H](Cc2c[nH]c3ccccc23)C(=O)N[C@@H](Cc2ccc(O)cc2)C(=O)N[C@@H](CCCN)C(=O)N[C@H](C(=O)NCC(N)=O)CSCC(=O)N[C@@H](Cc2ccc(F)cc2)C(=O)N(C)[C@@H](Cc2ccccc2)C(=O)N1C]

The crude material of Example 9263 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 33.2 mg, and its estimated purity by LCMS analysis was 100%.

Analysis condition A: Retention time=1.63 min; ESI-MS (+) m/z 905.6 (M+2H).

Analysis condition B: Retention time=3.31 min; ESI-MS (+) m/z 907.10 (M+2H).

Preparation of Example 9264

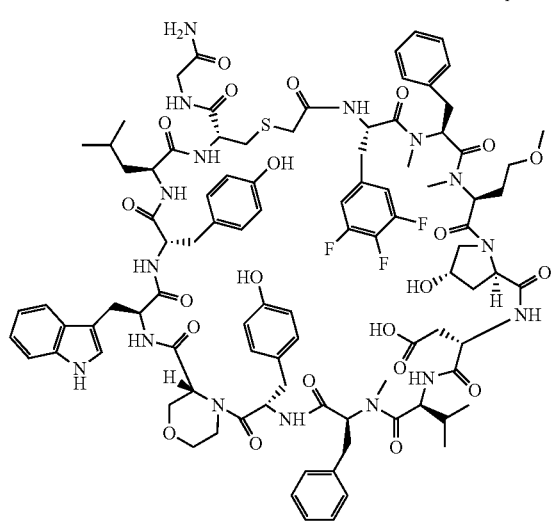

Example 9264

The crude material of Example 9264 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 60-100% B over 25 minutes, then a 10-minute hold at 100% B; Flow: 20 mL/min. Fractions containing the desired product were combined and dried via centrifugal evaporation. The yield of the product was 22.9 mg, and its estimated purity by LCMS analysis was 98%.

Analysis condition A: Retention time=1.74 min; ESI-MS (+) m/z 968.25 (M+2H).

Analysis condition B: Retention time=2.38 min; ESI-MS (+) m/z 968.45 (M+2H).

Preparation of Example 9265

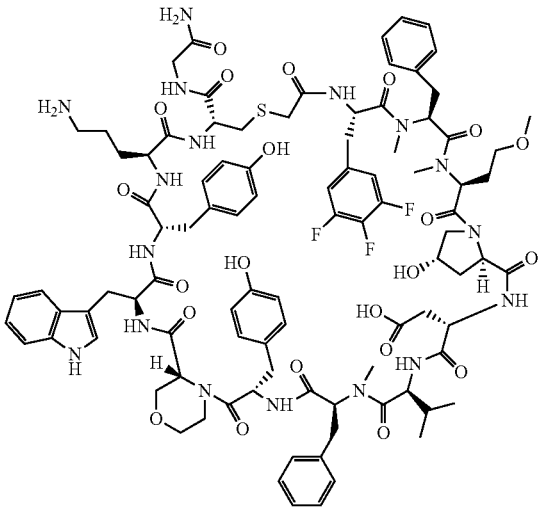

Example 9265

The crude material of Example 9265 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 60-100% B over 25 minutes, then a 10-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-65% B over 30 minutes, then a 5-minute hold at 100% B; Flow: 20 mL/min. Fractions containing the desired product were combined and dried via centrifugal evaporation. The yield of the product was 17.6 mg, and its estimated purity by LCMS analysis was 95%.

Analysis condition A: Retention time=1.68 min; ESI-MS (+) m/z 969.15 (M+2H).

Analysis condition B: Retention time=3.32 min; ESI-MS (+) m/z 969.05 (M+2H).

Preparation of Example 9266

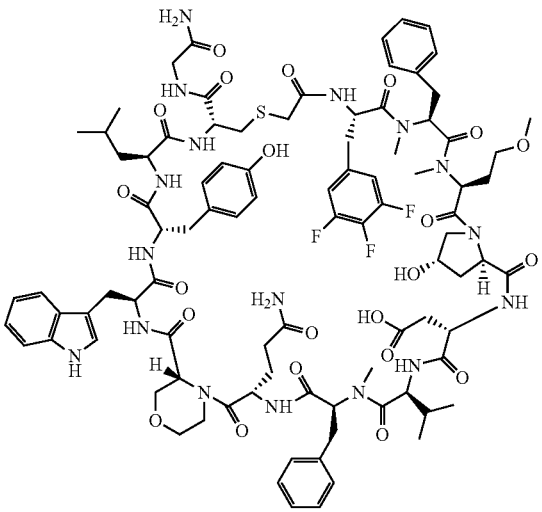

Example 9266

The crude material of Example 9266 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 60-100% B over 25 minutes, then a 10-minute hold at 100% B; Flow: 20 mL/min. Fractions containing the desired product were combined and dried via centrifugal evaporation. The yield of the product was 16.5 mg, and its estimated purity by LCMS analysis was 100%.

Analysis condition A: Retention time=1.68 min; ESI-MS (−) m/z 950.2 (M−2H).

Analysis condition B: Retention time=2.85 min; ESI-MS (+) m/z 951.8 (M+2H).

Preparation of Example 9267

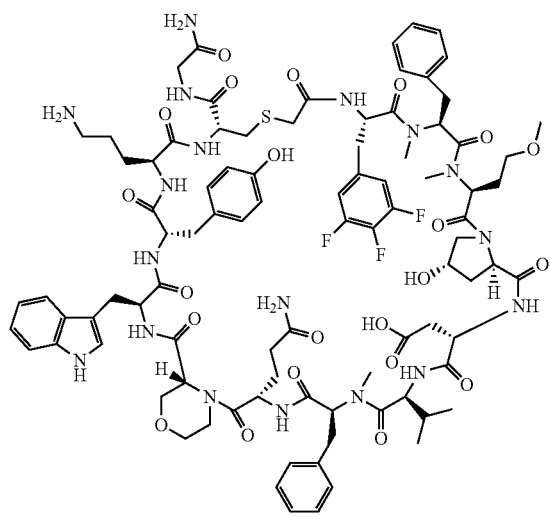

Example 9267

The crude material of Example 9267 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 26.1 mg, and its estimated purity by LCMS analysis was 98%.

Analysis condition A: Retention time=1.67 min; ESI-MS (+) m/z 951.50 (M+2H).

Analysis condition B: Retention time=3.26 min; ESI-MS (+) m/z 951.55 (M+2H).

Preparation of Example 9268

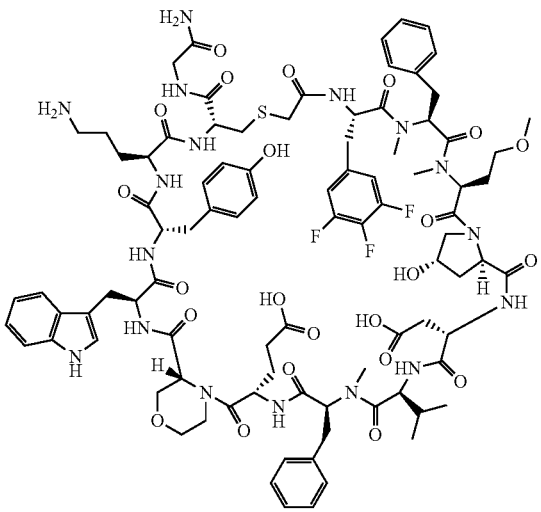

Example 9268

The crude material of Example 9268 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 18.2 mg, and its estimated purity by LCMS analysis was 99%.

Analysis condition A: Retention time=1.61 min; ESI-MS (+) m/z 951.85 (M+2H).

Analysis condition B: Retention time=3.18 min; ESI-MS (+) m/z 951.95 (M+2H).

Preparation of Example 9269

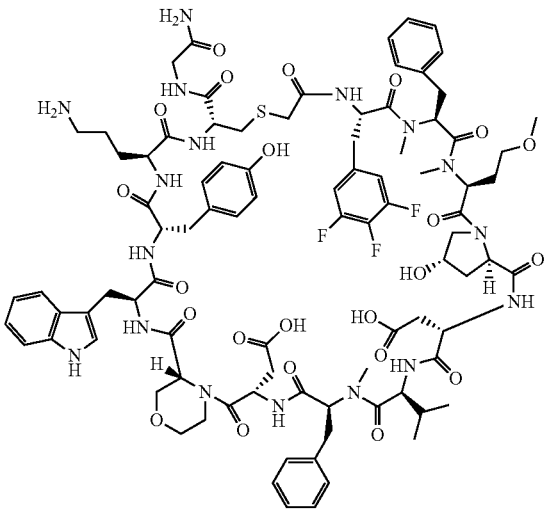

Example 9269

The crude material of Example 9269 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 12.4 mg, and its estimated purity by LCMS analysis was 100%.

Analysis condition A: Retention time=1.40 min; ESI-MS (+) m/z 945.35 (M+2H).

Analysis condition B: Retention time=2.74 min; ESI-MS (+) m/z 945.35 (M+2H).

Preparation of Example 9270

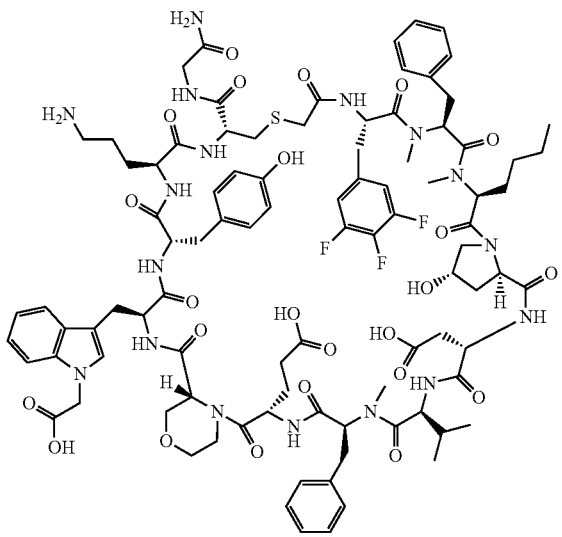

Example 9270

The crude material of Example 9270 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 29.7 mg, and its estimated purity by LCMS analysis was 100%.

Analysis condition A: Retention time=1.32 min; ESI-MS (+) m/z 980.35 (M+2H).

Analysis condition B: Retention time=2.74 min; ESI-MS (+) m/z 980.45 (M+2H).

Preparation of Example 9271

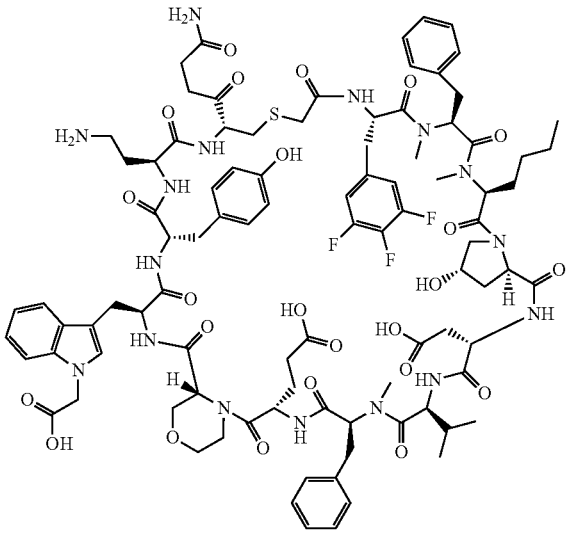

Example 9271

The crude material of Example 9271 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 39.6 mg, and its estimated purity by LCMS analysis was 94%.

Analysis condition A: Retention time=1.52 min; ESI-MS (+) m/z 973.40 (M+2H).

Analysis condition B: Retention time=3.12 min; ESI-MS (+) m/z 973.35 (M+2H).

Preparation of Example 9272

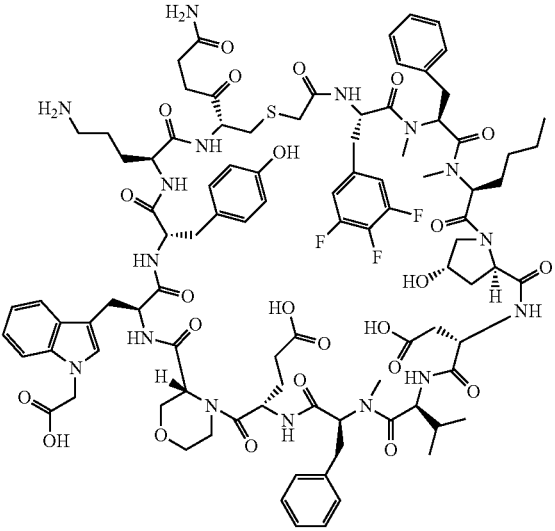

Example 9272

The crude material of Example 9272 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 5.8 mg, and its estimated purity by LCMS analysis was 99%.

Analysis condition A: Retention time=1.82 min; ESI-MS (+) m/z 973.50 (M+2H).

Analysis condition B: Retention time=3.08 min; ESI-MS (+) m/z 973.45 (M+2H).

Preparation of Example 9273

Example 9273

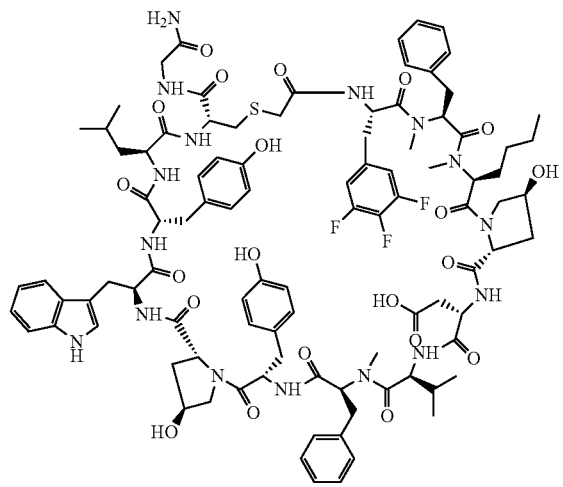

The crude material of Example 9273 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 48.5 mg, and its estimated purity by LCMS analysis was 99%.

Analysis condition A: Retention time=1.60 min; ESI-MS (+) m/z 967.70 (M+2H).

Analysis condition B: Retention time=2.99 min; ESI-MS (+) m/z 967.70 (M+2H).

Preparation of Example 9274

Example 9274

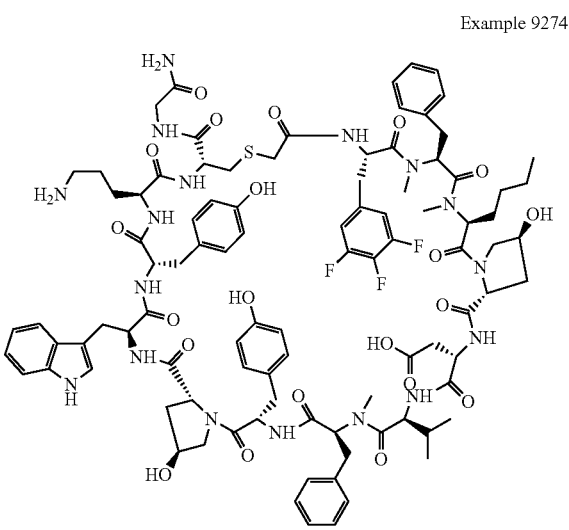 [SMILES: CCCC[C@H]1C(=O)N2C[C@@H](O)C[C@@H]2C(=O)N[C@@H](CC(=O)O)C(=O)N[C@@H](C(C)C)C(=O)N(C)[C@@H](Cc2ccccc2)C(=O)N[C@@H](Cc2ccc(O)cc2)C(=O)N2C[C@@H](O)C[C@@H]2C(=O)N[C@@H](Cc2c[nH]c3ccccc23)C(=O)N[C@@H](Cc2ccc(O)cc2)C(=O)N[C@@H](CCCN)C(=O)N[C@H](C(=O)NCC(N)=O)CSCC(=O)N[C@@H](Cc2cc(F)c(F)c(F)c2)C(=O)N(C)[C@@H](Cc2ccccc2)C(=O)N1C]

The crude material of Example 9274 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 30 minutes, then a 5-minute hold at 100% B; Flow: 20 mL/min. Fractions containing the desired product were combined and dried via centrifugal evaporation. The yield of the product was 46.8 mg, and its estimated purity by LCMS analysis was 94%.

Analysis condition A: Retention time=1.60 min; ESI-MS (+) m/z 968.80 (M+2H).

Analysis condition B: Retention time=3.04 min; ESI-MS (+) m/z 968.20 (M+2H).

Preparation of Example 9275

Example 9275

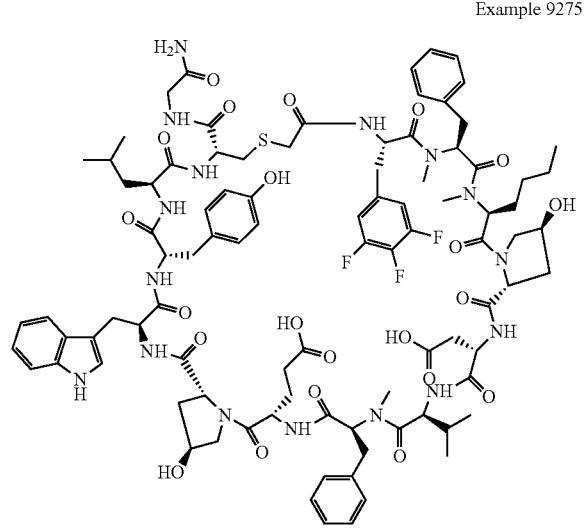 [SMILES: CCCC[C@H]1C(=O)N2C[C@@H](O)C[C@@H]2C(=O)N[C@@H](CC(=O)O)C(=O)N[C@@H](C(C)C)C(=O)N(C)[C@@H](Cc2ccccc2)C(=O)N[C@@H](CCC(=O)O)C(=O)N2C[C@@H](O)C[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2cc(F)c(F)c(F)c2)C(=O)N(C)[C@@H](Cc2ccccc2)C(=O)N1C]

The crude material of Example 9275 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 50.3 mg, and its estimated purity by LCMS analysis was 100%.

Analysis condition A: Retention time=1.55 min; ESI-MS (+) m/z 950.70 (M+2H).

Analysis condition B: Retention time=2.87 min; ESI-MS (+) m/z 950.70 (M+2H).

Preparation of Example 9276

Example 9276

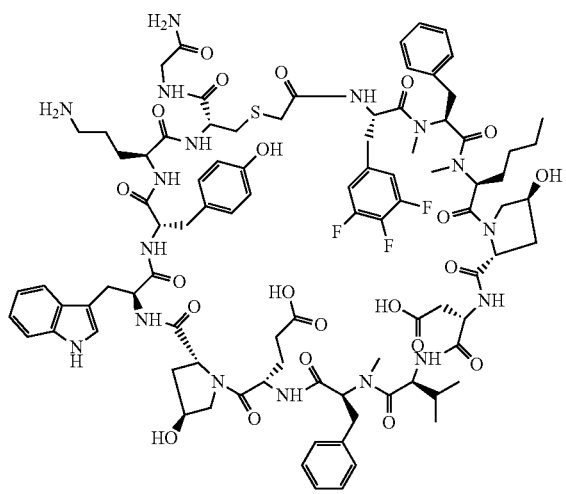

The crude material of Example 9276 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 28.9 mg, and its estimated purity by LCMS analysis was 99%.

Analysis condition A: Retention time=1. min; ESI-MS(+) m/z 951.20 (M+2H).

Analysis condition B: Retention time=2.96 min; ESI-MS (+) m/z 951.15 (M+2H).

Preparation of Example 9277

Example 9277

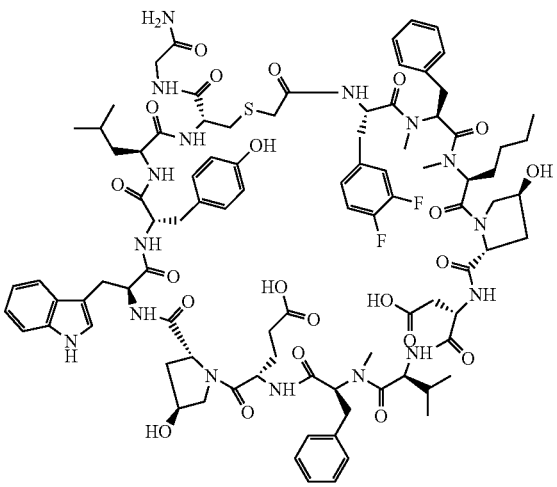

The crude material of Example 9277 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 43.1 mg, and its estimated purity by LCMS analysis was 100%.

Analysis condition A: Retention time=1.50 min; ESI-MS (+) m/z 941.70 (M+2H).

Analysis condition B: Retention time=2.75 min; ESI-MS (+) m/z 941.70 (M+2H).

Preparation of Example 9278

Example 9278

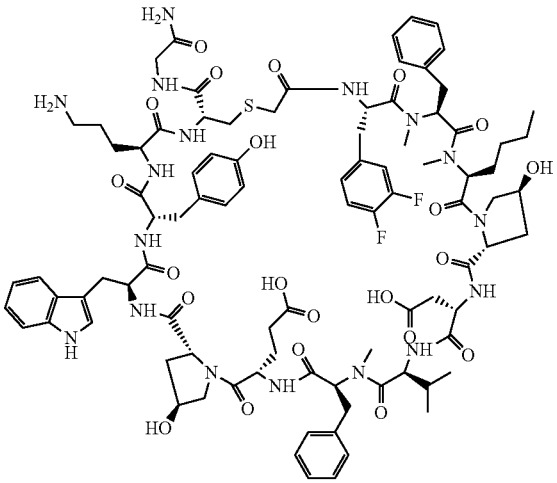

The crude material of Example 9278 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 30.8 mg, and its estimated purity by LCMS analysis was 100%.

Analysis condition A: Retention time=1.50 min; ESI-MS (+) m/z 942.20 (M+2H).
Analysis condition B: Retention time=2.91 min; ESI-MS (+) m/z 942.20 (M+2H).

Preparation of Example 9279

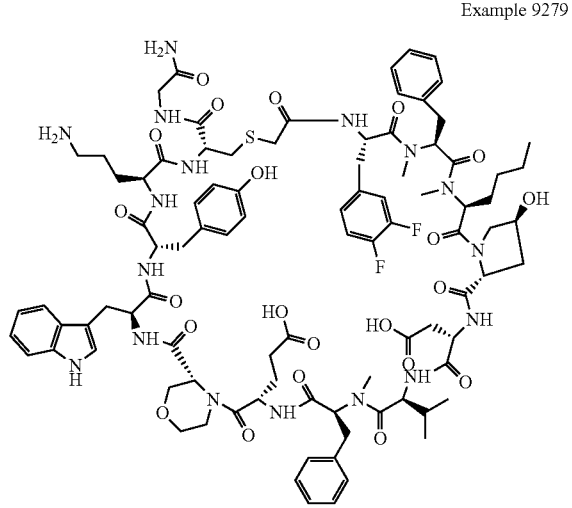 [SMILES: CCCC[C@H]1C(=O)N2C[C@@H](O)C[C@@H]2C(=O)N[C@@H](CC(=O)O)C(=O)N[C@@H](C(C)C)C(=O)N(C)[C@@H](Cc2ccccc2)C(=O)N[C@@H](CCC(=O)O)C(=O)N2CCOC[C@@H]2C(=O)N[C@@H](Cc2c[nH]c3ccccc23)C(=O)N[C@@H](Cc2ccc(O)cc2)C(=O)N[C@@H](CCCN)C(=O)N[C@H](C(=O)NCC(N)=O)CSCC(=O)N[C@@H](Cc2ccc(F)c(F)c2)C(=O)N(C)[C@@H](Cc2ccccc2)C(=O)N1C]

Example 9279

The crude material of Example 9279 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 52.6 mg, and its estimated purity by LCMS analysis was 100%.
Analysis condition A: Retention time=1.63 min; ESI-MS (+) m/z 942.3 (M+2H).
Analysis condition B: Retention time=2.86 min; ESI-MS (+) m/z 942.8 (M+2H).

Preparation of Example 9280

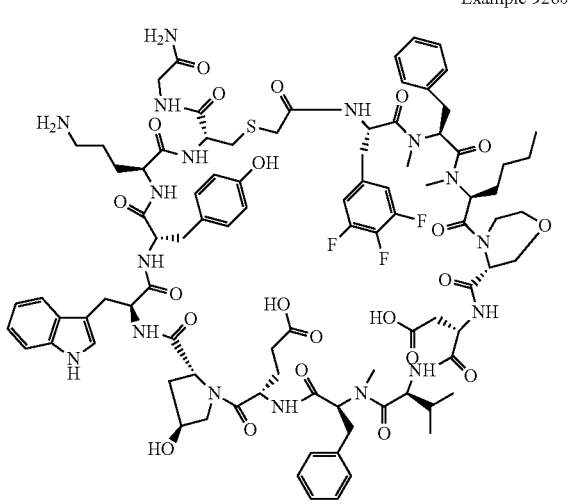

Example 9280

The crude material of Example 9280 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 42.2 mg, and its estimated purity by LCMS analysis was 96%.
Analysis condition A: Retention time=1.68 min; ESI-MS (+) m/z 951.3 (M+2H).
Analysis condition B: Retention time=2.76 min; ESI-MS (+) m/z 951.6 (M+2H).

Preparation of Example 9281

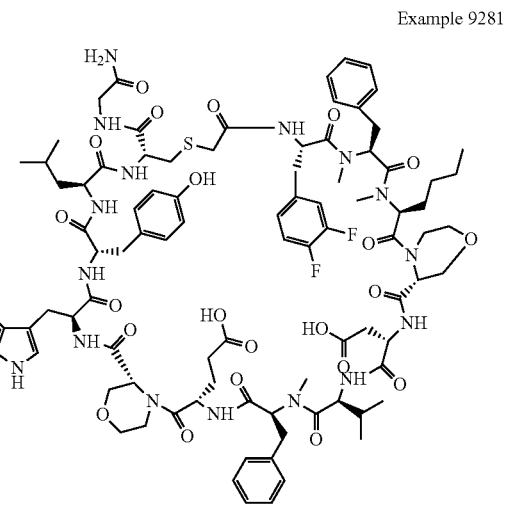

Example 9281

The crude material of Example 9281 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 56.9 mg, and its estimated purity by LCMS analysis was 95%.
Analysis condition A: Retention time=1.51 min; ESI-MS (+) m/z 942.25 (M+2H).
Analysis condition B: Retention time=2.93 min; ESI-MS (+) m/z 942.25 (M+2H).

Preparation of Example 9282

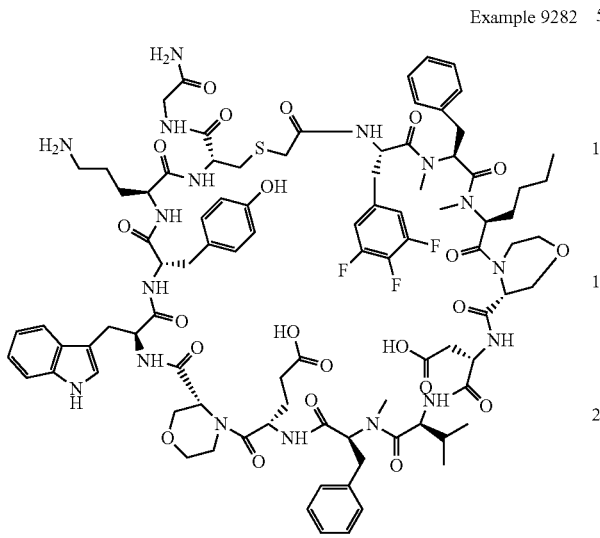

Example 9282

The crude material of Example 9282 was purified via preparative LC/MS with the following conditions: Column: XBridge C18, 19×150 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 28.4 mg, and its estimated purity by LCMS analysis was 97%.

Analysis condition A: Retention time=1.60 min; ESI-MS (+) m/z 951.4 (M+2H).

Analysis condition B: Retention time=2.78 min; ESI-MS (+) m/z 951.4 (M+2H).

Preparation of Example 9283

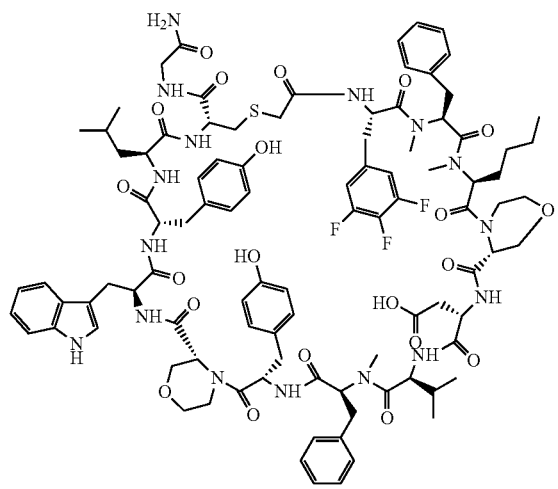

Example 9283

The crude material of Example 9283 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-85% B over 30 minutes, then a 5-minute hold at 100% B; Flow: 20 mL/min. Fractions containing the desired product were combined and dried via centrifugal evaporation. The yield of the product was 52.5 mg, and its estimated purity by LCMS analysis was 95%.

Analysis condition A: Retention time=1.84 min; ESI-MS (+) m/z 967.65 (M+2H).

Analysis condition B: Retention time=3.42 min; ESI-MS (+) m/z 967.90 (M+2H).

Preparation of Example 9284

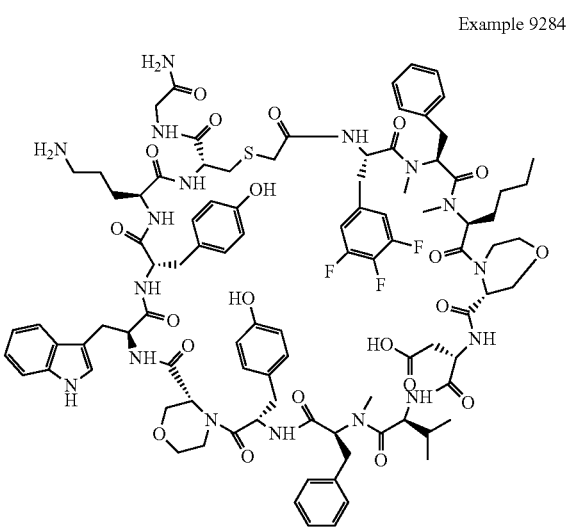 [SMILES: CCCC[C@H]1C(=O)N2CCOC[C@@H]2C(=O)N[C@@H](CC(=O)O)C(=O)N[C@@H](C(C)C)C(=O)N(C)[C@@H](Cc2ccccc2)C(=O)N[C@@H](Cc2ccc(O)cc2)C(=O)N2CCOC[C@@H]2C(=O)N[C@@H](Cc2c[nH]c3ccccc23)C(=O)N[C@@H](Cc2ccc(O)cc2)C(=O)N[C@@H](CCCN)C(=O)N[C@H](C(=O)NCC(N)=O)CSCC(=O)N[C@@H](Cc2cc(F)c(F)c(F)c2)C(=O)N(C)[C@@H](Cc2ccccc2)C(=O)N1C]

Example 9284

The crude material of Example 9284 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 39.1 mg, and its estimated purity by LCMS analysis was 100%.

Analysis condition A: Retention time=1.72 min; ESI-MS (+) m/z 967.90 (M+2H).

Analysis condition B: Retention time=3.16 min; ESI-MS (+) m/z 968.25 (M+2H).

Preparation of Example 9285

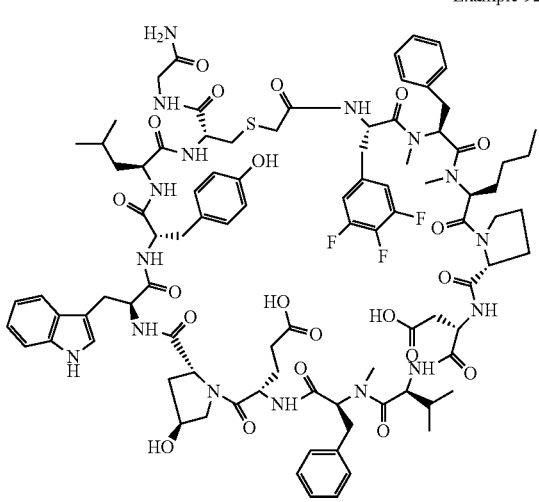

Example 9285

The crude material of Example 9285 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 50.9 mg, and its estimated purity by LCMS analysis was 100%.

Analysis condition A: Retention time=1.58 min; ESI-MS (+) m/z 942.75 (M+2H).

Analysis condition B: Retention time=2.89 min; ESI-MS (+) m/z 942.75 (M+2H).

Preparation of Example 9286

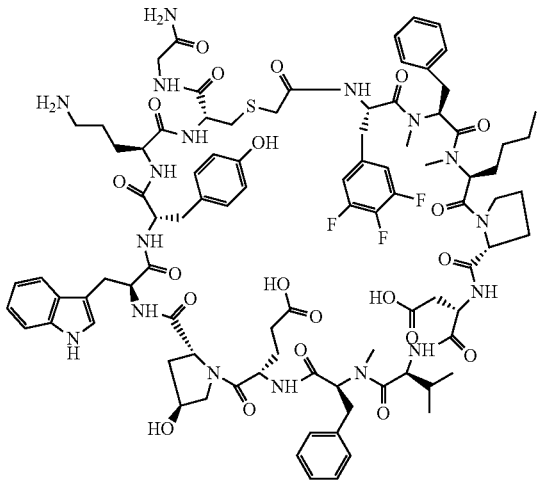

Example 9286

The crude material of Example 9286 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 59.1 mg, and its estimated purity by LCMS analysis was 100%.

Analysis condition A: Retention time=1.75 min; ESI-MS (−) m/z 941.10 (M−2H).

Analysis condition B: Retention time=3.33 min; ESI-MS (+) m/z 943.35 (M+2H).

Preparation of Example 9287

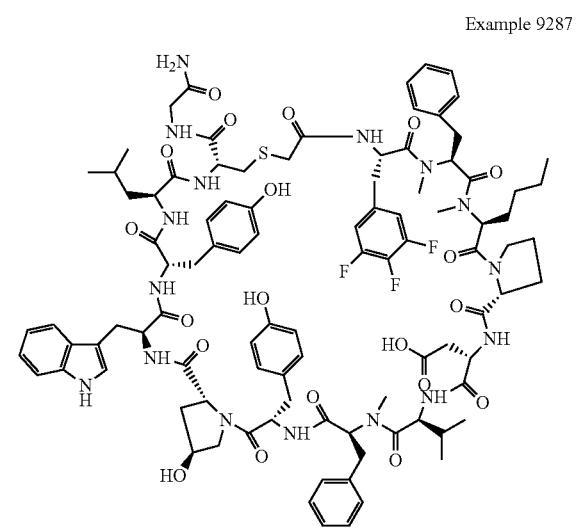 [SMILES: CCCC[C@H]1C(=O)N2CCC[C@@H]2C(=O)N[C@@H](CC(=O)O)C(=O)N[C@@H](C(C)C)C(=O)N(C)[C@@H](Cc2ccccc2)C(=O)N[C@@H](Cc2ccc(O)cc2)C(=O)N2C[C@@H](O)C[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2cc(F)c(F)c(F)c2)C(=O)N(C)[C@@H](Cc2ccccc2)C(=O)N1C]

Example 9287

The crude material of Example 9287 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-65% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 47.8 mg, and its estimated purity by LCMS analysis was 100%.

Analysis condition A: Retention time=1.85 min; ESI-MS (+) m/z 960.40 (M+2H).

Analysis condition B: Retention time=2.50 min; ESI-MS (+) m/z 959.50 (M+2H).

Preparation of Example 9288

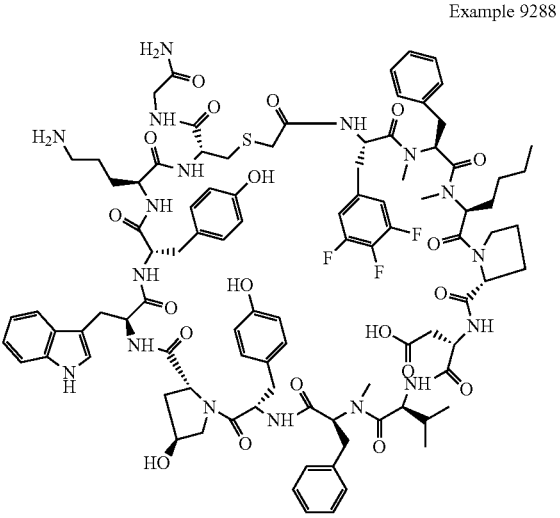 [SMILES: CCCC[C@H]1C(=O)N2CCC[C@@H]2C(=O)N[C@@H](CC(=O)O)C(=O)N[C@@H](C(C)C)C(=O)N(C)[C@@H](Cc2ccccc2)C(=O)N[C@@H](Cc2ccc(O)cc2)C(=O)N2C[C@@H](O)C[C@@H]2C(=O)N[C@@H](Cc2c[nH]c3ccccc23)C(=O)N[C@@H](Cc2ccc(O)cc2)C(=O)N[C@@H](CCCN)C(=O)N[C@H](C(=O)NCC(N)=O)CSCC(=O)N[C@@H](Cc2cc(F)c(F)c(F)c2)C(=O)N(C)[C@@H](Cc2ccccc2)C(=O)N1C]

Example 9288

The crude material of Example 9288 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 33.4 mg, and its estimated purity by LCMS analysis was 100%.

Analysis condition A: Retention time=1.81 min; ESI-MS (−) m/z 958.10 (M−2H).

Analysis condition B: Retention time=3.48 min; ESI-MS (+) m/z 960.15 (M+2H).

Preparation of Example 9289

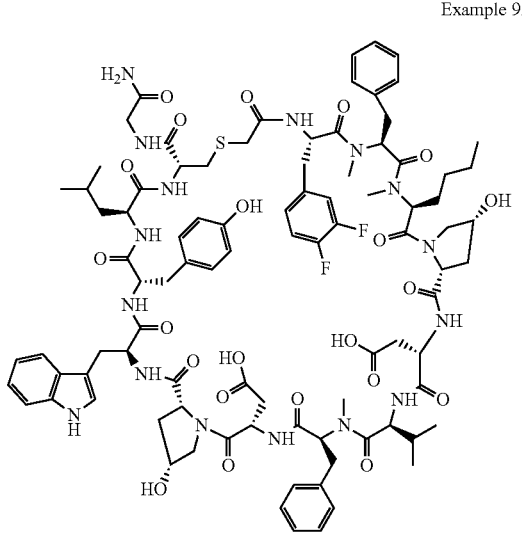

Example 9289

Example 9289 was prepared according to the method outlined in Example 10541. The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 24.8 mg, and its estimated purity by LCMS analysis was 99%.

Analysis condition A: Retention time=1.72 min; ESI-MS (−) m/z 931.75 (M−2H).

Analysis condition B: Retention time=2.33 min; ESI-MS (+) m/z 933.60 (M+2H).

Preparation of Examples 9290 and 9291

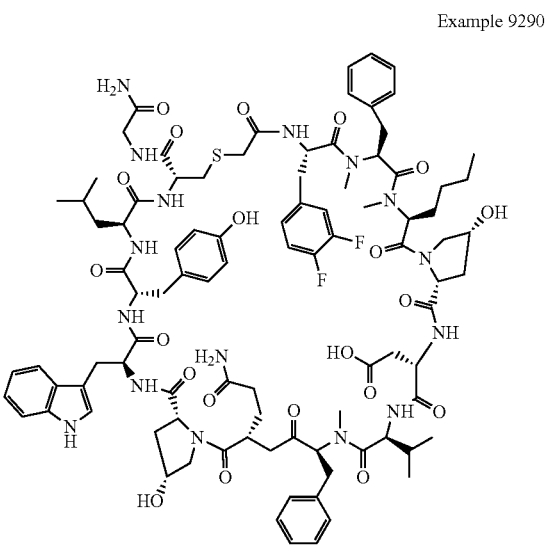 [SMILES: CCCC[C@H]1C(=O)N2C[C@H](O)C[C@@H]2C(=O)N[C@@H](CC(=O)O)C(=O)N[C@@H](C(C)C)C(=O)N(C)[C@@H](Cc2ccccc2)C(=O)N[C@@H](CC(=O)O)C(=O)N2C[C@H](O)C[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccc(F)c(F)c2)C(=O)N(C)[C@@H](Cc2ccccc2)C(=O)N1C]

Example 9290

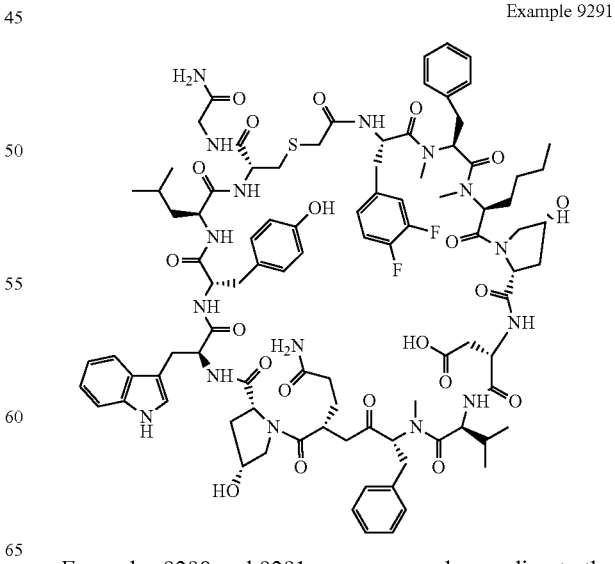

Example 9291

Examples 9290 and 9291 were prepared according to the method outlined in Example 10541. The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired products were combined and dried via centrifugal evaporation. The yield of Examples 9290 was 4.8 mg, and its estimated purity by LCMS analysis was 100%. The yield of Examples 9291 was 9.3 mg, and its estimated purity by LCMS analysis was 100%.

Examples 9290

Analysis condition A: Retention time=1.76 min; ESI-MS (−) m/z 938.90 (M−2H).

Analysis condition B: Retention time=3.36 min; ESI-MS (+) m/z 941.10 (M+2H).

Examples 9291

Analysis condition A: Retention time=1.79 min; ESI-MS (+) m/z 938.10 (M−2H).

Preparation of Examples 9292 and 9293

Example 9292

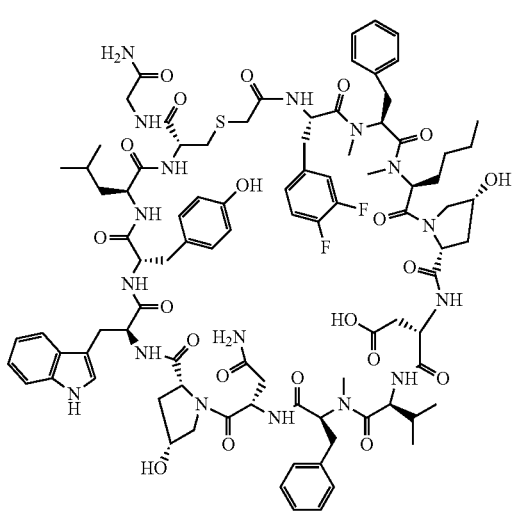

Example 9293

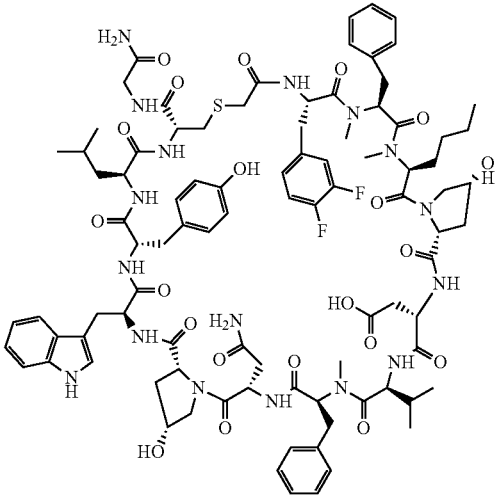

Examples 9292 and 9293 were prepared according to the method outlined in Example 10541. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 30 minutes, then a 5-minute hold at 100% B; Flow: 20 mL/min. Fractions containing the desired products were combined and dried via centrifugal evaporation. The yield of Examples 9292 was 3.1 mg, and its estimated purity by LCMS analysis was 100%. The yield of Examples 9293 was 2.9 mg, and its estimated purity by LCMS analysis was 100%.

Examples 9292

Analysis condition B: Retention time=3.39 min; ESI-MS (+) m/z 934.25 (M+2H).

Examples 9293

Analysis condition B: Retention time=3.39 min; ESI-MS (+) m/z 934.15 (M+2H).

Preparation of Examples 9294 and 9295

Example 9294

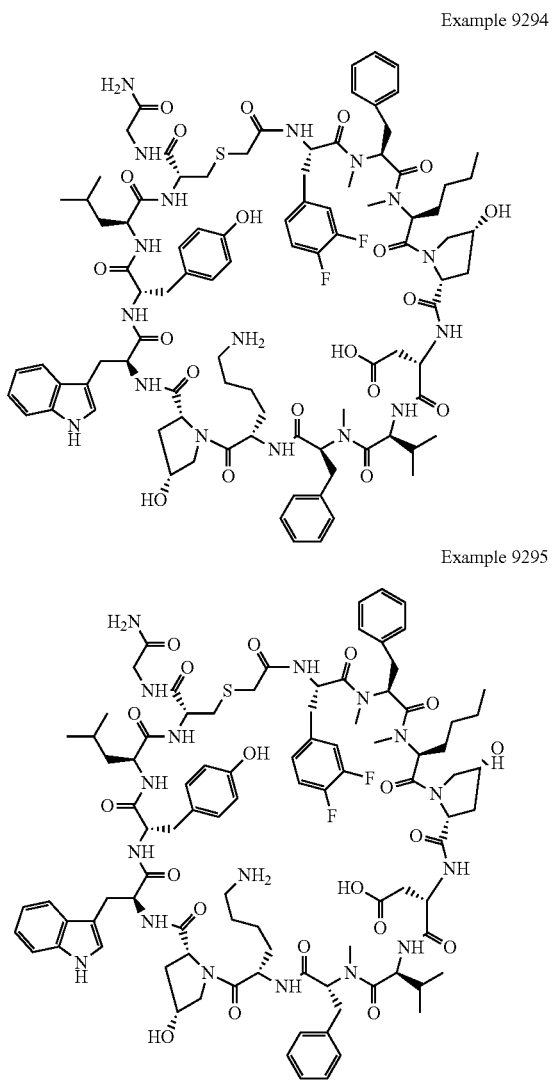

Example 9295

Examples 9294 and 9295 were prepared according to the method outlined in Example 10541. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The material was further purified via preparative LC/MS with the following conditions: Column: waters xbridge c-18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 30 minutes, then a 5-minute hold at 100% B; Flow: 20 mL/min. Fractions containing the desired products were combined and dried via centrifugal evaporation. The yield of Examples 9294 was 5.2 mg, and its estimated purity by LCMS analysis was 100%. The yield of Examples 9295 was 3.1 mg, and its estimated purity by LCMS analysis was 100%.

Examples 9294

Analysis condition A: Retention time=1.82 min; ESI-MS (+) m/z 940.95 (M+2H).

Examples 9295

Analysis condition A: Retention time=1.89 min; ESI-MS (+) m/z 940.90 (M+2H).

Preparation of Examples 9296 and 9297

Example 9296

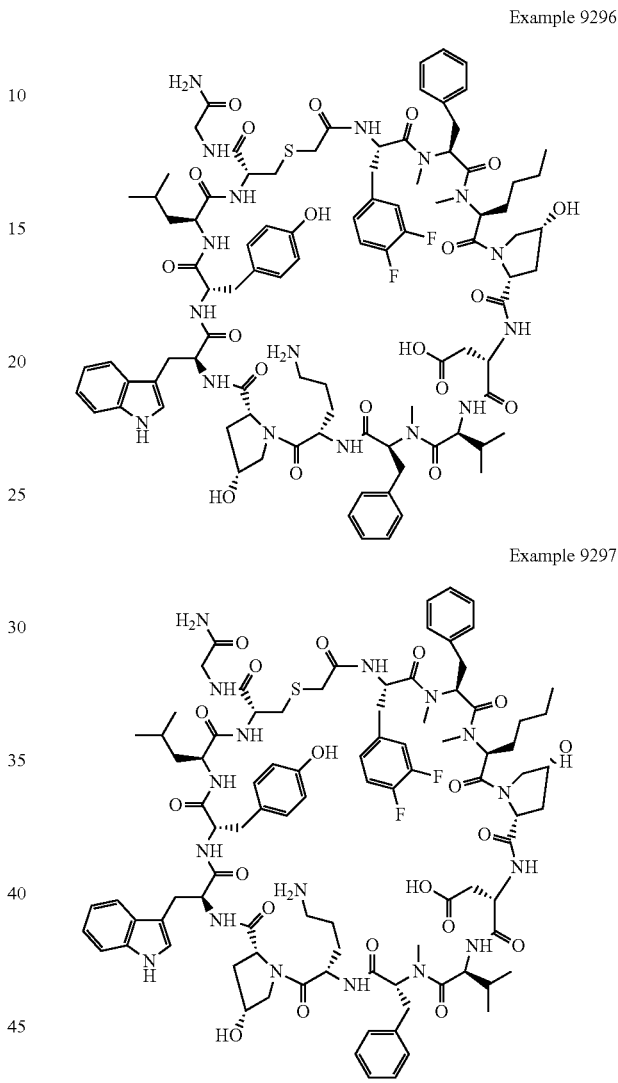

Example 9297

Examples 9296 and 9297 were prepared according to the method outlined in Example 10541. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-100% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired products were combined and dried via centrifugal evaporation. The yield of Examples 9296 was 11.6 mg, and its estimated purity by LCMS analysis was 100%. The yield of Examples 9297 was 10.1 mg, and its estimated purity by LCMS analysis was 97%.

Examples 9296

Analysis condition A: Retention time=1.89 min; ESI-MS (+) m/z 933.25 (M+2H).
Analysis condition B: Retention time=2.56 min; ESI-MS (+) m/z 933.15 (M+2H).

Examples 9297

Analysis condition A: Retention time=1.93 min; ESI-MS (+) m/z 933.05 (M+2H).

Preparation of Examples 9298 and 9299

Examples 9298 and 9299 were prepared according to the method outlined in Example 10541. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 30 minutes, then a 5-minute hold at 100% B; Flow: 20 mL/min. Fractions containing the desired products were combined and dried via centrifugal evaporation. The yield of Examples 9298 was 4.1 mg, and its estimated purity by LCMS analysis was 100%. The yield of Examples 9299 was 4.6 mg, and its estimated purity by LCMS analysis was 100%.

Examples 9298

Analysis condition A: Retention time=1.81 min; ESI-MS (+) m/z 927.30 (M+2H).

Examples 9299

Analysis condition A: Retention time=1.83 min; ESI-MS (+) m/z 926.85 (M+2H).
Analysis condition B: Retention time=3.13 min; ESI-MS (+) m/z 927.7 (M+2H).

Preparation of Examples 9300 and 9301

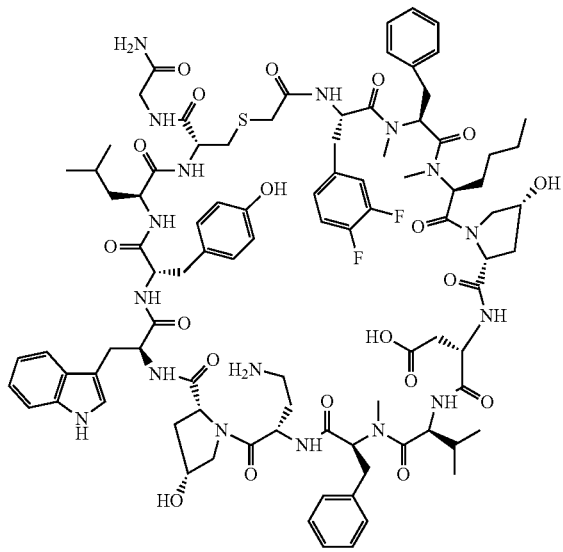

Example 9298

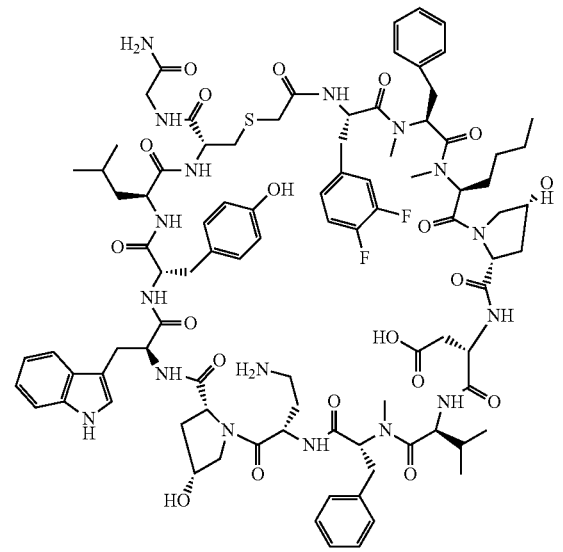

Example 9299

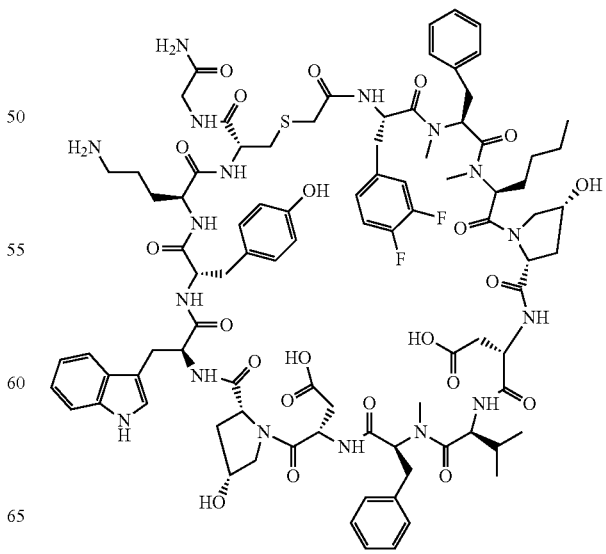

Example 9300

Example 9301

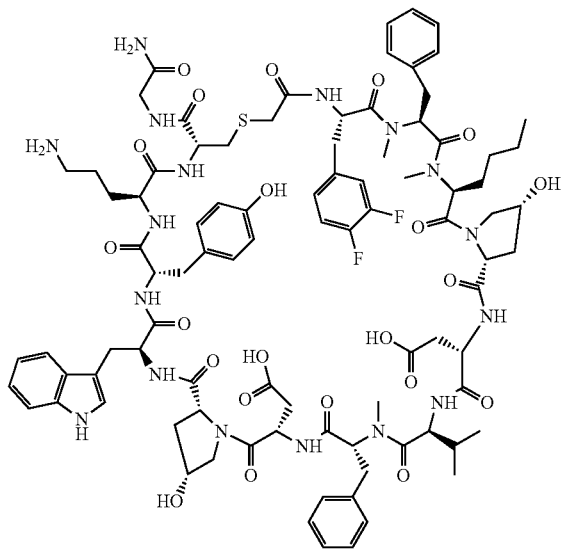

Examples 9300 and 9301 were prepared according to the method outlined in Example 10541. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 30 minutes, then a 5-minute hold at 100% B; Flow: 20 mL/min. Fractions containing the desired products were combined and dried via centrifugal evaporation. The yield of Examples 9300 was 8.4 mg, and its estimated purity by LCMS analysis was 93%. The yield of Examples 9301 was 2.1 mg, and its estimated purity by LCMS analysis was 98%.

Examples 9300

Analysis condition A: Retention time=1.76 min; ESI-MS (+) m/z 935.10 (M+2H).

Analysis condition B: Retention time=3.24 min; ESI-MS (+) m/z 934.85 (M+2H).

Examples 9301

Analysis condition A: Retention time=1.79 min; ESI-MS (+) m/z 935.55 (M+2H).

Analysis condition B: Retention time=3.35 min; ESI-MS (+) m/z 935.05 (M+2H).

Preparation of Examples 9302 and 9303

Example 9302

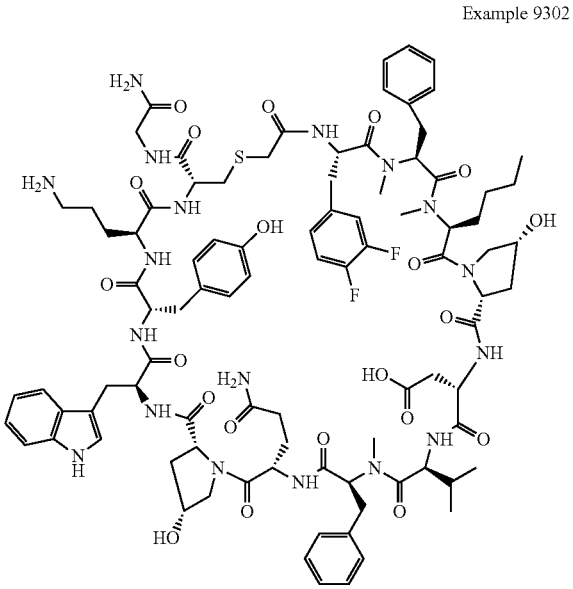 [SMILES: CCCC[C@H]1C(=O)N2C[C@H](O)C[C@@H]2C(=O)N[C@@H](CC(=O)O)C(=O)N[C@@H](C(C)C)C(=O)N(C)[C@@H](Cc2ccccc2)C(=O)N[C@@H](CC(=O)O)C(=O)N2C[C@H](O)C[C@@H]2C(=O)N[C@@H](Cc2c[nH]c3ccccc23)C(=O)N[C@@H](Cc2ccc(O)cc2)C(=O)N[C@@H](CCC(=O)O)C(=O)N[C@H](C(=O)NCC(N)=O)CSCC(=O)N[C@@H](Cc2ccc(F)c(F)c2)C(=O)N(C)[C@@H](Cc2ccccc2)C(=O)N1C]

Example 9303

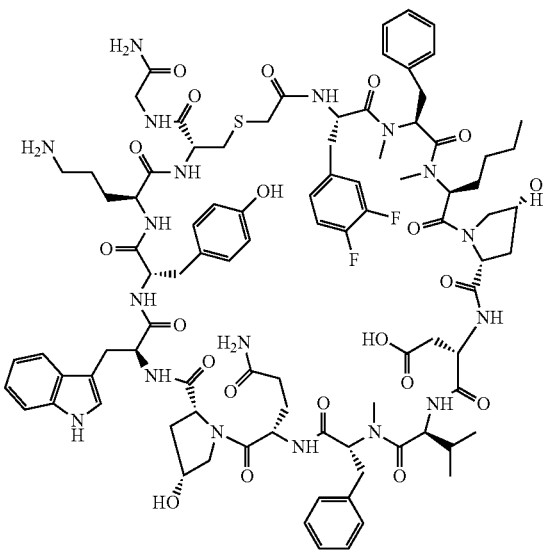

Examples 9302 and 9303 were prepared according to the method outlined in Example 10541. The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 30 minutes, then a 5-minute hold at 100% B; Flow: 20 mL/min. Fractions containing the desired products were combined and dried via centrifugal evaporation. The yield of Examples 9302 was 14.2 mg, and its estimated purity by LCMS analysis was 100%. The yield of Examples 9303 was 9.1 mg, and its estimated purity by LCMS analysis was 100%.

Examples 9302

Analysis condition A: Retention time=1.71 min; ESI-MS (−) m/z 939.55 (M−2H).

Examples 9303

Analysis condition A: Retention time=1.76 min; ESI-MS (−) m/z 939.25 (M−2H).

Preparation of Examples 9304 and 9305

Example 9304

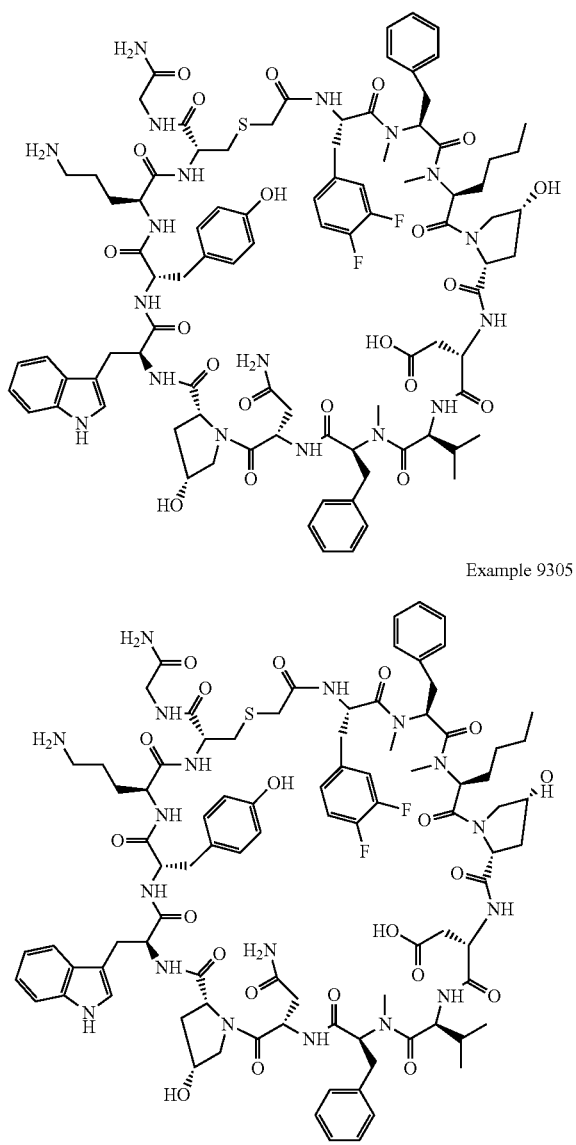

Example 9305

Examples 9304 and 9305 were prepared according to the method outlined in Example 10541. The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 30 minutes, then a 5-minute hold at 100% B; Flow: 20 mL/min. Fractions containing the desired products were combined and dried via centrifugal evaporation. The yield of Examples 9304 was 8.9 mg, and its estimated purity by LCMS analysis was 100%. The yield of Examples 9305 was 10.8 mg, and its estimated purity by LCMS analysis was 100%.

Examples 9304

Analysis condition A: Retention time=1.76 min; ESI-MS (+) m/z 934.75 (M+2H).

Examples 9305

Analysis condition A: Retention time=1.78 min; ESI-MS (+) m/z (M+2H).

Preparation of Examples 9306 and 9307

Example 9306

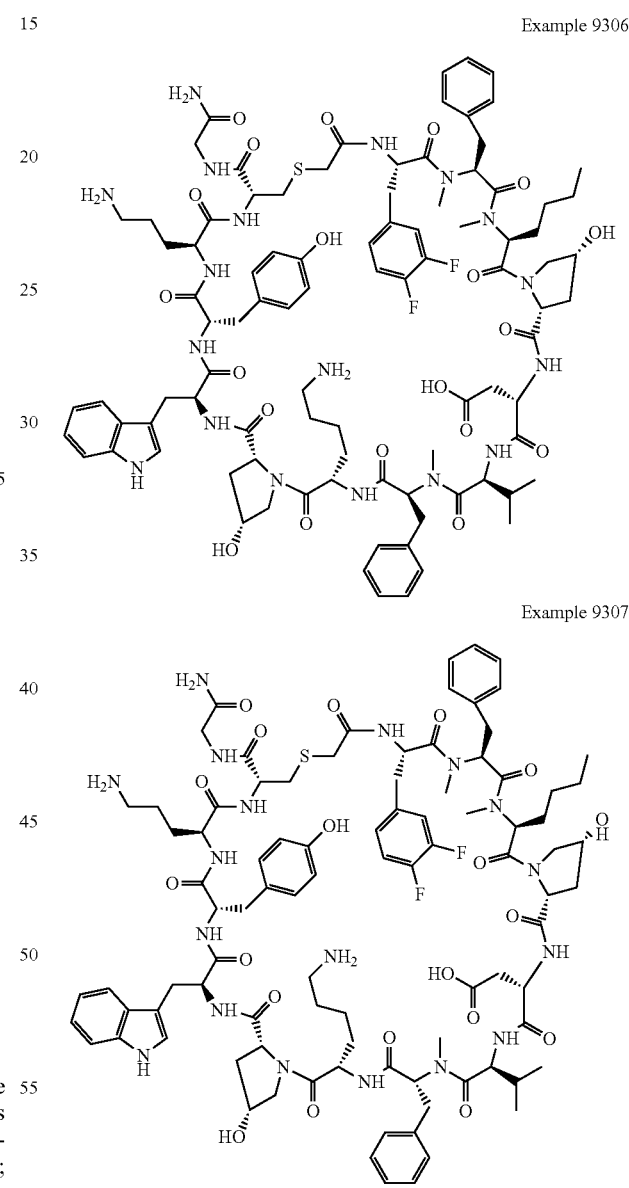

Example 9307

Examples 9306 and 9307 were prepared according to the method outlined in Example 10541. The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 30 minutes, then a 5-minute hold at 100% B; Flow: 20 mL/min.

Fractions containing the desired products were combined and dried via centrifugal evaporation. The yield of Examples 9306 was 1.3 mg, and its estimated purity by LCMS analysis was 100%. The yield of Examples 9307 was 2.1 mg, and its estimated purity by LCMS analysis was 96%.

Examples 9306

Analysis condition A: Retention time=1.78 min; ESI-MS (+) m/z 940.9 (M+2H).
Analysis condition B: Retention time=3.27 min; ESI-MS (+) m/z 941.0 (M+2H).

Examples 9307

Analysis condition A: Retention time=1.82 min; ESI-MS (+) m/z 941.5 (M+2H).
Analysis condition B: Retention time=3.30 min; ESI-MS (+) m/z 940.9 (M+2H).

Preparation of Examples 9308 and 9309

Example 9308

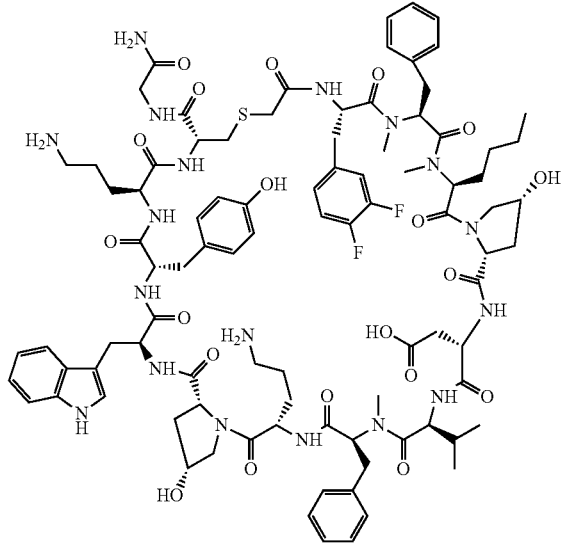

Examples 9308 and 9309 were prepared according to the method outlined in Example 10541. The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×150 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 40 minutes, then a 5-minute hold at 100% B; Flow: 20 mL/min. Fractions containing the desired products were combined and dried via centrifugal evaporation. The yield of Examples 9308 was 2.2 mg, and its estimated purity by LCMS analysis was 97%. The yield of Examples 9309 was 4.0 mg, and its estimated purity by LCMS analysis was 96%.

Examples 9308

Analysis condition A: Retention time=1.79 min; ESI-MS (+) m/z 934.3 (M+2H).
Analysis condition B: Retention time=3.25 min; ESI-MS (+) m/z 934.3 (M+2H).

Examples 9309

Analysis condition A: Retention time=1.81 min; ESI-MS (+) m/z 934.2 (M+2H).
Analysis condition B: Retention time=3.28 min; ESI-MS (+) m/z 934.2 (M+2H).

Preparation of Examples 9310 and 9311

Example 9309

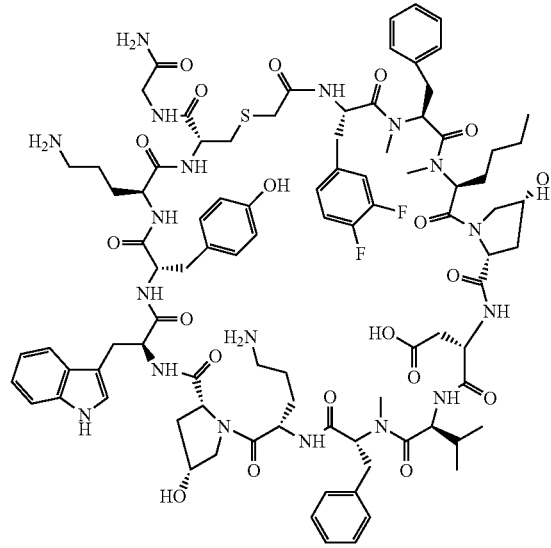

Example 9310

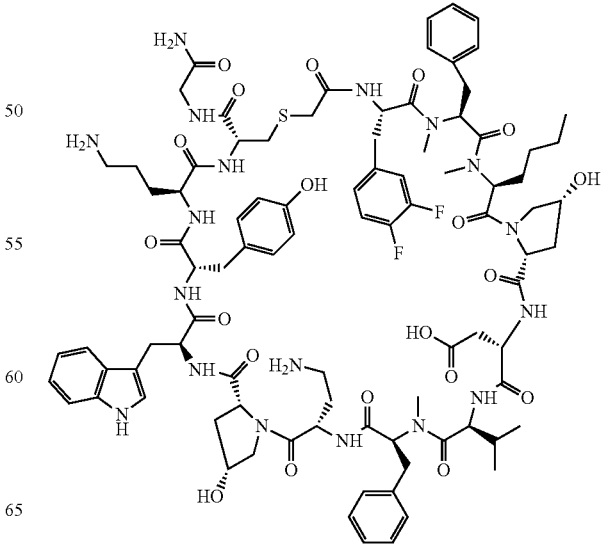

Example 9311

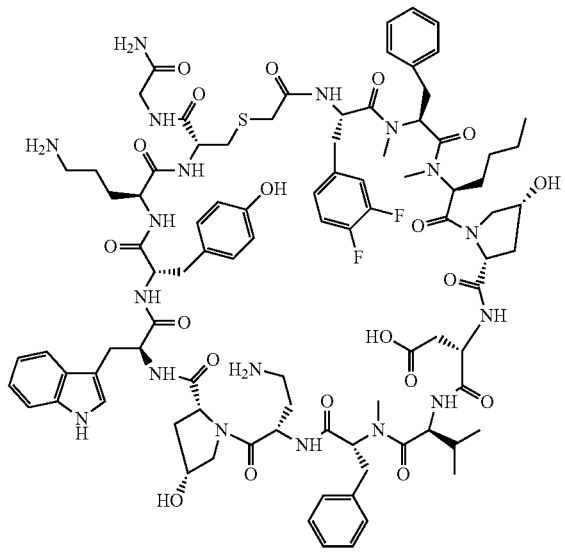

Examples 9310 and 9311 were prepared according to the method outlined in Example 10541. The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 40 minutes, then a 5-minute hold at 100% B; Flow: 20 mL/min. Fractions containing the desired products were combined and dried via centrifugal evaporation. The yield of Examples 9310 was 3.1 mg, and its estimated purity by LCMS analysis was 96%. The yield of Examples 9311 was 1.4 mg, and its estimated purity by LCMS analysis was 96%.

Examples 9310

Analysis condition A: Retention time=1.79 min; ESI-MS (+) m/z 926.8 (M+2H).

Analysis condition B: Retention time=3.25 min; ESI-MS (+) m/z 926.8 (M+2H).

Examples 9311

Analysis condition A: Retention time=1.83 min; ESI-MS (+) m/z 927.0 (M+2H).

Analysis condition B: Retention time=3.29 min; ESI-MS (+) m/z 926.8 (M+2H).

Preparation of Examples 9312 and 9313

Example 9312

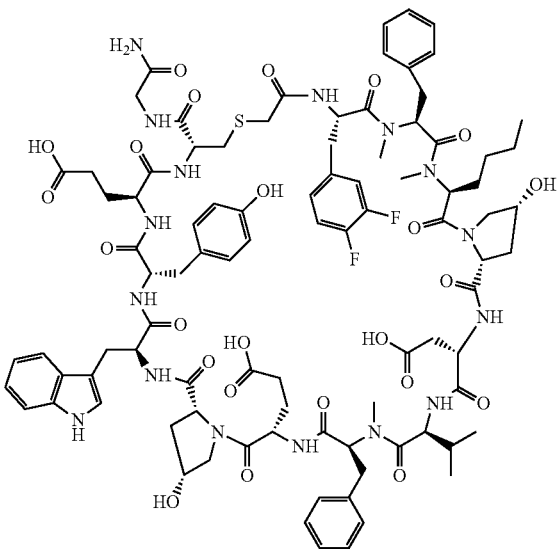

Example 9313

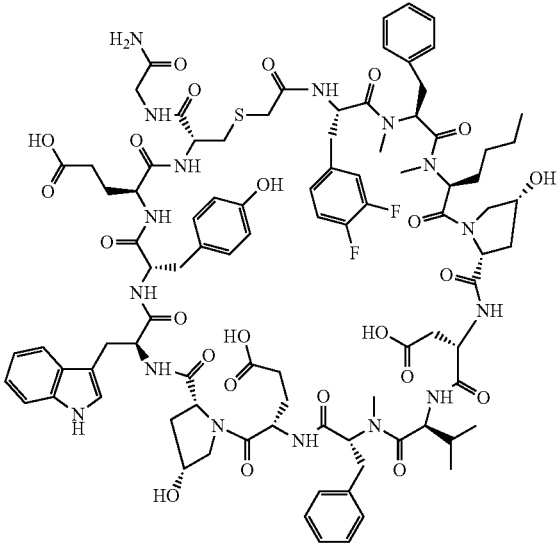

Examples 9312 and 9313 were prepared according to the method outlined in Example 10541. The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired products were combined and dried via centrifugal evaporation. The yield of Examples 9312 was 3.3 mg, and its estimated purity by LCMS analysis was 100%. The yield of Examples 9313 was 1.0 mg, and its estimated purity by LCMS analysis was 100%.

Examples 9312

Analysis condition A: Retention time=1.29 min; ESI-MS (+) m/z 949.7 (M+2H).
Analysis condition B: Retention time=2.60 min; ESI-MS (+) m/z 949.9 (M+2H).

Examples 9313

Analysis condition A: Retention time=1.33 min; ESI-MS (+) m/z 949.8 (M+2H).
Analysis condition B: Retention time=2.63 min; ESI-MS (+) m/z 950.0 (M+2H).

Preparation of Example 9314

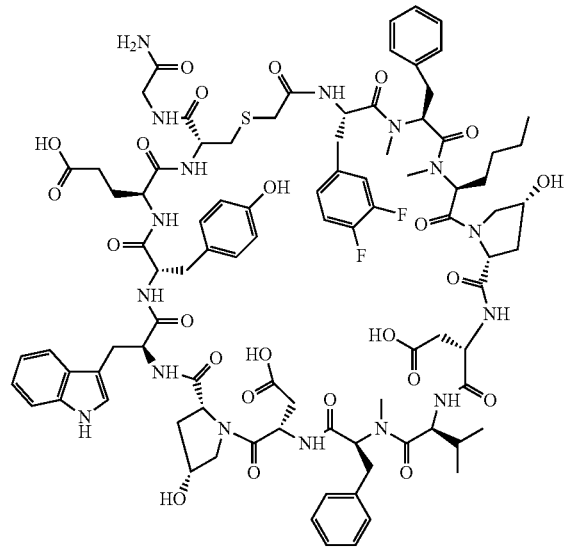

Example 9314

Examples 9314 was prepared according to the method outlined in Example 10541. The crude material was purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 30 minutes, then a 5-minute hold at 100% B; Flow: 20 mL/min. Fractions containing the desired product were combined and dried via centrifugal evaporation. The yield of the product was 2.9 mg, and its estimated purity by LCMS analysis was 96%.

Examples 9314

Analysis condition A: Retention time=1.35 min; ESI-MS (+) m/z 942.9 (M+2H).
Analysis condition B: Retention time=2.61 min; ESI-MS (+) m/z 942.9 (M+2H).

Preparation of Examples 9315 and 9316

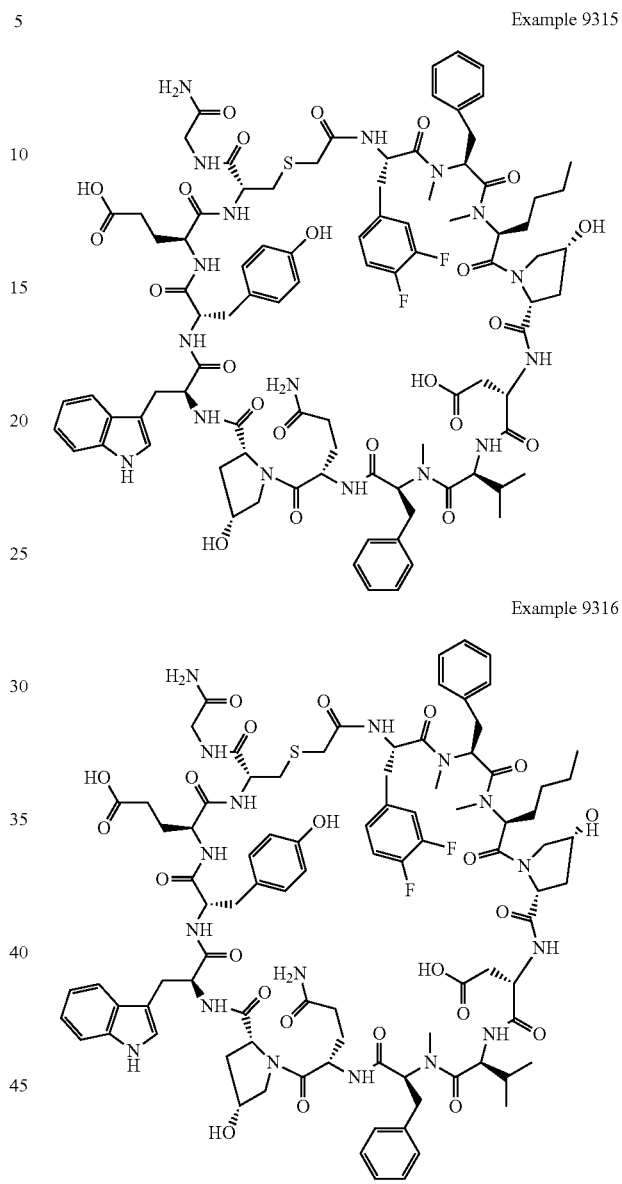

Example 9315

Example 9316

Examples 9315 and 9316 were prepared according to the method outlined in Example 10541. The crude material was purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 35-75% B over 20 minutes, then a 5-minute hold at 100% B; Flow: 20 mL/min. Fractions containing the desired product were combined and dried via centrifugal evaporation. The yield of Examples 9315 was 2.1 mg, and its estimated purity by LCMS analysis was 100%. The yield of Examples 9316 was 1.3 mg, and its estimated purity by LCMS analysis was 96%.

Examples 9315

Analysis condition A: Retention time=1.41 min; ESI-MS (+) m/z 948.3 (M+2H).

Analysis condition B: Retention time=2.76 min; ESI-MS (+) m/z 948.8 (M+2H).

Examples 9316

Analysis condition A: Retention time=1.46 min; ESI-MS (+) m/z 948.4 (M+2H).

Analysis condition B: Retention time=2.81 min; ESI-MS (+) m/z 948.9 (M+2H).

Preparation of Examples 9317

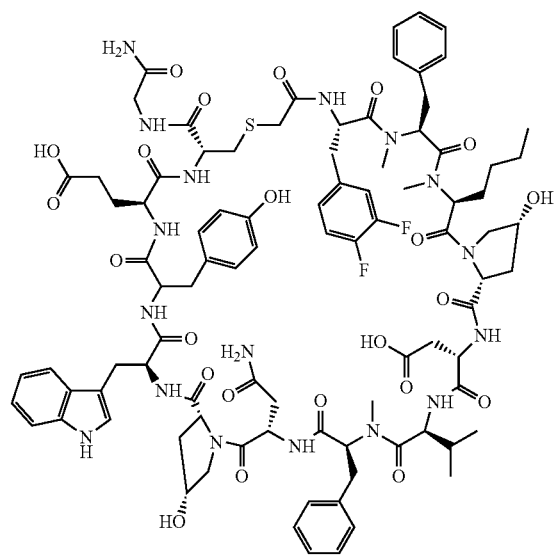

Example 9317

Examples 9317 was prepared according to the method outlined in Example 10541. The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 30 minutes, then a 5-minute hold at 100% B; Flow: 20 mL/min. Fractions containing the desired product were combined and dried via centrifugal evaporation. The yield of the product was 18.0 mg, and its estimated purity by LCMS analysis was 99%.

Analysis condition A: Retention time=1.78 min; ESI-MS (+) m/z 942.30 (M+2H).

Analysis condition B: Retention time=2.21 min; ESI-MS (+) m/z 942.05 (M+2H).

Preparation of Example 9318

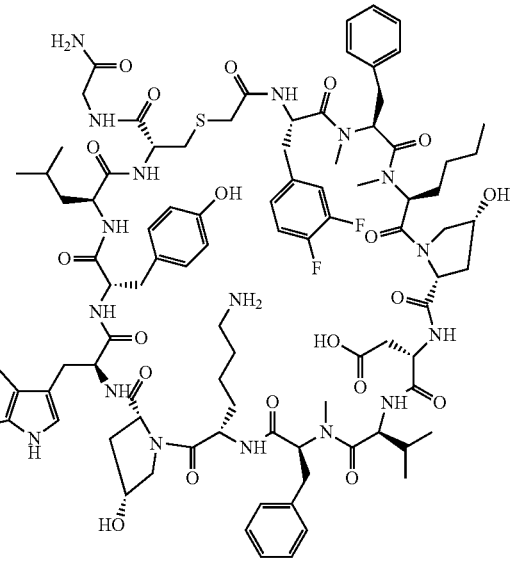

Example 9318

The crude material of Example 9318 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 15.9 mg, and its estimated purity by LCMS analysis was 95%.

Analysis condition A: Retention time=2.11 min; ESI-MS (+) m/z 941.45 (M+2H).

Preparation of Example 9319

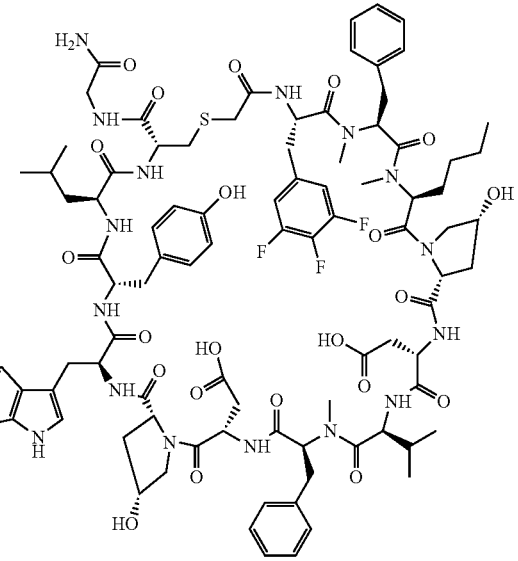

Example 9319

The crude material of Example 9319 was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 19.6 mg, and its estimated purity by LCMS analysis was 99%.

Analysis condition A: Retention time=1.49 min; ESI-MS (+) m/z 944.7 (M+2H).

Analysis condition B: Retention time=2.77 min; ESI-MS (+) m/z 944.2 (M+2H).

Preparation of Example 9320

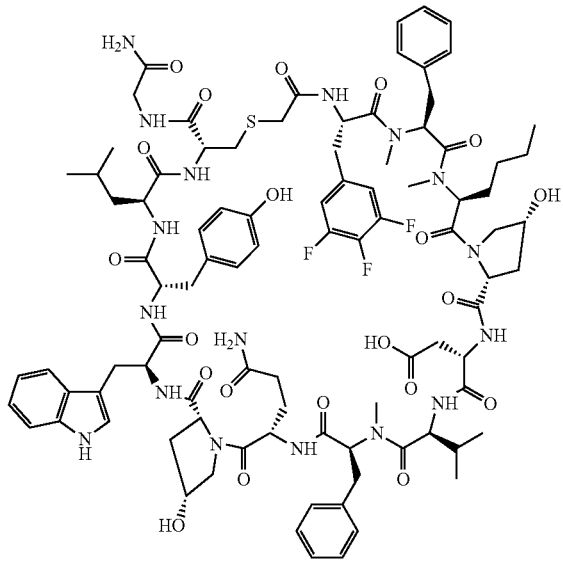

Example 9320

The crude material of Example 9320 was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 55-95% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 10.5 mg, and its estimated purity by LCMS analysis was 100%.

Analysis condition A: Retention time=1.61 min; ESI-MS (+) m/z 950.4 (M+2H).

Analysis condition B: Retention time=2.96 min; ESI-MS (+) m/z 950.6 (M+2H).

Preparation of Example 9321

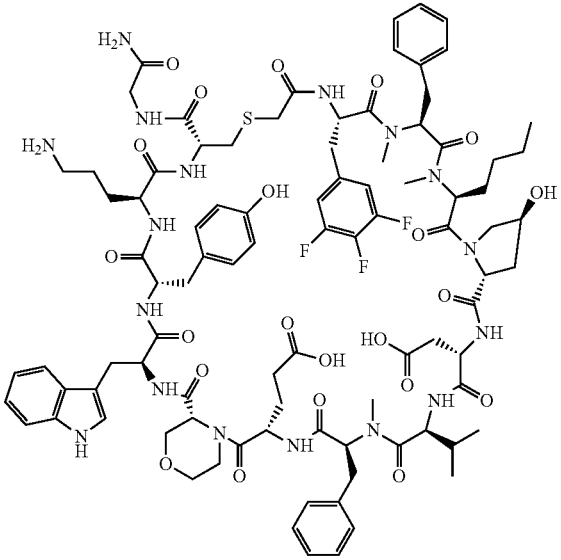

Example 9321

The crude material of Example 9321 was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 10.1-90% B over 30 minutes, then a 5-minute hold at 100% B; Flow: 20 mL/min. Fractions containing the desired product were combined and dried via centrifugal evaporation. The yield of the product was 38.9 mg, and its estimated purity by LCMS analysis was 100%.

Analysis condition A: Retention time=1.58 min; ESI-MS (+) m/z 951.7 (M+2H).

Analysis condition B: Retention time=3.00 min; ESI-MS (+) m/z 951.8 (M+2H).

Preparation of Example 9322

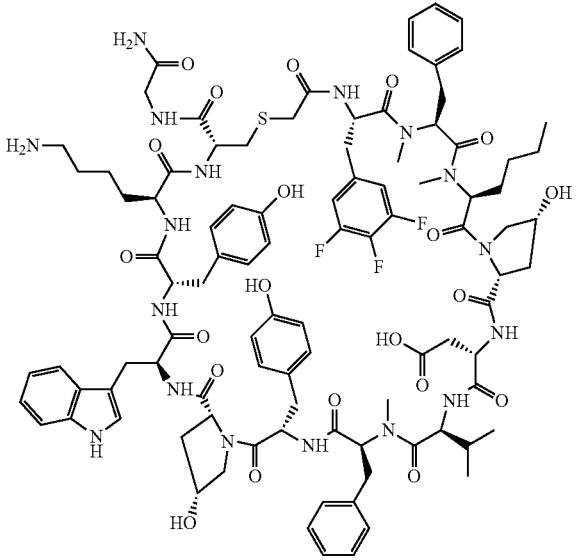

Example 9322

The crude material of Example 9322 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 29.9 mg, and its estimated purity by LCMS analysis was 94%.

Analysis condition A: Retention time=1.69 min; ESI-MS (+) m/z 975.0 (M+2H).

Analysis condition B: Retention time=3.09 min; ESI-MS (+) m/z 975.1 (M+2H).

Preparation of Example 9323

Example 9323

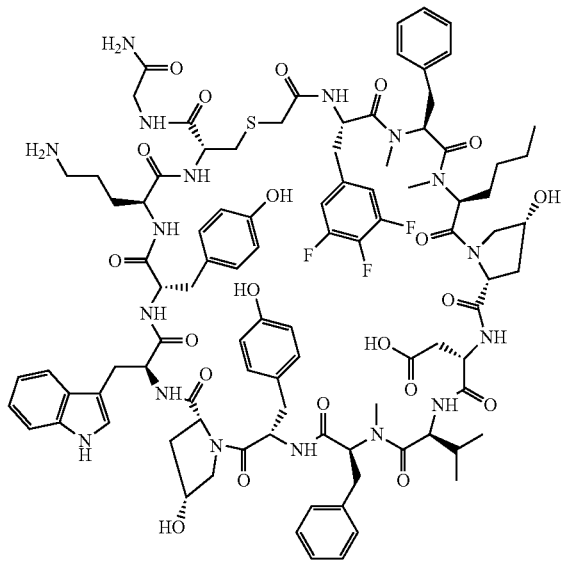

The crude material of Example 9323 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 15.7 mg, and its estimated purity by LCMS analysis was 99%.

Analysis condition A: Retention time=1.68 min; ESI-MS (+) m/z 968.2 (M+2H).

Analysis condition B: Retention time=3.09 min; ESI-MS (+) m/z 968.4 (M+2H).

Preparation of Example 9324

Example 9324

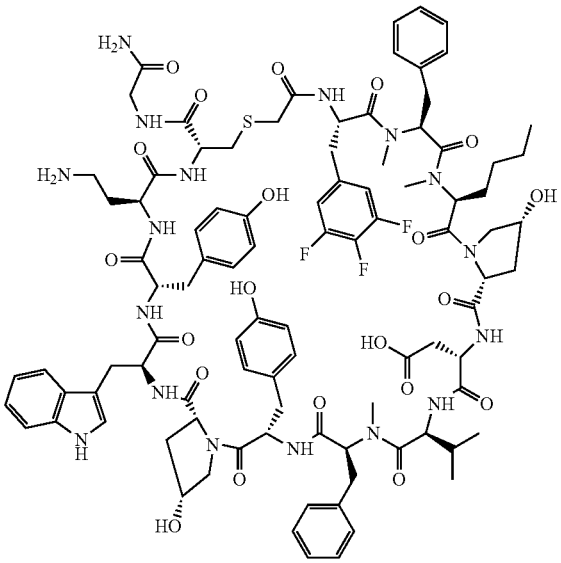

The crude material of Example 9324 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 19.4 mg, and its estimated purity by LCMS analysis was 99%.

Analysis condition A: Retention time=1.67 min; ESI-MS (+) m/z 961.2 (M+2H).

Analysis condition B: Retention time=3.08 min; ESI-MS (+) m/z 961.5 (M+2H).

Preparation of Example 9325

Example 9325

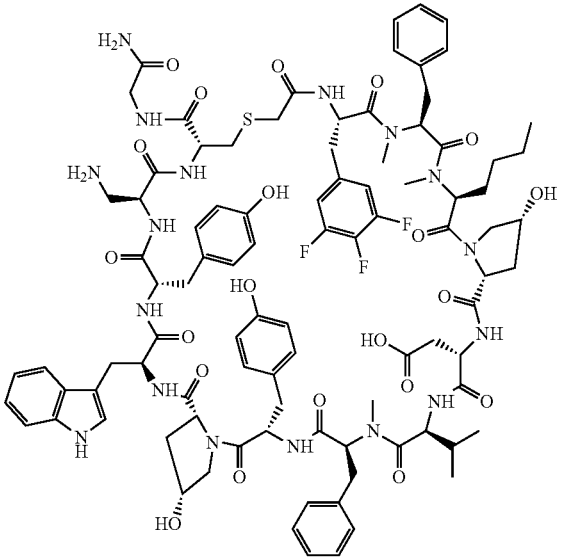

The crude material of Example 9325 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 29.5 mg, and its estimated purity by LCMS analysis was 99%.

Analysis condition A: Retention time=1.64 min; ESI-MS (−) m/z 952.2 (M−2H).

Analysis condition B: Retention time=3.02 min; ESI-MS (+) m/z 954.3 (M+2H).

Preparation of Example 9326

Example 9326

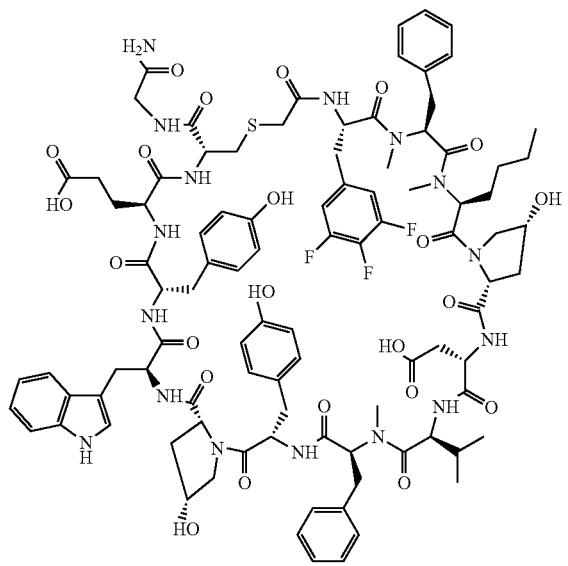

The crude material of Example 9326 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 15 minutes, then a 5-minute hold at 100% B; Flow: 20 mL/min. Fractions containing the desired product were combined and dried via centrifugal evaporation. The yield of the product was 35.5 mg, and its estimated purity by LCMS analysis was 96%.

Analysis condition A: Retention time=1.48 min; ESI-MS (+) m/z 976.0 (M+2H).

Analysis condition B: Retention time=2.82 min; ESI-MS (+) m/z 976.2 (M+2H).

Preparation of Example 9327

Example 9327

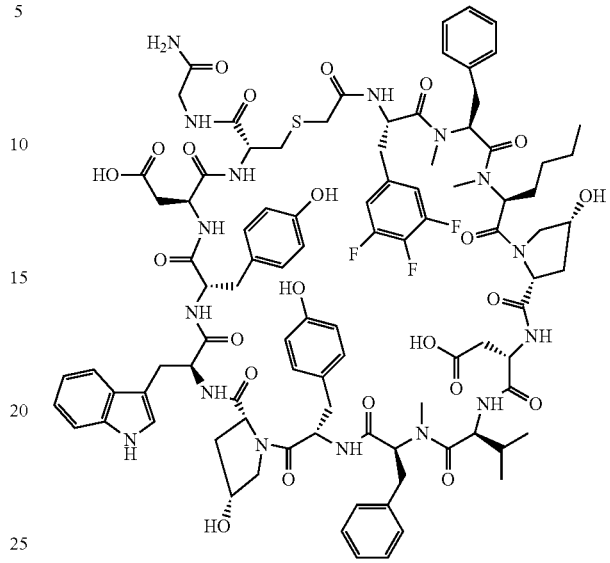

The crude material of Example 9327 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 13.2 mg, and its estimated purity by LCMS analysis was 100%.

Analysis condition A: Retention time=1.46 min; ESI-MS (+) m/z 968.6 (M+2H).

Analysis condition B: Retention time=2.86 min; ESI-MS (+) m/z 968.9 (M+2H).

Preparation of Example 9328

Example 9328

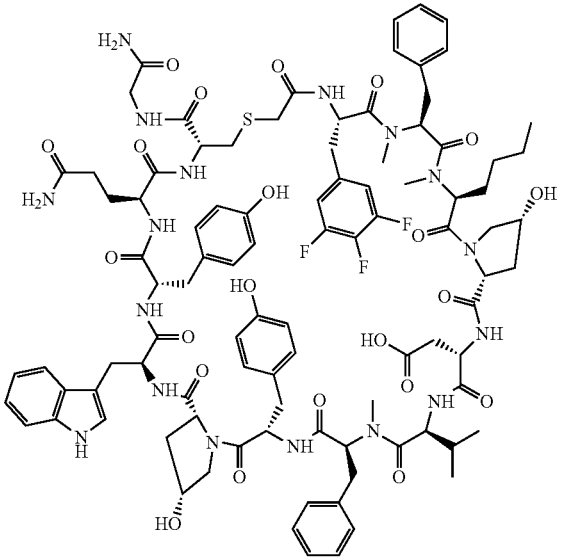

The crude material of Example 9328 was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 60-90% B over 25 minutes, then a 5-minute hold at 100% B; Flow: 20 mL/min. Fractions containing the desired product were combined and dried via centrifugal evaporation. The yield of the product was 34.0 mg, and its estimated purity by LCMS analysis was 95%.

Analysis condition A: Retention time=1.56 min; ESI-MS (+) m/z 975.2 (M+2H).

Analysis condition B: Retention time=2.96 min; ESI-MS (+) m/z 975.6 (M+2H).

Preparation of Example 9329

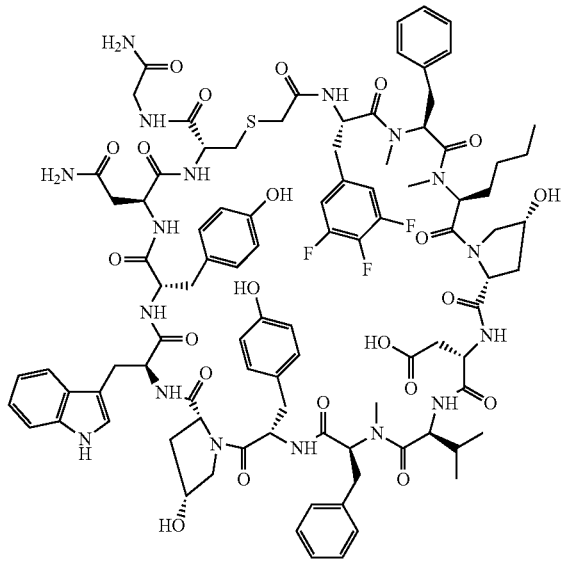

Example 9329

The crude material of Example 9329 was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 60-90% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 21.8 mg, and its estimated purity by LCMS analysis was 100%.

Analysis condition A: Retention time=1.58 min; ESI-MS (+) m/z 968.0 (M+2H).

Analysis condition B: Retention time=2.98 min; ESI-MS (+) m/z 968.2 (M+2H).

Preparation of Example 9330

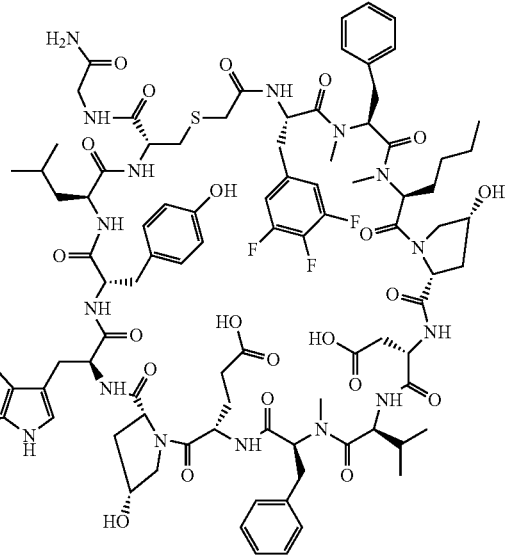

Example 9330

The crude material of Example 9330 was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 20.4 mg, and its estimated purity by LCMS analysis was 100%.

Analysis condition A: Retention time=1.53 min; ESI-MS (+) m/z 951.1 (M+2H).

Analysis condition B: Retention time=2.78 min; ESI-MS (+) m/z 950.7 (M+2H).

Preparation of Example 9331

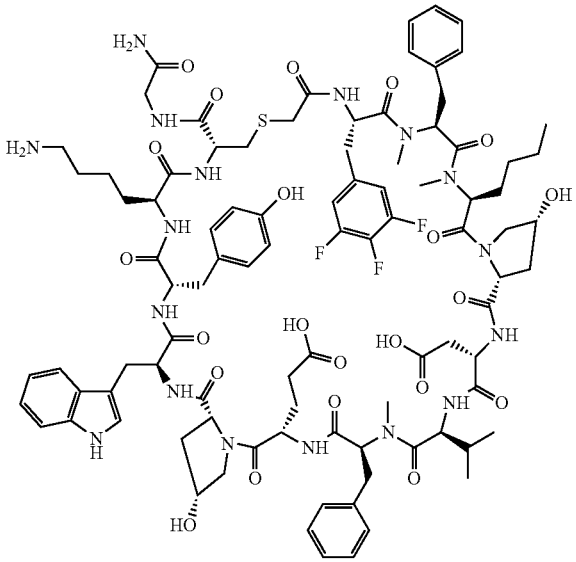

Example 9331

The crude material of Example 9331 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 22.0 mg, and its estimated purity by LCMS analysis was 100%.

Analysis condition A: Retention time=1.53 min; ESI-MS (+) m/z 958.5 (M+2H).

Analysis condition B: Retention time=2.91 min; ESI-MS (+) m/z 958.3 (M+2H).

Preparation of Example 9332

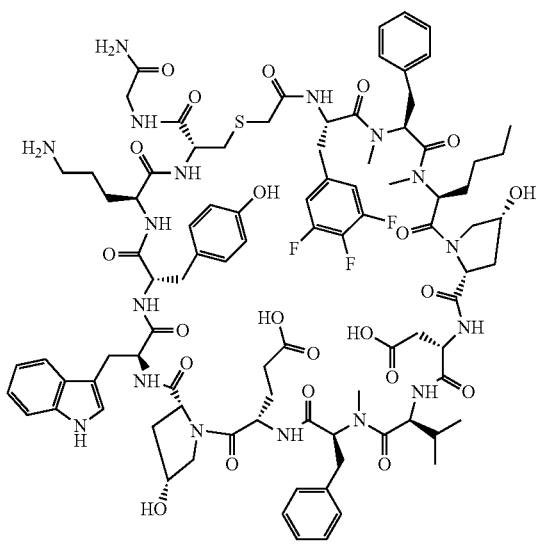
Example 9332

The crude material of Example 9332 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 30.4 mg, and its estimated purity by LCMS analysis was 99%.

Analysis condition A: Retention time=1.57 min; ESI-MS (+) m/z 951.6 (M+2H).

Analysis condition B: Retention time=2.92 min; ESI-MS (+) m/z 951.0 (M+2H).

Preparation of Example 9333

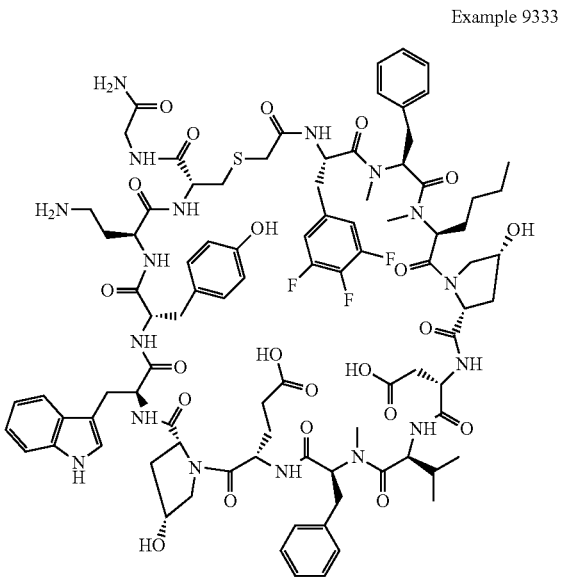 [SMILES: CCCC[C@H]1C(=O)N2C[C@H](O)C[C@@H]2C(=O)N[C@@H](CC(=O)O)C(=O)N[C@@H](C(C)C)C(=O)N(C)[C@@H](Cc2ccccc2)C(=O)N[C@@H](CCC(=O)O)C(=O)N2C[C@H](O)C[C@@H]2C(=O)N[C@@H](Cc2c[nH]c3ccccc23)C(=O)N[C@@H](Cc2ccc(O)cc2)C(=O)N[C@@H](CCN)C(=O)N[C@H](C(=O)NCC(N)=O)CSCC(=O)N[C@@H](Cc2cc(F)c(F)c(F)c2)C(=O)N(C)[C@@H](Cc2ccccc2)C(=O)N1C]
Example 9333

The crude material of Example 9333 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 26.3 mg, and its estimated purity by LCMS analysis was 100%.

Analysis condition A: Retention time=1.54 min; ESI-MS (+) m/z 944.2 (M+2H).

Analysis condition B: Retention time=2.91 min; ESI-MS (+) m/z 944.3 (M+2H).

Preparation of Example 9334

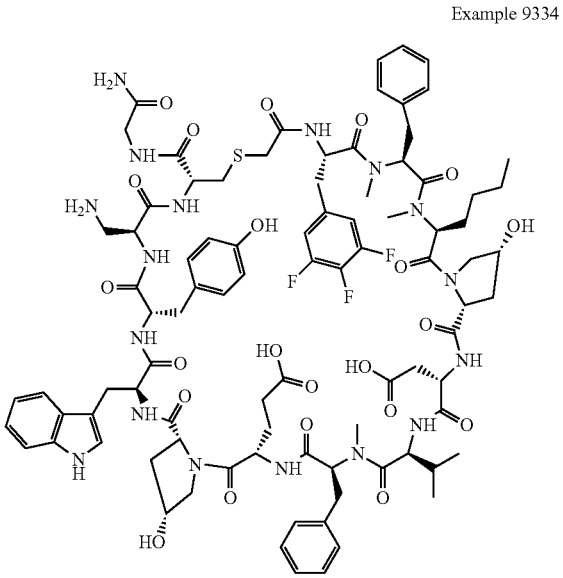 [SMILES: CCCC[C@H]1C(=O)N2C[C@H](O)C[C@@H]2C(=O)N[C@@H](CC(=O)O)C(=O)N[C@@H](C(C)C)C(=O)N(C)[C@@H](Cc2ccccc2)C(=O)N[C@@H](CCC(=O)O)C(=O)N2C[C@H](O)C[C@@H]2C(=O)N[C@@H](Cc2c[nH]c3ccccc23)C(=O)N[C@@H](Cc2ccc(O)cc2)C(=O)N[C@@H](CN)C(=O)N[C@H](C(=O)NCC(N)=O)CSCC(=O)N[C@@H](Cc2cc(F)c(F)c(F)c2)C(=O)N(C)[C@@H](Cc2ccccc2)C(=O)N1C]
Example 9334

The crude material of Example 9334 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 27.1 mg, and its estimated purity by LCMS analysis was 100%.

Analysis condition A: Retention time=1.50 min; ESI-MS (+) m/z 937.5 (M+2H).

Analysis condition B: Retention time=2.83 min; ESI-MS (+) m/z 937.4 (M+2H).

Preparation of Example 9335

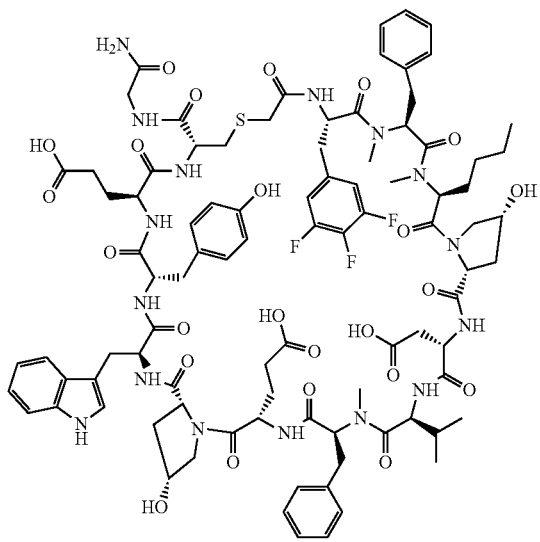

Example 9335

The crude material of Example 9335 was purified via preparative LC/MS with the following conditions: Column: XBridge C18, 19×mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 34.6 mg, and its estimated purity by LCMS analysis was 100%.

Analysis condition A: Retention time=1.32 min; ESI-MS (+) m/z 959.3 (M+2H).

Analysis condition B: Retention time=2.58 min; ESI-MS (+) m/z 959.0 (M+2H).

Preparation of Example 9336

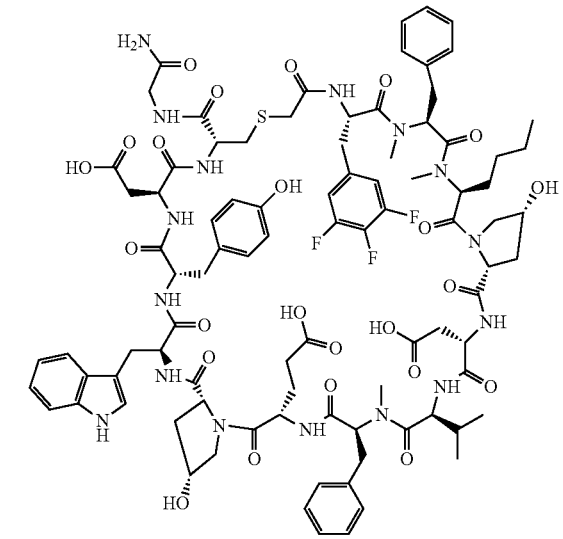

Example 9336

The crude material of Example 9336 was purified via preparative LC/MS with the following conditions: Column: XBridge C18, 19×mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 28.6 mg, and its estimated purity by LCMS analysis was 100%.

Analysis condition A: Retention time=1.34 min; ESI-MS (+) m/z 952.0 (M+2H).

Analysis condition B: Retention time=2.64 min; ESI-MS (+) m/z 951.7 (M+2H).

Preparation of Example 9337

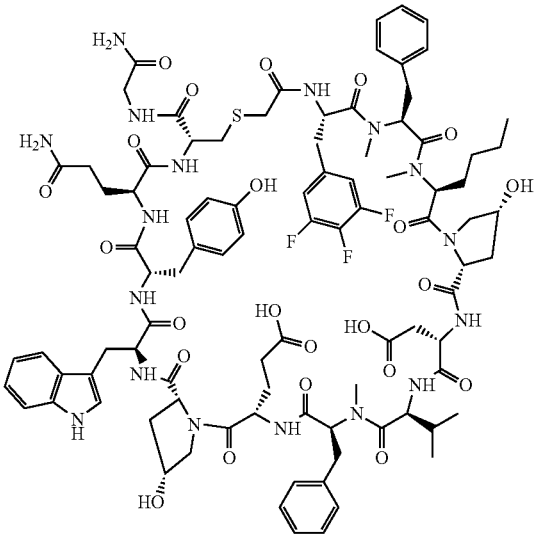

Example 9337

The crude material of Example 9337 was purified via preparative LC/MS with the following conditions: Column: XBridge C18, 19×mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 32.9 mg, and its estimated purity by LCMS analysis was 98%.

Analysis condition A: Retention time=1.46 min; ESI-MS (+) m/z 959.2 (M+2H).

Analysis condition B: Retention time=2.74 min; ESI-MS (+) m/z 958.8 (M+2H).

Preparation of Example 9338

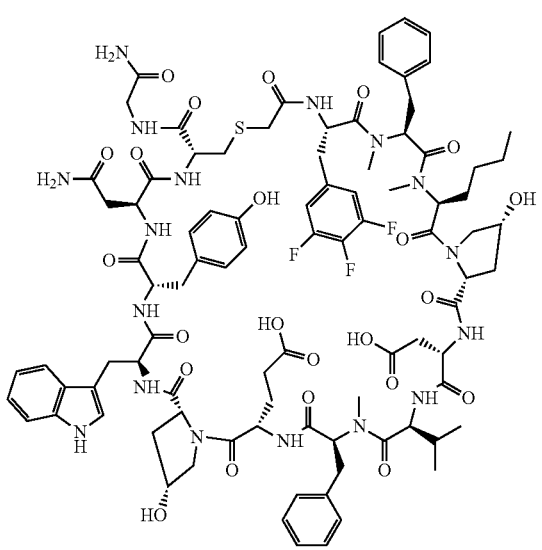

Example 9338

The crude material of Example 9338 was purified via preparative LC/MS with the following conditions: Column: XBridge C18, 19×mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 38.5 mg, and its estimated purity by LCMS analysis was 100%.

Analysis condition A: Retention time=1.47 min; ESI-MS (+) m/z 951.5 (M+2H).

Analysis condition B: Retention time=2.75 min; ESI-MS (+) m/z 951.7 (M+2H).

Preparation of Example 9345

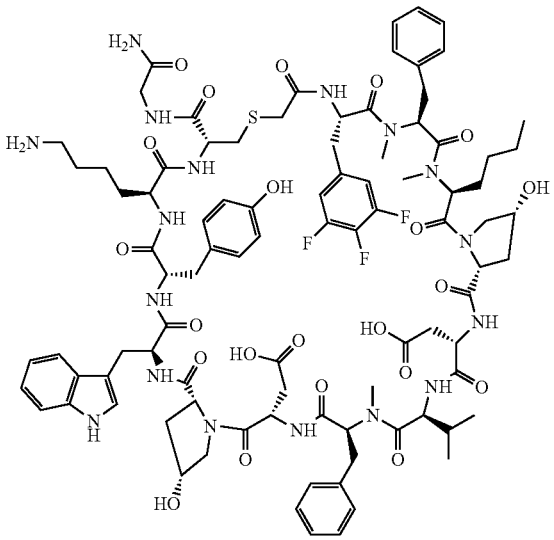

Example 9345

The crude material of Example 9345 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 43.1 mg, and its estimated purity by LCMS analysis was 96%.

Analysis condition B: Retention time=3.35 min; ESI-MS (+) m/z 951.35 (M+2H).

Preparation of Example 9346

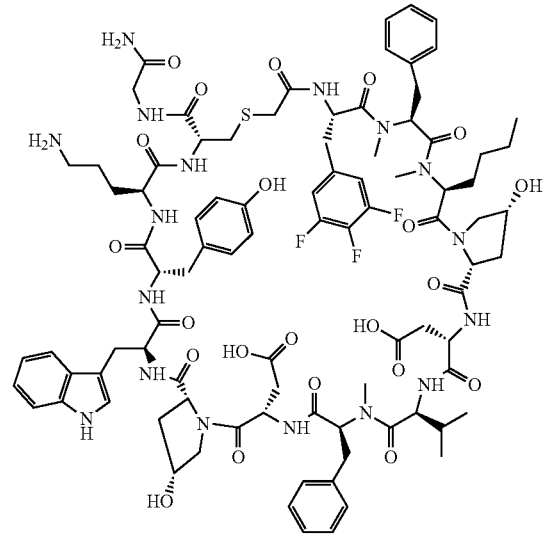

Example 9346

The crude material of Example 9346 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 39.6 mg, and its estimated purity by LCMS analysis was 99%.

Analysis condition B: Retention time=3.26 min; ESI-MS (+) m/z 944.35 (M+2H).

Preparation of Example 9347

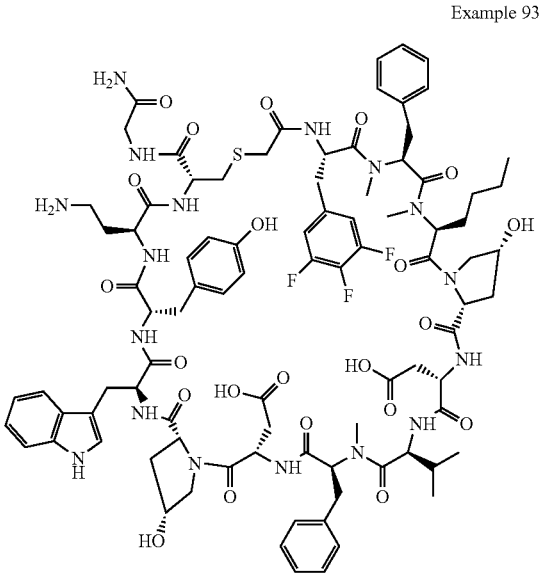

Example 9347

The crude material of Example 9347 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 45.0 mg, and its estimated purity by LCMS analysis was 95%.

Analysis condition B: Retention time=3.26 min; ESI-MS (+) m/z 937.30 (M+2H).

Preparation of Example 9348

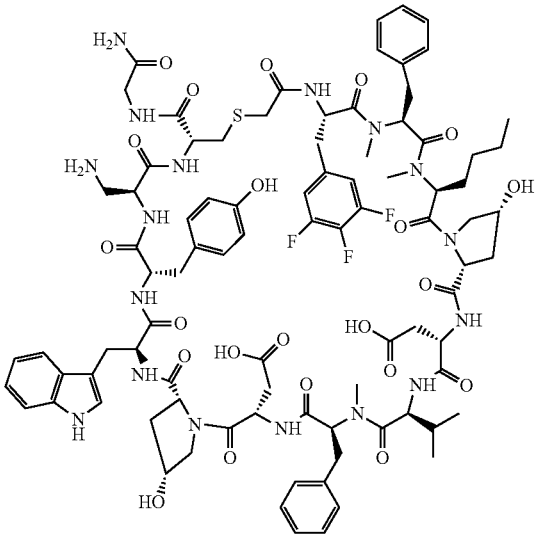

Example 9348

The crude material of Example 9348 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 39.4 mg, and its estimated purity by LCMS analysis was 100%.

Analysis condition B: Retention time=3.17 min; ESI-MS (+) m/z 930.35 (M+2H).

Preparation of Example 9349

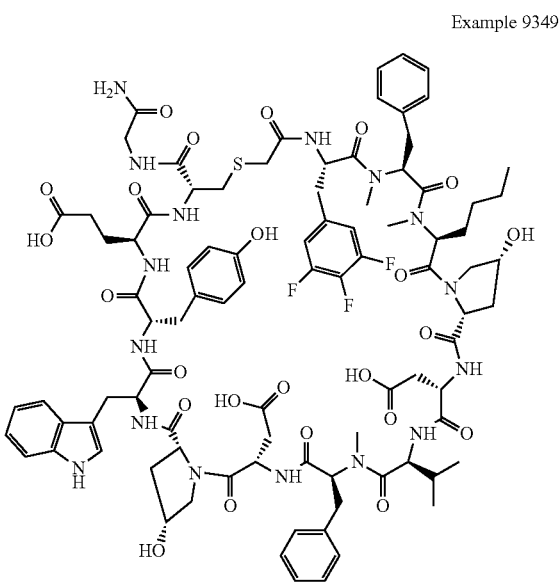 [SMILES: CCCC[C@H]1C(=O)N2C[C@H](O)C[C@@H]2C(=O)N[C@@H](CC(=O)O)C(=O)N[C@@H](C(C)C)C(=O)N(C)[C@@H](Cc2ccccc2)C(=O)N[C@@H](CC(=O)O)C(=O)N2C[C@H](O)C[C@@H]2C(=O)N[C@@H](Cc2c[nH]c3ccccc23)C(=O)N[C@@H](Cc2ccc(O)cc2)C(=O)N[C@@H](CCC(=O)O)C(=O)N[C@H](C(=O)NCC(N)=O)CSCC(=O)N[C@@H](Cc2cc(F)c(F)c(F)c2)C(=O)N(C)[C@@H](Cc2ccccc2)C(=O)N1C]

Example 9349

The crude material of Example 9349 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 39.0 mg, and its estimated purity by LCMS analysis was 100%.

Analysis condition A: Retention time=1.46 min; ESI-MS (+) m/z 951.70 (M+2H).

Analysis condition B: Retention time=2.95 min; ESI-MS (+) m/z 951.65 (M+2H).

Preparation of Example 9350

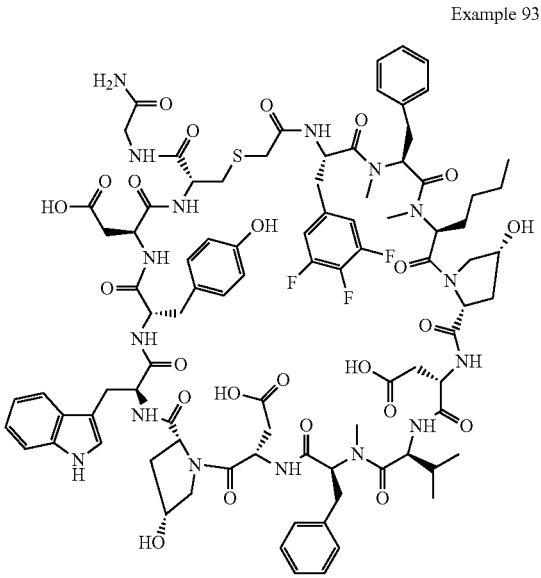

Example 9350

The crude material of Example 9350 was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 37.7 mg, and its estimated purity by LCMS analysis was 96%.

Analysis condition A: Retention time=1.46 min; ESI-MS (−) m/z 942.8 (M−2H).

Analysis condition B: Retention time=2.69 min; ESI-MS (+) m/z 944.8 (M+2H).

Preparation of Example 9351

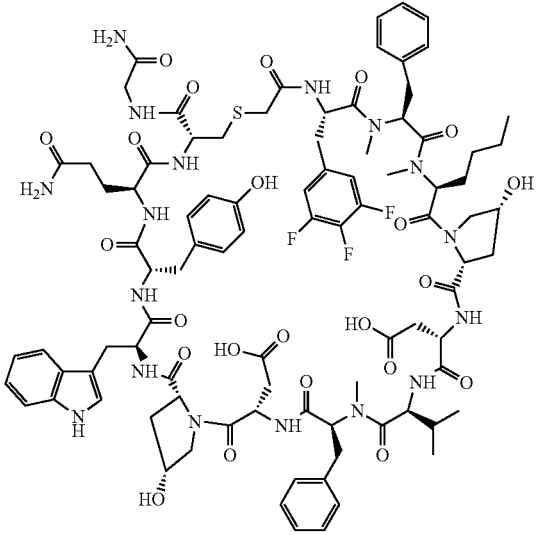

Example 9351

The crude material of Example 9351 was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 45.3 mg, and its estimated purity by LCMS analysis was 98%.

Analysis condition A: Retention time=1.52 min; ESI-MS (−) m/z 950.0 (M−2H).

Analysis condition B: Retention time=2.70 min; ESI-MS (+) m/951.3 (M+2H).

Preparation of Example 9352

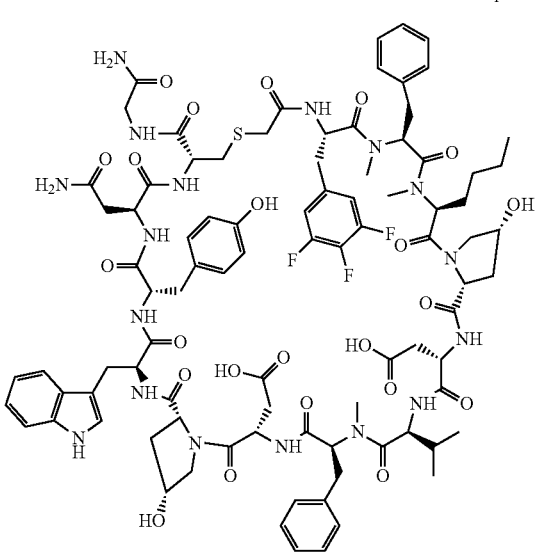

Example 9352

The crude material of Example 9352 was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 40.1 mg, and its estimated purity by LCMS analysis was 100%.

Analysis condition A: Retention time=1.60 min; ESI-MS (−) m/z 942.8 (M−2H).

Analysis condition B: Retention time=2.73 min; ESI-MS (+) m/z 944.6 (M+2H).

Preparation of Example 9353

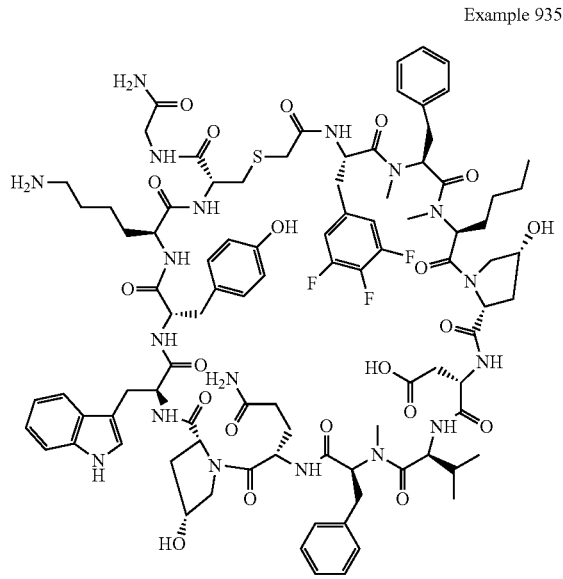

Example 9353

The crude material of Example 9353 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 34.7 mg, and its estimated purity by LCMS analysis was 100%.

Analysis condition A: Retention time=1.67 min; ESI-MS (−) m/z 955.8 (M−2H).

Analysis condition B: Retention time=2.94 min; ESI-MS (+) m/z 957.8 (M+2H).

Preparation of Example 9354

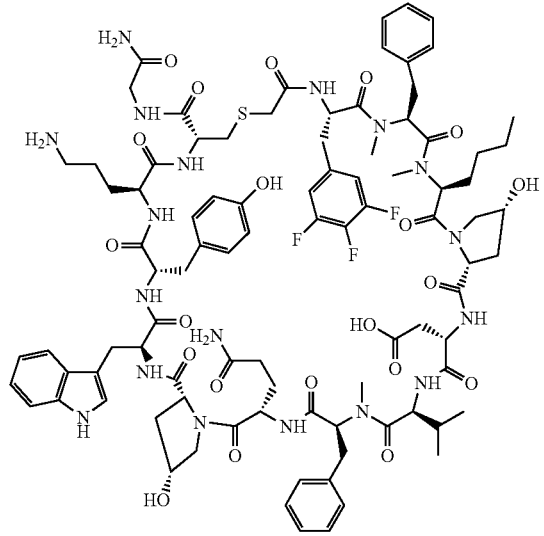

Example 9354

The crude material of Example 9354 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 20 minutes, then a 5-minute hold at 100% B; Flow: 20 mL/min. Fractions containing the desired product were combined and dried via centrifugal evaporation. The yield of the product was 37.8 mg, and its estimated purity by LCMS analysis was 100%.

Analysis condition A: Retention time=1.70 min; ESI-MS (+) m/z 951.2 (M+2H).

Analysis condition B: Retention time=2.95 min; ESI-MS (+) m/z 950.6 (M+2H).

Preparation of Example 9355

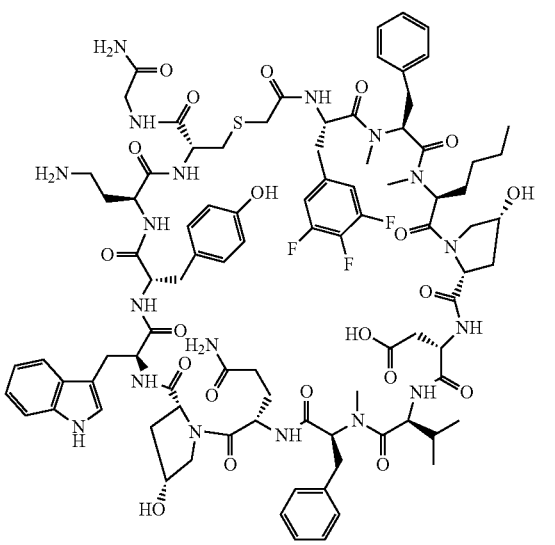

Example 9355

The crude material of Example 9355 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 32.9 mg, and its estimated purity by LCMS analysis was 100%.

Analysis condition A: Retention time=1.71 min; ESI-MS (+) m/z 941.9 (M+2H).

Analysis condition B: Retention time=2.95 min; ESI-MS (−) m/z 941.6 (M−2H).

Preparation of Example 9356

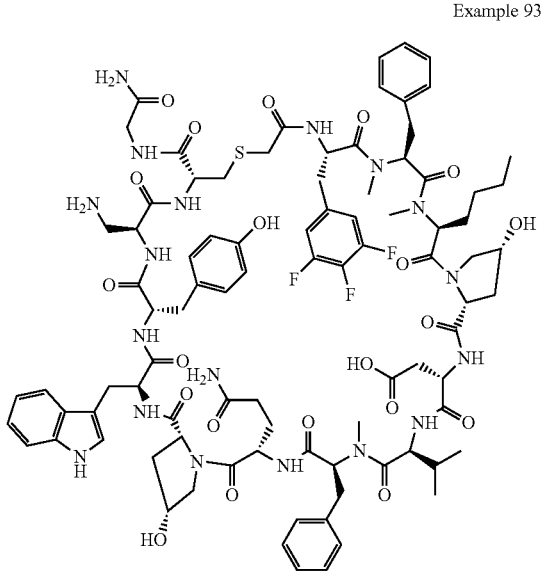

Example 9356

The crude material of Example 9356 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 15.7 mg, and its estimated purity by LCMS analysis was 97%.

Analysis condition A: Retention time=1.58 min; ESI-MS (−) m/z 934.7 (M−2H).

Analysis condition B: Retention time=2.82 min; ESI-MS (+) m/z 936.8 (M+2H).

Preparation of Example 9357

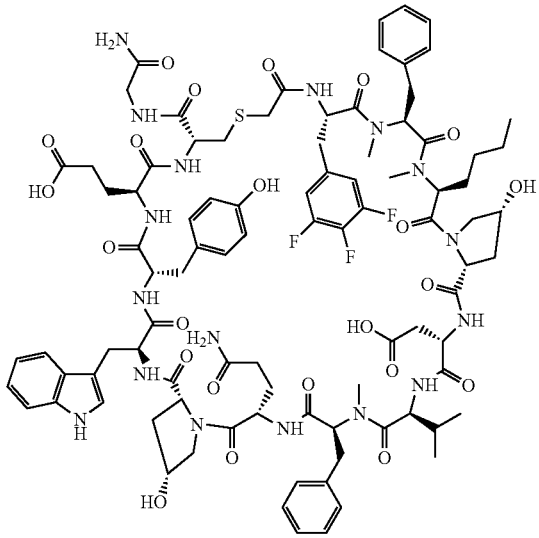

Example 9357

The crude material of Example 9357 was purified via preparative LC/MS with the following conditions: Column: XBridge C18, 19×200 mm, 5-μm particles; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 49.0 mg, and its estimated purity by LCMS analysis was 98%.

Analysis condition A: Retention time=1.50 min; ESI-MS (−) m/z 956.3 (M−2H).

Analysis condition B: Retention time=2.73 min; ESI-MS (+) m/z 958.4 (M+2H).

Preparation of Example 9358

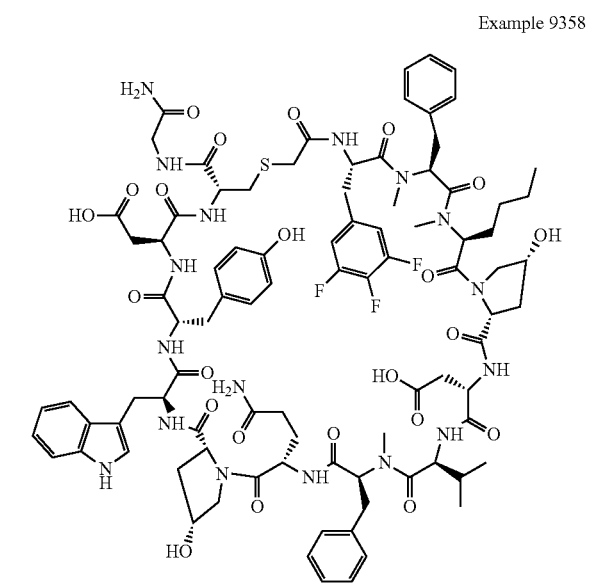 [SMILES: CCCC[C@H]1C(=O)N2C[C@H](O)C[C@@H]2C(=O)N[C@@H](CC(=O)O)C(=O)N[C@@H](C(C)C)C(=O)N(C)[C@@H](Cc2ccccc2)C(=O)N[C@@H](CCC(N)=O)C(=O)N2C[C@H](O)C[C@@H]2C(=O)N[C@@H](Cc2c[nH]c3ccccc23)C(=O)N[C@@H](Cc2ccc(O)cc2)C(=O)N[C@@H](CC(=O)O)C(=O)N[C@H](C(=O)NCC(N)=O)CSCC(=O)N[C@@H](Cc2cc(F)c(F)c(F)c2)C(=O)N(C)[C@@H](Cc2ccccc2)C(=O)N1C]

Example 9358

The crude material of Example 9358 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 48.5 mg, and its estimated purity by LCMS analysis was 100%.

Analysis condition A: Retention time=1.50 min; ESI-MS (−) m/z 949.9 (M−2H).

Analysis condition B: Retention time=2.76 min; ESI-MS (+) m/z 951.3 (M+2H).

Preparation of Example 9359

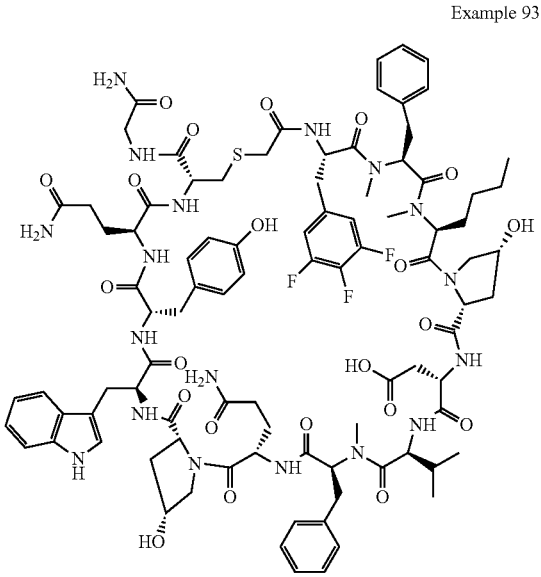

Example 9359

The crude material of Example 9359 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 17.4 mg, and its estimated purity by LCMS analysis was 96%.

Analysis condition A: Retention time=1.59 min; ESI-MS (−) m/z 955.7 (M−2H).

Analysis condition B: Retention time=2.86 min; ESI-MS (+) m/z 957.8 (M+2H).

Preparation of Example 9360

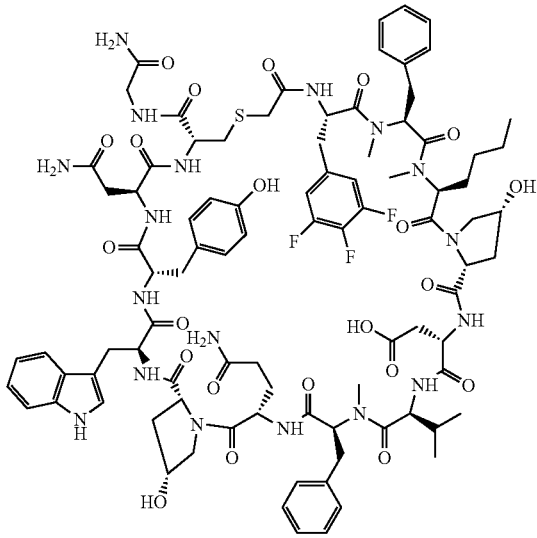

Example 9360

The crude material of Example 9360 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 20 minutes, then a 5-minute hold at 100% B; Flow: 20 mL/min. Fractions containing the desired product were combined and dried via centrifugal evaporation. The yield of the product was 34.7 mg, and its estimated purity by LCMS analysis was 100%.

Analysis condition A: Retention time=1.65 min; ESI-MS (−) m/z 948.9 (M−2H).

Analysis condition B: Retention time=2.89 min; ESI-MS (+) m/z 950.8 (M+2H).

Preparation of Example 9361

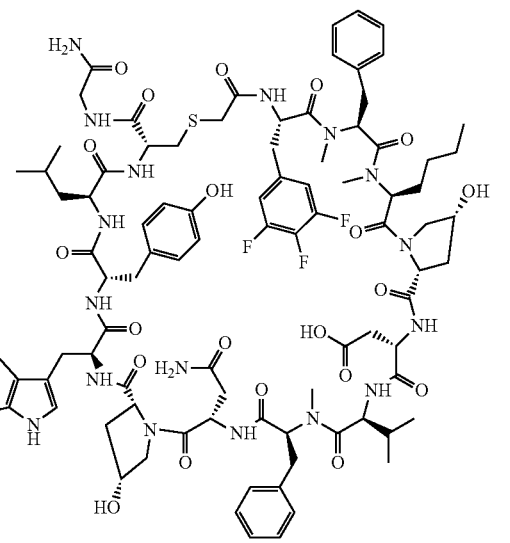

Example 9361

The crude material of Example 9361 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 38.0 mg, and its estimated purity by LCMS analysis was 100%.

Analysis condition A: Retention time=1.73 min; ESI-MS (−) m/z 941.2 (M−2H).

Analysis condition B: Retention time=2.97 min; ESI-MS (+) m/z 943.4 (M+2H).

Preparation of Example 9362

Example 9362

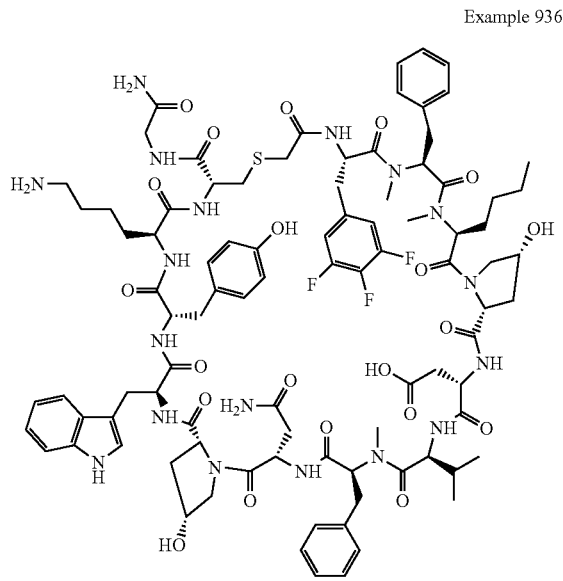

The crude material of Example 9362 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 37.0 mg, and its estimated purity by LCMS analysis was 98%.

Analysis condition A: Retention time=1.72 min; ESI-MS (+) m/z 948.6 (M+2H).

Analysis condition B: Retention time=2.98 min; ESI-MS (+) m/z 950.9 (M+2H).

Preparation of Example 9363

Example 9363

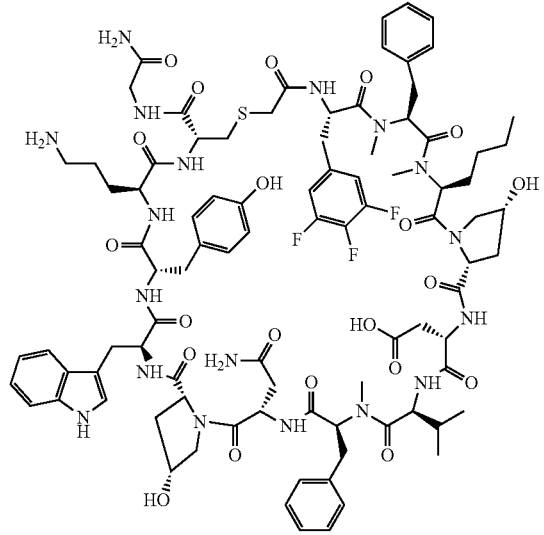

The crude material of Example 9363 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 28.1 mg, and its estimated purity by LCMS analysis was 100%.

Analysis condition A: Retention time=1.68 min; ESI-MS (−) m/z 941.5 (M−2H).

Analysis condition B: Retention time=2.98 min; ESI-MS (+) m/z 943.4 (M+2H).

Preparation of Example 9364

Example 9364

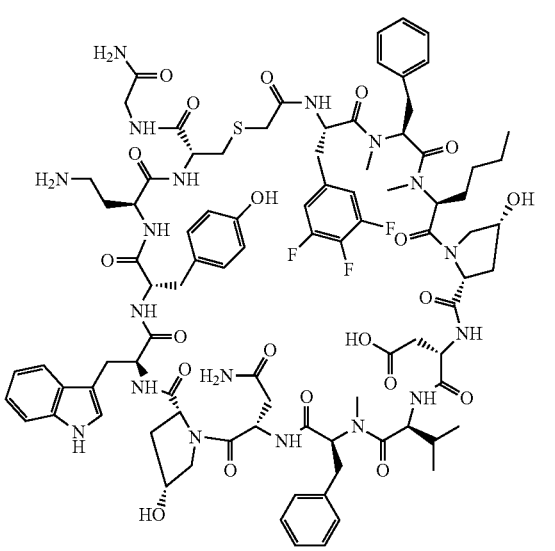

The crude material of Example 9364 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 42.7 mg, and its estimated purity by LCMS analysis was 99%.

Analysis condition A: Retention time=1.71 min; ESI-MS (+) m/z 934.7 (M+2H).

Analysis condition B: Retention time=2.97 min; ESI-MS (+) m/z 936.8 (M+2H).

Preparation of Example 9365

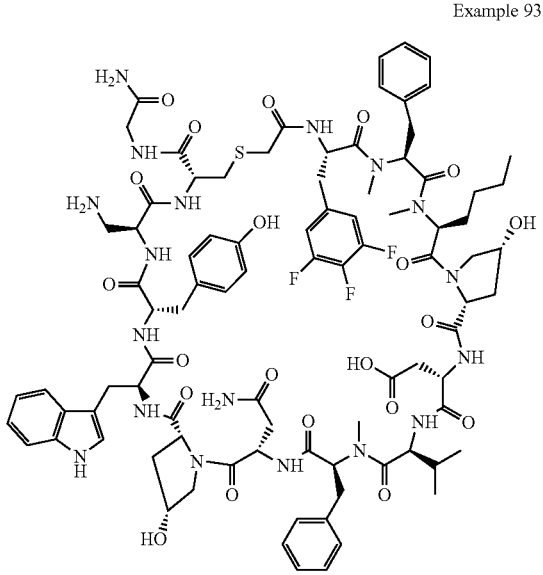

Example 9365

The crude material of Example 9365 was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 48-88% B over 30 minutes, then a 5-minute hold at 100% B; Flow: 20 mL/min. Fractions containing the desired product were combined and dried via centrifugal evaporation. The yield of the product was 18.5 mg, and its estimated purity by LCMS analysis was 98%.

Analysis condition A: Retention time=1.67 min; ESI-MS (−) m/z 927.8 (M−2H).

Analysis condition B: Retention time=2.93 min; ESI-MS (+) m/z 929.6 (M+2H).

Preparation of Example 9366

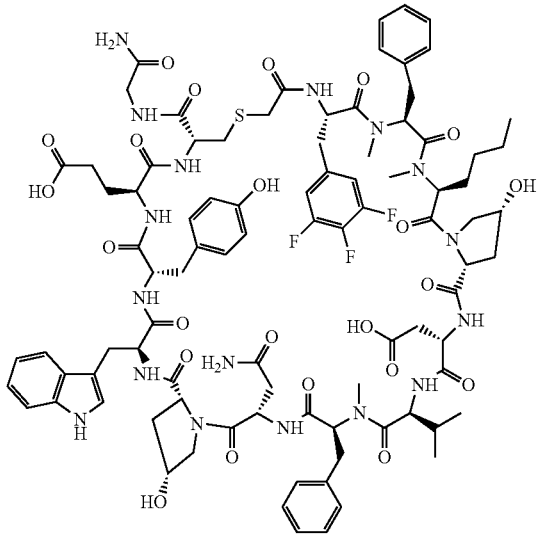

Example 9366

The crude material of Example 9366 was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 39.6 mg, and its estimated purity by LCMS analysis was 99%.

Analysis condition A: Retention time=1.56 min; ESI-MS (−) m/z 949.2 (M−2H).

Analysis condition B: Retention time=2.78 min; ESI-MS (+) m/z 951.2 (M+2H).

Preparation of Example 9367

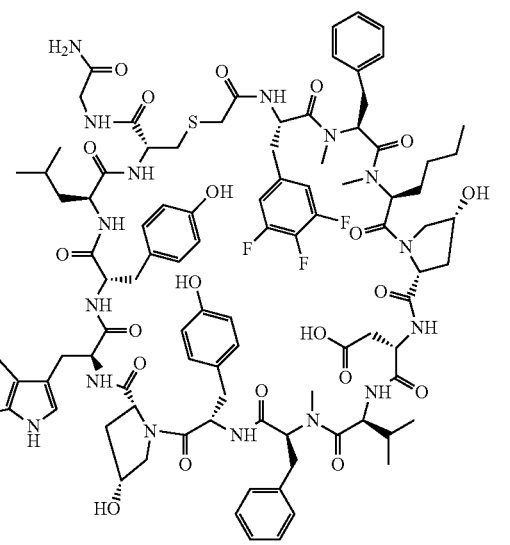

Example 9367

The crude material of Example 9367 was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 55-95% B over 30 minutes, then a 5-minute hold at 100% B; Flow: 20 mL/min. Fractions containing the desired product were combined and dried via centrifugal evaporation. The yield of the product was 23.0 mg, and its estimated purity by LCMS analysis was 98%.

Analysis condition A: Retention time=1.77 min; ESI-MS (−) m/z 965.8 (M−2H).

Analysis condition B: Retention time=2.98 min; ESI-MS (+) m/z 967.5 (M+2H).

Preparation of Example 9368

Example 9368

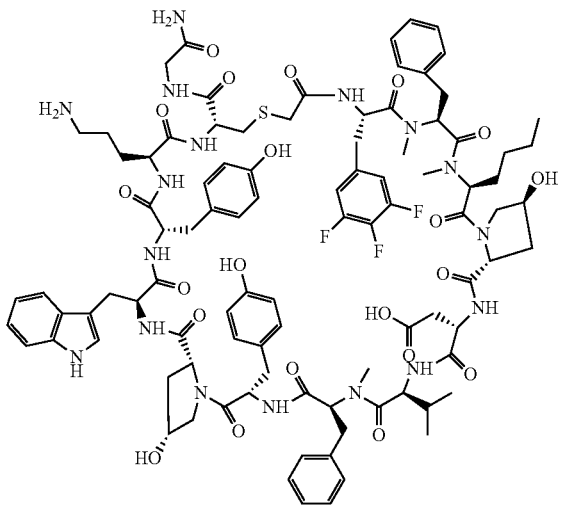

The crude material of Example 9368 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 55-95% B over 30 minutes, then a 5-minute hold at 100% B; Flow: 20 mL/min. Fractions containing the desired product were combined and dried via centrifugal evaporation. The yield of the product was 38.8 mg, and its estimated purity by LCMS analysis was 95%.

Analysis condition A: Retention time=1.65 min; ESI-MS (+) m/z 968.7 (M+2H).

Analysis condition B: Retention time=2.90 min; ESI-MS (+) m/z 968.4 (M+2H).

Preparation of Example 9369

Example 9369

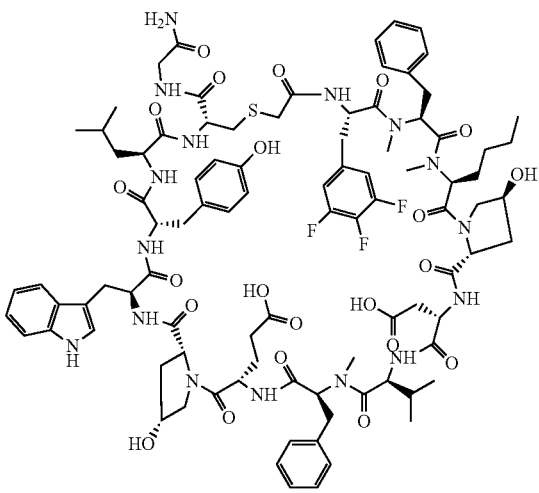

The crude material of Example 9369 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 55-95% B over 30 minutes, then a 5-minute hold at 100% B; Flow: 20 mL/min. Fractions containing the desired product were combined and dried via centrifugal evaporation. The yield of the product was 28.3 mg, and its estimated purity by LCMS analysis was 97%.

Analysis condition A: Retention time=1.62 min; ESI-MS (+) m/z 948.6 (M+2H).

Analysis condition B: Retention time=2.78 min; ESI-MS (+) m/z 950.8 (M+2H).

Preparation of Example 9370

Example 9370

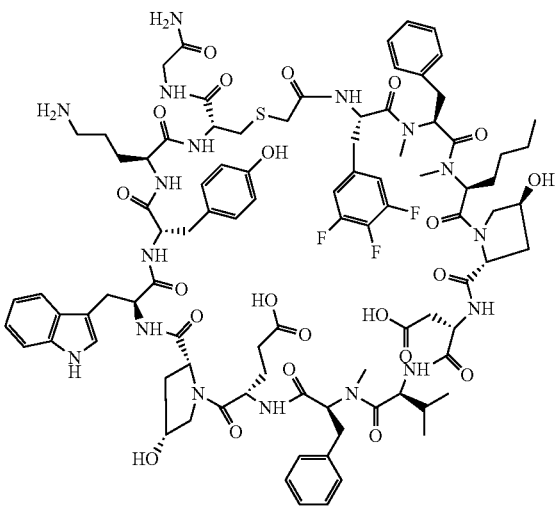

The crude material of Example 9370 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 55-95% B over 30 minutes, then a 5-minute hold at 100% B; Flow: 20 mL/min. Fractions containing the desired product were combined and dried via centrifugal evaporation. The yield of the product was 47.0 mg, and its estimated purity by LCMS analysis was 99%.

Analysis condition A: Retention time=1.58 min; ESI-MS (+) m/z 952.1 (M+2H).

Analysis condition B: Retention time=2.83 min; ESI-MS (+) m/z 951.2 (M+2H).

Preparation of Example 9371

Example 9371

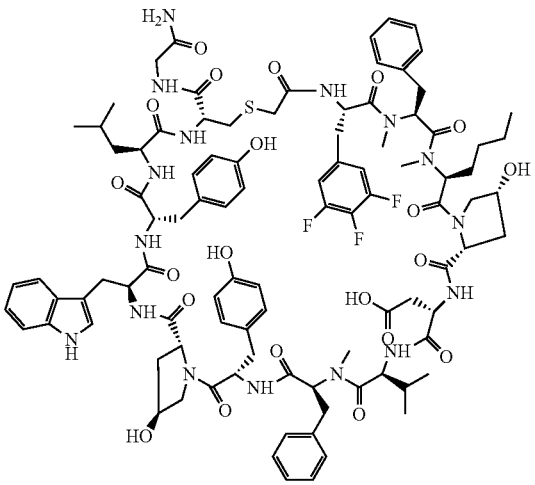

The crude material of Example 9371 was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 55-95% B over 30 minutes, then a 5-minute hold at 100% B; Flow: 20 mL/min. Fractions containing the desired product were combined and dried via centrifugal evaporation. The yield of the product was 29.3 mg, and its estimated purity by LCMS analysis was 94%.

Analysis condition A: Retention time=1.69 min; ESI-MS (−) m/z 966.0 (M−2H).

Analysis condition B: Retention time=2.85 min; ESI-MS (+) m/z 968.2 (M+2H).

Preparation of Example 9372

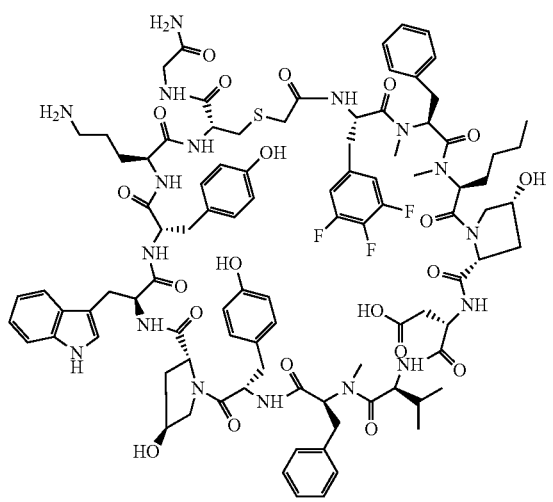

Example 9372

The crude material of Example 9372 was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 55-95% B over 30 minutes, then a 5-minute hold at 100% B; Flow: 20 mL/min. Fractions containing the desired product were combined and dried via centrifugal evaporation. The yield of the product was 26.0 mg, and its estimated purity by LCMS analysis was 100%.

Analysis condition A: Retention time=1.77 min; ESI-MS (−) m/z 966.1 (M−2H).

Analysis condition B: Retention time=2.95 min; ESI-MS (+) m/z 968.3 (M+2H).

Preparation of Example 9373

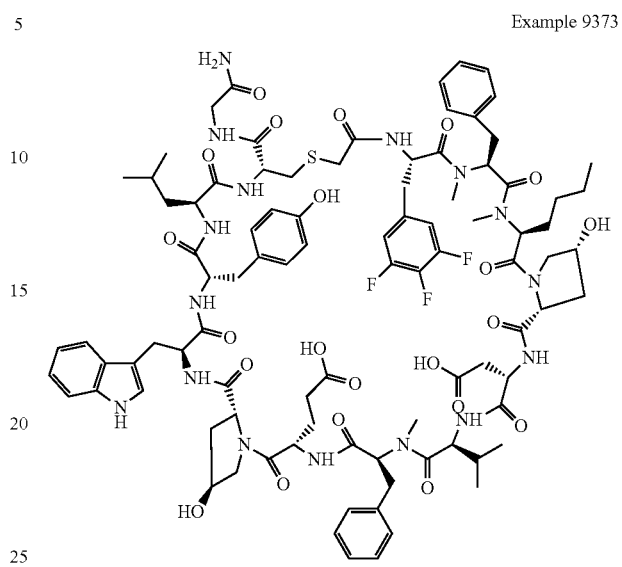

Example 9373

The crude material of Example 9373 was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 23.4 mg, and its estimated purity by LCMS analysis was 100%.

Analysis condition A: Retention time=1.56 min; ESI-MS (+) m/z 950.6 (M+2H).

Analysis condition B: Retention time=2.68 min; ESI-MS (+) m/z 950.5 (M+2H).

Preparation of Example 9374

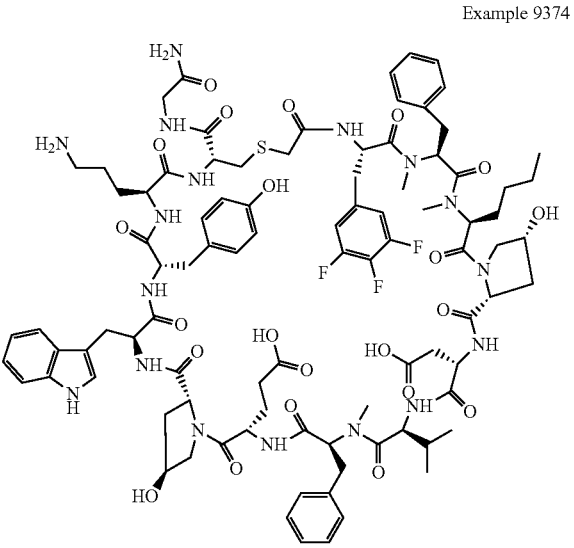 [SMILES: CCCC[C@H]1C(=O)N2C[C@H](O)C[C@@H]2C(=O)N[C@@H](CC(=O)O)C(=O)N[C@@H](C(C)C)C(=O)N(C)[C@@H](Cc2ccccc2)C(=O)N[C@@H](CCC(=O)O)C(=O)N2C[C@@H](O)C[C@@H]2C(=O)N[C@@H](Cc2c[nH]c3ccccc23)C(=O)N[C@@H](Cc2ccc(O)cc2)C(=O)N[C@@H](CCCN)C(=O)N[C@H](C(=O)NCC(N)=O)CSCC(=O)N[C@@H](Cc2cc(F)c(F)c(F)c2)C(=O)N(C)[C@@H](Cc2ccccc2)C(=O)N1C]

Example 9374

The crude material of Example 9374 was purified via preparative LC/MS with the following conditions: Column:

XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 55-95% B over 30 minutes, then a 5-minute hold at 100% B; Flow: 20 mL/min. Fractions containing the desired product were combined and dried via centrifugal evaporation. The yield of the product was 23.6 mg, and its estimated purity by LCMS analysis was 100%.

Analysis condition A: Retention time=1.67 min; ESI-MS (−) m/z 949.3 (M−2H).

Analysis condition B: Retention time=2.82 min; ESI-MS (+) m/z 951.2 (M+2H).

Series 10000

Example 10012-10043, Example 10045-10052, Example 10122-10147 and Example 10196-10219 were prepared by following the "General Synthetic Sequence A".

Example 10044, Example 10053-10121 and Example 10148-10195 were prepared by following the "General Synthetic Sequence D".

Preparation of Example 10012

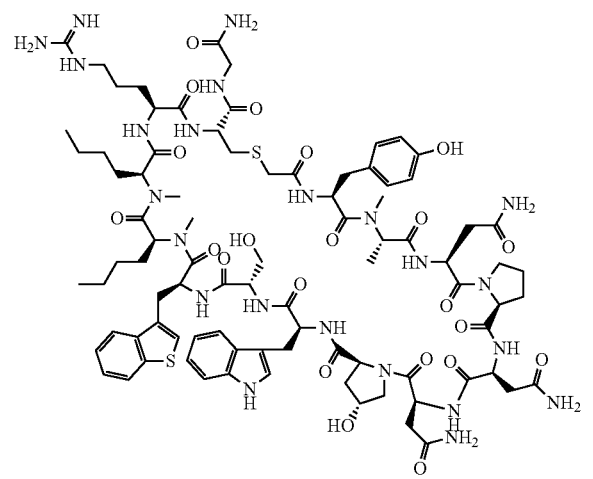

Example 10012

The crude material of Example 10012 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 3.9 mg, and its estimated purity by LCMS analysis was 98%.

Analysis condition A: Retention time=1.54 min; ESI-MS (+) m/z 954.0 (M+2H).

Analysis condition B: Retention time=2.72 min; ESI-MS (+) m/z 953.5 (M+2H).

ESI-HRMS(+) m/z: Calculated: 949.9269 (M+2H); Found: 949.9263 (M+2H).

Preparation of Example 10013

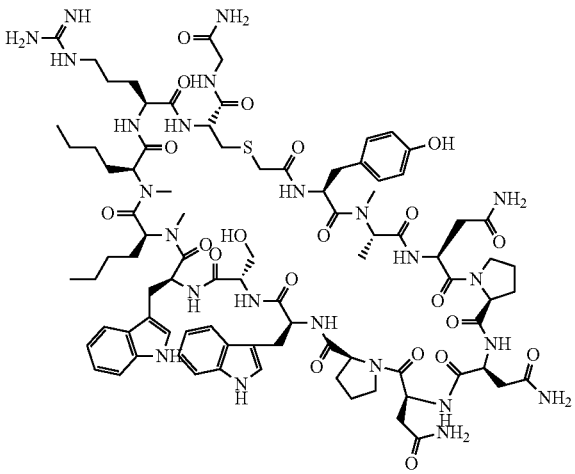

Example 10013

The crude material of Example 10013 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 10.2 mg, and its estimated purity by LCMS analysis was 99%.

Analysis condition A: Retention time=1.46 min; ESI-MS (+) m/z 936.9 (M+2H).

Analysis condition B: Retention time=2.58 min; ESI-MS (+) m/z 937.5 (M+2H).

ESI-HRMS(+) m/z: Calculated: 936.4541 (M+2H); Found: 936.4540 (M+2H).

Preparation of Example 10014

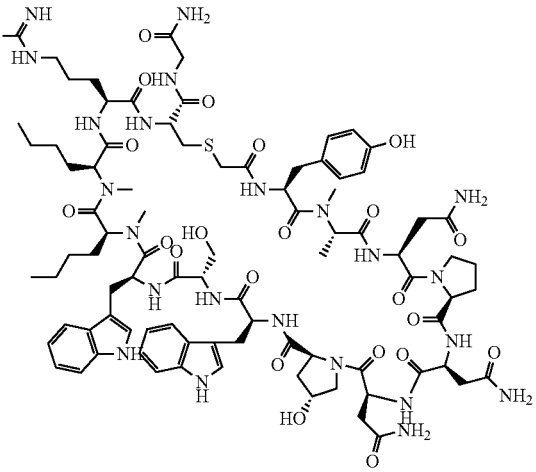

Example 10014

The crude material of Example 10014 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 2.0 mg, and its estimated purity by LCMS analysis was 100%.

Analysis condition A: Retention time=1.44 min; ESI-MS (+) m/z 945.3 (M+2H).

Analysis condition B: Retention time=2.56 min; ESI-MS (+) m/z 945.1 (M+2H).

ESI-HRMS(+) m/z: Calculated: 944.4516 (M+2H); Found: 944.4522 (M+2H).

Preparation of Example 10015

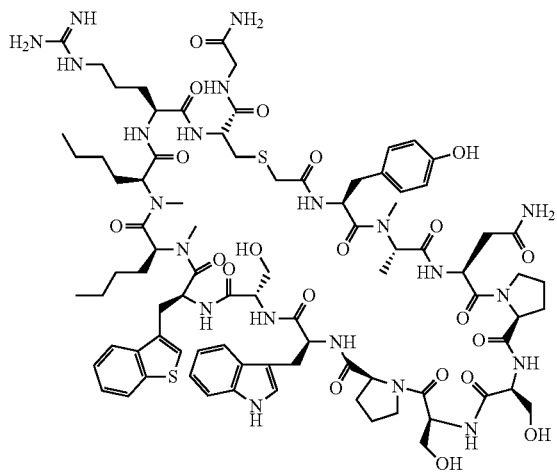

Example 10015

The crude material of Example 10015 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 2.2 mg, and its estimated purity by LCMS analysis was 96%.

Analysis condition A: Retention time=1.61 min; ESI-MS (+) m/z 918.5 (M+2H).

Analysis condition B: Retention time=2.79 min; ESI-MS (+) m/z 918.5 (M+2H).

ESI-HRMS(+) m/z: Calculated: 917.9238 (M+2H); Found: 917.9246 (M+2H).

Preparation of Example 10016

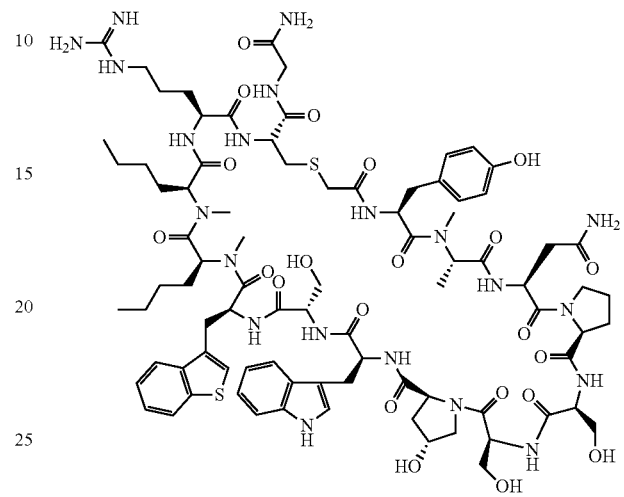

Example 10016

The crude material of Example 10016 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 5.6 mg, and its estimated purity by LCMS analysis was 98%.

Analysis condition A: Retention time=1.61 min; ESI-MS (−) m/z 924.4 (M−2H).

Analysis condition B: Retention time=2.77 min; ESI-MS (+) m/z 926.6 (M+2H).

ESI-HRMS(+) m/z: Calculated: 925.9213 (M+2H); Found: 925.9217 (M+2H).

Preparation of Example 10017

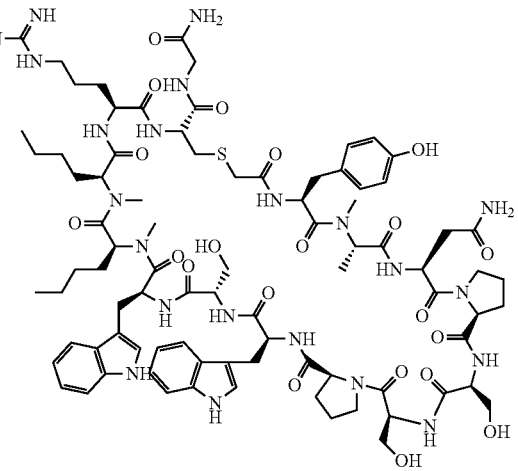

Example 10017

The crude material of Example 10017 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 10.3 mg, and its estimated purity by LCMS analysis was 100%.

Analysis condition A: Retention time=1.53 min; ESI-MS (+) m/z 910.4 (M+2H).

Analysis condition B: Retention time=2.64 min; ESI-MS (+) m/z 910.0 (M+2H).

ESI-HRMS(+) m/z: Calculated: 909.4432 (M+2H); Found: 909.4430 (M+2H).

Preparation of Example 10018

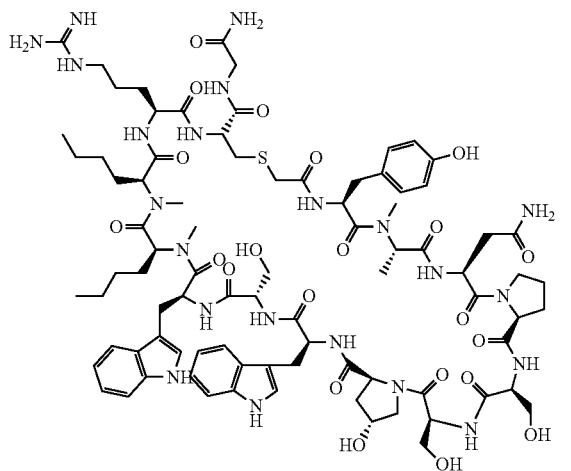

Example 10018

The crude material of Example 10018 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 4.5 mg, and its estimated purity by LCMS analysis was 99%.

Analysis condition A: Retention time=1.45 min; ESI-MS (+) m/z 918.9 (M+2H).

Analysis condition B: Retention time=2.61 min; ESI-MS (+) m/z 918.0 (M+2H).

ESI-HRMS(+) m/z: Calculated: 917.4407 (M+2H); Found: 917.4411 (M+2H).

Preparation of Example 10019

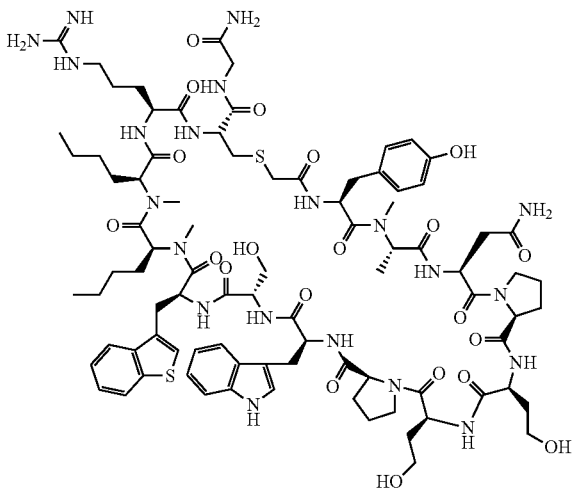

Example 10019

The crude material of Example 10019 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 11.3 mg, and its estimated purity by LCMS analysis was 95%.

Analysis condition A: Retention time=1.64 min; ESI-MS (+) m/z 1864.6 (M+H).

Analysis condition B: Retention time=2.79 min; ESI-MS (+) m/z 933.0 (M+2H).

ESI-HRMS(+) m/z: Calculated: 931.9395 (M+2H); Found: 931.9389 (M+2H).

Preparation of Example 10020

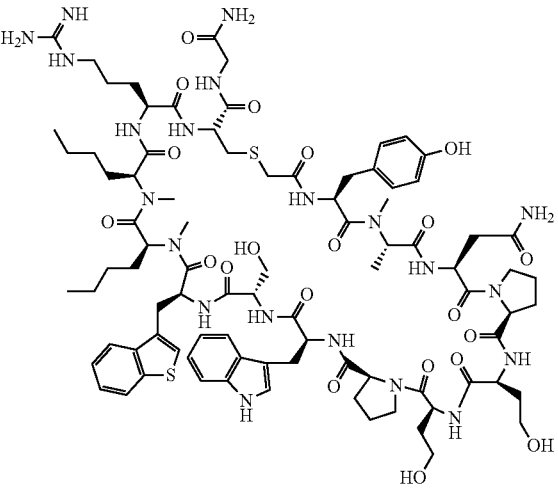

Example 10020

The crude material of Example 10020 was purified via preparative LC/MS with the following conditions: Column:

XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 7.2 mg, and its estimated purity by LCMS analysis was 98%.

Analysis condition A: Retention time=1.68 min; ESI-MS (+) m/z 940.8 (M+2H).

Analysis condition B: Retention time=2.81 min; ESI-MS (+) m/z 940.6 (M+2H).

ESI-HRMS(+) m/z: Calculated: 939.9369 (M+2H); Found: 939.9374 (M+2H).

Preparation of Examples 10021 and 10022

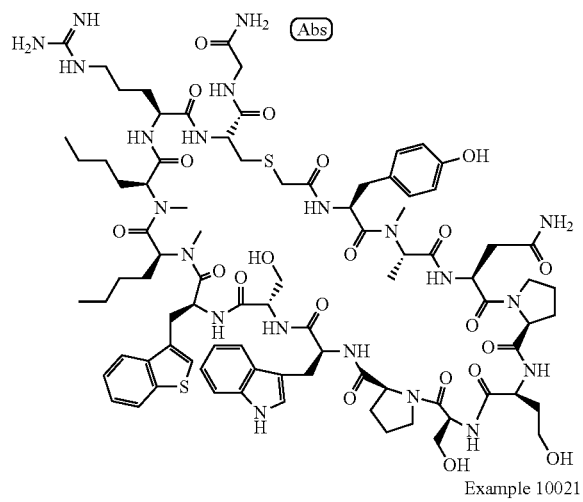

Example 10022

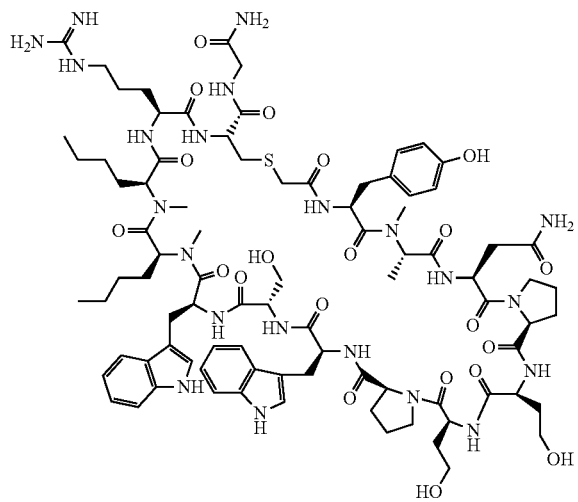

Example 10021

The crude material of Example 10021 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 7.2 mg, and its estimated purity by LCMS analysis was 90%.

Analysis condition A: Retention time=1.52 min; ESI-MS (−) m/z 922.0 (M−2H).

Analysis condition B: Retention time=2.64 min; ESI-MS (+) m/z 924.1 (M+2H).

ESI-HRMS(+) m/z: Calculated: 923.4589 (M+2H); Found: 923.4589 (M+2H).

Preparation of Example 10022

The crude material of Example 10022 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 7.8 mg, and its estimated purity by LCMS analysis was 99%.

Analysis condition A: Retention time=1.61 min; ESI-MS (−) m/z 924.0 (M−2H).

Analysis condition B: Retention time=2.77 min; ESI-MS (+) m/z 925.9 (M+2H).

ESI-HRMS(+) m/z: Calculated: 924.9316 (M+2H); Found: 924.9323 (M+2H).

Preparation of Example 10023

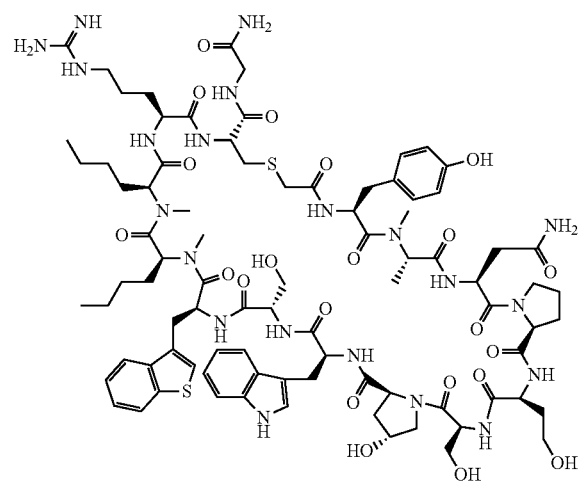

Example 10023

The crude material of Example 10023 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 9.5 mg, and its estimated purity by LCMS analysis was 100%.

Analysis condition A: Retention time=1.61 min; ESI-MS (−) m/z 932.1 (M−2H).

Analysis condition B: Retention time=2.76 min; ESI-MS (+) m/z 934.1 (M+2H).

ESI-HRMS(+) m/z: Calculated: 932.9291 (M+2H); Found: 932.9300 (M+2H).

Preparation of Example 10024

Example 10024

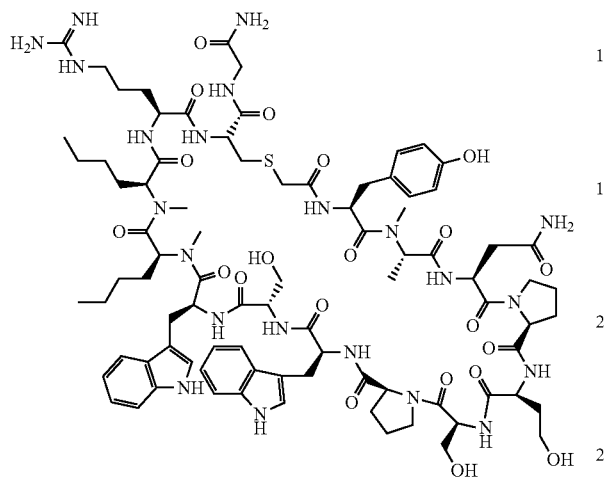

The crude material of Example 10024 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 12.4 mg, and its estimated purity by LCMS analysis was 100%.

Analysis condition A: Retention time=1.46 min; ESI-MS (+) m/z 925.1 (M+2H).

Analysis condition B: Retention time=2.60 min; ESI-MS (+) m/z 925.4 (M+2H).

ESI-HRMS(+) m/z: Calculated: 924.4485 (M+2H); Found: 924.4496 (M+2H).

Preparation of Example 10025

Example 10025

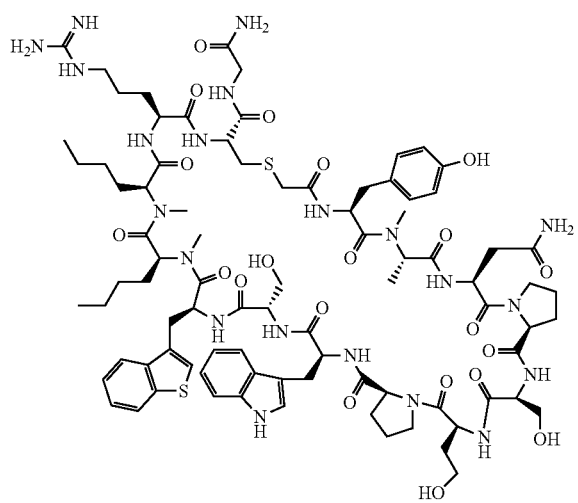

The crude material of Example 10025 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 22.3 mg, and its estimated purity by LCMS analysis was 100%.

Analysis condition A: Retention time=1.66 min; ESI-MS (−) m/z 923.6 (M−2H).

Analysis condition B: Retention time=2.82 min; ESI-MS (+) m/z 925.6 (M+2H).

ESI-HRMS(+) m/z: Calculated: 924.9316 (M+2H); Found: 924.9320 (M+2H).

Preparation of Example 10034

Example 10034

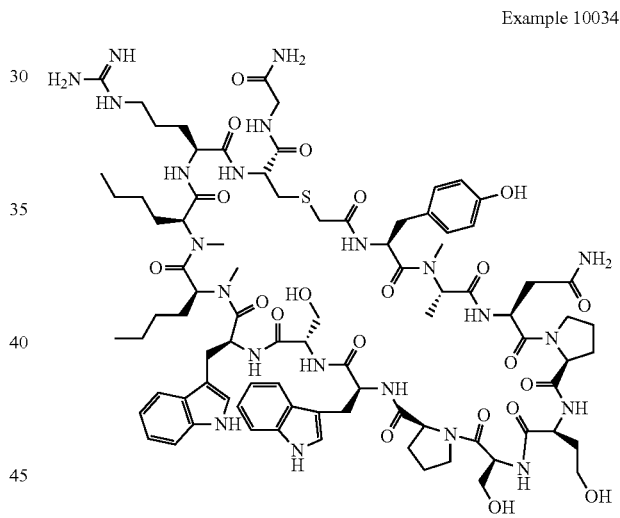

The crude material of Example 10034 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 9.5 mg, and its estimated purity by LCMS analysis was 90%.

Analysis condition A: Retention time=1.61 min; ESI-MS (+) m/z 916.60 (M+2H).

Analysis condition B: Retention time=2.19 min; ESI-MS (+) m/z 916.55 (M+2H).

ESI-HRMS(+) m/z: Calculated: 916.4511 (M+2H); Found: 916.4492 (M+2H).

Preparation of Example 10035

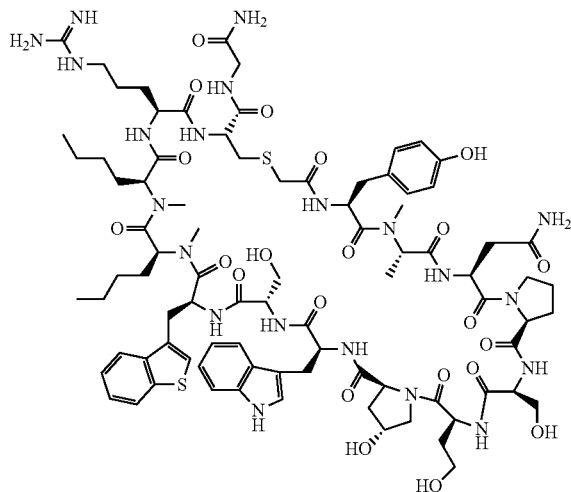

Example 10035

The crude material of Example 10035 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 6.6 mg, and its estimated purity by LCMS analysis was 100%.

Analysis condition A: Retention time=1.68 min; ESI-MS (−) m/z 931.6 (M−2H).

Analysis condition B: Retention time=3.10 min; ESI-MS (+) m/z 934.10 (M+2H).

ESI-HRMS(+) m/z: Calculated: 932.9291 (M+2H); Found: 932.9265 (M+2H).

Preparation of Example 10036

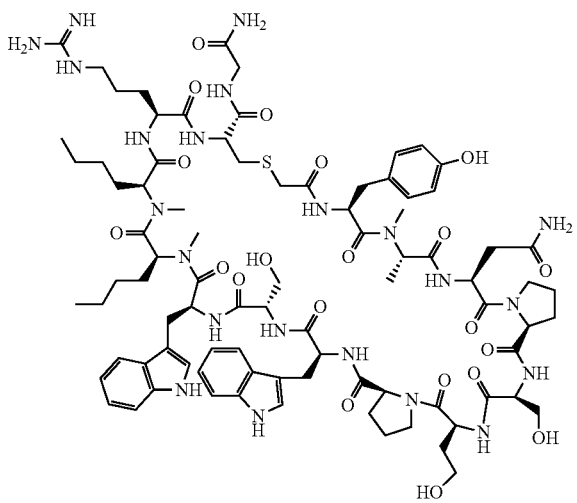

Example 10036

The crude material of Example 10036 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 21.1 mg, and its estimated purity by LCMS analysis was 91%.

Analysis condition A: Retention time=1.78 min; ESI-MS (+) m/z 916.80 (M+2H).

Analysis condition B: Retention time=2.61 min; ESI-MS (+) m/z 916.80 (M+2H).

ESI-HRMS(+) m/z: Calculated: 916.4511 (M+2H); Found: 916.4490 (M+2H).

Preparation of Example 10037

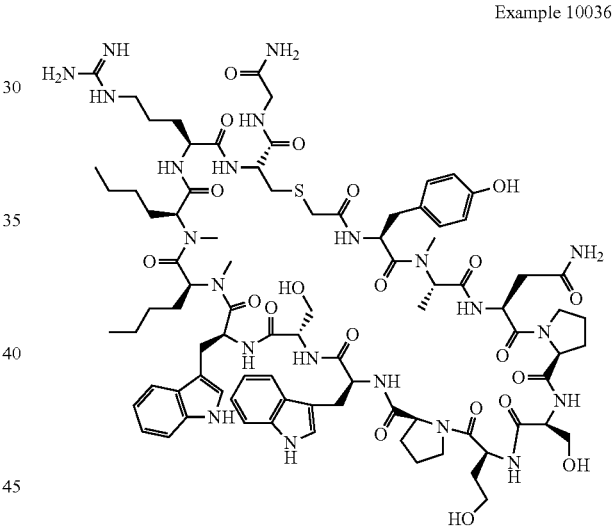

Example 10036

The crude material of Example 10037 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 12.5 mg, and its estimated purity by LCMS analysis was 100%.

Analysis condition A: Retention time=1.63 min; ESI-MS (+) m/z 924.55 (M+2H).

Analysis condition B: Retention time=2.95 min; ESI-MS (+) m/z 924.65 (M+2H).

ESI-HRMS(+) m/z: Calculated: 924.4485 (M+2H); Found: 924.4468 (M+2H).

Preparation of Example 10042

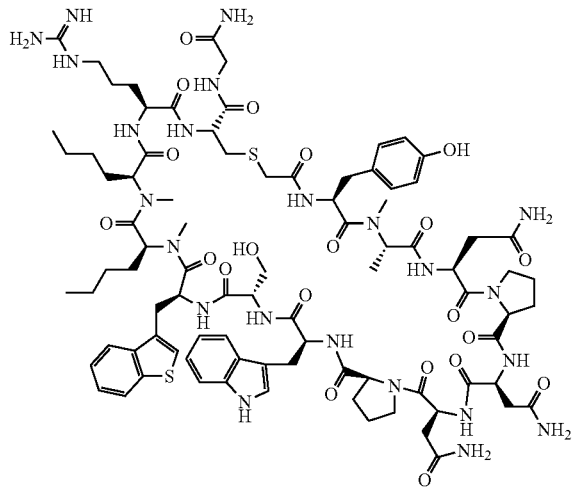

Example 10042

The crude material of Example 10042 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 19.7 mg, and its estimated purity by LCMS analysis was 100%.

Analysis condition A: Retention time=1.68 min; ESI-MS (+) m/z 945.40 (M+2H).

Analysis condition B: Retention time=3.13 min; ESI-MS (+) m/z 945.40 (M+2H).

ESI-HRMS(+) m/z: Calculated: 944.9347 (M+2H); Found: 944.9326 (M+2H).

Preparation of Example 10043

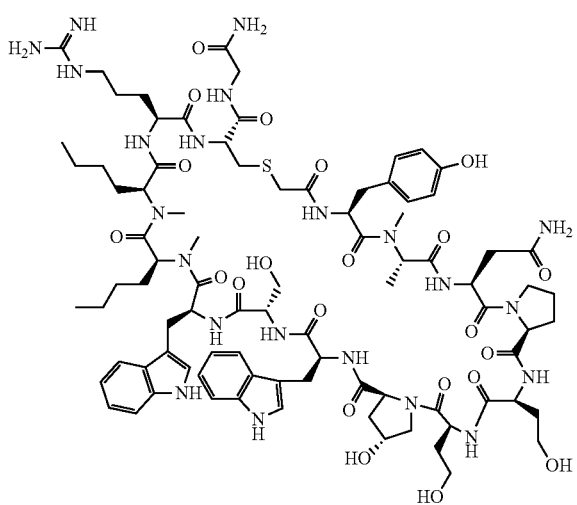

Example 10043

The crude material of Example 10043 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 19.0 mg, and its estimated purity by LCMS analysis was 100%.

Analysis condition A: Retention time=1.78 min; ESI-MS (+) m/z 931.80 (M+2H).

Analysis condition B: Retention time=2.57 min; ESI-MS (+) m/z 932.00 (M+2H).

ESI-HRMS(+) m/z: Calculated: 931.4563 (M+2H); Found: 931.4546 (M+2H).

Preparation of Example 10044

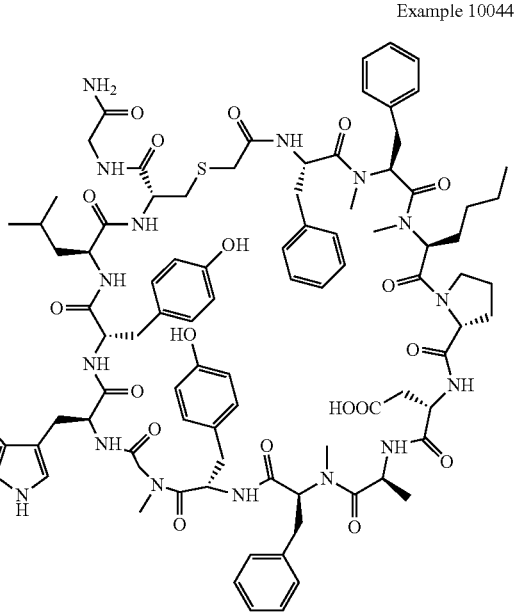

Example 10044

The crude material of Example 10044 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 29.4 mg, and its estimated purity by LCMS analysis was 100%.

Analysis condition A: Retention time=1.68 min; ESI-MS (+) m/z 897.95 (M+2H).

Analysis condition B: Retention time=3.31 min; ESI-MS (+) m/z 897.85 (M+2H).

Preparation of Example 10045

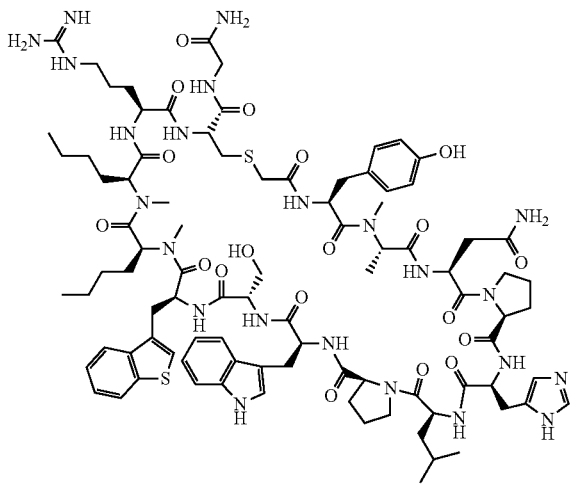

Example 10045

The crude material of Example 10045 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 28.5 mg, and its estimated purity by LCMS analysis was 97%.

Analysis condition A: Retention time=1.70 min; ESI-MS (+) m/z 956.3 (M+2H).

Analysis condition B: Retention time=3.18 min; ESI-MS (+) m/z 956.3 (M+2H).

ESI-HRMS(+) m/z: Calculated: 955.9633 (M+2H); Found: 955.9613 (M+2H).

Preparation of Example 10047

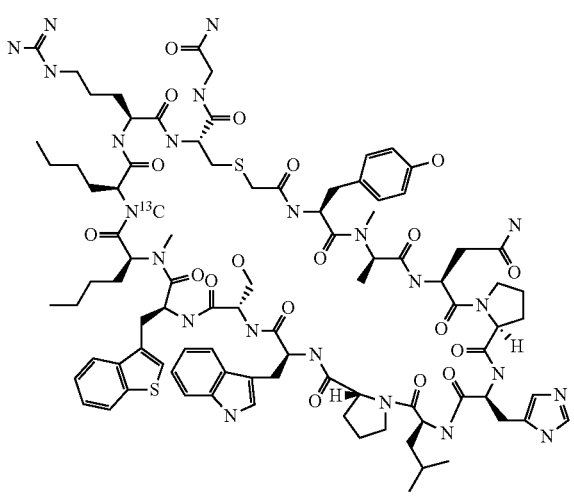

Example 10047

The crude material of Example 10047 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 38.6 mg, and its estimated purity by LCMS analysis was 98%.

Analysis condition A: Retention time=1.71 min; ESI-MS (+) m/z 957.35 (M+2H).

Analysis condition B: Retention time=3.17 min; ESI-MS (+) m/z 957.30 (M+2H).

ESI-HRMS(+) m/z: Calculated: 956.4672 (M+2H); Found: 956.4629 (M+2H).

Preparation of Example 10049

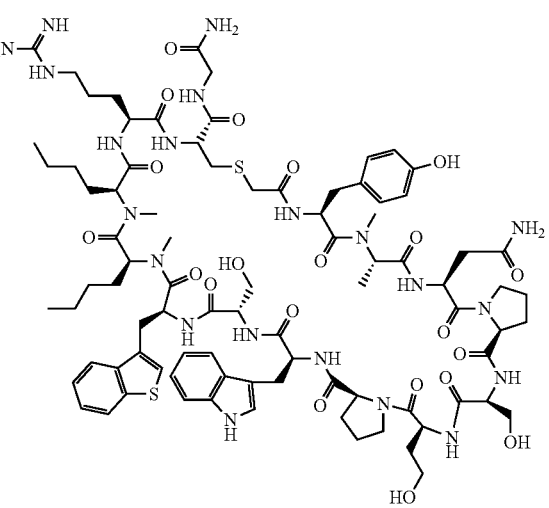

Example 10049

The crude material of Example 10049 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 36.2 mg, and its estimated purity by LCMS analysis was 98%.

Analysis condition A: Retention time=1.69 min; ESI-MS (+) m/z 932.45 (M+2H).

Analysis condition B: Retention time=3.14 min; ESI-MS (+) m/z 932.45 (M+2H).

ESI-HRMS(+) m/z: Calculated: 931.9395 (M+2H); Found: 931.9380 (M+2H).

Preparation of Example 10050

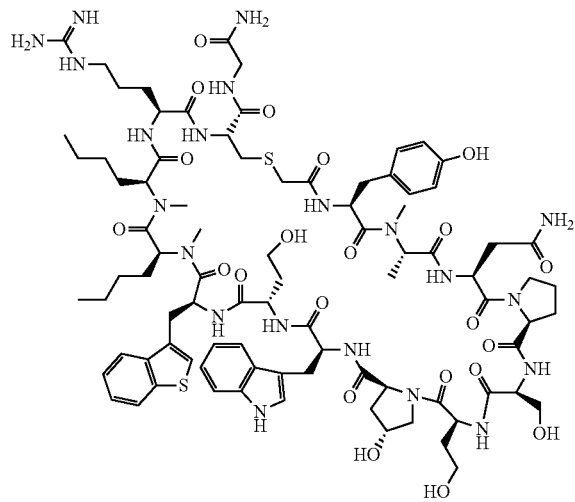

Example 10050

The crude material of Example 10050 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 12.0 mg, and its estimated purity by LCMS analysis was 99%.

Analysis condition A: Retention time=1.70 min; ESI-MS (+) m/z 940.40 (M+2H).

Analysis condition B: Retention time=3.14 min; ESI-MS (+) m/z 940.40 (M+2H).

ESI-HRMS(+) m/z: Calculated: 939.9369 (M+2H); Found: 939.9354 (M+2H).

Preparation of Example 10051

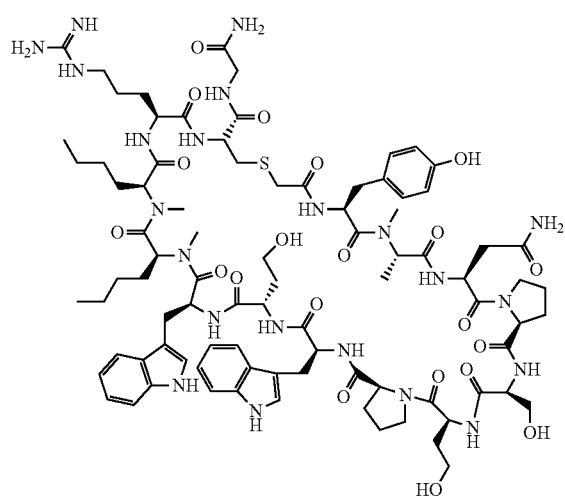

Example 10051

The crude material of Example 10051 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 20.1 mg, and its estimated purity by LCMS analysis was 99%.

Analysis condition A: Retention time=1.57 min; ESI-MS (+) m/z 923.90 (M+2H).

Analysis condition B: Retention time=2.95 min; ESI-MS (+) m/z 923.90 (M+2H).

ESI-HRMS(+) m/z: Calculated: 923.4589 (M+2H); Found: 923.4565 (M+2H).

Preparation of Example 10052

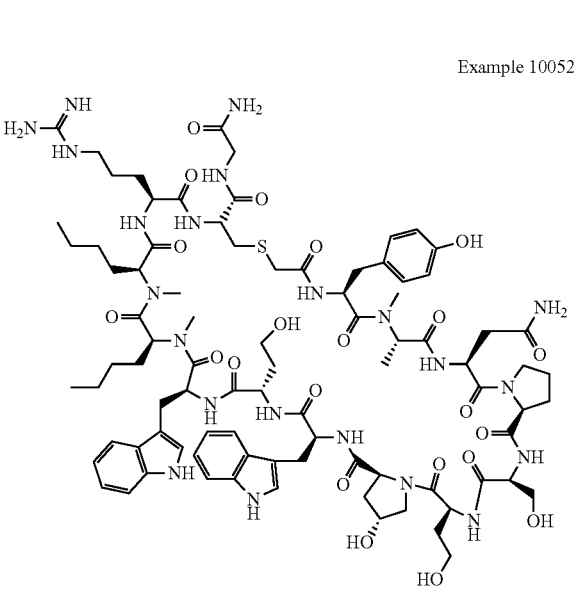

Example 10052

The crude material of Example 10052 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 22.2 mg, and its estimated purity by LCMS analysis was 100%.

Analysis condition A: Retention time=1.54 min; ESI-MS (+) m/z 931.90 (M+2H).

Analysis condition B: Retention time=2.94 min; ESI-MS (+) m/z 931.90 (M+2H).

ESI-HRMS(+) m/z: Calculated: 931.4563 (M+2H); Found: 931.4547 (M+2H).

Preparation of Example 10053

Example 10053

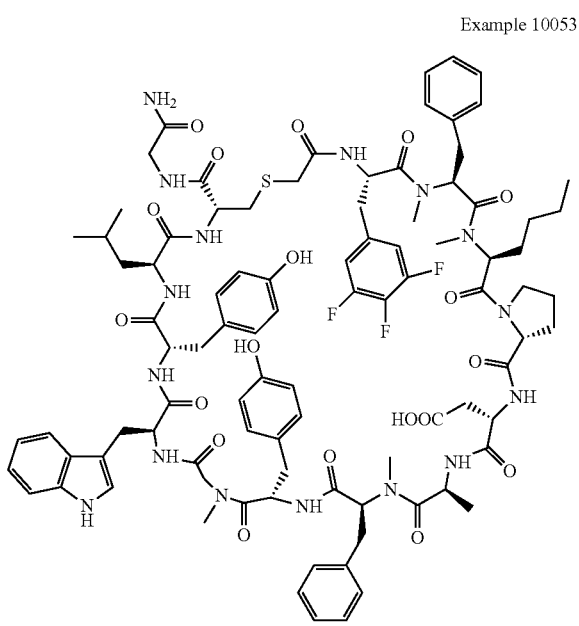 [SMILES: CCCC[C@H]1C(=O)N2CCC[C@@H]2C(=O)N[C@@H](CC(=O)O)C(=O)N[C@@H](C)C(=O)N(C)[C@@H](Cc2ccccc2)C(=O)N[C@@H](Cc2ccc(O)cc2)C(=O)N(C)CC(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2cc(F)c(F)c(F)c2)C(=O)N(C)[C@@H](Cc2ccccc2)C(=O)N1C]

The crude material of Example 10053 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 36.3 mg, and its estimated purity by LCMS analysis was 100%.

Analysis condition A: Retention time=1.79 min; ESI-MS (+) m/z 924.90 (M+2H).

Analysis condition B: Retention time=3.37 min; ESI-MS (+) m/z 925.00 (M+2H).

Preparation of Example 10054

Example 10054

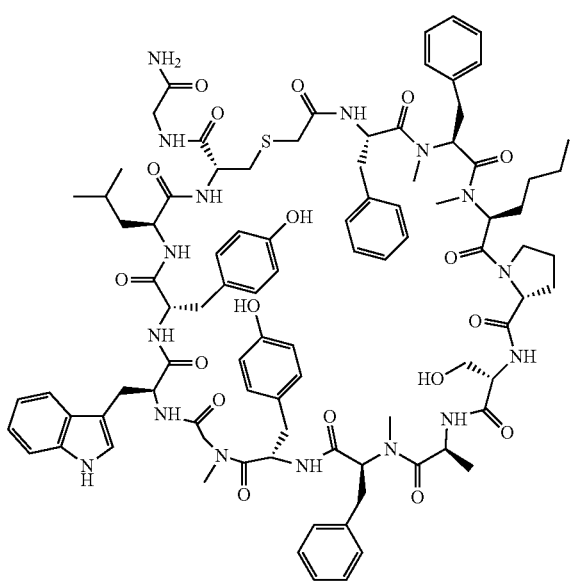

The crude material of Example 10054 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 32.5 mg, and its estimated purity by LCMS analysis was 97%.

Analysis condition A: Retention time=1.89 min; ESI-MS (+) m/z 883.95 (M+2H).

Analysis condition B: Retention time=3.38 min; ESI-MS (+) m/z 883.85 (M+2H).

Preparation of Example 10055

Example 10055

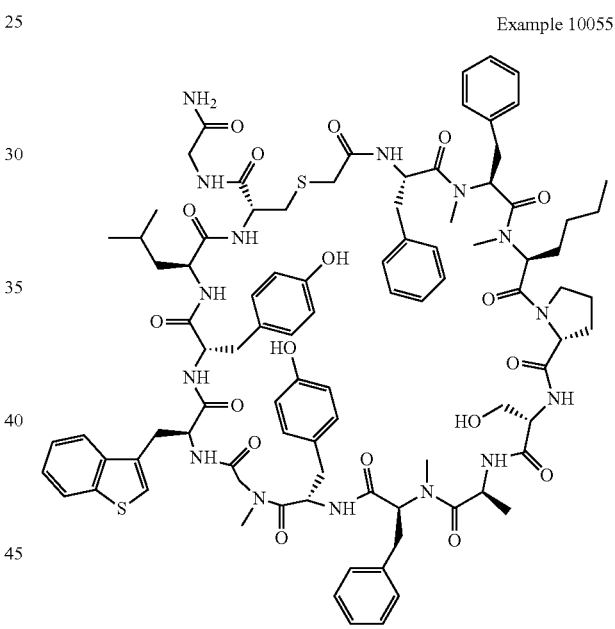

The crude material of Example 10055 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 29.6 mg, and its estimated purity by LCMS analysis was 100%.

Analysis condition A: Retention time=1.96 min; ESI-MS (+) m/z 892.15 (M+2H).

Analysis condition B: Retention time=3.09 min; ESI-MS (+) m/z 892.20 (M+2H).

Preparation of Example 10056

Example 10056

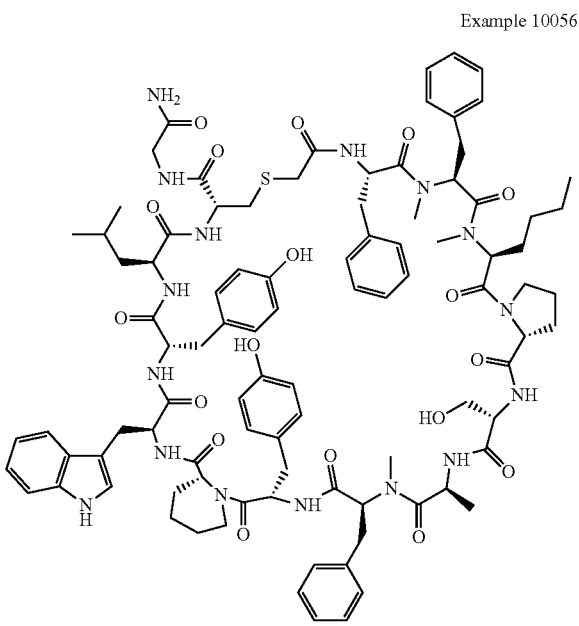 [SMILES: CCCC[C@H]1C(=O)N2CCC[C@@H]2C(=O)N[C@@H](CO)C(=O)N[C@@H](C)C(=O)N(C)[C@@H](Cc2ccccc2)C(=O)N[C@@H](Cc2ccc(O)cc2)C(=O)N2CCCC[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccccc2)C(=O)N(C)[C@@H](Cc2ccccc2)C(=O)N1C]

The crude material of Example 10056 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 41.0 mg, and its estimated purity by LCMS analysis was 100%.

Analysis condition A: Retention time=1.91 min; ESI-MS (+) m/z 903.50 (M+2H).

Analysis condition B: Retention time=3.40 min; ESI-MS (+) m/z 903.65 (M+2H).

ESI-HRMS(+) m/z: Calculated: 903.4416 (M+2H); Found: 903.4412 (M+2H).

Preparation of Example 10057

Example 10057

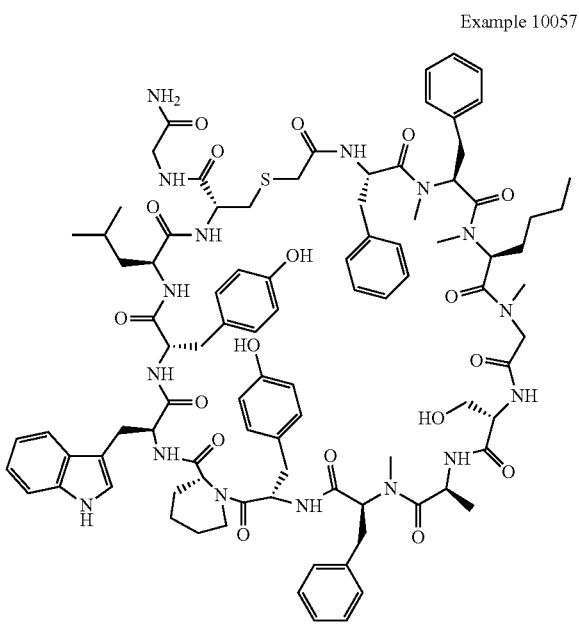 [SMILES: CCCC[C@H]1C(=O)N(C)CC(=O)N[C@@H](CO)C(=O)N[C@@H](C)C(=O)N(C)[C@@H](Cc2ccccc2)C(=O)N[C@@H](Cc2ccc(O)cc2)C(=O)N2CCCC[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccccc2)C(=O)N(C)[C@@H](Cc2ccccc2)C(=O)N1C]

The crude material of Example 10057 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 23.0 mg, and its estimated purity by LCMS analysis was 98%.

Analysis condition A: Retention time=1.79 min; ESI-MS (+) m/z 890.70 (M+2H).

Analysis condition B: Retention time=3.26 min; ESI-MS (+) m/z 891.05 (M+2H).

Preparation of Example 10058

Example 10058

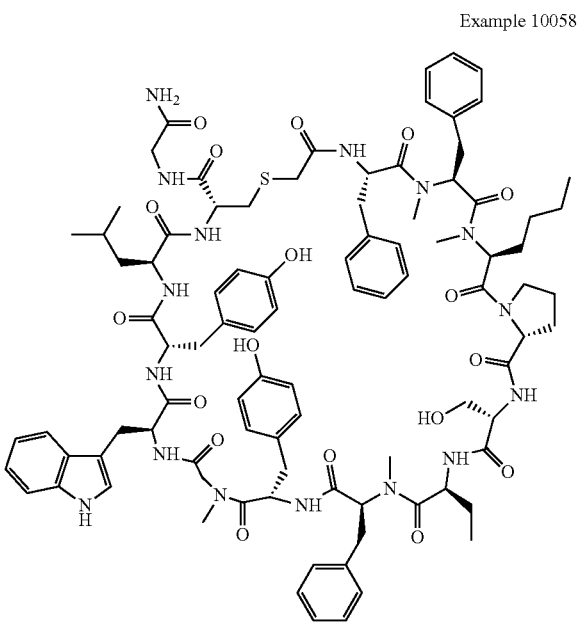 [SMILES: CCCC[C@H]1C(=O)N2CCC[C@@H]2C(=O)N[C@@H](CO)C(=O)N[C@@H](CC)C(=O)N(C)[C@@H](Cc2ccccc2)C(=O)N[C@@H](Cc2ccc(O)cc2)C(=O)N(C)CC(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccccc2)C(=O)N(C)[C@@H](Cc2ccccc2)C(=O)N1C]

The crude material of Example 10058 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 21.6 mg, and its estimated purity by LCMS analysis was 100%.

Analysis condition A: Retention time=1.92 min; ESI-MS (+) m/z 890.60 (M+2H).

Analysis condition B: Retention time=3.43 min; ESI-MS (+) m/z 890.65 (M+2H).

Preparation of Example 10059

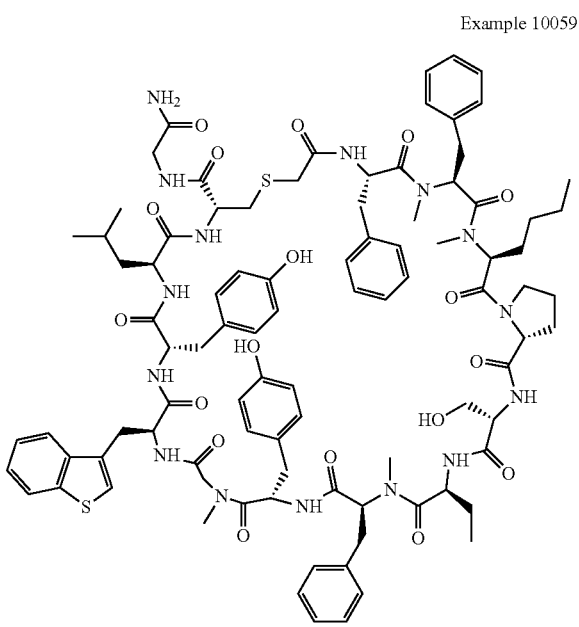 [SMILES: CCCC[C@H]1C(=O)N2CCC[C@@H]2C(=O)N[C@@H](CO)C(=O)N[C@@H](CC)C(=O)N(C)[C@@H](Cc2ccccc2)C(=O)N[C@@H](Cc2ccc(O)cc2)C(=O)N(C)CC(=O)N[C@@H](Cc2csc3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccccc2)C(=O)N(C)[C@@H](Cc2ccccc2)C(=O)N1C]

Example 10059

The crude material of Example 10059 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 26.7 mg, and its estimated purity by LCMS analysis was 100%.

Analysis condition A: Retention time=2.03 min; ESI-MS (+) m/z 899.00 (M+2H).

Analysis condition B: Retention time=3.15 min; ESI-MS (+) m/z 899.10 (M+2H).

ESI-HRMS(+) m/z: Calculated: 898.9144 (M+2H); Found: 898.9140 (M+2H).

Preparation of Example 10060

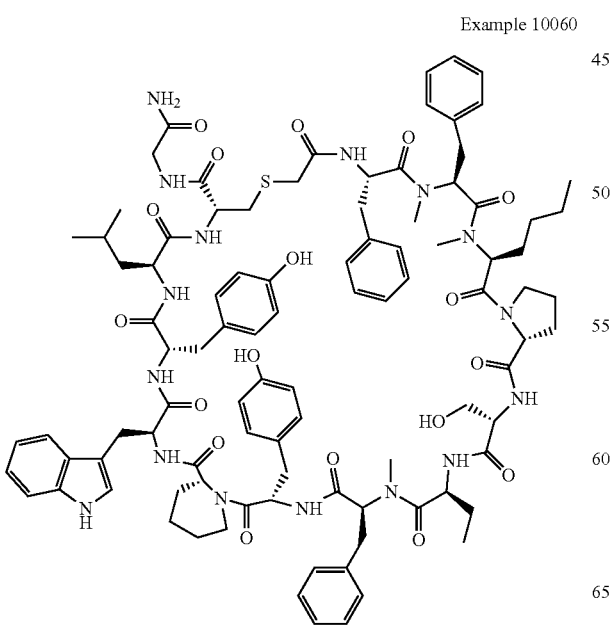

Example 10060

The crude material of Example 10060 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 27.4 mg, and its estimated purity by LCMS analysis was 100%.

Analysis condition A: Retention time=1.97 min; ESI-MS (+) m/z 910.60 (M+2H).

Analysis condition B: Retention time=3.46 min; ESI-MS (+) m/z 910.60 (M+2H).

ESI-HRMS(+) m/z: Calculated: 910.4495 (M+2H); Found: 910.4492 (M+2H).

Preparation of Example 10061

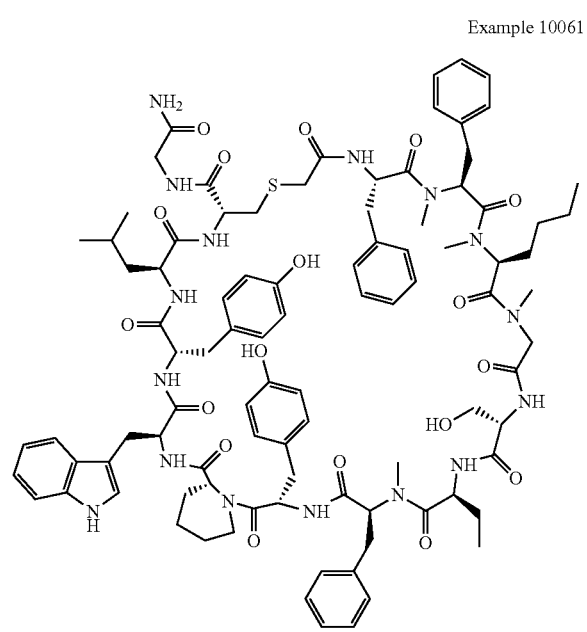 [SMILES: CCCC[C@H]1C(=O)N(C)CC(=O)N[C@@H](CO)C(=O)N[C@@H](CC)C(=O)N(C)[C@@H](Cc2ccccc2)C(=O)N[C@@H](Cc2ccc(O)cc2)C(=O)N2CCCC[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccccc2)C(=O)N(C)[C@@H](Cc2ccccc2)C(=O)N1C]

Example 10061

The crude material of Example 10061 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 29.3 mg, and its estimated purity by LCMS analysis was 97%.

Analysis condition A: Retention time=1.84 min; ESI-MS (+) m/z 897.60 (M+2H).

Analysis condition B: Retention time=3.33 min; ESI-MS (+) m/z 897.60 (M+2H).

Preparation of Example 10062

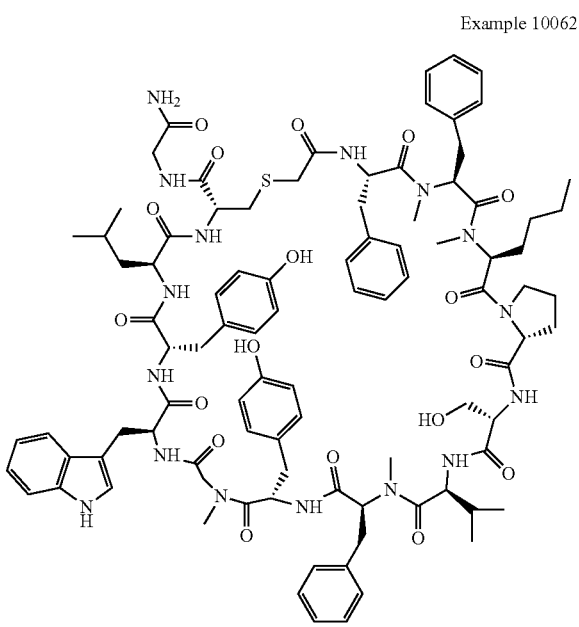 [SMILES: CCCC[C@H]1C(=O)N2CCC[C@@H]2C(=O)N[C@@H](CO)C(=O)N[C@@H](C(C)C)C(=O)N(C)[C@@H](Cc2ccccc2)C(=O)N[C@@H](Cc2ccc(O)cc2)C(=O)N(C)CC(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccccc2)C(=O)N(C)[C@@H](Cc2ccccc2)C(=O)N1C]

Example 10062

The crude material of Example 10062 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 28.7 mg, and its estimated purity by LCMS analysis was 100%.

Analysis condition A: Retention time=1.95 min; ESI-MS (+) m/z 897.30 (M+2H).

Analysis condition B: Retention time=3.49 min; ESI-MS (+) m/z 897.75 (M+2H).

Preparation of Example 10063

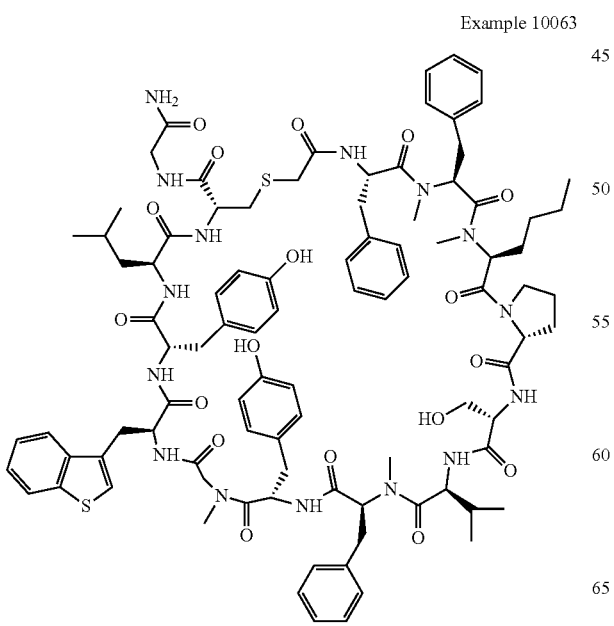

Example 10063

The crude material of Example 10063 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 26.8 mg, and its estimated purity by LCMS analysis was 100%.

Analysis condition A: Retention time=2.07 min; ESI-MS (+) m/z 906.05 (M+2H).

Analysis condition B: Retention time=3.16 min; ESI-MS (+) m/z 906.20 (M+2H).

ESI-HRMS(+) m/z: Calculated: 905.9222 (M+2H); Found: 905.9215 (M+2H).

Preparation of Example 10064

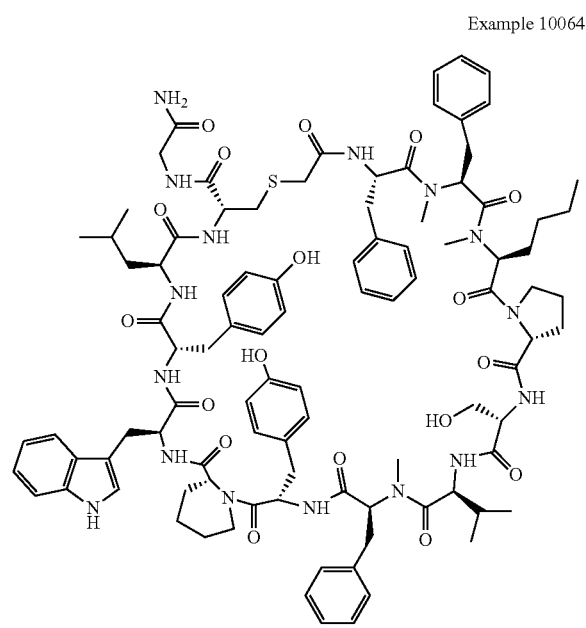 [SMILES: CCCC[C@H]1C(=O)N2CCC[C@@H]2C(=O)N[C@@H](CO)C(=O)N[C@@H](C(C)C)C(=O)N(C)[C@@H](Cc2ccccc2)C(=O)N[C@@H](Cc2ccc(O)cc2)C(=O)N2CCCC[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccccc2)C(=O)N(C)[C@@H](Cc2ccccc2)C(=O)N1C]

Example 10064

The crude material of Example 10064 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 23.4 mg, and its estimated purity by LCMS analysis was 100%.

Analysis condition A: Retention time=2.01 min; ESI-MS (+) m/z 917.85 (M+2H).

Analysis condition B: Retention time=3.05 min; ESI-MS (+) m/z 917.70 (M+2H).

ESI-HRMS(+) m/z: Calculated: 917.4573 (M+2H); Found: 917.4568 (M+2H).

Preparation of Example 10065

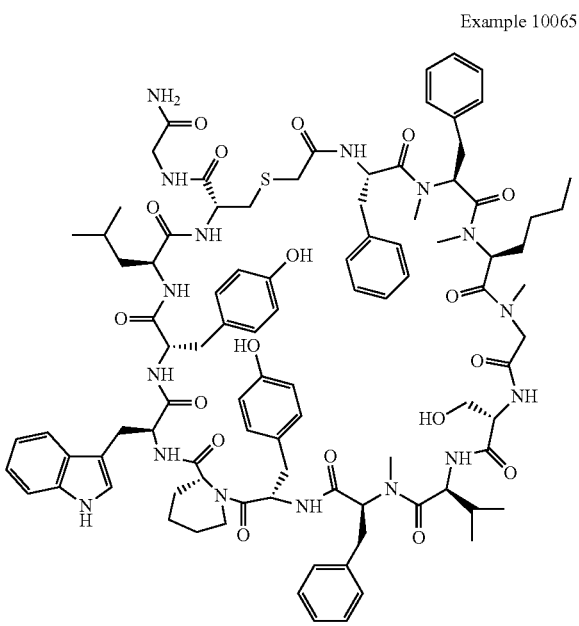 [SMILES: CCCC[C@H]1C(=O)N(C)CC(=O)N[C@@H](CO)C(=O)N[C@@H](C(C)C)C(=O)N(C)[C@@H](Cc2ccccc2)C(=O)N[C@@H](Cc2ccc(O)cc2)C(=O)N2CCCC[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccccc2)C(=O)N(C)[C@@H](Cc2ccccc2)C(=O)N1C]

Example 10065

The crude material of Example 10065 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 21.4 mg, and its estimated purity by LCMS analysis was 100%.

Analysis condition A: Retention time=1.89 min; ESI-MS (+) m/z 904.75 (M+2H).

Analysis condition B: Retention time=3.36 min; ESI-MS (+) m/z 904.45 (M+2H).

ESI-HRMS(+) m/z: Calculated: 904.4495 (M+2H); Found: 904.4494 (M+2H).

Preparation of Example 10066

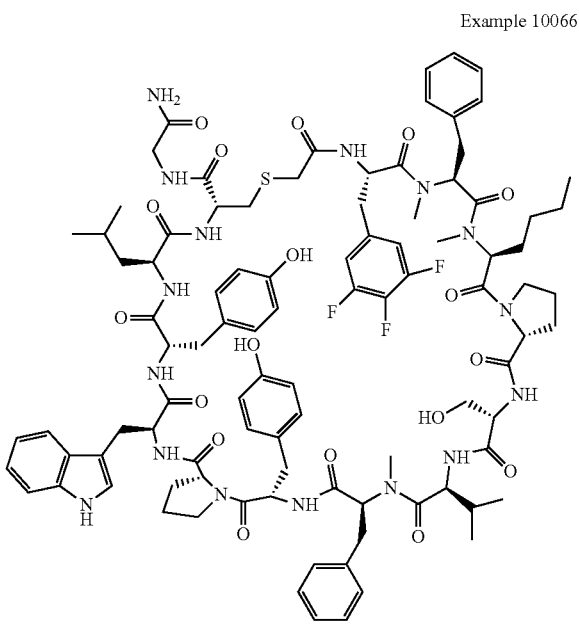 [SMILES: CCCC[C@H]1C(=O)N2CCC[C@@H]2C(=O)N[C@@H](CO)C(=O)N[C@@H](C(C)C)C(=O)N(C)[C@@H](Cc2ccccc2)C(=O)N[C@@H](Cc2ccc(O)cc2)C(=O)N2CCC[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2cc(F)c(F)c(F)c2)C(=O)N(C)[C@@H](Cc2ccccc2)C(=O)N1C]

Example 10066

The crude material of Example 10066 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 25.4 mg, and its estimated purity by LCMS analysis was 98%.

Analysis condition A: Retention time=2.02 min; ESI-MS (+) m/z 937.65 (M+2H).

Analysis condition B: Retention time=3.07 min; ESI-MS (+) m/z 937.65 (M+2H).

Preparation of Example 10067

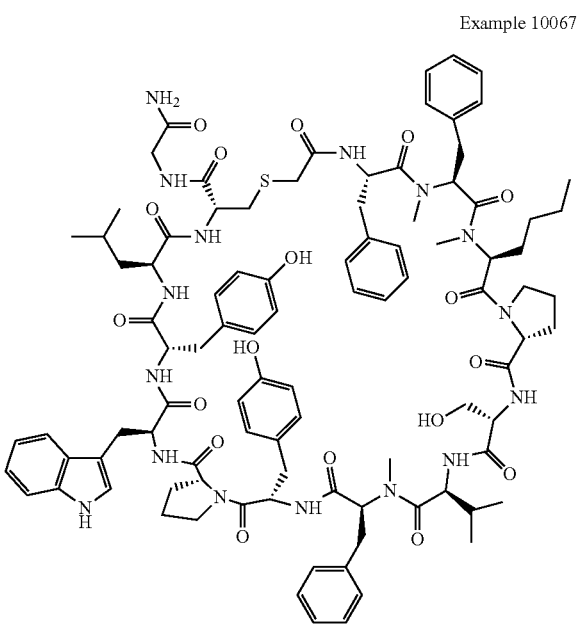 [SMILES: CCCC[C@H]1C(=O)N2CCC[C@@H]2C(=O)N[C@@H](CO)C(=O)N[C@@H](C(C)C)C(=O)N(C)[C@@H](Cc2ccccc2)C(=O)N[C@@H](Cc2ccc(O)cc2)C(=O)N2CCC[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccccc2)C(=O)N(C)[C@@H](Cc2ccccc2)C(=O)N1C]

Example 10067

The crude material of Example 10067 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 22.1 mg, and its estimated purity by LCMS analysis was 100%.

Analysis condition A: Retention time=1.95 min; ESI-MS (+) m/z 910.55 (M+2H).

Analysis condition B: Retention time=3.43 min; ESI-MS (+) m/z 910.60 (M+2H).

Preparation of Example 10068

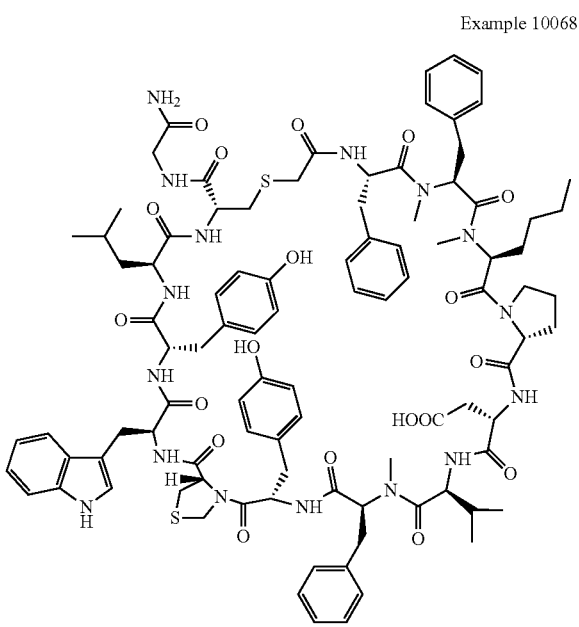 [SMILES: CCCC[C@H]1C(=O)N2CCC[C@@H]2C(=O)N[C@@H](CC(=O)O)C(=O)N[C@@H](C(C)C)C(=O)N(C)[C@@H](Cc2ccccc2)C(=O)N[C@@H](Cc2ccc(O)cc2)C(=O)N2CSC[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccccc2)C(=O)N(C)[C@@H](Cc2ccccc2)C(=O)N1C]

Example 10068

The crude material of Example 10068 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 13.7 mg, and its estimated purity by LCMS analysis was 100%.

Analysis condition A: Retention time=1.83 min; ESI-MS (+) m/z 933.60 (M+2H).

Analysis condition B: Retention time=2.53 min; ESI-MS (+) m/z 933.60 (M+2H).

ESI-HRMS(+) m/z: Calculated: 933.4251 (M+2H); Found: 933.4239 (M+2H).

Preparation of Example 10069

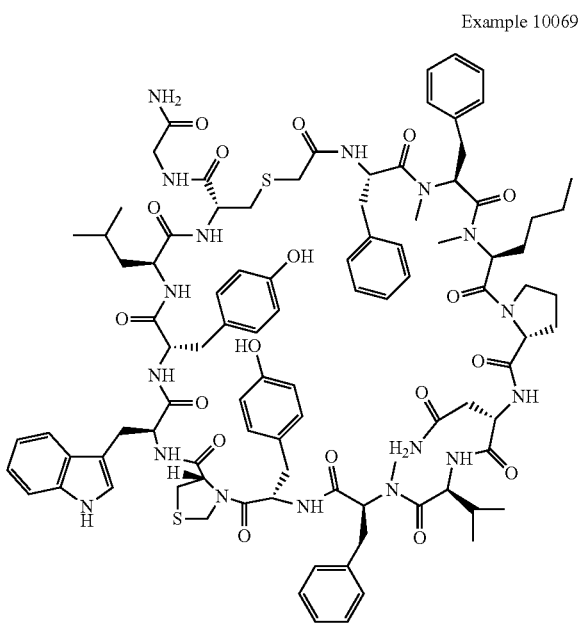 [SMILES: CCCC[C@H]1C(=O)N2CCC[C@@H]2C(=O)N[C@H]2CC(=O)NN(C(=O)[C@H](C(C)C)NC2=O)[C@@H](Cc2ccccc2)C(=O)N[C@@H](Cc2ccc(O)cc2)C(=O)N2CSC[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccccc2)C(=O)N(C)[C@@H](Cc2ccccc2)C(=O)N1C]

Example 10069

The crude material of Example 10069 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 15.4 mg, and its estimated purity by LCMS analysis was 100%.

Analysis condition A: Retention time=2.02 min; ESI-MS (+) m/z 933.20 (M+2H).

ESI-HRMS(+) m/z: Calculated: 932.9331 (M+2H); Found: 932.9326 (M+2H).

Preparation of Example 10070

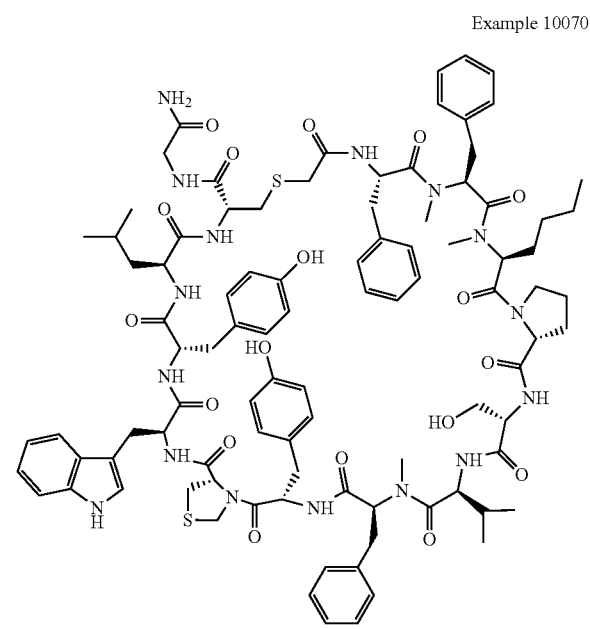 [SMILES: CCCC[C@H]1C(=O)N2CCC[C@@H]2C(=O)N[C@@H](CO)C(=O)N[C@@H](C(C)C)C(=O)N(C)[C@@H](Cc2ccccc2)C(=O)N[C@@H](Cc2ccc(O)cc2)C(=O)N2CSC[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccccc2)C(=O)N(C)[C@@H](Cc2ccccc2)C(=O)N1C]

Example 10070

The crude material of Example 10070 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 12.0 mg, and its estimated purity by LCMS analysis was 97%.

Analysis condition A: Retention time=2.05 min; ESI-MS (+) m/z 920.00 (M+2H).

Analysis condition B: Retention time=2.79 min; ESI-MS (+) m/z 919.60 (M+2H).

ESI-HRMS(+) m/z: Calculated: 919.4277 (M+2H); Found: 919.4267 (M+2H).

Preparation of Example 10071

Example 10071

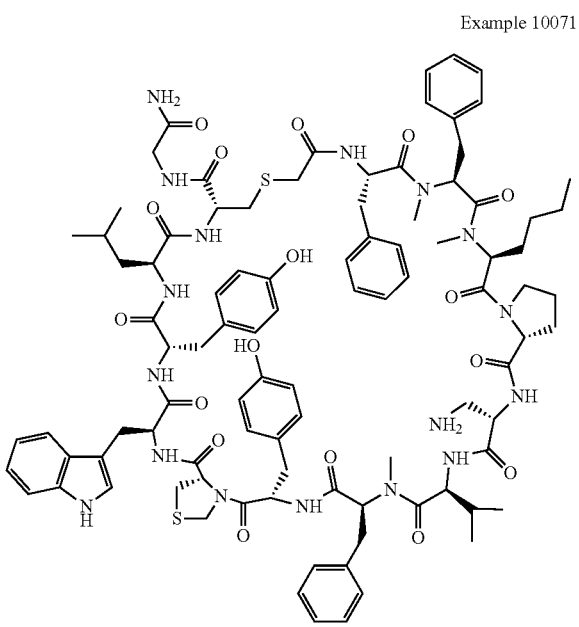 [SMILES: CCCC[C@H]1C(=O)N2CCC[C@@H]2C(=O)N[C@@H](CN)C(=O)N[C@@H](C(C)C)C(=O)N(C)[C@@H](Cc2ccccc2)C(=O)N[C@@H](Cc2ccc(O)cc2)C(=O)N2CSC[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccccc2)C(=O)N(C)[C@@H](Cc2ccccc2)C(=O)N1C]

The crude material of Example 10071 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 16.0 mg, and its estimated purity by LCMS analysis was 100%.

Analysis condition A: Retention time=1.94 min; ESI-MS (+) m/z 918.75 (M+2H).

Analysis condition B: Retention time=3.46 min; ESI-MS (+) m/z 919.75 (M+2H).

ESI-HRMS(+) m/z: Calculated: 918.9357 (M+2H); Found: 918.9330 (M+2H).

Preparation of Example 10072

Example 10072

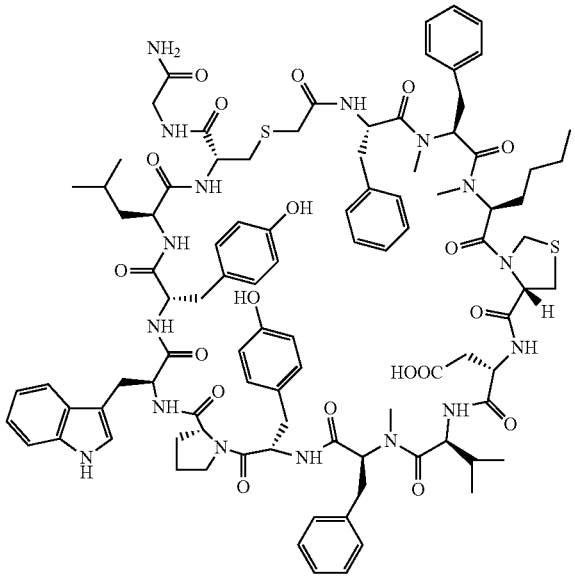

The crude material of Example 10072 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 9.5 mg, and its estimated purity by LCMS analysis was 95%.

Analysis condition A: Retention time=1.80 min; ESI-MS (+) m/z 933.55 (M+2H).

Analysis condition B: Retention time=2.48 min; ESI-MS (+) m/z 933.00 (M+2H).

ESI-HRMS(+) m/z: Calculated: 933.4251 (M+2H); Found: 933.4245 (M+2H).

Preparation of Example 10073

Example 10073

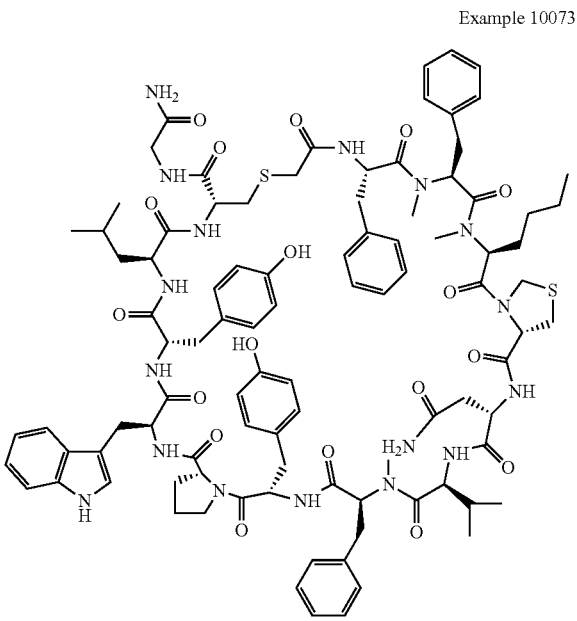 [SMILES: CCCC[C@H]1C(=O)N2CSC[C@@H]2C(=O)N[C@H]2CC(=O)NN(C(=O)[C@H](C(C)C)NC2=O)[C@@H](Cc2ccccc2)C(=O)N[C@@H](Cc2ccc(O)cc2)C(=O)N2CCC[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccccc2)C(=O)N(C)[C@@H](Cc2ccccc2)C(=O)N1C]

The crude material of Example 10073 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 5.8 mg, and its estimated purity by LCMS analysis was 100%.

Analysis condition A: Retention time=1.97 min; ESI-MS (+) m/z 933.45 (M+2H).

Analysis condition B: Retention time=2.67 min; ESI-MS (+) m/z 932.90 (M+2H).

ESI-HRMS(+) m/z: Calculated: 932.9331 (M+2H); Found: 932.9324 (M+2H).

Preparation of Example 10074

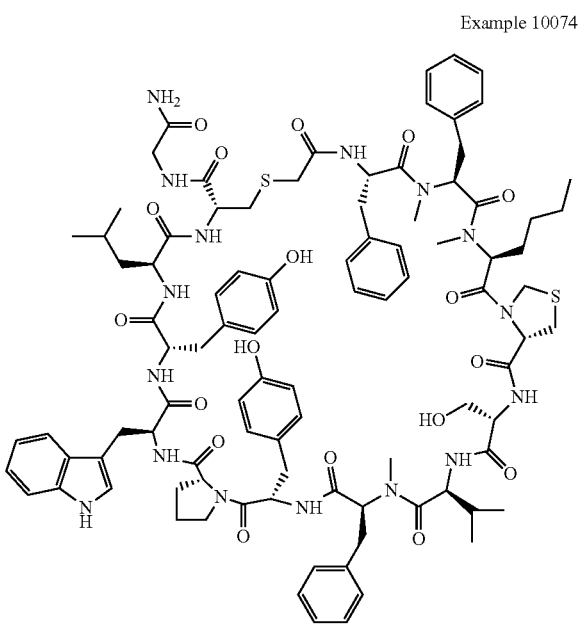 [SMILES: CCCC[C@H]1C(=O)N2CSC[C@@H]2C(=O)N[C@@H](CN)C(=O)N[C@@H](C(C)C)C(=O)N(C)[C@@H](Cc2ccccc2)C(=O)N[C@@H](Cc2ccc(O)cc2)C(=O)N2CCC[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccccc2)C(=O)N(C)[C@@H](Cc2ccccc2)C(=O)N1C]

Example 10074

The crude material of Example 10074 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 3.0 mg, and its estimated purity by LCMS analysis was 100%.

Analysis condition A: Retention time=2.01 min; ESI-MS (+) m/z 919.60 (M+2H).

ESI-HRMS(+) m/z: Calculated: 919.4277 (M+2H); Found: 919.4265 (M+2H).

Preparation of Example 10075

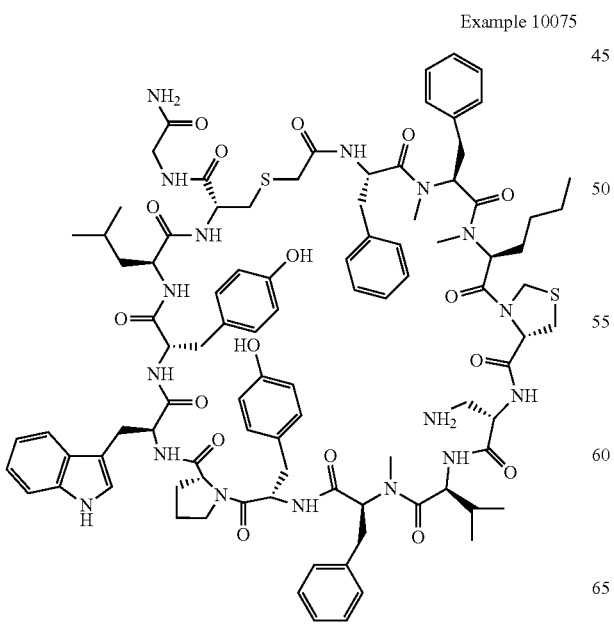

Example 10075

The crude material of Example 10075 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 8.0 mg, and its estimated purity by LCMS analysis was 100%.

Analysis condition A: Retention time=1.90 min; ESI-MS (+) m/z 919.10 (M+2H).

Analysis condition B: Retention time=2.62 min; ESI-MS (+) m/z 919.00 (M+2H).

ESI-HRMS(+) m/z: Calculated: 918.9357 (M+2H); Found: 918.9337 (M+2H).

Preparation of Example 10076

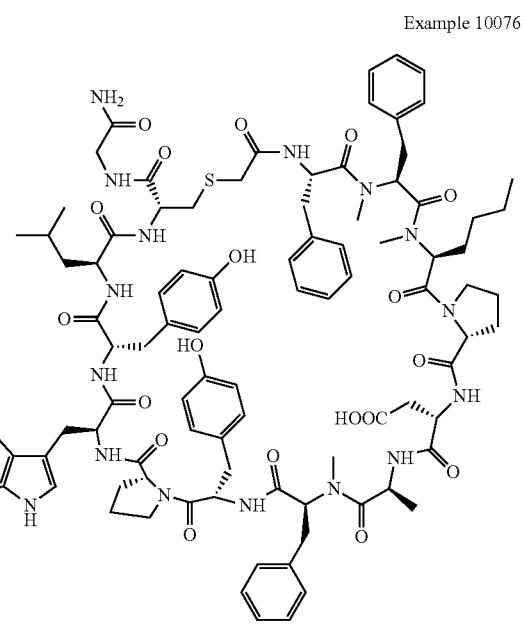

Example 10076

The crude material of Example 10076 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 18.9 mg, and its estimated purity by LCMS analysis was 100%.

Analysis condition A: Retention time=1.75 min; ESI-MS (+) m/z 910.85 (M+2H).

Analysis condition B: Retention time=2.36 min; ESI-MS (+) m/z 910.60 (M+2H).

ESI-HRMS(+) m/z: Calculated: 910.4313 (M+2H); Found: 910.4301 (M+2H).

Preparation of Example 10077

Example 10077

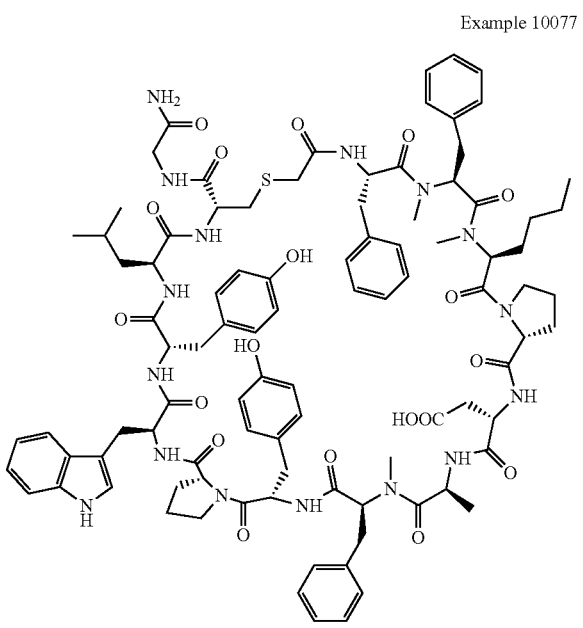 [SMILES: CCCC[C@H]1C(=O)N2CCC[C@@H]2C(=O)N[C@@H](CC(=O)O)C(=O)N[C@@H](C)C(=O)N(C)[C@@H](Cc2ccccc2)C(=O)N[C@@H](Cc2ccc(O)cc2)C(=O)N2CCC[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccccc2)C(=O)N(C)[C@@H](Cc2ccccc2)C(=O)N1C]

The crude material of Example 10077 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 6.3 mg, and its estimated purity by LCMS analysis was 98%.

Analysis condition A: Retention time=2.44 min; ESI-MS (+) m/z 924.65 (M+2H).

Analysis condition B: Retention time=3.37 min; ESI-MS (+) m/z 924.70 (M+2H).

ESI-HRMS(+) m/z: Calculated: 924.4469 (M+2H); Found: 924.4455 (M+2H).

Preparation of Example 10078

Example 10078

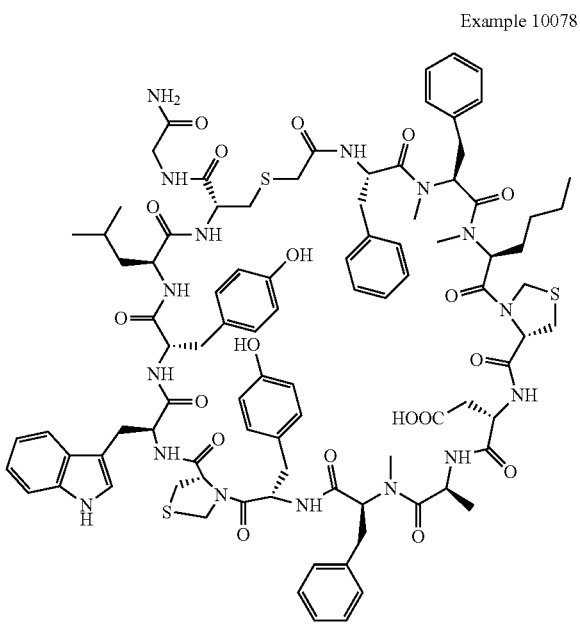 [SMILES: CCCC[C@H]1C(=O)N2CSC[C@@H]2C(=O)N[C@@H](CC(=O)O)C(=O)N[C@@H](C)C(=O)N(C)[C@@H](Cc2ccccc2)C(=O)N[C@@H](Cc2ccc(O)cc2)C(=O)N2CSC[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccccc2)C(=O)N(C)[C@@H](Cc2ccccc2)C(=O)N1C]

The crude material of Example 10078 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 4.6 mg, and its estimated purity by LCMS analysis was 96%.

Analysis condition A: Retention time=1.84 min; ESI-MS (+) m/z 929.05 (M+2H).

Analysis condition B: Retention time=3.46 min; ESI-MS (+) m/z 929.20 (M+2H).

ESI-HRMS(+) m/z: Calculated: 928.3877 (M+2H); Found: 928.3871 (M+2H).

Preparation of Example 10079

Example 10079

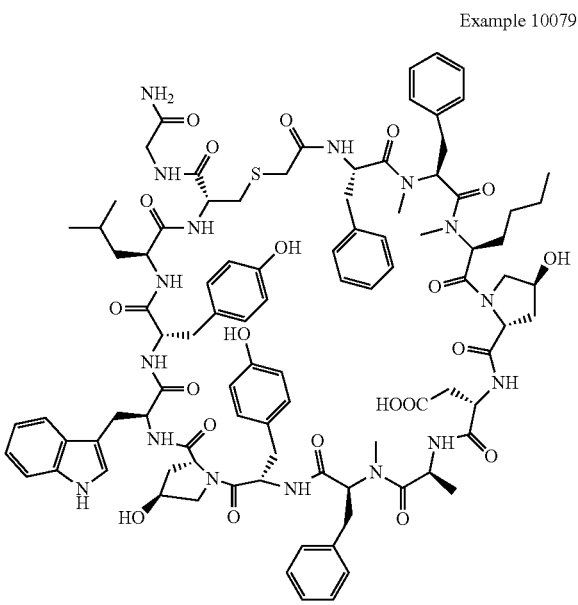 [SMILES: CCCC[C@H]1C(=O)N2C[C@@H](O)C[C@@H]2C(=O)N[C@@H](CC(=O)O)C(=O)N[C@@H](C)C(=O)N(C)[C@@H](Cc2ccccc2)C(=O)N[C@@H](Cc2ccc(O)cc2)C(=O)N2C[C@@H](O)C[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccccc2)C(=O)N(C)[C@@H](Cc2ccccc2)C(=O)N1C]

The crude material of Example 10079 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 13.1 mg, and its estimated purity by LCMS analysis was 99%.

Analysis condition A: Retention time=1.65 min; ESI-MS (+) m/z 926.55 (M+2H).

Analysis condition B: Retention time=3.18 min; ESI-MS (+) m/z 926.60 (M+2H).

ESI-HRMS(+) m/z: Calculated: 926.4262 (M+2H); Found: 926.4252 (M+2H).

Preparation of Example 10080

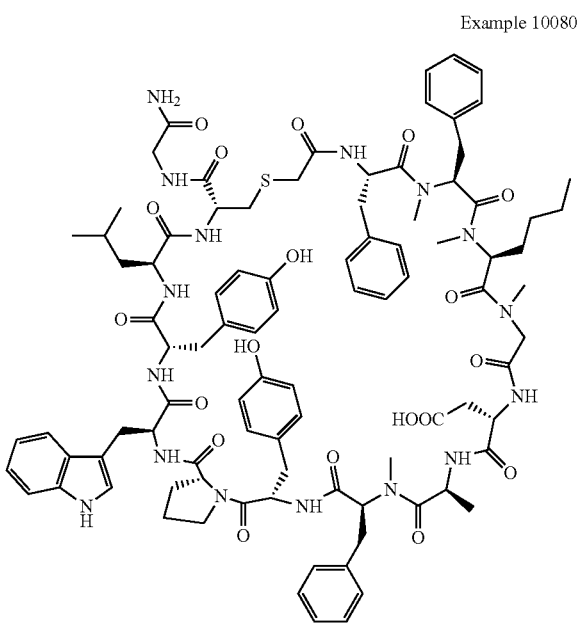 [SMILES: CCCC[C@H]1C(=O)N(C)CC(=O)N[C@@H](CC(=O)O)C(=O)N[C@@H](C)C(=O)N(C)[C@@H](Cc2ccccc2)C(=O)N[C@@H](Cc2ccc(O)cc2)C(=O)N2CCC[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccccc2)C(=O)N(C)[C@@H](Cc2ccccc2)C(=O)N1C]

Example 10080

The crude material of Example 10080 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 0.5 mg, and its estimated purity by LCMS analysis was 100%.

Analysis condition A: Retention time=1.59 min; ESI-MS (+) m/z 897.70 (M+2H).

Analysis condition B: Retention time=3.14 min; ESI-MS (+) m/z 897.70 (M+2H).

ESI-HRMS(+) m/z: Calculated: 897.4234 (M+2H); Found: 897.4224 (M+2H).

Preparation of Example 10081

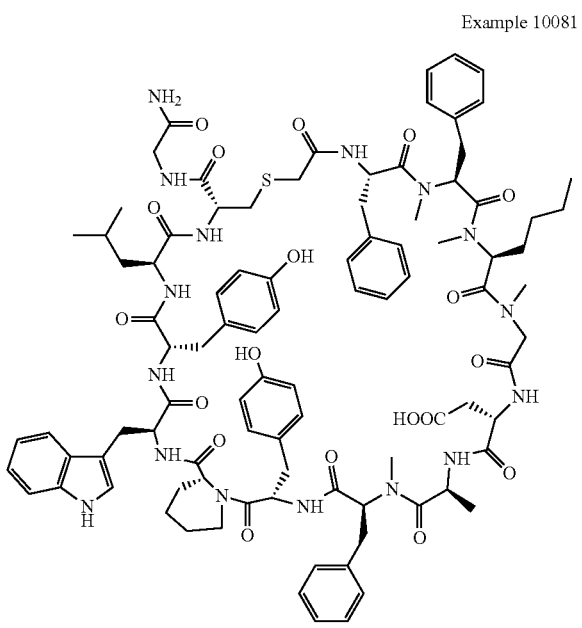 [SMILES: CCCC[C@H]1C(=O)N(C)CC(=O)N[C@@H](CC(=O)O)C(=O)N[C@@H](C)C(=O)N(C)[C@@H](Cc2ccccc2)C(=O)N[C@@H](Cc2ccc(O)cc2)C(=O)N2CCCC[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccccc2)C(=O)N(C)[C@@H](Cc2ccccc2)C(=O)N1C]

Example 10081

The crude material of Example 10081 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 21.3 mg, and its estimated purity by LCMS analysis was 96%.

Analysis condition A: Retention time=1.72 min; ESI-MS (+) m/z 904.60 (M+2H).

Analysis condition B: Retention time=2.32 min; ESI-MS (+) m/z 904.55 (M+2H).

ESI-HRMS(+) m/z: Calculated: 904.4313 (M+2H); Found: 904.4304 (M+2H).

Preparation of Example 10082

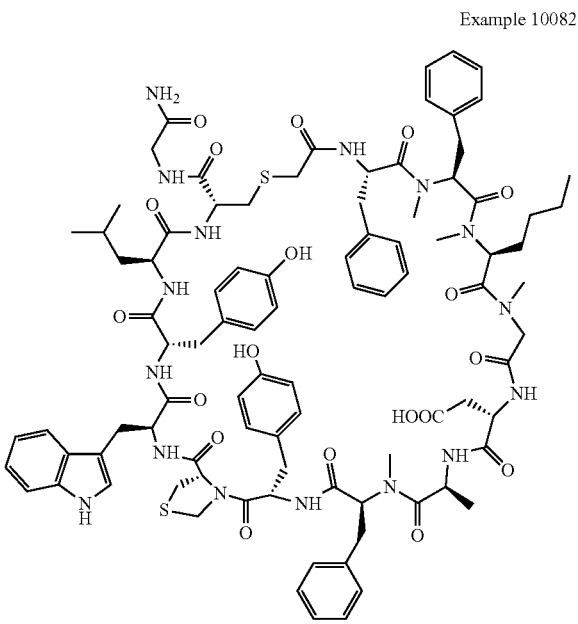 [SMILES: CCCC[C@H]1C(=O)N(C)CC(=O)N[C@@H](CC(=O)O)C(=O)N[C@@H](C)C(=O)N(C)[C@@H](Cc2ccccc2)C(=O)N[C@@H](Cc2ccc(O)cc2)C(=O)N2CSC[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccccc2)C(=O)N(C)[C@@H](Cc2ccccc2)C(=O)N1C]

Example 10082

The crude material of Example 10082 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 24.1 mg, and its estimated purity by LCMS analysis was 100%.

Analysis condition A: Retention time=1.73 min; ESI-MS (+) m/z 906.70 (M+2H).

Analysis condition B: Retention time=3.29 min; ESI-MS (+) m/z 906.65 (M+2H).

ESI-HRMS(+) m/z: Calculated: 906.4017 (M+2H); Found: 906.4014 (M+2H).

Preparation of Example 10083

Example 10083

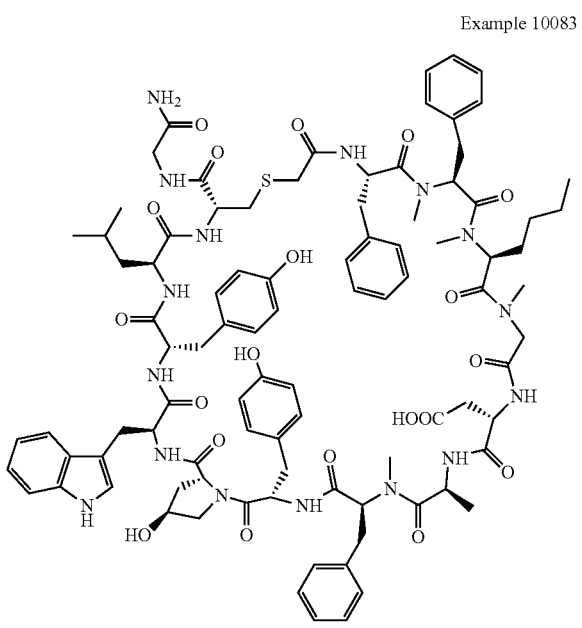 [SMILES: CCCC[C@H]1C(=O)N(C)CC(=O)N[C@@H](CC(=O)O)C(=O)N[C@@H](C)C(=O)N(C)[C@@H](Cc2ccccc2)C(=O)N[C@@H](Cc2ccc(O)cc2)C(=O)N2C[C@@H](O)C[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccccc2)C(=O)N(C)[C@@H](Cc2ccccc2)C(=O)N1C]

The crude material of Example 10083 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 8.3 mg, and its estimated purity by LCMS analysis was 100%.

Analysis condition A: Retention time=1.48 min; ESI-MS (+) m/z 905.80 (M+2H).

Analysis condition B: Retention time=2.90 min; ESI-MS (+) m/z 905.70 (M+2H).

ESI-HRMS(+) m/z: Calculated: 905.4209 (M+2H); Found: 905.4196 (M+2H).

Preparation of Example 10084

Example 10084

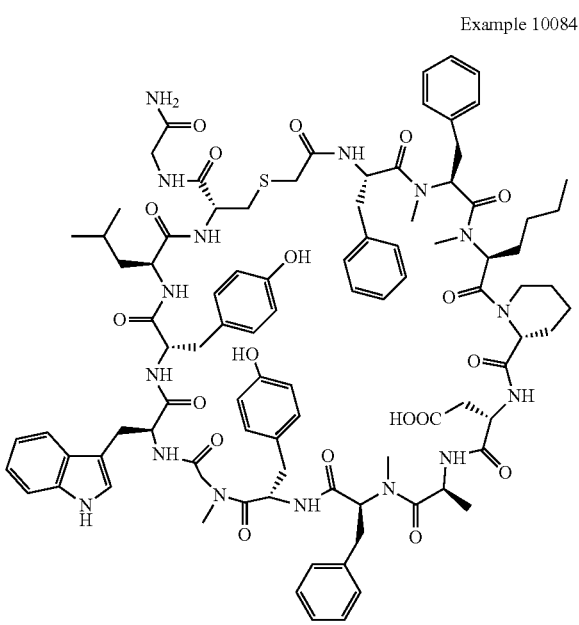 [SMILES: CCCC[C@H]1C(=O)N2CCCC[C@@H]2C(=O)N[C@@H](CC(=O)O)C(=O)N[C@@H](C)C(=O)N(C)[C@@H](Cc2ccccc2)C(=O)N[C@@H](Cc2ccc(O)cc2)C(=O)N(C)CC(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccccc2)C(=O)N(C)[C@@H](Cc2ccccc2)C(=O)N1C]

The crude material of Example 10084 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 12.6 mg, and its estimated purity by LCMS analysis was 98%.

Analysis condition A: Retention time=1.81 min; ESI-MS (+) m/z 904.45 (M+2H).

Analysis condition B: Retention time=3.36 min; ESI-MS (+) m/z 904.60 (M+2H).

ESI-HRMS(+) m/z: Calculated: 904.4313 (M+2H); Found: 904.4304 (M+2H).

Preparation of Example 10085

Example 10085

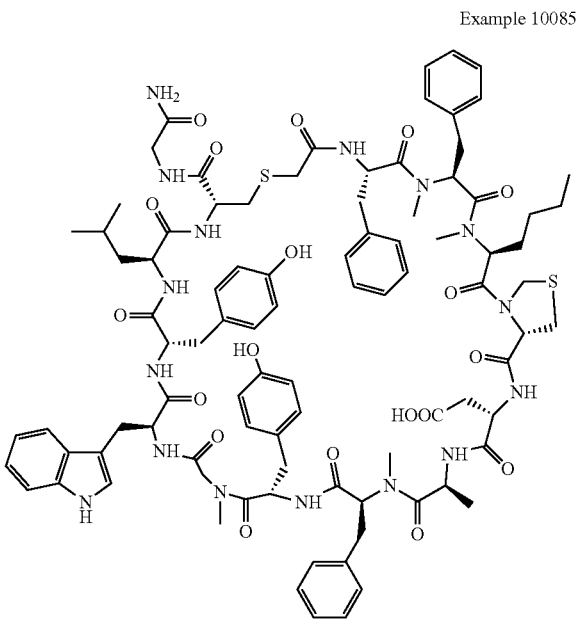 [SMILES: CCCC[C@H]1C(=O)N2CSC[C@@H]2C(=O)N[C@@H](CC(=O)O)C(=O)N[C@@H](C)C(=O)N(C)[C@@H](Cc2ccccc2)C(=O)N[C@@H](Cc2ccc(O)cc2)C(=O)N(C)CC(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccccc2)C(=O)N(C)[C@@H](Cc2ccccc2)C(=O)N1C]

The crude material of Example 10085 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 10.6 mg, and its estimated purity by LCMS analysis was 100%.

Analysis condition A: Retention time=1.77 min; ESI-MS (+) m/z 907.35 (M+2H).

Analysis condition B: Retention time=3.38 min; ESI-MS (+) m/z 906.50 (M+2H).

ESI-HRMS(+) m/z: Calculated: 906.4017 (M+2H); Found: 906.4011 (M+2H).

Preparation of Example 10086

Example 10086

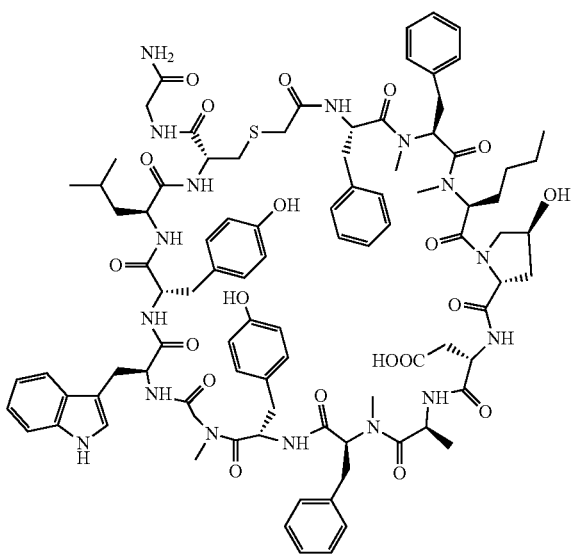

The crude material of Example 10086 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 10.6 mg, and its estimated purity by LCMS analysis was 100%.

Analysis condition A: Retention time=1.63 min; ESI-MS (+) m/z 905.65 (M+2H).

Analysis condition B: Retention time=2.98 min; ESI-MS (+) m/z 905.65 (M+2H).

ESI-HRMS(+) m/z: Calculated: 905.4209 (M+2H); Found: 905.4198 (M+2H).

Preparation of Example 10087

Example 10087

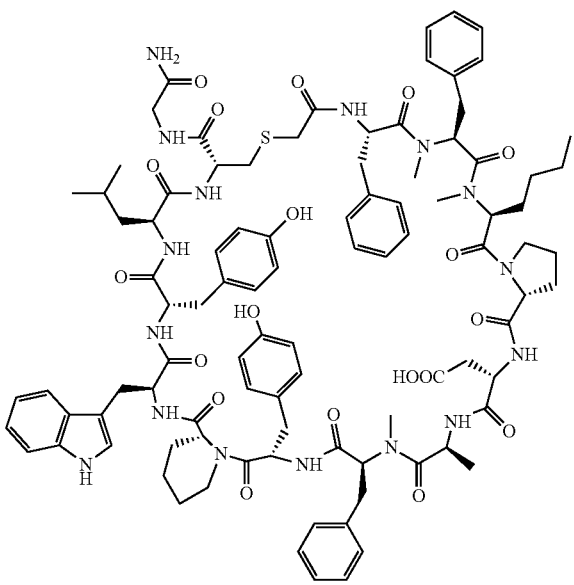

The crude material of Example 10087 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 20.1 mg, and its estimated purity by LCMS analysis was 100%.

Analysis condition A: Retention time=1.80 min; ESI-MS (+) m/z 917.45 (M+2H).

Analysis condition B: Retention time=3.40 min; ESI-MS (+) m/z 917.70 (M+2H).

ESI-HRMS(+) m/z: Calculated: 917.4391 (M+2H); Found: 917.4378 (M+2H).

Preparation of Example 10088

Example 10088

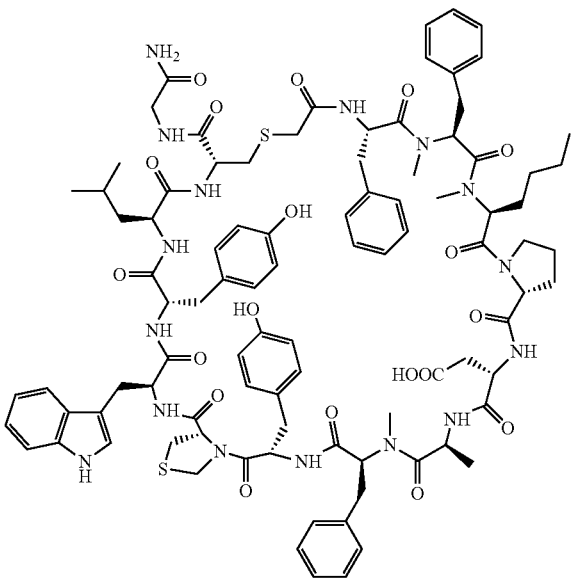

The crude material of Example 10088 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 8.3 mg, and its estimated purity by LCMS analysis was 100%.

Analysis condition A: Retention time=1.72 min; ESI-MS (+) m/z 919.90 (M+2H).

Analysis condition B: Retention time=3.33 min; ESI-MS (+) m/z 919.95 (M+2H).

ESI-HRMS(+) m/z: Calculated: 919.4095 (M+2H); Found: 919.4090 (M+2H).

Preparation of Example 10089

Example 10089

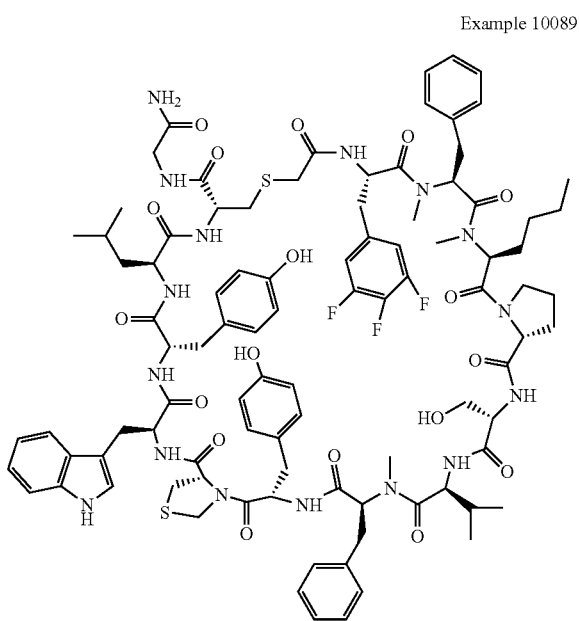 [SMILES: CCCC[C@H]1C(=O)N2CCC[C@@H]2C(=O)N[C@@H](CO)C(=O)N[C@@H](C(C)C)C(=O)N(C)[C@@H](Cc2ccccc2)C(=O)N[C@@H](Cc2ccc(O)cc2)C(=O)N2CSC[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2cc(F)c(F)c(F)c2)C(=O)N(C)[C@@H](Cc2ccccc2)C(=O)N1C]

The crude material of Example 10089 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 13.6 mg, and its estimated purity by LCMS analysis was 99%.

Analysis condition A: Retention time=2.14 min; ESI-MS (−) m/z 945.30 (M−2H).

Analysis condition B: Retention time=3.19 min; ESI-MS (+) m/z 947.10 (M+2H).

ESI-HRMS(+) m/z: Calculated: 946.4135 (M+2H); Found: 946.4148 (M+2H).

Preparation of Example 10090

Example 10090

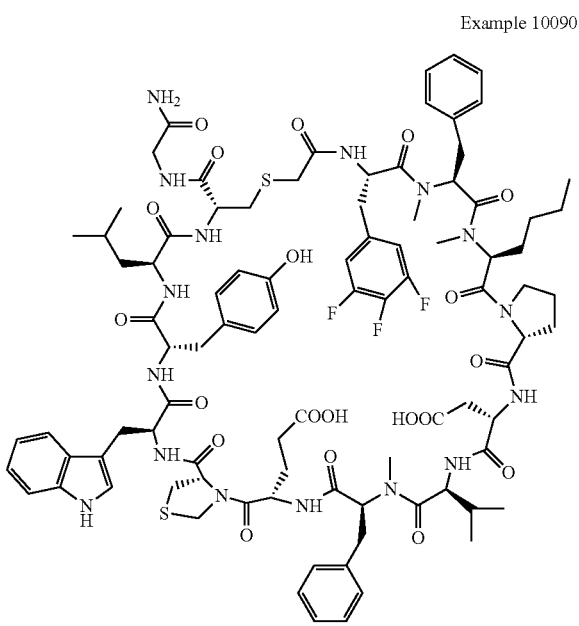 [SMILES: CCCC[C@H]1C(=O)N2CCC[C@@H]2C(=O)N[C@@H](CC(=O)O)C(=O)N[C@@H](C(C)C)C(=O)N(C)[C@@H](Cc2ccccc2)C(=O)N[C@@H](CCC(=O)O)C(=O)N2CSC[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2cc(F)c(F)c(F)c2)C(=O)N(C)[C@@H](Cc2ccccc2)C(=O)N1C]

The crude material of Example 10090 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 7.6 mg, and its estimated purity by LCMS analysis was 97%.

Analysis condition B: Retention time=2.98 min; ESI-MS (+) m/z 944.20 (M+2H).

ESI-HRMS(+) m/z: Calculated: 943.4006 (M+2H); Found: 943.4012 (M+2H).

Preparation of Example 10091

Example 10091

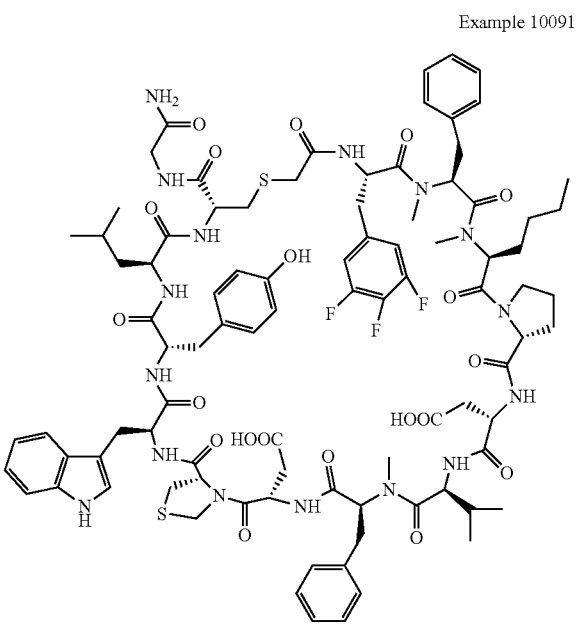 [SMILES: CCCC[C@H]1C(=O)N2CCC[C@@H]2C(=O)N[C@@H](CC(=O)O)C(=O)N[C@@H](C(C)C)C(=O)N(C)[C@@H](Cc2ccccc2)C(=O)N[C@@H](CC(=O)O)C(=O)N2CSC[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2cc(F)c(F)c(F)c2)C(=O)N(C)[C@@H](Cc2ccccc2)C(=O)N1C]

The crude material of Example 10091 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 17.7 mg, and its estimated purity by LCMS analysis was 95%.

Analysis condition A: Retention time=1.75 min; ESI-MS (−) m/z 935.2 (M−2H).

Analysis condition B: Retention time=3.01 min; ESI-MS (+) m/z 936.7 (M+2H).

ESI-HRMS(+) m/z: Calculated: 936.3928 (M+2H); Found: 936.3937 (M+2H).

Preparation of Example 10092

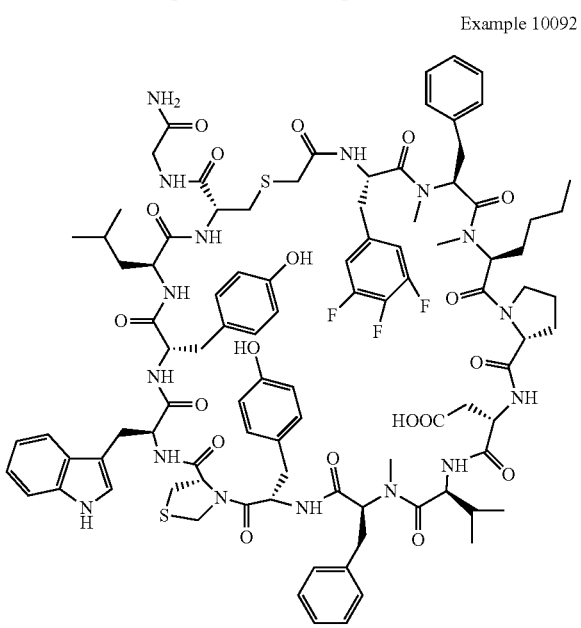 [SMILES: CCCC[C@H]1C(=O)N2CCC[C@@H]2C(=O)N[C@@H](CC(=O)O)C(=O)N[C@@H](C(C)C)C(=O)N(C)[C@@H](Cc2ccccc2)C(=O)N[C@@H](Cc2ccc(O)cc2)C(=O)N2CSC[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2cc(F)c(F)c(F)c2)C(=O)N(C)[C@@H](Cc2ccccc2)C(=O)N1C]

Example 10092

The crude material of Example 10092 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 20.5 mg, and its estimated purity by LCMS analysis was 94%.

Analysis condition B: Retention time=3.14 min; ESI-MS (+) m/z 961.2 (M+2H).

ESI-HRMS(+) m/z: Calculated: 960.4110 (M+2H); Found: 960.4109 (M+2H).

Preparation of Example 10093

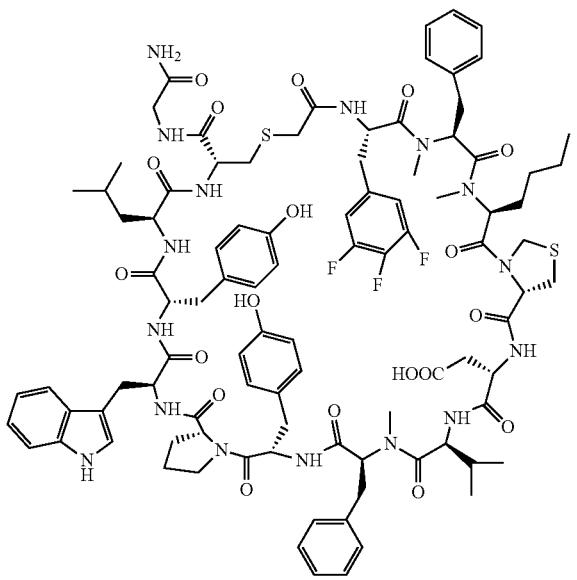

Example 10093

The crude material of Example 10093 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 6.5 mg, and its estimated purity by LCMS analysis was 99%.

Analysis condition A: Retention time=1.82 min; ESI-MS (−) m/z 959.0 (M−2H).

Analysis condition B: Retention time=3.09 min; ESI-MS (+) m/z 960.9 (M+2H).

ESI-HRMS(+) m/z: Calculated: 944.4110 (M+2H); Found: 960.4109 (M+2H).

Preparation of Example 10094

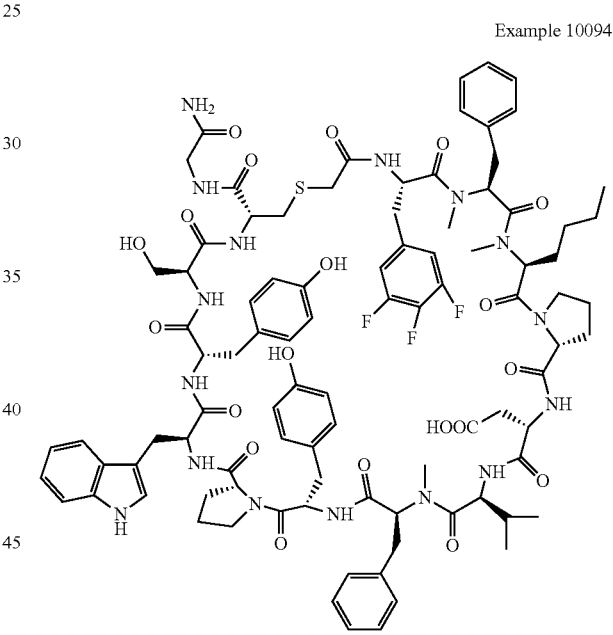

Example 10094

The crude material of Example 10094 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 25.4 mg, and its estimated purity by LCMS analysis was 96%.

Analysis condition A: Retention time=1.93 min; ESI-MS (+) m/z 938.70 (M+2H).

Analysis condition B: Retention time=3.09 min; ESI-MS (+) m/z 939.30 (M+2H).

ESI-HRMS(+) m/z: Calculated: 938.4068 (M+2H); Found: 938.4065 (M+2H).

Preparation of Example 10095

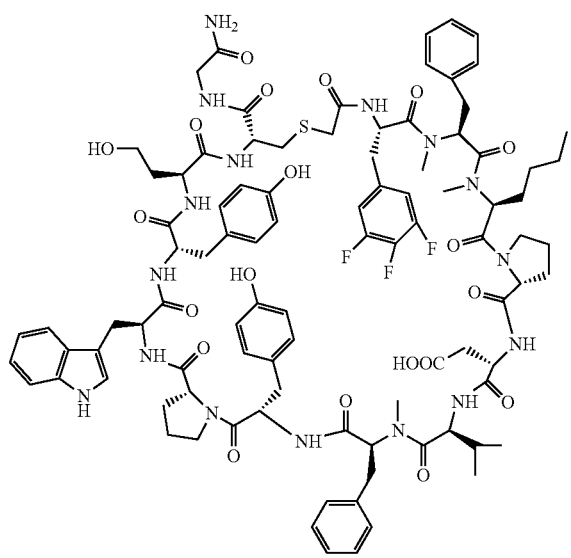

Example 10095

The crude material of Example 10095 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 10.7 mg, and its estimated purity by LCMS analysis was 100%.

Analysis condition A: Retention time=1.75 min; ESI-MS (+) m/z 946.30 (M+2H).

Analysis condition B: Retention time=3.08 min; ESI-MS (+) m/z 946.60 (M+2H).

ESI-HRMS(+) m/z: Calculated: 945.4146 (M+2H); Found: 945.4132 (M+2H).

Preparation of Example 10096

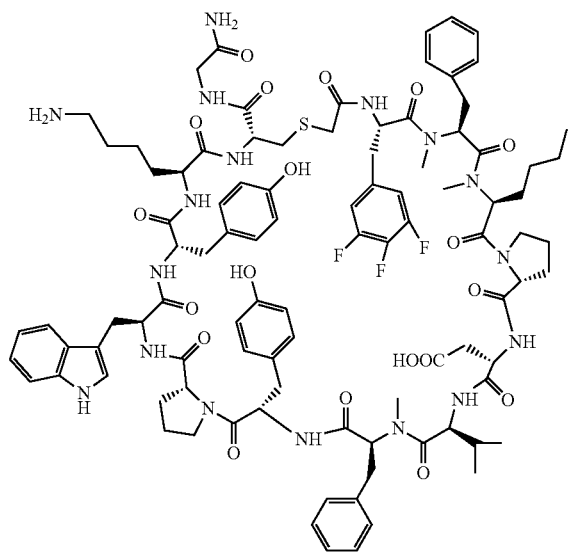

Example 10096

The crude material of Example 10096 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 32.5 mg, and its estimated purity by LCMS analysis was 100%.

Analysis condition A: Retention time=1.82 min; ESI-MS (+) m/z 959.10 (M+2H).

Analysis condition B: Retention time=3.13 min; ESI-MS (+) m/z 959.30 (M+2H).

ESI-HRMS(+) m/z: Calculated: 958.9382 (M+2H); Found: 958.9363 (M+2H).

Preparation of Example 10097

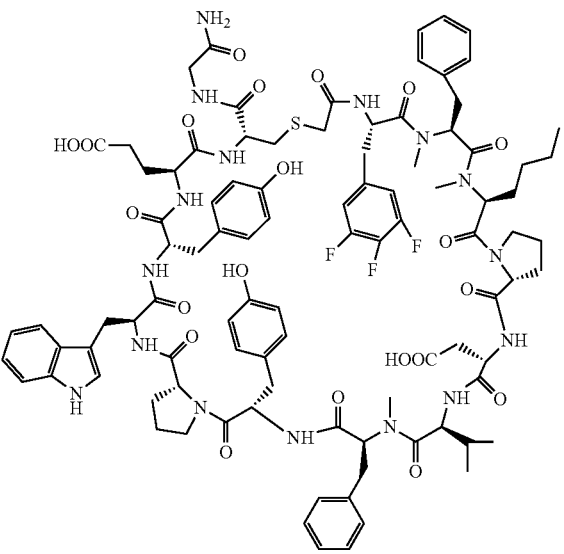

Example 10097

The crude material of Example 10097 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 44.4 mg, and its estimated purity by LCMS analysis was 100%.

Analysis condition A: Retention time=1.60 min; ESI-MS (+) m/z 959.70 (M+2H).

Analysis condition B: Retention time=3.11 min; ESI-MS (+) m/z 959.70 (M+2H).

ESI-HRMS(+) m/z: Calculated: 959.4121 (M+2H); Found: 959.4115 (M+2H).

Preparation of Example 10098

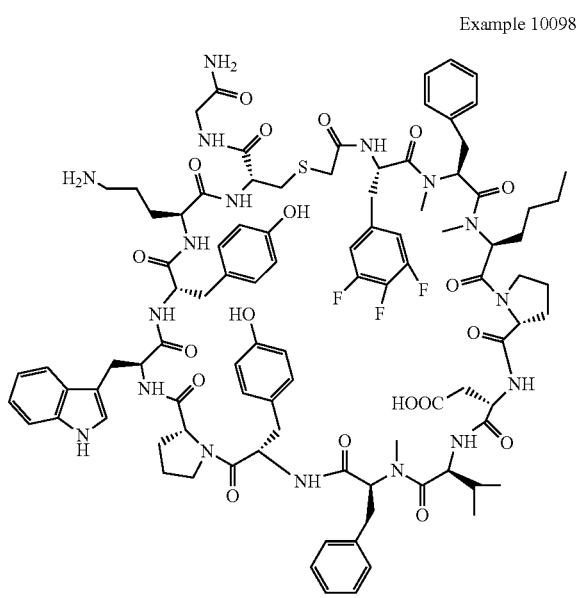 [SMILES: CCCC[C@H]1C(=O)N2CCC[C@@H]2C(=O)N[C@@H](CC(=O)O)C(=O)N[C@@H](C(C)C)C(=O)N(C)[C@@H](Cc2ccccc2)C(=O)N[C@@H](Cc2ccc(O)cc2)C(=O)N2CCC[C@@H]2C(=O)N[C@@H](Cc2c[nH]c3ccccc23)C(=O)N[C@@H](Cc2ccc(O)cc2)C(=O)N[C@@H](CCCN)C(=O)N[C@H](C(=O)NCC(N)=O)CSCC(=O)N[C@@H](Cc2cc(F)c(F)c(F)c2)C(=O)N(C)[C@@H](Cc2ccccc2)C(=O)N1C]

Example 10098

The crude material of Example 10098 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 36.5 mg, and its estimated purity by LCMS analysis was 100%.

Analysis condition A: Retention time=1.91 min; ESI-MS (+) m/z 952.10 (M+2H).

Analysis condition B: Retention time=3.30 min; ESI-MS (+) m/z 952.20 (M+2H).

ESI-HRMS(+) m/z: Calculated: 951.9304 (M+2H); Found: 951.9286 (M+2H).

Preparation of Example 10099

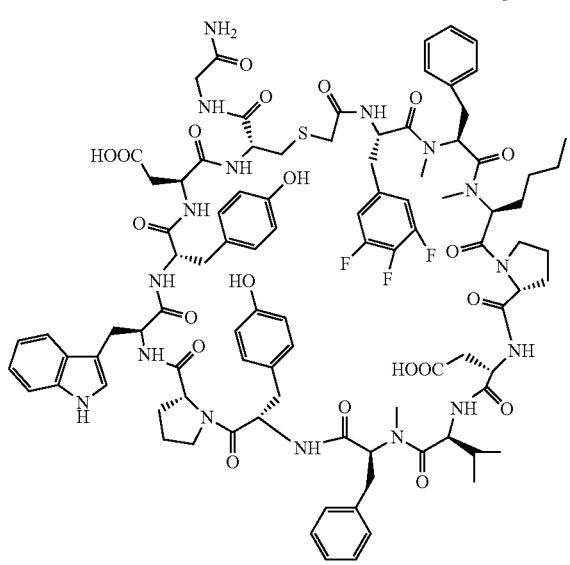

Example 10099

The crude material of Example 10099 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 36.7 mg, and its estimated purity by LCMS analysis was 100%.

Analysis condition A: Retention time=1.65 min; ESI-MS (+) m/z 952.80 (M+2H).

Analysis condition B: Retention time=2.98 min; ESI-MS (+) m/z 953.20 (M+2H).

ESI-HRMS(+) m/z: Calculated: 952.4042 (M+2H); Found: 952.4045 (M+2H).

Preparation of Example 10100

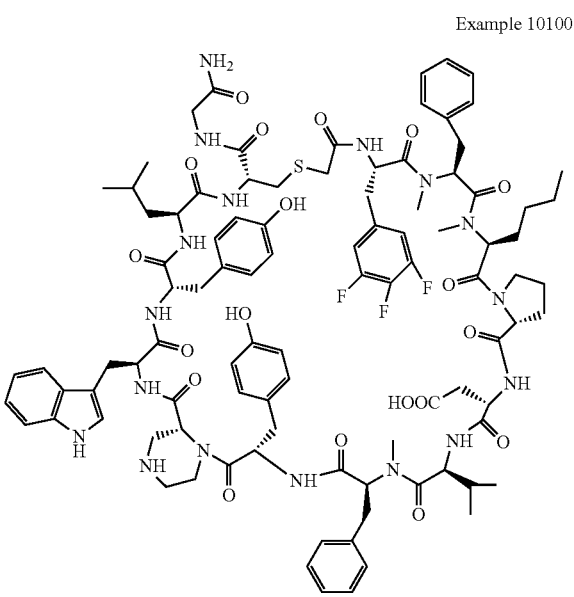 [SMILES: CCCC[C@H]1C(=O)N2CCC[C@@H]2C(=O)N[C@@H](CC(=O)O)C(=O)N[C@@H](C(C)C)C(=O)N(C)[C@@H](Cc2ccccc2)C(=O)N[C@@H](Cc2ccc(O)cc2)C(=O)N2CCNC[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2cc(F)c(F)c(F)c2)C(=O)N(C)[C@@H](Cc2ccccc2)C(=O)N1C]

Example 10100

The crude material of Example 10100 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 23.5 mg, and its estimated purity by LCMS analysis was 94%.

Analysis condition A: Retention time=1.83 min; ESI-MS (+) m/z 959.20 (M+2H).

Analysis condition B: Retention time=3.34 min; ESI-MS (+) m/z 959.25 (M+2H).

ESI-HRMS(+) m/z: Calculated: 958.9382 (M+2H); Found: 958.9368 (M+2H).

Preparation of Example 10102

Example 10102

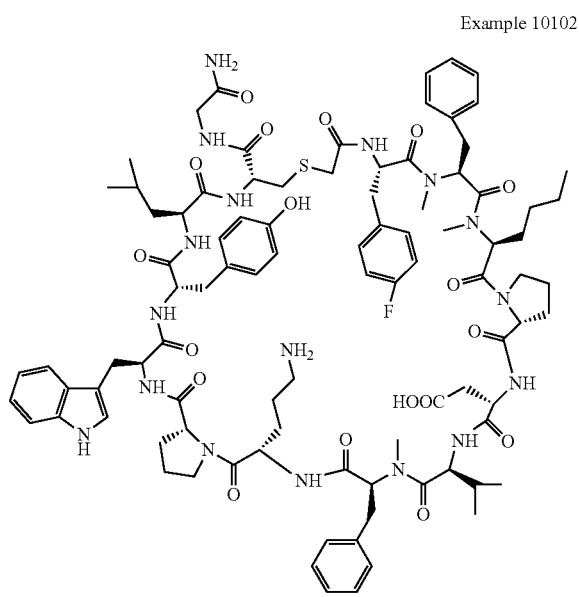 [SMILES: CCCC[C@H]1C(=O)N2CCC[C@@H]2C(=O)N[C@@H](CC(=O)O)C(=O)N[C@@H](C(C)C)C(=O)N(C)[C@@H](Cc2ccccc2)C(=O)N[C@@H](CCCN)C(=O)N2CCC[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccc(F)cc2)C(=O)N(C)[C@@H](Cc2ccccc2)C(=O)N1C]

The crude material of Example 10102 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 36.1 mg, and its estimated purity by LCMS analysis was 100%.

Analysis condition A: Retention time=1.90 min; ESI-MS (+) m/z 909.05 (M+2H).

ESI-HRMS(+) m/z: Calculated: 908.9502 (M+2H); Found: 908.9476 (M+2H).

Preparation of Example 10103

Example 10103

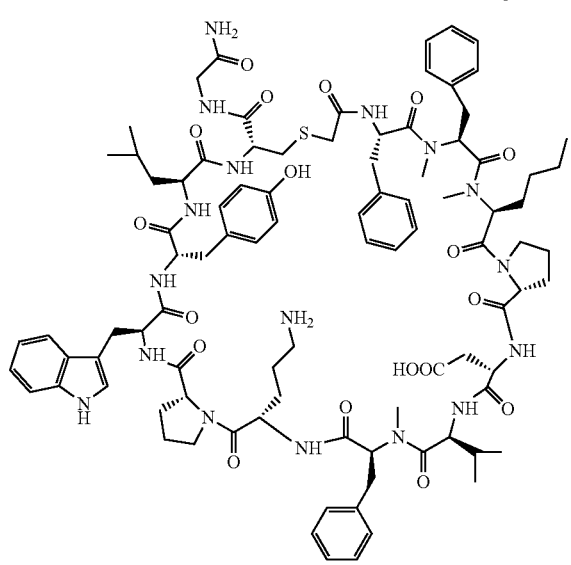

The crude material of Example 10103 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 27.2 mg, and its estimated purity by LCMS analysis was 100%.

Analysis condition A: Retention time=1.88 min; ESI-MS (+) m/z 900.35 (M+2H).

Analysis condition B: Retention time=2.57 min; ESI-MS (+) m/z 900.10 (M+2H).

ESI-HRMS(+) m/z: Calculated: 899.9549 (M+2H); Found: 899.9521 (M+2H).

Preparation of Example 10104

Example 10104

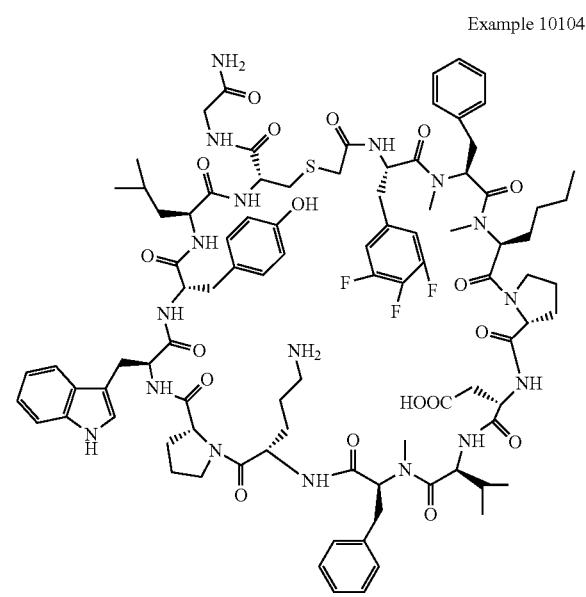 [SMILES: CCCC[C@H]1C(=O)N2CCC[C@@H]2C(=O)N[C@@H](CC(=O)O)C(=O)N[C@@H](C(C)C)C(=O)N(C)[C@@H](Cc2ccccc2)C(=O)N[C@@H](CCCN)C(=O)N2CCC[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2cc(F)c(F)c(F)c2)C(=O)N(C)[C@@H](Cc2ccccc2)C(=O)N1C]

The crude material of Example 10104 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 40.8 mg, and its estimated purity by LCMS analysis was 100%.

Analysis condition A: Retention time=1.94 min; ESI-MS (+) m/z 927.45 (M+2H).

Analysis condition B: Retention time=3.44 min; ESI-MS (+) m/z 927.40 (M+2H).

ESI-HRMS(+) m/z: Calculated: 926.9408 (M+2H); Found: 926.9375 (M+2H).

Preparation of Example 10105

Example 10105

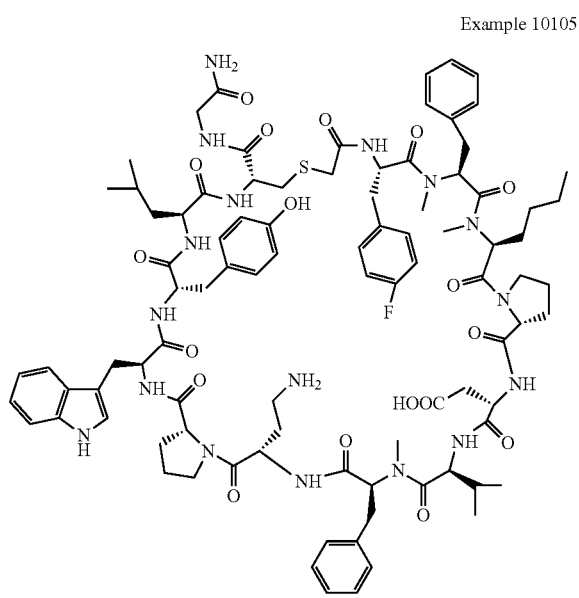 [SMILES: CCCC[C@H]1C(=O)N2CCC[C@@H]2C(=O)N[C@@H](CC(=O)O)C(=O)N[C@@H](C(C)C)C(=O)N(C)[C@@H](Cc2ccccc2)C(=O)N[C@@H](CCN)C(=O)N2CCC[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccc(F)cc2)C(=O)N(C)[C@@H](Cc2ccccc2)C(=O)N1C]

The crude material of Example 10105 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 39.2 mg, and its estimated purity by LCMS analysis was 99%.

Analysis condition A: Retention time=1.88 min; ESI-MS (+) m/z 901.95 (M+2H).

Analysis condition B: Retention time=3.44 min; ESI-MS (+) m/z 902.15 (M+2H).

ESI-HRMS(+) m/z: Calculated: 901.9424 (M+2H); Found: 901.9385 (M+2H).

Preparation of Example 10106

Example 10106

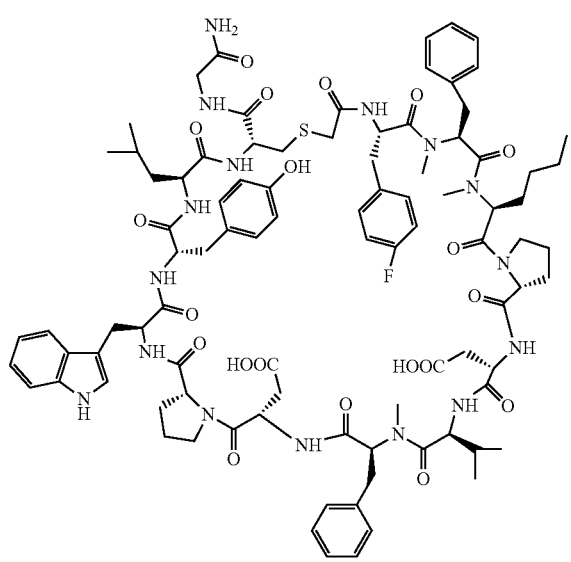

The crude material of Example 10106 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 40.1 mg, and its estimated purity by LCMS analysis was 100%.

Analysis condition A: Retention time=1.61 min; ESI-MS (+) m/z 910.20 (M+2H).

ESI-HRMS(+) m/z: Calculated: 909.4240 (M+2H); Found: 909.4215 (M+2H).

Preparation of Example 10107

Example 10107

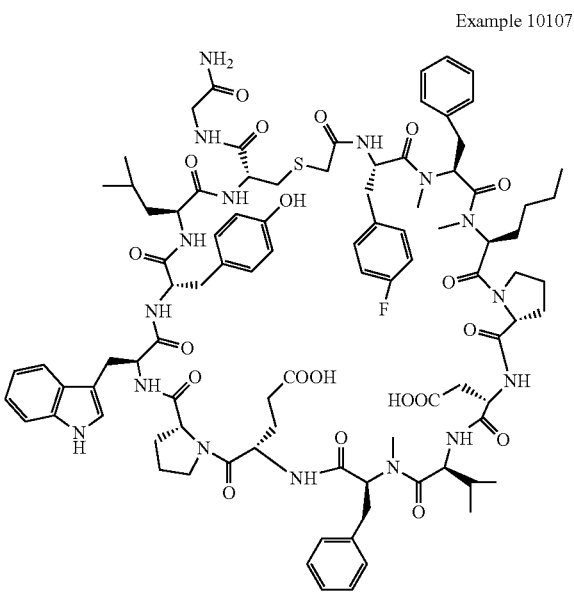 [SMILES: CCCC[C@H]1C(=O)N2CCC[C@@H]2C(=O)N[C@@H](CC(=O)O)C(=O)N[C@@H](C(C)C)C(=O)N(C)[C@@H](Cc2ccccc2)C(=O)N[C@@H](CCC(=O)O)C(=O)N2CCC[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccc(F)cc2)C(=O)N(C)[C@@H](Cc2ccccc2)C(=O)N1C]

The crude material of Example 10107 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 42.7 mg, and its estimated purity by LCMS analysis was 99%.

Analysis condition A: Retention time=1.68 min; ESI-MS (+) m/z 917.50 (M+2H).

Analysis condition B: Retention time=2.75 min; ESI-MS (+) m/z 917.10 (M+2H).

ESI-HRMS(+) m/z: Calculated: 916.4318 (M+2H); Found: 916.4293 (M+2H).

Preparation of Example 10108

Example 10108

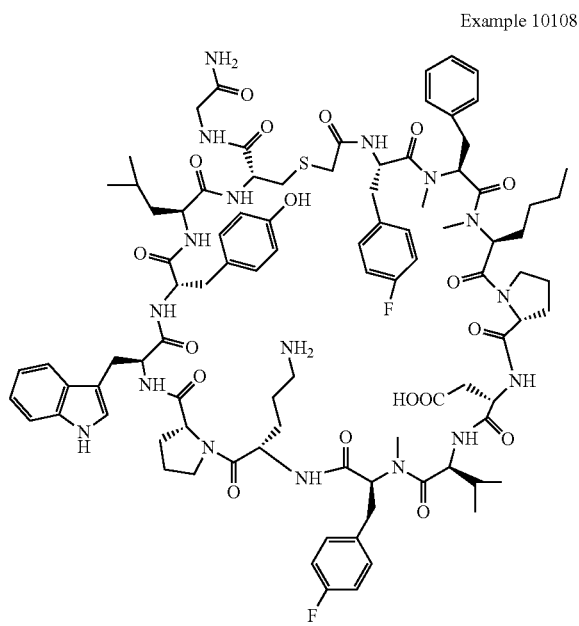 [SMILES: CCCC[C@H]1C(=O)N2CCC[C@@H]2C(=O)N[C@@H](CC(=O)O)C(=O)N[C@@H](C(C)C)C(=O)N(C)[C@@H](Cc2ccc(F)cc2)C(=O)N[C@@H](CCCN)C(=O)N2CCC[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccc(F)cc2)C(=O)N(C)[C@@H](Cc2ccccc2)C(=O)N1C]

The crude material of Example 10108 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 31.4 mg, and its estimated purity by LCMS analysis was 100%.

Analysis condition A: Retention time=1.84 min; ESI-MS (+) m/z 918.90 (M+2H).

Analysis condition B: Retention time=3.06 min; ESI-MS (+) m/z 918.40 (M+2H).

ESI-HRMS(+) m/z: Calculated: 917.9455 (M+2H); Found: 917.9416 (M+2H).

Preparation of Example 10109

Example 10109

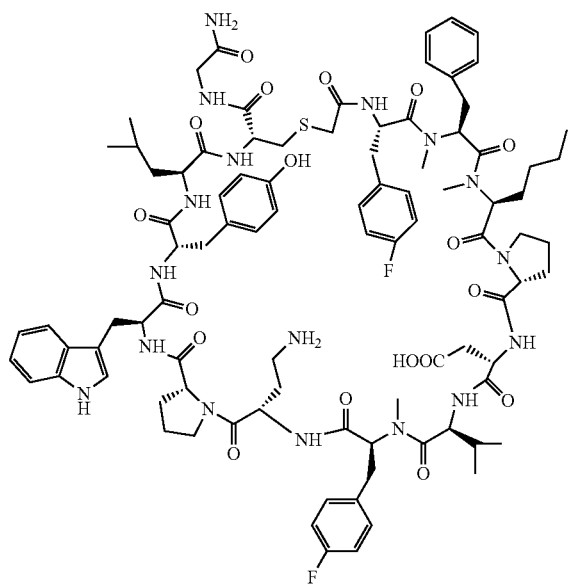

The crude material of Example 10109 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 45.9 mg, and its estimated purity by LCMS analysis was 100%.

Analysis condition A: Retention time=1.86 min; ESI-MS (+) m/z 912.40 (M+2H).

Analysis condition B: Retention time=3.07 min; ESI-MS (+) m/z 911.50 (M+2H).

ESI-HRMS(+) m/z: Calculated: 910.9377 (M+2H); Found: 910.9345 (M+2H).

Preparation of Example 10110

Example 10110

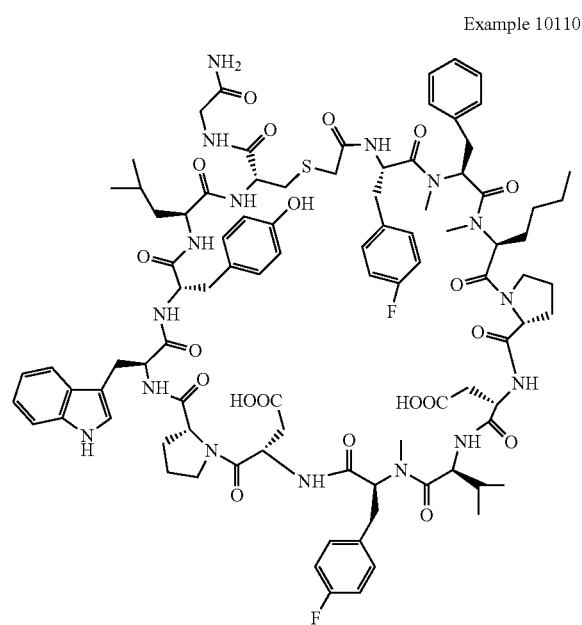 [SMILES: CCCC[C@H]1C(=O)N2CCC[C@@H]2C(=O)N[C@@H](CC(=O)O)C(=O)N[C@@H](C(C)C)C(=O)N(C)[C@@H](Cc2ccc(F)cc2)C(=O)N[C@@H](CC(=O)O)C(=O)N2CCC[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccc(F)cc2)C(=O)N(C)[C@@H](Cc2ccccc2)C(=O)N1C]

The crude material of Example 10110 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 30.6 mg, and its estimated purity by LCMS analysis was 99%.

Analysis condition A: Retention time=1.58 min; ESI-MS (+) m/z 919.60 (M+2H).

Analysis condition B: Retention time=2.73 min; ESI-MS (+) m/z 919.50 (M+2H).

ESI-HRMS(+) m/z: Calculated: 918.4193 (M+2H); Found: 918.4171 (M+2H).

Preparation of Example 10111

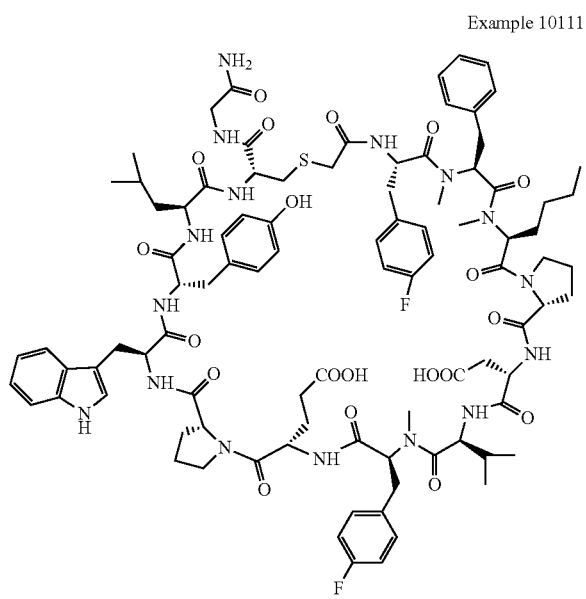 [SMILES: CCCC[C@H]1C(=O)N2CCC[C@@H]2C(=O)N[C@@H](CC(=O)O)C(=O)N[C@@H](C(C)C)C(=O)N(C)[C@@H](Cc2ccc(F)cc2)C(=O)N[C@@H](CCC(=O)O)C(=O)N2CCC[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccc(F)cc2)C(=O)N(C)[C@@H](Cc2ccccc2)C(=O)N1C]

Example 10111

The crude material of Example 10111 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 22.8 mg, and its estimated purity by LCMS analysis was 100%.

Analysis condition A: Retention time=1.68 min; ESI-MS (+) m/z 925.95 (M+2H).

Analysis condition B: Retention time=3.21 min; ESI-MS (+) m/z 926.00 (M+2H).

ESI-HRMS(+) m/z: Calculated: 925.4271 (M+2H); Found: 925.4250 (M+2H).

Preparation of Example 10112

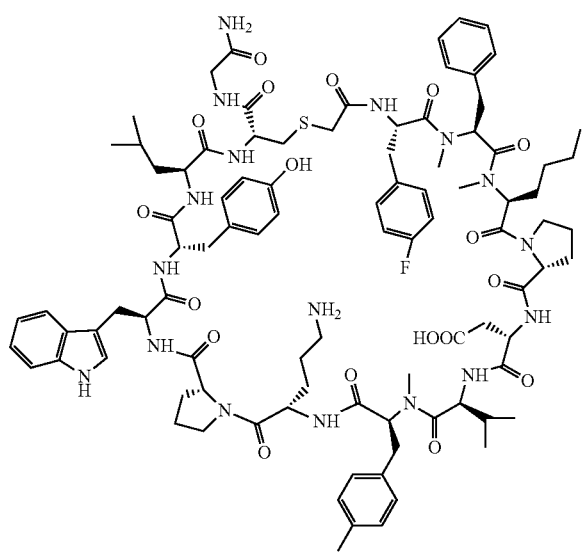

Example 10112

The crude material of Example 10112 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 41.6 mg, and its estimated purity by LCMS analysis was 96%.

Analysis condition A: Retention time=1.89 min; ESI-MS (+) m/z 916.50 (M+2H).

Analysis condition B: Retention time=3.11 min; ESI-MS (+) m/z 916.50 (M+2H).

ESI-HRMS(+) m/z: Calculated: 915.9580 (M+2H); Found: 915.9549 (M+2H).

Preparation of Example 10113

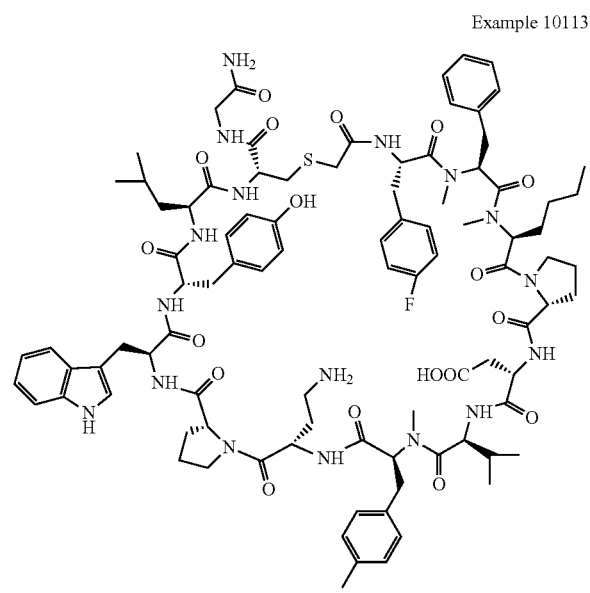 [SMILES: CCCC[C@H]1C(=O)N2CCC[C@@H]2C(=O)N[C@@H](CC(=O)O)C(=O)N[C@@H](C(C)C)C(=O)N(C)[C@@H](Cc2ccc(C)cc2)C(=O)N[C@@H](CCN)C(=O)N2CCC[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccc(F)cc2)C(=O)N(C)[C@@H](Cc2ccccc2)C(=O)N1C]

Example 10113

The crude material of Example 10113 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 31.0 mg, and its estimated purity by LCMS analysis was 100%.

Analysis condition A: Retention time=1.96 min; ESI-MS (+) m/z 909.40 (M+2H).

ESI-HRMS(+) m/z: Calculated: 908.9502 (M+2H); Found: 908.9469 (M+2H).

Preparation of Example 10114

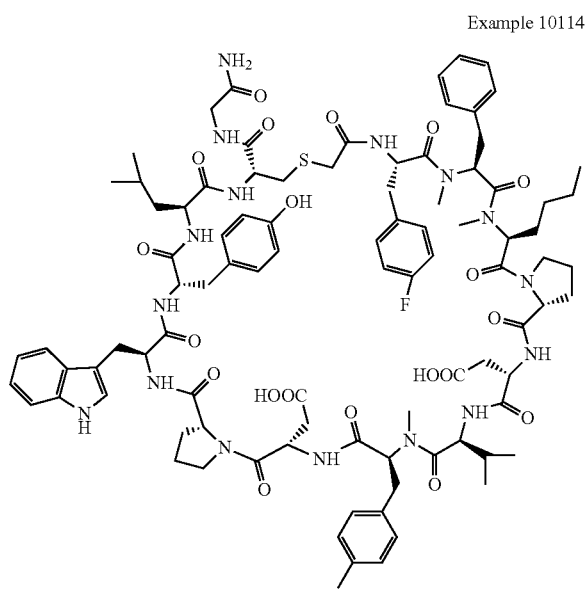 [SMILES: CCCC[C@H]1C(=O)N2CCC[C@@H]2C(=O)N[C@@H](CC(=O)O)C(=O)N[C@@H](C(C)C)C(=O)N(C)[C@@H](Cc2ccc(C)cc2)C(=O)N[C@@H](CC(=O)O)C(=O)N2CCC[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccc(F)cc2)C(=O)N(C)[C@@H](Cc2ccccc2)C(=O)N1C]

Example 10114

The crude material of Example 10114 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 39.5 mg, and its estimated purity by LCMS analysis was 99%.

Analysis condition A: Retention time=1.63 min; ESI-MS (+) m/z 916.8 (M+2H).

Analysis condition B: Retention time=2.78 min; ESI-MS (+) m/z 917.0 (M+2H).

ESI-HRMS(+) m/z: Calculated: 916.4318 (M+2H); Found: 916.4293 (M+2H).

Preparation of Example 10115

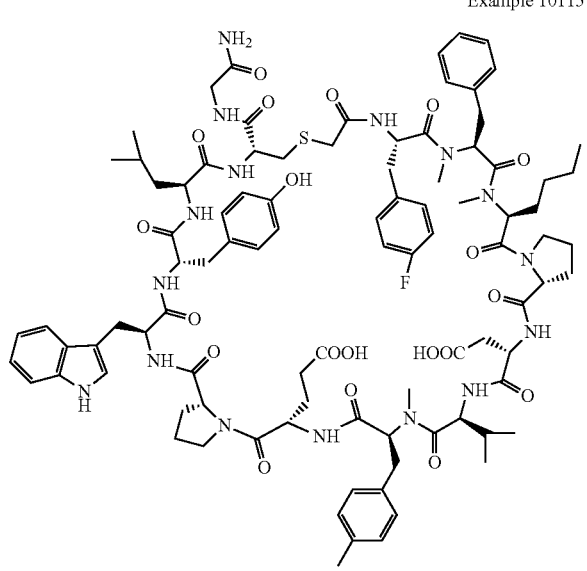

Example 10115

The crude material of Example 10115 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 31.5 mg, and its estimated purity by LCMS analysis was 99%.

Analysis condition A: Retention time=1.72 min; ESI-MS (+) m/z 923.95 (M+2H).

Analysis condition B: Retention time=3.26 min; ESI-MS (+) m/z 923.95 (M+2H).

ESI-HRMS(+) m/z: Calculated: 923.4397 (M+2H); Found: 923.4369 (M+2H).

Preparation of Example 10116

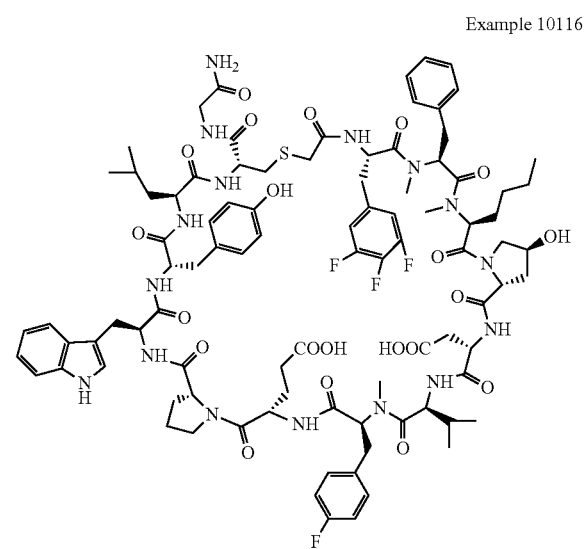 [SMILES: CCCC[C@H]1C(=O)N2C[C@@H](O)C[C@@H]2C(=O)N[C@@H](CC(=O)O)C(=O)N[C@@H](C(C)C)C(=O)N(C)[C@@H](Cc2ccc(F)cc2)C(=O)N[C@@H](CCC(=O)O)C(=O)N2CCC[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2cc(F)c(F)c(F)c2)C(=O)N(C)[C@@H](Cc2ccccc2)C(=O)N1C]

Example 10116

The crude material of Example 10116 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 35.8 mg, and its estimated purity by LCMS analysis was 99%.

Analysis condition A: Retention time=1.67 min; ESI-MS (+) m/z 951.90 (M+2H).

Analysis condition B: Retention time=3.18 min; ESI-MS (+) m/z 951.90 (M+2H).

ESI-HRMS(+) m/z: Calculated: 951.4152 (M+2H); Found: 951.4133 (M+2H).

Preparation of Example 10117

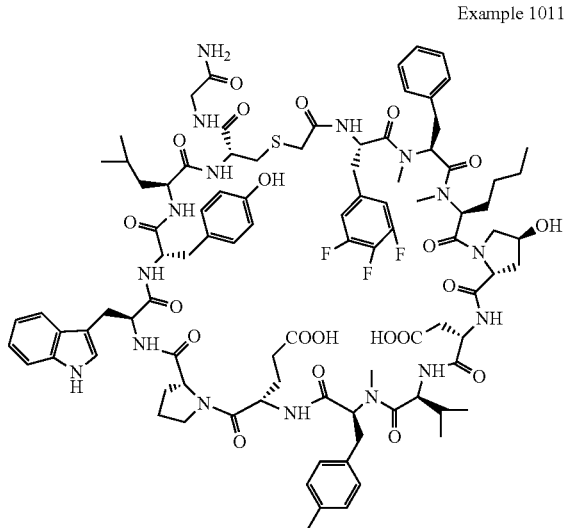

Example 10117

The crude material of Example 10117 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 32.9 mg, and its estimated purity by LCMS analysis was 97%.

Analysis condition A: Retention time=1.62 min; ESI-MS (+) m/z 950.70 (M+2H).

Analysis condition B: Retention time=2.80 min; ESI-MS (+) m/z 950.10 (M+2H).

ESI-HRMS(+) m/z: Calculated: 949.4277 (M+2H); Found: 949.4250 (M+2H).

Preparation of Example 10118

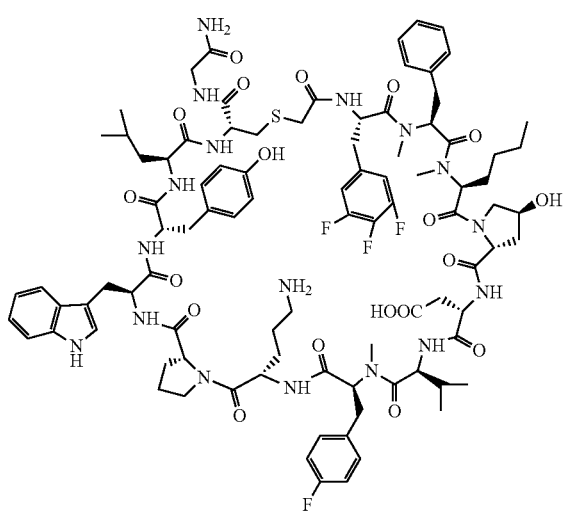

Example 10118

The crude material of Example 10118 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 26.8 mg, and its estimated purity by LCMS analysis was 98%.

Analysis condition A: Retention time=1.84 min; ESI-MS (+) m/z 944.45 (M+2H).

Analysis condition B: Retention time=3.34 min; ESI-MS (+) m/z 944.35 (M+2H).

ESI-HRMS(+) m/z: Calculated: 943.9335 (M+2H); Found: 943.9302 (M+2H).

Preparation of Example 10119

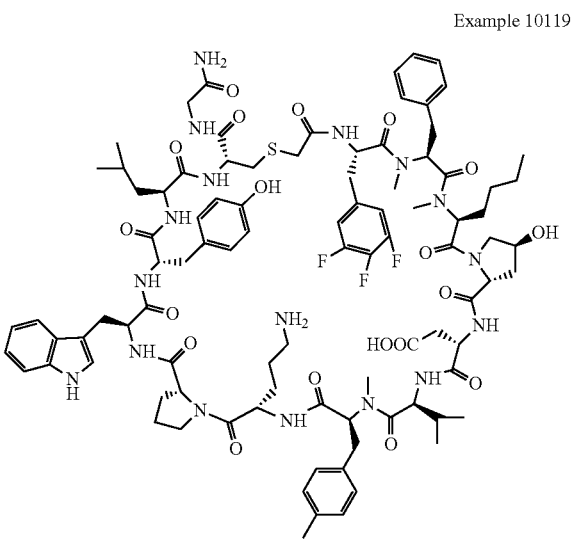 [SMILES: CCCC[C@H]1C(=O)N2C[C@@H](O)C[C@@H]2C(=O)N[C@@H](CC(=O)O)C(=O)N[C@@H](C(C)C)C(=O)N(C)[C@@H](Cc2ccc(C)cc2)C(=O)N[C@@H](CCCN)C(=O)N2CCC[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2cc(F)c(F)c(F)c2)C(=O)N(C)[C@@H](Cc2ccccc2)C(=O)N1C]

Example 10119

The crude material of Example 10119 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 32.8 mg, and its estimated purity by LCMS analysis was 96%.

Analysis condition A: Retention time=1.89 min; ESI-MS (+) m/z 942.45 (M+2H).

Analysis condition B: Retention time=3.41 min; ESI-MS (+) m/z 942.35 (M+2H).

ESI-HRMS(+) m/z: Calculated: 941.9461 (M+2H); Found: 941.9436 (M+2H).

Preparation of Example 10120

Example 10120

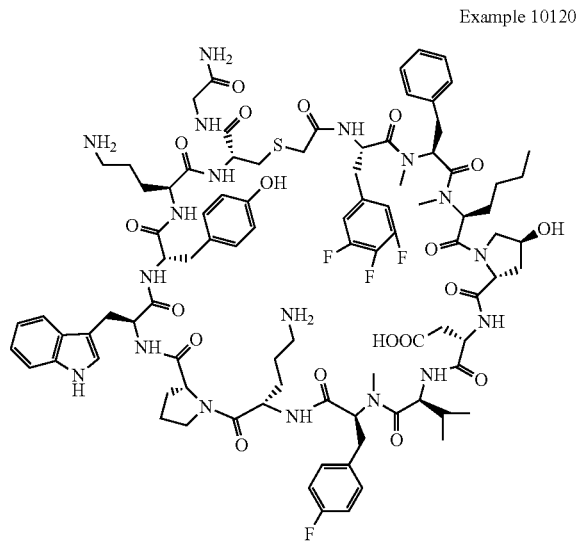 [SMILES: CCCC[C@H]1C(=O)N2C[C@@H](O)C[C@@H]2C(=O)N[C@@H](CC(=O)O)C(=O)N[C@@H](C(C)C)C(=O)N(C)[C@@H](Cc2ccc(F)cc2)C(=O)N[C@@H](CCCN)C(=O)N2CCC[C@@H]2C(=O)N[C@@H](Cc2c[nH]c3ccccc23)C(=O)N[C@@H](Cc2ccc(O)cc2)C(=O)N[C@@H](CCCN)C(=O)N[C@H](C(=O)NCC(N)=O)CSCC(=O)N[C@@H](Cc2cc(F)c(F)c(F)c2)C(=O)N(C)[C@@H](Cc2ccccc2)C(=O)N1C]

Preparation of Example 10121

Example 10121

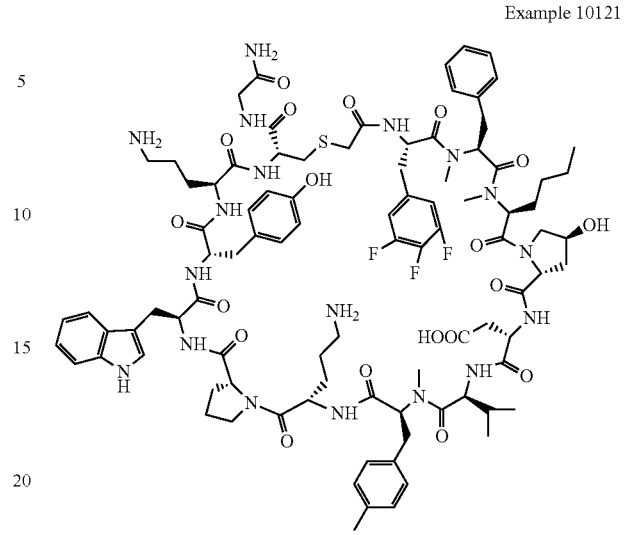

The crude material of Example 10120 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 47.5 mg, and its estimated purity by LCMS analysis was 99%.

Analysis condition A: Retention time=1.72 min; ESI-MS (+) m/z 944.90 (M+2H).

Analysis condition B: Retention time=3.41 min; ESI-MS (+) m/z 944.85 (M+2H).

ESI-HRMS(+) m/z: Calculated: 944.4311 (M+2H); Found: 944.4283 (M+2H).

The crude material of Example 10121 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 48.0 mg, and its estimated purity by LCMS analysis was 99%.

Analysis condition A: Retention time=1.79 min; ESI-MS (+) m/z 942.65 (M+2H).

Analysis condition B: Retention time=2.47 min; ESI-MS (+) m/z 942.80 (M+2H).

ESI-HRMS(+) m/z: Calculated: 942.4437 (M+2H); Found: 942.4407 (M+2H).

Preparation of Example 10122

Example 10122

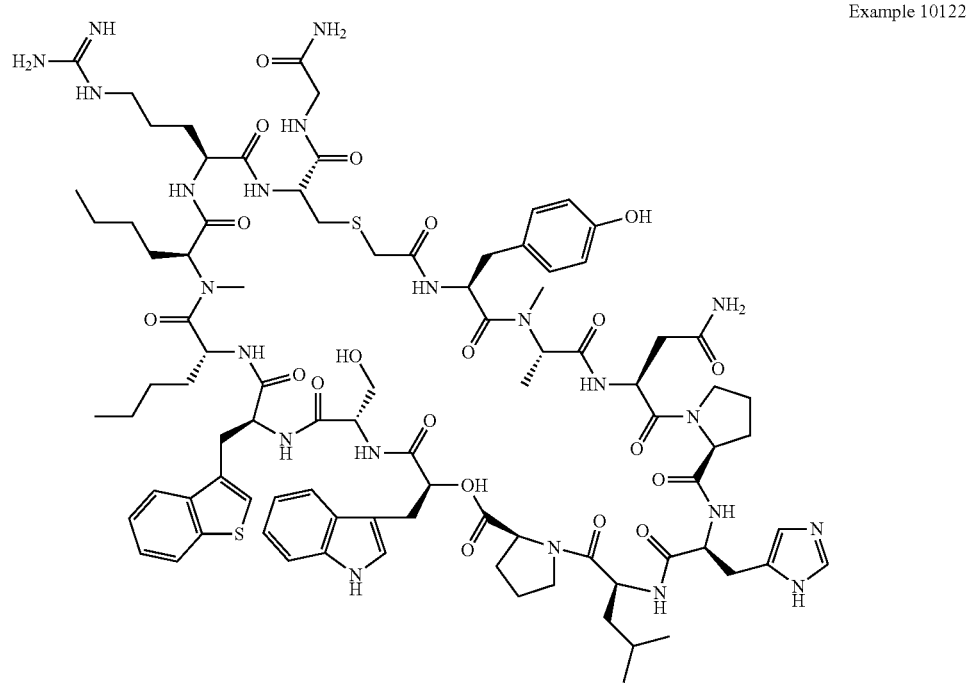

The crude material of Example 10122 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 28.9 mg, and its estimated purity by LCMS analysis was 98%.

Analysis condition A: Retention time=1.67 min; ESI-MS (+) m/z 949.80 (M+2H).

Analysis condition B: Retention time=2.73 min; ESI-MS (+) m/z 949.60 (M+2H).

ESI-HRMS(+) m/z: Calculated: 948.9555 (M+2H); Found: 948.9532 (M+2H).

Preparation of Example 10123

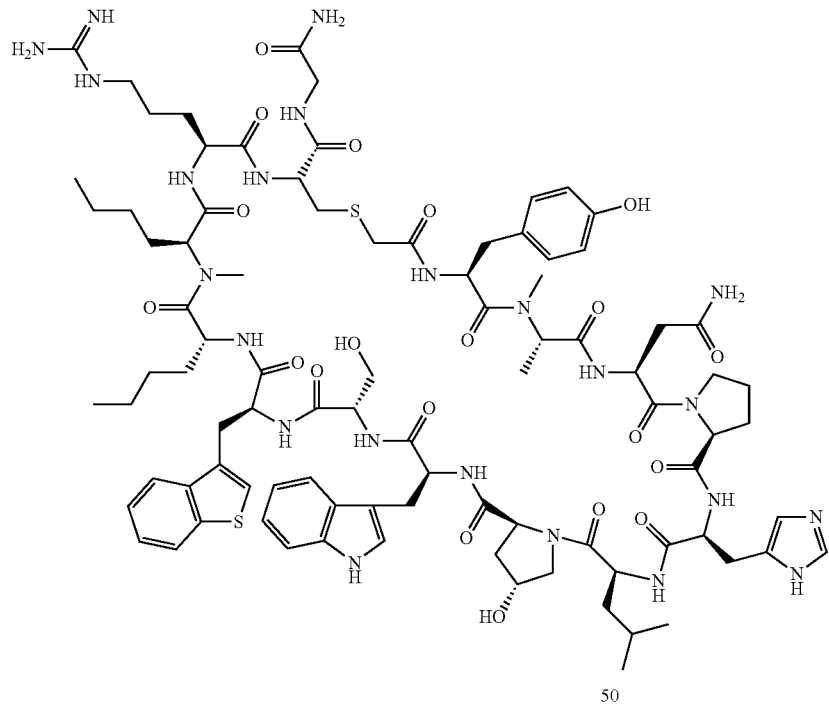

Example 10123

The crude material of Example 10123 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 30.5 mg, and its estimated purity by LCMS analysis was 96%.

Analysis condition A: Retention time=1.61 min; ESI-MS (+) m/z 957.15 (M+2H).

Analysis condition B: Retention time=2.27 min; ESI-MS (+) m/z 957.30 (M+2H).

Preparation of Example 10126

Example 10126

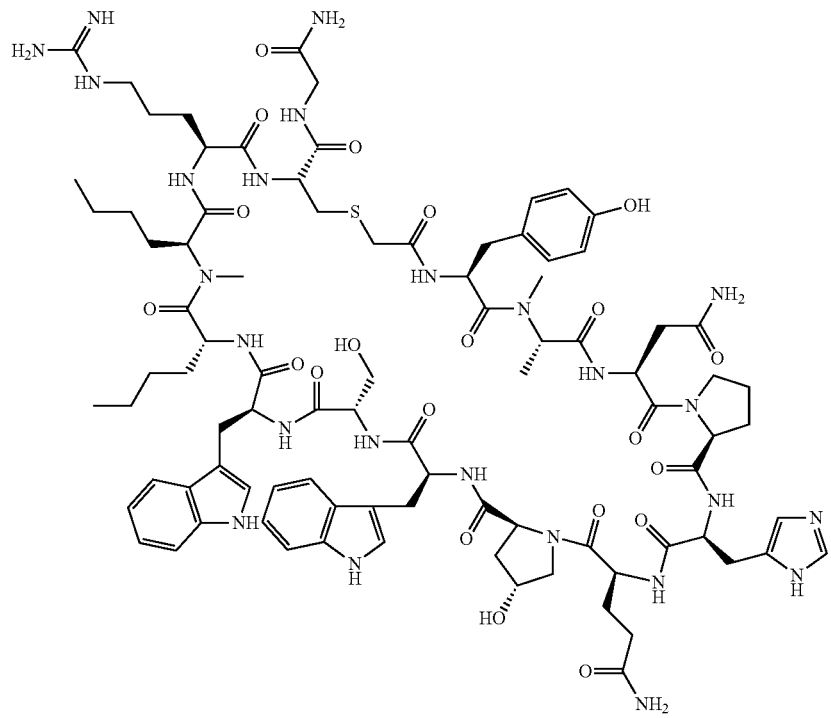

The crude material of Example 10126 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 10.7 mg, and its estimated purity by LCMS analysis was 100%.

Analysis condition A: Retention time=1.46 min; ESI-MS (+) m/z 956.60 (M+2H).

Analysis condition B: Retention time=2.50 min; ESI-MS (+) m/z 956.60 (M+2H).

Preparation of Example 10127

Example 10127

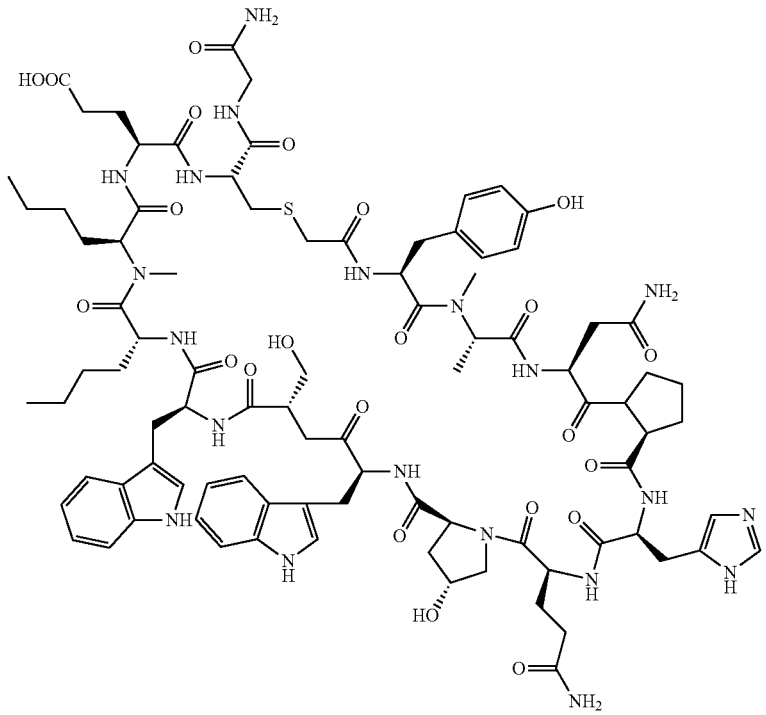

The crude material of Example 10127 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 15.0 mg, and its estimated purity by LCMS analysis was 98%.

Analysis condition A: Retention time=1.45 min; ESI-MS (+) m/z 942.95 (M+2H).

Analysis condition B: Retention time=2.89 min; ESI-MS (+) m/z 942.80 (M+2H).

ESI-HRMS(+) m/z: Calculated: 942.4303 (M+2H); Found: 942.4284 (M+2H).

Preparation of Example 10128

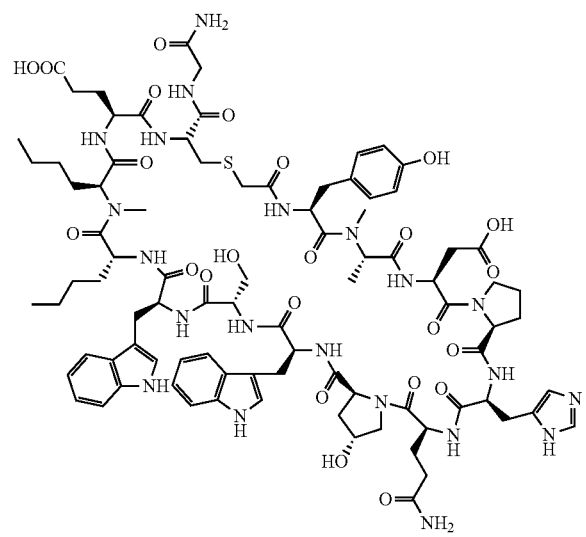

Example 10128

The crude material of Example 10128 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 22.2 mg, and its estimated purity by LCMS analysis was 100%.

Analysis condition A: Retention time=1.45 min; ESI-MS (+) m/z 943.45 (M+2H).

Analysis condition B: Retention time=2.84 min; ESI-MS (+) m/z 943.10 (M+2H).

ESI-HRMS(+) m/z: Calculated: 942.9223 (M+2H); Found: 942.9201 (M+2H).

Preparation of Example 10129

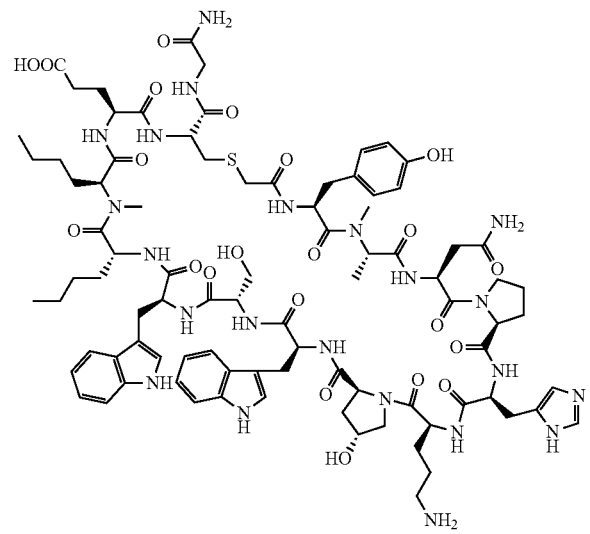

Example 10129

The crude material of Example 10129 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 26.0 mg, and its estimated purity by LCMS analysis was 92%.

Analysis condition A: Retention time=1.51 min; ESI-MS (+) m/z 935.65 (M+2H).

Analysis condition B: Retention time=3.04 min; ESI-MS (+) m/z 935.60 (M+2H).

ESI-HRMS(+) m/z: Calculated: 935.4407 (M+2H); Found: 935.4384 (M+2H).

Preparation of Example 10130

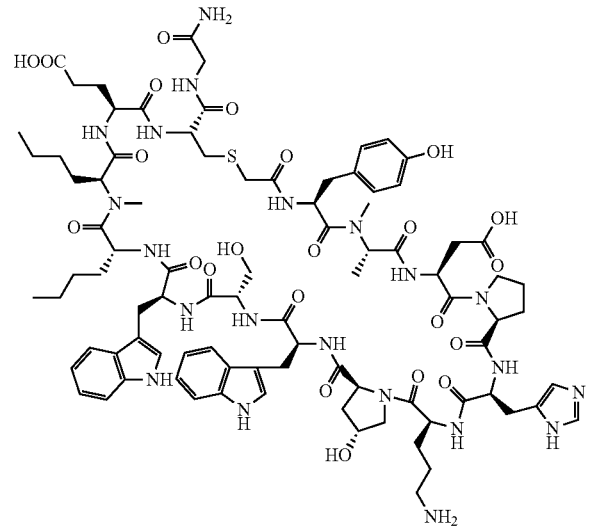

Example 10130

The crude material of Example 10130 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 28.2 mg, and its estimated purity by LCMS analysis was 97%.

Analysis condition A: Retention time=1.49 min; ESI-MS (+) m/z 935.80 (M+2H).

Analysis condition B: Retention time=2.96 min; ESI-MS (+) m/z 936.15 (M+2H).

ESI-HRMS(+) m/z: Calculated: 935.9327 (M+2H); Found: 935.9300 (M+2H).

Preparation of Example 10131

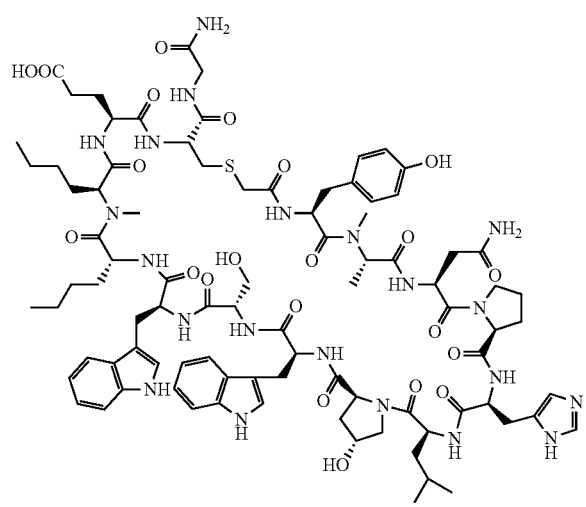

Example 10131

The crude material of Example 10131 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 9.7 mg, and its estimated purity by LCMS analysis was 96%.

Analysis condition A: Retention time=1.53 min; ESI-MS (+) m/z 935.10 (M+2H).

Analysis condition B: Retention time=2.94 min; ESI-MS (+) m/z 936.20 (M+2H).

ESI-HRMS(+) m/z: Calculated: 934.9431 (M+2H); Found: 934.9411 (M+2H).

Preparation of Example 10132

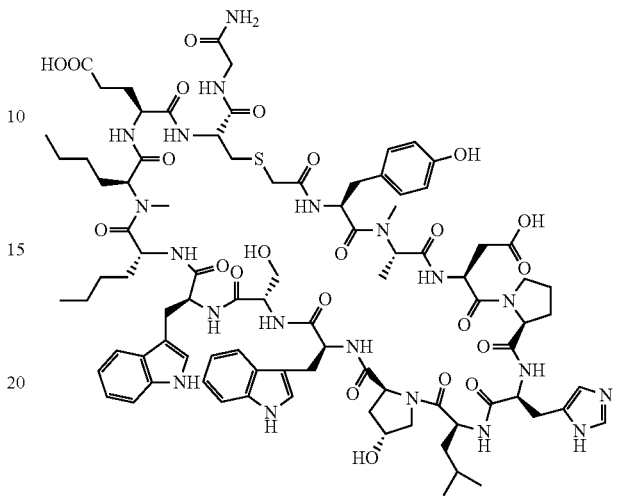

Example 10132

The crude material of Example 10132 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 26.6 mg, and its estimated purity by LCMS analysis was 99%.

Analysis condition A: Retention time=1.49 min; ESI-MS (+) m/z 935.55 (M+2H).

Analysis condition B: Retention time=2.88 min; ESI-MS (+) m/z 935.65 (M+2H).

ESI-HRMS(+) m/z: Calculated: 935.4341 (M+2H); Found: 935.4325 (M+2H).

Preparation of Example 10136

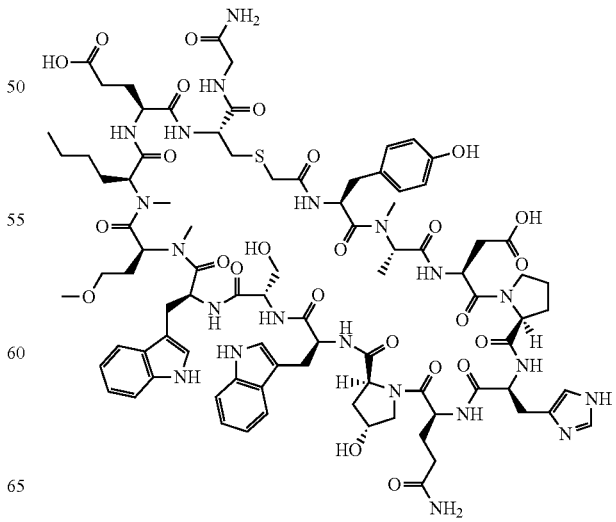

Example 10136

The crude material of Example 10136 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 10.8 mg, and its estimated purity by LCMS analysis was 99%.

Analysis condition A: Retention time=1.27 min; ESI-MS (+) m/z 951.00 (M+2H).

Analysis condition B: Retention time=2.64 min; ESI-MS (+) m/z 951.20 (M+2H).

ESI-HRMS(+) m/z: Calculated: 950.9198 (M+2H); Found: 950.9178 (M+2H).

Preparation of Example 10137

Example 10137

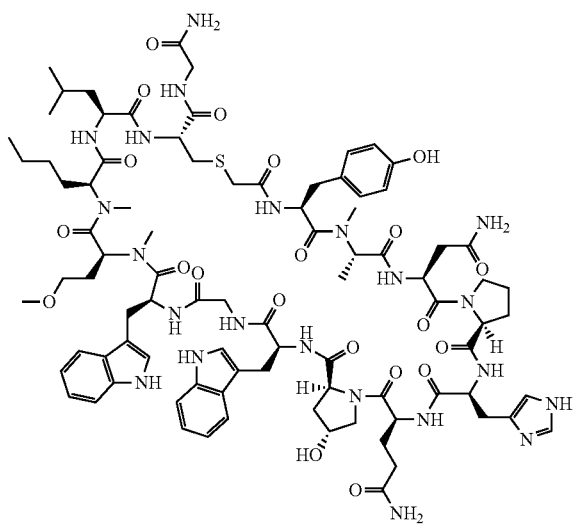

The crude material of Example 10137 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 22.3 mg, and its estimated purity by LCMS analysis was 99%.

Analysis condition A: Retention time=1.42 min; ESI-MS (+) m/z 928.30 (M+2H).

Analysis condition B: Retention time=2.52 min; ESI-MS (+) m/z 928.00 (M+2H).

ESI-HRMS(+) m/z: Calculated: 927.4432 (M+2H); Found: 927.4417 (M+2H).

Preparation of Example 10138

Example 10138

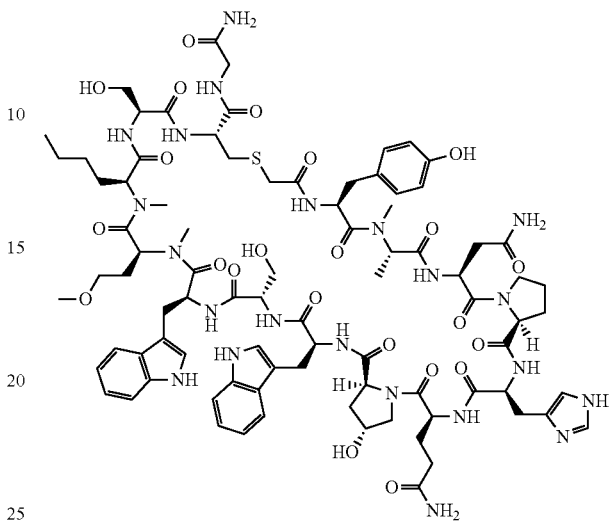

The crude material of Example 10138 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 7.5 mg, and its estimated purity by LCMS analysis was 100%.

Analysis condition A: Retention time=1.39 min; ESI-MS (+) m/z 929.40 (M+2H).

Analysis condition B: Retention time=2.83 min; ESI-MS (+) m/z 929.75 (M+2H).

Preparation of Example 10139

Example 10139

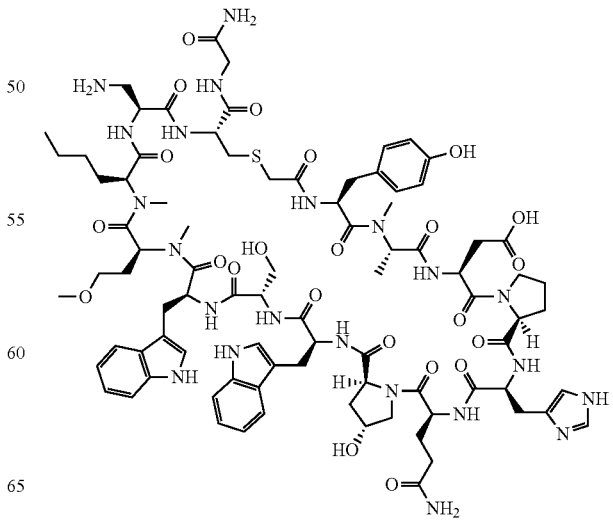

The crude material of Example 10139 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 26.4 mg, and its estimated purity by LCMS analysis was 99%.

Analysis condition A: Retention time=1.37 min; ESI-MS (+) m/z 929.60 (M+2H).

Analysis condition B: Retention time=1.96 min; ESI-MS (+) m/z 929.70 (M+2H).

Preparation of Example 10140

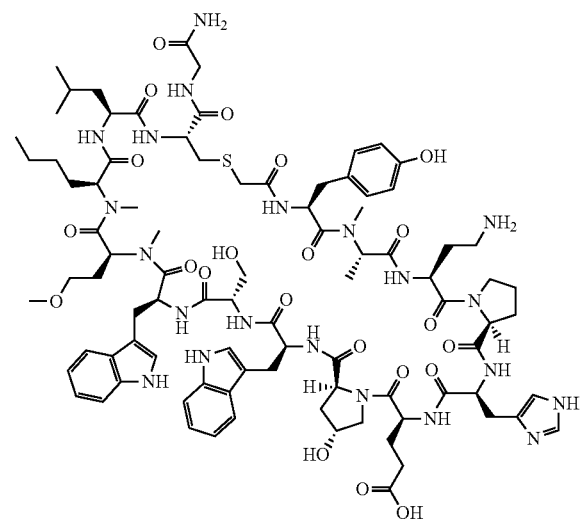

Example 10140

The crude material of Example 10140 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 25.4 mg, and its estimated purity by LCMS analysis was 100%.

Analysis condition A: Retention time=1.48 min; ESI-MS (+) m/z 936.20 (M+2H).

Analysis condition B: Retention time=2.13 min; ESI-MS (+) m/z 936.20 (M+2H).

ESI-HRMS(+) m/z: Calculated: 935.9509 (M+2H); Found: 935.9480 (M+2H).

Preparation of Example 10141

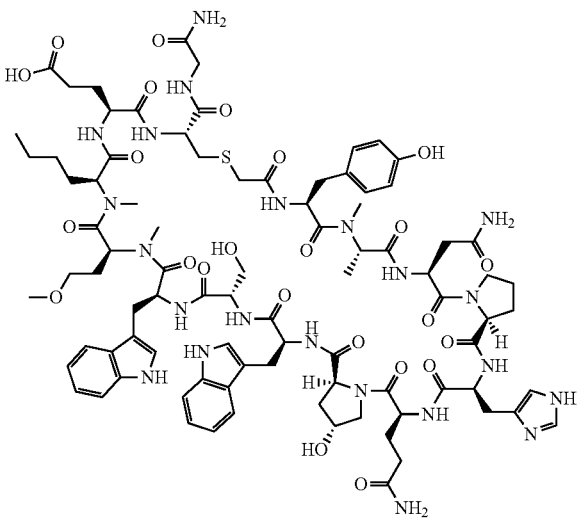

Example 10141

The crude material of Example 10141 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 27.0 mg, and its estimated purity by LCMS analysis was 98%.

Analysis condition A: Retention time=1.36 min; ESI-MS (+) m/z 950.60 (M+2H).

Analysis condition B: Retention time=1.79 min; ESI-MS (+) m/z 950.60 (M+2H).

ESI-HRMS(+) m/z: Calculated: 950.4278 (M+2H); Found: 950.4262 (M+2H).

Preparation of Example 10142

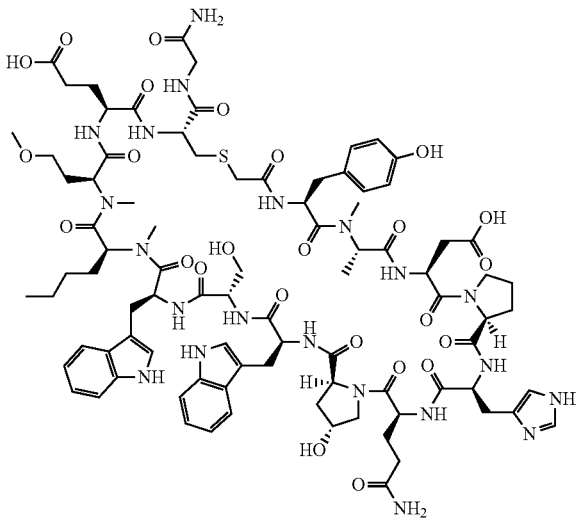

Example 10142

The crude material of Example 10142 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 19.9 mg, and its estimated purity by LCMS analysis was 100%.

Analysis condition B: Retention time=1.51 min; ESI-MS (+) m/z 951.90 (M+2H).

ESI-HRMS(+) m/z: Calculated: 950.9198 (M+2H); Found: 950.9182 (M+2H).

Preparation of Example 10143

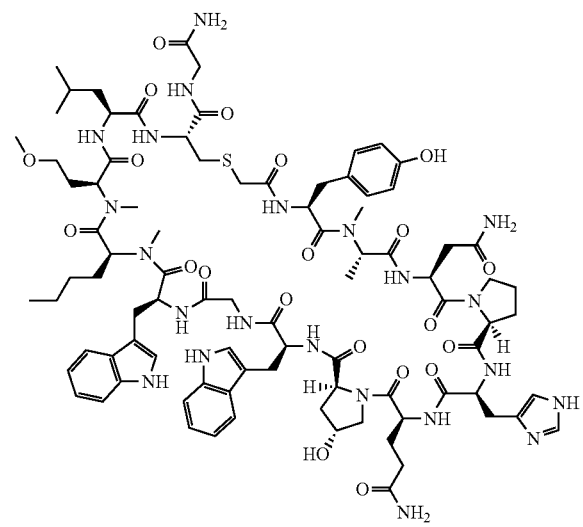

Example 10143

The crude material of Example 10143 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 20.1 mg, and its estimated purity by LCMS analysis was 97%.

Analysis condition A: Retention time=1.45 min; ESI-MS (+) m/z 928.40 (M+2H).

Analysis condition B: Retention time=2.54 min; ESI-MS (+) m/z 928.30 (M+2H).

ESI-HRMS(+) m/z: Calculated: 927.4432 (M+2H); Found: 927.4418 (M+2H).

Preparation of Example 10144

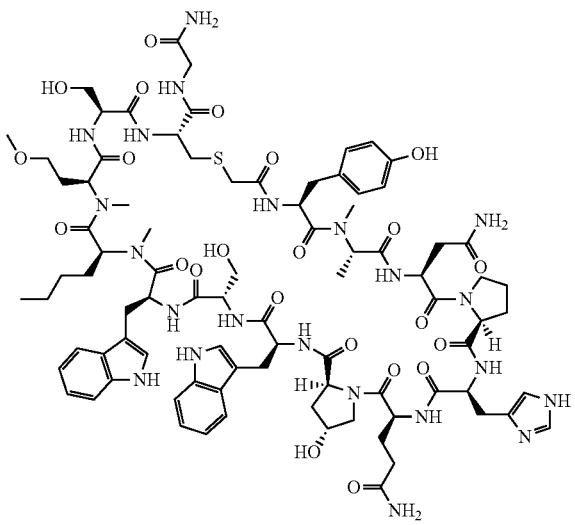

Example 10144

The crude material of Example 10144 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 14.8 mg, and its estimated purity by LCMS analysis was 100%.

Analysis condition A: Retention time=1.36 min; ESI-MS (+) m/z 929.9 (M+2H).

Analysis condition B: Retention time=2.41 min; ESI-MS (+) m/z 930.5 (M+2H).

ESI-HRMS(+) m/z: Calculated: 929.4225 (M+2H); Found: 929.4217 (M+2H).

Preparation of Example 10145

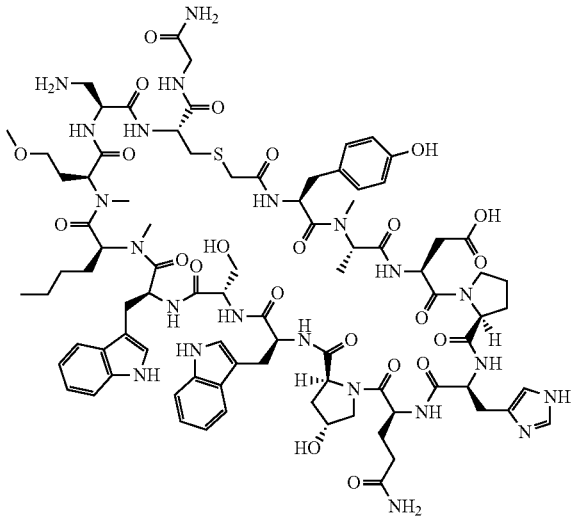

Example 10145

The crude material of Example 10145 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 18.4 mg, and its estimated purity by LCMS analysis was 100%.

Analysis condition A: Retention time=1.41 min; ESI-MS (+) m/z 929.55 (M+2H).

Analysis condition B: Retention time=1.99 min; ESI-MS (+) m/z 930.65 (M+2H).

ESI-HRMS(+) m/z: Calculated: 929.4225 (M+2H); Found: 929.4194 (M+2H).

Preparation of Example 10146

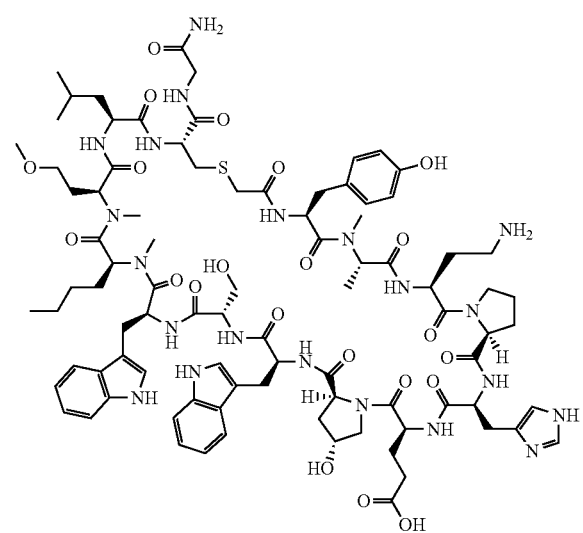

Example 10146

The crude material of Example 10146 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 13.2 mg, and its estimated purity by LCMS analysis was 100%.

Analysis condition A: Retention time=1.42 min; ESI-MS (+) m/z 936.8 (M+2H).

Analysis condition B: Retention time=2.53 min; ESI-MS (+) m/z 936.7 (M+2H).

ESI-HRMS(+) m/z: Calculated: 935.9509 (M+2H); Found: 935.9490 (M+2H).

Preparation of Example 10147

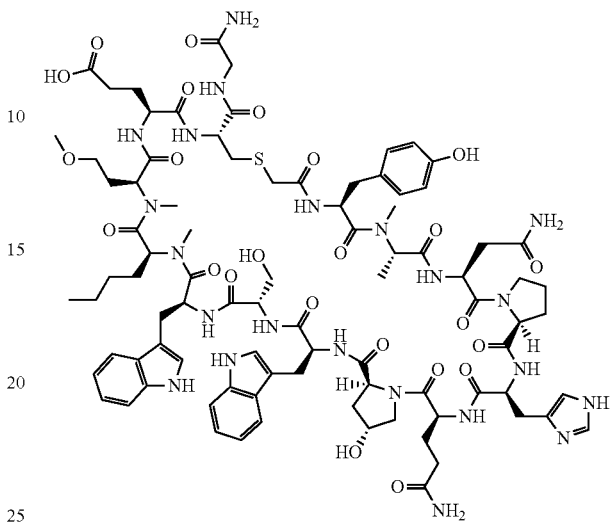

Example 10147

The crude material of Example 10147 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 20.4 mg, and its estimated purity by LCMS analysis was 98%.

Analysis condition A: Retention time=1.23 min; ESI-MS (+) m/z 951.2 (M+2H).

Analysis condition B: Retention time=2.33 min; ESI-MS (+) m/z 951.6 (M+2H).

ESI-HRMS(+) m/z: Calculated: 950.4278 (M+2H); Found: 950.4256 (M+2H).

Preparation of Example 10148

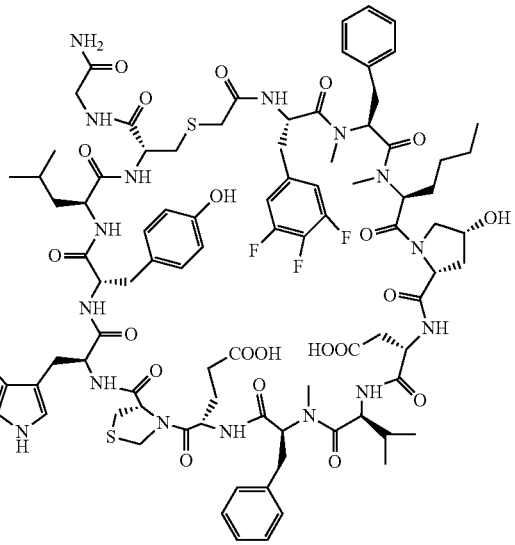

Example 10148

The crude material of Example 10148 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 3.7 mg, and its estimated purity by LCMS analysis was 99%.

Analysis condition B: Retention time=1.71 min; ESI-MS (−) m/z 950.9 (M−2H).

ESI-HRMS(+) m/z: Calculated: 951.3981 (M+2H); Found: 951.3967 (M+2H).

Preparation of Example 10149

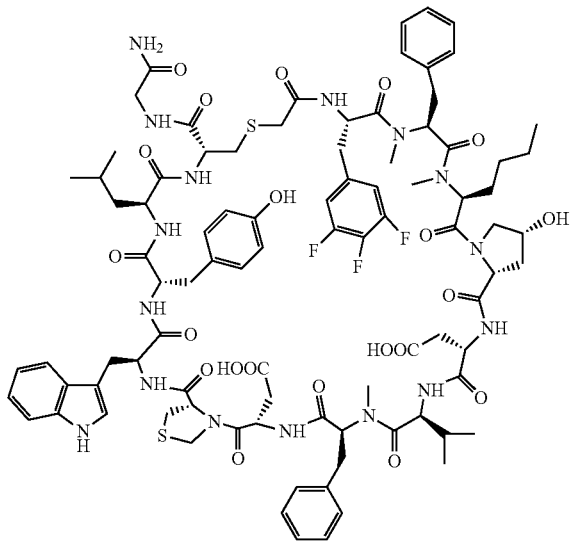

Example 10149

The crude material of Example 10149 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 8.2 mg, and its estimated purity by LCMS analysis was 95%.

Analysis condition A: Retention time=1.73 min; ESI-MS (−) m/z 943.5 (M−2H).

Analysis condition B: Retention time=2.89 min; ESI-MS (+) m/z 945.4 (M+2H).

ESI-HRMS(+) m/z: Calculated: 944.3903 (M+2H); Found: 944.3894 (M+2H).

Preparation of Example 10150

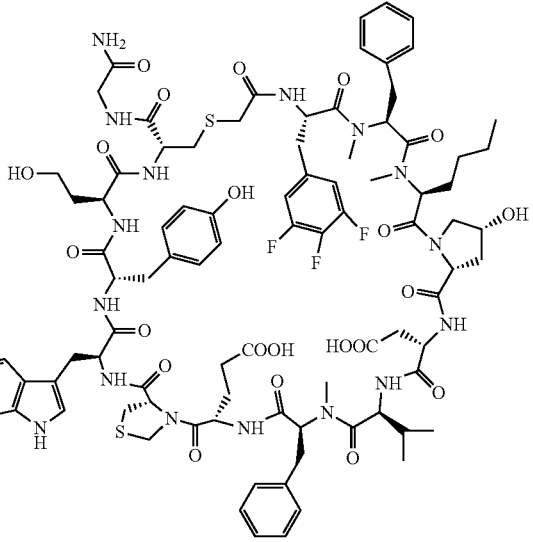

Example 10150

The crude material of Example 10150 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 4.7 mg, and its estimated purity by LCMS analysis was 96%.

Analysis condition A: Retention time=1.61 min; ESI-MS (−) m/z 944.2 (M−2H).

Analysis condition B: Retention time=2.84 min; ESI-MS (+) m/z 946.4 (M+2H).

ESI-HRMS(+) m/z: Calculated: 945.3799 (M+2H); Found: 945.3791 (M+2H).

Preparation of Example 10151

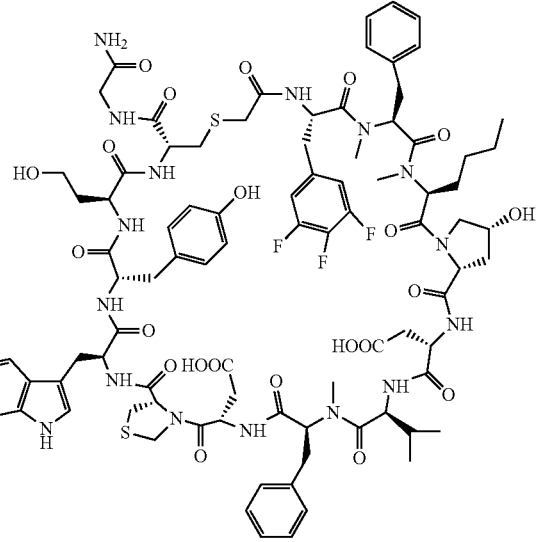

Example 10151

The crude material of Example 10151 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 11.7 mg, and its estimated purity by LCMS analysis was 100%.

Analysis condition A: Retention time=1.59 min; ESI-MS (−) m/z 937.3 (M−2H).

Analysis condition B: Retention time=2.83 min; ESI-MS (+) m/z 939.8 (M+2H).

ESI-HRMS(+) m/z: Calculated: 938.3721 (M+2H); Found: 938.3719 (M+2H).

Preparation of Example 10152

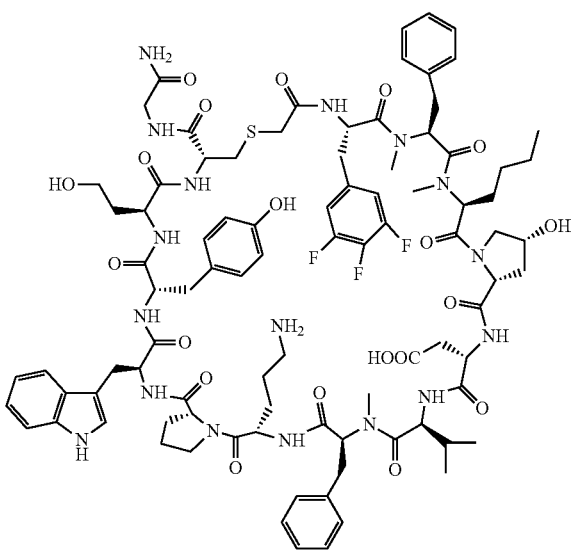

Example 10152

The crude material of Example 10152 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 17.0 mg, and its estimated purity by LCMS analysis was 100%.

Analysis condition A: Retention time=1.72 min; ESI-MS (−) m/z 928.1 (M−2H).

Analysis condition B: Retention time=3.06 min; ESI-MS (+) m/z 930.0 (M+2H).

ESI-HRMS(+) m/z: Calculated: 928.9200 (M+2H); Found: 928.9183 (M+2H).

Preparation of Example 10153

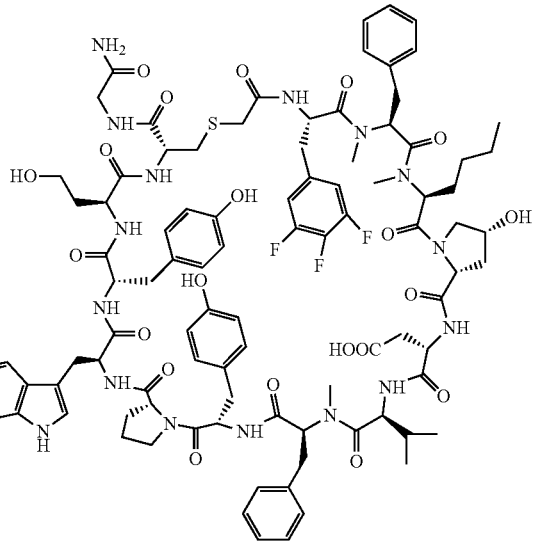

Example 10153

The crude material of Example 10153 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 20.9 mg, and its estimated purity by LCMS analysis was 100%.

Analysis condition A: Retention time=1.68 min; ESI-MS (−) m/z 952.6 (M−2H).

Analysis condition B: Retention time=2.95 min; ESI-MS (+) m/z 954.8 (M+2H).

ESI-HRMS(+) m/z: Calculated: 953.4121 (M+2H); Found: 953.4107 (M+2H).

Preparation of Example 10154

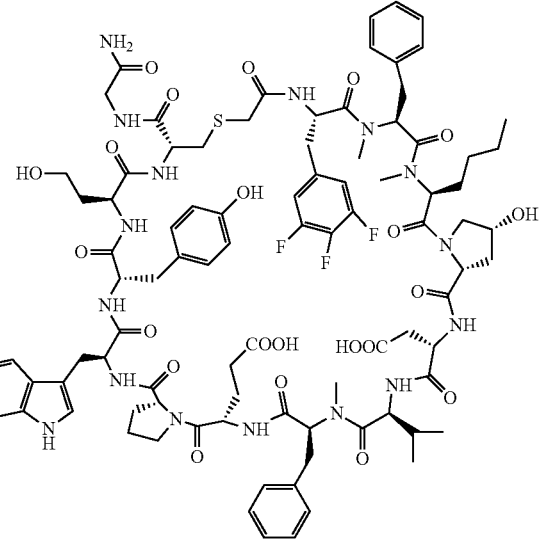

Example 10154

The crude material of Example 10154 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 36.0 mg, and its estimated purity by LCMS analysis was 99%.

Analysis condition A: Retention time=1.48 min; ESI-MS (+) m/z 936.7 (M+2H).

Analysis condition B: Retention time=2.74 min; ESI-MS (+) m/z 937.5 (M+2H).

ESI-HRMS(+) m/z: Calculated: 936.4017 (M+2H); Found: 936.4008 (M+2H).

Preparation of Example 10155

Example 10155

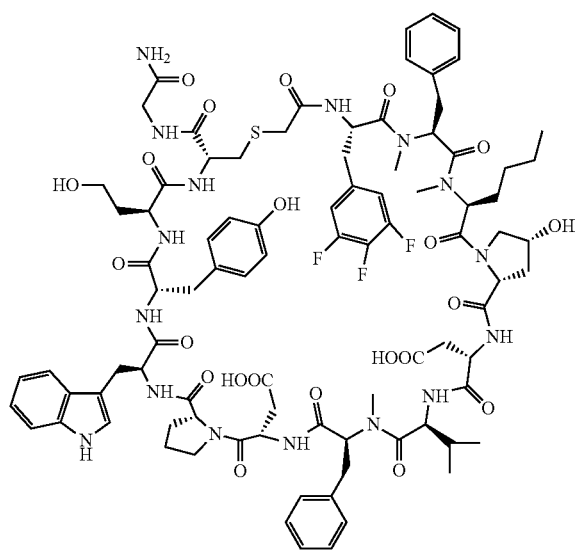

The crude material of Example 10155 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 31.4 mg, and its estimated purity by LCMS analysis was 94%.

Analysis condition A: Retention time=1.54 min; ESI-MS (−) m/z 928.6 (M−2H).

Analysis condition B: Retention time=2.69 min; ESI-MS (+) m/z 930.3 (M+2H).

ESI-HRMS(+) m/z: Calculated: 929.3939 (M+2H); Found: 929.3927 (M+2H).

Preparation of (R)-4-(((9H-fluoren-9-yl)methoxy) carbonyl)morpholine-3-carboxylic acid Scheme:

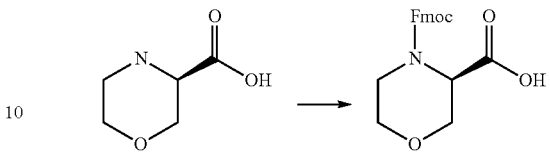

To a solution of (R)-morpholine-3-carboxylic acid (2 g, 15.25 mmol) in THF (50.8 mL) and water (25.4 mL) was added sodium bicarbonate (1.922 g, 22.88 mmol) and FMOC-OSU (5.14 g, 15.25 mmol). The resulting mixture was stirred for 28 h. After removal of THF, the white suspension was diluted with sat.NaHCO₃/water and ether. Filter through celite. Washed with water and ether. Separate ether and aqueous layer. The aqueous layer was acidified with 1 N HCl, extracted with ethyl acetate, washed with brine, dried over Na₂SO₄, concentrated to give 3.19 g (R)-4-(((9H-fluoren-9-yl)methoxy)carbonyl)morpholine-3-carboxylic acid as white solid.

Preparation of Example 10156

Example 10156

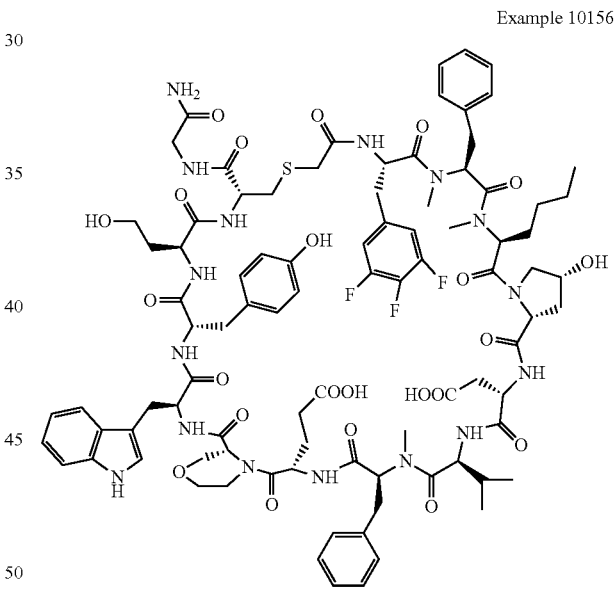

The crude material of Example 10156 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 18.1 mg, and its estimated purity by LCMS analysis was 97%.

Analysis condition A: Retention time=1.60 min; ESI-MS (−) m/z 943.3 (M−2H).

Analysis condition B: Retention time=2.83 min; ESI-MS (+) m/z 945.8 (M+2H).

ESI-HRMS(+) m/z: Calculated: 944.3991 (M+2H); Found: 944.3984 (M+2H).

Preparation of Example 10157

Example 10157

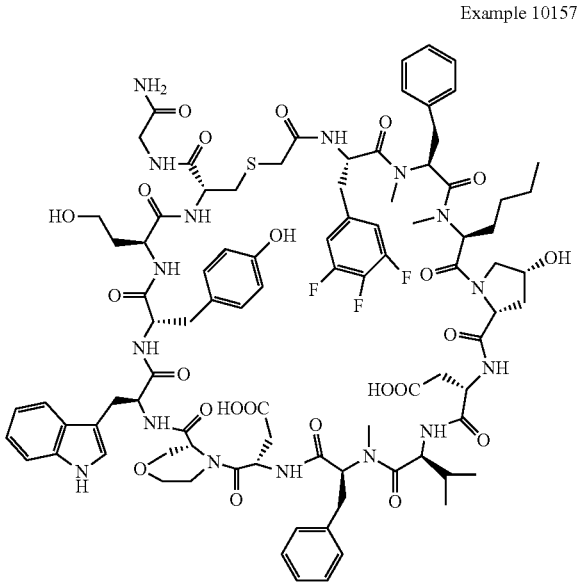 [SMILES: CCCC[C@H]1C(=O)N2C[C@H](O)C[C@@H]2C(=O)N[C@@H](CC(=O)O)C(=O)N[C@@H](C(C)C)C(=O)N(C)[C@@H](Cc2ccccc2)C(=O)N[C@@H](CC(=O)O)C(=O)N2CCOC[C@@H]2C(=O)N[C@@H](Cc2c[nH]c3ccccc23)C(=O)N[C@@H](Cc2ccc(O)cc2)C(=O)N[C@@H](CCO)C(=O)N[C@H](C(=O)NCC(N)=O)CSCC(=O)N[C@@H](Cc2cc(F)c(F)c(F)c2)C(=O)N(C)[C@@H](Cc2ccccc2)C(=O)N1C]

The crude material of Example 10157 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 20.1 mg, and its estimated purity by LCMS analysis was 95%.

Analysis condition A: Retention time=1.59 min; ESI-MS (−) m/z 936.6 (M−2H).

Analysis condition B: Retention time=2.81 min; ESI-MS (+) m/z 938.7 (M+2H).

ESI-HRMS(+) m/z: Calculated: 937.3913 (M+2H); Found: 937.3905 (M+2H).

Preparation of Example 10158

Example 10158

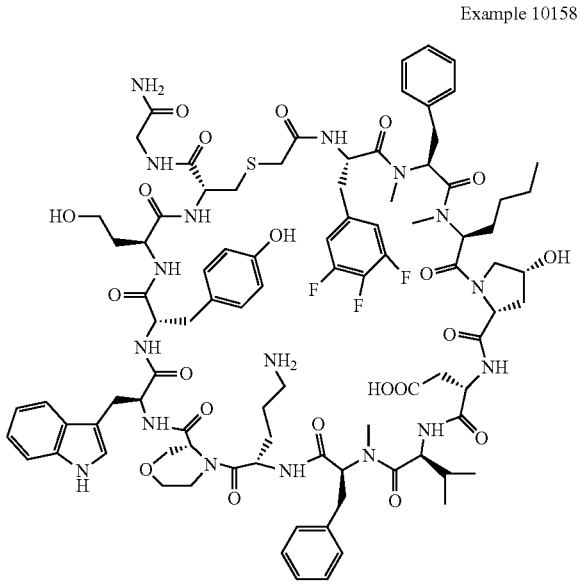 [SMILES: CCCC[C@H]1C(=O)N2C[C@H](O)C[C@@H]2C(=O)N[C@@H](CC(=O)O)C(=O)N[C@@H](C(C)C)C(=O)N(C)[C@@H](Cc2ccccc2)C(=O)N[C@@H](CCCN)C(=O)N2CCOC[C@@H]2C(=O)N[C@@H](Cc2c[nH]c3ccccc23)C(=O)N[C@@H](Cc2ccc(O)cc2)C(=O)N[C@@H](CCO)C(=O)N[C@H](C(=O)NCC(N)=O)CSCC(=O)N[C@@H](Cc2cc(F)c(F)c(F)c2)C(=O)N(C)[C@@H](Cc2ccccc2)C(=O)N1C]

The crude material of Example 10158 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 20.1 mg, and its estimated purity by LCMS analysis was 97%.

Analysis condition A: Retention time=1.77 min; ESI-MS (+) m/z 937.4 (M+2H).

Analysis condition B: Retention time=2.99 min; ESI-MS (+) m/z 937.4 (M+2H).

ESI-HRMS(+) m/z: Calculated: 936.9175 (M+2H); Found: 936.9158 (M+2H).

Preparation of Example 10159

Example 10159

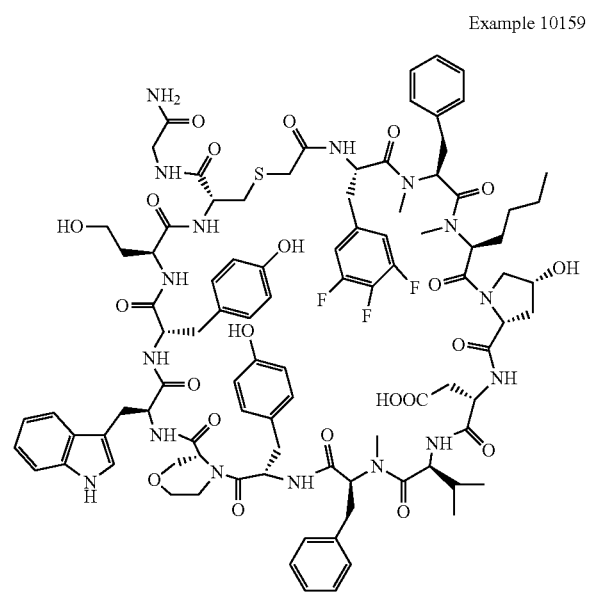 [SMILES: CCCC[C@H]1C(=O)N2C[C@H](O)C[C@@H]2C(=O)N[C@@H](CC(=O)O)C(=O)N[C@@H](C(C)C)C(=O)N(C)[C@@H](Cc2ccccc2)C(=O)N[C@@H](Cc2ccc(O)cc2)C(=O)N2CCOC[C@@H]2C(=O)N[C@@H](Cc2c[nH]c3ccccc23)C(=O)N[C@@H](Cc2ccc(O)cc2)C(=O)N[C@@H](CCO)C(=O)N[C@H](C(=O)NCC(N)=O)CSCC(=O)N[C@@H](Cc2cc(F)c(F)c(F)c2)C(=O)N(C)[C@@H](Cc2ccccc2)C(=O)N1C]

The crude material of Example 10159 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 16.2 mg, and its estimated purity by LCMS analysis was 100%.

Analysis condition A: Retention time=1.73 min; ESI-MS (+) m/z 960.4 (M+2H).

Analysis condition B: Retention time=3.01 min; ESI-MS (+) m/z 962.5 (M+2H).

ESI-HRMS(+) m/z: Calculated: 961.4095 (M+2H); Found: 961.4093 (M+2H).

Preparation of Example 10160

Example 10160

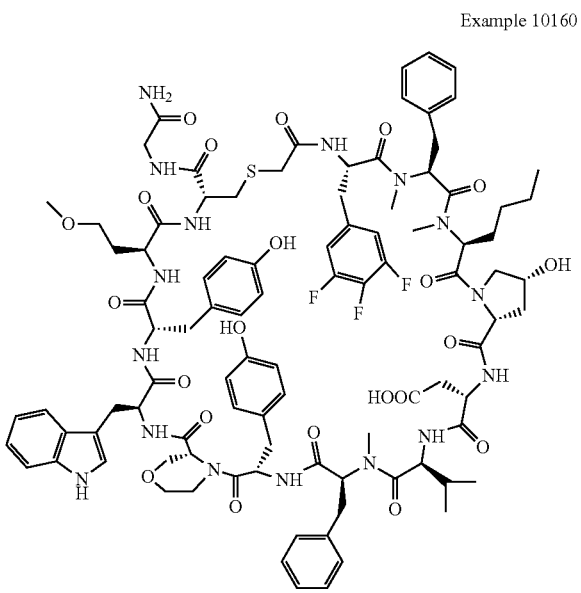 [SMILES: CCCC[C@H]1C(=O)N2C[C@H](O)C[C@@H]2C(=O)N[C@@H](CC(=O)O)C(=O)N[C@@H](C(C)C)C(=O)N(C)[C@@H](Cc2ccccc2)C(=O)N[C@@H](Cc2ccc(O)cc2)C(=O)N2CCOC[C@@H]2C(=O)N[C@@H](Cc2c[nH]c3ccccc23)C(=O)N[C@@H](Cc2ccc(O)cc2)C(=O)N[C@@H](CCOC)C(=O)N[C@H](C(=O)NCC(N)=O)CSCC(=O)N[C@@H](Cc2cc(F)c(F)c(F)c2)C(=O)N(C)[C@@H](Cc2ccccc2)C(=O)N1C]

The crude material of Example 10161 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 18.6 mg, and its estimated purity by LCMS analysis was 100%.

Analysis condition A: Retention time=1.80 min; ESI-MS (+) m/z 968.80 (M+2H).

Analysis condition B: Retention time=3.44 min; ESI-MS (+) m/z 968.80 (M+2H).

ESI-HRMS(+) m/z: Calculated: 968.4173 (M+2H); Found: 968.4154 (M+2H).

Preparation of Example 10161

Example 10161

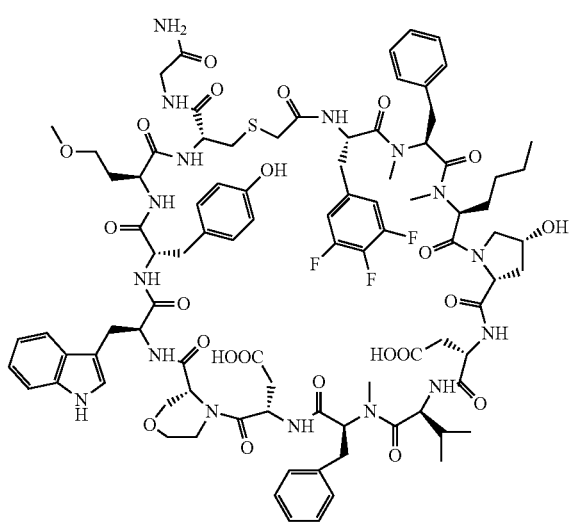

The crude material of Example 10161 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 19.4 mg, and its estimated purity by LCMS analysis was 95%.

Analysis condition A: Retention time=1.65 min; ESI-MS (+) m/z 944.65 (M+2H).

Analysis condition B: Retention time=3.20 min; ESI-MS (+) m/z 944.80 (M+2H).

ESI-HRMS(+) m/z: Calculated: 944.3991 (M+2H); Found: 944.3977 (M+2H).

Preparation of Example 10162

Example 10162

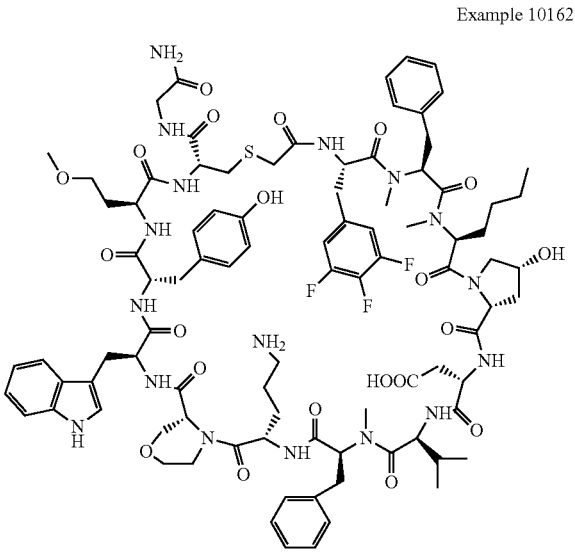 [SMILES: CCCC[C@H]1C(=O)N2C[C@H](O)C[C@@H]2C(=O)N[C@@H](CC(=O)O)C(=O)N[C@@H](C(C)C)C(=O)N(C)[C@@H](Cc2ccccc2)C(=O)N[C@@H](CCCN)C(=O)N2CCOC[C@@H]2C(=O)N[C@@H](Cc2c[nH]c3ccccc23)C(=O)N[C@@H](Cc2ccc(O)cc2)C(=O)N[C@@H](CCOC)C(=O)N[C@H](C(=O)NCC(N)=O)CSCC(=O)N[C@@H](Cc2cc(F)c(F)c(F)c2)C(=O)N(C)[C@@H](Cc2ccccc2)C(=O)N1C]

The crude material of Example 10162 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 33.5 mg, and its estimated purity by LCMS analysis was 100%.

Analysis condition A: Retention time=1.85 min; ESI-MS (+) m/z 944.45 (M+2H).

ESI-HRMS(+) m/z: Calculated: 943.9253 (M+2H); Found: 943.9225 (M+2H).

Preparation of Example 10163

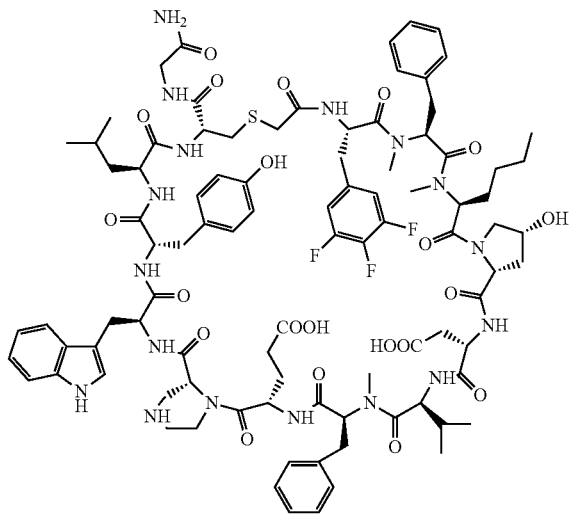

Example 10163

The crude material of Example 10163 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 3.5 mg, and its estimated purity by LCMS analysis was 100%.

Analysis condition A: Retention time=1.59 min; ESI-MS (+) m/z 950.30 (M+2H).

Analysis condition B: Retention time=2.90 min; ESI-MS (+) m/z 950.70 (M+2H).

ESI-HRMS(+) m/z: Calculated: 949.9253 (M+2H); Found: 949.9239 (M+2H).

Preparation of Example 10164

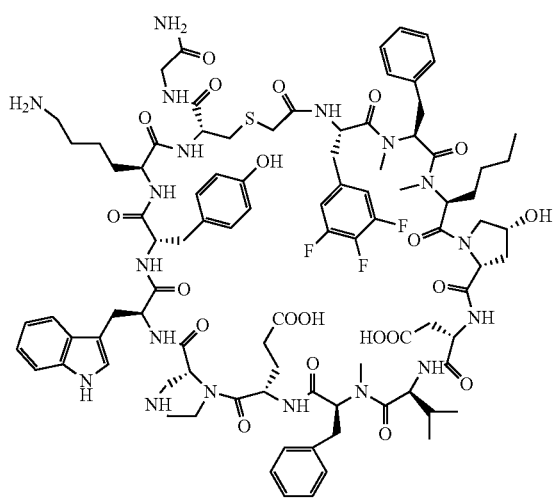

Example 10164

The crude material of Example 10164 was purified via preparative LC/MS with the following conditions: Column: XBridge C8, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 11.6 mg, and its estimated purity by LCMS analysis was 100%.

Analysis condition A: Retention time=1.75 min; ESI-MS (+) m/z 958.10 (M+2H).

Analysis condition B: Retention time=2.98 min; ESI-MS (+) m/z 958.00 (M+2H).

ESI-HRMS(+) m/z: Calculated: 957.4308 (M+2H); Found: 957.4300 (M+2H).

Preparation of Example 10165

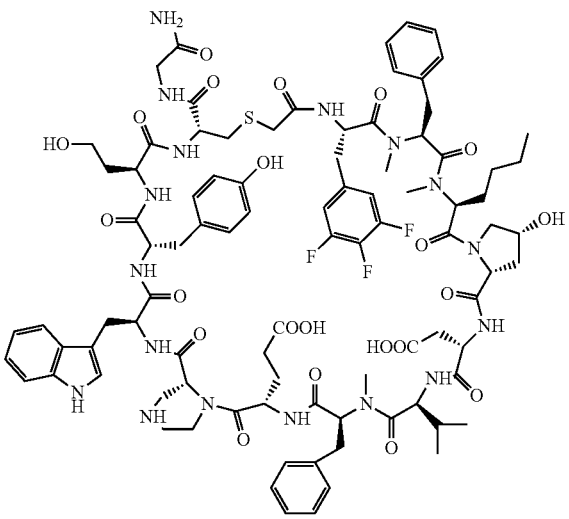

Example 10165

The crude material of Example 10165 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 3.2 mg, and its estimated purity by LCMS analysis was 95%.

Analysis condition A: Retention time=1.63 min; ESI-MS (+) m/z 945.40 (M+2H).

Analysis condition B: Retention time=2.85 min; ESI-MS (+) m/z 944.70 (M+2H).

ESI-HRMS(+) m/z: Calculated: 943.9071 (M+2H); Found: 943.9067 (M+2H).

Preparation of Example 10166

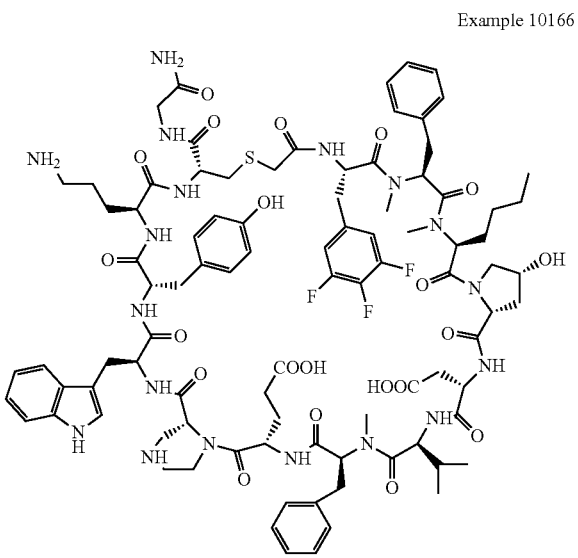 [SMILES: CCCC[C@H]1C(=O)N2C[C@H](O)C[C@@H]2C(=O)N[C@@H](CC(=O)O)C(=O)N[C@@H](C(C)C)C(=O)N(C)[C@@H](Cc2ccccc2)C(=O)N[C@@H](CCC(=O)O)C(=O)N2CCNC[C@@H]2C(=O)N[C@@H](Cc2c[nH]c3ccccc23)C(=O)N[C@@H](Cc2ccc(O)cc2)C(=O)N[C@@H](CCCN)C(=O)N[C@H](C(=O)NCC(N)=O)CSCC(=O)N[C@@H](Cc2cc(F)c(F)c(F)c2)C(=O)N(C)[C@@H](Cc2ccccc2)C(=O)N1C]
Example 10166

The crude material of Example 10166 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 12.6 mg, and its estimated purity by LCMS analysis was 99%.

Analysis condition A: Retention time=1.73 min; ESI-MS (+) m/z 951.50 (M+2H).

Analysis condition B: Retention time=2.98 min; ESI-MS (+) m/z 951.00 (M+2H).

Preparation of Example 10167

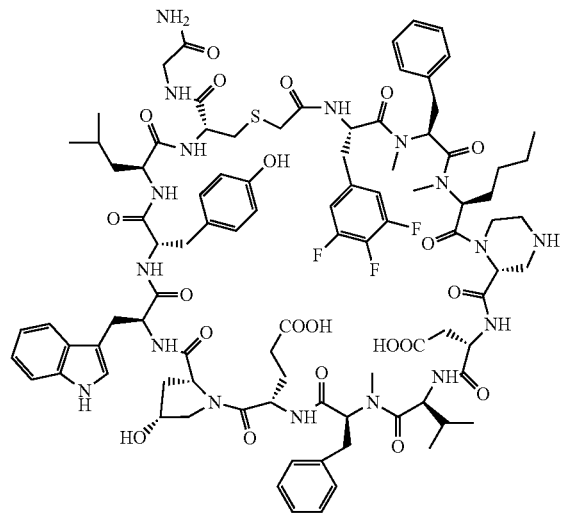
Example 10167

The crude material of Example 10167 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 48.2 mg, and its estimated purity by LCMS analysis was 98%.

Analysis condition A: Retention time=1.61 min; ESI-MS (+) m/z 949.50 (M+2H).

Analysis condition B: Retention time=2.77 min; ESI-MS (+) m/z 949.50 (M+2H).

Preparation of Example 10168

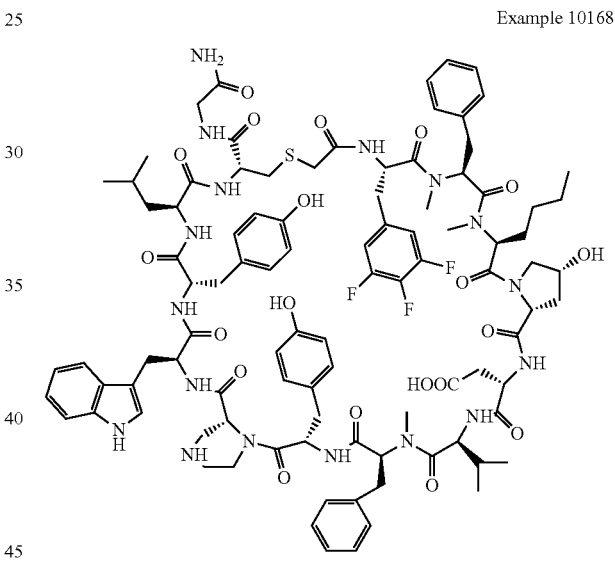
Example 10168

The crude material of Example 10168 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 24.9 mg, and its estimated purity by LCMS analysis was 100%.

Analysis condition A: Retention time=1.74 min; ESI-MS (+) m/z 967.80 (M+2H).

Analysis condition B: Retention time=3.10 min; ESI-MS (+) m/z 968.10 (M+2H).

ESI-HRMS(+) m/z: Calculated: 966.9357 (M+2H); Found: 966.9339 (M+2H).

Preparation of Example 10169

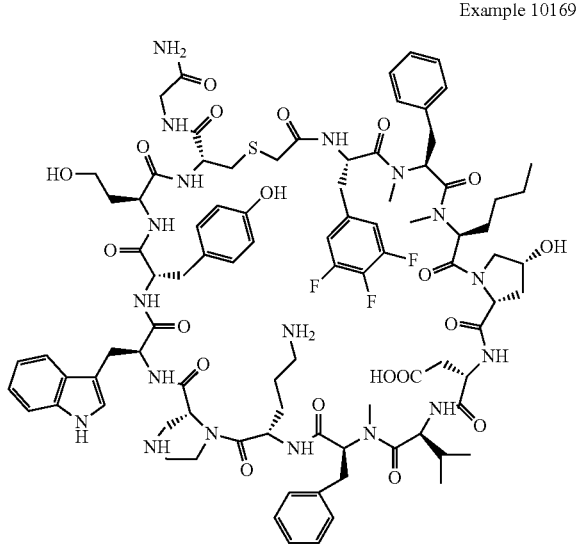 [SMILES: CCCC[C@H]1C(=O)N2C[C@H](O)C[C@@H]2C(=O)N[C@@H](CC(=O)O)C(=O)N[C@@H](C(C)C)C(=O)N(C)[C@@H](Cc2ccccc2)C(=O)N[C@@H](CCCN)C(=O)N2CCNC[C@@H]2C(=O)N[C@@H](Cc2c[nH]c3ccccc23)C(=O)N[C@@H](Cc2ccc(O)cc2)C(=O)N[C@@H](CCO)C(=O)N[C@H](C(=O)NCC(N)=O)CSCC(=O)N[C@@H](Cc2cc(F)c(F)c(F)c2)C(=O)N(C)[C@@H](Cc2ccccc2)C(=O)N1C]

Example 10169

The crude material of Example 10169 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 18.9 mg, and its estimated purity by LCMS analysis was 97%.

Analysis condition A: Retention time=1.75 min; ESI-MS (+) m/z 937.10 (M+2H).

Analysis condition B: Retention time=3.17 min; ESI-MS (+) m/z 937.30 (M+2H).

ESI-HRMS(+) m/z: Calculated: 936.4255 (M+2H); Found: 936.4226 (M+2H).

Preparation of Example 10170

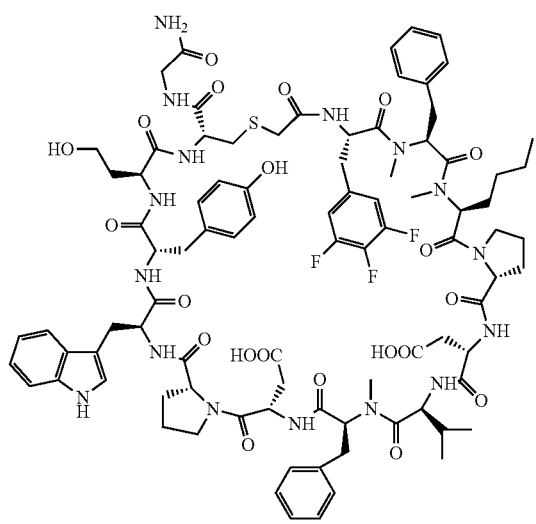

Example 10170

The crude material of Example 10170 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 25.1 mg, and its estimated purity by LCMS analysis was 100%.

Analysis condition A: Retention time=1.70 min; ESI-MS (+) m/z 919.20 (M+2H).

Analysis condition B: Retention time=2.39 min; ESI-MS (+) m/z 920.05 (M+2H).

ESI-HRMS(+) m/z: Calculated: 921.3964 (M+2H); Found: 921.3936 (M+2H).

Preparation of Example 10171

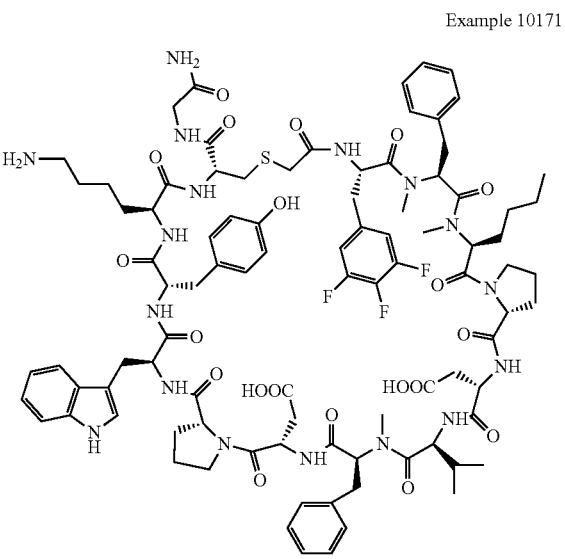 [SMILES: CCCC[C@H]1C(=O)N2CCC[C@@H]2C(=O)N[C@@H](CC(=O)O)C(=O)N[C@@H](C(C)C)C(=O)N(C)[C@@H](Cc2ccccc2)C(=O)N[C@@H](CC(=O)O)C(=O)N2CCC[C@@H]2C(=O)N[C@@H](Cc2c[nH]c3ccccc23)C(=O)N[C@@H](Cc2ccc(O)cc2)C(=O)N[C@@H](CCCCN)C(=O)N[C@H](C(=O)NCC(N)=O)CSCC(=O)N[C@@H](Cc2cc(F)c(F)c(F)c2)C(=O)N(C)[C@@H](Cc2ccccc2)C(=O)N1C]

Example 10171

The crude material of Example 10171 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 35.2 mg, and its estimated purity by LCMS analysis was 100%.

Analysis condition A: Retention time=1.59 min; ESI-MS (+) m/z 935.50 (M+2H).

Analysis condition B: Retention time=2.93 min; ESI-MS (+) m/z 935.50 (M+2H).

ESI-HRMS(+) m/z: Calculated: 934.9200 (M+2H); Found: 934.9167 (M+2H).

Preparation of Example 10172

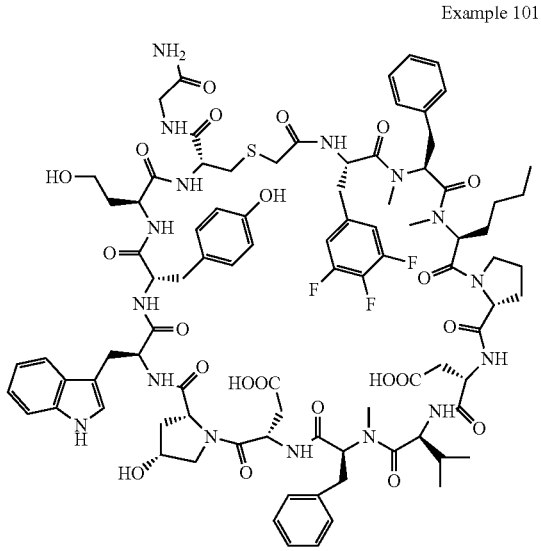

Example 10172

The crude material of Example 10172 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 32.9 mg, and its estimated purity by LCMS analysis was 98%.

Analysis condition A: Retention time=1.69 min; ESI-MS (−) m/z 927.65 (M−2H).

Analysis condition B: Retention time=2.35 min; ESI-MS (+) m/z 929.65 (M+2H).

ESI-HRMS(+) m/z: Calculated: 929.3939 (M+2H); Found: 929.3927 (M+2H).

Preparation of Example 10173

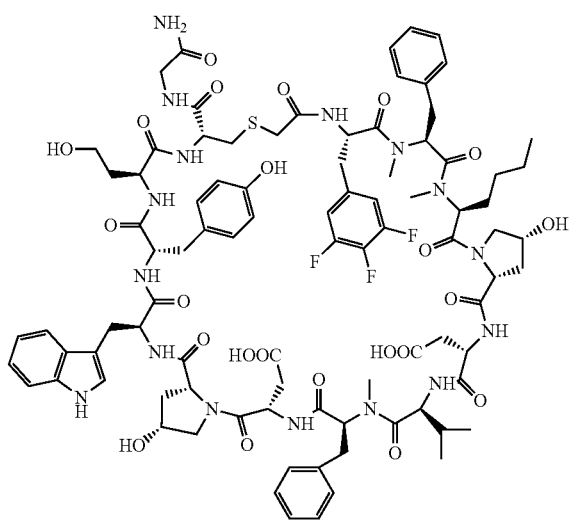

Example 10173

The crude material of Example 10173 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 18.6 mg, and its estimated purity by LCMS analysis was 100%.

Analysis condition A: Retention time=1.45 min; ESI-MS (+) m/z 938.0 (M+2H).

Analysis condition B: Retention time=2.70 min; ESI-MS (+) m/z 938.3 (M+2H).

ESI-HRMS(+) m/z: Calculated: 937.3913 (M+2H); Found: 937.3897 (M+2H).

Preparation of Example 10174

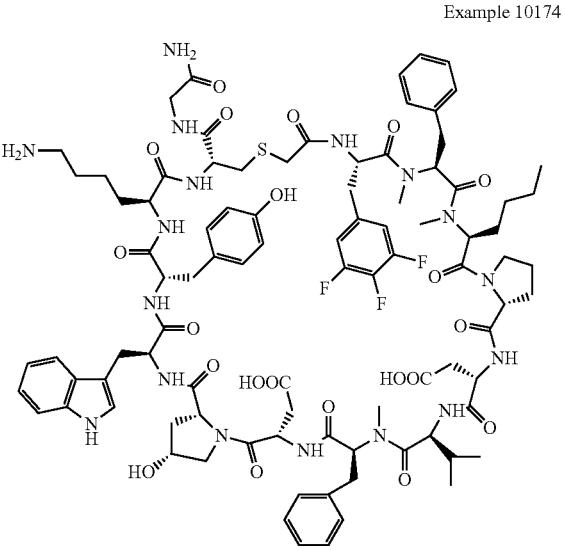 [SMILES: CCCC[C@H]1C(=O)N2CCC[C@@H]2C(=O)N[C@@H](CC(=O)O)C(=O)N[C@@H](C(C)C)C(=O)N(C)[C@@H](Cc2ccccc2)C(=O)N[C@@H](CC(=O)O)C(=O)N2C[C@H](O)C[C@@H]2C(=O)N[C@@H](Cc2c[nH]c3ccccc23)C(=O)N[C@@H](Cc2ccc(O)cc2)C(=O)N[C@@H](CCCCN)C(=O)N[C@H](C(=O)NCC(N)=O)CSCC(=O)N[C@@H](Cc2cc(F)c(F)c(F)c2)C(=O)N(C)[C@@H](Cc2ccccc2)C(=O)N1C]

Example 10174

The crude material of Example 10174 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 16.7 mg, and its estimated purity by LCMS analysis was 96%.

Analysis condition A: Retention time=1.58 min; ESI-MS (+) m/z 944.1 (M+2H).

Analysis condition B: Retention time=2.95 min; ESI-MS (+) m/z 943.5 (M+2H).

ESI-HRMS(+) m/z: Calculated: 942.9175 (M+2H); Found: 942.9151 (M+2H).

Preparation of Example 10175

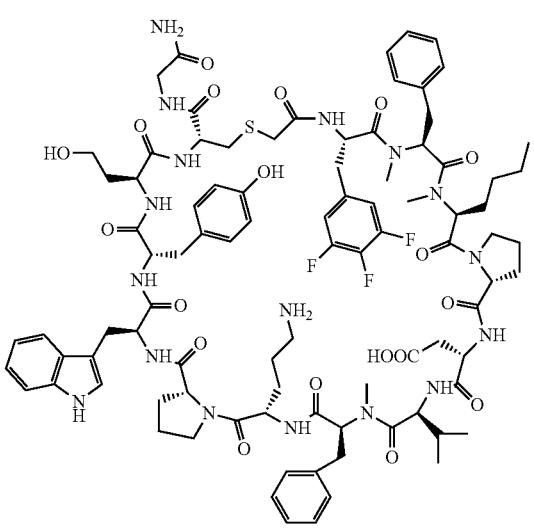

Example 10175

The crude material of Example 10175 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 38.7 mg, and its estimated purity by LCMS analysis was 95%.

Analysis condition A: Retention time=1.89 min; ESI-MS (−) m/z 918.8 (M−2H).

Analysis condition B: Retention time=3.34 min; ESI-MS (+) m/z 921.15 (M+2H).

ESI-HRMS(+) m/z: Calculated: 920.9226 (M+2H); Found: 920.9186 (M+2H).

Preparation of Example 10176

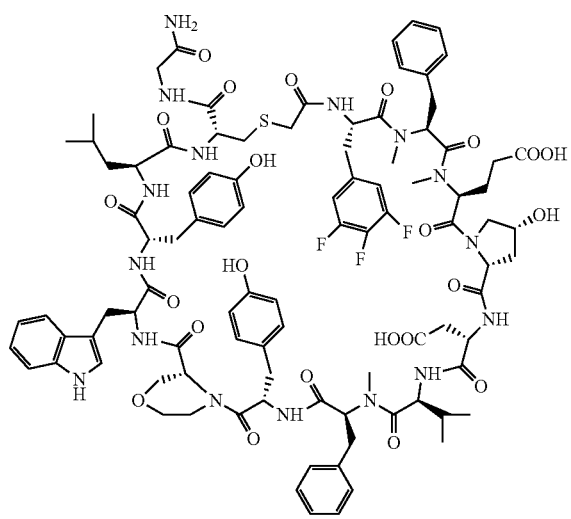

Example 10176

The crude material of Example 10176 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 18.1 mg, and its estimated purity by LCMS analysis was 97%.

Analysis condition A: Retention time=1.37 min; ESI-MS (−) m/z 973.9 (M−2H).

Analysis condition B: Retention time=2.57 min; ESI-MS (+) m/z 976.1 (M+2H).

ESI-HRMS(+) m/z: Calculated: 975.4070 (M+2H); Found: 975.4049 (M+2H).

Preparation of Example 10177

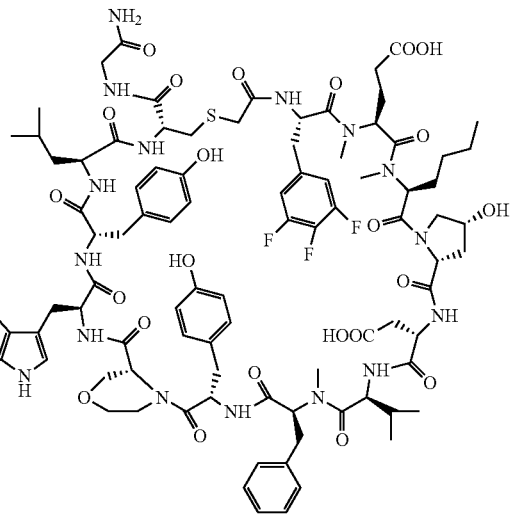

Example 10177

The crude material of Example 10177 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 28.6 mg, and its estimated purity by LCMS analysis was 96%.

Analysis condition A: Retention time=1.55 min; ESI-MS (+) m/z 959.5 (M+2H).

Analysis condition B: Retention time=2.95 min; ESI-MS (+) m/z 959.2 (M+2H).

ESI-HRMS(+) m/z: Calculated: 958.4148 (M+2H); Found: 958.4130 (M+2H).

Preparation of Example 10178

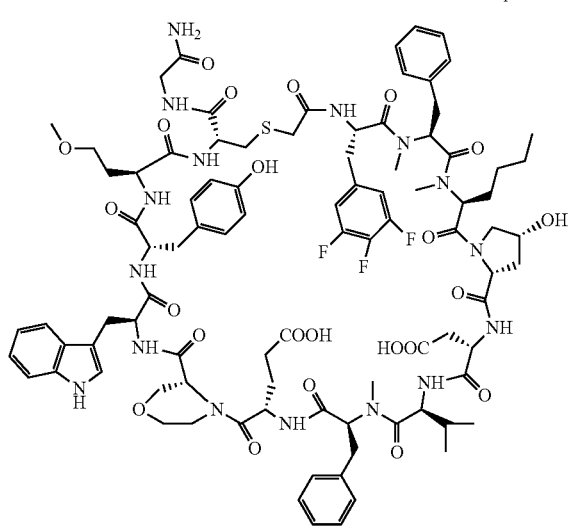

Example 10178

The crude material of Example 10178 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 46.3 mg, and its estimated purity by LCMS analysis was 100%.

Analysis condition A: Retention time=1.49 min; ESI-MS (+) m/z 952.4 (M+2H).

Analysis condition B: Retention time=2.81 min; ESI-MS (+) m/z 952.5 (M+2H).

ESI-HRMS(+) m/z: Calculated: 951.4070 (M+2H); Found: 951.4050 (M+2H).

Preparation of Example 10179

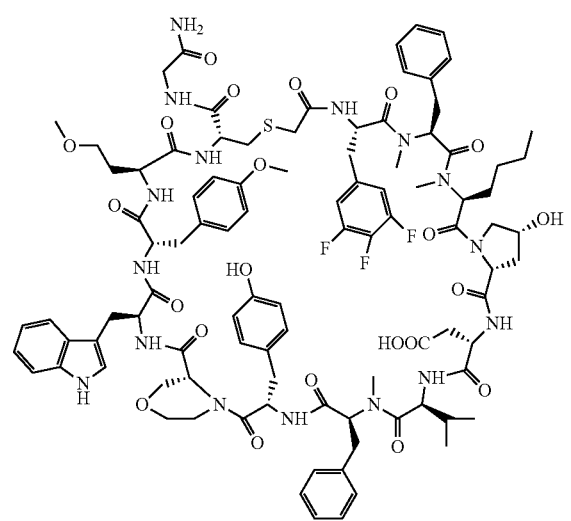

Example 10179

The crude material of Example 10179 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 28.1 mg, and its estimated purity by LCMS analysis was 100%.

Analysis condition A: Retention time=1.74 min; ESI-MS (+) m/z 976.5 (M+2H).

Analysis condition B: Retention time=3.12 min; ESI-MS (+) m/z 976.1 (M+2H).

ESI-HRMS(+) m/z: Calculated: 975.4252 (M+2H); Found: 975.4227 (M+2H).

Preparation of Example 10180

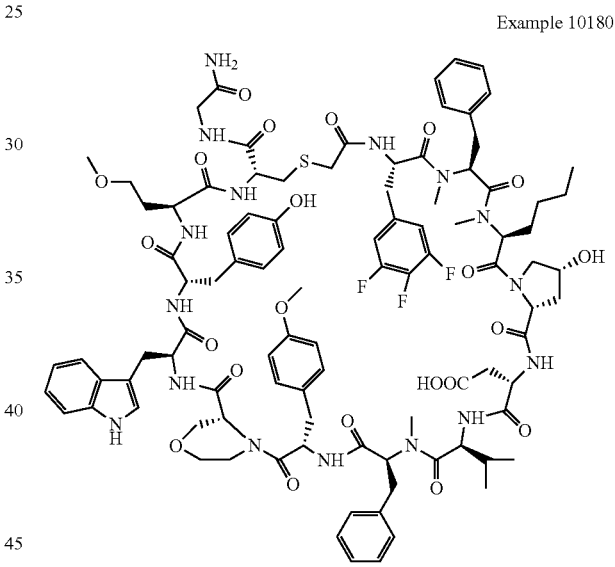

Example 10180

The crude material of Example 10180 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 26.8 mg, and its estimated purity by LCMS analysis was 100%.

Analysis condition A: Retention time=1.79 min; ESI-MS (+) m/z 975.7 (M+2H).

Analysis condition B: Retention time=3.37 min; ESI-MS (+) m/z 975.8 (M+2H).

ESI-HRMS(+) m/z: Calculated: 975.4252 (M+2H); Found: 975.4225 (M+2H).

Preparation of Example 10181

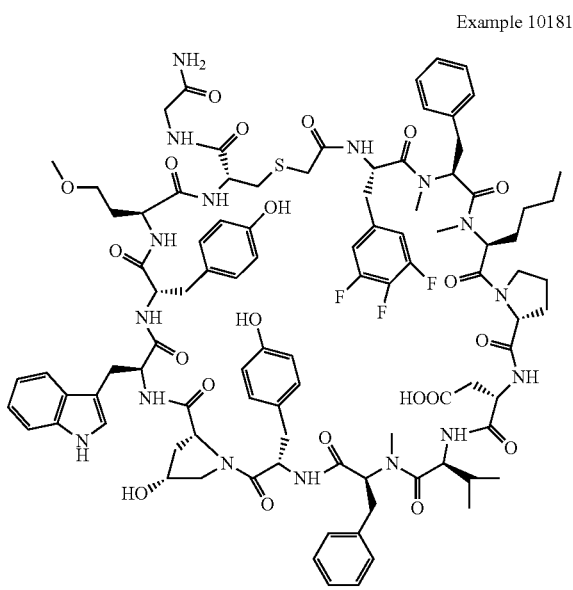 [SMILES: CCCC[C@H]1C(=O)N2CCC[C@@H]2C(=O)N[C@@H](CC(=O)O)C(=O)N[C@@H](C(C)C)C(=O)N(C)[C@@H](Cc2ccccc2)C(=O)N[C@@H](Cc2ccc(O)cc2)C(=O)N2C[C@H](O)C[C@@H]2C(=O)N[C@@H](Cc2c[nH]c3ccccc23)C(=O)N[C@@H](Cc2ccc(O)cc2)C(=O)N[C@@H](CCOC)C(=O)N[C@H](C(=O)NCC(N)=O)CSCC(=O)N[C@@H](Cc2cc(F)c(F)c(F)c2)C(=O)N(C)[C@@H](Cc2ccccc2)C(=O)N1C]

Example 10181

The crude material of Example 10181 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 25.5 mg, and its estimated purity by LCMS analysis was 96%.

Analysis condition A: Retention time=1.77 min; ESI-MS (+) m/z 960.70 (M+2H).

Analysis condition B: Retention time=3.37 min; ESI-MS (+) m/z 960.75 (M+2H).

ESI-HRMS(+) m/z: Calculated: 960.4199 (M+2H); Found: 960.4173 (M+2H).

Preparation of Example 10182

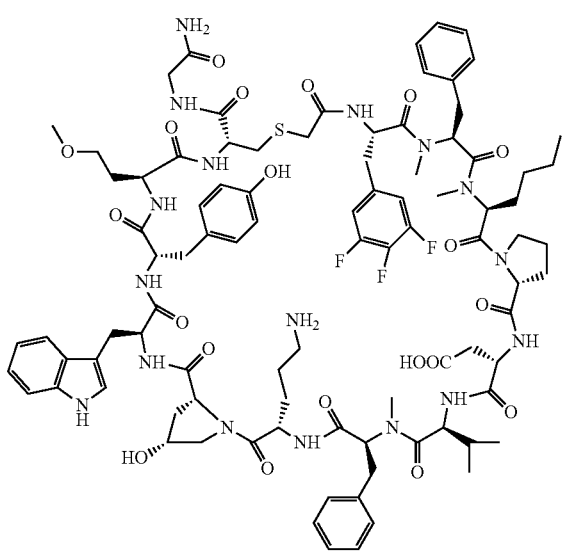

Example 10182

The crude material of Example 10182 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 23.9 mg, and its estimated purity by LCMS analysis was 100%.

Analysis condition A: Retention time=1.80 min; ESI-MS (+) m/z 936.25 (M+2H).

Analysis condition B: Retention time=3.47 min; ESI-MS (+) m/z 936.20 (M+2H).

ESI-HRMS(+) m/z: Calculated: 935.9279 (M+2H); Found: 935.9249 (M+2H).

Preparation of Example 10183

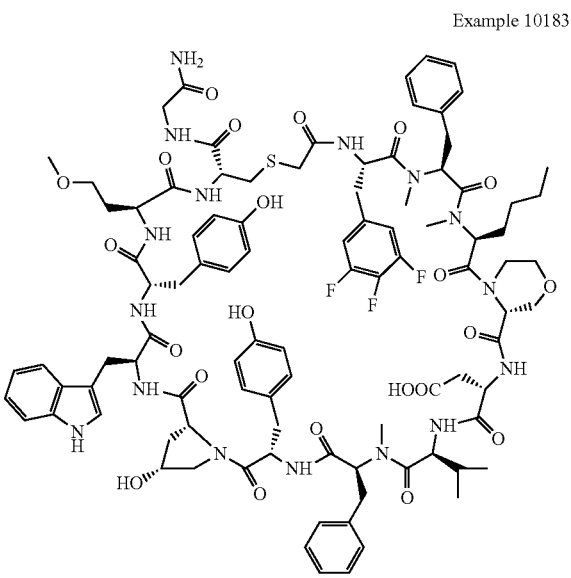 [SMILES: CCCC[C@H]1C(=O)N2CCOC[C@@H]2C(=O)N[C@@H](CC(=O)O)C(=O)N[C@@H](C(C)C)C(=O)N(C)[C@@H](Cc2ccccc2)C(=O)N[C@@H](Cc2ccc(O)cc2)C(=O)N2C[C@H](O)C[C@@H]2C(=O)N[C@@H](Cc2c[nH]c3ccccc23)C(=O)N[C@@H](Cc2ccc(O)cc2)C(=O)N[C@@H](CCOC)C(=O)N[C@H](C(=O)NCC(N)=O)CSCC(=O)N[C@@H](Cc2cc(F)c(F)c(F)c2)C(=O)N(C)[C@@H](Cc2ccccc2)C(=O)N1C]

Example 10183

The crude material of Example 10183 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 16.0 mg, and its estimated purity by LCMS analysis was 100%

Analysis condition A: Retention time=1.72 min; ESI-MS (+) m/z 960.75 (M+2H).

Analysis condition B: Retention time=3.29 min; ESI-MS (+) m/z 960.75 (M+2H).

ESI-HRMS(+) m/z: Calculated: 968.4173 (M+2H); Found: 968.4135 (M+2H).

Preparation of Example 10184

Example 10184

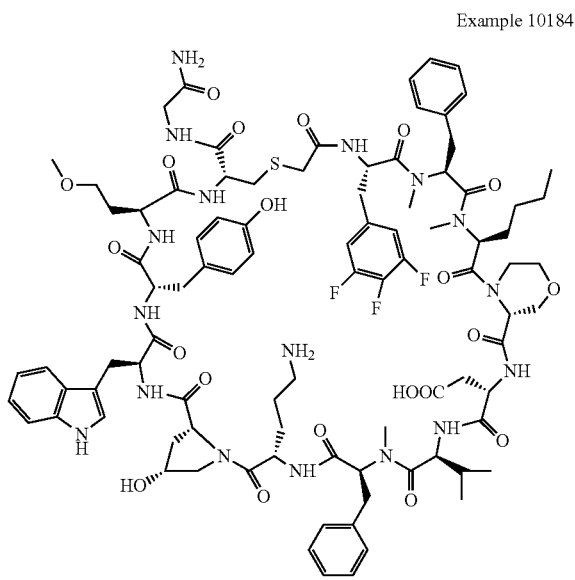 [SMILES: CCCC[C@H]1C(=O)N2CCOC[C@@H]2C(=O)N[C@@H](CC(=O)O)C(=O)N[C@@H](C(C)C)C(=O)N(C)[C@@H](Cc2ccccc2)C(=O)N[C@@H](CCCN)C(=O)N2C[C@H](O)C[C@@H]2C(=O)N[C@@H](Cc2c[nH]c3ccccc23)C(=O)N[C@@H](Cc2ccc(O)cc2)C(=O)N[C@@H](CCOC)C(=O)N[C@H](C(=O)NCC(N)=O)CSCC(=O)N[C@@H](Cc2cc(F)c(F)c(F)c2)C(=O)N(C)[C@@H](Cc2ccccc2)C(=O)N1C]

The crude material of Example 10184 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 23.5 mg, and its estimated purity by LCMS analysis was 94%.

Analysis condition A: Retention time=1.74 min; ESI-MS (+) m/z 944.20 (M+2H).

Analysis condition B: Retention time=3.37 min; ESI-MS (+) m/z 944.20 (M+2H).

ESI-HRMS(+) m/z: Calculated: 943.9253 (M+2H); Found: 943.9220 (M+2H).

Preparation of Example 10185

Example 10185

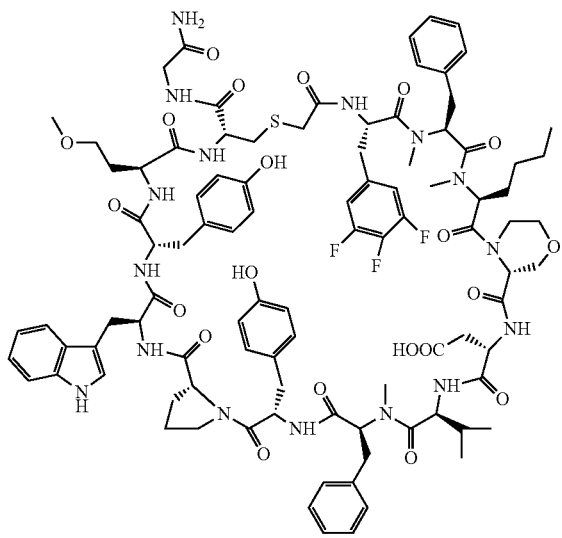

The crude material of Example 10185 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 16.6 mg, and its estimated purity by LCMS analysis was 96%.

Analysis condition A: Retention time=1.71 min; ESI-MS (+) m/z 960.65 (M+2H).

Analysis condition B: Retention time=3.23 min; ESI-MS (+) m/z 960.70 (M+2H).

ESI-HRMS(+) m/z: Calculated: 960.4199 (M+2H); Found: 960.4174 (M+2H).

Preparation of Example 10186

Example 10186

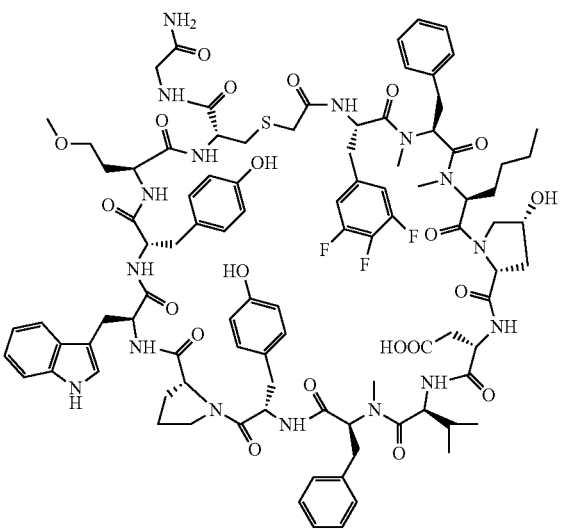

The crude material of Example 10186 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 31.7 mg, and its estimated purity by LCMS analysis was 99%.

Analysis condition A: Retention time=1.72 min; ESI-MS (+) m/z 960.70 (M+2H).

Analysis condition B: Retention time=3.30 min; ESI-MS (+) m/z 960.70 (M+2H).

ESI-HRMS(+) m/z: Calculated: 960.4199 (M+2H); Found: 960.4169 (M+2H).

Preparation of Example 10187

Example 10187

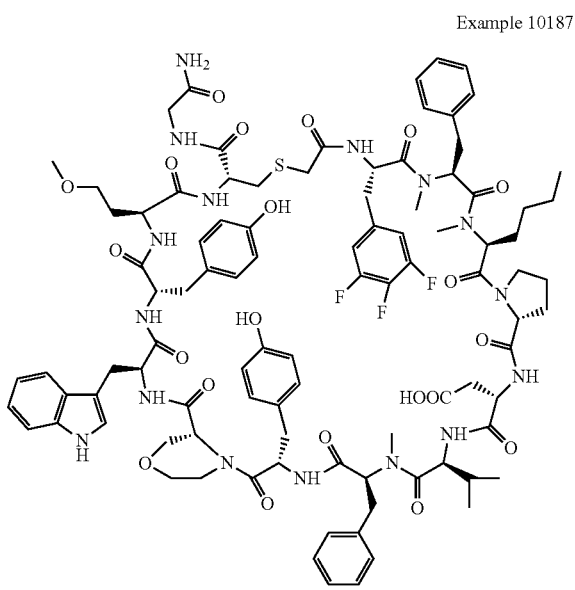 [SMILES: CCCC[C@H]1C(=O)N2CCC[C@@H]2C(=O)N[C@@H](CC(=O)O)C(=O)N[C@@H](C(C)C)C(=O)N(C)[C@@H](Cc2ccccc2)C(=O)N[C@@H](Cc2ccc(O)cc2)C(=O)N2CCOC[C@@H]2C(=O)N[C@@H](Cc2c[nH]c3ccccc23)C(=O)N[C@@H](Cc2ccc(O)cc2)C(=O)N[C@@H](CCOC)C(=O)N[C@H](C(=O)NCC(N)=O)CSCC(=O)N[C@@H](Cc2cc(F)c(F)c(F)c2)C(=O)N(C)[C@@H](Cc2ccccc2)C(=O)N1C]

The crude material of Example 10187 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 50.2 mg, and its estimated purity by LCMS analysis was 100%.

Analysis condition A: Retention time=1.82 min; ESI-MS (+) m/z 960.70 (M+2H).

Analysis condition B: Retention time=3.42 min; ESI-MS (+) m/z 960.75 (M+2H).

ESI-HRMS(+) m/z: Calculated: 960.4199 (M+2H); Found: 960.4168 (M+2H).

Preparation of Example 10188

Example 10188

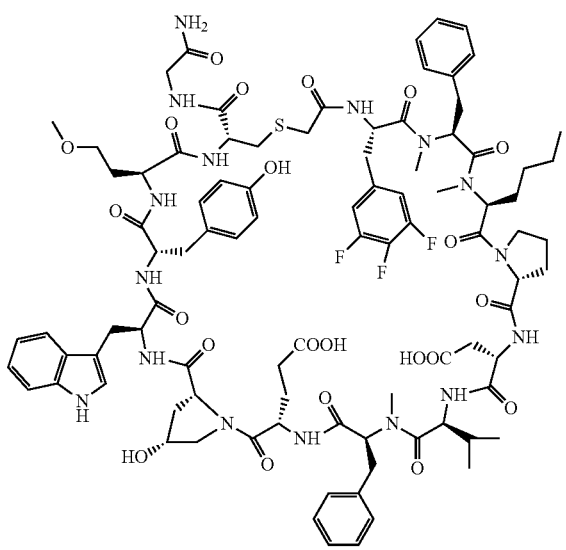

The crude material of Example 10188 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 28.2 mg, and its estimated purity by LCMS analysis was 100%.

Analysis condition A: Retention time=1.67 min; ESI-MS (+) m/z 943.65 (M+2H).

Analysis condition B: Retention time=3.18 min; ESI-MS (+) m/z 943.65 (M+2H).

ESI-HRMS(+) m/z: Calculated: 943.4095 (M+2H); Found: 943.4072 (M+2H).

Preparation of Example 10189

Example 10189

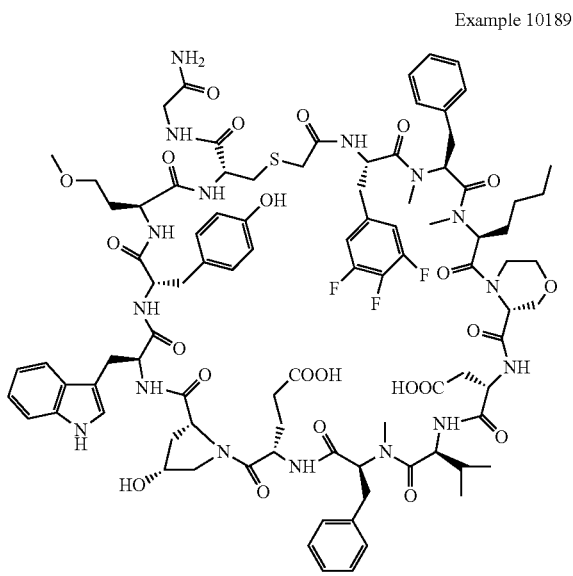 [SMILES: CCCC[C@H]1C(=O)N2CCOC[C@@H]2C(=O)N[C@@H](CC(=O)O)C(=O)N[C@@H](C(C)C)C(=O)N(C)[C@@H](Cc2ccccc2)C(=O)N[C@@H](CCC(=O)O)C(=O)N2C[C@H](O)C[C@@H]2C(=O)N[C@@H](Cc2c[nH]c3ccccc23)C(=O)N[C@@H](Cc2ccc(O)cc2)C(=O)N[C@@H](CCOC)C(=O)N[C@H](C(=O)NCC(N)=O)CSCC(=O)N[C@@H](Cc2cc(F)c(F)c(F)c2)C(=O)N(C)[C@@H](Cc2ccccc2)C(=O)N1C]

The crude material of Example 10189 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 22.5 mg, and its estimated purity by LCMS analysis was 100%.

Analysis condition A: Retention time=1.50 min; ESI-MS (+) m/z 952.0 (M+2H).

Analysis condition B: Retention time=2.74 min; ESI-MS (+) m/z 952.0 (M+2H).

ESI-HRMS(+) m/z: Calculated: 951.4070 (M+2H); Found: 951.4054 (M+2H).

Preparation of Example 10190

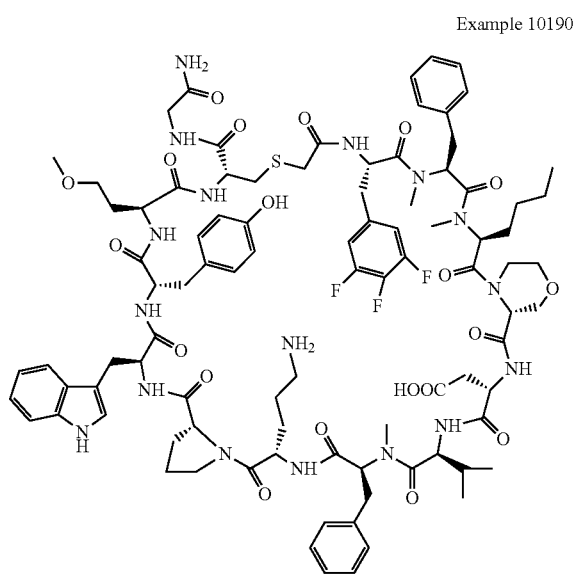 [SMILES: CCCC[C@H]1C(=O)N2CCOC[C@@H]2C(=O)N[C@@H](CC(=O)O)C(=O)N[C@@H](C(C)C)C(=O)N(C)[C@@H](Cc2ccccc2)C(=O)N[C@@H](CCCN)C(=O)N2CCC[C@@H]2C(=O)N[C@@H](Cc2c[nH]c3ccccc23)C(=O)N[C@@H](Cc2ccc(O)cc2)C(=O)N[C@@H](CCOC)C(=O)N[C@H](C(=O)NCC(N)=O)CSCC(=O)N[C@@H](Cc2cc(F)c(F)c(F)c2)C(=O)N(C)[C@@H](Cc2ccccc2)C(=O)N1C]

Example 10190

The crude material of Example 10190 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 29.2 mg, and its estimated purity by LCMS analysis was 100%.

Analysis condition A: Retention time=1.77 min; ESI-MS (−) m/z 935.2 (M−2H).

Analysis condition B: Retention time=2.97 min; ESI-MS (−) m/z 934.3 (M−2H).

ESI-HRMS(+) m/z: Calculated: 935.9279 (M+2H); Found: 935.9238 (M+2H).

Preparation of Example 10191

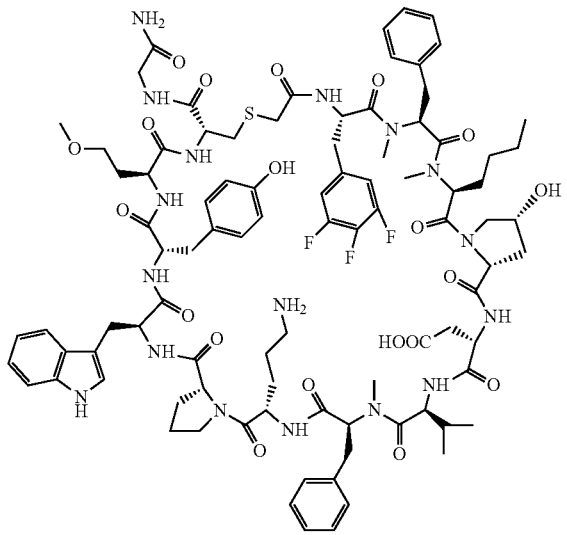

Example 10191

The crude material of Example 10191 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 38.4 mg, and its estimated purity by LCMS analysis was 100%.

Analysis condition A: Retention time=1.79 min; ESI-MS (−) m/z 934.1 (M−2H).

Analysis condition B: Retention time=2.99 min; ESI-MS (+) m/z 936.1 (M+2H).

ESI-HRMS(+) m/z: Calculated: 935.9279 (M+2H); Found: 935.9237 (M+2H).

Preparation of Example 10192

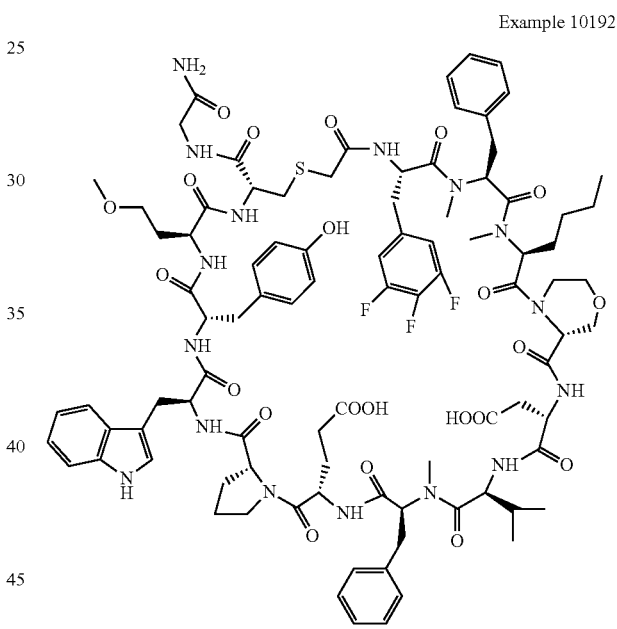

Example 10192

The crude material of Example 10192 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 24.6 mg, and its estimated purity by LCMS analysis was 100%.

Analysis condition A: Retention time=1.58 min; ESI-MS (−) m/z 942.1 (M−2H).

Analysis condition B: Retention time=2.66 min; ESI-MS (+) m/z 943.7 (M+2H).

ESI-HRMS(+) m/z: Calculated: 943.4095 (M+2H); Found: 943.4064 (M+2H).

Preparation of Example 10193

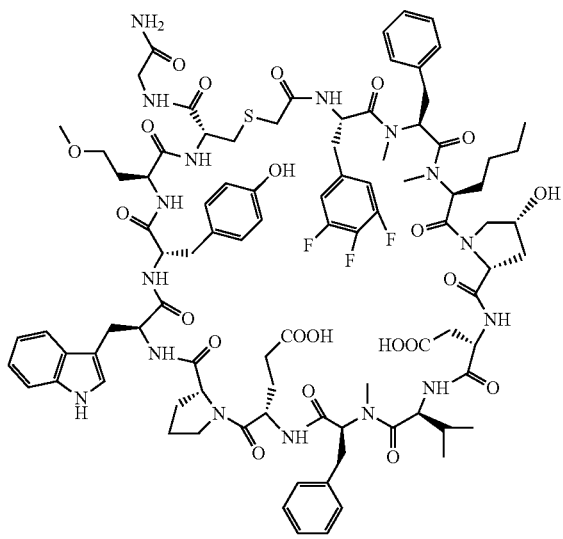

Example 10193

The crude material of Example 10193 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 51.5 mg, and its estimated purity by LCMS analysis was 98%.

Analysis condition A: Retention time=1.62 min; ESI-MS (−) m/z 941.6 (M−2H).

Analysis condition B: Retention time=2.68 min; ESI-MS (+) m/z 943.7 (M+2H).

ESI-HRMS(+) m/z: Calculated: 943.4095 (M+2H); Found: 943.4070 (M+2H).

Preparation of Example 10194

Example 10194

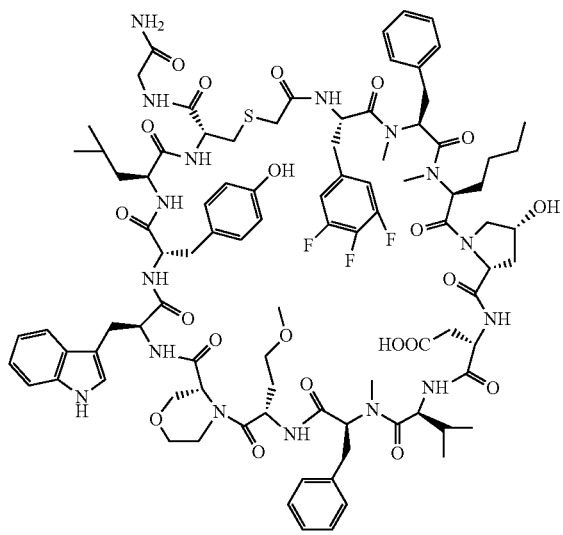

The crude material of Example 10194 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 9.5 mg, and its estimated purity by LCMS analysis was 100%.

Analysis condition A: Retention time=1.82 min; ESI-MS (−) m/z 942.3 (M−2H).

Analysis condition B: Retention time=2.97 min; ESI-MS (+) m/z 943.9 (M+2H).

ESI-HRMS(+) m/z: Calculated: 943.4277 (M+2H); Found: 943.4248 (M+2H).

Preparation of Example 10195

Example 10195

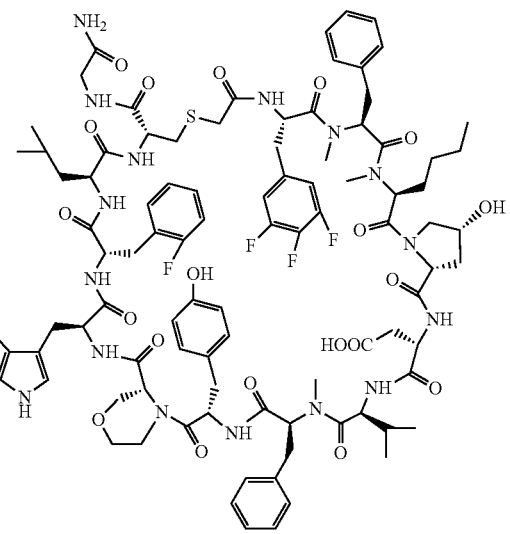

The crude material of Example 10195 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 10.1 mg, and its estimated purity by LCMS analysis was 100%.

Analysis condition A: Retention time=1.88 min; ESI-MS (−) m/z 967.4 (M−2H).

Analysis condition B: Retention time=3.01 min; ESI-MS (+) m/z 968.8 (M+2H).

ESI-HRMS(+) m/z: Calculated: 968.4255 (M+2H); Found: 968.4234 (M+2H).

Preparation of Example 10196

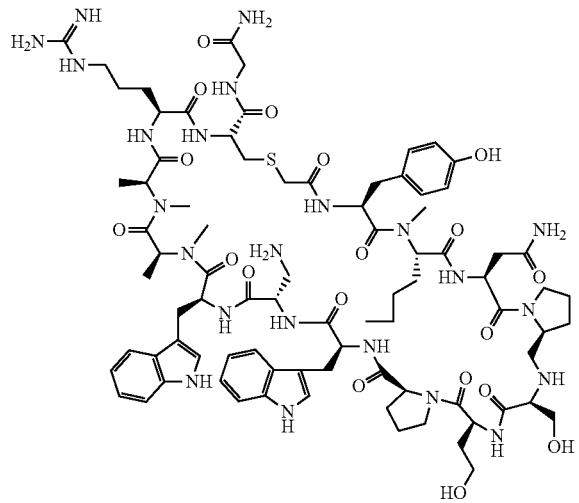

Example 10196

The crude material of Example 10196 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 5.3 mg, and its estimated purity by LCMS analysis was 97%.

Analysis condition A: Retention time=1.61 min; ESI-MS (+) m/z 895.7 (M+2H).

Analysis condition B: Retention time=2.28 min; ESI-MS (+) m/z 895.2 (M+2H).

ESI-HRMS(+) m/z: Calculated: 894.9356 (M+2H); Found: 894.9339 (M+2H).

Preparation of Example 10197

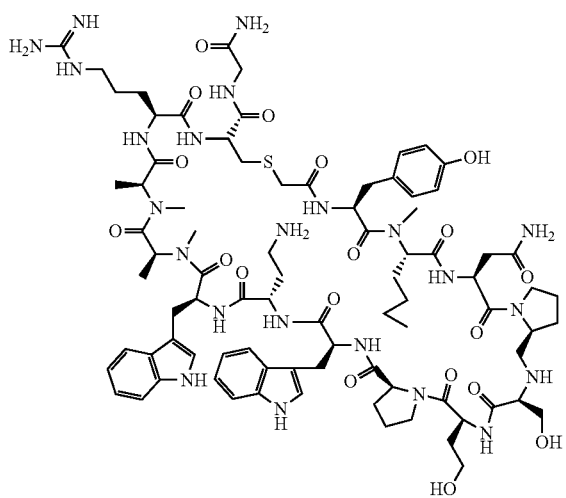

Example 10197

The crude material of Example 10197 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 16.1 mg, and its estimated purity by LCMS analysis was 100%.

Analysis condition A: Retention time=1.24 min; ESI-MS (+) m/z 902.15 (M+2H).

Analysis condition B: Retention time=1.83 min; ESI-MS (+) m/z 902.10 (M+2H).

ESI-HRMS(+) m/z: Calculated: 901.9434 (M+2H); Found: 901.9418 (M+2H).

Preparation of Example 10198

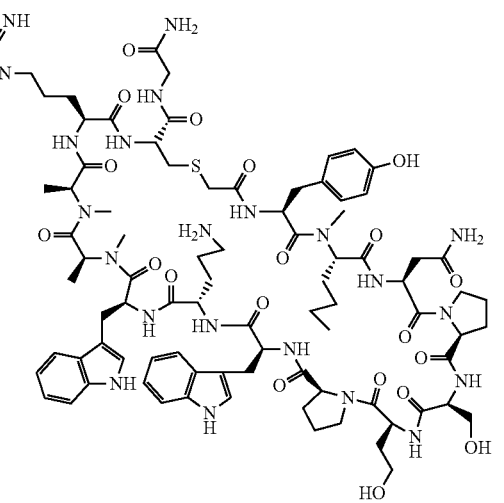

Example 10198

The crude material of Example 10198 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 10.4 mg, and its estimated purity by LCMS analysis was 100%.

Analysis condition A: Retention time=1.24 min; ESI-MS (+) m/z 909.05 (M+2H).

Analysis condition B: Retention time=2.58 min; ESI-MS (+) m/z 909.05 (M+2H).

ESI-HRMS(+) m/z: Calculated: 908.9512 (M+2H); Found: 908.9496 (M+2H).

Preparation of Example 10199

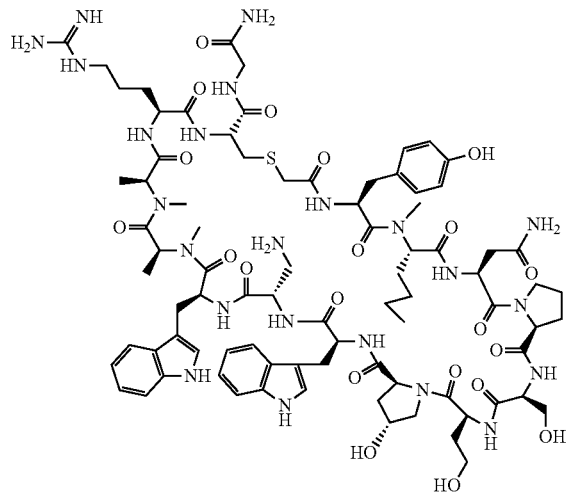

Example 10199

The crude material of Example 10199 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 35.4 mg, and its estimated purity by LCMS analysis was 99%.

Analysis condition A: Retention time=1.61 min; ESI-MS (+) m/z 903.4 (M+2H).

Analysis condition B: Retention time=2.22 min; ESI-MS (+) m/z 903.2 (M+2H).

ESI-HRMS(+) m/z: Calculated: 902.9330 (M+2H); Found: 902.9322 (M+2H).

Preparation of Example 10200

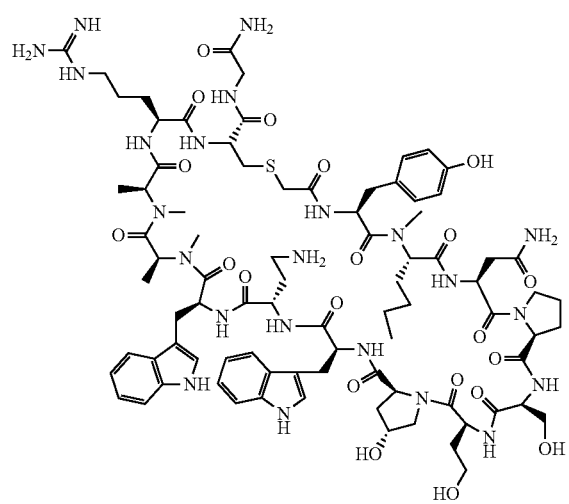

Example 10200

The crude material of Example 10200 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 26.7 mg, and its estimated purity by LCMS analysis was 98%.

Analysis condition A: Retention time=1.47 min; ESI-MS (+) m/z 910.3 (M+2H).

Analysis condition B: Retention time=2.15 min; ESI-MS (+) m/z 910.3 (M+2H).

ESI-HRMS(+) m/z: Calculated: 909.9409 (M+2H); Found: 909.9391 (M+2H).

Preparation of Example 10201

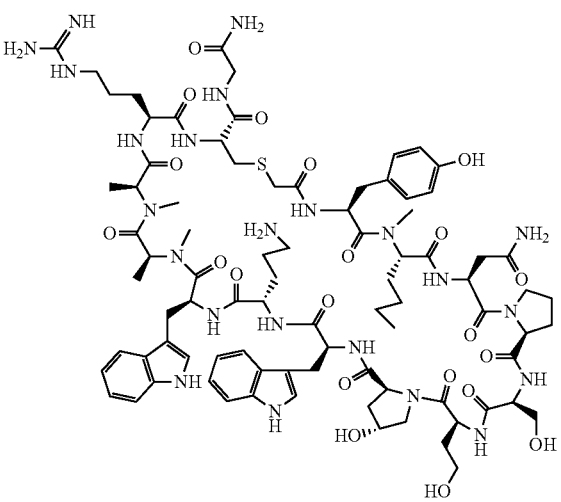

Example 10121

The crude material of Example 10201 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 45.2 mg, and its estimated purity by LCMS analysis was 100%.

Analysis condition A: Retention time=1.54 min; ESI-MS (+) m/z 917.4 (M+2H).

Analysis condition B: Retention time=2.22 min; ESI-MS (+) m/z 917.7 (M+2H).

ESI-HRMS(+) m/z: Calculated: 916.9457 (M+2H); Found: 916.9488 (M+2H).

Preparation of Example 10202

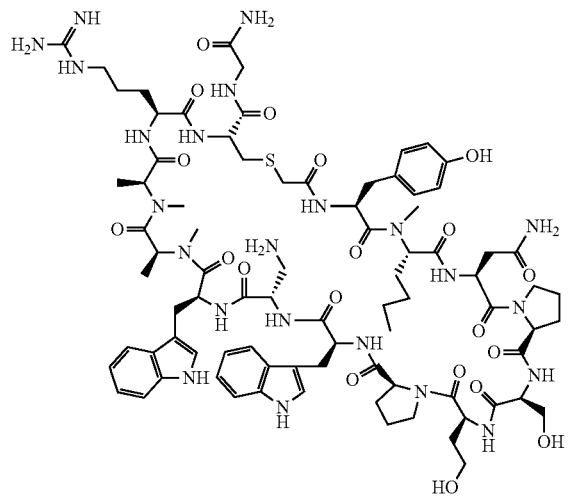

Example 10202

The crude material of Example 10202 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 6.3 mg, and its estimated purity by LCMS analysis was 100%.

Analysis condition A: Retention time=1.45 min; ESI-MS (+) m/z 888.3 (M+2H).

Analysis condition B: Retention time=2.18 min; ESI-MS (+) m/z 888.5 (M+2H).

ESI-HRMS(+) m/z: Calculated: 887.9277 (M+2H); Found: 887.9263 (M+2H).

Preparation of Example 10203

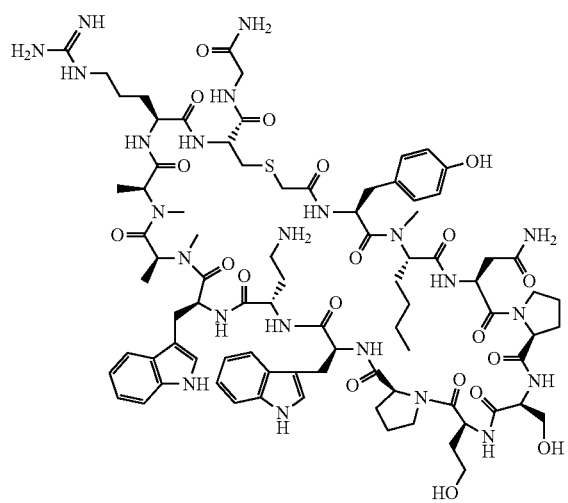

Example 10203

The crude material of Example 10203 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 29.8 mg, and its estimated purity by LCMS analysis was 96%.

Analysis condition A: Retention time=1.48 min; ESI-MS (+) m/z 895.6 (M+2H).

Analysis condition B: Retention time=2.12 min; ESI-MS (+) m/z 895.3 (M+2H).

ESI-HRMS(+) m/z: Calculated: 894.9356 (M+2H); Found: 894.9343 (M+2H).

Preparation of Example 10204

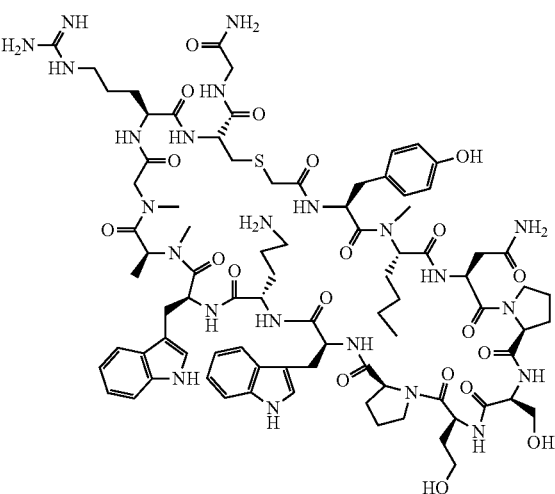

Example 10204

The crude material of Example 10204 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 11.8 mg, and its estimated purity by LCMS analysis was 96%.

Analysis condition A: Retention time=1.46 min; ESI-MS (+) m/z 902.7 (M+2H).

Analysis condition B: Retention time=2.11 min; ESI-MS (+) m/z 902.3 (M+2H).

ESI-HRMS(+) m/z: Calculated: 901.9434 (M+2H); Found: 901.9419 (M+2H).

Preparation of Example 10205

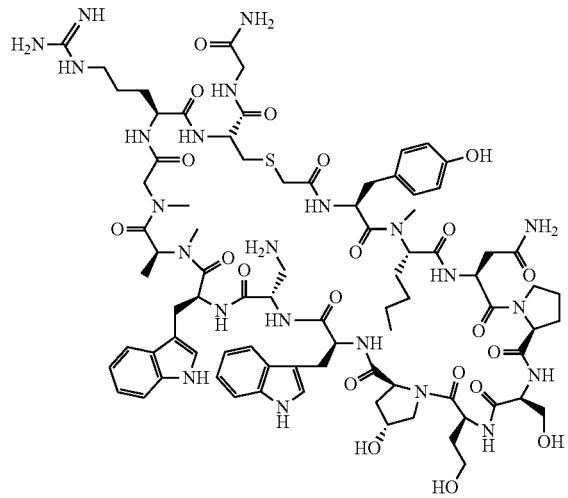

Example 10205

The crude material of Example 10205 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 13.5 mg, and its estimated purity by LCMS analysis was 98%.

Analysis condition A: Retention time=1.51 min; ESI-MS (+) m/z 896.1 (M+2H).

Analysis condition B: Retention time=2.12 min; ESI-MS (+) m/z 896.4 (M+2H).

ESI-HRMS(+) m/z: Calculated: 895.9252 (M+2H); Found: 895.9240 (M+2H).

Preparation of Example 10206

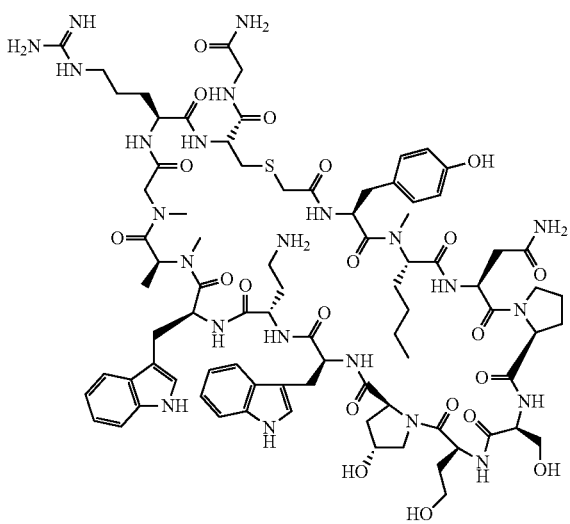

Example 10206

The crude material of Example 10206 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 10.0 mg, and its estimated purity by LCMS analysis was 100%.

Analysis condition A: Retention time=1.42 min; ESI-MS (+) m/z 903.5 (M+2H).

Analysis condition B: Retention time=2.07 min; ESI-MS (+) m/z 903.7 (M+2H).

ESI-HRMS(+) m/z: Calculated: 902.9330 (M+2H); Found: 902.9324 (M+2H).

Preparation of Example 10207

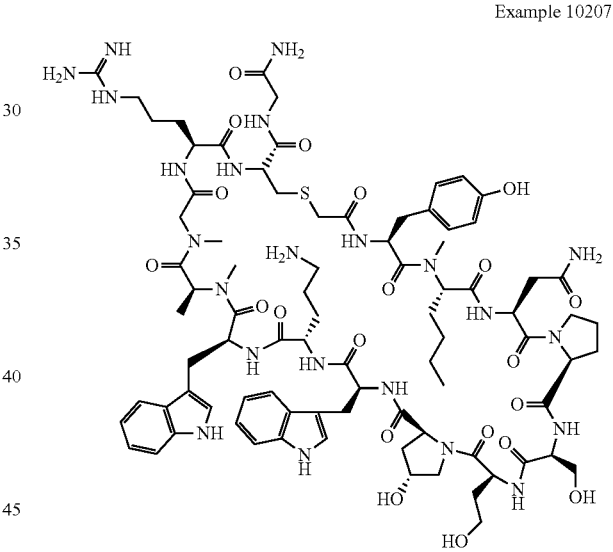

Example 10207

The crude material of Example 10207 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 22.2 mg, and its estimated purity by LCMS analysis was 94%.

Analysis condition A: Retention time=1.46 min; ESI-MS (+) m/z 910.4 (M+2H).

Analysis condition B: Retention time=2.05 min; ESI-MS (+) m/z 910.4 (M+2H).

ESI-HRMS(+) m/z: Calculated: 909.9409 (M+2H); Found: 909.9397 (M+2H).

Preparation of Example 10208

Example 10208

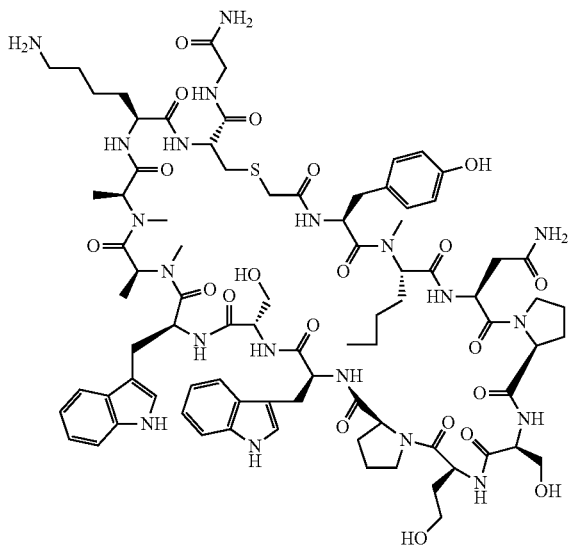

The crude material of Example 10208 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 9.1 mg, and its estimated purity by LCMS analysis was 96%.

Analysis condition A: Retention time=1.51 min; ESI-MS (+) m/z 881.9 (M+2H).

Analysis condition B: Retention time=2.29 min; ESI-MS (+) m/z 882.1 (M+2H).

ESI-HRMS(+) m/z: Calculated: 881.4245 (M+2H); Found: 881.4237 (M+2H).

Preparation of Example 10209

Example 10209

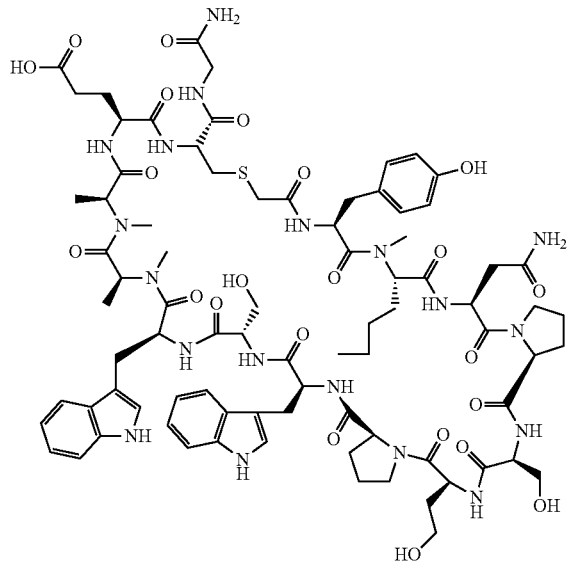

The crude material of Example 10209 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 13.3 mg, and its estimated purity by LCMS analysis was 96%.

Analysis condition A: Retention time=1.52 min; ESI-MS (+) m/z 882.3 (M+2H).

Analysis condition B: Retention time=2.25 min; ESI-MS (+) m/z 882.4 (M+2H).

ESI-HRMS(+) m/z: Calculated: 881.8983 (M+2H); Found: 881.8978 (M+2H).

Preparation of Example 10210

Example 10210

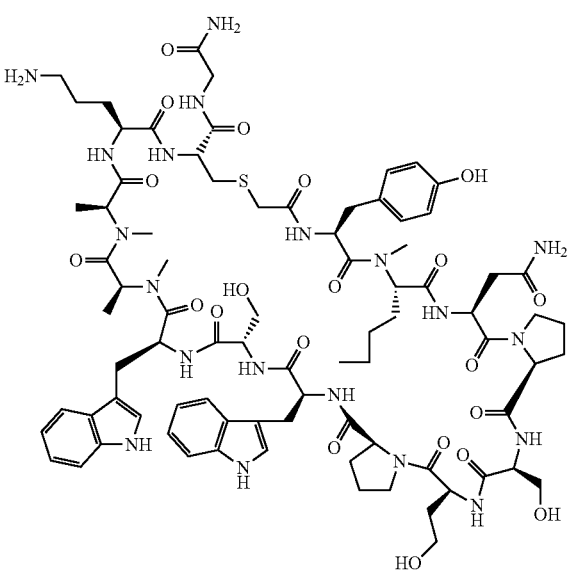

The crude material of Example 10210 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 30.0 mg, and its estimated purity by LCMS analysis was 100%.

Analysis condition A: Retention time=1.34 min; ESI-MS (+) m/z 874.50 (M+2H).

Analysis condition B: Retention time=1.95 min; ESI-MS (+) m/z 874.50 (M+2H).

ESI-HRMS(+) m/z: Calculated: 874.4167 (M+2H); Found: 874.4162 (M+2H).

Preparation of Example 10211

Example 10211

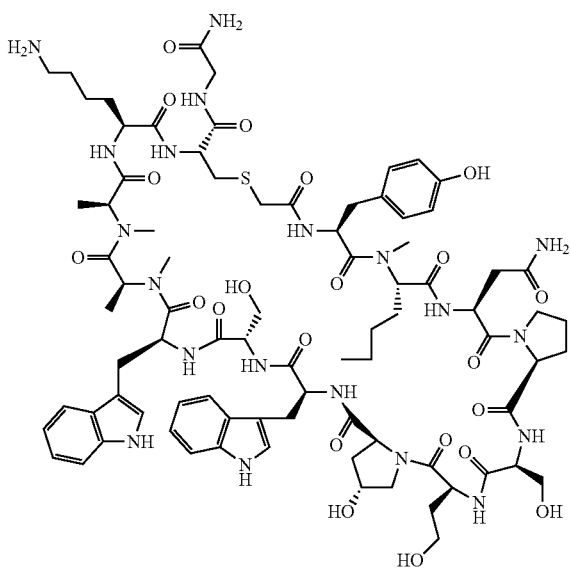

The crude material of Example 10211 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 18.8 mg, and its estimated purity by LCMS analysis was 100%.

Analysis condition A: Retention time=1.57 min; ESI-MS (+) m/z 890.4 (M+2H).

Analysis condition B: Retention time=2.29 min; ESI-MS (+) m/z 889.8 (M+2H).

ESI-HRMS(+) m/z: Calculated: 889.4220 (M+2H); Found: 889.4208 (M+2H).

Preparation of Example 10212

Example 10212

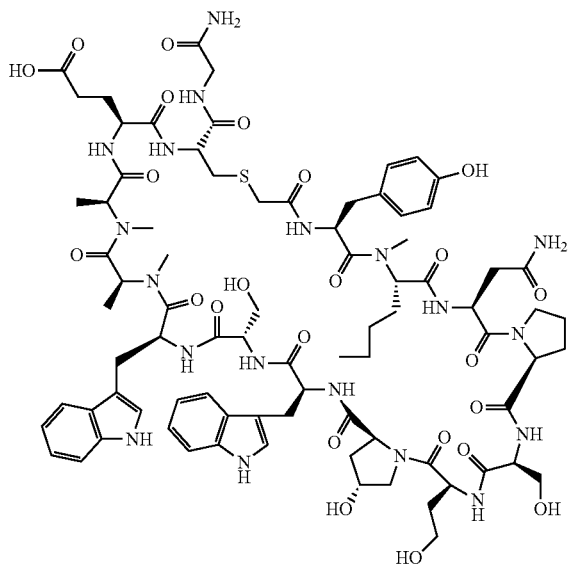

The crude material of Example 10212 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 10.7 mg, and its estimated purity by LCMS analysis was 100%.

Analysis condition A: Retention time=1.56 min; ESI-MS (+) m/z 890.6 (M+2H).

Analysis condition B: Retention time=2.60 min; ESI-MS (+) m/z 890.35 (M+2H).

ESI-HRMS(+) m/z: Calculated: 889.8958 (M+2H); Found: 889.8954 (M+2H).

Preparation of Example 10213

Example 10213

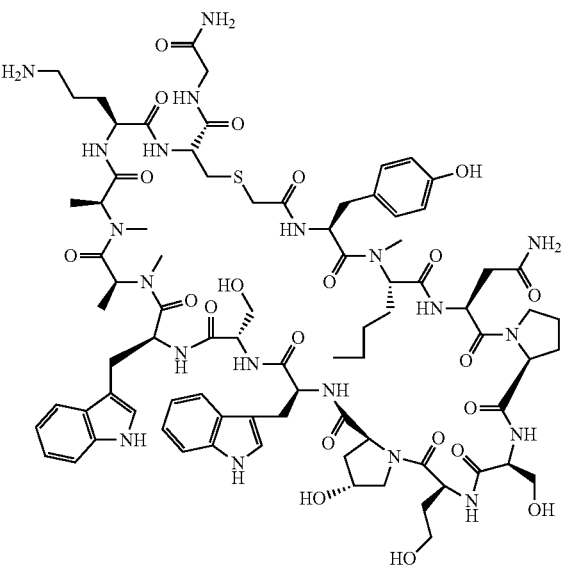

The crude material of Example 10213 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 13.1 mg, and its estimated purity by LCMS analysis was 100%.

Analysis condition A: Retention time=1.48 min; ESI-MS (+) m/z 882.7 (M+2H).

Analysis condition B: Retention time=2.26 min; ESI-MS (+) m/z 882.8 (M+2H).

ESI-HRMS(+) m/z: Calculated: 882.4141 (M+2H); Found: 882.4134 (M+2H).

Preparation of Example 10214

Example 10214

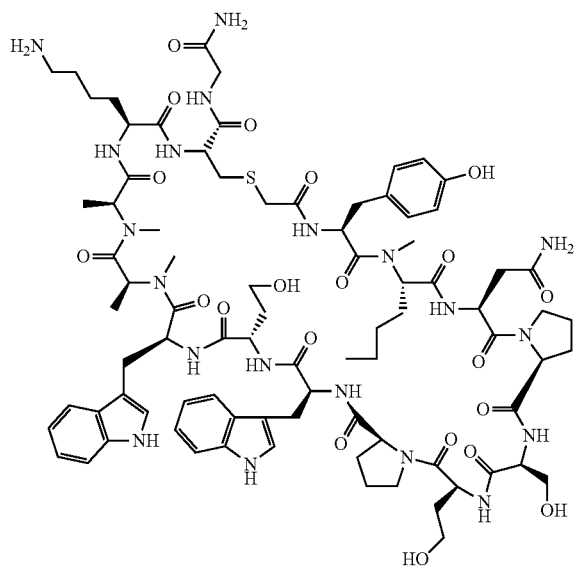

The crude material of Example 10214 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 13.8 mg, and its estimated purity by LCMS analysis was 97%.

Analysis condition A: Retention time=1.31 min; ESI-MS (+) m/z 888.80 (M+2H).

Analysis condition B: Retention time=2.72 min; ESI-MS (+) m/z 888.85 (M+2H).

ESI-HRMS(+) m/z: Calculated: 888.4323 (M+2H); Found: 888.4312 (M+2H).

Preparation of Example 10215 example 10215

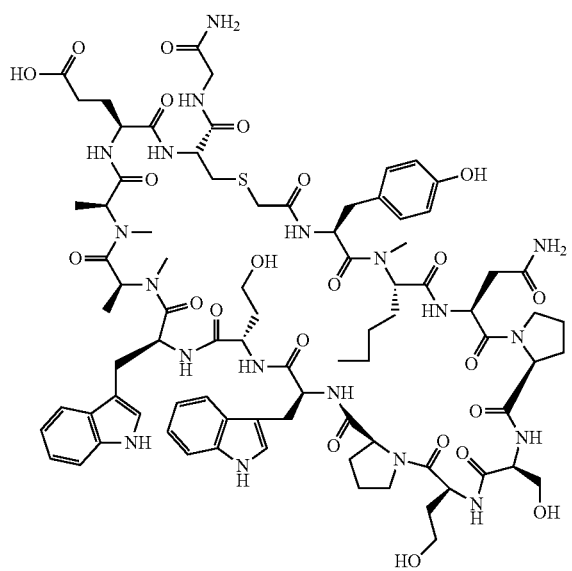

The crude material of Example 10215 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 7.9 mg, and its estimated purity by LCMS analysis was 96%.

Analysis condition A: Retention time=1.46 min; ESI-MS (+) m/z 889.4 (M+2H).

Analysis condition B: Retention time=2.24 min; ESI-MS (+) m/z 889.6 (M+2H).

ESI-HRMS(+) m/z: Calculated: 889.9061 (M+2H); Found: 889.9052 (M+2H).

Preparation of Example 10216

Example 10216

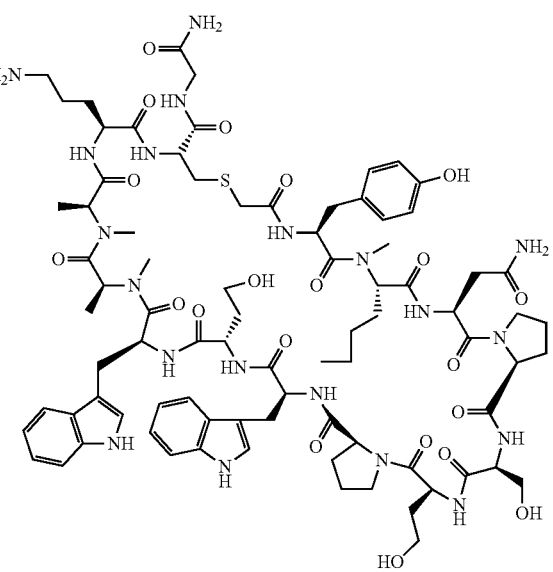

The crude material of Example 10216 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 15.8 mg, and its estimated purity by LCMS analysis was 96%.

Analysis condition A: Retention time=1.31 min; ESI-MS (+) m/z 881.45 (M+2H).

Analysis condition B: Retention time=2.72 min; ESI-MS (+) m/z 881.70 (M+2H).

ESI-HRMS(+) m/z: Calculated: 881.4245 (M+2H); Found: 881.4238 (M+2H).

Preparation of Example 10217

Example 10217

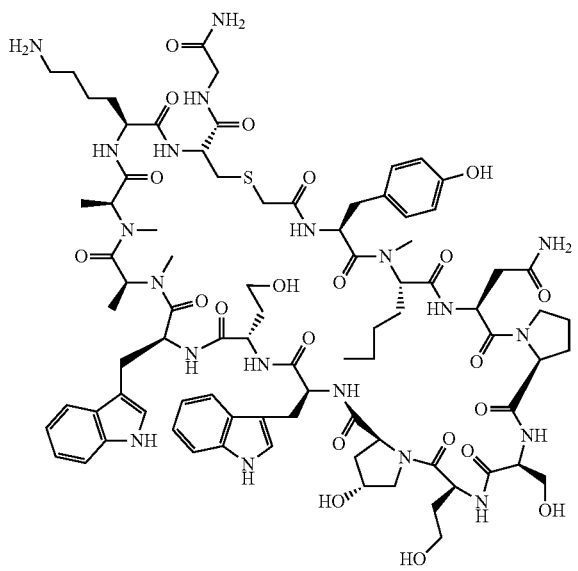

The crude material of Example 10217 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 19.7 mg, and its estimated purity by LCMS analysis was 100%.

Analysis condition A: Retention time=1.29 min; ESI-MS (+) m/z 896.60 (M+2H).

Analysis condition B: Retention time=2.65 min; ESI-MS (+) m/z 896.55 (M+2H).

Preparation of Example 10218

Example 10218

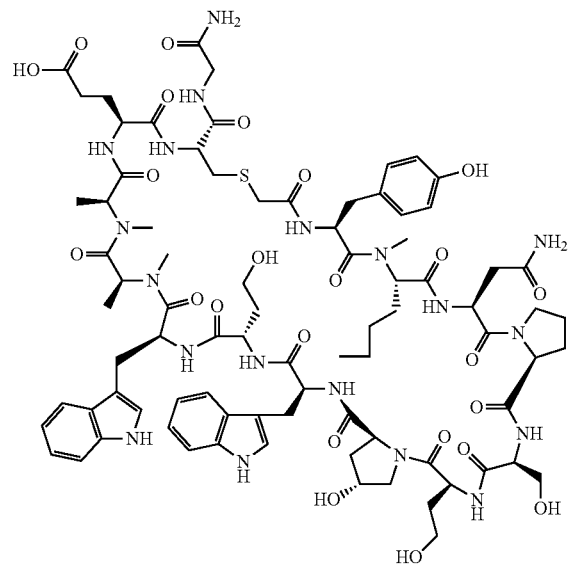

The crude material of Example 10218 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 8.3 mg, and its estimated purity by LCMS analysis was 100%.

Analysis condition A: Retention time=1.46 min; ESI-MS (−) m/z 895.30 (M−2H).

Analysis condition B: Retention time=2.20 min; ESI-MS (−) m/z 895.60 (M−2H).

ESI-HRMS(+) m/z: Calculated: 896.9036 (M+2H); Found: 896.9030 (M+2H).

Preparation of Example 10219

Example 10219

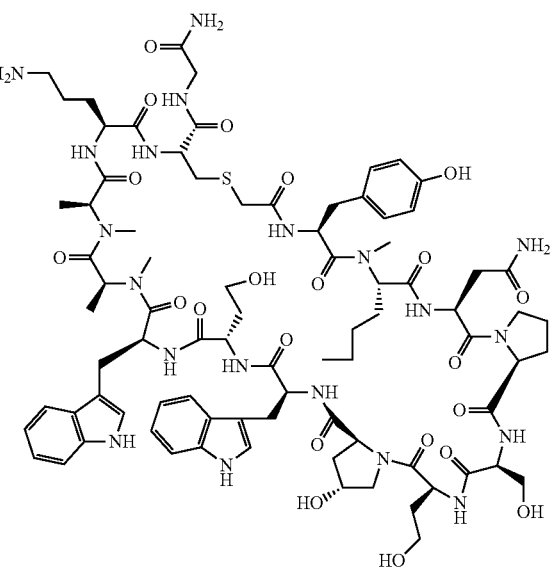

The crude material of Example 10219 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 6.8 mg, and its estimated purity by LCMS analysis was 100%.

Analysis condition A: Retention time=1.29 min; ESI-MS (−) m/z 889.45 (M−2H).

Analysis condition B: Retention time=1.90 min; ESI-MS (−) m/z 890.35 (M−2H).

ESI-HRMS(+) m/z: Calculated: 889.4220 (M+2H); Found: 889.4208 (M+2H).

Preparation of Example 10530

Example 10530

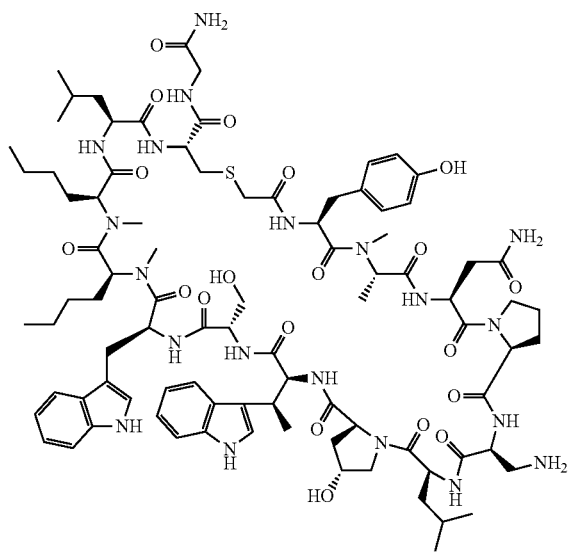

Example 10530 was prepared following "General Synthetic Sequence A" but using "Cyclization Method B" instead of "Cyclization Method A". The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-65% B over 30 minutes, then a 5-minute hold at 100% B; Flow: 20 mL/min. Fractions containing the desired product were combined and dried via centrifugal evaporation.

The yield of the product was 1.3 mg, and its estimated purity by LCMS analysis was 95%.

Analysis condition A: Retention time=2.01 min; ESI-MS (+) m/z 915.4 (M+2H).

Analysis condition B: Retention time=2.94 min; ESI-MS (+) m/z 915.8 (M+2H.).

Preparation of Example 10531

Example 10531

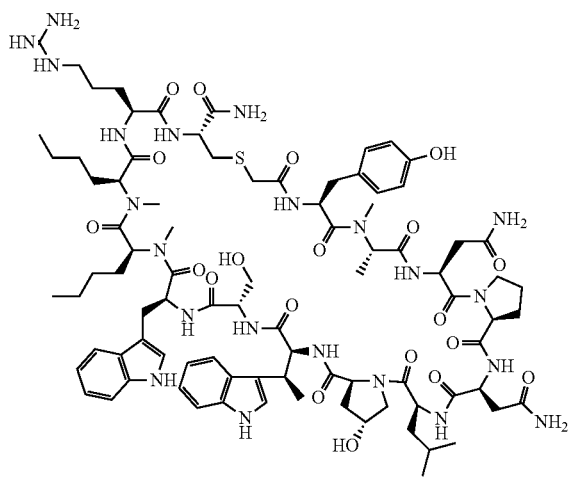

Example 10531 was prepared following "General Synthetic Sequence A" but using "Cyclization Method B" instead of "Cyclization Method A". The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 11.5 mg, and its estimated purity by LCMS analysis was 100%.

Analysis condition A: Retention time=1.56 min; ESI-MS (+) m/z 922.7 (M+2H).

Analysis condition B: Retention time=2.94 min; ESI-MS (+) m/z 922.5 (M+2H).

ESI-HRMS(+) m/z: Calculated: 922.4692 (M+2H); Found: 922.4669 (M+2H).

Preparation of Example 10532

Example 10532

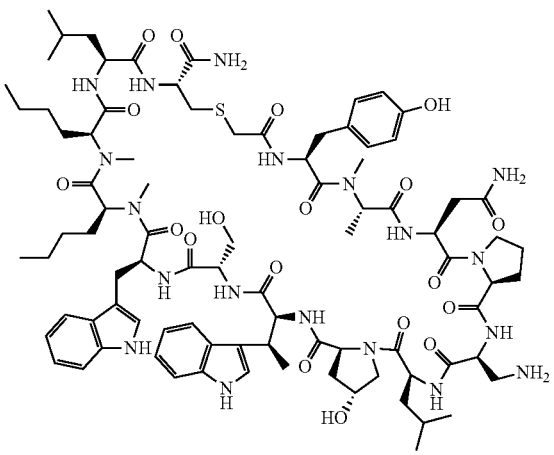

Example 10532 was prepared following "General Synthetic Sequence A" but using "Cyclization Method B" instead of "Cyclization Method A". The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 16.8 mg, and its estimated purity by LCMS analysis was 98%.

Analysis condition A: Retention time=1.77 min; ESI-MS (+) m/z 887.2 (M+2H).

Analysis condition B: Retention time=3.16 min; ESI-MS (+) m/z 887.2 (M+2H).

ESI-HRMS(+) m/z: Calculated: 866.9633 (M+2H); Found: 866.9610 (M+2H).

Preparation of Example 10533

Example 10533

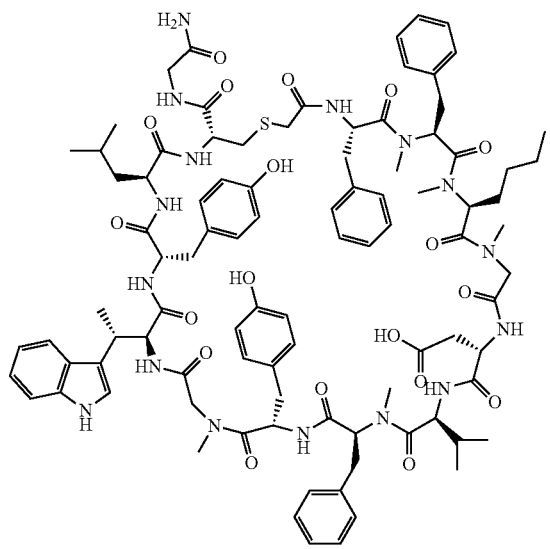

Example 10533 was prepared following "General Synthetic Sequence A" with the following changes: "Symphony Method A: Single-coupling procedure" was modified by increasing the time of agitation of the coupling from 15 minutes to 3 hours for the Fmoc-Val-OH coupling step. "Symphony Method A: Single-coupling procedure" was used for Fmoc-Phe-OH coupling step but the time of agitation during the coupling step was increased from 15 min to 1 h. "Global Deprotection A" was modified by changing the "deprotection solution" from a solution of [trifluoroacetic acid (22 mL), phenol (1.325 g), water (1.25 mL) and triisopropylsilane (0.5 mL)] to a solution of [trifluoroacetic acid (23.75 mL), 1,4-Dithio-DL-threitol (625 mg), triisopropylsilane (0.625 mL)]. "Cyclization Method B" was used instead of "Cyclization Method A". The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 14.0 mg, and its estimated purity by LCMS analysis was 98%.

Analysis condition A: Retention time=1.70 min; ESI-MS (+) m/z 905.9 (M+2H).

Analysis condition B: Retention time=3.27 min; ESI-MS (+) m/z 905.9 (M+2H).

Preparation of Example 10534

Example 10534

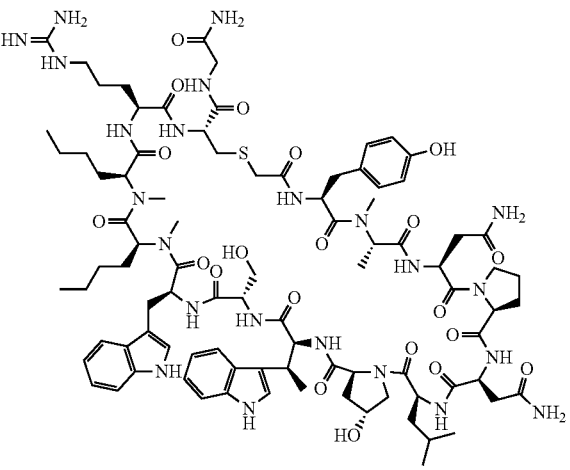

Example 10534 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-85% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 10.6 mg, and its estimated purity by LCMS analysis was 100%.

Analysis condition A: Retention time=1.56 min; ESI-MS (+) m/z 951.5 (M+2H).

Analysis condition B: Retention time=2.94 min; ESI-MS (+) m/z 951.4 (M+2H).

ESI-HRMS(+) m/z: Calculated: 950.9800 (M+2H); Found: 950.9786 (M+2H).

Preparation of Example 10535

Example 10535

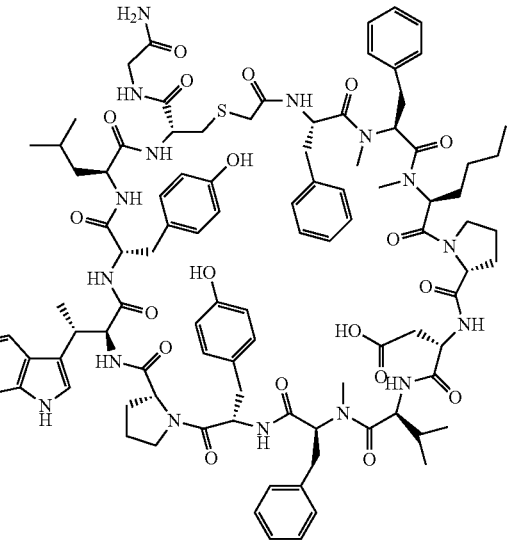

Example 10535 was prepared according to the method used for Example 10533. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 10.2 mg, and its estimated purity by LCMS analysis was 100%.

Analysis condition A: Retention time=1.76 min; ESI-MS (+) m/z 932.0 (M+2H).

Analysis condition B: Retention time=3.34 min; ESI-MS (+) m/z 931.9 (M+2H).

ESI-HRMS(+) m/z: Calculated: 931.4547 (M+2H); Found: 931.4535 (M+2H).

Preparation of Example 10536

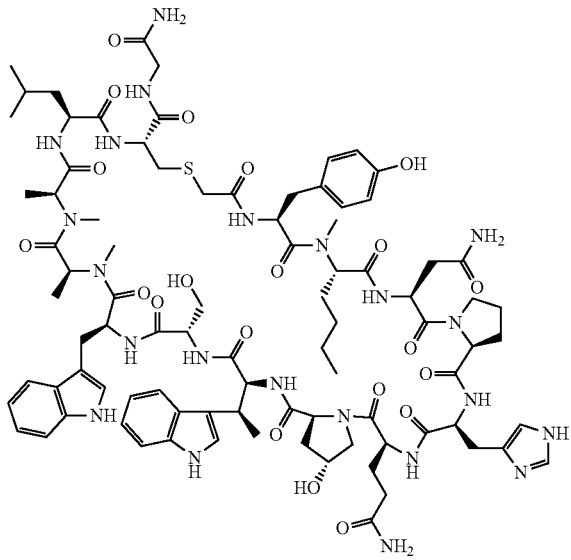

Example 10536

Example 10536 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 30 minutes, then a 3-minute hold at 100% B; Flow: 20 mL/min. Fractions containing the desired product were combined and dried via centrifugal evaporation. The yield of the product was 2.7 mg, and its estimated purity by LCMS analysis was 100%.

Analysis condition A: Retention time=1.35 min; ESI-MS (+) m/z 927.8 (M+2H).

Analysis condition B: Retention time=2.62 min; ESI-MS (+) m/z 927.6 (M+2H).

Preparation of Example 10539

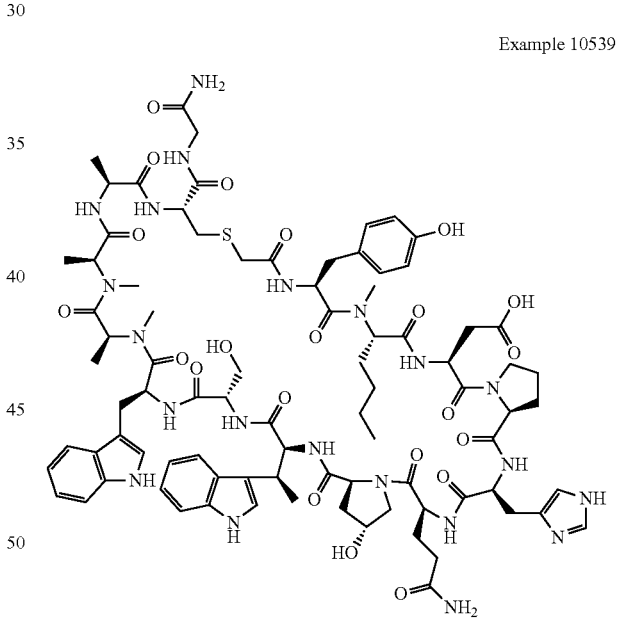

Example 10539

Example 10539 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-65% B over 30 minutes, then a 5-minute hold at 100% B; Flow: 20 mL/min. Fractions containing the desired product were combined and dried via centrifugal evaporation. The yield of the product was 7.2 mg, and its estimated purity by LCMS analysis was 96%.

Analysis condition A: Retention time=1.19 min; ESI-MS (+) m/z 906.3 (M+2H).

Analysis condition B: Retention time=2.32 min; ESI-MS (+) m/z 906.6 (M+2H).

ESI-HRMS(+) m/z: Calculated: 906.9118 (M+2H); Found: 906.9105 (M+2H).

Preparation of Example 10540

Example 10540

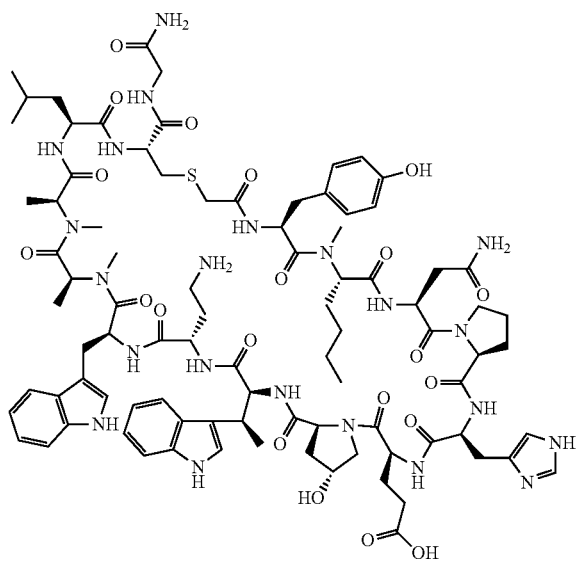

Example 10540 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 3-minute hold at 100% B; Flow: 20 mL/min. Fractions containing the desired product were combined and dried via centrifugal evaporation. The yield of the product was 15.2 mg, and its estimated purity by LCMS analysis was 100%.

Analysis condition A: Retention time=1.71 min; ESI-MS (+) m/z 934.6 (M+2H).

Analysis condition B: Retention time=2.52 min; ESI-MS (+) m/z 934.3 (M+2H).

ESI-HRMS(+) m/z: Calculated: 934.4511 (M+2H); Found: 934.4494 (M+2H).

Preparation of Example 10542

Example 10542

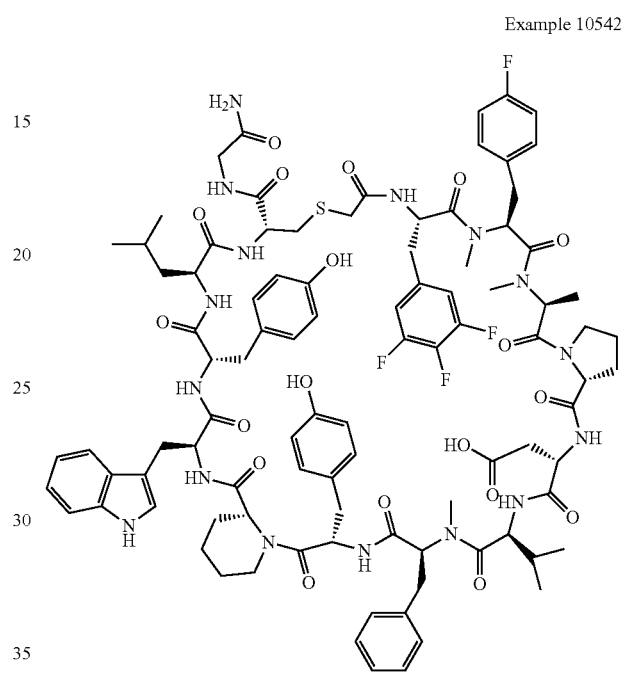

Example 10542 was prepared according to the method outlined in Example 10537. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×150 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 3.0 mg, and its estimated purity by LCMS analysis was 100%.

Analysis condition A: Retention time=1.92 min; ESI-MS (+) m/z 946.4 (M+2H).

Analysis condition B: Retention time=2.91 min; ESI-MS (+) m/z 946.4 (M+2H).

ESI-HRMS(+) m/z: Calculated: 946.4124 (M+2H) Found: 946.4113 (M+2H).

Preparation of Example 10543

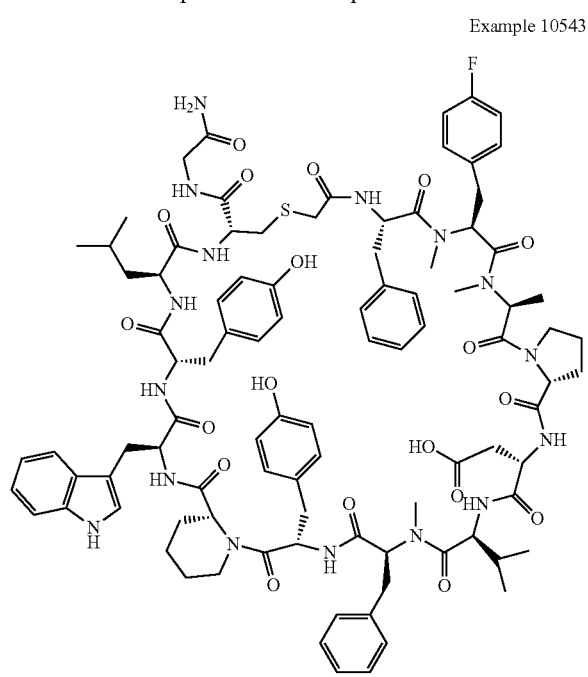

Example 10543

Example 10543 was prepared according to the method outlined in Example 10537. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 10.0 mg, and its estimated purity by LCMS analysis was 93%.

Analysis condition A: Retention time=1.67 min; ESI-MS (+) m/z 919.9 (M+2H).

Analysis condition B: Retention time=3.26 min; ESI-MS (+) m/z 919.9 (M+2H).

ESI-HRMS(+) m/z: Calculated: 919.4266 (M+2H); Found: 919.4253 (M+2H).

Preparation of Example 10544

Example 10544

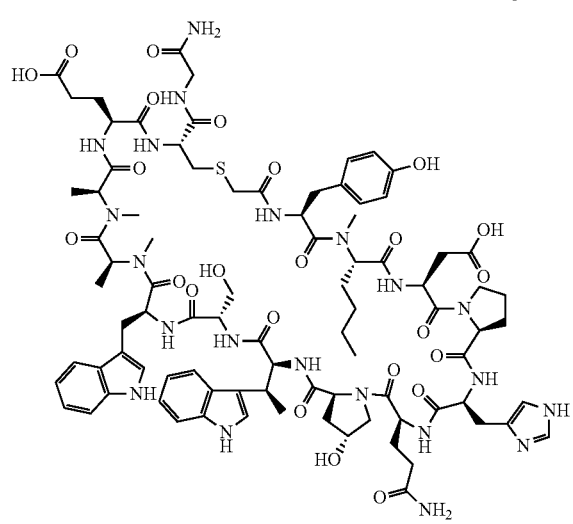

Example 10544 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 15.4 mg, and its estimated purity by LCMS analysis was 99%.

Analysis condition A: Retention time=1.36 min; ESI-MS (+) m/z 936.4 (M+2H).

Analysis condition B: Retention time=2.14 min; ESI-MS (+) m/z 936.4 (M+2H).

ESI-HRMS(+) m/z: Calculated: 935.9145 (M+2H); Found: 935.9138 (M+2H).

Preparation of Examples 10551 and Example 10640

Example 10551

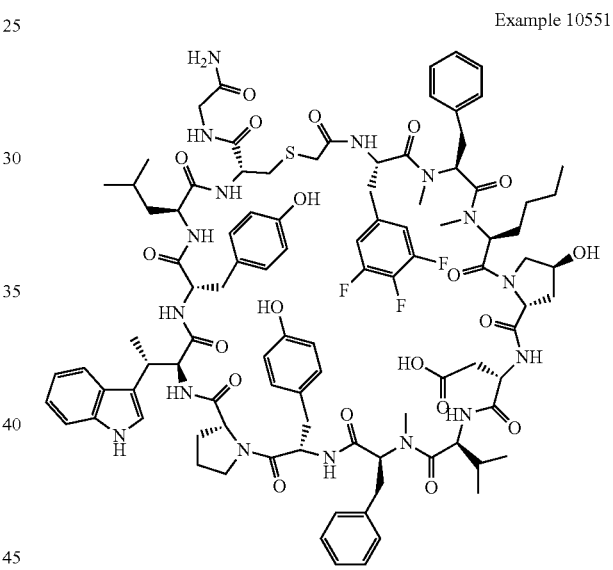

Example 10640

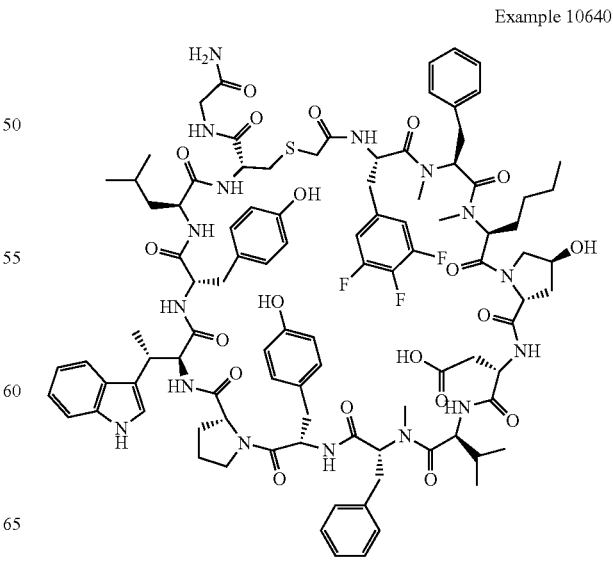

Example 10551 and Example 10640 were prepared according to the method outlined in Example 10541 except dipeptide fragment Fmoc-L-Val-L-'''Phe-OH was used instead of dipeptide fragment Fmoc-L-CyclopentylGly-L-'''Phe-OH. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. The diastereomers were separated and dried via centrifugal evaporation to give 7.3 mg of Example 10551 (First eluting peak) with an estimated purity by LCMS analysis was 95% and 10.3 mg of Example 10640 (Second eluting peak) with an estimated purity by LCMS analysis was 98%.

Example 10551

Analysis condition A: Retention time=1.67 min; ESI-MS (+) m/z 966.9 (M+2H).

Analysis condition B: Retention time=3.28 min; ESI-MS (+) m/z 966.9 (M+2H).

ESI-HRMS(+) m/z: Calculated: 966.4381 (M+2H); Found: 966.4368 (M+2H).

Example 10640

Analysis condition A: Retention time=1.78 min; ESI-MS (+) m/z 967.0 (M+2H).

ESI-HRMS(+) m/z: Calculated: 966.4381 (M+2H); Found: 966.4368 (M+2H).

Preparation of Example 10552

Example 10552

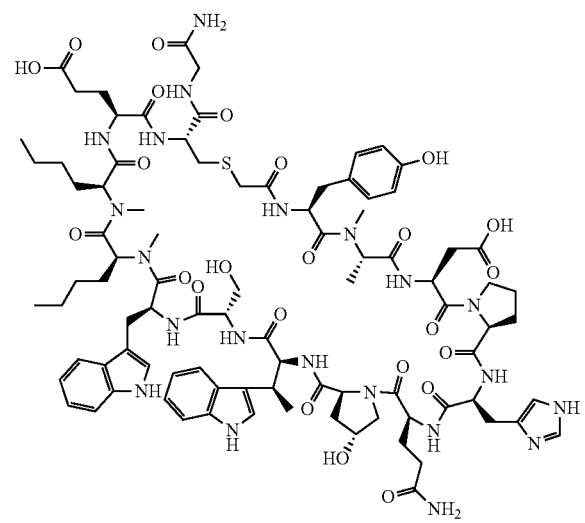

Example 10552 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 11.7 mg, and its estimated purity by LCMS analysis was 95%.

Analysis condition A: Retention time=1.70 min; ESI-MS (+) m/z 956.9 (M+2H).

Analysis condition B: Retention time=2.47 min; ESI-MS (+) m/z 956.9 (M+2H).

ESI-HRMS(+) m/z: Calculated: 956.9380 (M+2H); Found: 956.9363 (M+2H).

Preparation of Example 10553

Example 10553

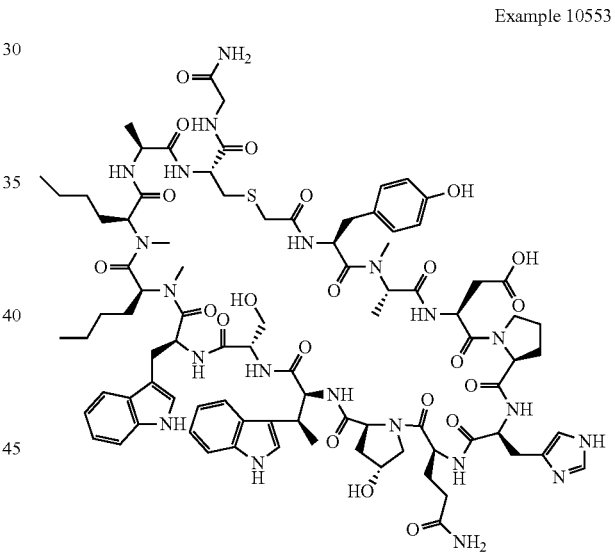

Example 10553 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min.

Fractions containing the desired product were combined and dried via centrifugal evaporation. The yield of the product was 15.5 mg, and its estimated purity by LCMS analysis was 100%.

Analysis condition A: Retention time=1.55 min; ESI-MS (+) m/z 928.2 (M+2H).

Analysis condition B: Retention time=2.21 min; ESI-MS (+) m/z 928.1 (M+2H).

ESI-HRMS(+) m/z: Calculated: 927.9352 (M+2H); Found: 927.9321 (M+2H).

Preparation of Example 10554

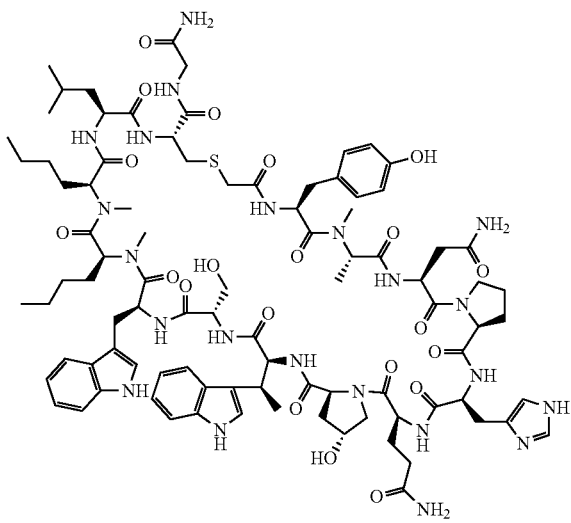

Example 10554

Example 10554 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 30 minutes, then a 5-minute hold at 100% B; Flow: 20 mL/min. Fractions containing the desired product were combined and dried via centrifugal evaporation. The yield of the product was 13.8 mg, and its estimated purity by LCMS analysis was 98%.

Analysis condition A: Retention time=1.87 min; ESI-MS (+) m/z 948.8 (M+2H).

Analysis condition B: Retention time=2.72 min; ESI-MS (+) m/z 948.3 (M+2H).

ESI-HRMS(+) m/z: Calculated: 948.4667 (M+2H); Found: 948.4634 (M+2H).

Preparation of Example 10555

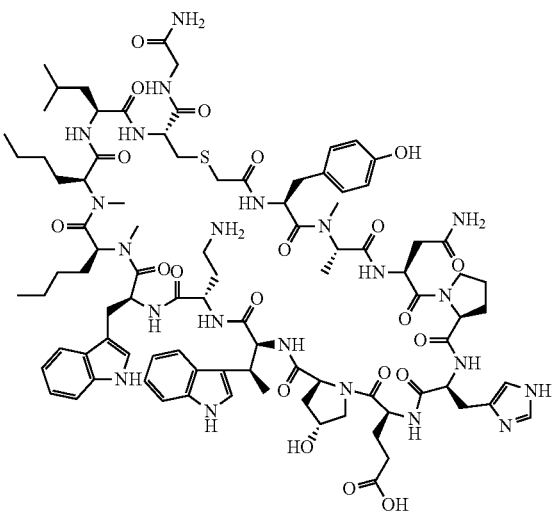

Example 10555

Example 10555 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 13.6 mg, and its estimated purity by LCMS analysis was 100%.

Analysis condition A: Retention time=1.89 min; ESI-MS (+) m/z 955.3 (M+2H).

Analysis condition B: Retention time=2.75 min; ESI-MS (+) m/z 955.6 (M+2H).

ESI-HRMS(+) m/z: Calculated: 955.4745 (M+2H); Found: 955.4722 (M+2H).

Preparation of Example 10556

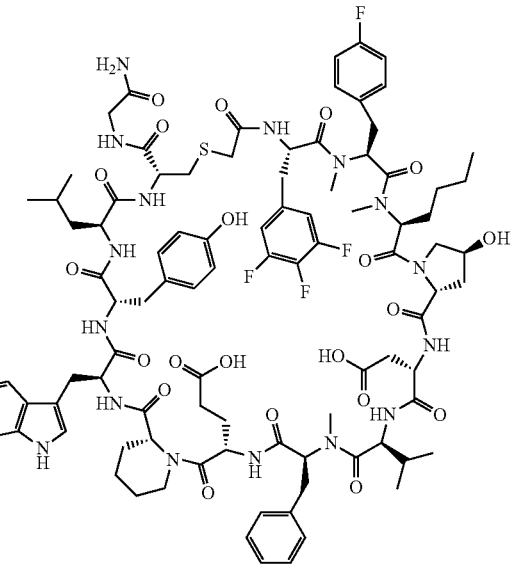

Example 10556

Example 10556 was prepared according to the method outlined in Example 10537. The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 60-100% B over 15 minutes, then a 5-minute hold at 100% B; Flow: 20 mL/min. Fractions containing the desired product were combined and dried via centrifugal evaporation. The yield of the product was 18.3 mg, and its estimated purity by LCMS analysis was 100%.

Analysis condition A: Retention time=1.94 min; ESI-MS (+) m/z 958.8 (M+2H).

Analysis condition B: Retention time=2.78 min; ESI-MS (+) m/z 958.8 (M+2H).

Preparation of Example 10557

Example 10557

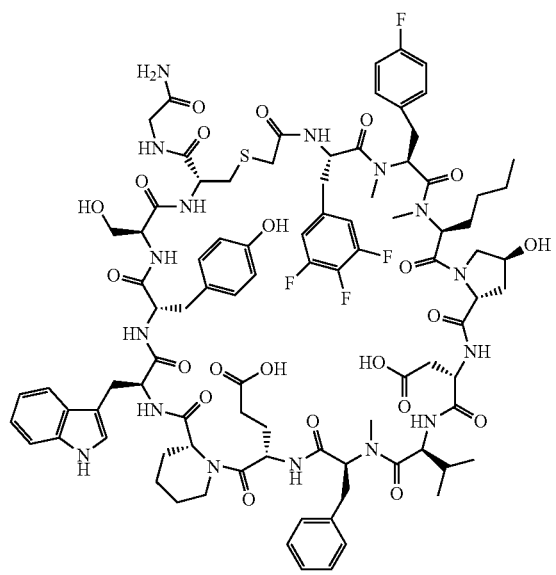

Example 10557 was prepared according to the method outlined in Example 10537. The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 60-100% B over 30 minutes, then a 5-minute hold at 100% B; Flow: 20 mL/min. Fractions containing the desired product were combined and dried via centrifugal evaporation. The yield of the product was 26.5 mg, and its estimated purity by LCMS analysis was 100%.

Analysis condition A: Retention time=1.94 min; ESI-MS (+) m/z 946.0 (M+2H).

Analysis condition B: Retention time=2.77 min; ESI-MS (+) m/z 946.0 (M+2H).

Preparation of Example 10558

Example 10558

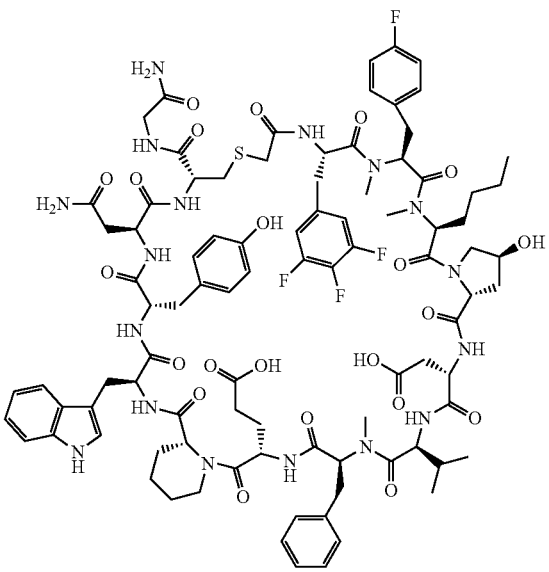

Example 10558 was prepared according to the method outlined in Example 10537. The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 55-95% B over 30 minutes, then a 5-minute hold at 100% B; Flow: 20 mL/min. Fractions containing the desired product were combined and dried via centrifugal evaporation. The yield of the product was 7.8 mg, and its estimated purity by LCMS analysis was 100%.

Analysis condition A: Retention time=1.93 min; ESI-MS (+) m/z 958.9 (M+2H).

Analysis condition B: Retention time=2.75 min; ESI-MS (+) m/z 958.9 (M+2H).

Preparation of Example 10559

Example 10559

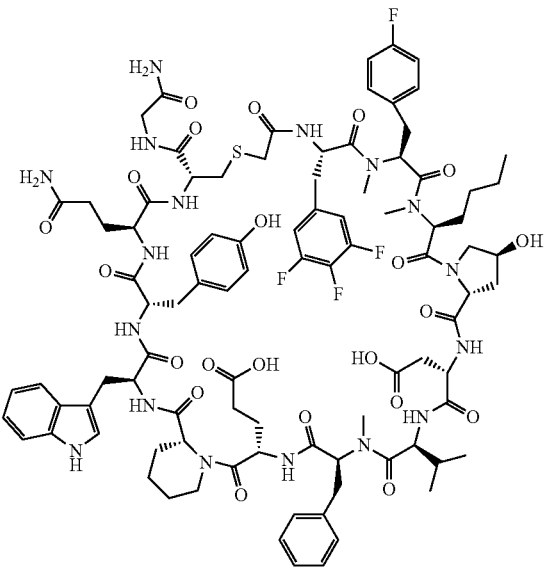

Example 10559 was prepared according to the method outlined in Example 10537. The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 55-95% B over 30 minutes, then a 5-minute hold at 100% B; Flow: 20 mL/min. Fractions containing the desired product were combined and dried via centrifugal evaporation. The yield of the product was 26.0 mg, and its estimated purity by LCMS analysis was 100%.

Analysis condition A: Retention time=1.92 min; ESI-MS (+) m/z 965.9 (M+2H).

Analysis condition B: Retention time=2.77 min; ESI-MS (+) m/z 966.1 (M+2H).

Preparation of Example 10560

Example 10560

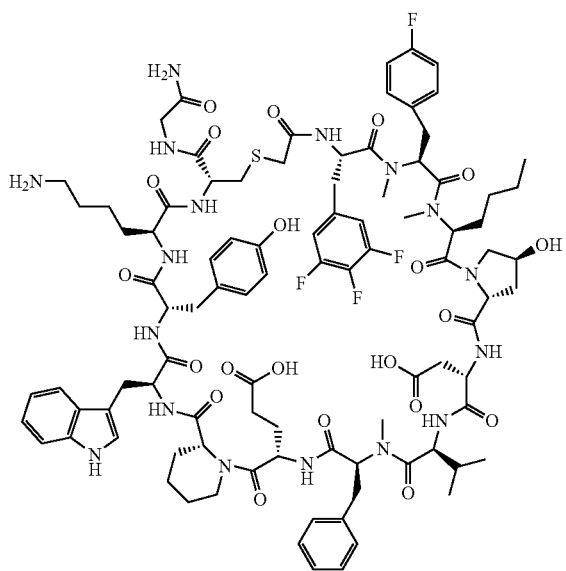

Example 10560 was prepared according to the method outlined in Example 10537. The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 60-100% B over 30 minutes, then a 5-minute hold at 100% B; Flow: 20 mL/min. Fractions containing the desired product were combined and dried via centrifugal evaporation. The yield of the product was 35.7 mg, and its estimated purity by LCMS analysis was 100%.

Analysis condition A: Retention time=2.08 min; ESI-MS (+) m/z 966.0 (M+2H).

Analysis condition B: Retention time=2.87 min; ESI-MS (+) m/z 966.1 (M+2H).

Preparation of Example 10561

Example 10561

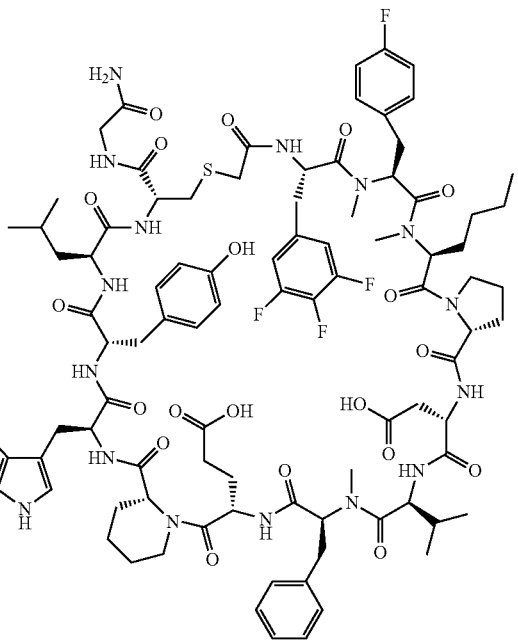

Example 10561 was prepared according to the method outlined in Example 10537. The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 22.2 mg, and its estimated purity by LCMS analysis was 95%.

Analysis condition A: Retention time=2.14 min; ESI-MS (+) m/z 951.4 (M+2H).

Analysis condition B: Retention time=2.85 min; ESI-MS (+) m/z 950.6 (M+2H).

Preparation of Example 10562

Example 10562

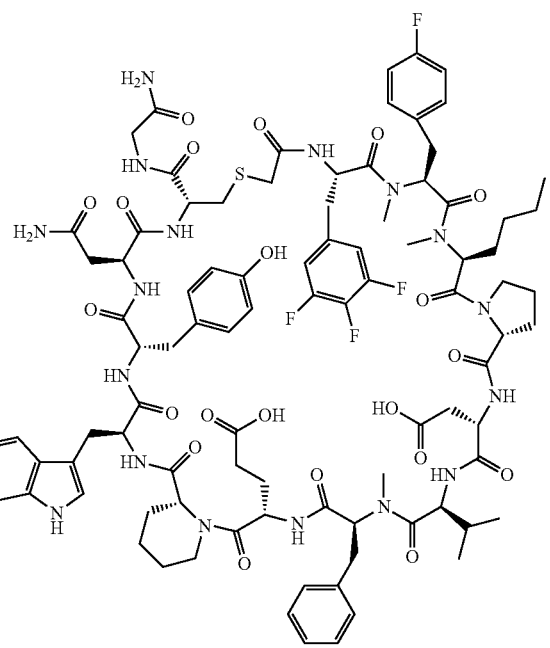

Example 10562 was prepared according to the method outlined in Example 10537. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 10.2 mg, and its estimated purity by LCMS analysis was 100%.

Analysis condition A: Retention time=1.80 min; ESI-MS (+) m/z 951.0 (M+2H).

Analysis condition B: Retention time=3.32 min; ESI-MS (+) m/z 950.3 (M+2H).

Preparation of Example 10563

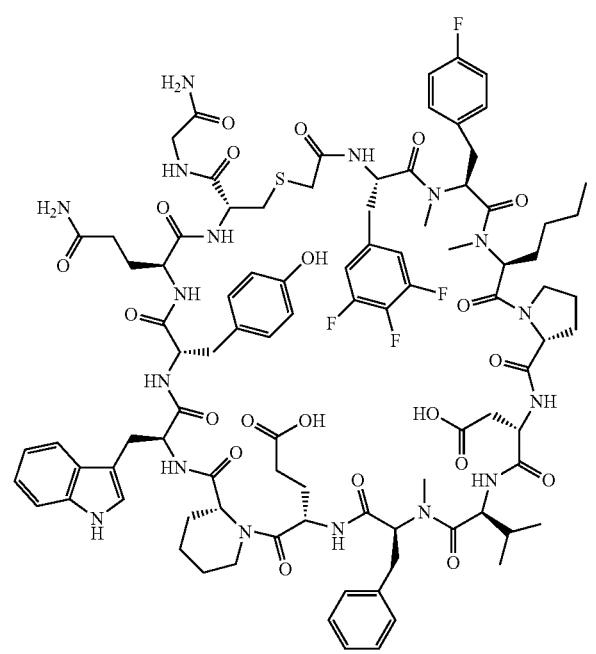

Example 10563

Example 10563 was prepared according to the method outlined in Example 10537. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 32.0 mg, and its estimated purity by LCMS analysis was 98%.

Analysis condition A: Retention time=1.77 min; ESI-MS (+) m/z 958.1 (M+2H).

Analysis condition B: Retention time=3.33 min; ESI-MS (+) m/z 958.4 (M+2H).

Preparation of Example 10564

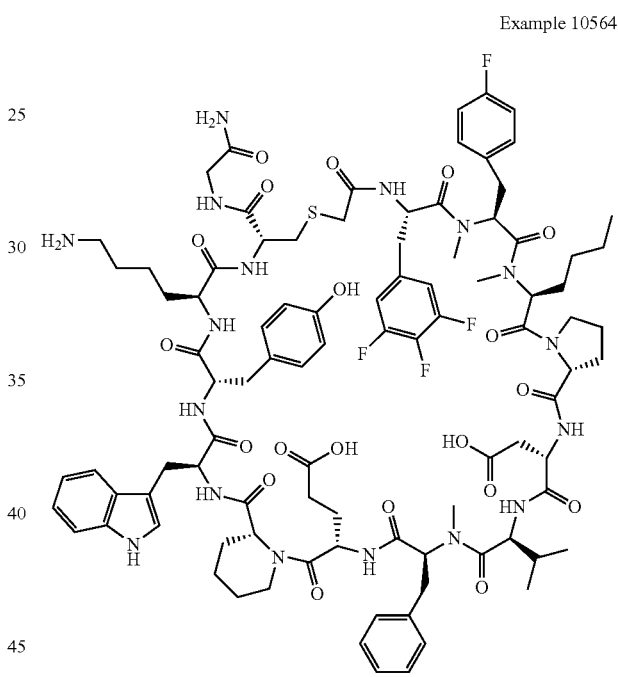

Example 10564

Example 10564 was prepared according to the method outlined in Example 10537. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 30.3 mg, and its estimated purity by LCMS analysis was 100%.

Analysis condition A: Retention time=1.88 min; ESI-MS (+) m/z 957.9 (M+2H).

Analysis condition B: Retention time=2.52 min; ESI-MS (+) m/z 957.9 (M+2H).

Preparation of Example 10565

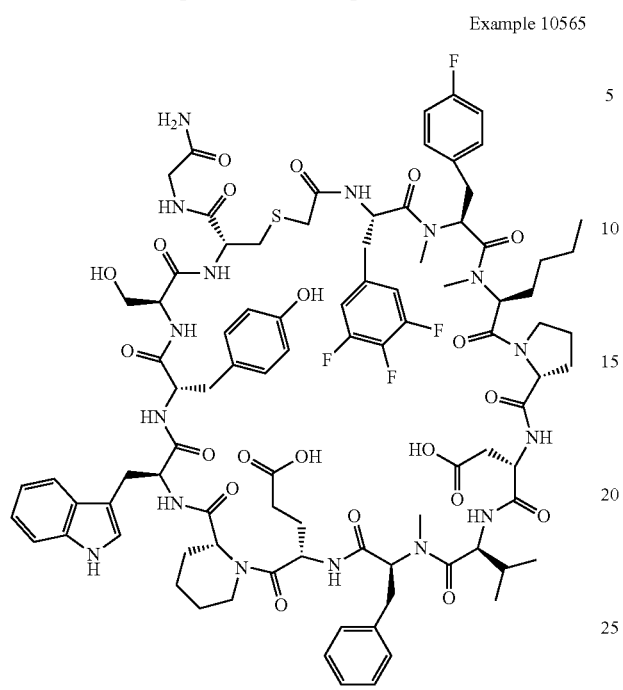

Example 10565

Example 10565 was prepared according to the method outlined in Example 10537. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 29.7 mg, and its estimated purity by LCMS analysis was 100%.

Analysis condition A: Retention time=1.84 min; ESI-MS (+) m/z 937.6 (M+2H).

Analysis condition B: Retention time=3.38 min; ESI-MS (+) m/z 937.6 (M+2H).

Preparation of Example 10566

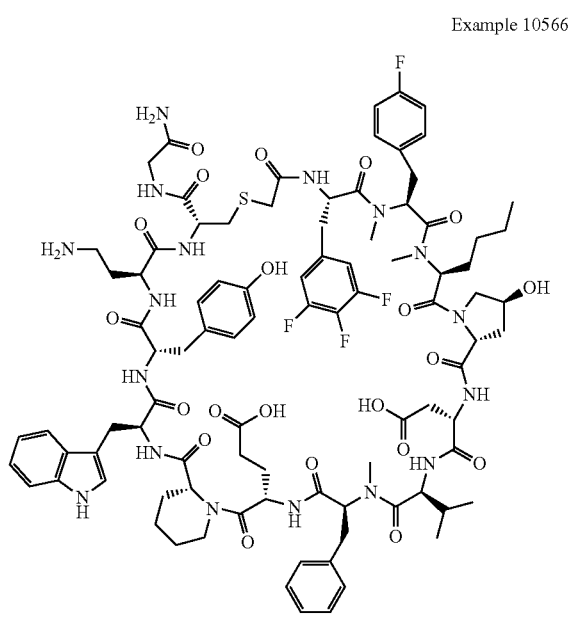 [SMILES: CCCC[C@H]1C(=O)N2C[C@@H](O)C[C@@H]2C(=O)N[C@@H](CC(=O)O)C(=O)N[C@@H](C(C)C)C(=O)N(C)[C@@H](Cc2ccccc2)C(=O)N[C@@H](CCC(=O)O)C(=O)N2CCCC[C@@H]2C(=O)N[C@@H](Cc2c[nH]c3ccccc23)C(=O)N[C@@H](Cc2ccc(O)cc2)C(=O)N[C@@H](CCN)C(=O)N[C@H](C(=O)NCC(N)=O)CSCC(=O)N[C@@H](Cc2cc(F)c(F)c(F)c2)C(=O)N(C)[C@@H](Cc2ccc(F)cc2)C(=O)N1C]

Example 10566

Example 10566 was prepared according to the method outlined in Example 10537. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 28.1 mg, and its estimated purity by LCMS analysis was 96%.

Analysis condition A: Retention time=1.70 min; ESI-MS (+) m/z 952.4 (M+2H).

Analysis condition B: Retention time=3.36 min; ESI-MS (+) m/z 952.5 (M+2H).

ESI-HRMS(+) m/z: Calculated: 951.9128 (M+2H); Found: 951.9113 (M+2H).

Preparation of Example 10567

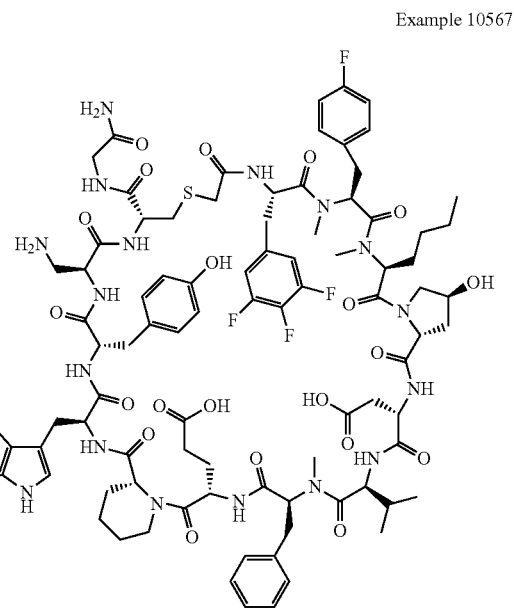

Example 10567

Example 10567 was prepared according to the method outlined in Example 10537. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 15.6 mg, and its estimated purity by LCMS analysis was 99%.

Analysis condition A: Retention time=1.70 min; ESI-MS (+) m/z 945.4 (M+2H).

Analysis condition B: Retention time=3.35 min; ESI-MS (+) m/z 945.4 (M+2H).

ESI-HRMS(+) m/z: Calculated: 944.9050 (M+2H); Found: 944.9027 (M+2H).

Preparation of Example 10568

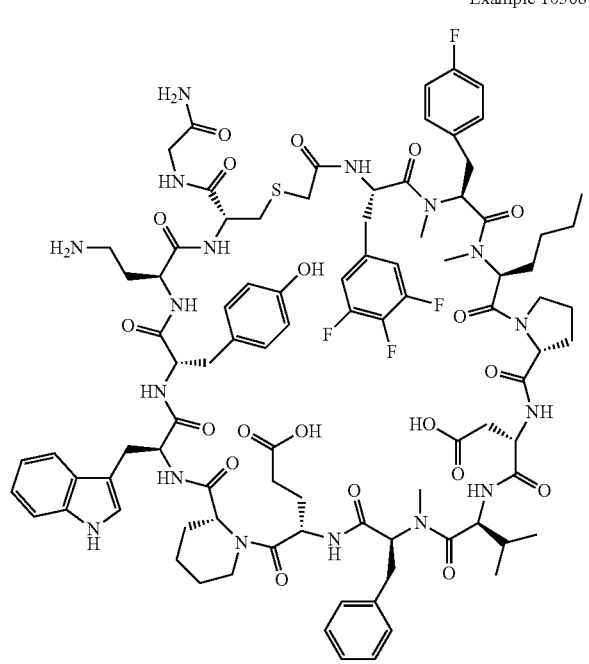

Example 10568

Example 10568 was prepared according to the method outlined in Example 10537. The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 28.8 mg, and its estimated purity by LCMS analysis was 96%.

Analysis condition A: Retention time=1.81 min; ESI-MS (+) m/z 944.5 (M+2H).

Analysis condition B: Retention time=3.45 min; ESI-MS (+) m/z 944.5 (M+2H).

ESI-HRMS(+) m/z: Calculated: 943.9153 (M+2H); Found: 943.9124 (M+2H).

Preparation of Example 10569

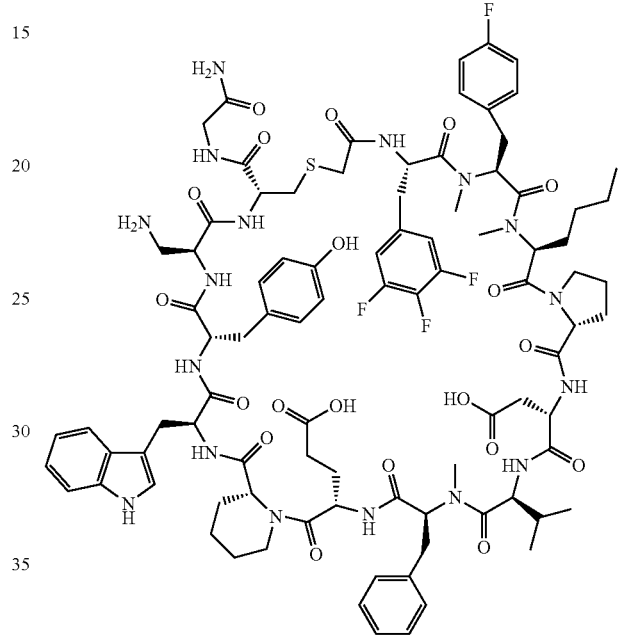

Example 10569

Example 10569 was prepared according to the method outlined in Example 10537. The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 19.3 mg, and its estimated purity by LCMS analysis was 97%.

Analysis condition A: Retention time=1.79 min; ESI-MS (+) m/z 937.2 (M+2H).

Analysis condition B: Retention time=3.39 min; ESI-MS (+) m/z 937.6 (M+2H).

ESI-HRMS(+) m/z: Calculated: 936.9075 (M+2H); Found: 936.9049 (M+2H).

Preparation of Example 10570

Example 10570

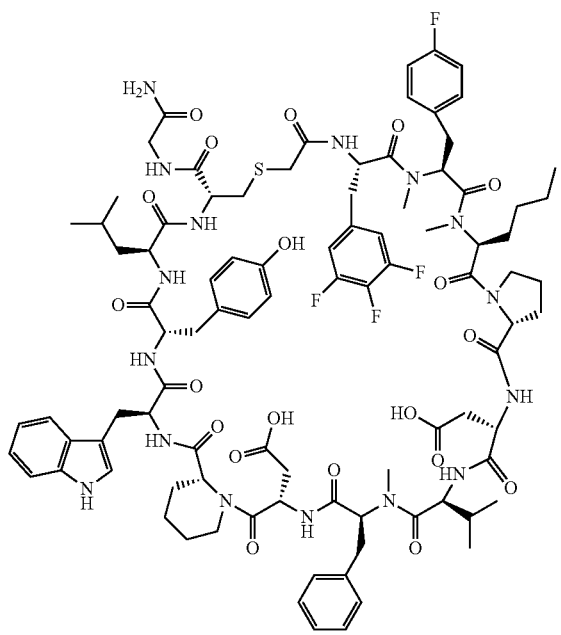

Example 10570 was prepared according to the method outlined in Example 10537. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 12.8 mg, and its estimated purity by LCMS analysis was 100%.

Analysis condition A: Retention time=1.77 min; ESI-MS (+) m/z 944.0 (M+2H).

Analysis condition B: Retention time=3.39 min; ESI-MS (+) m/z 943.9 (M+2H).

ESI-HRMS(+) m/z: Calculated: 943.4177 (M+2H); Found: 943.4163 (M+2H).

Preparation of Example 10571

Example 10571

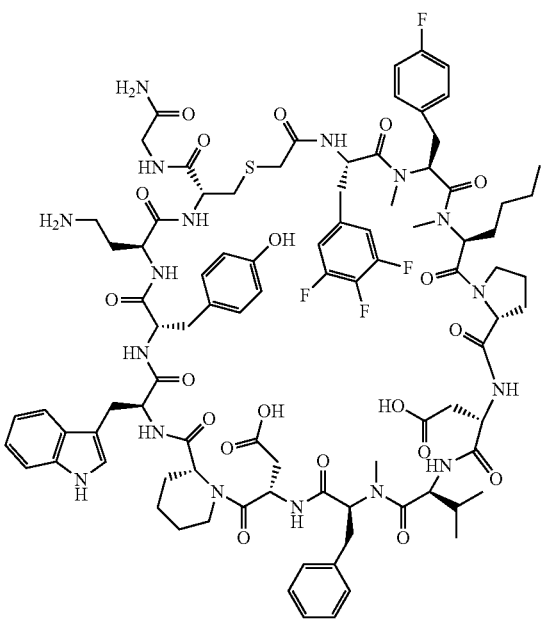

Example 10571 was prepared according to the method outlined in Example 10537. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 29.7 mg, and its estimated purity by LCMS analysis was 99%.

Analysis condition A: Retention time=1.83 min; ESI-MS (+) m/z 937.2 (M+2H).

Analysis condition B: Retention time=3.44 min; ESI-MS (+) m/z 937.4 (M+2H).

ESI-HRMS(+) m/z: Calculated: 936.9075 (M+2H); Found: 936.9053 (M+2H).

Preparation of Example 10572

Example 10572

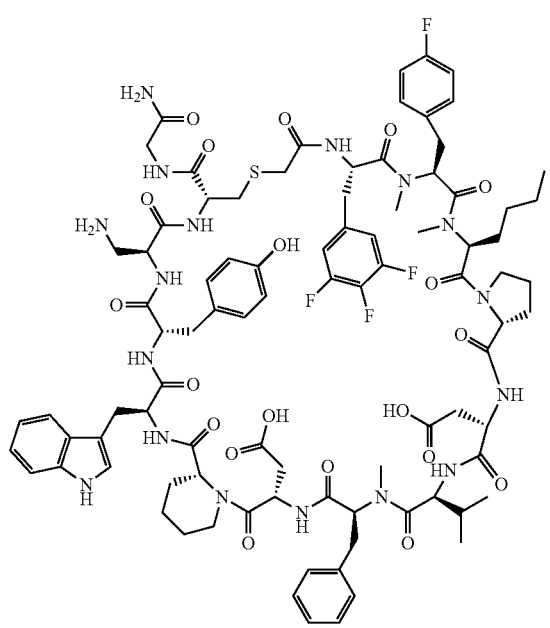

Example 10572 was prepared according to the method outlined in Example 10537. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 22.9 mg, and its estimated purity by LCMS analysis was 96%.

Analysis condition A: Retention time=1.76 min; ESI-MS (+) m/z 930.0 (M+2H).

Analysis condition B: Retention time=3.31 min; ESI-MS (+) m/z 930.4 (M+2H).

ESI-HRMS(+) m/z: Calculated: 929.8997 (M+2H); Found: 929.8971 (M+2H).

Preparation of Example 10573

Example 10573

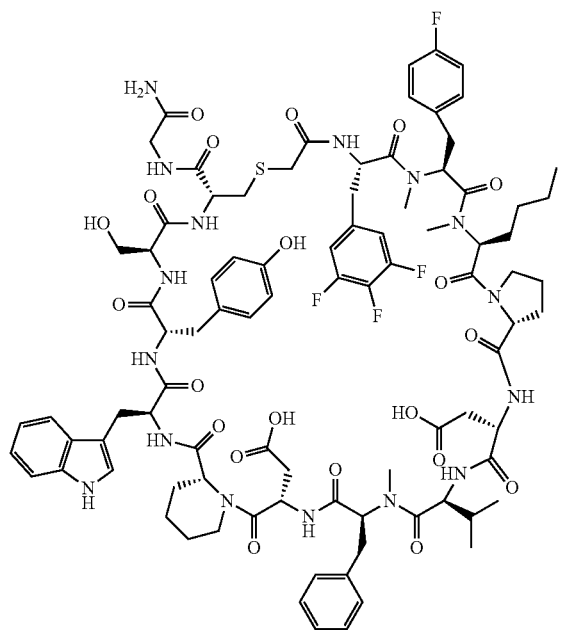

Example 10573 was prepared according to the method outlined in Example 10537. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 22.8 mg, and its estimated purity by LCMS analysis was 98%.

Analysis condition A: Retention time=1.72 min; ESI-MS (+) m/z 930.8 (M+2H).

Analysis condition B: Retention time=3.25 min; ESI-MS (+) m/z 930.9 (M+2H).

ESI-HRMS(+) m/z: Calculated: 930.3917 (M+2H); Found: 930.3903 (M+2H).

Preparation of Example 10574

Example 10574

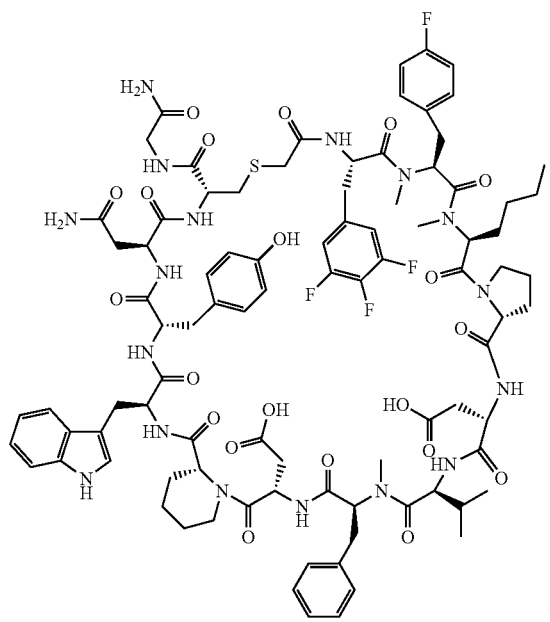

Example 10574 was prepared according to the method outlined in Example 10537. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 26.1 mg, and its estimated purity by LCMS analysis was 99%.

Analysis condition A: Retention time=1.71 min; ESI-MS (+) m/z 944.4 (M+2H).

Analysis condition B: Retention time=3.24 min; ESI-MS (+) m/z 944.3 (M+2H).

ESI-HRMS(+) m/z: Calculated: 943.8971 (M+2H); Found: 943.8959 (M+2H).

Preparation of Example 10575

Example 10575

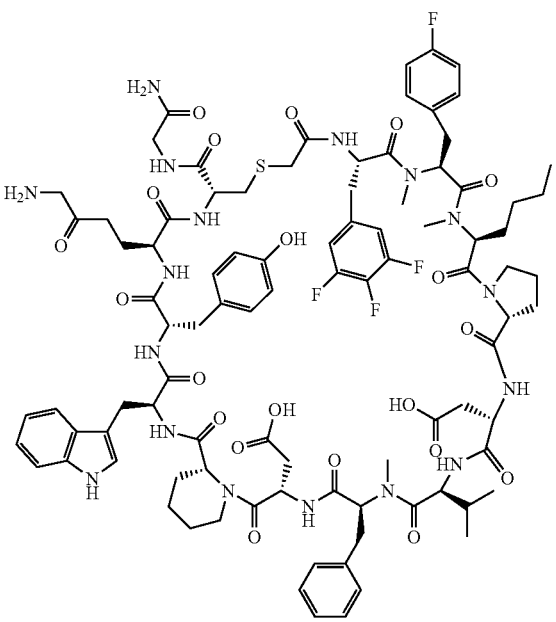

Example 10575 was prepared according to the method outlined in Example 10537. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 30.0 mg, and its estimated purity by LCMS analysis was 99%.

Analysis condition A: Retention time=1.67 min; ESI-MS (+) m/z 951.4 (M+2H).

Analysis condition B: Retention time=3.22 min; ESI-MS (+) m/z 951.4 (M+2H).

ESI-HRMS(+) m/z: Calculated: 950.9050 (M+2H); Found: 950.9041 (M+2H).

Preparation of Example 10576

Example 10576

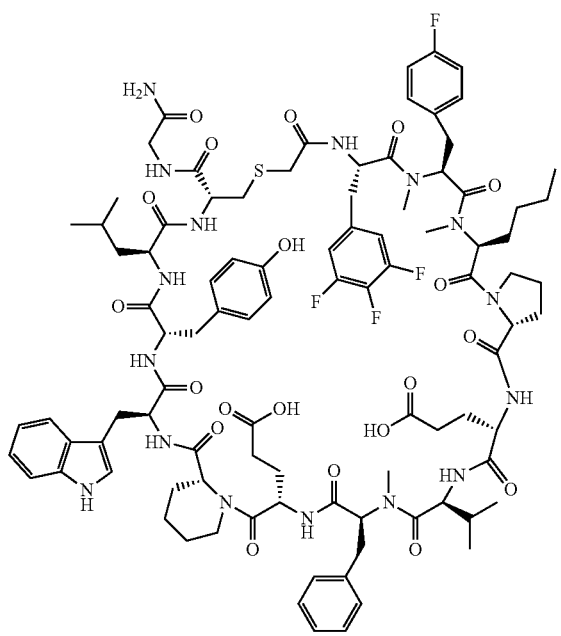

Example 10576 was prepared according to the method outlined in Example 10537. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 31.8 mg, and its estimated purity by LCMS analysis was 96%.

Analysis condition A: Retention time=1.77 min; ESI-MS (+) m/z 957.9 (M+2H).

Analysis condition B: Retention time=3.30 min; ESI-MS (+) m/z 957.9 (M+2H).

ESI-HRMS(+) m/z: Calculated: 957.4334 (M+2H); Found: 957.4322 (M+2H).

Preparation of Example 10577

Example 10577

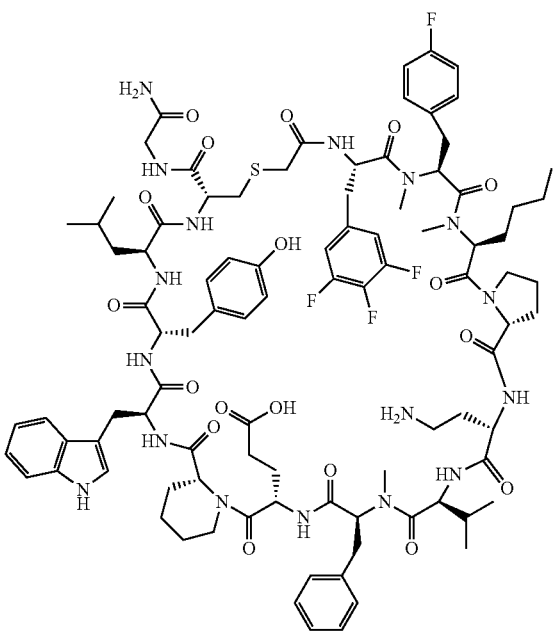

Example 10577 was prepared according to the method outlined in Example 10537. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 28.0 mg, and its estimated purity by LCMS analysis was 98%.

Analysis condition A: Retention time=1.94 min; ESI-MS (+) m/z 943.4 (M+2H).

ESI-HRMS(+) m/z: Calculated: 942.9439 (M+2H) Found: 942.9416 (M+2H).

Preparation of Example 10578

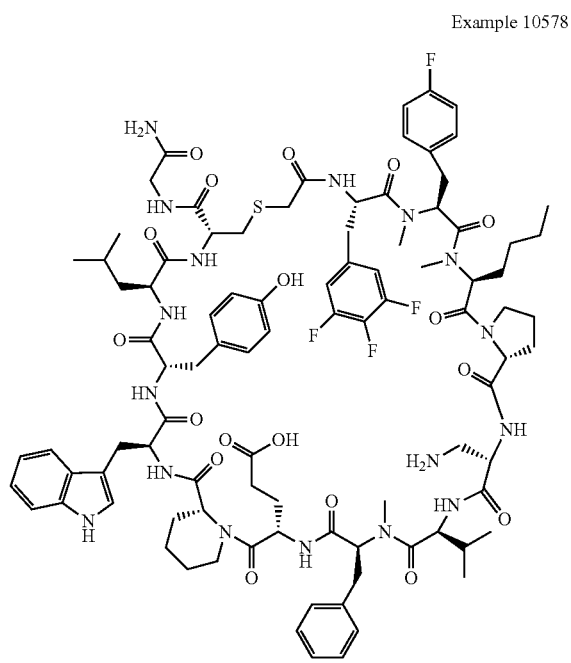 [SMILES: CCCC[C@H]1C(=O)N2CCC[C@@H]2C(=O)N[C@@H](CN)C(=O)N[C@@H](C(C)C)C(=O)N(C)[C@@H](Cc2ccccc2)C(=O)N[C@@H](CCC(=O)O)C(=O)N2CCCC[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2cc(F)c(F)c(F)c2)C(=O)N(C)[C@@H](Cc2ccc(F)cc2)C(=O)N1C]

Example 10578

Example 10578 was prepared according to the method outlined in Example 10537. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 23.3 mg, and its estimated purity by LCMS analysis was 96%.

Analysis condition A: Retention time=1.95 min; ESI-MS (+) m/z 936.3 (M+2H).

ESI-HRMS(+) m/z: Calculated: 935.9361 (M+2H); Found: 935.9335 (M+2H).

Preparation of Example 10579

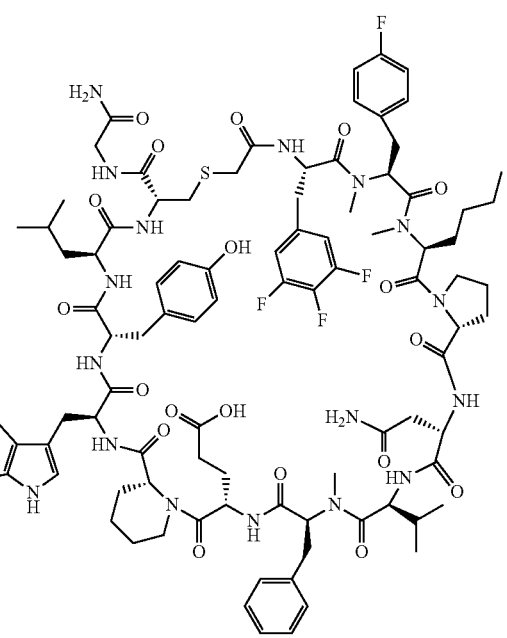

Example 10579

Example 10579 was prepared according to the method outlined in Example 10537. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 55-95% B over 30 minutes, then a 5-minute hold at 100% B; Flow: 20 mL/min. Fractions containing the desired product were combined and dried via centrifugal evaporation. The yield of the product was 24.9 mg, and its estimated purity by LCMS analysis was 98%.

Analysis condition A: Retention time=1.94 min; ESI-MS (+) m/z 950.1 (M+2H).

Analysis condition B: Retention time=3.46 min; ESI-MS (+) m/z 950.1 (M+2H).

ESI-HRMS(+) m/z: Calculated: 949.9335 (M+2H); Found: 949.9317 (M+2H).

Preparation of Example 10580

Example 10580

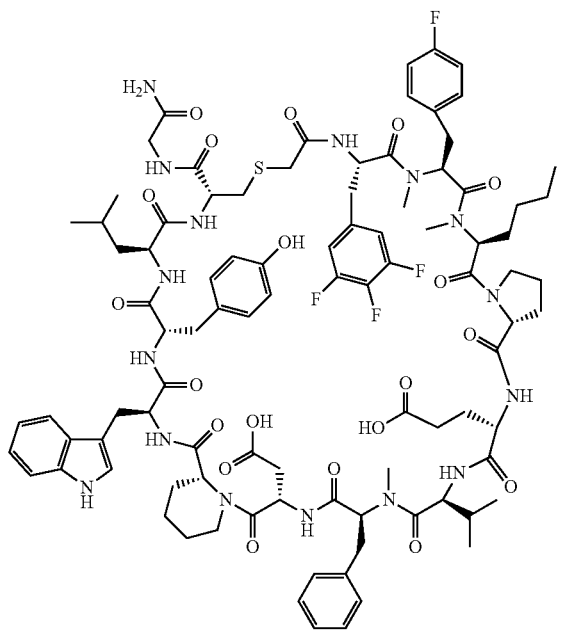

Example 10581

Preparation of Example 10581

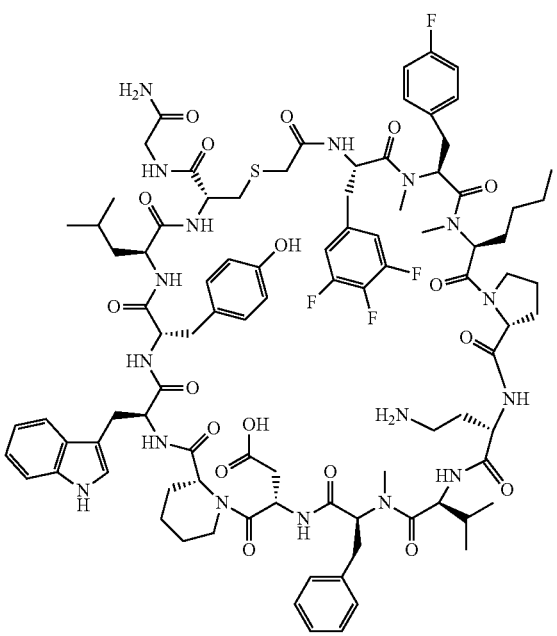

Example 10580 was prepared according to the method outlined in Example 10537. The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 30.2 mg, and its estimated purity by LCMS analysis was 98%.

Example 10581 was prepared according to the method outlined in Example 10537. The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 55-95% B over 30 minutes, then a 5-minute hold at 100% B; Flow: 20 mL/min. Fractions containing the desired product were combined and dried via centrifugal evaporation. The yield of the product was 39.7 mg, and its estimated purity by LCMS analysis was 99%.

Analysis condition A: Retention time=1.81 min; ESI-MS (+) m/z 951.0 (M+2H).

Analysis condition A: Retention time=1.94 min; ESI-MS (+) m/z 936.3 (M+2H).

Analysis condition B: Retention time=3.34 min; ESI-MS (+) m/z 950.1 (M+2H).

Analysis condition B: Retention time=3.46 min; ESI-MS (+) m/z 936.4 (M+2H).

ESI-HRMS(+) m/z: Calculated: 950.4255 (M+2H); Found: 950.4237 (M+2H).

ESI-HRMS(+) m/z: Calculated: 935.9361 (M+2H); Found: 935.9339 (M+2H).

Preparation of Example 10582

Preparation of Example 10583

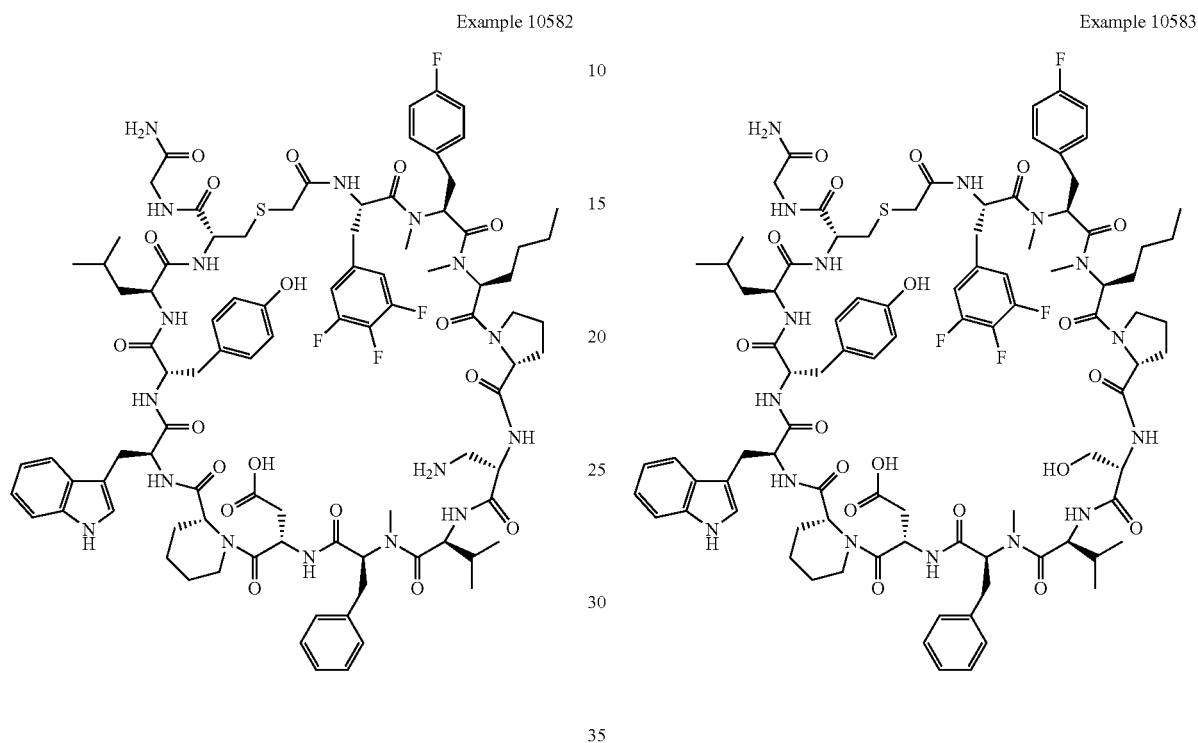

Example 10582

Example 10583

Example 10582 was prepared according to the method outlined in Example 10537. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 27.1 mg, and its estimated purity by LCMS analysis was 99%.

Analysis condition A: Retention time=1.95 min; ESI-MS (+) m/z 929.3 (M+2H).

ESI-HRMS(+) m/z: Calculated: 928.9282 (M+2H); Found: 928.9258 (M+2H).

Example 10583 was prepared according to the method outlined in Example 10537. The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 14.8 mg, and its estimated purity by LCMS analysis was 96%.

Analysis condition A: Retention time=1.95 min; ESI-MS (+) m/z 929.9 (M+2H).

Analysis condition B: Retention time=3.46 min; ESI-MS (+) m/z 929.9 (M+2H).

Preparation of Example 10584

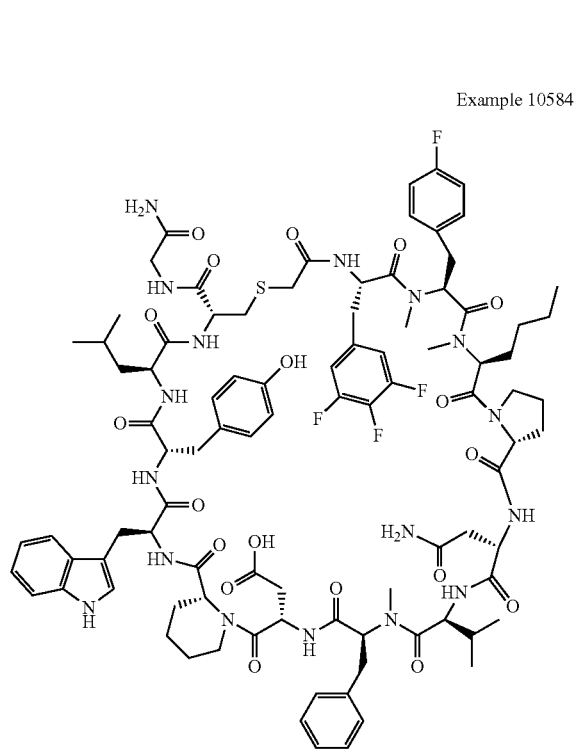 [SMILES: CCCC[C@H]1C(=O)N2CCC[C@@H]2C(=O)N[C@@H](CC(N)=O)C(=O)N[C@@H](C(C)C)C(=O)N(C)[C@@H](Cc2ccccc2)C(=O)N[C@@H](CC(=O)O)C(=O)N2CCCC[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2cc(F)c(F)c(F)c2)C(=O)N(C)[C@@H](Cc2ccc(F)cc2)C(=O)N1C]

Example 10584

Example 10584 was prepared according to the method outlined in Example 10537. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 55-95% B over 30 minutes, then a 5-minute hold at 100% B; Flow: 20 mL/min. Fractions containing the desired product were combined and dried via centrifugal evaporation. The yield of the product was 29.3 mg, and its estimated purity by LCMS analysis was 95%.

Analysis condition A: Retention time=1.91 min; ESI-MS (+) m/z 943.4 (M+2H).

Analysis condition B: Retention time=3.43 min; ESI-MS (+) m/z 943.4 (M+2H).

Preparation of Example 10585

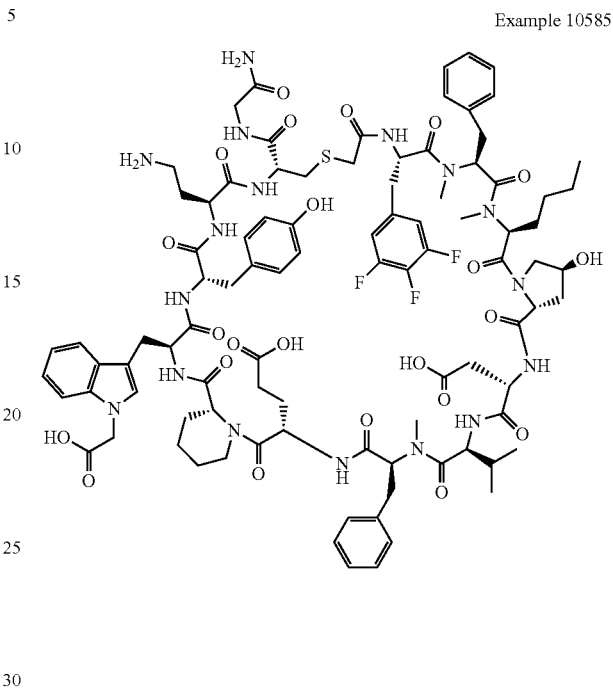

Example 10585

Example 10585 was prepared according to the method outlined in Example 10537. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 19.0 mg, and its estimated purity by LCMS analysis was 96%.

Analysis condition A: Retention time=1.48 min; ESI-MS (+) m/z 972.3 (M+2H).

Analysis condition B: Retention time=3.12 min; ESI-MS (+) m/z 972.5 (M+2H).

ESI-HRMS(+) m/z: Calculated: 971.9202 (M+2H); Found: 971.9183 (M+2H).

Preparation of Example 10586

Preparation of Example 10587

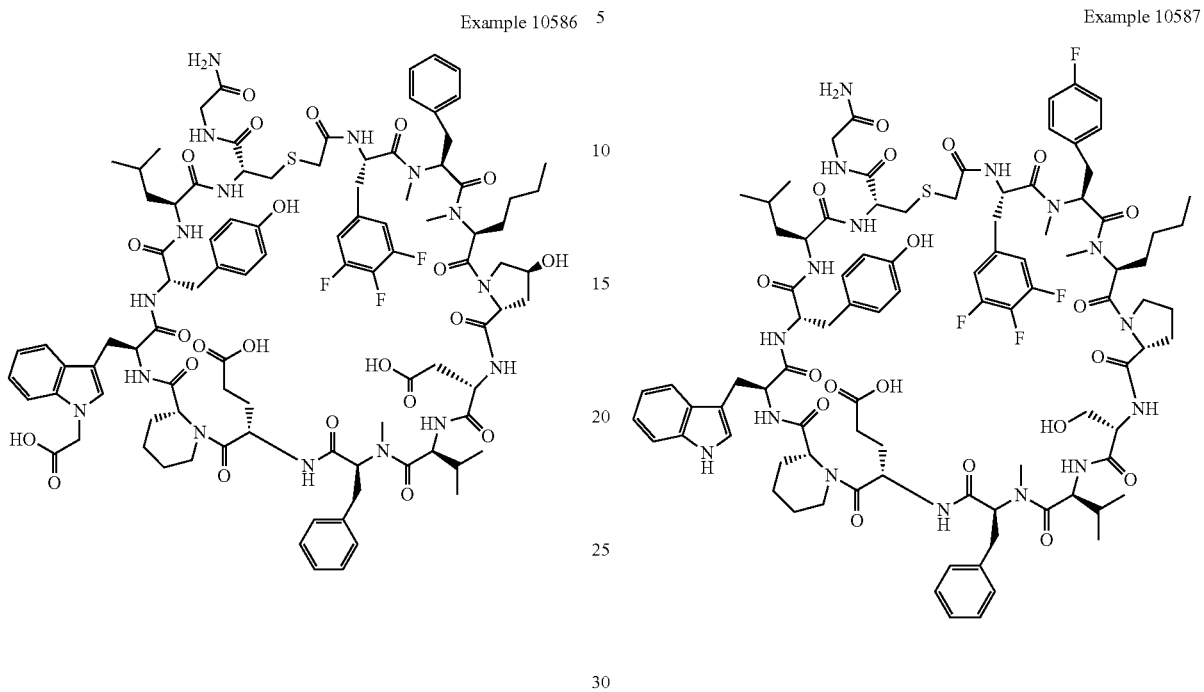

Example 10586

Example 10587

Example 10586 was prepared according to the method outlined in Example 10537. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 28.7 mg, and its estimated purity by LCMS analysis was 98%.

Example 10587 was prepared according to the method outlined in Example 10537. The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 19.4 mg, and its estimated purity by LCMS analysis was 100%.

Analysis condition A: Retention time=1.41 min; ESI-MS (+) m/z 978.7 (M+2H).

Analysis condition A: Retention time=1.98 min; ESI-MS (+) m/z 936.4 (M+2H).

Analysis condition B: Retention time=2.77 min; ESI-MS (+) m/z 978.7 (M+2H).

Analysis condition B: Retention time=3.46 min; ESI-MS (+) m/z 936.4 (M+2H).

ESI-HRMS(+) m/z: Calculated: 978.4304 (M+2H); Found: 978.4291 (M+2H).

ESI-HRMS(+) m/z: Calculated: 936.4281 (M+2H) Found: 936.4261 (M+2H).

Preparation of Example 10588

Preparation of Example 10589

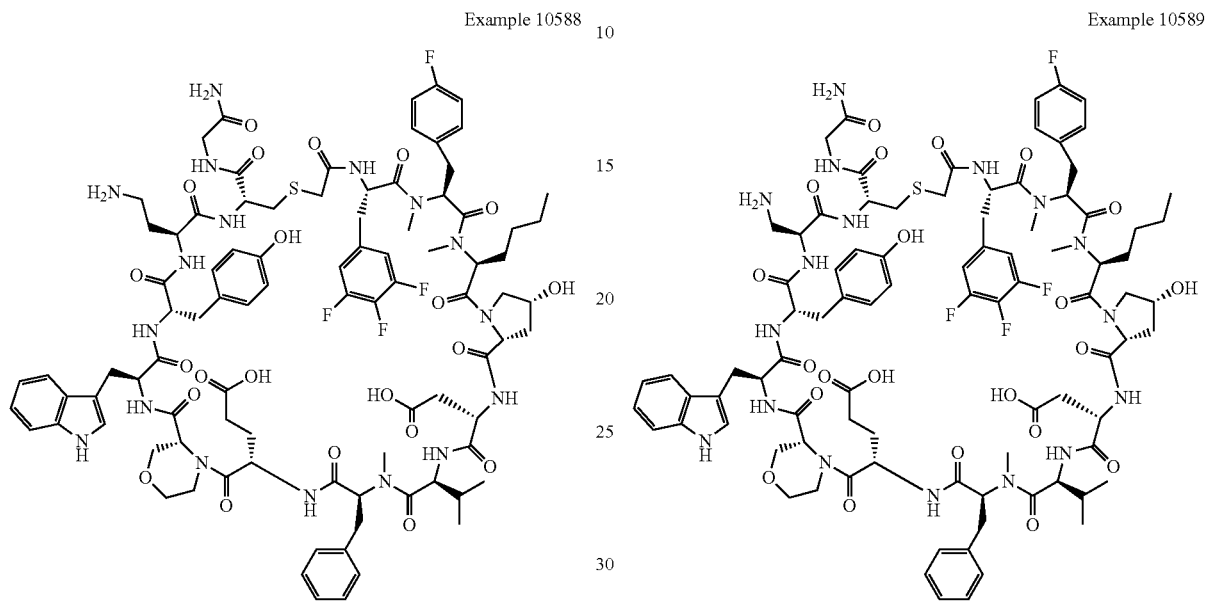

Example 10588

Example 10589

Example 10588 was prepared according to the method outlined in Example 10537. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 6.9 mg, and its estimated purity by LCMS analysis was 100%.

Example 10589 was prepared according to the method outlined in Example 10537. The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 45-90% B over 30 minutes, then a 5-minute hold at 100% B; Flow: 20 mL/min. Fractions containing the desired product were combined and dried via centrifugal evaporation. The yield of the product was 6.1 mg, and its estimated purity by LCMS analysis was 96%.

Analysis condition A: Retention time=1.98 min; ESI-MS (−) m/z 949.9 (M−2H).

Analysis condition A: Retention time=1.70 min; ESI-MS (+) m/z 944.9 (M+2H).

Analysis condition B: Retention time=2.93 min; ESI-MS (+) m/z 951.9 (M+2H).

Analysis condition B: Retention time=2.88 min; ESI-MS (+) m/z 944.9 (M+2H).

Preparation of Example 10590

Preparation of Example 10591

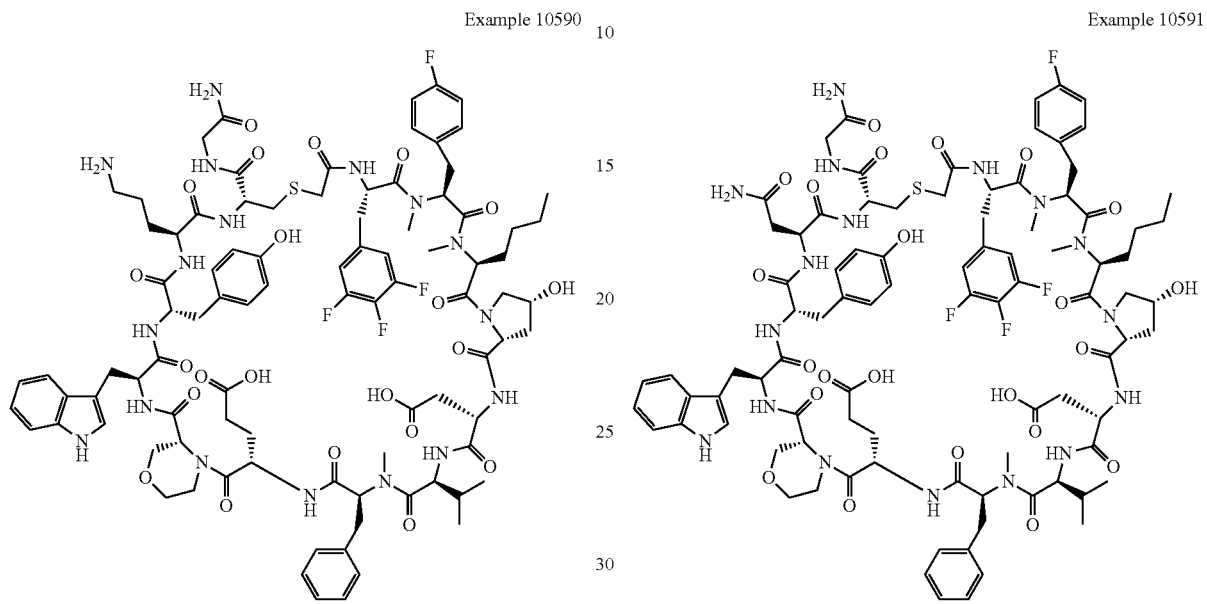

Example 10590

Example 10591

Example 10590 was prepared according to the method outlined in Example 10537. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-60% B over 30 minutes, then a 5-minute hold at 100% B; Flow: 20 mL/min. Fractions containing the desired product were combined and dried via centrifugal evaporation. The yield of the product was 12.4 mg, and its estimated purity by LCMS analysis was 98%.

Example 10591 was prepared according to the method outlined in Example 10537. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 8.2 mg, and its estimated purity by LCMS analysis was 95%.

Analysis condition A: Retention time=1.71 min; ESI-MS (+) m/z 959.2 (M+2H).

Analysis condition A: Retention time=1.71 min; ESI-MS (−) m/z 957.5 (M−2H).

Analysis condition B: Retention time=2.90 min; ESI-MS (+) m/z 958.7 (M+2H).

Analysis condition B: Retention time=2.90 min; ESI-MS (−) m/z 957.5 (M−2H).

Preparation of Example 10592

Preparation of Example 10593

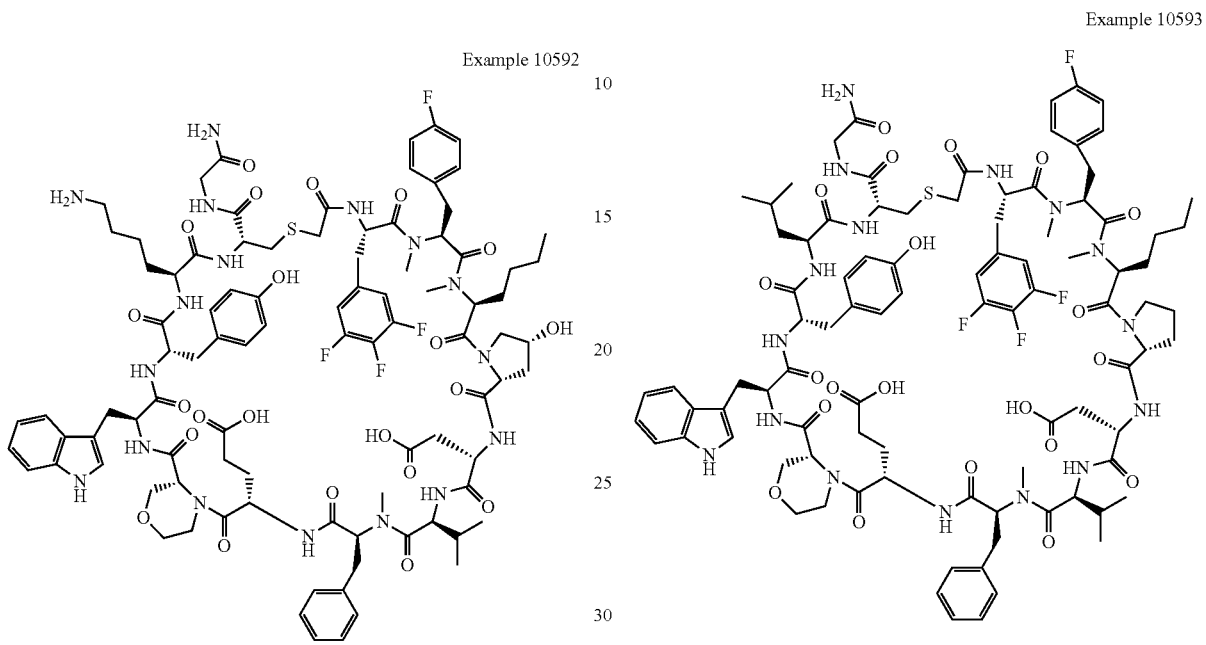

Example 10592

Example 10593

Example 10592 was prepared according to the method outlined in Example 10537. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 13.0 mg, and its estimated purity by LCMS analysis was 100%.

Example 10593 was prepared according to the method outlined in Example 10537. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 24.6 mg, and its estimated purity by LCMS analysis was 100%.

Analysis condition A: Retention time=1.70 min; ESI-MS (+) m/z 966.3 (M+2H).

Analysis condition A: Retention time=1.70 min; ESI-MS (−) m/z 949.5 (M−2H).

Analysis condition B: Retention time=2.91 min; ESI-MS (+) m/z 966.2 (M+2H).

Analysis condition B: Retention time=2.87 min; ESI-MS (+) m/z 952.0 (M+2H).

Preparation of Example 10594

Preparation of Example 10595

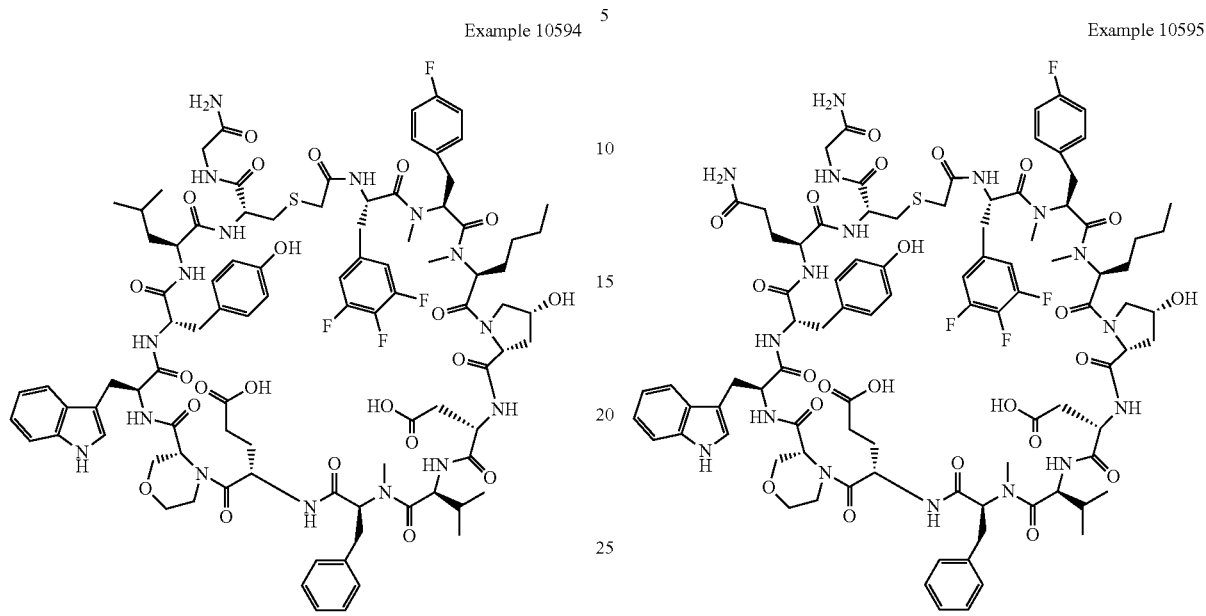

Example 10594

Example 10595

Example 10594 was prepared according to the method outlined in Example 10537. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-65% B over 30 minutes, then a 5-minute hold at 100% B; Flow: 20 mL/min. Fractions containing the desired product were combined and dried via centrifugal evaporation. The yield of the product was 10.2 mg, and its estimated purity by LCMS analysis was 97%.

Example 10595 was prepared according to the method outlined in Example 10537. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 6.6 mg, and its estimated purity by LCMS analysis was 100%.

Analysis condition A: Retention time=1.73 min; ESI-MS (+) m/z 958.9 (M+2H).

Analysis condition A: Retention time=1.59 min; ESI-MS (+) m/z 966.2 (M+2H).

Analysis condition B: Retention time=3.3 min; ESI-MS (+) m/z 958.9 (M+2H).

Analysis condition B: Retention time=2.77 min; ESI-MS (+) m/z 966.0 (M+2H).

Preparation of Example 10596

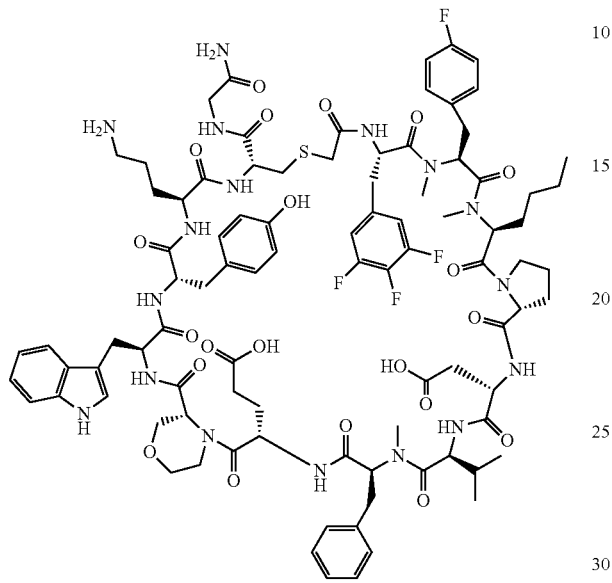

Example 10596

Example 10596 was prepared according to the method outlined in Example 10537. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 25.0 mg, and its estimated purity by LCMS analysis was 100%.

Analysis condition A: Retention time=1.80 min; ESI-MS (−) m/z 951.0 (M−2H).

Analysis condition B: Retention time=2.97 min; ESI-MS (+) m/z 952.4 (M+2H).

Preparation of Example 10597

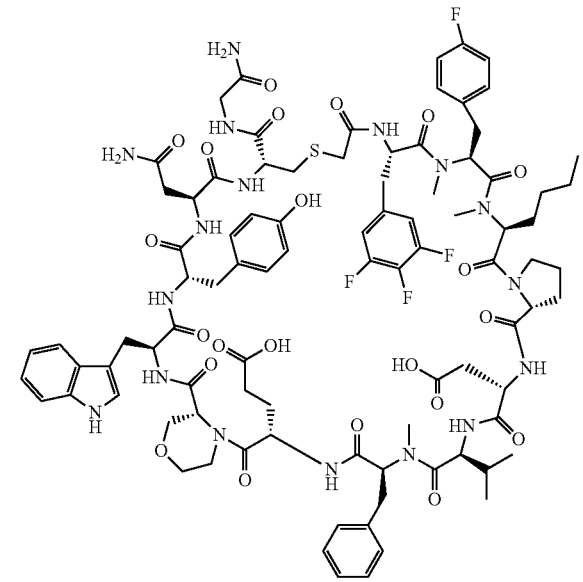

Example 10597

Example 10597 was prepared according to the method outlined in Example 10537. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 19.2 mg, and its estimated purity by LCMS analysis was 95%.

Analysis condition A: Retention time=1.73 min; ESI-MS (−) m/z 950.5 (M−2H).

Analysis condition B: Retention time=2.93 min; ESI-MS (+) m/z 952.2 (M+2H).

Preparation of Example 10598

Example 10598

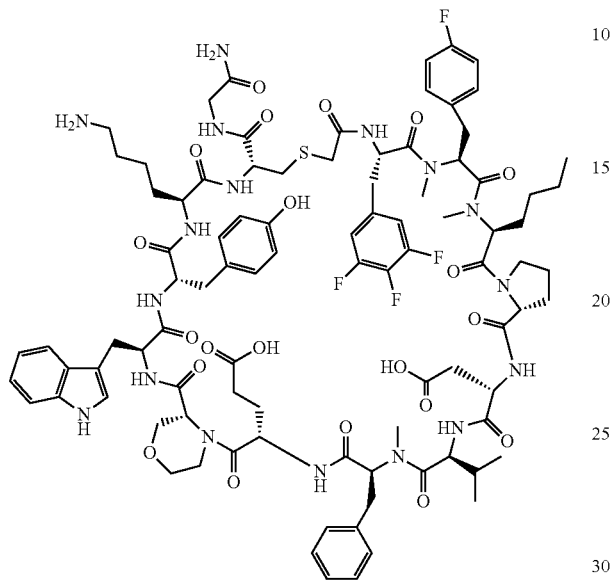

Example 10598 was prepared according to the method outlined in Example 10537. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 50-100% B over 30 minutes, then a 5-minute hold at 100% B; Flow: 20 mL/min. Fractions containing the desired product were combined and dried via centrifugal evaporation. The yield of the product was 24.5 mg, and its estimated purity by LCMS analysis was 98%.

Analysis condition A: Retention time=1.75 min; ESI-MS (+) m/z 959.5 (M+2H).

Analysis condition B: Retention time=2.97 min; ESI-MS (+) m/z 959.7 (M+2H).

Preparation of Example 10599

Example 10599

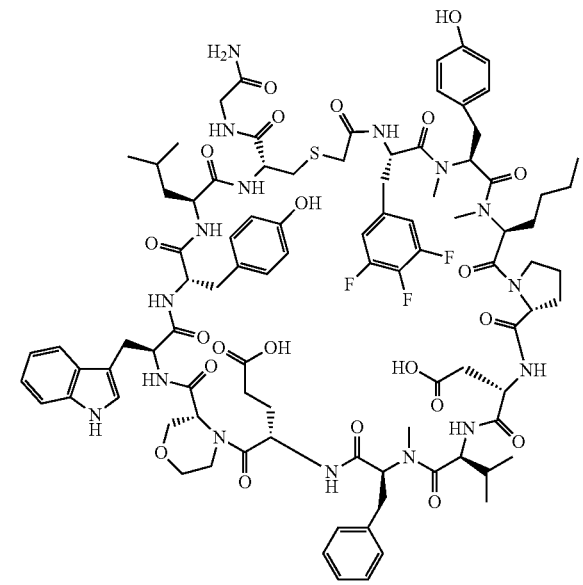

Example 10599 was prepared according to the method outlined in Example 10537. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 34.2 mg, and its estimated purity by LCMS analysis was 98%.

Analysis condition A: Retention time=1.77 min; ESI-MS (−) m/z 948.0 (M−2H).

Analysis condition B: Retention time=2.82 min; ESI-MS (+) m/z 949.6 (M+2H).

Preparation of Example 10600

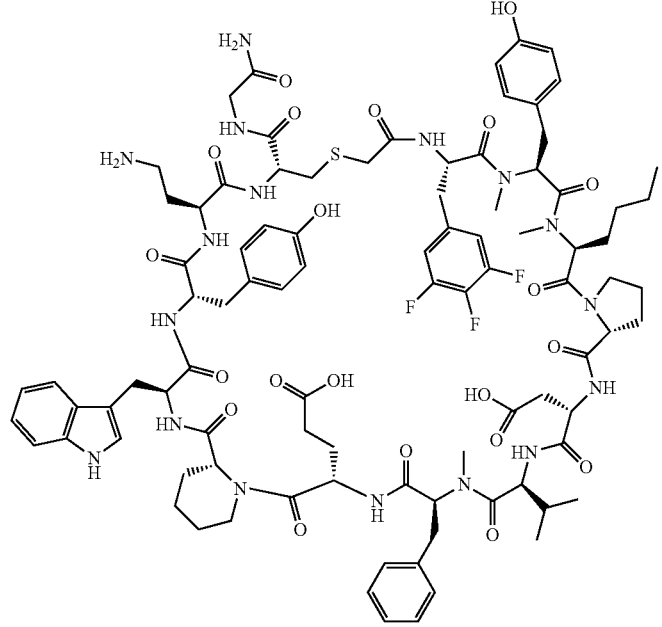

Example 10600

Example 10600 was prepared according to the method outlined in Example 10537. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 22.2 mg, and its estimated purity by LCMS analysis was 100%.

Analysis condition A: Retention time=1.75 min; ESI-MS (−) m/z 942.6 (M−2H).

Analysis condition B: Retention time=2.98 min; ESI-MS (+) m/z 943.5 (M+2H).

Preparation of Example 10601

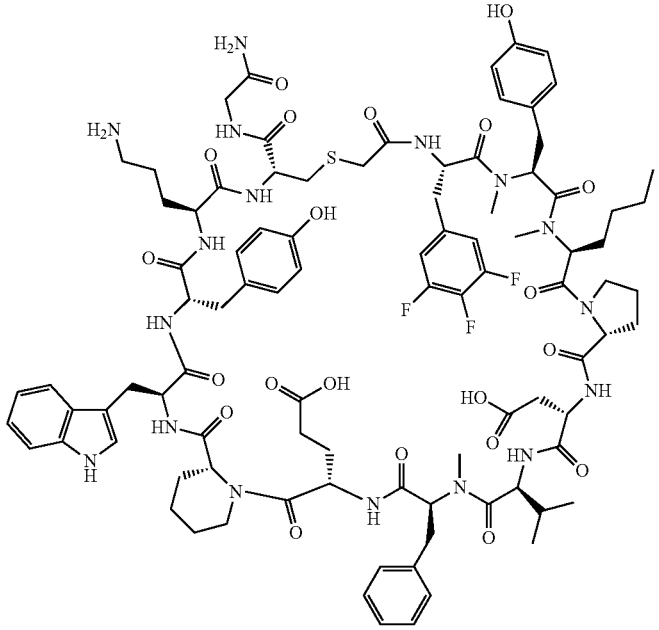

Example 10601

Example 10601 was prepared according to the method outlined in Example 10537. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 25.3 mg, and its estimated purity by LCMS analysis was 100%.

Analysis condition A: Retention time=1.67 min; ESI-MS (+) m/z 950.8 (M+2H).

Analysis condition B: Retention time=2.98 min; ESI-MS (+) m/z 950.6 (M+2H).

Preparation of Example 10602

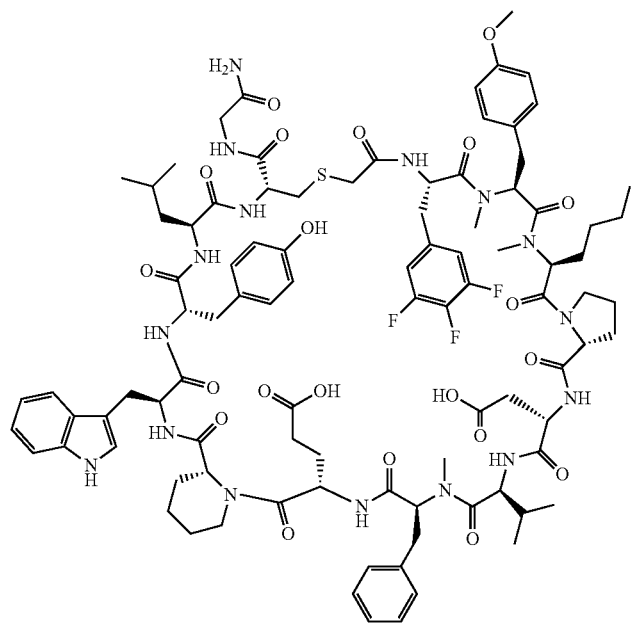

Example 10602

Example 10602 was prepared according to the method outlined in Example 10537. The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 26.5 mg, and its estimated purity by LCMS analysis was 100%.

Analysis condition A: Retention time=1.18 min; ESI-MS (−) m/z 955.6 (M−2H).

Analysis condition B: Retention time=2.84 min; ESI-MS (+) m/z 956.9 (M+2H).

Preparation of Example 10603

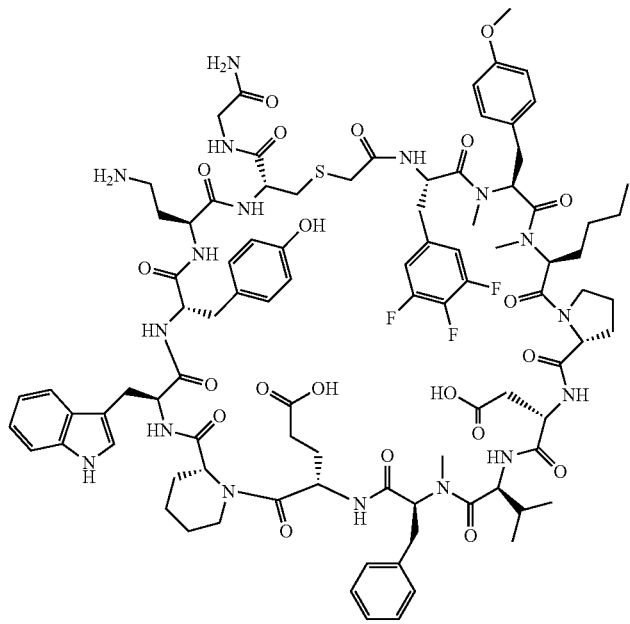

Example 10603

Example 10603 was prepared according to the method outlined in Example 10537. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 31.9 mg, and its estimated purity by LCMS analysis was 100%.

Analysis condition A: Retention time=1.75 min; ESI-MS (+) m/z 950.5 (M+2H).

Analysis condition B: Retention time=2.96 min; ESI-MS (+) m/z 949.9 (M+2H).

Preparation of Example 10604

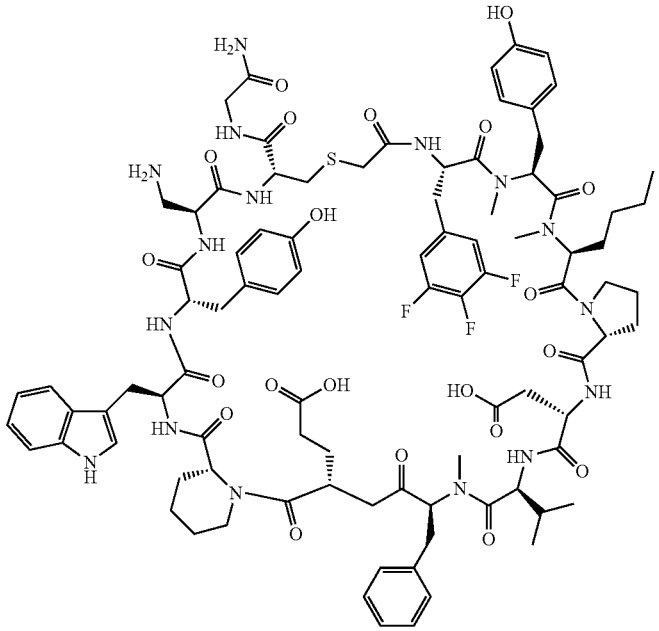

Example 10604

Example 10604 was prepared according to the method outlined in Example 10537. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 21.3 mg, and its estimated purity by LCMS analysis was 94%.

Analysis condition A: Retention time=1.74 min; ESI-MS (−) m/z 934.5 (M−2H).

Analysis condition B: Retention time=2.95 min; ESI-MS (+) m/z 936.7 (M+2H).

Preparation of Example 10605

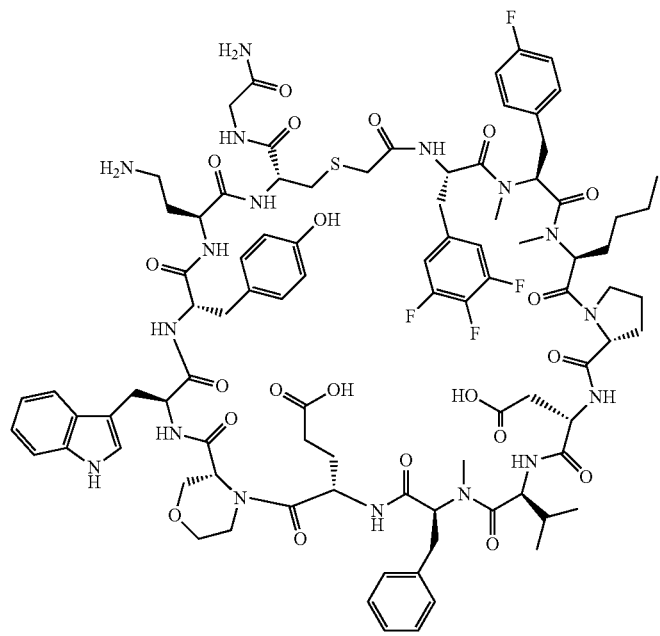

Example 10605

Example 10605 was prepared according to the method outlined in Example 10537. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 55-95% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 15 minutes, then a 5-minute hold at 100% B; Flow: 20 mL/min. Fractions containing the desired product were combined and dried via centrifugal evaporation. The yield of the product was 10.2 mg, and its estimated purity by LCMS analysis was 100%.

Analysis condition A: Retention time=1.80 min; ESI-MS (−) m/z 943.0 (M−2H).

Analysis condition B: Retention time=3.06 min; ESI-MS (+) m/z 945.5 (M+2H).

Preparation of Example 10606

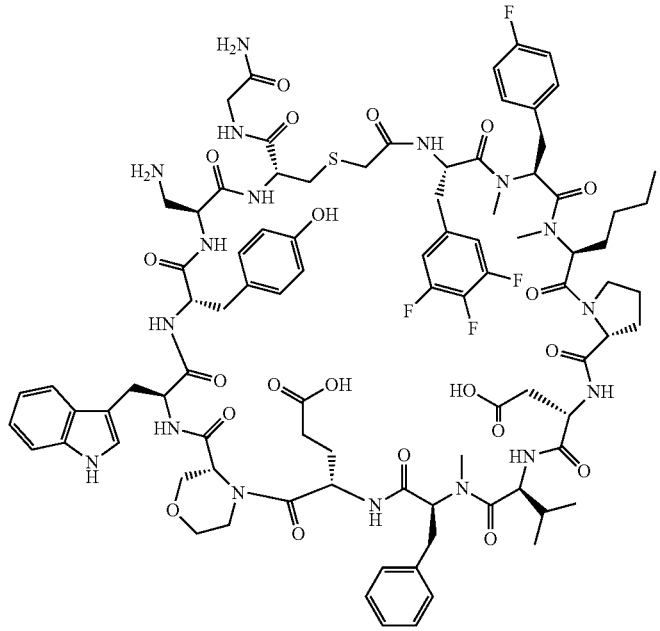

Example 10606

Example 10606 was prepared according to the method outlined in Example 10537. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 minutes, then a 5-minute hold at 100% B; Flow: 20 mL/min. Fractions containing the desired product were combined and dried via centrifugal evaporation. The yield of the product was 11.6 mg, and its estimated purity by LCMS analysis was 100%.

Analysis condition A: Retention time=1.73 min; ESI-MS (+) m/z 938.4 (M+2H).

Analysis condition B: Retention time=2.94 min; ESI-MS (+) m/z 938.5 (M+2H).

Preparation of Example 10607

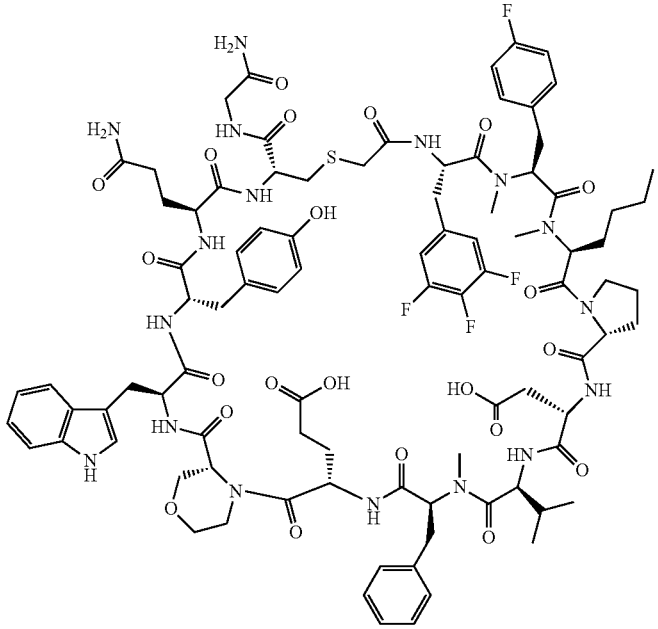

Example 10607

Example 10607 was prepared according to the method outlined in Example 10537. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 3.4 mg, and its estimated purity by LCMS analysis was 95%.

Analysis condition A: Retention time=1.62 min; ESI-MS (+) m/z 959.5 (M+2H).

Analysis condition B: Retention time=2.97 min; ESI-MS (+) m/z 959.3 (M+2H).

ESI-HRMS(+) m/z: Calculated: 958.9024 (M+2H); Found: 958.9002 (M+2H).

Preparation of Example 10608

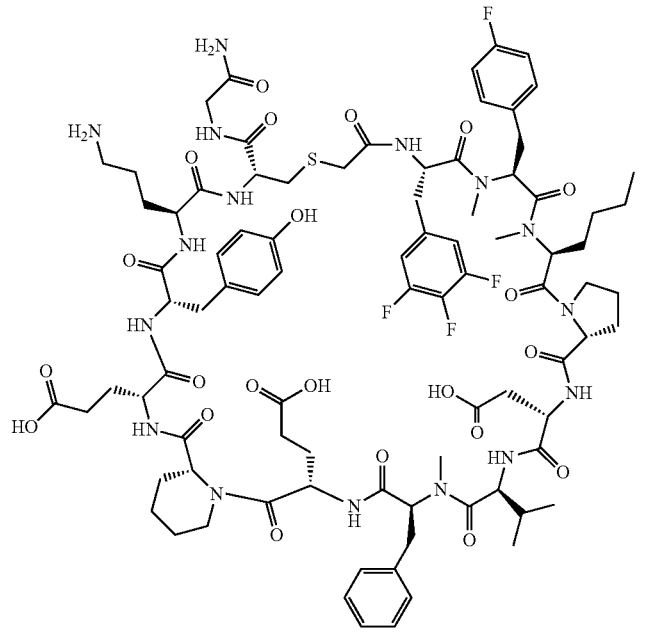

Example 10608

Example 10608 was prepared according to the method outlined in Example 10537. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 39.9 mg, and its estimated purity by LCMS analysis was 100%.

Analysis condition A: Retention time=1.57 min; ESI-MS (−) m/z 920.5 (M−2H).

Analysis condition B: Retention time=3.10 min; ESI-MS (+) m/z 922.5 (M+2H).

ESI-HRMS(+) m/z: Calculated: 922.4048 (M+2H); Found: 922.4025 (M+2H).

Preparation of Example 10609

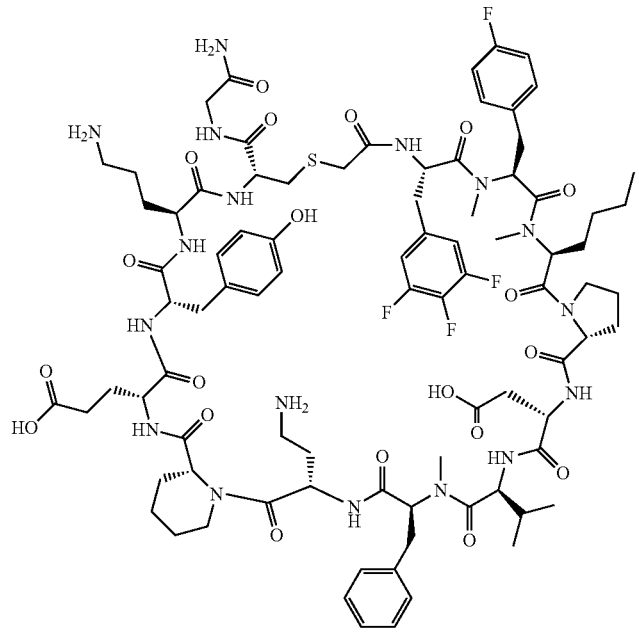

Example 10609

Example 10609 was prepared according to the method outlined in Example 10537. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min. Fractions containing the desired product were combined and dried via centrifugal evaporation. The yield of the product was 22.7 mg, and its estimated purity by LCMS analysis was 99%.

Analysis condition A: Retention time=1.60 min; ESI-MS (+) m/z 908.4 (M+2H).

Analysis condition B: Retention time=3.06 min; ESI-MS (+) m/z 908.4 (M+2H).

ESI-HRMS(+) m/z: Calculated: 907.9153 (M+2H); Found: 907.9127 (M+2H).

Preparation of Example 10610

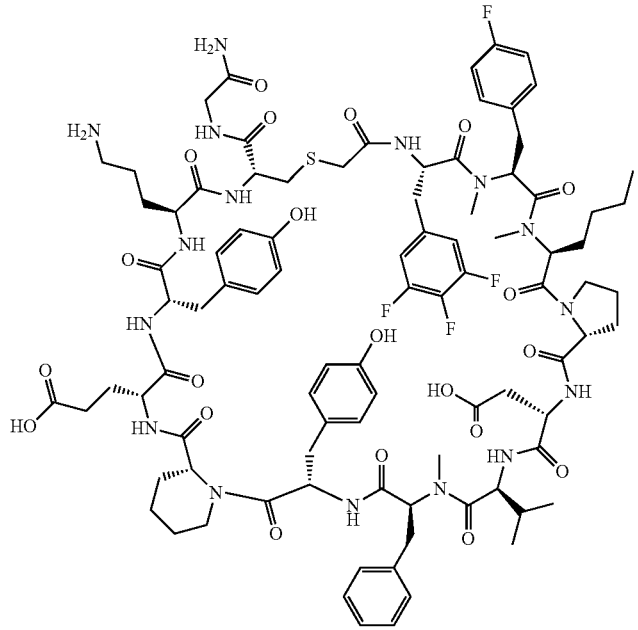

Example 10610

Example 10610 was prepared according to the method outlined in Example 10537. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 20 minutes, then a 5-minute hold at 100% B; Flow: 20 mL/min. Fractions containing the desired product were combined and dried via centrifugal evaporation. The yield of the product was 26.8 mg, and its estimated purity by LCMS analysis was 96%.

Analysis condition A: Retention time=1.63 min; ESI-MS (−) m/z 937.4 (M−2H).

Analysis condition B: Retention time=2.25 min; ESI-MS (−) m/z 936.5 (M−2H).

ESI-HRMS(+) m/z: Calculated: 939.4152 (M+2H); Found: 939.4132 (M+2H).

Preparation of Example 10611

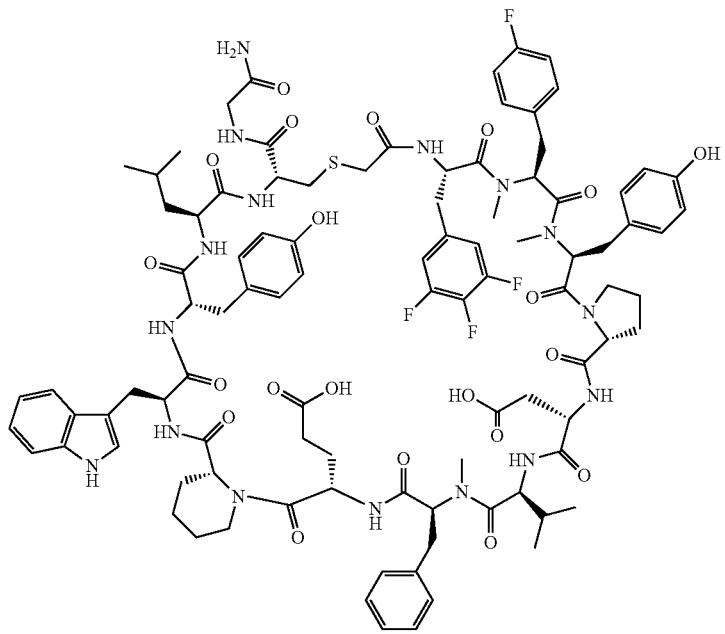

Example 10611

Example 10611 was prepared according to the method outlined in Example 10537. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 17.7 mg, and its estimated purity by LCMS analysis was 100%.

Analysis condition A: Retention time=1.40 min; ESI-MS (−) m/z 973.4 (M−2H).

Analysis condition B: Retention time=2.64 min; ESI-MS (+) m/z 975.4 (M+2H).

ESI-HRMS(+) m/z: Calculated: 975.4152 (M+2H); Found: 975.4136 (M+2H).

Preparation of Example 10612

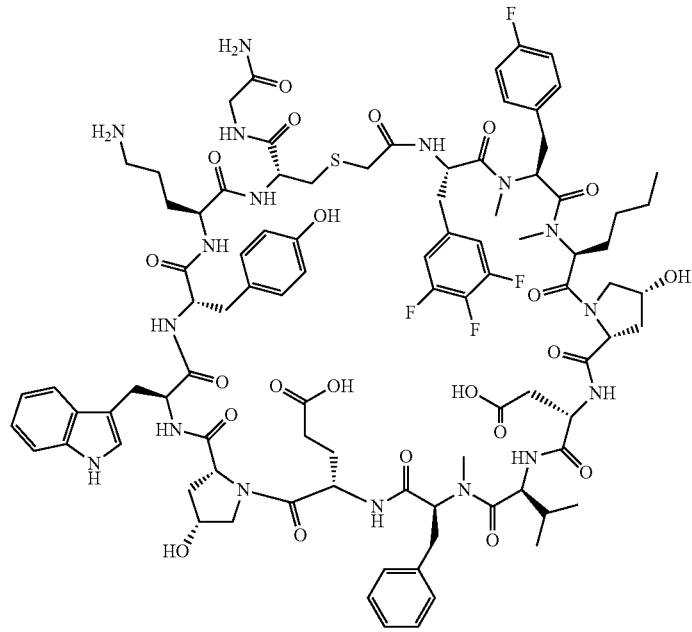

Example 10612

Example 10612 was prepared according to the method outlined in Example 10537. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 11.8 mg, and its estimated purity by LCMS analysis was 100%.

Analysis condition A: Retention time=1.58 min; ESI-MS (−) m/z 958.1 (M−2H).

Analysis condition B: Retention time=2.92 min; ESI-MS (+) m/z 960.5 (M+2H).

ESI-HRMS(+) m/z: Calculated: 959.9102 (M+2H); Found: 959.9085 (M+2H).

Preparation of Example 10613

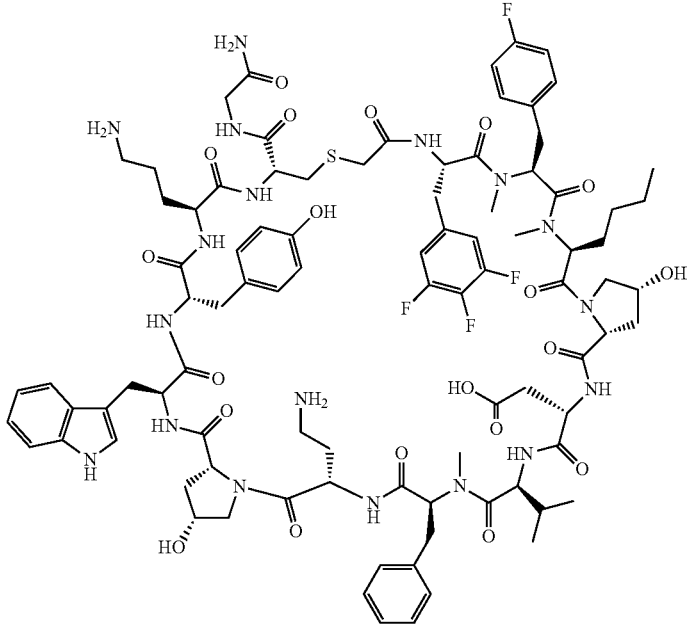

Example 10613

Example 10613 was prepared according to the method outlined in Example 10537. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 12.2 mg, and its estimated purity by LCMS analysis was 99%.

Analysis condition A: Retention time=1.76 min; ESI-MS (+) m/z 945.4 (M+2H).

Analysis condition B: Retention time=3.20 min; ESI-MS (+) m/z 945.7 (M+2H).

ESI-HRMS(+) m/z: Calculated: 945.4208 (M+2H); Found: 945.4181 (M+2H).

Preparation of Example 10614

Example 10614

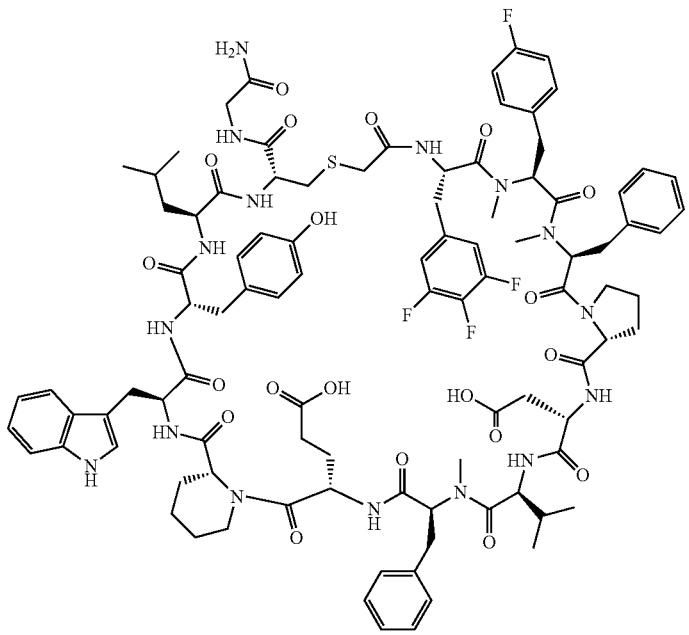

Example 10614 was prepared according to the method outlined in Example 10537. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 20 minutes, then a 5-minute hold at 100% B; Flow: 20 mL/min. Fractions containing the desired product were combined and dried via centrifugal evaporation. The yield of the product was 16.6 mg, and its estimated purity by LCMS analysis was 99%.

Analysis condition A: Retention time=1.59 min; ESI-MS (−) m/z 965.6 (M−2H).

Analysis condition B: Retention time=2.90 min; ESI-MS (+) m/z 967.4 (M+2H).

ESI-HRMS(+) m/z: Calculated: 967.4177 (M+2H); Found: 967.4156 (M+2H).

Preparation of Example 10615

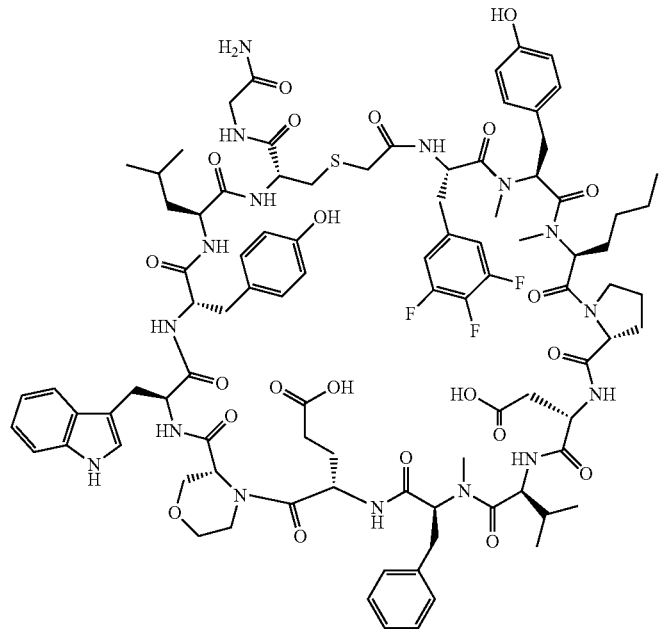

Example 10615

Example 10615 was prepared according to the method outlined in Example 10537. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 21.1 mg, and its estimated purity by LCMS analysis was 99%.

Analysis condition A: Retention time=1.72 min; ESI-MS (−) m/z 948.6 (M−2H).

Analysis condition B: Retention time=2.88 min; ESI-MS (−) m/z 948.0 (M−2H).

ESI-HRMS(+) m/z: Calculated: 950.4173 (M+2H); Found: 950.4165 (M+2H).

Preparation of Example 10616

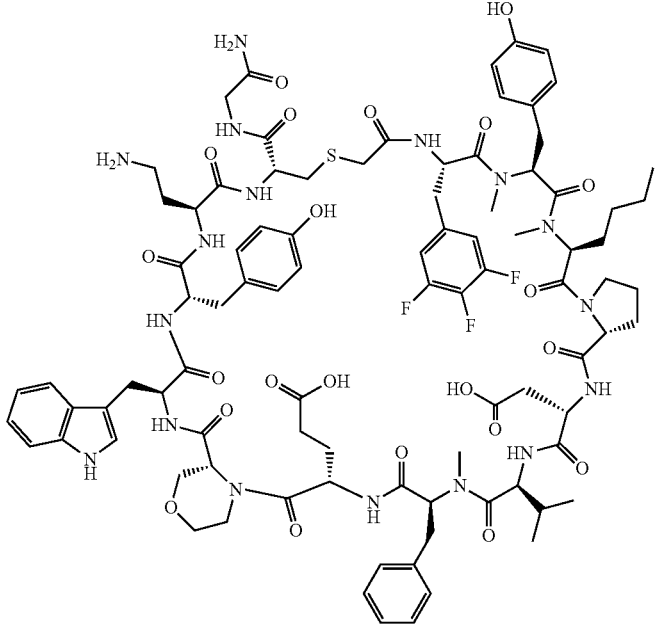

Example 10616

Example 10616 was prepared according to the method outlined in Example 10537. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 29.3 mg, and its estimated purity by LCMS analysis was 96%.

Analysis condition A: Retention time=1.74 min; ESI-MS (−) m/z 942.0 (M−2H).

Analysis condition B: Retention time=2.99 min; ESI-MS (−) m/z 942.0 (M−2H).

ESI-HRMS(+) m/z: Calculated: 943.9071 (M+2H); Found: 943.9057 (M+2H).

Preparation of Example 10617

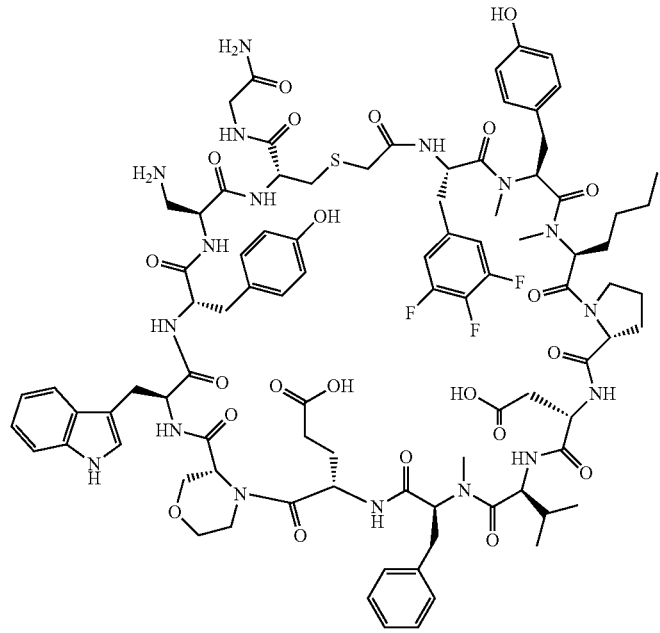

Example 10617

Example 10617 was prepared according to the method outlined in Example 10537. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 18.6 mg, and its estimated purity by LCMS analysis was 100%.

Analysis condition B: Retention time=2.78 min; ESI-MS (−) m/z 934.4 (M−2H).

Preparation of Example 10618

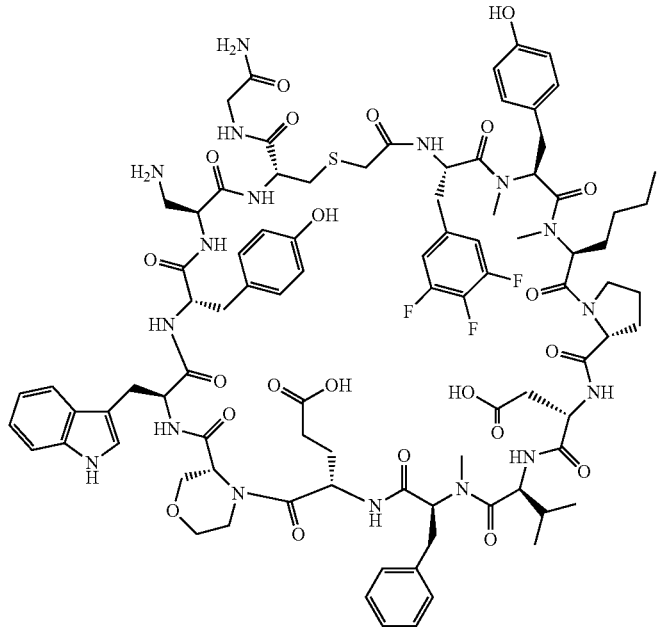

Example 10618

Example 10618 was prepared according to the method outlined in Example 10537. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 37.3 mg, and its estimated purity by LCMS analysis was 97%.

Analysis condition A: Retention time=1.73 min; ESI-MS (+) m/z 951.2 (M+2H).

Analysis condition B: Retention time=2.98 min; ESI-MS (+) m/z 950.4 (M+2H).

Preparation of Example 10619

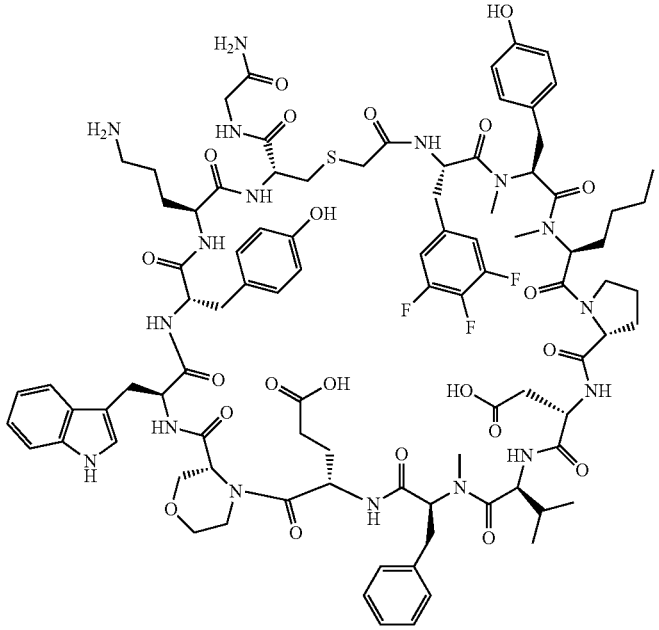

Example 10619

Example 10619 was prepared according to the method outlined in Example 10537. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 30.5 mg, and its estimated purity by LCMS analysis was 100%.

Analysis condition A: Retention time=1.65 min; ESI-MS (−) m/z 955.5 (M−2H).

Analysis condition B: Retention time=2.84 min; ESI-MS (+) m/z 957.6 (M+2H).

ESI-HRMS(+) m/z: Calculated: 957.9046 (M+2H); Found: 957.9030 (M+2H).

Preparation of Example 10620

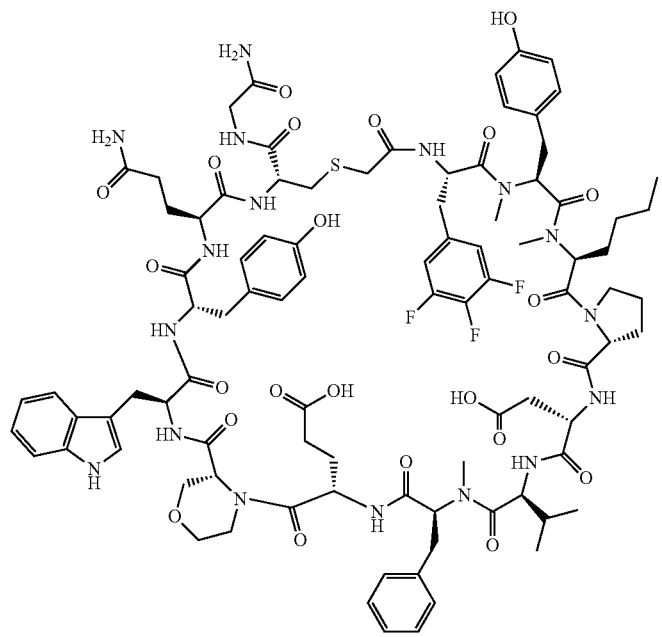

Example 10620

Example 10620 was prepared according to the method outlined in Example 10537. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 23.6 mg, and its estimated purity by LCMS analysis was 99%.

Analysis condition A: Retention time=1.68 min; ESI-MS (−) m/z 656.6 (M−2H).

Analysis condition B: Retention time=2.73 min; ESI-MS (−) m/z 955.9 (M−2H).

ESI-HRMS(+) m/z: Calculated: 958.4148 (M+2H); Found: 958.4128 (M+2H).

Preparation of Example 10621

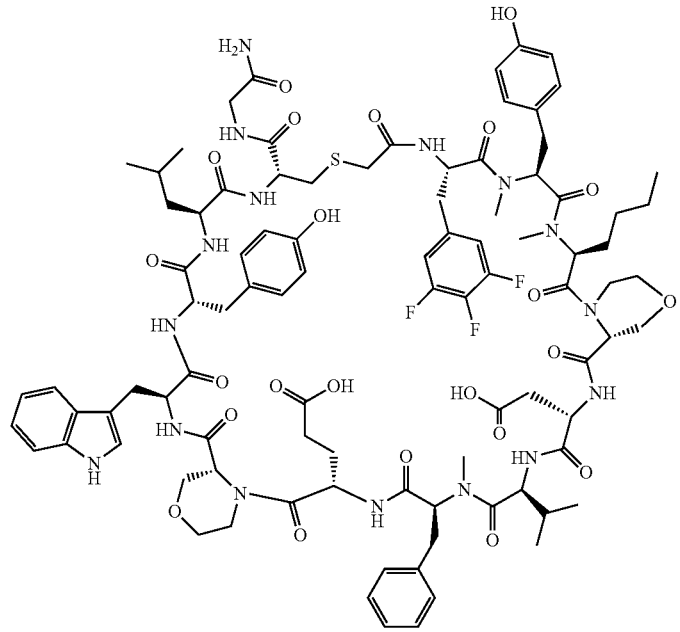

Example 10621

Example 10621 was prepared according to the method outlined in Example 10537. The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 27.5 mg, and its estimated purity by LCMS analysis was 100%.

Analysis condition A: Retention time=1.62 min; ESI-MS (−) m/z 957.6 (M−2H).

Analysis condition B: Retention time=2.82 min; ESI-MS (+) m/z 958.7 (M+2H).

ESI-HRMS(+) m/z: Calculated: 958.9124 (M+2H); Found: 958.9115 (M+2H).

Preparation of Example 10622

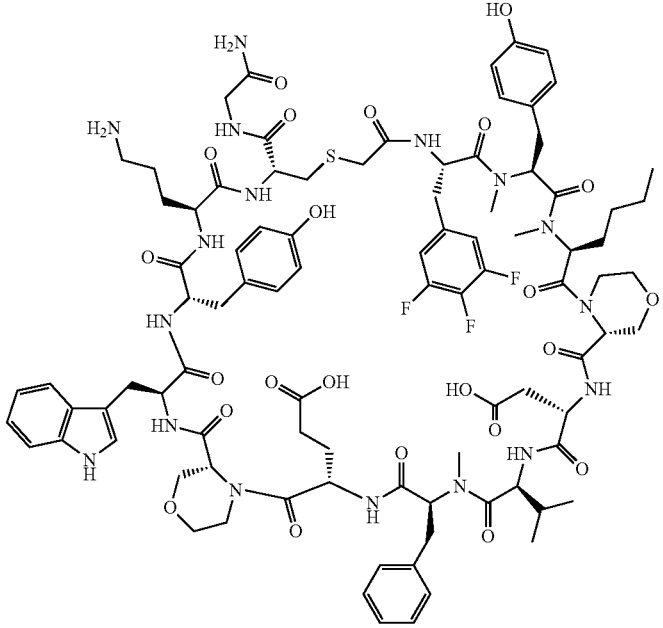

Example 10622

Example 10622 was prepared according to the method outlined in Example 10537. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 35.6 mg, and its estimated purity by LCMS analysis was 100%.

Analysis condition A: Retention time=1.92 min; ESI-MS (+) m/z 936.5 (M+2H).

Analysis condition B: Retention time=3.11 min; ESI-MS (−) m/z 933.5 (M−2H).

Preparation of Example 10623

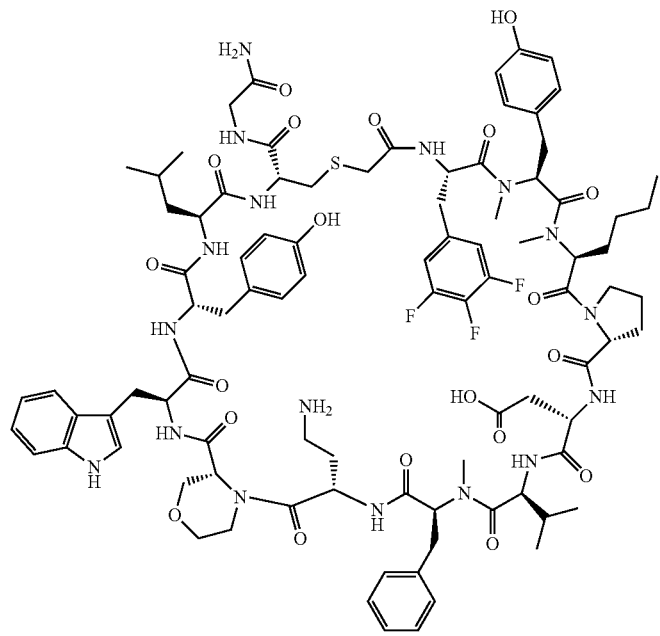

Example 10623

Example 10623 was prepared according to the method outlined in Example 10537. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 39.9 mg, and its estimated purity by LCMS analysis was 96%.

Analysis condition A: Retention time=1.90 min; ESI-MS (+) m/z 930.0 (M+2H).

Analysis condition B: Retention time=3.11 min; ESI-MS (−) m/z 927.0 (M−2H).

ESI-HRMS(+) m/z: Calculated: 929.4177 (M+2H); Found: 929.4155 (M+2H).

Preparation of Example 10624

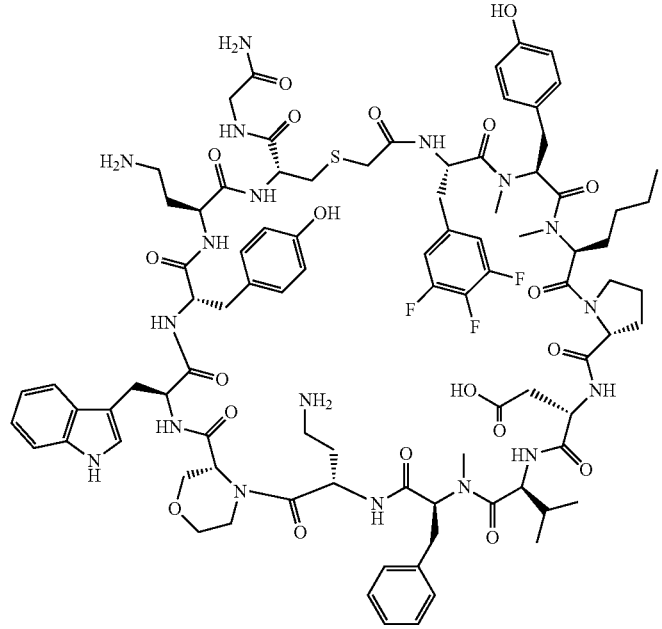

Example 10624

Example 10624 was prepared according to the method outlined in Example 10537. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 27.3 mg, and its estimated purity by LCMS analysis was 100%.

Analysis condition B: Retention time=2.98 min; ESI-MS (+) m/z 943.4 (M+2H).

ESI-HRMS(+) m/z: Calculated: 943.9071 (M+2H) Found: 943.9056 (M+2H).

Preparation of Example 10625

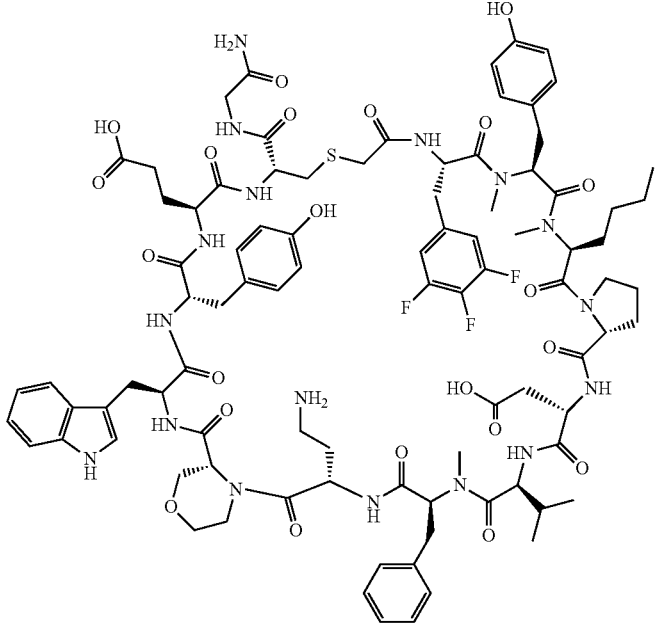

Example 10625

Example 10625 was prepared according to the method outlined in Example 10537. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 30.6 mg, and its estimated purity by LCMS analysis was 97%.

Analysis condition A: Retention time=1.89 min; ESI-MS (+) m/z 936.5 (M+2H).

Analysis condition B: Retention time=3.11 min; ESI-MS (+) m/z 935.9 (M+2H).

ESI-HRMS(+) m/z: Calculated: 936.4255 (M+2H); Found: 936.4238 (M+2H).

Preparation of Example 10626

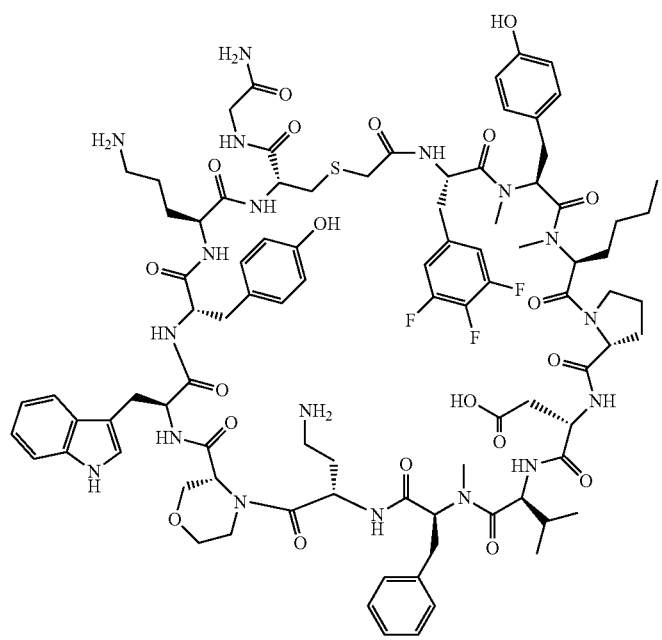

Example 10626

Example 10626 was prepared according to the method outlined in Example 10537. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the desired product were combined and dried via centrifugal evaporation. The yield of the product was 4.8 mg, and its estimated purity by LCMS analysis was 100%.

Analysis condition A: Retention time=1.82 min; ESI-MS (−) m/z 942.5 (M−2H).

Analysis condition B: Retention time=3.08 min; ESI-MS (+) m/z 943.6 (M+2H).

Preparation of Example 10627

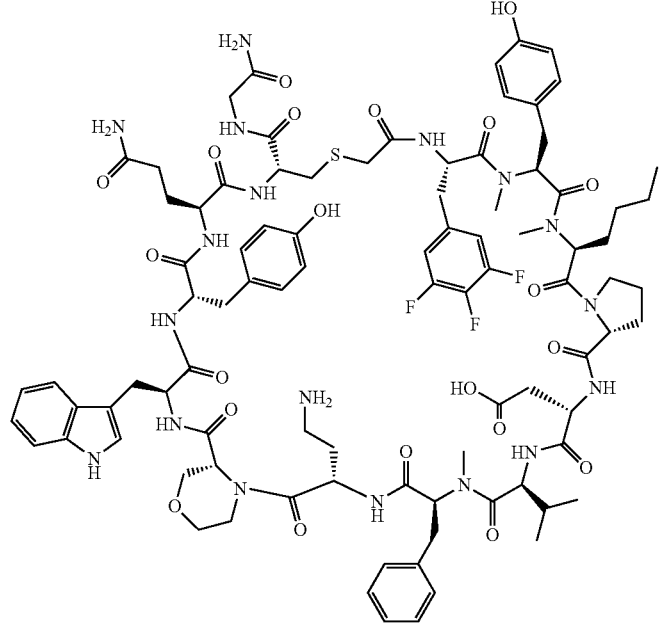

Example 10627

Example 10627 was prepared according to the method outlined in Example 10537. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 25.9 mg, and its estimated purity by LCMS analysis was 97%.

Analysis condition A: Retention time=1.79 min; ESI-MS (+) m/z 944.9 (M+2H).

Analysis condition B: Retention time=3.04 min; ESI-MS (+) m/z 944.1 (M+2H).

ESI-HRMS(+) m/z: Calculated: 944.4230 (M+2H); Found: 944.4208 (M+2H).

Preparation of Example 10628

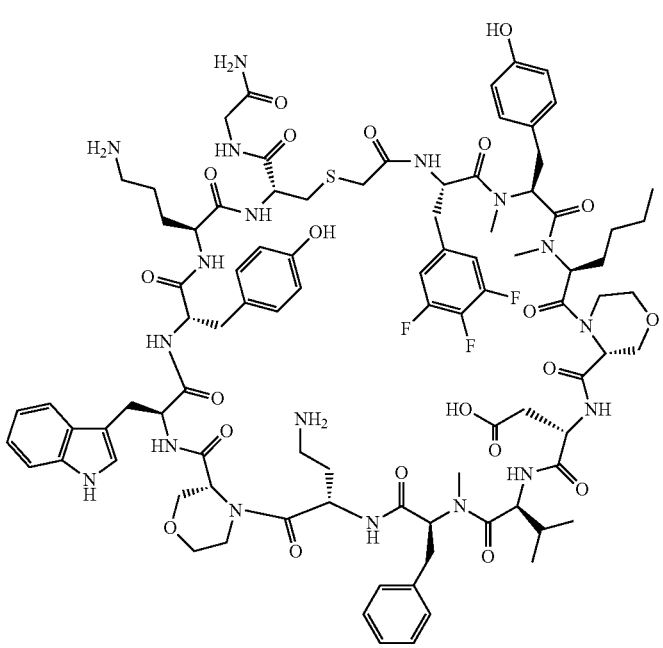

Example 10628

Example 10628 was prepared according to the method outlined in Example 10537. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 32.3 mg, and its estimated purity by LCMS analysis was 100%.

Analysis condition A: Retention time=1.70 min; ESI-MS (−) m/z 950.8 (M−2H).

Analysis condition B: Retention time=2.91 min; ESI-MS (+) m/z 951.6 (M+2H).

ESI-HRMS(+) m/z: Calculated: 951.9046 (M+2H); Found: 951.9030 (M+2H).

Preparation of Example 10629

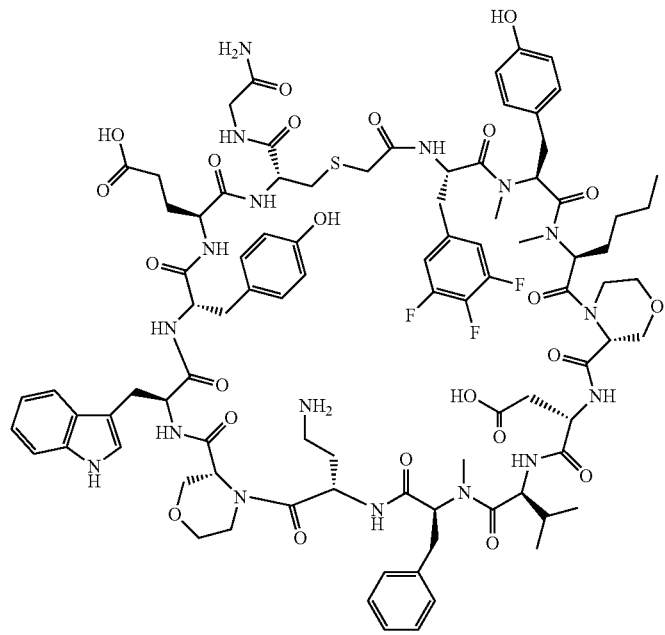

Example 10629

Example 10629 was prepared according to the method outlined in Example 10537. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 14.0 mg, and its estimated purity by LCMS analysis was 100%.

Analysis condition B: Retention time=2.85 min; ESI-MS (+) m/z 950.0 (M+2H).

Analysis condition C: Retention time=1.86 min; ESI-MS (+) m/z 950.7 (M+2H).

ESI-HRMS(+) m/z: Calculated: 950.4173 (M+2H); Found: 950.4166 (M+2H).

Preparation of Example 10630

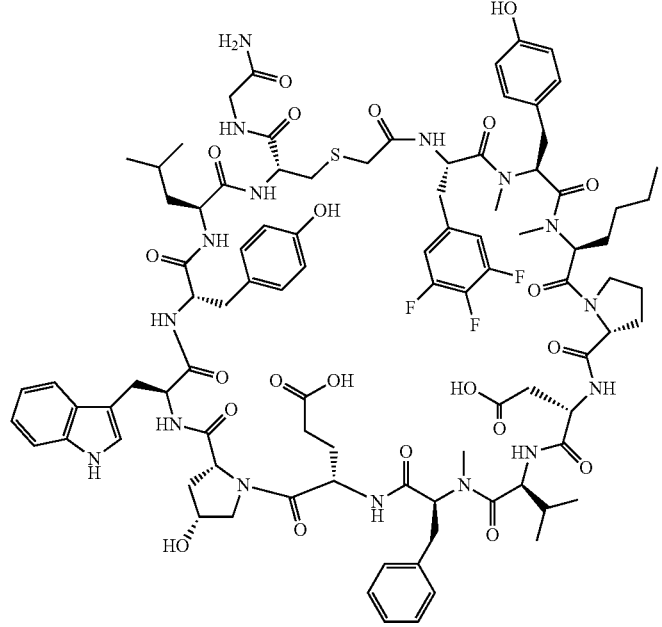

Example 10630

Example 10630 was prepared according to the method outlined in Example 10537. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 36.4 mg, and its estimated purity by LCMS analysis was 100%.

Analysis condition A: Retention time=1.64 min; ESI-MS (−) m/z 949.0 (M−2H).

Analysis condition B: Retention time=2.79 min; ESI-MS (+) m/z 950.6 (M+2H).

ESI-HRMS(+) m/z: Calculated: 950.8968 (M+2H); Found: 950.8961 (M+2H).

Preparation of Example 10631

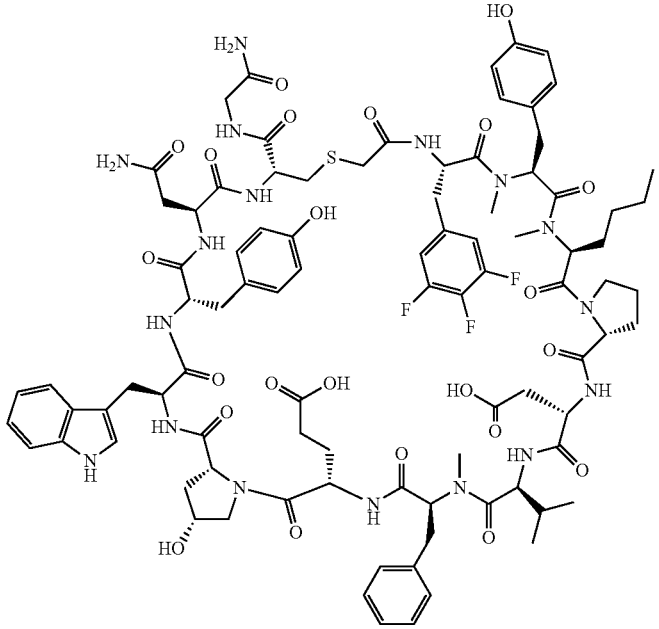

Example 10631

Example 10631 was prepared according to the method outlined in Example 10537. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 23.2 mg, and its estimated purity by LCMS analysis was 100%.

Analysis condition A: Retention time=1.57 min; ESI-MS (−) m/z 955.9 (M−2H).

Analysis condition B: Retention time=2.79 min; ESI-MS (−) m/z 956.1 (M−2H).

ESI-HRMS(+) m/z: Calculated: 957.9046 (M+2H); Found: 957.9032 (M+2H).

Preparation of Example 10632

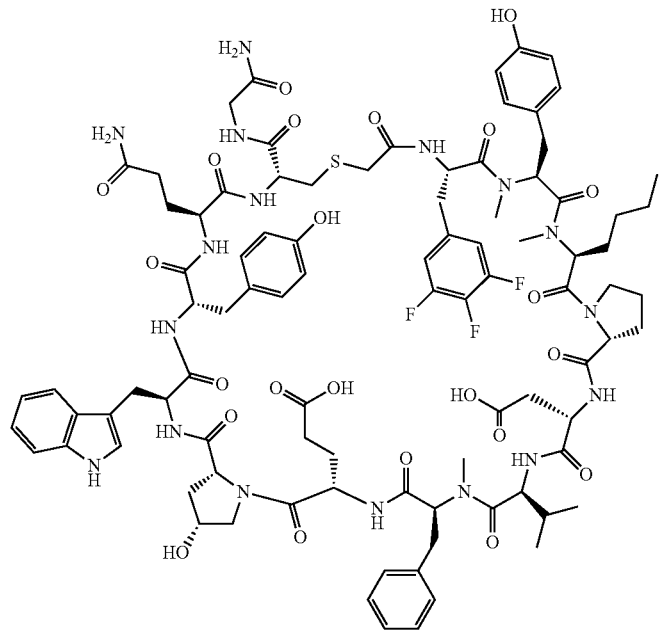

Example 10632

Example 10632 was prepared according to the method outlined in Example 10537. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 20.8 mg, and its estimated purity by LCMS analysis was 100%.

Analysis condition A: Retention time=1.64 min; ESI-MS (−) m/z 949.2 (M−2H).

Analysis condition B: Retention time=2.89 min; ESI-MS (−) m/z 948.4 (M−2H).

ESI-HRMS(+) m/z: Calculated: 950.9157 (M+2H); Found: 950.9138 (M+2H).

Preparation of Example 10633

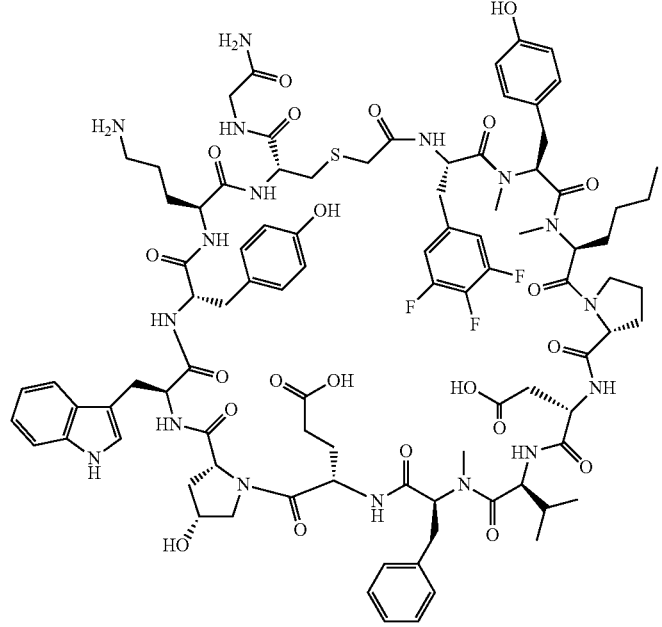

Example 10633

Example 10633 was prepared according to the method outlined in Example 10537. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 27.8 mg, and its estimated purity by LCMS analysis was 100%.

Analysis condition A: Retention time=1.56 min; ESI-MS (−) m/z 957.4 (M−2H).

Analysis condition B: Retention time=2.67 min; ESI-MS (−) m/z 956.0 (M−2H).

ESI-HRMS(+) m/z: Calculated: 958.3966 (M+2H); Found: 958.3953 (M+2H).

Preparation of Example 10634

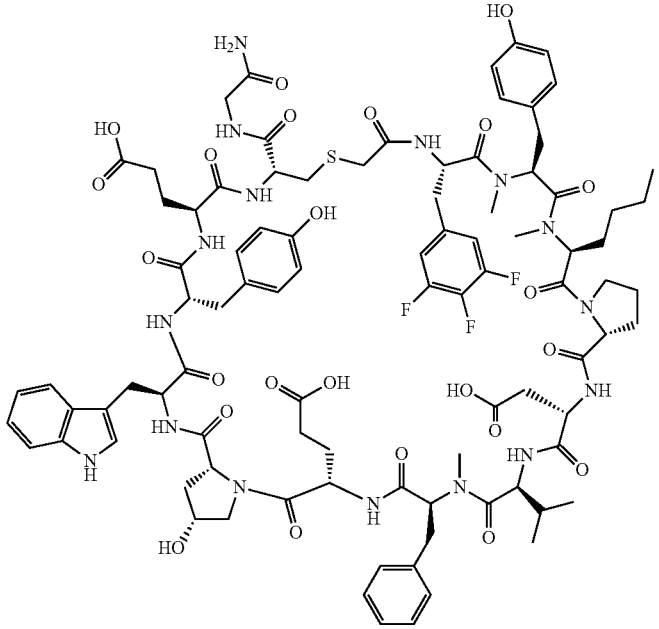

Example 10634

Example 10634 was prepared according to the method outlined in Example 10537. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 32.1 mg, and its estimated purity by LCMS analysis was 100%.

Analysis condition A: Retention time=1.61 min; ESI-MS (−) m/z 956.7 (M−2H).

Analysis condition B: Retention time=2.74 min; ESI-MS (+) m/z 958.2 (M+2H).

ESI-HRMS(+) m/z: Calculated: 958.4148 (M+2H); Found: 958.4144 (M+2H).

Preparation of Example 10635

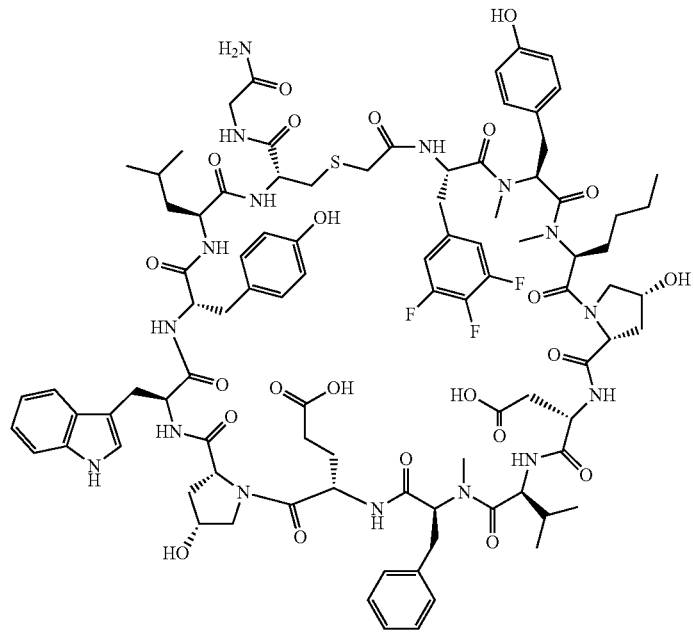

Example 10635

Example 10635 was prepared according to the method outlined in Example 10537. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 25.3 mg, and its estimated purity by LCMS analysis was 99%.

Analysis condition A: Retention time=1.53 min; ESI-MS (−) m/z 956.6 (M−2H).

Analysis condition B: Retention time=2.69 min; ESI-MS (+) m/z 959.5 (M+2H).

ESI-HRMS(+) m/z: Calculated: 958.8942 (M+2H); Found: 958.8936 (M+2H).

Preparation of Example 10636

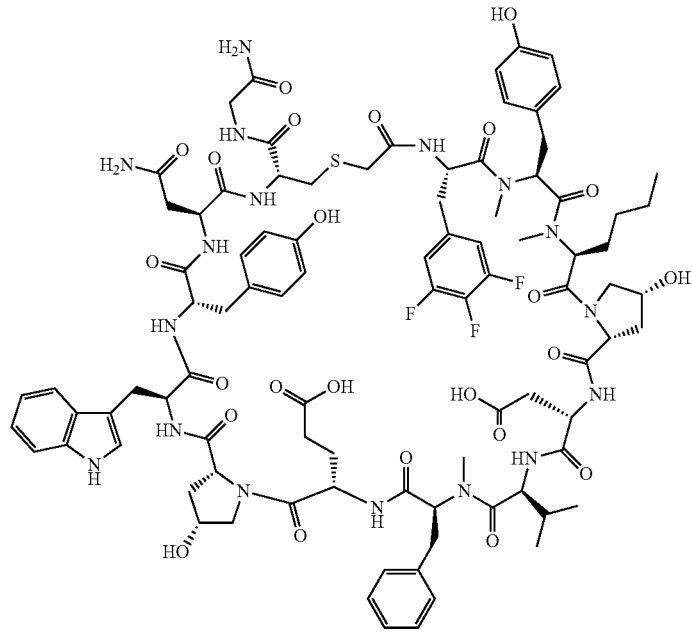

Example 10636

Example 10636 was prepared according to the method outlined in Example 10537. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 22.0 mg, and its estimated purity by LCMS analysis was 96%.

Analysis condition A: Retention time=1.51 min; ESI-MS (−) m/z 964.5 (M−2H).

Analysis condition B: Retention time=2.69 min; ESI-MS (+) m/z 965.6 (M+2H).

ESI-HRMS(+) m/z: Calculated: 965.9020 (M+2H); Found: 965.9010 (M+2H).

Preparation of Example 10637

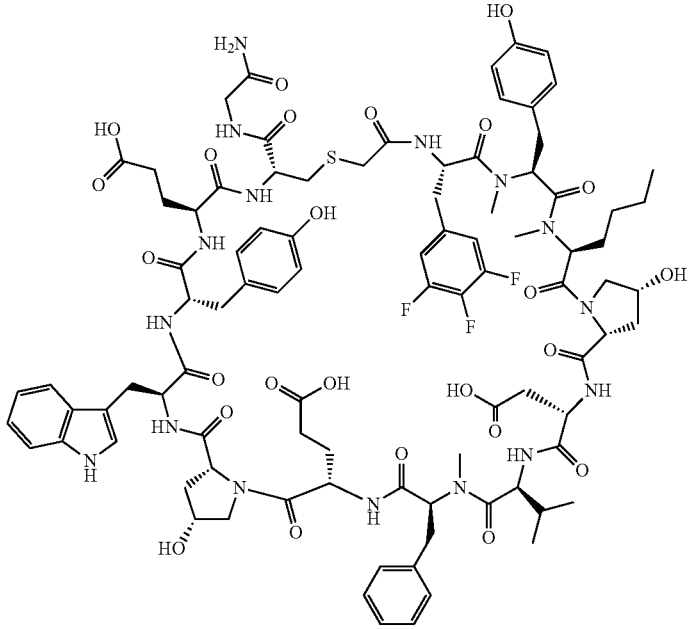

Example 10637

Example 10637 was prepared according to the method outlined in Example 10537. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 35.4 mg, and its estimated purity by LCMS analysis was 98%.

Analysis condition A: Retention time=1.51 min; ESI-MS (+) m/z 966.5 (M+2H).

Analysis condition B: Retention time=2.57 min; ESI-MS (+) m/z 966.6 (M+2H).

ESI-HRMS(+) m/z: Calculated: 966.3941 (M+2H); Found: 966.3934 (M+2H).

Preparation of Example 10638

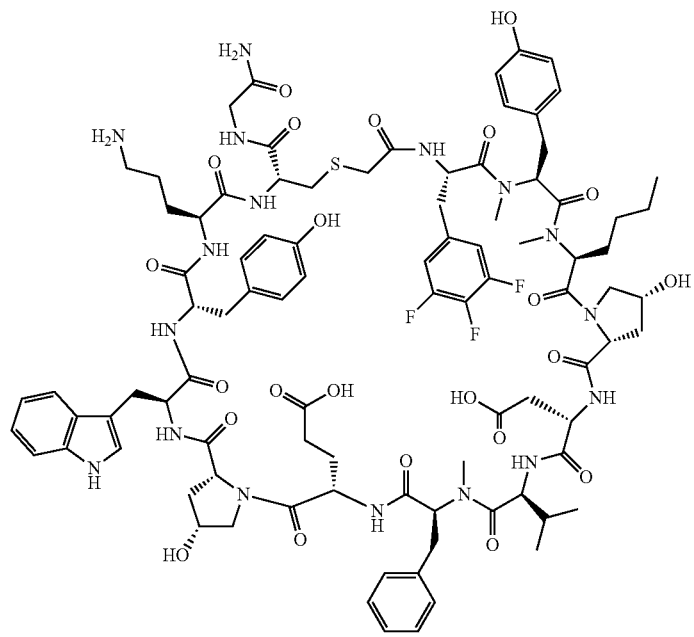

Example 10638

Example 10638 was prepared according to the method outlined in Example 10537. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 29.6 mg, and its estimated purity by LCMS analysis was 99%.

Analysis condition A: Retention time=1.63 min; ESI-MS (−) m/z 956.9 (M−2H).

Analysis condition B: Retention time=2.81 min; ESI-MS (−) m/z 956.5 (M−2H).

ESI-HRMS(+) m/z: Calculated: 958.9124 (M+2H); Found: 958.9121 (M+2H).

Analysis LCMS Condition XX:

Column: Waters Xbridge C18, 2.1×50 mm; Mobile Phase A: 5:95 acetonitrile:water with 10 mM ammonium acetate; Mobile Phase B: 95:5 acetonitrile:water with 10 mM ammonium acetate; Temperature: 35° C.; Gradient: 0-100% B over 8 minutes, then a 1-minute hold at 100% B; Flow: 0.8 mL/min; Detection: UV at 220 nm.

Preparation of Example 11001

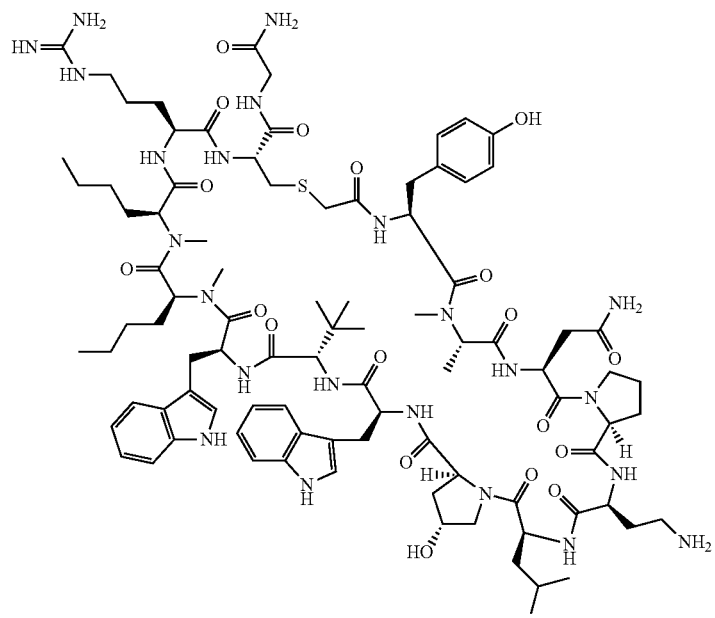

Molecular Weight: 1899.26

Example 11001 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D". (S)-2-((((9H-fluoren-9-yl)methoxy)carbonyl)amino)-3,3-dimethylbutanoic acid was used in the "Custom amino acids-coupling procedure".

The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 25 minutes, then a 5-minute hold at 100% B; Flow: 30 mL/min. Fractions containing the desired product were combined and dried via centrifugal evaporation. The yield of the product was 10.2 mg, and its estimated purity by LCMS analysis was 98.2%.

Analysis LCMS Condition XX: Retention time=4.66 min; ESI-MS(+) m/z 949.52 (M+2H).

Preparation of Example 11002

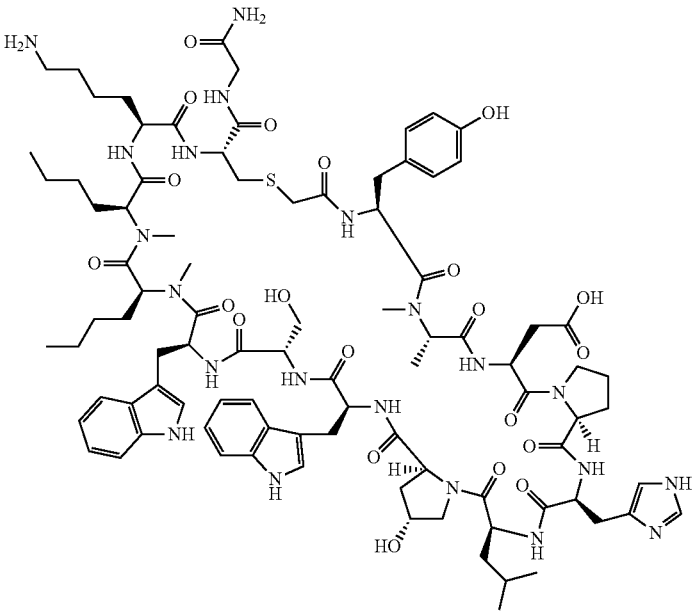

Molecular Weight: 1883.18

Example 11002 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D".

The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 25 minutes, then a 5-minute hold at 100% B; Flow: 30 mL/min. Fractions containing the desired product were combined and dried via centrifugal evaporation. The yield of the product was 38 mg, and its estimated purity by LCMS analysis was 93.6%.

Analysis LCMS Condition XX: Retention time=3.64 min; ESI-MS(+) m/z 941.70 (M+2H).

ESI-HRMS(+) m/z: Calculated: 941.9691 (M+2H) Found: 941.9683 (M+2H).

Preparation of Example 11003

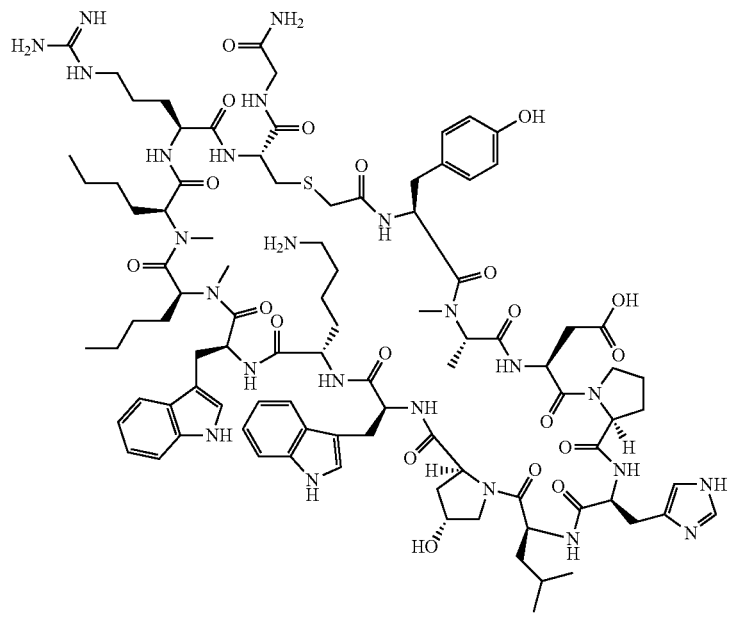

Molecular Weight: 1952.28

Example 11003 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D".

The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 25 minutes, then a 5-minute hold at 100% B; Flow: 30 mL/min. Fractions containing the desired product were combined and dried via centrifugal evaporation. The yield of the product was 50 mg, and its estimated purity by LCMS analysis was 95.6%.

Analysis LCMS Condition XX: Retention time=3.55 min; ESI-MS(+) m/z 976.30 (M+2H).

ESI-HRMS(+) m/z: Calculated: 976.5036 (M+2H) Found: 976.5027 (M+2H).

Preparation of Example 11004

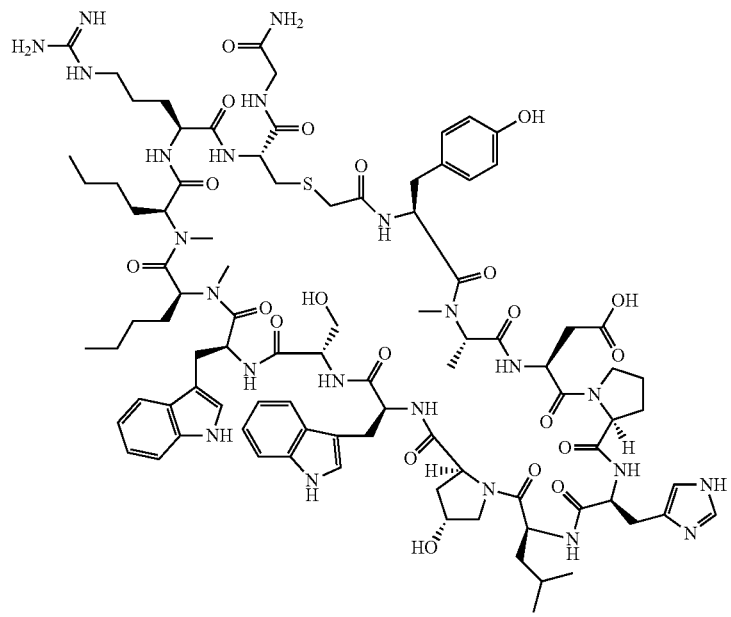

Molecular Weight: 1884.12

Example 11004 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D".

The crude material was purified via preparative LC/MS with the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 25 minutes, then a 5-minute hold at 100% B; Flow: 30 mL/min. Fractions containing the desired product were combined and dried via centrifugal evaporation. The yield of the product was 70 mg, and its estimated purity by LCMS analysis was 96.5%.

Analysis LCMS Condition XX: Retention time=3.78 min; ESI-MS(+) m/z 942.30 (M+2H).

ESI-HRMS(+) m/z: Calculated: 942.4541 (M+2H) Found: 942.4525 (M+2H).

Methods for Testing the Ability of Macrocyclic Peptides to Compete for the Binding of PD-1 to PD-L1 Using Homogenous Time-Resolved Fluorescence (HTRF) Binding Assays The ability of the macrocyclic peptides of the present disclosure to bind to PD-L1 was investigated using a PD-1/PD-L1 Homogenous Time-Resolved Fluorescence (HTRF) binding assay.

Methods

Homogenous Time-Resolved Fluorescence (HTRF) Assays of Binding of Soluble PD-1 to Soluble PD-L1. Soluble PD-1 and soluble PD-L1 refers to proteins with carboxyl-end truncations that remove the transmembrane-spanning regions and are fused to heterologous sequences, specifically the Fc portion of the human immunoglobuling G sequence (Ig) or the hexahistidine epitope tag (His). All binding studies were performed in an HTRF assay buffer consisting of dPBS supplemented with 0.1% (w/v) bovine serum albumin and 0.05% (v/v) Tween-20. For the PD-1-Ig/PD-L1-His binding assay, inhibitors were pre-incubated with PD-L1-His (10 nM final) for 15 m in 4 μl of assay buffer, followed by addition of PD-1-Ig (20 nM final) in 1 μl of assay buffer and further incubation for 15 m. PD-L1 fusion proteins from either human, cynomolgus macaques, or mouse were used. HTRF detection was achieved using europium crypate-labeled anti-Ig monoclonal antibody (1 nM final) and allophycocyanin (APC) labeled anti-His monoclonal antibody (20 nM final). Antibodies were diluted in HTRF detection buffer and 5 μl was dispensed on top of binding reaction. The reaction was allowed to equilibrate for 30 minutes and signal (665 nm/620 nm ratio) was obtained using an EnVision fluorometer. Additional binding assays were established between PD-1-Ig/PD-L2-His (20 and 5 nM, respectively), CD80-His/PD-L1-Ig (100 and 10 nM, respectively) and CD80-His/CTLA4-Ig (10 and 5 nM, respectively). Competition studies between biotinylated Compound No. 71 and human PD-L1-His were performed as follows. Macrocyclic peptide inhibitors were pre-incubated with PD-L1-His (10 nM final) for 60 minutes in 4 μl of assay buffer followed by addition of biotinylated Compound No. 71 (0.5 nM final) in 1 μl of assay buffer. Binding was allowed to equilibrate for 30 minutes followed by addition of europium crypated labeled Streptavidin (2.5 pM final) and APC-labeled anti-His (20 nM final) in 5 μl of HTRF buffer. The reaction was allowed to equilibrate for 30 m and signal (665 nm/620 nm ratio) was obtained using an EnVision fluorometer.

Recombinant Proteins. Carboxyl-truncated human PD-1 (amino acids 25-167) with a C-terminal human Ig epitope tag [hPD-1 (25-167)-3S-IG] and human PD-L1 (amino acids 18-239) with a C-terminal His epitope tag [hPD-L1(19-239)-tobacco vein mottling virus protease cleavage site (TVMV)-His] were expressed in HEK293T cells and purified sequentially by rProteinA affinity chromatography and size exclusion chromatography. Human PD-L2-His (Sino Biologicals), CD80-His (Sino Biologicals), CTLA4-Ig (RnD Systems) were all obtained through commercial sources.

```
Sequence of Recombinant Human PD-1-Ig
hPD1(25-167)-3S-IG
                                                   (SEQ ID NO: 1)
    1 LDSPDRPWNP PTFSPALLVV TEGDNATFTC SPSNTSESFV LNWYRMSPSN

51 QTDKLAAFPE DRSQPGQDCR FRVTQLPNGR DFHMSVVRAR RNDSGTYLCG

101 AISLAPKAQI KESLRAELRV TERRAEVPTA HPSPSPRPAG QFQGSPGGGG

151 GREPKSSDKT HTSPPSPAPE LLGGSSVFLF PPKPKDTLMI SRTPEVTCVV

201 VDVSHEDPEV KFNWYVDGVE VHNAKTKPRE EQYNSTYRVV SVLTVLHQDW

251 LNGKEYKCKV SNKALPAPIE KTISKAKGQP REPQVYTLPP SRDELTKNQV

301 SLTCLVKGFY PSDIAVEWES NGQPENNYKT TPPVLDSDGS FFLYSKLTVD

351 KSRWQQGNVF SCSVMHEALH NHYTQKSLSL SPGK

Sequence of Recombinant Human PD-L1-TVMV-His (PD-L1-His)
hPDL1(19-239)-TVMV-His
                                                   (SEQ ID NO: 2)
    1 PTVTVPKDLY VVEYGSNMTI ECKFPVEKQL DLAALIVYWE MEDKNIIQFV

51 HGEEDLKVQH SSYRQRARLL KDQLSLGNAA LQITDVKLQD AGVYRCMISY

101 GGADYKRITV KVNAPYNKIN QRILVVDPVT SEHELTCQAE GYPKAEVIWT

151 SSDHQVLSGK TTTTNSKREE KLFNVTSTLR INTTTNEIFY CTFRRLDPEE

201 NHTAELVIPE LPLAHPPNER TGSSETVRFQ GHHHHHH
```

The results are shown in Table 1. As shown, the macrocyclic peptides of the present disclosure demonstrated potent inhibition of PD-1-Ig binding activity to PD-L1-TVMV-His (PD-L1-His). A=0.001-0.0099 µM; B=0.01-0.0999 µM; C=0.10-0.99 µM; D=1-10 µM.

TABLE 1

| Example Number | HTRF Human PD-L1/PD-1 Binding Assay IC50 (µM) | Range |
| --- | --- | --- |
| 1240 |  | D |
| 1241 | 1.0000 | D |
| 1244 |  | C |
| 1245 |  | B |
| 1246 |  | A |
| 1247 |  | B |
| 1248 |  | B |
| 1250 |  | A |
| 1251 |  | A |
| 1252 |  | A |
| 1255 | 0.0026 | A |
| 1256 |  | A |
| 1257 |  | A |
| 1258 |  | A |
| 1259 |  | A |
| 1260 |  | A |
| 1261 |  | A |
| 1262 |  | A |
| 1272 |  | A |
| 1273 |  | A |
| 1275 |  | A |
| 1276 | 0.4685 | C |

TABLE 1-continued

| Example Number | HTRF Human PD-L1/PD-1 Binding Assay IC50 (µM) | Range |
| --- | --- | --- |
| 1277 |  | B |
| 1278 |  | B |
| 1279 |  | B |

TABLE 1-continued

| Example Number | HTRF Human PD-L1/PD-1 Binding Assay IC50 (µM) | Range |
| --- | --- | --- |
| 1280 |  | B |
| 1281 |  | A |
| 1283 |  | B |
| 1285 |  | A |
| 1289 |  | A |
| 1290 |  | B |
| 1291 |  | A |
| 1292 |  | B |
| 1293 |  | B |
| 1294 |  | B |
| 1295 |  | B |
| 1296 |  | A |
| 1297 |  | A |
| 1298 |  | A |
| 1299 |  | A |
| 1300 |  | A |
| 1301 |  | B |
| 1302 |  | A |
| 1303 |  | B |
| 1304 |  | B |
| 1305 |  | A |
| 1306 |  | B |
| 1309 |  | B |
| 1500 |  | A |
| 1501 |  | B |
| 1502 |  | B |
| 1503 |  | A |
| 1504 |  | B |
| 1505 |  | A |
| 1506 |  | A |

TABLE 1-continued

| Example Number | HTRF Human PD-L1/PD-1 Binding Assay IC50 (μM) | Range |
|---|---|---|
| 1507 | | A |
| 1508 | | A |
| 1509 | | B |
| 1510 | | A |
| 1511 | | A |
| 1512 | | B |
| 1513 | 0.0053 | A |
| 1514 | | A |
| 1515 | | A |
| 1519 | | A |
| 1520 | | A |
| 1521 | | A |
| 1522 | | B |
| 1523 | | A |
| 1525 | | A |
| 1526 | | A |
| 1528 | | B |
| 1529 | | A |
| 1530 | | B |
| 1531 | | B |
| 1532 | | A |
| 1533 | | A |
| 1534 | 1.0000 | D |
| 1535 | | B |
| 1536 | | B |
| 1537 | | B |
| 1538 | | B |
| 1541 | 0.4514 | C |
| 1542 | | B |
| 1828 | | C |
| 3210 | 1.0000 | D |
| 3211 | | B |
| 3212 | | B |
| 3213 | | B |
| 3216 | | B |
| 3217 | | B |
| 3218 | | A |
| 3219 | | B |
| 3220 | | B |
| 3221 | | B |
| 3222 | 0.0045 | A |
| 3223 | | A |
| 3224 | | B |
| 3225 | | A |
| 3226 | 1.8590 | D |
| 3227 | | A |
| 3228 | | B |
| 3229 | | A |
| 3230-A | | D |
| 3230-B | | C |
| 3230-C | | C |
| 3230-D | 10.0000 | D |
| 3231 | | A |
| 3232 | | D |
| 3233 | | D |
| 3234 | 10.0000 | D |
| 3235 | | D |
| 3236 | | B |
| 3237 | | B |
| 3238 | | C |
| 3239 | | B |
| 3240 | | C |
| 3241 | | B |
| 3242 | | C |
| 3243 | | B |
| 3244 | | B |
| 3245 | | D |
| 3246 | | B |
| 3614 | | B |
| 3616 | | B |
| 3637 | | A |
| 3638-A | | D |
| 3638-B | | B |
| 3639 | | D |
| 3640-A | | C |
| 3640-B | | C |
| 3641 | | B |
| 3642 | | B |
| 3643 | | B |
| 3644 | | A |
| 3645 | | B |
| 3646 | | B |
| 3647 | | B |
| 3648 | | B |
| 5148 | | A |
| 5150 | | A |
| 5151 | | B |
| 5152 | | B |
| 5153 | | A |
| 5154 | | B |
| 5155 | | A |
| 5156 | 0.7670 | C |
| 5158 | | B |
| 5159 | | A |
| 5160 | | B |
| 5161 | | A |
| 5162 | | A |
| 5163 | | A |
| 5164 | | A |
| 5165 | | A |
| 5166 | | B |
| 5167 | | A |
| 5168 | | A |
| 5169 | | A |
| 5170 | | A |
| 5171 | | A |
| 5172 | | A |
| 5173 | | A |
| 5174 | | A |
| 5175 | | A |
| 5176 | | A |
| 5177 | | B |
| 5178 | | A |
| 5179 | | A |
| 5180 | | A |
| 5181 | | B |
| 5182 | | B |
| 5183 | | B |
| 5184 | | B |
| 5185 | | A |
| 5186 | | A |
| 5187 | | A |
| 5188 | | A |
| 5189 | | B |
| 5190 | | A |
| 5191 | | A |
| 5192 | | A |
| 5193 | | A |
| 5194 | 0.0036 | A |
| 5196 | | A |
| 5197 | | A |
| 5198 | | B |
| 5199 | | A |
| 5200 | | A |
| 5201 | | A |
| 5202 | | A |
| 5203 | | A |
| 5204 | | A |
| 5205 | | A |
| 5206 | | A |
| 5207 | | B |
| 5208 | | A |
| 5209 | | A |
| 5211 | | B |
| 5212 | | B |
| 5213 | | A |
| 5214 | | A |
| 5215 | | A |
| 5216 | | A |
| 5217 | | B |
| 5218 | | B |
| 5219 | | A |

TABLE 1-continued

| Example Number | HTRF Human PD-L1/PD-1 Binding Assay IC50 (µM) | Range |
|---|---|---|
| 5220 | | C |
| 5221 | | A |
| 5222 | 1.0000 | D |
| 5223 | | A |
| 5224 | | A |
| 5225 | | A |
| 5226 | | A |
| 5227 | | A |
| 5228 | | A |
| 5229 | | A |
| 5230 | | A |
| 5231 | | A |
| 5232 | | A |
| 5233 | | A |
| 5234 | | A |
| 5235 | | A |
| 5236 | | A |
| 5237 | | A |
| 5238 | | A |
| 5239 | | A |
| 5240 | | A |
| 5241 | | B |
| 5242 | | A |
| 5243 | | C |
| 5244 | 5.0050 | D |
| 5245 | | A |
| 5246 | | A |
| 5247 | | A |
| 5248 | | A |
| 5249 | | B |
| 5250 | | A |
| 5251 | | A |
| 5252 | | A |
| 5253 | | A |
| 5254 | | B |
| 5255 | | A |
| 5256 | | B |
| 5257 | | B |
| 5258 | | A |
| 5259 | | A |
| 5260 | | A |
| 5261 | | A |
| 5262 | 0.1014 | C |
| 5263 | | D |
| 5264 | | D |
| 5265 | | B |
| 6118 | | A |
| 6119 | | A |
| 6126 | | A |
| 6134 | | A |
| 6135 | | A |
| 6136 | | B |
| 6137 | | B |
| 6140 | | A |
| 6141 | | A |
| 6143 | | A |
| 6144 | | A |
| 6146 | | A |
| 6150 | | A |
| 6156 | | A |
| 6158 | | A |
| 6162 | | A |
| 6167 | | A |
| 6168 | | B |
| 6170 | | A |
| 6172 | | A |
| 6176 | | B |
| 6180 | | A |
| 6189 | | A |
| 6200 | | A |
| 6202 | | B |
| 6203 | | A |
| 6204 | | A |
| 6209 | | A |
| 6211 | | B |
| 6213 | | A |
| 6216 | | A |
| 6221 | | A |
| 6222 | 0.0036 | A |
| 6224 | | B |
| 6228 | | A |
| 6232 | | A |
| 6235 | | A |
| 6236 | | A |
| 6238 | | A |
| 6244 | | A |
| 6247 | | A |
| 6249 | | A |
| 6250 | | A |
| 6256 | | A |
| 6258 | | B |
| 6262 | | A |
| 6265 | | A |
| 6266 | | B |
| 6267 | | A |
| 6269 | | B |
| 6271 | | A |
| 6272 | | A |
| 6274 | | A |
| 6276 | | A |
| 6283 | | A |
| 6284 | | A |
| 6288 | | A |
| 6289 | | A |
| 6293 | | A |
| 6296 | | A |
| 6297 | | A |
| 6301 | | A |
| 6303 | | A |
| 6309 | 0.0111 | B |
| 6310 | | B |
| 6324 | | A |
| 6329 | | A |
| 6331 | | A |
| 6334 | | A |
| 6335 | | A |
| 6338 | | B |
| 6341 | | A |
| 6342 | | A |
| 6343 | | A |
| 6344 | | A |
| 6415 | 0.1773 | C |
| 6416 | | B |
| 7067 | | B |
| 7068 | | B |
| 7069 | | A |
| 7070 | | A |
| 7071 | | A |
| 7072 | | A |
| 7073 | | A |
| 7075 | | A |
| 7077 | | A |
| 7078 | | B |
| 7079 | | A |
| 7080 | | B |
| 7081 | | A |
| 7082 | | A |
| 7083 | | B |
| 7084 | | A |
| 7085 | | A |
| 7086 | | A |
| 7087 | | A |
| 7088 | | A |
| 7089 | | A |
| 7090 | | A |
| 7091 | | A |
| 7092 | | B |
| 7093 | | A |
| 7094 | | A |
| 7095 | | A |
| 7096 | | A |
| 7097 | | A |

TABLE 1-continued

| Example Number | HTRF Human PD-L1/PD-1 Binding Assay IC50 (μM) | Range |
|---|---|---|
| 7098 | | A |
| 7099 | | B |
| 7100 | | A |
| 7101 | | A |
| 7102 | | A |
| 7103 | | B |
| 7104 | | B |
| 7105 | | B |
| 7106 | | A |
| 7107 | 0.3040 | C |
| 7108 | | A |
| 7109 | | A |
| 7110 | | A |
| 7111 | | A |
| 7112 | | A |
| 7113 | | A |
| 7114 | | C |
| 7115 | | C |
| 7116 | 1.0000 | D |
| 7117 | | B |
| 7118 | | A |
| 7119 | | A |
| 7120 | | A |
| 7121 | | A |
| 7122 | | A |
| 7123 | | B |
| 7124 | | B |
| 7125 | | B |
| 7126 | | D |
| 7127 | | B |
| 7128 | | B |
| 7129 | | A |
| 7130 | | B |
| 7131 | | A |
| 7132 | | C |
| 7132 | | B |
| 7133 | | B |
| 7135 | 0.0056 | A |
| 7136 | | A |
| 7137 | | A |
| 7138 | | A |
| 7139 | | A |
| 7140 | | A |
| 7141 | | A |
| 7142 | | A |
| 7143 | | A |
| 7144 | | A |
| 7145 | | A |
| 7146 | | B |
| 7147 | | A |
| 7148 | | A |
| 7151 | | A |
| 7152 | | B |
| 7153 | | A |
| 7154 | | B |
| 9115 | | B |
| 9116 | | B |
| 9117 | | B |
| 9118 | 0.0270 | B |
| 9119 | | B |
| 9120 | | B |
| 9121 | | B |
| 9122 | | B |
| 9123 | | A |
| 9124 | | B |
| 9125 | | B |
| 9126 | | A |
| 9127 | | A |
| 9128 | | A |
| 9129 | | A |
| 9130 | | A |
| 9131 | | A |
| 9132 | | B |
| 9133 | | A |
| 9134 | | A |
| 9135 | | A |
| 9136 | | B |
| 9137 | | A |
| 9138 | | A |
| 9139 | | A |
| 9140 | | A |
| 9141 | | B |
| 9142 | | A |
| 9143 | | B |
| 9144 | | A |
| 9145 | | A |
| 9146 | | A |
| 9147 | | A |
| 9148 | | D |
| 9149 | 1.0000 | D |
| 9150 | | A |
| 9155 | | A |
| 9156 | | A |
| 9157 | | A |
| 9158 | | A |
| 9159 | | A |
| 9160 | | B |
| 9161 | | A |
| 9162 | | A |
| 9163 | | A |
| 9164 | | A |
| 9165 | | A |
| 9166 | | D |
| 9167 | 1.0000 | D |
| 9168 | | A |
| 9169 | | A |
| 9170 | | B |
| 9171 | | A |
| 9172 | | C |
| 9173 | | C |
| 9174 | | C |
| 9175 | 0.3640 | C |
| 9176 | | C |
| 9177 | | C |
| 9178 | | C |
| 9179 | | C |
| 9180 | | A |
| 9181 | | A |
| 9182 | | A |
| 9183 | | A |
| 9184 | | B |
| 9185 | | A |
| 9186 | | B |
| 9187 | | A |
| 9188 | | A |
| 9189 | | A |
| 9190 | | B |
| 9191 | | B |
| 9192 | 0.0140 | B |
| 9193 | | A |
| 9194 | | A |
| 9195 | | A |
| 9196 | 0.0045 | A |
| 9213 | | B |
| 9214 | | C |
| 9215 | | B |
| 9216 | | B |
| 9217 | | C |
| 9218 | | B |
| 9219 | | C |
| 9220 | | C |
| 9221 | | C |
| 9222 | 0.1438 | C |
| 9223 | | C |
| 9224 | | C |
| 9225 | | A |
| 9226 | | B |
| 9227 | | A |
| 9228 | | B |
| 9229 | | A |
| 9230 | | B |
| 9231 | | A |

TABLE 1-continued

| Example Number | HTRF Human PD-L1/PD-1 Binding Assay IC50 (μM) | Range |
|---|---|---|
| 9232 | | A |
| 9233 | | A |
| 9234 | | A |
| 9235 | | A |
| 9236 | | A |
| 9237 | | A |
| 9238 | | A |
| 9239 | 0.0038 | A |
| 9240 | | A |
| 9241 | | D |
| 9242 | | D |
| 9243 | | D |
| 9244 | | D |
| 9245 | | D |
| 9246 | | D |
| 9247 | | D |
| 9248 | | D |
| 9249 | | C |
| 9250 | | D |
| 9251 | | C |
| 9252 | | C |
| 9253 | | D |
| 9254 | | D |
| 9255 | | D |
| 9256 | | D |
| 9257 | | D |
| 9258 | 7.2840 | D |
| 9259 | | D |
| 9260 | | D |
| 9261 | | D |
| 9262 | | D |
| 9263 | | D |
| 9264 | | A |
| 9265 | | A |
| 9266 | | A |
| 9267 | | A |
| 9268 | | A |
| 9269 | | A |
| 9270 | | A |
| 9271 | | A |
| 9272 | | A |
| 9273 | | A |
| 9274 | | A |
| 9275 | | A |
| 9276 | | A |
| 9277 | | A |
| 9278 | | A |
| 9279 | | A |
| 9280 | | B |
| 9281 | | A |
| 9282 | | B |
| 9283 | | A |
| 9284 | | A |
| 9285 | | A |
| 9286 | | A |
| 9287 | | A |
| 9288 | | A |
| 9289 | | A |
| 9290 | | A |
| 9291 | | A |
| 9292 | | A |
| 9293 | | A |
| 9294 | | A |
| 9295 | | A |
| 9296 | | A |
| 9297 | | A |
| 9298 | | A |
| 9299 | | A |
| 9300 | | A |
| 9301 | | A |
| 9302 | | A |
| 9303 | | A |
| 9304 | 0.0117 | B |
| 9305 | | B |
| 9306 | | A |
| 9307 | | A |
| 9308 | | A |
| 9309 | | A |
| 9310 | | A |
| 9311 | | A |
| 9312 | | B |
| 9313 | 0.0027 | A |
| 9314 | | A |
| 9315 | | B |
| 9316 | | B |
| 9317 | | A |
| 9318 | | A |
| 9319 | | A |
| 9320 | | A |
| 9321 | | A |
| 9322 | | A |
| 9323 | | A |
| 9324 | | A |
| 9325 | | A |
| 9326 | | B |
| 9327 | | B |
| 9328 | | B |
| 9329 | | A |
| 9330 | | B |
| 9331 | | A |
| 9332 | | B |
| 9333 | | B |
| 9334 | | B |
| 9335 | | B |
| 9336 | | B |
| 9337 | | B |
| 9338 | | A |
| 9345 | | A |
| 9346 | | A |
| 9347 | 0.0109 | B |
| 9348 | | B |
| 9349 | | B |
| 9350 | | B |
| 9351 | | B |
| 9352 | | A |
| 9353 | | A |
| 9354 | | A |
| 9355 | | A |
| 9356 | 0.1505 | C |
| 9357 | | B |
| 9358 | | B |
| 9360 | | A |
| 9361 | | A |
| 9362 | | A |
| 9363 | | A |
| 9364 | | B |
| 9365 | | B |
| 9366 | | B |
| 9367 | | B |
| 9368 | | A |
| 9369 | | A |
| 9370 | 0.0057 | A |
| 9371 | | A |
| 9372 | | A |
| 9373 | | B |
| 9374 | | B |
| 10012 | | B |
| 10013 | 0.0634 | B |
| 10014 | | B |
| 10015 | | A |
| 10016 | | B |
| 10017 | | B |
| 10018 | | B |
| 10019 | | B |
| 10020 | | A |
| 10021 | | B |
| 10022 | 0.1340 | C |
| 10023 | | B |
| 10024 | | B |
| 10025 | | A |
| 10034 | | A |
| 10035 | | A |

TABLE 1-continued

| Example Number | HTRF Human PD-L1/PD-1 Binding Assay IC50 (µM) | Range |
|---|---|---|
| 10036 | | A |
| 10037 | | A |
| 10042 | | B |
| 10043 | | A |
| 10044 | | B |
| 10045 | | B |
| 10047 | | B |
| 10049 | | A |
| 10050 | | A |
| 10051 | | A |
| 10052 | | A |
| 10053 | | B |
| 10054 | | C |
| 10055 | | C |
| 10056 | | C |
| 10057 | 0.2154 | C |
| 10058 | | B |
| 10059 | | B |
| 10060 | | B |
| 10061 | | B |
| 10062 | | B |
| 10063 | | B |
| 10064 | | B |
| 10065 | | B |
| 10066 | | A |
| 10067 | | A |
| 10068 | | A |
| 10069 | 0.0126 | B |
| 10070 | | B |
| 10071 | | B |
| 10072 | | A |
| 10073 | | B |
| 10074 | | B |
| 10075 | | B |
| 10076 | | B |
| 10077 | | B |
| 10078 | | B |
| 10079 | | B |
| 10080 | | B |
| 10081 | | B |
| 10082 | | C |
| 10083 | 0.1576 | C |
| 10084 | | C |
| 10085 | | C |
| 10086 | | B |
| 10087 | | B |
| 10088 | | B |
| 10089 | | A |
| 10090 | | A |
| 10091 | 0.0025 | A |
| 10092 | | A |
| 10093 | | A |
| 10094 | | A |
| 10095 | | A |
| 10096 | | A |
| 10097 | | A |
| 10098 | | A |
| 10099 | | A |
| 10100 | | A |
| 10102 | | A |
| 10103 | | A |
| 10104 | | A |
| 10105 | | A |
| 10106 | | A |
| 10107 | | A |
| 10108 | | A |
| 10109 | | B |
| 10110 | | A |
| 10111 | | A |
| 10112 | | C |
| 10113 | | C |
| 10114 | | C |
| 10115 | | C |
| 10116 | | A |
| 10117 | | C |
| 10118 | | A |
| 10119 | | C |
| 10120 | | A |
| 10121 | | C |
| 10122 | | D |
| 10123 | | C |
| 10126 | | D |
| 10127 | | D |
| 10128 | | D |
| 10129 | | D |
| 10130 | | D |
| 10131 | 2.9010 | D |
| 10132 | | C |
| 10136 | | A |
| 10137 | | B |
| 10138 | 0.1796 | C |
| 10139 | | A |
| 10140 | | B |
| 10141 | | B |
| 10142 | | B |
| 10143 | 0.0109 | B |
| 10144 | | A |
| 10145 | | A |
| 10146 | | B |
| 10147 | | A |
| 10148 | | A |
| 10149 | | A |
| 10150 | | A |
| 10151 | | A |
| 10152 | | A |
| 10153 | | A |
| 10154 | | A |
| 10155 | | A |
| 10156 | | A |
| 10157 | 0.0041 | A |
| 10158 | | A |
| 10159 | | A |
| 10160 | | A |
| 10161 | | A |
| 10162 | | A |
| 10163 | | B |
| 10164 | | A |
| 10165 | | A |
| 10166 | | A |
| 10167 | | A |
| 10168 | | A |
| 10169 | | A |
| 10170 | | A |
| 10171 | | B |
| 10172 | | B |
| 10173 | | B |
| 10174 | | A |
| 10175 | | A |
| 10176 | 0.0110 | B |
| 10177 | | B |
| 10178 | | A |
| 10179 | | B |
| 10180 | | B |
| 10181 | | A |
| 10182 | | A |
| 10183 | | B |
| 10184 | | B |
| 10185 | | A |
| 10186 | | B |
| 10187 | | A |
| 10188 | | A |
| 10189 | | B |
| 10190 | 0.0082 | A |
| 10191 | | A |
| 10192 | | B |
| 10193 | | A |
| 10194 | | B |
| 10195 | | A |
| 10196 | | D |
| 10197 | | D |
| 10198 | | D |
| 10199 | | D |

TABLE 1-continued

| Example Number | HTRF Human PD-L1/PD-1 Binding Assay IC50 (µM) | Range |
|---|---|---|
| 10200 | | D |
| 10201 | | D |
| 10202 | | D |
| 10203 | | D |
| 10204 | | D |
| 10205 | | D |
| 10206 | | D |
| 10207 | | D |
| 10208 | | D |
| 10209 | | D |
| 10210 | | D |
| 10211 | | D |
| 10212 | | D |
| 10213 | | D |
| 10214 | | D |
| 10215 | | D |
| 10216 | | D |
| 10217 | | D |
| 10218 | | D |
| 10219 | | D |
| 10530 | 0.0150 | B |
| 10531 | | A |
| 10532 | | A |
| 10533 | | A |
| 10534 | | A |
| 10535 | | A |
| 10536 | | D |
| 10539 | | D |
| 10540 | | D |
| 10542 | | A |
| 10543 | 0.0100 | B |
| 10544 | | D |
| 10551 | | A |
| 10552 | | A |
| 10553 | | A |
| 10554 | | A |
| 10555 | | A |
| 10556 | | A |
| 10557 | | A |
| 10558 | | A |
| 10559 | | A |
| 10560 | | A |
| 10561 | | A |
| 10562 | | A |
| 10563 | | A |
| 10564 | | A |
| 10565 | | A |
| 10566 | | A |
| 10567 | | A |
| 10568 | | A |
| 10569 | | A |
| 10570 | | A |
| 10571 | | A |
| 10572 | | A |
| 10573 | | A |
| 10574 | | A |
| 10575 | | A |
| 10576 | | A |
| 10577 | | A |
| 10578 | | A |
| 10579 | | A |
| 10580 | | A |
| 10581 | | B |
| 10582 | | A |
| 10583 | | A |
| 10584 | | A |
| 10585 | | A |
| 10586 | | A |
| 10587 | | A |
| 10588 | | A |
| 10589 | | A |
| 10590 | | A |
| 10591 | | A |
| 10592 | | A |
| 10593 | | A |
| 10594 | | A |
| 10595 | | A |
| 10596 | | A |
| 10597 | | A |
| 10598 | | A |
| 10599 | | A |
| 10600 | | A |
| 10601 | | A |
| 10602 | | A |
| 10603 | | A |
| 10604 | | A |
| 10605 | | A |
| 10606 | | A |
| 10607 | | A |
| 10608 | | D |
| 10609 | | C |
| 10610 | | C |
| 10611 | | A |
| 10612 | | A |
| 10613 | | A |
| 10614 | | B |
| 10615 | | B |
| 10616 | 0.0106 | B |
| 10617 | | B |
| 10618 | | B |
| 10619 | | B |
| 10620 | | B |
| 10621 | | B |
| 10622 | | B |
| 10623 | | A |
| 10624 | | B |
| 10625 | | B |
| 10626 | | B |
| 10627 | | B |
| 10628 | | B |
| 10629 | | B |
| 10630 | | A |
| 10631 | | B |
| 10632 | | A |
| 10633 | | B |
| 10634 | | B |
| 10635 | | A |
| 10636 | | A |
| 10637 | | B |
| 10638 | 0.0125 | B |
| 10640 | | B |
| 11001 | | B |
| 11002 | | A |
| 11003 | | A |
| 11004 | | B |

Numerous modifications and variations of the subject matter described and claimed herein are possible in light of the above teachings. It is therefore understood that within the scope of the appended claims, the subject matter recited in the claims may be practiced otherwise than as specifically described herein.

The present disclosure is not to be limited in scope by the embodiments disclosed herein, which are intended as single illustrations of individual aspects of the disclosure, and any that are functionally equivalent are within the scope of the disclosure. Various modifications to the models and methods of the disclosure, in addition to those described herein, will become apparent to those skilled in the art from the foregoing description and teachings, and are similarly intended to fall within the scope of the disclosure. Such modifications or other embodiments can be practiced without departing from the true scope and spirit of the disclosure.

The entire disclosure of each document cited (including patents, patent applications, journal articles, abstracts, laboratory manuals, books, GENBANK® Accession numbers, SWISS-PROT® Accession numbers, or other disclosures) herein is hereby incorporated by reference in its entirety. Further, the hard copy of the Sequence Listing submitted herewith, in addition to its corresponding Computer Readable Form, are incorporated herein by reference in their entireties.

What is claimed is:
1. A compound selected from
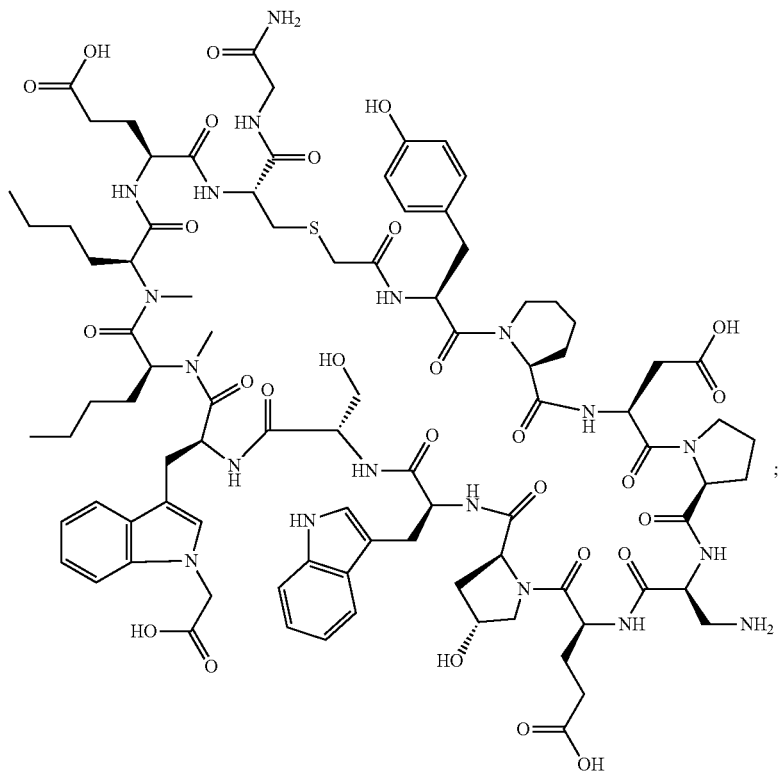
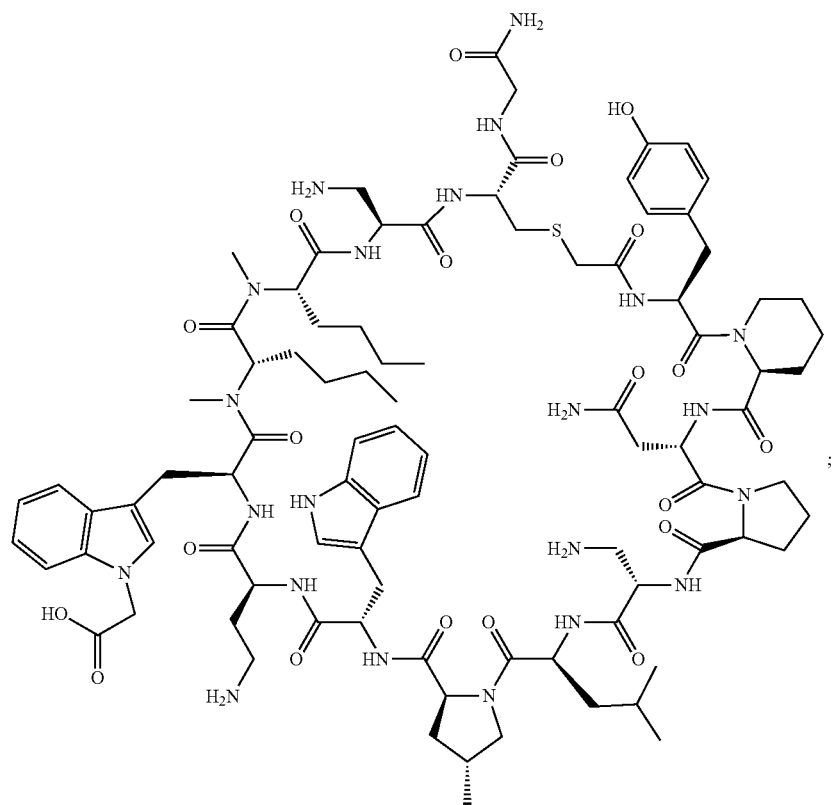

-continued
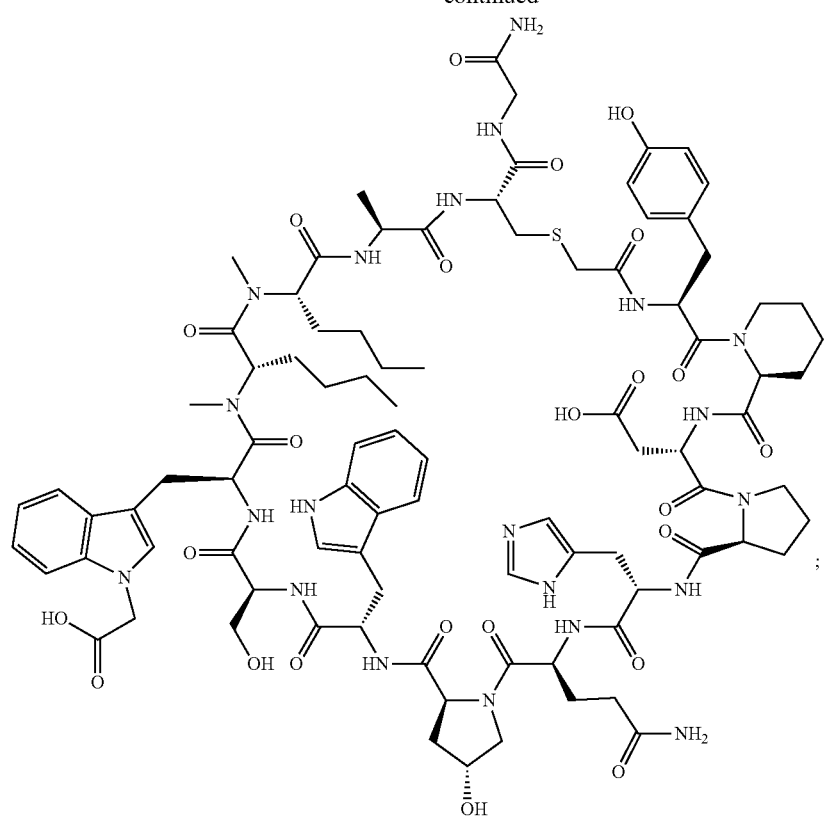
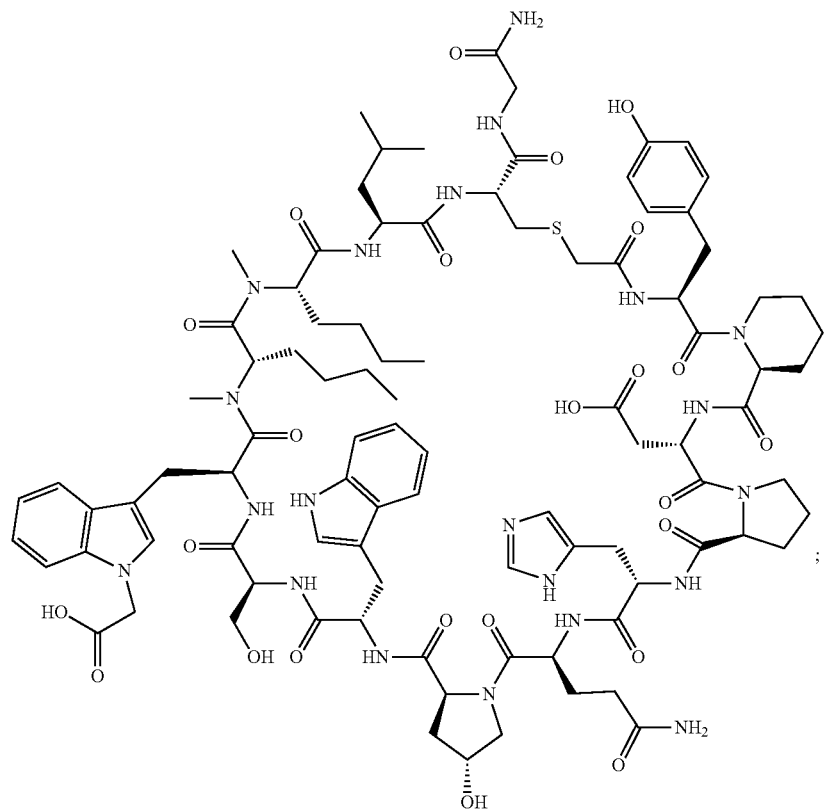

-continued
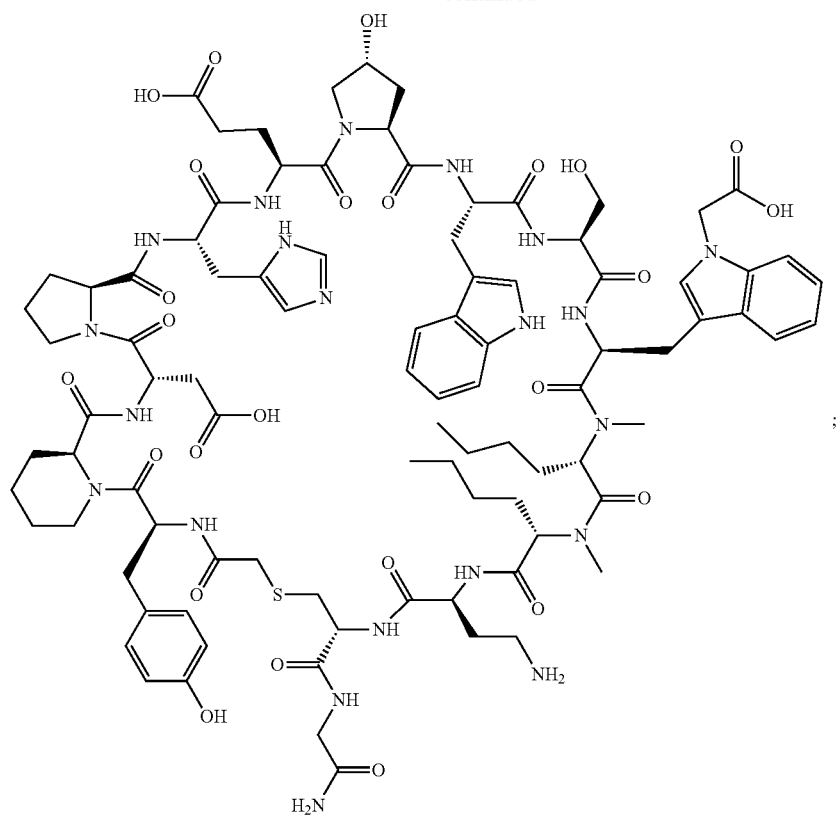
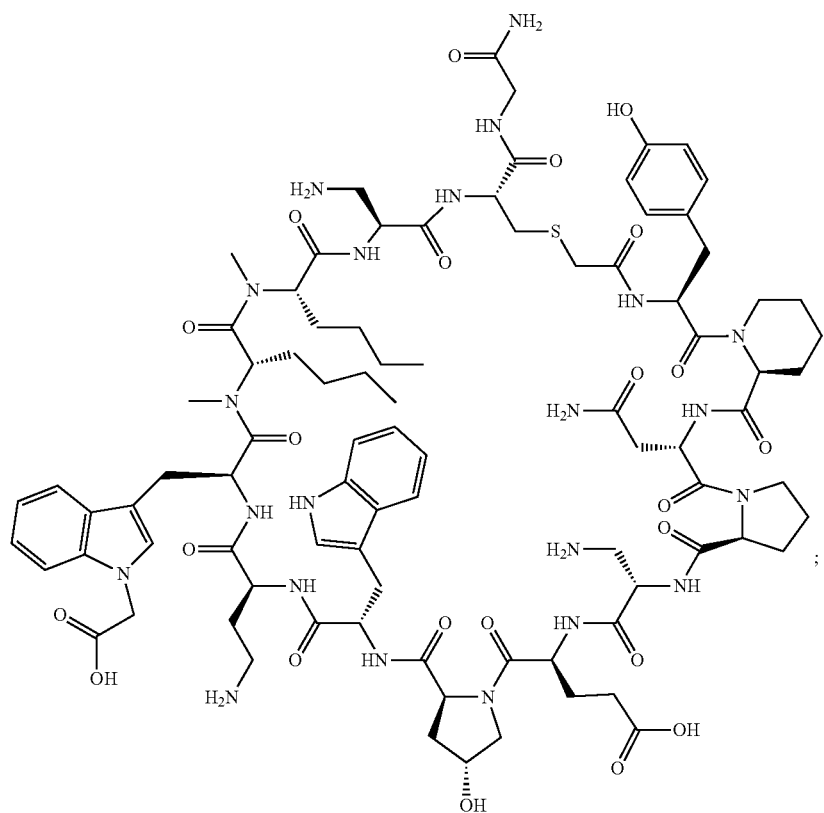

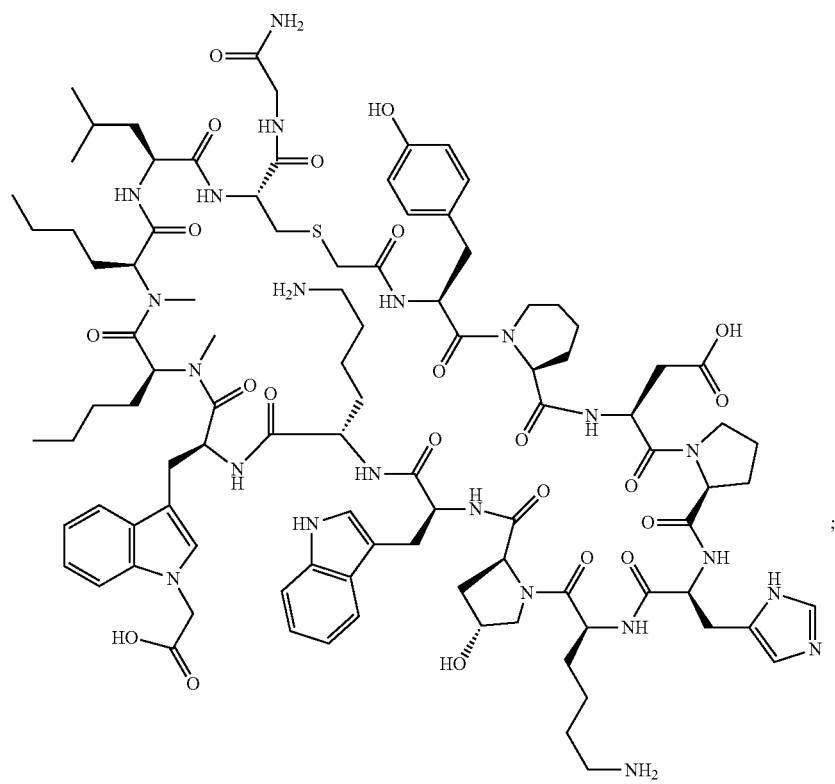
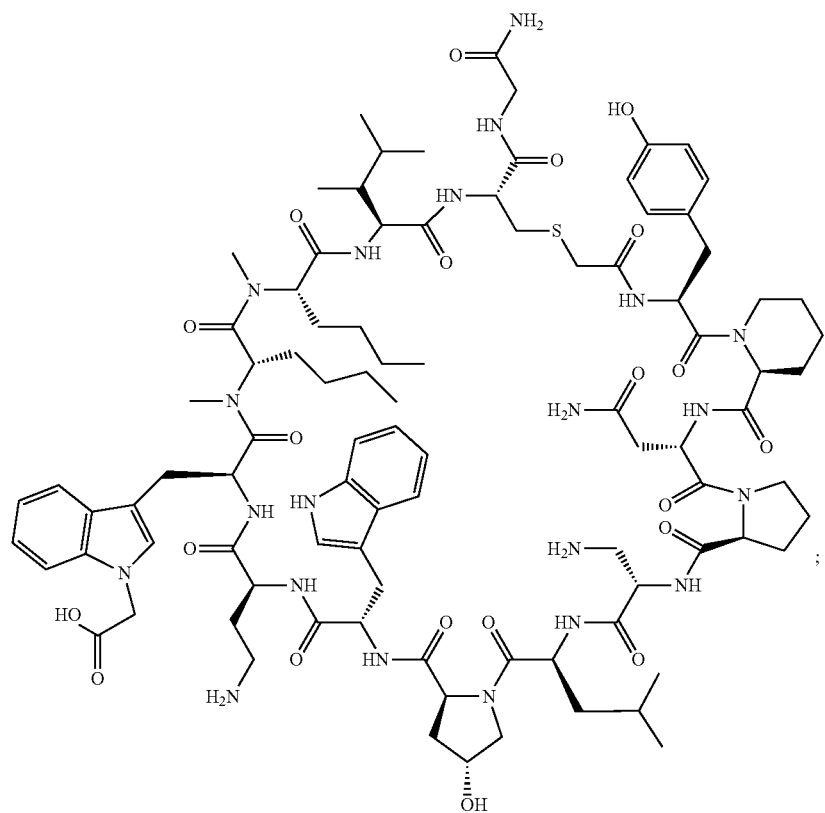

-continued
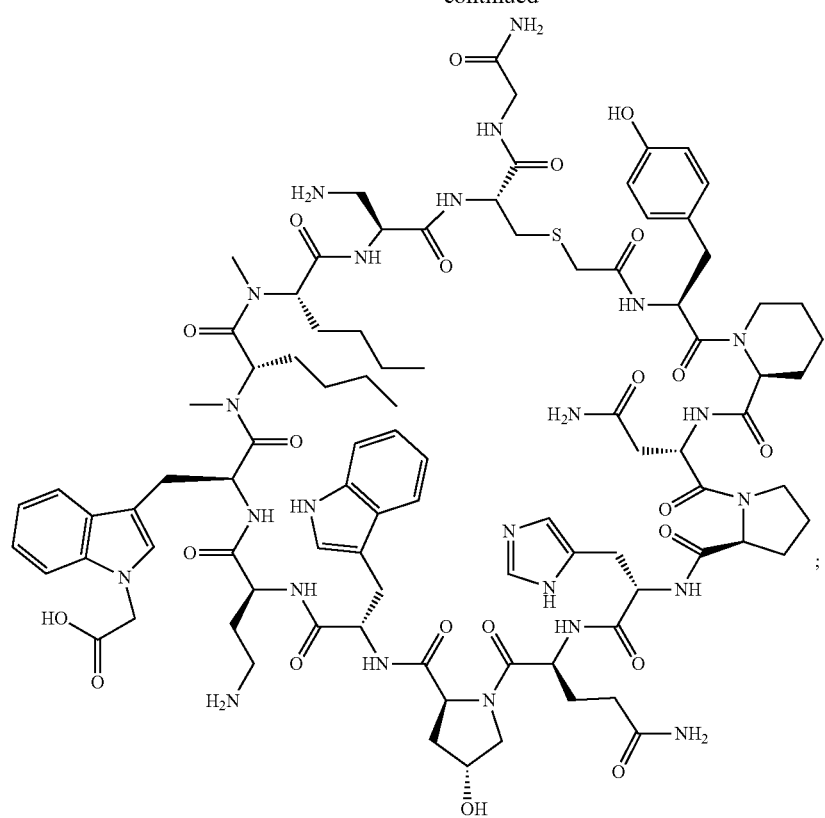
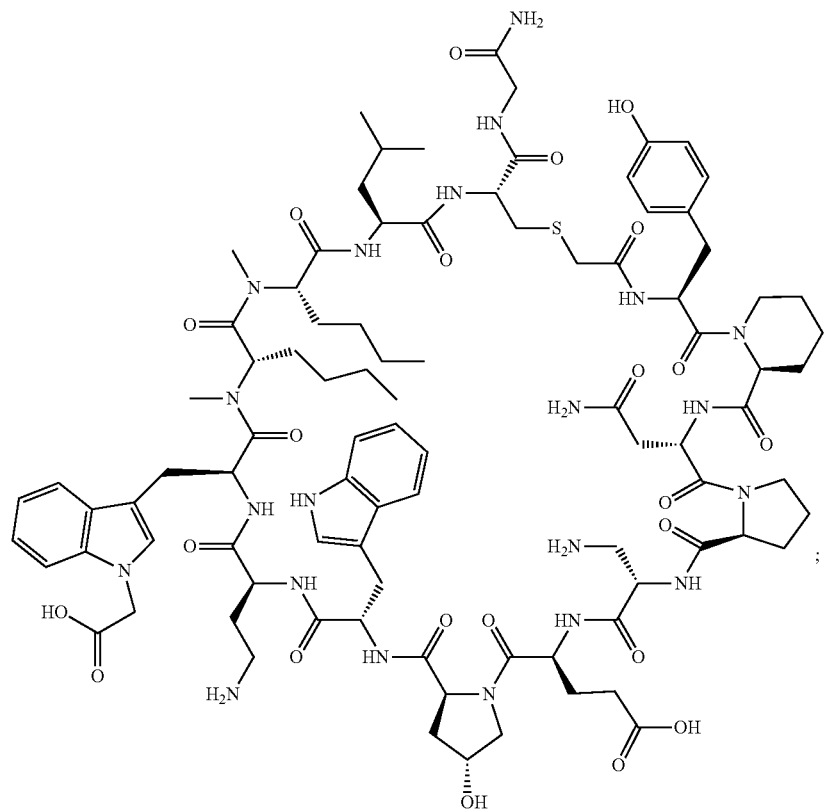

-continued
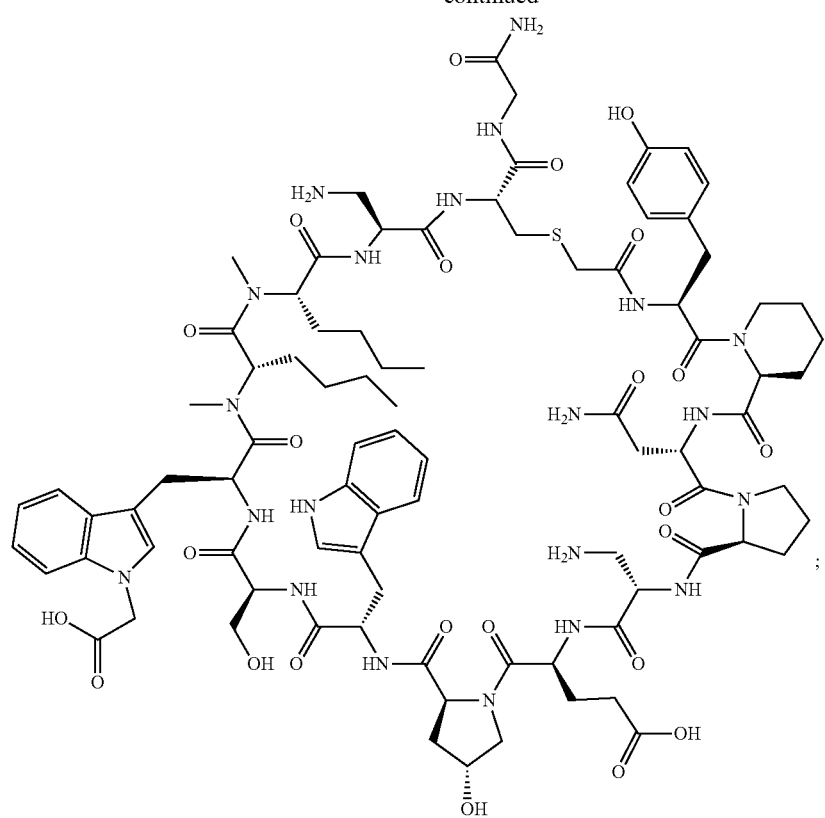
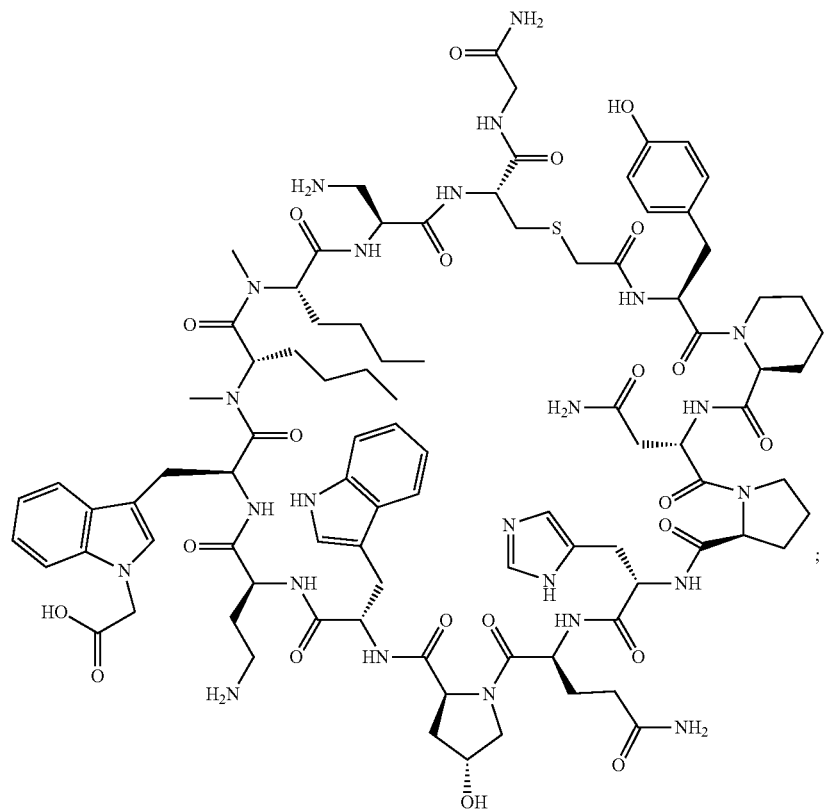

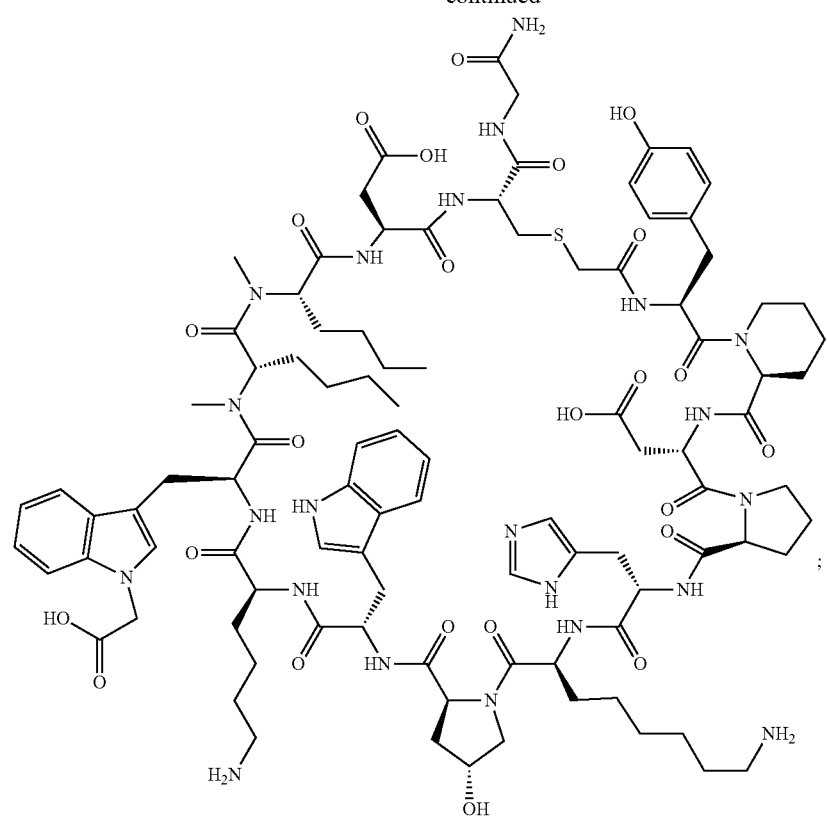
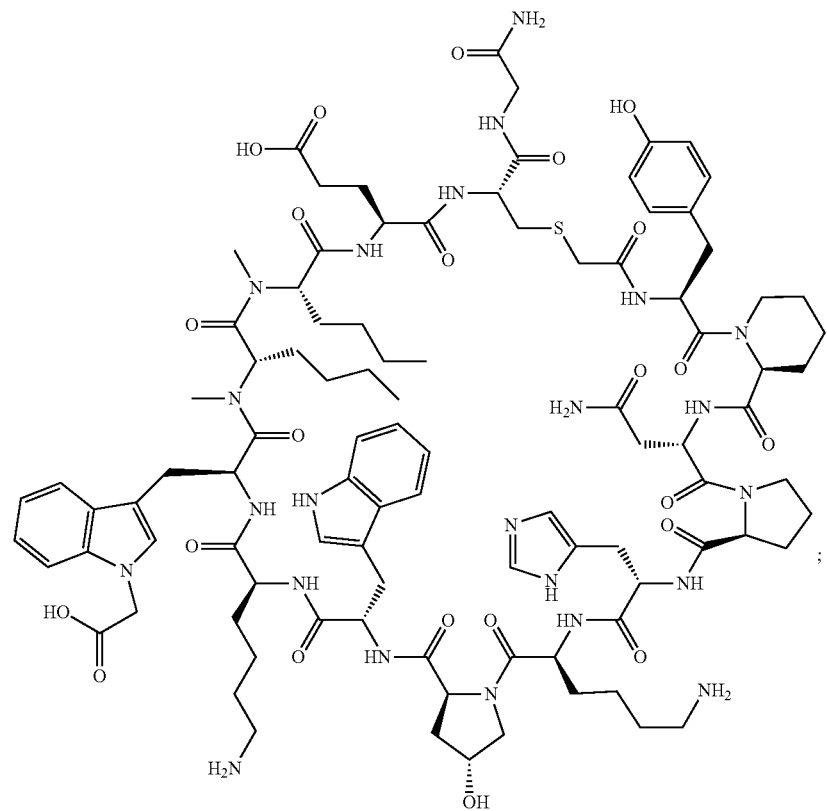

-continued
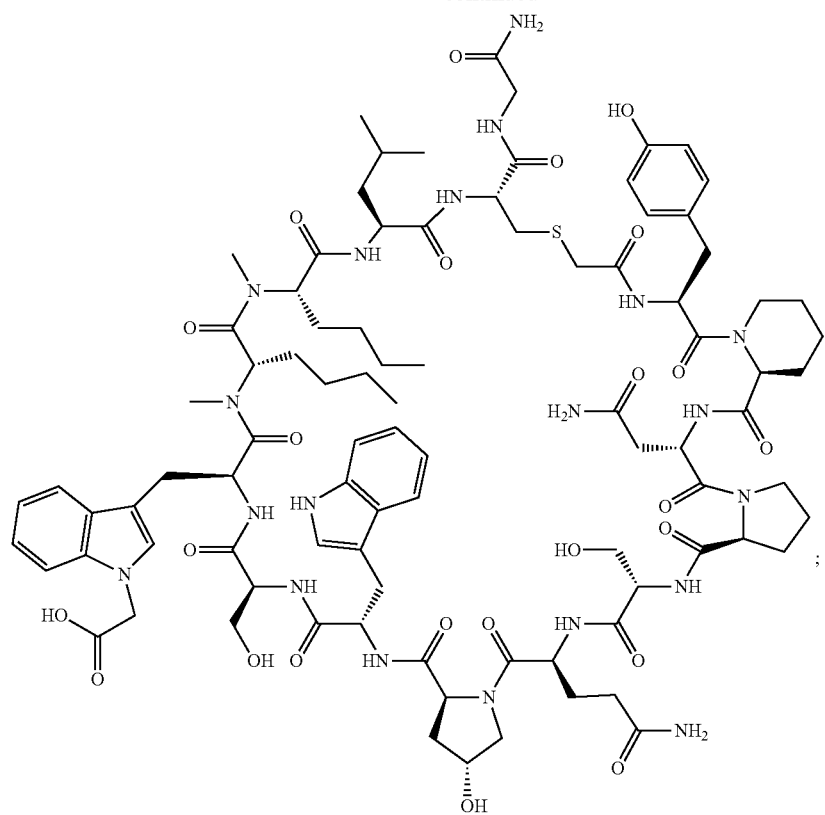
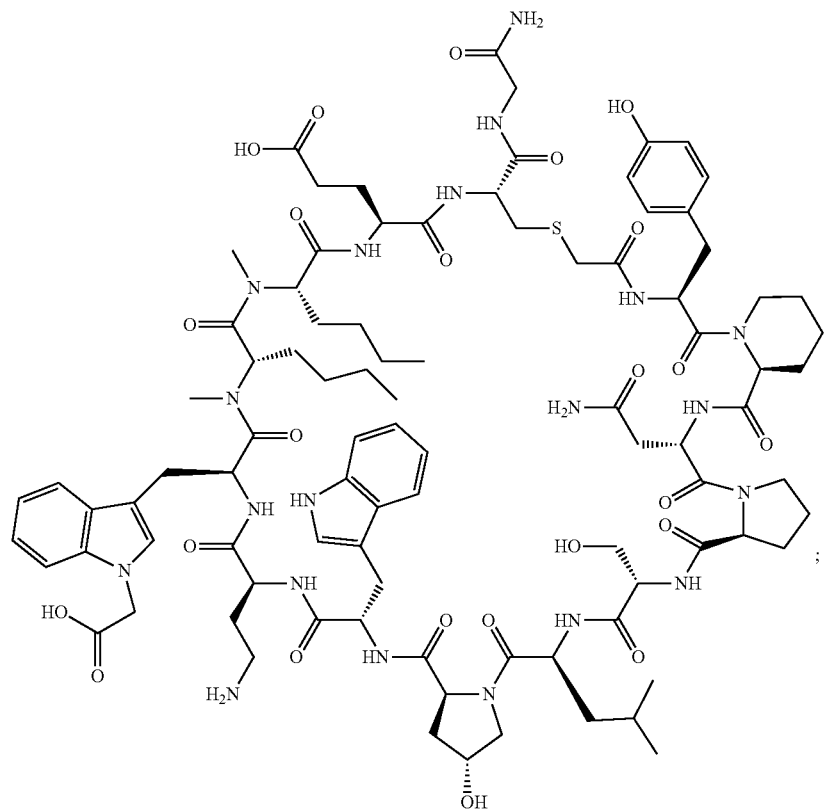

-continued
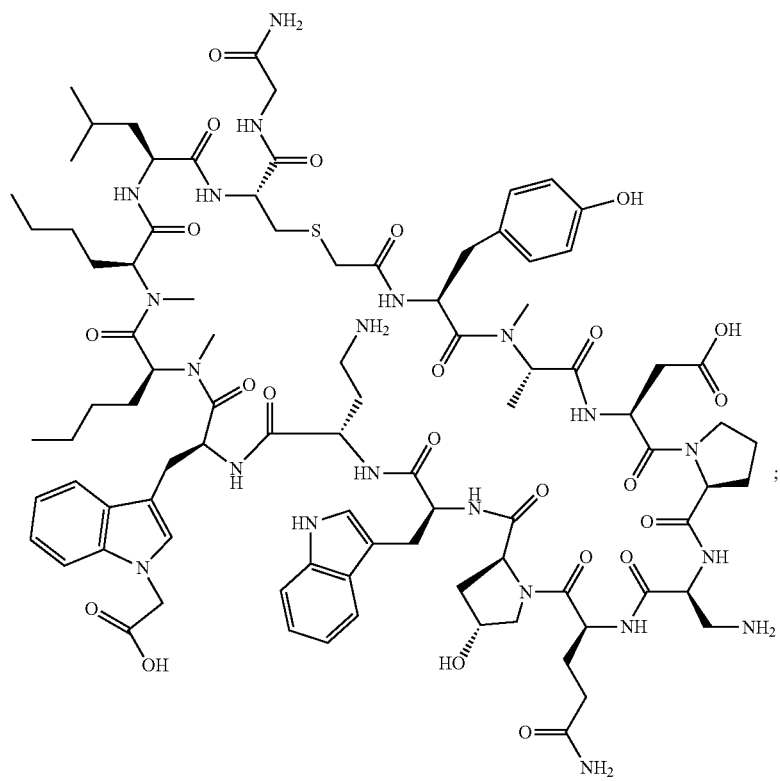
;
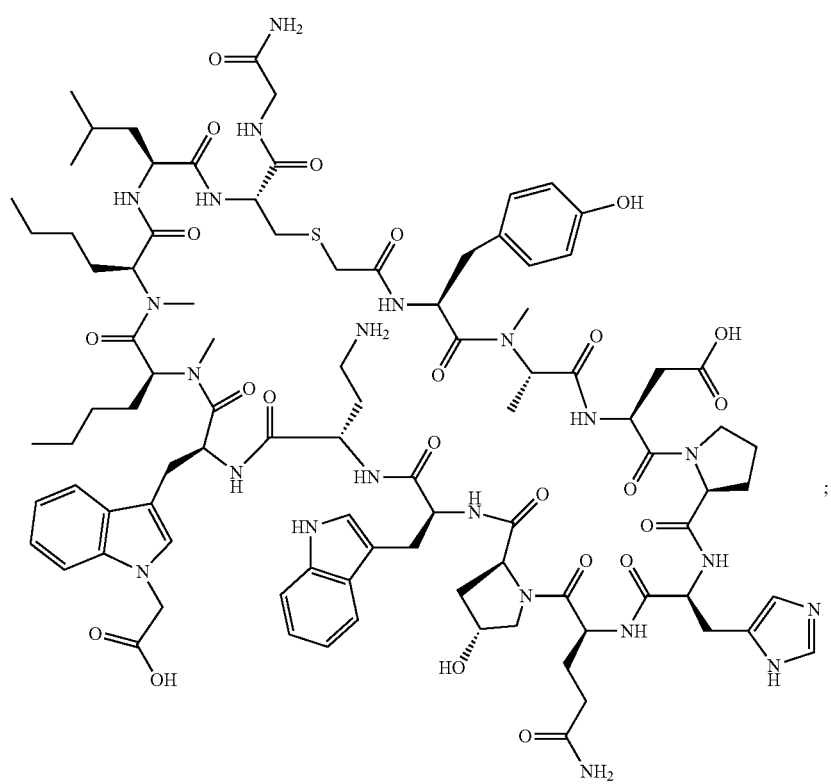
;

-continued
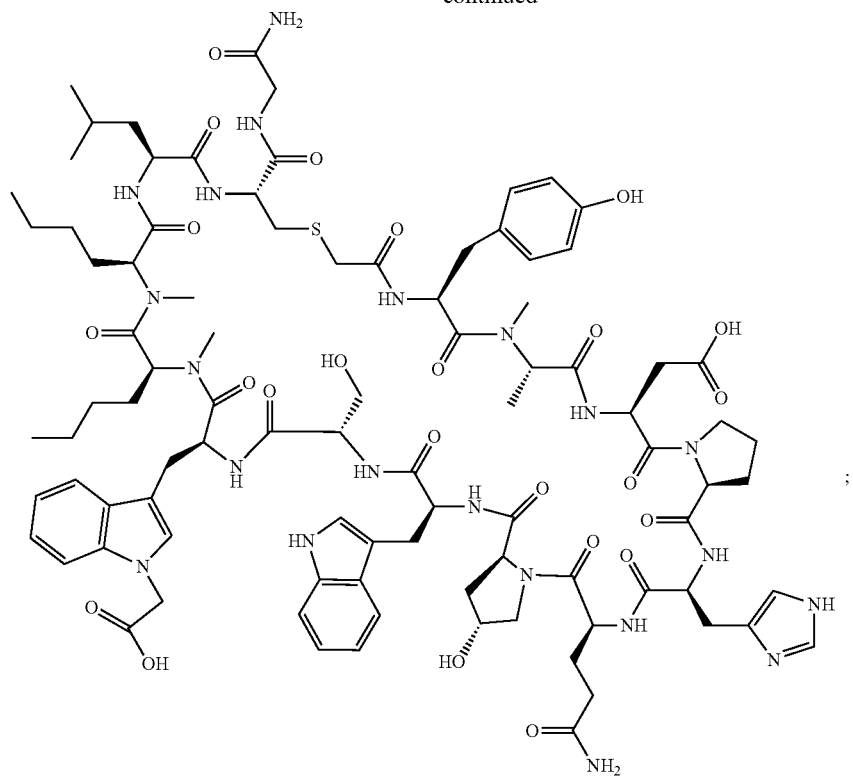
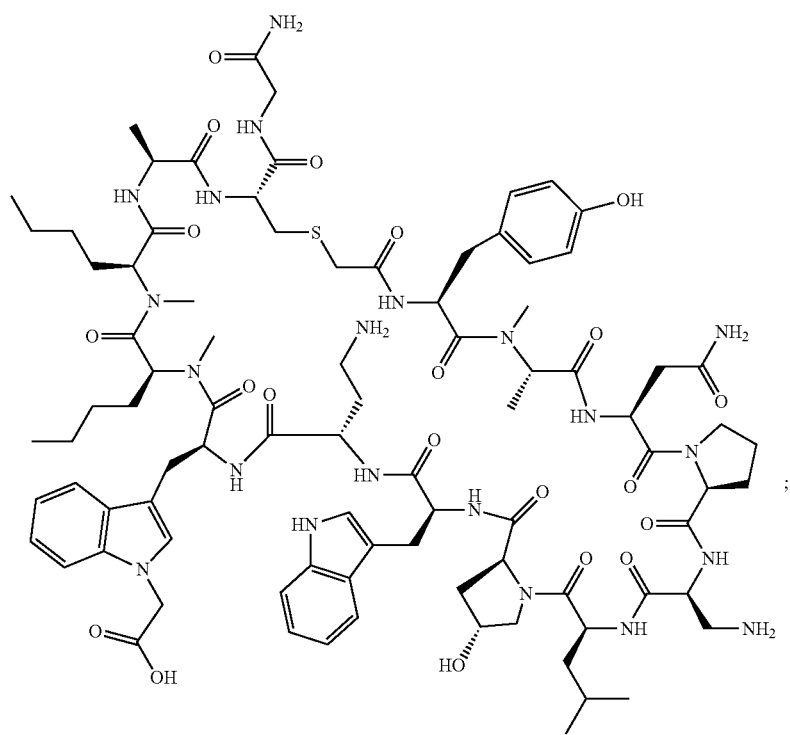

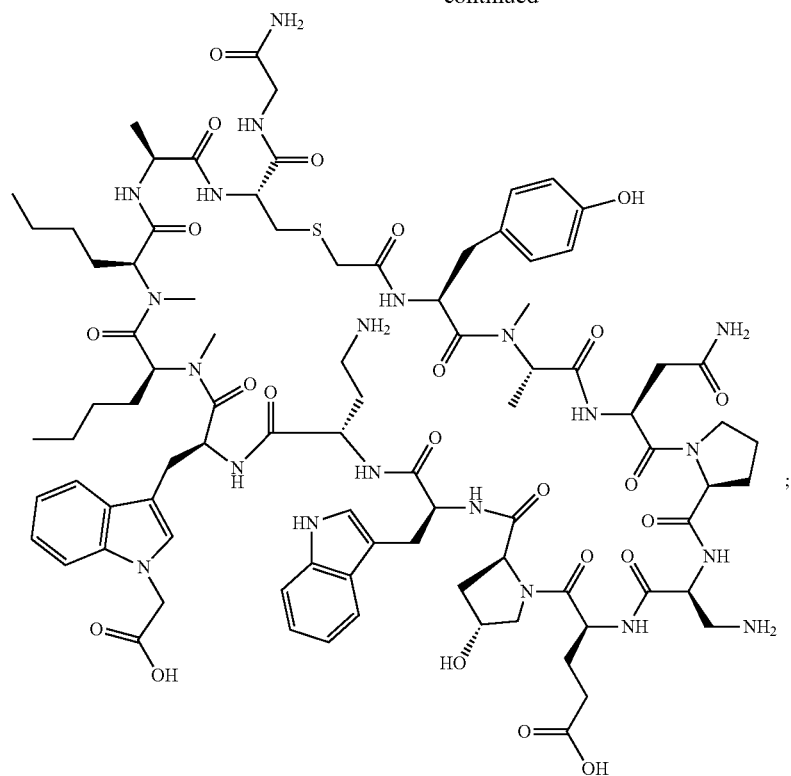
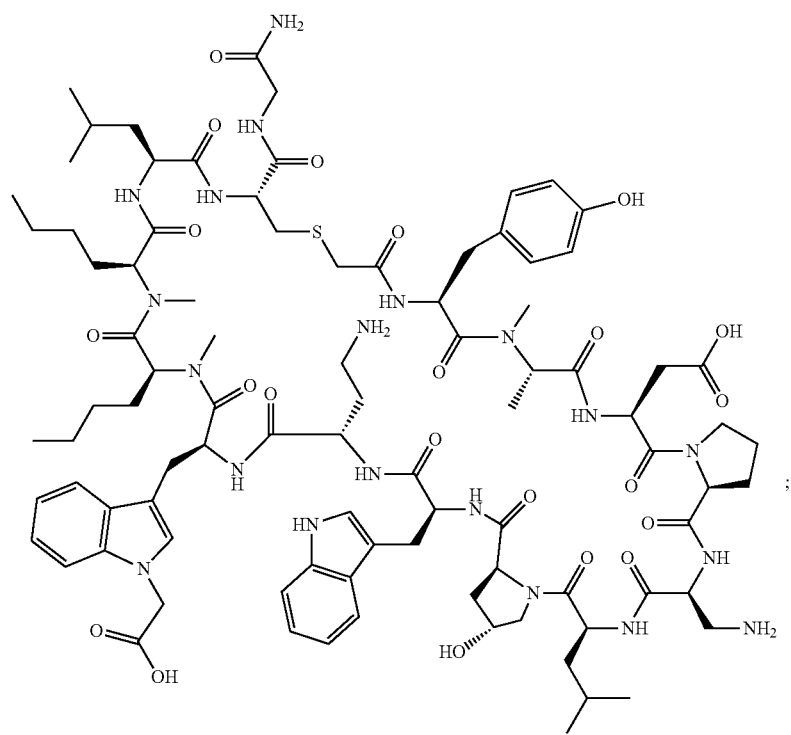

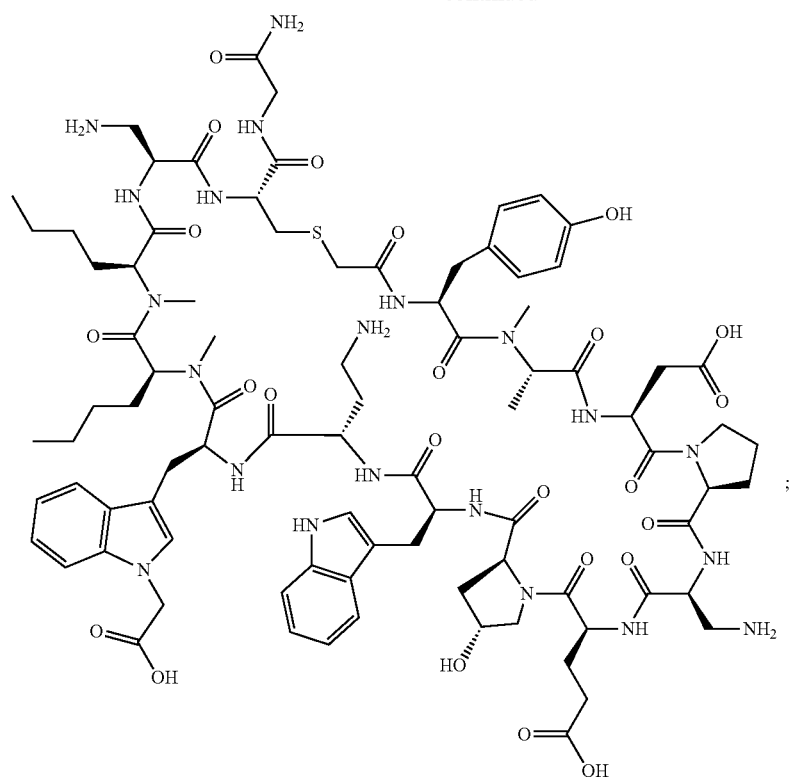
;
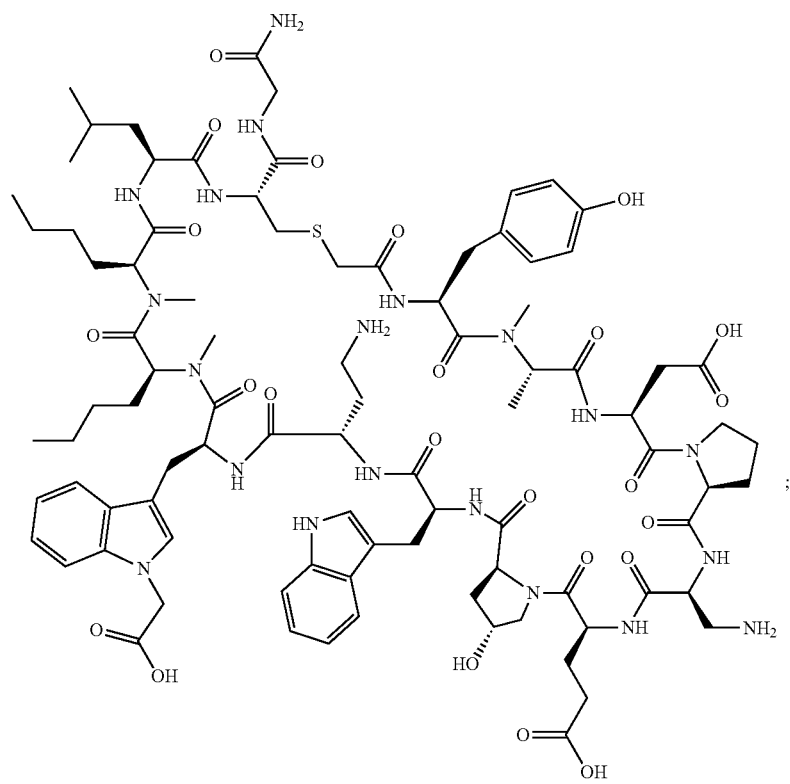
;

-continued
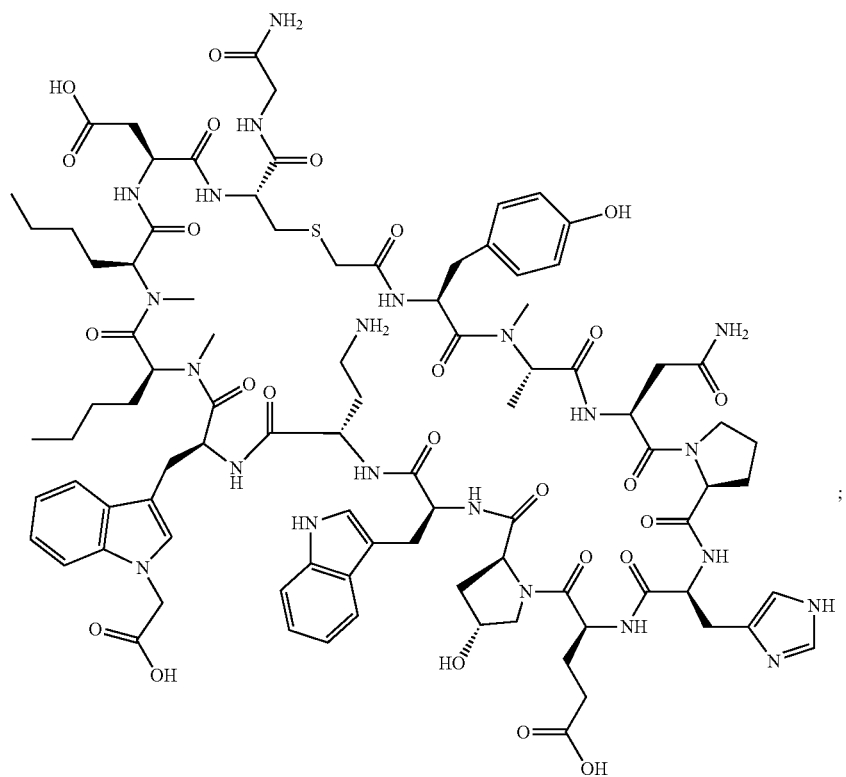
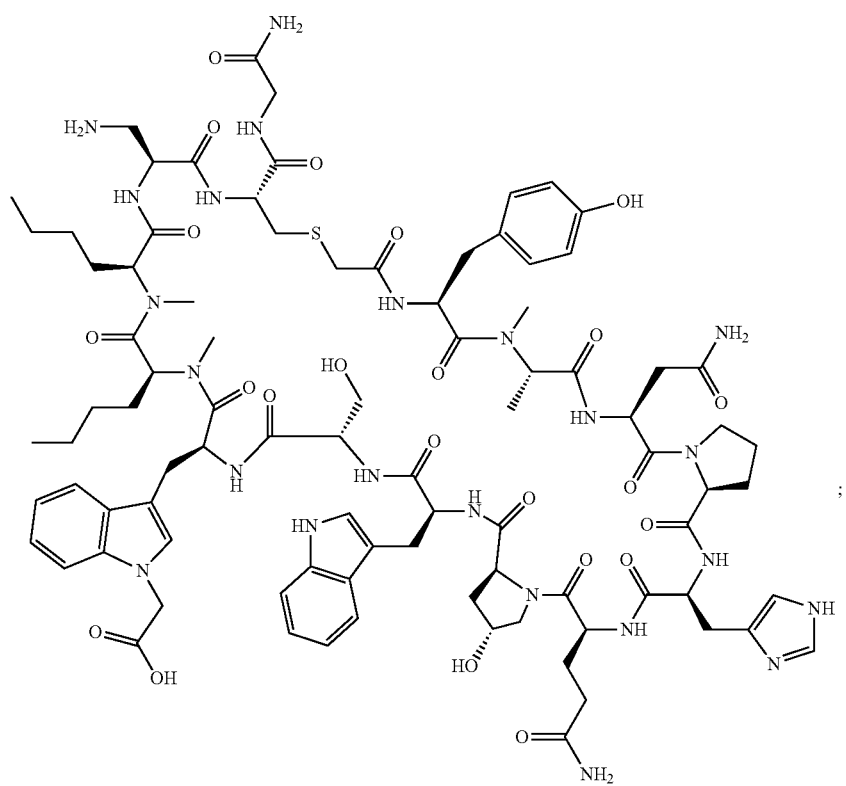

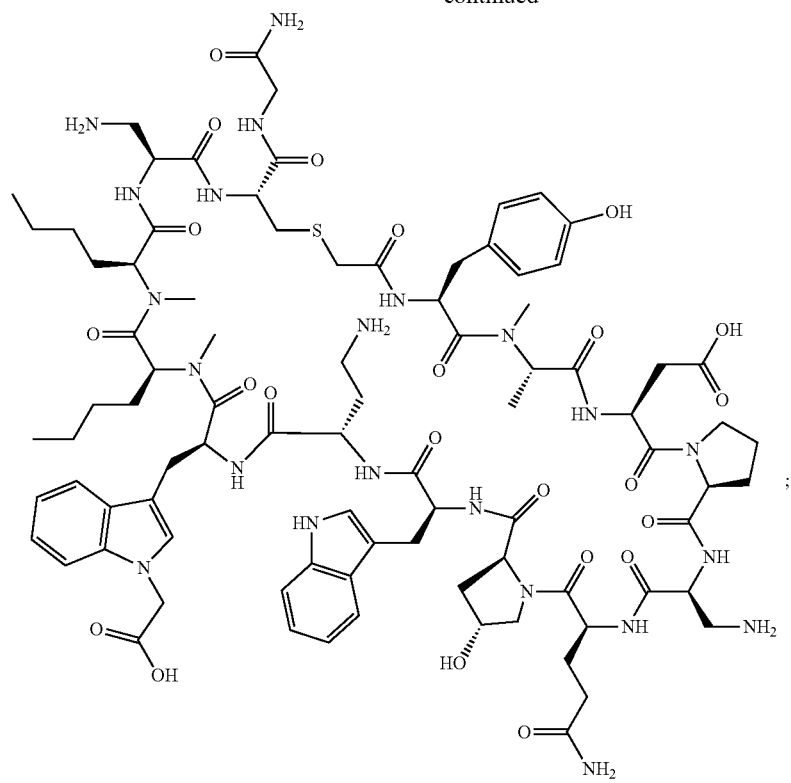
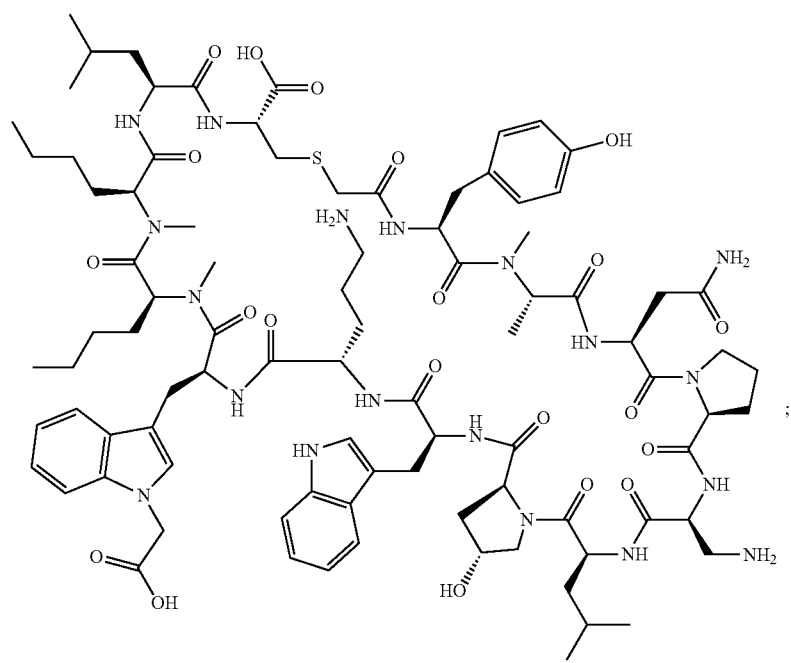

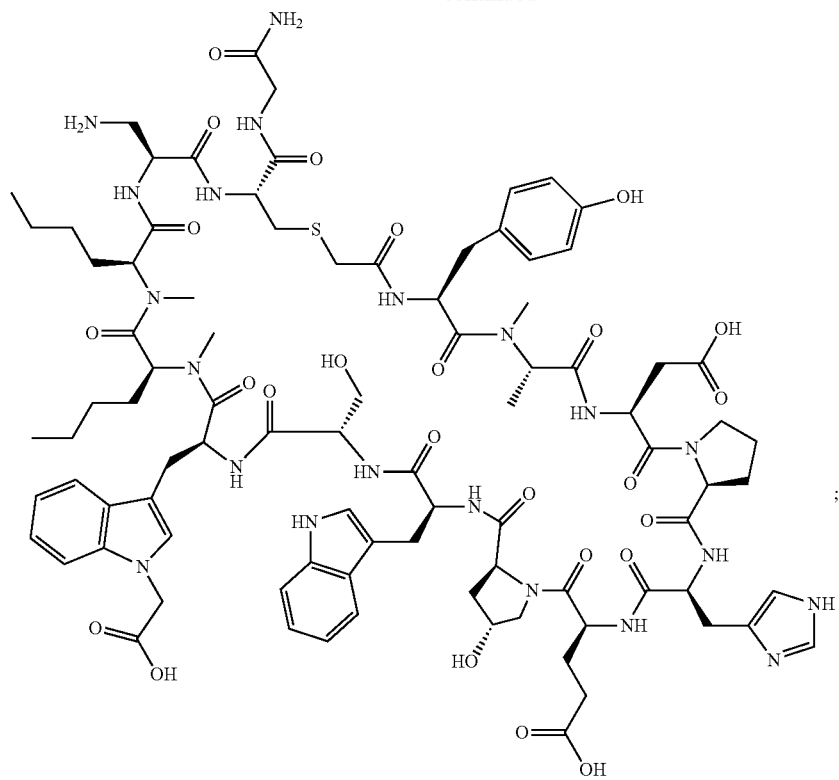
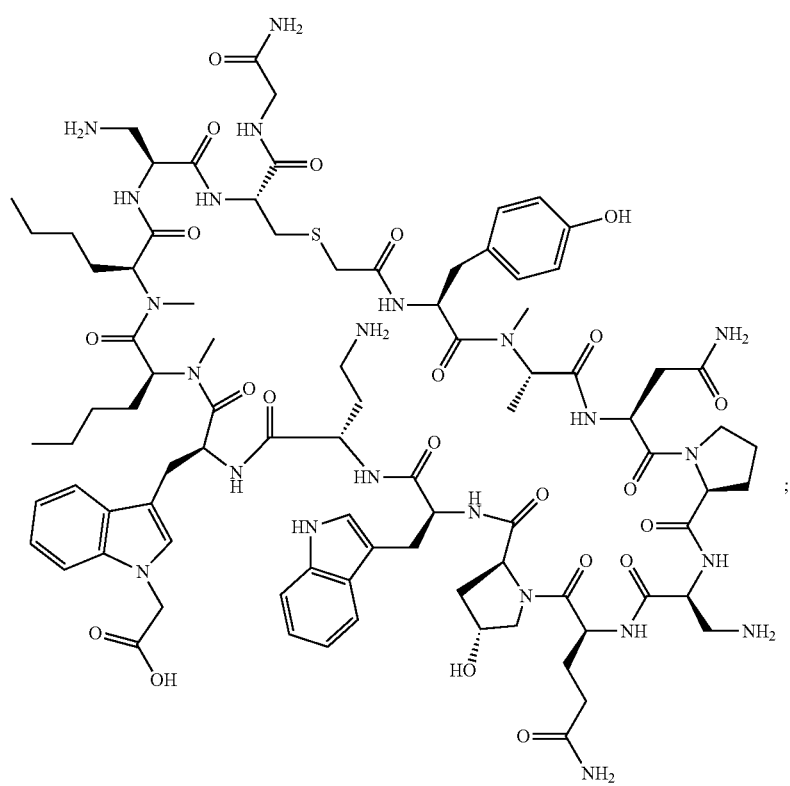 [SMILES: CCCC[C@H]1C(=O)N(C)[C@@H](CCCC)C(=O)N[C@@H](CN)C(=O)N[C@H](C(=O)NCC(N)=O)CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](CN)C(=O)N[C@@H](CCC(N)=O)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

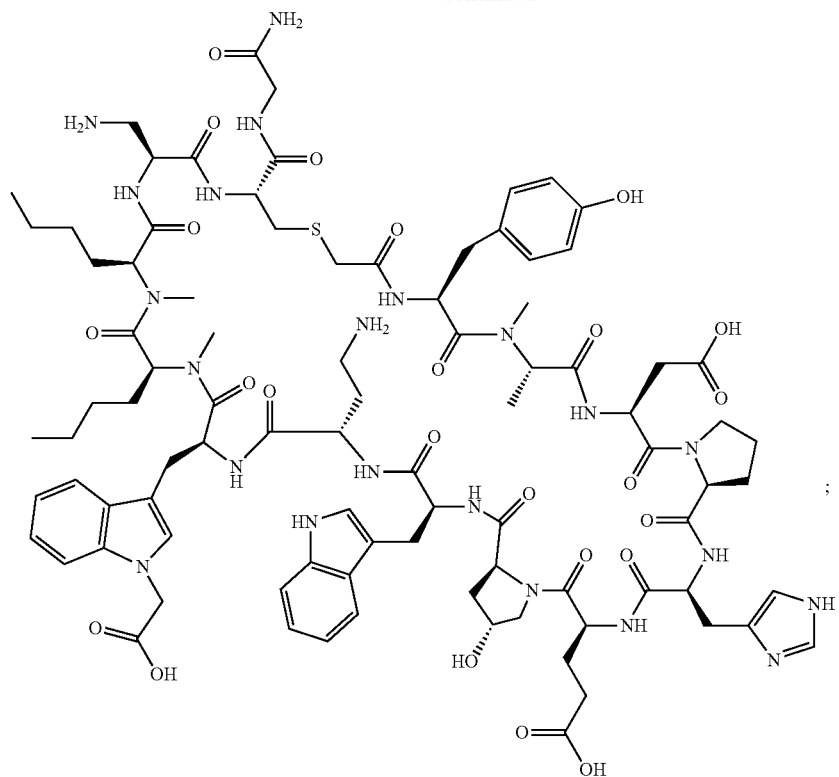
;
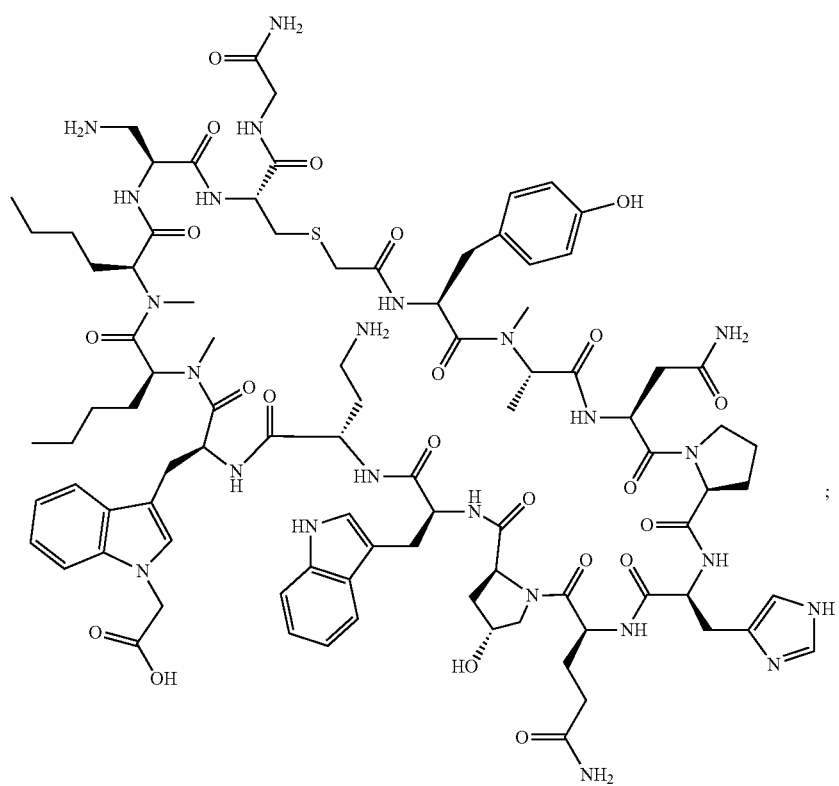
;

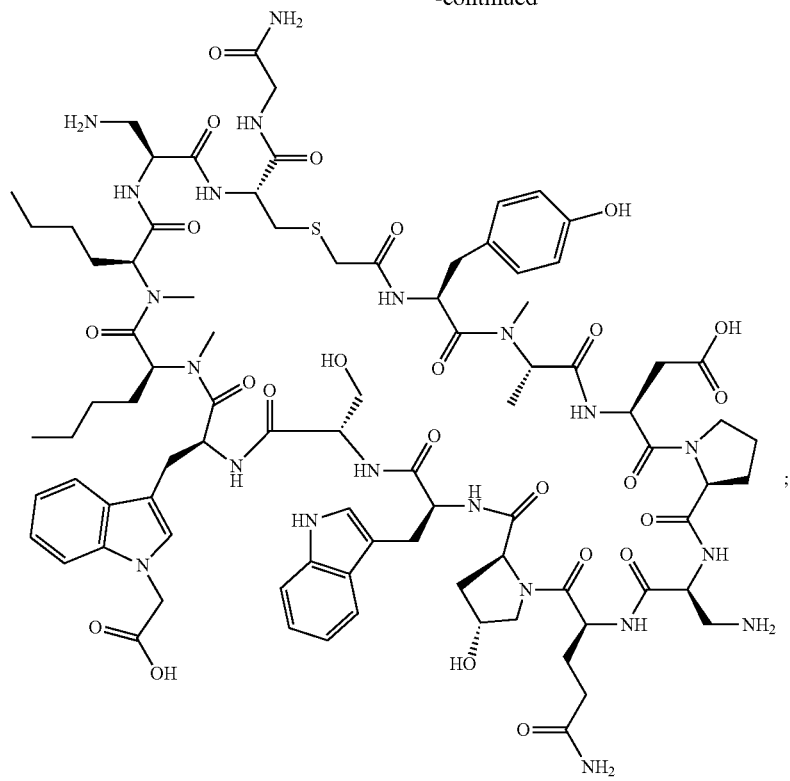
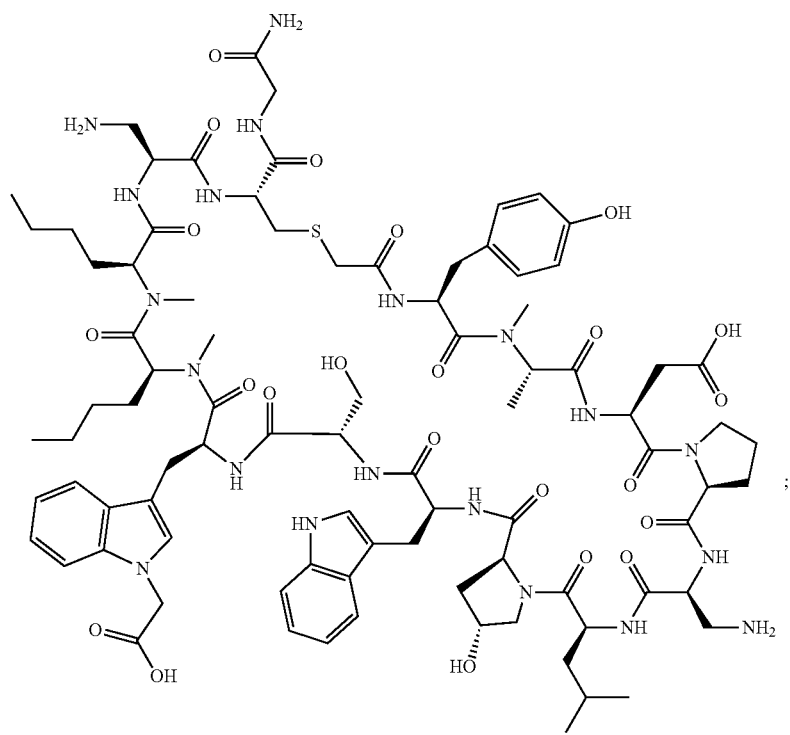

-continued
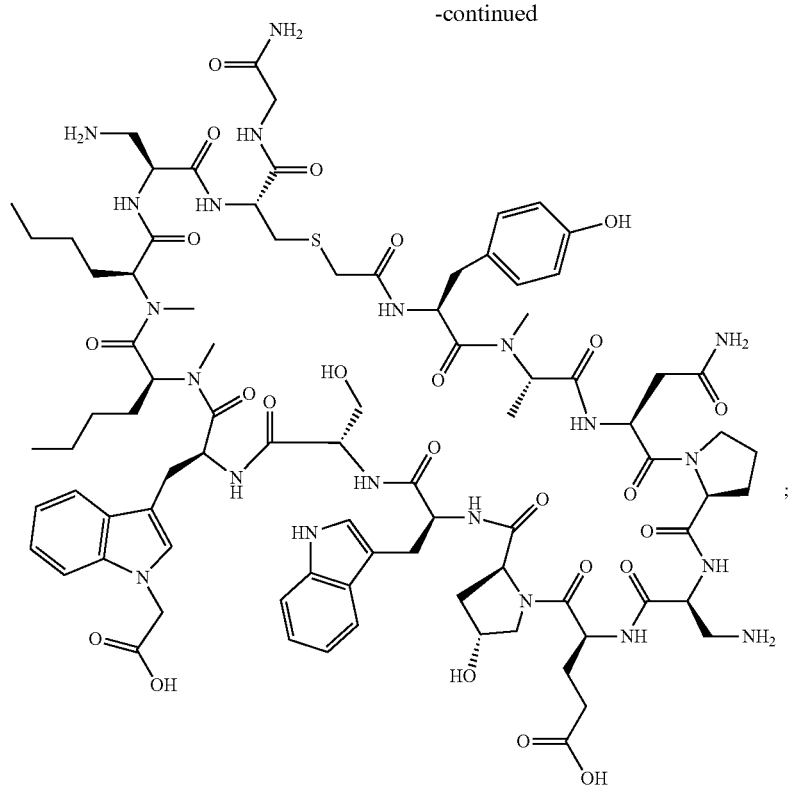
;
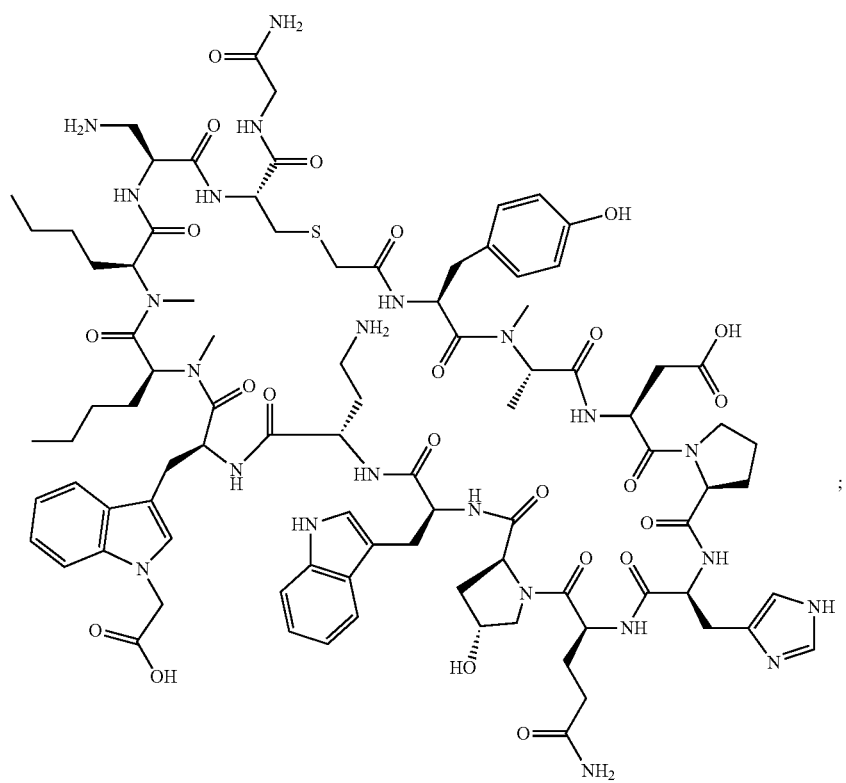
;

-continued
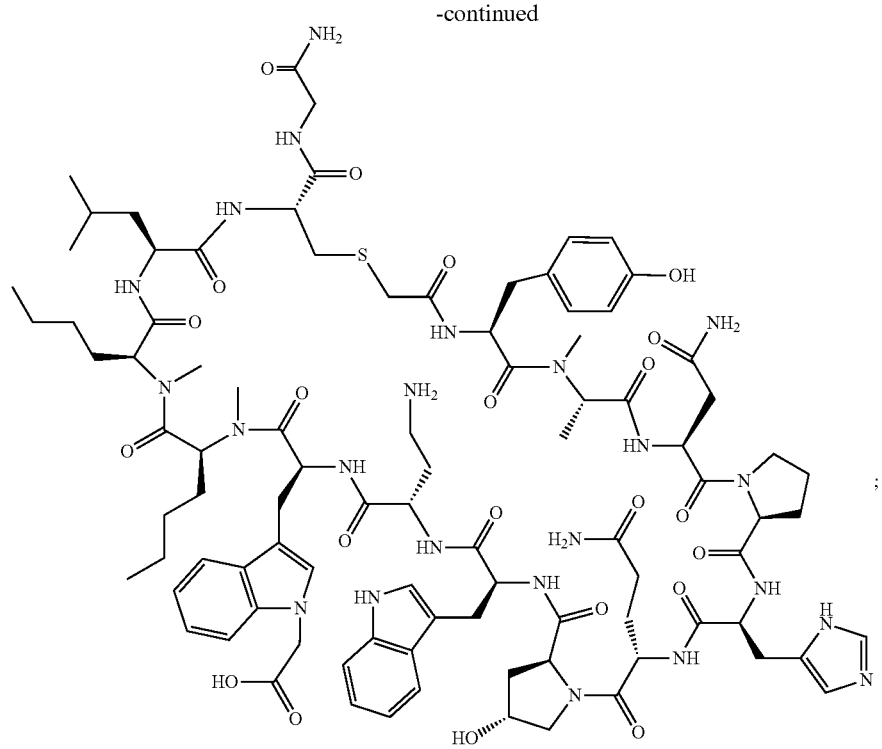
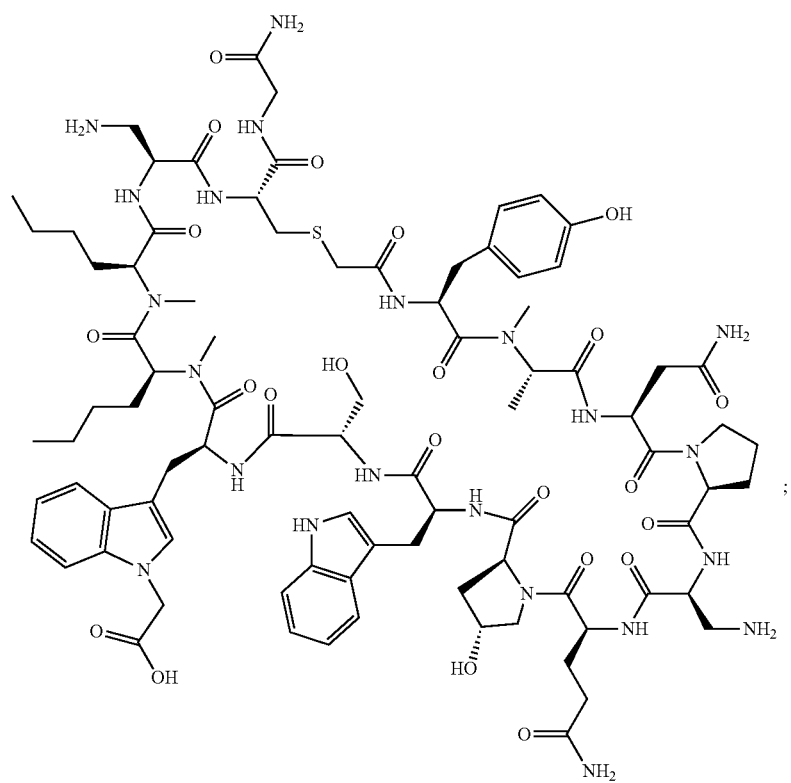

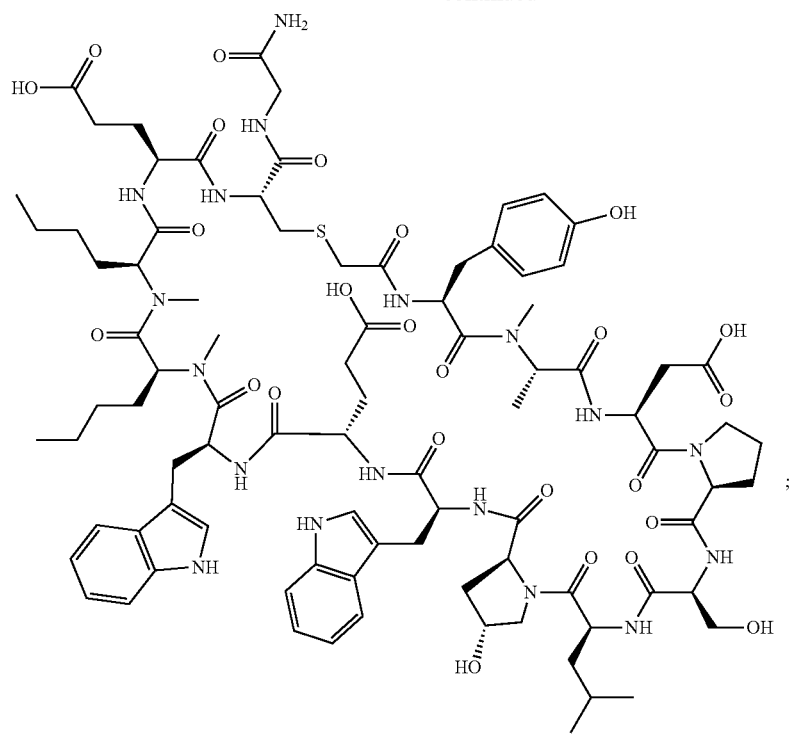
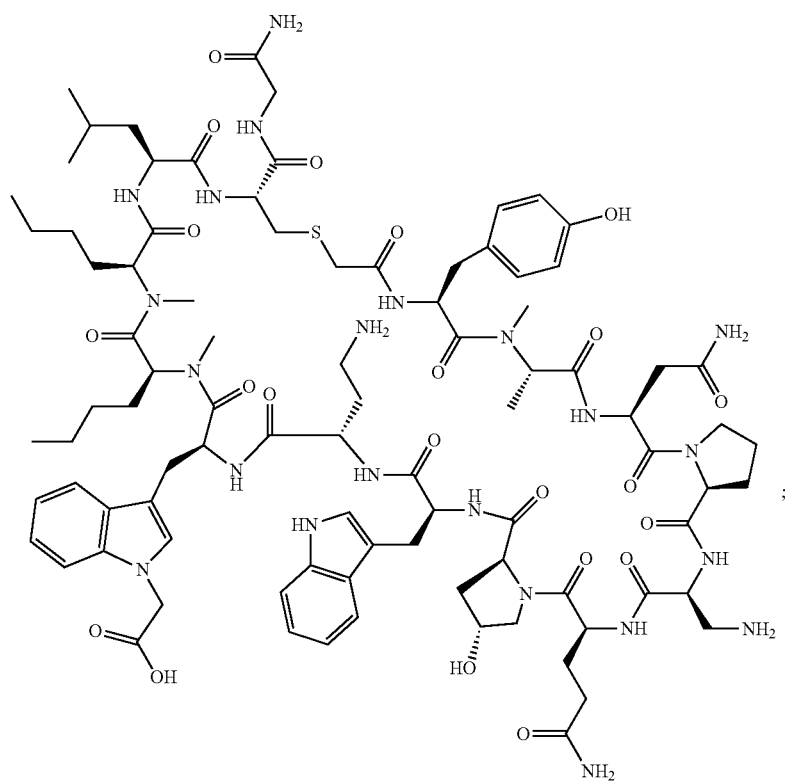

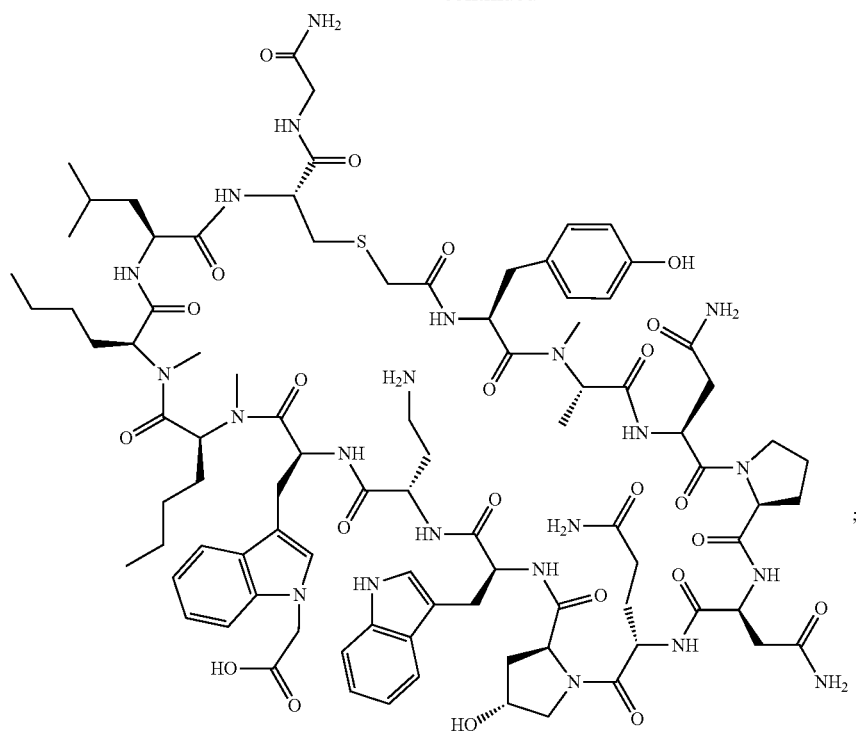
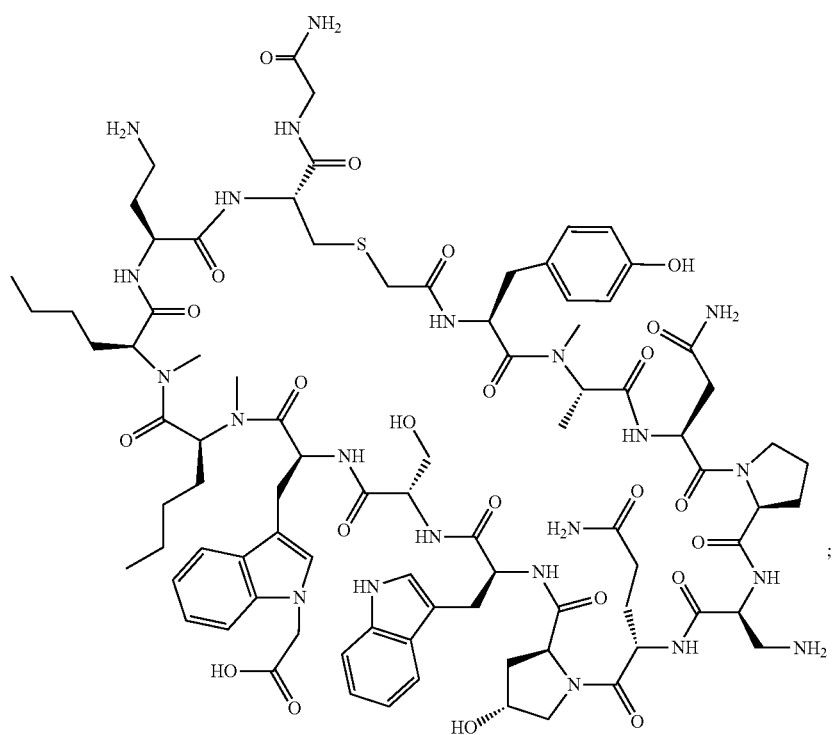

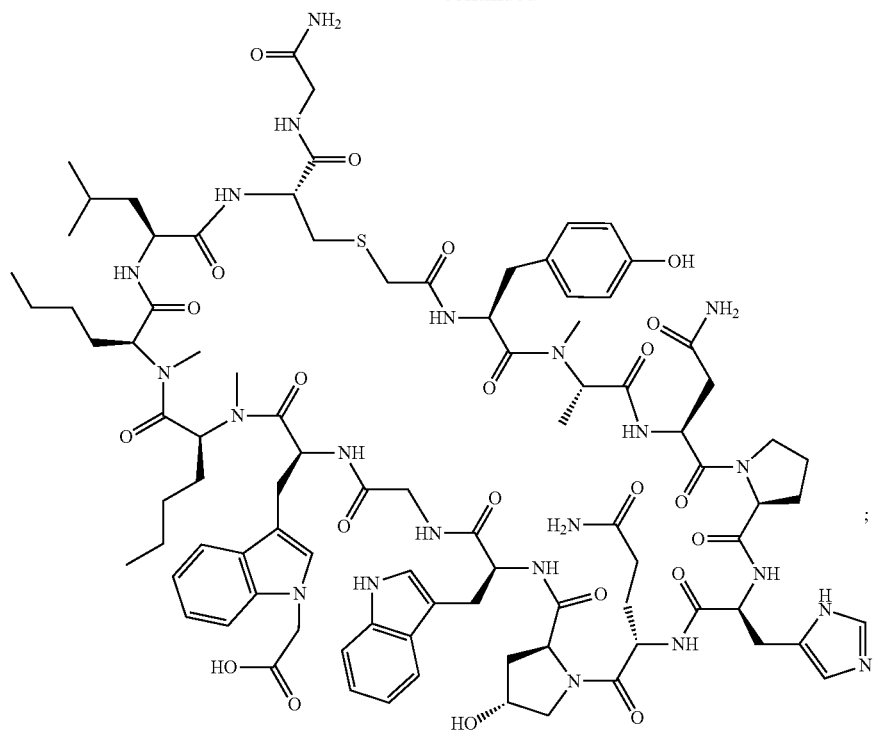
;
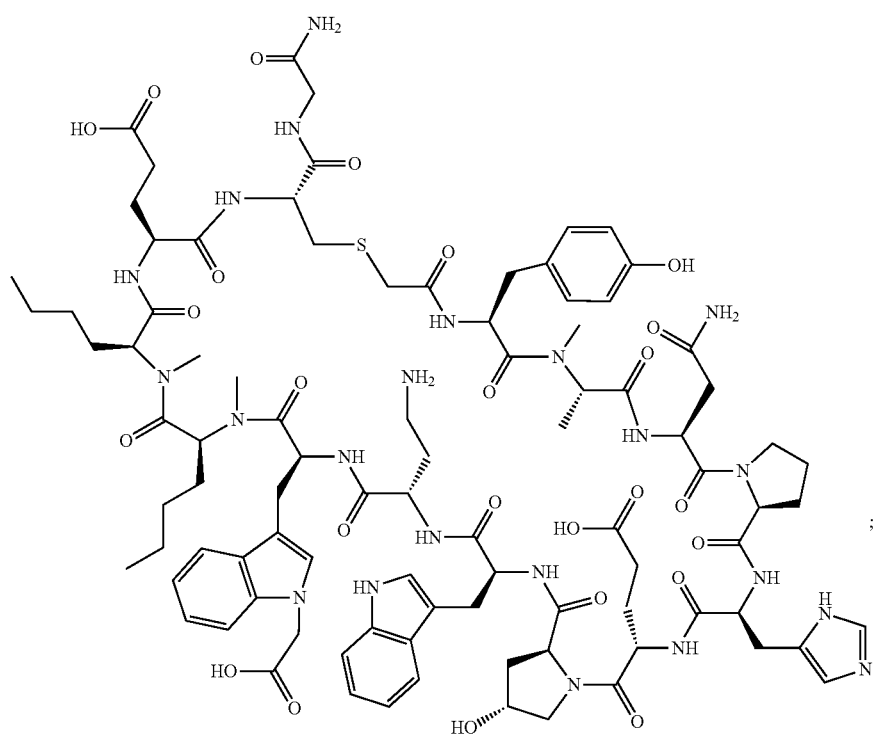
;

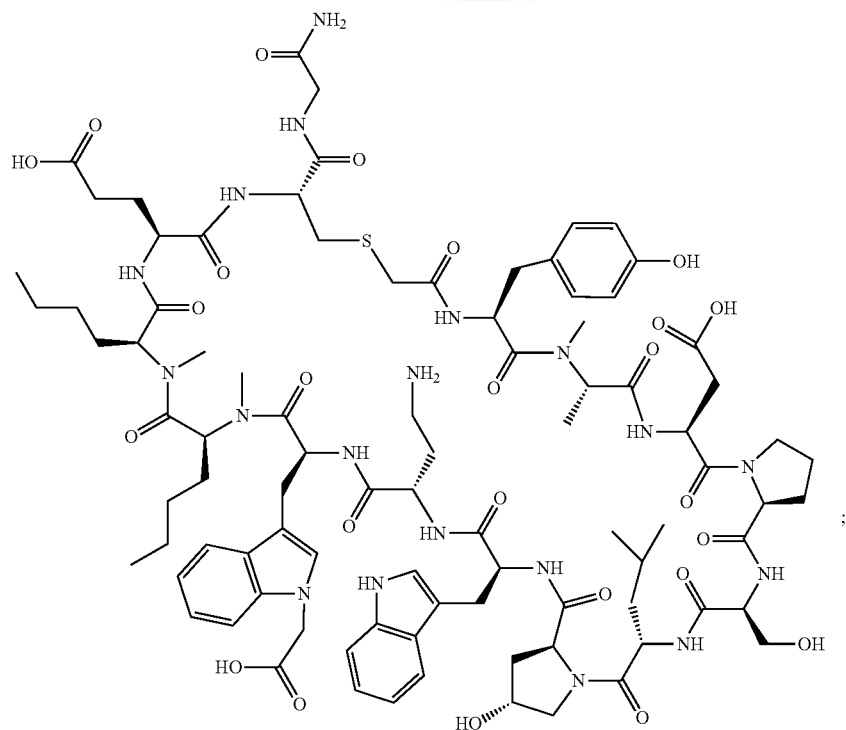
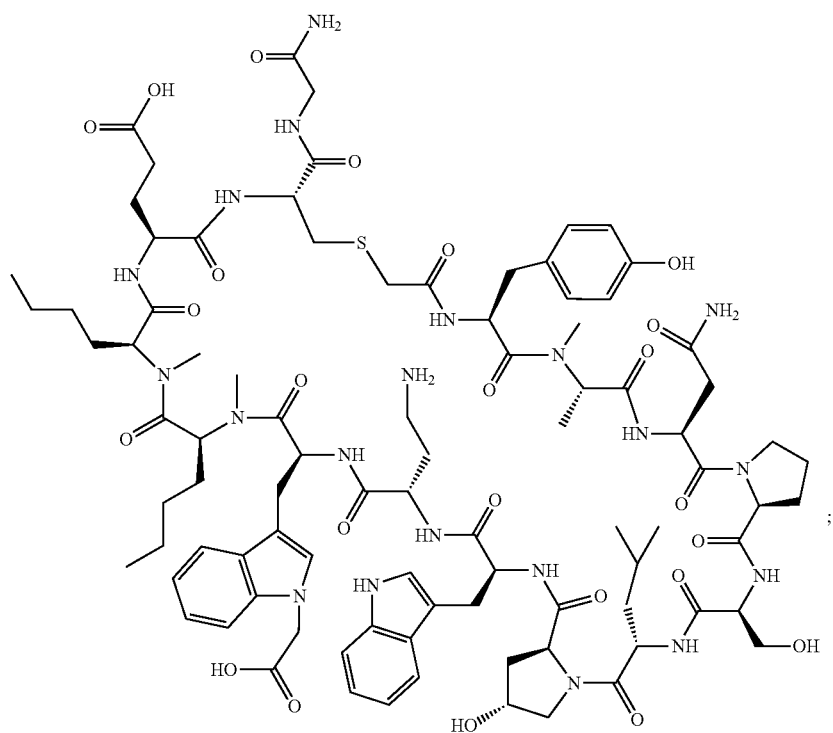

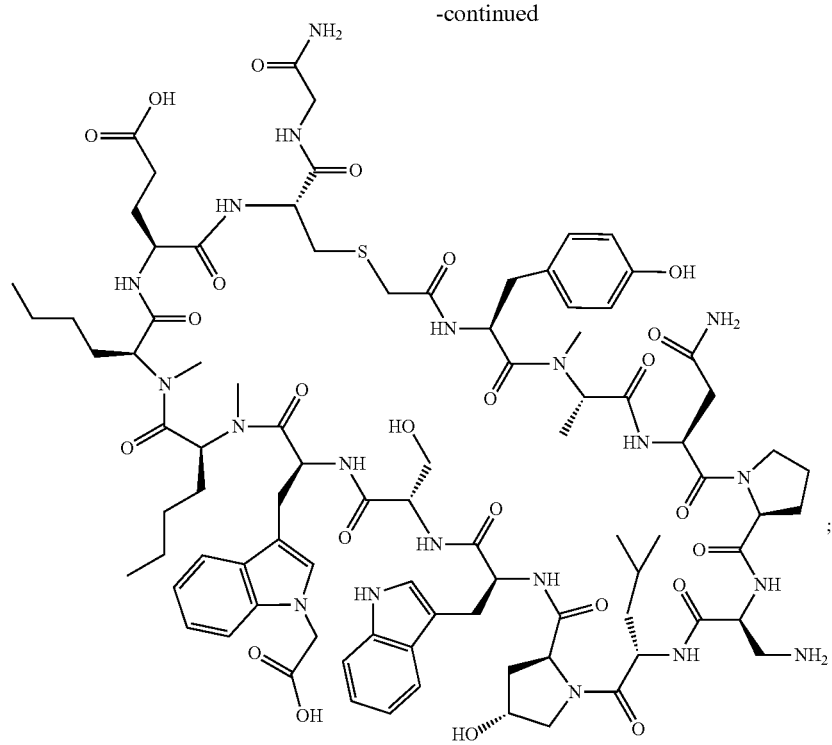
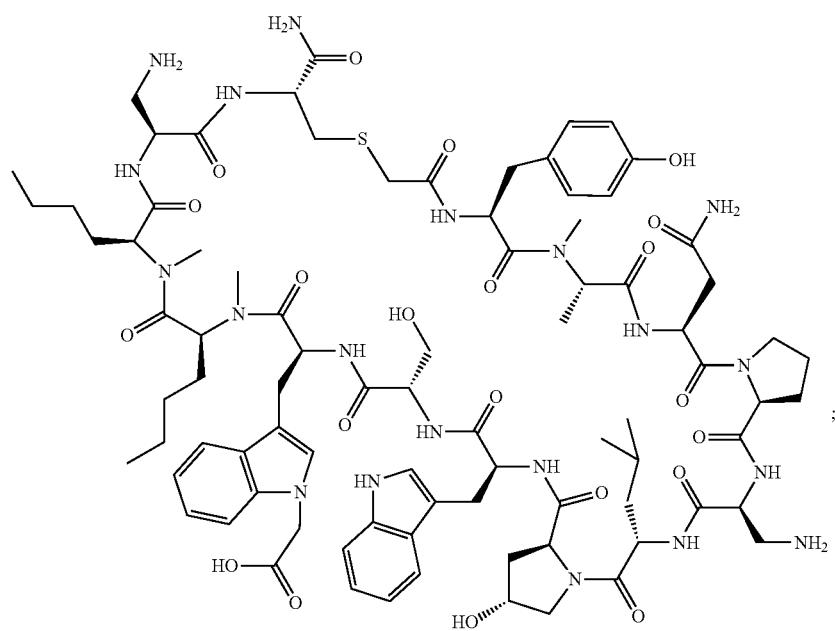

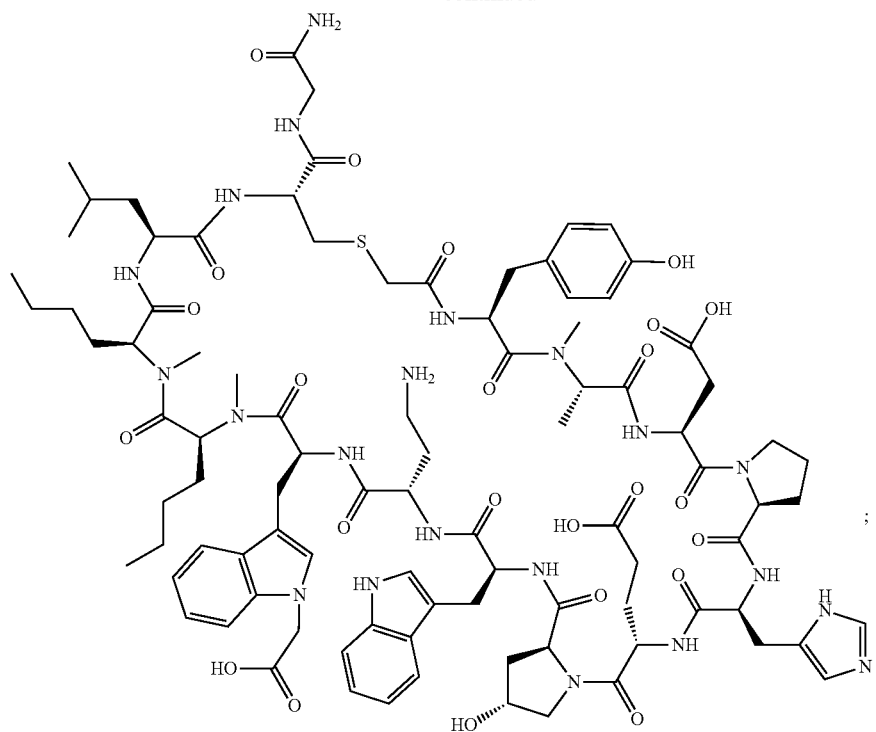
;
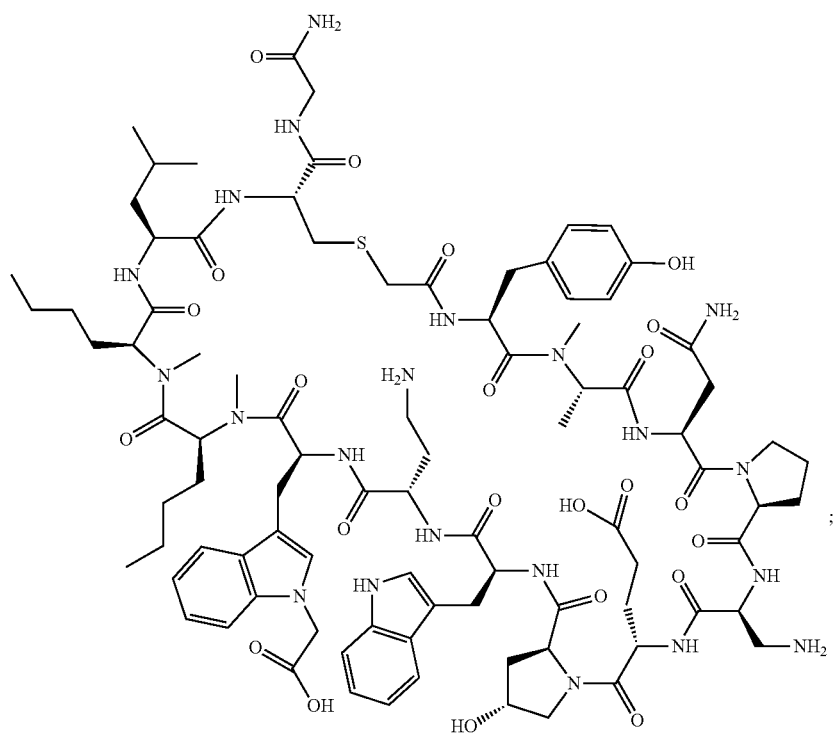
;

-continued
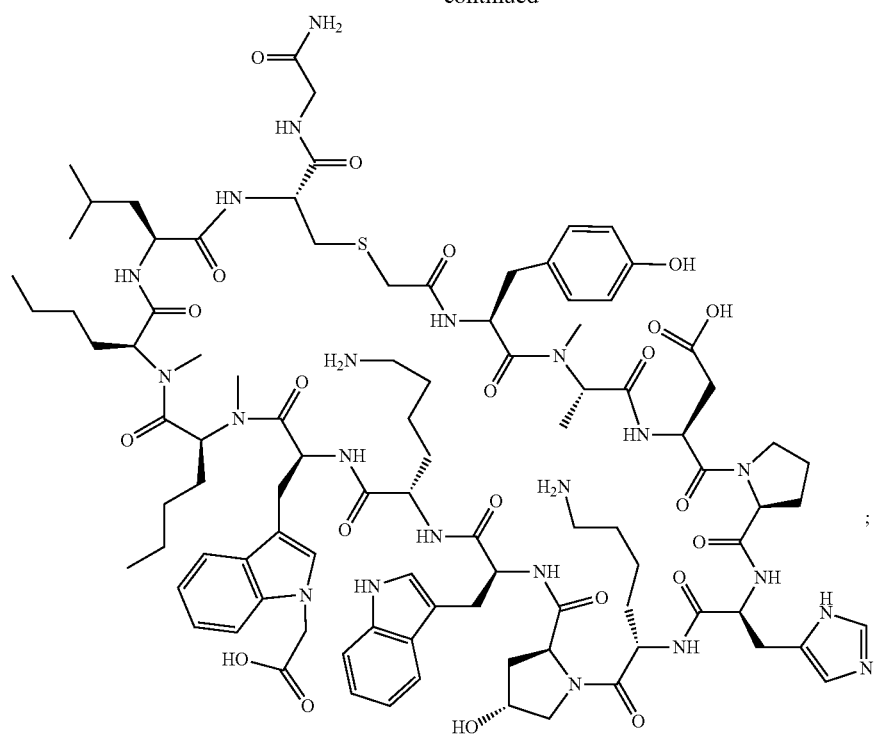
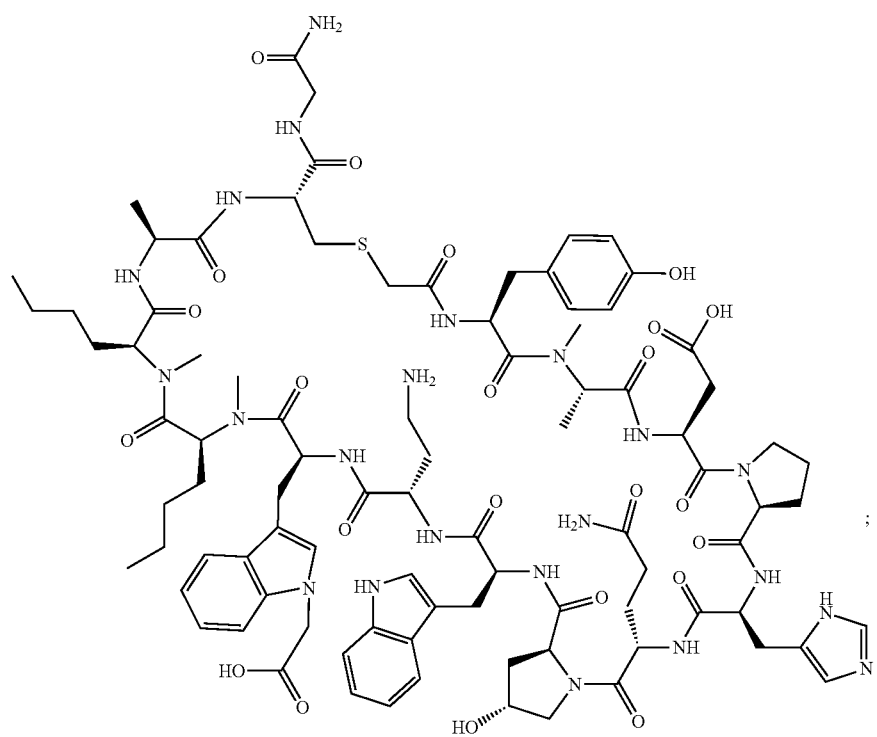

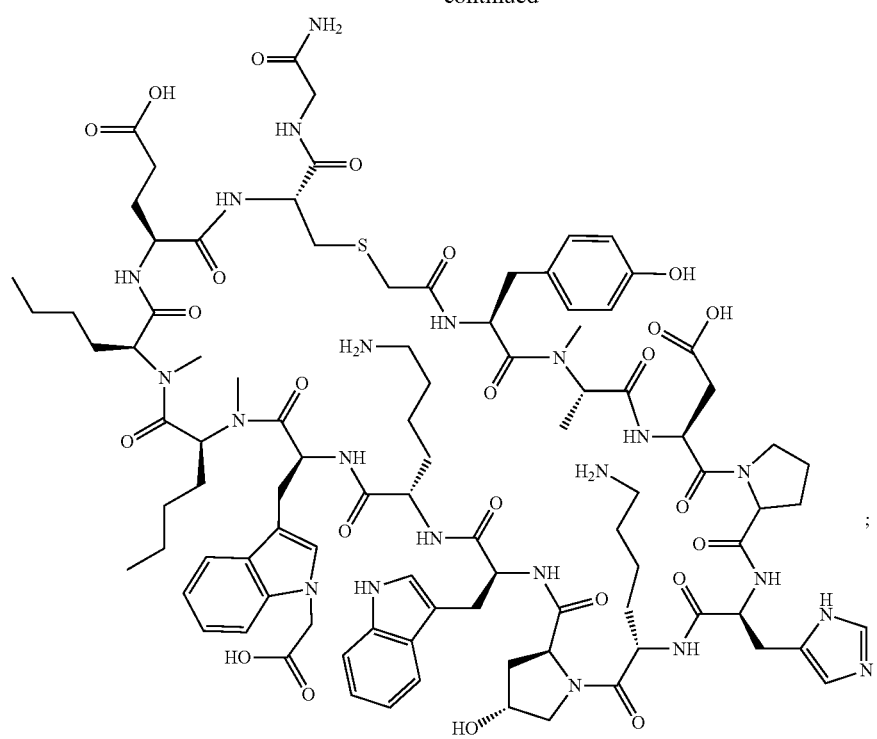
;
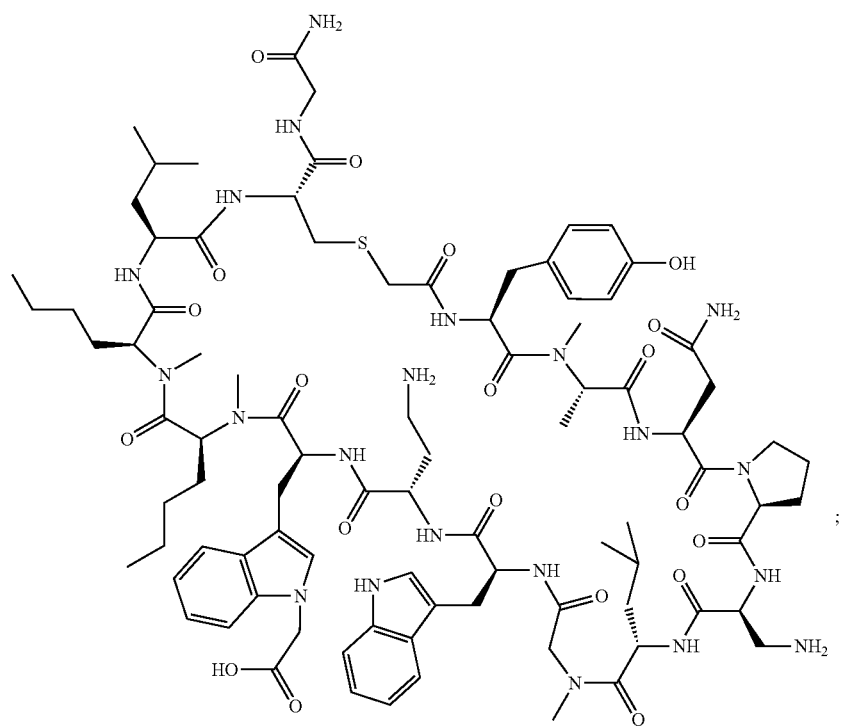
;

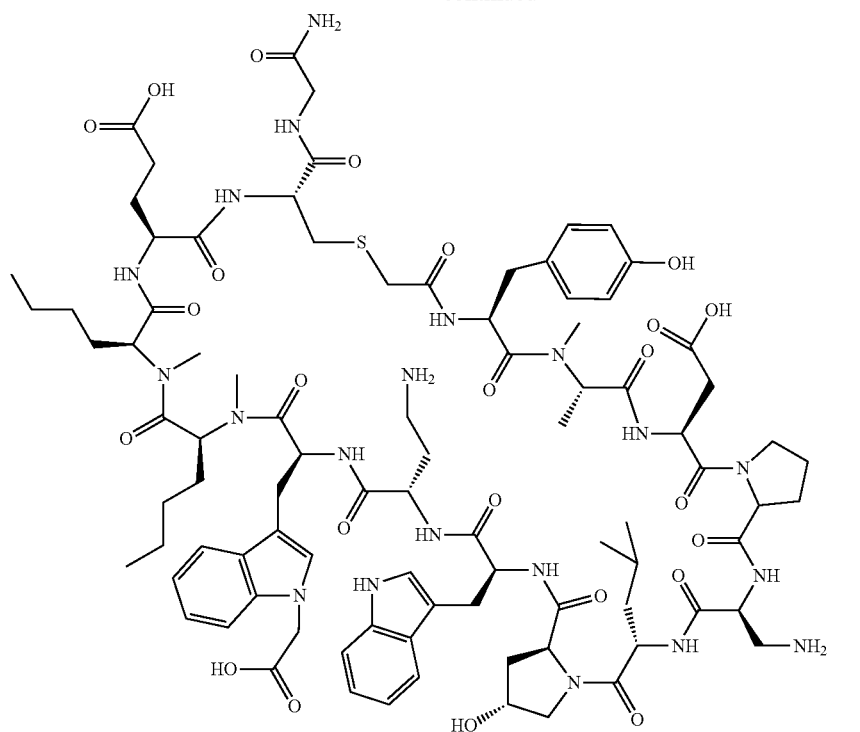
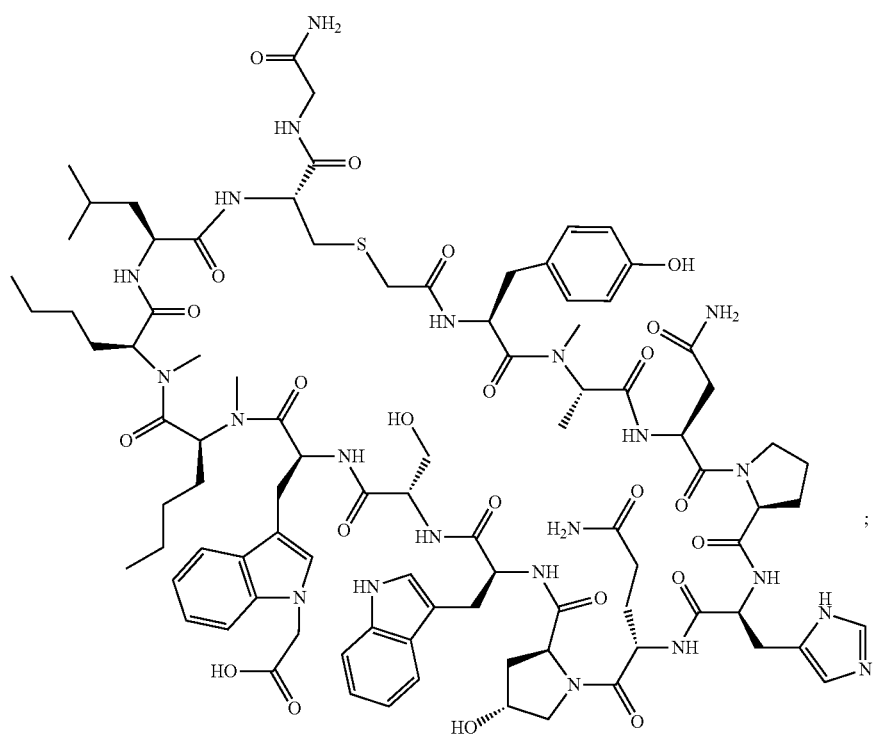

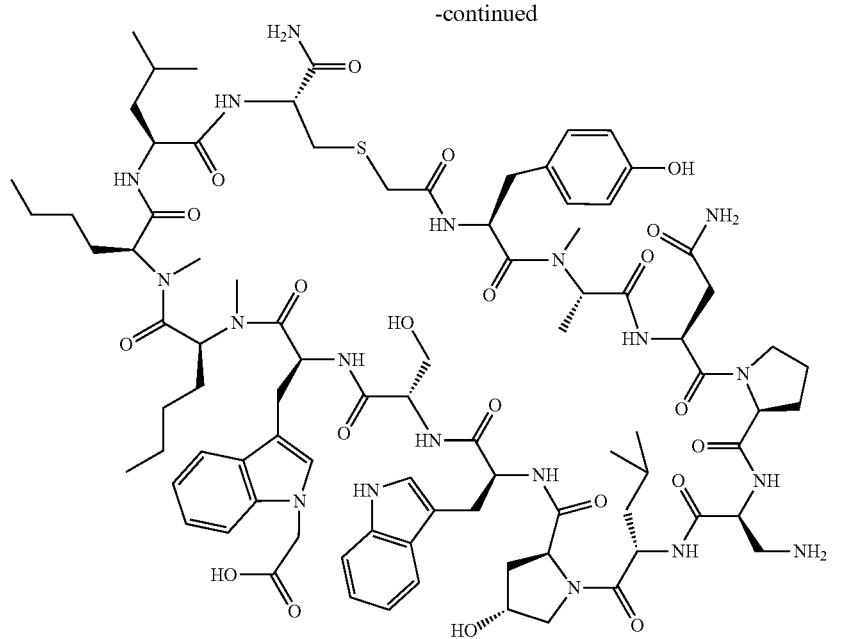
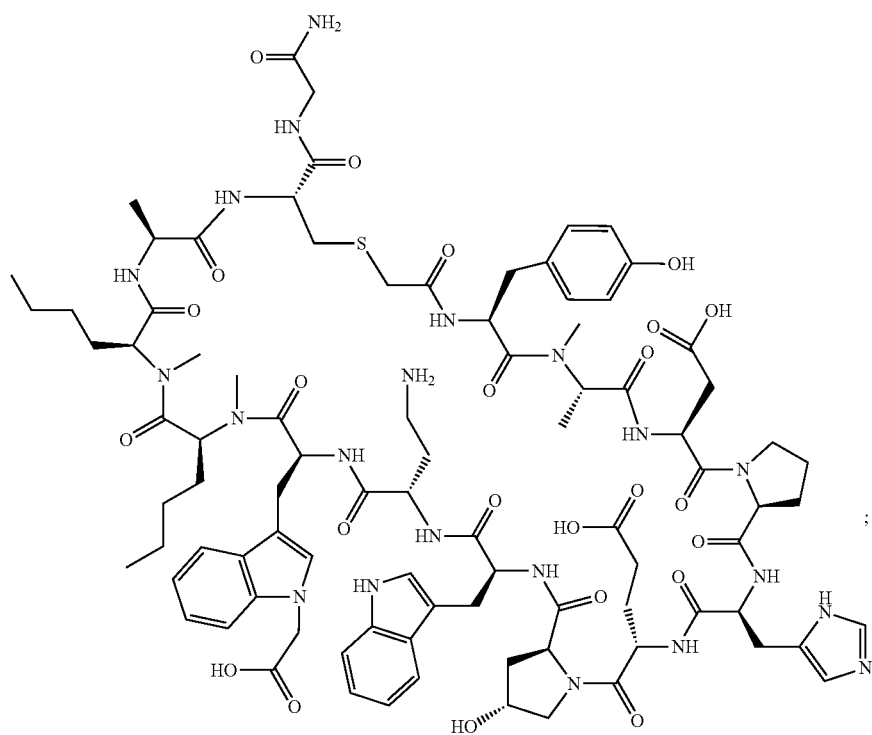

-continued
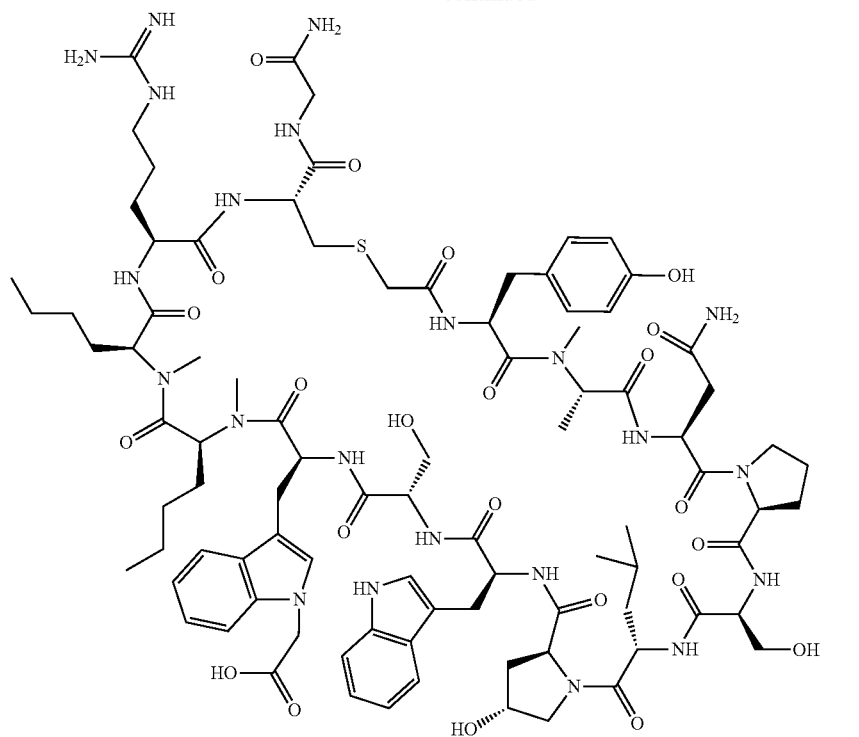
;
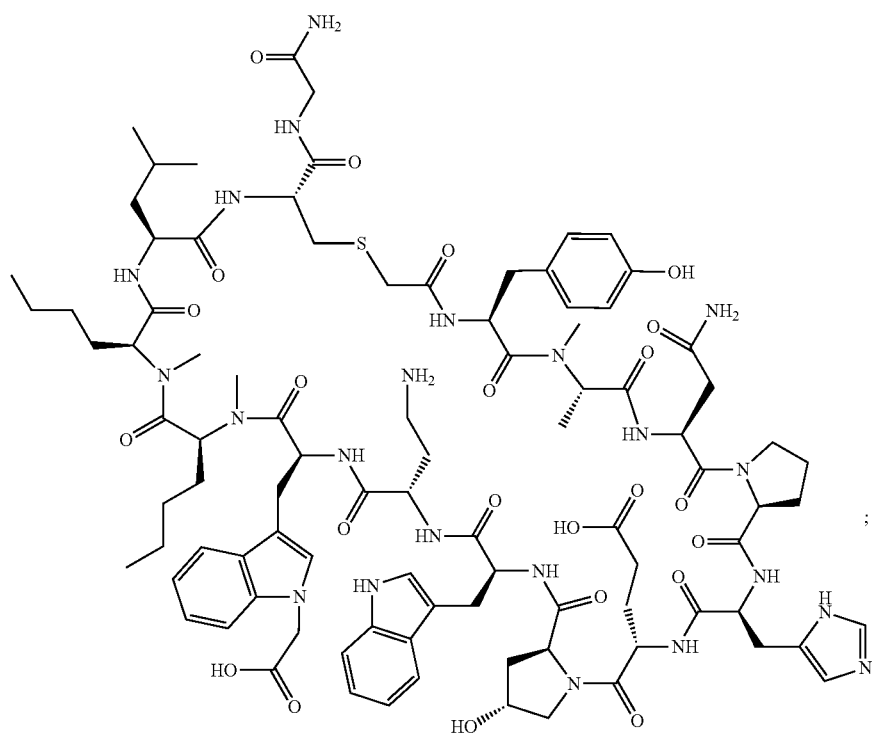
;

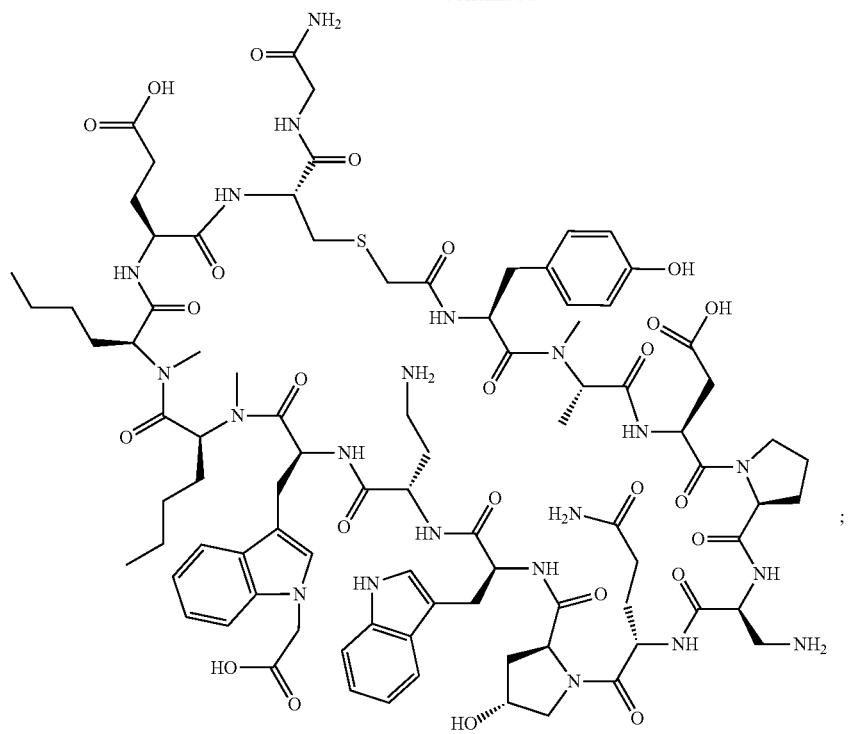
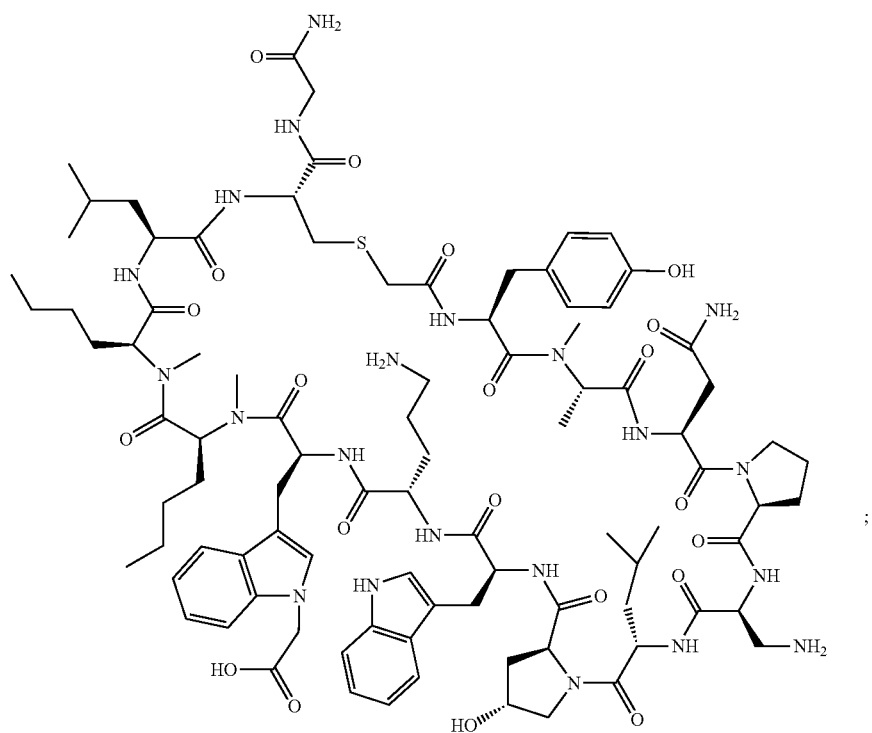

-continued
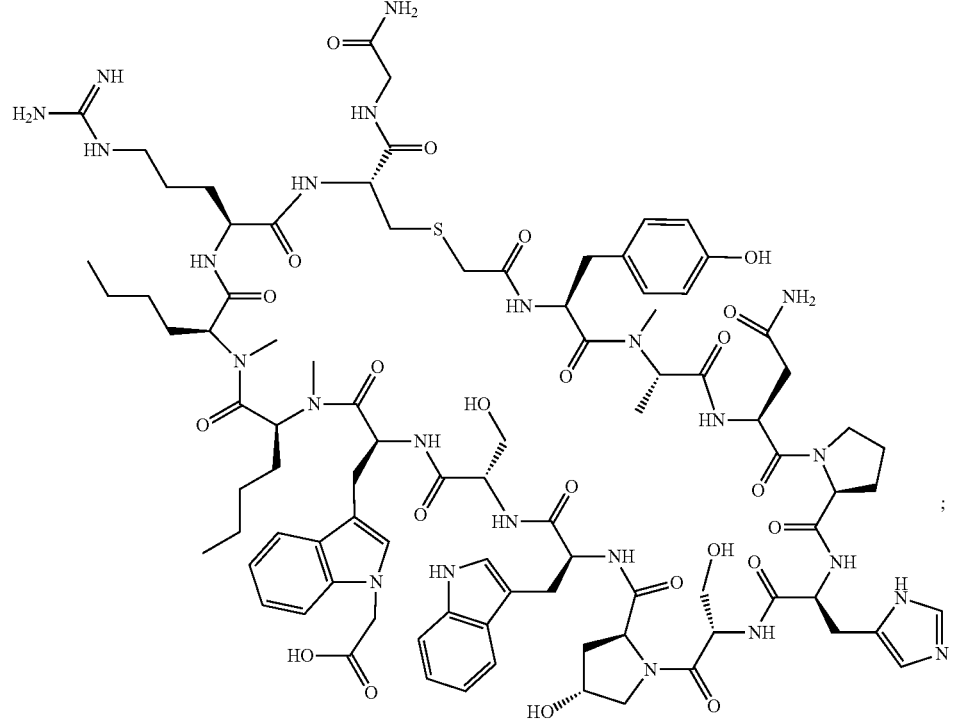
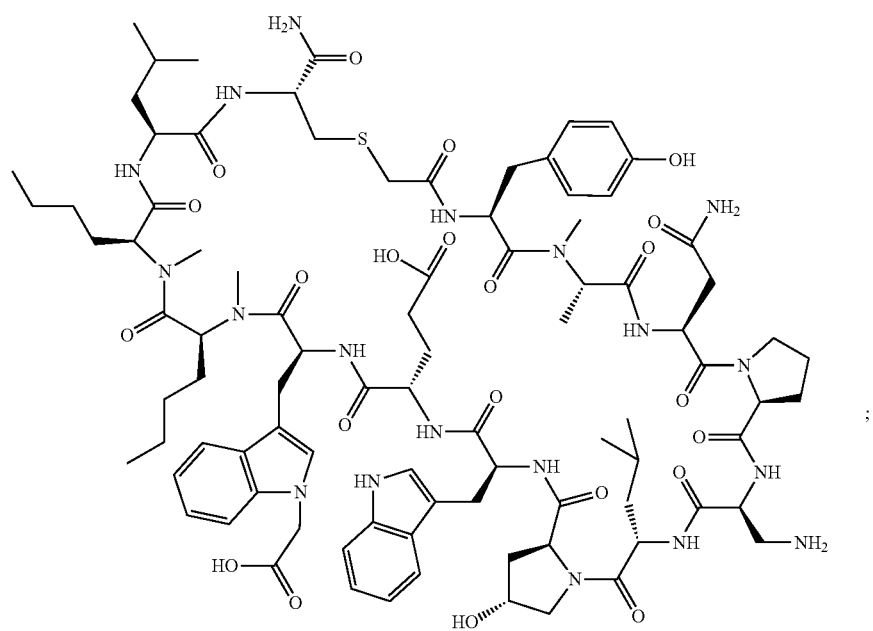

-continued
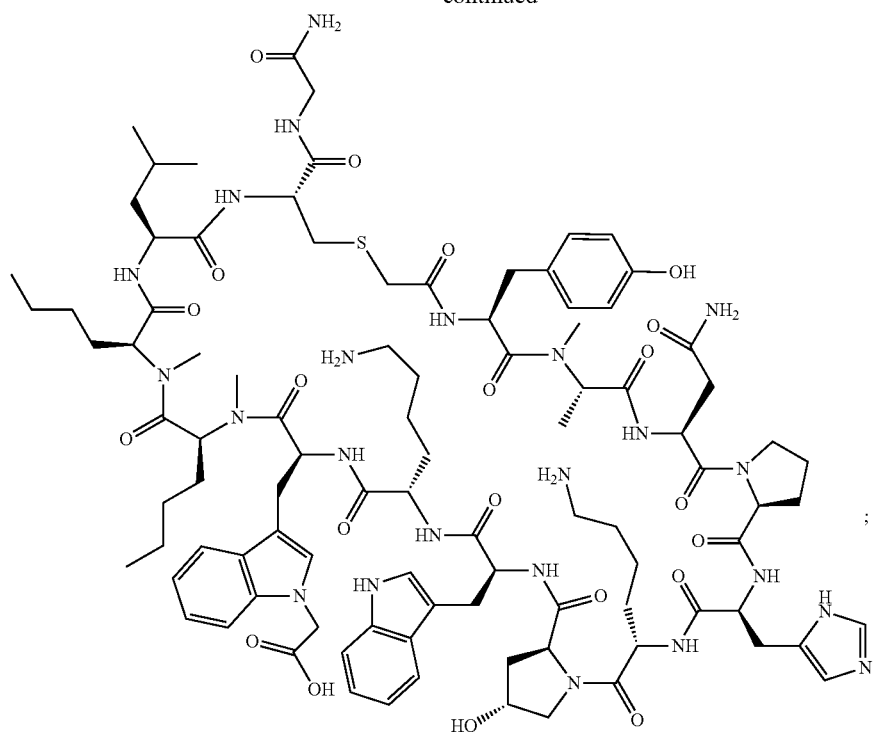
;
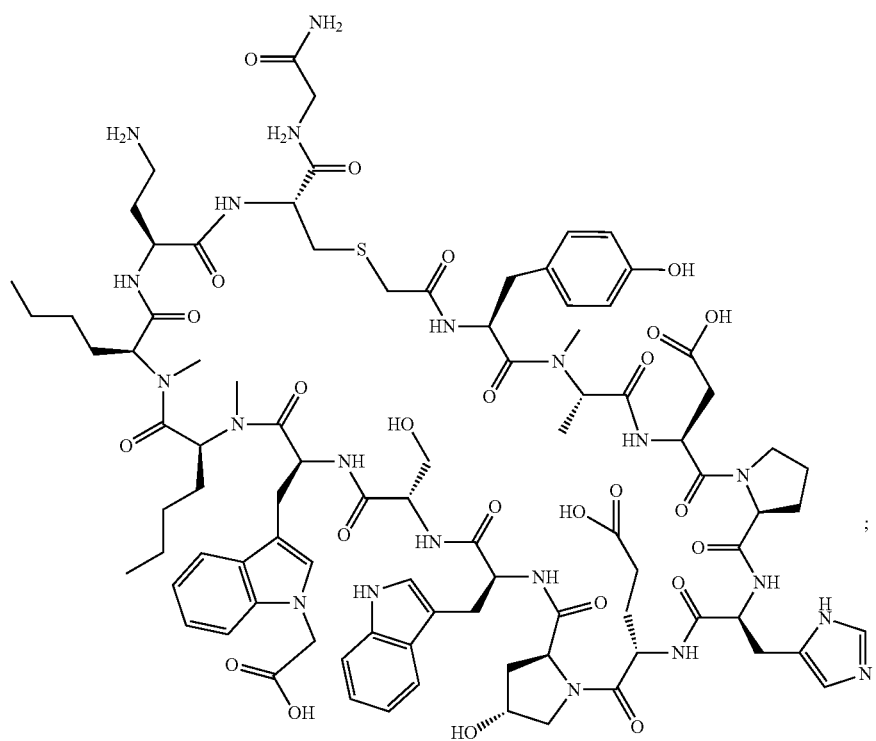
;

1005
-continued
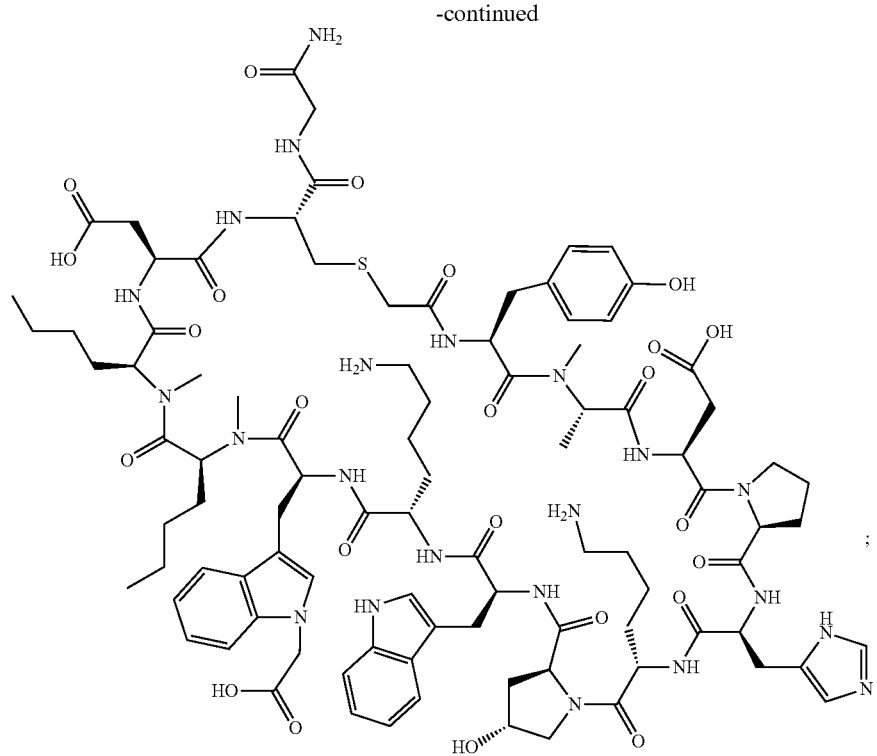
;
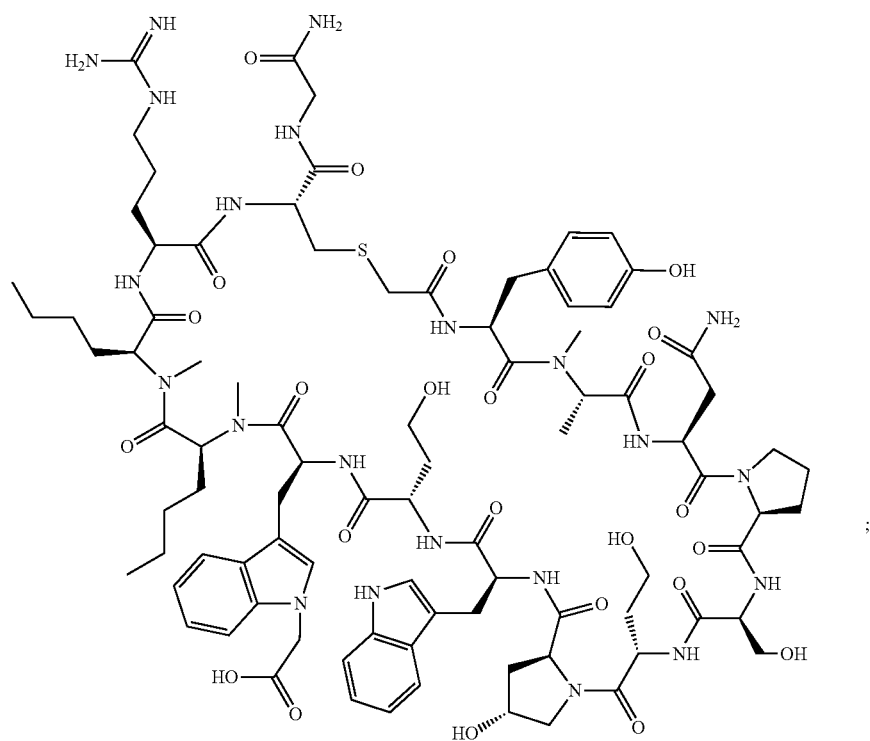
;

1007
-continued
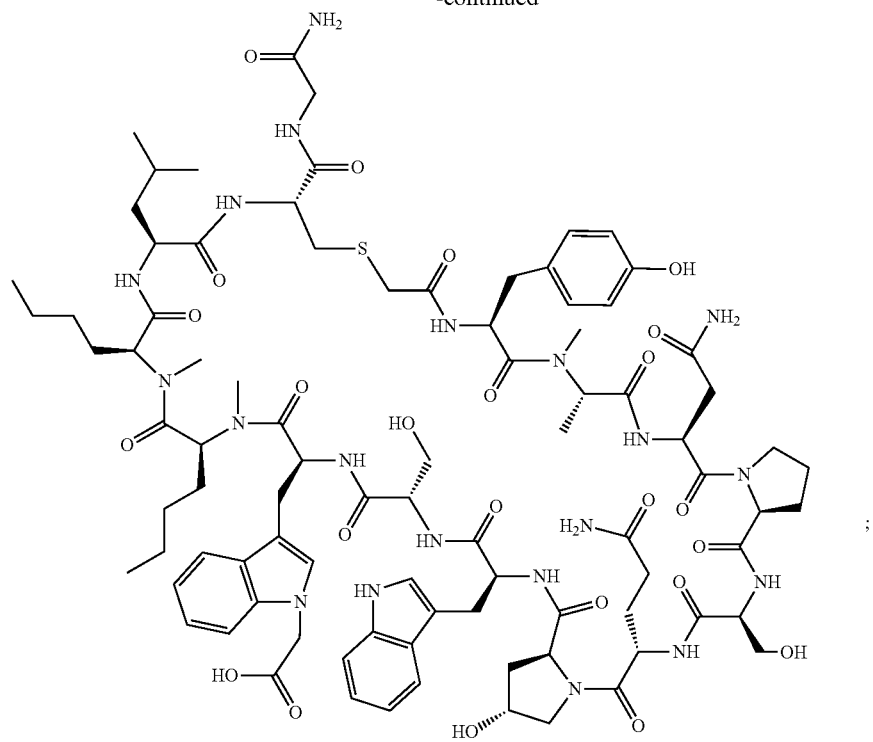
;
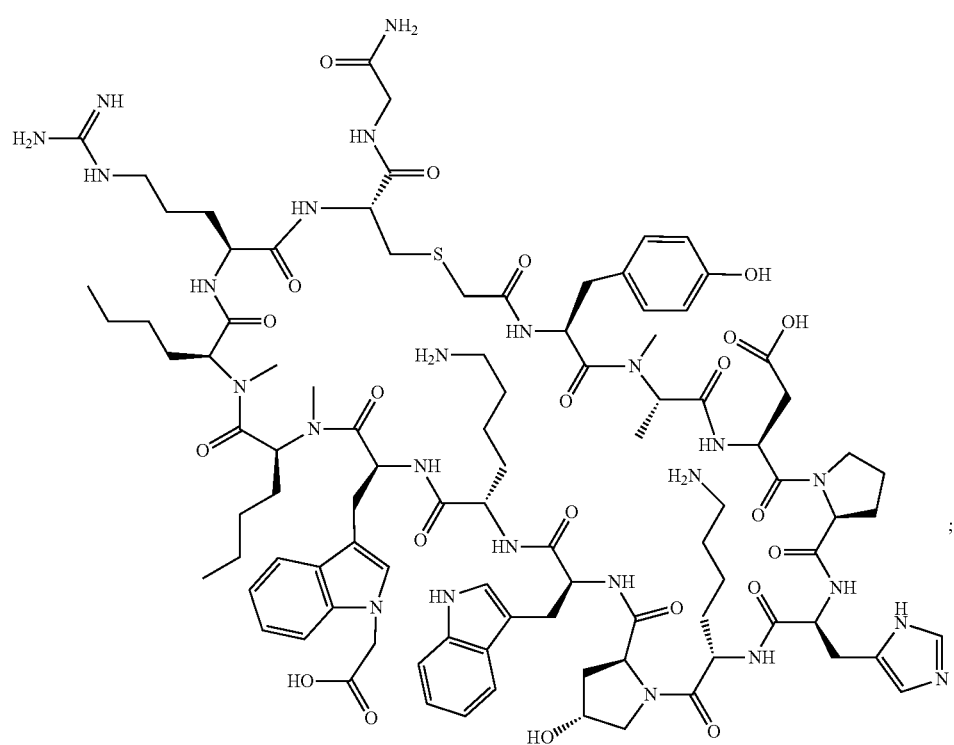 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](Cc2cnc[nH]2)C(=O)N[C@@H](CCCCN)C(=O)N2C[C@H](O)C[C@H]2C(=O)N[C@@H](Cc2c[nH]c3ccccc23)C(=O)N[C@@H](CCCCN)C(=O)N[C@@H](Cc2cn(CC(=O)O)c3ccccc23)C(=O)N1C]
;

1009
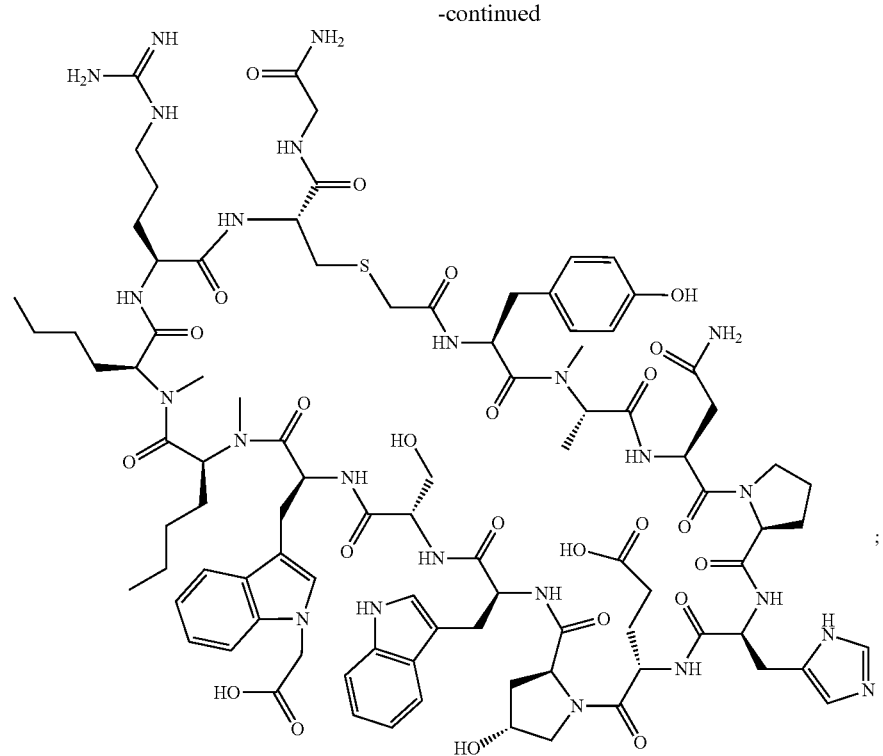
;
1010
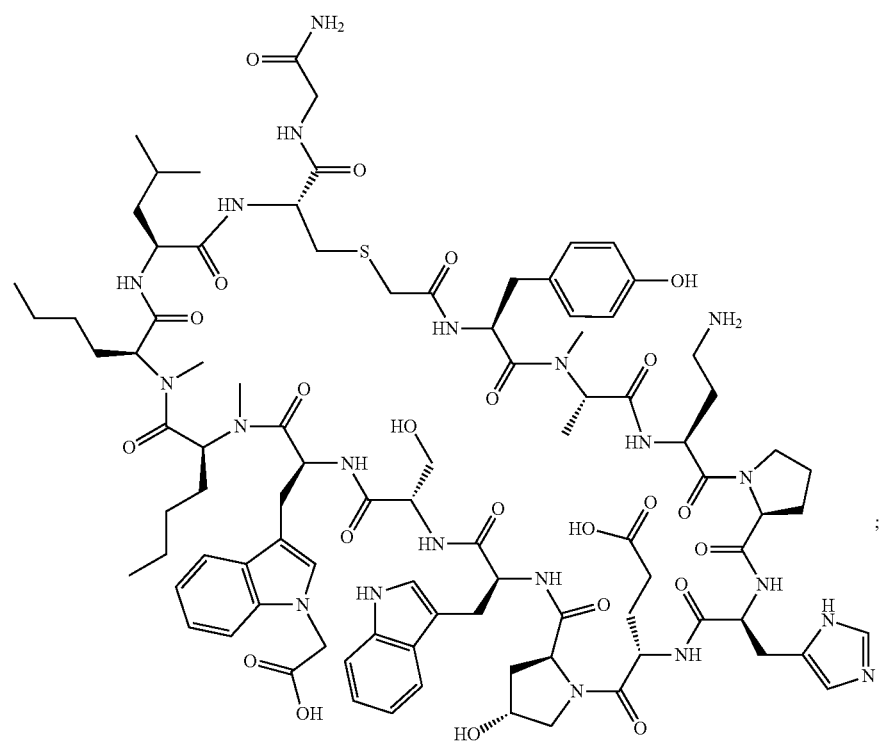
;

-continued
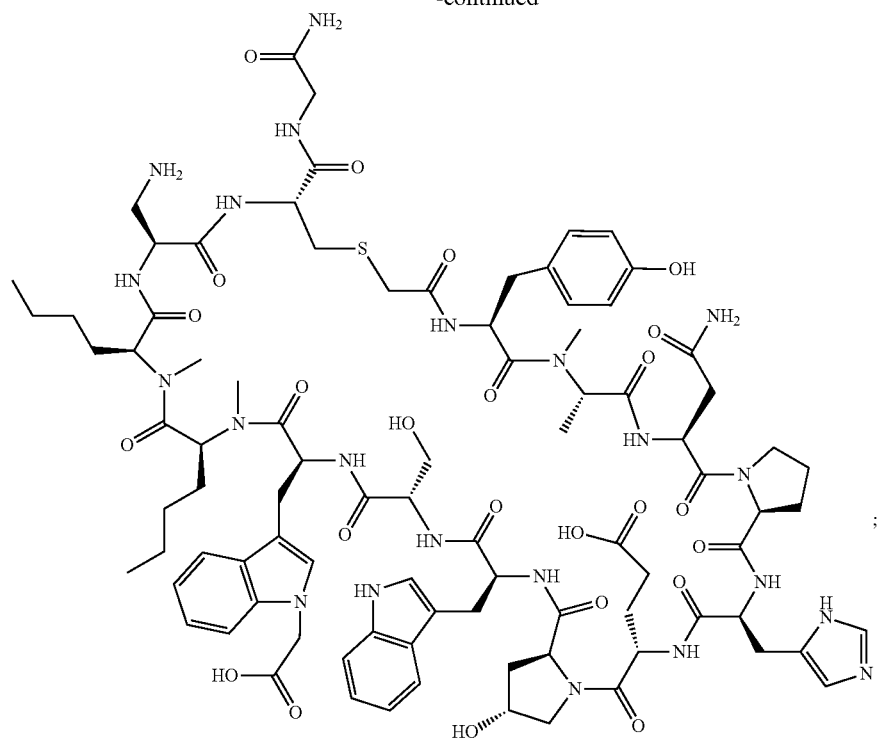
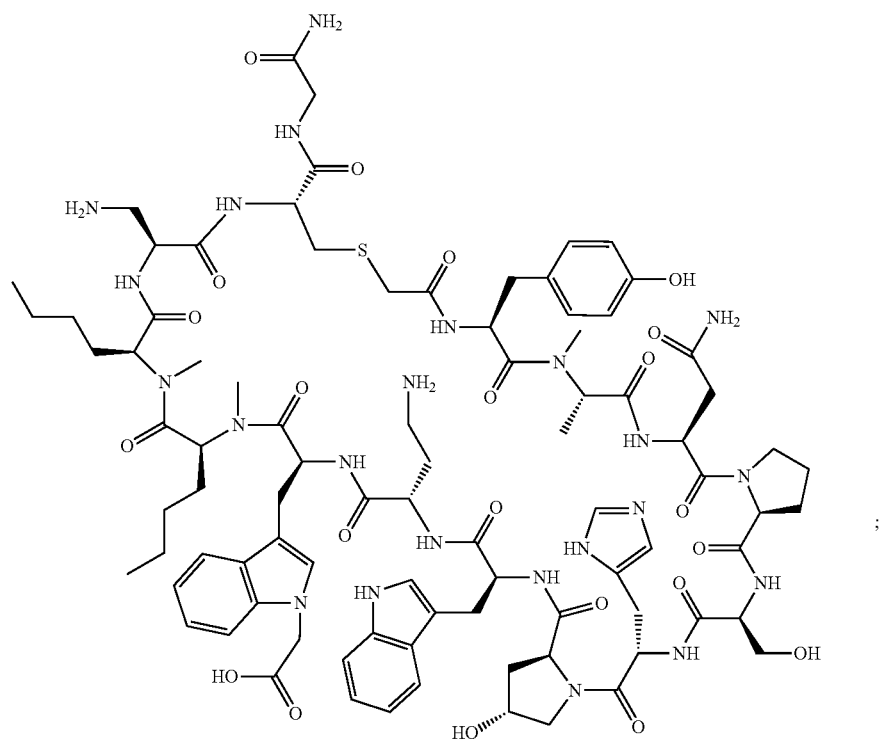

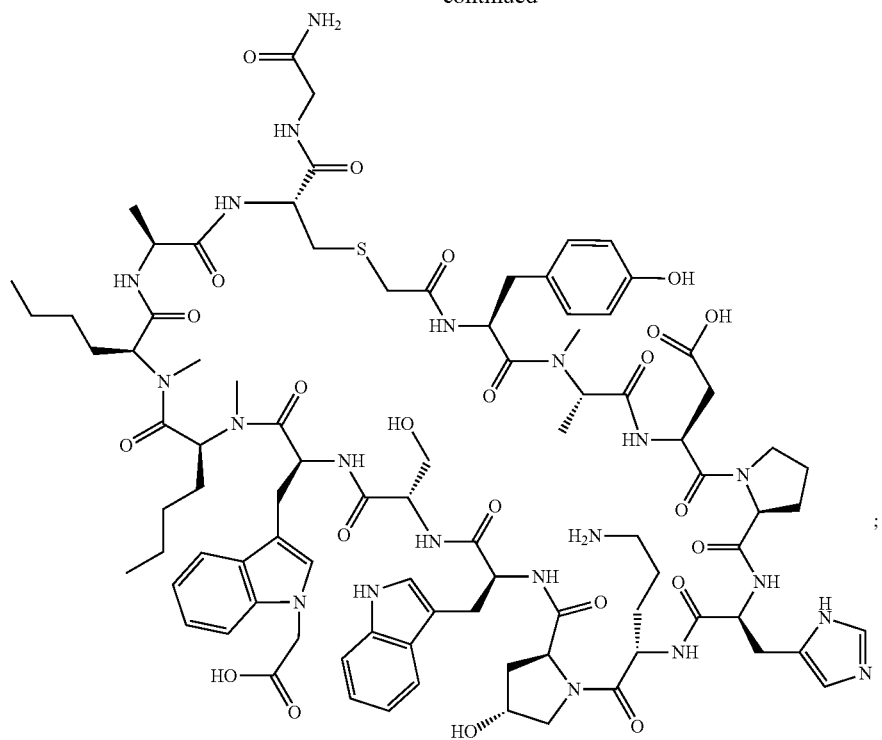
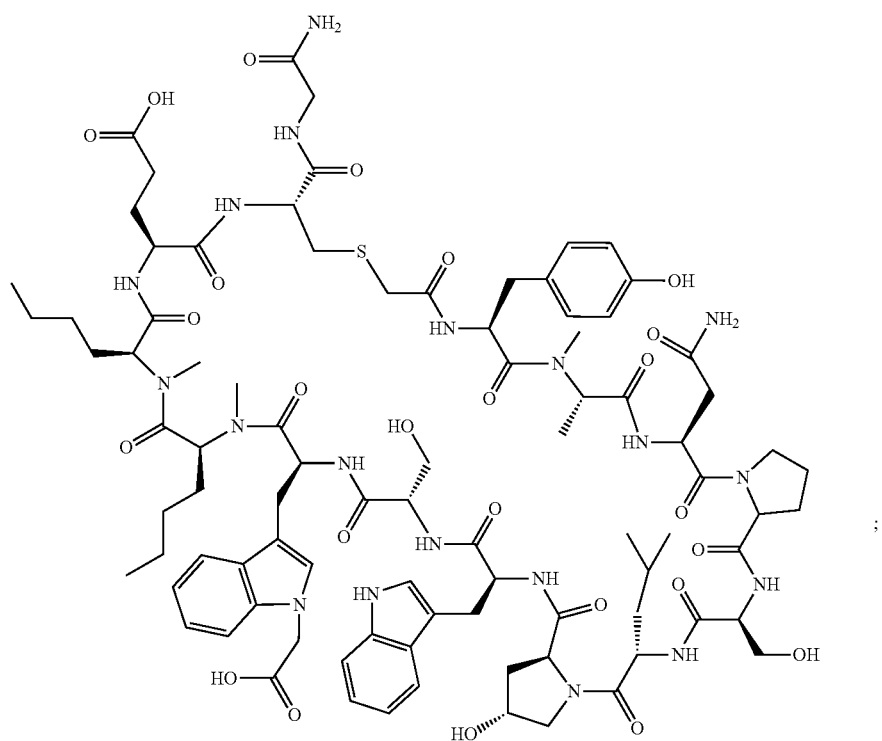

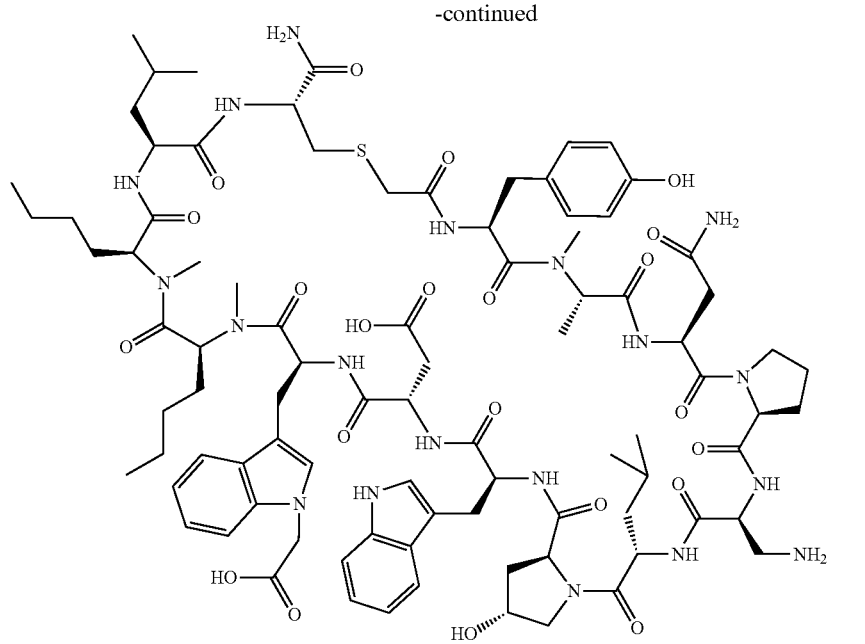
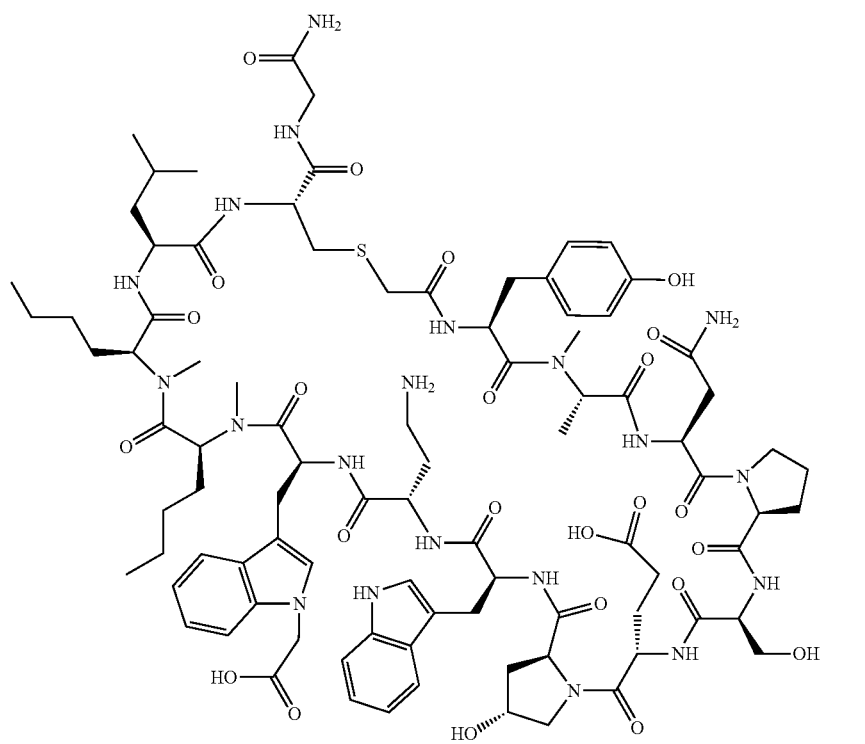

-continued
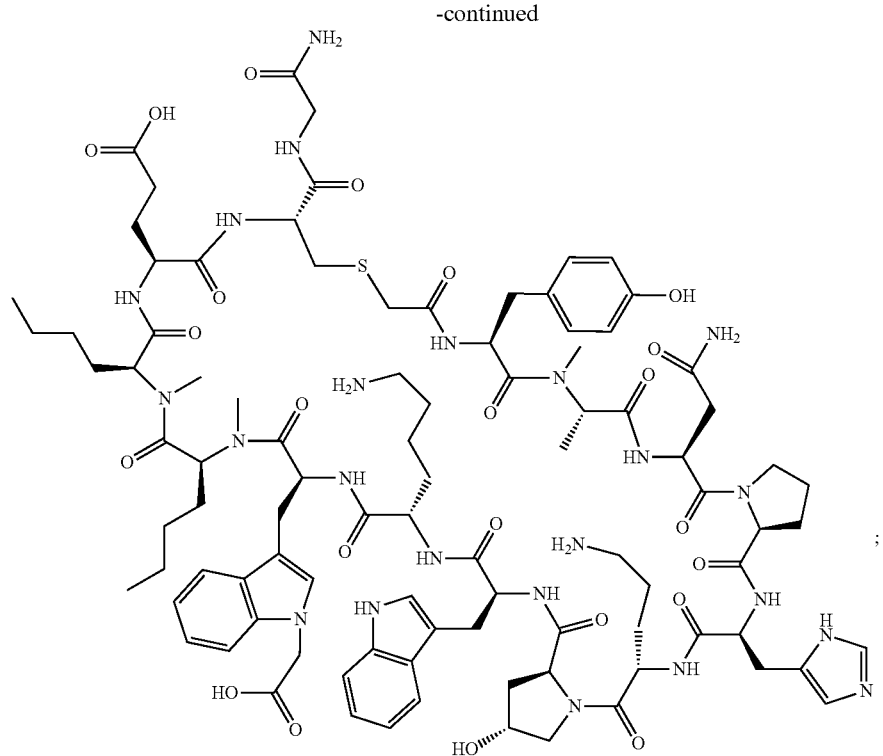
;
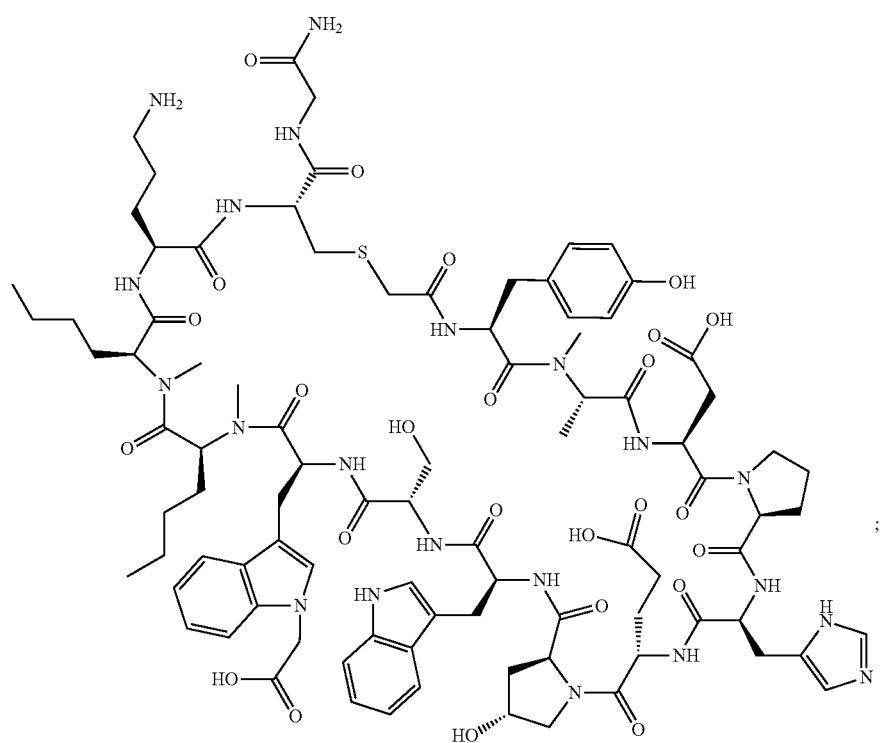
;

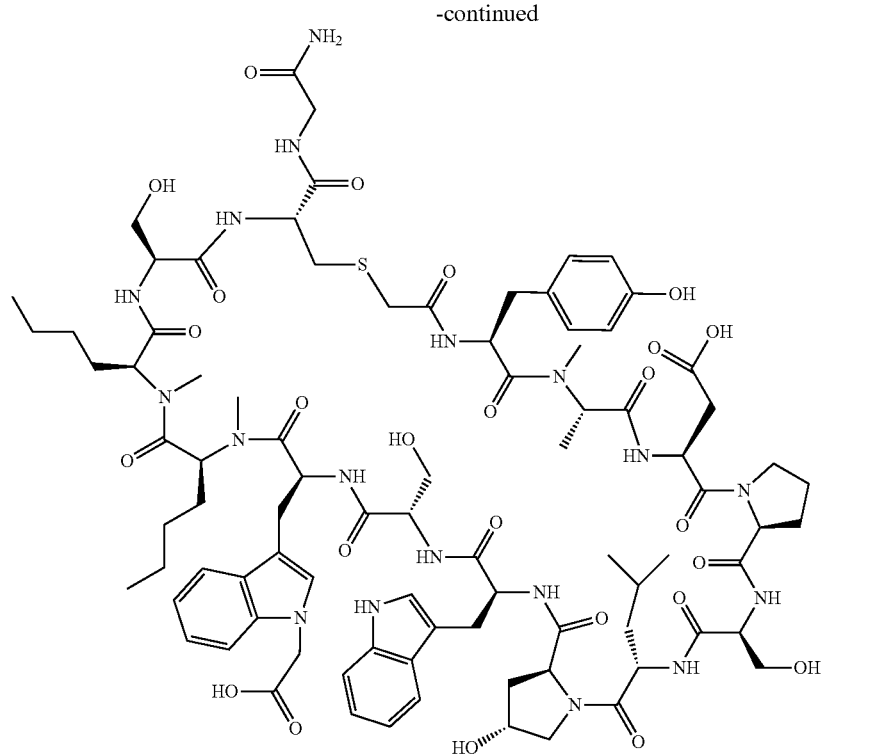
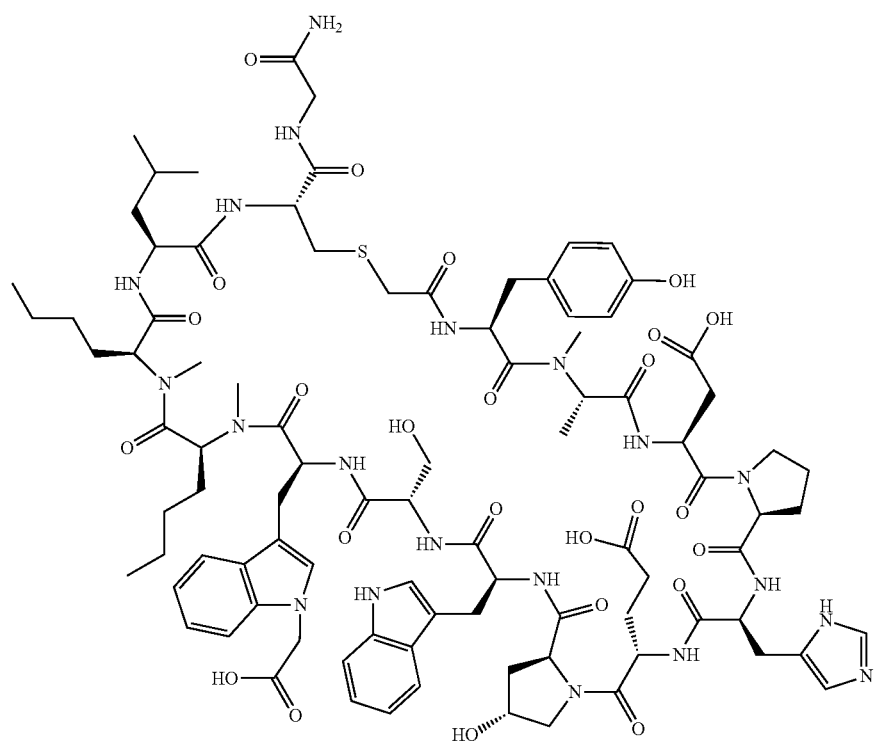

1021
-continued
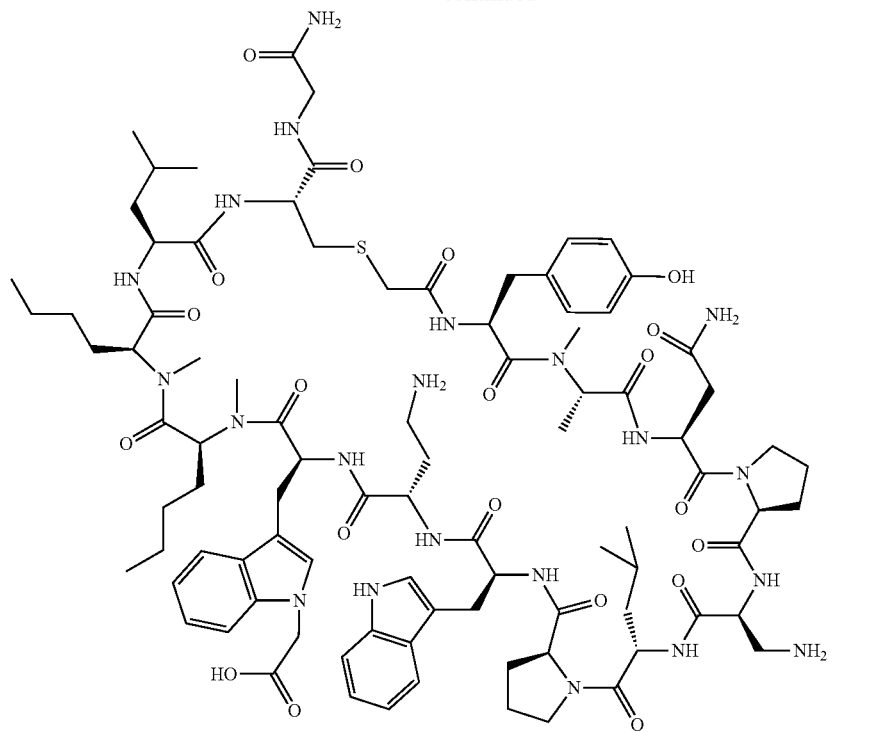
1022
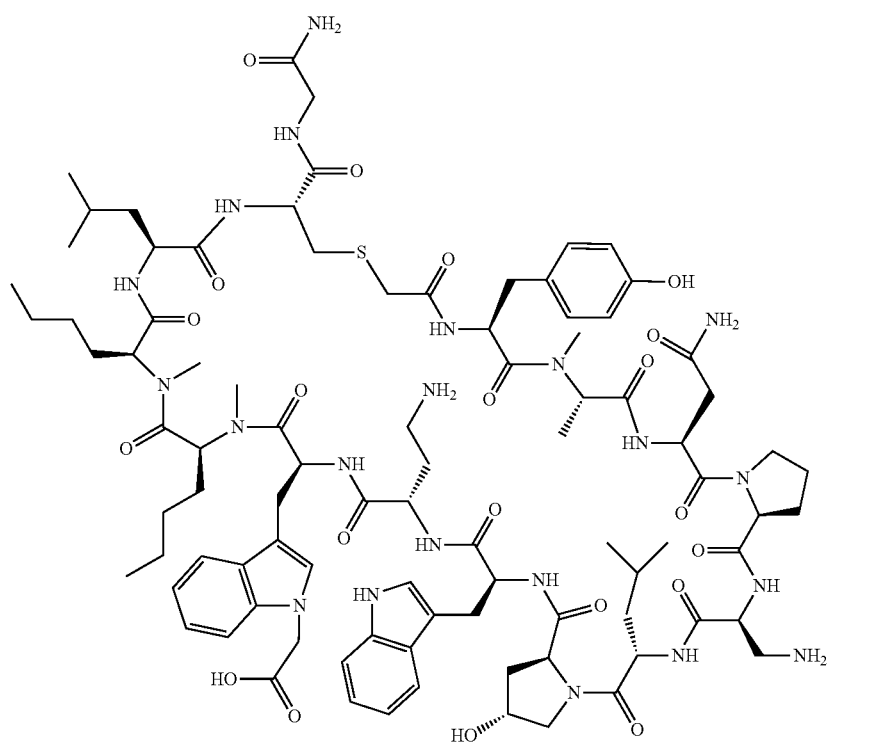
;

-continued
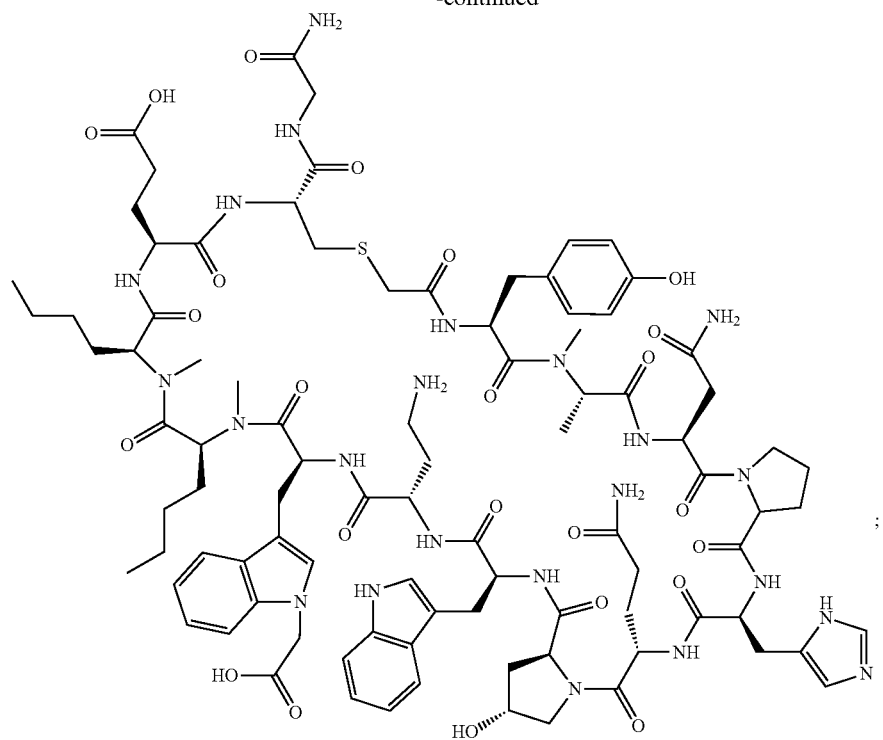
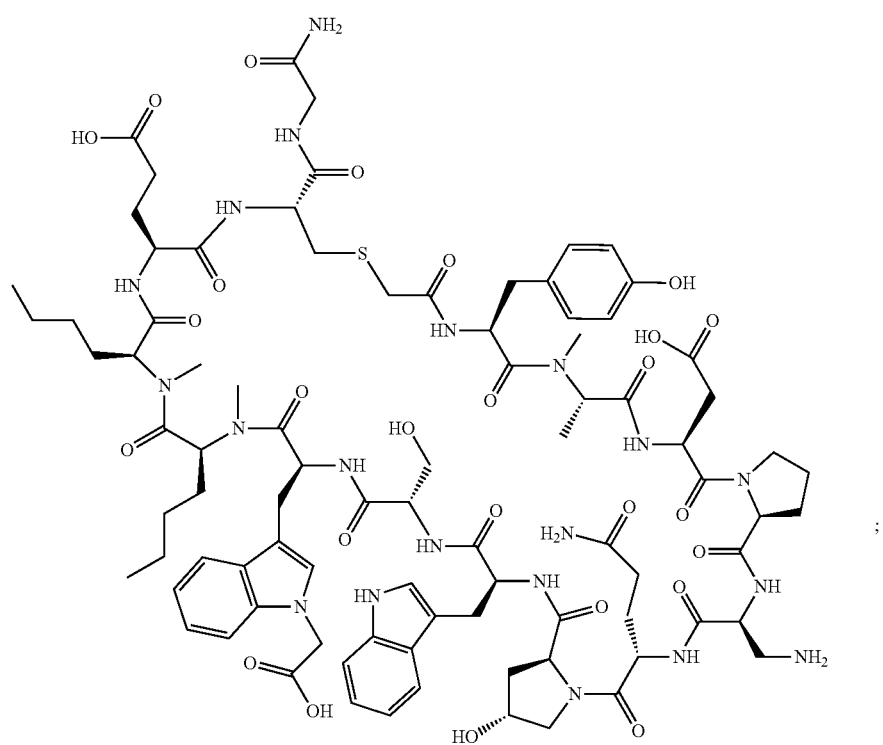

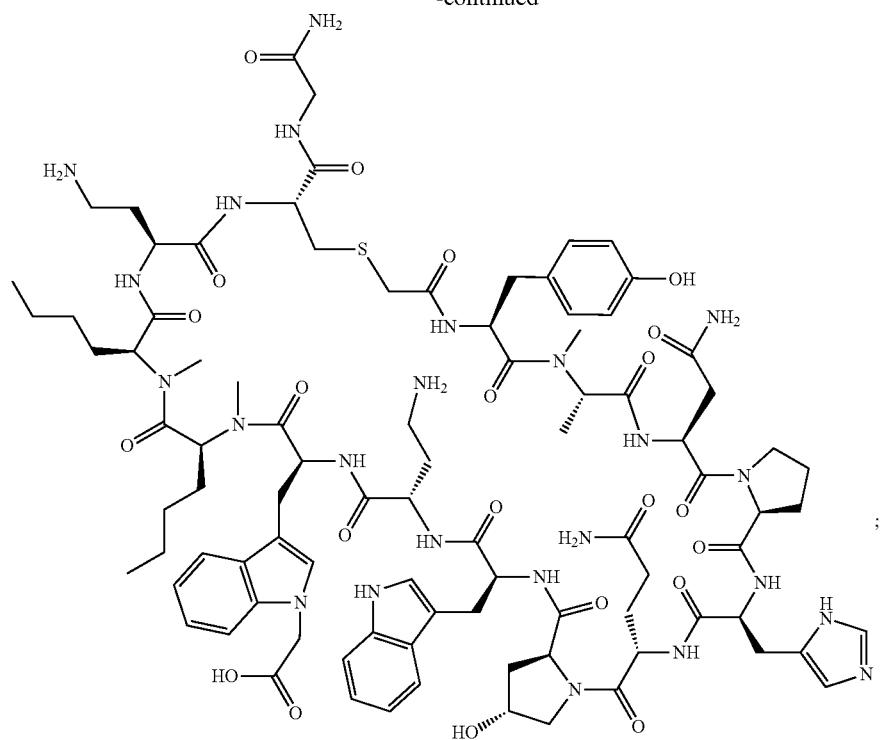
;
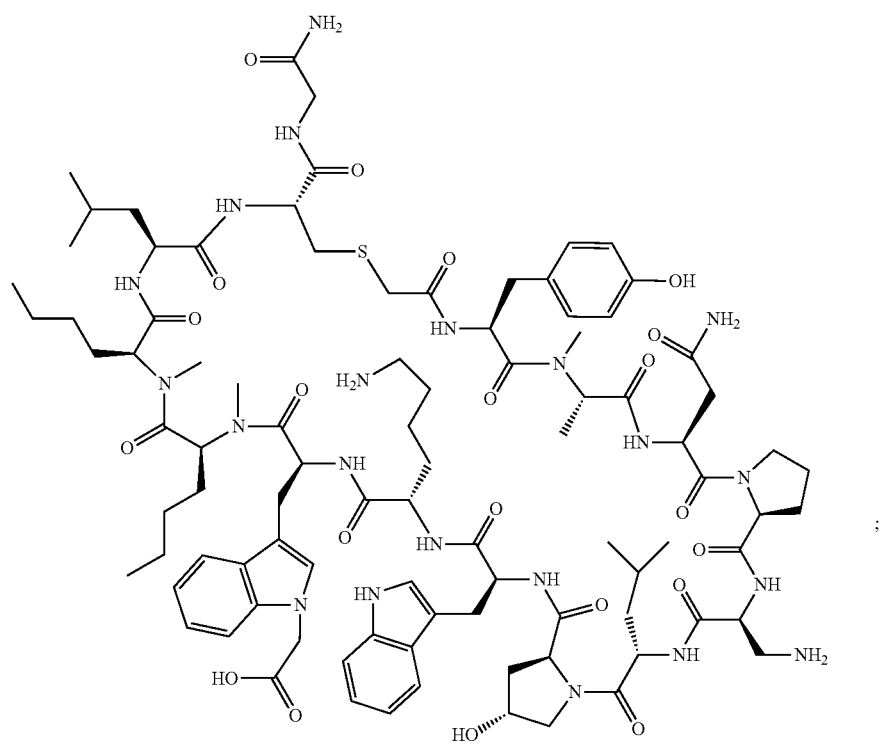
;

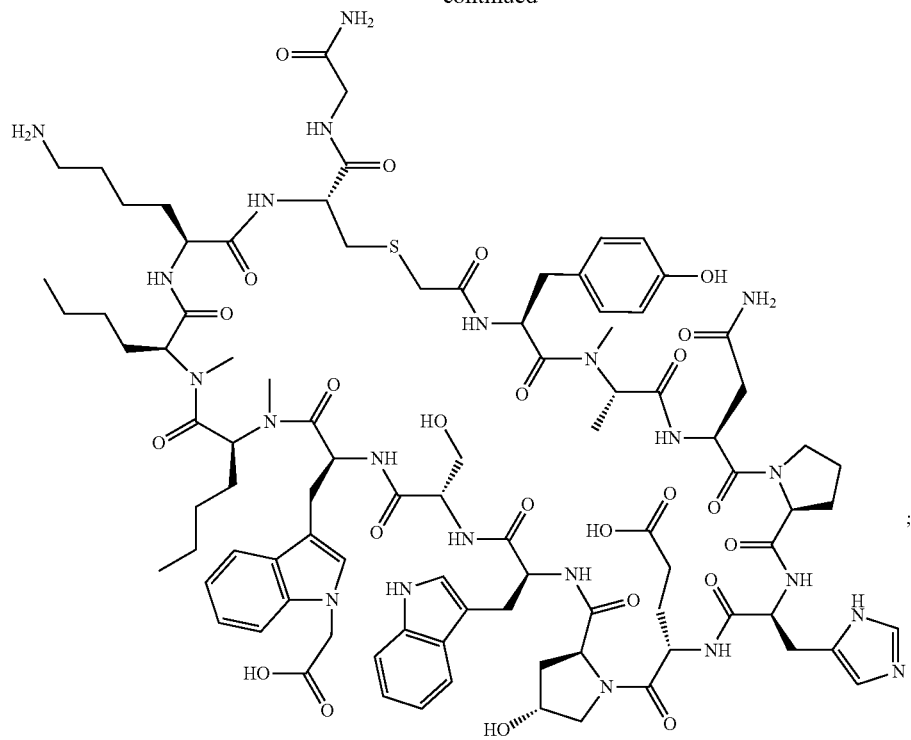
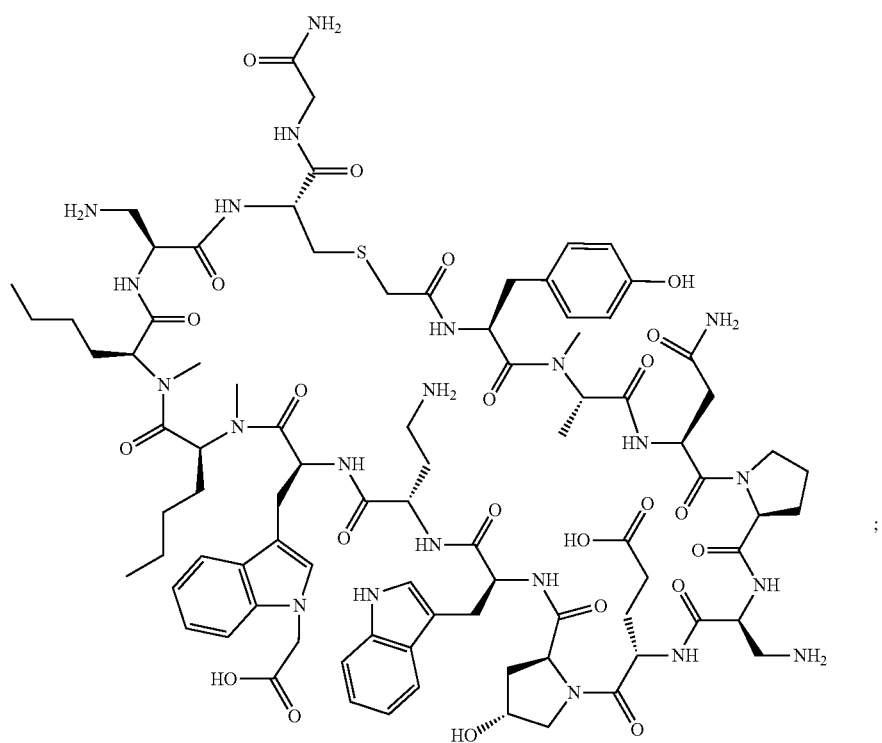

-continued
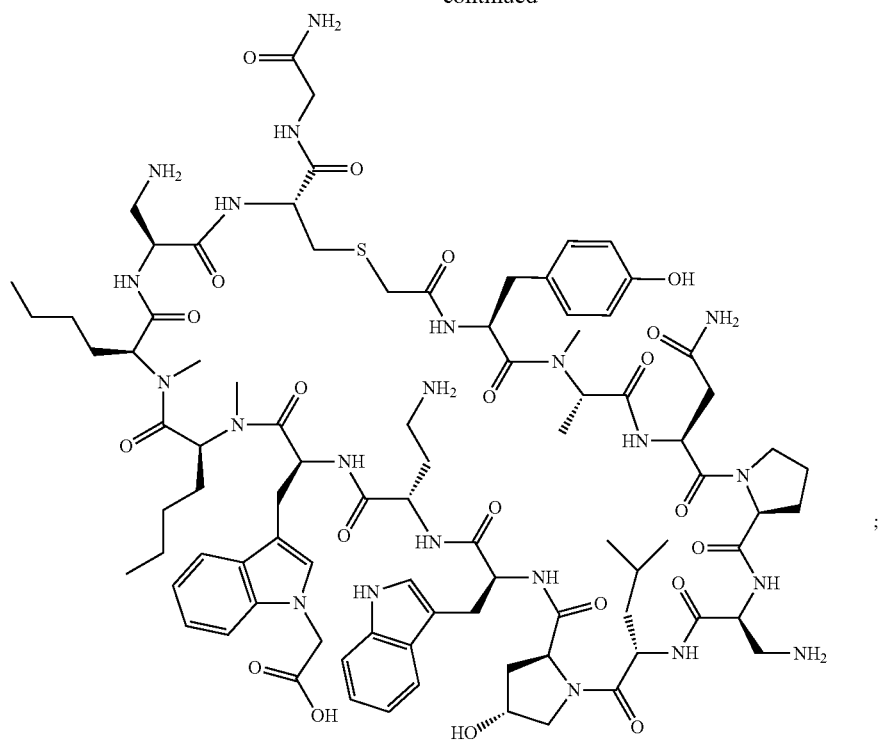
;
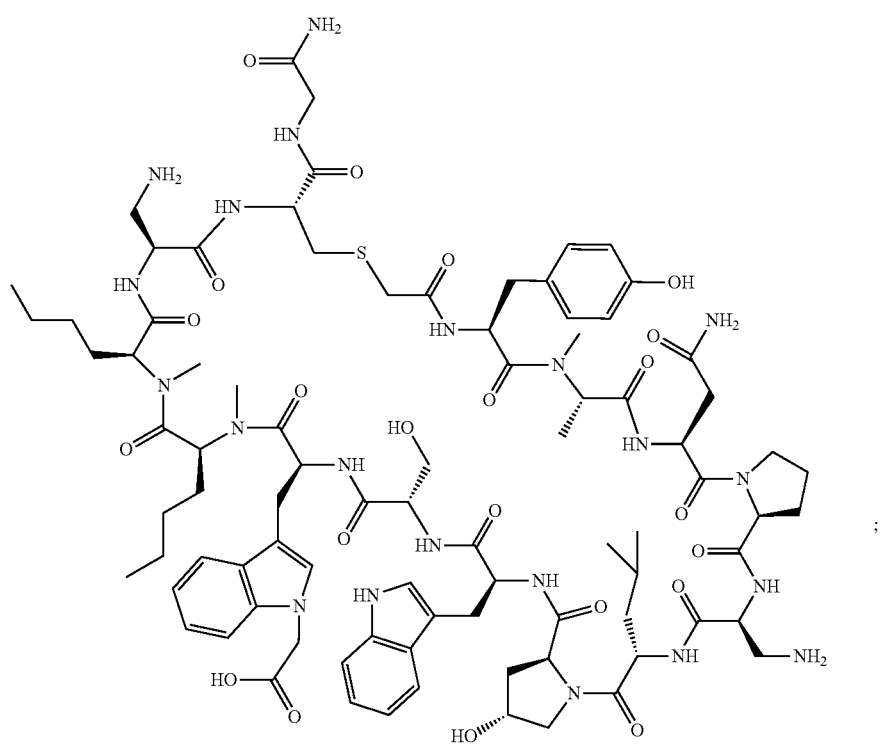
;

1031
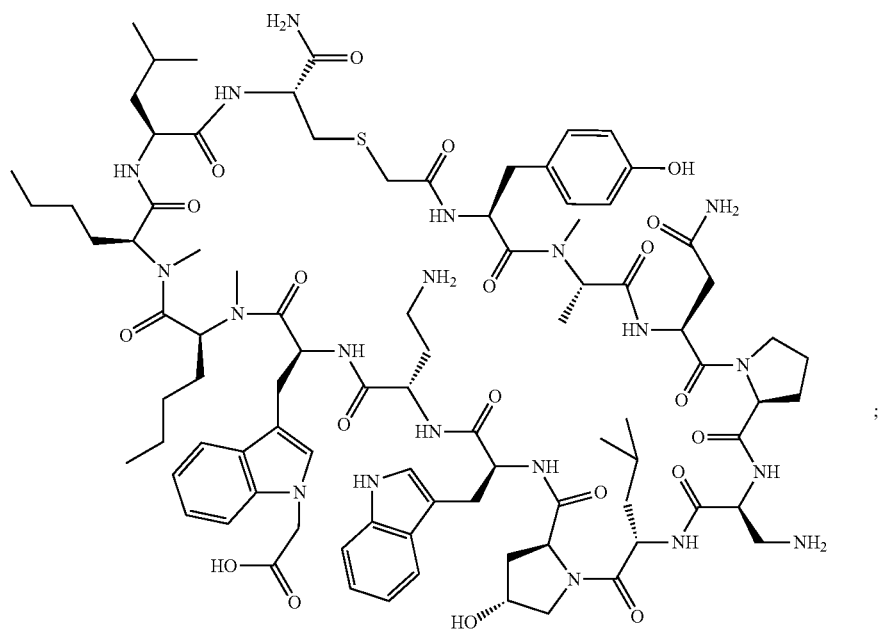
;
1032
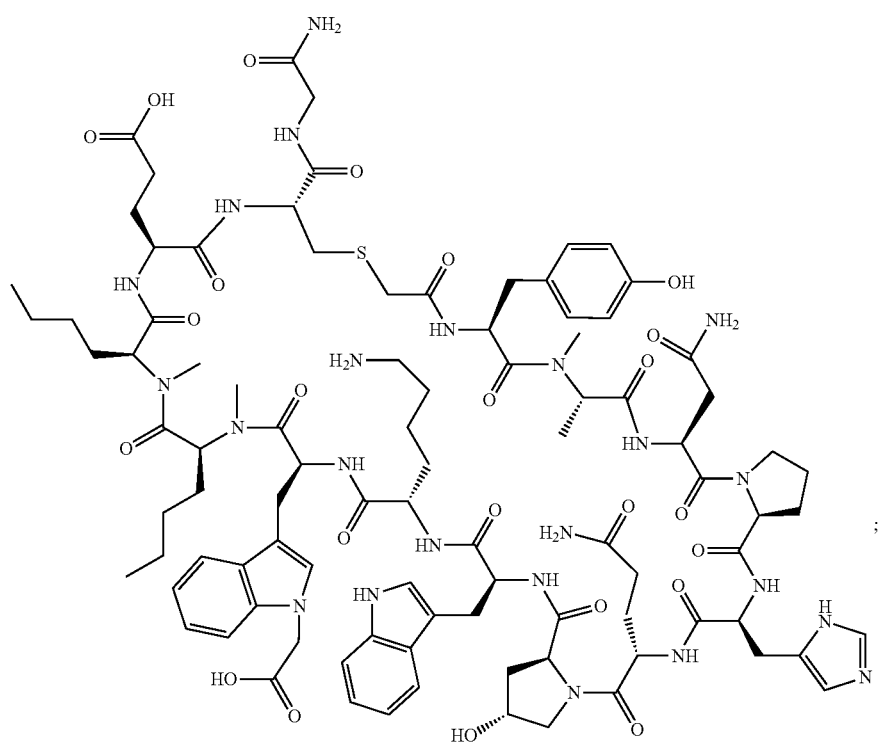
;

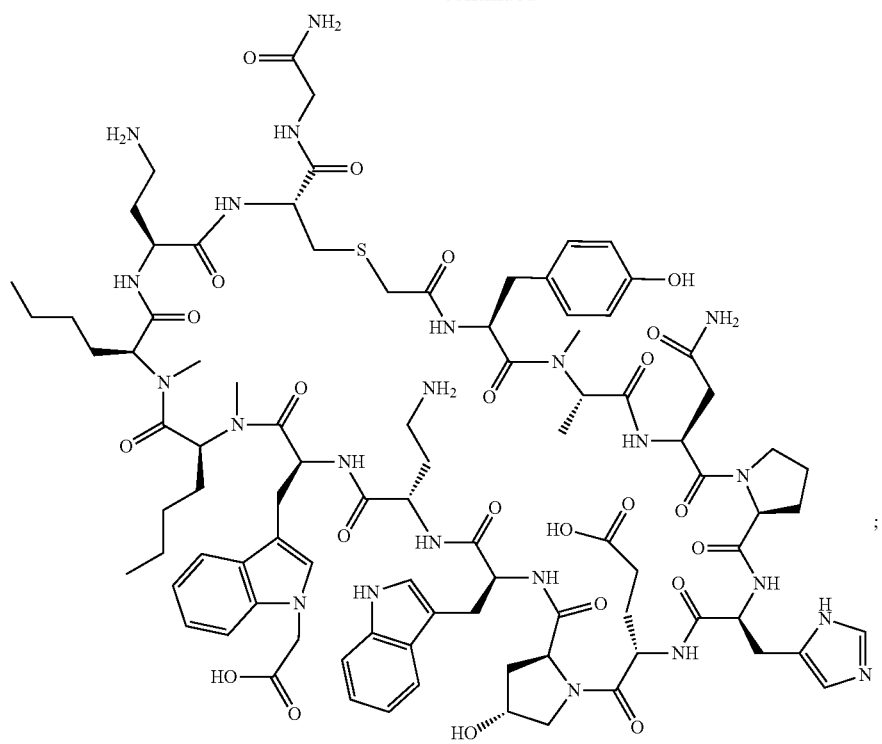
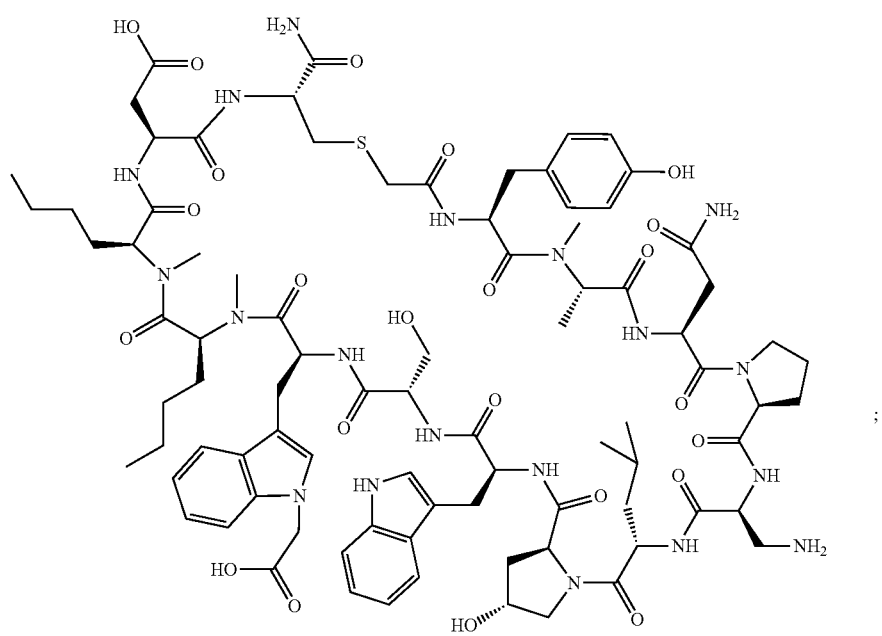

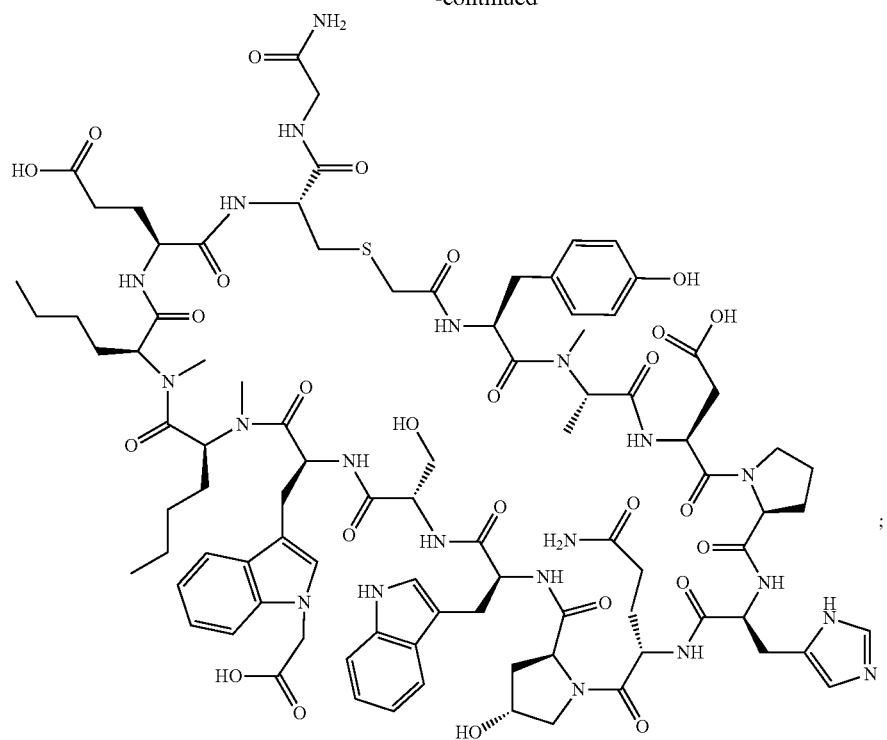
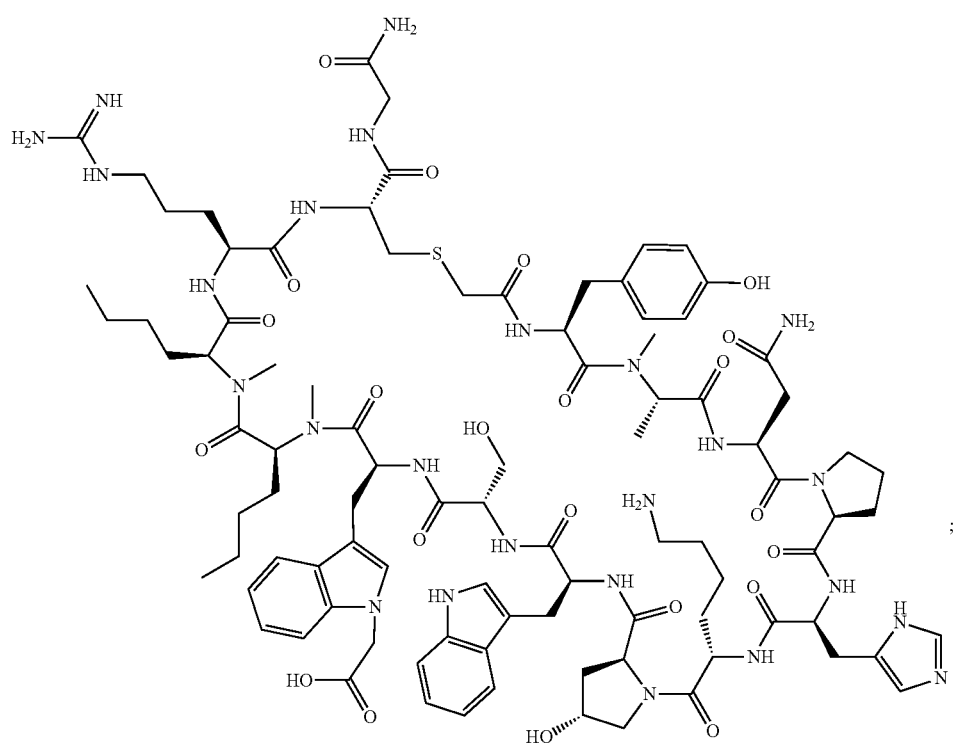 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](C(C)C)C(=O)N[C@@H](Cc2cn(CC(=O)O)c3ccccc23)C(=O)N1C]

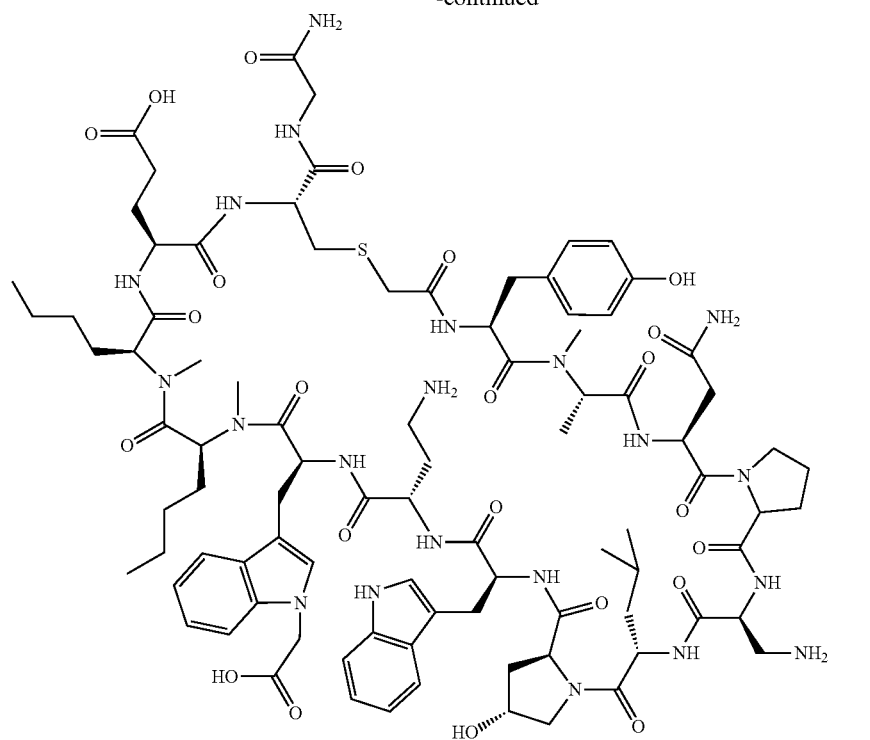
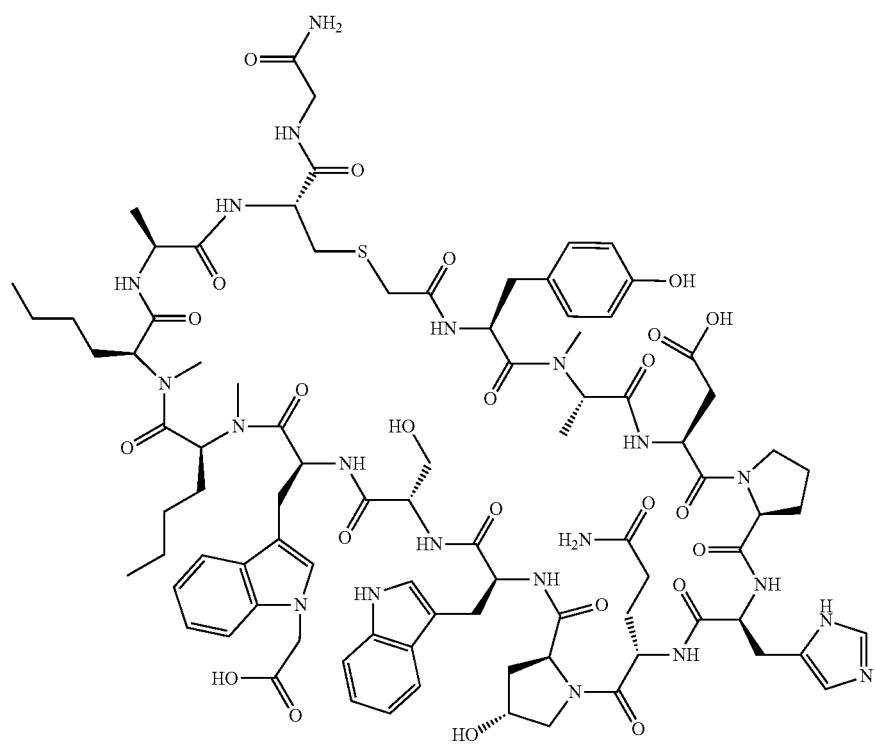

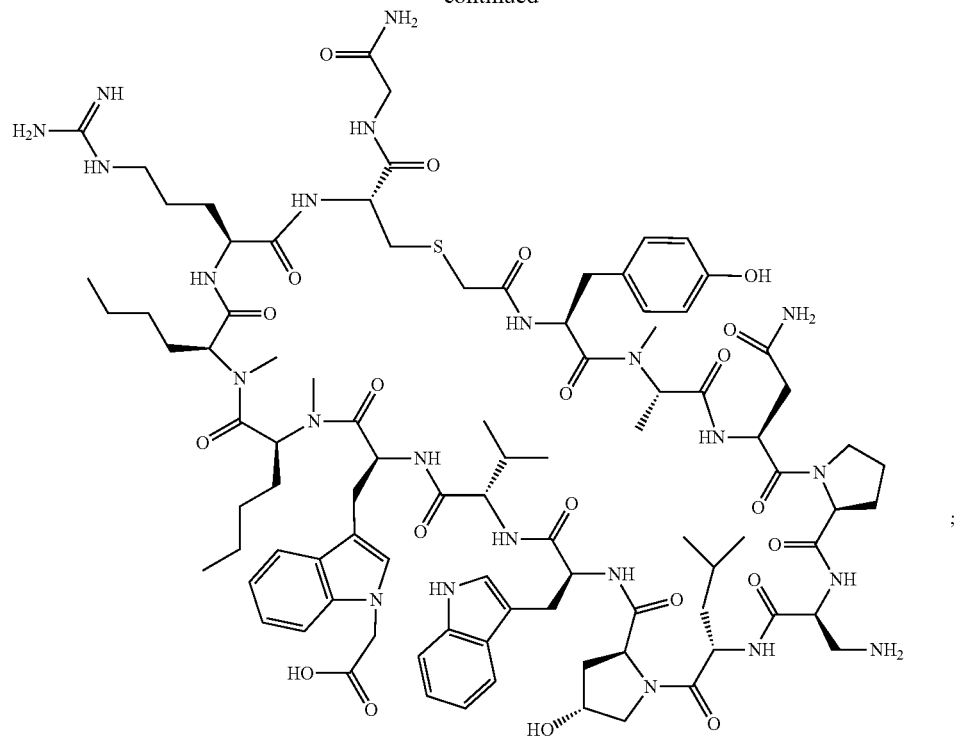
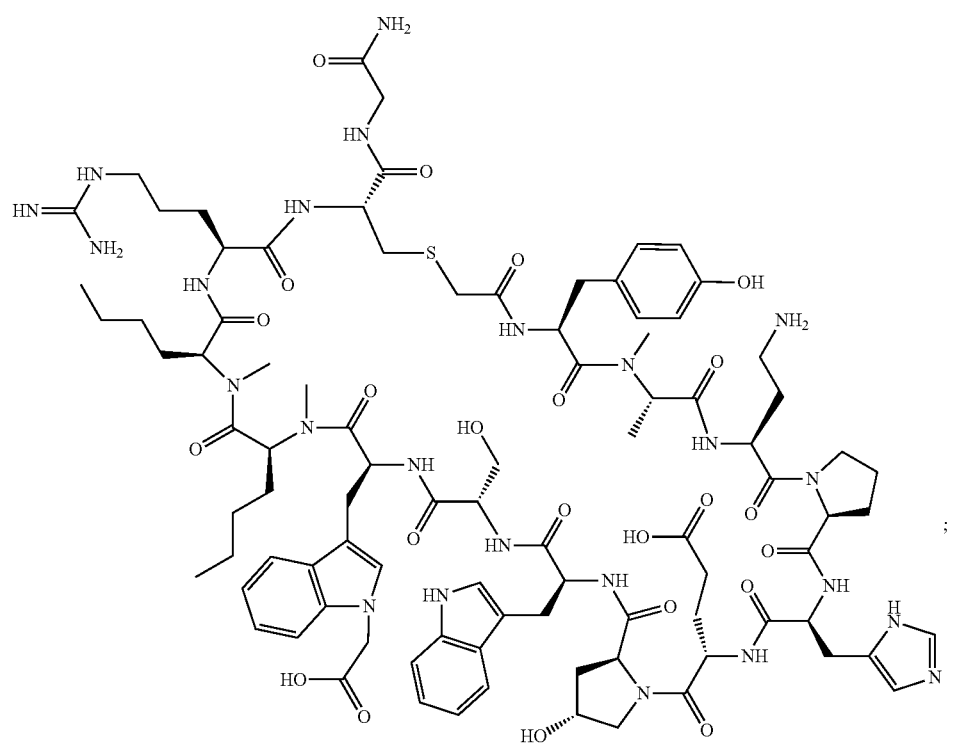

-continued
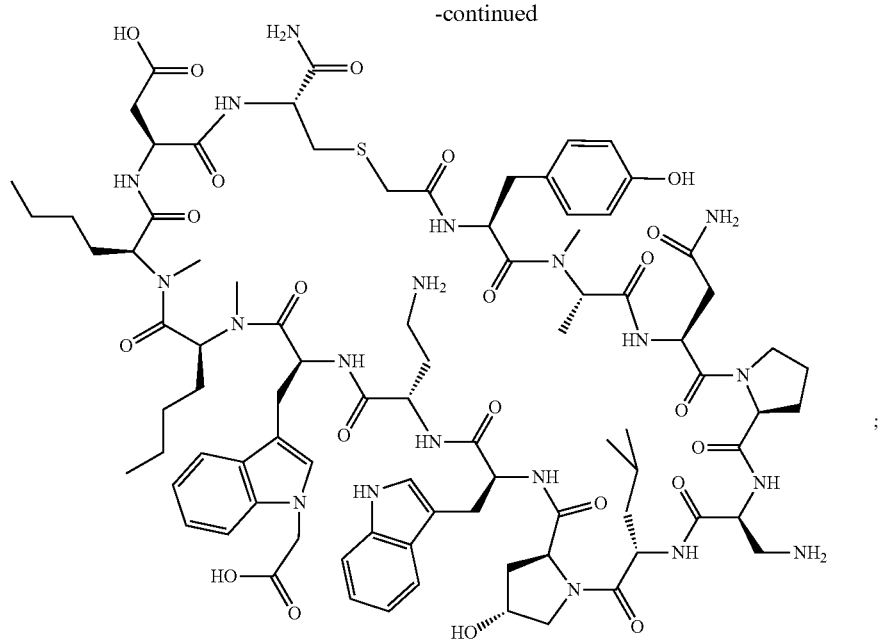
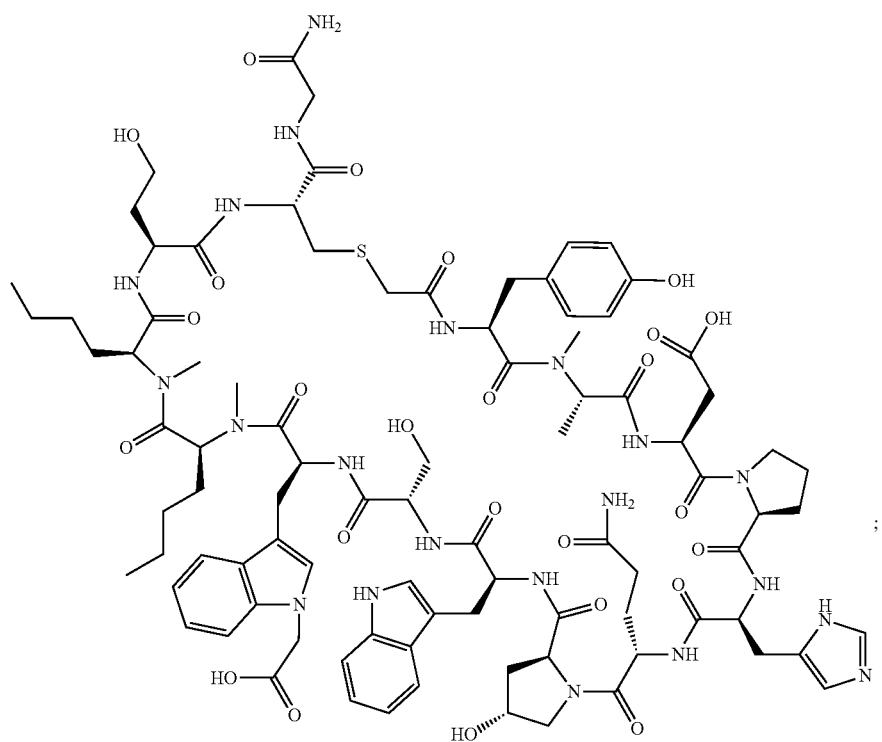

-continued
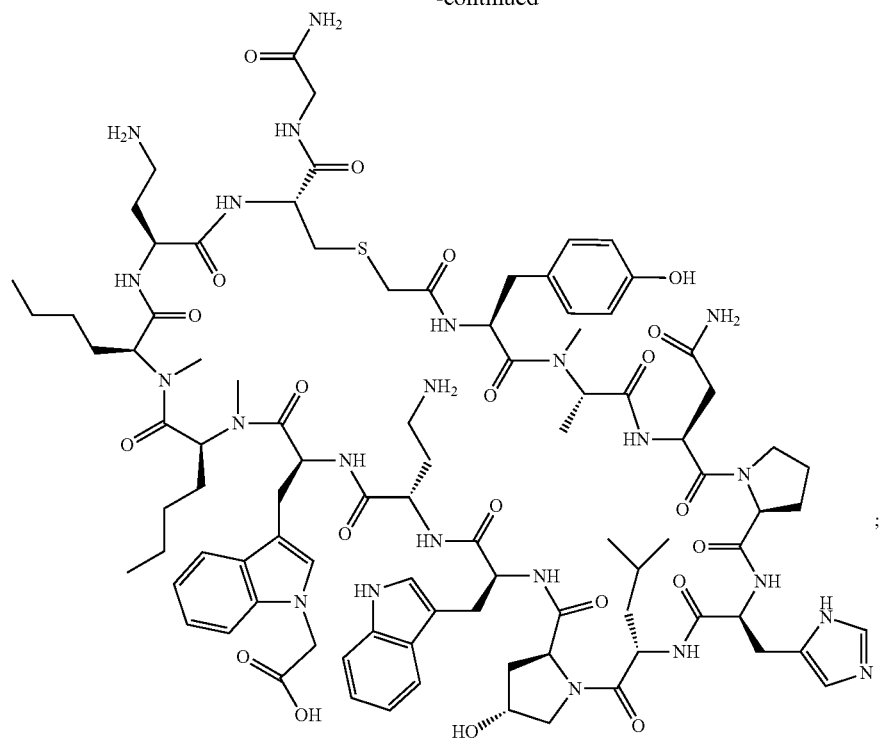
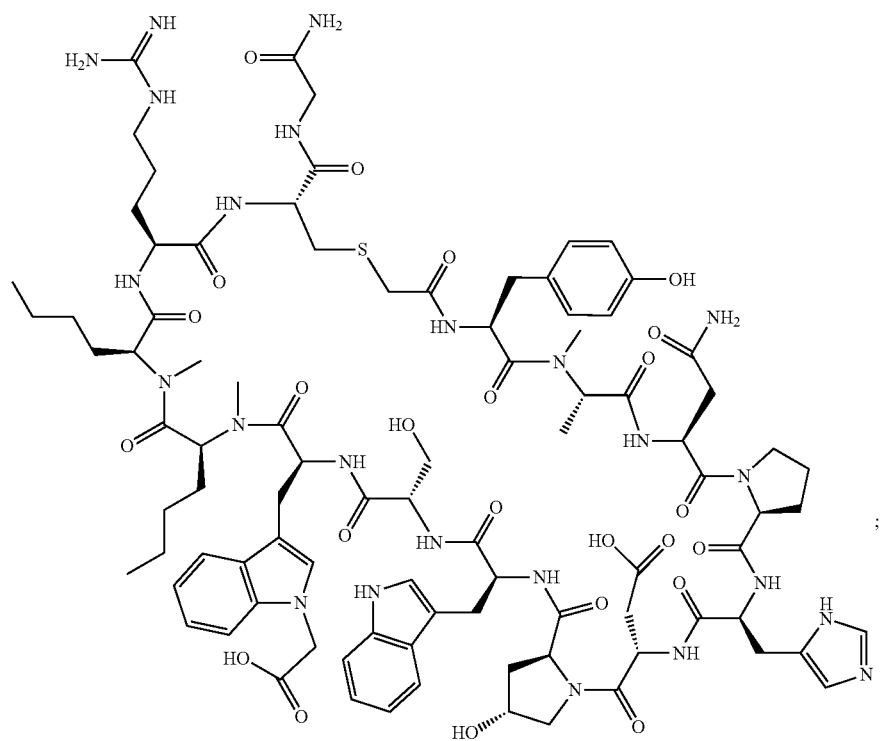

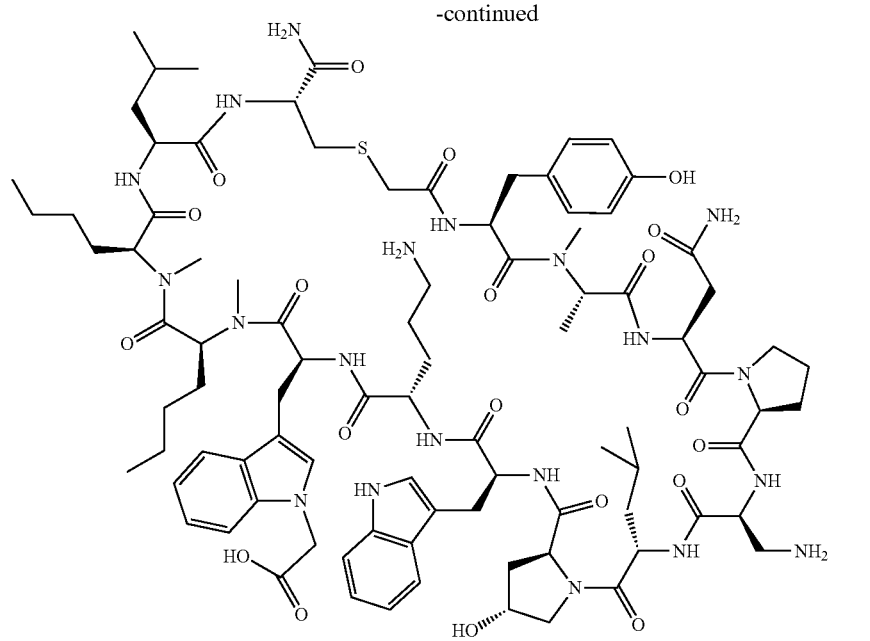
;
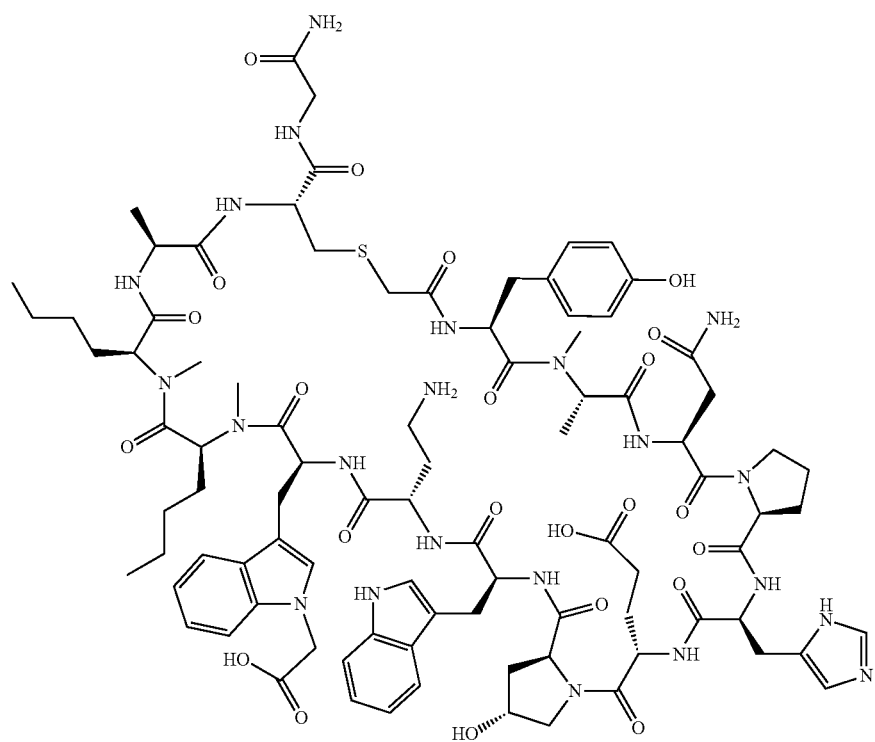
;

-continued
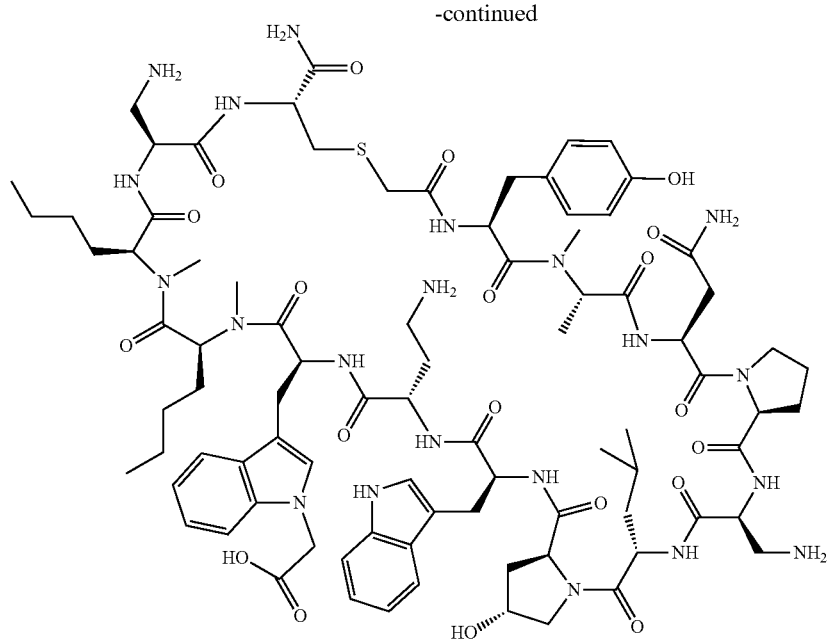
;
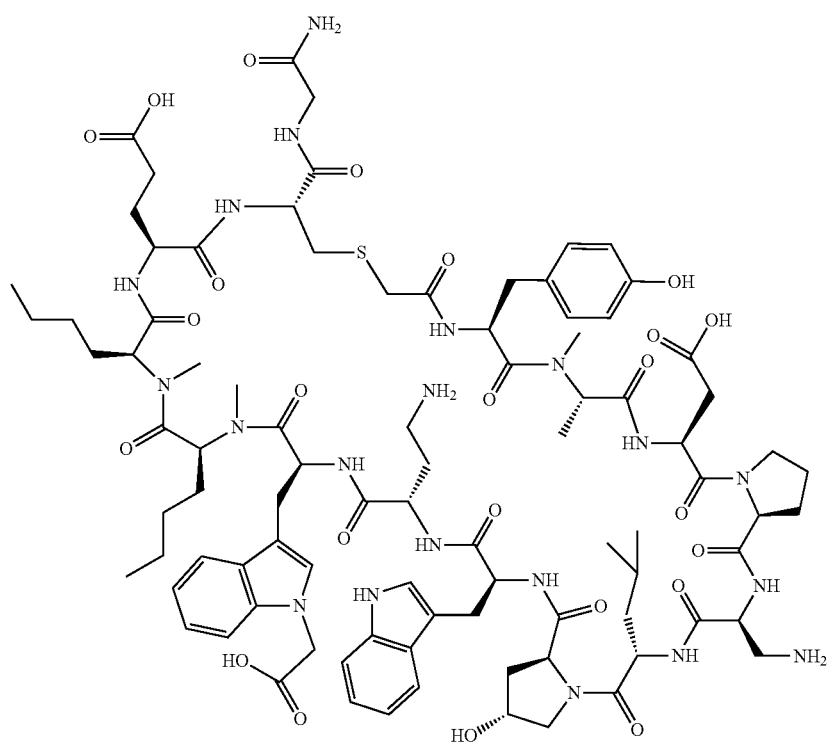
;

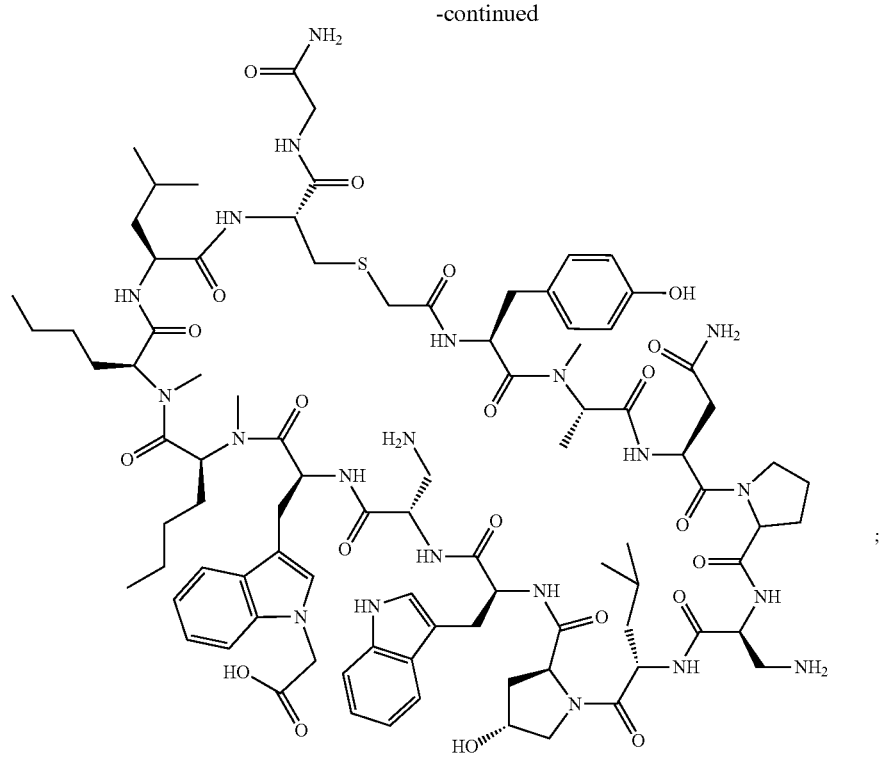
;
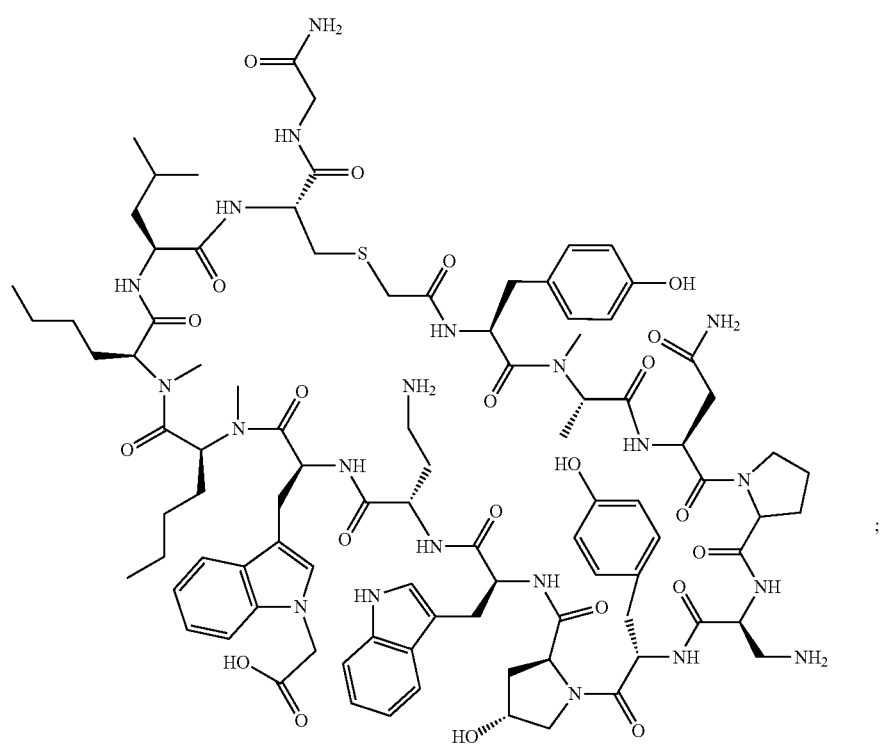
;

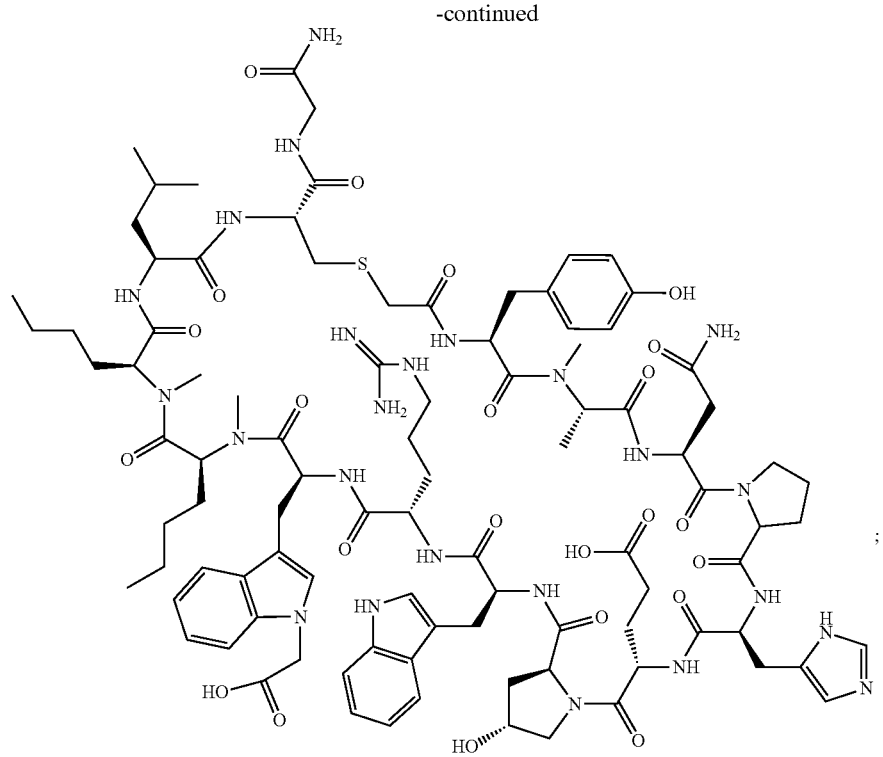
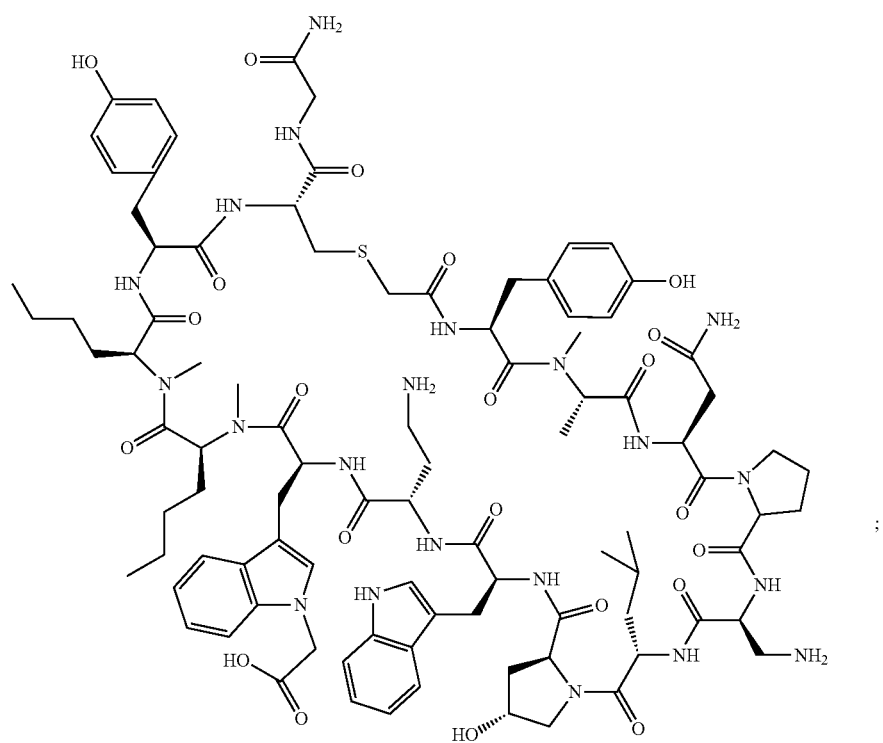

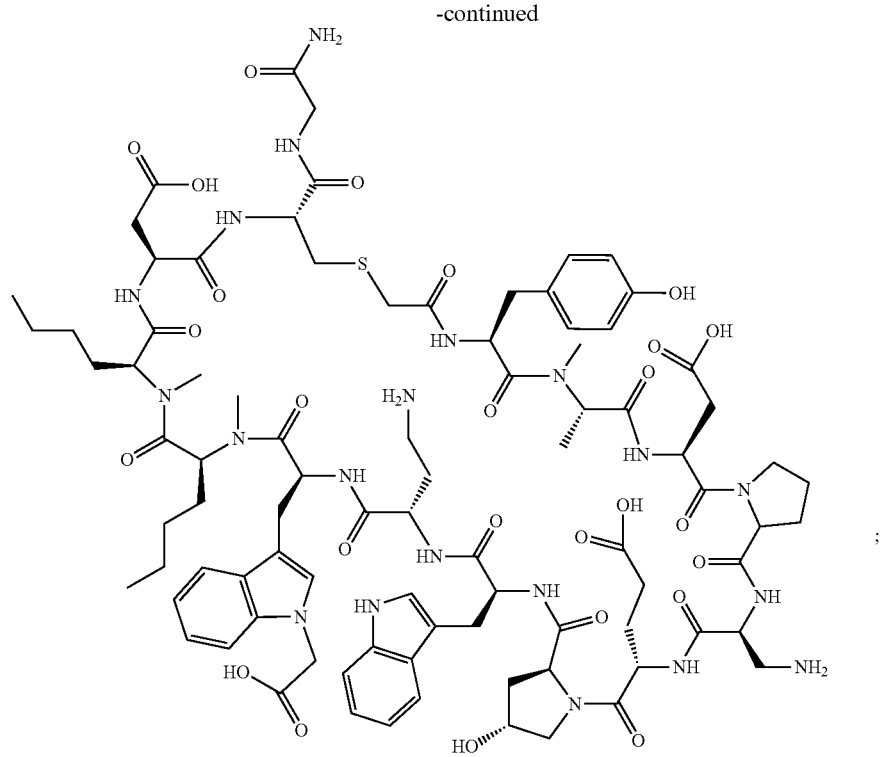
;
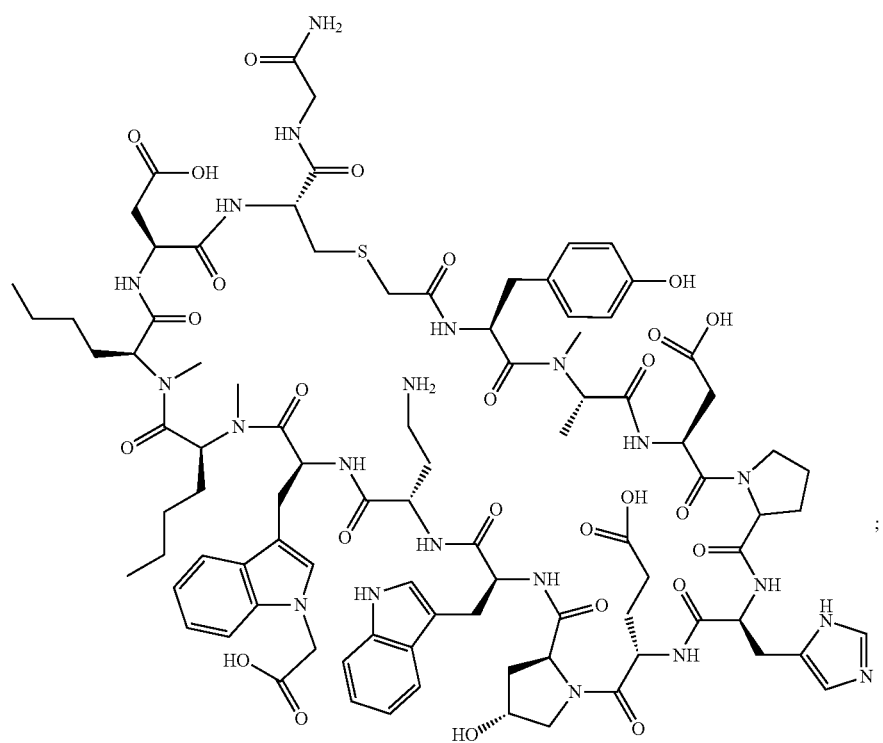
;

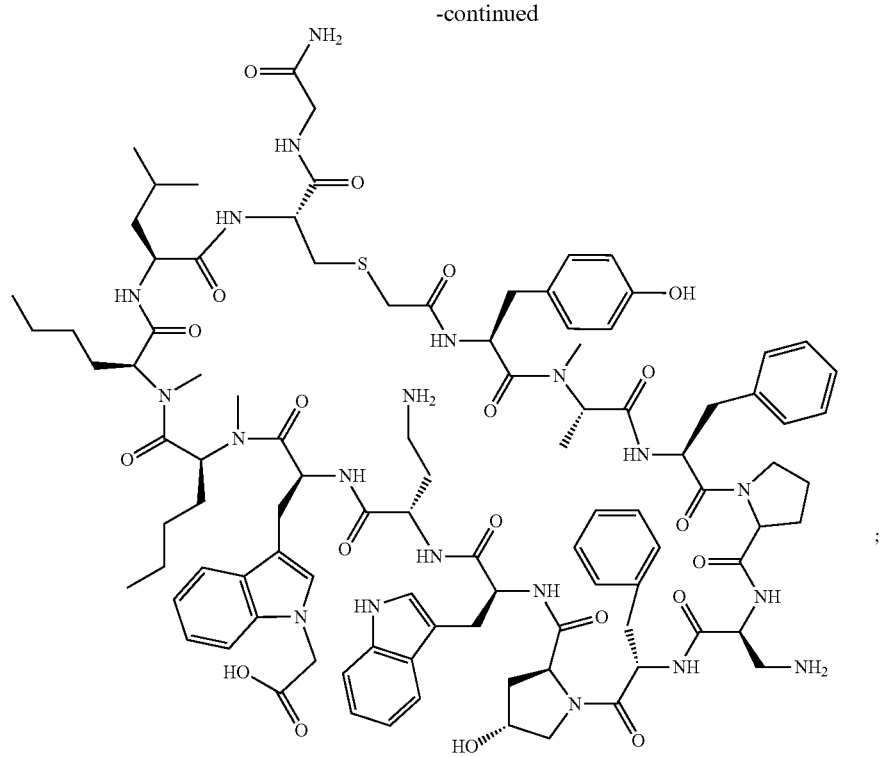
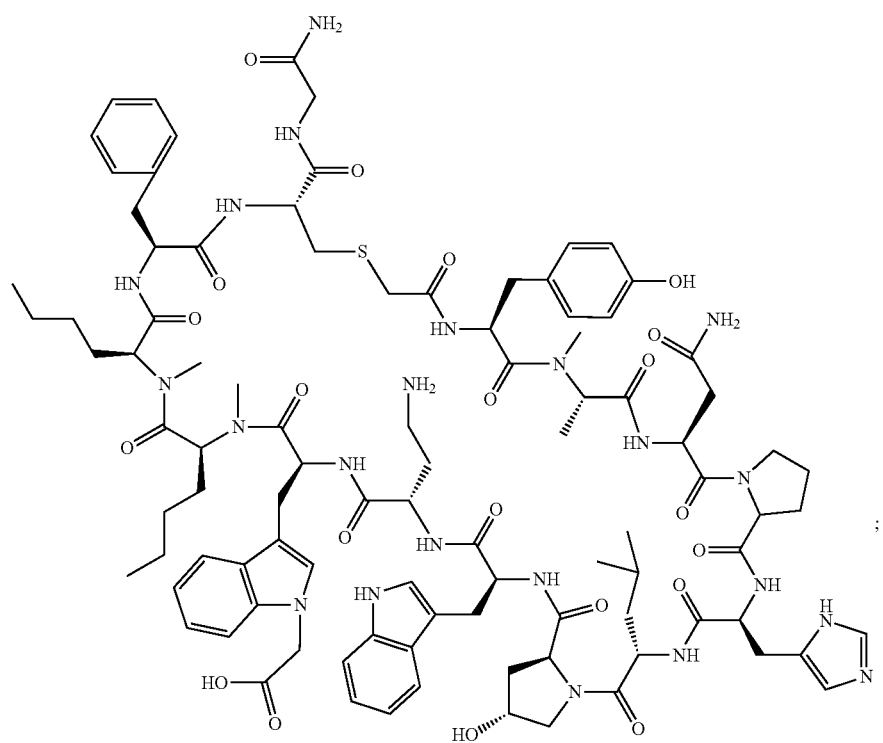

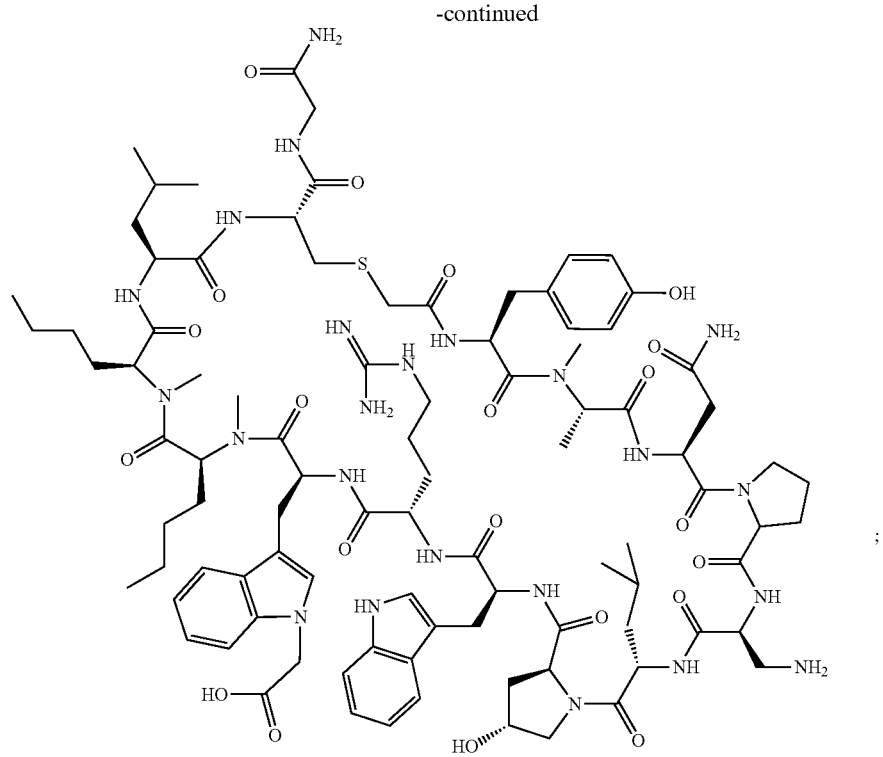
;
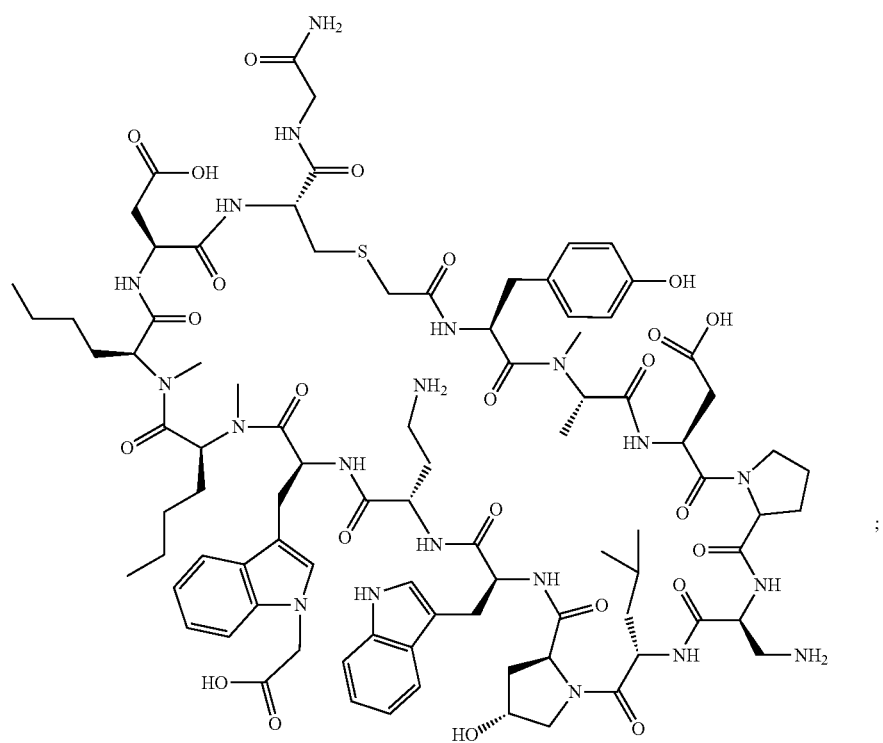
;

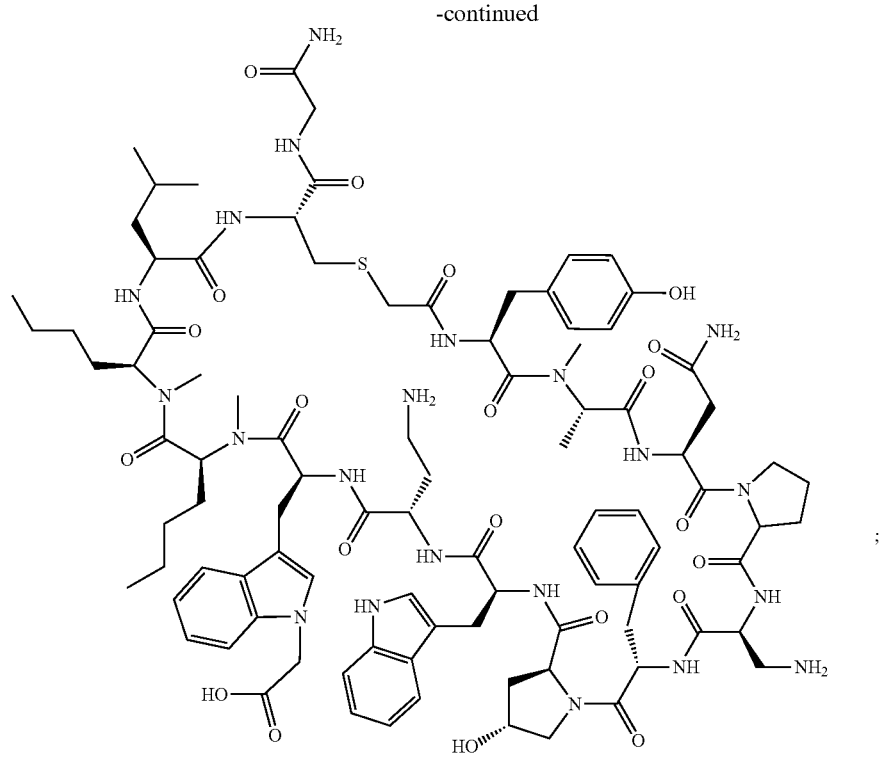
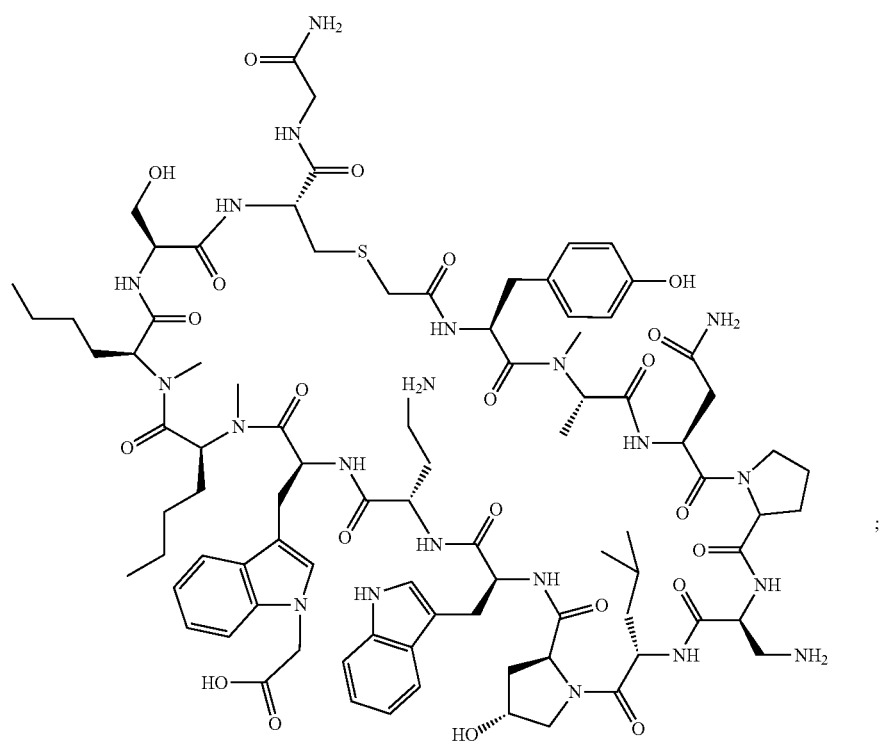

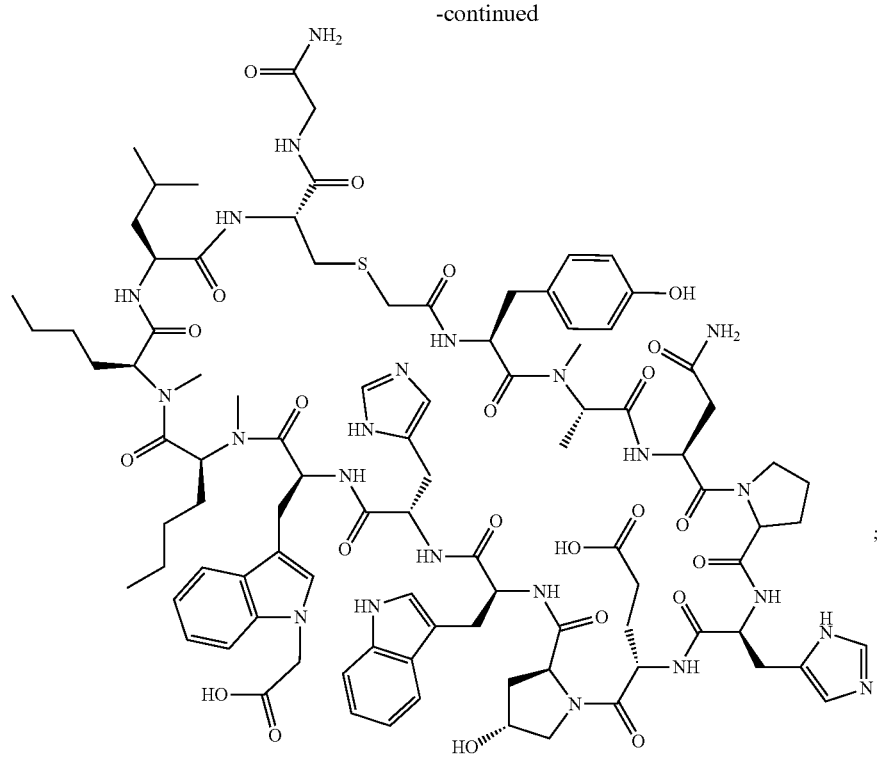
;
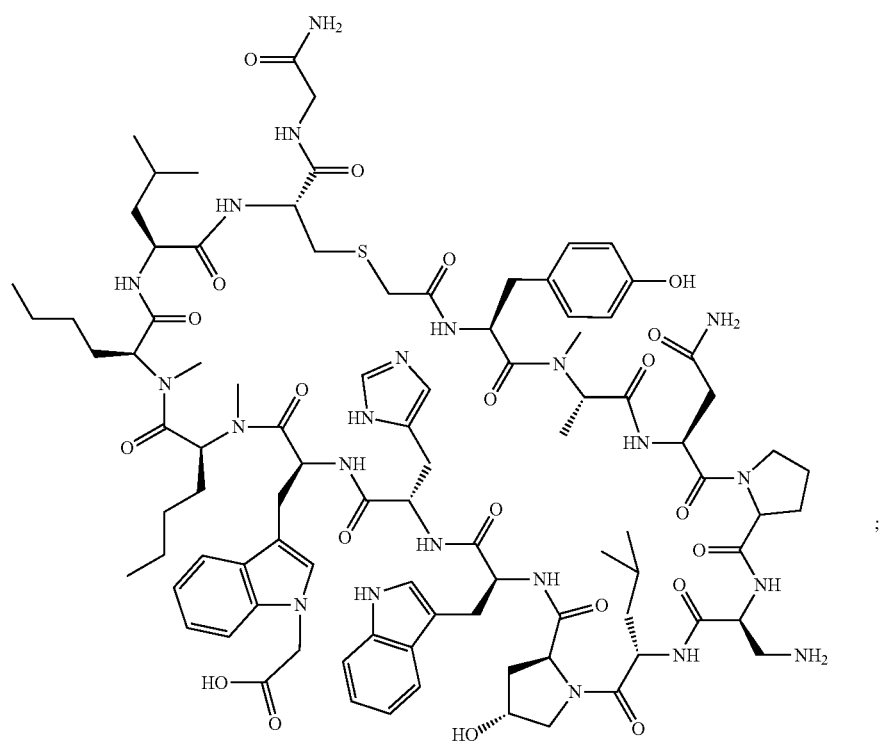
;

-continued
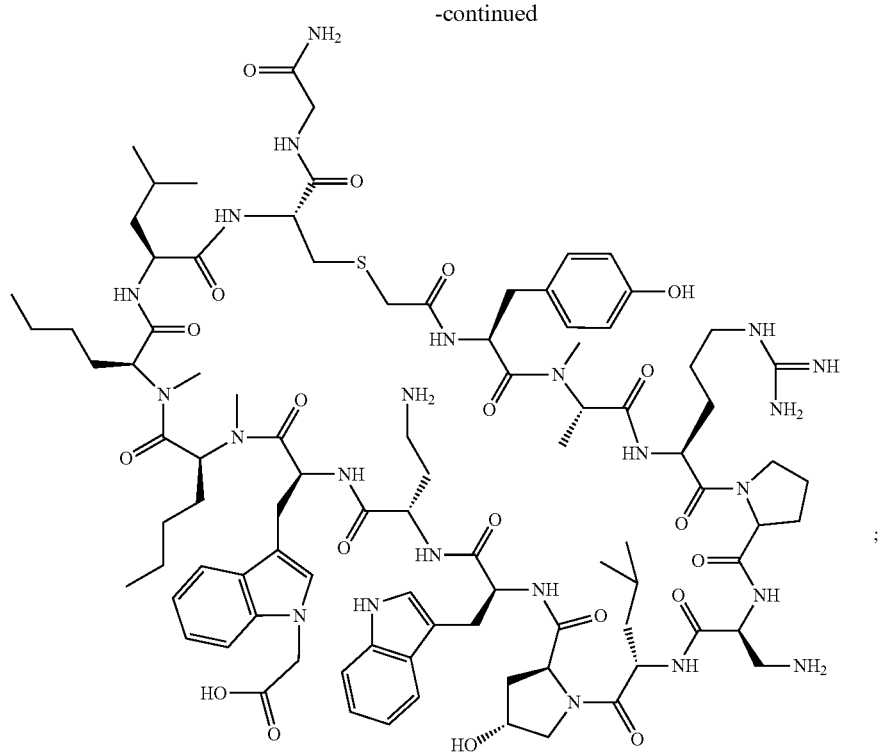
;
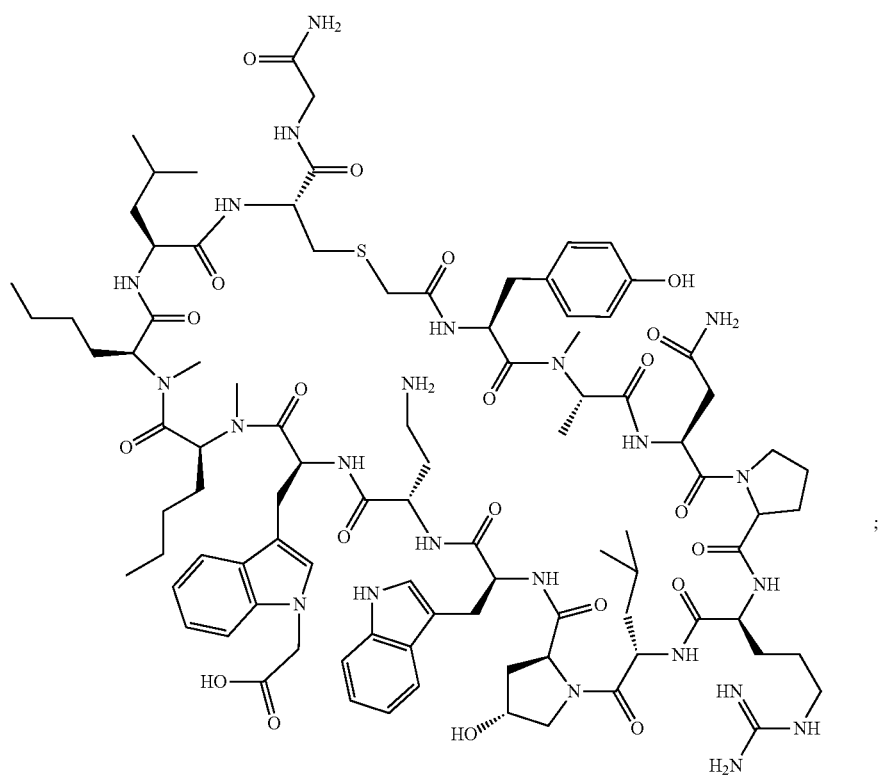
;

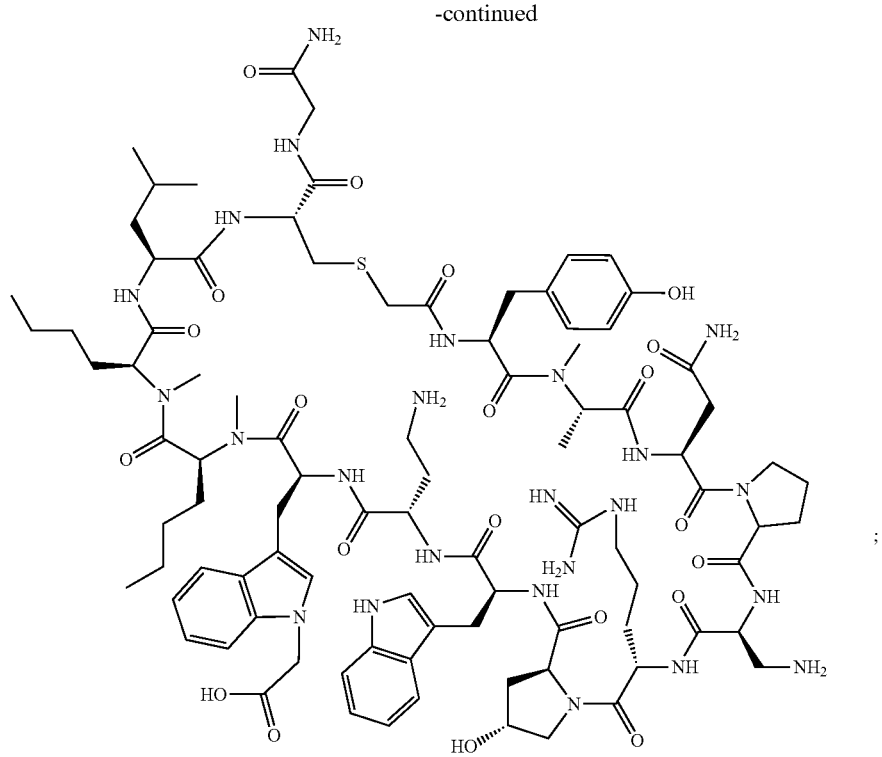
;
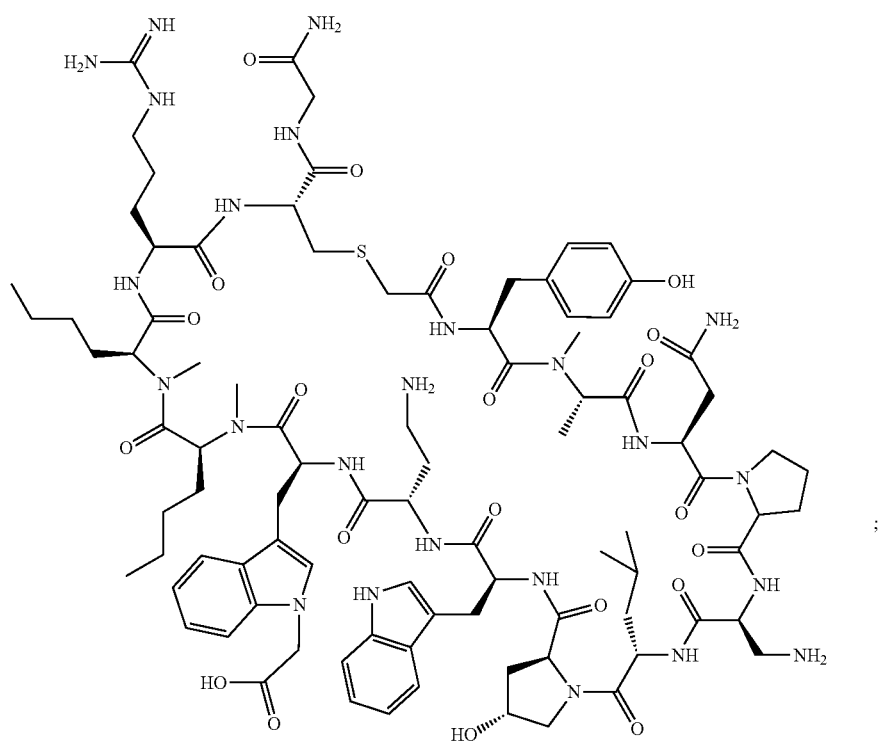
;

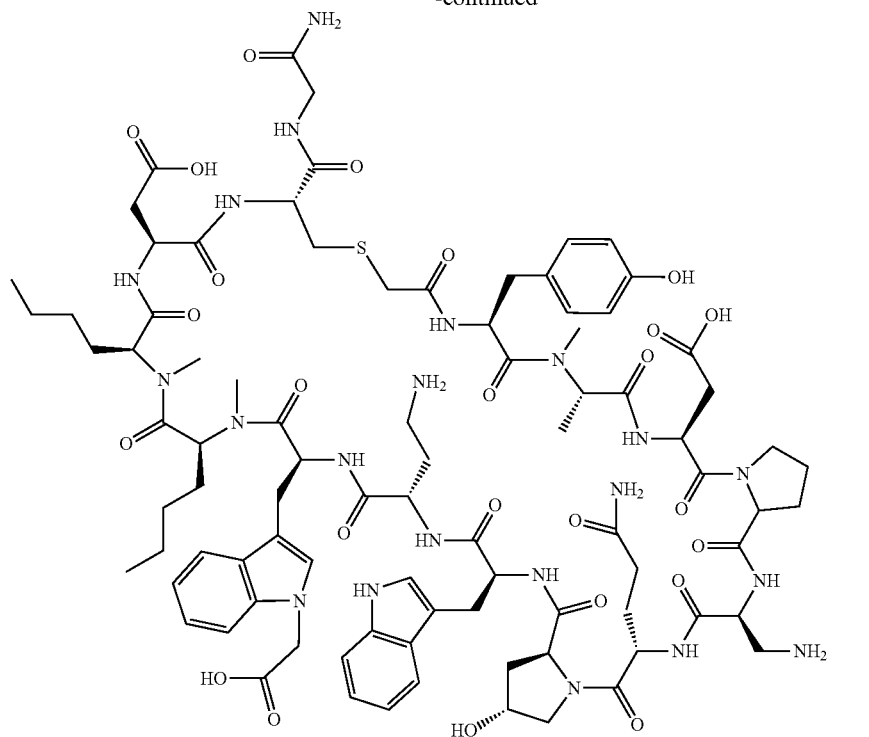;
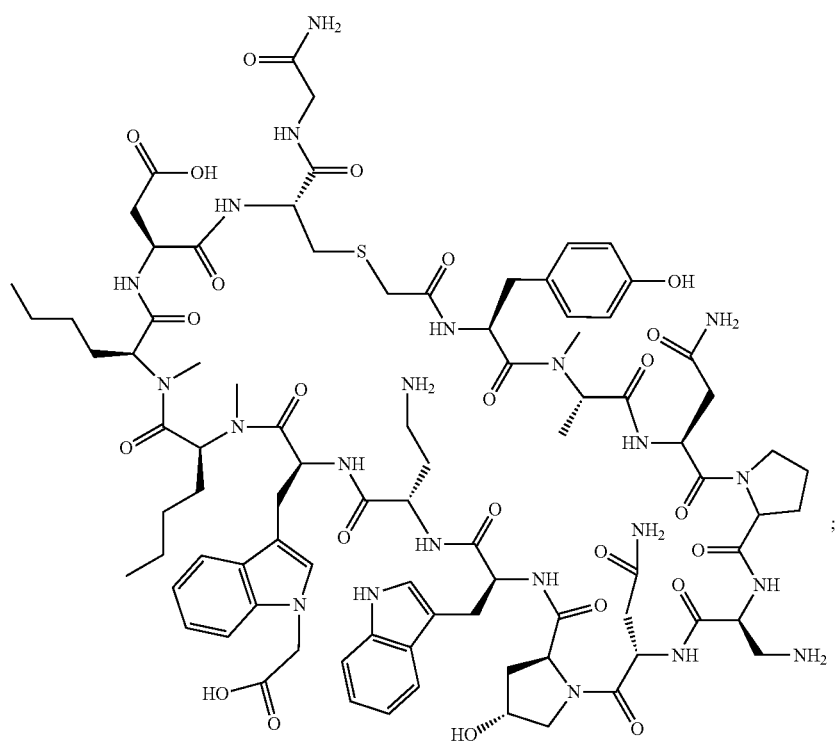;

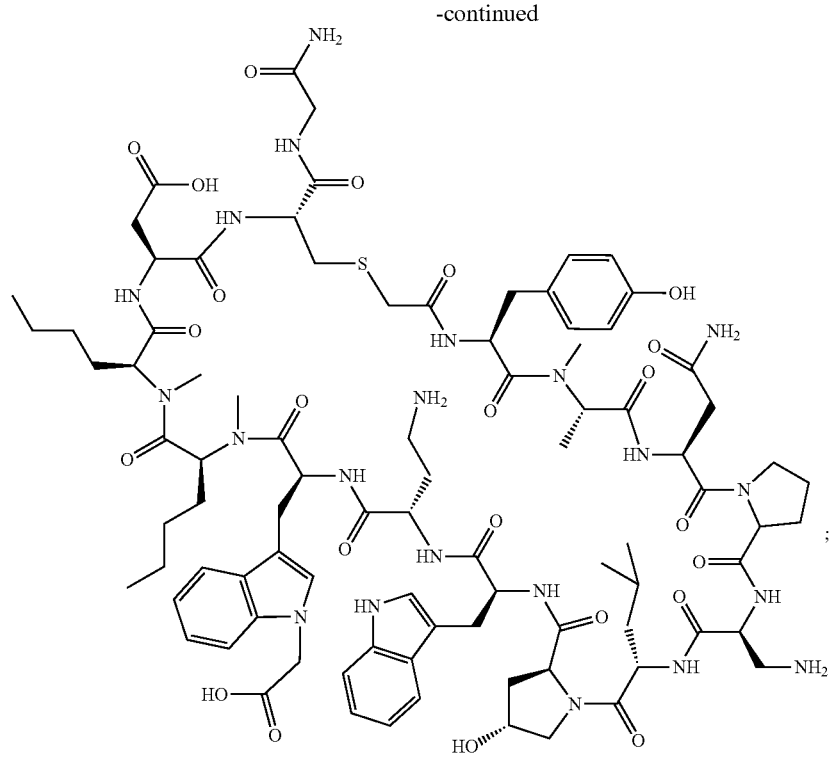
;
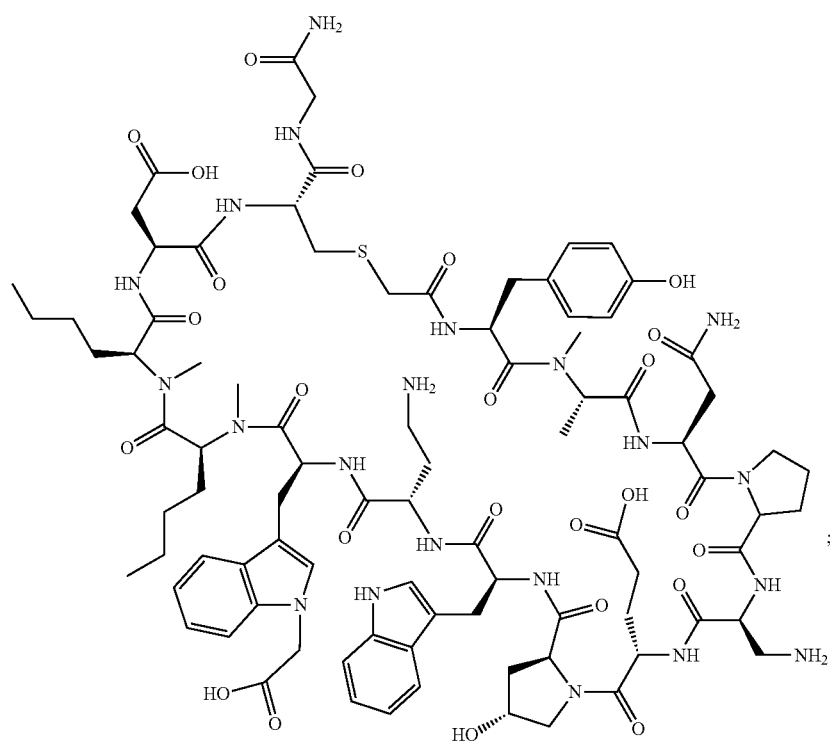
;

-continued
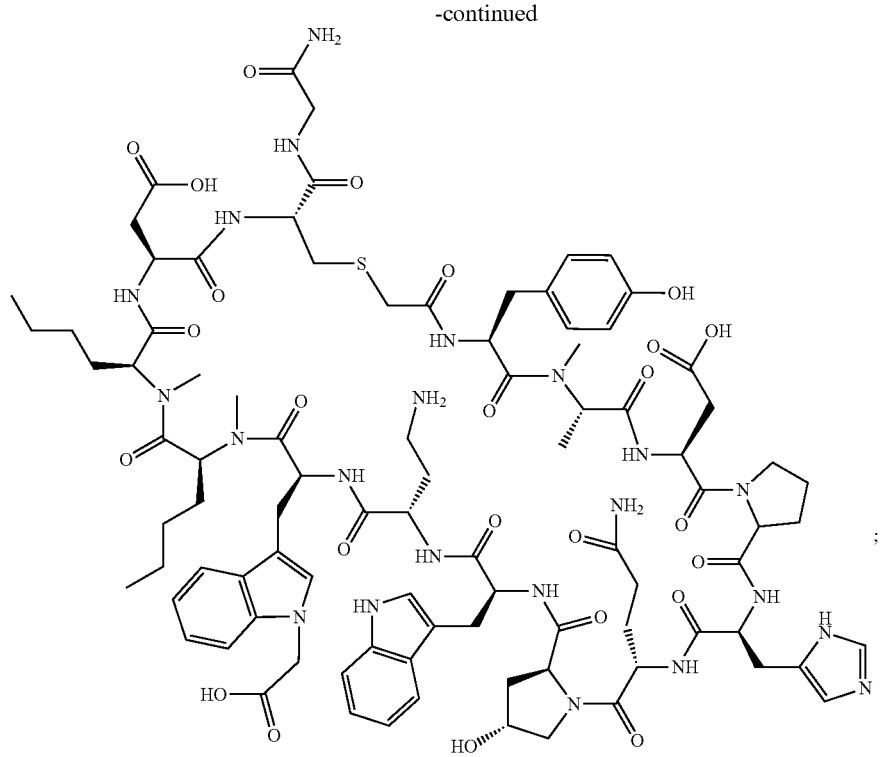
;
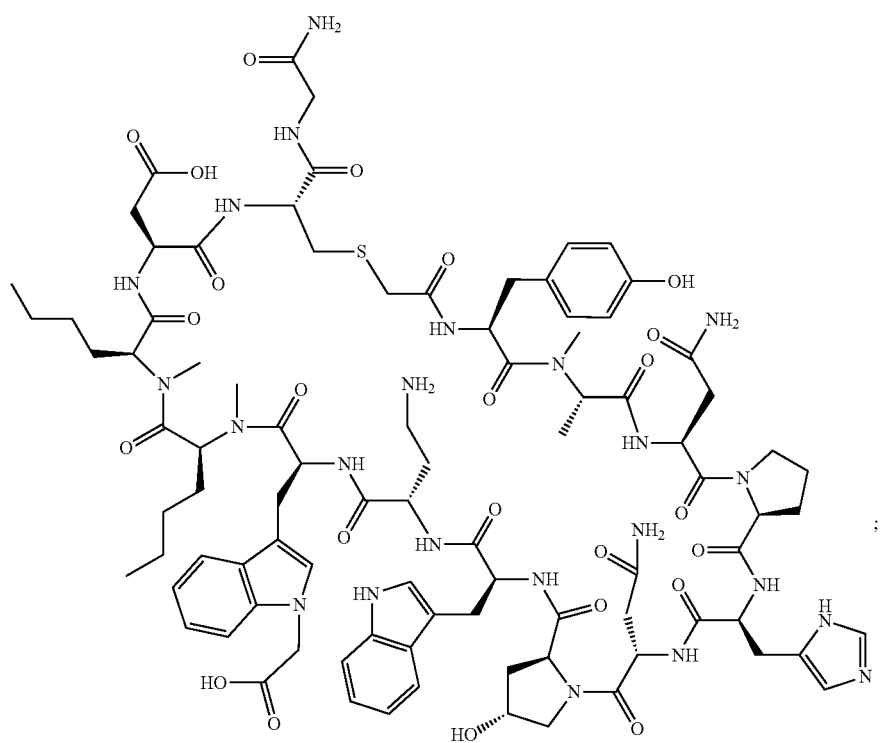
;

-continued
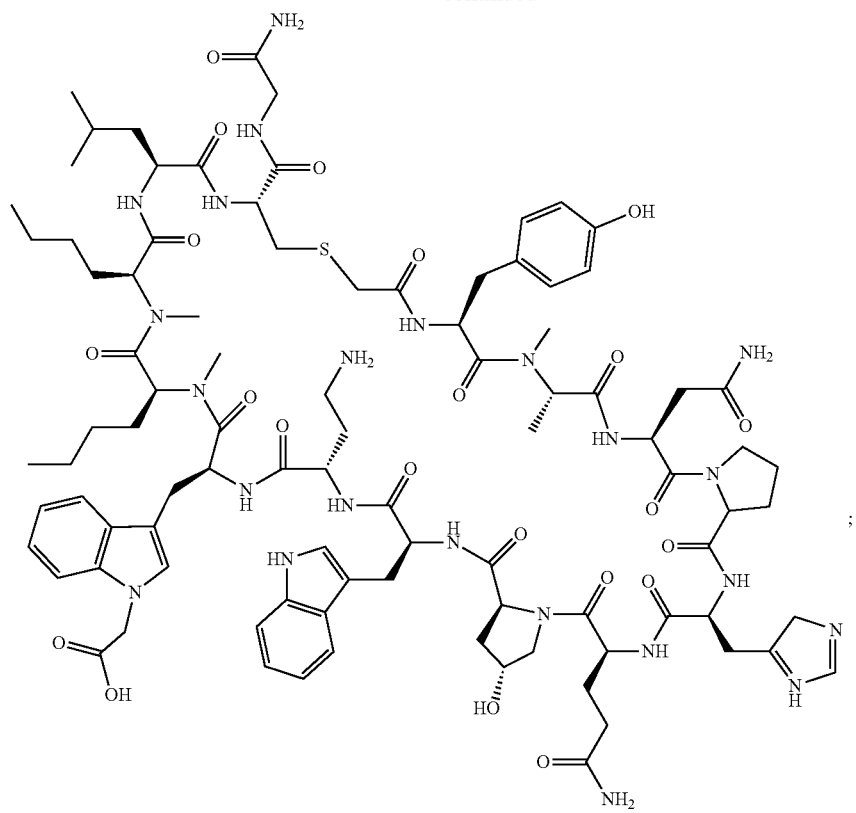
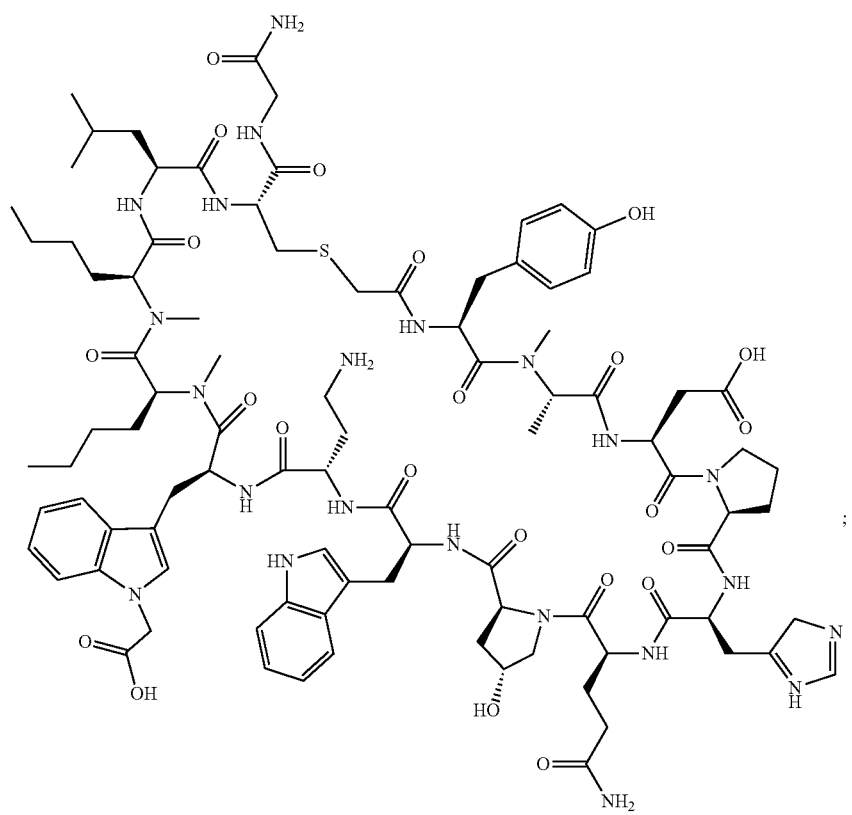 [SMILES: CCCC[C@H]1C(=O)N(C)[C@@H](CCCC)C(=O)N[C@@H](CC(C)C)C(=O)N[C@H](C(=O)NCC(N)=O)CSCC(=O)N[C@@H](Cc2ccc(O)cc2)C(=O)N(C)[C@@H](C)C(=O)N[C@@H](CC(=O)O)C(=O)N2CCC[C@H]2C(=O)N[C@@H](CC2=NC=NC2)C(=O)N[C@@H](CCC(N)=O)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

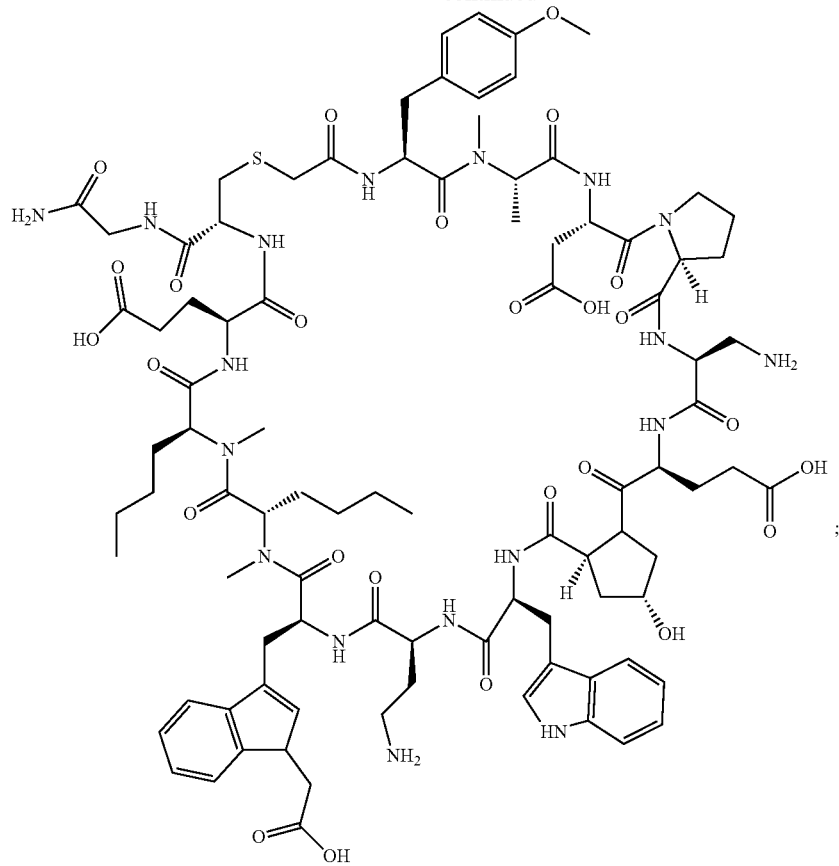
-continued
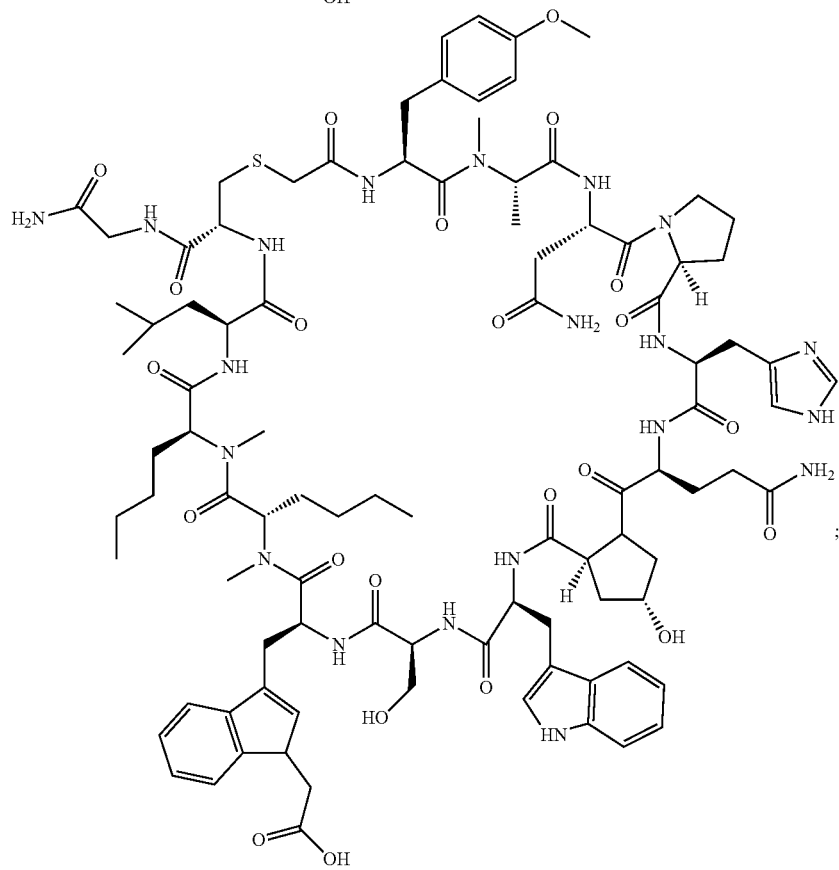
;

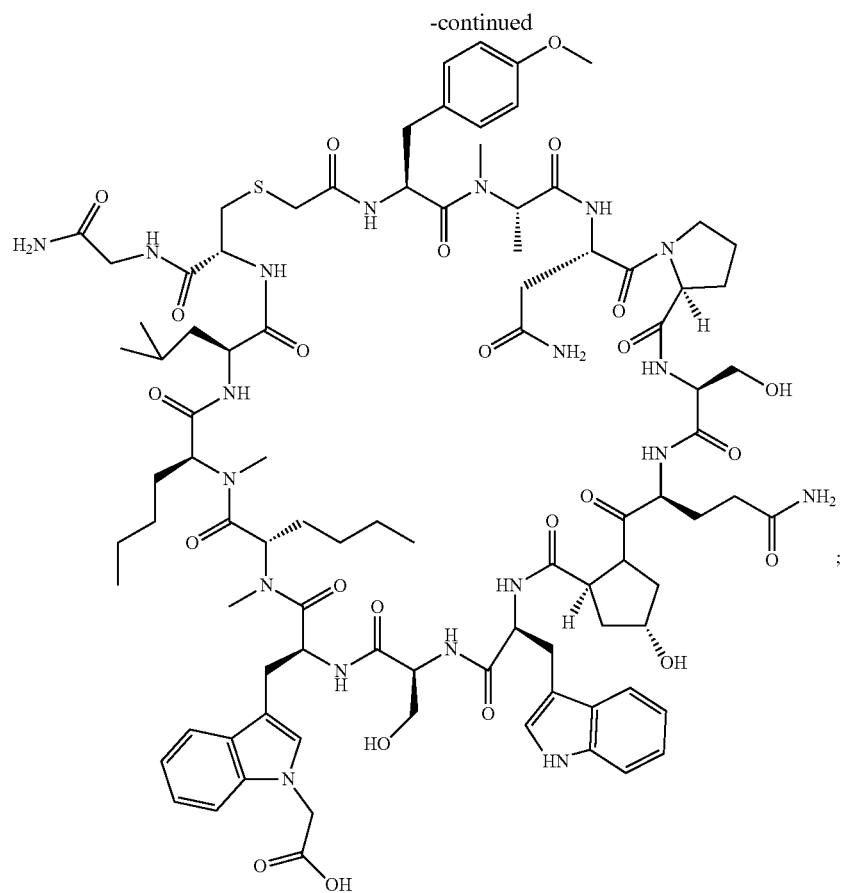
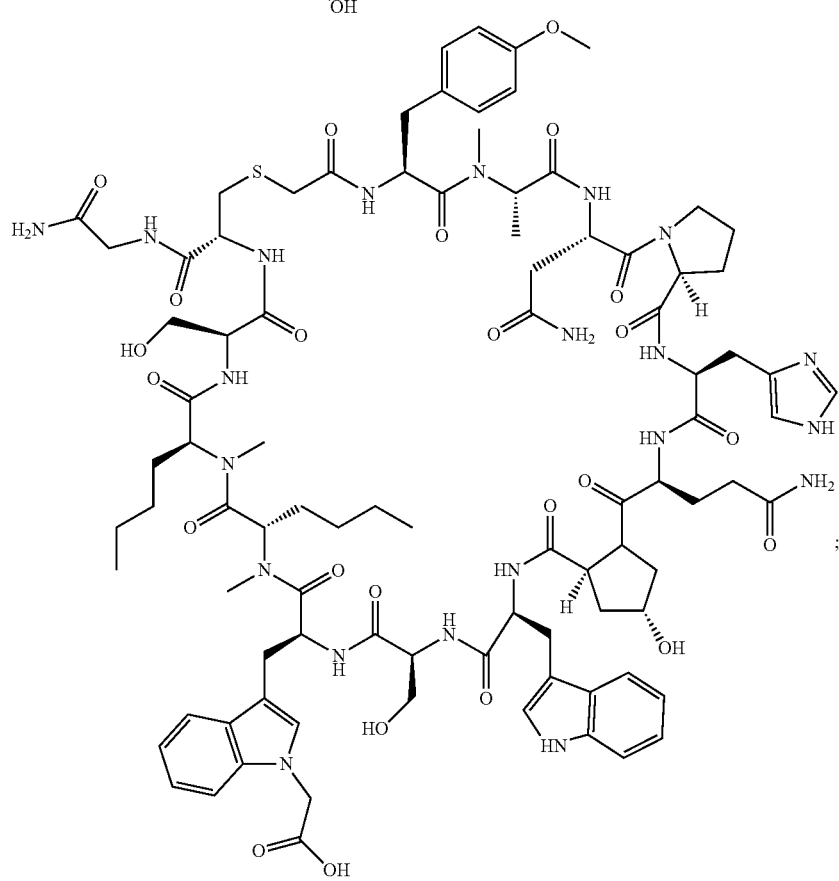

-continued
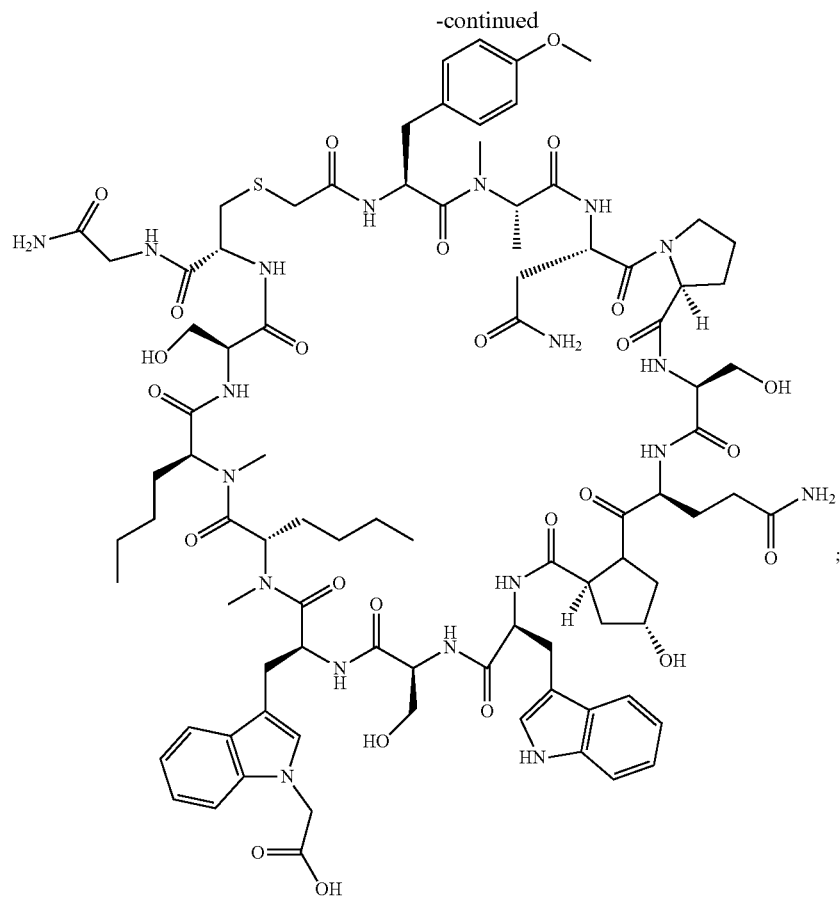
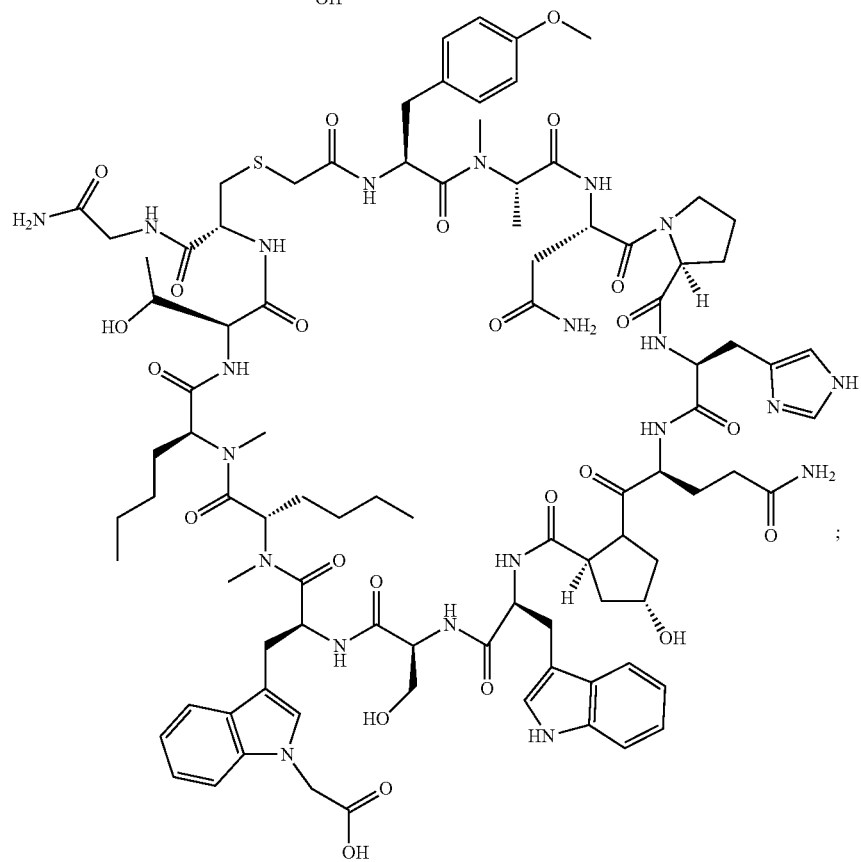

1081
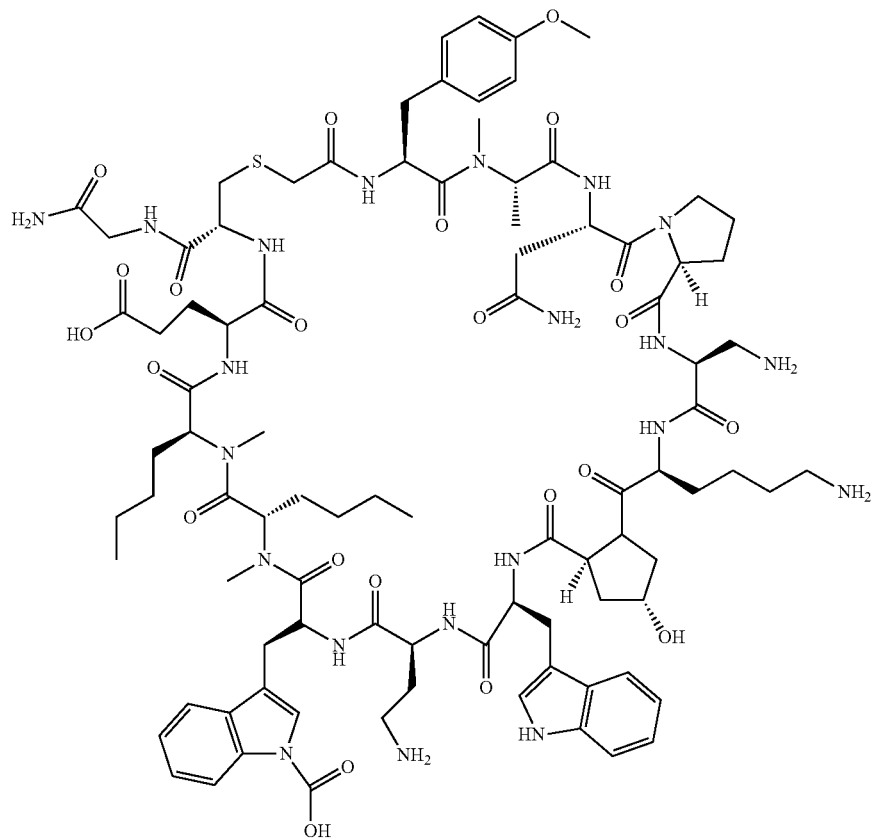
;
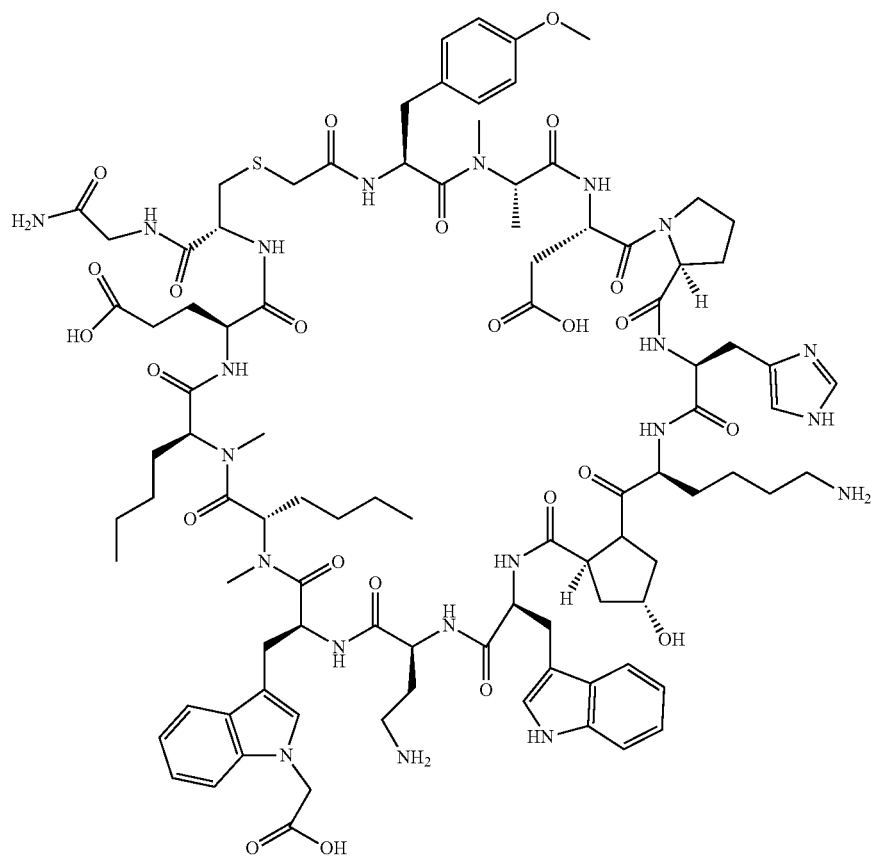
;

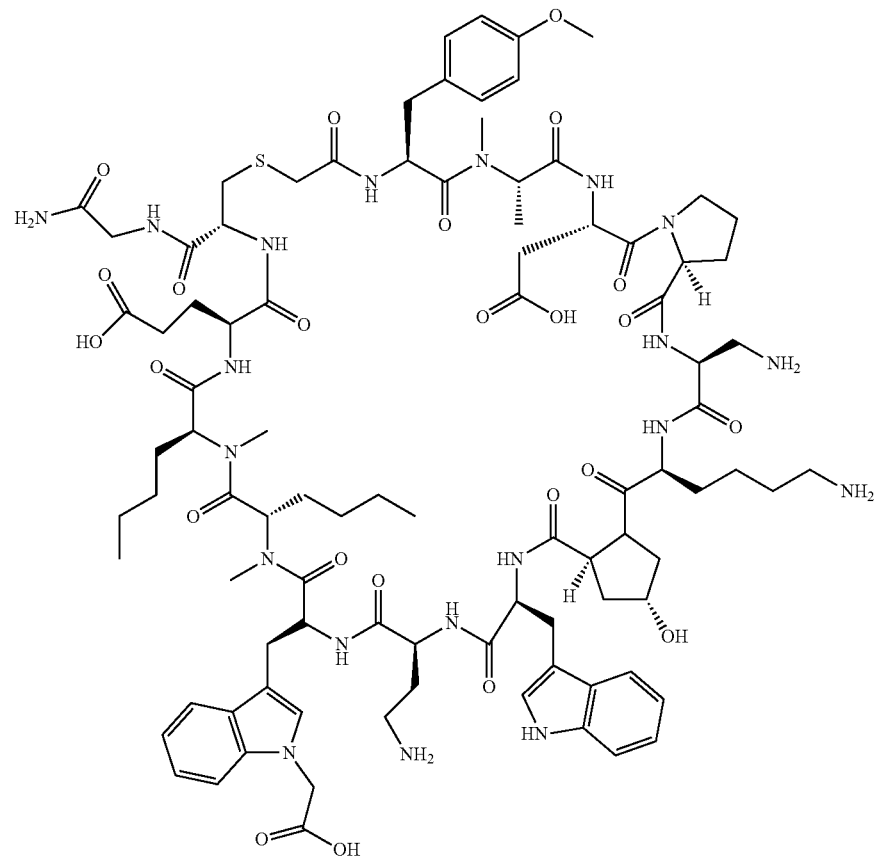
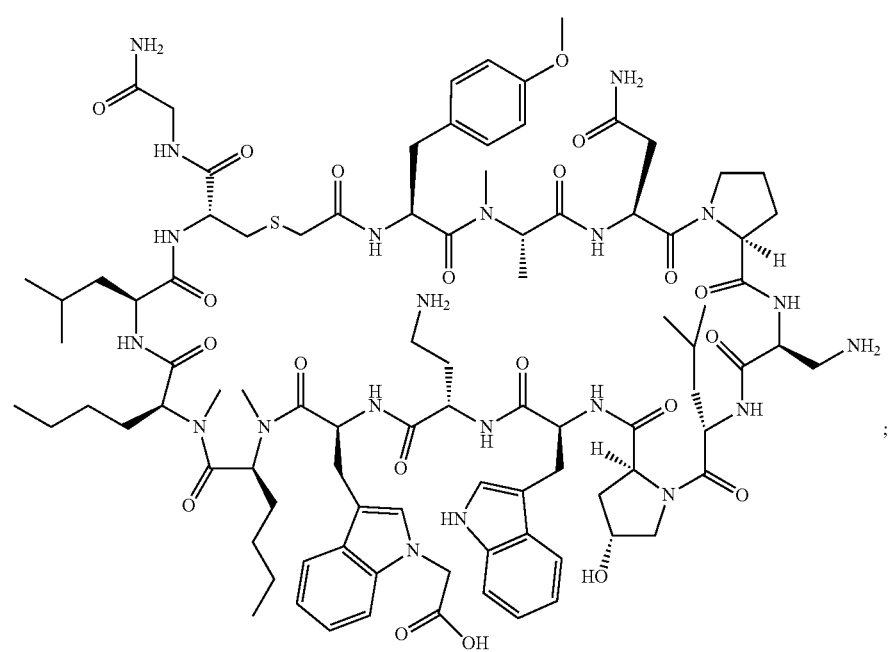

-continued
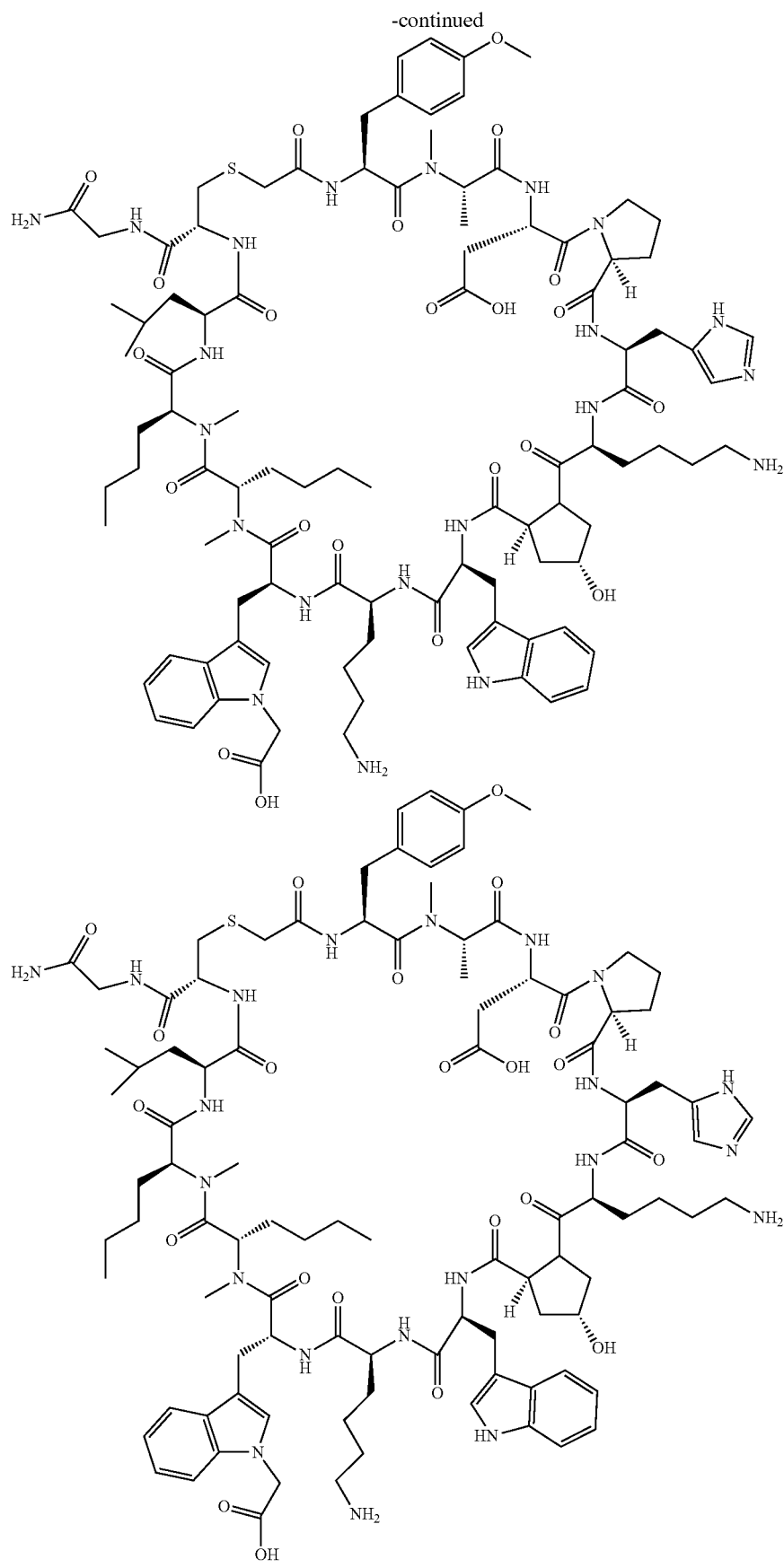
; and
;
or a pharmaceutically acceptable salt thereof.

2. A method of treating septic shock in a subject in need thereof, the method comprising administering to the subject a therapeutically effective amount of a compound of claim 1.

3. A method blocking the interaction of PD-L1 with PD-1 and/or CD80 in a subject, the method comprising administering to the subject a therapeutically effective amount of a compound of claim 1.

\* \* \* \* \*